US010688099B2

(12) United States Patent
Naryshkin

(10) Patent No.: US 10,688,099 B2
(45) Date of Patent: Jun. 23, 2020

(54) METHODS FOR MODULATING THE AMOUNT OF RNA TRANSCRIPTS

(71) Applicant: PTC Therapeutics, Inc., South Plainfield, NJ (US)

(72) Inventor: Nikolai Naryshkin, East Brunswick, NJ (US)

(73) Assignee: PTC Therapeutics, Inc., South Plainfield, NJ (US)

( * ) Notice: Subject to any disclaimer, the term of this patent is extended or adjusted under 35 U.S.C. 154(b) by 0 days.

(21) Appl. No.: 16/248,020

(22) Filed: Jan. 15, 2019

(65) Prior Publication Data

US 2019/0134045 A1 May 9, 2019

Related U.S. Application Data

(63) Continuation of application No. 15/105,661, filed as application No. PCT/US2014/071252 on Dec. 18, 2014, now Pat. No. 10,195,202.

(60) Provisional application No. 61/918,591, filed on Dec. 19, 2013.

(51) Int. Cl.
*A61K 31/519* (2006.01)
*A61K 31/4545* (2006.01)
*A61K 31/496* (2006.01)
*A61K 31/5377* (2006.01)
*C07D 471/04* (2006.01)
*C07D 487/04* (2006.01)
*C07D 519/00* (2006.01)
*A61K 31/551* (2006.01)

(52) U.S. Cl.
CPC ........ *A61K 31/519* (2013.01); *A61K 31/4545* (2013.01); *A61K 31/496* (2013.01); *A61K 31/5377* (2013.01); *A61K 31/551* (2013.01); *C07D 471/04* (2013.01); *C07D 487/04* (2013.01); *C07D 519/00* (2013.01)

(58) Field of Classification Search
None
See application file for complete search history.

(56) References Cited

U.S. PATENT DOCUMENTS

| 3,558,618 | A | 1/1971 | Trepanier et al. |
| 4,122,274 | A | 10/1978 | Juby |
| 4,342,870 | A | 8/1982 | Kennis et al. |
| 5,089,633 | A | 2/1992 | Powers et al. |
| 5,599,816 | A | 2/1997 | Chu et al. |
| 6,630,488 | B1 | 10/2003 | Lamothe et al. |
| 6,977,255 | B2 | 12/2005 | Robertson et al. |
| 7,326,711 | B2 | 2/2008 | Wang et al. |
| 7,399,767 | B2 | 7/2008 | Zhang et al. |
| 7,569,337 | B2 | 8/2009 | Auberson |
| 7,897,792 | B2 | 3/2011 | Iikura et al. |
| 8,337,941 | B2 | 12/2012 | Gubernator et al. |
| 8,633,019 | B2 | 1/2014 | Paushkin et al. |
| 9,371,336 | B2 | 6/2016 | Lee et al. |
| 9,399,649 | B2 | 6/2016 | Chen et al. |
| 2003/0199526 | A1 | 10/2003 | Choquette et al. |
| 2008/0255162 | A1 | 10/2008 | Bruendl et al. |
| 2015/0005289 | A1 | 1/2015 | Qi et al. |
| 2015/0119380 | A1 | 4/2015 | Woll et al. |
| 2015/0080383 | A1 | 5/2015 | Yang et al. |

FOREIGN PATENT DOCUMENTS

| EP | 1227084 A1 | 6/1998 |
| WO | WO 1993/23398 | 11/1993 |
| WO | WO 1998/025930 | 6/1998 |
| WO | WO 2004/009558 | 1/2004 |
| WO | WO 2008/077188 A1 | 7/2008 |
| WO | WO 2009/151546 | 5/2009 |
| WO | WO 2010/19236 | 8/2009 |
| WO | WO 2007/109211 | 9/2009 |
| WO | WO 2009/156861 | 12/2009 |
| WO | WO 2010/000032 A1 | 1/2010 |
| WO | WO 2011/050245 | 4/2011 |
| WO | WO 2011/62853 | 5/2011 |
| WO | WO 2011/85990 | 7/2011 |
| WO | WO 2013/059606 | 4/2013 |
| WO | WO 2013/101974 | 7/2013 |
| WO | WO 2013/112788 | 8/2013 |
| WO | WO 2013/119916 | 8/2013 |
| WO | WO 2013/130689 | 9/2013 |
| WO | WO 2013/142236 | 9/2013 |
| WO | WO 2015/024876 A2 | 2/2015 |
| WO | WO 2015/095446 | 6/2015 |
| WO | WO 2015/095449 | 6/2015 |

OTHER PUBLICATIONS

Coady et al., 2010, "Trans-splicing-mediated improvement in a severe mouse model of spinal muscular atrophy," J Neurosci., vol. 30(1), pp. 126-130 (2010).
Greene et al., 1991, Protective Groups in Organic Synthesis (1991), Wiley, New York, pp. v-xxi and 1-17.
Hua et al., 2012, "Peripheral SMN restoration is essential for long-term rescue of a severe SMA mouse model," Nature, vol. 478(7367): pp. 123-126 (2012).
Jarecki et al., 2005, "Diverse small-molecule modulators of SMN expression found by high throughput compound screening: early leads towards a therapeutic for spinal muscular atrophy," *Human Molecular Genetics*, 14(14):2003-2018 (2005).
Knight et al., 2004, "Isoform-specific phosphoinositide 3-kinase inhibitors from an arylmorpholine scaffold," *Bioorganic & Medicinal Chemistry*, 12:4749-4759 (2004).
Kocar et al., 2002, "Transformations of 3-aminopyridazines. Synthesis of 4-oxo-4H-pyrimido [1,2-b]pyridazine and 1-(substituted pyridazin-3-yi)-1H-1,2,3-triazole derivatives,"ARKIVOC 2002 (viii) 143-156.

(Continued)

*Primary Examiner* — Savitha M Rao
*Assistant Examiner* — Gregg Polansky
(74) *Attorney, Agent, or Firm* — Jones Day

(57) ABSTRACT

Described herein are methods for modulating the amount of a gene product and compounds for use in such methods. More particularly, described herein are methods for modulating the amount of an RNA transcript or protein product as the result of gene expression and compounds for use in such methods.

7 Claims, 3 Drawing Sheets

Specification includes a Sequence Listing.

(56) References Cited

OTHER PUBLICATIONS

Le et al., 2005, "SMND7, the major product of the centromeric survival motor neuron (SMN2) gene, extends survival in mice with spinal muscular atrophy and associates with full-length SMN," *Human Molecular Genetics*, vol. 14(6) pp. 845-857 (2005).

Liu et al., 1996, "A novel nuclear structure containing the survival of motor neurons protein," EMBO J., vol. 15(14), pp. 3555-3565 (1996).

Makhortova, et al. 2011, "A Screen for Regulators of Survival of Motor Neuron Protein Levels," *Nat Chern Bioi*, 7(8):544-552 (2011).

Passini et al., 2001, "Antisense Oligonucleotides Delivered to the Mouse CNS Ameliorate Symptoms of Severe Spinal Muscular Atrophy," Sci Transl Med., vol. 3(72) (2001).

Peng et al., 2011, "Identification of pyrido [1, 2-α] pyrimidine-4-ones as new molecules improving the transcriptional functions of estrogen-related receptor α", *Journal of medicinal chemistry*, 54.21 (2011): 7729-7733.

PubChem compound CID 377422. Mar. 26, 2005. [Retrieved from the Internet Oct. 27, 2014: <http://pubchem.ncbi.nlm.nih.gov//compound/377422?from=summary>).

PCT International Preliminary Report dated Aug. 21, 2014 in connection with PCT/US2013/025292.

PCT International Search Report dated Oct. 24, 2013 with Publication No. WO 2013-119916 A3 in connection with PCT/US2013/025292.

PCT International Search Report dated Aug. 30, 2013 in connection with PCT/US2013/025292.

PCT Written Opinion of the International Searching Authority dated Aug. 30, 2013 in connection with PCT/US2013/025292.

Naryshkin et al., 2014, "SMN2 splicing modifiers improve motor function and longevity in mice with spinal muscular atrophy," *Science*, 345.6197 (2014): 688-693 (including supplementary materials).

Palacino, et al., 2015, "SMN2 splice modulators enhance U1-pre-mRNA association and rescue SMA mice," *Nature chemical biology*, 11.7 (2015): 511-517 (including supplementary materials).

European Patent Office, a Communication pursuant to Article 94(3) EPC, European Application No. 14877918.4, date of mailing Mar. 23, 2018.

METHODS FOR MODULATING THE AMOUNT OF RNA TRANSCRIPTS

CROSS-REFERENCE

This application is a continuation of U.S. patent application Ser. No. 15/105,661, filed Jun. 17, 2016, currently allowed, which is a U.S. national stage application of International Patent Application No. PCT/US2014/071252, filed Dec. 18, 2014, which claims the benefit of priority to U.S. Provisional Application Ser. No. 61/918,591, filed Dec. 19, 2013, each of which is incorporated herein by reference in its entirety and for all purposes.

INTRODUCTION

Described herein are methods for modulating the amount of a gene product and compounds for use in such methods. More particularly, described herein are methods for modulating the amount of an RNA transcript or protein product as the result of gene expression and compounds for use in such methods.

BACKGROUND

A number of diseases are associated with aberrant expression of a gene product (e.g., an RNA transcript or protein) of a gene. The resulting aberrant amounts of RNA transcripts may lead to disease due to corresponding changes in protein expression. Changes in the amount of a particular RNA transcript may be the result of several factors. First, changes in the amount of RNA transcripts may be due to an aberrant level of transcription of a particular gene, such as by the perturbation of a transcription factor or a portion of the transcription process, resulting in a change in the expression level of a particular RNA transcript. Secondly, changes in the splicing of particular RNA transcripts, such as by perturbation of a particular splicing process or mutations in the gene that lead to modified splicing can change the levels of a particular RNA transcript. Changes to the stability of a particular RNA transcript or to components that maintain RNA transcript stability, such as the process of poly-A tail incorporation or an effect on certain factors or proteins that bind to and stabilize RNA transcripts, may lead to changes in the levels of a particular RNA transcript. Also, the level of translation of particular RNA transcripts can affect the amount of those transcripts, affecting or upregulating RNA transcript decay processes. Finally, aberrant RNA transport or RNA sequestration may also lead to changes in functional levels of RNA transcripts, and may have an effect on the stability, further processing, or translation of the RNA transcripts.

Often, diseases associated with changes to RNA transcript amount are treated with a focus on the aberrant protein expression. However, if the processes responsible for the aberrant changes in RNA levels, such as components of the splicing process or associated transcription factors or associated stability factors, could be targeted by treatment with a small molecule, it would be possible to restore protein expression levels such that the unwanted effects of the expression of aberrant levels of RNA transcripts or associated proteins. Therefore, there is a need for methods of modulating the amount of RNA transcripts encoded by certain genes as a way to prevent or treat diseases associated with aberrant expression of the RNA transcripts or associated proteins.

SUMMARY

In one aspect, provided herein are methods for modulating the amount of one or more RNA transcripts (e.g., rRNA, tRNA, miRNA, siRNA, lncRNA, pre-mRNA, or mRNA transcripts) or proteins thereof expressed as the product of one or more of genes, comprising contacting a cell with a compound of Formula (I)

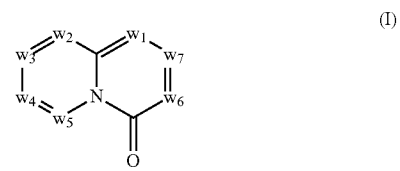

or a form thereof, wherein $w_1$, $w_2$, $w_3$, $w_4$, $w_5$, $w_6$ and $w_7$ are as defined herein. In one embodiment, provided herein are methods for modulating the amount of one, two, three or more RNA transcripts of a gene, by way of nonlimiting example, disclosed in Tables 1-4, 6 and 8-11, infra, comprising contacting a cell with a compound of Formula (I) or a form thereof. In another embodiment, provided herein are methods for modulating one, two, three or more RNA transcripts of one, two, three or more genes, by way of nonlimiting example, disclosed in Tables 1-4, 6 and 8-11, infra, comprising contacting a cell with a compound of Formula (I) or a form thereof. In certain embodiments, the cell is contacted with the compound of Formula (I) or a form thereof in a cell culture. In other embodiments, the cell is contacted with the compound of Formula (I) or a form thereof in a subject (e.g., a non-human animal subject or a human subject). In certain embodiments, a compound of Formula (I) is a compound of Formula (II), Formula (III), Formula (IV), Formula (V), Formula (VI), Formula (VII), Formula (VIII), Formula (IX), Formula (X), Formula (XI), Formula (XII), Formula (XIII), or Formula (XIV) described infra. In some embodiments, a compound of Formula (I) is a compound selected from a compound described herein.

In another aspect, provided herein are methods for modulating the amount of one, two, three or more RNA transcripts of a gene comprising administering to a patient in need thereof a compound of Formula (I) or a form thereof, or a pharmaceutical composition comprising a compound of Formula (I) or a form thereof and a pharmaceutically acceptable carrier, excipient or diluent. In one embodiment, provided herein are methods for modulating the amount of one, two, three or more RNA transcripts of a gene, by way of nonlimiting example, disclosed in Tables 1-4, 6 and 8-11, infra, comprising administering to a patient in need thereof a compound of Formula (I) or a form thereof, or a pharmaceutical composition comprising a compound of Formula (I) or a form thereof and a pharmaceutically acceptable carrier, excipient or diluent. In another embodiment, provided herein are methods for modulating the amount of one, two, three or more RNA transcripts of one, two, three or more genes disclosed in Tables 1-4, 6 and 8-11, infra, comprising administering to a patient in need thereof a compound of Formula (I) or a form thereof, or a pharmaceutical composition comprising a compound of Formula (I) or a form thereof, and a pharmaceutically acceptable carrier, excipient or diluent. In certain embodiments, a compound of Formula (I) is a compound of Formula (II), Formula (III), Formula (IV), Formula (V), Formula (VI), Formula (VII), Formula (VIII), Formula (IX), Formula (X), Formula (XI), Formula (XII), Formula (XIII), or Formula (XIV) described infra. In some embodiments, a compound of Formula (I) is a compound selected from a compound described herein.

In another aspect, provided herein are methods for preventing and/or treating a disease associated with the aberrant expression of a gene product, comprising administering to a patient in need thereof a compound of Formula (I) or a form thereof, or a pharmaceutical composition comprising a compound of Formula (I) or a form thereof and a pharmaceutically acceptable carrier, excipient or diluent. In one embodiment, provided herein are methods for preventing and/or treating a disease associated with aberrant expression of a gene product (e.g., an RNA transcript or protein) a gene, by way of nonlimiting example, disclosed in Tables 1-4, 6 and 8-11, infra, comprising administering to a patient in need thereof a compound of Formula (I) or a form thereof, or a pharmaceutical composition comprising a compound of Formula (I) or a form thereof and a pharmaceutically acceptable carrier, excipient or diluent. In certain embodiments, a compound of Formula (I) is a compound of Formula (II), Formula (III), Formula (IV), Formula (V), Formula (VI), Formula (VII), Formula (VIII), Formula (IX), Formula (X), Formula (XI), Formula (XII), Formula (XIII), or Formula (XIV) described infra. In some embodiments, a compound of Formula (I) is a compound selected from a compound described herein.

In another aspect, provided herein are methods for preventing and/or treating a disease in which a change in the level of expression of one, two, three or more RNA isoforms encoded by a gene is beneficial to the prevention and/or treatment of the disease, comprising administering to a patient in need thereof a compound of Formula (I) or a form thereof, or a pharmaceutical composition comprising a compound of Formula (I) or a form thereof and a pharmaceutically acceptable carrier, excipient or diluent. In one embodiment, provided herein are methods for preventing and/or treating a disease in which the increase in the expression one, two, three or more RNA isoforms encoded by gene, by way of nonlimiting example, disclosed in Tables 1-4, 6 and 8-11, infra, is beneficial to the prevention and/or treatment of the disease, comprising administering to a patient in need thereof a compound of Formula (I) or a form thereof, or a pharmaceutical composition comprising a compound of Formula (I) or a form thereof and a pharmaceutically acceptable carrier, excipient or diluent. In another embodiment, provided herein are methods for preventing and/or treating a disease in which the decrease in the expression one, two, three or more RNA isoforms encoded by a gene, by way of nonlimiting example, disclosed in Tables 1-4, 6 and 8-11, infra, is beneficial to the prevention and/or treatment of the disease, comprising administering to a patient in need thereof a compound of Formula (I) or a form thereof, or a pharmaceutical composition comprising a compound of Formula (I) or a form thereof and a pharmaceutically acceptable carrier, excipient or diluent. In certain embodiments, a compound of Formula (I) is a compound of Formula (II), Formula (III), Formula (IV), Formula (V), Formula (VI), Formula (VII), Formula (VIII), Formula (IX), Formula (X), Formula (XI), Formula (XII), Formula (XIII), or Formula (XIV) described infra. In some embodiments, a compound of Formula (I) is a compound selected from a compound described herein.

In another aspect, provided herein are methods for preventing and/or treating a disease in which a change in the level of expression of one, two, three or more protein isoforms encoded by a gene is beneficial to the prevention and/or treatment of the disease, comprising administering to a patient in need thereof a compound of Formula (I) or a form thereof, or a pharmaceutical composition comprising a compound of Formula (I) or a form thereof and a pharmaceutically acceptable carrier, excipient or diluent. In one embodiment, provided herein are methods for preventing and/or treating a disease in which the increase in the expression one, two, three or more protein isoforms encoded by a gene, by way of nonlimiting example, disclosed in Tables 1-4, 6 and 8-11, infra, is beneficial to the prevention and/or treatment of the disease, comprising administering to a patient in need thereof a compound of Formula (I) or a form thereof, or a pharmaceutical composition comprising a compound of Formula (I) or a form thereof and a pharmaceutically acceptable carrier, excipient or diluent. In another embodiment, provided herein are methods for preventing and/or treating a disease in which the decrease in the expression one, two, three or more protein isoforms encoded by a gene, by way of nonlimiting example, disclosed in Tables 1-4, 6 and 8-11, infra, is beneficial to the prevention and/or treatment of the disease, comprising administering to a patient in need thereof a compound of Formula (I) or a form thereof, or a pharmaceutical composition comprising a compound of Formula (I) or a form thereof and a pharmaceutically acceptable carrier, excipient or diluent. In certain embodiments, a compound of Formula (I) is a compound of Formula (II), Formula (III), Formula (IV), Formula (V), Formula (VI), Formula (VII), Formula (VIII), Formula (IX), Formula (X), Formula (XI), Formula (XII), Formula (XIII), or Formula (XIV) described infra. In some embodiments, a compound of Formula (I) is a compound selected from a compound described herein.

DETAILED DESCRIPTION

Figure 1:
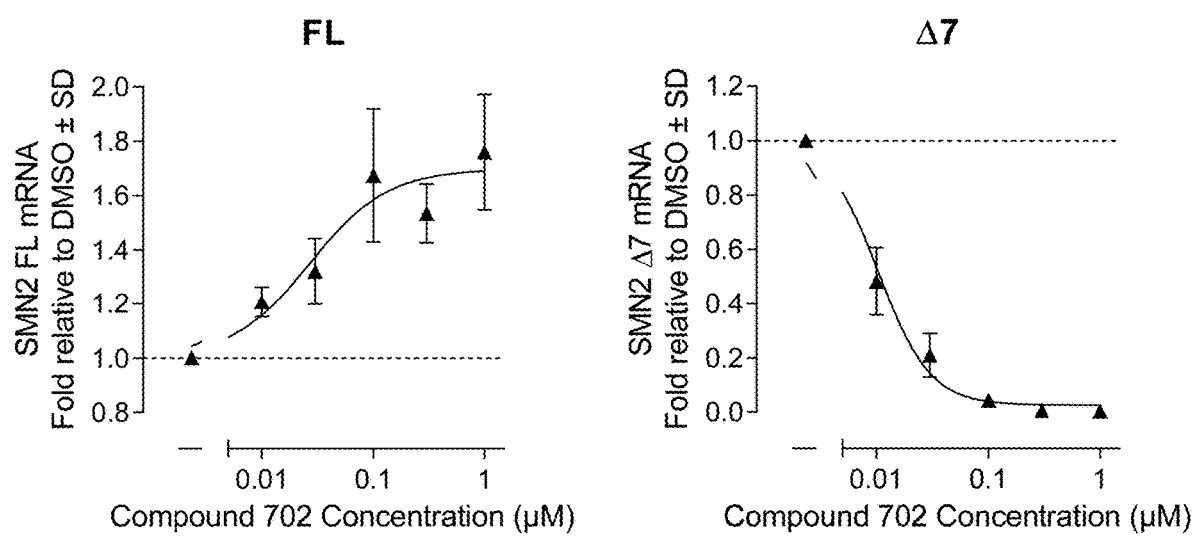
FIG. 1. Effect of Compound 702 treatment for 24 hours showing dose dependent expression of full length (FL) and exon 7 lacking ($\Delta 7$) mRNA in SMA Type I patient fibroblasts.

In one aspect, provided herein are methods for modulating the amount of one or more RNA transcripts of one or more of genes, comprising contacting a cell with a compound of Formula (I) or a form thereof. In certain embodiments, a compound of Formula (I) or a form thereof modulates the amount of one or more of the RNA transcripts of one or more of the genes, by way of nonlimiting example, in Tables 1-4, 6 and 8-11, infra.

In another aspect, provided herein are methods for modulating an aberrant amount of RNA transcripts of a gene(s) comprising administering to a patient in need thereof a compound of Formula (I) or a form thereof, or a pharmaceutical composition comprising a compound of Formula (I) or a form thereof and a pharmaceutically acceptable carrier, excipient or diluent. In certain embodiments, a compound of Formula (I) or a form thereof modulates the amount of one, two, three or more of the RNA transcripts of one, two, three or more of the genes, by way of nonlimiting example, in Tables 1-4, 6 and 8-11, infra.

In another aspect, provided herein are methods for preventing and/or treating a disease associated with the aberrant expression of a gene, comprising administering to a patient in need thereof a compound of Formula (I) or a form thereof, or a pharmaceutical composition comprising a compound of Formula (I) or a form thereof and a pharmaceutically acceptable carrier, excipient or diluent. In certain embodiments, the disease is associated with the aberrant expression of a gene, by way of nonlimiting example, in Tables 1-4, 6 and 8-11, infra. In certain embodiments, the disease is not associated with the aberrant expression of the SMN2 gene.

In another aspect, provided herein are methods for preventing and/or treating a disease in which a change in the level of expression of one, two, three or more RNA isoforms of a gene(s) is beneficial to the prevention and/or treatment of the disease, comprising administering to a patient in need thereof a compound of Formula (I) or a form thereof, or a pharmaceutical composition comprising a compound of Formula (I) or a form thereof and a pharmaceutically acceptable carrier, excipient or diluent. In certain embodiments, an increase in the level of expression of one, two, three or more RNA isoforms of one, two, three or more genes, by way of nonlimiting example, in Tables 1-4, 6 and 8-11, infra, is beneficial to prevent and/or treat a disease. In other embodiments, a decrease in the level of expression of one, two, three or more RNA isoforms of one, two or more genes, by way of nonlimiting example, in Tables 1-4, 6 and 8-11, infra, is beneficial to prevent and/or treat a disease.

In another aspect, provided herein are methods for preventing and/or treating a disease in which a change in the level of expression of one, two, three or more protein isoforms of a gene(s) is beneficial to the prevention and/or treatment of the disease, comprising administering to a patient in need thereof a compound of Formula (I) or a form thereof, or a pharmaceutical composition comprising a compound of Formula (I) or a form thereof and a pharmaceutically acceptable carrier, excipient or diluent. In certain embodiments, an increase in the level of expression of one, two, three or more protein isoforms of one, two, three or more genes, by way of nonlimiting example, in Tables 1-4, 6 and 8-11, infra, is beneficial to prevent and/or treat a disease. In other embodiments, a decrease in the level of expression of one, two, three or more protein isoforms of one, two or more genes, by way of nonlimiting example, in Tables 1-4, 6 and 8-11, infra, is beneficial to prevent and/or treat a disease.

Compounds

Provided herein are compounds of Formula (I) for use in the methods described herein:

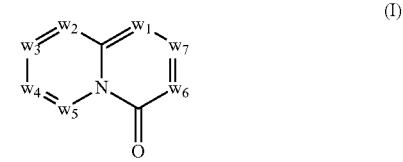

(I)

or a form thereof, wherein:

$w_1$ and $w_5$ are independently C—$R_a$ or N;

$w_2$ is C—$R_b$ or N;

$w_3$, $w_4$ and $w_7$ are independently C—$R_1$, C—$R_2$, C—$R_a$ or N;

$w_6$ is C—$R_1$, C—$R_2$, C—Re or N;

wherein one of $w_3$, $w_4$, $w_6$ and $w_7$ is C—$R_1$ and one other of $w_3$, $w_4$, $w_6$ and $w_7$ is C—$R_2$, provided that, when $w_3$ is C—$R_1$, then $w_6$ is C—$R_2$ and $w_4$ and $w_7$ are independently C—$R_a$ or N; or, when $w_3$ is C—$R_2$, then $w_6$ is C—$R_1$ and $w_4$ and $w_7$ are independently C—$R_a$ or N; or, when $w_4$ is C—$R_1$, then $w_7$ is C—$R_2$ and $w_3$ is C—$R_a$ or N and $w_6$ is C—$R_c$ or N; or, when $w_4$ is C—$R_2$, then $w_7$ is C—$R_1$ and $w_3$ is C—$R_a$ or N and $w_6$ is C—Re or N; and, wherein any one, two or three of $w_1$, $w_2$, $w_3$, $w_4$, $w_5$, $w_6$ and $w_7$ may optionally be N;

$R_1$ is $C_{1-8}$alkyl, amino, $C_{1-8}$alkyl-amino, ($C_{1-8}$alkyl)$_2$-amino, $C_{1-8}$alkoxy-$C_{1-8}$alkyl-amino, ($C_{1-8}$alkoxy-$C_{1-8}$alkyl)$_2$-amino, ($C_{1-8}$alkoxy-$C_{1-8}$alkyl)($C_{1-8}$alkyl)amino, amino-$C_{1-8}$alkyl, $C_{1-8}$alkyl-amino-$C_{1-8}$alkyl, ($C_{1-8}$alkyl)$_2$-amino-$C_{1-8}$alkyl, $C_{1-8}$alkoxy-$C_{1-8}$alkyl-amino-$C_{1-8}$alkyl, ($C_{1-8}$alkoxy-$C_{1-8}$alkyl)$_2$-amino-$C_{1-8}$alkyl, ($C_{1-8}$alkoxy-$C_{1-8}$alkyl)($C_{1-8}$alkyl)amino-$C_{1-8}$alkyl, amino-$C_{1-8}$alkyl-amino, (amino-$C_{1-8}$alkyl)$_2$-amino, (amino-$C_{1-8}$alkyl)($C_{1-8}$alkyl)amino, $C_{1-8}$alkyl-amino-$C_{1-8}$alkyl-amino, ($C_{1-8}$alkyl-amino-$C_{1-8}$alkyl)$_2$-amino, ($C_{1-8}$alkyl-amino-$C_{1-8}$alkyl)($C_{1-8}$alkyl)amino, ($C_{1-8}$alkyl)$_2$-amino-$C_{1-8}$alkyl-amino, [($C_{1-8}$alkyl)$_2$-amino-$C_{1-8}$alkyl]($C_{1-8}$alkyl)amino, amino-$C_{1-8}$alkoxy, $C_{1-8}$alkyl-amino-$C_{1-8}$alkoxy, ($C_{1-8}$alkyl)$_2$-amino-$C_{1-8}$alkoxy, $C_{1-8}$alkoxy-$C_{1-8}$alkyl-amino-$C_{1-8}$alkoxy, $C_{1-8}$alkoxy-$C_{1-8}$alkyl-amino-$C_{1-8}$alkoxy, ($C_{1-8}$alkoxy-$C_{1-8}$alkyl)($C_{1-8}$alkyl)amino-$C_{1-8}$alkoxy, amino-$C_{2-8}$alkenyl, $C_{1-8}$alkyl-amino-$C_{2-8}$alkenyl, ($C_{1-8}$alkyl)$_2$-amino-$C_{2-8}$alkenyl, amino-$C_{2-8}$alkynyl, $C_{1-8}$alkyl-amino-$C_{2-8}$alkynyl, ($C_{1-8}$alkyl)$_2$-amino-$C_{2-8}$alkynyl, halo-$C_{1-8}$alkyl-amino, (halo-$C_{1-8}$alkyl)$_2$-amino, (halo-$C_{1-8}$alkyl)($C_{1-8}$alkyl)amino, hydroxy-$C_{1-8}$alkyl, hydroxy-$C_{1-8}$alkoxy-$C_{1-8}$alkyl, hydroxy-$C_{1-8}$alkyl-amino, (hydroxy-$C_{1-8}$alkyl)$_2$-amino, (hydroxy-$C_{1-8}$alkyl)($C_{1-8}$alkyl)amino, hydroxy-$C_{1-8}$alkyl-amino-$C_{1-8}$alkyl, (hydroxy-$C_{1-8}$alkyl)$_2$-amino-$C_{1-8}$alkyl, (hydroxy-$C_{1-8}$alkyl)($C_{1-8}$alkyl)amino-$C_{1-8}$alkyl, hydroxy-$C_{1-8}$alkyl-amino-$C_{1-8}$alkoxy, (hydroxy-$C_{1-8}$alkyl)$_2$-amino-$C_{1-8}$alkoxy, (hydroxy-$C_{1-8}$alkyl)($C_{1-8}$alkyl)amino-$C_{1-8}$alkoxy, hydroxy-$C_{1-8}$alkyl-amino-$C_{1-8}$alkyl-amino, (hydroxy-$C_{1-8}$alkyl-amino-$C_{1-8}$alkyl)$_2$-amino, (hydroxy-$C_{1-8}$alkyl)$_2$-amino-$C_{1-8}$alkyl-amino, (hydroxy-$C_{1-8}$alkyl-amino-$C_{1-8}$alkyl)($C_{1-8}$alkyl)amino, (hydroxy-$C_{1-8}$alkyl)($C_{1-8}$alkyl)amino-$C_{1-8}$alkyl-amino, [(hydroxy-$C_{1-8}$alkyl)$_2$-amino-$C_{1-8}$alkyl]($C_{1-8}$alkyl)amino, [(hydroxy-$C_{1-8}$alkyl)($C_{1-8}$alkyl)amino-$C_{1-8}$alkyl]($C_{1-8}$alkyl)amino, heterocyclyl, heterocyclyl-$C_{1-8}$alkyl, heterocyclyl-$C_{1-8}$alkoxy, heterocyclyl-amino, (heterocyclyl)($C_{1-8}$alkyl)amino, heterocyclyl-amino-$C_{1-8}$alkyl, heterocyclyl-$C_{1-8}$alkyl-amino, (heterocyclyl-$C_{1-8}$alkyl)$_2$-amino, (heterocyclyl-$C_{1-8}$alkyl)($C_{1-8}$alkyl)amino, heterocyclyl-$C_{1-8}$alkyl-amino-$C_{1-8}$alkyl, (heterocyclyl-$C_{1-8}$alkyl)$_2$-amino-$C_{1-8}$alkyl, (heterocyclyl-$C_{1-8}$alkyl)($C_{1-8}$alkyl)amino-$C_{1-8}$alkyl, heterocyclyl-oxy, heterocyclyl-carbonyl, heterocyclyl-carbonyl-oxy, $C_{3-14}$cycloalkyl, aryl-$C_{1-8}$ alkyl-amino, (aryl-$C_{1-8}$alkyl)$_2$-amino, (aryl-$C_{1-8}$alkyl)($C_{1-8}$alkyl)amino, aryl-$C_{1-8}$alkyl-amino-$C_{1-8}$alkyl, (aryl-$C_{1-8}$ alkyl)$_2$-amino-$C_{1-8}$alkyl, (aryl-$C_{1-8}$alkyl)($C_{1-8}$alkyl)amino-$C_{1-8}$alkyl, heteroaryl, heteroaryl-$C_{1-8}$alkyl, heteroaryl-$C_{1-8}$alkoxy, heteroaryl-amino, heteroaryl-$C_{1-8}$alkyl-amino, (heteroaryl-$C_{1-8}$alkyl)$_2$-amino, (heteroaryl-$C_{1-8}$ alkyl)($C_{1-8}$alkyl)amino, heteroaryl-$C_{1-8}$alkyl-amino-$C_{1-8}$alkyl, (heteroaryl-$C_{1-8}$alkyl)$_2$-amino-$C_{1-8}$alkyl or (heteroaryl-$C_{1-8}$alkyl)($C_{1-8}$alkyl)amino-$C_{1-8}$alkyl;

wherein, each instance of heterocyclyl, $C_{3-14}$cycloalkyl, aryl and heteroaryl is optionally substituted with one, two or three $R_3$ substituents and optionally, with one additional $R_4$ substituent; or, wherein, each instance of heterocyclyl, $C_{3-14}$cycloalkyl, aryl and heteroaryl is optionally substituted with one, two, three or four $R_3$ substituents;

$R_2$ is aryl, aryl-amino, aryl-amino-carbonyl, heterocyclyl, heteroaryl or heteroaryl-amino;

wherein, each instance of aryl, heterocyclyl and heteroaryl is optionally substituted with one, two or three $R_6$ substituents and optionally, with one additional $R_7$ substituent;

$R_a$ is, in each instance, independently selected from hydrogen, halogen, $C_{1-8}$alkyl or deuterium;

$R_b$ is hydrogen, halogen, $C_{1-8}$alkyl, $C_{1-8}$alkoxy or deuterium;

$R_c$ is hydrogen, halogen, $C_{1-8}$alkyl or deuterium;

$R_3$ is, in each instance, independently selected from cyano, halogen, hydroxy, oxo, $C_{1-8}$alkyl, halo-$C_{1-8}$alkyl, $C_{1-8}$alkyl-carbonyl, $C_{1-8}$alkoxy, halo-$C_{1-8}$alkoxy, $C_{1-8}$alkoxy-$C_{1-8}$alkyl, $C_{1-8}$alkoxy-carbonyl, amino, $C_{1-8}$alkyl-amino, ($C_{1-8}$alkyl)$_2$-amino, amino-$C_{1-8}$alkyl, $C_{1-8}$alkyl-amino-$C_{1-8}$alkyl, ($C_{1-8}$alkyl)$_2$-amino-$C_{1-8}$alkyl, amino-$C_{1-8}$alkyl-amino, $C_{1-8}$alkyl-amino-$C_{1-8}$alkyl-amino, ($C_{1-8}$alkyl-amino-$C_{1-8}$alkyl)$_2$-amino, ($C_{1-8}$alkyl)$_2$-amino-$C_{1-8}$alkyl-amino, [($C_{1-8}$alkyl)$_2$-amino-$C_{1-8}$alkyl]$_2$-amino, ($C_{1-8}$alkyl-amino-$C_{1-8}$alkyl)($C_{1-8}$alkyl)amino, [($C_{1-8}$alkyl)$_2$-amino-$C_{1-8}$alkyl]($C_{1-8}$alkyl)amino, $C_{1-8}$alkoxy-$C_{1-8}$alkyl-amino, ($C_{1-8}$alkoxy-$C_{1-8}$alkyl)$_2$-amino, ($C_{1-8}$alkoxy-$C_{1-8}$ alkyl)($C_{1-8}$alkyl)amino, $C_{1-8}$alkyl-carbonyl-amino, $C_{1-8}$alkoxy-carbonyl-amino, hydroxy-$C_{1-8}$alkyl, hydroxy-$C_{1-8}$alkoxy-$C_{1-8}$alkyl, hydroxy-$C_{1-8}$alkyl-amino, (hydroxy-$C_{1-8}$alkyl)$_2$-amino or (hydroxy-$C_{1-8}$alkyl)($C_{1-8}$alkyl)amino;

$R_4$ is $C_{3-14}$cycloalkyl, $C_{3-14}$cycloalkyl-$C_{1-8}$alkyl, $C_{3-14}$cycloalkyl-amino, aryl-$C_{1-8}$alkyl, aryl-$C_{1-8}$alkoxy-carbonyl, aryl-sulfonyloxy-$C_{1-8}$alkyl, heterocyclyl or heterocyclyl-$C_{1-8}$ alkyl; wherein, each instance of $C_{3-14}$cycloalkyl, aryl and heterocyclyl is optionally substituted with one, two or three $R_5$ substituents;

$R_5$ is, in each instance, independently selected from halogen, hydroxy, cyano, nitro, $C_{1-8}$alkyl, halo-$C_{1-8}$alkyl, $C_{1-8}$alkoxy, halo-$C_{1-8}$alkoxy, amino, $C_{1-8}$alkyl-amino, ($C_{1-8}$alkyl)$_2$-amino or $C_{1-8}$alkyl-thio;

$R_6$ is, in each instance, independently selected from halogen, hydroxy, cyano, nitro, $C_{1-8}$alkyl, $C_{2-8}$alkenyl, halo-$C_{1-8}$ alkyl, hydroxy-$C_{1-8}$alkyl, $C_{1-8}$alkoxy, halo-$C_{1-8}$alkoxy, $C_{1-8}$alkoxy-$C_{1-8}$alkyl, amino, $C_{1-8}$alkyl-amino, ($C_{1-8}$alkyl)$_2$-amino or $C_{1-8}$alkyl-thio; and, $R_7$ is $C_{3-14}$cycloalkyl, $C_{3-14}$cycloalkyl-oxy, aryl, heterocyclyl or heteroaryl.

In one embodiment of the use of a compound of Formula (I), $w_1$ is C—$R_a$.

In another embodiment of the use of a compound of Formula (I), $w_1$ is N.

In one embodiment of the use of a compound of Formula (I), $w_2$ is C—$R_b$.

In another embodiment of the use of a compound of Formula (I), $w_2$ is N.

In one embodiment of the use of a compound of Formula (I), $w_3$ is C—$R_a$.

In another embodiment of the use of a compound of Formula (I), $w_3$ is N.

In one embodiment of the use of a compound of Formula (I), $w_4$ is C—$R_a$.

In another embodiment of the use of a compound of Formula (I), $w_4$ is N.

In one embodiment of the use of a compound of Formula (I), $w_5$ is C—$R_a$.

In another embodiment of the use of a compound of Formula (I), $w_5$ is N.

In one embodiment of the use of a compound of Formula (I), $w_6$ is C—$R_c$.

In another embodiment of the use of a compound of Formula (I), $w_6$ is N.

In one embodiment of the use of a compound of Formula (I), $w_7$ is C—$R_a$.

In another embodiment of the use of a compound of Formula (I), $w_7$ is N.

In one embodiment of the use of a compound of Formula (I), $w_3$ is C—$R_1$ and $w_6$ is C—$R_2$.

In another embodiment of the use of a compound of Formula (I), $w_3$ is C—$R_2$ and $w_6$ is C—$R_1$.

In one embodiment of the use of a compound of Formula (I), $w_4$ is C—$R_1$ and $w_7$ is C—$R_2$.

In another embodiment of the use of a compound of Formula (I), $w_4$ is C—$R_2$ and $w_7$ is C—$R_1$.

In one embodiment of the use of a compound of Formula (I), $w_3$ is C—$R_1$, $w_6$ is C—$R_2$ and $w_1$, $w_4$, $w_5$ and $w_7$ are independently C—$R_a$ or N and $w_2$ is C—$R_b$ or N.

In another embodiment of the use of a compound of Formula (I), $w_3$ is C—$R_2$, $w_6$ is C—$R_1$ and $w_1$, $w_4$, $w_5$ and $w_7$ are independently C—$R_a$ or N and $w_2$ is C—$R_b$ or N.

In one embodiment of the use of a compound of Formula (I), $w_4$ is C—$R_1$, $w_7$ is C—$R_2$, $w_1$, $w_3$ and $w_5$ are independently C—$R_a$ or N, $w_2$ is C—$R_b$ or N and $w_6$ is C—Re or N.

In another embodiment of the use of a compound of Formula (I), $w_4$ is C—$R_2$, $w_7$ is C—$R_1$, $w_1$, $w_3$ and $w_5$ are independently C—$R_a$ or N, $w_2$ is C—$R_b$ or N and $w_6$ is C—Re or N.

In one embodiment of the use of a compound of Formula (I), $w_1$ and $w_2$ are N.

In one embodiment of the use of a compound of Formula (I), $w_1$ and $w_3$ are N.

In one embodiment of the use of a compound of Formula (I), $w_1$ and $w_4$ are N.

In one embodiment of the use of a compound of Formula (I), $w_1$ and $w_5$ are N.

In one embodiment of the use of a compound of Formula (I), $w_1$ and $w_6$ are N.

In one embodiment of the use of a compound of Formula (I), $w_1$ and $w_7$ are N.

In one embodiment of the use of a compound of Formula (I), $R_1$ is $C_{1-8}$alkyl, amino, $C_{1-8}$alkyl-amino, $(C_{1-8}$alkyl$)_2$-amino, $C_{1-8}$alkoxy-$C_{1-8}$alkyl-amino, $(C_{1-8}$alkoxy-$C_{1-8}$alkyl$)_2$-amino, $(C_{1-8}$alkoxy-$C_{1-8}$alkyl$)(C_{1-8}$alkyl$)$amino, amino-$C_{1-8}$alkyl, $C_{1-8}$alkyl-amino-$C_{1-8}$alkyl, $(C_{1-8}$alkyl$)_2$-amino-$C_{1-8}$alkyl, $C_{1-8}$alkoxy-$C_{1-8}$alkyl-amino-$C_{1-8}$alkyl, $(C_{1-8}$alkoxy-$C_{1-8}$alkyl$)_2$-amino-$C_{1-8}$alkyl, $(C_{1-8}$alkoxy-$C_{1-8}$alkyl$)(C_{1-8}$alkyl$)$amino-$C_{1-8}$alkyl, amino-$C_{1-8}$alkyl-amino, (amino-$C_{1-8}$alkyl$)_2$-amino, (amino-$C_{1-8}$alkyl$)(C_{1-8}$alkyl$)$amino, $C_{1-8}$alkyl-amino-$C_{1-8}$alkyl-amino, $(C_{1-8}$alkyl-amino-$C_{1-8}$alkyl$)_2$-amino, $(C_{1-8}$alkyl-amino-$C_{1-8}$alkyl$)(C_{1-8}$alkyl$)$amino, $(C_{1-8}$alkyl$)_2$-amino-$C_{1-8}$alkyl-amino, $[(C_{1-8}$alkyl$)_2$-amino-$C_{1-8}$alkyl$](C_{1-8}$alkyl$)$amino, amino-$C_{1-8}$alkoxy, $C_{1-8}$alkyl-amino-$C_{1-8}$alkoxy, $(C_{1-8}$alkyl$)_2$-amino-$C_{1-8}$alkoxy, $C_{1-8}$alkoxy-$C_{1-8}$alkyl-amino-$C_{1-8}$alkoxy, $(C_{1-8}$alkoxy-$C_{1-8}$alkyl$)_2$-amino-$C_{1-8}$alkoxy, $(C_{1-8}$alkoxy-$C_{1-8}$alkyl$)(C_{1-8}$alkyl$)$amino-$C_{1-8}$alkoxy, amino-$C_{2-8}$alkenyl, $C_{1-8}$alkyl-amino-$C_{2-8}$alkenyl, $(C_{1-8}$alkyl$)_2$-amino-$C_{2-8}$alkenyl, amino-$C_{2-8}$alkynyl, $C_{1-8}$alkyl-amino-$C_{2-8}$alkynyl, $(C_{1-8}$alkyl$)_2$-amino-$C_{2-8}$alkynyl, halo-$C_{1-8}$alkyl-amino, (halo-$C_{1-8}$alkyl$)_2$-amino, (halo-$C_{1-8}$alkyl$)(C_{1-8}$alkyl$)$amino, hydroxy-$C_{1-8}$alkyl, hydroxy-$C_{1-8}$alkoxy-$C_{1-8}$alkyl, hydroxy-$C_{1-8}$alkyl-amino, (hydroxy-$C_{1-8}$alkyl$)_2$-amino, (hydroxy-$C_{1-8}$alkyl$)(C_{1-8}$alkyl$)$amino, hydroxy-$C_{1-8}$alkyl-amino-$C_{1-8}$alkyl, (hydroxy-$C_{1-8}$alkyl$)_2$-amino-$C_{1-8}$alkyl, (hydroxy-$C_{1-8}$alkyl$)(C_{1-8}$alkyl$)$amino-$C_{1-8}$alkyl, hydroxy-$C_{1-8}$alkyl-amino-$C_{1-8}$alkoxy, (hydroxy-$C_{1-8}$alkyl$)_2$-amino-$C_{1-8}$alkoxy, (hydroxy-$C_{1-8}$alkyl$)(C_{1-8}$alkyl$)$amino-$C_{1-8}$alkoxy, hydroxy-$C_{1-8}$alkyl-amino-$C_{1-8}$alkyl-amino, (hydroxy-$C_{1-8}$alkyl-amino-$C_{1-8}$alkyl$)_2$-amino, (hydroxy-$C_{1-8}$alkyl$)_2$-amino-$C_{1-8}$alkyl-amino, (hydroxy-$C_{1-8}$alkyl-amino-$C_{1-8}$alkyl$)(C_{1-8}$alkyl$)$amino, (hydroxy-$C_{1-8}$alkyl$)(C_{1-8}$alkyl$)$amino-$C_{1-8}$alkyl-amino, $[$(hydroxy-$C_{1-8}$alkyl$)_2$-amino-$C_{1-8}$alkyl$](C_{1-8}$alkyl$)$amino, $[$(hydroxy-$C_{1-8}$alkyl$)(C_{1-8}$alkyl$)$amino-$C_{1-8}$alkyl$](C_{1-8}$alkyl$)$amino, heterocyclyl, heterocyclyl-$C_{1-8}$alkyl, heterocyclyl-$C_{1-8}$alkoxy, heterocyclyl-amino, (heterocyclyl)($C_{1-8}$alkyl)amino, heterocyclyl-amino-$C_{1-8}$alkyl, heterocyclyl-$C_{1-8}$alkyl-amino, (heterocyclyl-$C_{1-8}$alkyl$)_2$-amino, (heterocyclyl-$C_{1-8}$alkyl$)(C_{1-8}$alkyl$)$amino, heterocyclyl-$C_{1-8}$alkyl-amino-$C_{1-8}$alkyl, (heterocyclyl-$C_{1-8}$alkyl$)_2$-amino-$C_{1-8}$alkyl, (heterocyclyl-$C_{1-8}$alkyl$)(C_{1-8}$alkyl$)$amino-$C_{1-8}$alkyl, heterocyclyl-oxy, heterocyclyl-carbonyl, heterocyclyl-carbonyl-oxy, $C_{3-14}$cycloalkyl, aryl-$C_{1-8}$ alkyl-amino, (aryl-$C_{1-8}$alkyl$)_2$-amino, (aryl-$C_{1-8}$alkyl$)(C_{1-8}$alkyl$)$amino, aryl-$C_{1-8}$alkyl-amino-$C_{1-8}$alkyl, (aryl-$C_{1-8}$ alkyl$)_2$-amino-$C_{1-8}$alkyl, (aryl-$C_{1-8}$alkyl$)(C_{1-8}$alkyl$)$amino-$C_{1-8}$alkyl, heteroaryl, heteroaryl-$C_{1-8}$alkyl, heteroaryl-$C_{1-8}$alkoxy, heteroaryl-amino, heteroaryl-$C_{1-8}$alkyl-amino, (heteroaryl-$C_{1-8}$alkyl$)_2$-amino, (heteroaryl-$C_{1-8}$alkyl$)(C_{1-8}$alkyl$)$amino, heteroaryl-$C_{1-8}$alkyl-amino-$C_{1-8}$alkyl, (heteroaryl-$C_{1-8}$alkyl$)_2$-amino-$C_{1-8}$alkyl or (heteroaryl-$C_{1-8}$alkyl$)(C_{1-8}$alkyl$)$amino-$C_{1-8}$alkyl; wherein, each instance of heterocyclyl, $C_{3-14}$cycloalkyl, aryl and heteroaryl is optionally substituted with $R_3$ and $R_4$ substituents.

In another embodiment of the use of a compound of Formula (I), $R_1$ is amino, $(C_{1-8}$alkyl$)_2$-amino, $C_{1-8}$alkoxy-$C_{1-8}$alkyl-amino, $(C_{1-8}$alkoxy-$C_{1-8}$alkyl$)_2$-amino, amino-$C_{1-8}$alkyl, $C_{1-8}$alkyl-amino-$C_{1-8}$alkyl, $(C_{1-8}$alkyl$)_2$-amino-$C_{1-8}$alkyl, $C_{1-8}$alkoxy-$C_{1-8}$alkyl-amino-$C_{1-8}$alkyl, $(C_{1-8}$alkoxy-$C_{1-8}$alkyl$)_2$-amino-$C_{1-8}$alkyl, $(C_{1-8}$alkoxy-$C_{1-8}$alkyl$)(C_{1-8}$alkyl$)$amino-$C_{1-8}$alkyl, amino-$C_{1-8}$alkyl-amino, (amino-$C_{1-8}$alkyl$)_2$-amino, (amino-$C_{1-8}$alkyl$)(C_{1-8}$alkyl$)$amino, $C_{1-8}$alkyl-amino-$C_{1-8}$alkyl-amino, $(C_{1-8}$alkyl-amino-$C_{1-8}$alkyl$)_2$-amino, $(C_{1-8}$alkyl-amino-$C_{1-8}$alkyl$)(C_{1-8}$alkyl$)$amino, $(C_{1-8}$alkyl$)_2$-amino-$C_{1-8}$alkyl-amino, $[(C_{1-8}$alkyl$)_2$-amino-$C_{1-8}$alkyl$](C_{1-8}$alkyl$)$amino, amino-$C_{1-8}$alkoxy, $C_{1-8}$alkyl-amino-$C_{1-8}$alkoxy, $(C_{1-8}$alkyl$)_2$-amino-$C_{1-8}$alkoxy, $C_{1-8}$alkoxy-$C_{1-8}$alkyl-amino-$C_{1-8}$alkoxy, $(C_{1-8}$alkoxy-$C_{1-8}$alkyl$)_2$-amino-$C_{1-8}$alkoxy, $(C_{1-8}$alkoxy-$C_{1-8}$alkyl$)(C_{1-8}$alkyl$)$amino-$C_{1-8}$alkoxy, amino-$C_{2-8}$alkenyl, $C_{1-8}$alkyl-amino-$C_{2-8}$alkenyl, $(C_{1-8}$alkyl$)_2$-amino-$C_{2-8}$alkenyl, amino-$C_{2-8}$alkynyl, $C_{1-8}$alkyl-amino-$C_{2-8}$alkynyl, $(C_{1-8}$ alkyl$)_2$-amino-$C_{2-8}$alkynyl, halo-$C_{1-8}$alkyl-amino, (halo-$C_{1-8}$alkyl$)_2$-amino, (halo-$C_{1-8}$alkyl$)(C_{1-8}$alkyl$)$amino, hydroxy-$C_{1-8}$alkyl, hydroxy-$C_{1-8}$alkoxy-$C_{1-8}$alkyl, hydroxy-$C_{1-8}$alkyl-amino, (hydroxy-$C_{1-8}$alkyl$)_2$-amino, (hydroxy-$C_{1-8}$alkyl$)(C_{1-8}$alkyl$)$amino, hydroxy-$C_{1-8}$alkyl-amino-$C_{1-8}$alkyl, (hydroxy-$C_{1-8}$alkyl$)_2$-amino-$C_{1-8}$alkyl, (hydroxy-$C_{1-8}$alkyl$)(C_{1-8}$alkyl$)$amino-$C_{1-8}$alkyl, hydroxy-$C_{1-8}$alkyl-amino-$C_{1-8}$alkoxy, (hydroxy-$C_{1-8}$alkyl$)_2$-amino-$C_{1-8}$alkoxy, (hydroxy-$C_{1-8}$alkyl$)(C_{1-8}$alkyl$)$amino-$C_{1-8}$alkoxy, hydroxy-$C_{1-8}$alkyl-amino-$C_{1-8}$alkyl-amino, (hydroxy-$C_{1-8}$alkyl-amino-$C_{1-8}$alkyl$)_2$-amino, (hydroxy-$C_{1-8}$alkyl$)_2$-amino-$C_{1-8}$alkyl-amino, (hydroxy-$C_{1-8}$alkyl-amino-$C_{1-8}$alkyl$)(C_{1-8}$alkyl$)$amino, (hydroxy-$C_{1-8}$alkyl$)(C_{1-8}$alkyl$)$amino-$C_{1-8}$alkyl-amino, $[$(hydroxy-$C_{1-8}$alkyl$)_2$-amino-$C_{1-8}$alkyl$](C_{1-8}$alkyl$)$amino, $[$(hydroxy-$C_{1-8}$alkyl$)(C_{1-8}$alkyl$)$amino-$C_{1-8}$alkyl$](C_{1-8}$alkyl$)$amino, heterocyclyl, heterocyclyl-$C_{1-8}$alkyl, heterocyclyl-$C_{1-8}$alkoxy, heterocyclyl-amino, (heterocyclyl)($C_{1-8}$alkyl)amino, heterocyclyl-amino-$C_{1-8}$alkyl, heterocyclyl-$C_{1-8}$alkyl-amino, (heterocyclyl-$C_{1-8}$alkyl$)_2$-amino, (heterocyclyl-$C_{1-8}$alkyl$)(C_{1-8}$alkyl$)$amino, heterocyclyl-$C_{1-8}$alkyl-amino-$C_{1-8}$alkyl, (heterocyclyl-$C_{1-8}$alkyl$)_2$-amino-$C_{1-8}$alkyl, (heterocyclyl-$C_{1-8}$alkyl$)(C_{1-8}$alkyl$)$amino-$C_{1-8}$alkyl, heterocyclyl-oxy, heterocyclyl-carbonyl, heterocyclyl-carbonyl-oxy, $C_{3-14}$cycloalkyl, aryl-$C_{1-8}$ alkyl-amino, (aryl-$C_{1-8}$alkyl$)_2$-amino, (aryl-$C_{1-8}$alkyl$)(C_{1-8}$alkyl$)$amino, aryl-$C_{1-8}$alkyl-amino-$C_{1-8}$alkyl, (aryl-$C_{1-8}$ alkyl$)_2$-amino-$C_{1-8}$alkyl, (aryl-$C_{1-8}$alkyl$)(C_{1-8}$alkyl$)$amino-$C_{1-8}$alkyl, heteroaryl, heteroaryl-$C_{1-8}$alkyl, heteroaryl-$C_{1-8}$alkoxy, heteroaryl-$C_{1-8}$alkyl-amino, (heteroaryl-$C_{1-8}$alkyl$)_2$-amino, (heteroaryl-$C_{1-8}$alkyl$)(C_{1-8}$alkyl$)$amino, heteroaryl-$C_{1-8}$alkyl-amino-$C_{1-8}$alkyl, (heteroaryl-$C_{1-8}$alkyl$)_2$-amino-$C_{1-8}$alkyl or (heteroaryl-$C_{1-8}$alkyl$)(C_{1-8}$alkyl$)$amino-$C_{1-8}$alkyl; wherein, each instance of heterocyclyl, $C_{3-14}$cycloalkyl, aryl and heteroaryl is optionally substituted with $R_3$ and $R_4$ substituents.

In another embodiment of the use of a compound of Formula (I), $R_1$ is $C_{1-8}$alkyl, amino, $C_{1-8}$alkyl-amino, $(C_{1-8}$alkyl$)_2$-amino, $C_{1-8}$alkoxy-$C_{1-8}$alkyl-amino, $(C_{1-8}$alkoxy-$C_{1-8}$alkyl$)_2$-amino, $(C_{1-8}$alkoxy-$C_{1-8}$alkyl$)(C_{1-8}$alkyl$)$amino, amino-$C_{1-8}$alkyl, $C_{1-8}$alkyl-amino-$C_{1-8}$alkyl, $(C_{1-8}$alkyl$)_2$-amino-$C_{1-8}$alkyl, $C_{1-8}$alkoxy-$C_{1-8}$alkyl-amino-$C_{1-8}$alkyl, $(C_{1-8}$alkoxy-$C_{1-8}$alkyl$)_2$-amino-$C_{1-8}$alkyl, $(C_{1-8}$alkoxy-$C_{1-8}$alkyl$)(C_{1-8}$alkyl$)$amino-$C_{1-8}$alkyl, amino-$C_{1-8}$alkyl-amino, (amino-$C_{1-8}$alkyl$)_2$-amino, (amino-$C_{1-8}$alkyl$)(C_{1-8}$alkyl$)$ amino, $C_{1-8}$alkyl-amino-$C_{1-8}$alkyl-amino, ($C_{1-8}$alkyl-amino-$C_{1-8}$alkyl)$_2$-amino, ($C_{1-8}$alkyl-amino-$C_{1-8}$alkyl)($C_{1-8}$alkyl)amino, ($C_{1-8}$alkyl)$_2$-amino-$C_{1-8}$alkyl-amino, [($C_{1-8}$alkyl)$_2$-amino-$C_{1-8}$alkyl]($C_{1-8}$alkyl)amino, amino-$C_{1-8}$alkoxy, $C_{1-8}$alkyl-amino-$C_{1-8}$alkoxy, ($C_{1-8}$alkyl)$_2$-amino-$C_{1-8}$alkoxy, $C_{1-8}$alkoxy-$C_{1-8}$alkyl-amino-$C_{1-8}$alkoxy, ($C_{1-8}$alkoxy-$C_{1-8}$alkyl)$_2$-amino-$C_{1-8}$alkoxy, ($C_{1-8}$alkoxy-$C_{1-8}$alkyl)($C_{1-8}$alkyl)amino-$C_{1-8}$alkoxy, amino-$C_{2-8}$alkenyl, $C_{1-8}$alkyl-amino-$C_{2-8}$alkenyl, ($C_{1-8}$alkyl)$_2$-amino-$C_{2-8}$alkenyl, amino-$C_{2-8}$alkynyl, $C_{1-8}$alkyl-amino-$C_{2-8}$alkynyl, ($C_{1-8}$ alkyl)$_2$-amino-$C_{2-8}$alkynyl, halo-$C_{1-8}$alkyl-amino, (halo-$C_{1-8}$alkyl)$_2$-amino, (halo-$C_{1-8}$alkyl)($C_{1-8}$alkyl)amino, hydroxy-$C_{1-8}$alkyl, hydroxy-$C_{1-8}$alkoxy-$C_{1-8}$alkyl, hydroxy-$C_{1-8}$alkyl-amino, (hydroxy-$C_{1-8}$alkyl)$_2$-amino, (hydroxy-$C_{1-8}$alkyl)($C_{1-8}$alkyl)amino, hydroxy-$C_{1-8}$alkyl-amino-$C_{1-8}$alkyl, (hydroxy-$C_{1-8}$alkyl)$_2$-amino-$C_{1-8}$alkyl, (hydroxy-$C_{1-8}$alkyl)($C_{1-8}$alkyl)amino-$C_{1-8}$alkyl, hydroxy-$C_{1-8}$alkyl-amino-$C_{1-8}$alkoxy, (hydroxy-$C_{1-8}$alkyl)$_2$-amino-$C_{1-8}$alkoxy, (hydroxy-$C_{1-8}$alkyl)($C_{1-8}$alkyl)amino-$C_{1-8}$alkoxy, hydroxy-$C_{1-8}$alkyl-amino-$C_{1-8}$alkyl-amino, (hydroxy-$C_{1-8}$alkyl-amino-$C_{1-8}$alkyl)$_2$-amino, (hydroxy-$C_{1-8}$alkyl)$_2$-amino-$C_{1-8}$alkyl-amino, (hydroxy-$C_{1-8}$alkyl-amino-$C_{1-8}$alkyl)($C_{1-8}$alkyl)amino, (hydroxy-$C_{1-8}$alkyl)($C_{1-8}$alkyl)amino-$C_{1-8}$alkyl-amino, [(hydroxy-$C_{1-8}$alkyl)$_2$-amino-$C_{1-8}$alkyl]($C_{1-8}$alkyl)amino or [(hydroxy-$C_{1-8}$alkyl)($C_{1-8}$alkyl)amino-$C_{1-8}$alkyl]($C_{1-8}$alkyl)amino.

In another embodiment of the use of a compound of Formula (I), $R_1$ is heterocyclyl, heterocyclyl-$C_{1-8}$alkyl, heterocyclyl-$C_{1-8}$alkoxy, heterocyclyl-amino, (heterocyclyl)($C_{1-8}$alkyl)amino, heterocyclyl-amino-$C_{1-8}$alkyl, heterocyclyl-$C_{1-8}$alkyl-amino, (heterocyclyl-$C_{1-8}$alkyl)$_2$-amino, (heterocyclyl-$C_{1-8}$alkyl)($C_{1-8}$alkyl)amino, heterocyclyl-$C_{1-8}$alkyl-amino-$C_{1-8}$alkyl, (heterocyclyl-$C_{1-8}$alkyl)$_2$-amino-$C_{1-8}$alkyl, (heterocyclyl-$C_{1-8}$alkyl)($C_{1-8}$alkyl)amino-$C_{1-8}$alkyl, heterocyclyl-oxy, heterocyclyl-carbonyl, heterocyclyl-carbonyl-oxy, $C_{3-14}$cycloalkyl, aryl-$C_{1-8}$alkyl-amino, (aryl-$C_{1-8}$alkyl)$_2$-amino, (aryl-$C_{1-8}$alkyl)($C_{1-8}$alkyl)amino, aryl-$C_{1-8}$alkyl-amino-$C_{1-8}$alkyl, (aryl-$C_{1-8}$alkyl)$_2$-amino-$C_{1-8}$alkyl, (aryl-$C_{1-8}$alkyl)($C_{1-8}$alkyl)amino-$C_{1-8}$alkyl, heteroaryl, heteroaryl-$C_{1-8}$alkyl, heteroaryl-$C_{1-8}$alkoxy, heteroaryl-amino, heteroaryl-$C_{1-8}$alkyl-amino, (heteroaryl-$C_{1-8}$alkyl)$_2$-amino, (heteroaryl-$C_{1-8}$alkyl)($C_{1-8}$alkyl)amino, heteroaryl-$C_{1-8}$alkyl-amino-$C_{1-8}$alkyl, (heteroaryl-$C_{1-8}$alkyl)$_2$-amino-$C_{1-8}$alkyl or (heteroaryl-$C_{1-8}$alkyl)($C_{1-8}$alkyl)amino-$C_{1-8}$alkyl; wherein, each instance of heterocyclyl, $C_{3-14}$cycloalkyl, aryl and heteroaryl is optionally substituted with $R_3$ and $R_4$ substituents.

In another embodiment of the use of a compound of Formula (I), $R_1$ is heterocyclyl, heterocyclyl-$C_{1-8}$alkyl, heterocyclyl-$C_{1-8}$alkoxy, heterocyclyl-amino, (heterocyclyl)($C_{1-8}$alkyl)amino, heterocyclyl-amino-$C_{1-8}$alkyl, heterocyclyl-$C_{1-8}$alkyl-amino, (heterocyclyl-$C_{1-8}$alkyl)$_2$-amino, (heterocyclyl-$C_{1-8}$alkyl)($C_{1-8}$alkyl)amino, heterocyclyl-$C_{1-8}$alkyl-amino-$C_{1-8}$alkyl, (heterocyclyl-$C_{1-8}$alkyl)$_2$-amino-$C_{1-8}$alkyl, (heterocyclyl-$C_{1-8}$alkyl)($C_{1-8}$alkyl)amino-$C_{1-8}$alkyl, heterocyclyl-oxy, heterocyclyl-carbonyl or heterocyclyl-carbonyl-oxy; wherein, each instance of heterocyclyl is optionally substituted with $R_3$ and $R_4$ substituents.

In another embodiment of the use of a compound of Formula (I), $R_1$ is heterocyclyl optionally substituted with $R_3$ and $R_4$ substituents.

In another embodiment of the use of a compound of Formula (I), $R_1$ is $C_{3-14}$cycloalkyl optionally substituted with $R_3$ and $R_4$ substituents.

In another embodiment of the use of a compound of Formula (I), $R_1$ is aryl-$C_{1-8}$alkyl-amino, (aryl-$C_{1-8}$alkyl)$_2$-amino, (aryl-$C_{1-8}$alkyl)($C_{1-8}$alkyl)amino, aryl-$C_{1-8}$alkyl-amino-$C_{1-8}$ alkyl, (aryl-$C_{1-8}$alkyl)$_2$-amino-$C_{1-8}$alkyl or (aryl-$C_{1-8}$alkyl)($C_{1-8}$alkyl)amino-$C_{1-8}$alkyl; wherein, each instance of aryl is optionally substituted with $R_3$ and $R_4$ substituents.

In another embodiment of the use of a compound of Formula (I), $R_1$ is aryl-$C_{1-8}$alkyl-amino optionally substituted with $R_3$ and $R_4$ substituents.

In another embodiment of the use of a compound of Formula (I), $R_1$ is heteroaryl, heteroaryl-$C_{1-8}$alkyl, heteroaryl-$C_{1-8}$alkoxy, heteroaryl-amino, heteroaryl-$C_{1-8}$alkyl-amino, (heteroaryl-$C_{1-8}$alkyl)$_2$-amino, (heteroaryl-$C_{1-8}$alkyl)($C_{1-8}$alkyl)amino, heteroaryl-$C_{1-8}$alkyl-amino-$C_{1-8}$alkyl, (heteroaryl-$C_{1-8}$alkyl)$_2$-amino-$C_{1-8}$alkyl or (heteroaryl-$C_{1-8}$alkyl)($C_{1-8}$alkyl)amino-$C_{1-8}$alkyl; wherein, each instance of heterocyclyl, $C_{3-14}$cycloalkyl, aryl and heteroaryl is optionally substituted with $R_3$ and $R_4$ substituents.

In another embodiment of the use of a compound of Formula (I), $R_1$ is heteroaryl optionally substituted with $R_3$ and $R_4$ substituents.

In one embodiment of the use of a compound of Formula (I), $R_1$ is heterocyclyl selected from azetidinyl, tetrahydrofuranyl, pyrrolidinyl, piperidinyl, piperazinyl, 1,4-diazepanyl, 1,2,5,6-tetrahydropyridinyl, 1,2,3,6-tetrahydropyridinyl, hexahydropyrrolo[3,4-b]pyrrol-(1H)-yl, (3aS,6aS)-hexahydropyrrolo[3,4-b]pyrrol-(1H)-yl, (3 aR,6aR)-hexahydropyrrolo[3,4-b]pyrrol-(1H)-yl, hexahydropyrrolo[3,4-b]pyrrol-(2H)-yl, (3aS,6aS)-hexahydropyrrolo[3,4-b]pyrrol-(2H)-yl, hexahydropyrrolo[3,4-c]pyrrol-(1H)-yl, (3 aR,6aS)-hexahydropyrrolo[3,4-c]pyrrol-(1H)-yl, octahydro-5H-pyrrolo[3,2-c]pyridinyl, octahydro-6H-pyrrolo[3,4-b]pyridinyl, (4aR,7aR)-octahydro-6H-pyrrolo[3,4-b]pyridinyl, (4aS,7aS)-octahydro-6H-pyrrolo[3,4-b]pyridinyl, hexahydropyrrolo[1,2-a]pyrazin-(2H)-one, hexahydropyrrolo[1,2-a]pyrazin-(1H)-yl, (7R,8aS)-hexahydropyrrolo[1,2-a]pyrazin-(1H)-yl, (8aS)-hexahydropyrrolo[1,2-a]pyrazin-(1H)-yl, (8aR)-hexahydropyrrolo[1,2-a]pyrazin-(1H)-yl, (8aS)-octahydropyrrolo[1,2-a]pyrazin-(1H)-yl, (8aR)-octahydropyrrolo[1,2-a]pyrazin-(1H)-yl, octahydro-2H-pyrido[1,2-a]pyrazinyl, 3-azabicyclo[3.1.0]hexyl, (1R,5S)-3-azabicyclo[3.1.0]hexyl, 8-azabicyclo[3.2.1]octyl, (1R,5S)-8-azabicyclo[3.2.1]octyl, 8-azabicyclo[3.2.1]oct-2-enyl, (1R,5S)-8-azabicyclo[3.2.1]oct-2-enyl, 9-azabicyclo[3.3.1]nonyl, (1R,5S)-9-azabicyclo[3.3.1]nonyl, 2,5-diazabicyclo[2.2.1]heptyl, (1S,4S)-2,5-diazabicyclo[2.2.1]heptyl, 2,5-diazabicyclo[2.2.2]octyl, 3,8-diazabicyclo[3.2.1]octyl, (1R,5S)-3,8-diazabicyclo[3.2.1]octyl, 1,4-diazabicyclo[3.2.2]nonyl, azaspiro[3.3]heptyl, 2,6-diazaspiro[3.3]heptyl, 2,7-diazaspiro[3.5]nonyl, 5,8-diazaspiro[3.5]nonyl, 2,7-diazaspiro[4.4]nonyl or 6,9-diazaspiro[4.5]decyl; wherein, each instance of heterocyclyl is optionally substituted with $R_3$ and $R_4$ substituents.

In another embodiment of the use of a compound of Formula (I), $R_1$ is heterocyclyl selected from azetidin-1-yl, tetrahydrofuran-3-yl, pyrrolidin-1-yl, piperidin-1-yl, piperidin-4-yl, piperazin-1-yl, 1,4-diazepan-1-yl, 1,2,5,6-tetrahydropyridin-5-yl, 1,2,3,6-tetrahydropyridin-4-yl, hexahydropyrrolo[3,4-b]pyrrol-1(2H)-yl, (3 aS, 6aS)-hexahydropyrrolo[3,4-b]pyrrol-1(2H)-yl, (3 aS,6aS)-hexahydropyrrolo[3,4-b]pyrrol-5(1H)-yl, (3aR,6aR)-hexahydropyrrolo[3,4-b]pyrrol-5(1H)-yl, hexahydropyrrolo[3,4-c]pyrrol-2(1H)-yl, (3 aR,6aS)-hexahydropyrrolo[3,4-c]pyrrol-2(1H)-yl, octahydro-5H-pyrrolo[3,2-c]pyridin-5-yl, octahydro-6H-pyrrolo[3,4-b]pyridin-6-yl, (4aR,7aR)-octahydro-6H-pyrrolo[3,4-b]pyridin-6-yl, (4aS,7aS)-octahydro-6H-pyrrolo[3,4-b]pyridin-6-yl, hexahydropyrrolo[1,2-a]pyrazin-6(2H)-one, hexahydropyrrolo[1,2-a]pyrazin-2(1H)-yl, (7R,8aS)-hexahydropyrrolo[1,2-a]pyrazin-2(1H)-yl, (8aS)-hexahydropyrrolo[1,2-a]pyrazin-2(1H)-yl, (8aR)-hexahydropyrrolo[1,2-a]pyrazin-2(1H)-yl, (8aS)-octahydropyrrolo[1,2-a]pyrazin-2(1H)-yl, (8aR)-octahydropyrrolo[1,2-a]pyrazin-2(1H)-yl, octahydro-2H-pyrido[1,2-a]pyrazin-2-yl, 3-azabicyclo[3.1.0]hex-3-yl, 8-azabicyclo[3.2.1]oct-3-yl, (1R,5S)-8-azabicyclo[3.2.1]oct-3-yl, 8-azabicyclo[3.2.1]oct-2-en-3-yl, (1R,5S)-8-azabicyclo[3.2.1]oct-2-en-3-yl, 9-azabicyclo[3.3.1]non-3-yl, (1R,5S)-9-azabicyclo[3.3.1]non-3-yl, 2,5-diazabicyclo[2.2.1]hept-2-yl, (1S,4S)-2,5-diazabicyclo[2.2.1]hept-2-yl, 2,5-diazabicyclo[2.2.2]oct-2-yl, 3,8-diazabicyclo[3.2.1]oct-3-yl, (1R,5S)-3,8-diazabicyclo[3.2.1]oct-3-yl, 1,4-diazabicyclo[3.2.2]non-4-yl, azaspiro[3.3]hept-2-yl, 2,6-diazaspiro[3.3]hept-2-yl, 2,7-diazaspiro[3.5]non-7-yl, 5,8-diazaspiro[3.5]non-8-yl, 2,7-diazaspiro[4.4]non-2-yl or 6,9-diazaspiro[4.5]dec-9-yl; wherein, each instance of heterocyclyl is optionally substituted with $R_3$ and $R_4$ substituents.

In another embodiment of the use of a compound of Formula (I), $R_1$ is substituted heterocyclyl selected from 4-methyl-1,4-diazepan-1-yl, (3 aS,6aS)-1-methylhexahydropyrrolo[3,4-b]pyrrol-5 (1H)-yl, (3 aS, 6aS)-5-methylhexahydropyrrolo[3,4-b]pyrrol-1(2H)-yl, (3aR,6aR)-1-methylhexahydropyrrolo[3,4-b]pyrrol-5(1H)-yl, (3 aR,6aS)-5-methylhexahydropyrrolo[3,4-c]pyrrol-2(1H)-yl, (3aR,6aS)-5-(2-hydroxyethyl)hexahydropyrrolo[3,4-c]pyrrol-2(1H)-yl, (3 aR,6aS)-5-(propan-2-yl)hexahydropyrrolo[3,4-c]pyrrol-2(1H)-yl, (3 aR,6aS)-5-ethylhexahydropyrrolo[3,4-c]pyrrol-2(1H)-yl, (4aR,7aR)-1-methyloctahydro-6H-pyrrolo[3,4-b]pyridin-6-yl, (4aR,7aR)-1-ethyloctahydro-6H-pyrrolo[3,4-b]pyridin-6-yl, (4aR,7aR)-1-(2-hydroxyethyl)octahydro-6H-pyrrolo[3,4-b]pyridin-6-yl, (4aS,7aS)-1-methyloctahydro-6H-pyrrolo[3,4-b]pyridin-6-yl, (4aS,7aS)-1-(2-hydroxyethyl)octahydro-6H-pyrrolo[3,4-b]pyridin-6-yl, (7R,8aS)-7-hydroxyhexahydropyrrolo[1,2-a]pyrazin-2(1H)-yl, (8aS)-8a-methyloctahydropyrrolo[1,2-a]pyrazin-2(1H)-yl, (8aR)-8a-methyloctahydropyrrolo[1,2-a]pyrazin-2(1H)-yl, (1R,5S,6s)-6-(dimethylamino)-3-azabicyclo[3.1.0]hex-3-yl, (1R,5S)-8-methyl-8-azabicyclo[3.2.1]oct-3-yl, 9-methyl-9-azabicyclo[3.3.1]non-3-yl, (3-exo)-9-methyl-9-azabicyclo[3.3.1]non-3-yl, (1R,5S)-9-methyl-9-azabicyclo[3.3.1]non-3-yl, (1S,4S)-5-methyl-2,5-diazabicyclo[2.2.1]hept-2-yl or (1S,4S)-5-ethyl-2,5-diazabicyclo[2.2.1]hept-2-yl.

In one embodiment of the use of a compound of Formula (I), $R_1$ is heterocyclyl-$C_{1-8}$alkyl, wherein heterocyclyl is selected from morpholinyl, piperidinyl, piperazinyl, imidazolyl or pyrrolidinyl; and, wherein, each instance of heterocyclyl is optionally substituted with $R_3$ and $R_4$ substituents.

In another embodiment of the use of a compound of Formula (I), $R_1$ is heterocyclyl-$C_{1-8}$alkyl selected from morpholin-4-yl-methyl, morpholin-4-yl-ethyl, morpholin-4-yl-propyl, piperidin-1-yl-methyl, piperazin-1-yl-methyl, piperazin-1-yl-ethyl, piperazin-1-yl-propyl, piperazin-1-yl-butyl, imidazol-1-yl-methyl, imidazol-1-yl-ethyl, imidazol-1-yl-propyl, imidazol-1-yl-butyl, pyrrolidin-1-yl-methyl, pyrrolidin-1-yl-ethyl, pyrrolidin-1-yl-propyl or pyrrolidin-1-yl-butyl; wherein, each instance of heterocyclyl is optionally substituted with $R_3$ and $R_4$ substituents.

In one embodiment of the use of a compound of Formula (I), $R_1$ is heterocyclyl-$C_{1-8}$alkoxy, wherein heterocyclyl is selected from pyrrolidinyl, piperidinyl or morpholinyl; and, wherein, each instance of heterocyclyl is optionally substituted with $R_3$ and $R_4$ substituents.

In another embodiment of the use of a compound of Formula (I), $R_1$ is heterocyclyl-$C_{1-8}$alkoxy selected from pyrrolidin-2-yl-methoxy, pyrrolidin-2-yl-ethoxy, pyrrolidin-1-yl-methoxy, pyrrolidin-1-yl-ethoxy, piperidin-1-yl-methoxy, piperidin-1-yl-ethoxy, morpholin-4-yl-methoxy or morpholin-4-yl-ethoxy; wherein, each instance of heterocyclyl is optionally substituted with $R_3$ and $R_4$ substituents.

In one embodiment of the use of a compound of Formula (I), $R_1$ is heterocyclyl-amino, wherein heterocyclyl is selected from azetidinyl, pyrrolidinyl, piperidinyl, 9-azabicyclo[3.3.1]nonyl or (1R,5S)-9-azabicyclo[3.3.1]nonyl; and, wherein, each instance of heterocyclyl is optionally substituted with $R_3$ and $R_4$ substituents.

In another embodiment of the use of a compound of Formula (I), $R_1$ is heterocyclyl-amino selected from azetidin-3-yl-amino, pyrrolidin-3-yl-amino, piperidin-4-yl-amino, 9-azabicyclo[3.3.1]non-3-yl-amino, (1R,5S)-9-azabicyclo[3.3.1]non-3-yl-amino, 9-methyl-9-azabicyclo[3.3.1]non-3-yl-amino, (3-exo)-9-methyl-9-azabicyclo[3.3.1]non-3-yl-amino or (1R,5S)-9-methyl-9-azabicyclo[3.3.1]non-3-yl-amino; wherein, each instance of heterocyclyl is optionally substituted with $R_3$ and $R_4$ substituents.

In one embodiment of the use of a compound of Formula (I), $R_1$ is (heterocyclyl)($C_{1-8}$alkyl)amino, wherein heterocyclyl is selected from pyrrolidinyl or piperidinyl; and, wherein, each instance of heterocyclyl is optionally substituted with $R_3$ and $R_4$ substituents.

In another embodiment of the use of a compound of Formula (I), $R_1$ is (heterocyclyl)($C_{1-8}$alkyl)amino selected from (pyrrolidin-3-yl)(methyl)amino or (piperidin-4-yl)(methyl)amino; wherein, each instance of heterocyclyl is optionally substituted with $R_3$ and $R_4$ substituents.

In one embodiment of the use of a compound of Formula (I), $R_1$ is heterocyclyl-amino-$C_{1-8}$alkyl, wherein heterocyclyl is selected from tetrahydrofuranyl; and, wherein, each instance of heterocyclyl is optionally substituted with $R_3$ and $R_4$ substituents.

In another embodiment of the use of a compound of Formula (I), $R_1$ is heterocyclyl-amino-$C_{1-8}$alkyl, selected from 3-(tetrahydrofuran-3-yl-amino)propyl; wherein, each instance of heterocyclyl is optionally substituted with $R_3$ and $R_4$ substituents.

In one embodiment of the use of a compound of Formula (I), $R_1$ is heterocyclyl-$C_{1-8}$alkyl-amino-$C_{1-8}$alkyl, wherein heterocyclyl is selected from tetrahydrofuranyl, thienyl or pyridinyl; and, wherein, each instance of heterocyclyl is optionally substituted with $R_3$ and $R_4$ substituents.

In another embodiment of the use of a compound of Formula (I), $R_1$ is heterocyclyl-$C_{1-8}$alkyl-amino-$C_{1-8}$alkyl, selected from 3-[(tetrahydrofuran-2-ylmethyl)amino]propyl, 3-[(thienyl-3-ylmethyl)amino]propyl, 3-[(pyridin-2-ylmethyl)amino]propyl or 3-[(pyridin-4-ylmethyl)amino]propyl; wherein, each instance of heterocyclyl is optionally substituted with $R_3$ and $R_4$ substituents.

In one embodiment of the use of a compound of Formula (I), $R_1$ is heterocyclyl-oxy, wherein heterocyclyl is selected from pyrrolidinyl or piperidinyl; and, wherein, each instance of heterocyclyl is optionally substituted with $R_3$ and $R_4$ substituents.

In another embodiment of the use of a compound of Formula (I), $R_1$ is heterocyclyl-oxy selected from pyrrolidin- 3-yl-oxy or piperidin-4-yl-oxy; wherein, each instance of heterocyclyl is optionally substituted with $R_3$ and $R_4$ substituents.

In one embodiment of the use of a compound of Formula (I), $R_1$ is heterocyclyl-carbonyl, wherein heterocyclyl is selected from piperazinyl; and, wherein, each instance of heterocyclyl is optionally substituted with $R_3$ and $R_4$ substituents.

In another embodiment of the use of a compound of Formula (I), $R_1$ is heterocyclyl-carbonyl selected from piperazin-1-yl-carbonyl; wherein, each instance of heterocyclyl is optionally substituted with $R_3$ and $R_4$ substituents.

In one embodiment of the use of a compound of Formula (I), $R_1$ is heterocyclyl-carbonyl-oxy, wherein heterocyclyl is selected from piperazinyl; and, wherein, each instance of heterocyclyl is optionally substituted with $R_3$ and $R_4$ substituents.

In another embodiment of the use of a compound of Formula (I), $R_1$ is heterocyclyl-carbonyl-oxy selected from piperazin-1-yl-carbonyl-oxy; wherein, each instance of heterocyclyl is optionally substituted with $R_3$ and $R_4$ substituents.

In one embodiment of the use of a compound of Formula (I), $R_1$ is $C_{3-14}$cycloalkyl selected from cyclopropyl, cyclobutyl, cyclopentyl, cyclohexyl, cyclohexenyl or cycloheptyl; wherein, each instance of $C_{3-14}$cycloalkyl is optionally substituted with $R_3$ and $R_4$ substituents.

In another embodiment of the use of a compound of Formula (I), $R_1$ is $C_{3-8}$cycloalkyl selected from cyclopropyl, cyclobutyl, cyclopentyl, cyclohexyl, cyclohexenyl or cycloheptyl; wherein, each instance of $C_{3-8}$cycloalkyl is optionally substituted with $R_3$ and $R_4$ substituents.

In one embodiment of the use of a compound of Formula (I), $R_1$ is aryl-$C_{1-8}$alkyl-amino-$C_{1-8}$alkyl, wherein aryl is selected from phenyl; and, wherein, each instance of aryl is optionally substituted with $R_3$ and $R_4$ substituents.

In another embodiment of the use of a compound of Formula (I), $R_1$ is aryl-$C_{1-8}$alkyl-amino-$C_{1-8}$alkyl selected from 3-(benzylamino)propyl; wherein, each instance of aryl is optionally substituted with $R_3$ and $R_4$ substituents.

In one embodiment of the use of a compound of Formula (I), $R_1$ is heteroaryl, wherein heteroaryl is selected from pyridinyl; and, wherein, each instance of heteroaryl is optionally substituted with $R_3$ and $R_4$ substituents.

In another embodiment of the use of a compound of Formula (I), $R_1$ is heteroaryl selected from pyridin-4-yl; wherein, each instance of heteroaryl is optionally substituted with $R_3$ and $R_4$ substituents.

In one embodiment of the use of a compound of Formula (I), $R_1$ is heteroaryl-$C_{1-8}$alkyl, wherein heteroaryl is selected from 1H-imidazolyl; and, wherein, each instance of heteroaryl is optionally substituted with $R_3$ and $R_4$ substituents.

In another embodiment of the use of a compound of Formula (I), $R_1$ is heteroaryl-$C_{1-8}$alkyl selected from 1H-imidazol-1-yl-methyl; wherein, each instance of heteroaryl is optionally substituted with $R_3$ and $R_4$ substituents.

In one embodiment of the use of a compound of Formula (I), $R_1$ is (heteroaryl-$C_{1-8}$alkyl)($C_{1-8}$alkyl)amino, wherein heteroaryl is selected from pyridinyl; and, wherein, each instance of heteroaryl is optionally substituted with $R_3$ and $R_4$ substituents.

In another embodiment of the use of a compound of Formula (I), $R_1$ is (heteroaryl-$C_{1-8}$alkyl)($C_{1-8}$alkyl)amino selected from (pyridin-3-ylmethyl)(methyl)amino; wherein, each instance of heteroaryl is optionally substituted with $R_3$ and $R_4$ substituents.

In one embodiment of the use of a compound of Formula (I), $R_1$ is heteroaryl-$C_{1-8}$alkyl-amino-$C_{1-8}$alkyl, wherein heteroaryl is selected from thienyl or pyridinyl; and, wherein, each instance of heteroaryl is optionally substituted with $R_3$ and $R_4$ substituents.

In another embodiment of the use of a compound of Formula (I), $R_1$ is heteroaryl-$C_{1-8}$alkyl-amino-$C_{1-8}$alkyl selected from thien-3-yl-methyl-amino-propyl, pyridin-2-yl-methyl-amino-propyl, pyridin-3-yl-methyl-amino-propyl or pyridin-4-yl-methyl-amino-propyl; wherein, each instance of heteroaryl is optionally substituted with $R_3$ and $R_4$ substituents.

In one embodiment of the use of a compound of Formula (I), $R_3$ is selected from cyano, halogen, hydroxy, oxo, $C_{1-8}$alkyl, halo-$C_{1-8}$alkyl, $C_{1-8}$alkyl-carbonyl, $C_{1-8}$alkoxy, halo-$C_{1-8}$alkoxy, $C_{1-8}$alkoxy-$C_{1-8}$alkyl, $C_{1-8}$alkoxy-carbonyl, amino, $C_{1-8}$alkyl-amino, $(C_{1-8}$alkyl$)_2$-amino, amino-$C_{1-8}$ alkyl, $C_{1-8}$alkyl-amino-$C_{1-8}$alkyl, $(C_{1-8}$alkyl$)_2$-amino-$C_{1-8}$alkyl, amino-$C_{1-8}$alkyl-amino, $C_{1-8}$alkyl-amino-$C_{1-8}$ alkyl-amino, $(C_{1-8}$alkyl$)_2$-amino-$C_{1-8}$alkyl-amino, $C_{1-8}$alkoxy-$C_{1-8}$alkyl-amino, $C_{1-8}$alkyl-carbonyl-amino, $C_{1-8}$alkoxy-carbonyl-amino, hydroxy-$C_{1-8}$alkyl, hydroxy-$C_{1-8}$alkoxy-$C_{1-8}$alkyl, hydroxy-$C_{1-8}$alkyl-amino, (hydroxy-$C_{1-8}$alkyl$)_2$-amino or (hydroxy-$C_{1-8}$alkyl)($C_{1-8}$alkyl)amino.

In another embodiment of the use of a compound of Formula (I), $R_3$ is selected from cyano, halogen, hydroxy, oxo, $C_{1-8}$alkyl, halo-$C_{1-8}$alkyl, $C_{1-8}$alkoxy, $C_{1-8}$alkoxy-$C_{1-8}$alkyl, $C_{1-8}$alkoxy-carbonyl, amino, $C_{1-8}$alkyl-amino, $(C_{1-8}$alkyl$)_2$-amino, amino-$C_{1-8}$alkyl, $C_{1-8}$alkyl-amino-$C_{1-8}$alkyl, $(C_{1-8}$alkyl$)_2$-amino-$C_{1-8}$alkyl, $C_{1-8}$alkyl-amino-$C_{1-8}$alkyl-amino, $C_{1-8}$alkoxy-$C_{1-8}$alkyl-amino, $C_{1-8}$alkoxy-carbonyl-amino, hydroxy-$C_{1-8}$alkyl, hydroxy-$C_{1-8}$alkoxy-$C_{1-8}$alkyl, hydroxy-$C_{1-8}$alkyl-amino, (hydroxy-$C_{1-8}$alkyl$)_2$-amino or (hydroxy-$C_{1-8}$alkyl)($C_{1-8}$alkyl)amino.

In one embodiment of the use of a compound of Formula (I), $R_3$ is $C_{1-8}$alkyl selected from methyl, ethyl, propyl, isopropyl or tert-butyl.

In another embodiment of the use of a compound of Formula (I), $R_3$ is $C_{1-8}$alkyl selected from ethyl, propyl, isopropyl or tert-butyl.

In one embodiment of the use of a compound of Formula (I), $R_3$ is halo-$C_{1-8}$alkyl selected from trihalo-methyl, dihalo-methyl, halo-methyl, trihalo-ethyl, dihalo-ethyl, halo-ethyl, trihalo-propyl, dihalo-propyl or halo-propyl; wherein, halo is selected from fluoro, chloro, bromo or iodo.

In another embodiment of the use of a compound of Formula (I), $R_3$ is halo-$C_{1-8}$alkyl selected from trihalo-methyl, dihalo-methyl, halo-methyl, trihalo-ethyl, dihalo-ethyl, trihalo-propyl or dihalo-propyl; wherein, halo is selected from fluoro, chloro, bromo or iodo.

In one embodiment of the use of a compound of Formula (I), $R_3$ is hydroxy-$C_{1-8}$alkyl selected from hydroxy-methyl, hydroxy-ethyl, hydroxy-propyl, dihydroxy-propyl, hydroxy-butyl or dihydroxy-butyl.

In another embodiment of the use of a compound of Formula (I), $R_3$ is hydroxy-$C_{1-8}$alkyl selected from hydroxy-methyl, dihydroxy-propyl, hydroxy-butyl or dihydroxy-butyl.

In one embodiment of a the use of compound of Formula (I), $R_3$ is $C_{1-8}$alkoxy selected from methoxy, ethoxy, propoxy or isopropoxy.

In one embodiment of the use of a compound of Formula (I), $R_3$ is halo-$C_{1-8}$alkoxy selected from trihalo-methoxy, dihalo-methoxy, halo-methoxy, trihalo-ethoxy, dihalo-ethoxy, halo-ethoxy, trihalo-propoxy, dihalo-propoxy or halo-propoxy; wherein, halo is selected from fluoro, chloro, bromo or iodo.

In one embodiment of the use of a compound of Formula (I), $R_3$ is $C_{1-8}$alkoxy-carbonyl-amino selected from methoxy-carbonyl-amino, ethoxy-carbonyl-amino, propoxy-carbonyl-amino, isopropoxy-carbonyl-amino, tert-butoxy-carbonyl-amino.

In one embodiment of the use of a compound of Formula (I), $R_a$ is, in each instance, independently selected from hydrogen, halogen, $C_{1-8}$alkyl.

In one embodiment of the use of a compound of Formula (I), $R_a$ is, in each instance, optionally and independently deuterium.

In one embodiment of the use of a compound of Formula (I), $R_b$ is hydrogen, halogen, $C_{1-8}$alkyl, $C_{1-8}$alkoxy.

In one embodiment of the use of a compound of Formula (I), $R_c$ is, in each instance, independently selected from hydrogen, halogen, $C_{1-8}$alkyl.

In one embodiment of the use of a compound of Formula (I), $R_c$ is, in each instance, optionally and independently deuterium.

In one embodiment of the use of a compound of Formula (I), $R_b$ is deuterium.

In one embodiment of the use of a compound of Formula (I), $R_4$ is $C_{3-14}$cycloalkyl selected from cyclopropyl, cyclobutyl, cyclopentyl, cyclohexyl or cycloheptyl; wherein, each instance of $C_{3-14}$cycloalkyl is optionally substituted with $R_5$ substituents.

In another embodiment of the use of a compound of Formula (I), $R_4$ is $C_{3-8}$cycloalkyl selected from cyclopropyl, cyclobutyl, cyclopentyl, cyclohexyl or cycloheptyl; wherein, each instance of $C_{3-8}$cycloalkyl is optionally substituted with $R_5$ substituents.

In one embodiment of the use of a compound of Formula (I), $R_4$ is $C_{3-14}$cycloalkyl-$C_{1-8}$alkyl, wherein $C_{3-14}$cycloalkyl is selected from cyclopropyl, cyclobutyl, cyclopentyl, cyclohexyl or cycloheptyl; and, wherein, each instance of $C_{3-14}$cycloalkyl is optionally substituted with $R_5$ substituents.

In another embodiment of the use of a compound of Formula (I), $R_4$ is $C_{3-8}$cycloalkyl-$C_{1-8}$alkyl, wherein $C_{3-8}$cycloalkyl is selected from cyclopropyl, cyclobutyl, cyclopentyl, cyclohexyl or cycloheptyl; and, wherein, each instance of $C_{3-8}$cycloalkyl is optionally substituted with $R_5$ substituents.

In one embodiment of the use of a compound of Formula (I), $R_4$ is $C_{3-14}$cycloalkyl-amino, wherein $C_{3-14}$cycloalkyl is selected from cyclopropyl, cyclobutyl, cyclopentyl, cyclohexyl or cycloheptyl; and, wherein, each instance of $C_{3-14}$cycloalkyl is optionally substituted with $R_5$ substituents.

In another embodiment of the use of a compound of Formula (I), $R_4$ is $C_{3-8}$cycloalkyl-amino, wherein $C_{3-8}$cycloalkyl is selected from cyclopropyl, cyclobutyl, cyclopentyl, cyclohexyl or cycloheptyl; and, wherein, each instance of $C_{3-8}$cycloalkyl is optionally substituted with $R_5$ substituents.

In one embodiment of the use of a compound of Formula (I), $R_4$ is aryl-$C_{1-8}$alkyl, aryl-$C_{1-8}$alkoxy-carbonyl or aryl-sulfonyloxy-$C_{1-8}$alkyl, wherein aryl is selected from phenyl; and, wherein, each instance of aryl is optionally substituted with $R_5$ substituents.

In another embodiment of the use of a compound of Formula (I), $R_4$ is aryl-$C_{1-8}$alkyl or aryl-$C_{1-8}$alkoxy-carbonyl, wherein each instance of aryl is optionally substituted with $R_5$ substituents.

In one embodiment of the use of a compound of Formula (I), $R_4$ is heterocyclyl selected from oxetanyl, pyrrolidinyl, piperidinyl, piperazinyl, 1,3-dioxanyl or morpholinyl, wherein each instance of heterocyclyl is optionally substituted with $R_5$ substituents.

In another embodiment of the use of a compound of Formula (I), $R_4$ is heterocyclyl selected from oxetan-3-yl, pyrrolidin-1-yl, piperidin-1-yl, piperazin-1-yl, 1,3-dioxan-5-yl or morpholin-4-yl, wherein each instance of heterocyclyl is optionally substituted with $R_5$ substituents.

In one embodiment of the use of a compound of Formula (I), $R_4$ is heterocyclyl-$C_{1-8}$alkyl, wherein each instance of heterocyclyl is selected from pyrrolidinyl or piperidinyl; and, wherein, each instance of heterocyclyl is optionally substituted with $R_5$ substituents.

In another embodiment of the use of a compound of Formula (I), $R_4$ is heterocyclyl-$C_{1-8}$alkyl selected from pyrrolidin-1-yl-$C_{1-8}$alkyl or piperidin-1-yl-$C_{1-8}$alkyl, wherein each instance of heterocyclyl is optionally substituted with $R_5$ substituents.

In one embodiment of the use of a compound of Formula (I), $R_5$ is selected from halogen, hydroxy, cyano, nitro, halo-$C_{1-8}$alkyl, $C_{1-8}$alkoxy, halo-$C_{1-8}$alkoxy, amino, $C_{1-8}$alkyl-amino, ($C_{1-8}$alkyl)$_2$-amino or $C_{1-8}$alkyl-thio; wherein, halogen and halo is selected from fluoro, chloro, bromo or iodo.

In one embodiment of the use of a compound of Formula (I), $R_5$ is hydroxy.

In one embodiment of the use of a compound of Formula (I), $R_5$ is $C_{1-8}$alkyl selected from methyl, ethyl, propyl, isopropyl, n-butyl or tert-butyl.

In another embodiment of the use of a compound of Formula (I), $R_5$ is $C_{1-8}$alkyl selected from ethyl, propyl, isopropyl or tert-butyl.

In one embodiment of the use of a compound of Formula (I), $R_5$ is halo-$C_{1-8}$alkyl selected from trihalo-methyl, dihalo-methyl, halo-methyl, trihalo-ethyl, dihalo-ethyl, halo-ethyl, trihalo-propyl, dihalo-propyl or halo-propyl; wherein, halo is selected from fluoro, chloro, bromo or iodo.

In one embodiment of the use of a compound of Formula (I), $R_5$ is $C_{1-8}$alkoxy selected from methoxy, ethoxy, propoxy or isopropoxy.

In one embodiment of the use of a compound of Formula (I), $R_5$ is halo-$C_{1-8}$alkoxy selected from trihalo-methoxy, dihalo-methoxy, halo-methoxy, trihalo-ethoxy, dihalo-ethoxy, halo-ethoxy, trihalo-propoxy, dihalo-propoxy or halo-propoxy; wherein, halo is selected from fluoro, chloro, bromo or iodo.

In one embodiment of the use of a compound of Formula (I), $R_2$ is aryl selected from phenyl optionally substituted with $R_6$ and $R_7$ substituents.

In one embodiment of the use of a compound of Formula (I), $R_2$ is aryl-amino, wherein aryl is selected from phenyl; and, wherein, each instance of aryl is optionally substituted with $R_6$ and $R_7$ substituents.

In another embodiment of the use of a compound of Formula (I), $R_2$ is aryl-amino selected from phenyl-amino; wherein, each instance of aryl is optionally substituted with $R_6$ and $R_7$ substituents.

In one embodiment of the use of a compound of Formula (I), $R_2$ is aryl-amino-carbonyl, wherein aryl is selected from phenyl; and, wherein, each instance of aryl is optionally substituted with $R_6$ and $R_7$ substituents.

In another embodiment of the use of a compound of Formula (I), $R_2$ is aryl-amino-carbonyl selected from phenyl-amino-carbonyl; wherein, each instance of aryl is optionally substituted with $R_6$ and $R_7$ substituents.

In one embodiment of the use of a compound of Formula (I), $R_2$ is heterocyclyl selected from 1,2,3,6-tetrahydropyridinyl, 1,3-benzodioxolyl or 2,3-dihydro-1,4-benzodioxinyl; wherein, each instance of heterocyclyl is optionally substituted with $R_6$ and $R_7$ substituents.

In another embodiment of the use of a compound of Formula (I), $R_2$ is heterocyclyl selected from 1,2,3,6-tetrahydropyridin-4-yl, 1,3-benzodioxol-5-yl or 2,3-dihydro-1,4-benzodioxin-6-yl; wherein, each instance of heterocyclyl is optionally substituted with $R_6$ and $R_7$ substituents.

In one embodiment of the use of a compound of Formula (I), $R_2$ is heteroaryl selected from thienyl, 1H-pyrazolyl, 1H-imidazolyl, 1,3-thiazolyl, 1,2,4-oxadiazolyl, 1,3,4-oxadiazolyl, pyridinyl, pyrimidinyl, 1H-indolyl, 2H-indolyl, 1H-indazolyl, 2H-indazolyl, indolizinyl, benzofuranyl, benzothienyl, 1H-benzimidazolyl, 1,3-benzothiazolyl, 1,3-benzoxazolyl, 9H-purinyl, furo[3,2-b]pyridinyl, furo[3,2-c]pyridinyl, furo[2,3-c]pyridinyl, thieno[3,2-c]pyridinyl, thieno[2,3-d]pyrimidinyl, 1H-pyrrolo[2,3-b]pyridinyl, 1H-pyrrolo[2,3-c]pyridinyl, pyrrolo[1,2-a]pyrimidinyl, pyrrolo[1,2-a]pyrazinyl, pyrrolo[1,2-b]pyridazinyl, pyrazolo[1,5-a]pyridinyl, pyrazolo[1,5-a]pyrazinyl, imidazo[1,2-a]pyridinyl, imidazo[1,2-a]pyrimidinyl, imidazo[1,2-c]pyrimidinyl, imidazo[1,2-b]pyridazinyl, imidazo[1,2-a]pyrazinyl, imidazo[2,1-b][1,3]thiazolyl, imidazo[2,1-b][1,3,4]thiadiazolyl, [1,3]oxazolo[4,5-b]pyridinyl or quinoxalinyl; wherein, each instance of heteroaryl is optionally substituted with $R_6$ and $R_7$ substituents.

In another embodiment of the use of a compound of Formula (I), $R_2$ is heteroaryl selected from thien-2-yl, thien-3-yl, 1H-pyrazol-3-yl, 1H-pyrazol-4-yl, 1H-pyrazol-5-yl, 1H-imidazol-1-yl, 1H-imidazol-4-yl, 1,3-thiazol-2-yl, 1,2,4-oxadiazol-3-yl, 1,3,4-oxadiazol-2-yl, pyridin-2-yl, pyridin-3-yl, pyridin-4-yl, pyrimidin-4-yl, 1H-indol-3-yl, 1H-indol-4-yl, 1H-indol-5-yl, 1H-indol-6-yl, 1H-indazol-5-yl, 2H-indazol-5-yl, indolizin-2-yl, benzofuran-2-yl, benzofuran-5-yl, benzothien-2-yl, benzothien-3-yl, 1H-benzimidazol-2-yl, 1H-benzimidazol-6-yl, 1,3-benzoxazol-2-yl, 1,3-benzoxazol-5-yl, 1,3-benzoxazol-6-yl, 1,3-benzothiazol-2-yl, 1,3-benzothiazol-5-yl, 1,3-benzothiazol-6-yl, 9H-purin-8-yl, furo[3,2-b]pyridin-2-yl, furo[3,2-c]pyridin-2-yl, furo[2,3-c]pyridin-2-yl, thieno[3,2-c]pyridin-2-yl, thieno[2,3-d]pyrimidin-6-yl, 1H-pyrrolo[2,3-b]pyridin-5-yl, 1H-pyrrolo[2,3-c]pyridin-4-yl, pyrrolo[1,2-a]pyrimidin-7-yl, pyrrolo[1,2-a]pyrazin-7-yl, pyrrolo[1,2-b]pyridazin-2-yl, pyrazolo[1,5-a]pyridin-2-yl, pyrazolo[1,5-a]pyrazin-2-yl, imidazo[1,2-a]pyridin-2-yl, imidazo[1,2-a]pyridin-6-yl, imidazo[1,2-a]pyrimidin-2-yl, imidazo[1,2-a]pyrimidin-6-yl, imidazo[1,2-c]pyrimidin-2-yl, imidazo[1,2-b]pyridazin-2-yl, imidazo[1,2-a]pyrazin-2-yl, imidazo[2,1-b][1,3]thiazol-6-yl, imidazo[2,1-b][1,3,4]thiadiazol-6-yl, [1,3]oxazolo[4,5-b]pyridin-2-yl or quinoxalin-2-yl; wherein, each instance of heteroaryl is optionally substituted with $R_6$ and $R_7$ substituents.

In another embodiment of the use of a compound of Formula (I), $R_2$ is substituted heteroaryl selected from 4-methylthien-2-yl, 1-methyl-1H-pyrazol-3-yl, 4-methyl-1H-pyrazol-3-yl, 1-phenyl-1H-pyrazol-3-yl, 1-phenyl-1H-imidazol-4-yl, 2-methyl-1-(pyridin-2-yl)-1H-imidazol-4-yl, 4-methyl-1,3-thiazol-2-yl, 4-(trifluoromethyl)-1,3-thiazol-2-yl, 4-phenyl-1,3-thiazol-2-yl, 5-phenyl-1,2,4-oxadiazol-3-yl, 3-fluoropyridin-4-yl, 6-fluoropyridin-2-yl, 2-chloropyridin-4-yl, 4-chloropyridin-3-yl, 5-chloropyridin-2-yl, 6-methylpyridin-3-yl, 2-(trifluoromethyl)pyridin-3-yl, 4-(trifluoromethyl)pyridin-2-yl, 6-(trifluoromethyl)pyridin-2-yl, 2-methoxypyridin-4-yl, 4-methoxypyridin-3-yl, 6-methoxypyridin-2-yl, 4-ethoxypyridin-3-yl, 6-ethoxypyridin-2-yl, 6-(propan-2-yloxy)pyridin-2-yl, 6-(dimethylamino)pyridin-3-yl, 6-(methyl sulfanyl)pyridin-2-yl, 6-(cyclobutyloxy)pyridin-2-yl, 6-(pyrrolidin-1-yl)pyridin-2-yl, 2-methylpyrimidin-4-yl, 2-(propan-2-yl)pyrimidin-4-yl, 2-cyclopropylpyrimidin-4-yl, 1-methyl-1H-indol-3-yl, 2-methyl-2H-indazol-5-yl, 2-methyl-1-benzofuran-5-yl, 1-methyl-1H-benzimidazol-2-yl, 4-methyl-1H-benzimidazol-2-yl 5-fluoro-1H-benzimidazol-2-yl, 4-fluoro-1,3-benzoxazol-2-yl, 5-fluoro-1,3-benzoxazol-2-yl, 4-chloro-1,3-benzoxazol-2-yl, 4-iodo-1,3-benzoxazol-2-yl, 2-methyl-1,3-benzoxazol-6-yl, 4-methyl-1,3-benzoxazol-2-yl, 4-(trifluoromethyl)-1,3-benzoxazol-2-yl, 7-(trifluoromethyl)-1,3-benzoxazol-2-yl, 2-methyl-1,3-benzothiazol-2-yl, 2-methyl-1,3-benzothiazol-5-yl, 2-methyl-1,3-benzothiazol-6-yl, 4-chloro-1,3-benzothiazol-2-yl, 7-chloro-1,3-benzothiazol-2-yl, 4-(trifluoromethyl)-1,3-benzothiazol-2-yl, 5-methylfuro[3,2-b]pyridin-2-yl, 4,6-dimethylfuro[3,2-c]pyridin-2-yl, 5,7-dimethylfuro[2,3-c]pyridin-2-yl, 4,6-dimethylthieno[3,2-c]pyridin-2-yl, 2,4-dimethylthieno[2,3-d]pyrimidin-6-yl, 1-methylpyrrolo[1,2-a]pyrazin-7-yl, 3-methylpyrrolo[1,2-a]pyrazin-7-yl, 1,3-dimethylpyrrolo[1,2-a]pyrazin-7-yl, 2-methylpyrrolo[1,2-b]pyridazin-2-yl, 4,6-dimethylpyrazolo[1,5-a]pyrazin-2-yl, 5-methylpyrazolo[1,5-a]pyridin-2-yl, 4,6-dimethylpyrazolo[1,5-a]pyrazin-2-yl, 2-chloroimidazo[2,1-b][1,3]thiazol-6-yl, 2-methylimidazo[2,1-b][1,3]thiazol-6-yl, 3-methylimidazo[2,1-b][1,3]thiazol-6-yl, 2-ethylimidazo[2,1-b][1,3]thiazol-6-yl, 2-methylimidazo[2,1-b][1,3,4]thiadiazol-6-yl, 6-cyanoimidazo[1,2-a]pyridin-2-yl (also referred to as 2-imidazo[1,2-a]pyridine-6-carbonitrile), 6-fluoroimidazo[1,2-a]pyridin-2-yl, 8-fluoroimidazo[1,2-a]pyridin-2-yl, 6,8-difluoroimidazo[1,2-a]pyridin-2-yl, 7-(trifluoromethyl)imidazo[1,2-a]pyridin-2-yl, 8-(trifluoromethyl)imidazo[1,2-a]pyridin-2-yl, 6-chloroimidazo[1,2-a]pyridin-2-yl, 7-chloroimidazo[1,2-a]pyridin-2-yl, 8-chloroimidazo[1,2-a]pyridin-2-yl, 8-bromoimidazo[1,2-a]pyridin-2-yl, 2-methylimidazo[1,2-a]pyridin-2-yl, 5-methylimidazo[1,2-a]pyridin-2-yl, 6-methylimidazo[1,2-a]pyridin-2-yl, 7-methylimidazo[1,2-a]pyridin-2-yl, 8-methylimidazo[1,2-a]pyridin-2-yl, 7-ethylimidazo[1,2-a]pyridin-2-yl, 8-ethylimidazo[1,2-a]pyridin-2-yl, 6,8-dimethylimidazo[1,2-a]pyridin-2-yl, 8-ethyl-6-methylimidazo[1,2-a]pyridin-2-yl, 7-methoxyimidazo[1,2-a]pyridin-2-yl, 8-methoxyimidazo[1,2-a]pyridin-2-yl, 6-fluoro-8-methylimidazo[1,2-a]pyridin-2-yl, 8-fluoro-6-methylimidazo[1,2-a]pyridin-2-yl, 8-chloro-6-methylimidazo[1,2-a]pyridin-2-yl, 6-methyl-8-nitroimidazo[1,2-a]pyridin-2-yl, 8-cyclopropylimidazo[1,2-a]pyridin-2-yl, 2-methylimidazo[1,2-a]pyridin-6-yl, 2-ethylimidazo[1,2-a]pyridin-6-yl, 2,3-dimethylimidazo[1,2-a]pyridin-6-yl, 2,8-dimethylimidazo[1,2-a]pyridin-6-yl, 2-(trifluoromethyl)imidazo[1,2-a]pyridin-6-yl, 8-chloro-2-methylimidazo[1,2-a]pyridin-6-yl, 8-fluoro-2-methylimidazo[1,2-a]pyridin-6-yl, 6-fluoroimidazo[1,2-a]pyrimidin-2-yl, 6-chloroimidazo[1,2-a]pyrimidin-2-yl, 6-methylimidazo[1,2-a]pyrimidin-2-yl, 7-methylimidazo[1,2-a]pyrimidin-2-yl, 2-methylimidazo[1,2-a]pyrimidin-6-yl, 6-methylimidazo[1,2-b]pyridazin-2-yl, 2-methyl-3-(1,2,3,6-tetrahydropyridin-4-yl)imidazo[1,2-b]pyridazin-6-yl, 6-methylimidazo[1,2-a]pyrazin-2-yl, 8-methylimidazo[1,2-a]pyrazin-2-yl, 6,8-dimethylimidazo[1,2-a]pyrazin-2-yl, 6-chloro-8-methylimidazo[1,2-a]pyrazin-2-yl, 6-methyl-8-(trifluoromethyl)imidazo[1,2-a]pyrazin-2-yl, 8-(methylsulfanyl)imidazo[1,2-a]pyrazin-2-yl, 2-methylimidazo[2,1-b]

[1,3]thiazol-6-yl, 3-methylimidazo[2,1-b][1,3]thiazol-6-yl or 2-methylimidazo[2,1-b][1,3,4]thiadiazol-6-yl.

In another embodiment of the use of a compound of Formula (I),
$R_2$ is heteroaryl selected from thienyl, 1H-pyrazolyl, 1H-imidazolyl, 1,3-thiazolyl, 1,2,4-oxadiazolyl, 1,3,4-oxadiazolyl, pyridinyl, pyrimidinyl, 1H-indolyl, 2H-indolyl, 1H-indazolyl, 2H-indazolyl, indolizinyl, benzofuranyl, benzothienyl, 1H-benzimidazolyl, 1,3-benzothiazolyl, 1,3-benzoxazolyl, 9H-purinyl; wherein, each instance of heteroaryl is optionally substituted with $R_6$ and $R_7$ substituents.

In another embodiment of the use of a compound of Formula (I),
$R_2$ is heteroaryl selected from furo[3,2-b]pyridinyl, furo[3,2-c]pyridinyl, furo[2,3-c]pyridinyl, thieno[3,2-c]pyridinyl, thieno[2,3-d]pyrimidinyl, 1H-pyrrolo[2,3-b]pyridinyl, 1H-pyrrolo[2,3-c]pyridinyl, pyrrolo[1,2-a]pyrimidinyl, pyrrolo[1,2-a]pyrazinyl, pyrrolo[1,2-b]pyridazinyl, pyrazolo[1,5-a]pyridinyl, pyrazolo[1,5-a]pyrazinyl, imidazo[1,2-a]pyridinyl, imidazo[1,2-a]pyrimidinyl, imidazo[1,2-c]pyrimidinyl, imidazo[1,2-b]pyridazinyl, imidazo[1,2-a]pyrazinyl, imidazo[2,1-b][1,3]thiazolyl, imidazo[2,1-b][1,3,4]thiadiazolyl, [1,3]oxazolo[4,5-b]pyridinyl or quinoxalinyl; wherein, each instance of heteroaryl is optionally substituted with $R_6$ and $R_7$ substituents.

In one embodiment of the use of a compound of Formula (I), $R_2$ is heteroaryl-amino, wherein heteroaryl is selected from pyridinyl or pyrimidinyl; and, wherein, each instance of heteroaryl is optionally substituted with $R_6$ and $R_7$ substituents.

In another embodiment of the use of a compound of Formula (I), $R_2$ is heteroaryl-amino selected from pyridin-2-yl-amino, pyridin-3-yl-amino or pyrimidin-2-yl-amino; wherein, each instance of heteroaryl is optionally substituted with $R_6$ and $R_7$ substituents.

In one embodiment of the use of a compound of Formula (I), $R_6$ is selected from halogen, hydroxy, cyano, nitro, $C_{1-8}$alkyl, halo-$C_{1-8}$alkyl, hydroxy-$C_{1-8}$alkyl, $C_{1-8}$alkoxy, halo-$C_{1-8}$alkoxy, $C_{1-8}$alkoxy-$C_{1-8}$alkyl, $(C_{1-8}$alkyl$)_2$-amino or $C_{1-8}$alkyl-thio; wherein, halogen and halo is selected from fluoro, chloro, bromo or iodo.

In one embodiment of the use of a compound of Formula (I), $R_6$ is $C_{1-8}$alkyl selected from methyl, ethyl, propyl, isopropyl or tert-butyl.

In another embodiment of the use of a compound of Formula (I), $R_6$ is $C_{1-8}$alkyl selected from ethyl, propyl, isopropyl or tert-butyl.

In one embodiment of the use of a compound of Formula (I), $R_6$ is $C_{2-8}$alkenyl selected from ethenyl, allyl or buta-1,3-dienyl.

In another embodiment of the use of a compound of Formula (I), $R_6$ is $C_{2-8}$alkenyl selected from ethenyl or allyl.

In one embodiment of the use of a compound of Formula (I), $R_6$ is halo-$C_{1-8}$alkyl selected from trihalo-methyl, dihalo-methyl, halo-methyl, trihalo-ethyl, dihalo-ethyl, halo-ethyl, trihalo-propyl, dihalo-propyl or halo-propyl; wherein, halo is selected from fluoro, chloro, bromo or iodo.

In one embodiment of the use of a compound of Formula (I), $R_6$ is hydroxy-$C_{1-8}$alkyl selected from hydroxy-methyl, hydroxy-ethyl, hydroxy-propyl, dihydroxy-propyl, hydroxy-butyl or dihydroxy-butyl.

In another embodiment of the use of a compound of Formula (I), $R_6$ is hydroxy-$C_{1-8}$alkyl selected from hydroxy-methyl, dihydroxy-propyl, hydroxy-butyl or dihydroxy-butyl.

In one embodiment of the use of a compound of Formula (I), $R_6$ is $C_{1-8}$alkoxy selected from methoxy, ethoxy, propoxy or isopropoxy.

In one embodiment of the use of a compound of Formula (I), $R_6$ is halo-$C_{1-8}$alkoxy selected from trihalo-methoxy, dihalo-methoxy, halo-methoxy, trihalo-ethoxy, dihalo-ethoxy, halo-ethoxy, trihalo-propoxy, dihalo-propoxy or halo-propoxy; wherein, halo is selected from fluoro, chloro, bromo or iodo.

In one embodiment of the use of a compound of Formula (I), $R_7$ is $C_{3-14}$cycloalkyl, $C_{3-14}$cycloalkyl-oxy, aryl, heterocyclyl or heteroaryl; wherein $C_{3-14}$cycloalkyl is selected from cyclopropyl or cyclobutoxy; wherein aryl is selected from phenyl; wherein heterocyclyl is selected from oxetanyl, pyrrolidinyl or 1,2,3,6-tetrahydropyridinyl; and, wherein heteroaryl is selected from thienyl or pyridinyl.

In another embodiment of the use of a compound of Formula (I), $R_7$ is $C_{3-14}$cycloalkyl or $C_{3-14}$cycloalkyl-oxy, wherein each instance of $C_{3-14}$cycloalkyl is selected from cyclopropyl, cyclobutyl, cyclopentyl, cyclohexyl or cycloheptyl.

In another embodiment of the use of a compound of Formula (I), $R_7$ is $C_{3-8}$cycloalkyl or $C_{3-8}$cycloalkyl-oxy, wherein each instance of $C_{3-8}$cycloalkyl is selected from cyclopropyl, cyclobutyl, cyclopentyl, cyclohexyl or cycloheptyl.

In one embodiment of the use of a compound of Formula (I), $R_7$ is aryl selected from phenyl.

In one embodiment of the use of a compound of Formula (I), $R_7$ is heterocyclyl selected from oxetanyl, pyrrolidinyl or 1,2,3,6-tetrahydropyridinyl.

In another embodiment of the use of a compound of Formula (I), $R_7$ is heterocyclyl selected from oxetan-3-yl, pyrrolidin-1-yl or 1,2,3,6-tetrahydropyridin-4-yl.

In one embodiment of the use of a compound of Formula (I), $R_7$ is heteroaryl selected from thienyl or pyridinyl.

In another embodiment of the use of a compound of Formula (I), $R_7$ is heteroaryl selected from pyridinyl.

In one embodiment of the use of a compound of Formula (I), $R_7$ is heteroaryl selected from thien-2-yl or pyridin-2-yl.

In another embodiment of the use of a compound of Formula (I), $R_7$ is heteroaryl selected from pyridin-2-yl.

In one embodiment of the use of a compound of Formula (I), $R_c$ is hydrogen or $C_{1-8}$alkyl.

In another embodiment of the use of a compound of Formula (I),
$R_1$ is heterocyclyl, heterocyclyl-$C_{1-8}$alkyl, heterocyclyl-$C_{1-8}$alkoxy, heterocyclyl-amino, (heterocyclyl)($C_{1-8}$alkyl)amino, heterocyclyl-amino-$C_{1-8}$alkyl, heterocyclyl-$C_{1-8}$alkyl-amino, (heterocyclyl-$C_{1-8}$alkyl)$_2$-amino, (heterocyclyl-$C_{1-8}$alkyl)($C_{1-8}$alkyl)amino, heterocyclyl-$C_{1-8}$alkyl-amino-$C_{1-8}$alkyl, (heterocyclyl-$C_{1-8}$alkyl)$_2$-amino-$C_{1-8}$alkyl, (heterocyclyl-$C_{1-8}$alkyl)($C_{1-8}$alkyl)amino-$C_{1-8}$alkyl, heterocyclyl-oxy, heterocyclyl-carbonyl, heterocyclyl-carbonyl-oxy, $C_{3-14}$cycloalkyl, aryl-$C_{1-8}$alkyl-amino, (aryl-$C_{1-8}$alkyl)$_2$-amino, (aryl-$C_{1-8}$alkyl)($C_{1-8}$alkyl)amino, aryl-$C_{1-8}$alkyl-amino-$C_{1-8}$alkyl, (aryl-$C_{1-8}$alkyl)$_2$-amino-$C_{1-8}$alkyl, (aryl-$C_{1-8}$alkyl)($C_{1-8}$alkyl)amino-$C_{1-8}$alkyl, heteroaryl, heteroaryl-$C_{1-8}$alkyl, heteroaryl-$C_{1-8}$alkoxy, heteroaryl-amino, heteroaryl-$C_{1-8}$alkyl-amino, (heteroaryl-$C_{1-8}$alkyl)$_2$-amino, (heteroaryl-$C_{1-8}$alkyl)($C_{1-8}$alkyl)amino, heteroaryl-$C_{1-8}$alkyl-amino-$C_{1-8}$alkyl, (heteroaryl-$C_{1-8}$alkyl)$_2$-amino-$C_{1-8}$alkyl or (heteroaryl-$C_{1-8}$alkyl)($C_{1-8}$alkyl)amino-$C_{1-8}$alkyl; wherein, each instance of heterocyclyl, $C_{3-14}$cycloalkyl, aryl and heteroaryl is optionally substituted with $R_3$ and $R_4$ substituents; and, wherein, heterocyclyl is selected from azetidinyl, tetrahydrofuranyl, pyrrolidinyl, piperidinyl, piperazinyl, 1,4-diazepanyl, 1,2,5,6-tetrahydropyridinyl, 1,2,3,6-tetrahydropyridinyl, hexahydropyrrolo[3,4-b]pyrrol-(1H)-yl, (3aS,6aS)-hexahydropyrrolo[3,4-b]pyrrol-(1H)-yl, (3aR,6aR)-hexahydropyrrolo[3,4-b]pyrrol-(1H)-yl, hexahydropyrrolo[3,4-b]pyrrol-(2H)-yl, (3aS,6aS)-hexahydropyrrolo[3,4-b]pyrrol-(2H)-yl, hexahydropyrrolo[3,4-c]pyrrol-(1H)-yl, (3 aR,6aS)-hexahydropyrrolo[3,4-c]pyrrol-(1H)-yl, octahydro-5H-pyrrolo[3,2-c]pyridinyl, octahydro-6H-pyrrolo[3,4-b]pyridinyl, (4aR,7aR)-octahydro-6H-pyrrolo[3,4-b]pyridinyl, (4aS,7aS)-octahydro-6H-pyrrolo[3,4-b]pyridinyl, hexahydropyrrolo[1,2-a]pyrazin-(2H)-one, hexahydropyrrolo[1,2-a]pyrazin-(1H)-yl, (7R,8aS)-hexahydropyrrolo[1,2-a]pyrazin-(1H)-yl, (8aS)-hexahydropyrrolo[1,2-a]pyrazin-(1H)-yl, (8aR)-hexahydropyrrolo[1,2-a]pyrazin-(1H)-yl, (8aS)-octahydropyrrolo[1,2-a]pyrazin-(1H)-yl, (8aR)-octahydropyrrolo[1,2-a]pyrazin-(1H)-yl, octahydro-2H-pyrido[1,2-a]pyrazinyl, 3-azabicyclo[3.1.0]hexyl, (1R,5S)-3-azabicyclo[3.1.0]hexyl, 8-azabicyclo[3.2.1]octyl, (1R,5S)-8-azabicyclo[3.2.1]octyl, 8-azabicyclo[3.2.1]oct-2-enyl, (1R,5S)-8-azabicyclo[3.2.1]oct-2-enyl, 9-azabicyclo[3.3.1]nonyl, (1R,5S)-9-azabicyclo[3.3.1]nonyl, 2,5-diazabicyclo[2.2.1]heptyl, (1S,4S)-2,5-diazabicyclo[2.2.1]heptyl, 2,5-diazabicyclo[2.2.2]octyl, 3,8-diazabicyclo[3.2.1]octyl, (1R,5S)-3,8-diazabicyclo[3.2.1]octyl, 1,4-diazabicyclo[3.2.2]nonyl, azaspiro[3.3]heptyl, 2,6-diazaspiro[3.3]heptyl, 2,7-diazaspiro[3.5]nonyl, 5,8-diazaspiro[3.5]nonyl, 2,7-diazaspiro[4.4]nonyl or 6,9-diazaspiro[4.5]decyl.

In another embodiment of the use of a compound of Formula (I), $R_2$ is aryl, aryl-amino, aryl-amino-carbonyl, heterocyclyl, heteroaryl or heteroaryl-amino;

wherein, aryl is phenyl;

wherein, heterocyclyl is selected from 1,2,3,6-tetrahydropyridinyl, 1,3-benzodioxolyl or 2,3-dihydro-1,4-benzodioxinyl;

wherein, heteroaryl is selected from thienyl, 1H-pyrazolyl, 1H-imidazolyl, 1,3-thiazolyl, 1,2,4-oxadiazolyl, 1,3,4-oxadiazolyl, pyridinyl, pyrimidinyl, 1H-indolyl, 2H-indolyl, 1H-indazolyl, 2H-indazolyl, indolizinyl, benzofuranyl, benzothienyl, 1H-benzimidazolyl, 1,3-benzothiazolyl, 1,3-benzoxazolyl, 9H-purinyl, furo[3,2-b]pyridinyl, furo[3,2-c]pyridinyl, furo[2,3-c]pyridinyl, thieno[3,2-c]pyridinyl, thieno[2,3-d]pyrimidinyl, 1H-pyrrolo[2,3-b]pyridinyl, 1H-pyrrolo[2,3-c]pyridinyl, pyrrolo[1,2-a]pyrimidinyl, pyrrolo[1,2-a]pyrazinyl, pyrrolo[1,2-b]pyridazinyl, pyrazolo[1,5-a]pyridinyl, pyrazolo[1,5-a]pyrazinyl, imidazo[1,2-a]pyridinyl, imidazo[1,2-a]pyrimidinyl, imidazo[1,2-c]pyrimidinyl, imidazo[1,2-b]pyridazinyl, imidazo[1,2-a]pyrazinyl, imidazo[2,1-b][1,3]thiazolyl, imidazo[2,1-b][1,3,4]thiadiazolyl, [1,3]oxazolo[4,5-b]pyridinyl or quinoxalinyl; and, wherein, each instance of aryl, heterocyclyl and heteroaryl is optionally substituted with $R_6$ and $R_7$ substituents.

In another embodiment of the use of a compound of Formula (I), $R_1$ is heterocyclyl, heterocyclyl-$C_{1-8}$alkyl, heterocyclyl-$C_{1-8}$alkoxy, heterocyclyl-amino, (heterocyclyl)($C_{1-8}$alkyl)amino, heterocyclyl-amino-$C_{1-8}$alkyl, heterocyclyl-$C_{1-8}$alkyl-amino, (heterocyclyl-$C_{1-8}$alkyl)$_2$-amino, (heterocyclyl-$C_{1-8}$alkyl)($C_{1-8}$alkyl)amino, heterocyclyl-$C_{1-8}$alkyl-amino-$C_{1-8}$alkyl, (heterocyclyl-$C_{1-8}$alkyl)$_2$-amino-$C_{1-8}$alkyl, (heterocyclyl-$C_{1-8}$alkyl)($C_{1-8}$alkyl)amino-$C_{1-8}$alkyl, heterocyclyl-oxy, heterocyclyl-carbonyl, heterocyclyl-carbonyl-oxy, $C_{3-14}$cycloalkyl, aryl-$C_{1-8}$alkyl-amino, (aryl-$C_{1-8}$alkyl)$_2$-amino, (aryl-$C_{1-8}$alkyl)($C_{1-8}$alkyl)amino, aryl-$C_{1-8}$alkyl-amino-$C_{1-8}$alkyl, (aryl-$C_{1-8}$alkyl)$_2$-amino-$C_{1-8}$alkyl, (aryl-$C_{1-8}$alkyl)($C_{1-8}$alkyl)amino-$C_{1-8}$alkyl, heteroaryl, heteroaryl-$C_{1-8}$alkyl, heteroaryl-$C_{1-8}$alkoxy, heteroaryl-amino, heteroaryl-$C_{1-8}$alkyl-amino, (heteroaryl-$C_{1-8}$alkyl)$_2$-amino, (heteroaryl-$C_{1-8}$alkyl)($C_{1-8}$alkyl)amino, heteroaryl-$C_{1-8}$alkyl-amino-$C_{1-8}$alkyl, (heteroaryl-$C_{1-8}$alkyl)$_2$-amino-$C_{1-8}$alkyl or (heteroaryl-$C_{1-8}$alkyl)($C_{1-8}$alkyl)amino-$C_{1-8}$alkyl;

wherein, heterocyclyl is selected from azetidinyl, tetrahydrofuranyl, pyrrolidinyl, piperidinyl, piperazinyl, 1,4-diazepanyl, 1,2,5,6-tetrahydropyridinyl, 1,2,3,6-tetrahydropyridinyl, hexahydropyrrolo[3,4-b]pyrrol-(1H)-yl, (3aS,6aS)-hexahydropyrrolo[3,4-b]pyrrol-(1H)-yl, (3 aR,6aR)-hexahydropyrrolo[3,4-b]pyrrol-(1H)-yl, hexahydropyrrolo[3,4-b]pyrrol-(2H)-yl, (3aS,6aS)-hexahydropyrrolo[3,4-b]pyrrol-(2H)-yl, hexahydropyrrolo[3,4-c]pyrrol-(1H)-yl, (3 aR,6aS)-hexahydropyrrolo[3,4-c]pyrrol-(1H)-yl, octahydro-5H-pyrrolo[3,2-c]pyridinyl, octahydro-6H-pyrrolo[3,4-b]pyridinyl, (4aR,7aR)-octahydro-6H-pyrrolo[3,4-b]pyridinyl, (4aS,7aS)-octahydro-6H-pyrrolo[3,4-b]pyridinyl, hexahydropyrrolo[1,2-a]pyrazin-(2H)-one, hexahydropyrrolo[1,2-a]pyrazin-(1H)-yl, (7R,8aS)-hexahydropyrrolo[1,2-a]pyrazin-(1H)-yl, (8aS)-hexahydropyrrolo[1,2-a]pyrazin-(1H)-yl, (8aR)-hexahydropyrrolo[1,2-a]pyrazin-(1H)-yl, (8aS)-octahydropyrrolo[1,2-a]pyrazin-(1H)-yl, (8aR)-octahydropyrrolo[1,2-a]pyrazin-(1H)-yl, octahydro-2H-pyrido[1,2-a]pyrazinyl, 3-azabicyclo[3.1.0]hexyl, (1R,5S)-3-azabicyclo[3.1.0]hexyl, 8-azabicyclo[3.2.1]octyl, (1R,5S)-8-azabicyclo[3.2.1]octyl, 8-azabicyclo[3.2.1]oct-2-enyl, (1R,5S)-8-azabicyclo[3.2.1]oct-2-enyl, 9-azabicyclo[3.3.1]nonyl, (1R,5S)-9-azabicyclo[3.3.1]nonyl, 2,5-diazabicyclo[2.2.1]heptyl, (1S,4S)-2,5-diazabicyclo[2.2.1]heptyl, 2,5-diazabicyclo[2.2.2]octyl, 3,8-diazabicyclo[3.2.1]octyl, (1R,5S)-3,8-diazabicyclo[3.2.1]octyl, 1,4-diazabicyclo[3.2.2]nonyl, azaspiro[3.3]heptyl, 2,6-diazaspiro[3.3]heptyl, 2,7-diazaspiro[3.5]nonyl, 5,8-diazaspiro[3.5]nonyl, 2,7-diazaspiro[4.4]nonyl or 6,9-diazaspiro[4.5]decyl; and, wherein, each instance of heterocyclyl, $C_{3-14}$cycloalkyl, aryl and heteroaryl is optionally substituted with $R_3$ and $R_4$ substituents; and $R_2$ is aryl, aryl-amino, aryl-amino-carbonyl, heterocyclyl, heteroaryl or heteroaryl-amino;

wherein, heterocyclyl is selected from 1,2,3,6-tetrahydropyridin-4-yl, 1,3-benzodioxol-5-yl or 2,3-dihydro-1,4-benzodioxin-6-yl;

wherein, heteroaryl is selected from thienyl, 1H-pyrazolyl, 1H-imidazolyl, 1,3-thiazolyl, 1,2,4-oxadiazolyl, 1,3,4-oxadiazolyl, pyridinyl, pyrimidinyl, 1H-indolyl, 2H-indolyl, 1H-indazolyl, 2H-indazolyl, indolizinyl, benzofuranyl, benzothienyl, 1H-benzimidazolyl, 1,3-benzothiazolyl, 1,3-benzoxazolyl, 9H-purinyl, furo[3,2-b]pyridinyl, furo[3,2-c]pyridinyl, furo[2,3-c]pyridinyl, thieno[3,2-c]pyridinyl, thieno[2,3-d]pyrimidinyl, 1H-pyrrolo[2,3-b]pyridinyl, 1H-pyrrolo[2,3-c]pyridinyl, pyrrolo[1,2-a]pyrimidinyl, pyrrolo[1,2-a]pyrazinyl, pyrrolo[1,2-b]pyridazinyl, pyrazolo[1,5-a]pyridinyl, pyrazolo[1,5-a]pyrazinyl, imidazo[1,2-a]pyridinyl, imidazo[1,2-a]pyrimidinyl, imidazo[1,2-c]pyrimidinyl, imidazo[1,2-b]pyridazinyl, imidazo[1,2-a]pyrazinyl, imidazo[2,1-b][1,3]thiazolyl, imidazo[2,1-b][1,3,4]thiadiazolyl, [1,3]oxazolo[4,5-b]pyridinyl or quinoxalinyl; and, wherein, each instance of heterocyclyl and heteroaryl is optionally substituted with $R_6$ and $R_7$ substituents.

In another embodiment of the use of a compound of Formula (I), $R_1$ is $C_{1-8}$alkyl, amino, $C_{1-8}$alkyl-amino, $(C_{1-8}$alkyl$)_2$-amino, $C_{1-8}$alkoxy-$C_{1-8}$alkyl-amino, $(C_{1-8}$alkoxy-$C_{1-8}$alkyl$)_2$-amino, $(C_{1-8}$alkoxy-$C_{1-8}$alkyl$)(C_{1-8}$alkyl$)$amino, amino-$C_{1-8}$alkyl, $C_{1-8}$alkyl-amino-$C_{1-8}$alkyl, $(C_{1-8}$alkyl$)_2$-amino-$C_{1-8}$alkyl, $C_{1-8}$alkoxy-$C_{1-8}$alkyl-amino-$C_{1-8}$alkyl, $(C_{1-8}$alkoxy-$C_{1-8}$alkyl$)_2$-amino-$C_{1-8}$alkyl, $(C_{1-8}$alkoxy-$C_{1-8}$alkyl$)(C_{1-8}$alkyl$)$amino-$C_{1-8}$alkyl, amino-$C_{1-8}$alkyl-amino, (amino-$C_{1-8}$alkyl$)_2$-amino, (amino-$C_{1-8}$alkyl$)(C_{1-8}$alkyl$)$amino, $C_{1-8}$alkyl-amino-$C_{1-8}$alkyl-amino, $(C_{1-8}$alkyl-amino-$C_{1-8}$alkyl$)_2$-amino, $(C_{1-8}$alkyl-amino-$C_{1-8}$alkyl$)(C_{1-8}$alkyl$)$amino, $(C_{1-8}$alkyl$)_2$-amino-$C_{1-8}$alkyl-amino, $[(C_{1-8}$alkyl$)_2$-amino-$C_{1-8}$alkyl$](C_{1-8}$alkyl$)$amino, amino-$C_{1-8}$alkoxy, $C_{1-8}$alkyl-amino-$C_{1-8}$alkoxy, $(C_{1-8}$alkyl$)_2$-amino-$C_{1-8}$alkoxy, $C_{1-8}$alkoxy-$C_{1-8}$alkyl-amino-$C_{1-8}$alkoxy, $(C_{1-8}$alkoxy-$C_{1-8}$alkyl$)_2$-amino-$C_{1-8}$alkoxy, $(C_{1-8}$alkoxy-$C_{1-8}$alkyl$)(C_{1-8}$alkyl$)$amino-$C_{1-8}$alkoxy, amino-$C_{2-8}$alkenyl, $C_{1-8}$alkyl-amino-$C_{2-8}$alkenyl, $(C_{1-8}$alkyl$)_2$-amino-$C_{2-8}$alkenyl, amino-$C_{2-8}$alkynyl, $C_{1-8}$alkyl-amino-$C_{2-8}$alkynyl, $(C_{1-8}$alkyl$)_2$-amino-$C_{2-8}$alkynyl, halo-$C_{1-8}$alkyl-amino, (halo-$C_{1-8}$alkyl$)_2$-amino, (halo-$C_{1-8}$alkyl$)(C_{1-8}$alkyl$)$amino, hydroxy-$C_{1-8}$alkyl, hydroxy-$C_{1-8}$alkoxy-$C_{1-8}$alkyl, hydroxy-$C_{1-8}$alkyl-amino, (hydroxy-$C_{1-8}$alkyl$)_2$-amino, (hydroxy-$C_{1-8}$alkyl$)(C_{1-8}$alkyl$)$amino, hydroxy-$C_{1-8}$alkyl-amino-$C_{1-8}$alkyl, (hydroxy-$C_{1-8}$alkyl$)_2$-amino-$C_{1-8}$alkyl, (hydroxy-$C_{1-8}$alkyl$)(C_{1-8}$alkyl$)$amino-$C_{1-8}$alkyl, hydroxy-$C_{1-8}$alkyl-amino-$C_{1-8}$alkoxy, (hydroxy-$C_{1-8}$alkyl$)_2$-amino-$C_{1-8}$alkoxy, (hydroxy-$C_{1-8}$alkyl$)(C_{1-8}$alkyl$)$amino-$C_{1-8}$alkoxy, hydroxy-$C_{1-8}$alkyl-amino-$C_{1-8}$alkyl-amino, (hydroxy-$C_{1-8}$alkyl-amino-$C_{1-8}$alkyl$)_2$-amino, (hydroxy-$C_{1-8}$alkyl$)_2$-amino-$C_{1-8}$alkyl-amino, (hydroxy-$C_{1-8}$alkyl-amino-$C_{1-8}$alkyl$)(C_{1-8}$alkyl$)$amino, (hydroxy-$C_{1-8}$alkyl$)(C_{1-8}$alkyl$)$amino-$C_{1-8}$alkyl-amino, $[$(hydroxy-$C_{1-8}$alkyl$)_2$-amino-$C_{1-8}$alkyl$](C_{1-8}$alkyl$)$amino or $[$(hydroxy-$C_{1-8}$alkyl$)(C_{1-8}$alkyl$)$amino-$C_{1-8}$alkyl$](C_{1-8}$alkyl$)$amino; and $R_2$ is aryl, aryl-amino, aryl-amino-carbonyl, heterocyclyl, heteroaryl or heteroaryl-amino, wherein, each instance of aryl, heterocyclyl and heteroaryl is optionally substituted with $R_6$ and $R_7$ substituents.

In another embodiment of the use of a compound of Formula (I), $R_1$ is heterocyclyl, heterocyclyl-$C_{1-8}$alkyl, heterocyclyl-$C_{1-8}$alkoxy, heterocyclyl-amino, (heterocyclyl)($C_{1-8}$alkyl)amino, heterocyclyl-amino-$C_{1-8}$alkyl, heterocyclyl-$C_{1-8}$alkyl-amino, (heterocyclyl-$C_{1-8}$alkyl)$_2$-amino, (heterocyclyl-$C_{1-8}$alkyl)($C_{1-8}$alkyl)amino, heterocyclyl-$C_{1-8}$alkyl-amino-$C_{1-8}$alkyl, (heterocyclyl-$C_{1-8}$alkyl)$_2$-amino-$C_{1-8}$alkyl, (heterocyclyl-$C_{1-8}$alkyl)($C_{1-8}$alkyl)amino-$C_{1-8}$alkyl, heterocyclyl-oxy, heterocyclyl-carbonyl, heterocyclyl-carbonyl-oxy, $C_{3-14}$cycloalkyl, aryl-$C_{1-8}$alkyl-amino, (aryl-$C_{1-8}$alkyl)$_2$-amino, (aryl-$C_{1-8}$alkyl)($C_{1-8}$alkyl)amino, aryl-$C_{1-8}$alkyl-amino-$C_{1-8}$alkyl, (aryl-$C_{1-8}$alkyl)$_2$-amino-$C_{1-8}$alkyl, (aryl-$C_{1-8}$alkyl)($C_{1-8}$alkyl)amino-$C_{1-8}$alkyl, heteroaryl, heteroaryl-$C_{1-8}$alkyl, heteroaryl-$C_{1-8}$alkoxy, heteroaryl-amino, heteroaryl-$C_{1-8}$alkyl-amino, (heteroaryl-$C_{1-8}$alkyl)$_2$-amino, (heteroaryl-$C_{1-8}$alkyl)($C_{1-8}$alkyl)amino, heteroaryl-$C_{1-8}$alkyl-amino-$C_{1-8}$alkyl, (heteroaryl-$C_{1-8}$alkyl)$_2$-amino-$C_{1-8}$alkyl or (heteroaryl-$C_{1-8}$alkyl)($C_{1-8}$alkyl)amino-$C_{1-8}$alkyl; wherein, each instance of heterocyclyl, $C_{3-14}$cycloalkyl, aryl and heteroaryl is optionally substituted with $R_3$ and $R_4$ substituents; and $R_2$ is aryl, aryl-amino, aryl-amino-carbonyl, heterocyclyl, heteroaryl or heteroaryl-amino, wherein, each instance of aryl, heterocyclyl and heteroaryl is optionally substituted with $R_6$ and $R_7$ substituents.

In another embodiment of the use of a compound of Formula (I), $R_1$ is heterocyclyl, heterocyclyl-$C_{1-8}$alkyl, heterocyclyl-$C_{1-8}$alkoxy, heterocyclyl-amino, (heterocyclyl)($C_{1-8}$alkyl)amino, heterocyclyl-amino-$C_{1-8}$alkyl, heterocyclyl-$C_{1-8}$alkyl-amino, (heterocyclyl-$C_{1-8}$alkyl)$_2$-amino, (heterocyclyl-$C_{1-8}$alkyl)($C_{1-8}$alkyl)amino, heterocyclyl-$C_{1-8}$alkyl-amino-$C_{1-8}$alkyl, (heterocyclyl-$C_{1-8}$alkyl)$_2$-amino-$C_{1-8}$alkyl, (heterocyclyl-$C_{1-8}$alkyl)($C_{1-8}$alkyl)amino-$C_{1-8}$alkyl, heterocyclyl-oxy, heterocyclyl-carbonyl or heterocyclyl-carbonyl-oxy; wherein, each instance of heterocyclyl is optionally substituted with $R_3$ and $R_4$ substituents; and $R_2$ is aryl, aryl-amino, aryl-amino-carbonyl, heterocyclyl, heteroaryl or heteroaryl-amino, wherein, each instance of aryl, heterocyclyl and heteroaryl is optionally substituted with $R_6$ and $R_7$ substituents.

In another embodiment of the use of a compound of Formula (I), $R_1$ is heterocyclyl optionally substituted with $R_3$ and $R_4$ substituents; and $R_2$ is aryl, aryl-amino, aryl-amino-carbonyl, heterocyclyl, heteroaryl or heteroaryl-amino, wherein, each instance of aryl, heterocyclyl and heteroaryl is optionally substituted with $R_6$ and $R_7$ substituents.

In another embodiment of the use of a compound of Formula (I), $R_1$ is $C_{3-14}$cycloalkyl optionally substituted with $R_3$ and $R_4$ substituents; and $R_2$ is aryl, aryl-amino, aryl-amino-carbonyl, heterocyclyl, heteroaryl or heteroaryl-amino, wherein, each instance of aryl, heterocyclyl and heteroaryl is optionally substituted with $R_6$ and $R_7$ substituents.

In another embodiment of the use of a compound of Formula (I), $R_1$ is aryl-$C_{1-8}$alkyl-amino, (aryl-$C_{1-8}$alkyl)$_2$-amino, (aryl-$C_{1-8}$alkyl)($C_{1-8}$alkyl)amino, aryl-$C_{1-8}$alkyl-amino-$C_{1-8}$alkyl, (aryl-$C_{1-8}$alkyl)$_2$-amino-$C_{1-8}$alkyl or (aryl-$C_{1-8}$alkyl)($C_{1-8}$alkyl)amino-$C_{1-8}$alkyl; wherein, each instance of aryl is optionally substituted with $R_3$ and $R_4$ substituents; and $R_2$ is aryl, aryl-amino, aryl-amino-carbonyl, heterocyclyl, heteroaryl or heteroaryl-amino, wherein, each instance of aryl, heterocyclyl and heteroaryl is optionally substituted with $R_6$ and $R_7$ substituents.

In another embodiment of the use of a compound of Formula (I), $R_1$ is aryl-$C_{1-8}$alkyl-amino optionally substituted with $R_3$ and $R_4$ substituents; and $R_2$ is aryl, aryl-amino, aryl-amino-carbonyl, heterocyclyl, heteroaryl or heteroaryl-amino, wherein, each instance of aryl, heterocyclyl and heteroaryl is optionally substituted with $R_6$ and $R_7$ substituents.

In another embodiment of the use of a compound of Formula (I), $R_1$ is heteroaryl, heteroaryl-$C_{1-8}$alkyl, heteroaryl-$C_{1-8}$alkoxy, heteroaryl-amino, heteroaryl-$C_{1-8}$alkyl-amino, (heteroaryl-$C_{1-8}$alkyl)$_2$-amino, (heteroaryl-$C_{1-8}$alkyl)($C_{1-8}$alkyl)amino, heteroaryl-$C_{1-8}$alkyl-amino-$C_{1-8}$alkyl, (heteroaryl-$C_{1-8}$alkyl)$_2$-amino-$C_{1-8}$alkyl or (heteroaryl-$C_{1-8}$alkyl)($C_{1-8}$alkyl)amino-$C_{1-8}$alkyl; wherein, each instance of heterocyclyl, $C_{3-14}$cycloalkyl, aryl and heteroaryl is optionally substituted with $R_3$ and $R_4$ substituents; and $R_2$ is aryl, aryl-amino, aryl-amino-carbonyl, heterocyclyl, heteroaryl or heteroaryl-amino, wherein, each instance of aryl, heterocyclyl and heteroaryl is optionally substituted with $R_6$ and $R_7$ substituents.

In another embodiment of the use of a compound of Formula (I),

R₁ is heteroaryl optionally substituted with R₃ and R₄ substituents; and

R₂ is aryl, aryl-amino, aryl-amino-carbonyl, heterocyclyl, heteroaryl or heteroaryl-amino, wherein, each instance of aryl, heterocyclyl and heteroaryl is optionally substituted with R₆ and R₇ substituents.

In one embodiment, the compound of Formula (I), used in a method disclosed herein, is a compound selected from Formula (II), Formula (III), Formula (IV), Formula (V), Formula (VI), Formula (VII), Formula (VIII), Formula (IX), Formula (X), Formula (XI), Formula (XII), Formula (XIII) or Formula (XIV):

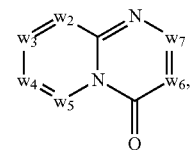 (II)

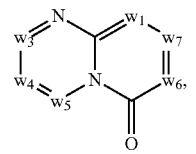 (III)

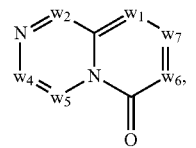 (IV)

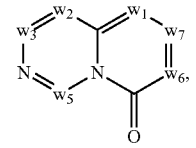 (V)

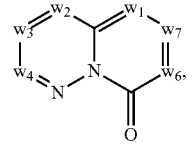 (VI)

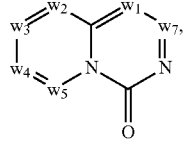 (VII)

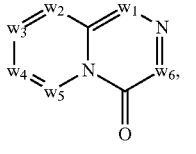 (VIII)

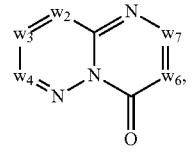 (IX)

-continued

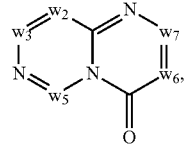 (X)

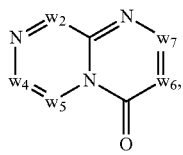 (XI)

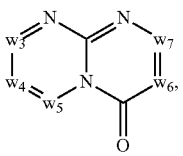 (XII)

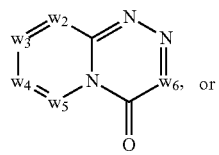 (XIII) or

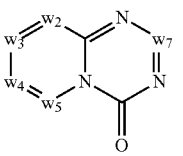 (XIV)

or a form thereof.

In an embodiment of the use of the compound of Formula (I), $w_3$ is C—R₁, $w_6$ is C—R₂, $w_1$, $w_4$, $w_5$ and $w_7$ are independently C—$R_a$ or N and $w_2$ is C—$R_b$ or N.

In another embodiment of the use of the compound of Formula (I), $w_3$ is C—R₂, $w_6$ is C—R₁, $w_1$, $w_4$, $w_5$ and $w_7$ are independently C—$R_a$ or N and $w_2$ is C—$R_b$ or N.

In another embodiment of the use of the compound of Formula (I), $w_4$ is C—R₁, $w_7$ is C—R₂, $w_1$, $w_3$ and $w_5$ are independently C—$R_a$ or N, $w_2$ is C—$R_b$ or N and $w_6$ is C—$R_c$ or N.

In another embodiment of the use of the compound of Formula (I), $w_4$ is C—R₂, $w_7$ is C—R₁, $w_1$, $w_3$ and $w_5$ are independently C—$R_a$ or N, $w_2$ is C—$R_b$ or N and $w_6$ is C—$R_c$ or N.

In an embodiment of the use of the compound of Formula (II), $w_3$ is C—R₁, $w_6$ is C—R₂, $w_4$, $w_5$ and $w_7$ are independently C—$R_a$ or N and $w_2$ is C—$R_b$ or N.

In another embodiment of the use of the compound of Formula (II), $w_3$ is C—R₂, $w_6$ is C—R₁, $w_4$, $w_5$ and $w_7$ are independently C—$R_a$ or N and $w_2$ is C—$R_b$ or N.

In another embodiment of the use of the compound of Formula (II), $w_4$ is C—R₁, $w_7$ is C—R₂, $w_3$ and $w_5$ are independently C—$R_a$ or N, $w_2$ is C—$R_b$ or N and $w_6$ is C—Re or N.

In another embodiment of the use of the compound of Formula (II), $w_4$ is C—R₂, $w_7$ is C—R₁, $w_3$ and $w_5$ are independently C—$R_a$ or N, $w_2$ is C—$R_b$ or N and $w_6$ is C—Re or N.

In an embodiment of the use of the compound of Formula (III), $w_3$ is C—R₁, $w_6$ is C—R₂ and $w_1$, $w_4$, $w_5$ and $w_7$ are independently C—$R_a$ or N.

In another embodiment of the use of the compound of Formula (III), $w_3$ is C—$R_2$, $w_6$ is C—$R_1$ and $w_1$, $w_4$, $w_5$ and $w_7$ are independently C—$R_a$ or N.

In another embodiment of the use of the compound of Formula (III), $w_4$ is C—$R_1$, $w_7$ is C—$R_2$, $w_1$, $w_3$ and $w_5$ are independently C—$R_a$ or N and $w_6$ is C—$R_c$ or N.

In another embodiment of the use of the compound of Formula (III), $w_4$ is C—$R_2$, $w_7$ is C—$R_1$, $w_1$, $w_3$ and $w_5$ are independently C—$R_a$ or N and $w_6$ is C—$R_c$ or N.

In an embodiment of the use of the compound of Formula (IV), $w_4$ is C—$R_1$, $w_7$ is C—$R_2$, $w_1$ and $w_5$ are independently C—$R_a$ or N, $w_2$ is C—$R_b$ or N and $w_6$ is C—$R_c$ or N.

In another embodiment of the use of the compound of Formula (IV), $w_4$ is C—$R_2$, $w_7$ is C—$R_1$, $w_1$ and $w_5$ are independently C—$R_a$ or N, $w_2$ is C—$R_b$ or N and $w_6$ is C—$R_c$ or N.

In an embodiment of the use of the compound of Formula (V), $w_3$ is C—$R_1$, $w_6$ is C—$R_2$, $w_1$, $w_5$ and $w_7$ are independently C—$R_a$ or N and $w_2$ is C—$R_b$ or N.

In another embodiment of the use of the compound of Formula (V), $w_3$ is C—$R_2$, $w_6$ is C—$R_1$, $w_1$, $w_5$ and $w_7$ are independently C—$R_a$ or N and $w_2$ is C—$R_b$ or N.

In another embodiment of the use of the compound of Formula (VI), $w_3$ is C—$R_1$, $w_6$ is C—$R_2$, $w_1$, $w_4$ and $w_7$ are independently C—$R_a$ or N and $w_2$ is C—$R_b$ or N.

In another embodiment of the use of the compound of Formula (VI), $w_3$ is C—$R_2$, $w_6$ is C—$R_1$, $w_1$, $w_4$ and $w_7$ are independently C—$R_a$ or N and $w_2$ is C—$R_b$ or N.

In another embodiment of the use of the compound of Formula (VI), $w_4$ is C—$R_1$, $w_7$ is C—$R_2$, $w_1$ and $w_3$ are independently C—$R_a$ or N, $w_2$ is C—$R_b$ or N and $w_6$ is C—Re or N.

In another embodiment of the use of the compound of Formula (VI), $w_4$ is C—$R_2$, $w_7$ is C—$R_1$, $w_1$ and $w_3$ are independently C—$R_a$ or N, $w_2$ is C—$R_b$ or N and $w_6$ is C—$R_c$ or N.

In another embodiment of the use of the compound of Formula (VII), $w_4$ is C—$R_1$, $w_7$ is C—$R_2$, $w_1$, $w_3$ and $w_5$ are C—$R_a$ or N and $w_2$ is C—$R_b$ or N.

In another embodiment of the use of the compound of Formula (VII), $w_4$ is C—$R_2$, $w_7$ is C—$R_1$, $w_1$, $w_3$ and $w_5$ are C—$R_a$ or N and $w_2$ is C—$R_b$ or N.

In another embodiment of the use of the compound of Formula (VIII), $w_3$ is C—$R_1$, $w_6$ is C—$R_2$, $w_1$, $w_4$ and $w_5$ are C—$R_a$ or N and $w_2$ is C—$R_b$ or N.

In another embodiment of the use of the compound of Formula (VIII), $w_3$ is C—$R_2$, $w_6$ is C—$R_1$, $w_1$, $w_4$ and $w_5$ are C—$R_a$ or N and $w_2$ is C—$R_b$ or N.

In an embodiment of the use of the compound of Formula (IX), $w_3$ is C—$R_1$, $w_6$ is C—$R_2$, $w_4$ and $w_7$ are independently C—$R_a$ or N and $w_2$ is C—$R_b$ or N.

In another embodiment of the use of the compound of Formula (IX), $w_3$ is C—$R_2$, $w_6$ is C—$R_1$, $w_4$ and $w_7$ are independently C—$R_a$ or N and $w_2$ is C—$R_b$ or N.

In another embodiment of the use of the compound of Formula (IX), $w_4$ is C—$R_1$, $w_7$ is C—$R_2$, $w_2$ is C—$R_b$ or N, $w_3$ is C—$R_a$ or N and $w_6$ is C—Re or N.

In another embodiment of the use of the compound of Formula (IX), $w_4$ is C—$R_2$, $w_7$ is C—$R_1$, $w_2$ is C—$R_b$ or N, $w_3$ is C—$R_a$ or N and $w_6$ is C—Re or N.

In an embodiment of the use of the compound of Formula (X), $w_3$ is C—$R_1$, $w_6$ is C—$R_2$, $w_2$ is C—$R_b$ or N and $w_5$ and $w_7$ are independently C—$R_a$ or N.

In another embodiment of the use of the compound of Formula (X), $w_3$ is C—$R_2$, $w_6$ is C—$R_1$, $w_2$ is C—$R_b$ or N and $w_5$ and $w_7$ are independently C—$R_a$ or N.

In an embodiment of the use of the compound of Formula (XI), $w_4$ is C—$R_1$, $w_7$ is C—$R_2$, $w_2$ is C—$R_b$ or N, $w_5$ is C—$R_a$ or N and $w_6$ is C—Re or N.

In another embodiment of the use of the compound of Formula (XI), $w_4$ is C—$R_2$, $w_7$ is C—$R_1$, $w_2$ is C—$R_b$ or N, $w_5$ is C—$R_a$ or N and $w_6$ is C—Re or N.

In an embodiment of the use of the compound of Formula (XII), $w_3$ is C—$R_1$, $w_6$ is C—$R_2$ and $w_4$, $w_5$ and $w_7$ are independently C—$R_a$ or N.

In another embodiment of the use of the compound of Formula (XII), $w_3$ is C—$R_2$, $w_6$ is C—$R_1$ and $w_4$, $w_5$ and $w_7$ are independently C—$R_a$ or N.

In another embodiment of the use of the compound of Formula (XII), $w_4$ is C—$R_1$, $w_7$ is C—$R_2$, $w_3$ and $w_5$ are independently C—$R_a$ or N and $w_6$ is C—$R_c$ or N.

In another embodiment of the use of the compound of Formula (XII), $w_4$ is C—$R_2$, $w_7$ is C—$R_1$, $w_3$ and $w_5$ are independently C—$R_a$ or N and $w_6$ is C—$R_c$ or N.

In an embodiment of the use of the compound of Formula (XIII), $w_3$ is C—$R_1$, $w_6$ is C—$R_2$, $w_2$ is C—$R_b$ or N and $w_4$ and $w_5$ are independently C—$R_a$ or N.

In another embodiment of the use of the compound of Formula (XIII), $w_3$ is C—$R_2$, $w_6$ is C—$R_1$, $w_2$ is C—$R_b$ or N and $w_4$ and $w_5$ are independently C—$R_a$ or N.

In an embodiment of the use of the compound of Formula (XIV), $w_4$ is C—$R_1$, $w_7$ is C—$R_2$, $w_2$ is C—$R_b$ or N and $w_3$ and $w_5$ are independently C—$R_a$ or N.

In another embodiment of the use of the compound of Formula (XIV), $w_4$ is C—$R_2$, $w_7$ is C—$R_1$, $w_2$ is C—$R_b$ or N and $w_3$ and $w_5$ are independently C—$R_a$ or N.

In another embodiment, the compound of Formula (I) used in a method disclosed herein is a compound selected from Formula (II), Formula (III), Formula (IX), Formula (XI) or Formula (XII):

-continued

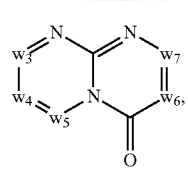
(XII)

or a form thereof.

In another embodiment, the compound of Formula (I) used in a method disclosed herein is a compound of Formula (II):

(II)

or a form thereof.

In another embodiment, the compound of Formula (I) used in a method disclosed herein is a compound of Formula (III):

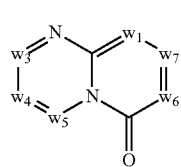
(III)

or a form thereof.

In another embodiment, the compound of Formula (I) used in a method disclosed herein is a compound of Formula (IV):

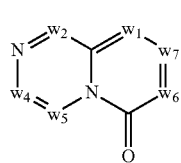
(IV)

or a form thereof.

In another embodiment, the compound of Formula (I) used in a method disclosed herein is a compound of Formula (V):

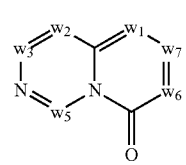
(V)

or a form thereof.

In another embodiment, the compound of Formula (I) used in a method disclosed herein is a compound of Formula (VI):

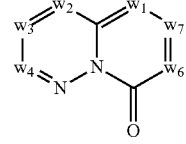
(VI)

or a form thereof.

In another embodiment, the compound of Formula (I) used in a method disclosed herein is a compound of Formula (VII):

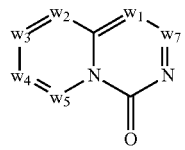
(VII)

or a form thereof.

In another embodiment, the compound of Formula (I) used in a method disclosed herein is a compound of Formula (VIII):

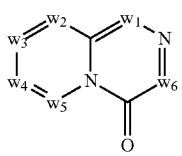
(VIII)

or a form thereof.

In another embodiment, the compound of Formula (I) used in a method disclosed herein is a compound of Formula (IX):

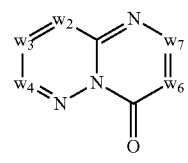
(IX)

or a form thereof.

In another embodiment, the compound of Formula (I) used in a method disclosed herein is a compound of Formula (X):

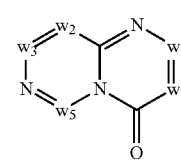
(X)

or a form thereof.

In another embodiment, the compound of Formula (I) used in a method disclosed herein is a compound of Formula (XI):

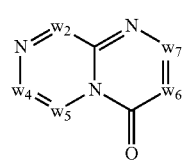

(XI)

or a form thereof.

In another embodiment, the compound of Formula (I) used in a method disclosed herein is a compound of Formula (XII):

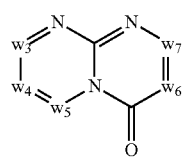

(XII)

or a form thereof.

In another embodiment, the compound of Formula (I) used in a method disclosed herein is a compound of Formula (XIII):

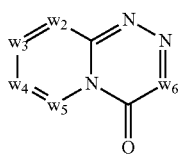

(XIII)

or a form thereof.

In another embodiment, the compound of Formula (I) used in a method disclosed herein is a compound of Formula (XIV):

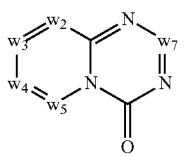

(XIV)

or a form thereof.

In one embodiment, the compound of Formula (I), Formula (II), Formula (III), Formula (IV), Formula (V), Formula (VI), Formula (VII), Formula (VIII), Formula (IX), Formula (X), Formula (XI), Formula (XII), Formula (XIII) or Formula (XIV) used in a method disclosed herein is a compound selected from Formula (Ia), Formula (IIa), Formula (IIIa), Formula (IVa), Formula (Va), Formula (VIa), Formula (VIIa), Formula (VIIIa), Formula (IXa), Formula (Xa), Formula (XIa), Formula (XIIa), Formula (XIIIa) or Formula (XIVa), respectively:

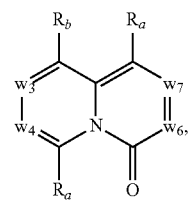

(Ia)

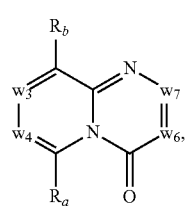

(IIa)

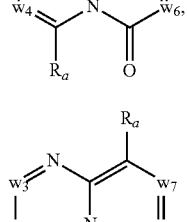

(IIIa)

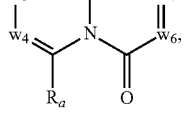

(IVa)

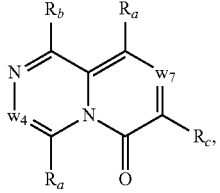

(Va)

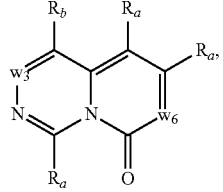

(VIa)

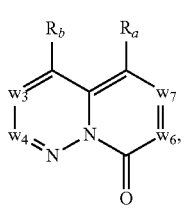

(VIIa)

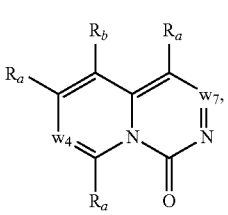

-continued (VIIIa)

(IXa)

(Xa)

(XIa)

(XIIa)

(XIIIa)

(XIVa)

or a form thereof.

In an embodiment of the use of the compound of Formula (Ia), one of $w_3$, $w_4$, $w_6$ and $w_7$ is C—$R_1$ and one other of $w_3$, $w_4$, $w_6$ and $w_7$ is C—$R_2$, provided that, when $w_3$ is C—$R_1$, then $w_6$ is C—$R_2$ and $w_4$ and $w_7$ are independently C—$R_a$ or N; or, when $w_3$ is C—$R_2$, then $w_6$ is C—$R_1$ and $w_4$ and $w_7$ are independently C—$R_a$ or N; or, when $w_4$ is C—$R_1$, then $w_7$ is C—$R_2$ and $w_3$ is C—$R_a$ or N and $w_6$ is C—$R_c$ or N; or, when $w_4$ is C—$R_2$, then $w_7$ is C—$R_1$ and $w_3$ is C—$R_a$ or N and $w_6$ is C—$R_c$ or N.

In an embodiment of the use of the compound of Formula (IIa), one of $w_3$, $w_4$, $w_6$ and $w_7$ is C—$R_1$ and one other of $w_3$, $w_4$, $w_6$ and $w_7$ is C—$R_2$, provided that, when $w_3$ is C—$R_1$, then $w_6$ is C—$R_2$ and $w_4$ and $w_7$ are independently C—$R_a$ or N; or, when $w_3$ is C—$R_2$, then $w_6$ is C—$R_1$ and $w_4$ and $w_7$ are independently C—$R_a$ or N; or, when $w_4$ is C—$R_1$, then $w_7$ is C—$R_2$ and $w_3$ is C—$R_a$ or N and $w_6$ is C—Re or N; or, when $w_4$ is C—$R_2$, then $w_7$ is C—$R_1$ and $w_3$ is C—$R_a$ or N and $w_6$ is C—$R_c$ or N.

In an embodiment of the use of the compound of Formula (IIIa), one of $w_3$, $w_4$, $w_6$ and $w_7$ is C—$R_1$ and one other of $w_3$, $w_4$, $w_6$ and $w_7$ is C—$R_2$, provided that, when $w_3$ is C—$R_1$, then $w_6$ is C—$R_2$ and $w_4$ and $w_7$ are independently C—$R_a$ or N; or, when $w_3$ is C—$R_2$, then $w_6$ is C—$R_1$ and $w_4$ and $w_7$ are independently C—$R_a$ or N; or, when $w_4$ is C—$R_1$, then $w_7$ is C—$R_2$ and $w_3$ is C—$R_a$ or N and $w_6$ is C—$R_c$ or N; or, when $w_4$ is C—$R_2$, then $w_7$ is C—$R_1$ and $w_3$ is C—$R_a$ or N and $w_6$ is C—$R_c$ or N.

In an embodiment of the use of the compound of Formula (IVa), one of $w_4$ and $w_7$ is C—$R_1$ and the other is C—$R_2$, provided that, when $w_4$ is C—$R_1$, then $w_7$ is C—$R_2$; or, when $w_4$ is C—$R_2$, then $w_7$ is C—$R_1$.

In an embodiment of the use of the compound of Formula (Va), one of $w_3$ and $w_6$ is C—$R_1$ and the other is C—$R_2$, provided that, when $w_3$ is C—$R_1$, then $w_6$ is C—$R_2$; or, when $w_3$ is C—$R_2$, then $w_6$ is C—$R_1$.

In an embodiment of the use of the compound of Formula (VIa), one of $w_3$, $w_4$, $w_6$ and $w_7$ is C—$R_1$ and one other of $w_3$, $w_4$, $w_6$ and $w_7$ is C—$R_2$, provided that, when $w_3$ is C—$R_1$, then $w_6$ is C—$R_2$ and $w_4$ and $w_7$ are independently C—$R_a$ or N; or, when $w_3$ is C—$R_2$, then $w_6$ is C—$R_1$ and $w_4$ and $w_7$ are independently C—$R_a$ or N; or, when $w_4$ is C—$R_1$, then $w_7$ is C—$R_2$ and $w_3$ is C—$R_a$ or N and $w_6$ is C—$R_c$ or N; or, when $w_4$ is C—$R_2$, then $w_7$ is C—$R_1$ and $w_3$ is C—$R_a$ or N and $w_6$ is C—$R_c$ or N.

In an embodiment of the use of the compound of Formula (VIIa), one of $w_4$ and $w_7$ is C—$R_1$ and the other is C—$R_2$, provided that, when $w_4$ is C—$R_1$, then $w_7$ is C—$R_2$; or, when $w_4$ is C—$R_2$, then $w_7$ is C—$R_1$.

In an embodiment of the use of the compound of Formula (VIIIa), one of $w_3$ and $w_6$ is C—$R_1$ and the other is C—$R_2$, provided that, when $w_3$ is C—$R_1$, then $w_6$ is C—$R_2$; or, when $w_3$ is C—$R_2$, then $w_6$ is C—$R_1$.

In an embodiment of the use of the compound of Formula (IXa), one of $w_3$, $w_4$, $w_6$ and $w_7$ is C—$R_1$ and one other of $w_3$, $w_4$, $w_6$ and $w_7$ is C—$R_2$, provided that, when $w_3$ is C—$R_1$, then $w_6$ is C—$R_2$ and $w_4$ and $w_7$ are independently C—$R_a$ or N; or, when $w_3$ is C—$R_2$, then $w_6$ is C—$R_1$ and $w_4$ and $w_7$ are independently C—$R_a$ or N; or, when $w_4$ is C—$R_1$, then $w_7$ is C—$R_2$ and $w_3$ is C—$R_a$ or N and $w_6$ is C—Re or N; or, when $w_4$ is C—$R_2$, then $w_7$ is C—$R_1$ and $w_3$ is C—$R_a$ or N and $w_6$ is C—Re or N.

In an embodiment of the use of the compound of Formula (Xa), one of $w_3$ and $w_6$ is C—$R_1$ and the other is C—$R_2$, provided that, when $w_3$ is C—$R_1$, then $w_6$ is C—$R_2$; or, when $w_3$ is C—$R_2$, then $w_6$ is C—$R_1$.

In an embodiment of the use of the compound of Formula (XIa), one of $w_4$ and $w_7$ is C—$R_1$ and the other is C—$R_2$, provided that, when $w_4$ is C—$R_1$, then $w_7$ is C—$R_2$; or, when $w_4$ is C—$R_2$, then $w_7$ is C—$R_1$.

In an embodiment of the use of the compound of Formula (XIIa), one of $w_3$, $w_4$, $w_6$ and $w_7$ is C—$R_1$ and one other of $w_3$, $w_4$, $w_6$ and $w_7$ is C—$R_2$, provided that,
when $w_3$ is C—$R_1$, then $w_6$ is C—$R_2$ and $w_4$ and $w_7$ are independently C—$R_a$ or N; or,
when $w_3$ is C—$R_2$, then $w_6$ is C—$R_1$ and $w_4$ and $w_7$ are independently C—$R_a$ or N; or,
when $w_4$ is C—$R_1$, then $w_7$ is C—$R_2$ and $w_3$ is C—$R_a$ or N and $w_6$ is C—$R_c$ or N; or,
when $w_4$ is C—$R_2$, then $w_7$ is C—$R_1$ and $w_3$ is C—$R_a$ or N and $w_6$ is C—$R_c$ or N.

In an embodiment of the use of the compound of Formula (XIIIa), one of $w_3$ and $w_6$ is C—$R_1$ and the other is C—$R_2$, provided that, when $w_3$ is C—$R_1$, then $w_6$ is C—$R_2$; or, when $w_3$ is C—$R_2$, then $w_6$ is C—$R_1$.

In an embodiment of the use of the compound of Formula (XIVa), one of $w_4$ and $w_7$ is C—$R_1$ and the other is C—$R_2$, provided that, when $w_4$ is C—$R_1$, then $w_7$ is C—$R_2$; or, when $w_4$ is C—$R_2$, then $w_7$ is C—$R_1$.

In another embodiment, the compound of Formula (I), Formula (II), Formula (III), Formula (IX), Formula (XI) or Formula (XII), used in a method disclosed herein, is a compound selected from Formula (Ia), Formula (IIa), Formula (IIIa), Formula (IXa), Formula (XIa) or Formula (XIIa), respectively:

(Ia)

(IIa)

(IIIa)

(IXa)

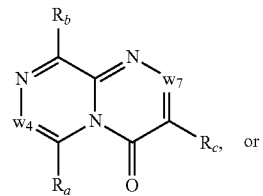

(XIa)

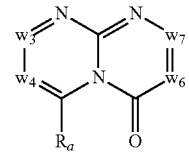

(XIIa)

or a form thereof.

In another embodiment, the compound of Formula (I) used in a method disclosed herein is a compound of Formula (Ia):

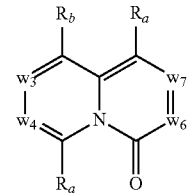

(Ia)

or a form thereof.

In another embodiment, the compound of Formula (II) used in a method disclosed herein is a compound of Formula (IIa):

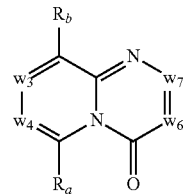

(IIa)

or a form thereof.

In another embodiment, the compound of Formula (III) used in a method disclosed herein is a compound of Formula (IIIa):

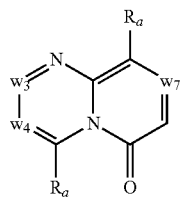

(IIIa)

or a form thereof.

In another embodiment, the compound of Formula (IV) used in a method disclosed herein is a compound of Formula (IVa):

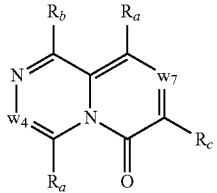
(IVa)

or a form thereof.

In another embodiment, the compound of Formula (V) used in a method disclosed herein is a compound of Formula (Va):

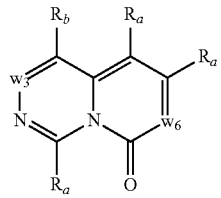
(Va)

or a form thereof.

In another embodiment, the compound of Formula (VI) used in a method disclosed herein is a compound of Formula (VIa):

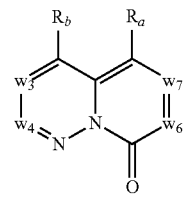
(VIa)

or a form thereof.

In another embodiment, the compound of Formula (VII) used in a method disclosed herein is a compound of Formula (VIIa):

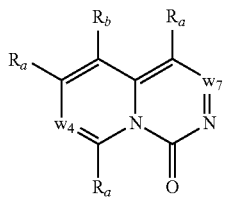
(VIIa)

or a form thereof.

In another embodiment, the compound of Formula (VIII) used in a method disclosed herein is a compound of Formula (VIIIa):

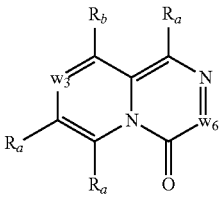
(VIIIa)

or a form thereof.

In another embodiment, the compound of Formula (IX) used in a method disclosed herein is a compound of Formula (IXa):

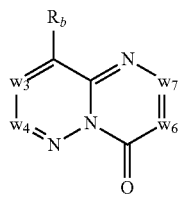
(IXa)

or a form thereof.

In another embodiment, the compound of Formula (X) used in a method disclosed herein is a compound of Formula (Xa):

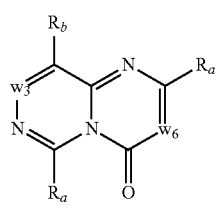
(Xa)

or a form thereof.

In another embodiment, the compound of Formula (XI) used in a method disclosed herein is a compound of Formula (XIa):

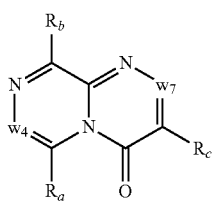
(XIa)

or a form thereof.

In another embodiment, the compound of Formula (XII) used in a method disclosed herein is a compound of Formula (XIIa):

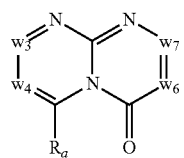
(XIIa)

or a form thereof.

In another embodiment, the compound of Formula (XIII) used in a method disclosed herein is a compound of Formula (XIIIa):

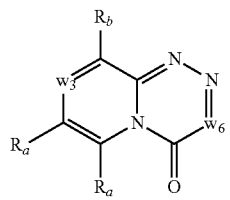
(XIIIa)

or a form thereof.

In another embodiment, the compound of Formula (XIV) used in a method disclosed herein is a compound of Formula (XIVa):

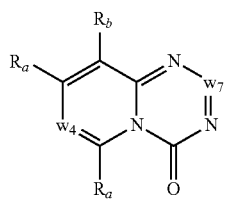
(XIVa)

or a form thereof.

In one embodiment, the compound of Formula (Ia) used in a method disclosed herein is a compound of Formula (Ia1), Formula (Ia2), Formula (Ia3) or Formula (Ia4):

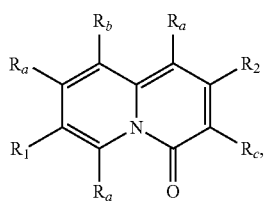
(Ia1)

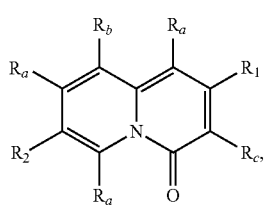
(Ia2)

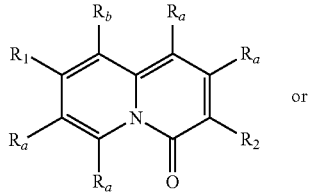
(Ia3)

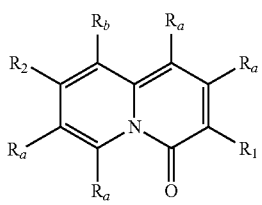
(Ia4)

or a form thereof.

In one embodiment, the compound of Formula (IIa) used in a method disclosed herein is a compound of Formula (IIa1), Formula (IIa2), Formula (IIa3) or Formula (IIa4):

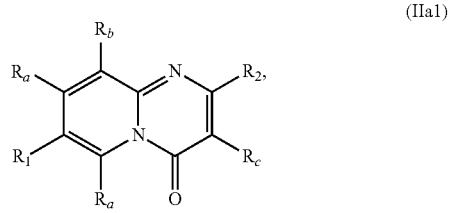
(IIa1)

(IIa2)

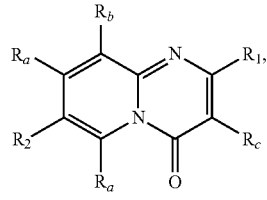
(IIa3)

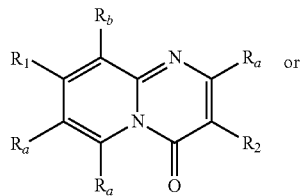
(IIa4)

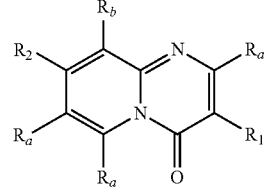

or a form thereof.

In one embodiment, the compound of Formula (IIIa) used in a method disclosed herein is a compound of Formula (IIIa1), Formula (IIIa2), Formula (IIIa3) or Formula (IIIa4):

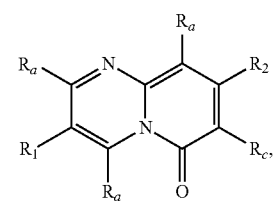

(IIIa1)

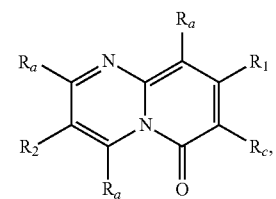

(IIIa2)

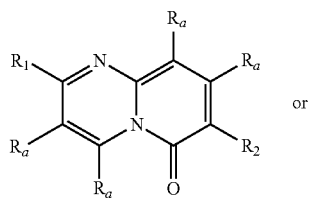

(IIIa3)

or

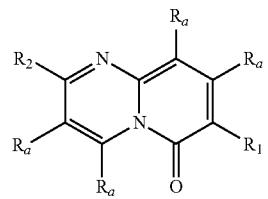

(IIIa4)

or a form thereof.

In one embodiment, the compound of Formula (IVa) used in a method disclosed herein is a compound of Formula (IVa1) or Formula (IVa2):

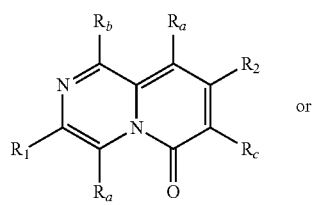

(IVa1)

or

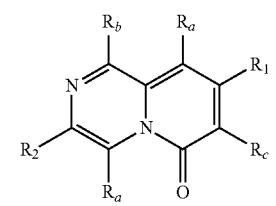

(IVa2)

or a form thereof.

In one embodiment, the compound of Formula (Va) used in a method disclosed herein is a compound of Formula (Va1) or Formula (Va2):

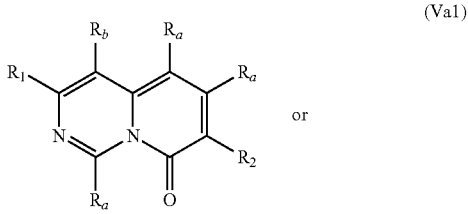

(Va1)

or

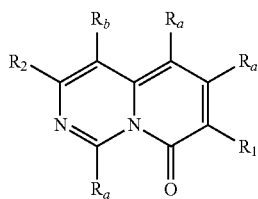

(Va2)

or a form thereof.

In one embodiment, the compound of Formula (VIa) used in a method disclosed herein is a compound of Formula (VIa1), Formula (VIa2), Formula (VIa3) or Formula (VIa4):

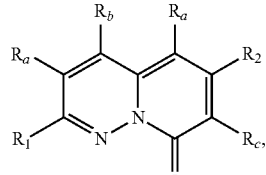

(VIa1)

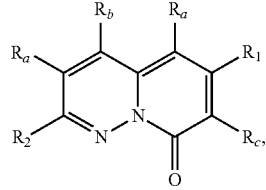

(VIa2)

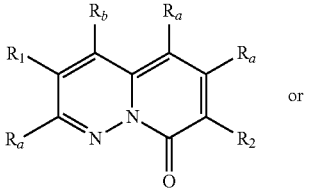

(VIa3)

or

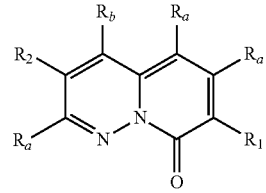

(VIa4)

or a form thereof.

In one embodiment, the compound of Formula (VIIa) used in a method disclosed herein is a compound of Formula (VIIa1) or Formula (VIIa2):

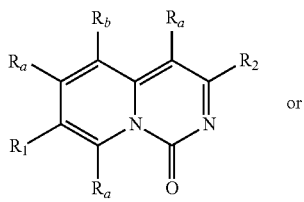

(VIIa1)

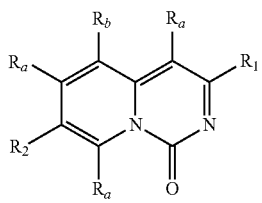

(VIIa2)

or a form thereof.

In one embodiment, the compound of Formula (VIIIa) used in a method disclosed herein is a compound of Formula (VIIIa1) or Formula (VIIIa2):

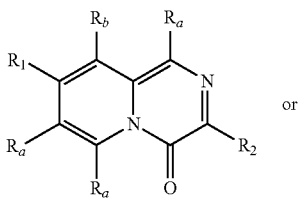

(VIIIa1)

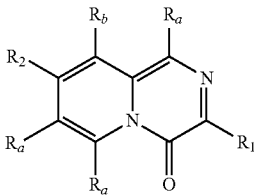

(VIIIa2)

or a form thereof.

In one embodiment, the compound of Formula (IXa) used in a method disclosed herein is a compound of Formula (IXa1), Formula (IXa2), Formula (IXa3) or Formula (IXa4):

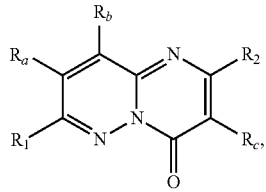

(IXa1)

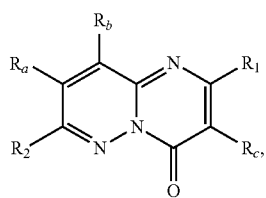

(IXa2)

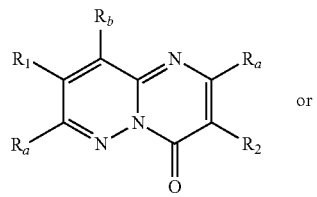

(IXa3)

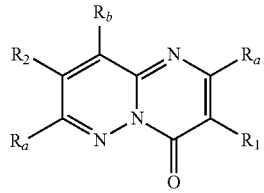

(IXa4)

or a form thereof.

In one embodiment, the compound of Formula (Xa) used in a method disclosed herein is a compound of Formula (Xa1) or Formula (Xa2):

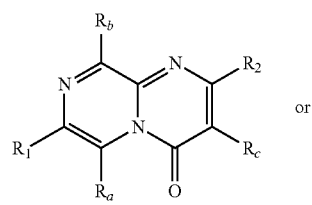

(Xa1)

(Xa2)

or a form thereof.

In one embodiment, the compound of Formula (XIa) used in a method disclosed herein is a compound of Formula (XIa1) or Formula (XIa2):

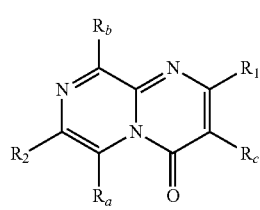

(XIa1)

(XIa2)

or a form thereof.

In one embodiment, the compound of Formula (XIIa) used in a method disclosed herein is a compound of Formula (XIIa1), Formula (XIIa2), Formula (XIIa3) or Formula (XIIa4):

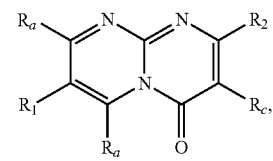
(XIIa1)

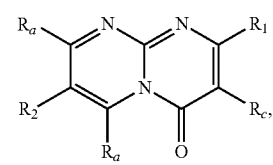
(XIIa2)

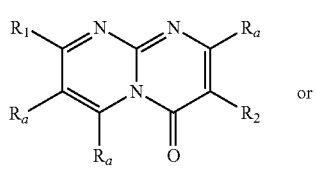
(XIIa3)

or

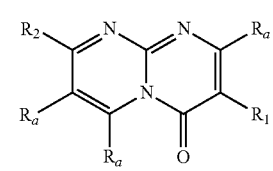
(XIIa4)

or a form thereof.

In one embodiment, the compound of Formula (XIIIa) used in a method disclosed herein is a compound of Formula (XIIIa1) or Formula (XIIIa2):

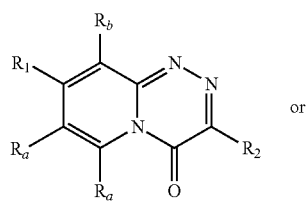
(XIIIa1)

or

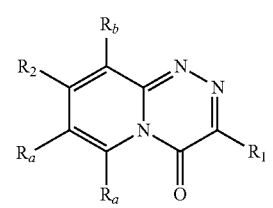
(XIIIa2)

or a form thereof.

In one embodiment, the compound of Formula (XIVa) used in a method disclosed herein is a compound of Formula (XIVa1) or Formula (XIVa2):

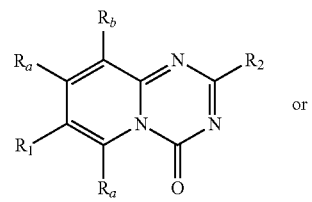
(XIVa1)

or

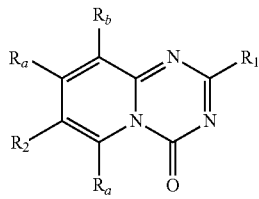
(XIVa2)

or a form thereof.

In one embodiment, the compound of Formula (Ia) used in a method disclosed herein is a compound of Formula (Ia1):

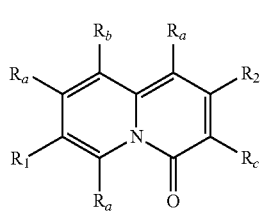
(Ia1)

or a form thereof.

In one embodiment, the compound of Formula (Ia) used in a method disclosed herein is a compound of Formula (Ia2):

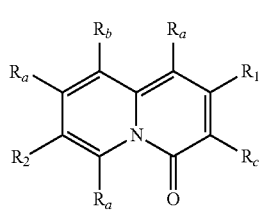
(Ia2)

or a form thereof.

In one embodiment, the compound of Formula (Ia) used in a method disclosed herein is a compound of Formula (Ia3):

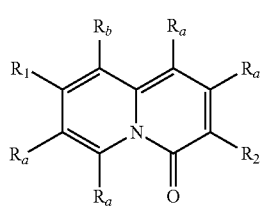
(Ia3)

or a form thereof.

In one embodiment, the compound of Formula (Ia) used in a method disclosed herein is a compound of Formula (Ia4):

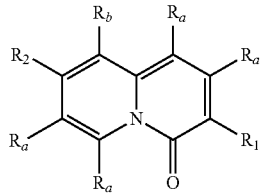

(Ia4)

or a form thereof.

In one embodiment, the compound of Formula (IIa) used in a method disclosed herein is a compound of Formula (IIa1):

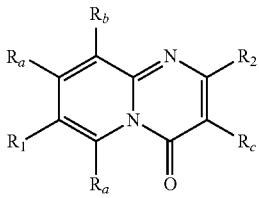

(IIa1)

or a form thereof.

In one embodiment, the compound of Formula (IIa) used in a method disclosed herein is a compound of Formula (IIa2):

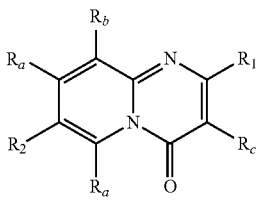

(IIa2)

or a form thereof.

In one embodiment, the compound of Formula (IIa) used in a method disclosed herein is a compound of Formula (IIa3):

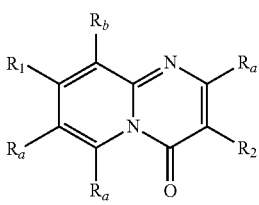

(IIa3)

or a form thereof.

In one embodiment, the compound of Formula (IIa) used in a method disclosed herein is a compound of Formula (IIa4):

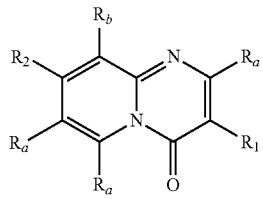

(IIa4)

or a form thereof.

In one embodiment, the compound of Formula (IIIa) used in a method disclosed herein is a compound of Formula (IIIa1):

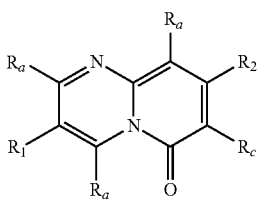

(IIIa1)

or a form thereof.

In one embodiment, the compound of Formula (IIIa) used in a method disclosed herein is a compound of Formula (IIIa2):

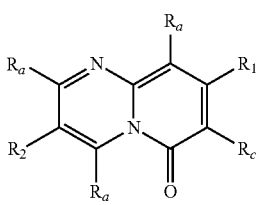

(IIIa2)

or a form thereof.

In one embodiment, the compound of Formula (IIIa) used in a method disclosed herein is a compound of Formula (IIIa3):

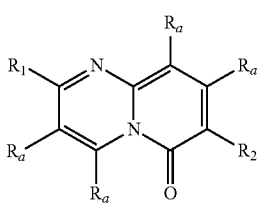

(IIIa3)

or a form thereof.

In one embodiment, the compound of Formula (IIIa) used in a method disclosed herein is a compound of Formula (IIIa4):

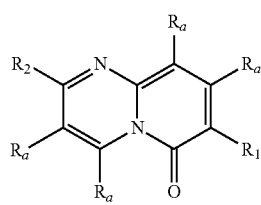

(IIIa4)

or a form thereof.

In one embodiment, the compound of Formula (IVa) used in a method disclosed herein is a compound of Formula (IVa1):

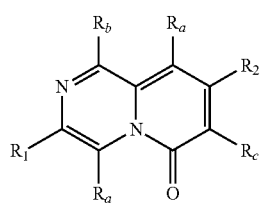

(IVa1)

or a form thereof.

In one embodiment, the compound of Formula (IVa) used in a method disclosed herein is a compound of Formula (IVa2):

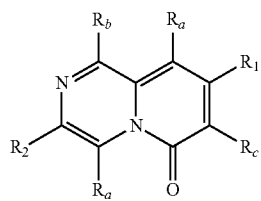

(IVa2)

or a form thereof.

In one embodiment, the compound of Formula (Va) used in a method disclosed herein is a compound of Formula (Va1):

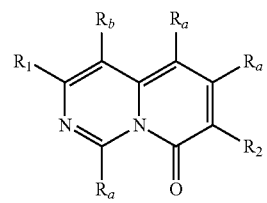

(Va1)

or a form thereof.

In one embodiment, the compound of Formula (Va) used in a method disclosed herein is a compound of Formula (Va2):

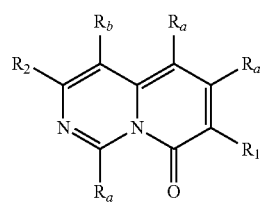

(Va2)

or a form thereof.

In one embodiment, the compound of Formula (VIa) used in a method disclosed herein is a compound of Formula (VIa1):

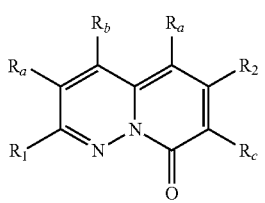

(VIa1)

or a form thereof.

In one embodiment, the compound of Formula (VIa) used in a method disclosed herein is a compound of Formula (VIa2):

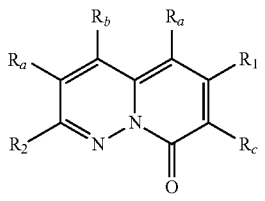

(VIa2)

or a form thereof.

In one embodiment, the compound of Formula (VIa) used in a method disclosed herein is a compound of Formula Formula (VIa3):

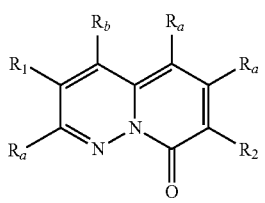

(VIa3)

or a form thereof.

In one embodiment, the compound of Formula (VIa) used in a method disclosed herein is a compound of Formula (VIa4):

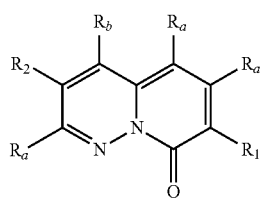

(VIa4)

or a form thereof.

In one embodiment, the compound of Formula (VIIa) used in a method disclosed herein is a compound of Formula (VIIa1):

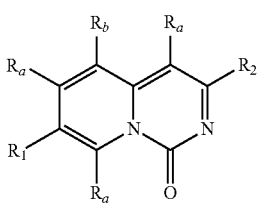

(VIIa1)

or a form thereof.

In one embodiment, the compound of Formula (VIIa) used in a method disclosed herein is a compound of Formula (VIIa2):

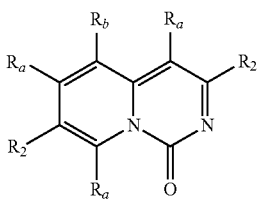

(VIIa2)

or a form thereof.

In one embodiment, the compound of Formula (VIIIa) used in a method disclosed herein is a compound of Formula (VIIIa1):

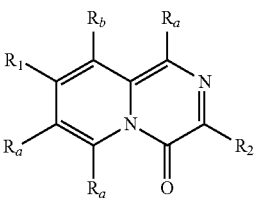

(VIIIa1)

or a form thereof.

In one embodiment, the compound of Formula (VIIIa) used in a method disclosed herein is a compound of Formula (VIIIa2):

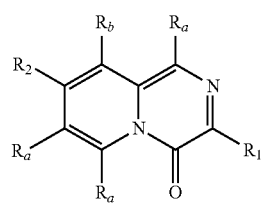

(VIIIa2)

or a form thereof.

In one embodiment, the compound of Formula (IXa) used in a method disclosed herein is a compound of Formula (IXa1):

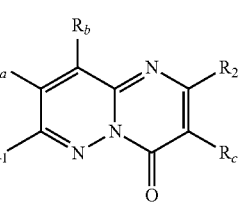

(IXa1)

or a form thereof.

In one embodiment, the compound of Formula (IXa) used in a method disclosed herein is a compound of Formula (IXa2):

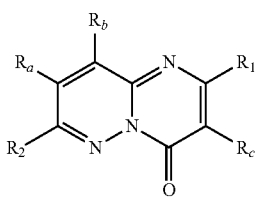

(IXa2)

or a form thereof.

In one embodiment, the compound of Formula (IXa) used in a method disclosed herein is a compound of Formula (IXa3):

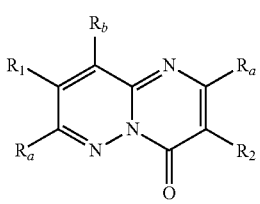

(IXa3)

or a form thereof.

In one embodiment, the compound of Formula (IXa) used in a method disclosed herein is a compound of Formula (IXa4):

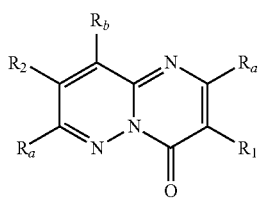
(IXa4)

or a form thereof.

In one embodiment, the compound of Formula (Xa) used in a method disclosed herein is a compound of Formula (Xa1):

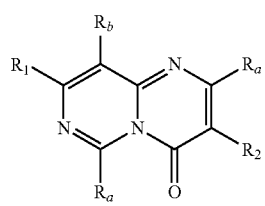
(Xa1)

or a form thereof.

In one embodiment, the compound of Formula (Xa) used in a method disclosed herein is a compound of Formula (Xa2):

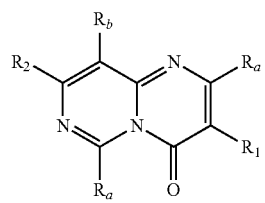
(Xa2)

or a form thereof.

In one embodiment, the compound of Formula (XIa) used in a method disclosed herein is a compound of Formula (XIa1):

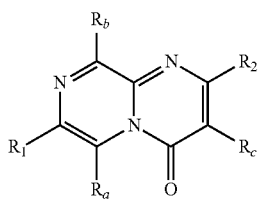
(XIa1)

or a form thereof.

In one embodiment, the compound of Formula (XIa) used in a method disclosed herein is a compound of Formula (XIa2):

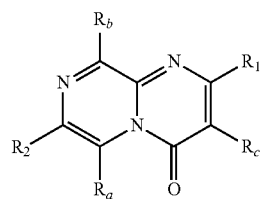
(XIa2)

or a form thereof.

In one embodiment, the compound of Formula (XIIa) used in a method disclosed herein is a compound of Formula (XIIa1):

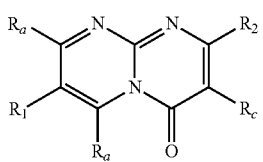
(XIIa1)

or a form thereof.

In one embodiment, the compound of Formula (XIIa) used in a method disclosed herein is a compound of Formula (XIIa2):

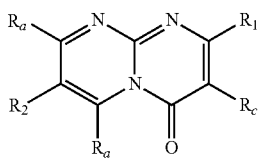
(XIIa2)

or a form thereof.

In one embodiment, the compound of Formula (XIIa) used in a method disclosed herein is a compound of Formula (XIIa3):

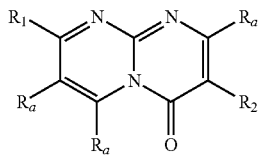
(XIIa3)

or a form thereof.

In one embodiment, the compound of Formula (XIIa) used in a method disclosed herein is a compound of Formula (XIIa4):

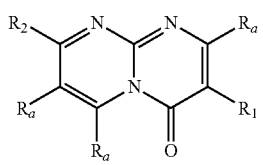
(XIIa4)

or a form thereof.

In one embodiment, the compound of Formula (XIIIa) used in a method disclosed herein is a compound of Formula (XIIIa1):

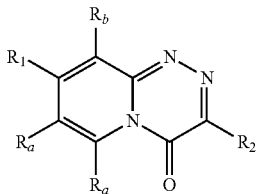
(XIIIa1)

or a form thereof.

In one embodiment, the compound of Formula (XIIIa) used in a method disclosed herein is a compound of Formula (XIIIa2):

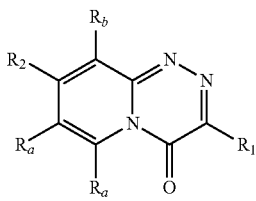
(XIIIa2)

or a form thereof.

In one embodiment, the compound of Formula (XIVa) used in a method disclosed herein is a compound of Formula (XIVa1):

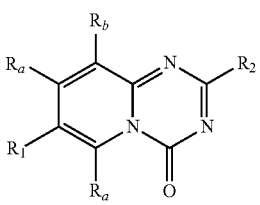
(XIVa1)

or a form thereof.

In one embodiment, the compound of Formula (XIVa) used in a method disclosed herein is a compound of Formula (XIVa2):

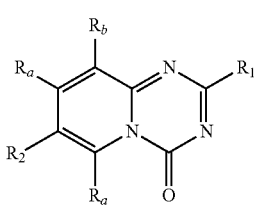
(XIVa2)

or a form thereof.

In another embodiment, the compound of Formula (I) used in a method disclosed herein is a compound selected from the group consisting of:

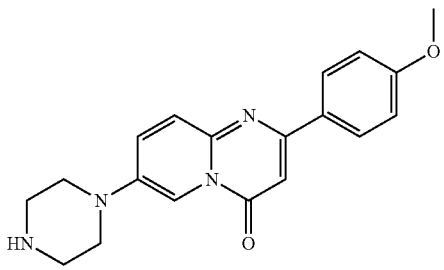
1

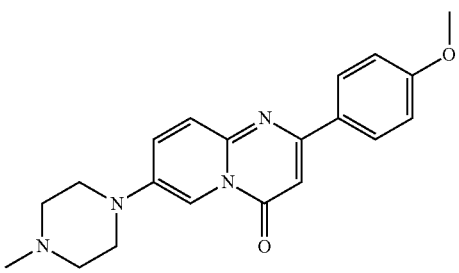
2

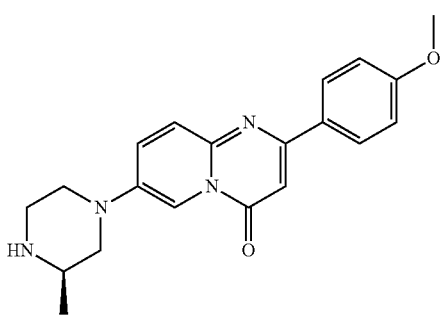
3

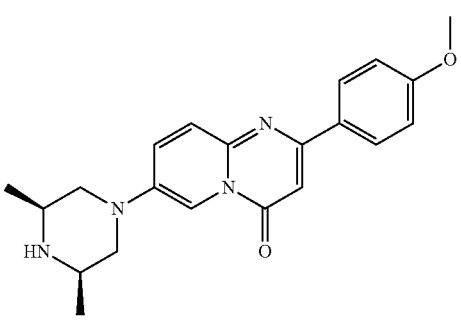
4

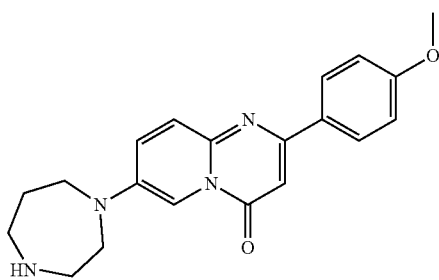
5

6
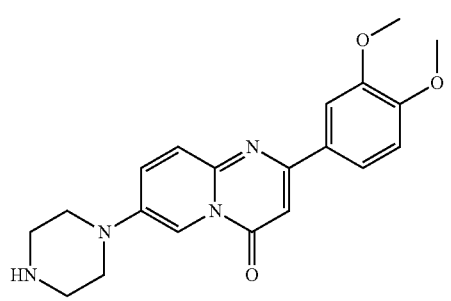
7
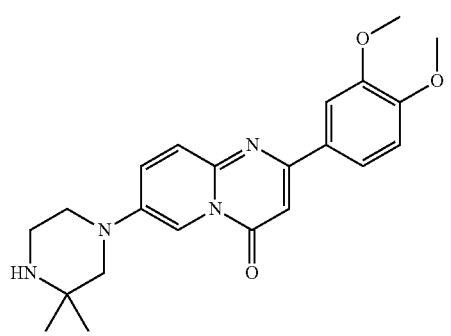
8
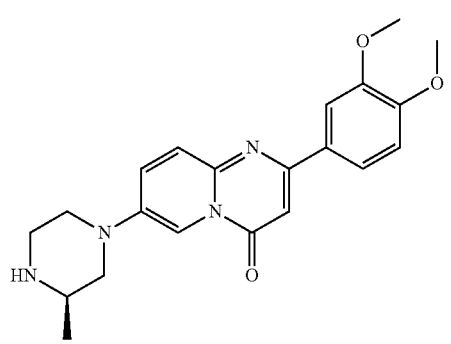
9
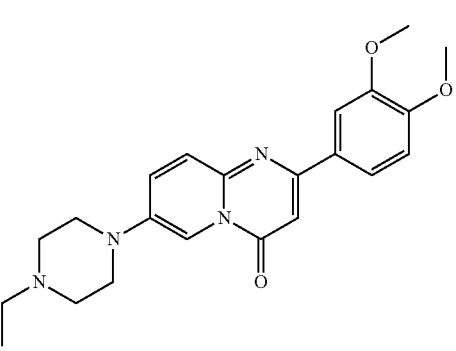
10
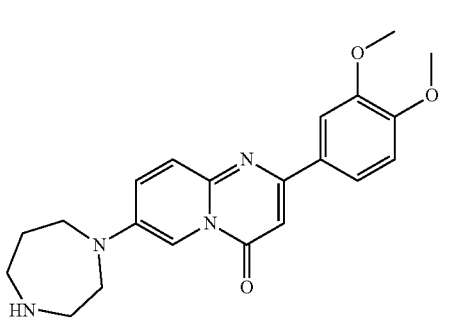
11
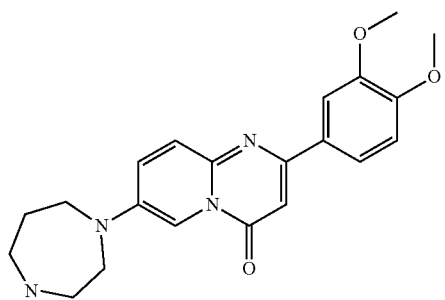
12
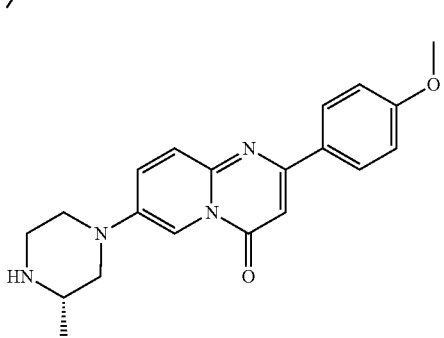
13
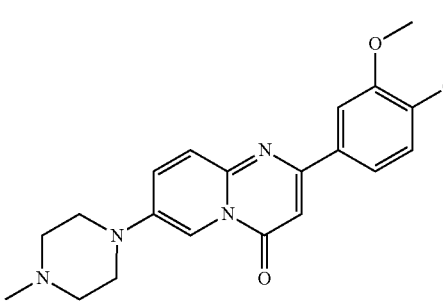
14
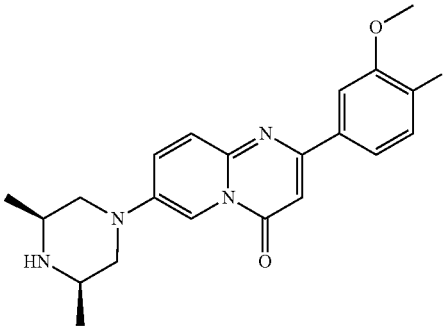
15
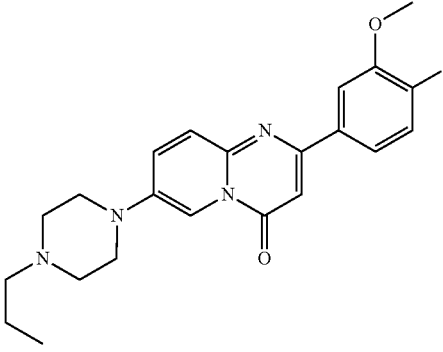

16
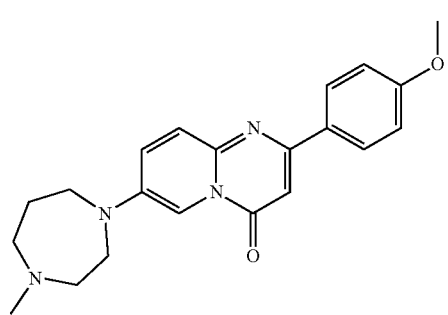
17
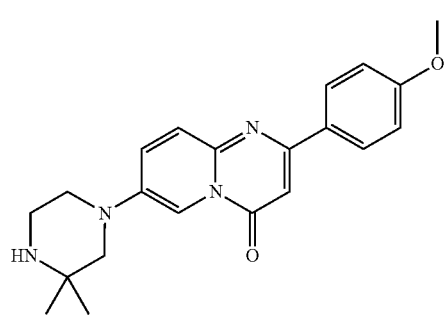
18
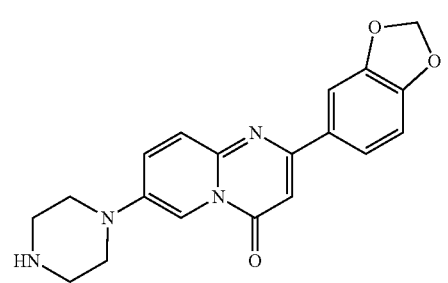
19
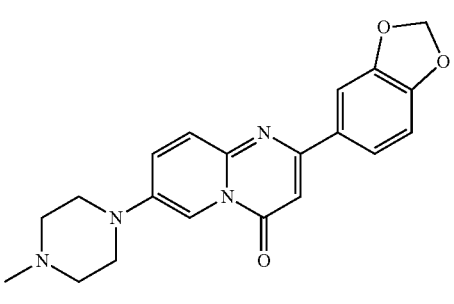
20
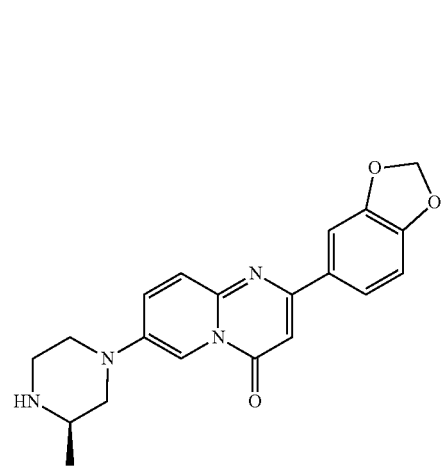
21
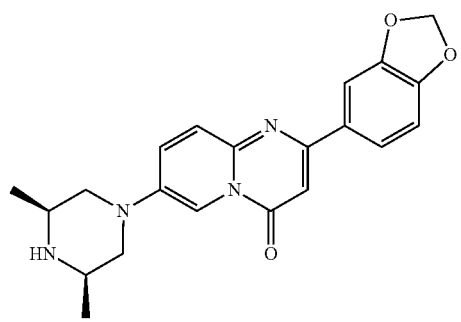
22
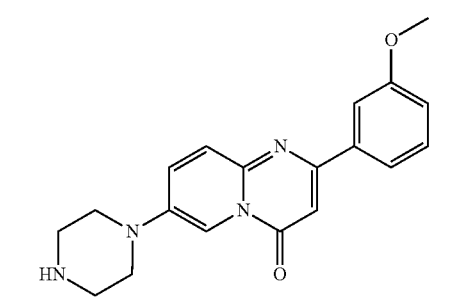
23
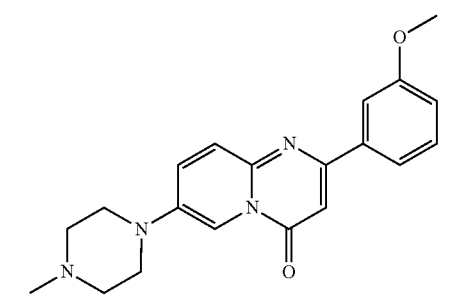
24
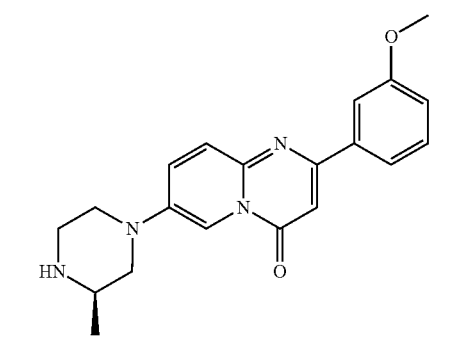
25
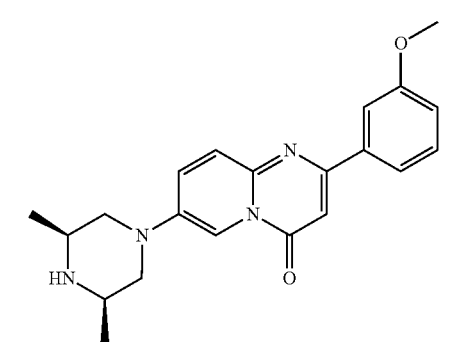

26
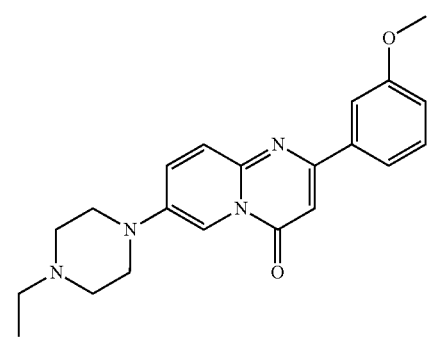
27
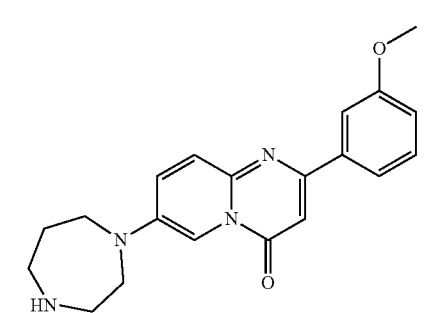
28
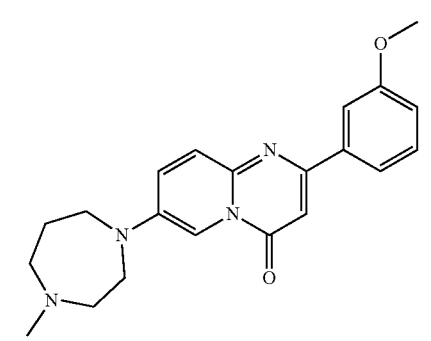
29
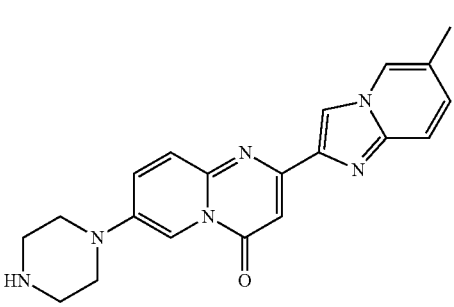
30
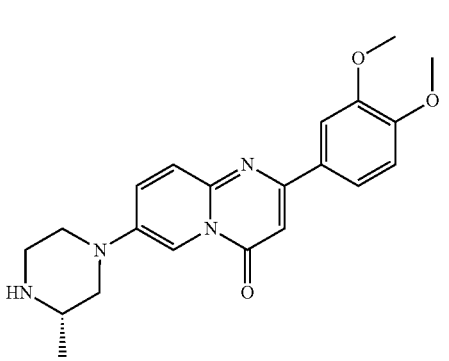
31
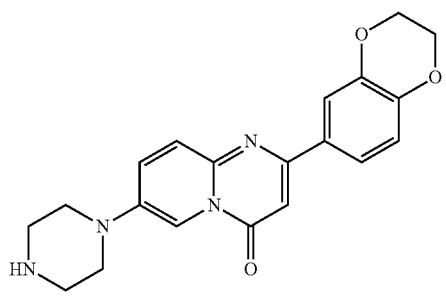
32
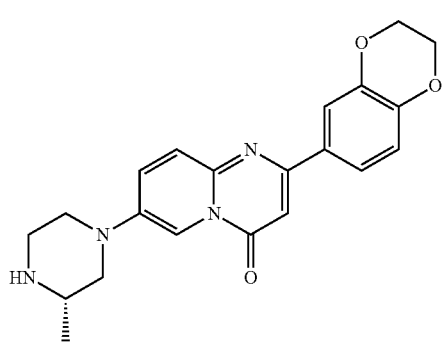
33
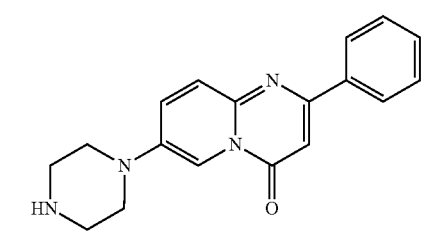
34
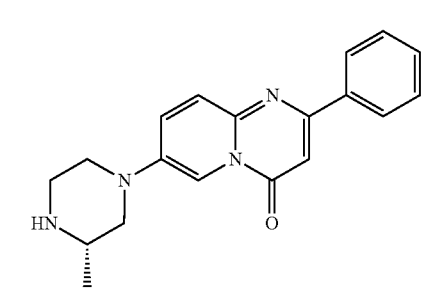
35
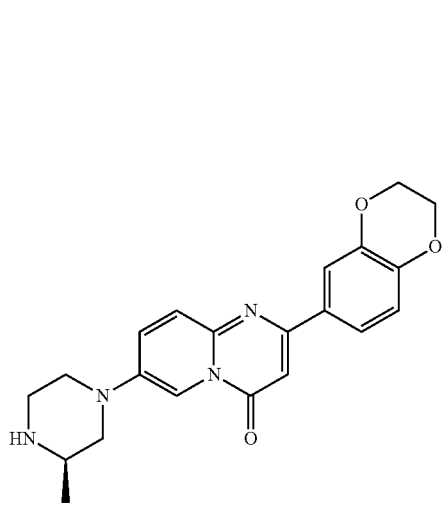

| 36 | 41 |
|---|---|
| 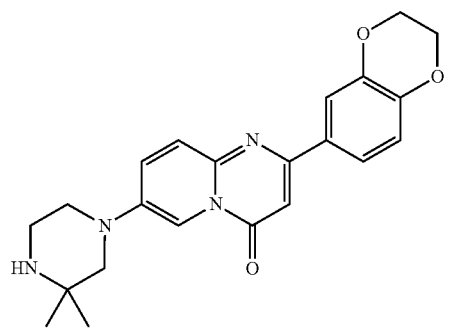 | 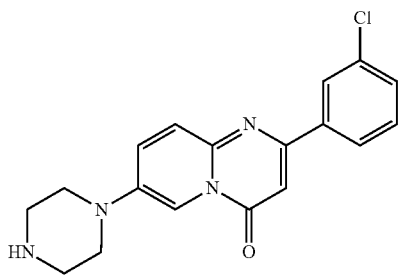 |
| 37 | 42 |
| 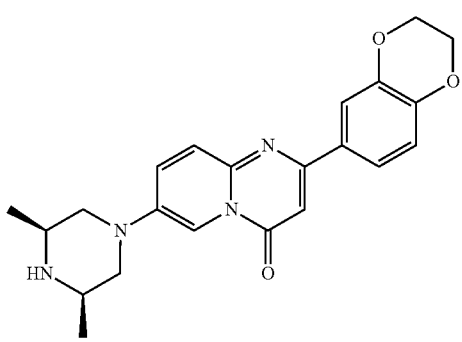 | 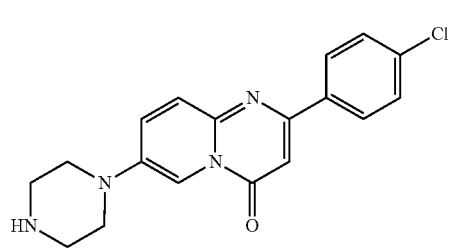 |
| 38 | 43 |
| 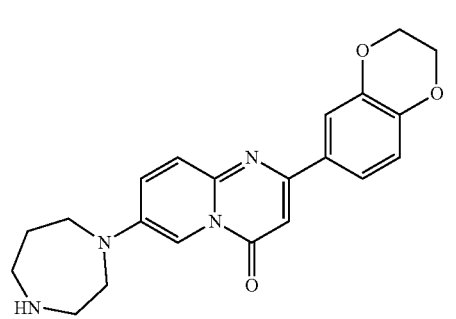 | 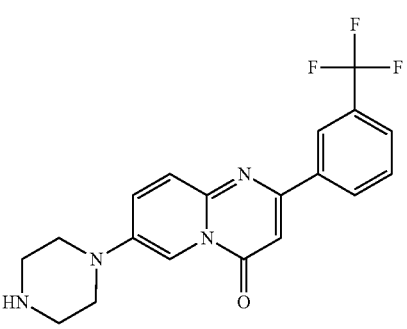 |
| 39 | 44 |
| 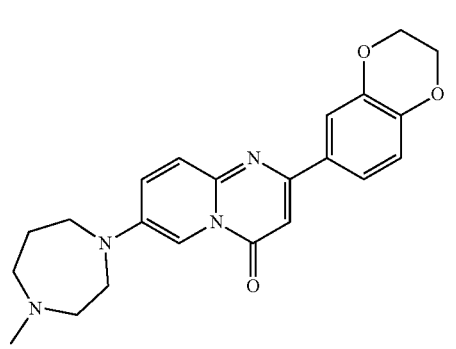 | 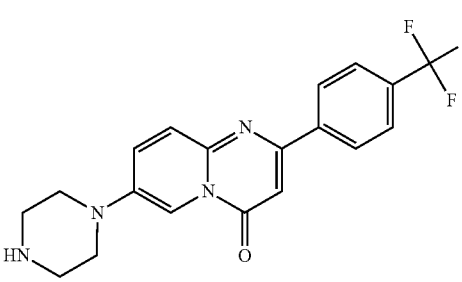 |
| 40 | 45 |
| 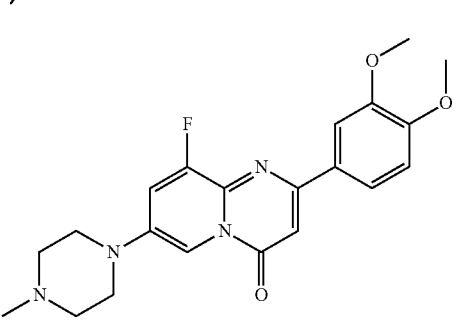 | 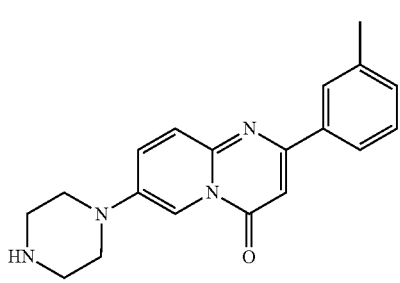 |
| | 46 |
| | 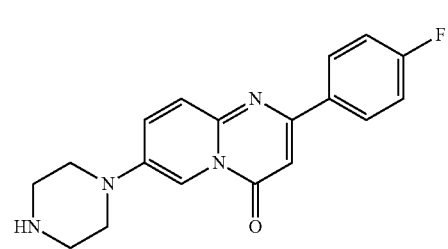 |

-continued
47
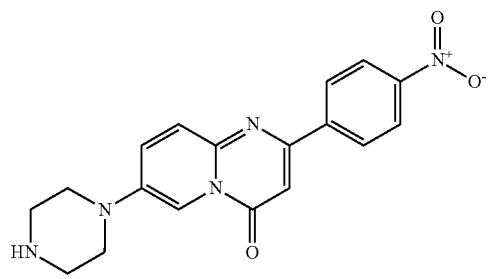
48
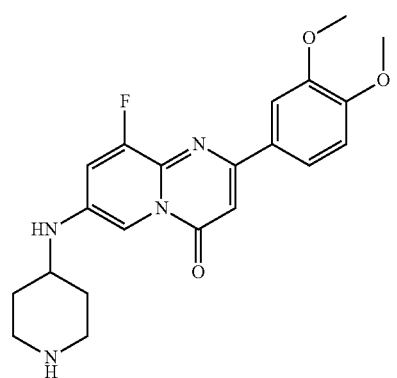
49
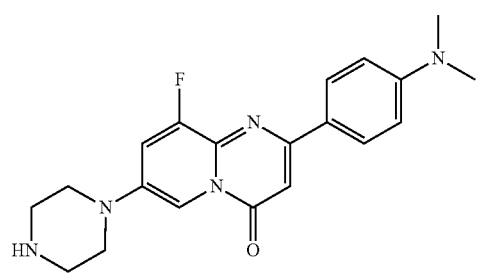
50
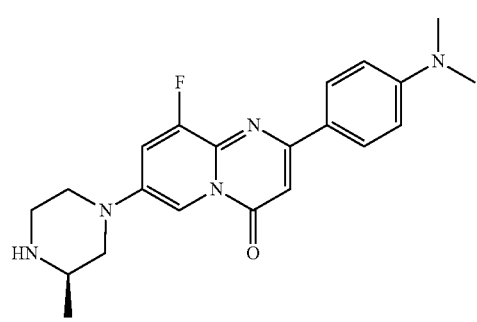
51
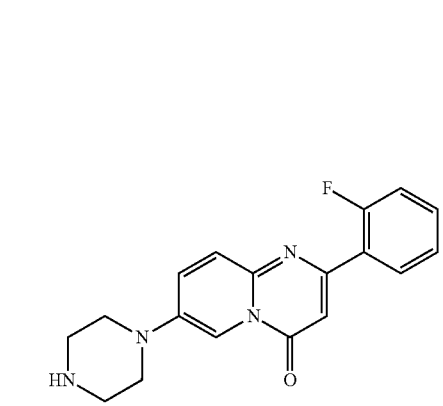
-continued
52
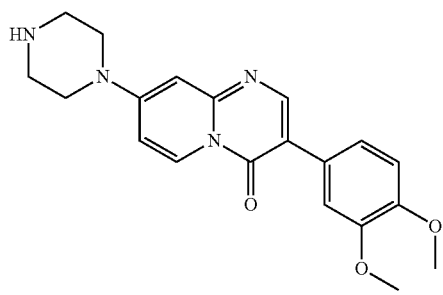
53
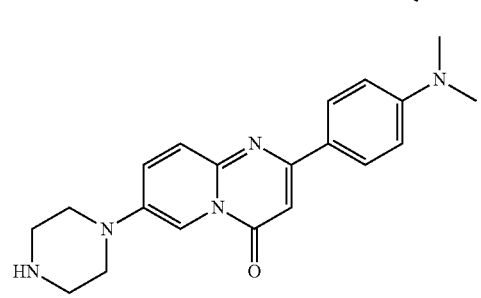
54
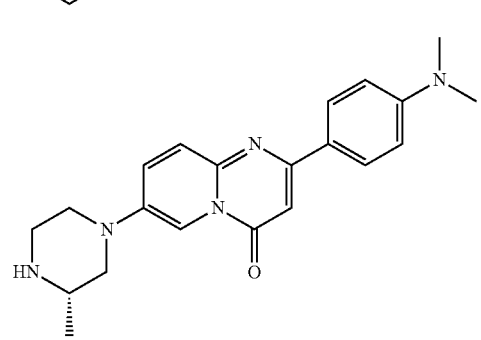
55
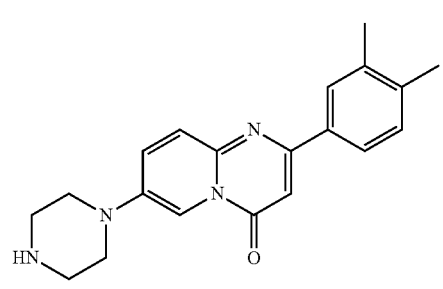
56
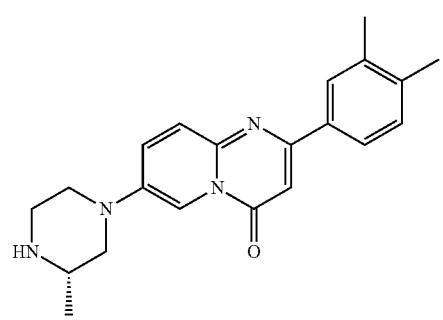

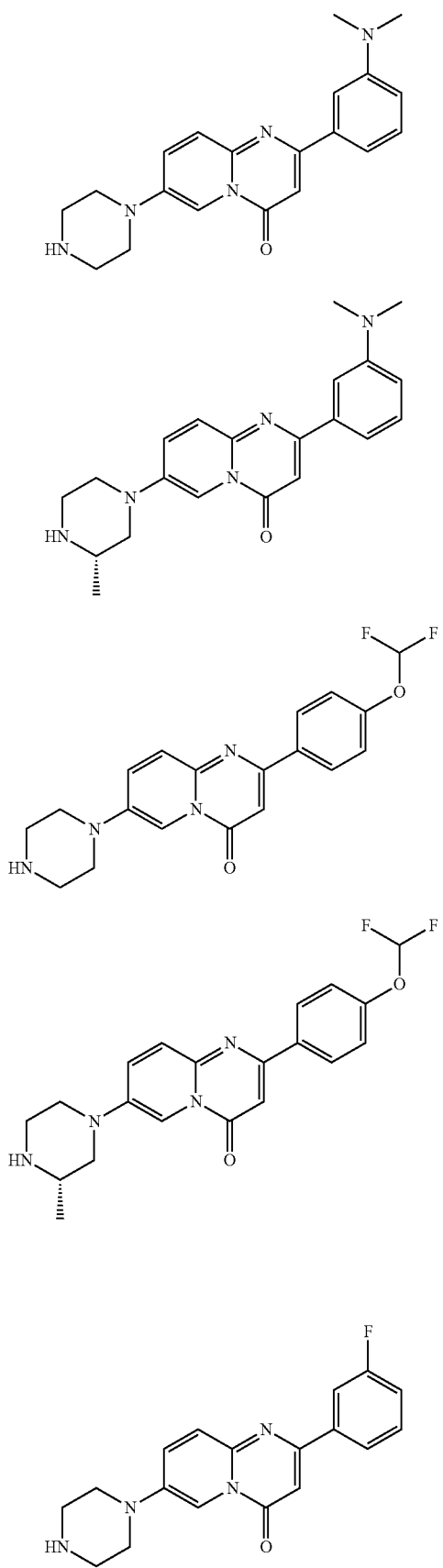
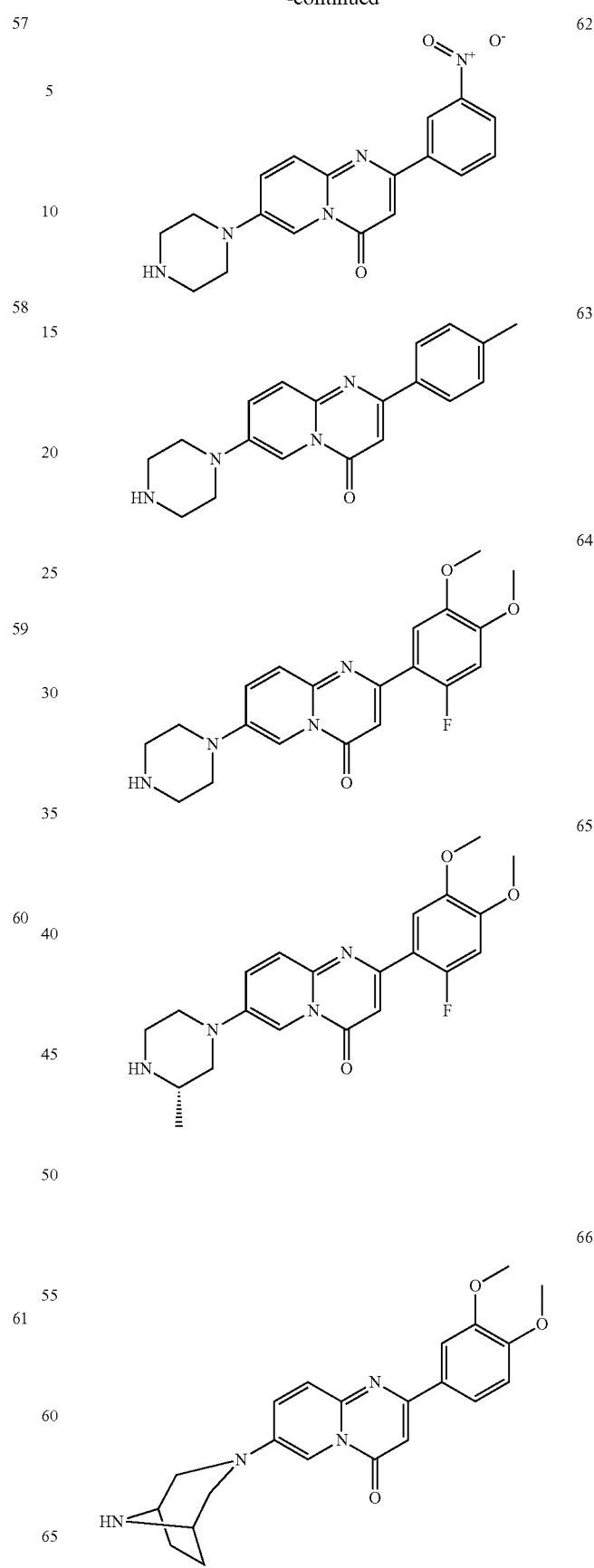

-continued
67
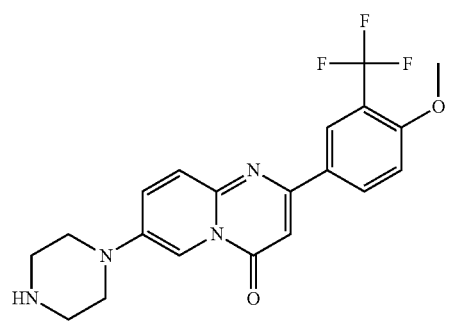
68
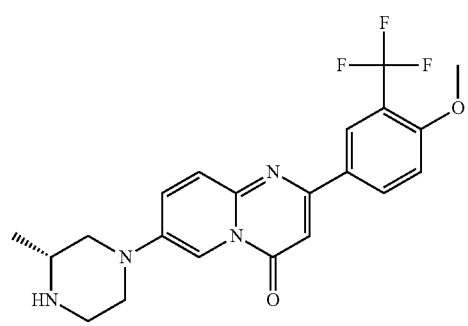
69
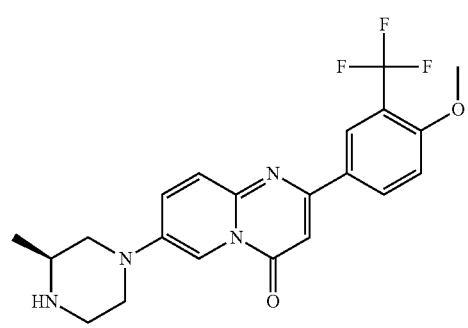
70
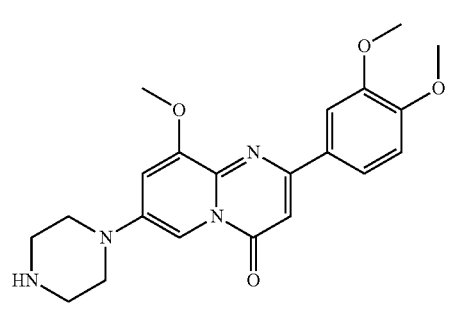
71
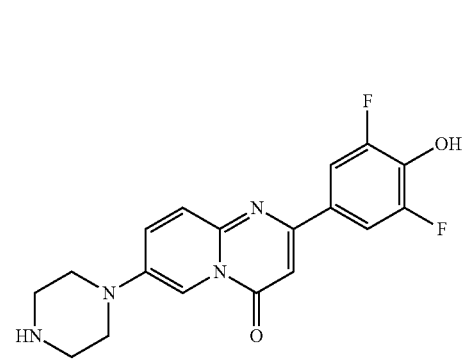
-continued
72
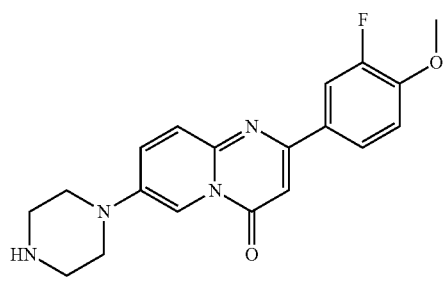
73
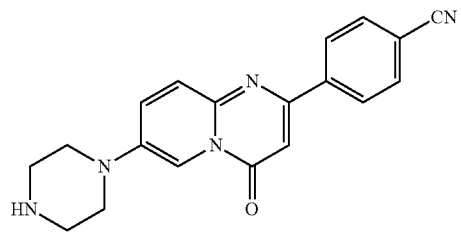
74
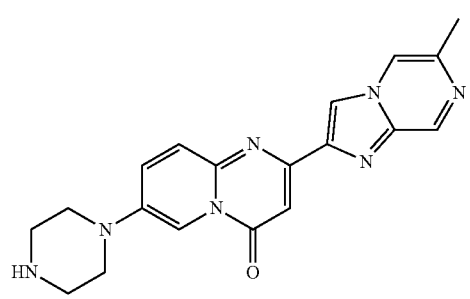
75
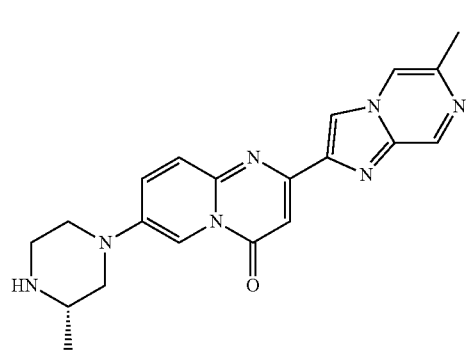
76
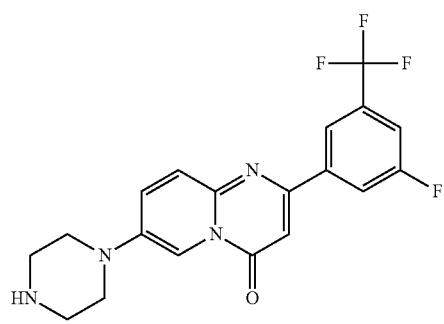

77
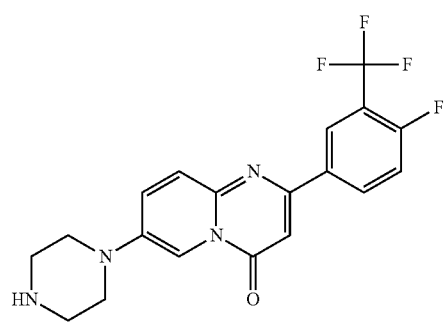
78
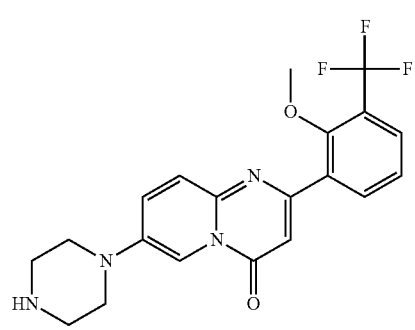
79
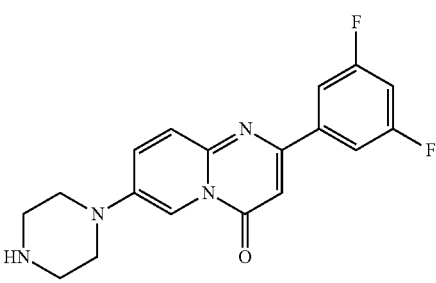
80
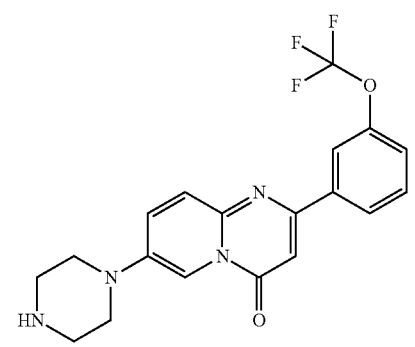
81
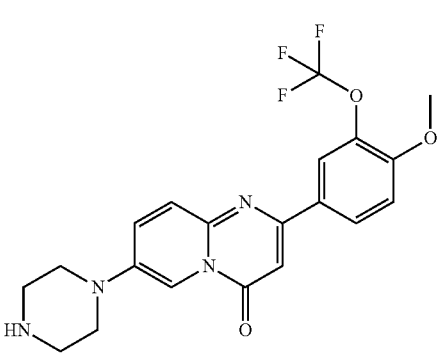
82
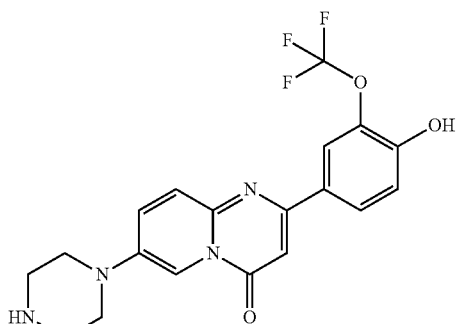
83
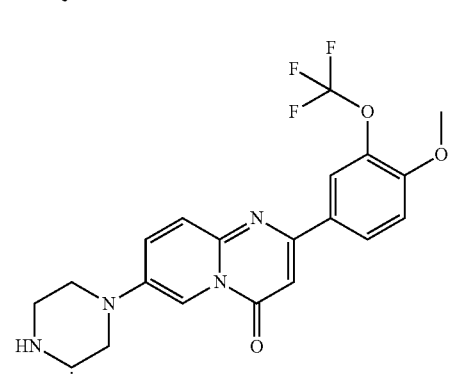
84
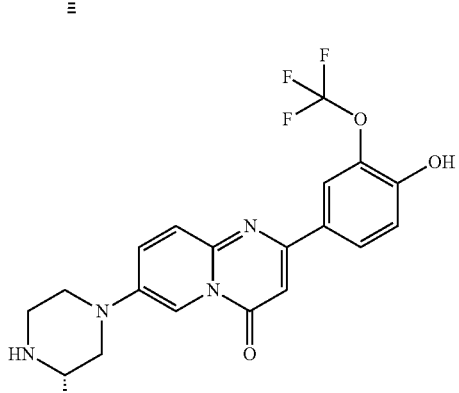
85
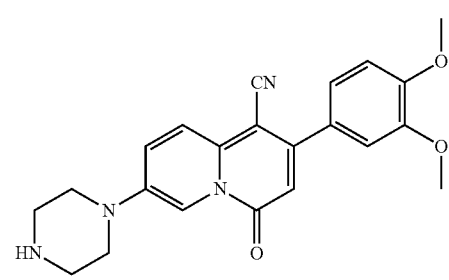

86
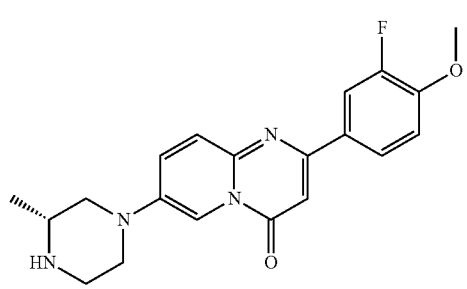
87
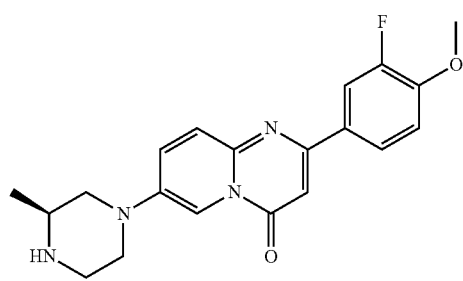
88
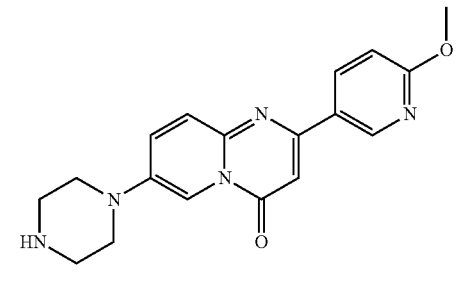
89
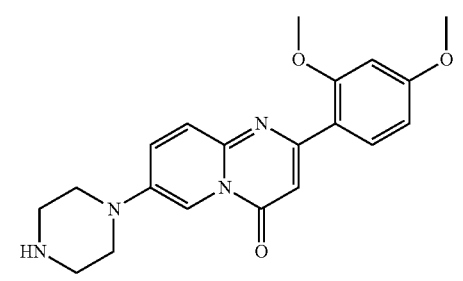
90
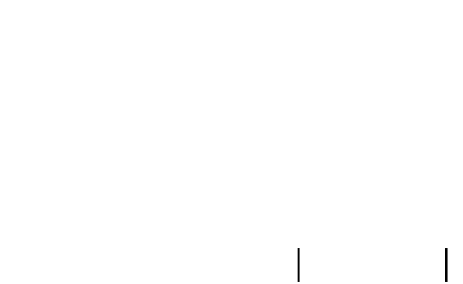
91
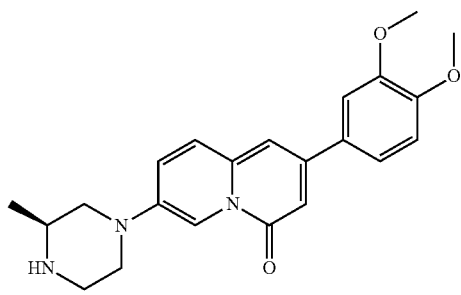
92
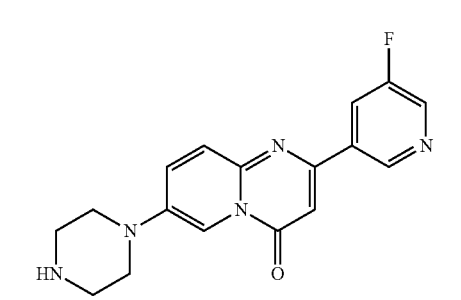
93
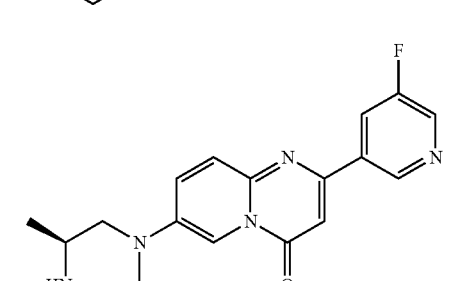
94
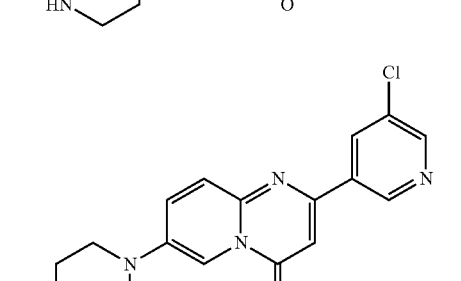
95
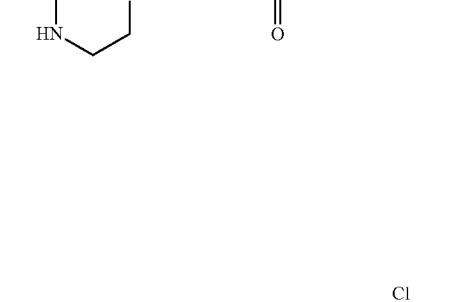

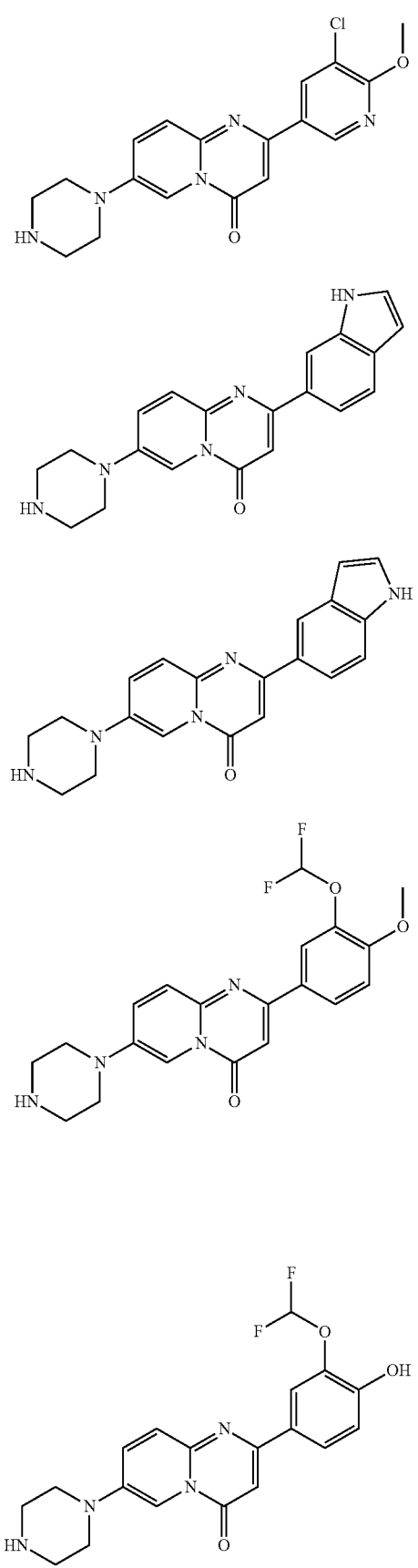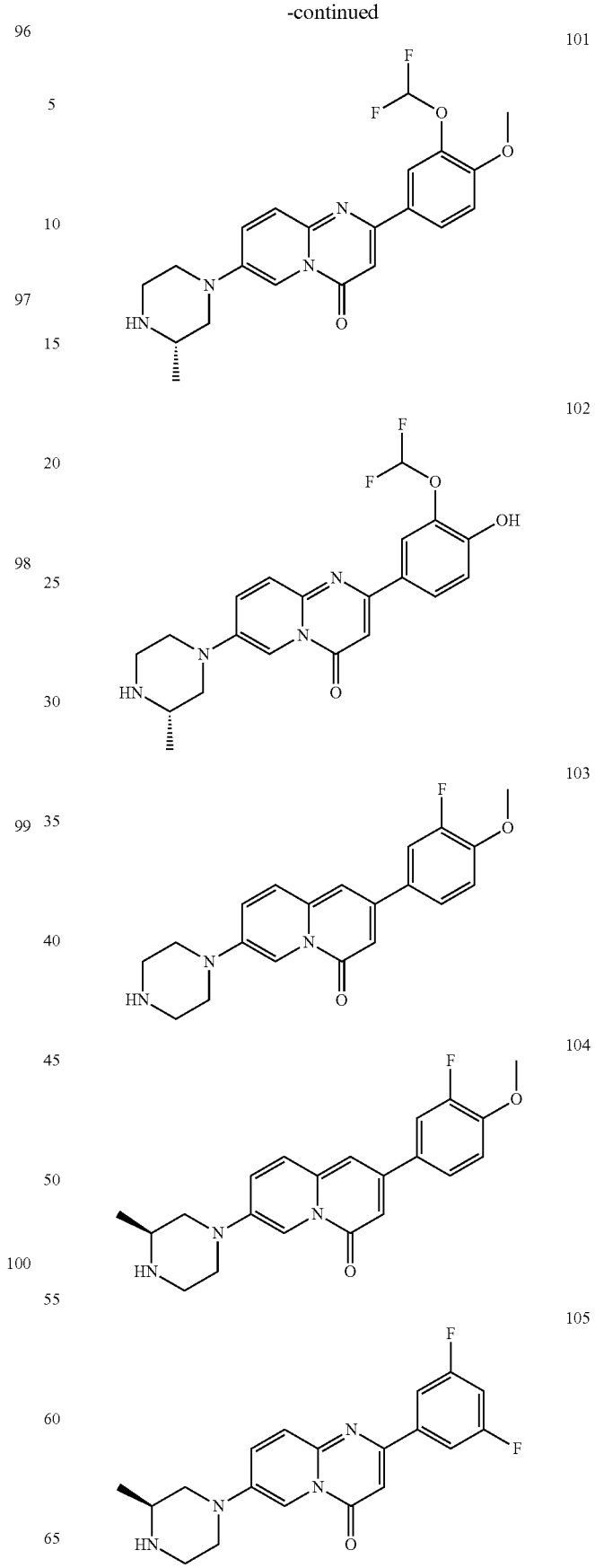

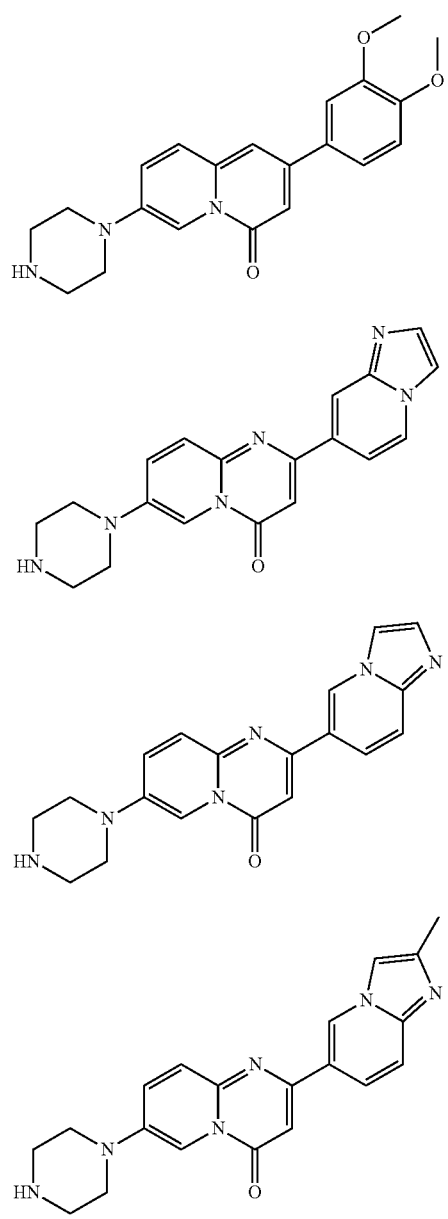
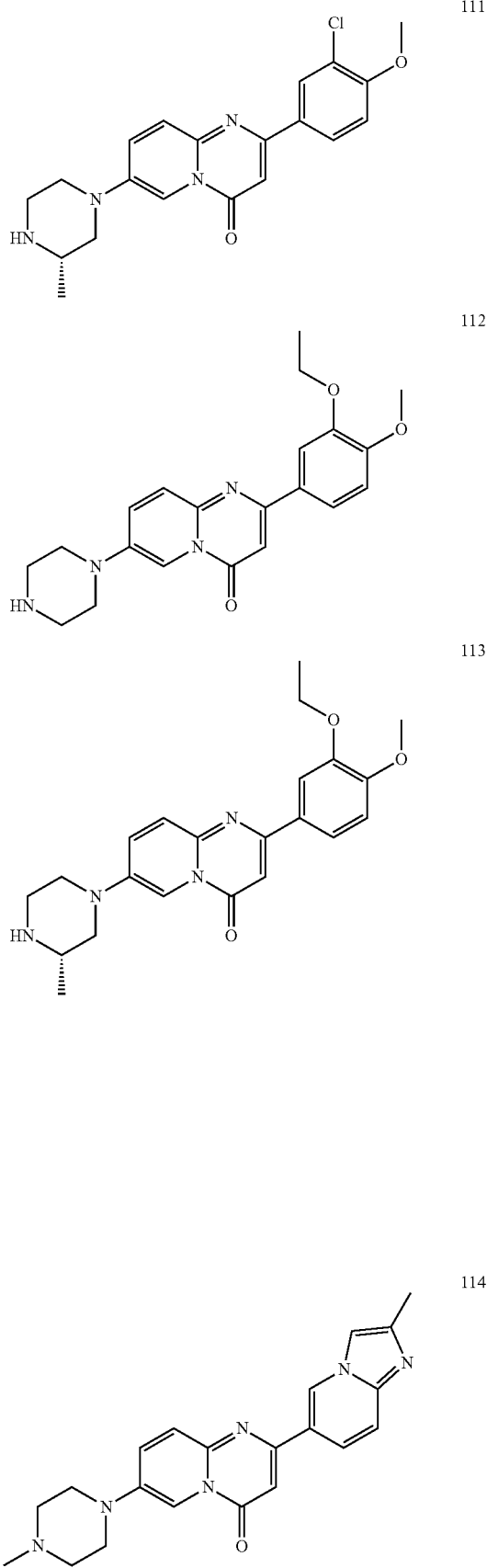

115 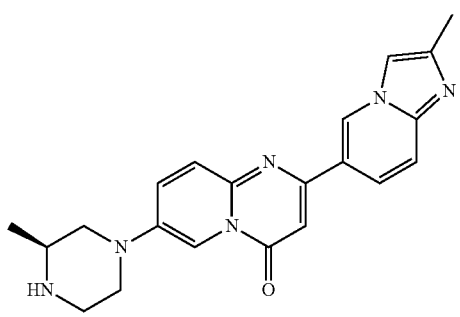
116 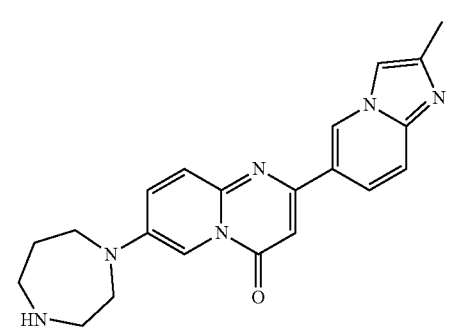
117 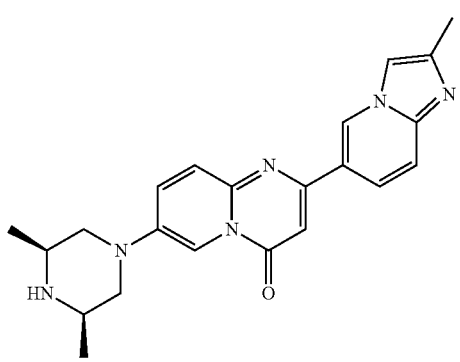
118 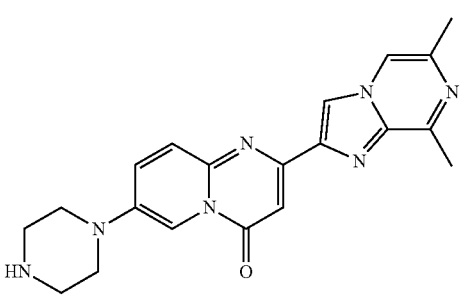
119 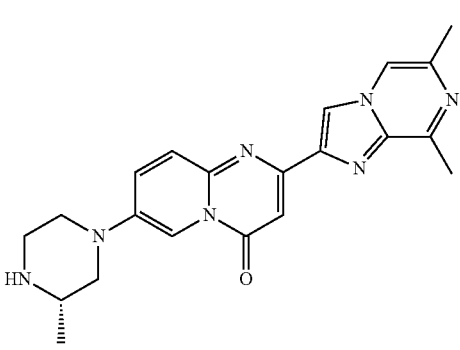
120 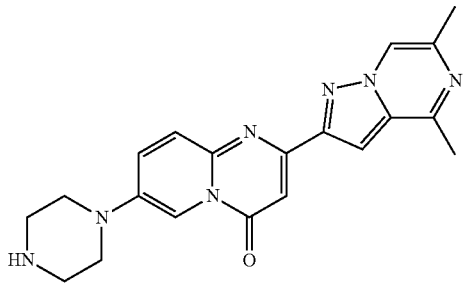
121 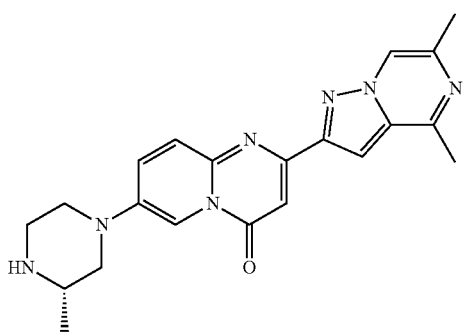
122 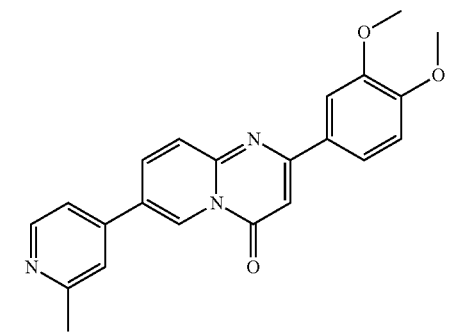
123 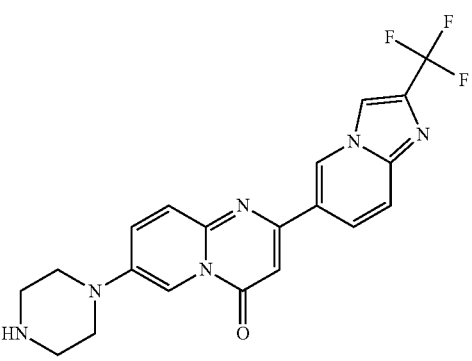

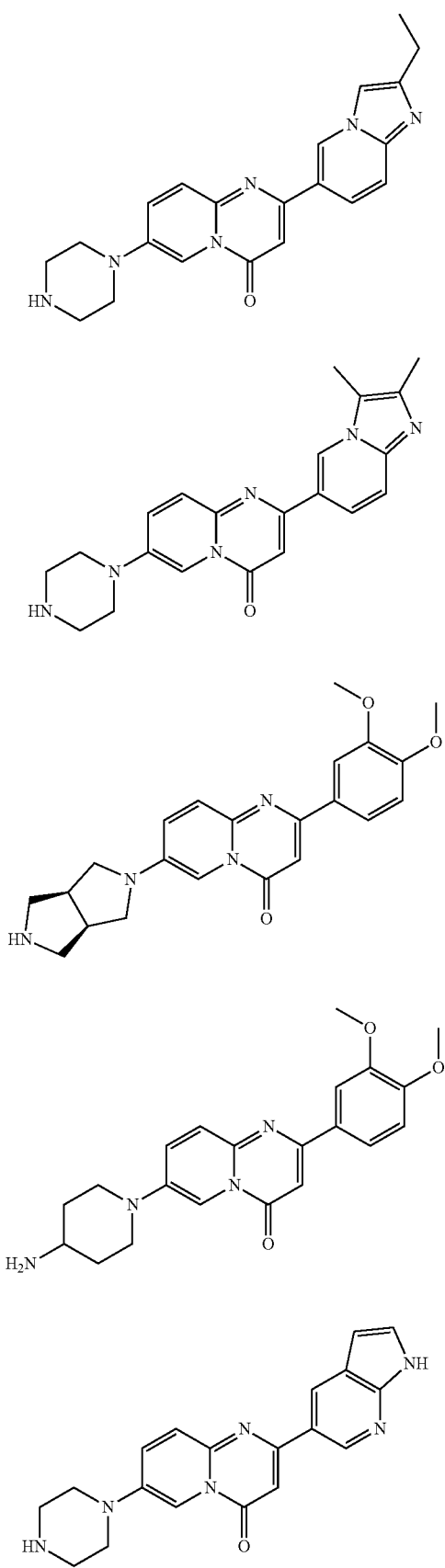

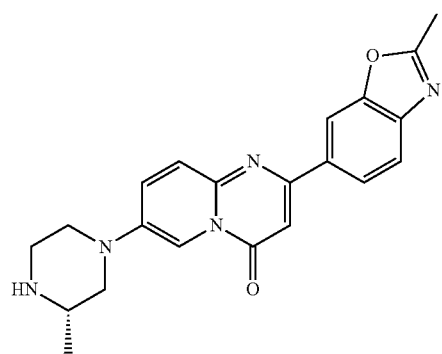
134
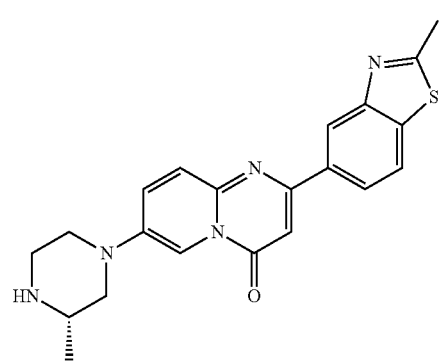
135
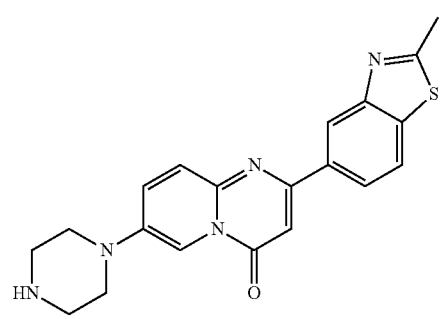
136
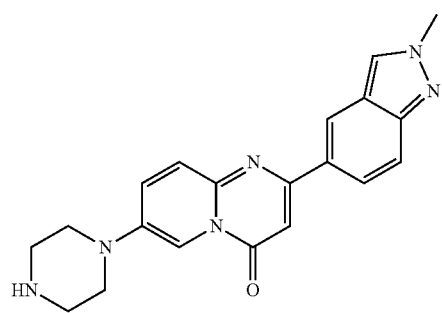
137
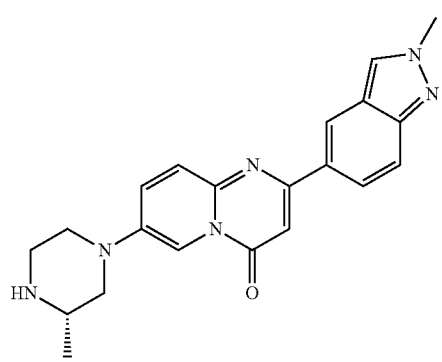
138
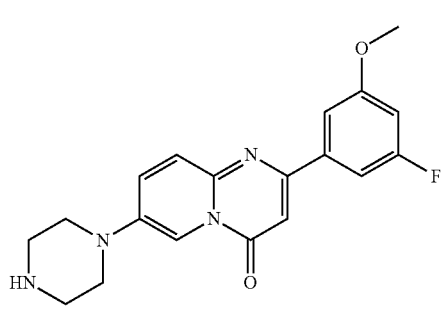
139
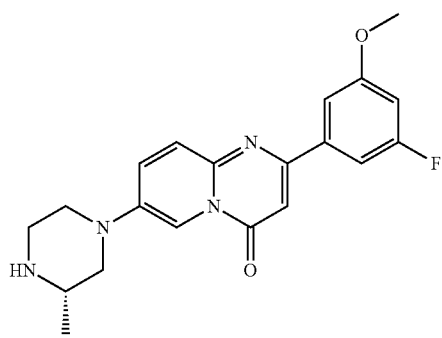
140
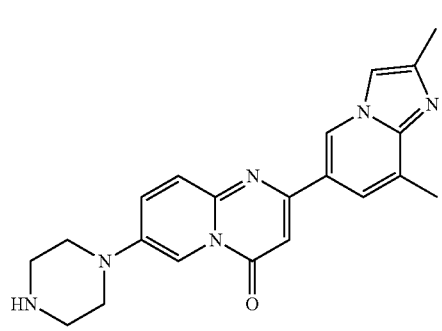
141
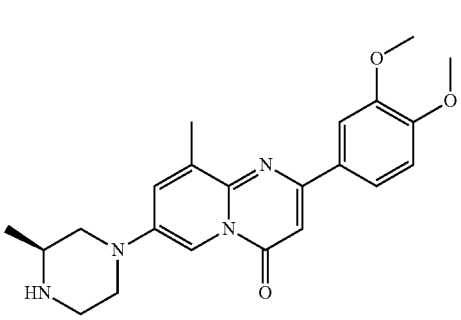
142

143
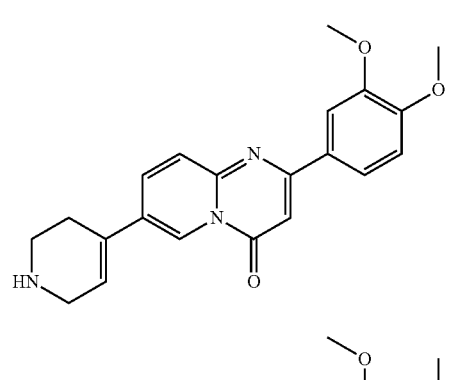
144
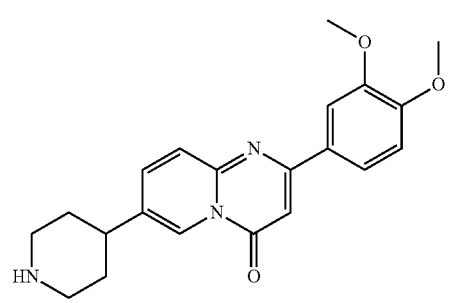
145
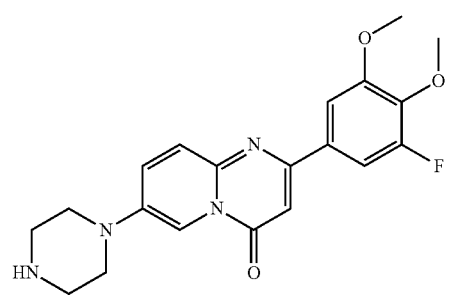
146
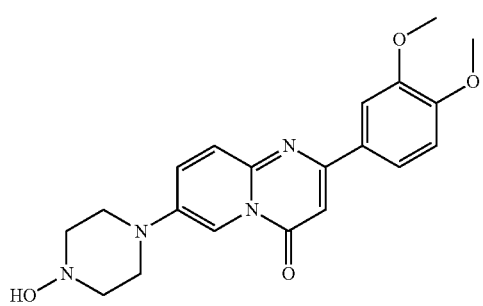
147
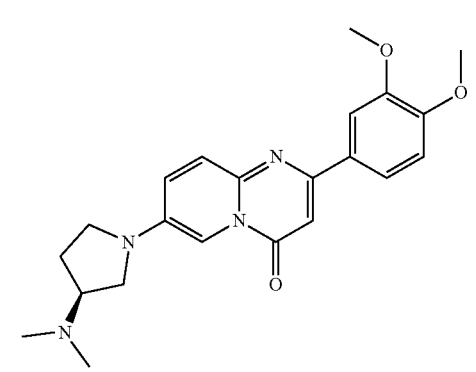
148
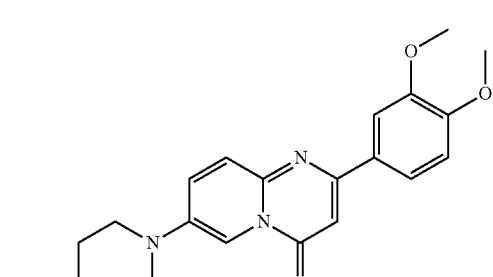
149
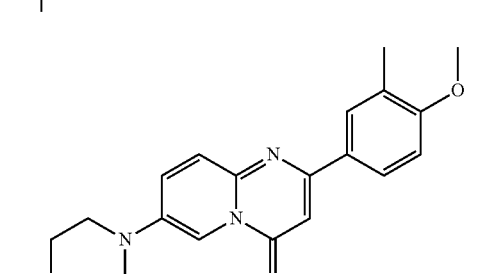
150
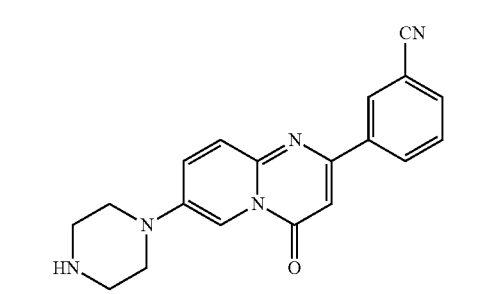
151
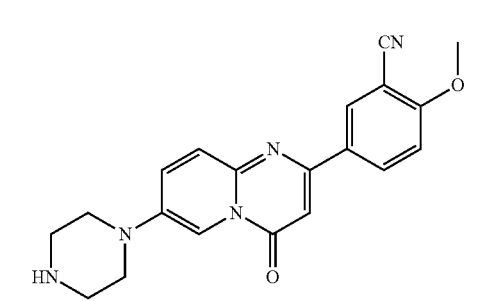
152
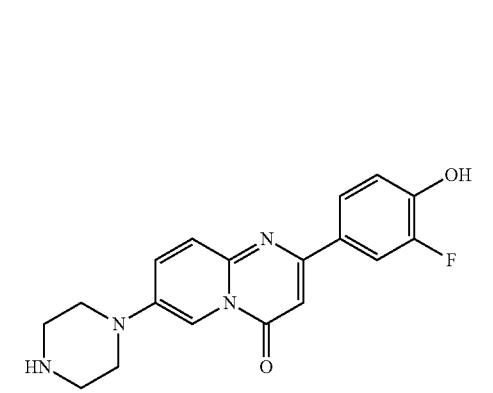

153 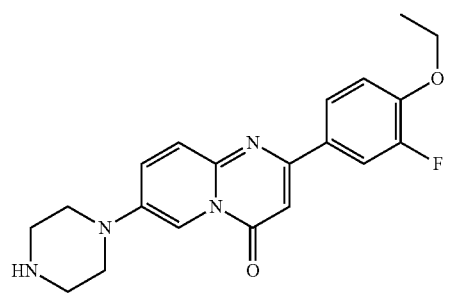
154 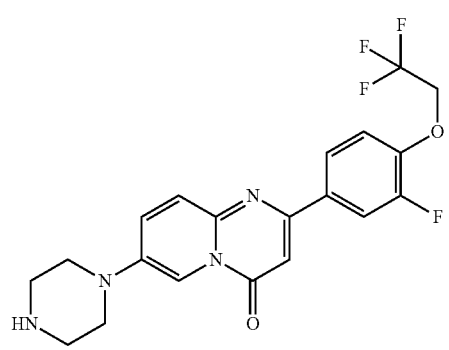
155 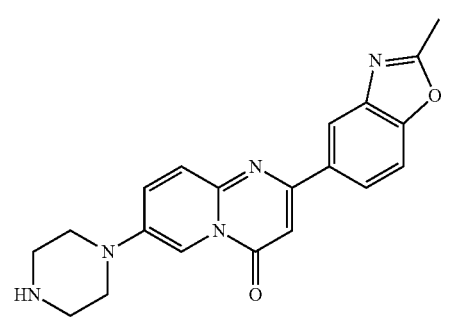
156 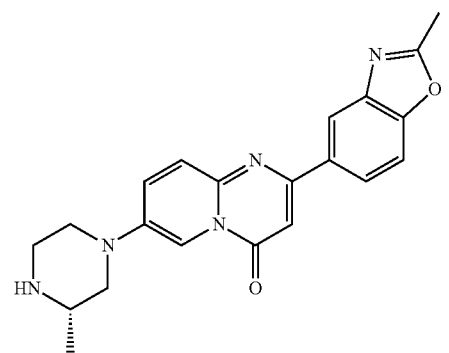
157 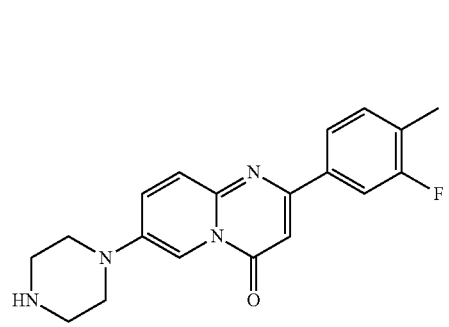
158 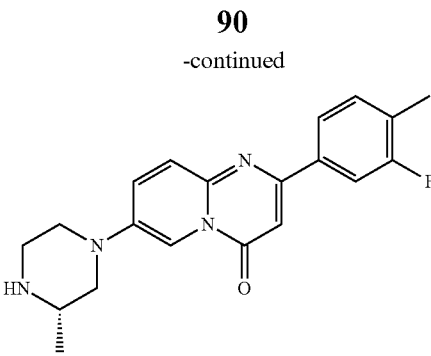
159 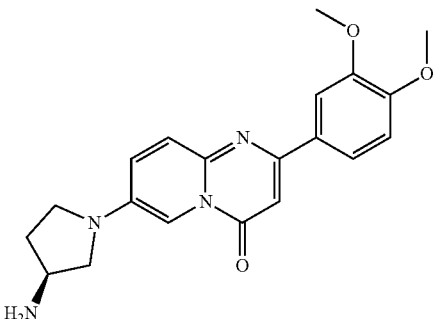
160 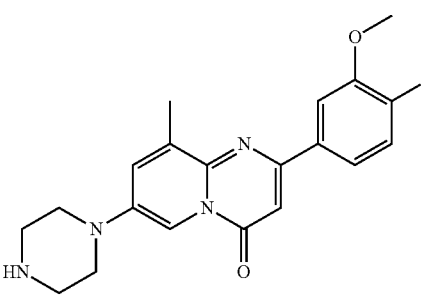
161 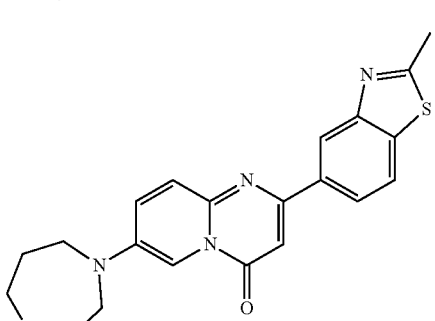
162 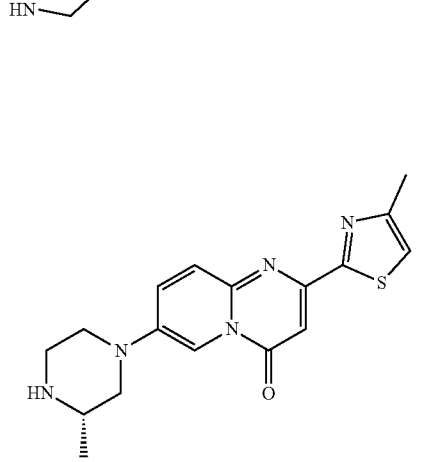

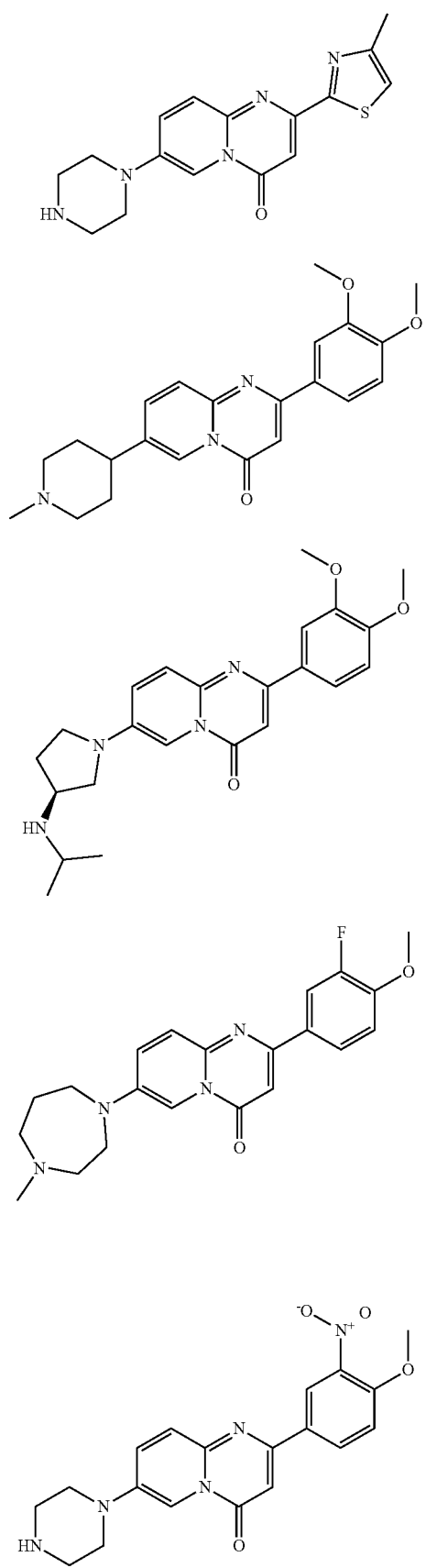
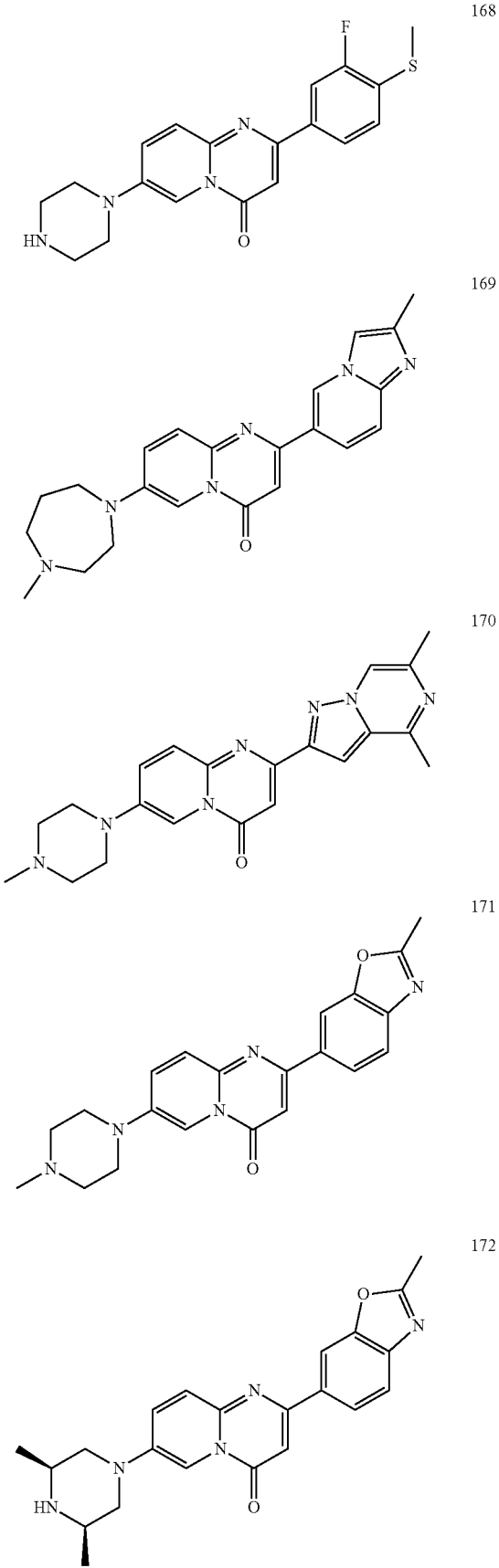

173 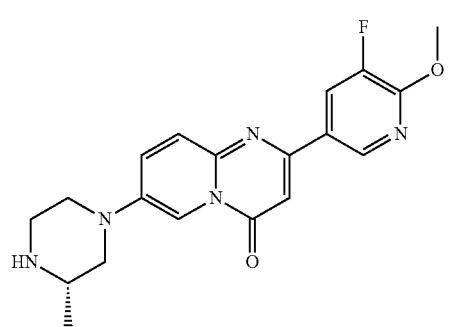
174 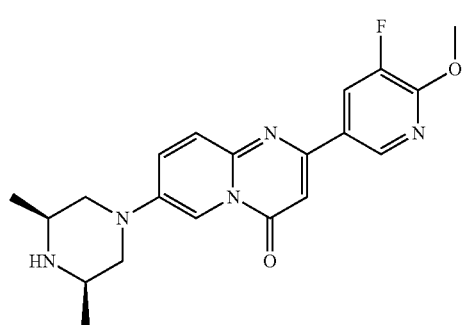
175 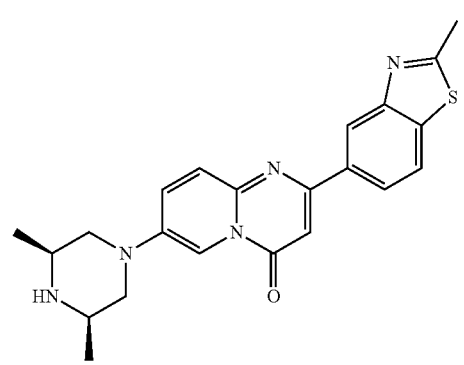
176 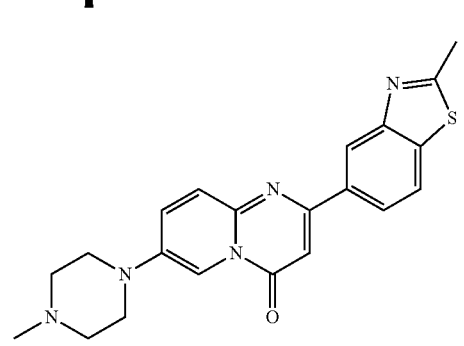
177 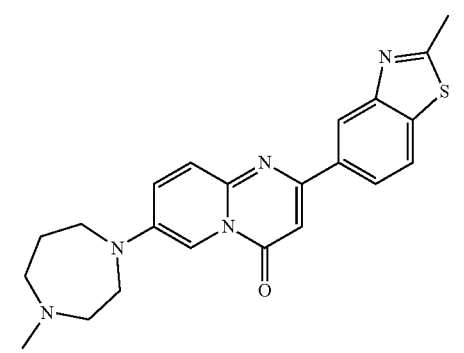
178 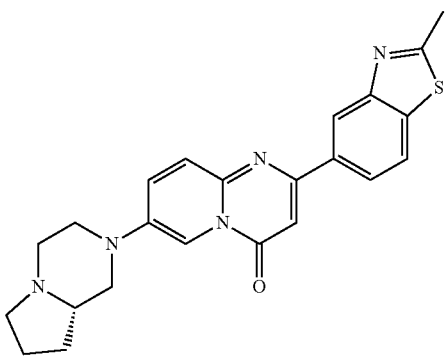
179 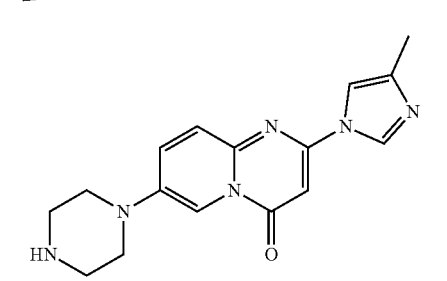
180 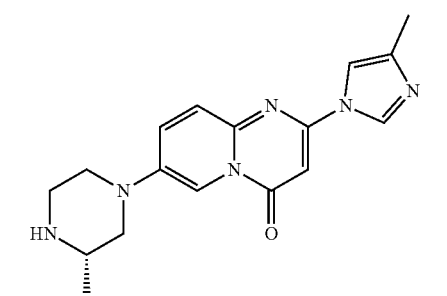
181 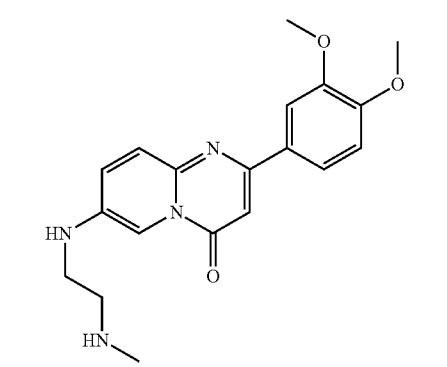
182 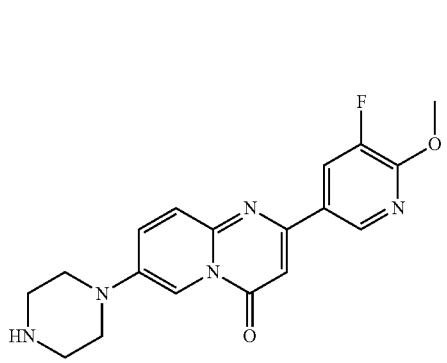

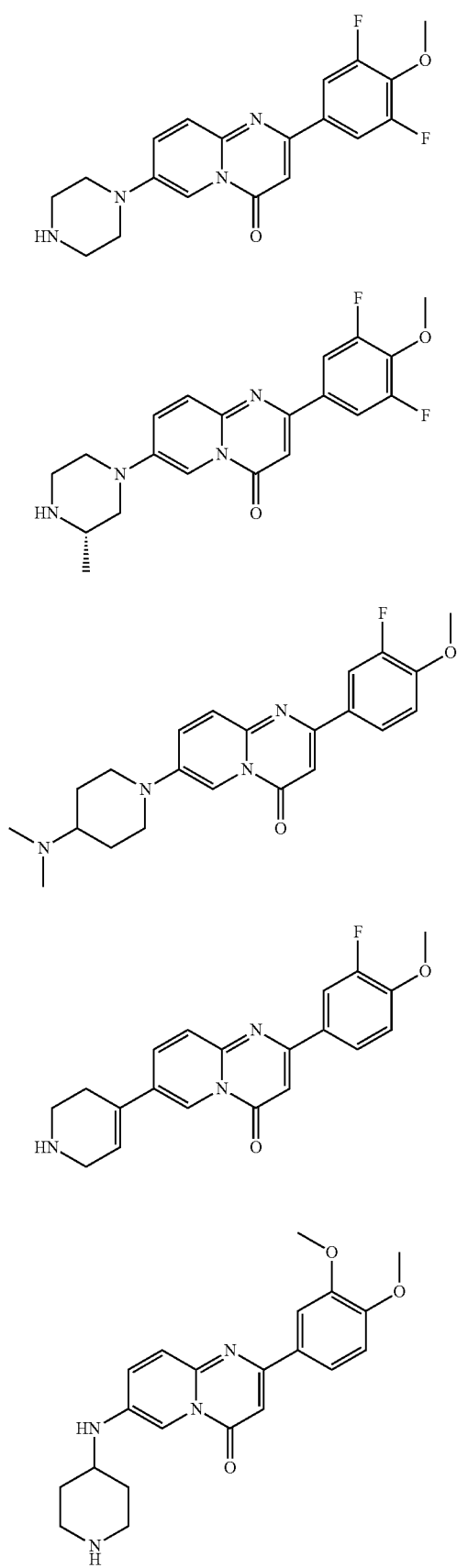
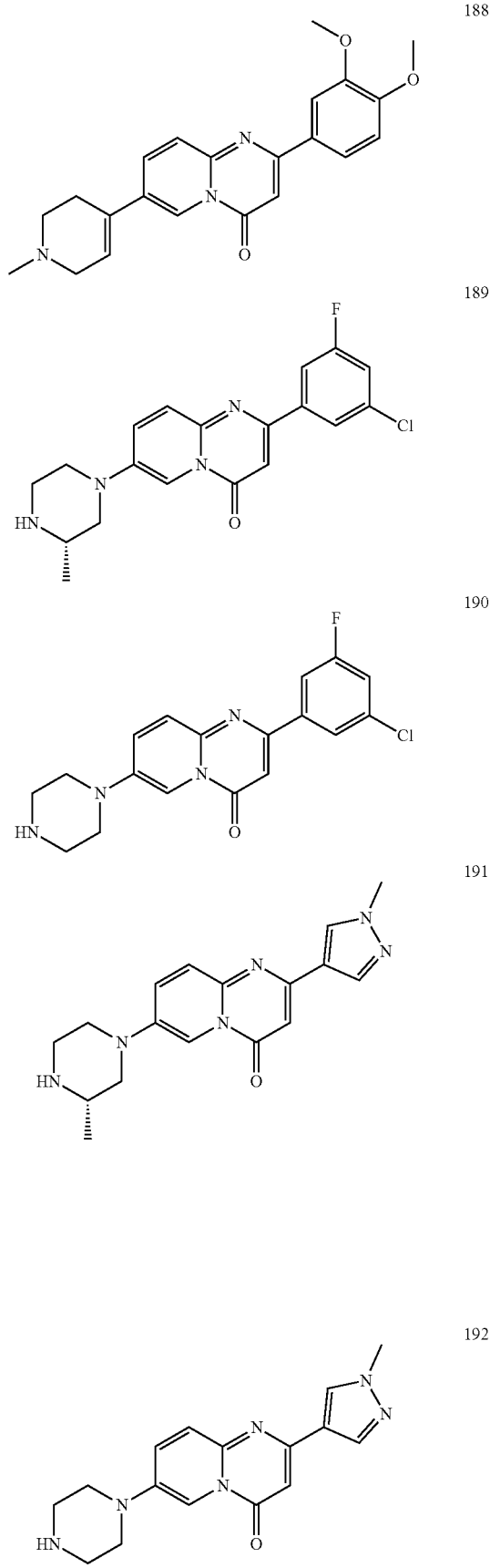

193
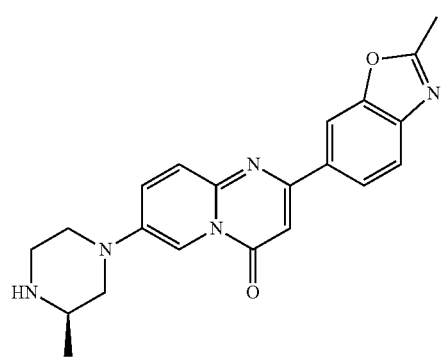
194
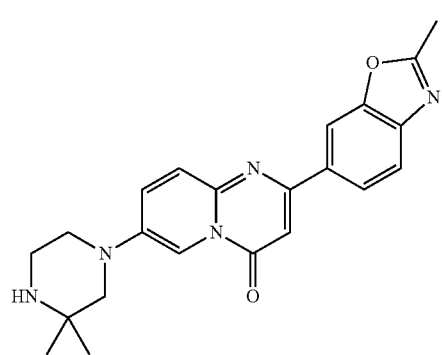
195
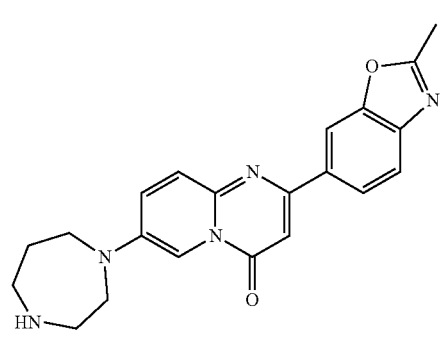
196
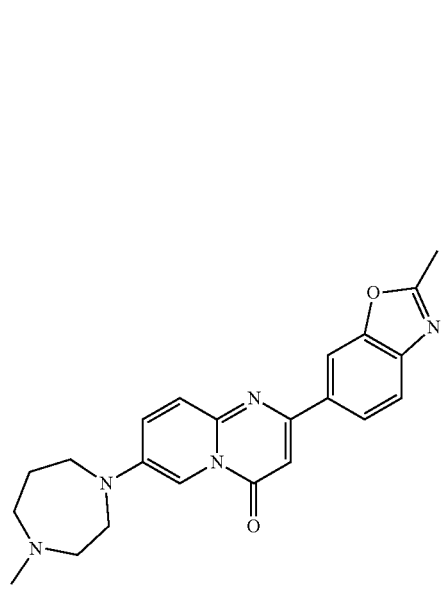
197
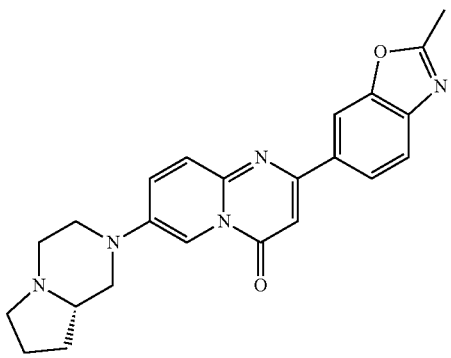
198
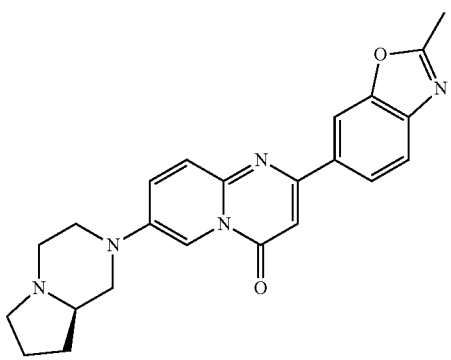
199
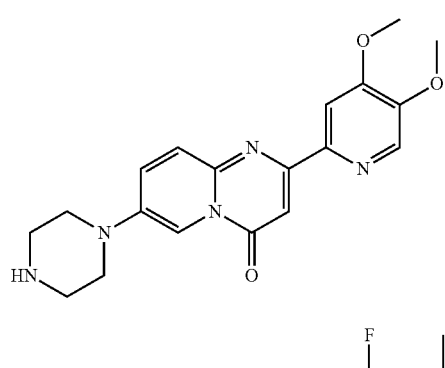
200
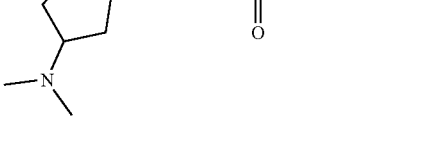
201
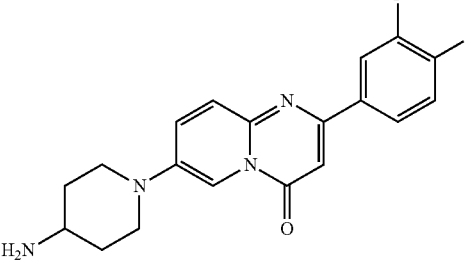

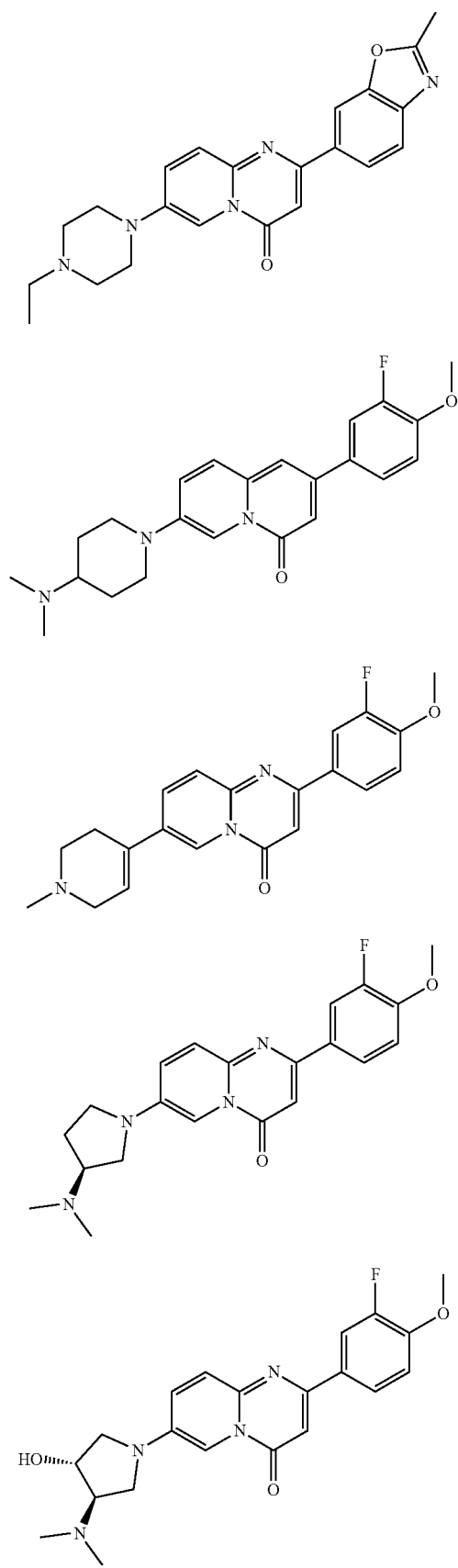

212
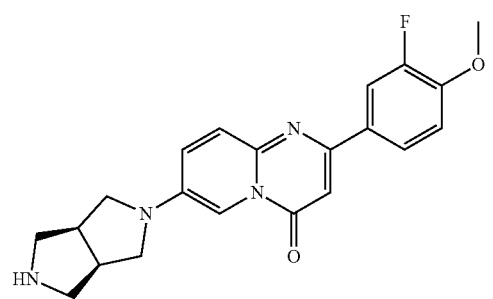
213
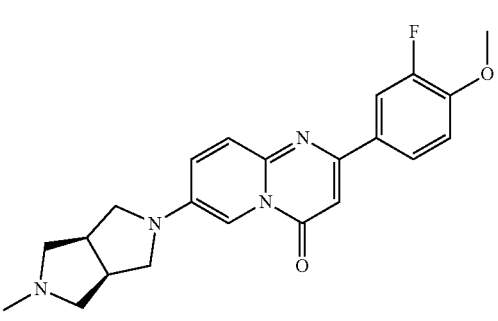
214
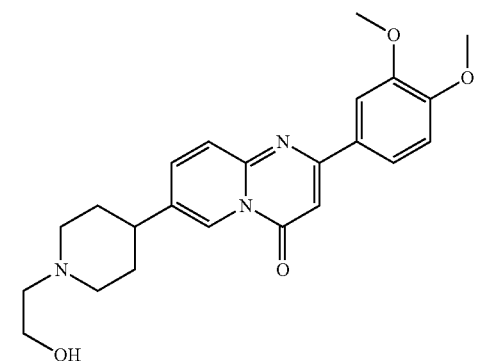
215
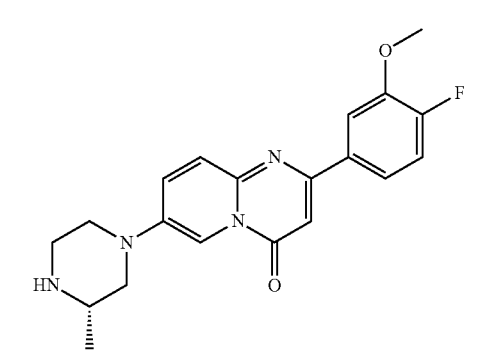
216
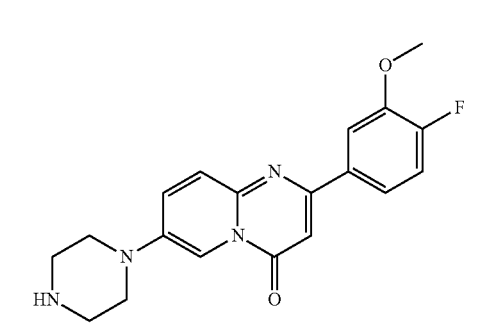
217
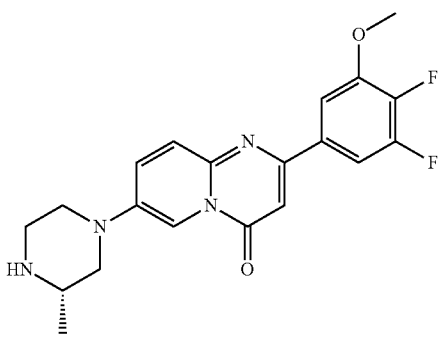
218
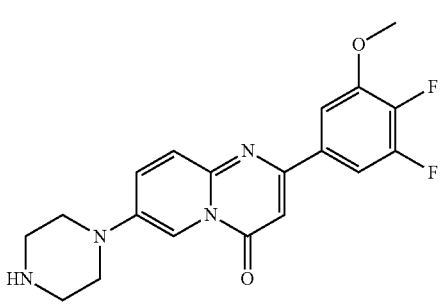
219
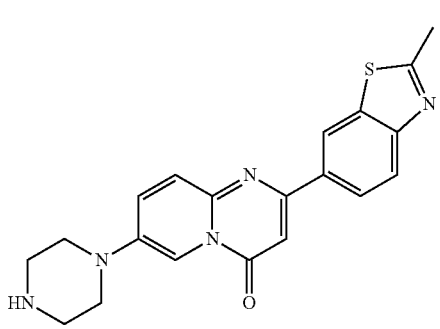
220
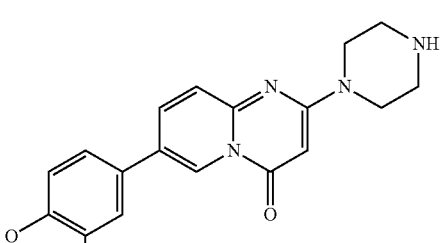
221
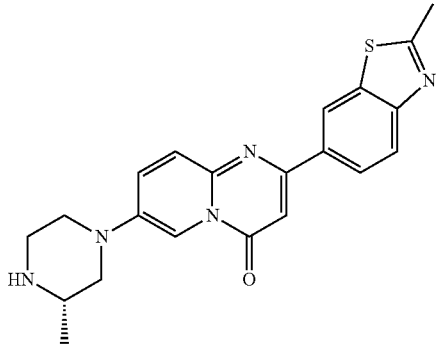

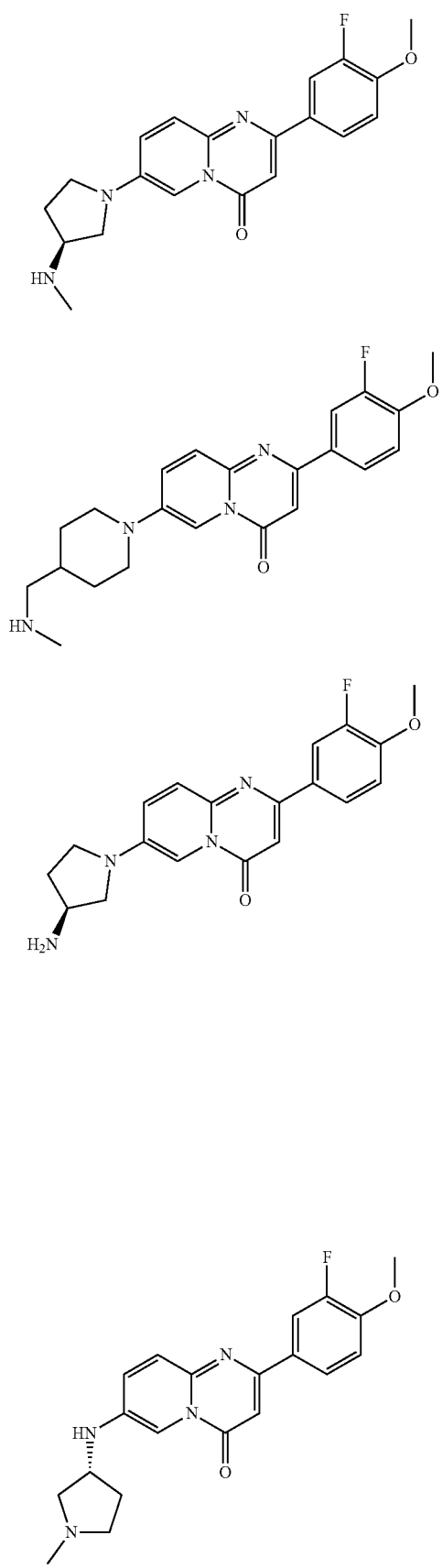
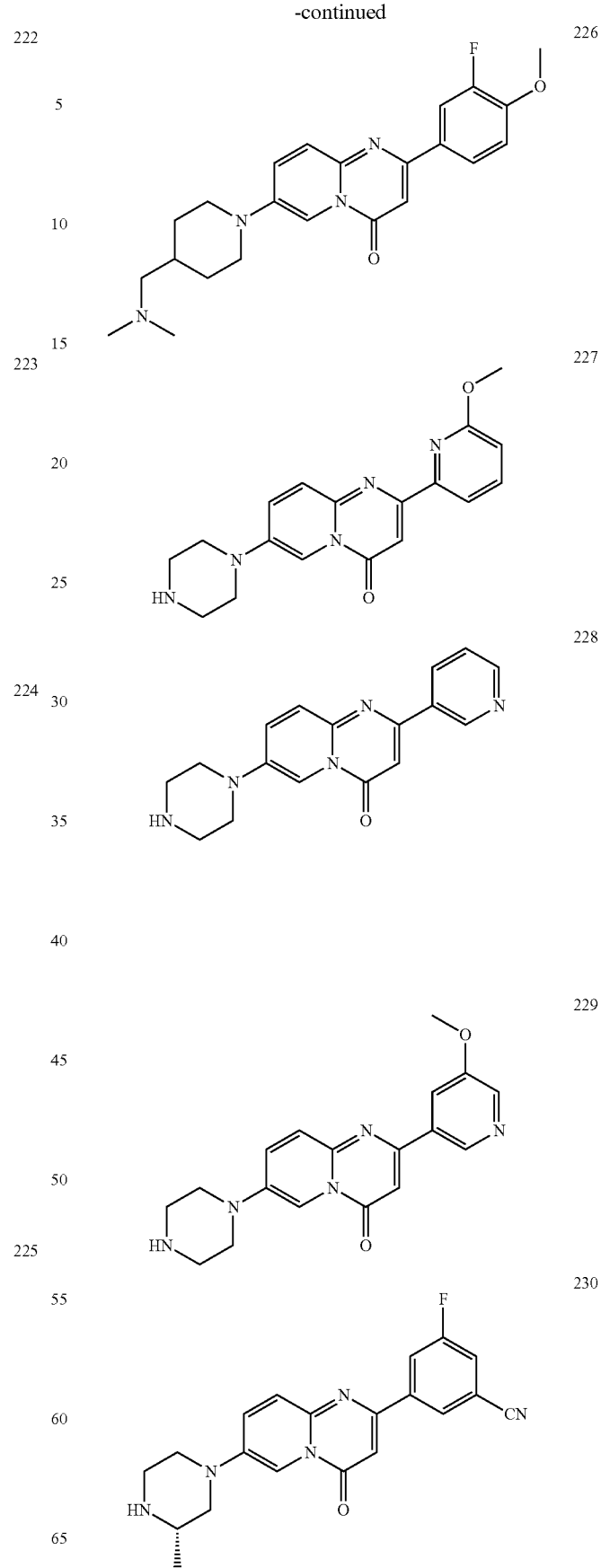

231
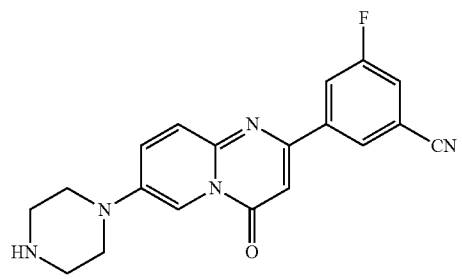
232
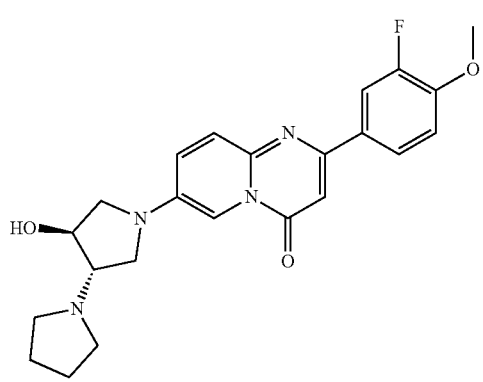
233
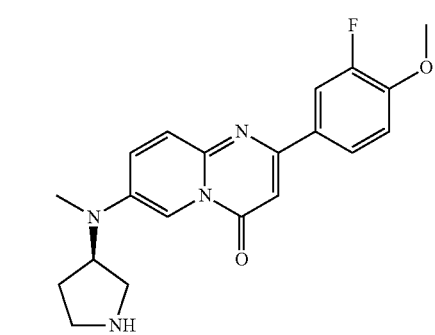
234
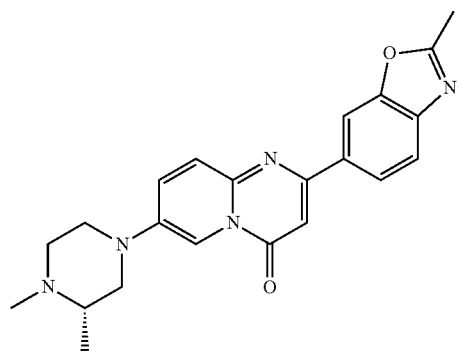
235
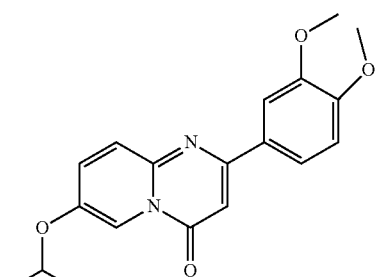
236
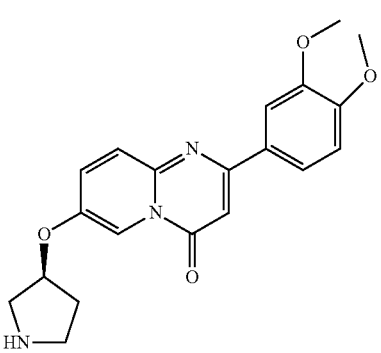
237
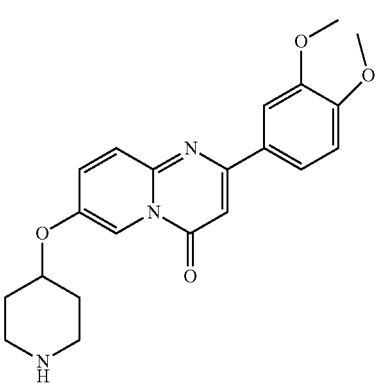
238
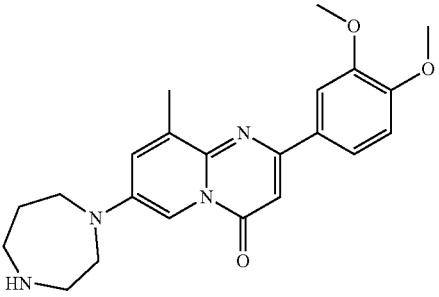

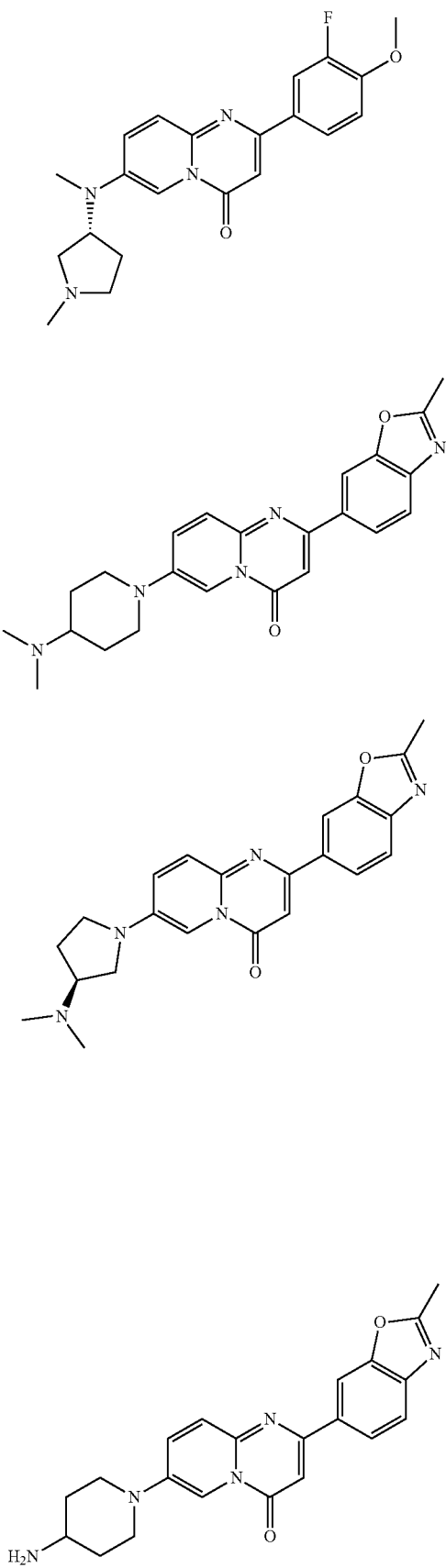
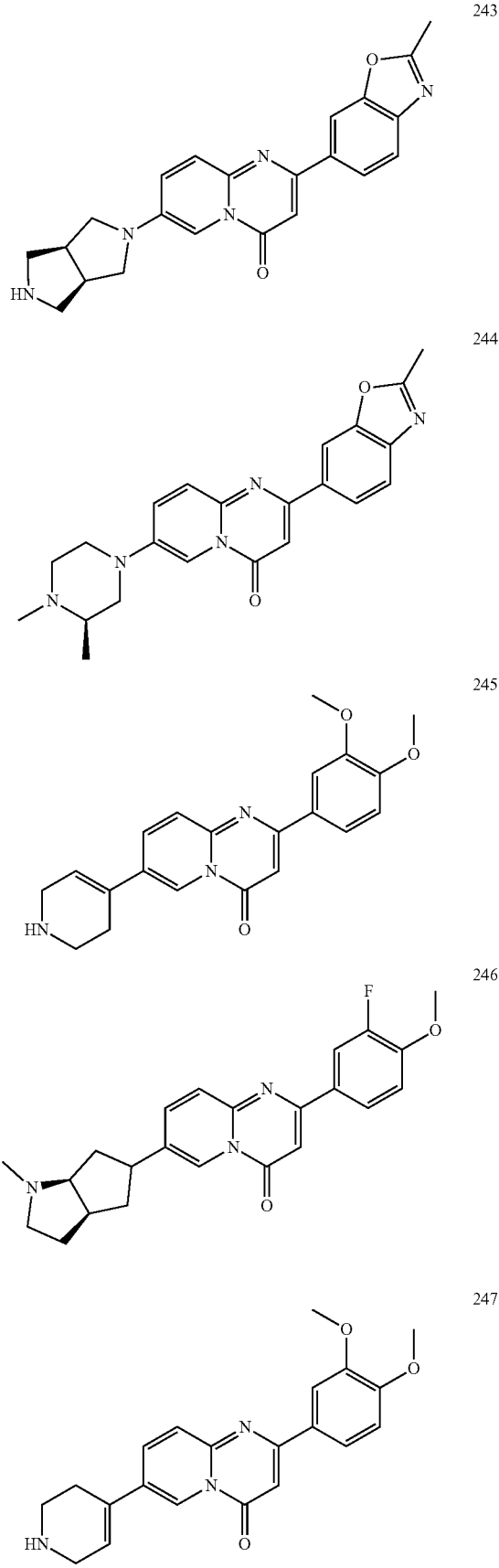

248 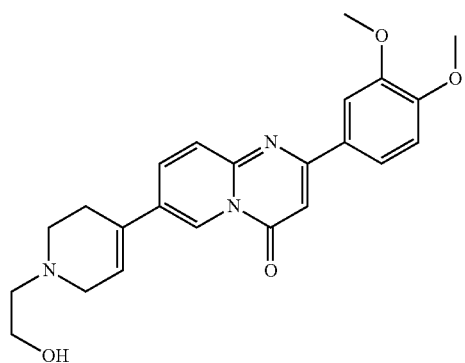
249 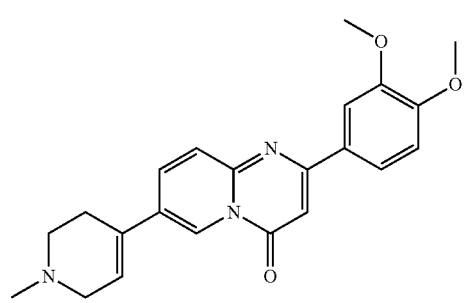
250 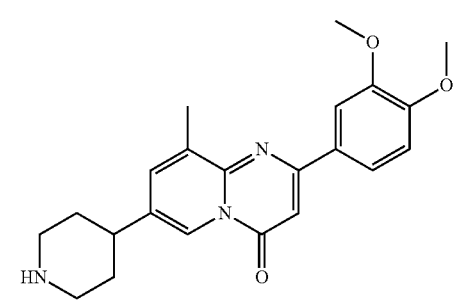
251 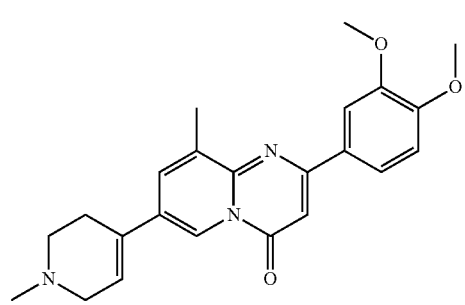
252 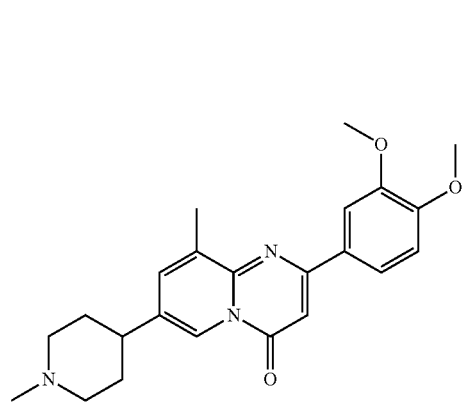
253 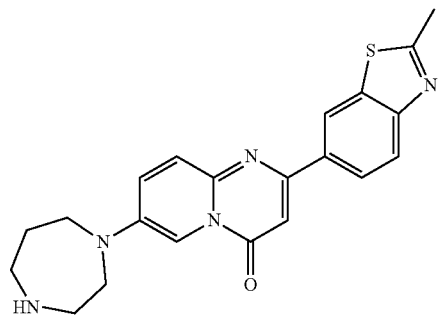
254 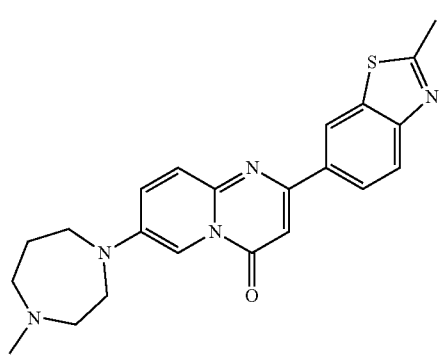
255 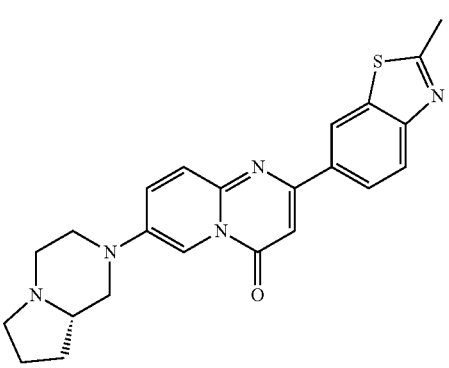
256 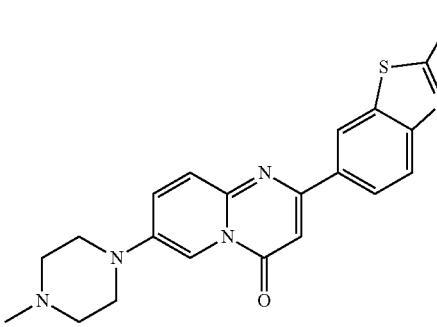
257 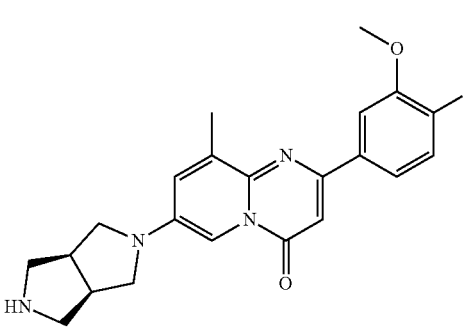

258
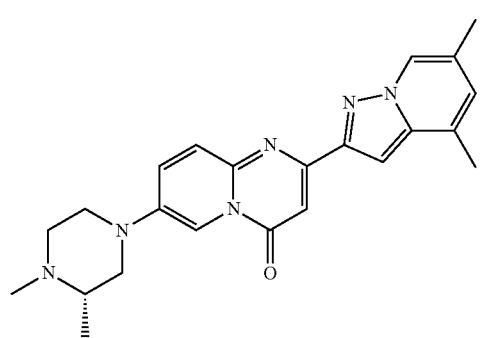
259
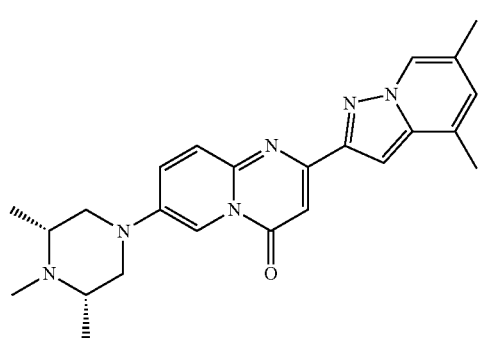
260
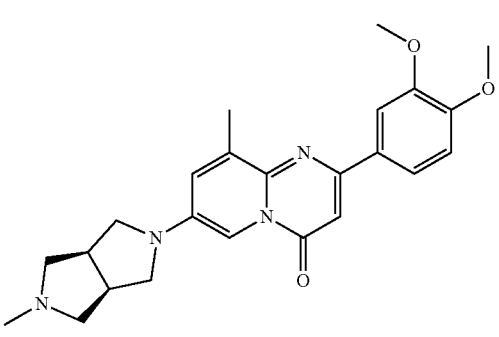
261
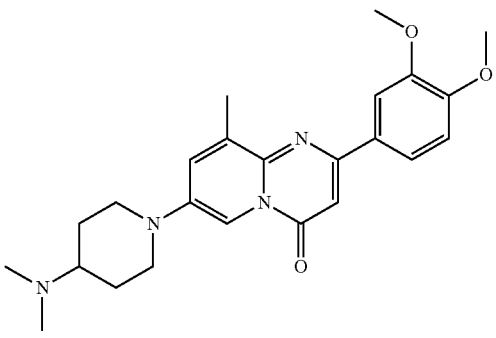
262
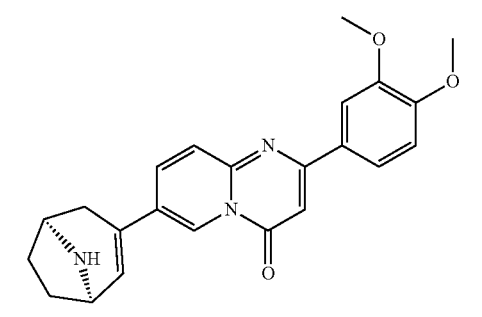
263
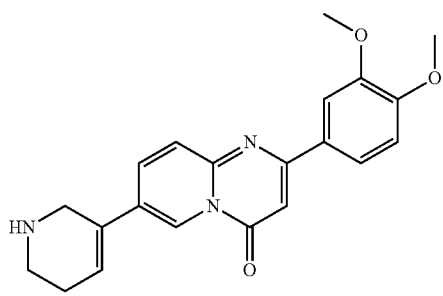
264
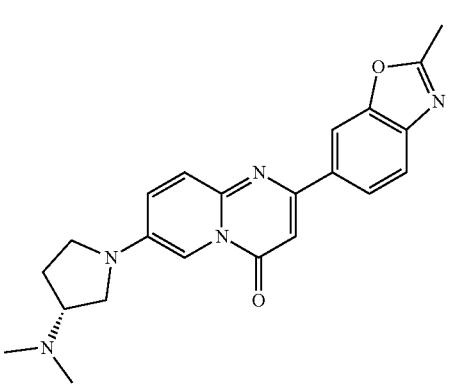
265
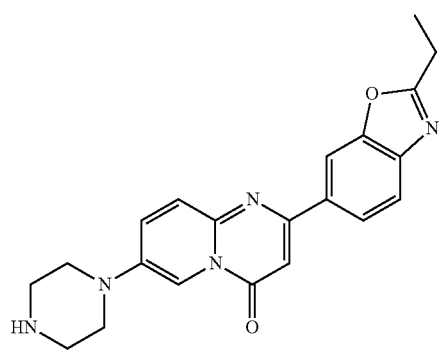
266
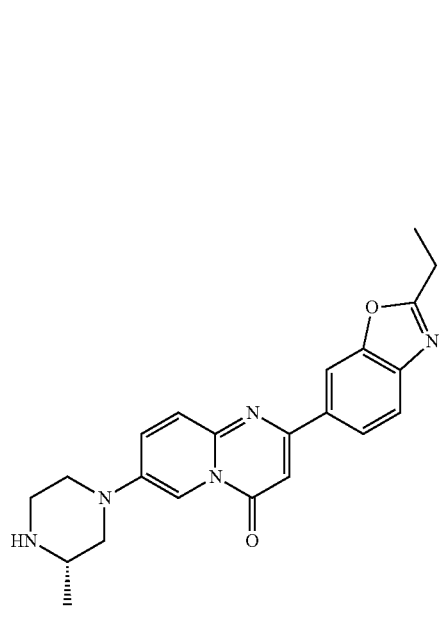

267 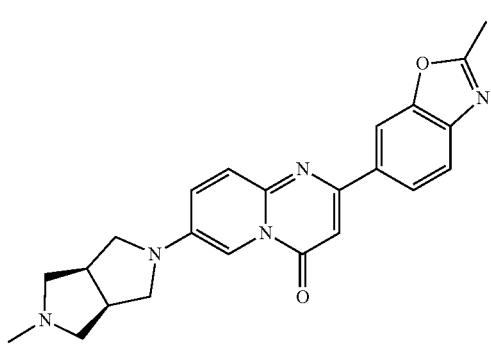
268 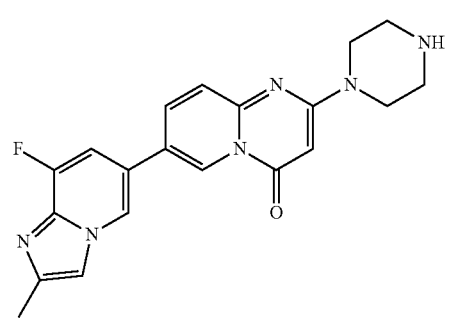
269 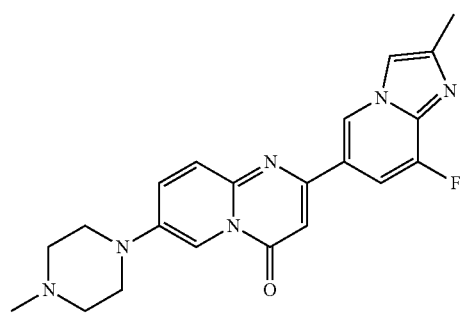
270 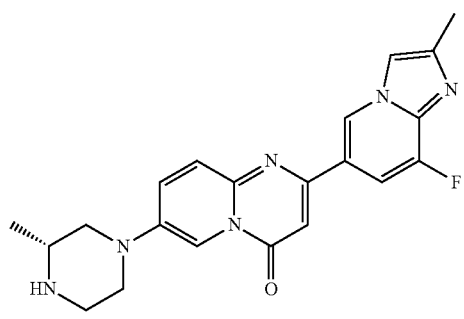
271 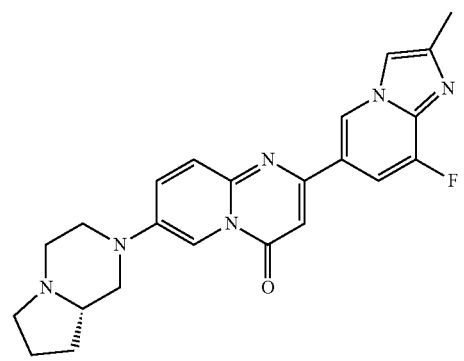
272 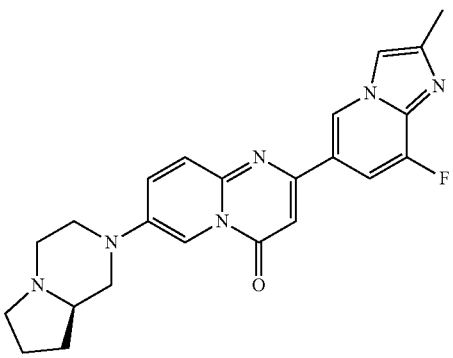
273 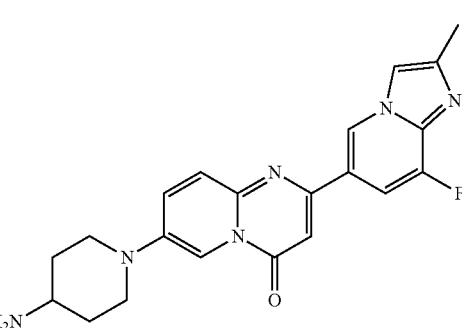
274 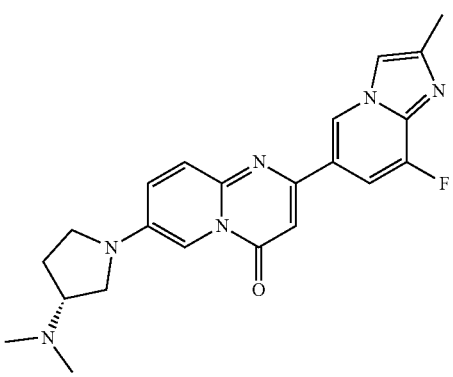
275 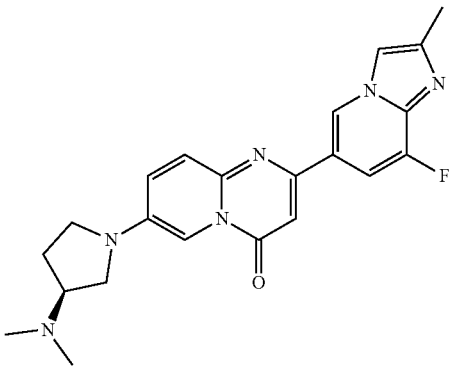

276 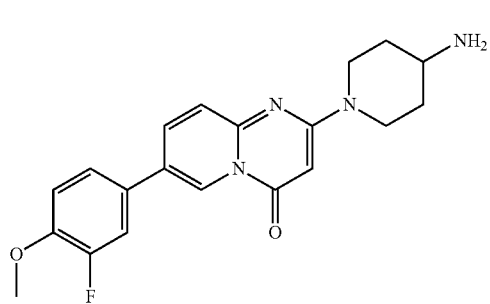
277 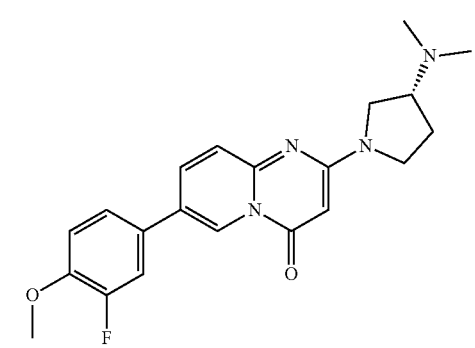
278 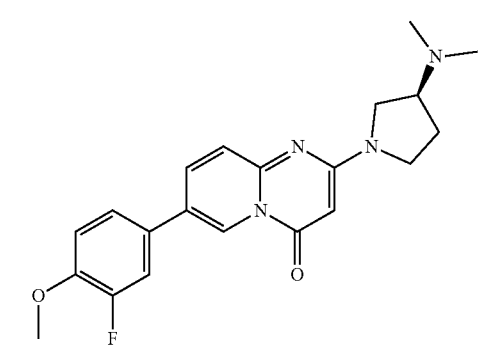
279 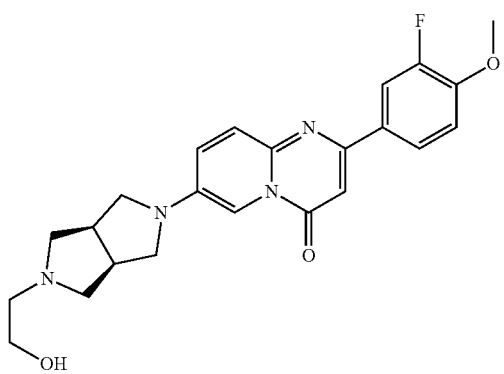
280 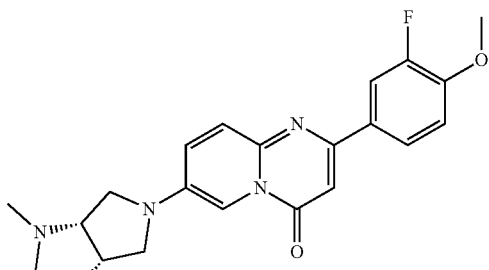
281 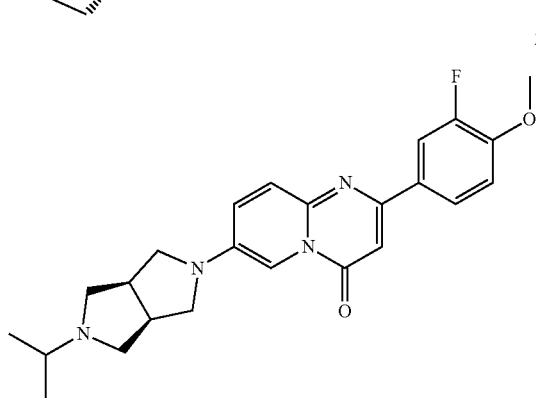
282 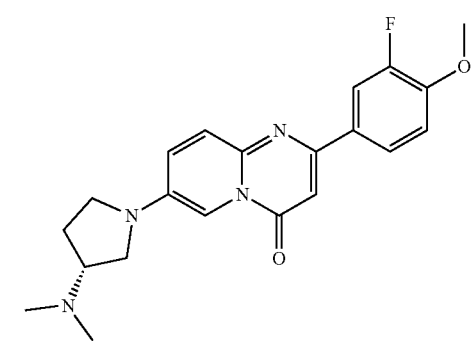
283 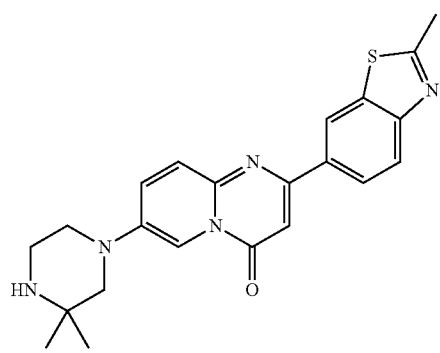

284 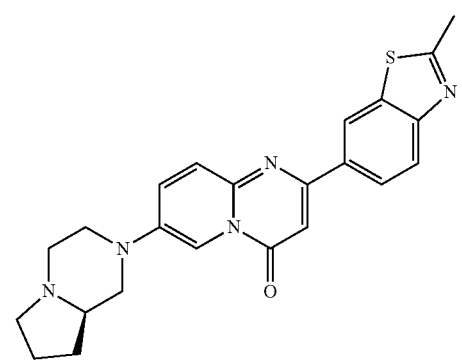
285 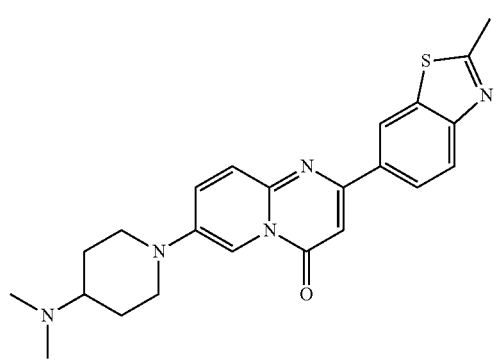
286 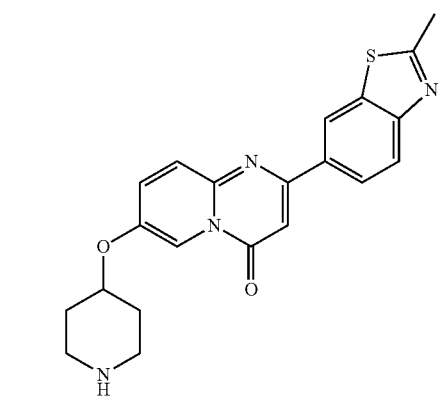
287 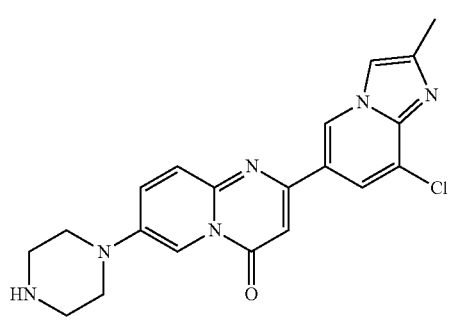
288 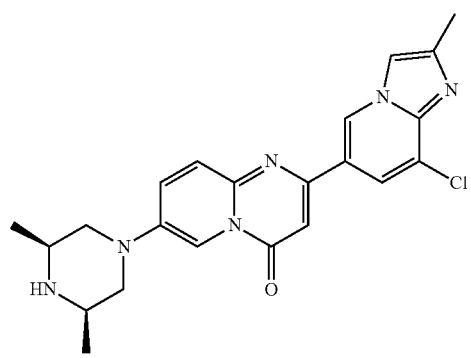
289 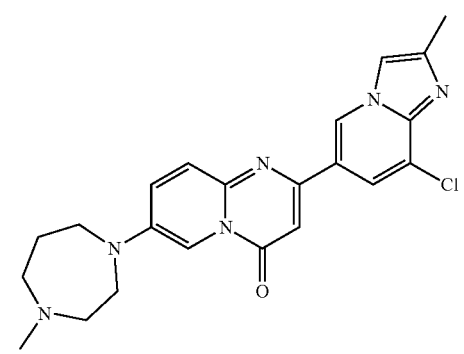
290 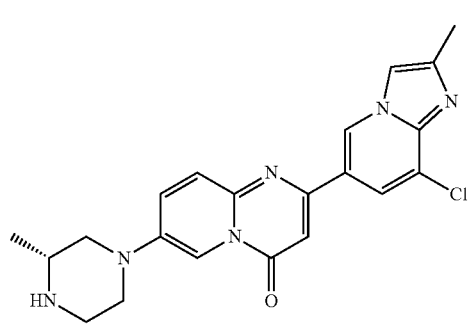
291 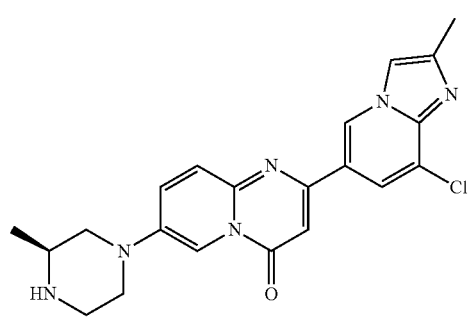

292 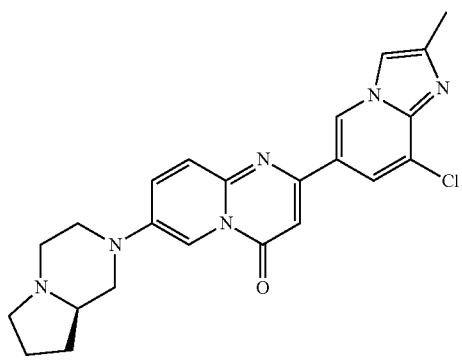
293 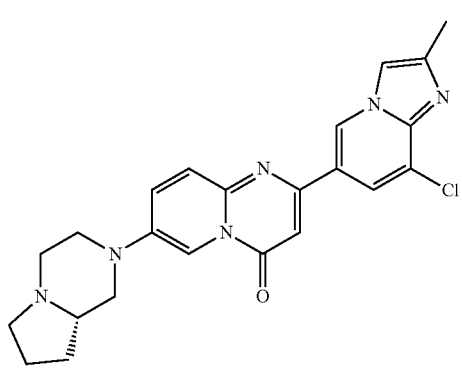
294 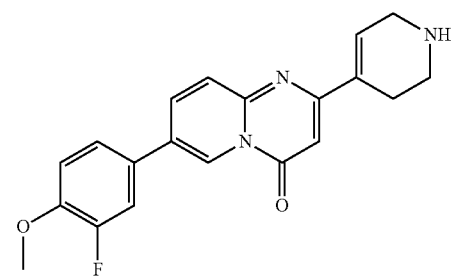
295 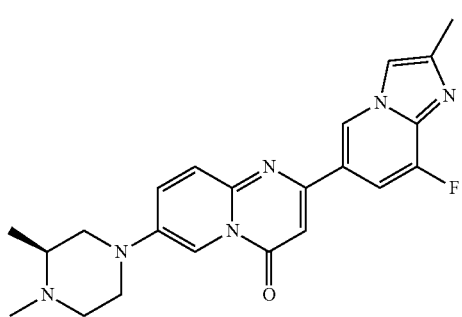
296 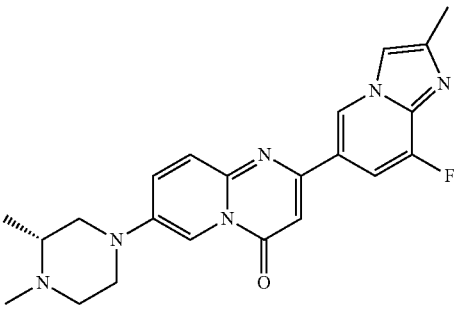
297 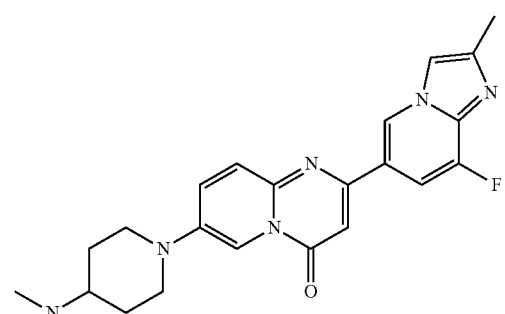
298 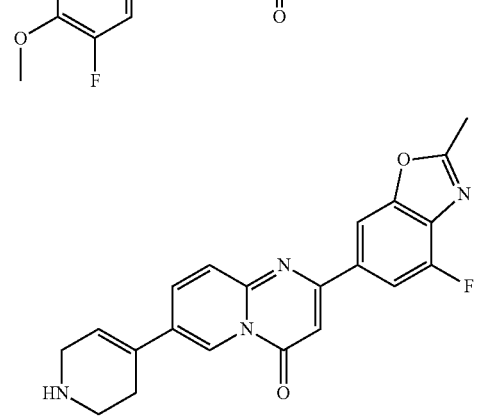
299 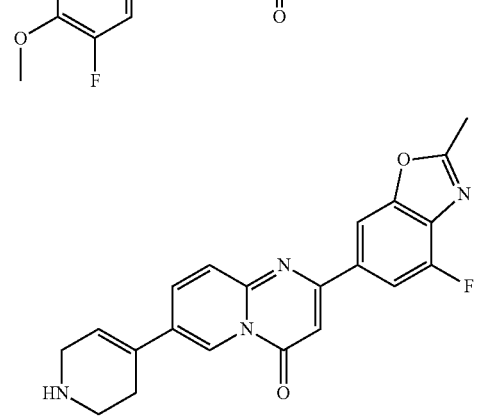
300 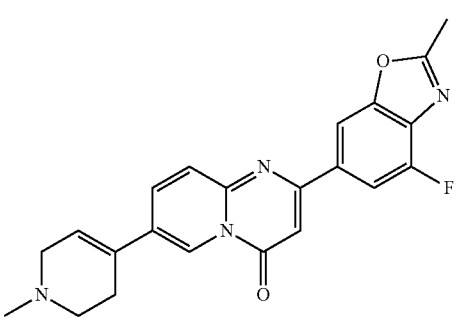

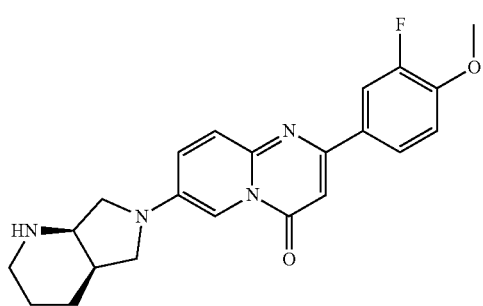
301
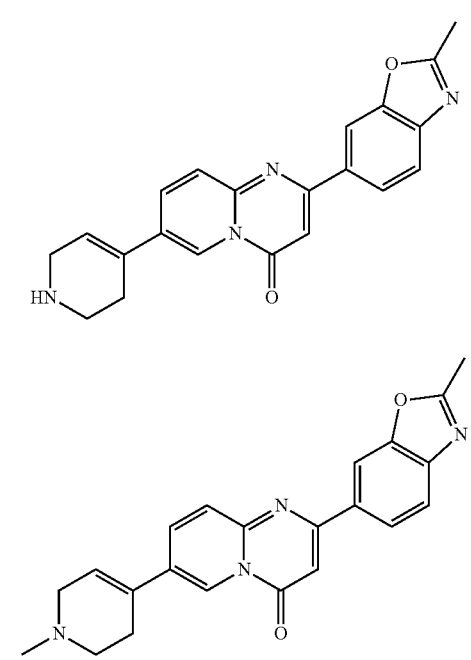
302
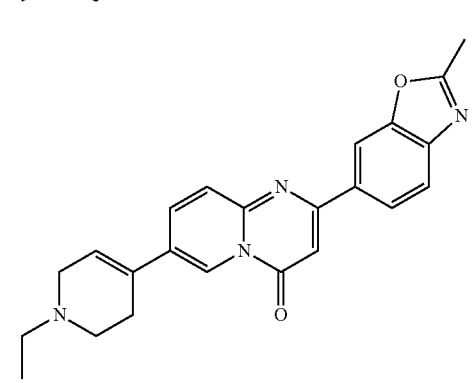
303
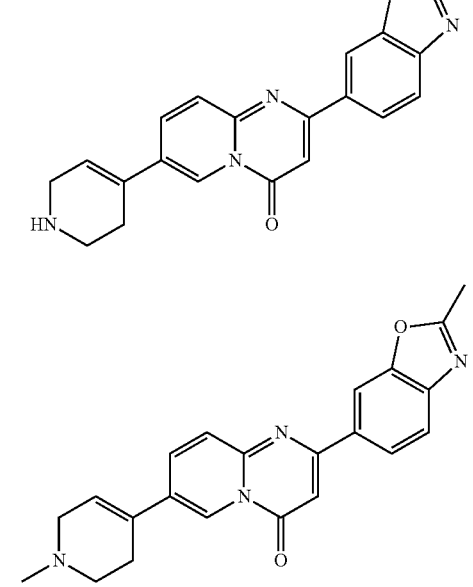
304
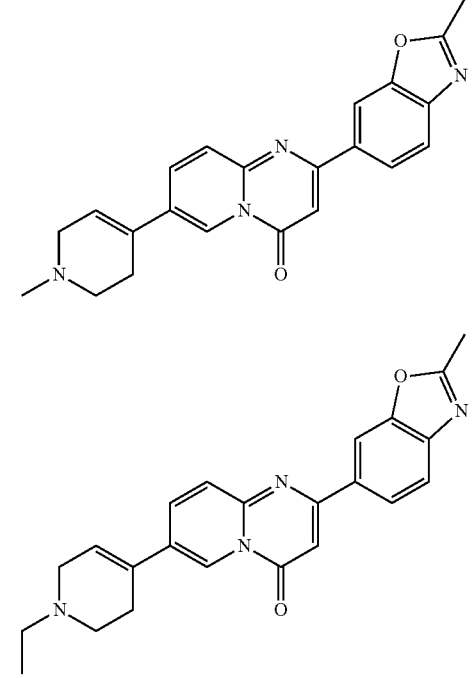
305
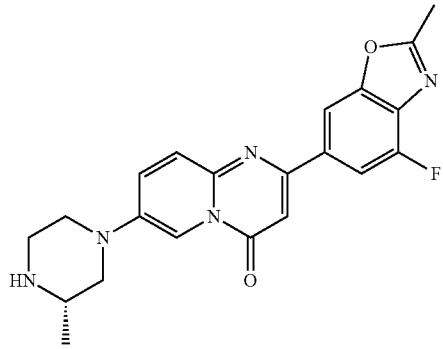
306
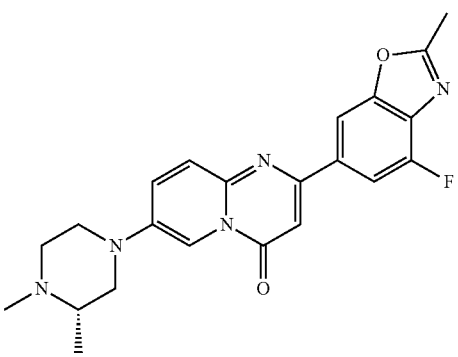
307
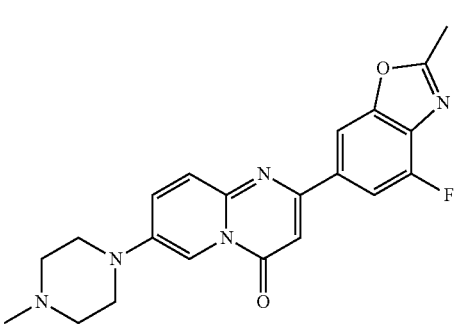
308
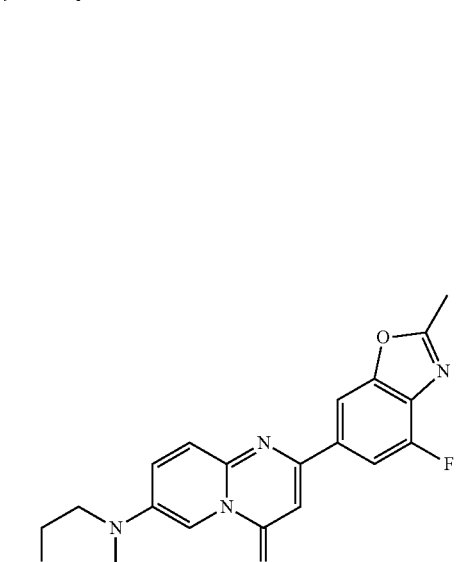
309

310
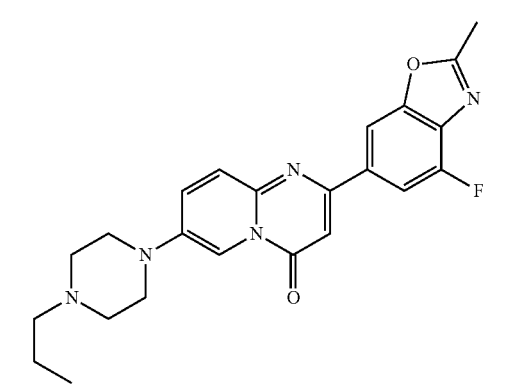
311
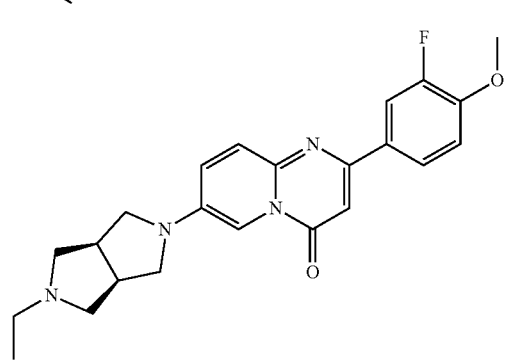
312
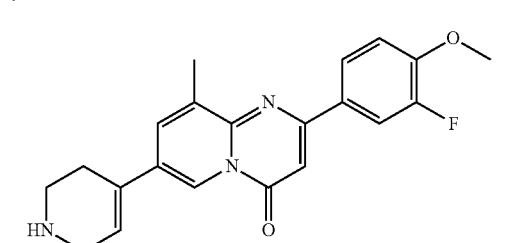
313
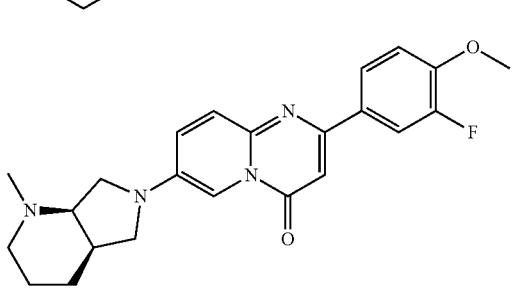
314
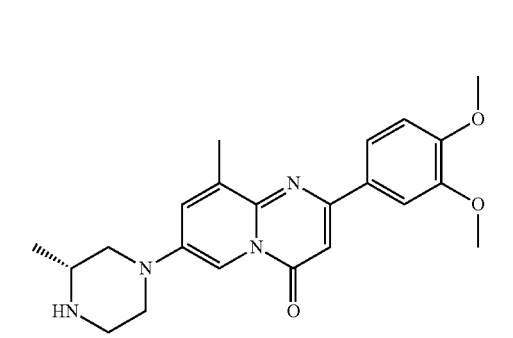
315
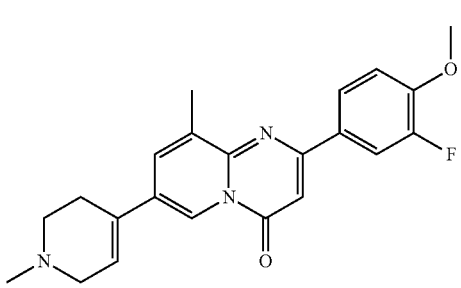
316
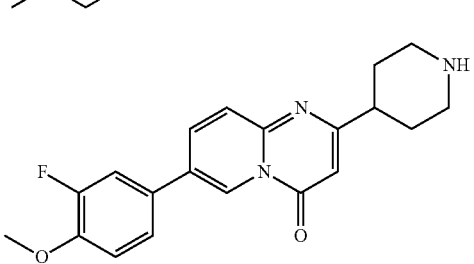
317
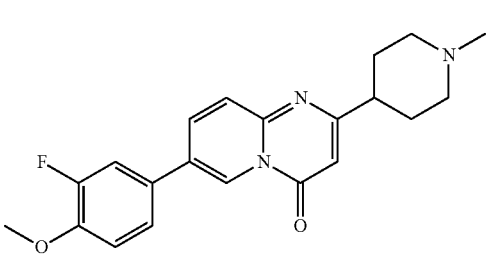
318
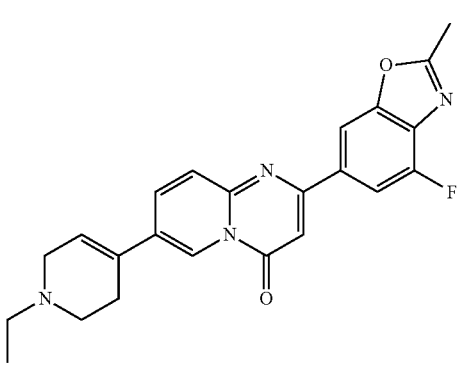
319

320 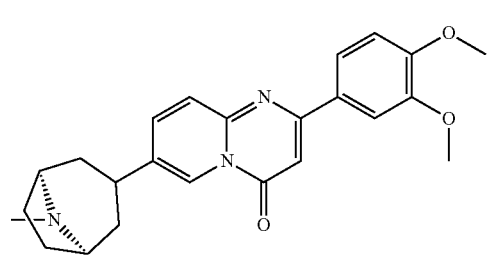
321 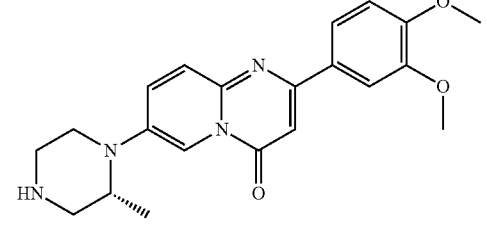
322 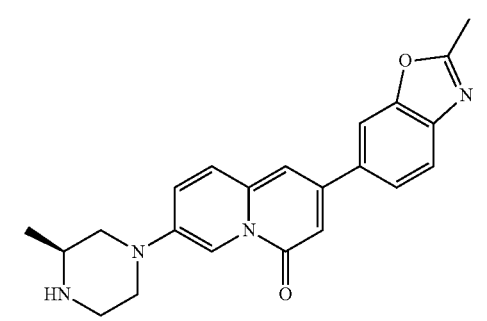
323 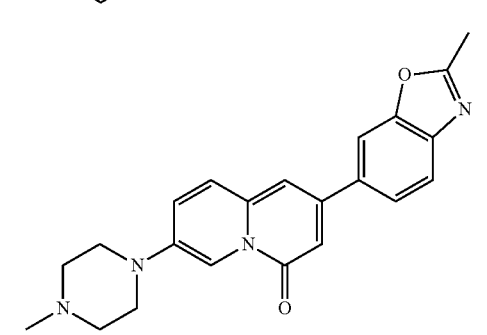
324 
325 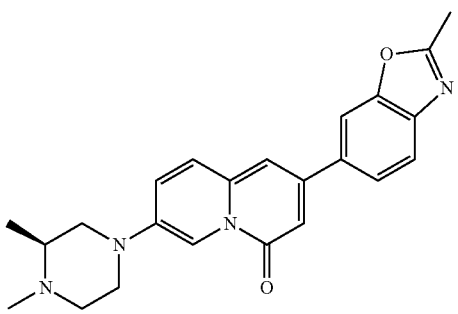
326 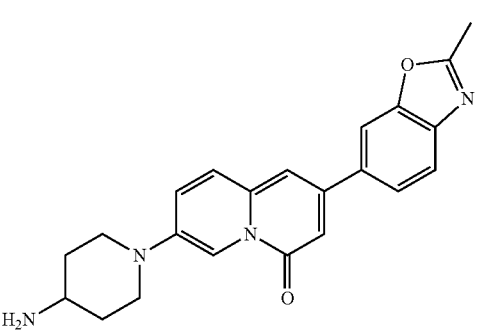
327 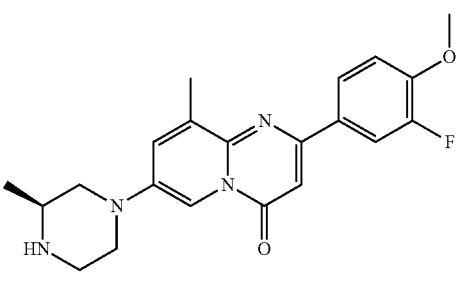
328 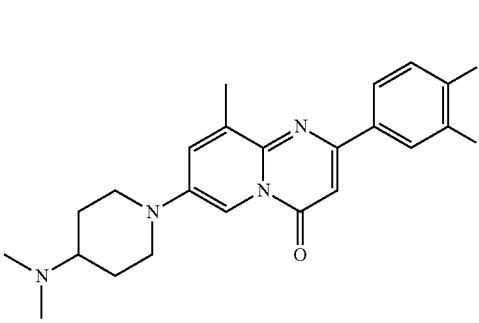
329 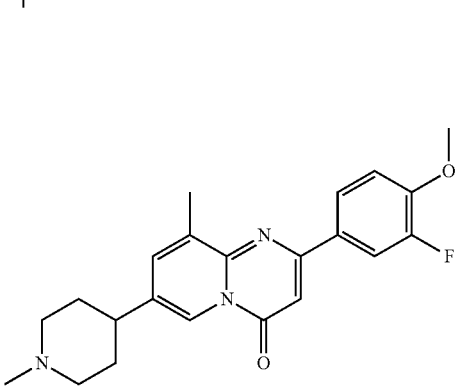

330 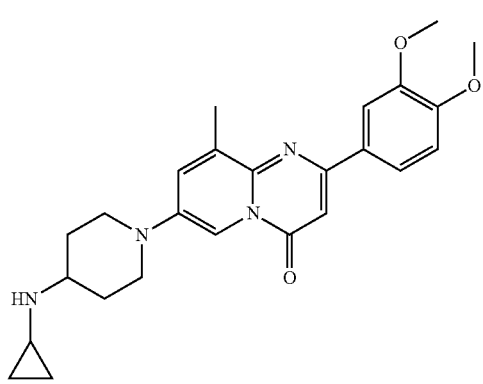
331 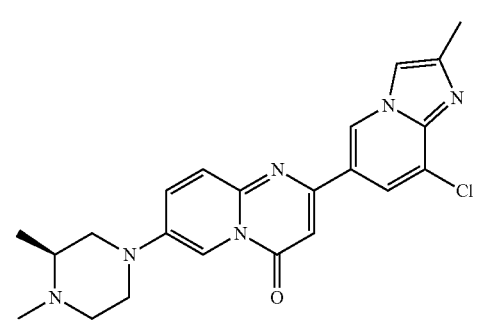
332 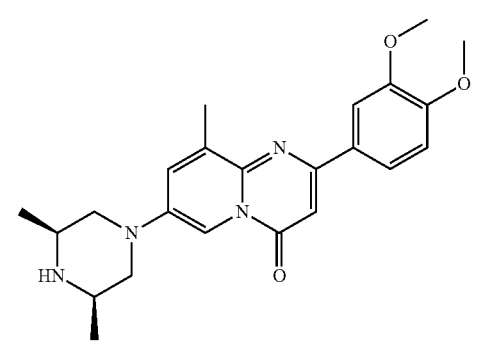
333 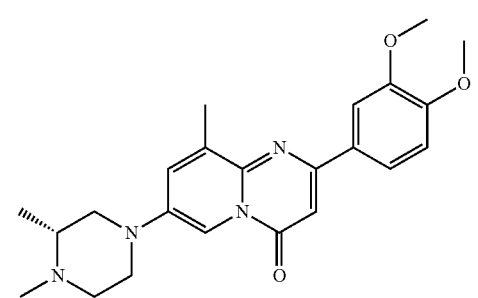
334 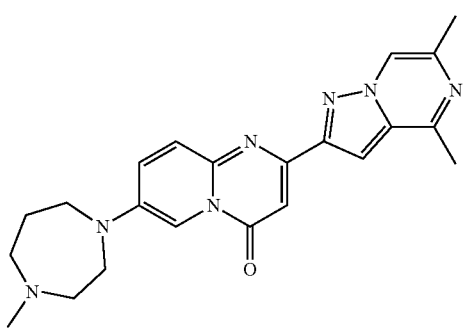
335 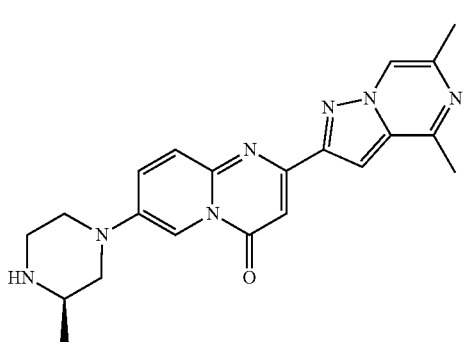
336 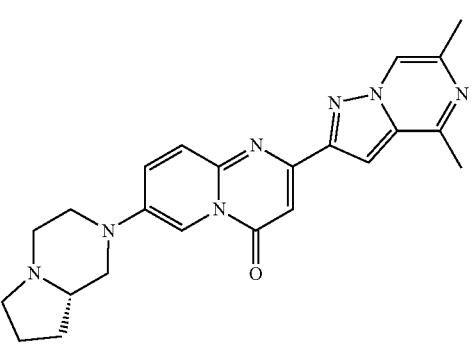
337 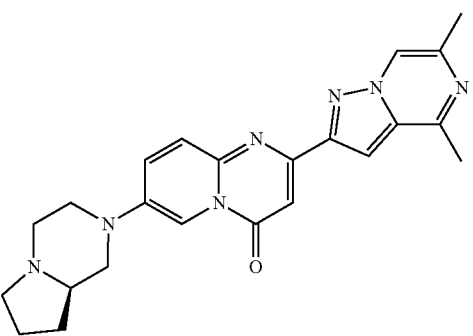

338
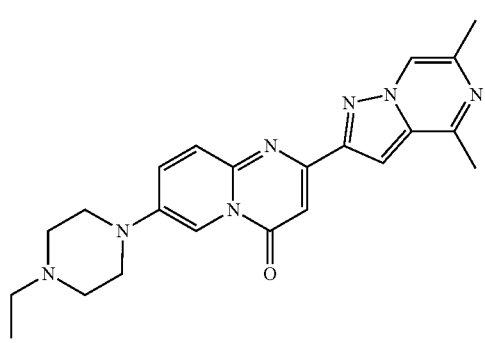
339
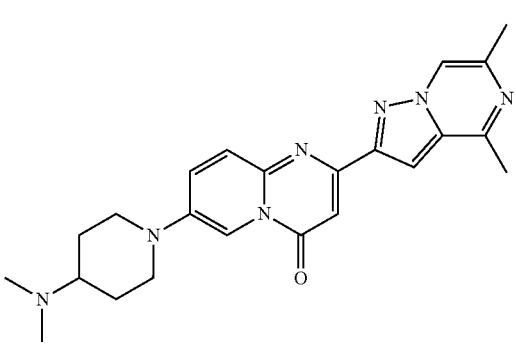
340
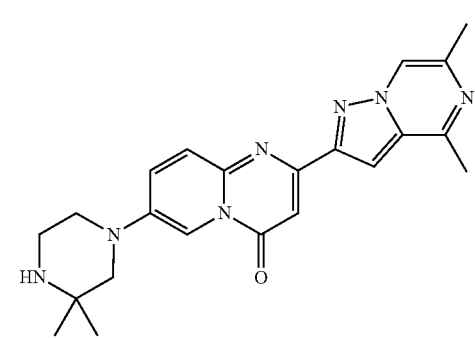
341
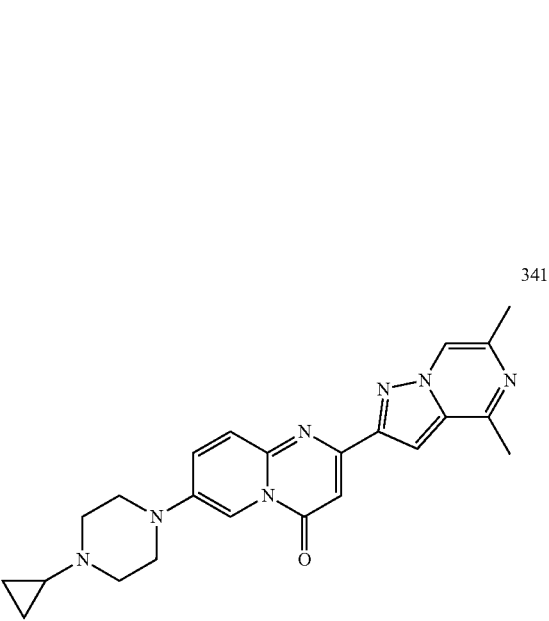
342
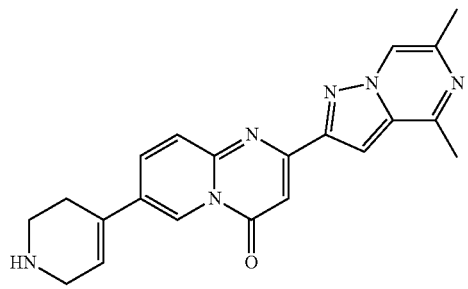
343
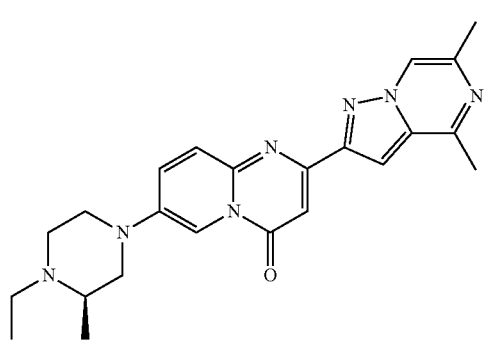
344
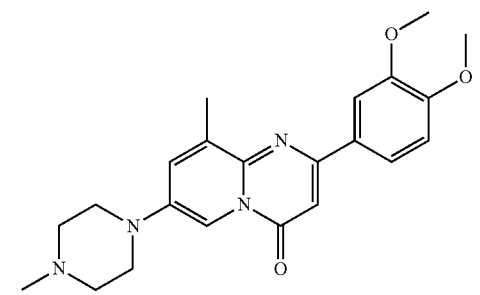
345
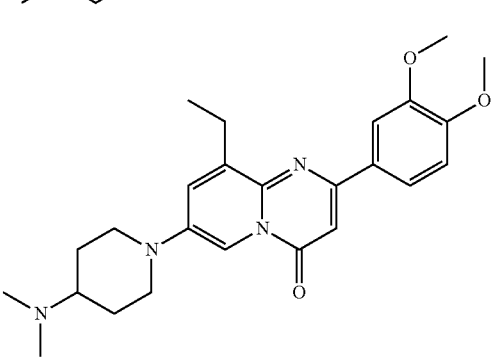
346
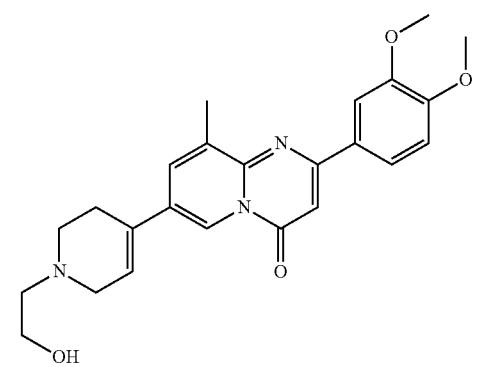

347
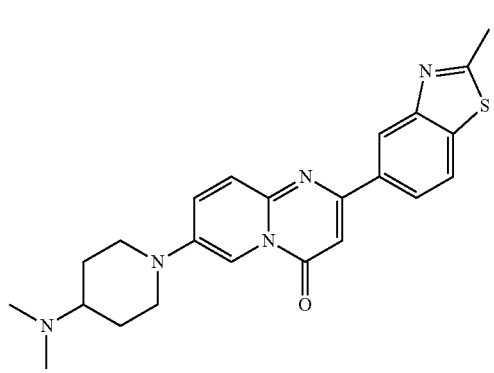
348
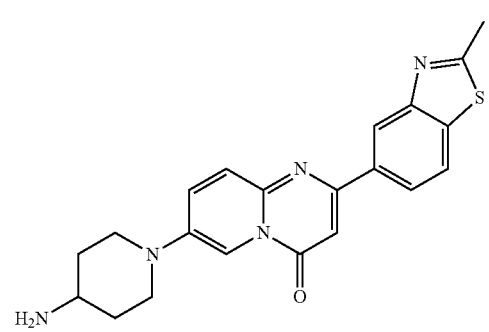
349
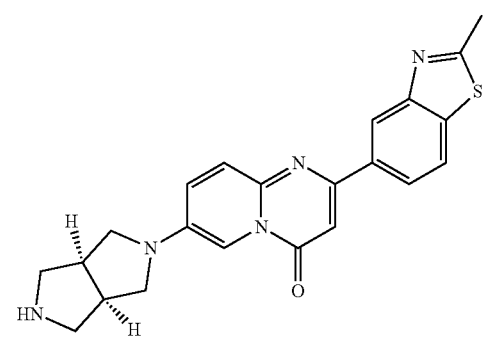
350
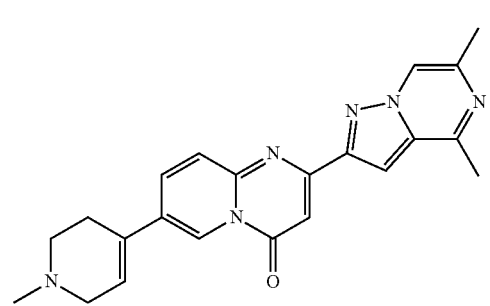
351
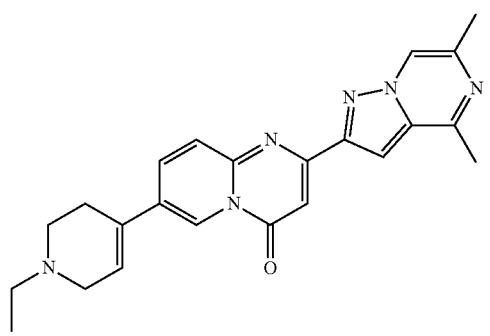
352
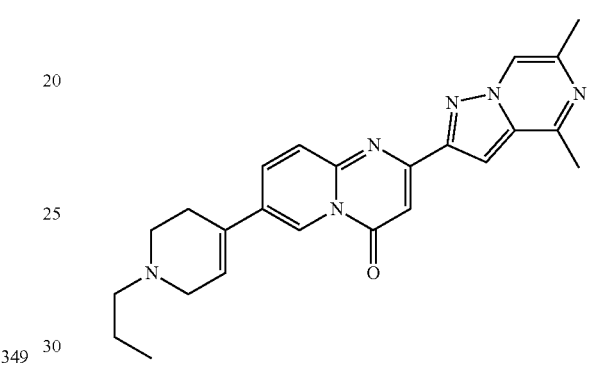
353
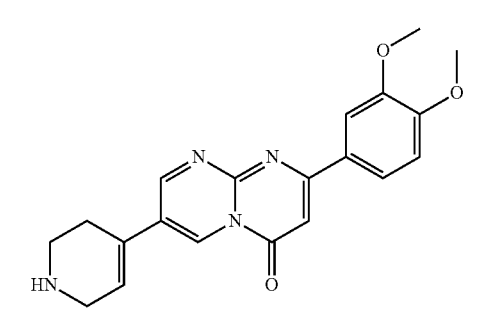
354
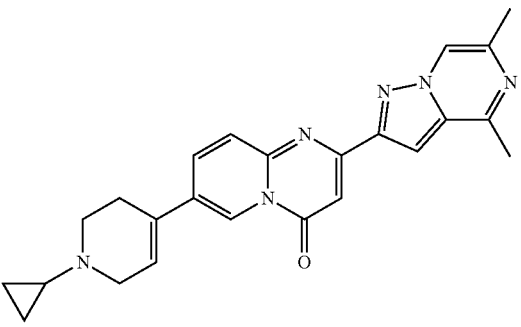

-continued
355
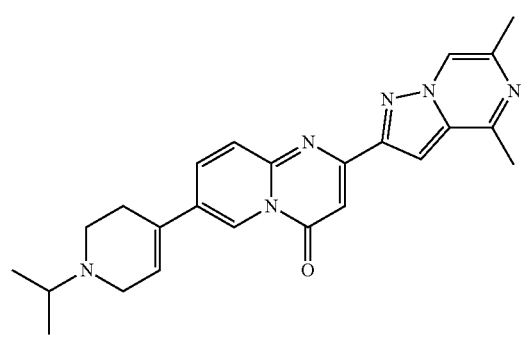
356
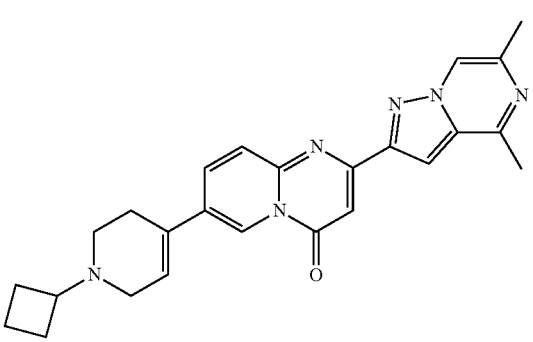
357
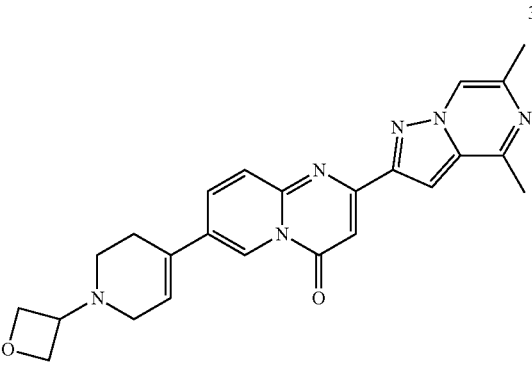
358
-continued
359
360
361
362
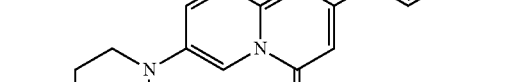

363
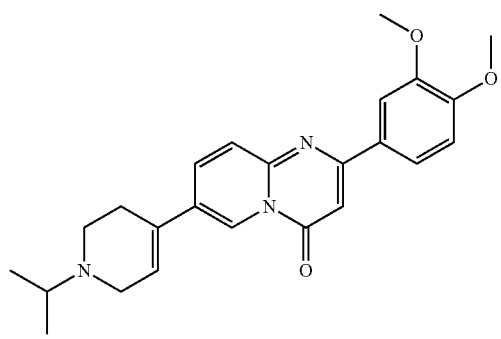
364
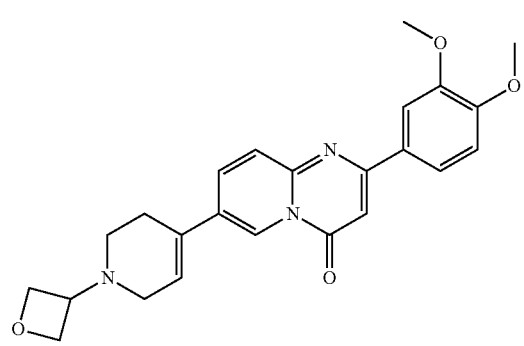
365
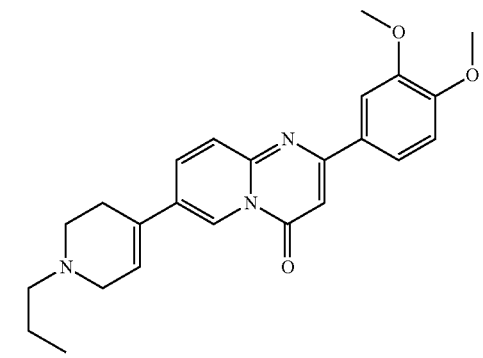
366
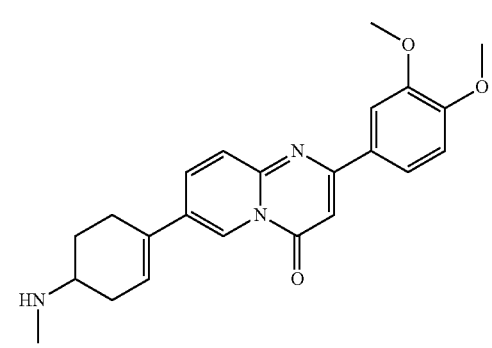
367
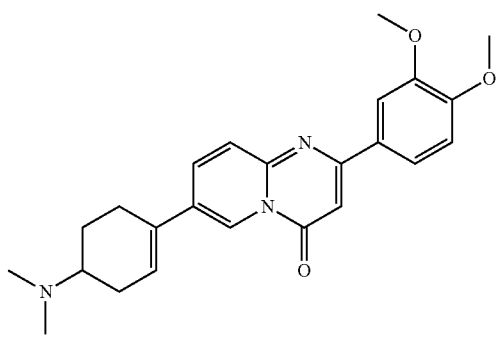
368
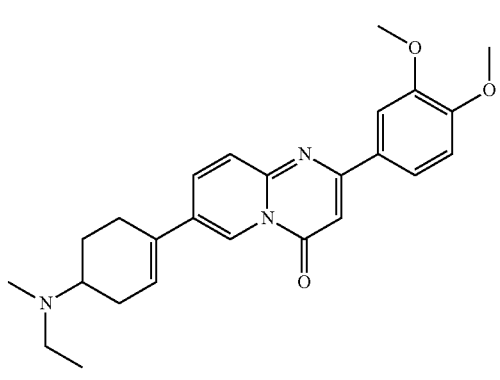
369
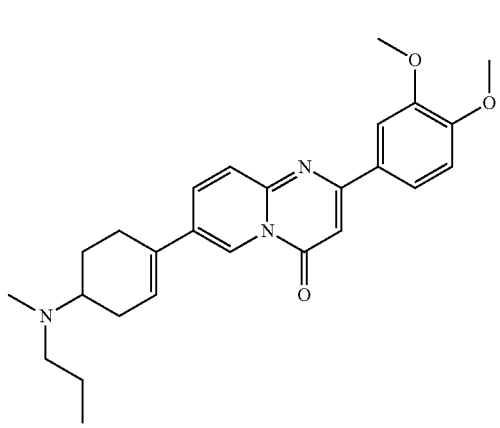
370
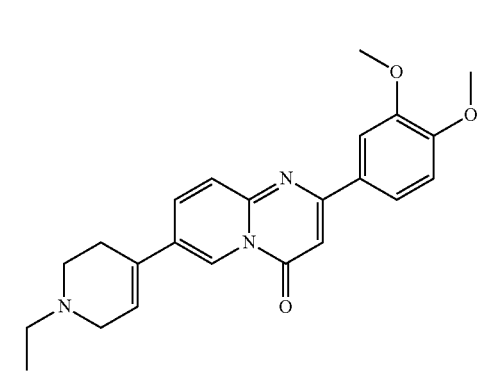

371 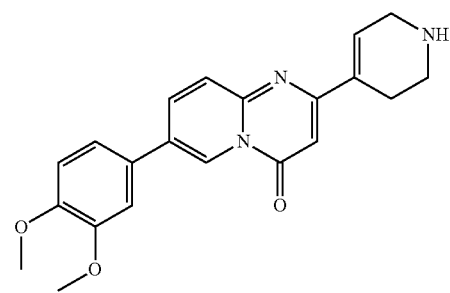
372 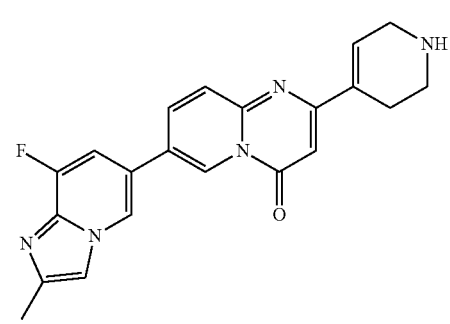
373 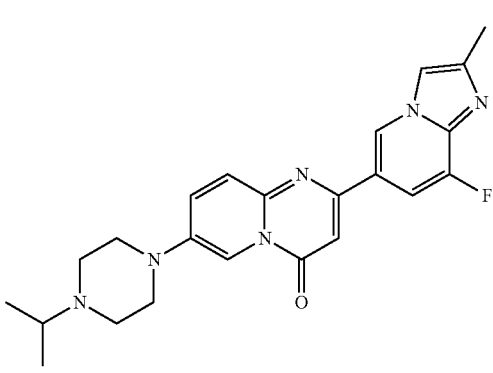
374 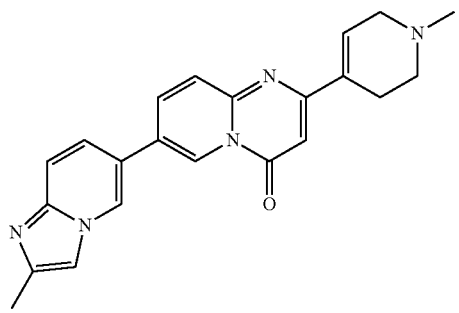
375 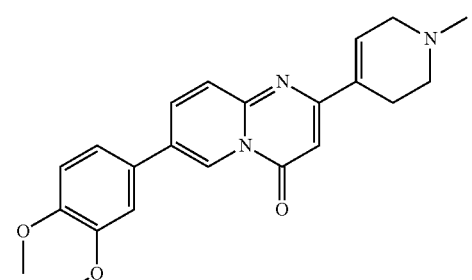
376 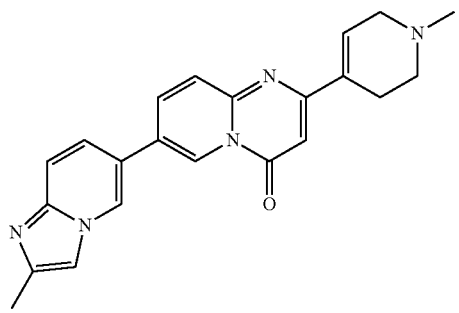
377 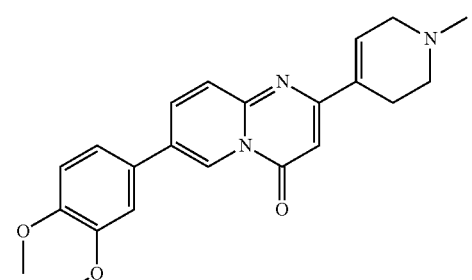
378 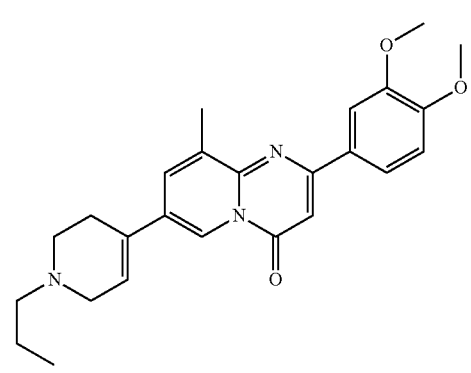
379 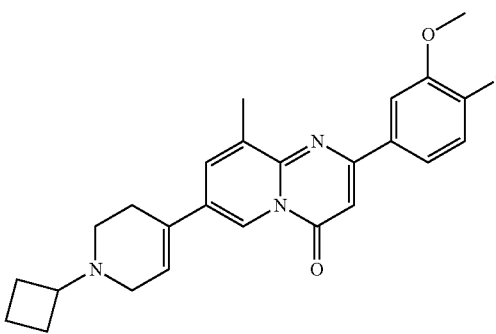
380 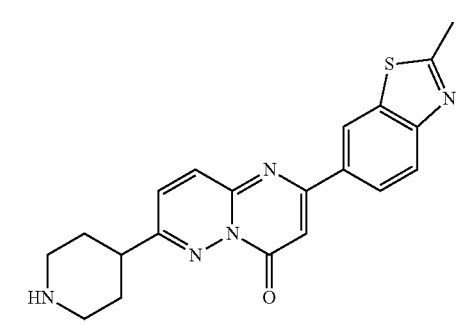

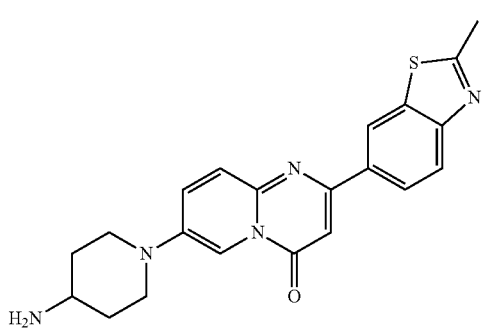
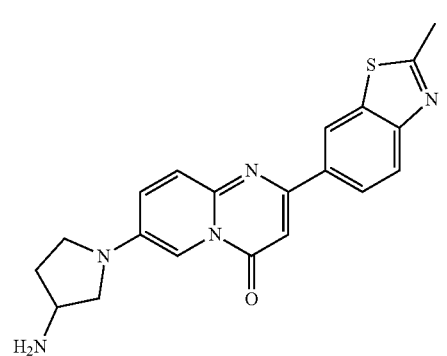
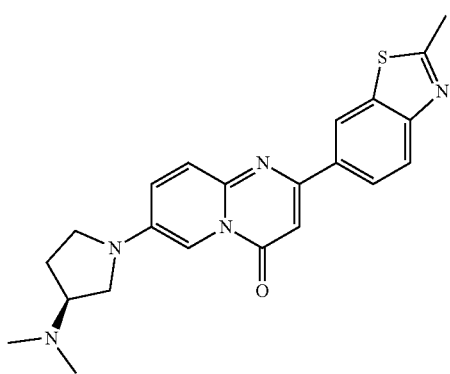
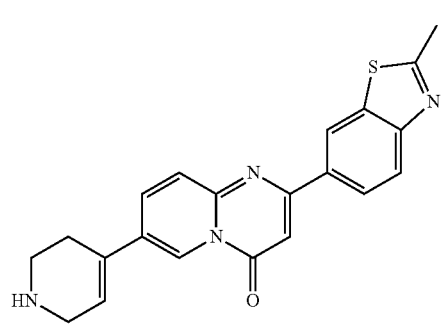
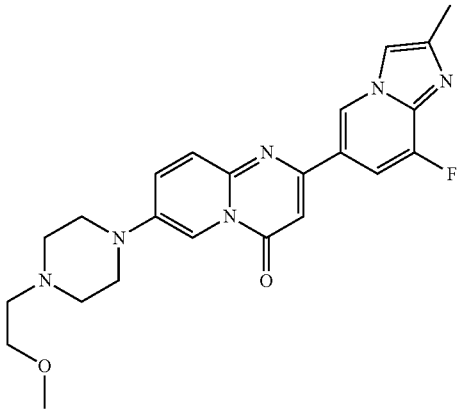
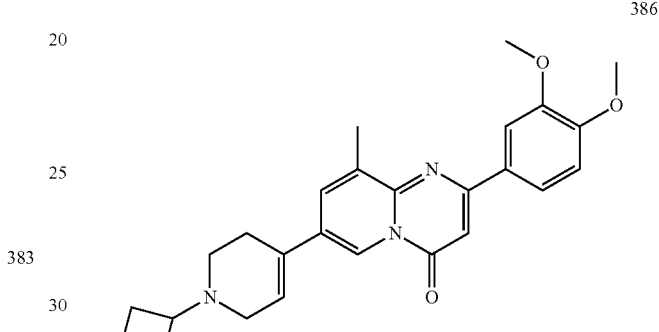
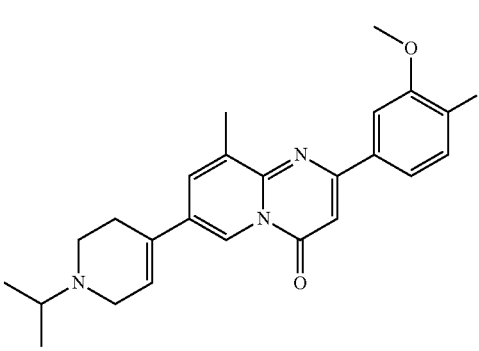
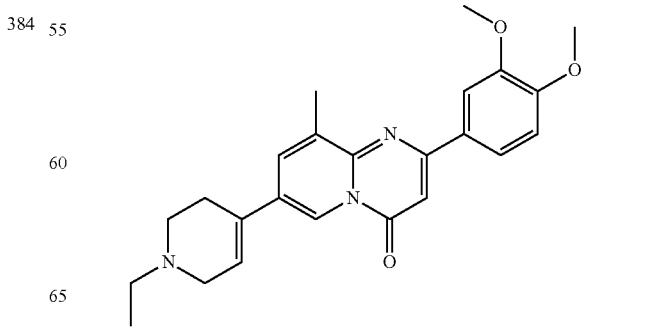

389
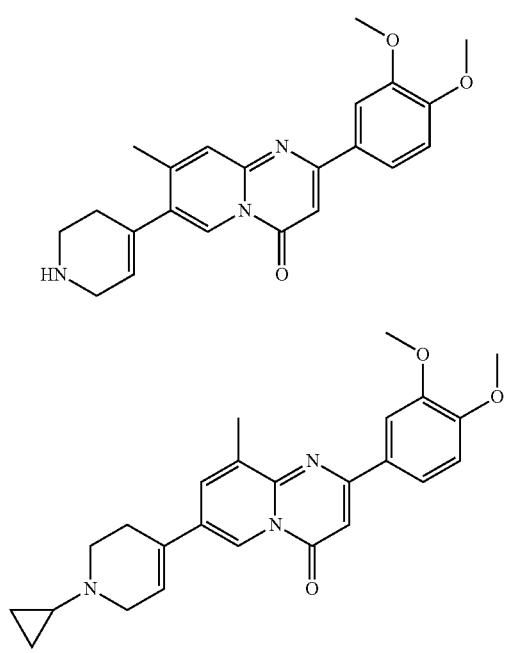
390
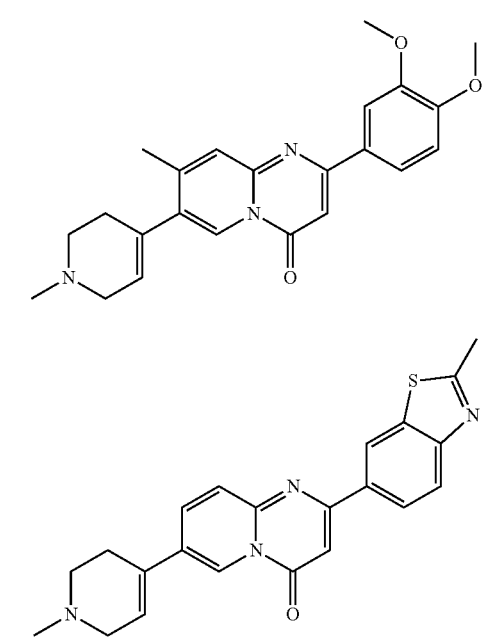
391
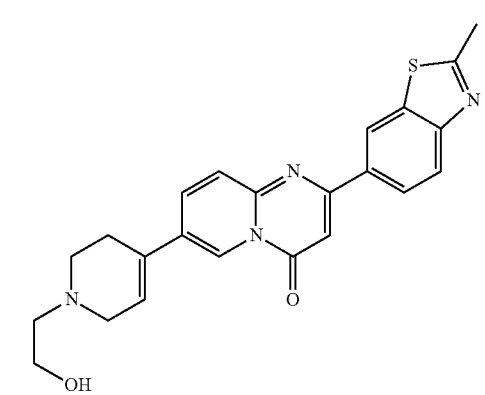
392
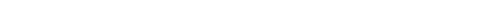
393
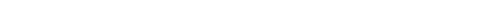
394
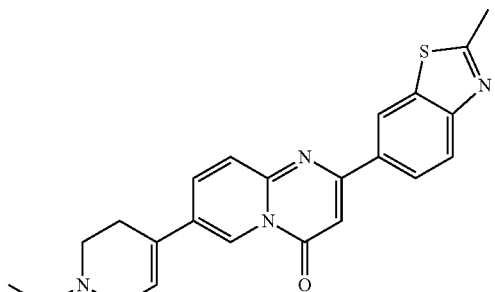
395
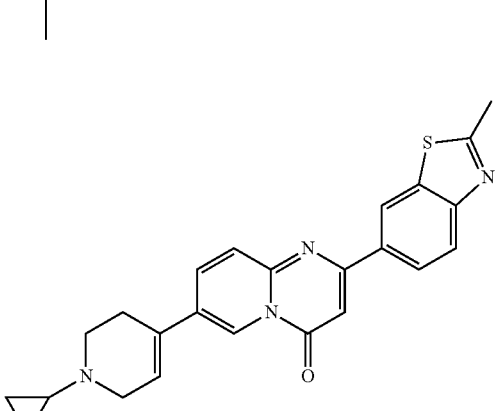
396
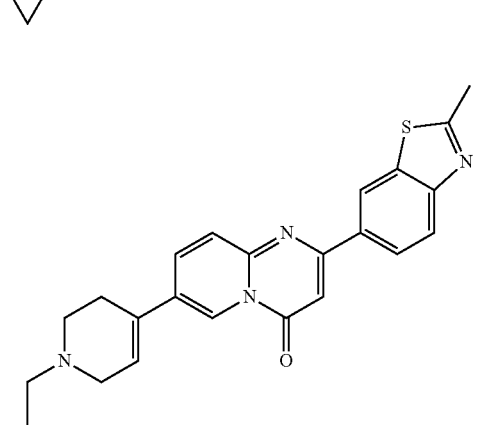
397
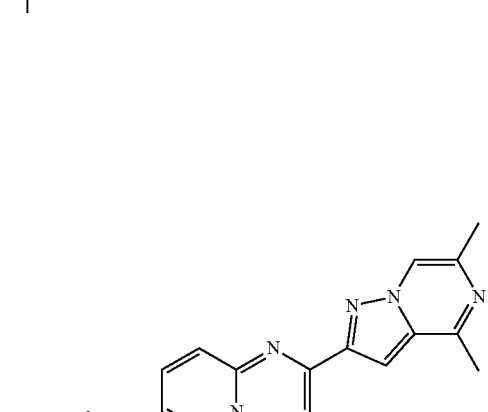

398
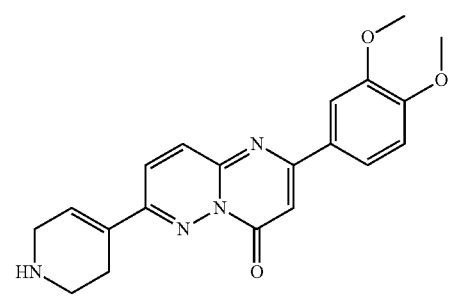
399
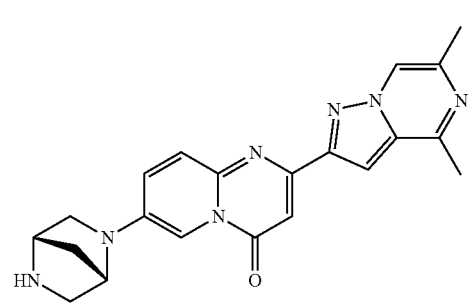
400
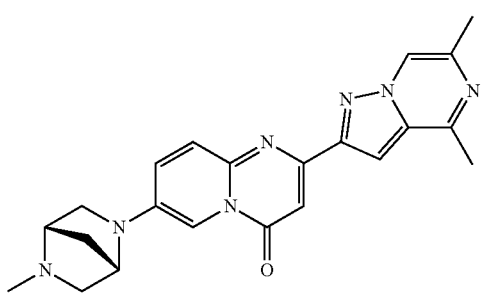
401
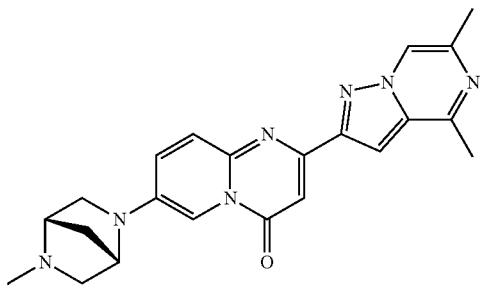
402
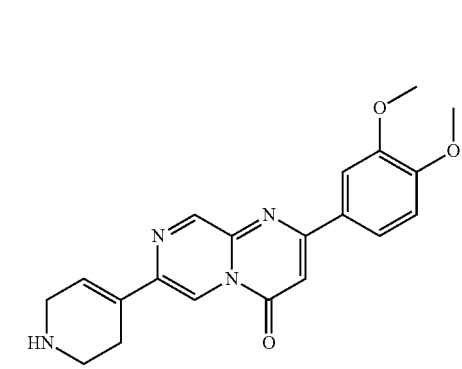
403
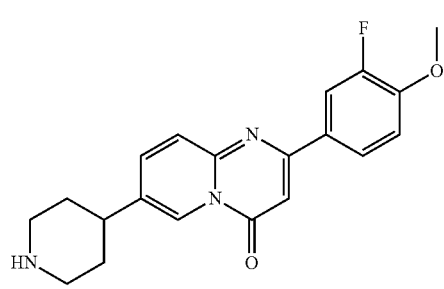
404
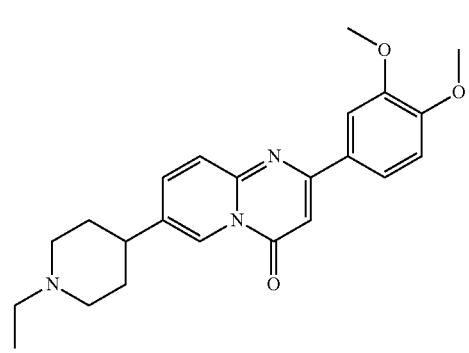
405
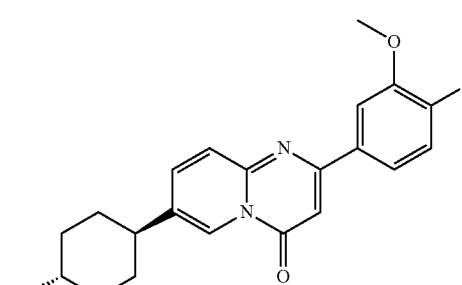
406
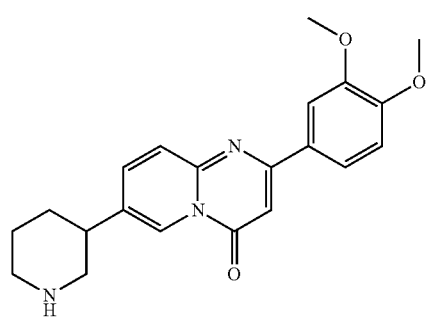

407
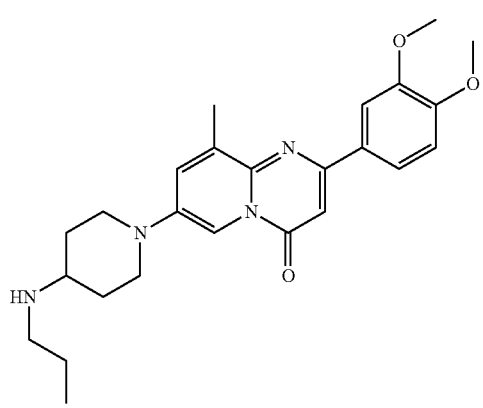
408
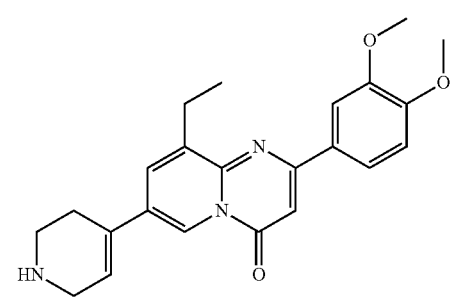
409
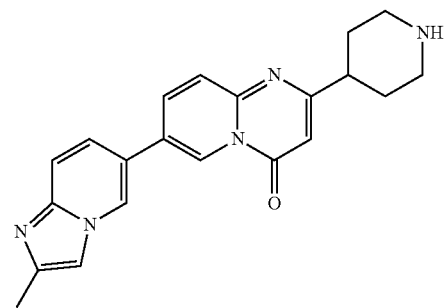
410
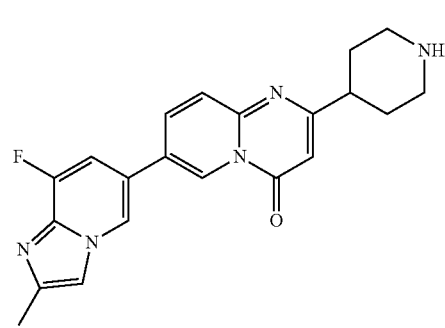
411
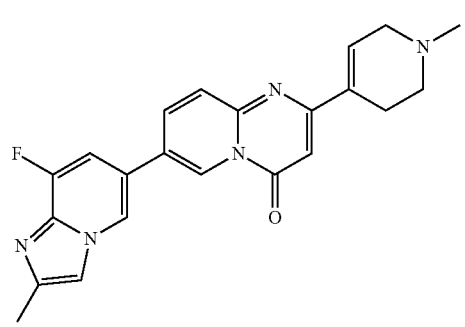
412
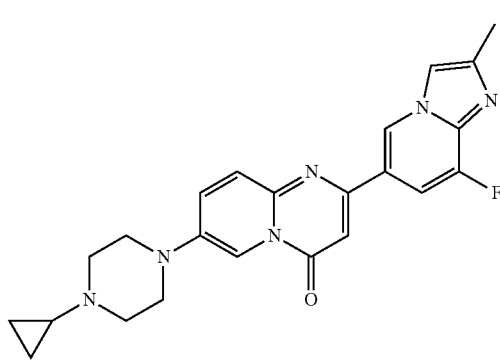
413
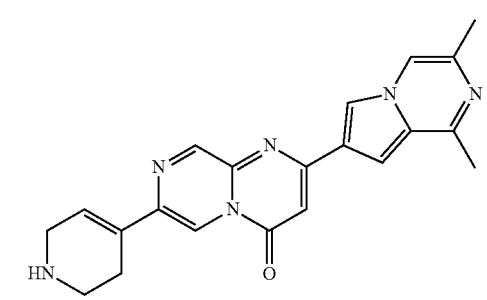
414
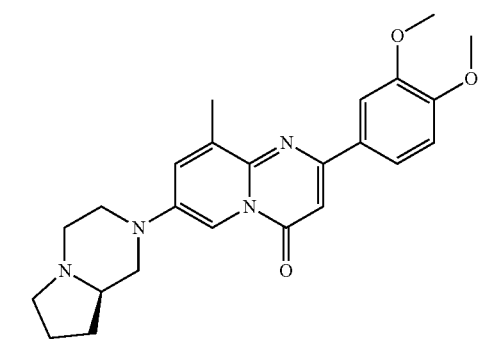
415
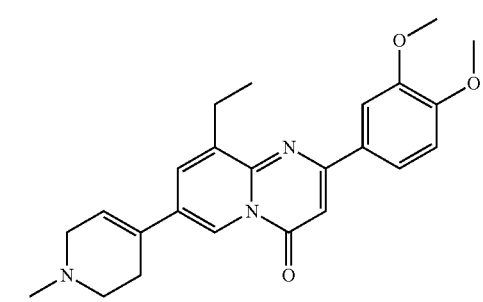
416
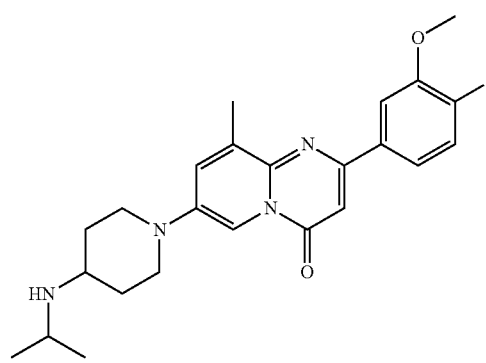

417 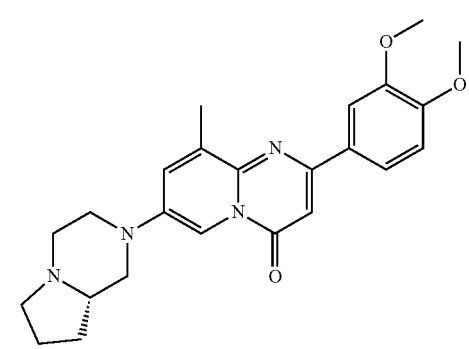
418 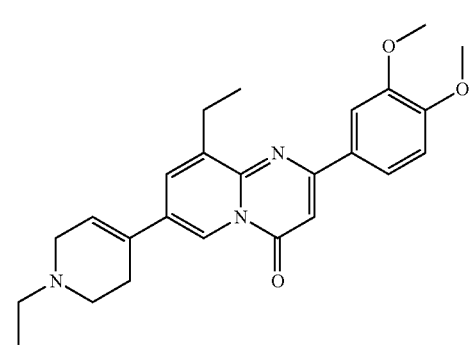
419 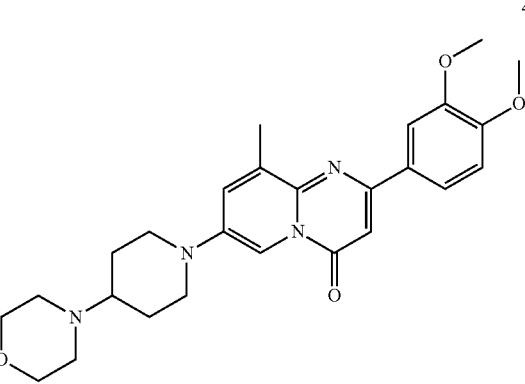
420 
421 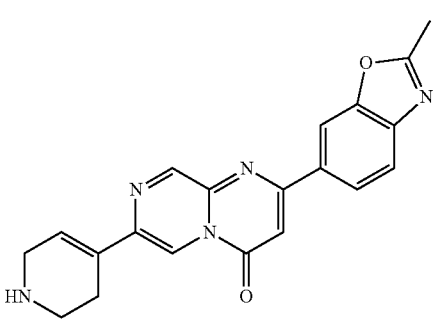
422 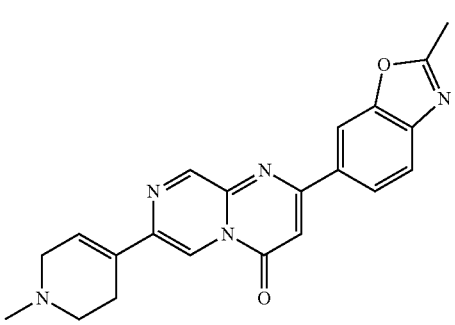
423 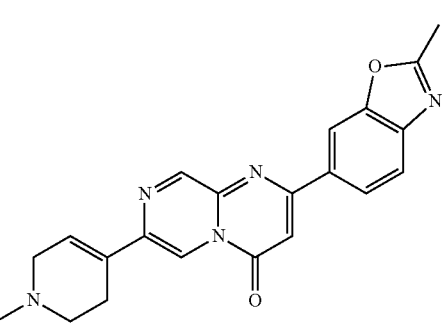
424 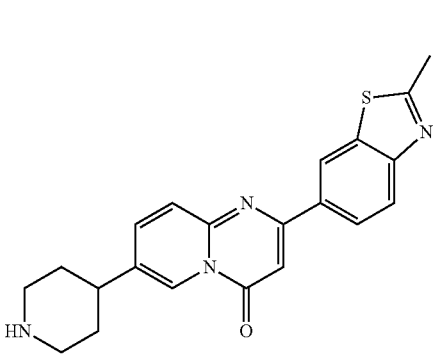
425 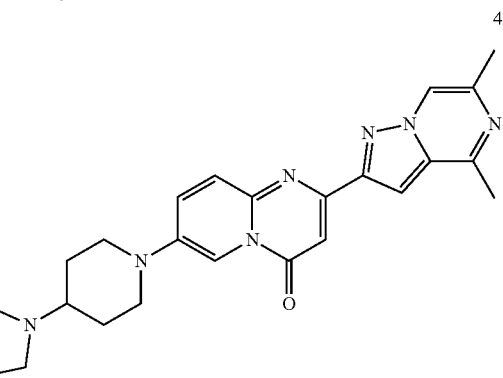

426
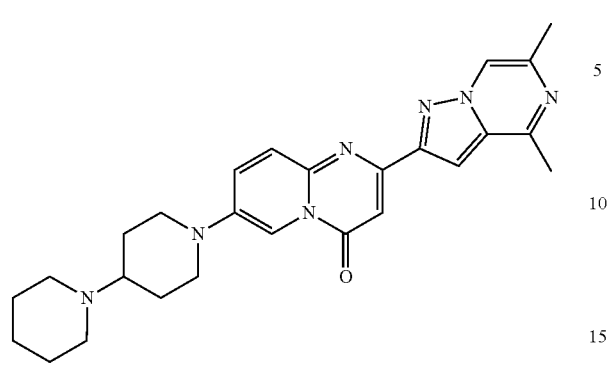
427
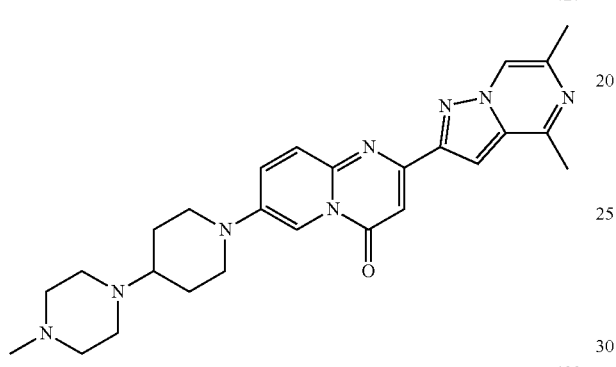
428
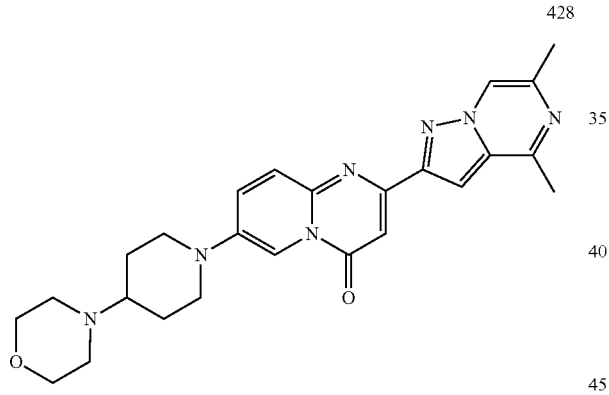
429
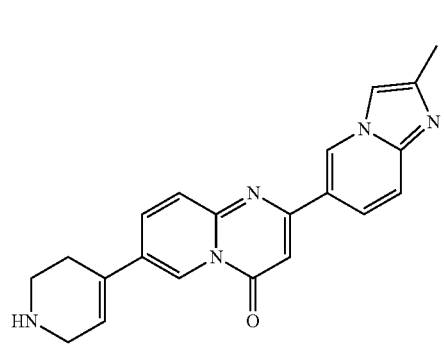
430
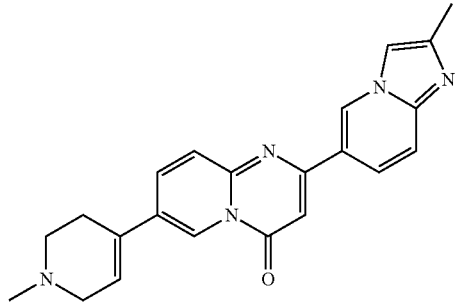
431
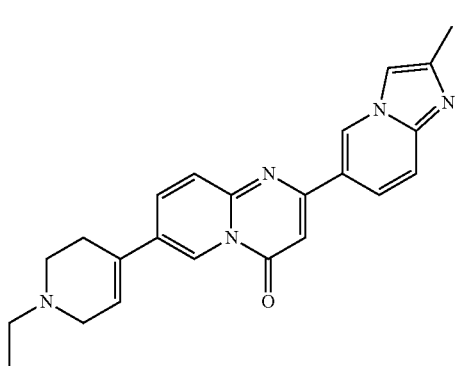
432
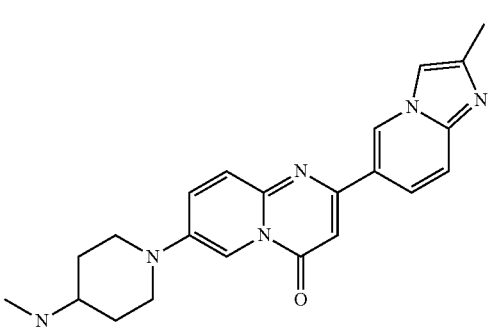
433
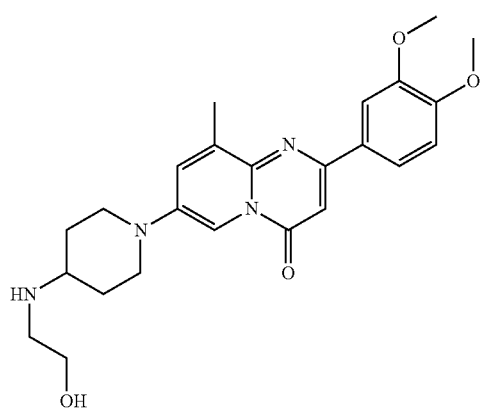

-continued
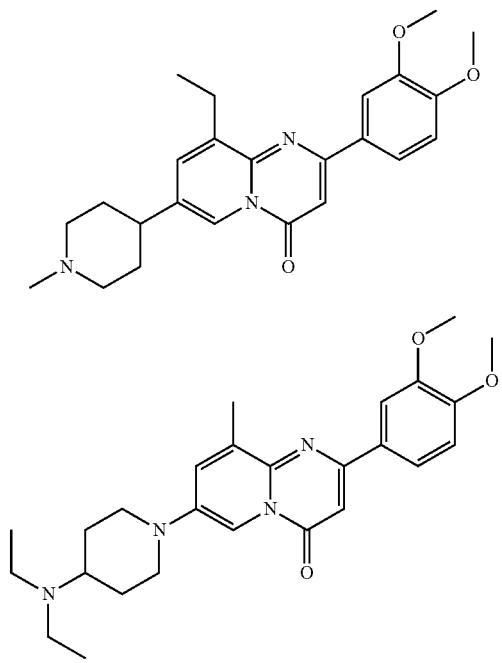
434
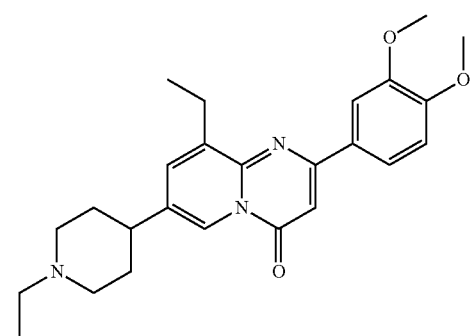
435
436
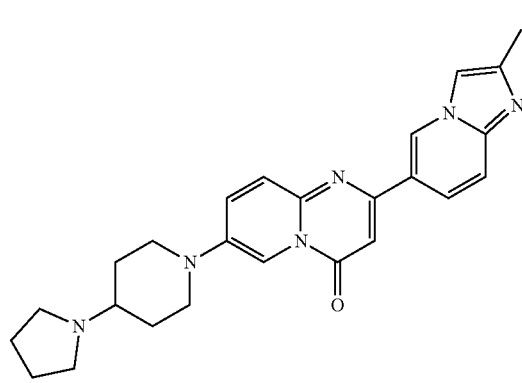
437
-continued
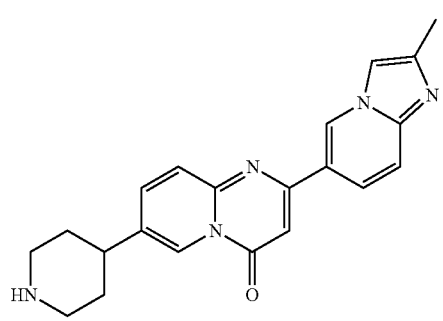
438
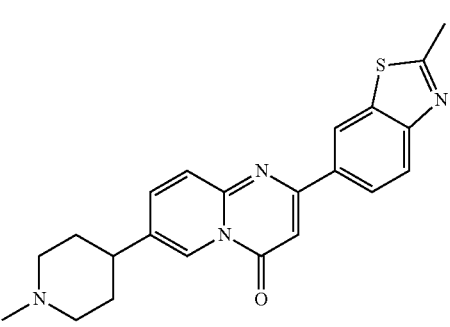
439
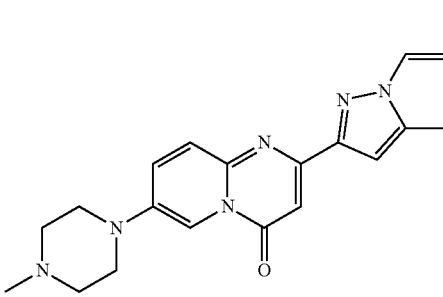
440
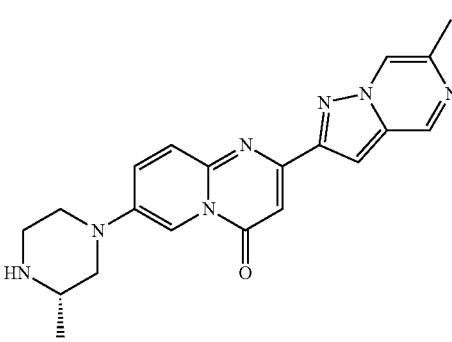
441
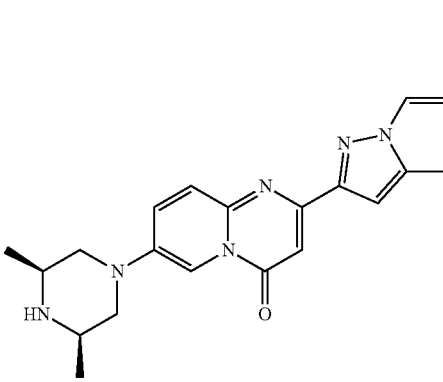
442

443 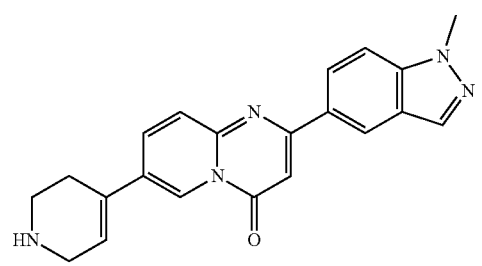
444 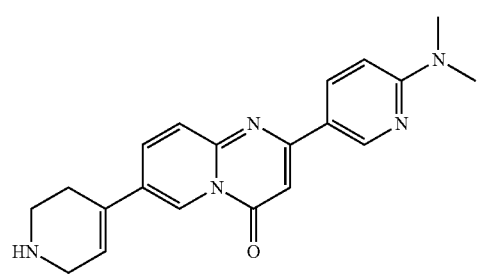
445 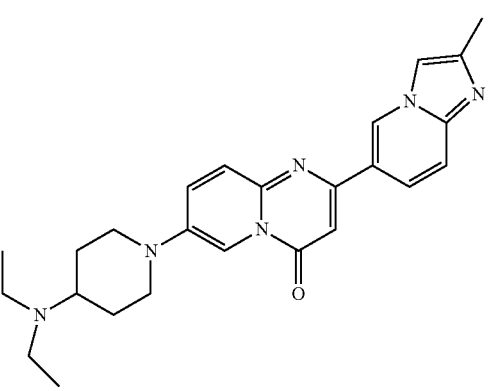
446 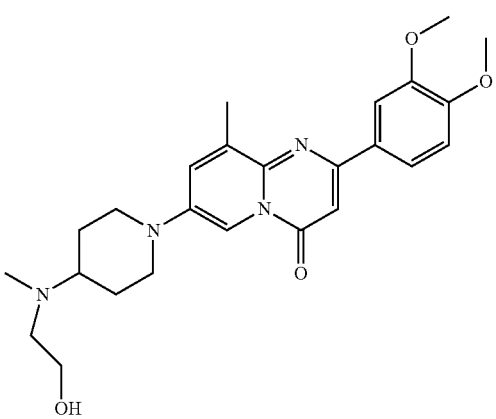
447 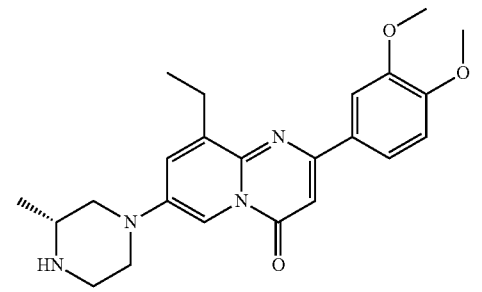
448 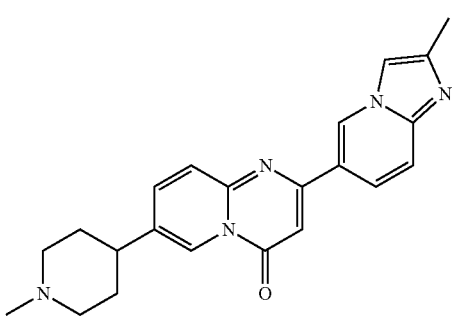
449 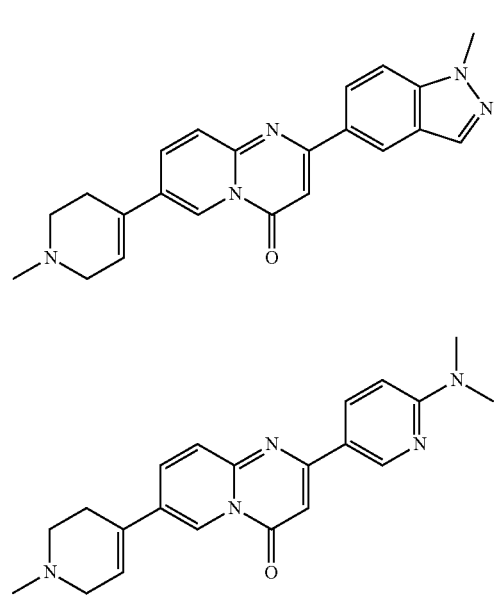
450 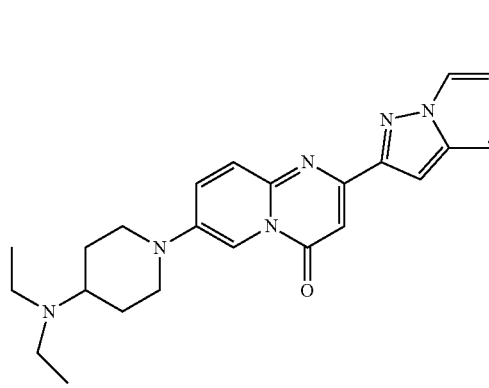
451 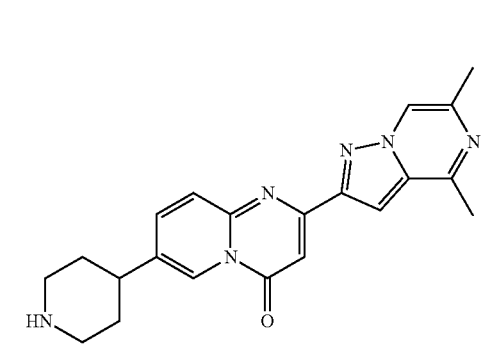
452

453
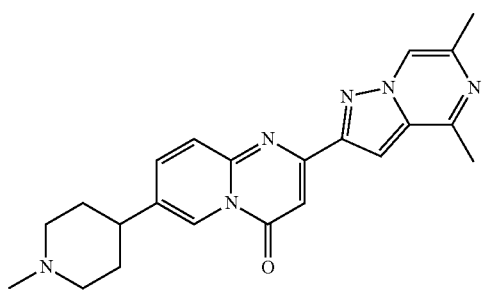
454
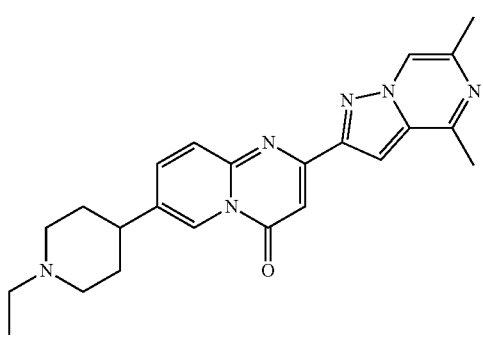
455
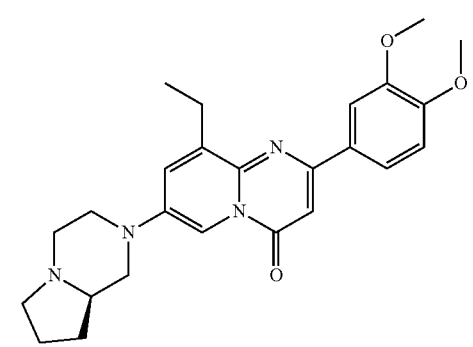
456
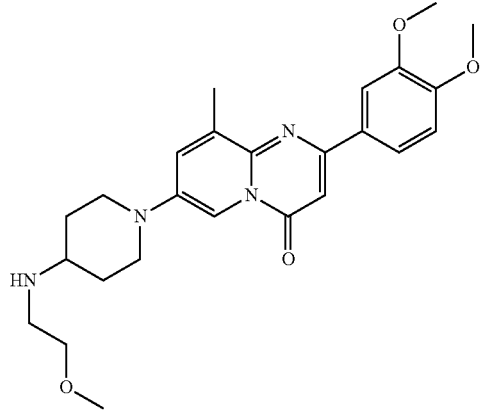
457
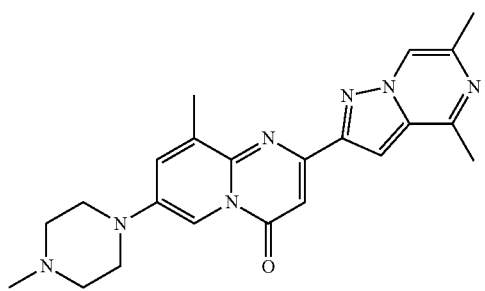
458
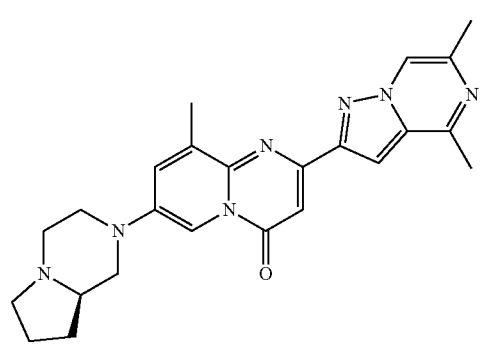
459
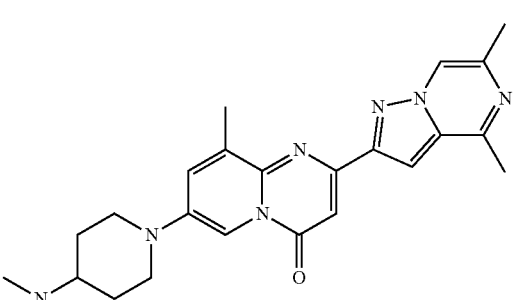
460
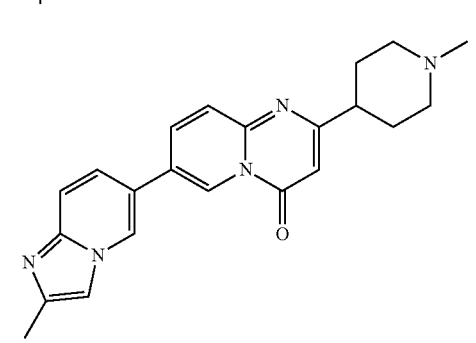
461
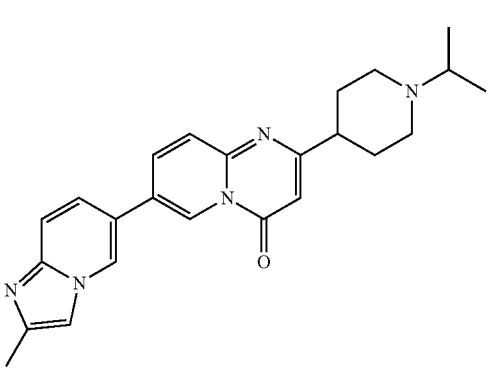

-continued
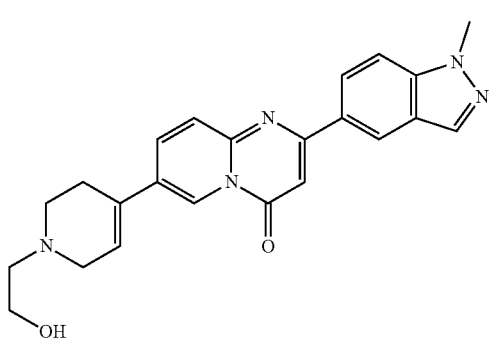
471
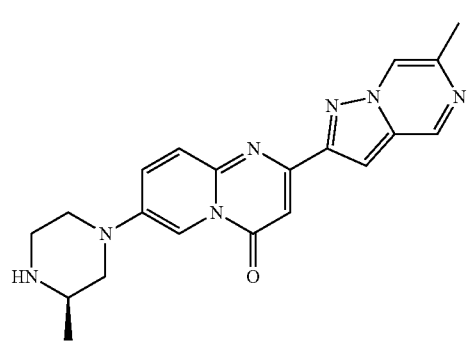
472
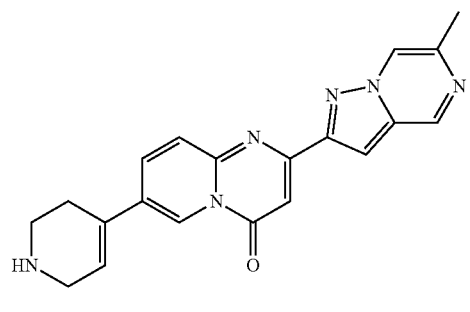
473
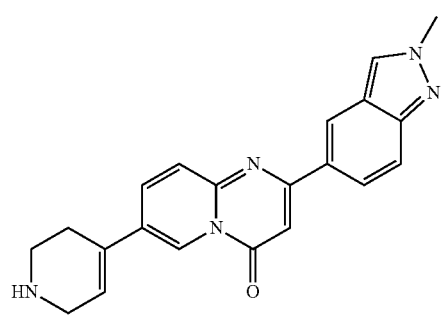
474
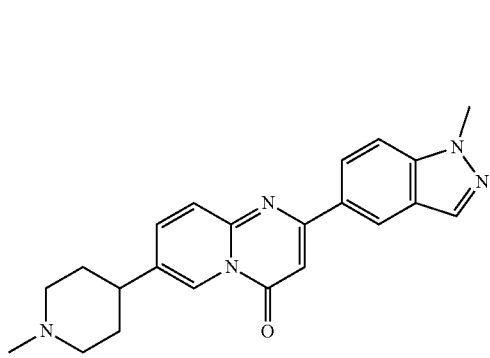
475
-continued
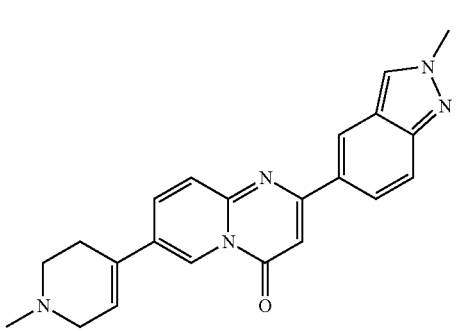
476
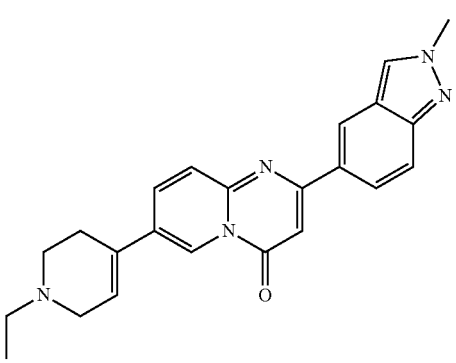
477
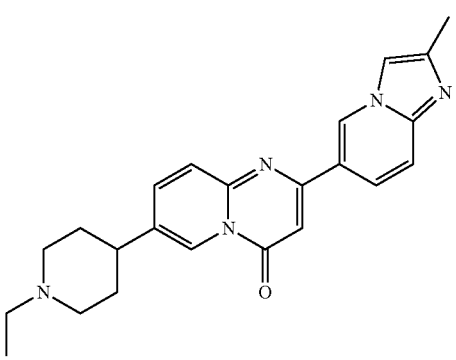
478
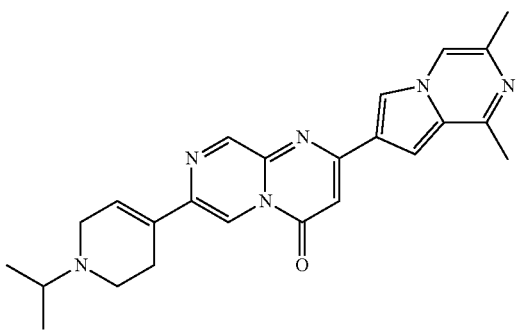
479

161
-continued
480
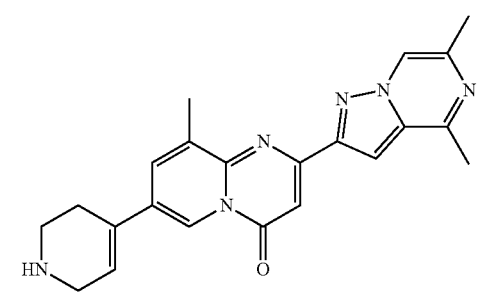
481
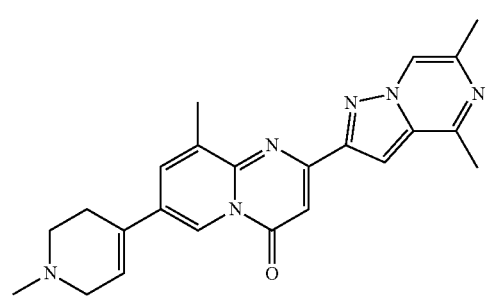
482
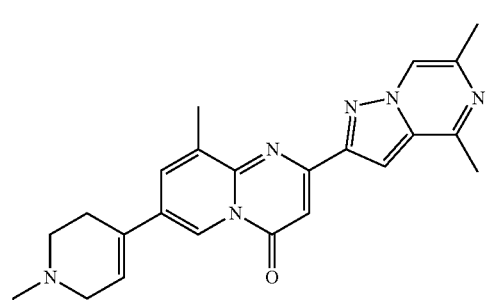
483
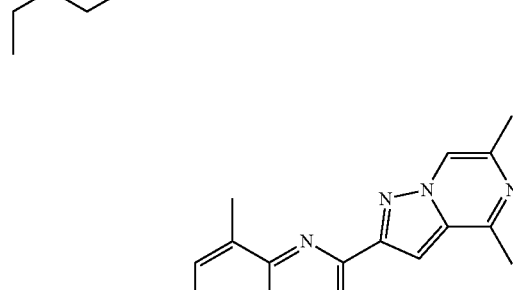
484
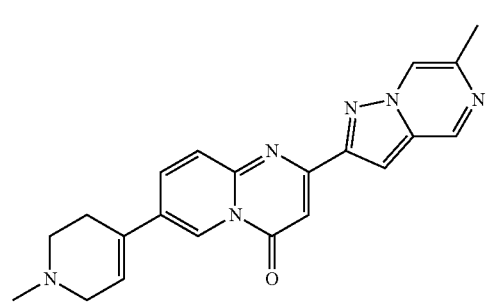
162
-continued
485
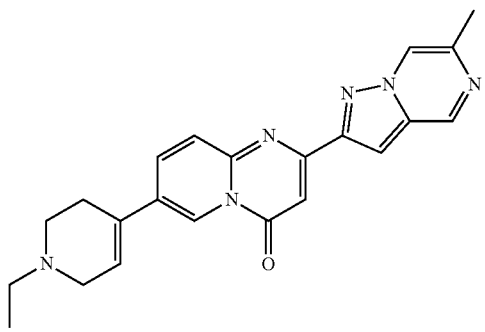
486
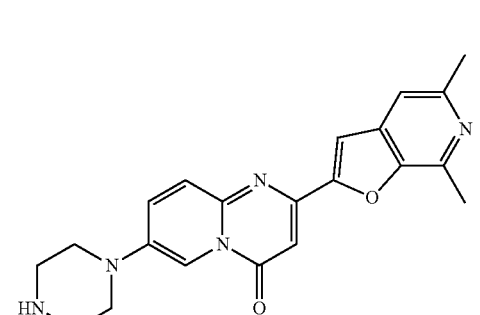
487
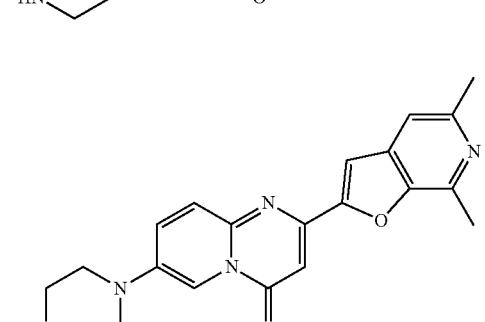
488
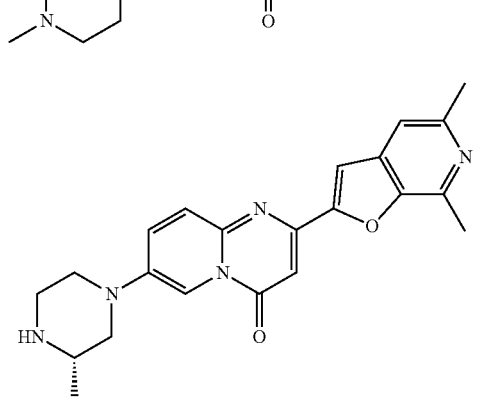
489
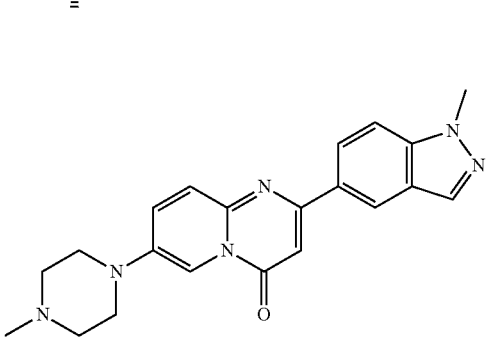

490 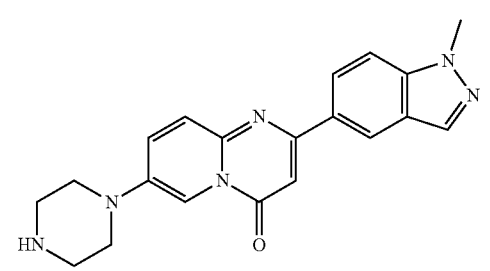
491 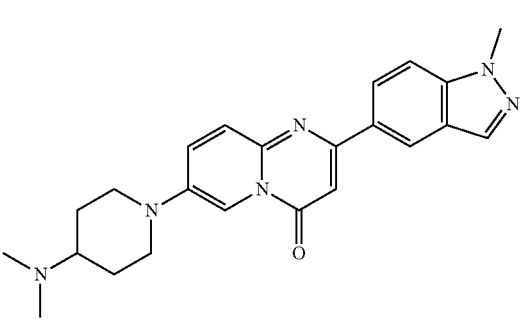
492 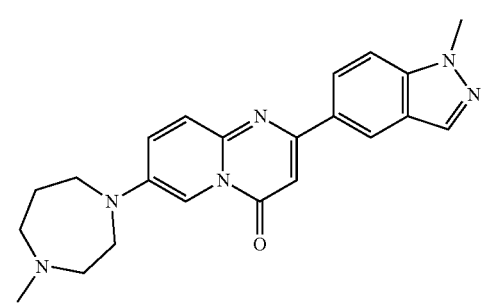
493 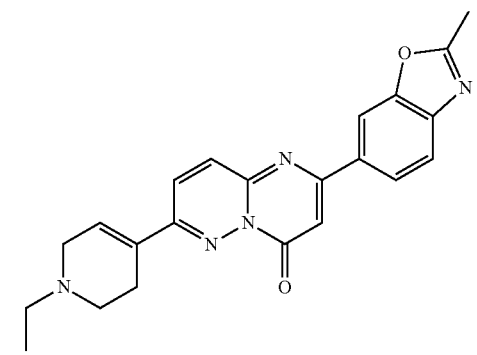
494 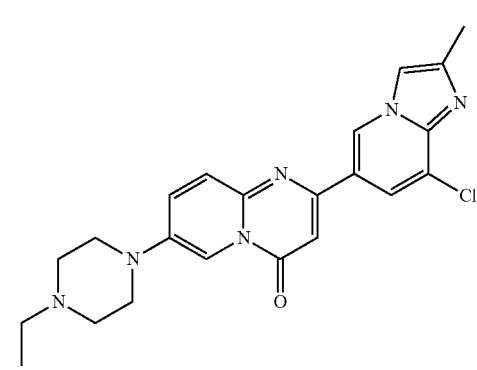
495 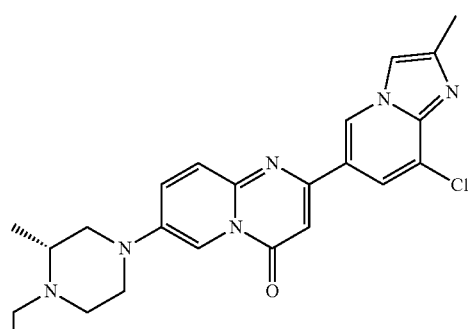
496 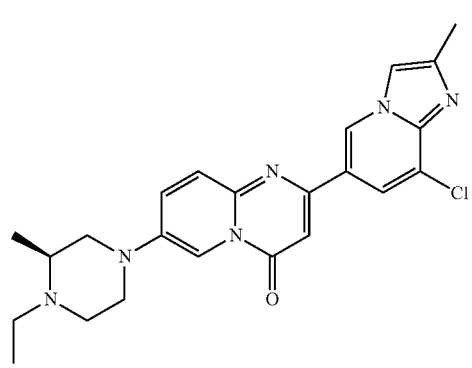
497 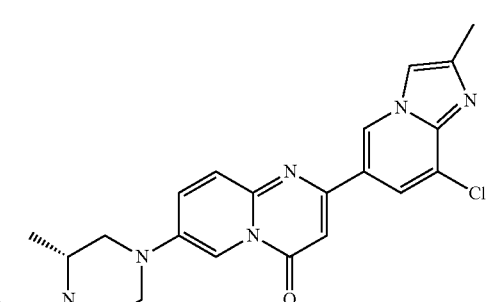
498 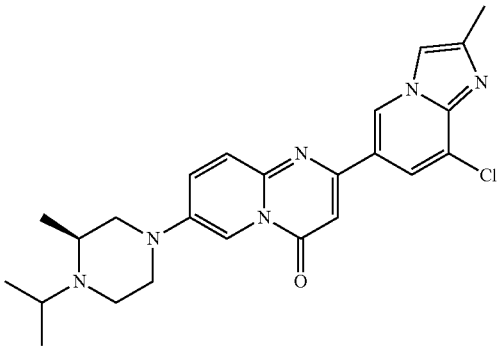

499
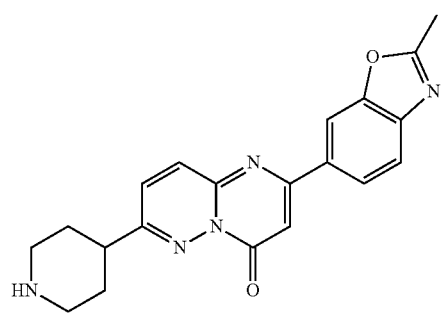
500
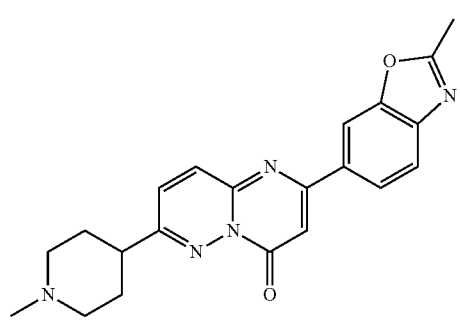
501
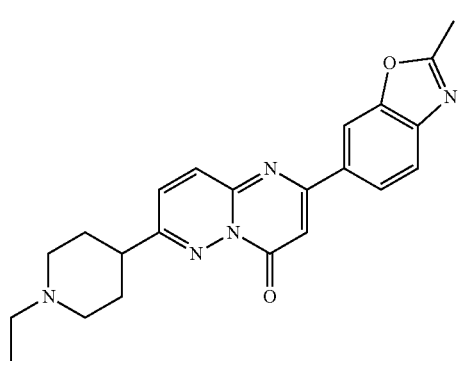
502
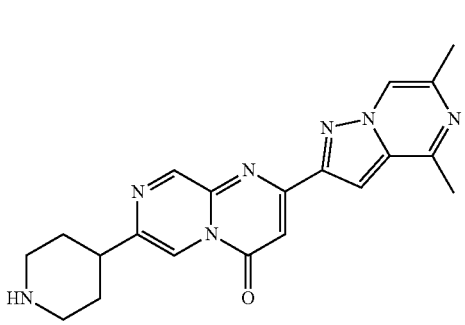
503
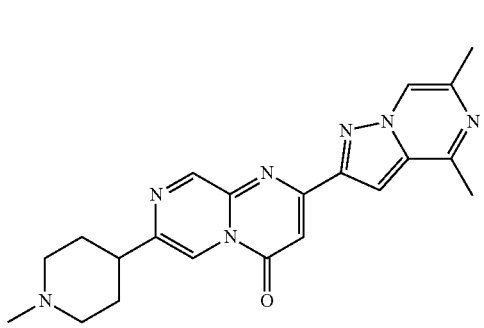
504
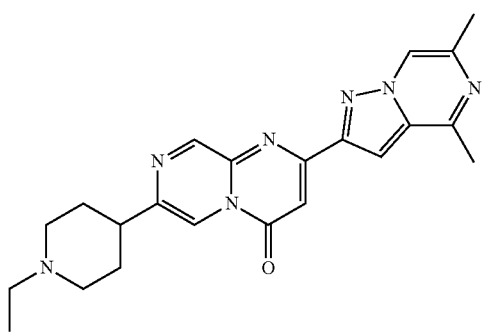
505
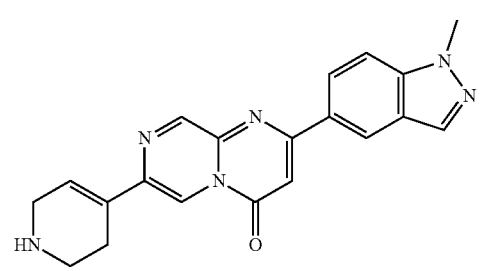
506
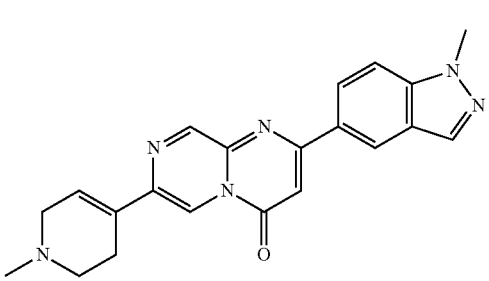
507
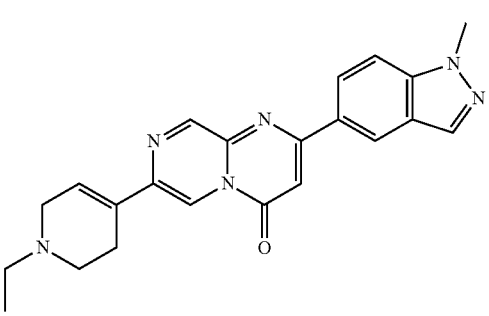
508
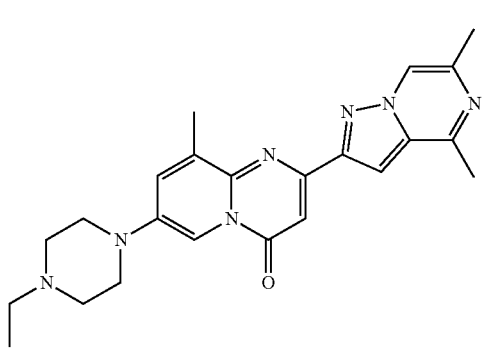

509
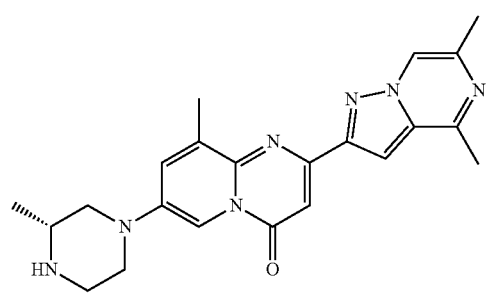
510
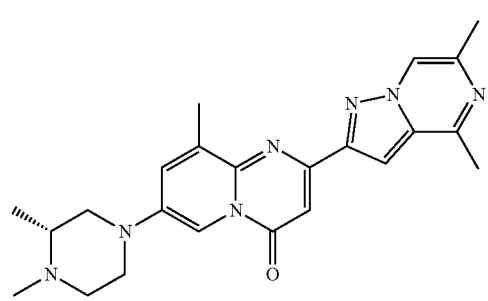
511
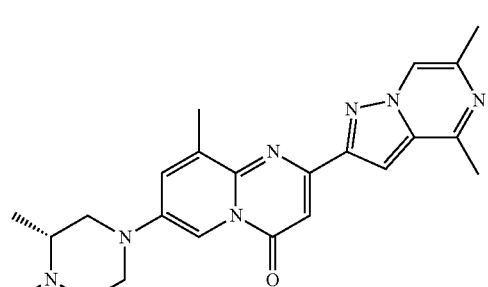
512
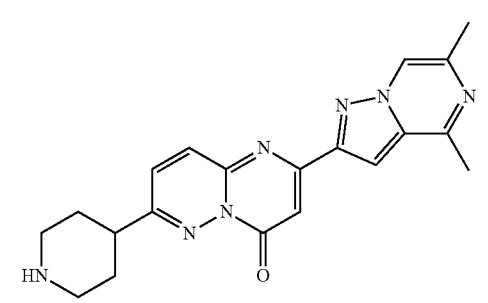
513
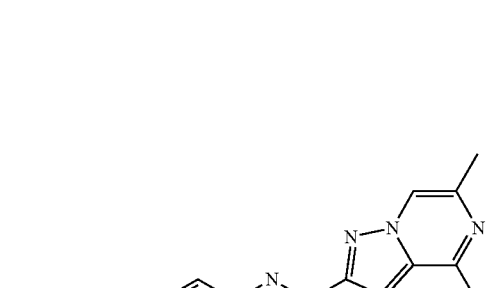
514
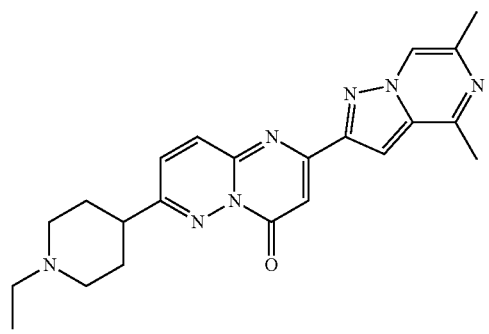
515
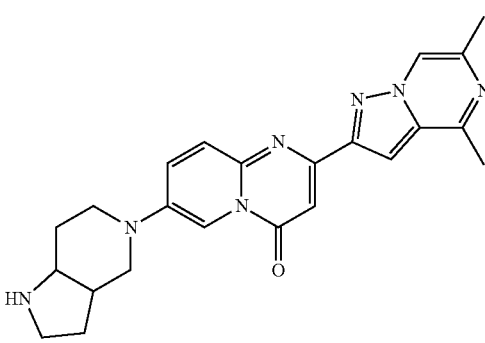
516
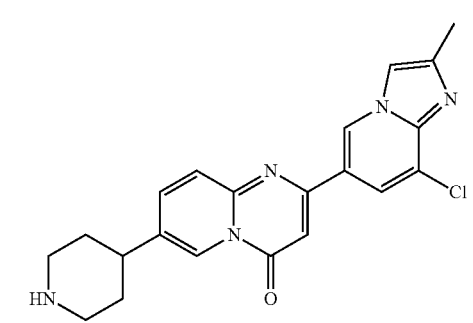
517
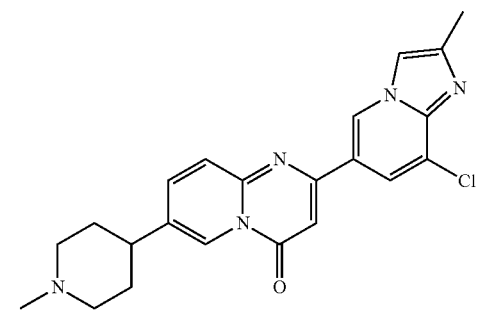
518
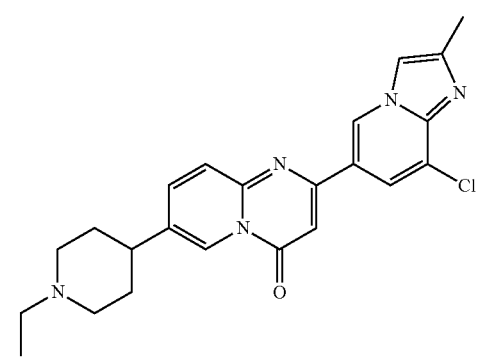

519 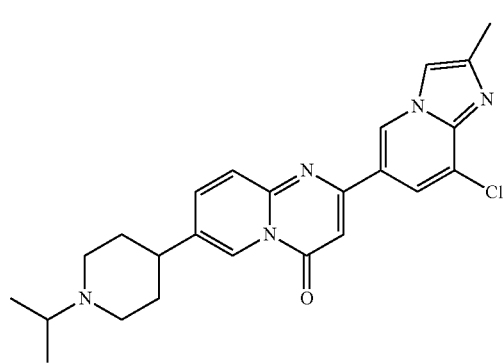
520 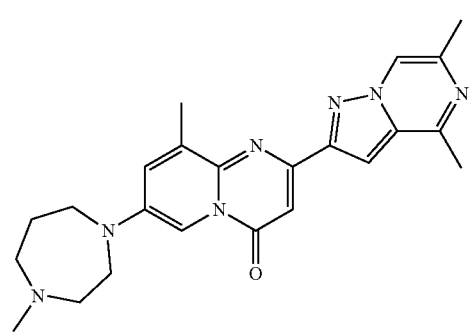
521 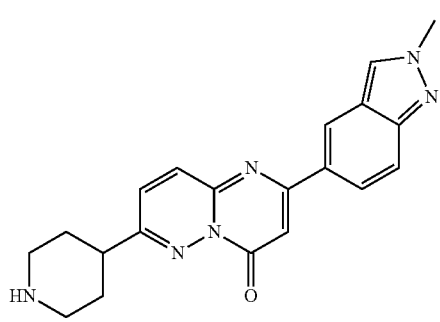
522 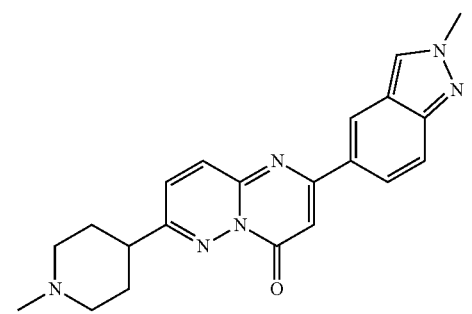
523 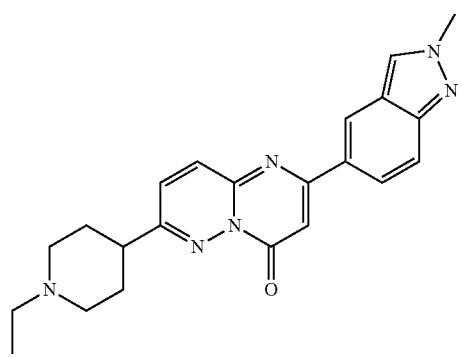
524 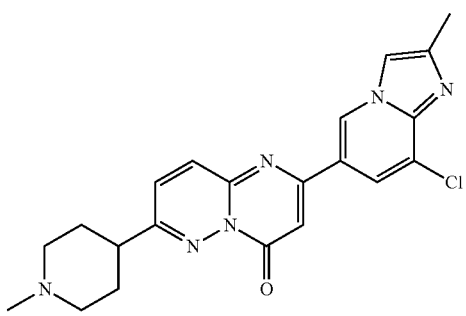
525 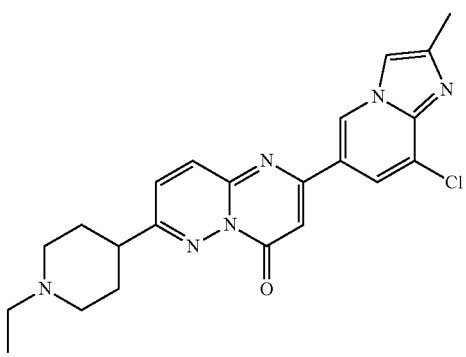
526 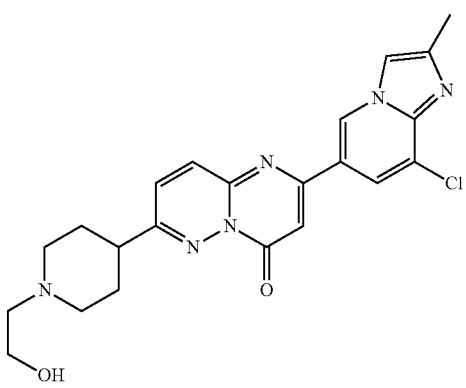

527
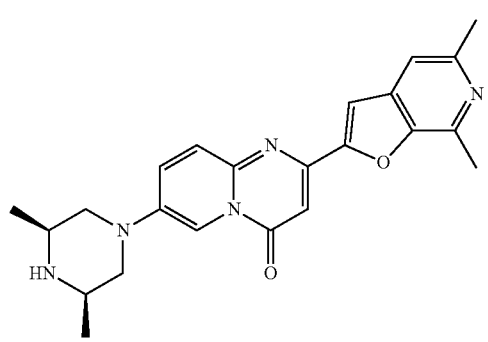
528
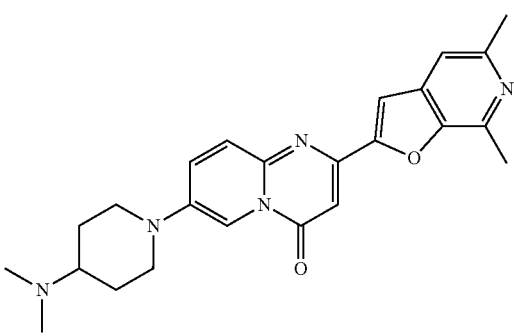
529
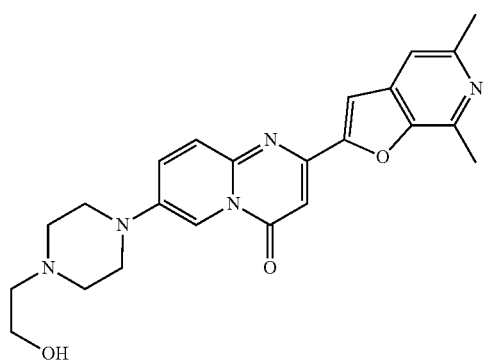
530
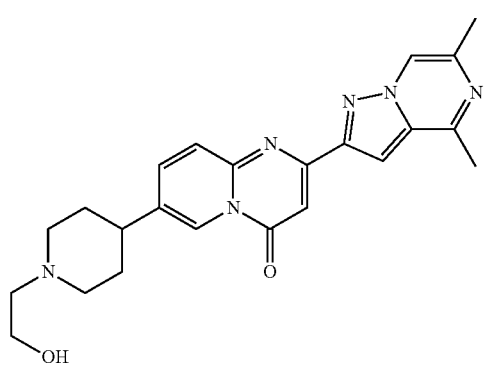
531
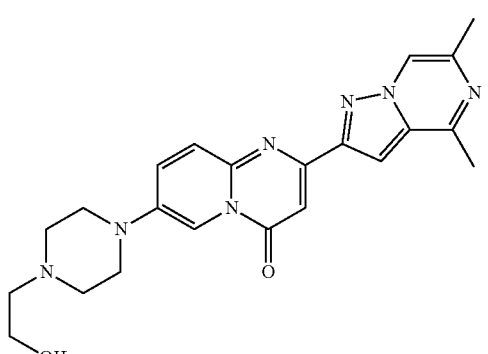
532
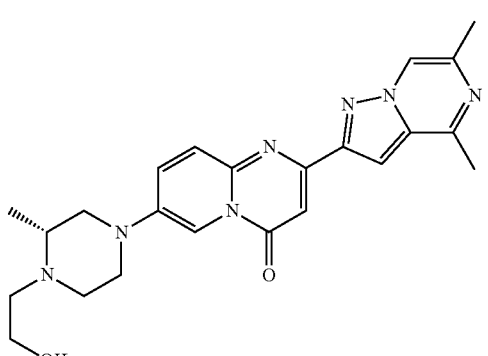
533
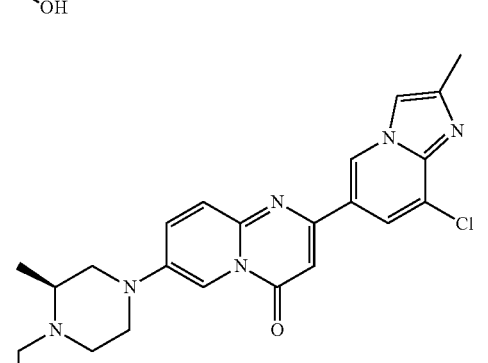
534
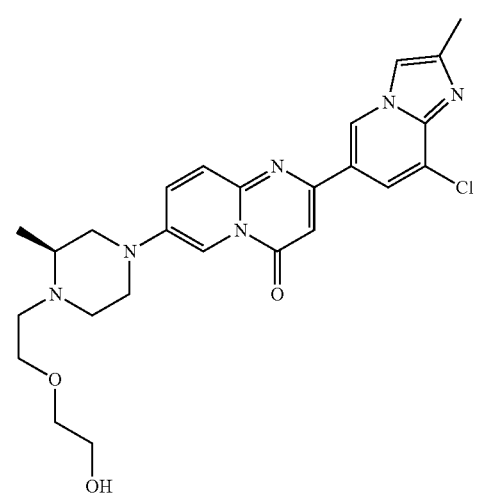

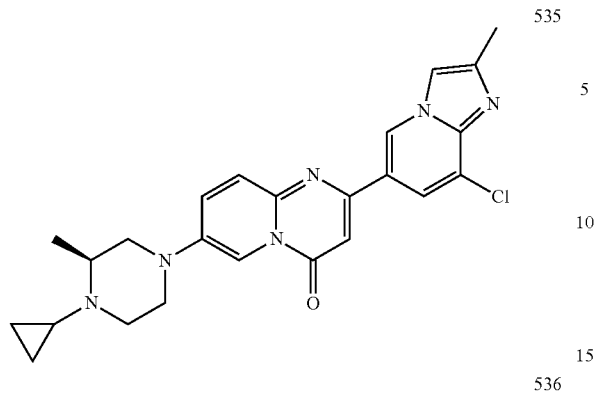
535
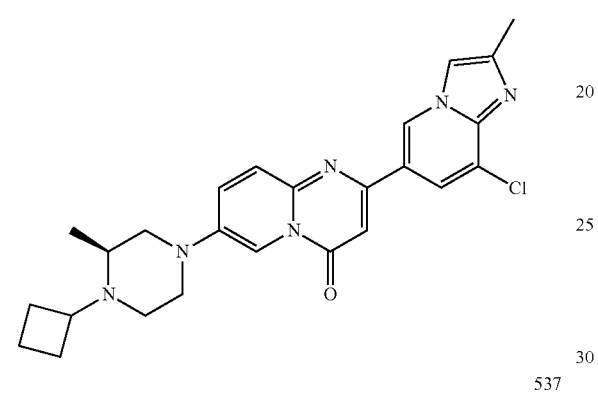
536
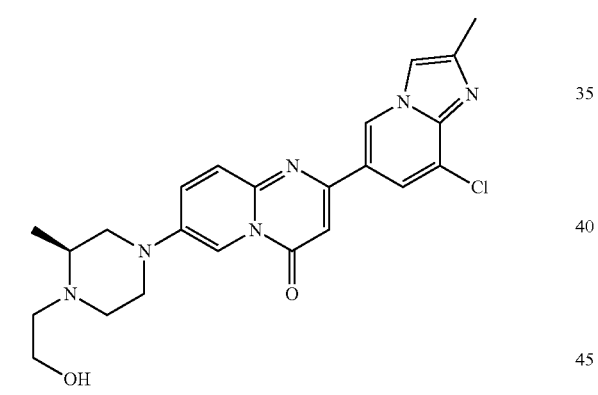
537
538
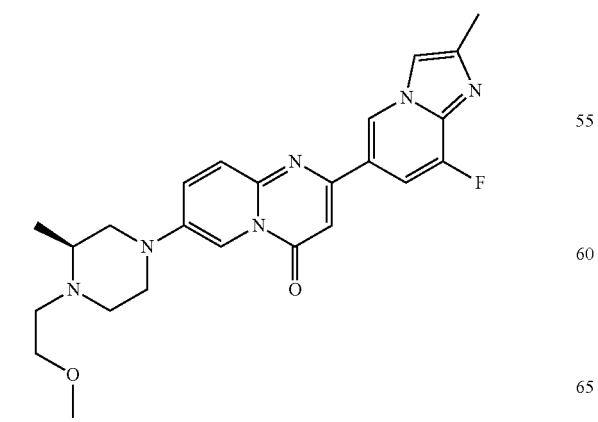
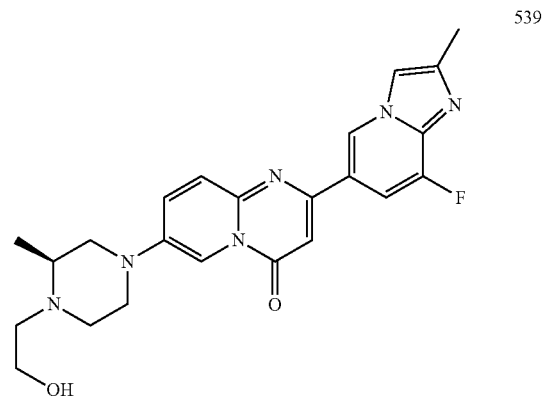
539
540
541
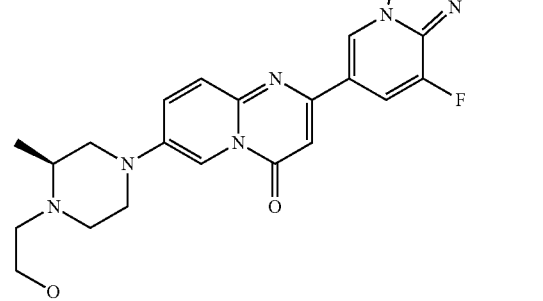
542

543
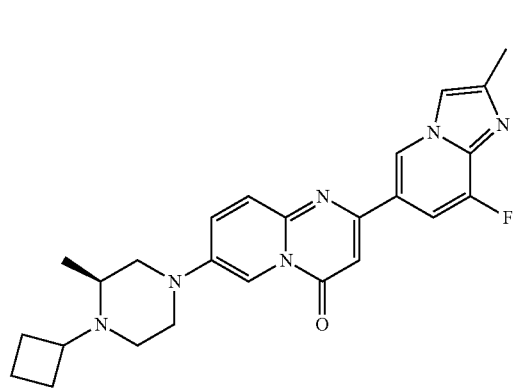
544
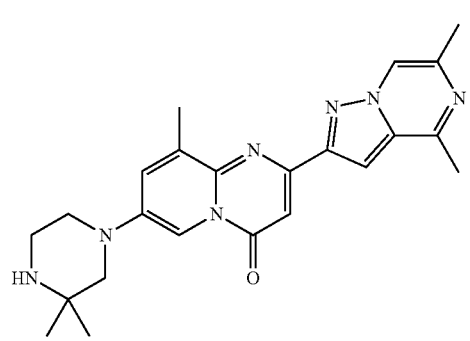
545
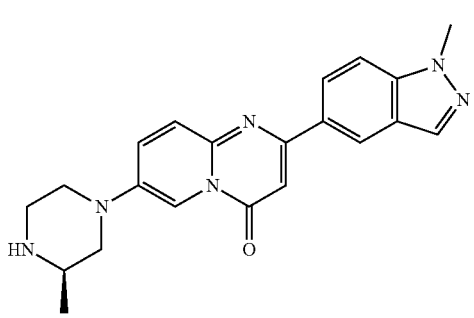
546
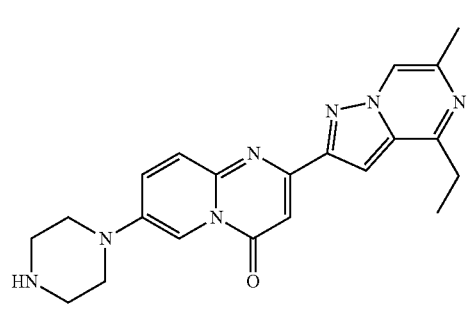
547
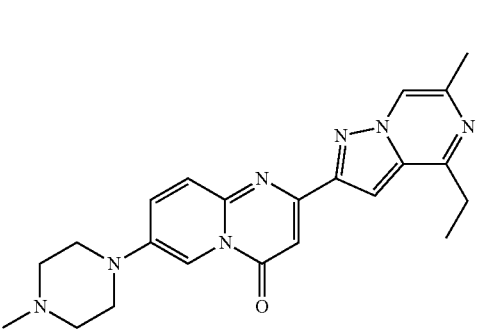
548
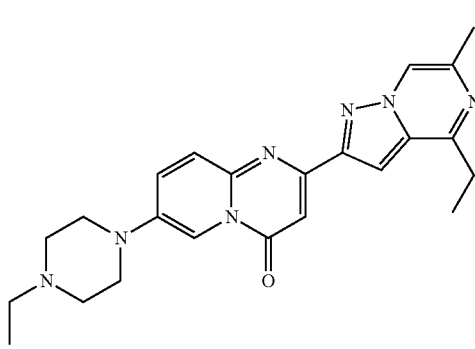
549
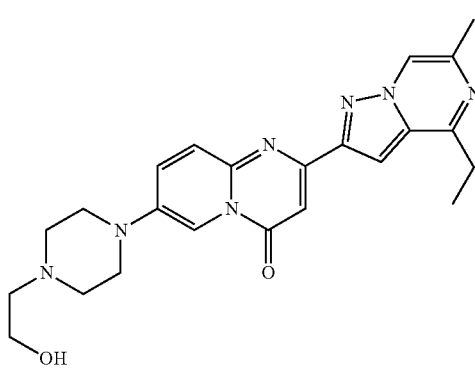
550
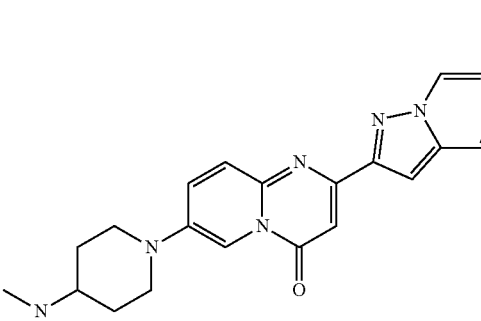
551
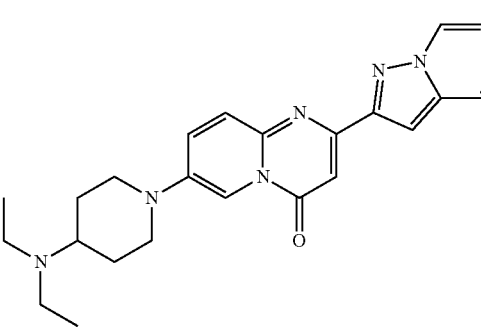

552
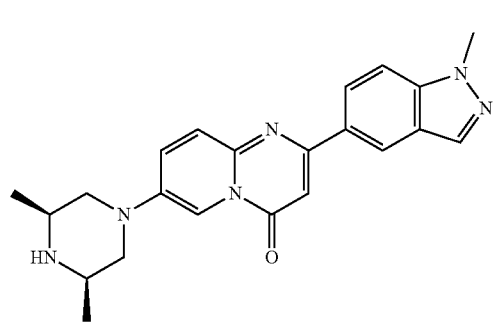
553
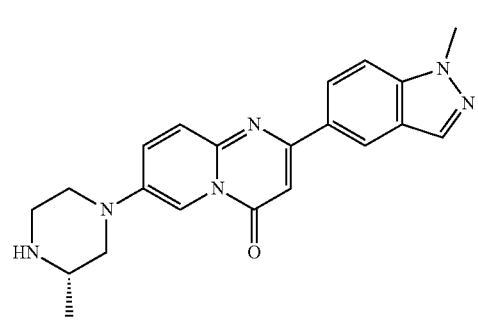
554
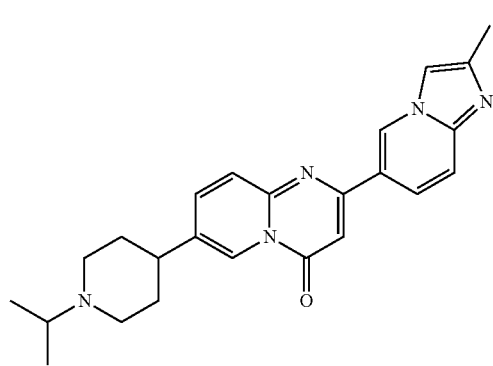
555
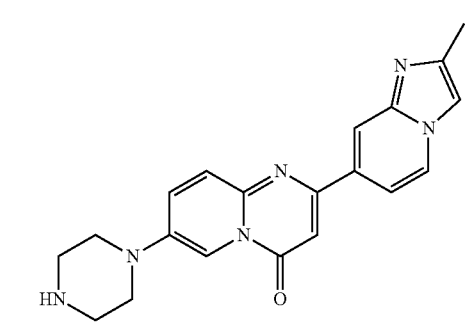
556
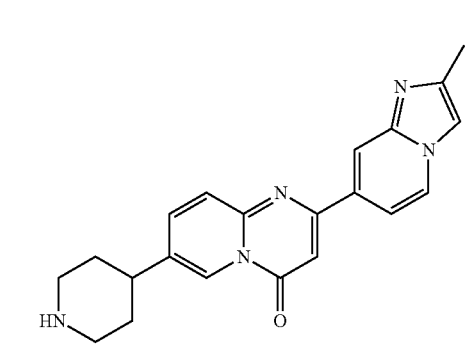
557
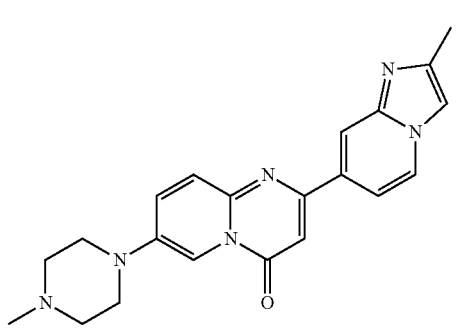
558
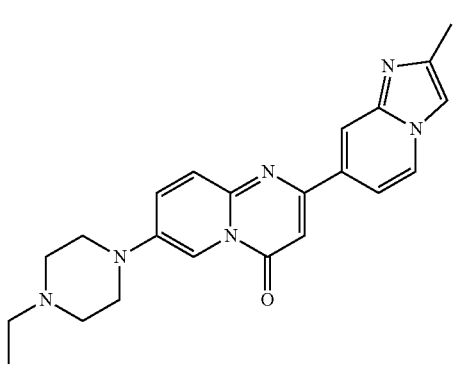
559
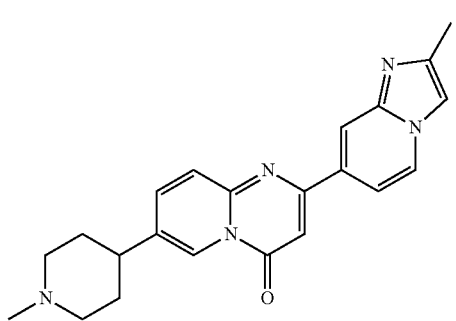
560
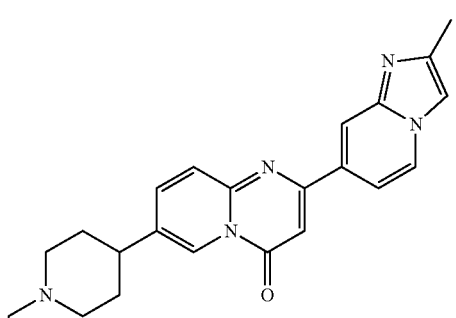
561
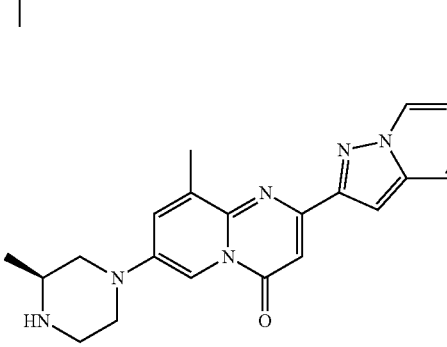

562
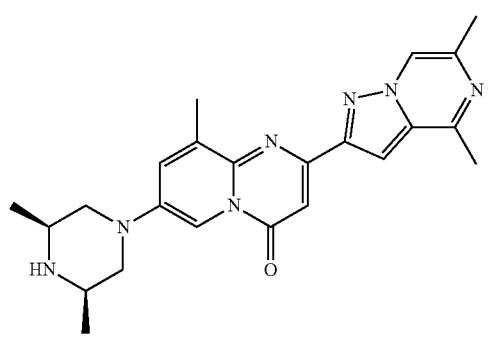
563
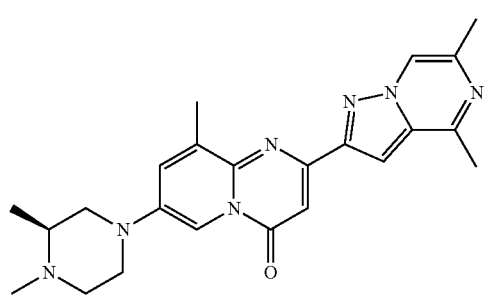
564
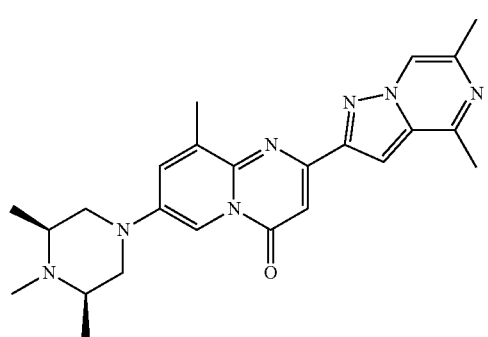
565
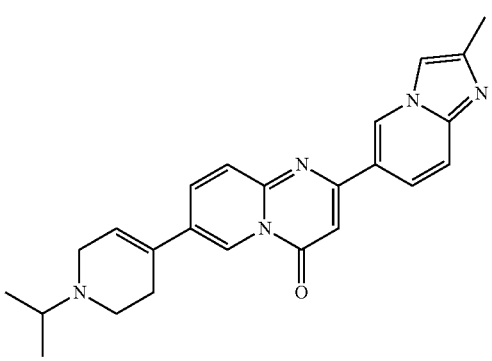
566
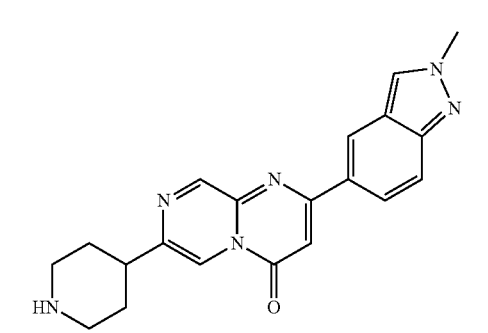
567
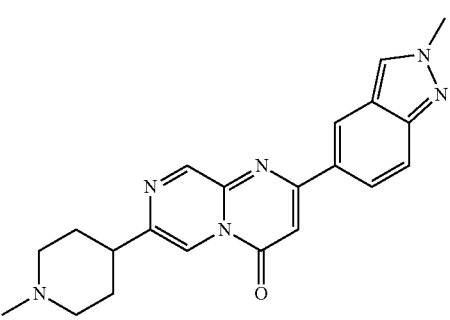
568
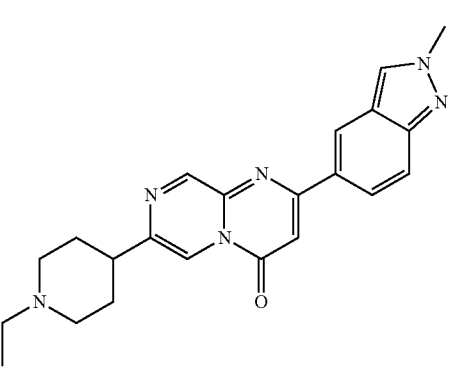
569
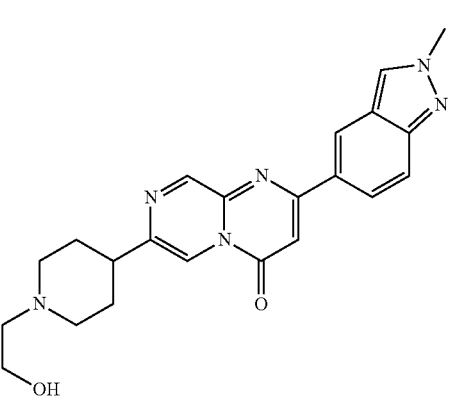
570
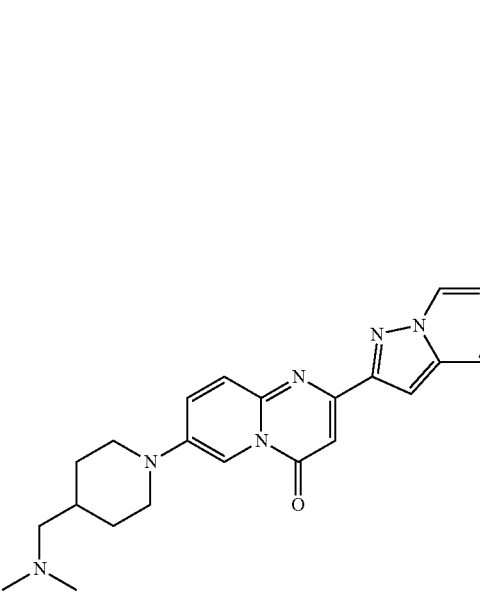

-continued
571
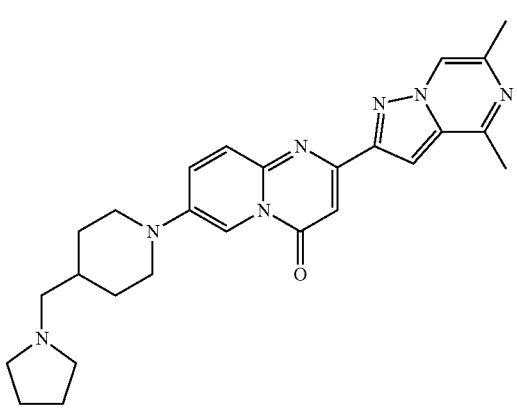
572
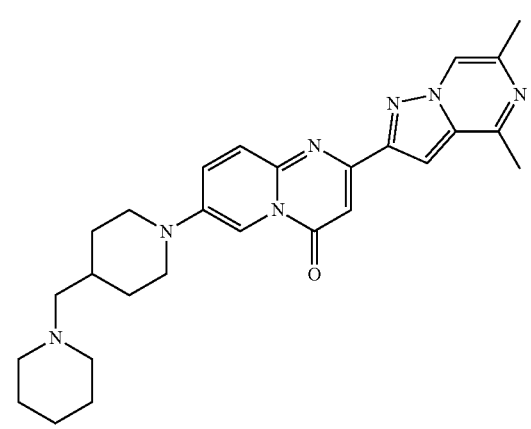
573
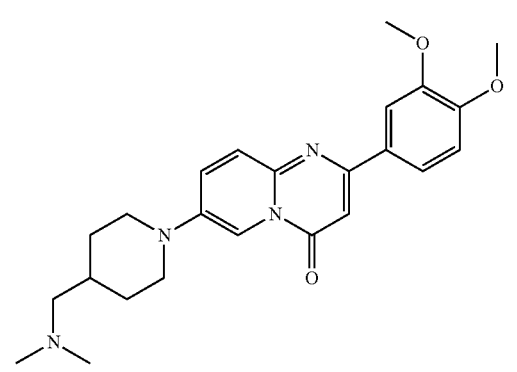
574
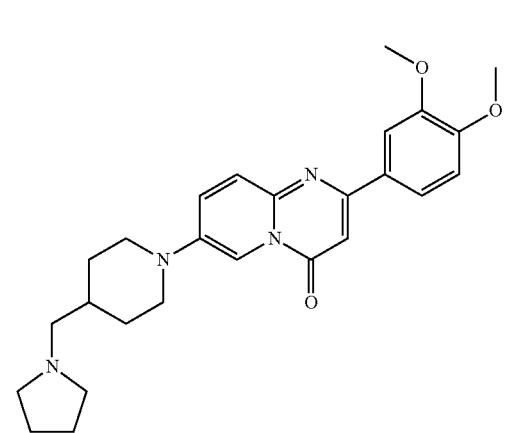
-continued
575
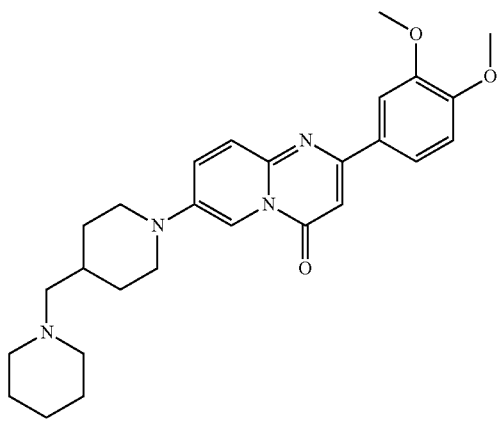
576
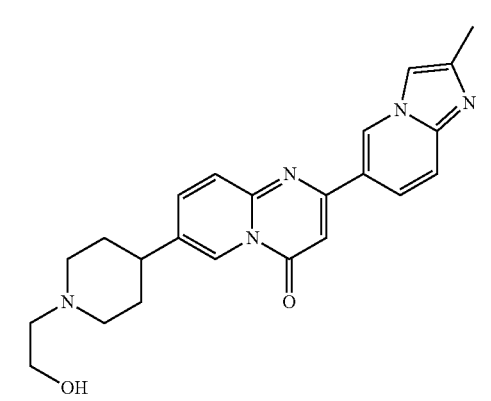
577
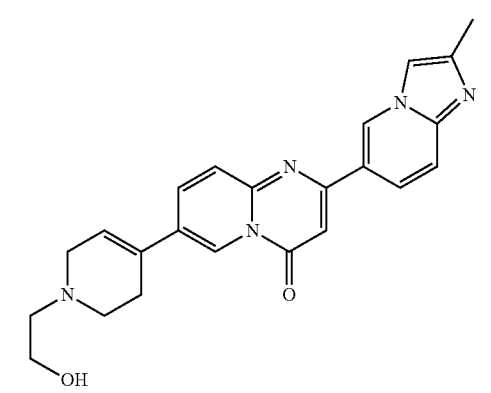
578
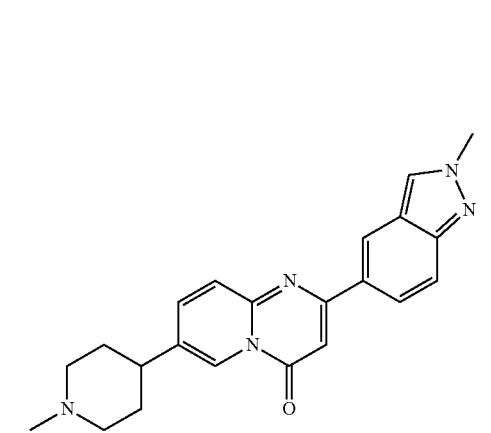

579
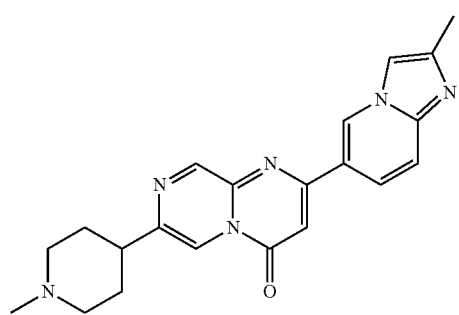
580
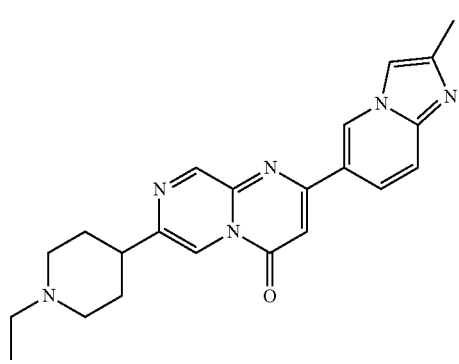
581
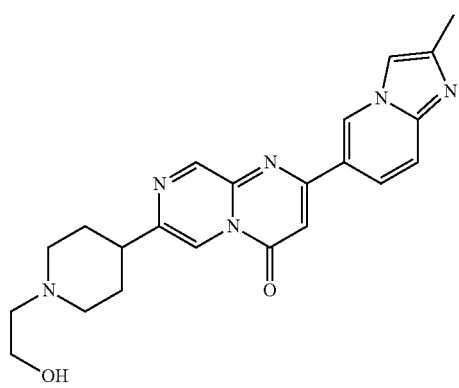
582
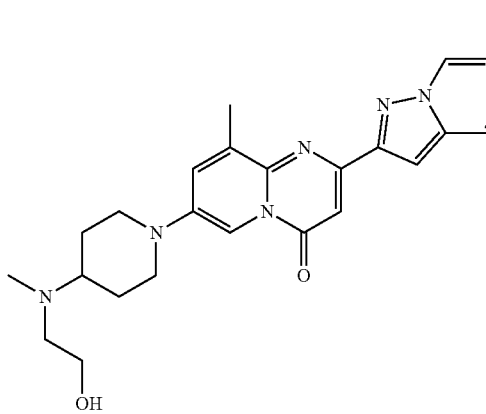
583
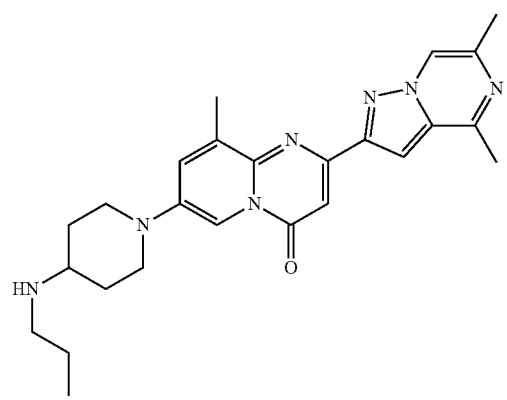
584
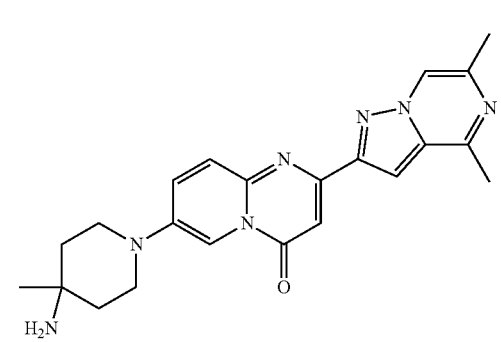
585
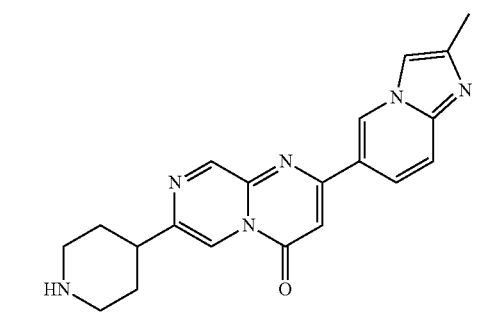
586
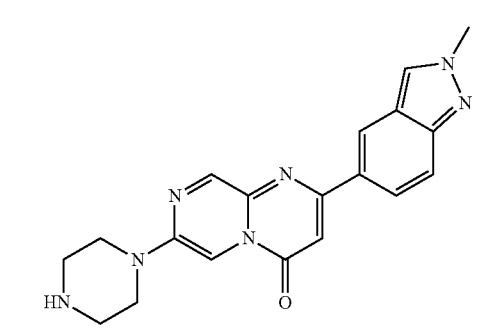

587 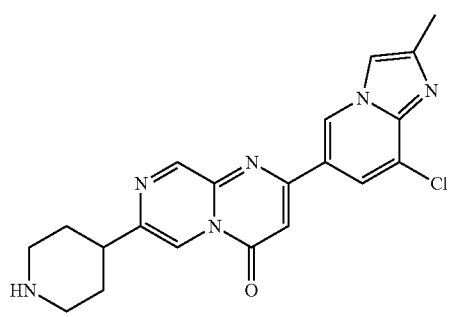
588 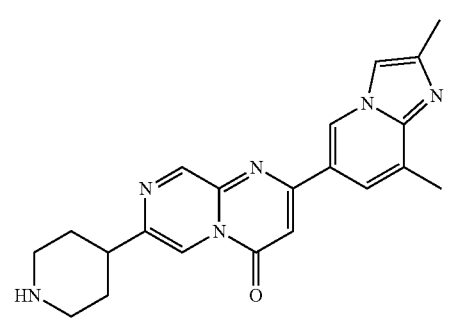
589 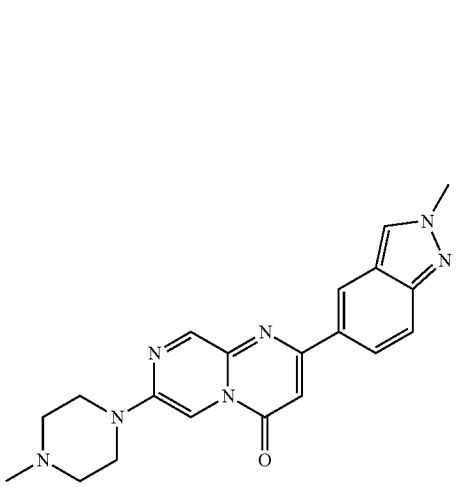
590 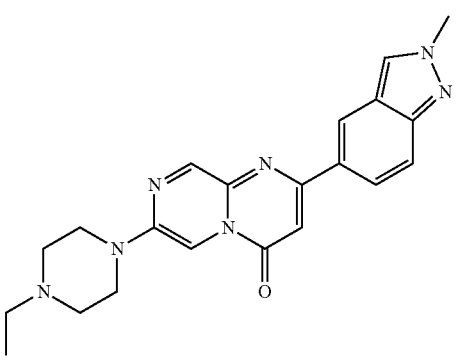
591 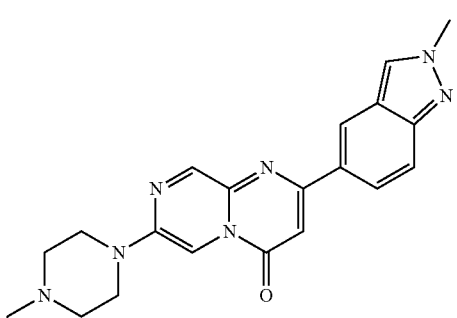
592 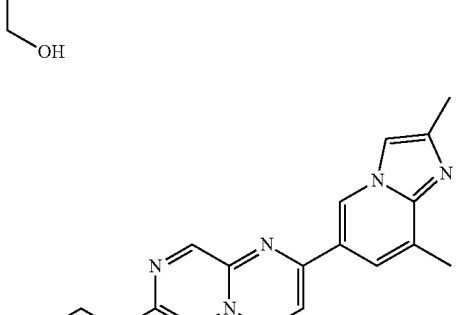
593 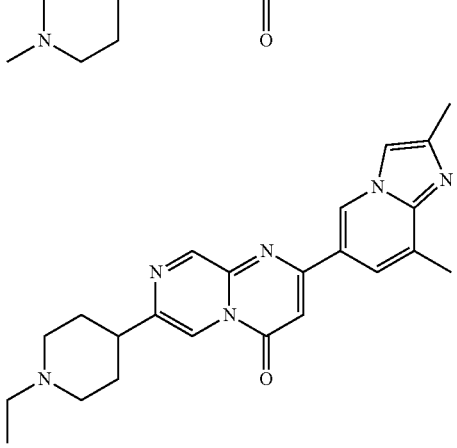
594 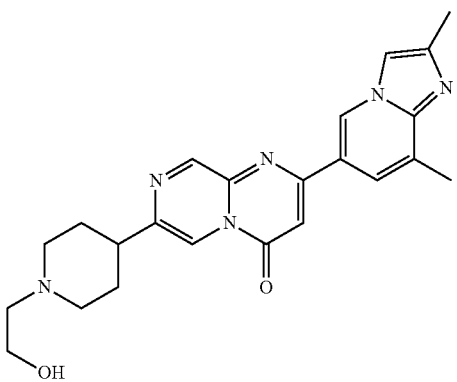

-continued
595
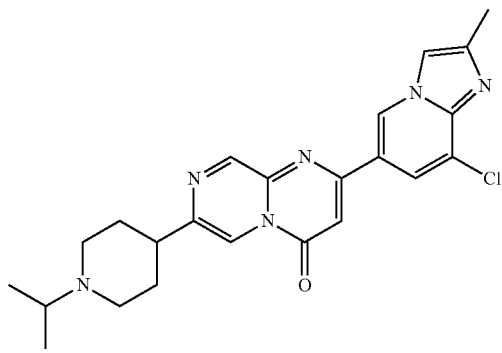
596
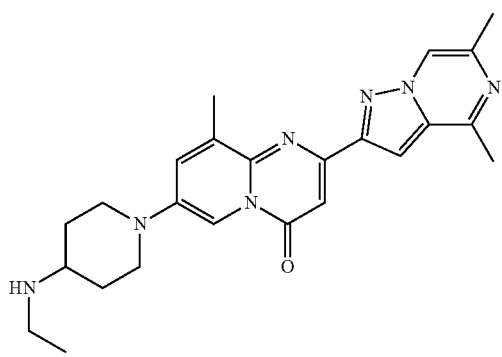
597
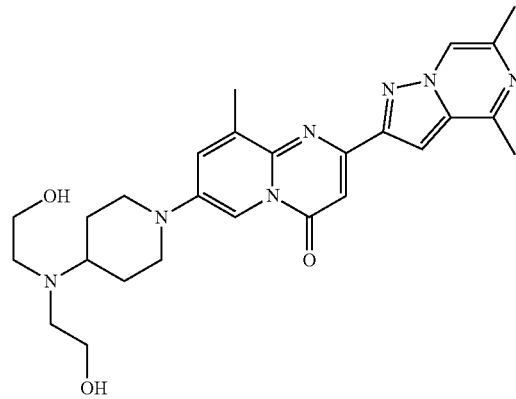
598
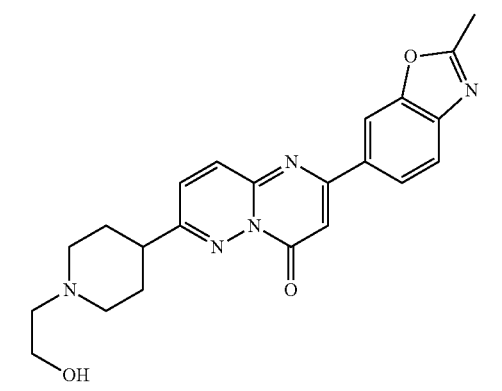
-continued
599
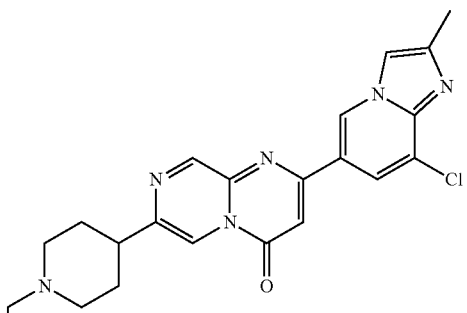
600
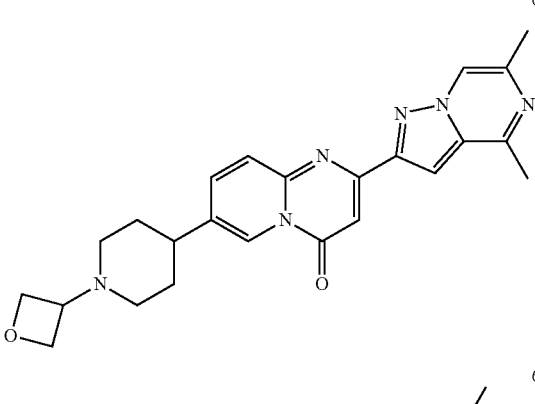
601
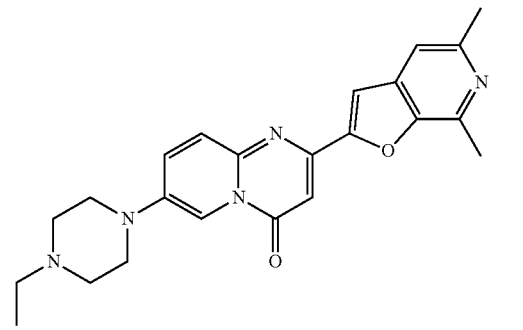
602
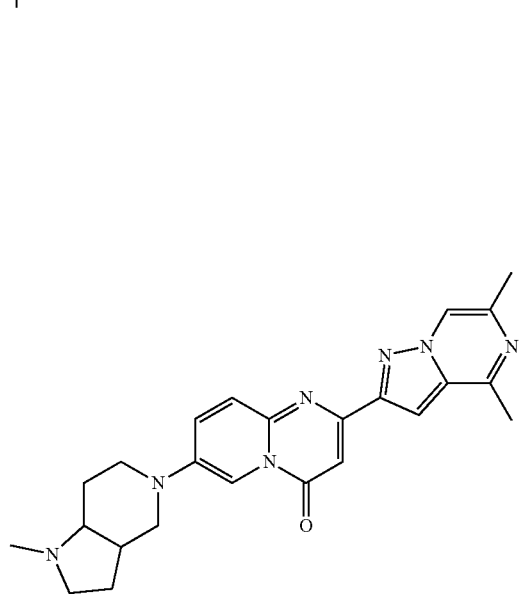

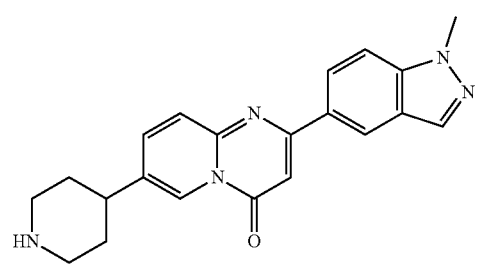
603
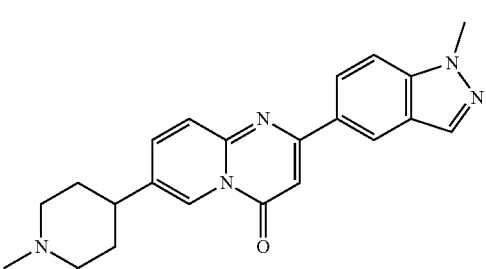
604
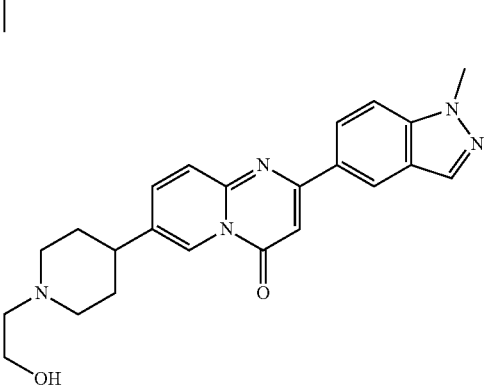
605
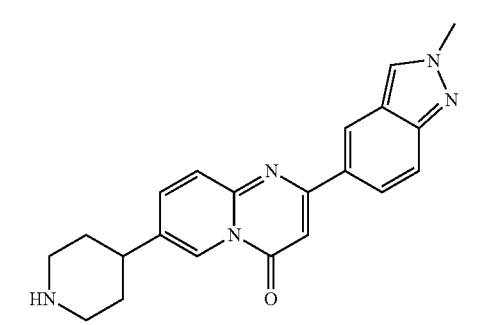
606
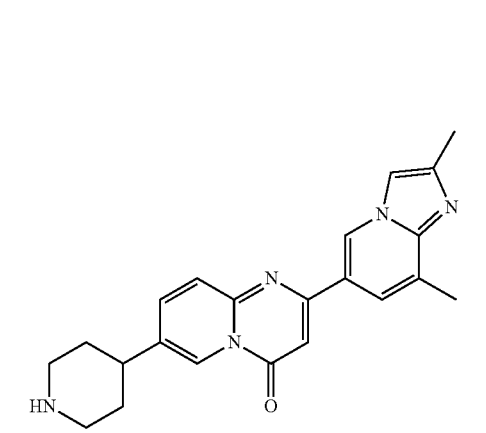
607
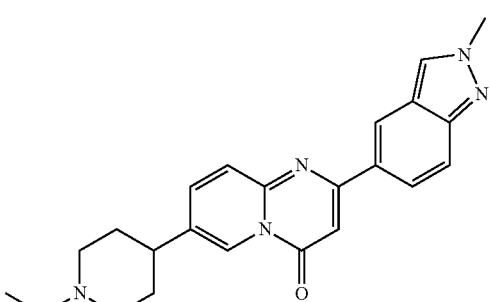
608
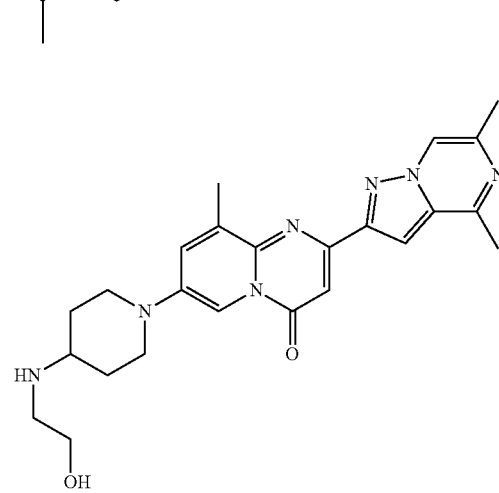
609
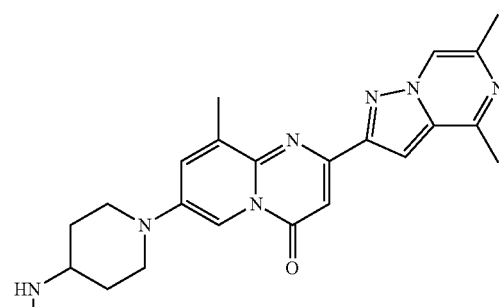
610
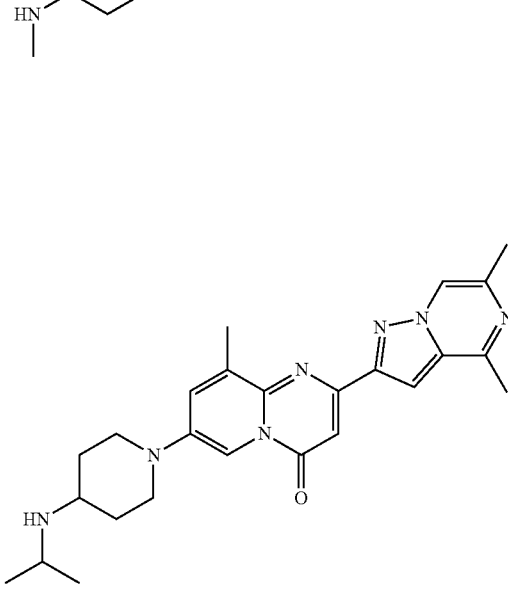
611

612 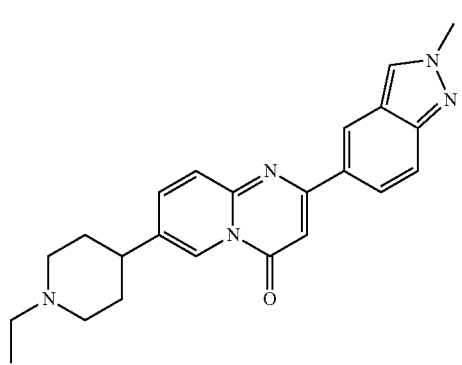
613 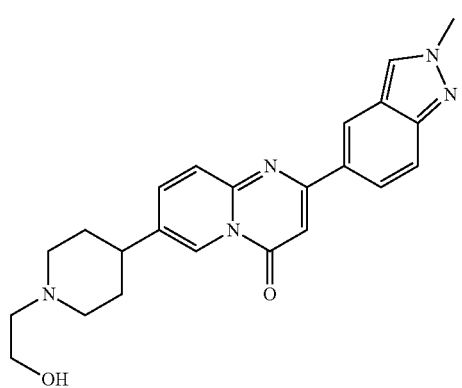
614 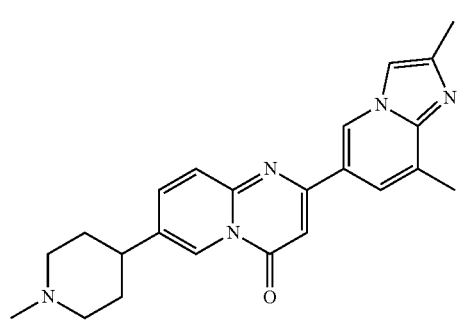
615 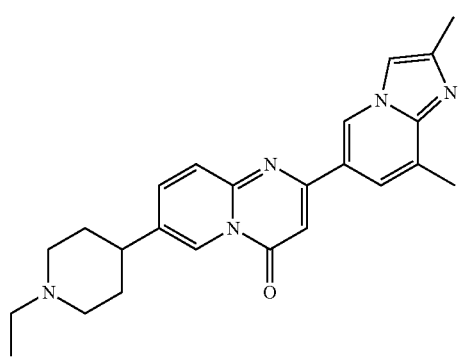
616 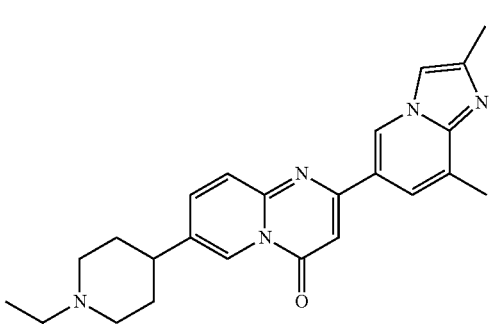
617 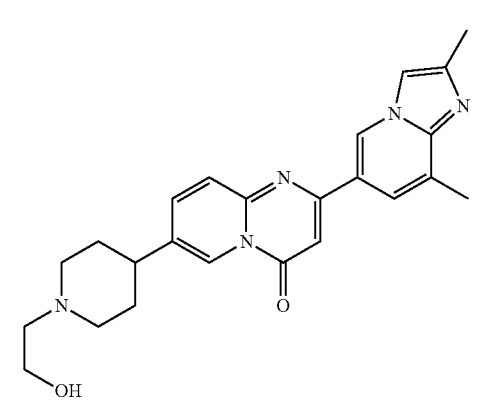
618 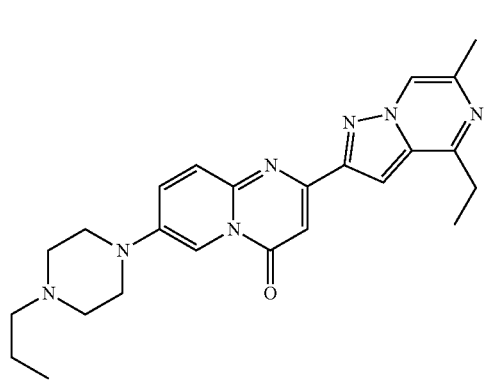
619 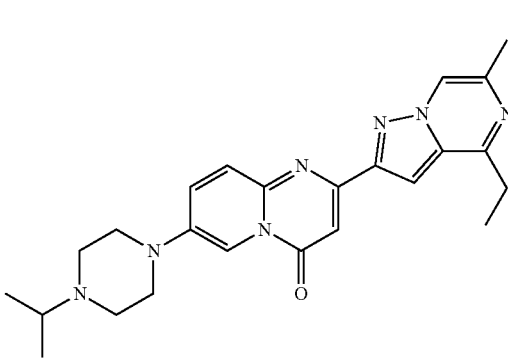

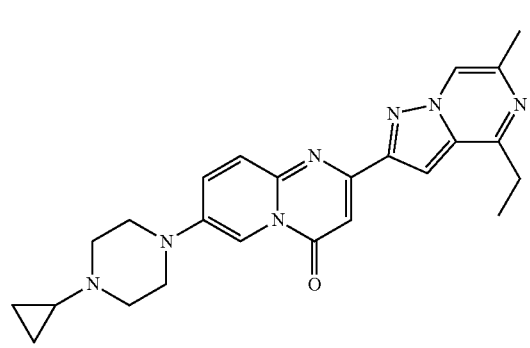
620
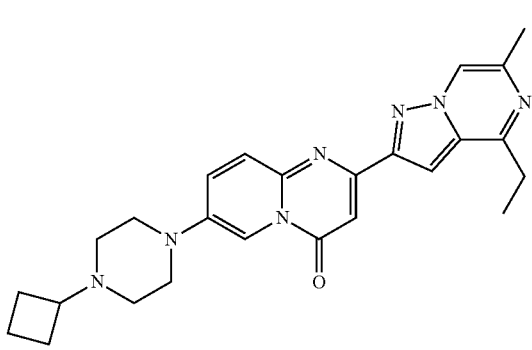
621
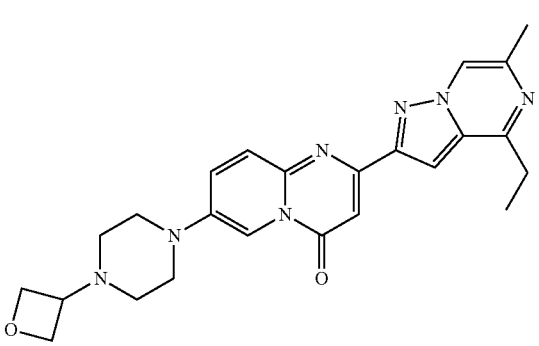
622
623
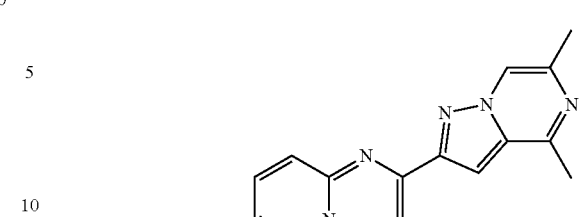
624
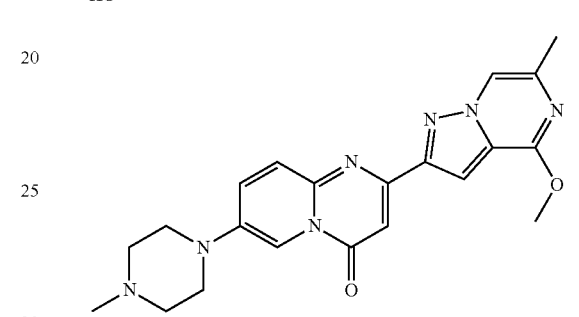
625
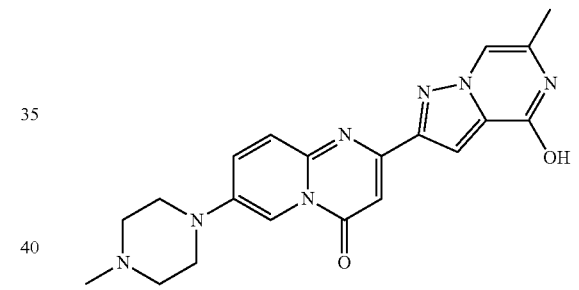
626
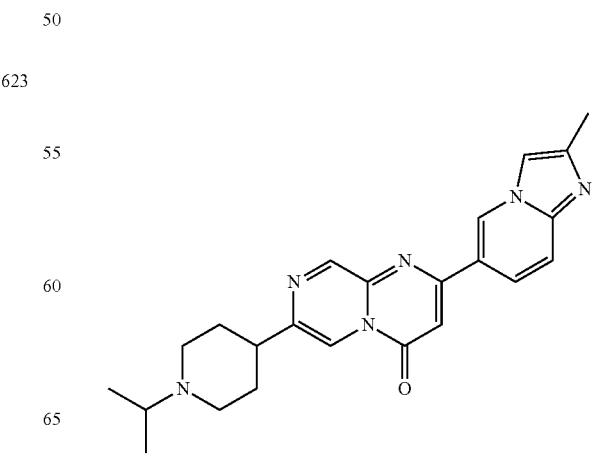
627

628
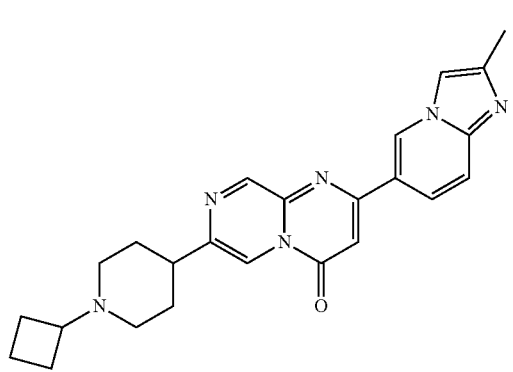
629
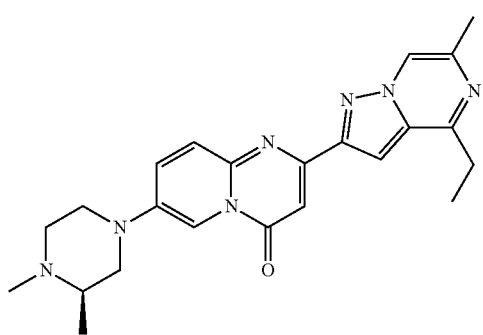
630
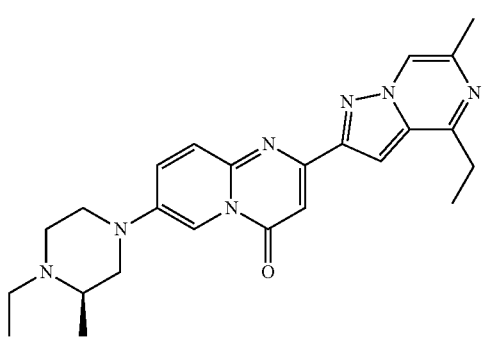
631
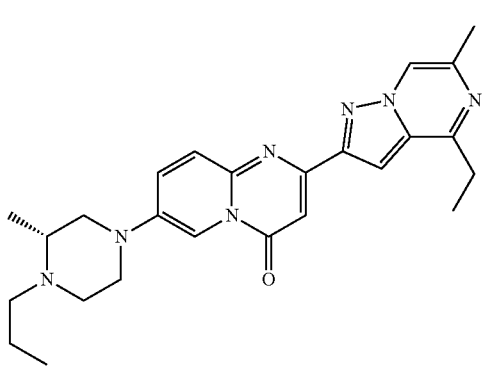
632
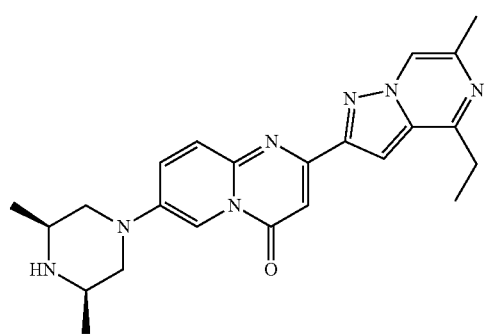
633
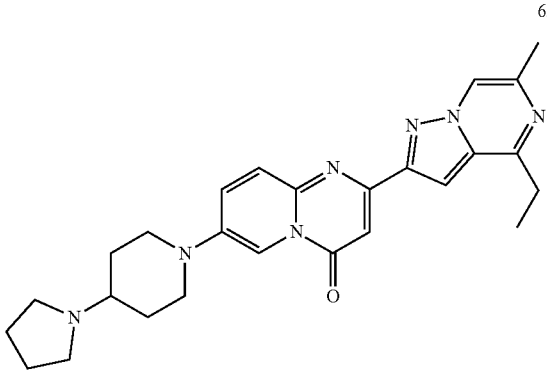
634
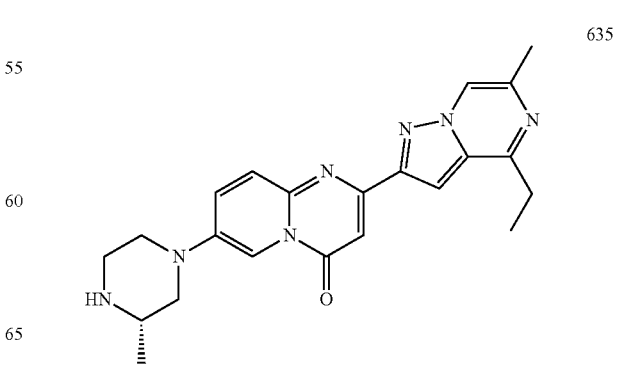
635
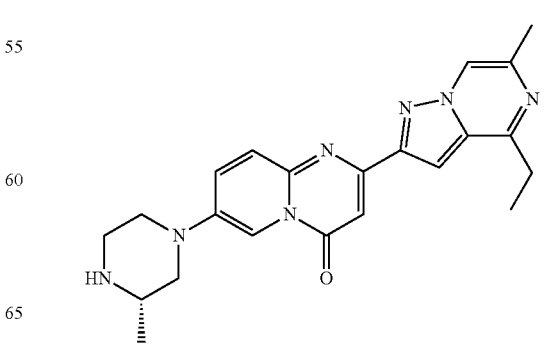

636
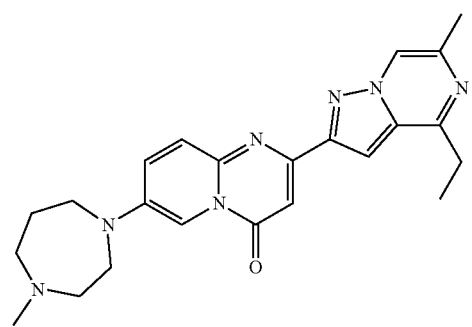
637
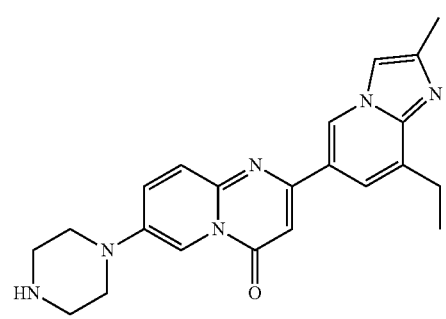
638
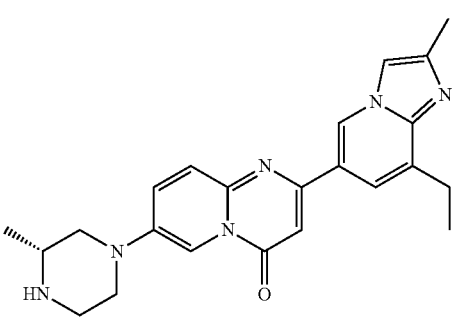
639
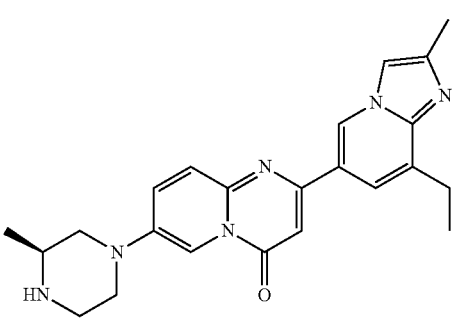
640
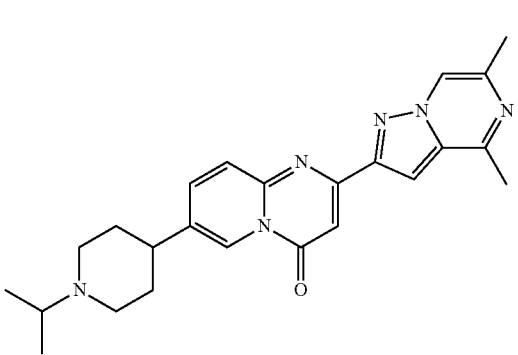
641
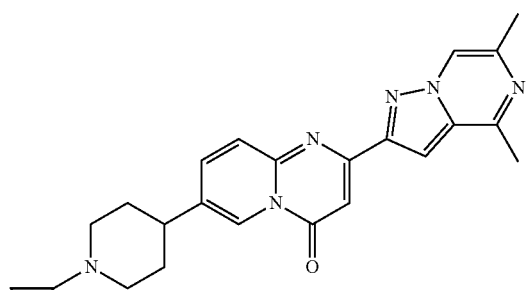
642
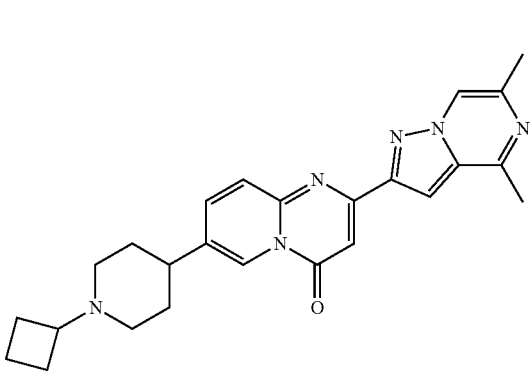
643
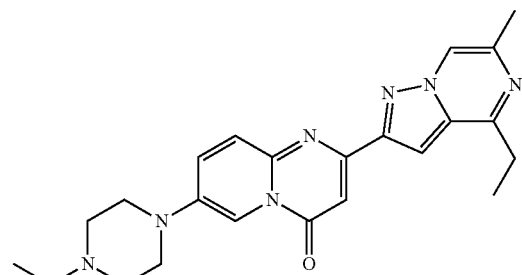
644
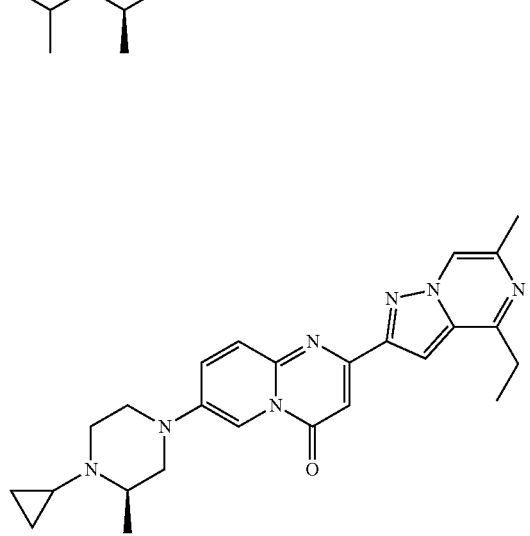

-continued
645
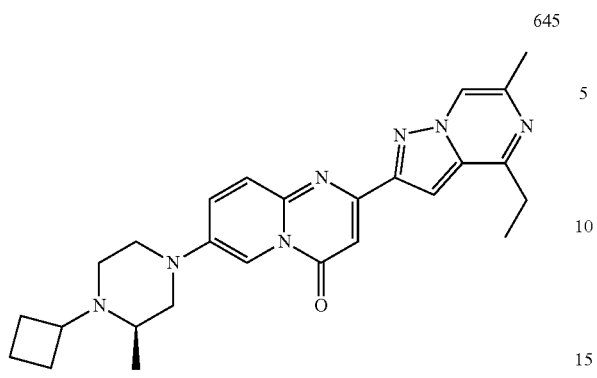
646
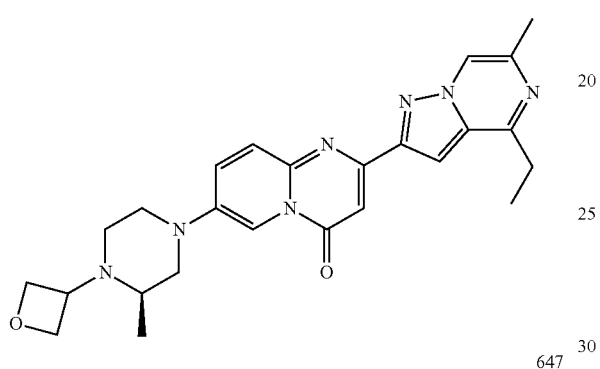
647
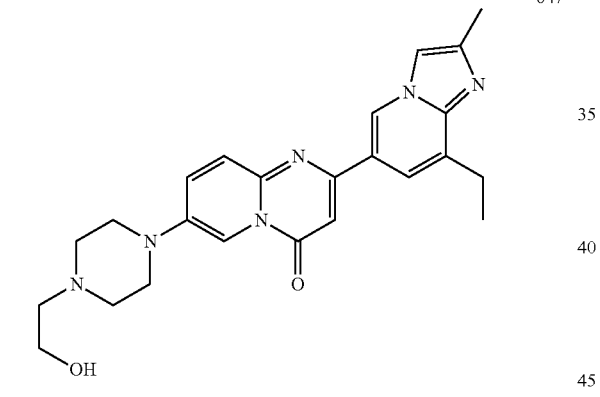
648
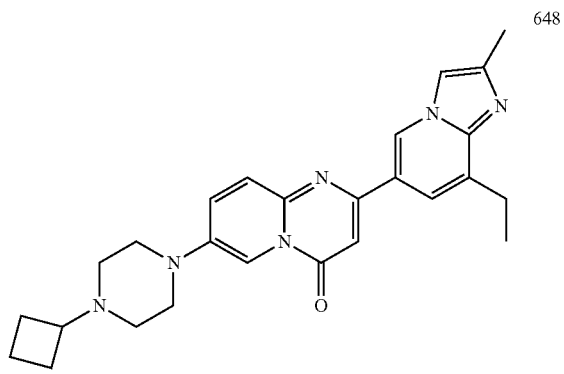
-continued
649
650
651
652
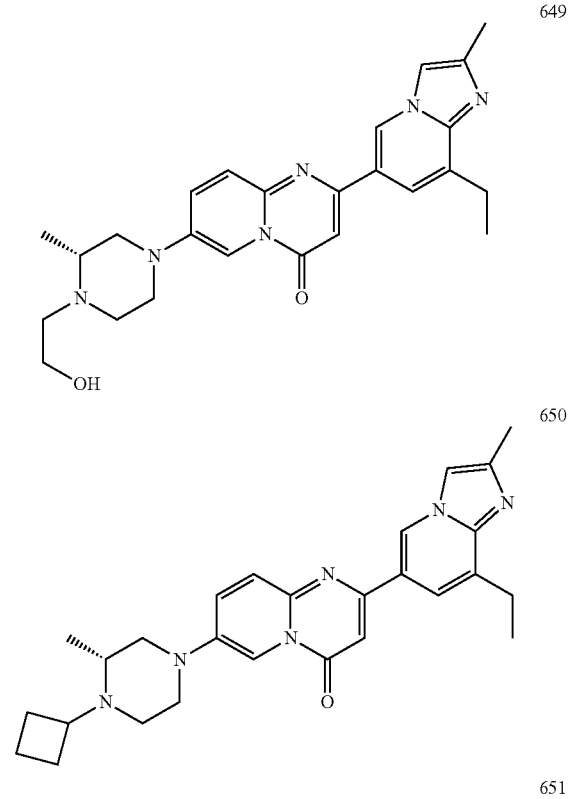
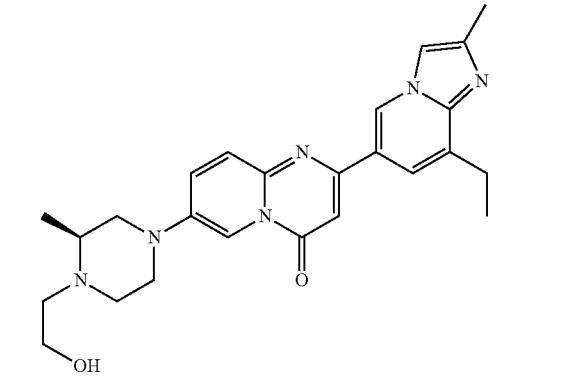

201
-continued
653
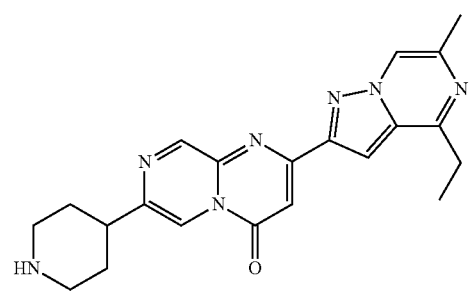
654
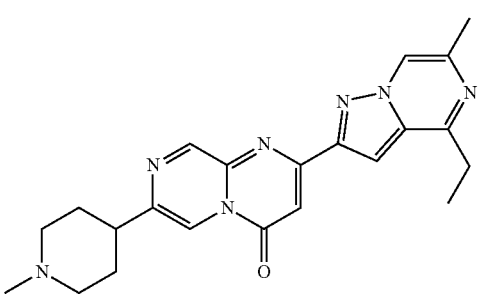
655
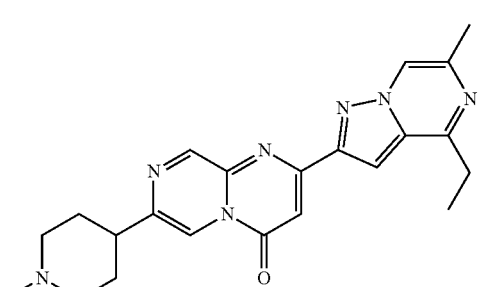
656
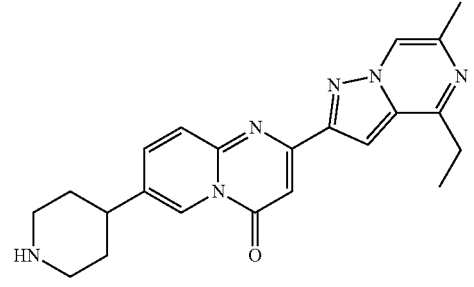
657
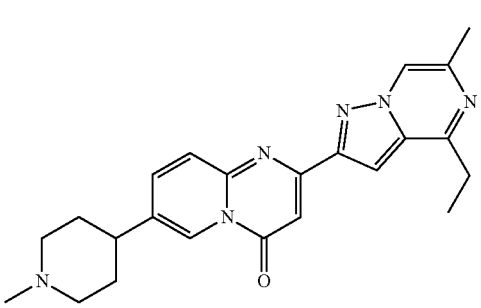
202
-continued
658
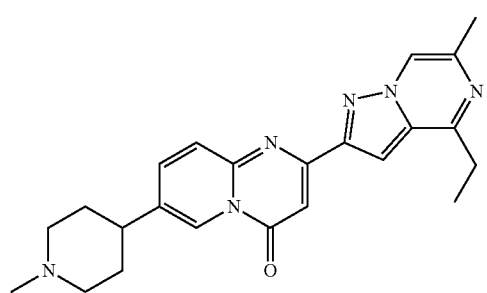
659
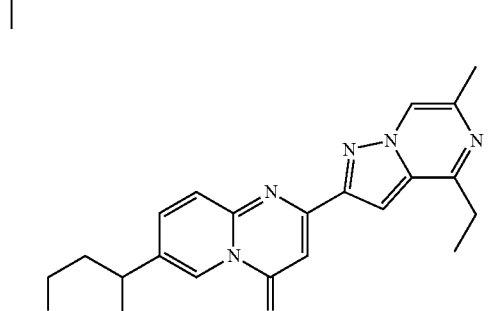
660
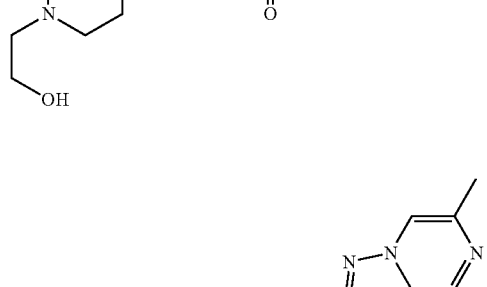
660
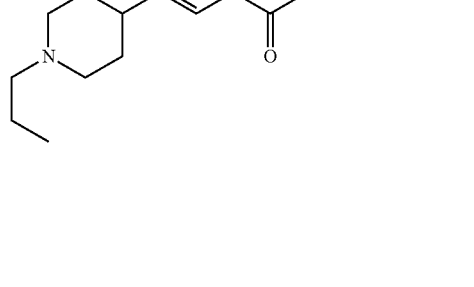
661
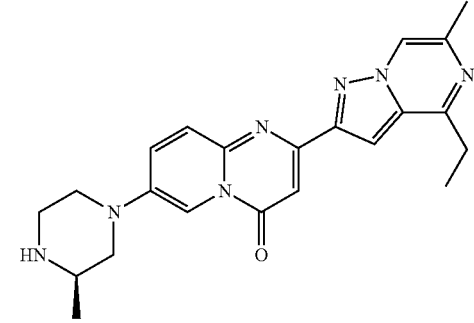

203
-continued
662
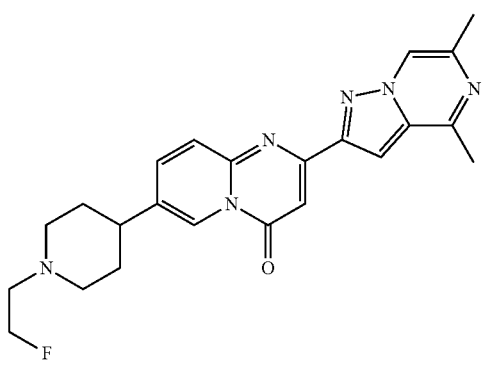
663
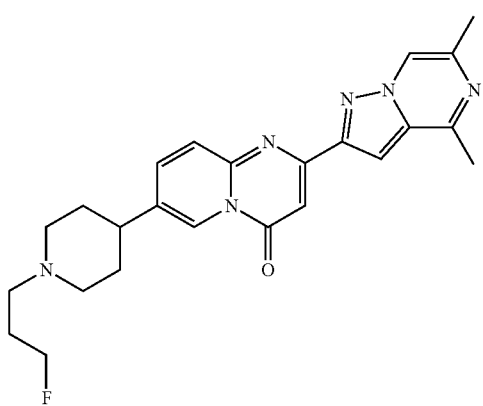
664
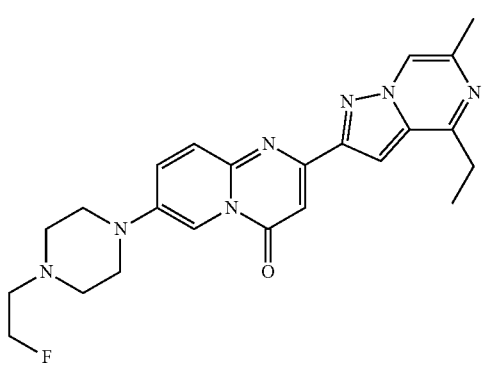
665
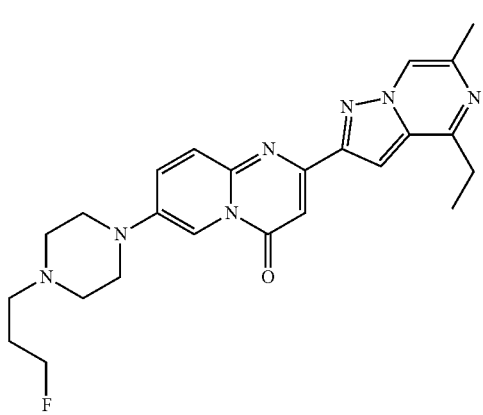
204
-continued
666
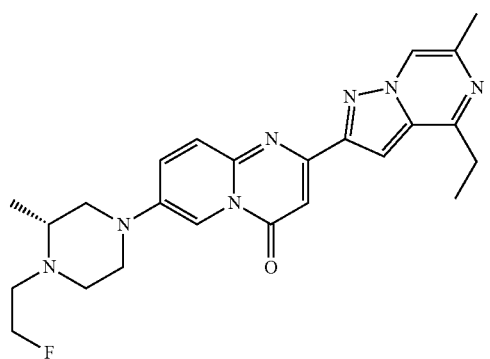
667
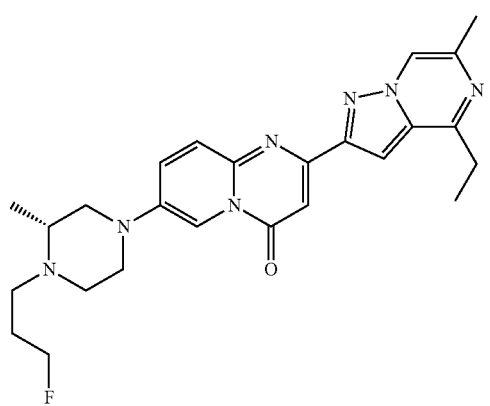
668
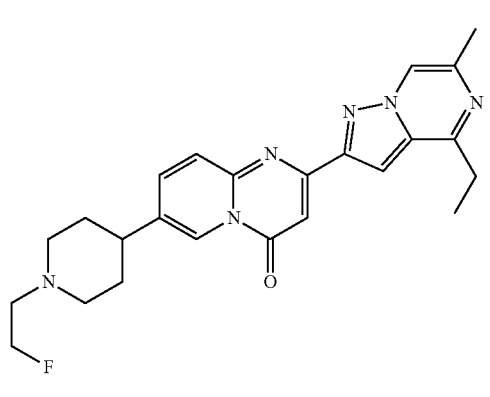
669
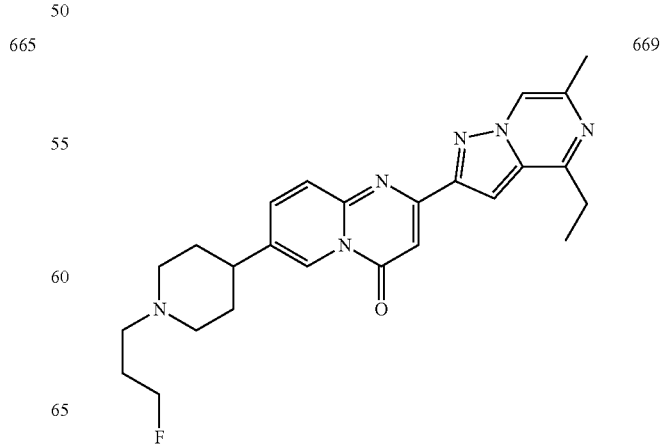

205
-continued
670
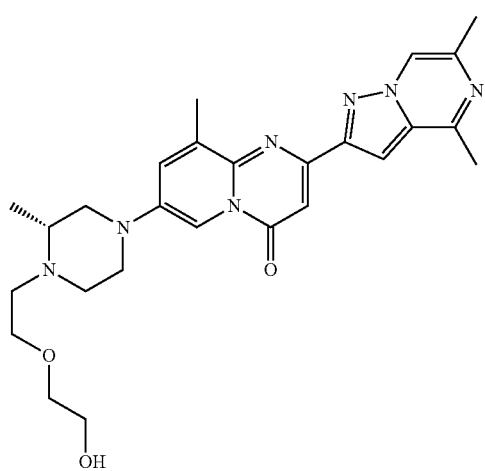
671
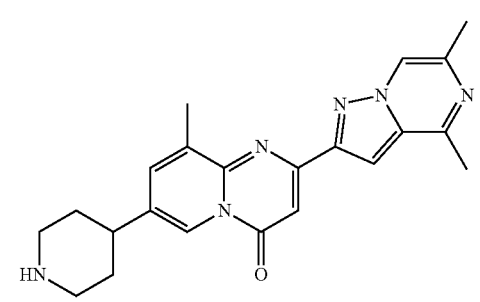
672
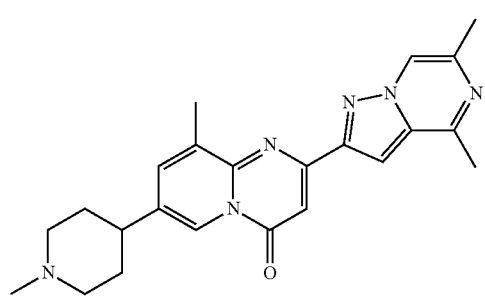
673
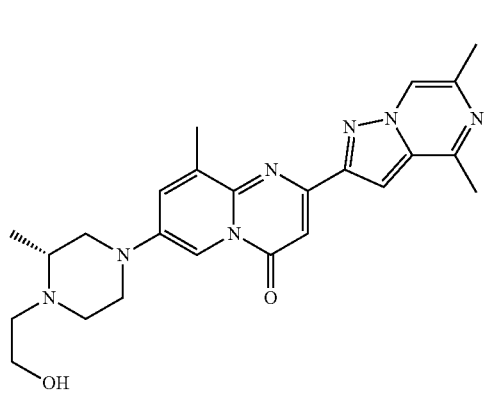
206
-continued
674
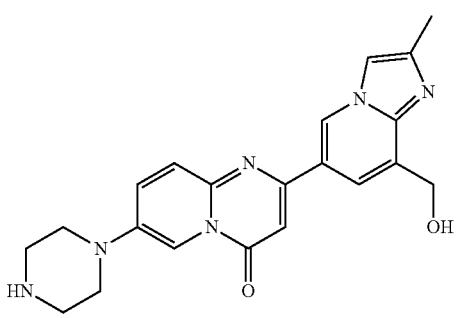
675
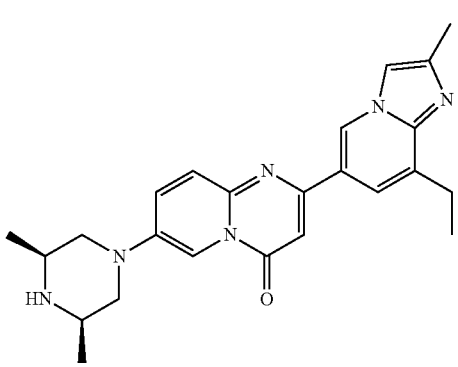
676
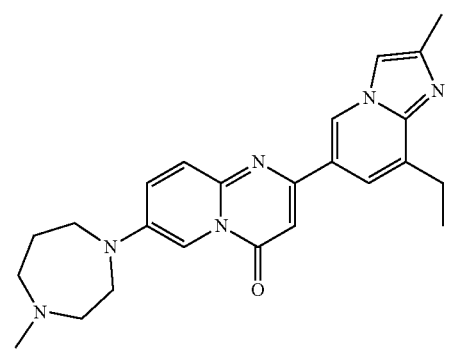
677
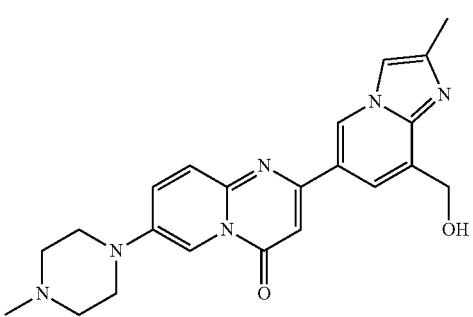

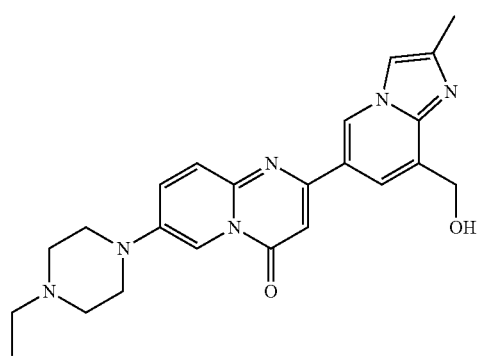
678
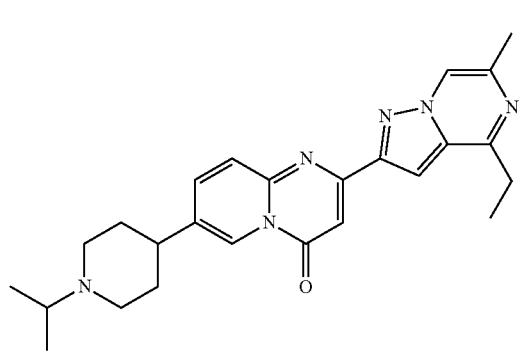
679
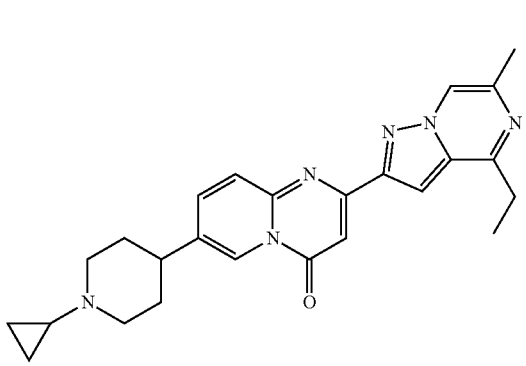
680
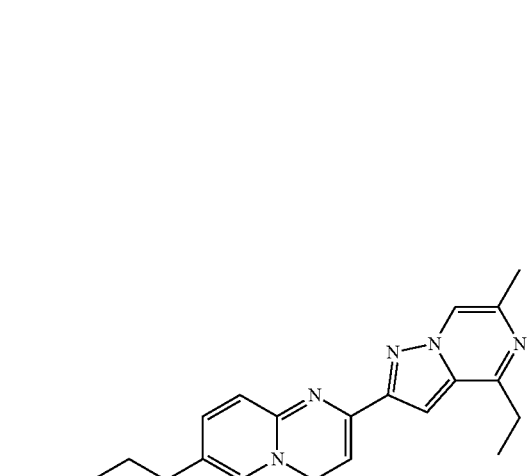
681
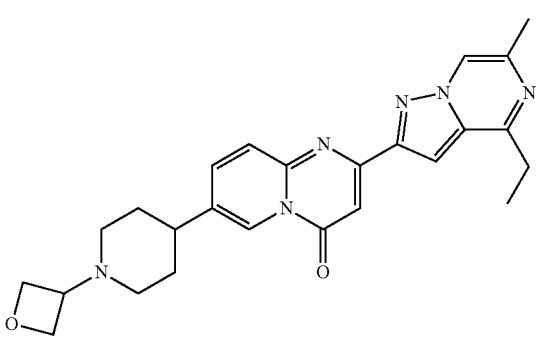
682
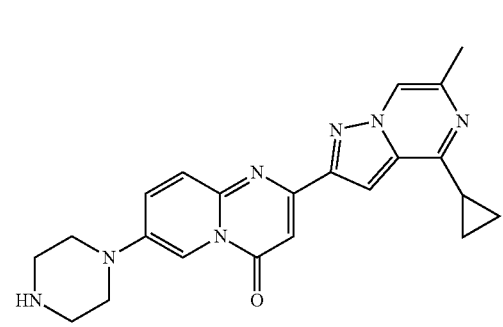
683
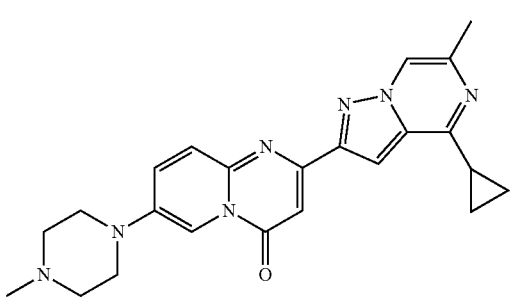
684
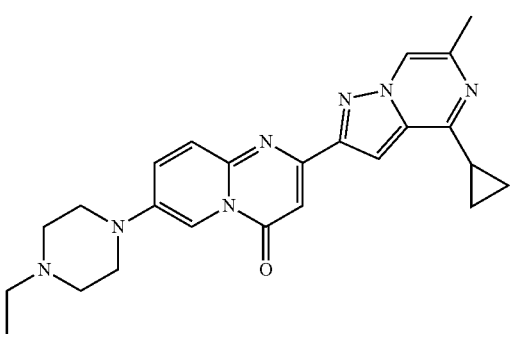
685

-continued
686
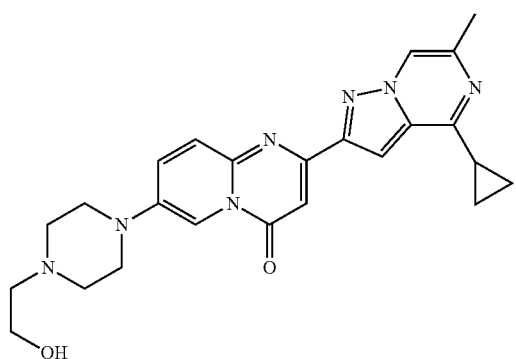
687
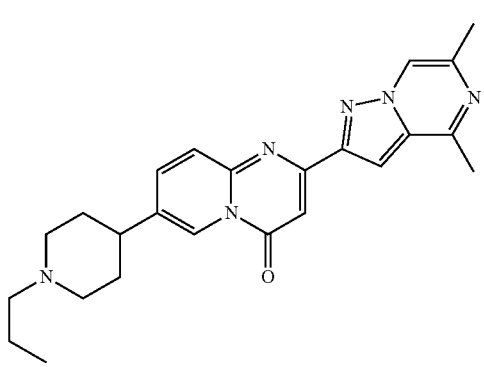
688
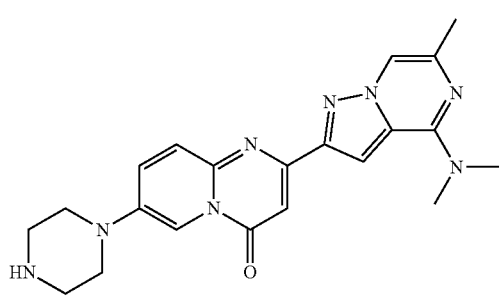
689
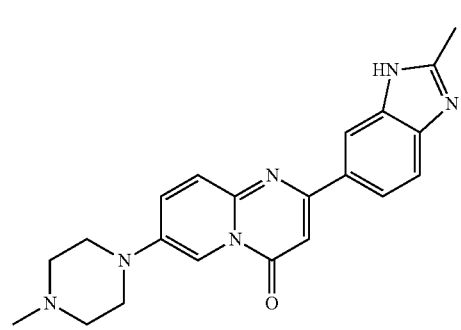
-continued
690
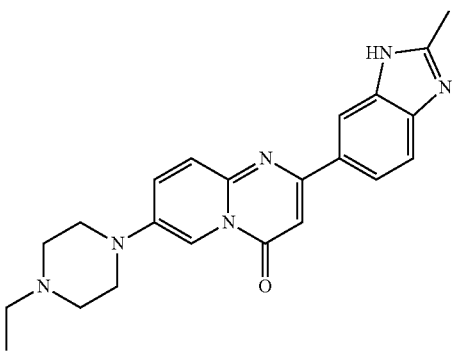
691
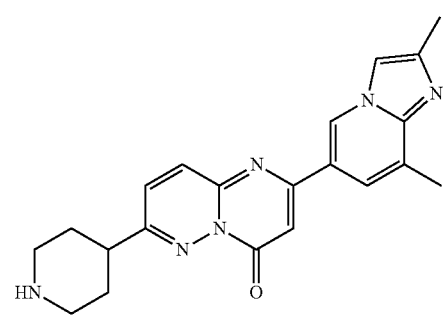
692
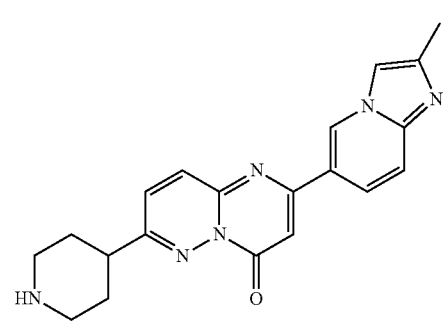
693
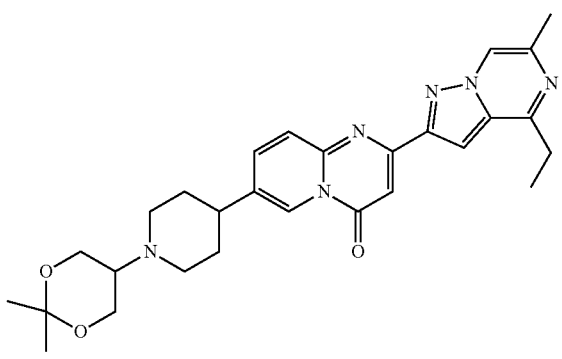

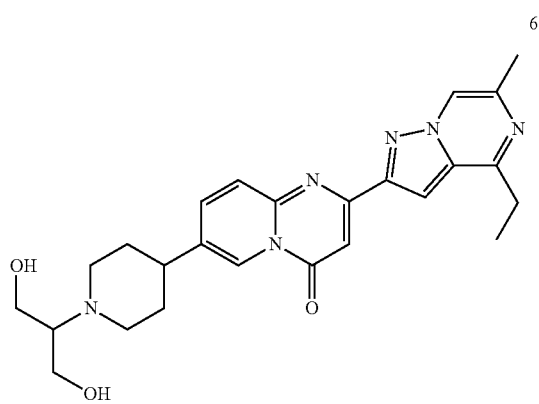
694
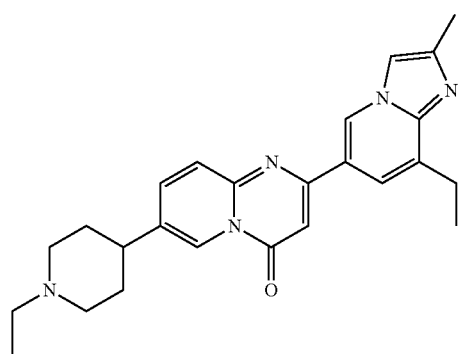
698
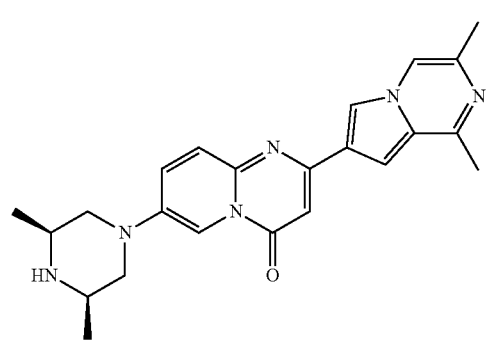
695
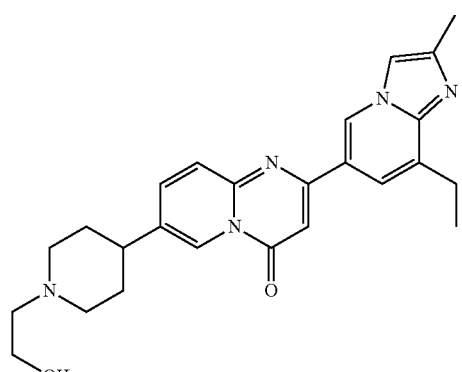
699
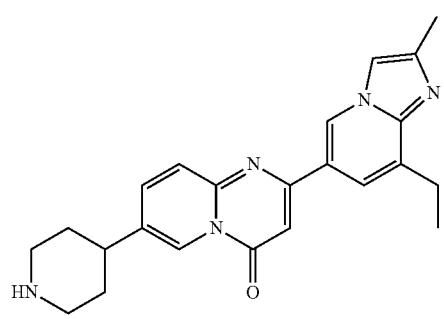
696
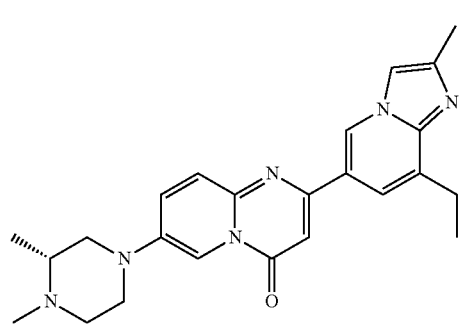
700
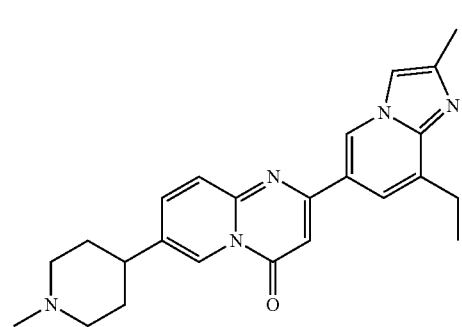
697
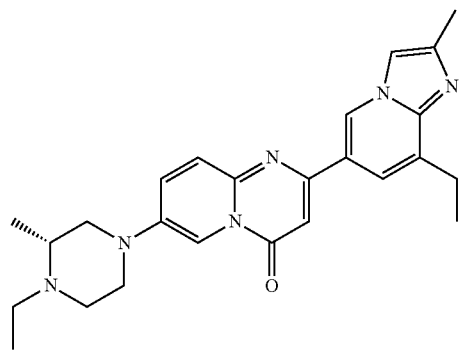
701

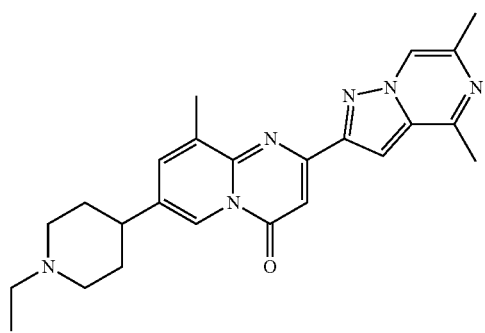
702
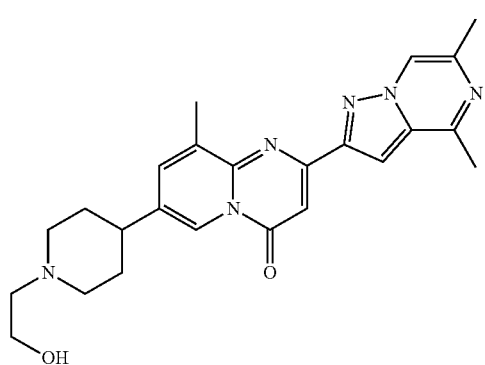
703
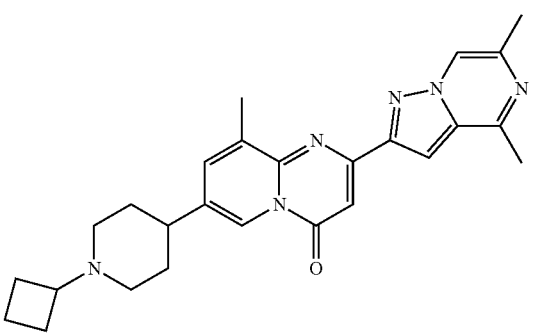
704
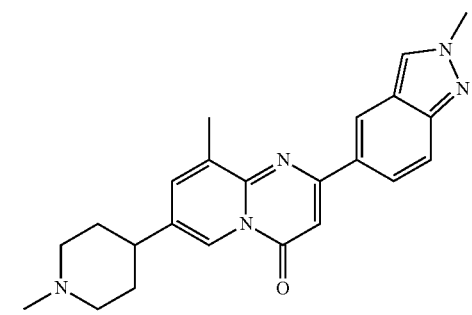
705
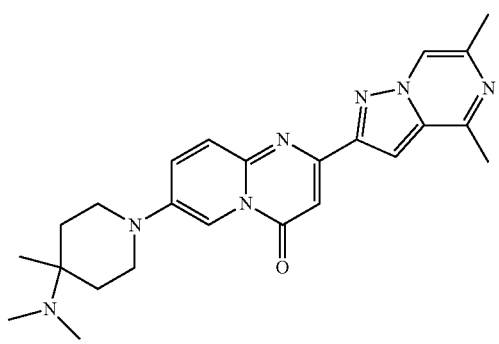
706
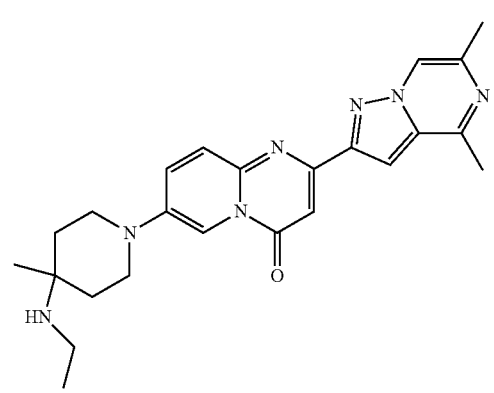
707
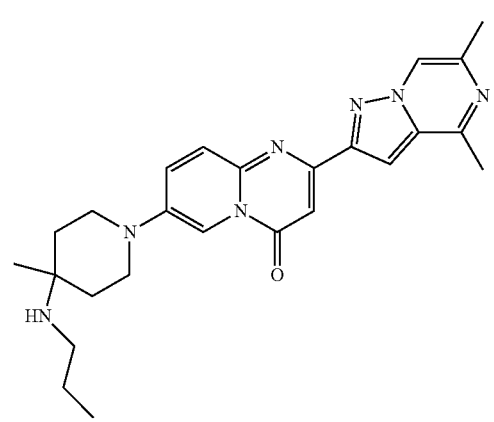
708
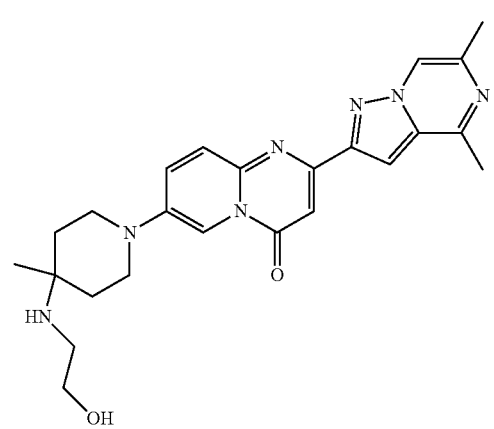
709

710
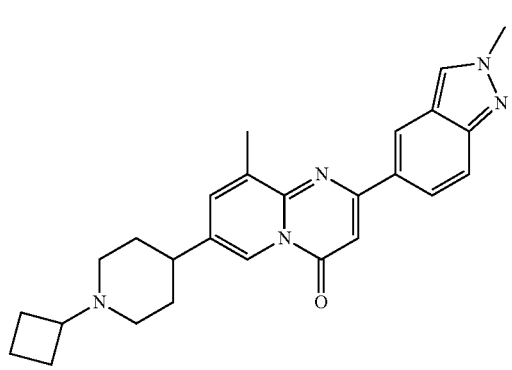
711
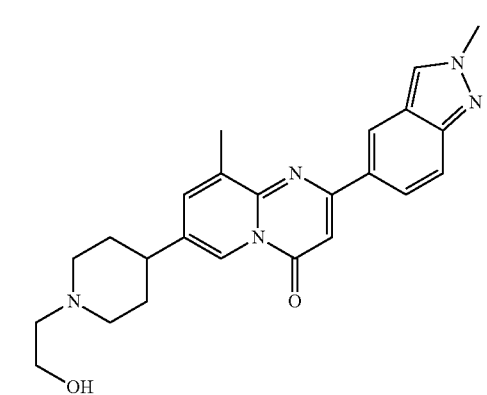
712
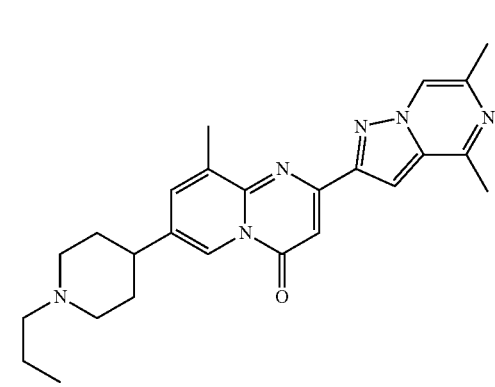
713
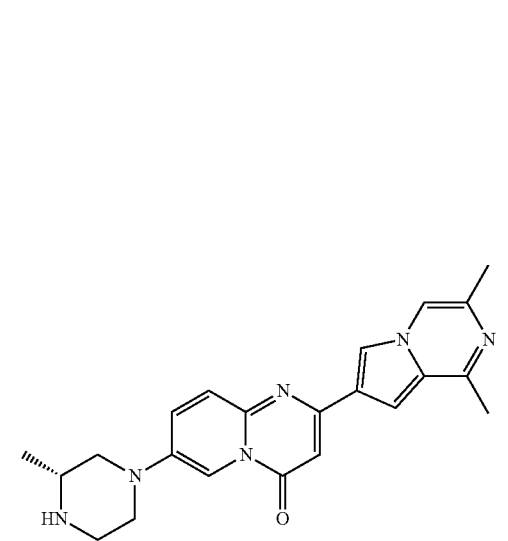
714
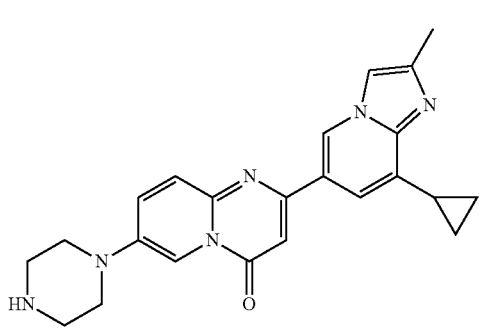
715
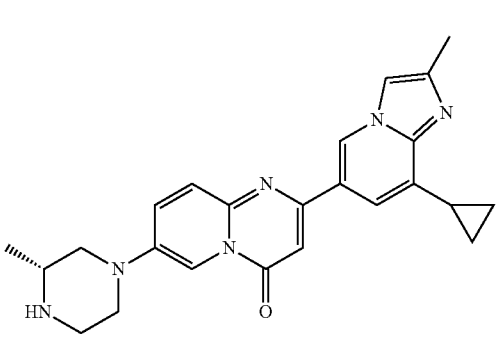
716
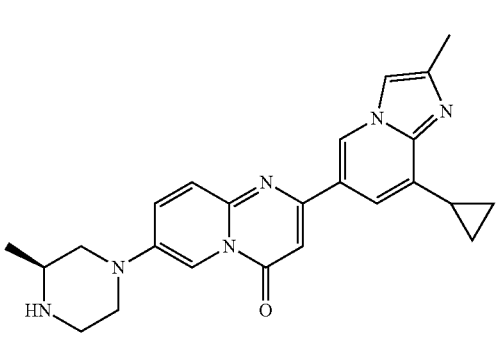
717
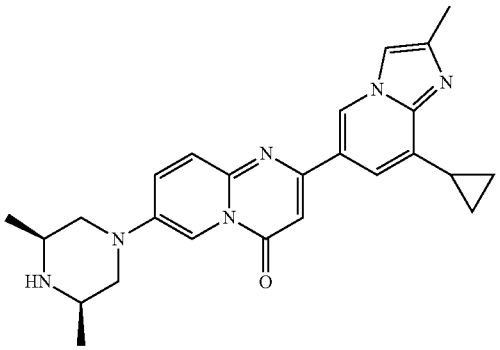

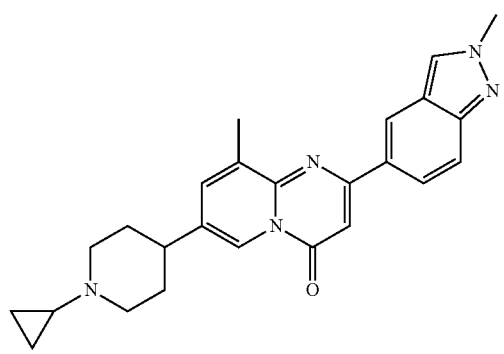
718
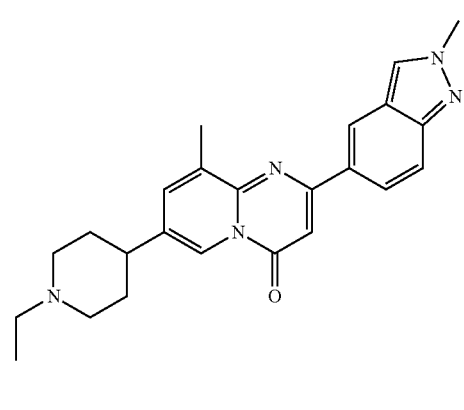
719
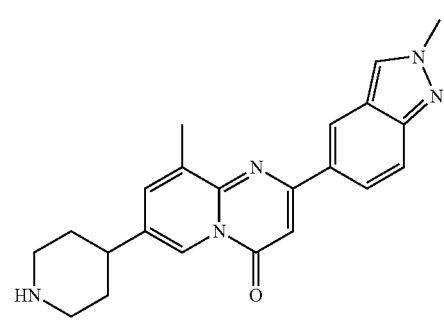
720
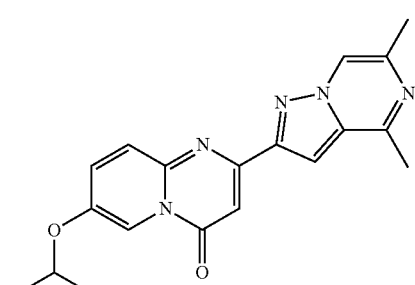
721
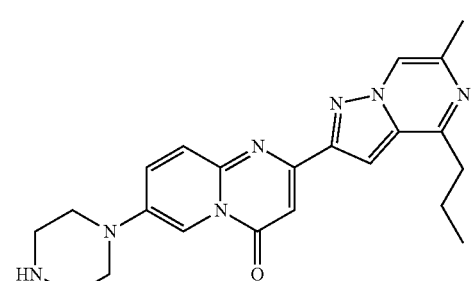
722
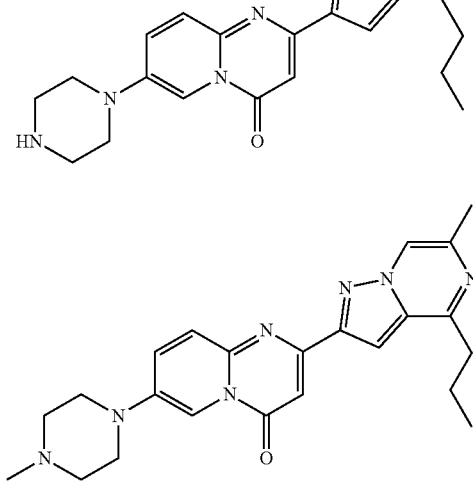
723
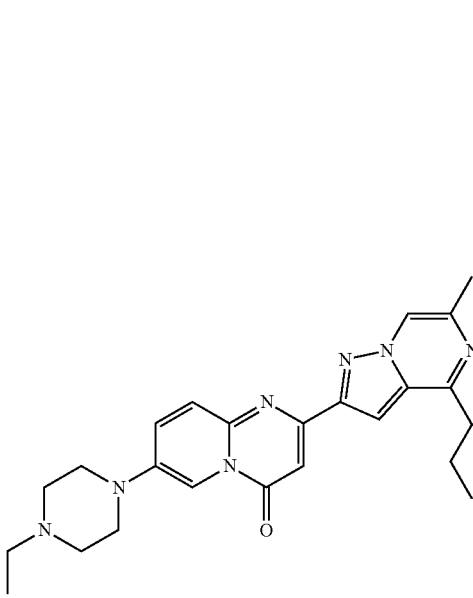
724
725

726 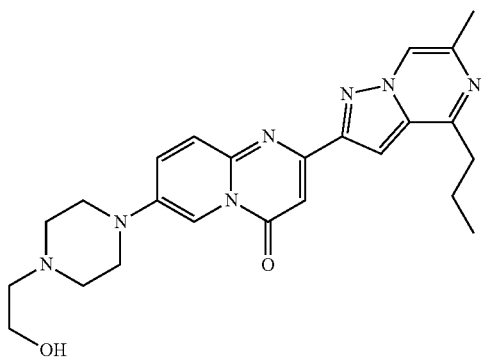
727 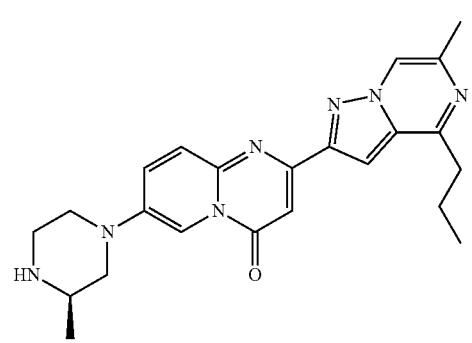
728 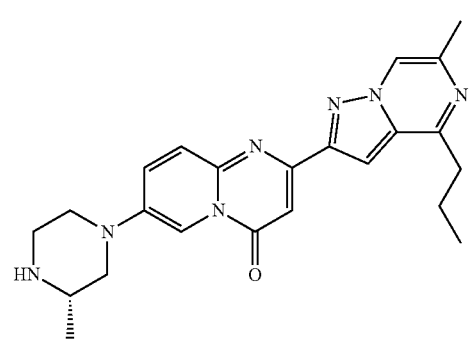
729 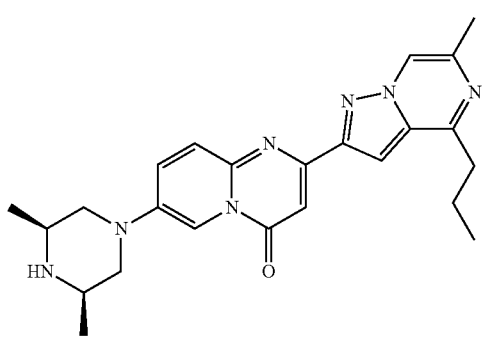
730 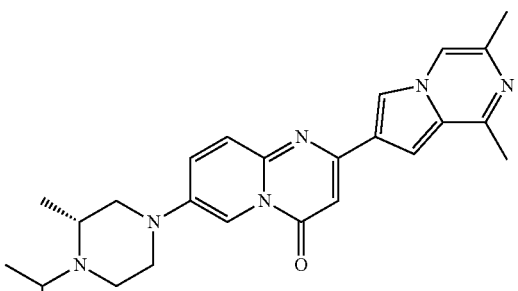
731 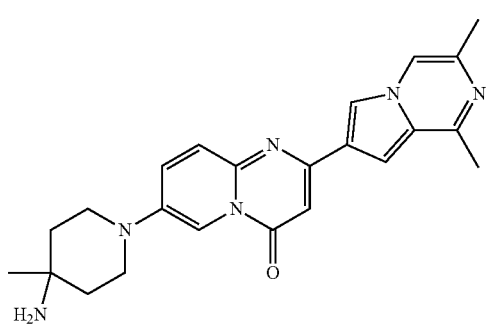
732 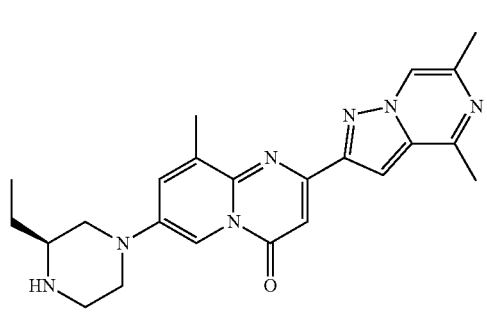
733 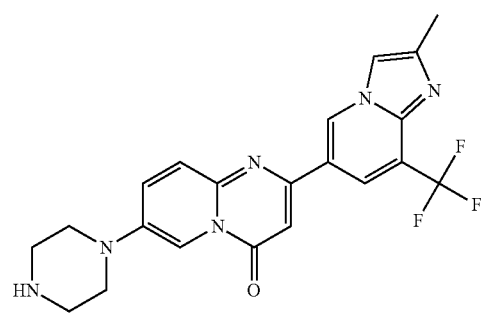
734 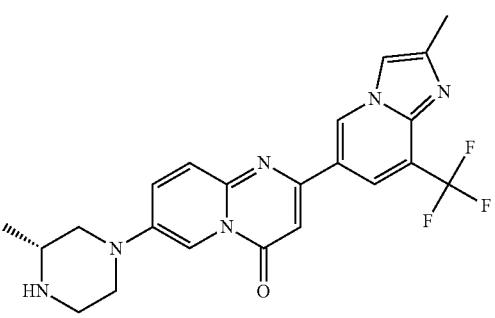

735
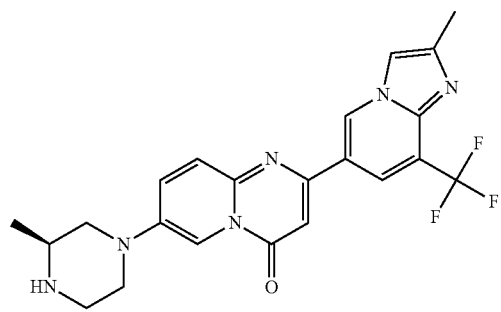
736
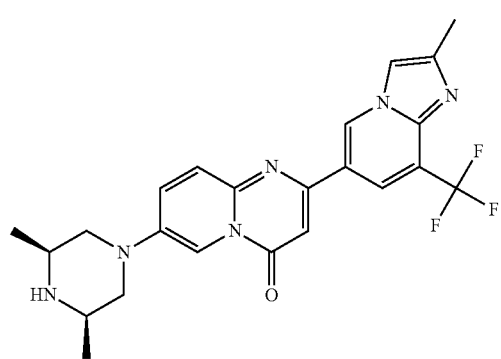
737
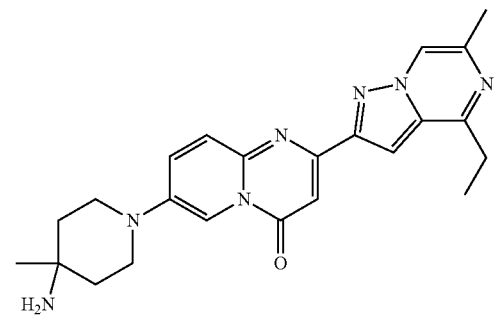
738
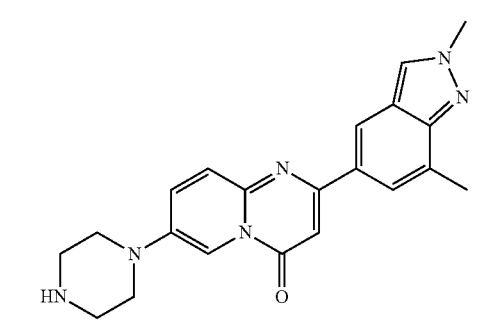
739
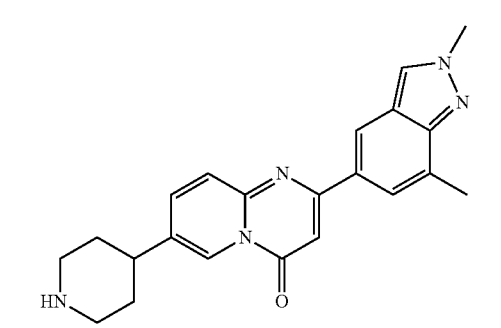
740
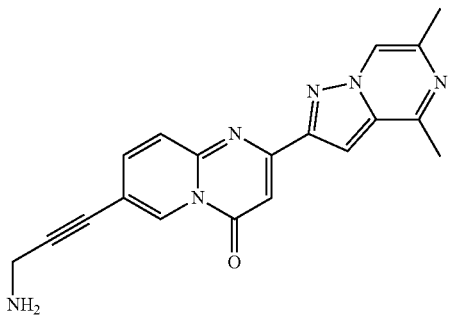
741
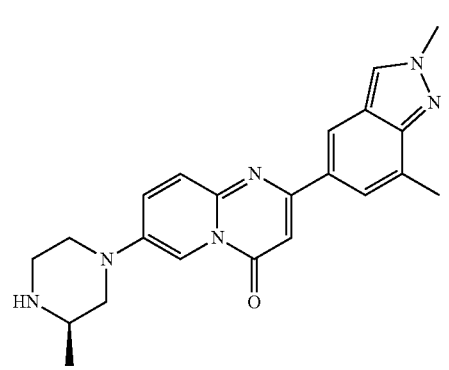
742
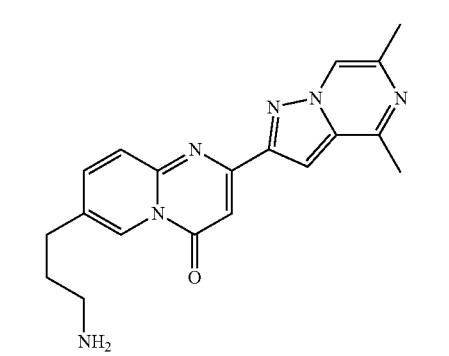
743
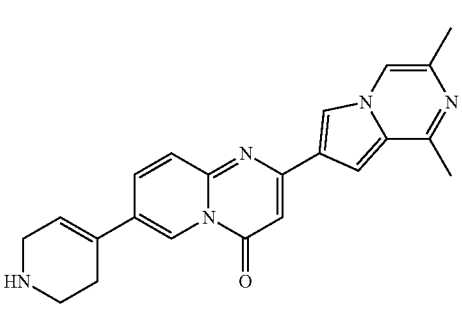
744
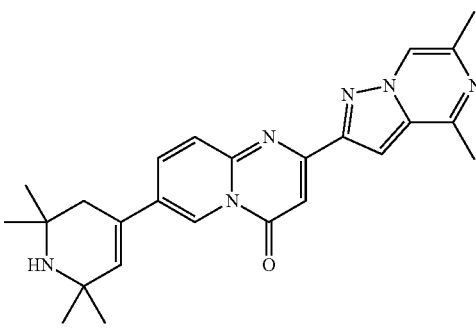

-continued
745
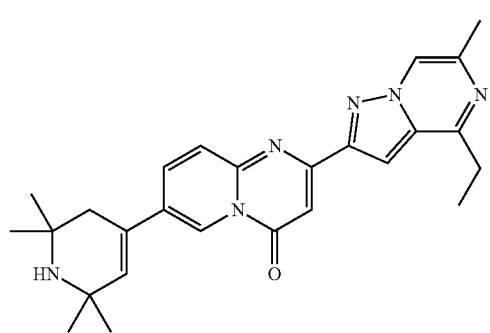
746
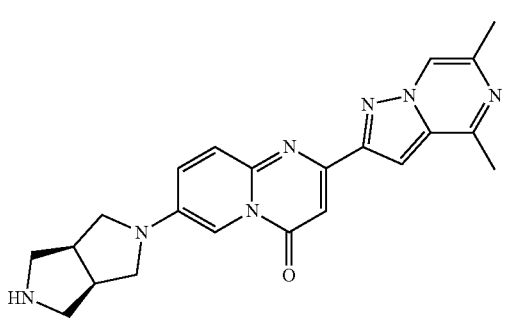
747
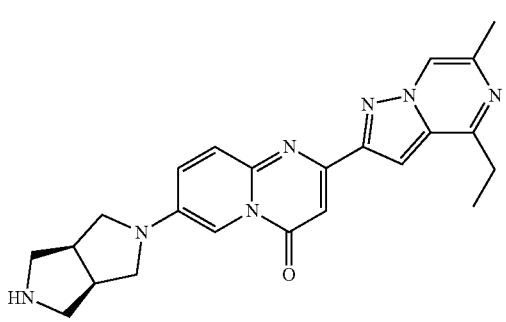
748
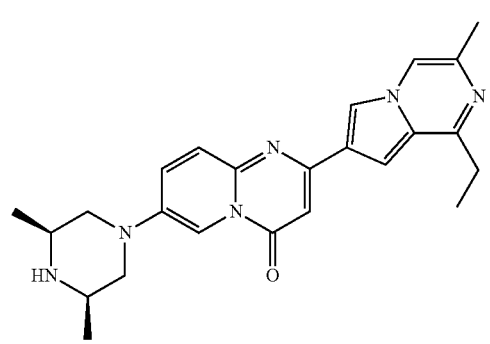
749
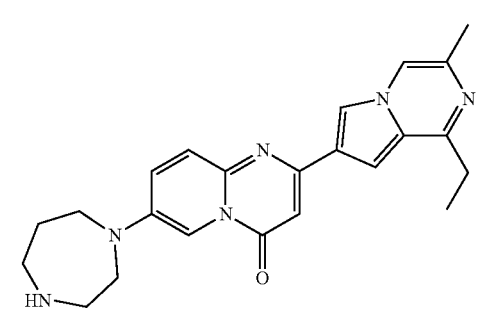
-continued
750
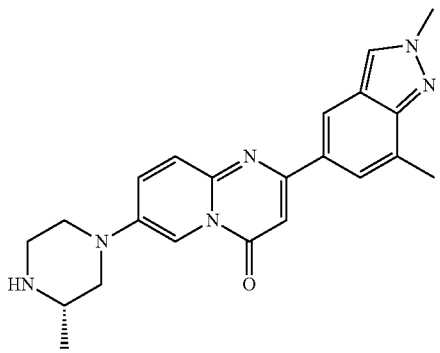
751
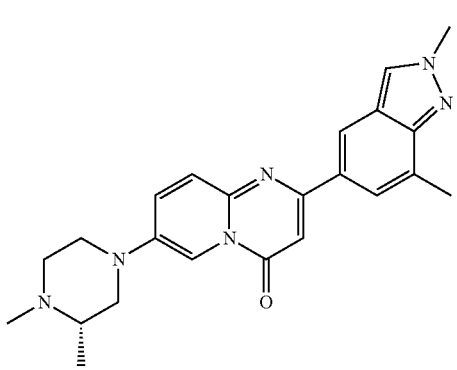
752
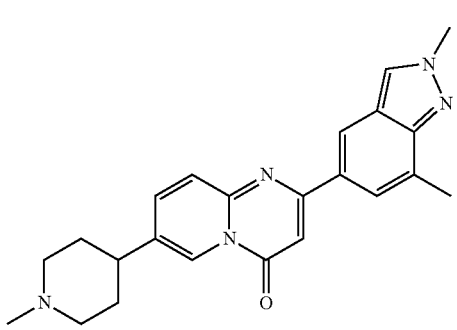
753
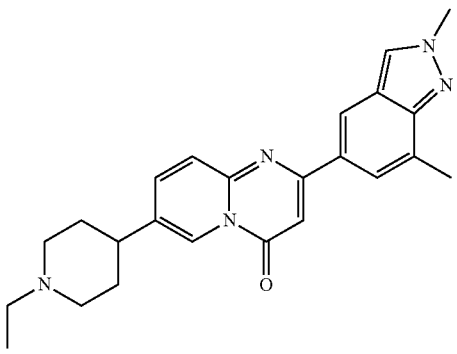

225
-continued
754
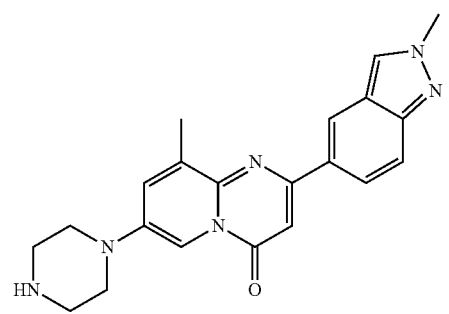
755
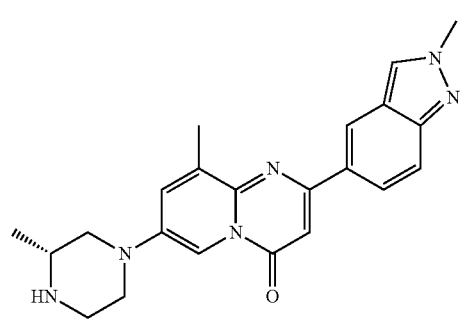
756
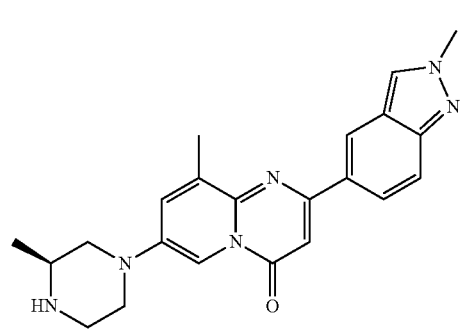
757
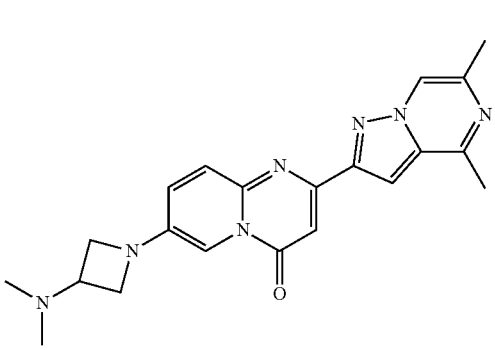
758
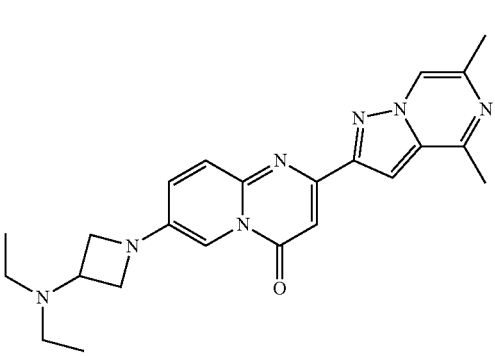
226
-continued
759
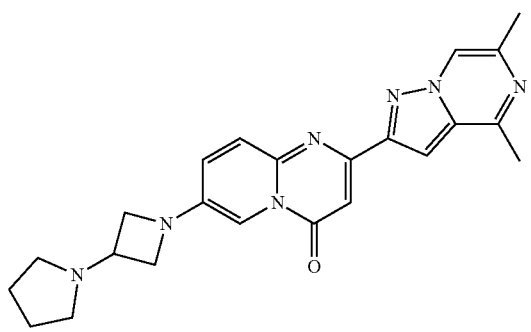
760
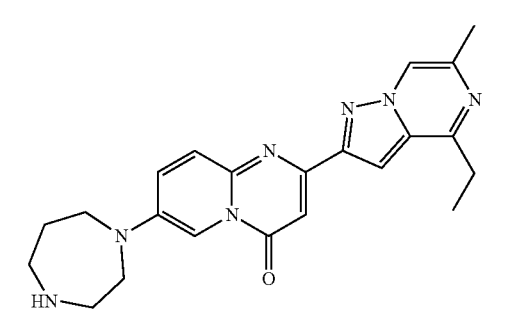
761
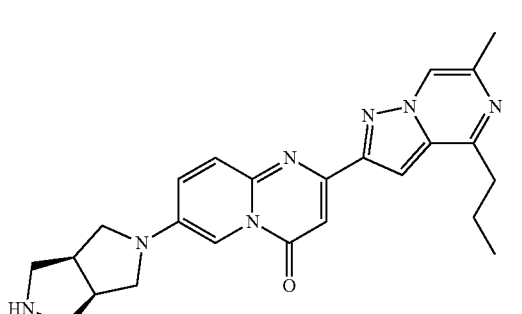
762
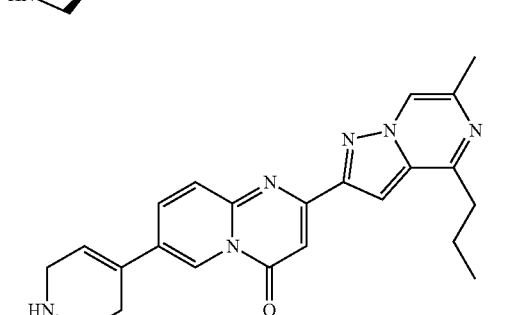
763
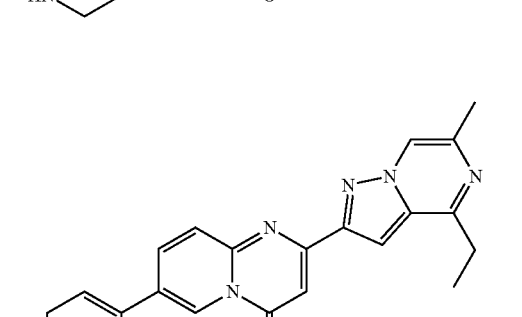

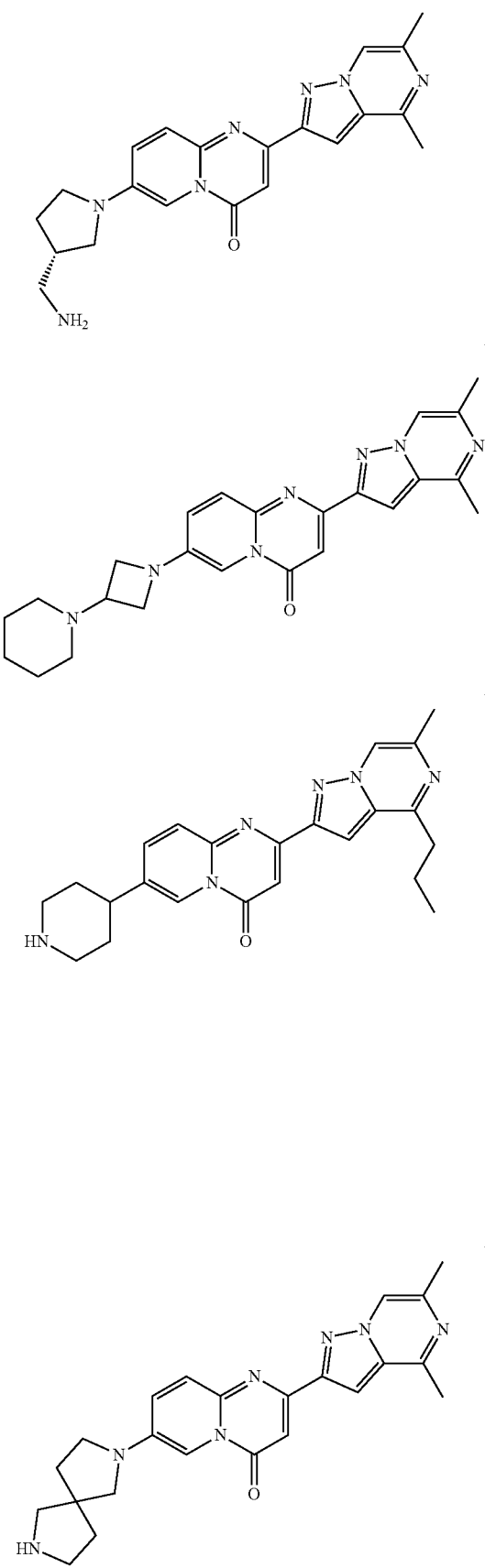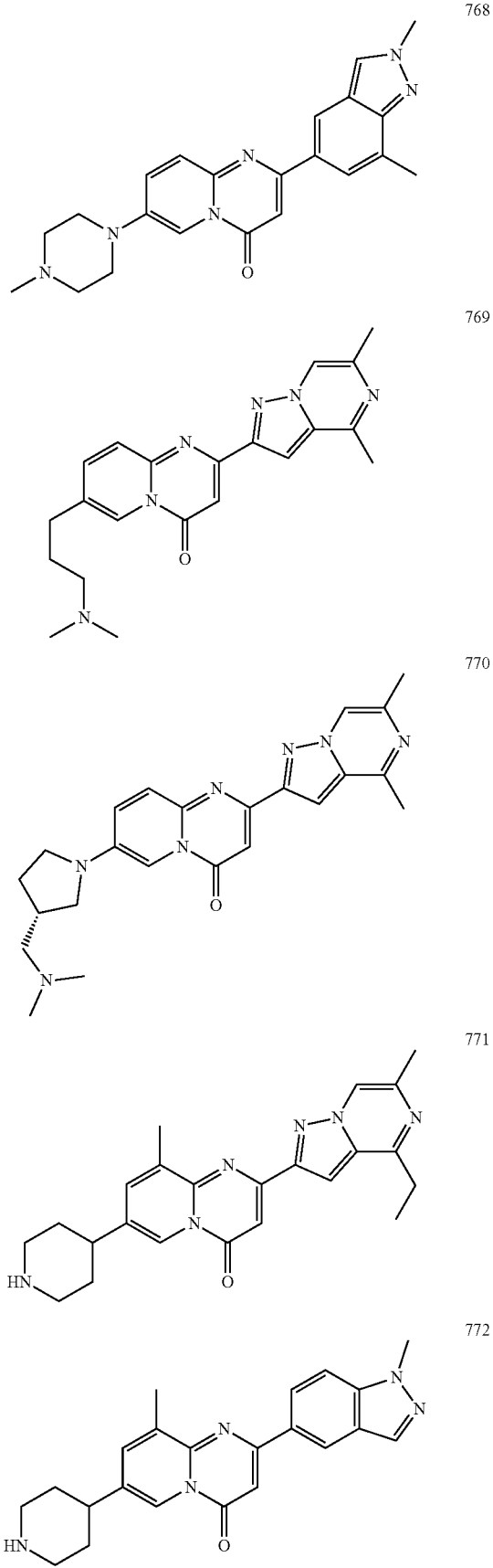

229
-continued
773
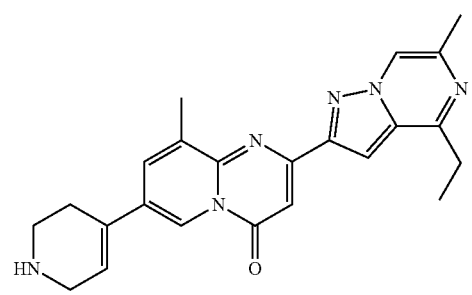
774
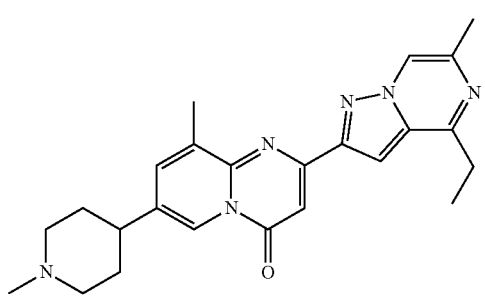
775
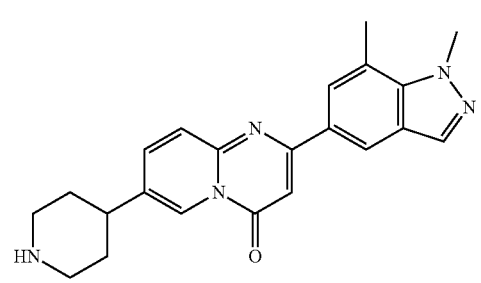
776
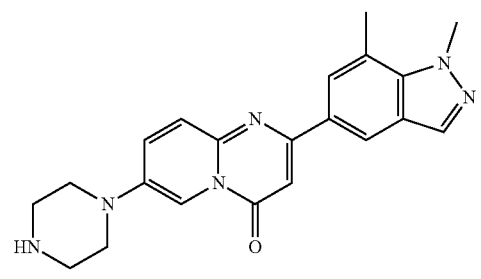
777
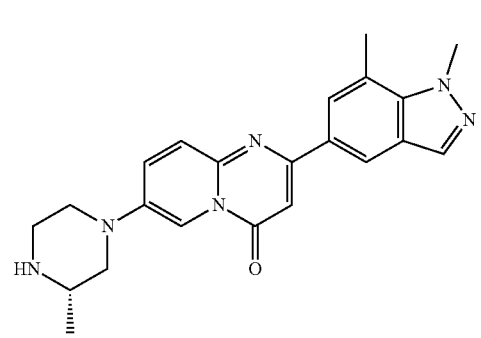
230
-continued
778
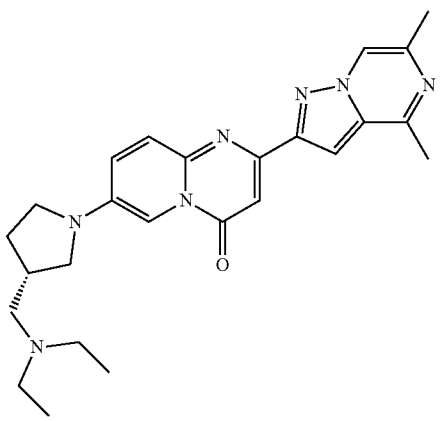
779
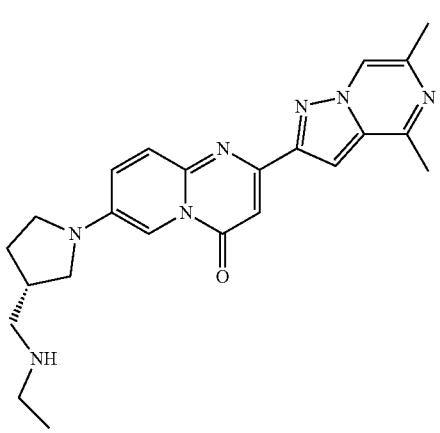
780
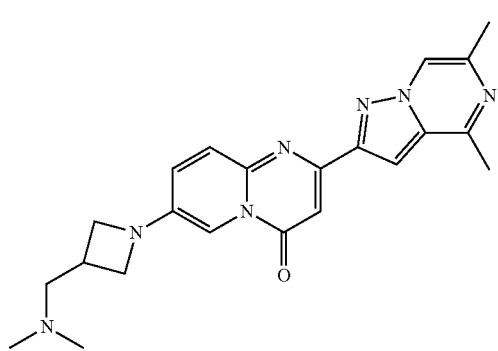
781
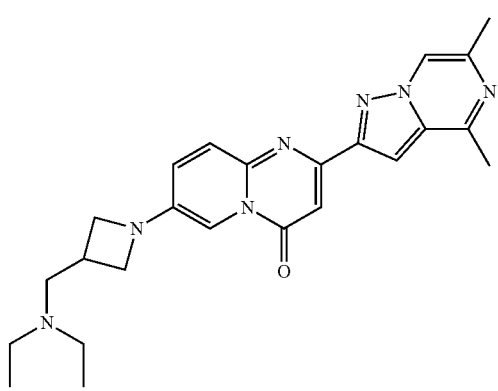

782
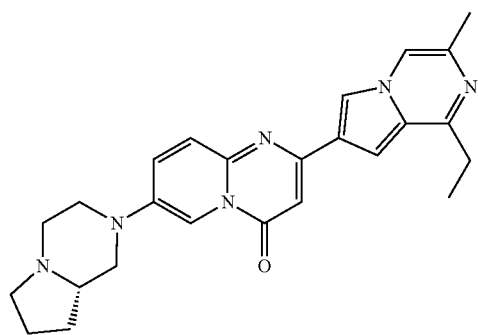
783
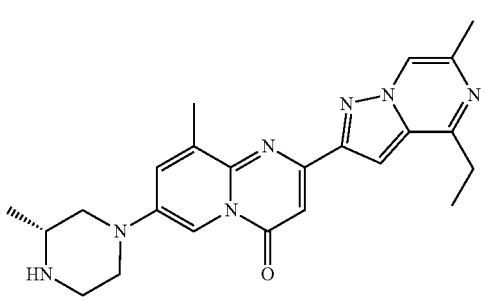
784
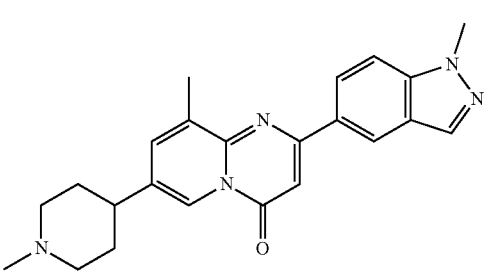
785
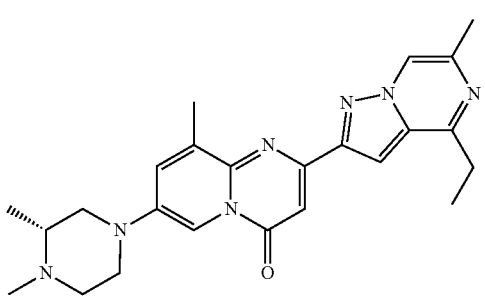
786
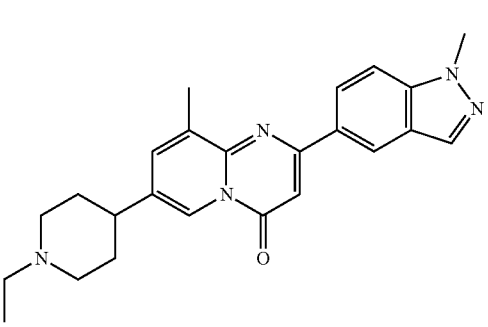
787
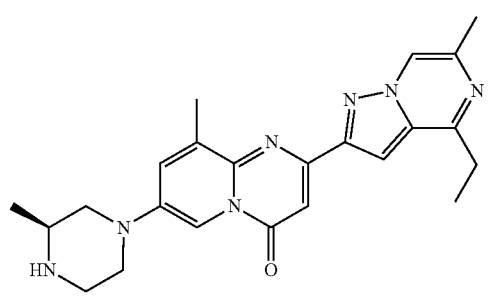
788
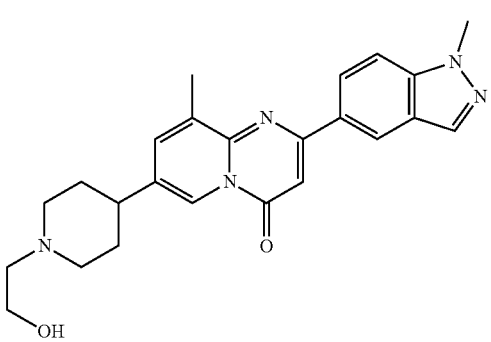
789
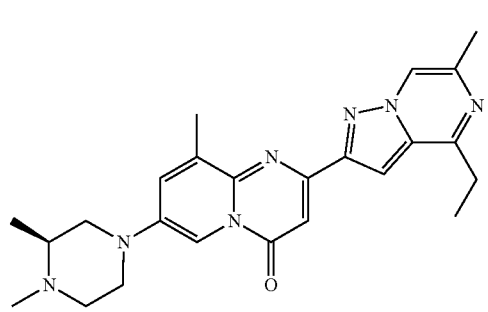
790
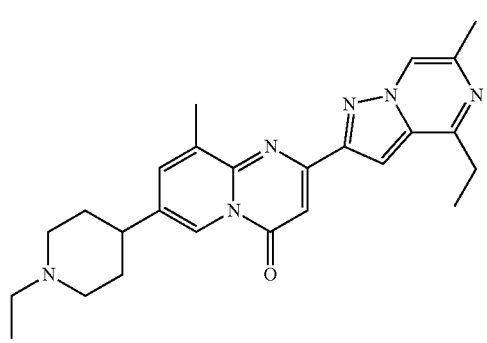
791
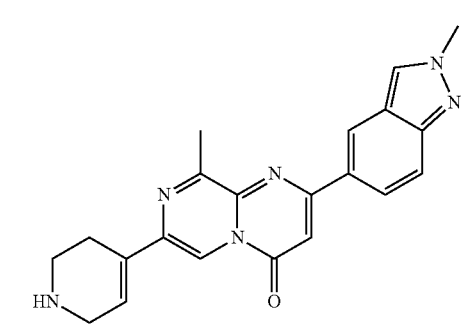

233
-continued
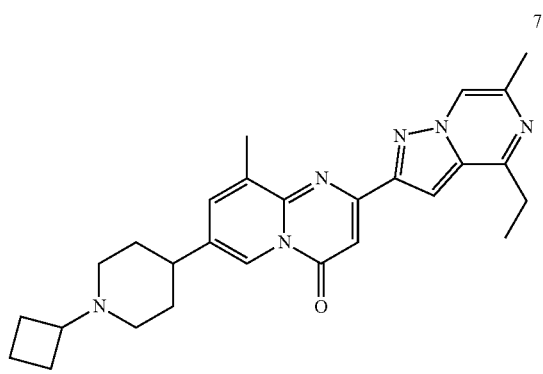
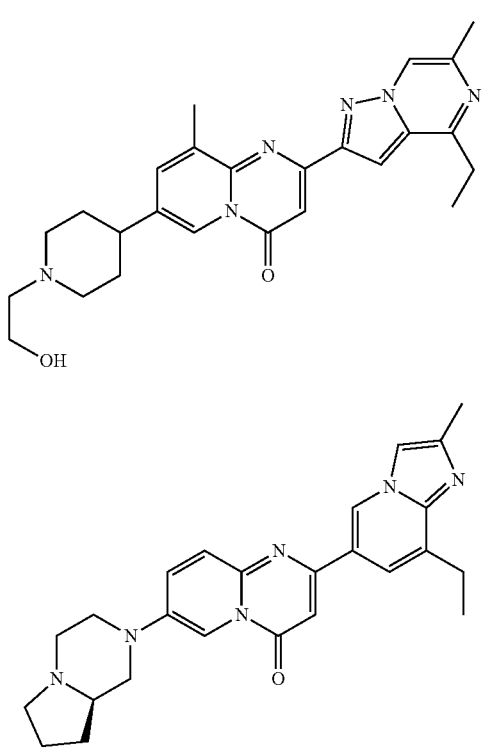
234
-continued
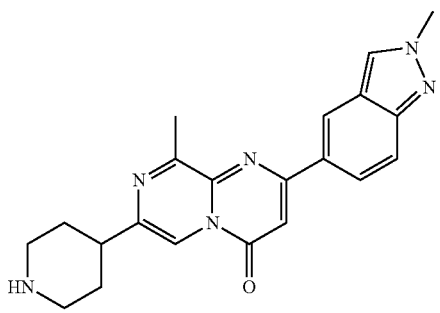
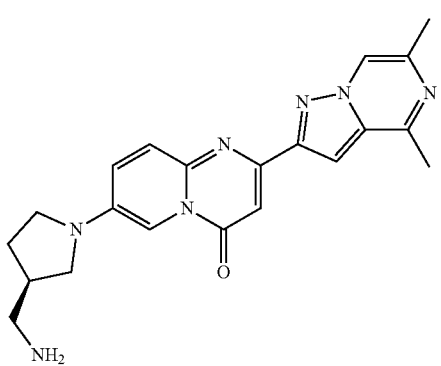
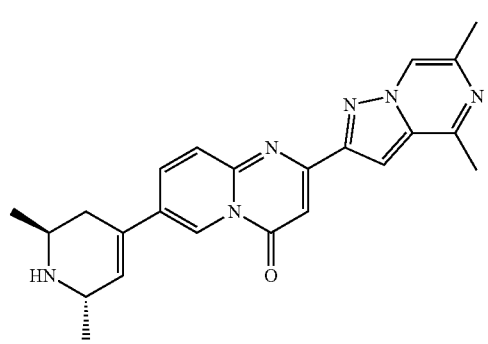
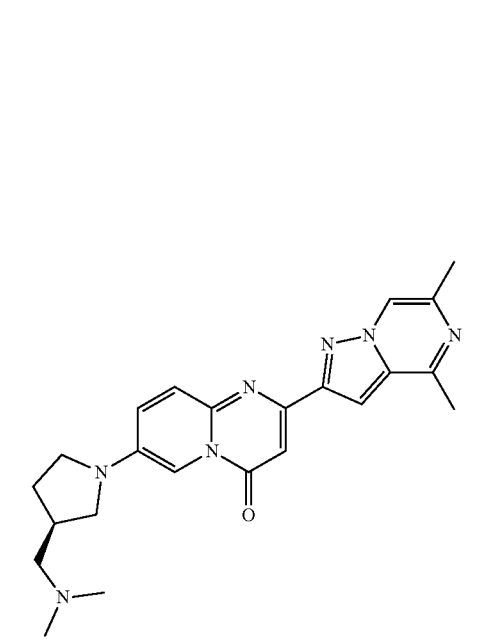

800
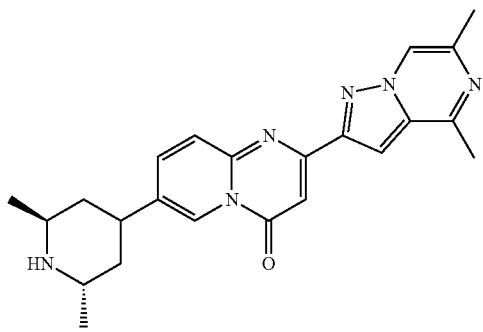
801
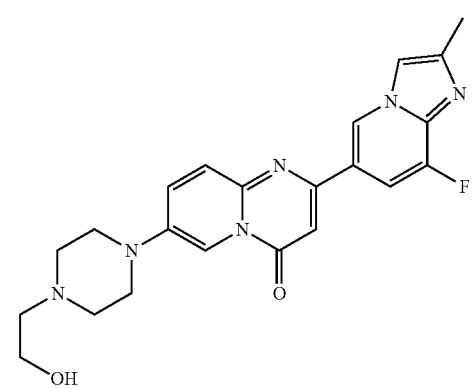
802
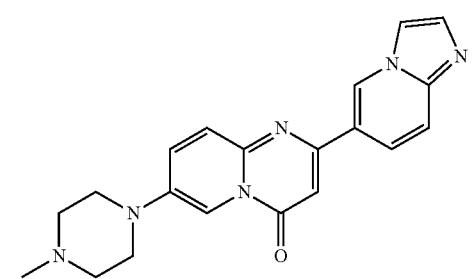
803
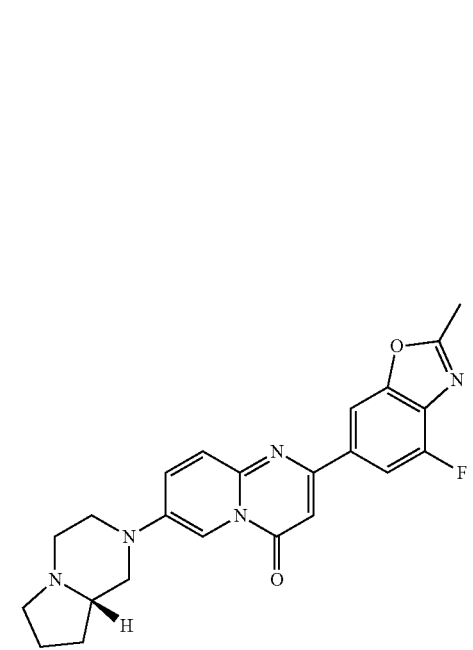
804
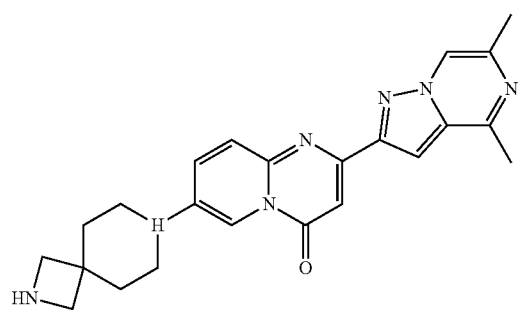
805
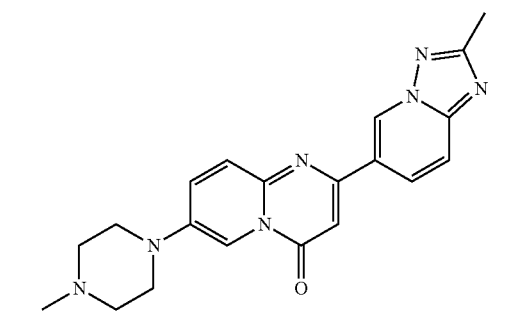
806
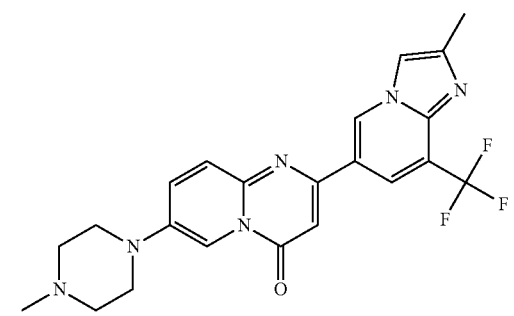
807
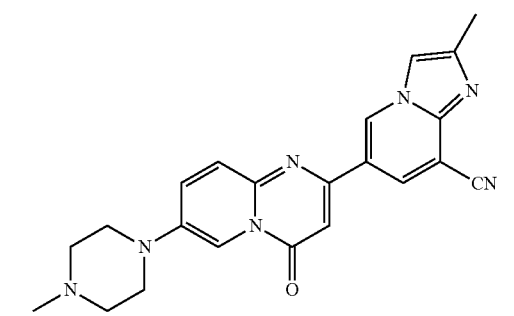
808
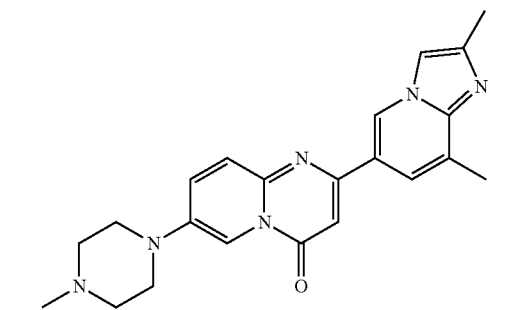

809
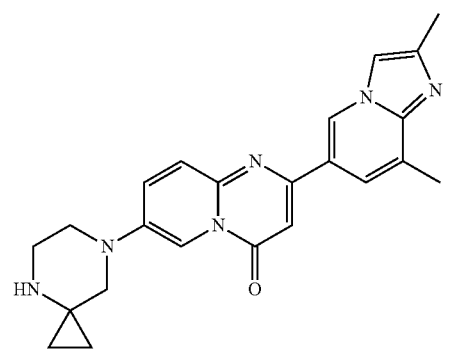
810
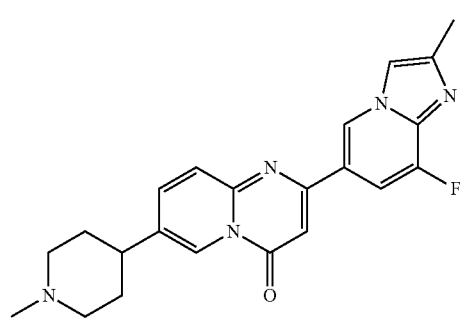
811
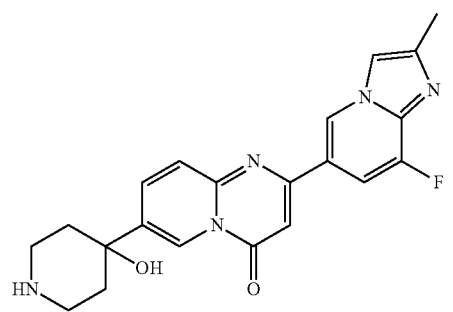
812
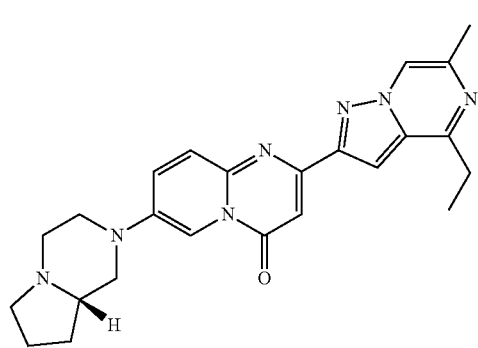
813
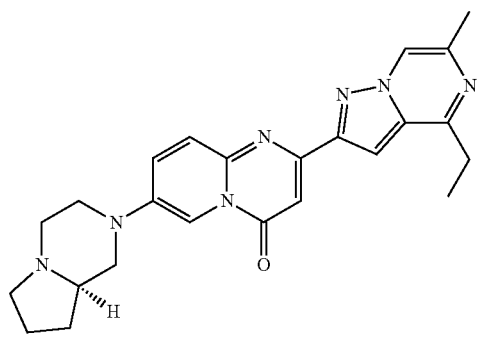
814
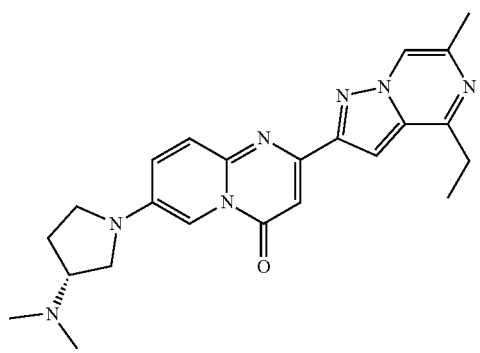
815
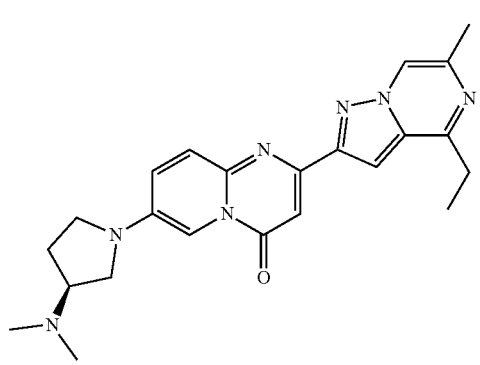
816
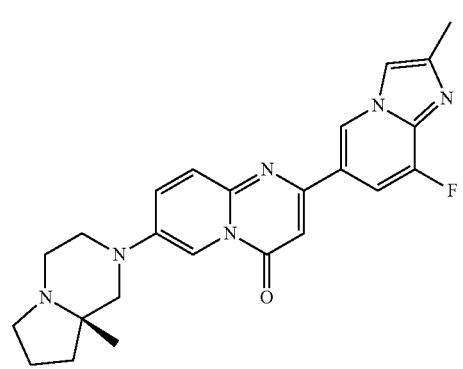

817 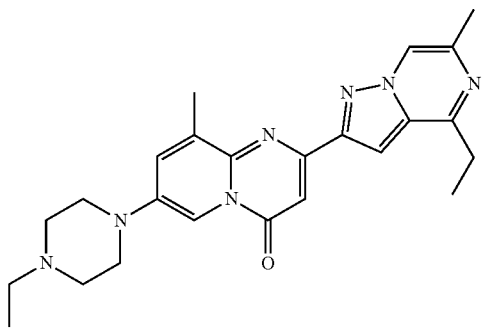
818 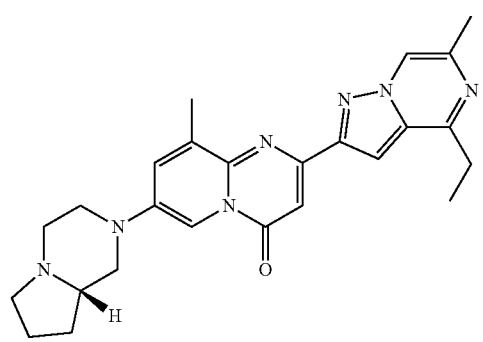
819 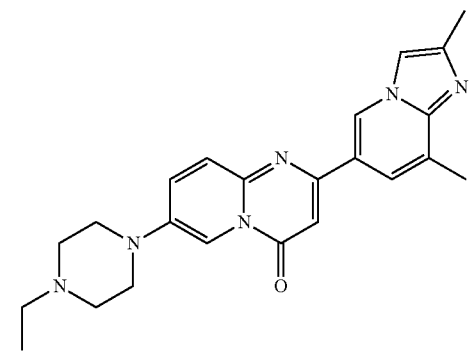
820 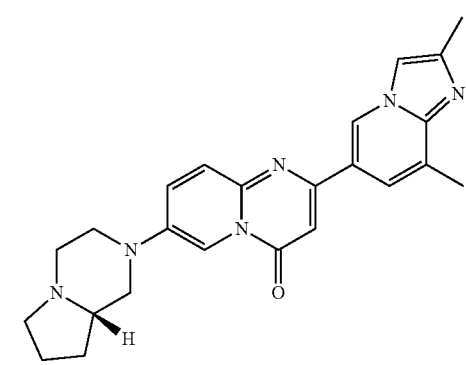
821 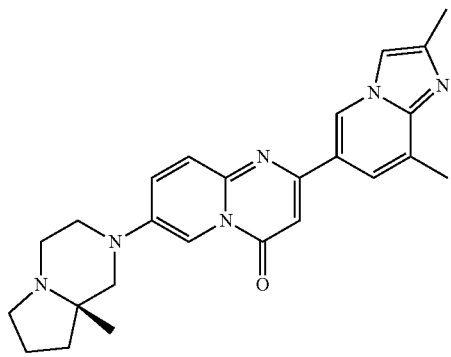
822 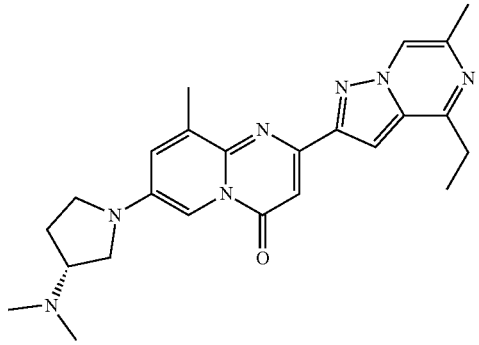
823 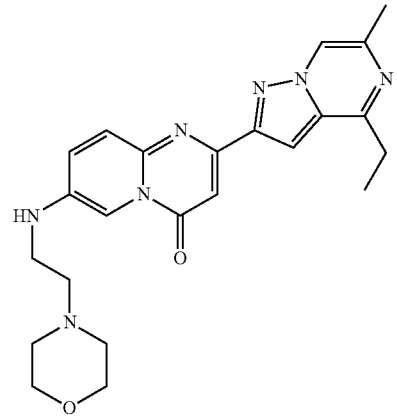
824 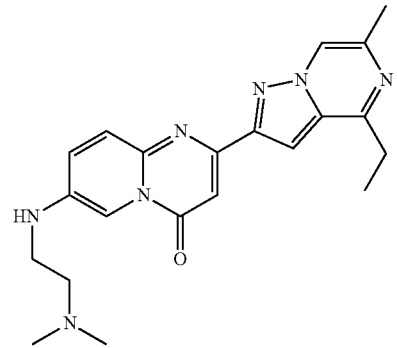

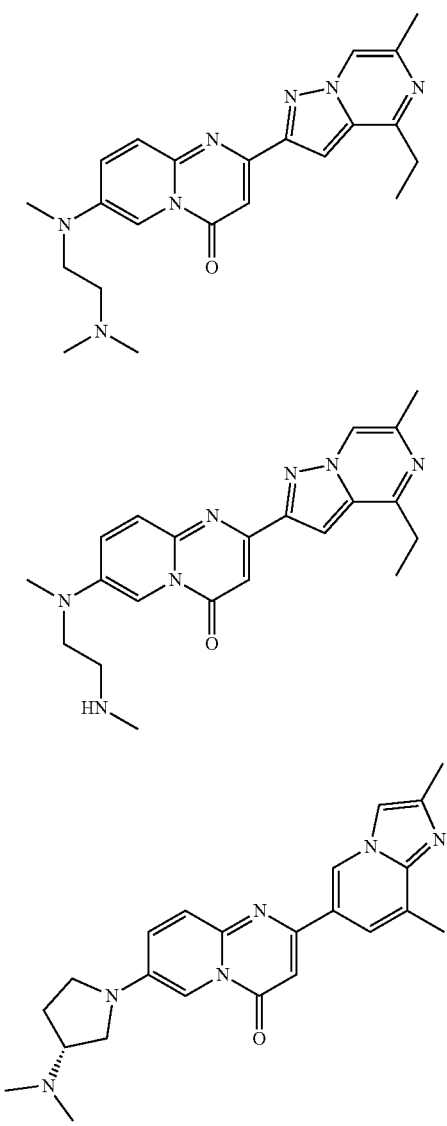
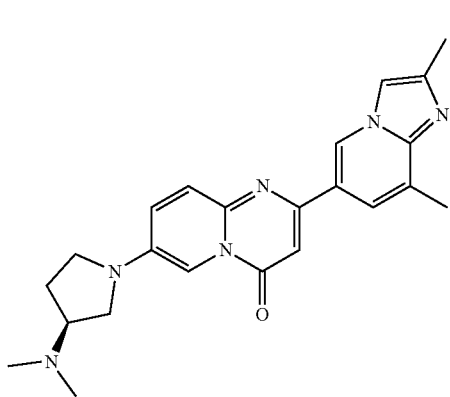
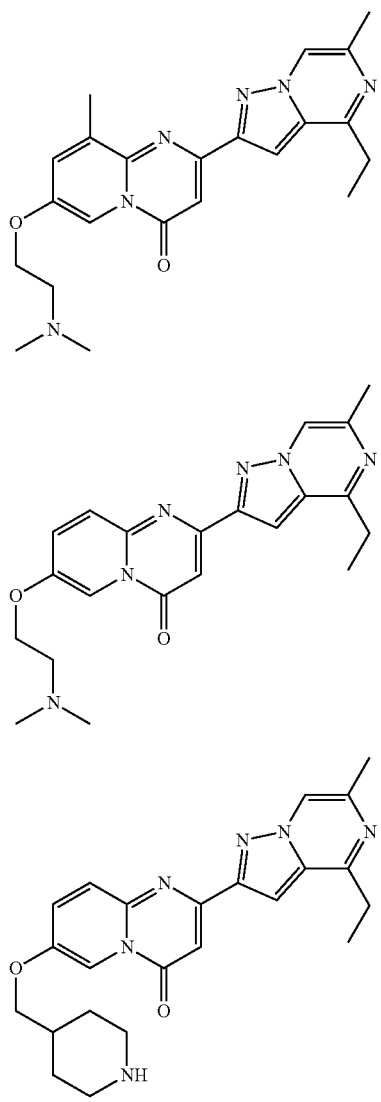

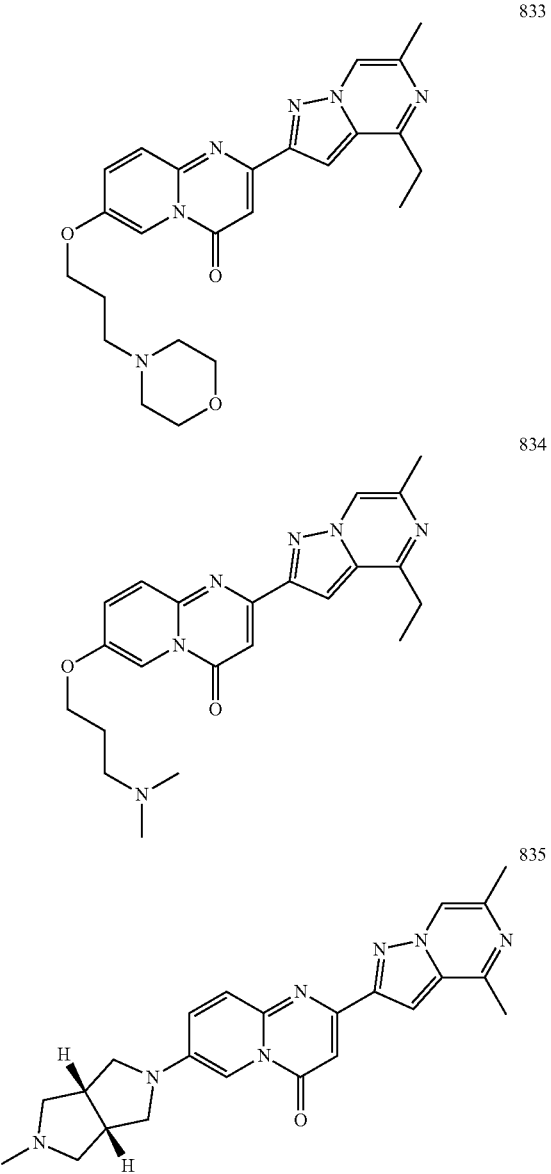

or a form thereof.

In another embodiment, the compound of Formula (I) used in a method disclosed herein is a compound selected from the group consisting of:

2-(4-methoxyphenyl)-7-(piperazin-1-yl)-4H-pyrido[1,2-a]pyrimidin-4-one
2-(4-methoxyphenyl)-7-(4-methylpiperazin-1-yl)-4H-pyrido[1,2-a]pyrimidin-4-one
2-(4-methoxyphenyl)-7-[(3R)-3-methylpiperazin-1-yl]-4H-pyrido[1,2-a]pyrimidin-4-one
7-[(3R,5S)-3,5-dimethylpiperazin-1-yl]-2-(4-methoxyphenyl)-4H-pyrido[1,2-a]pyrimidin-4-one
7-(1,4-diazepan-1-yl)-2-(4-methoxyphenyl)-4H-pyrido[1,2-a]pyrimidin-4-one
2-(3,4-dimethoxyphenyl)-7-(piperazin-1-yl)-4H-pyrido[1,2-a]pyrimidin-4-one
2-(3,4-dimethoxyphenyl)-7-(3,3-dimethylpiperazin-1-yl)-4H-pyrido[1,2-a]pyrimidin-4-one
2-(3,4-dimethoxyphenyl)-7-[(3R)-3-methylpiperazin-1-yl]-4H-pyrido[1,2-a]pyrimidin-4-one
2-(3,4-dimethoxyphenyl)-7-(4-ethylpiperazin-1-yl)-4H-pyrido[1,2-a]pyrimidin-4-one
7-(1,4-diazepan-1-yl)-2-(3,4-dimethoxyphenyl)-4H-pyrido[1,2-a]pyrimidin-4-one
2-(3,4-dimethoxyphenyl)-7-(4-methyl-1,4-diazepan-1-yl)-4H-pyrido[1,2-a]pyrimidin-4-one
2-(4-methoxyphenyl)-7-[(3S)-3-methylpiperazin-1-yl]-4H-pyrido[1,2-a]pyrimidin-4-one
2-(3,4-dimethoxyphenyl)-7-(4-methylpiperazin-1-yl)-4H-pyrido[1,2-a]pyrimidin-4-one
2-(3,4-dimethoxyphenyl)-7-[(3R,5S)-3,5-dimethylpiperazin-1-yl]-4H-pyrido[1,2-a]pyrimidin-4-one
2-(3,4-dimethoxyphenyl)-7-(4-propylpiperazin-1-yl)-4H-pyrido[1,2-a]pyrimidin-4-one
2-(4-methoxyphenyl)-7-(4-methyl-1,4-diazepan-1-yl)-4H-pyrido[1,2-a]pyrimidin-4-one
7-(3,3-dimethylpiperazin-1-yl)-2-(4-methoxyphenyl)-4H-pyrido[1,2-a]pyrimidin-4-one
2-(1,3-benzodioxol-5-yl)-7-(piperazin-1-yl)-4H-pyrido[1,2-a]pyrimidin-4-one
2-(1,3-benzodioxol-5-yl)-7-(4-methylpiperazin-1-yl)-4H-pyrido[1,2-a]pyrimidin-4-one
2-(1,3-benzodioxol-5-yl)-7-[(3R)-3-methylpiperazin-1-yl]-4H-pyrido[1,2-a]pyrimidin-4-one
2-(1,3-benzodioxol-5-yl)-7-[(3R,5S)-3,5-dimethylpiperazin-1-yl]-4H-pyrido[1,2-a]pyrimidin-4-one
2-(3-methoxyphenyl)-7-(piperazin-1-yl)-4H-pyrido[1,2-a]pyrimidin-4-one
2-(3-methoxyphenyl)-7-(4-methylpiperazin-1-yl)-4H-pyrido[1,2-a]pyrimidin-4-one
2-(3-methoxyphenyl)-7-[(3R)-3-methylpiperazin-1-yl]-4H-pyrido[1,2-a]pyrimidin-4-one
7-[(3R,5S)-3,5-dimethylpiperazin-1-yl]-2-(3-methoxyphenyl)-4H-pyrido[1,2-a]pyrimidin-4-one
7-(4-ethylpiperazin-1-yl)-2-(3-methoxyphenyl)-4H-pyrido[1,2-a]pyrimidin-4-one
7-(1,4-diazepan-1-yl)-2-(3-methoxyphenyl)-4H-pyrido[1,2-a]pyrimidin-4-one
2-(3-methoxyphenyl)-7-(4-methyl-1,4-diazepan-1-yl)-4H-pyrido[1,2-a]pyrimidin-4-one
2-(6-methylimidazo[1,2-a]pyridin-2-yl)-7-(piperazin-1-yl)-4H-pyrido[1,2-a]pyrimidin-4-one
2-(3,4-dimethoxyphenyl)-7-[(3S)-3-methylpiperazin-1-yl]-4H-pyrido[1,2-a]pyrimidin-4-one
2-(2,3-dihydro-1,4-benzodioxin-6-yl)-7-(piperazin-1-yl)-4H-pyrido[1,2-a]pyrimidin-4-one
2-(2,3-dihydro-1,4-benzodioxin-6-yl)-7-[(3S)-3-methylpiperazin-1-yl]-4H-pyrido[1,2-a]pyrimidin-4-one
2-phenyl-7-(piperazin-1-yl)-4H-pyrido[1,2-a]pyrimidin-4-one
7-[(3S)-3-methylpiperazin-1-yl]-2-phenyl-4H-pyrido[1,2-a]pyrimidin-4-one
2-(2,3-dihydro-1,4-benzodioxin-6-yl)-7-[(3R)-3-methylpiperazin-1-yl]-4H-pyrido[1,2-a]pyrimidin-4-one
2-(2,3-dihydro-1,4-benzodioxin-6-yl)-7-(3,3-dimethylpiperazin-1-yl)-4H-pyrido[1,2-a]pyrimidin-4-one
2-(2,3-dihydro-1,4-benzodioxin-6-yl)-7-[(3R,5S)-3,5-dimethylpiperazin-1-yl]-4H-pyrido[1,2-a]pyrimidin-4-one
7-(1,4-diazepan-1-yl)-2-(2,3-dihydro-1,4-benzodioxin-6-yl)-4H-pyrido[1,2-a]pyrimidin-4-one
2-(2,3-dihydro-1,4-benzodioxin-6-yl)-7-(4-methyl-1,4-diazepan-1-yl)-4H-pyrido[1,2-a]pyrimidin-4-one
2-(3,4-dimethoxyphenyl)-9-fluoro-7-(4-methylpiperazin-1-yl)-4H-pyrido[1,2-a]pyrimidin-4-one
2-(3-chlorophenyl)-7-(piperazin-1-yl)-4H-pyrido[1,2-a]pyrimidin-4-one 2-(4-chlorophenyl)-7-(piperazin-1-yl)-4H-pyrido[1,2-a]pyrimidin-4-one
7-(piperazin-1-yl)-2-[3-(trifluoromethyl)phenyl]-4H-pyrido[1,2-a]pyrimidin-4-one
7-(piperazin-1-yl)-2-[4-(trifluoromethyl)phenyl]-4H-pyrido[1,2-a]pyrimidin-4-one
2-(3-methylphenyl)-7-(piperazin-1-yl)-4H-pyrido[1,2-a]pyrimidin-4-one
2-(4-fluorophenyl)-7-(piperazin-1-yl)-4H-pyrido[1,2-a]pyrimidin-4-one
2-(4-nitrophenyl)-7-(piperazin-1-yl)-4H-pyrido[1,2-a]pyrimidin-4-one
2-(3,4-dimethoxyphenyl)-9-fluoro-7-(piperidin-4-ylamino)-4H-pyrido[1,2-a]pyrimidin-4-one
2-[4-(dimethylamino)phenyl]-9-fluoro-7-(piperazin-1-yl)-4H-pyrido[1,2-a]pyrimidin-4-one
2-[4-(dimethylamino)phenyl]-9-fluoro-7-[(3R)-3-methylpiperazin-1-yl]-4H-pyrido[1,2-a]pyrimidin-4-one
2-(2-fluorophenyl)-7-(piperazin-1-yl)-4H-pyrido[1,2-a]pyrimidin-4-one
3-(3,4-dimethoxyphenyl)-8-(piperazin-1-yl)-4H-pyrido[1,2-a]pyrimidin-4-one
2-[4-(dimethylamino)phenyl]-7-(piperazin-1-yl)-4H-pyrido[1,2-a]pyrimidin-4-one
2-[4-(dimethylamino)phenyl]-7-[(3S)-3-methylpiperazin-1-yl]-4H-pyrido[1,2-a]pyrimidin-4-one
2-(3,4-dimethylphenyl)-7-(piperazin-1-yl)-4H-pyrido[1,2-a]pyrimidin-4-one
2-(3,4-dimethylphenyl)-7-[(3S)-3-methylpiperazin-1-yl]-4H-pyrido[1,2-a]pyrimidin-4-one
2-[3-(dimethylamino)phenyl]-7-(piperazin-1-yl)-4H-pyrido[1,2-a]pyrimidin-4-one
2-[3-(dimethylamino)phenyl]-7-[(3S)-3-methylpiperazin-1-yl]-4H-pyrido[1,2-a]pyrimidin-4-one
2-[4-(difluoromethoxy)phenyl]-7-(piperazin-1-yl)-4H-pyrido[1,2-a]pyrimidin-4-one
2-[4-(difluoromethoxy)phenyl]-7-[(3S)-3-methylpiperazin-1-yl]-4H-pyrido[1,2-a]pyrimidin-4-one
2-(3-fluorophenyl)-7-(piperazin-1-yl)-4H-pyrido[1,2-a]pyrimidin-4-one
2-(3-nitrophenyl)-7-(piperazin-1-yl)-4H-pyrido[1,2-a]pyrimidin-4-one
2-(4-methylphenyl)-7-(piperazin-1-yl)-4H-pyrido[1,2-a]pyrimidin-4-one
2-(2-fluoro-4,5-dimethoxyphenyl)-7-(piperazin-1-yl)-4H-pyrido[1,2-a]pyrimidin-4-one
2-(2-fluoro-4,5-dimethoxyphenyl)-7-[(3S)-3-methylpiperazin-1-yl]-4H-pyrido[1,2-a]pyrimidin-4-one
7-(3,8-diazabicyclo[3.2.1]oct-3-yl)-2-(3,4-dimethoxyphenyl)-4H-pyrido[1,2-a]pyrimidin-4-one
2-[4-methoxy-3-(trifluoromethyl)phenyl]-7-(piperazin-1-yl)-4H-pyrido[1,2-a]pyrimidin-4-one
2-[4-methoxy-3-(trifluoromethyl)phenyl]-7-[(3R)-3-methylpiperazin-1-yl]-4H-pyrido[1,2-a]pyrimidin-4-one
2-[4-methoxy-3-(trifluoromethyl)phenyl]-7-[(3S)-3-methylpiperazin-1-yl]-4H-pyrido[1,2-a]pyrimidin-4-one
2-(3,4-dimethoxyphenyl)-9-methoxy-7-(piperazin-1-yl)-4H-pyrido[1,2-a]pyrimidin-4-one
2-(3,5-difluoro-4-hydroxyphenyl)-7-(piperazin-1-yl)-4H-pyrido[1,2-a]pyrimidin-4-one
2-(3-fluoro-4-methoxyphenyl)-7-(piperazin-1-yl)-4H-pyrido[1,2-a]pyrimidin-4-one
4-[4-oxo-7-(piperazin-1-yl)-4H-pyrido[1,2-a]pyrimidin-2-yl]benzonitrile
2-(6-methylimidazo[1,2-a]pyrazin-2-yl)-7-(piperazin-1-yl)-4H-pyrido[1,2-a]pyrimidin-4-one
2-(6-methylimidazo[1,2-a]pyrazin-2-yl)-7-[(3S)-3-methylpiperazin-1-yl]-4H-pyrido[1,2-a]pyrimidin-4-one
2-[3-fluoro-5-(trifluoromethyl)phenyl]-7-(piperazin-1-yl)-4H-pyrido[1,2-a]pyrimidin-4-one
2-[4-fluoro-3-(trifluoromethyl)phenyl]-7-(piperazin-1-yl)-4H-pyrido[1,2-a]pyrimidin-4-one
2-[2-methoxy-3-(trifluoromethyl)phenyl]-7-(piperazin-1-yl)-4H-pyrido[1,2-a]pyrimidin-4-one
2-(3,5-difluorophenyl)-7-(piperazin-1-yl)-4H-pyrido[1,2-a]pyrimidin-4-one
7-(piperazin-1-yl)-2-[3-(trifluoromethoxy)phenyl]-4H-pyrido[1,2-a]pyrimidin-4-one
2-[4-methoxy-3-(trifluoromethoxy)phenyl]-7-(piperazin-1-yl)-4H-pyrido[1,2-a]pyrimidin-4-one
2-[4-hydroxy-3-(trifluoromethoxy)phenyl]-7-(piperazin-1-yl)-4H-pyrido[1,2-a]pyrimidin-4-one
2-[4-methoxy-3-(trifluoromethoxy)phenyl]-7-[(3S)-3-methylpiperazin-1-yl]-4H-pyrido[1,2-a]pyrimidin-4-one
2-[4-hydroxy-3-(trifluoromethoxy)phenyl]-7-[(3S)-3-methylpiperazin-1-yl]-4H-pyrido[1,2-a]pyrimidin-4-one
2-(3,4-dimethoxyphenyl)-4-oxo-7-(piperazin-1-yl)-4H-quinolizine-1-carbonitrile
2-(3-fluoro-4-methoxyphenyl)-7-[(3R)-3-methylpiperazin-1-yl]-4H-pyrido[1,2-a]pyrimidin-4-one
2-(3-fluoro-4-methoxyphenyl)-7-[(3S)-3-methylpiperazin-1-yl]-4H-pyrido[1,2-a]pyrimidin-4-one
2-(6-methoxypyridin-3-yl)-7-(piperazin-1-yl)-4H-pyrido[1,2-a]pyrimidin-4-one
2-(2,4-dimethoxyphenyl)-7-(piperazin-1-yl)-4H-pyrido[1,2-a]pyrimidin-4-one
2-(2,4-dimethoxyphenyl)-7-[(3S)-3-methylpiperazin-1-yl]-4H-pyrido[1,2-a]pyrimidin-4-one
2-(3,4-dimethoxyphenyl)-7-[(3S)-3-methylpiperazin-1-yl]-4H-quinolizin-4-one
2-(5-fluoropyridin-3-yl)-7-(piperazin-1-yl)-4H-pyrido[1,2-a]pyrimidin-4-one
2-(5-fluoropyridin-3-yl)-7-[(3S)-3-methylpiperazin-1-yl]-4H-pyrido[1,2-a]pyrimidin-4-one
2-(5-chloropyridin-3-yl)-7-(piperazin-1-yl)-4H-pyrido[1,2-a]pyrimidin-4-one
2-(5-chloropyridin-3-yl)-7-[(3S)-3-methylpiperazin-1-yl]-4H-pyrido[1,2-a]pyrimidin-4-one
2-(5-chloro-6-methoxypyridin-3-yl)-7-(piperazin-1-yl)-4H-pyrido[1,2-a]pyrimidin-4-one
2-(1H-indol-6-yl)-7-(piperazin-1-yl)-4H-pyrido[1,2-a]pyrimidin-4-one
2-(1H-indol-5-yl)-7-(piperazin-1-yl)-4H-pyrido[1,2-a]pyrimidin-4-one
2-[3-(difluoromethoxy)-4-methoxyphenyl]-7-(piperazin-1-yl)-4H-pyrido[1,2-a]pyrimidin-4-one
2-[3-(difluoromethoxy)-4-hydroxyphenyl]-7-(piperazin-1-yl)-4H-pyrido[1,2-a]pyrimidin-4-one
2-[3-(difluoromethoxy)-4-methoxyphenyl]-7-[(3S)-3-methylpiperazin-1-yl]-4H-pyrido[1,2-a]pyrimidin-4-one
2-[3-(difluoromethoxy)-4-hydroxyphenyl]-7-[(3S)-3-methylpiperazin-1-yl]-4H-pyrido[1,2-a]pyrimidin-4-one
2-(3-fluoro-4-methoxyphenyl)-7-(piperazin-1-yl)-4H-quinolizin-4-one
2-(3-fluoro-4-methoxyphenyl)-7-[(3S)-3-methylpiperazin-1-yl]-4H-quinolizin-4-one
2-(3,5-difluorophenyl)-7-[(3S)-3-methylpiperazin-1-yl]-4H-pyrido[1,2-a]pyrimidin-4-one
2-(3,4-dimethoxyphenyl)-7-(piperazin-1-yl)-4H-quinolizin-4-one
2-(imidazo[1,2-a]pyridin-7-yl)-7-(piperazin-1-yl)-4H-pyrido[1,2-a]pyrimidin-4-one 2-(imidazo[1,2-a]pyridin-6-yl)-7-(piperazin-1-yl)-4H-pyrido[1,2-a]pyrimidin-4-one
2-(2-methylimidazo[1,2-a]pyridin-6-yl)-7-(piperazin-1-yl)-4H-pyrido[1,2-a]pyrimidin-4-one
2-(3-chloro-4-methoxyphenyl)-7-(piperazin-1-yl)-4H-pyrido[1,2-a]pyrimidin-4-one
2-(3-chloro-4-methoxyphenyl)-7-[(3S)-3-methylpiperazin-1-yl]-4H-pyrido[1,2-a]pyrimidin-4-one
2-(3-ethoxy-4-methoxyphenyl)-7-(piperazin-1-yl)-4H-pyrido[1,2-a]pyrimidin-4-one
2-(3-ethoxy-4-methoxyphenyl)-7-[(3S)-3-methylpiperazin-1-yl]-4H-pyrido[1,2-a]pyrimidin-4-one
2-(2-methylimidazo[1,2-a]pyridin-6-yl)-7-(4-methylpiperazin-1-yl)-4H-pyrido[1,2-a]pyrimidin-4-one
2-(2-methylimidazo[1,2-a]pyridin-6-yl)-7-[(3S)-3-methylpiperazin-1-yl]-4H-pyrido[1,2-a]pyrimidin-4-one
7-(1,4-diazepan-1-yl)-2-(2-methylimidazo[1,2-a]pyridin-6-yl)-4H-pyrido[1,2-a]pyrimidin-4-one
7-[(3R,5S)-3,5-dimethylpiperazin-1-yl]-2-(2-methylimidazo[1,2-a]pyridin-6-yl)-4H-pyrido[1,2-a]pyrimidin-4-one
2-(6,8-dimethylimidazo[1,2-a]pyrazin-2-yl)-7-(piperazin-1-yl)-4H-pyrido[1,2-a]pyrimidin-4-one
2-(6,8-dimethylimidazo[1,2-a]pyrazin-2-yl)-7-[(3S)-3-methylpiperazin-1-yl]-4H-pyrido[1,2-a]pyrimidin-4-one
2-(4,6-dimethylpyrazolo[1,5-a]pyrazin-2-yl)-7-(piperazin-1-yl)-4H-pyrido[1,2-a]pyrimidin-4-one
2-(4,6-dimethylpyrazolo[1,5-a]pyrazin-2-yl)-7-[(3S)-3-methylpiperazin-1-yl]-4H-pyrido[1,2-a]pyrimidin-4-one
2-(3,4-dimethoxyphenyl)-7-(2-methylpyridin-4-yl)-4H-pyrido[1,2-a]pyrimidin-4-one
7-(piperazin-1-yl)-2-[2-(trifluoromethyl)imidazo[1,2-a]pyridin-6-yl]-4H-pyrido[1,2-a]pyrimidin-4-one
2-(2-ethylimidazo[1,2-a]pyridin-6-yl)-7-(piperazin-1-yl)-4H-pyrido[1,2-a]pyrimidin-4-one
2-(2,3-dimethylimidazo[1,2-a]pyridin-6-yl)-7-(piperazin-1-yl)-4H-pyrido[1,2-a]pyrimidin-4-one
2-(3,4-dimethoxyphenyl)-7-[(3 aR,6aS)-hexahydropyrrolo[3,4-c]pyrrol-2(1H)-yl]-4H-pyrido[1,2-a]pyrimidin-4-one
7-(4-aminopiperidin-1-yl)-2-(3,4-dimethoxyphenyl)-4H-pyrido[1,2-a]pyrimidin-4-one
7-(piperazin-1-yl)-2-(1H-pyrrolo[2,3-b]pyridin-5-yl)-4H-pyrido[1,2-a]pyrimidin-4-one
2-(1-methyl-1H-pyrrolo[2,3-b]pyridin-5-yl)-7-(piperazin-1-yl)-4H-pyrido[1,2-a]pyrimidin-4-one
7-[(3R,5S)-3,5-dimethylpiperazin-1-yl]-2-(1-methyl-1H-pyrrolo[2,3-b]pyridin-5-yl)-4H-pyrido[1,2-a]pyrimidin-4-one
7-[(3R,5S)-3,5-dimethylpiperazin-1-yl]-2-(4,6-dimethylpyrazolo[1,5-a]pyrazin-2-yl)-4H-pyrido[1,2-a]pyrimidin-4-one
7-(1,4-diazepan-1-yl)-2-(4,6-dimethylpyrazolo[1,5-a]pyrazin-2-yl)-4H-pyrido[1,2-a]pyrimidin-4-one
2-(2-methyl-1,3-benzoxazol-6-yl)-7-(piperazin-1-yl)-4H-pyrido[1,2-a]pyrimidin-4-one
2-(2-methyl-1,3-benzoxazol-6-yl)-7-[(3S)-3-methylpiperazin-1-yl]-4H-pyrido[1,2-a]pyrimidin-4-one
2-(2-methyl-1,3-benzothiazol-5-yl)-7-[(3S)-3-methylpiperazin-1-yl]-4H-pyrido[1,2-a]pyrimidin-4-one
2-(2-methyl-1,3-benzothiazol-5-yl)-7-(piperazin-1-yl)-4H-pyrido[1,2-a]pyrimidin-4-one
2-(2-methyl-2H-indazol-5-yl)-7-(piperazin-1-yl)-4H-pyrido[1,2-a]pyrimidin-4-one
2-(2-methyl-2H-indazol-5-yl)-7-[(3S)-3-methylpiperazin-1-yl]-4H-pyrido[1,2-a]pyrimidin-4-one
2-(3-fluoro-5-methoxyphenyl)-7-(piperazin-1-yl)-4H-pyrido[1,2-a]pyrimidin-4-one
2-(3-fluoro-5-methoxyphenyl)-7-[(3S)-3-methylpiperazin-1-yl]-4H-pyrido[1,2-a]pyrimidin-4-one
2-(2,8-dimethylimidazo[1,2-a]pyridin-6-yl)-7-(piperazin-1-yl)-4H-pyrido[1,2-a]pyrimidin-4-one
2-(3,4-dimethoxyphenyl)-9-methyl-7-[(3S)-3-methylpiperazin-1-yl]-4H-pyrido[1,2-a]pyrimidin-4-one
2-(3,4-dimethoxyphenyl)-7-(1,2,3,6-tetrahydropyridin-4-yl)-4H-pyrido[1,2-a]pyrimidin-4-one
2-(3,4-dimethoxyphenyl)-7-(piperidin-4-yl)-4H-pyrido[1,2-a]pyrimidin-4-one
2-(3-fluoro-4,5-dimethoxyphenyl)-7-(piperazin-1-yl)-4H-pyrido[1,2-a]pyrimidin-4-one
2-(3,4-dimethoxyphenyl)-7-(4-hydroxypiperazin-1-yl)-4H-pyrido[1,2-a]pyrimidin-4-one
2-(3,4-dimethoxyphenyl)-7-[(3S)-3-(dimethylamino)pyrrolidin-1-yl]-4H-pyrido[1,2-a]pyrimidin-4-one
2-(3,4-dimethoxyphenyl)-7-[4-(dimethylamino)piperidin-1-yl]-4H-pyrido[1,2-a]pyrimidin-4-one
2-(4-methoxy-3-methylphenyl)-7-(piperazin-1-yl)-4H-pyrido[1,2-a]pyrimidin-4-one
3-[4-oxo-7-(piperazin-1-yl)-4H-pyrido[1,2-a]pyrimidin-2-yl]benzonitrile
2-methoxy-5-[4-oxo-7-(piperazin-1-yl)-4H-pyrido[1,2-a]pyrimidin-2-yl]benzonitrile
2-(3-fluoro-4-hydroxyphenyl)-7-(piperazin-1-yl)-4H-pyrido[1,2-a]pyrimidin-4-one
2-(4-ethoxy-3-fluorophenyl)-7-(piperazin-1-yl)-4H-pyrido[1,2-a]pyrimidin-4-one
2-[3-fluoro-4-(2,2,2-trifluoroethoxy)phenyl]-7-(piperazin-1-yl)-4H-pyrido[1,2-a]pyrimidin-4-one
2-(2-methyl-1,3-benzoxazol-5-yl)-7-(piperazin-1-yl)-4H-pyrido[1,2-a]pyrimidin-4-one
2-(2-methyl-1,3-benzoxazol-5-yl)-7-[(3S)-3-methylpiperazin-1-yl]-4H-pyrido[1,2-a]pyrimidin-4-one
2-(3-fluoro-4-methylphenyl)-7-(piperazin-1-yl)-4H-pyrido[1,2-a]pyrimidin-4-one
2-(3-fluoro-4-methylphenyl)-7-[(3S)-3-methylpiperazin-1-yl]-4H-pyrido[1,2-a]pyrimidin-4-one
7-[(3S)-3-aminopyrrolidin-1-yl]-2-(3,4-dimethoxyphenyl)-4H-pyrido[1,2-a]pyrimidin-4-one
2-(3,4-dimethoxyphenyl)-9-methyl-7-(piperazin-1-yl)-4H-pyrido[1,2-a]pyrimidin-4-one
7-(1,4-diazepan-1-yl)-2-(2-methyl-1,3-benzothiazol-5-yl)-4H-pyrido[1,2-a]pyrimidin-4-one
7-[(3S)-3-methylpiperazin-1-yl]-2-(4-methyl-1,3-thiazol-2-yl)-4H-pyrido[1,2-a]pyrimidin-4-one
2-(4-methyl-1,3-thiazol-2-yl)-7-(piperazin-1-yl)-4H-pyrido[1,2-a]pyrimidin-4-one
2-(3,4-dimethoxyphenyl)-7-(1-methylpiperidin-4-yl)-4H-pyrido[1,2-a]pyrimidin-4-one
2-(3,4-dimethoxyphenyl)-7-[(3S)-3-(propan-2-ylamino)pyrrolidin-1-yl]-4H-pyrido[1,2-a]pyrimidin-4-one
2-(3-fluoro-4-methoxyphenyl)-7-(4-methyl-1,4-diazepan-1-yl)-4H-pyrido[1,2-a]pyrimidin-4-one
2-(4-methoxy-3-nitrophenyl)-7-(piperazin-1-yl)-4H-pyrido[1,2-a]pyrimidin-4-one
2-[3-fluoro-4-(methylsulfanyl)phenyl]-7-(piperazin-1-yl)-4H-pyrido[1,2-a]pyrimidin-4-one
7-(4-methyl-1,4-diazepan-1-yl)-2-(2-methylimidazo[1,2-a]pyridin-6-yl)-4H-pyrido[1,2-a]pyrimidin-4-one
2-(4,6-dimethylpyrazolo[1,5-a]pyrazin-2-yl)-7-(4-methylpiperazin-1-yl)-4H-pyrido[1,2-a]pyrimidin-4-one
2-(2-methyl-1,3-benzoxazol-6-yl)-7-(4-methylpiperazin-1-yl)-4H-pyrido[1,2-a]pyrimidin-4-one 7-[(3R,5S)-3,5-dimethylpiperazin-1-yl]-2-(2-methyl-1,3-benzoxazol-6-yl)-4H-pyrido[1,2-a]pyrimidin-4-one
2-(5-fluoro-6-methoxypyridin-3-yl)-7-[(3S)-3-methylpiperazin-1-yl]-4H-pyrido[1,2-a]pyrimidin-4-one
7-[(3R,5S)-3,5-dimethylpiperazin-1-yl]-2-(5-fluoro-6-methoxypyridin-3-yl)-4H-pyrido[1,2-a]pyrimidin-4-one
7-[(3R,5S)-3,5-dimethylpiperazin-1-yl]-2-(2-methyl-1,3-benzothiazol-5-yl)-4H-pyrido[1,2-a]pyrimidin-4-one
2-(2-methyl-1,3-benzothiazol-5-yl)-7-(4-methylpiperazin-1-yl)-4H-pyrido[1,2-a]pyrimidin-4-one
2-(2-methyl-1,3-benzothiazol-5-yl)-7-(4-methyl-1,4-diazepan-1-yl)-4H-pyrido[1,2-a]pyrimidin-4-one
7-[(8aS)-hexahydropyrrolo[1,2-a]pyrazin-2(1H)-yl]-2-(2-methyl-1,3-benzothiazol-5-yl)-4H-pyrido[1,2-a]pyrimidin-4-one
2-(4-methyl-1H-imidazol-1-yl)-7-(piperazin-1-yl)-4H-pyrido[1,2-a]pyrimidin-4-one
2-(4-methyl-1H-imidazol-1-yl)-7-[(3S)-3-methylpiperazin-1-yl]-4H-pyrido[1,2-a]pyrimidin-4-one
2-(3,4-dimethoxyphenyl)-7-{[2-(methylamino)ethyl]amino}-4H-pyrido[1,2-a]pyrimidin-4-one
2-(5-fluoro-6-methoxypyridin-3-yl)-7-(piperazin-1-yl)-4H-pyrido[1,2-a]pyrimidin-4-one
2-(3,5-difluoro-4-methoxyphenyl)-7-(piperazin-1-yl)-4H-pyrido[1,2-a]pyrimidin-4-one
2-(3,5-difluoro-4-methoxyphenyl)-7-[(3S)-3-methylpiperazin-1-yl]-4H-pyrido[1,2-a]pyrimidin-4-one
7-[4-(dimethylamino)piperidin-1-yl]-2-(3-fluoro-4-methoxyphenyl)-4H-pyrido[1,2-a]pyrimidin-4-one
2-(3-fluoro-4-methoxyphenyl)-7-(1,2,3,6-tetrahydropyridin-4-yl)-4H-pyrido[1,2-a]pyrimidin-4-one
2-(3,4-dimethoxyphenyl)-7-(piperidin-4-ylamino)-4H-pyrido[1,2-a]pyrimidin-4-one
2-(3,4-dimethoxyphenyl)-7-(1-methyl-1,2,3,6-tetrahydropyridin-4-yl)-4H-pyrido[1,2-a]pyrimidin-4-one
2-(3-chloro-5-fluorophenyl)-7-[(3S)-3-methylpiperazin-1-yl]-4H-pyrido[1,2-a]pyrimidin-4-one
2-(3-chloro-5-fluorophenyl)-7-(piperazin-1-yl)-4H-pyrido[1,2-a]pyrimidin-4-one
7-[(3S)-3-methylpiperazin-1-yl]-2-(1-methyl-1H-pyrazol-4-yl)-4H-pyrido[1,2-a]pyrimidin-4-one
2-(1-methyl-1H-pyrazol-4-yl)-7-(piperazin-1-yl)-4H-pyrido[1,2-a]pyrimidin-4-one
2-(2-methyl-1,3-benzoxazol-6-yl)-7-[(3R)-3-methylpiperazin-1-yl]-4H-pyrido[1,2-a]pyrimidin-4-one
7-(3,3-dimethylpiperazin-1-yl)-2-(2-methyl-1,3-benzoxazol-6-yl)-4H-pyrido[1,2-a]pyrimidin-4-one
7-(1,4-diazepan-1-yl)-2-(2-methyl-1,3-benzoxazol-6-yl)-4H-pyrido[1,2-a]pyrimidin-4-one
2-(2-methyl-1,3-benzoxazol-6-yl)-7-(4-methyl-1,4-diazepan-1-yl)-4H-pyrido[1,2-a]pyrimidin-4-one
7-[(8aS)-hexahydropyrrolo[1,2-a]pyrazin-2(1H)-yl]-2-(2-methyl-1,3-benzoxazol-6-yl)-4H-pyrido[1,2-a]pyrimidin-4-one
7-[(8aR)-hexahydropyrrolo[1,2-a]pyrazin-2(1H)-yl]-2-(2-methyl-1,3-benzoxazol-6-yl)-4H-pyrido[1,2-a]pyrimidin-4-one
2-(4,5-dimethoxypyridin-2-yl)-7-(piperazin-1-yl)-4H-pyrido[1,2-a]pyrimidin-4-one
7-[3-(dimethylamino)pyrrolidin-1-yl]-2-(3-fluoro-4-methoxyphenyl)-4H-quinolizin-4-one
7-(4-aminopiperidin-1-yl)-2-(3-fluoro-4-methoxyphenyl)-4H-quinolizin-4-one
7-(4-ethylpiperazin-1-yl)-2-(2-methyl-1,3-benzoxazol-6-yl)-4H-pyrido[1,2-a]pyrimidin-4-one
7-[4-(dimethylamino)piperidin-1-yl]-2-(3-fluoro-4-methoxyphenyl)-4H-quinolizin-4-one
2-(3-fluoro-4-methoxyphenyl)-7-(1-methyl-1,2,3,6-tetrahydropyridin-4-yl)-4H-pyrido[1,2-a]pyrimidin-4-one
7-[(3S)-3-(dimethylamino)pyrrolidin-1-yl]-2-(3-fluoro-4-methoxyphenyl)-4H-pyrido[1,2-a]pyrimidin-4-one
7-[(3R,4R)-3-(dimethylamino)-4-hydroxypyrrolidin-1-yl]-2-(3-fluoro-4-methoxyphenyl)-4H-pyrido[1,2-a]pyrimidin-4-one
7-(4-aminopiperidin-1-yl)-2-(3-fluoro-4-methoxyphenyl)-4H-pyrido[1,2-a]pyrimidin-4-one
2-(3-fluoro-4-methoxyphenyl)-7-[4-(methylamino)piperidin-1-yl]-4H-pyrido[1,2-a]pyrimidin-4-one
2-(8-fluoro-2-methylimidazo[1,2-a]pyridin-6-yl)-7-(piperazin-1-yl)-4H-pyrido[1,2-a]pyrimidin-4-one
7-[(3R,5S)-3,5-dimethylpiperazin-1-yl]-2-(8-fluoro-2-methylimidazo[1,2-a]pyridin-6-yl)-4H-pyrido[1,2-a]pyrimidin-4-one
2-(8-fluoro-2-methylimidazo[1,2-a]pyridin-6-yl)-7-(4-methyl-1,4-diazepan-1-yl)-4H-pyrido[1,2-a]pyrimidin-4-one
2-(3-fluoro-4-methoxyphenyl)-7-[(3 aR, 6aS)-hexahydropyrrolo[3,4-c]pyrrol-2(1H)-yl]-4H-pyrido[1,2-a]pyrimidin-4-one
2-(3-fluoro-4-methoxyphenyl)-7-[(3 aR,6aS)-5-methylhexahydropyrrolo[3,4-c]pyrrol-2(1H)-yl]-4H-pyrido[1,2-a]pyrimidin-4-one
2-(3,4-dimethoxyphenyl)-7-[1-(2-hydroxyethyl)piperidin-4-yl]-4H-pyrido[1,2-a]pyrimidin-4-one
2-(4-fluoro-3-methoxyphenyl)-7-[(3S)-3-methylpiperazin-1-yl]-4H-pyrido[1,2-a]pyrimidin-4-one
2-(4-fluoro-3-methoxyphenyl)-7-(piperazin-1-yl)-4H-pyrido[1,2-a]pyrimidin-4-one
2-(3,4-difluoro-5-methoxyphenyl)-7-[(3S)-3-methylpiperazin-1-yl]-4H-pyrido[1,2-a]pyrimidin-4-one
2-(3,4-difluoro-5-methoxyphenyl)-7-(piperazin-1-yl)-4H-pyrido[1,2-a]pyrimidin-4-one
2-(2-methyl-1,3-benzothiazol-6-yl)-7-(piperazin-1-yl)-4H-pyrido[1,2-a]pyrimidin-4-one
7-(3-fluoro-4-methoxyphenyl)-2-(piperazin-1-yl)-4H-pyrido[1,2-a]pyrimidin-4-one
2-(2-methyl-1,3-benzothiazol-6-yl)-7-[(3S)-3-methylpiperazin-1-yl]-4H-pyrido[1,2-a]pyrimidin-4-one
2-(3-fluoro-4-methoxyphenyl)-7-[(3S)-3-(methylamino)pyrrolidin-1-yl]-4H-pyrido[1,2-a]pyrimidin-4-one
2-(3-fluoro-4-methoxyphenyl)-7-{4-[(methylamino)methyl]piperidin-1-yl}-4H-pyrido[1,2-a]pyrimidin-4-one
7-[(3S)-3-aminopyrrolidin-1-yl]-2-(3-fluoro-4-methoxyphenyl)-4H-pyrido[1,2-a]pyrimidin-4-one
2-(3-fluoro-4-methoxyphenyl)-7-{[(3R)-1-methylpyrrolidin-3-yl]amino}-4H-pyrido[1,2-a]pyrimidin-4-one
7-{4-[(dimethylamino)methyl]piperidin-1-yl}-2-(3-fluoro-4-methoxyphenyl)-4H-pyrido[1,2-a]pyrimidin-4-one
2-(6-methoxypyridin-2-yl)-7-(piperazin-1-yl)-4H-pyrido[1,2-a]pyrimidin-4-one
7-(piperazin-1-yl)-2-(pyridin-3-yl)-4H-pyrido[1,2-a]pyrimidin-4-one
2-(5-methoxypyridin-3-yl)-7-(piperazin-1-yl)-4H-pyrido[1,2-a]pyrimidin-4-one
3-fluoro-5-{7-[(3S)-3-methylpiperazin-1-yl]-4-oxo-4H-pyrido[1,2-a]pyrimidin-2-yl}benzonitrile
3-fluoro-5-[4-oxo-7-(piperazin-1-yl)-4H-pyrido[1,2-a]pyrimidin-2-yl]benzonitrile
2-(3-fluoro-4-methoxyphenyl)-7-[(3'S,4'S)-4'-hydroxy-1,3'-bipyrrolidin-1'-yl]-4H-pyrido[1,2-a]pyrimidin-4-one
2-(3-fluoro-4-methoxyphenyl)-7-{methyl[(3R)-pyrrolidin-3-yl]amino)}-4H-pyrido[1,2-a]pyrimidin-4-one
7-[(3S)-3,4-dimethylpiperazin-1-yl]-2-(2-methyl-1,3-benzoxazol-6-yl)-4H-pyrido[1,2-a]pyrimidin-4-one 2-(3,4-dimethoxyphenyl)-7-[(1-methylpiperidin-4-yl)oxy]-4H-pyrido[1,2-a]pyrimidin-4-one 2-(3,4-dimethoxyphenyl)-7-[(3S)-pyrrolidin-3-yloxy]-4H-pyrido[1,2-a]pyrimidin-4-one 2-(3,4-dimethoxyphenyl)-7-(piperidin-4-yloxy)-4H-pyrido[1,2-a]pyrimidin-4-one 7-(1,4-diazepan-1-yl)-2-(3,4-dimethoxyphenyl)-9-methyl-4H-pyrido[1,2-a]pyrimidin-4-one 2-(3-fluoro-4-methoxyphenyl)-7-{methyl[(3R)-1-methylpyrrolidin-3-yl]amino)}-4H-pyrido[1,2-a]pyrimidin-4-one 7-[4-(dimethylamino)piperidin-1-yl]-2-(2-methyl-1,3-benzoxazol-6-yl)-4H-pyrido[1,2-a]pyrimidin-4-one 7-[(3S)-3-(dimethylamino)pyrrolidin-1-yl]-2-(2-methyl-1,3-benzoxazol-6-yl)-4H-pyrido[1,2-a]pyrimidin-4-one 7-(4-aminopiperidin-1-yl)-2-(2-methyl-1,3-benzoxazol-6-yl)-4H-pyrido[1,2-a]pyrimidin-4-one 7-[(3 aR,6aS)-hexahydropyrrolo[3,4-c]pyrrol-2(1H)-yl]-2-(2-methyl-1,3-benzoxazol-6-yl)-4H-pyrido[1,2-a]pyrimidin-4-one 7-[(3R)-3,4-dimethylpiperazin-1-yl]-2-(2-methyl-1,3-benzoxazol-6-yl)-4H-pyrido[1,2-a]pyrimidin-4-one 2-(3,4-dimethoxyphenyl)-7-(1,2,3,6-tetrahydropyridin-4-yl)-4H-quinolizin-4-one 2-(3-fluoro-4-methoxyphenyl)-7-[(3 aR,6aR)-1-methylhexahydropyrrolo[3,4-b]pyrrol-5(1H)-yl]-4H-pyrido[1,2-a]pyrimidin-4-one 2-(3,4-dimethoxyphenyl)-9-methyl-7-(1,2,3,6-tetrahydropyridin-4-yl)-4H-pyrido[1,2-a]pyrimidin-4-one 2-(3,4-dimethoxyphenyl)-7-[1-(2-hydroxyethyl)-1,2,3,6-tetrahydropyridin-4-yl]-4H-pyrido[1,2-a]pyrimidin-4-one 2-(3,4-dimethoxyphenyl)-7-(1-methyl-1,2,3,6-tetrahydropyridin-4-yl)-4H-quinolizin-4-one 2-(3,4-dimethoxyphenyl)-9-methyl-7-(piperidin-4-yl)-4H-pyrido[1,2-a]pyrimidin-4-one 2-(3,4-dimethoxyphenyl)-9-methyl-7-(1-methyl-1,2,3,6-tetrahydropyridin-4-yl)-4H-pyrido[1,2-a]pyrimidin-4-one 2-(3,4-dimethoxyphenyl)-9-methyl-7-(1-methylpiperidin-4-yl)-4H-pyrido[1,2-a]pyrimidin-4-one 7-(1,4-diazepan-1-yl)-2-(2-methyl-1,3-benzothiazol-6-yl)-4H-pyrido[1,2-a]pyrimidin-4-one 2-(2-methyl-1,3-benzothiazol-6-yl)-7-(4-methyl-1,4-diazepan-1-yl)-4H-pyrido[1,2-a]pyrimidin-4-one 7-[(8aS)-hexahydropyrrolo[1,2-a]pyrazin-2(1H)-yl]-2-(2-methyl-1,3-benzothiazol-6-yl)-4H-pyrido[1,2-a]pyrimidin-4-one 2-(2-methyl-1,3-benzothiazol-6-yl)-7-(4-methylpiperazin-1-yl)-4H-pyrido[1,2-a]pyrimidin-4-one 2-(3,4-dimethoxyphenyl)-7-[(3 aR,6aS)-hexahydropyrrolo[3,4-c]pyrrol-2(1H)-yl]-9-methyl-4H-pyrido[1,2-a]pyrimidin-4-one 7-[(3S)-3,4-dimethylpiperazin-1-yl]-2-(4,6-dimethylpyrazolo[1,5-a]pyrazin-2-yl)-4H-pyrido[1,2-a]pyrimidin-4-one 2-(4,6-dimethylpyrazolo[1,5-a]pyrazin-2-yl)-7-[(3R,5S)-3,4,5-trimethylpiperazin-1-yl]-4H-pyrido[1,2-a]pyrimidin-4-one 2-(3,4-dimethoxyphenyl)-9-methyl-7-[(3 aR,6aS)-5-methylhexahydropyrrolo[3,4-c]pyrrol-2(1H)-yl]-4H-pyrido[1,2-a]pyrimidin-4-one 2-(3,4-dimethoxyphenyl)-7-[4-(dimethylamino)piperidin-1-yl]-9-methyl-4H-pyrido[12-a]pyrimidin-4-one 7-[(1R,5 S)-8-azabicyclo[3.2.1]oct-2-en-3-yl]-2-(3,4-dimethoxyphenyl)-4H-pyrido[1,2-a]pyrimidin-4-one 2-(3,4-dimethoxyphenyl)-7-(1,2,5,6-tetrahydropyridin-3-yl)-4H-pyrido[1,2-a]pyrimidin-4-one 7-[(3R)-3-(dimethylamino)pyrrolidin-1-yl]-2-(2-methyl-1,3-benzoxazol-6-yl)-4H-pyrido[1,2-a]pyrimidin-4-one 2-(2-ethyl-1,3-benzoxazol-6-yl)-7-(piperazin-1-yl)-4H-pyrido[1,2-a]pyrimidin-4-one 2-(2-ethyl-1,3-benzoxazol-6-yl)-7-[(3S)-3-methylpiperazin-1-yl]-4H-pyrido[1,2-a]pyrimidin-4-one 2-(2-methyl-1,3-benzoxazol-6-yl)-7-[(3aR,6aS)-5-methylhexahydropyrrolo[3,4-c]pyrrol-2(1H)-yl]-4H-pyrido[1,2-a]pyrimidin-4-one 7-(8-fluoro-2-methylimidazo[1,2-a]pyridin-6-yl)-2-(piperazin-1-yl)-4H-pyrido[1,2-a]pyrimidin-4-one 2-(8-fluoro-2-methylimidazo[1,2-a]pyridin-6-yl)-7-(4-methylpiperazin-1-yl)-4H-pyrido[1,2-a]pyrimidin-4-one 2-(8-fluoro-2-methylimidazo[1,2-a]pyridin-6-yl)-7-[(3R)-3-methylpiperazin-1-yl]-4H-pyrido[1,2-a]pyrimidin-4-one 2-(8-fluoro-2-methylimidazo[1,2-a]pyridin-6-yl)-7-[(8aS)-hexahydropyrrolo[1,2-a]pyrazin-2(1H)-yl]-4H-pyrido[1,2-a]pyrimidin-4-one 2-(8-fluoro-2-methylimidazo[1,2-a]pyridin-6-yl)-7-[(8aR)-hexahydropyrrolo[1,2-a]pyrazin-2(1H)-yl]-4H-pyrido[1,2-a]pyrimidin-4-one 7-(4-aminopiperidin-1-yl)-2-(8-fluoro-2-methylimidazo[1,2-a]pyridin-6-yl)-4H-pyrido[1,2-a]pyrimidin-4-one 7-[(3R)-3-(dimethylamino)pyrrolidin-1-yl]-2-(8-fluoro-2-methylimidazo[1,2-a]pyridin-6-yl)-4H-pyrido[1,2-a]pyrimidin-4-one 7-[(3S)-3-(dimethylamino)pyrrolidin-1-yl]-2-(8-fluoro-2-methylimidazo[1,2-a]pyridin-6-yl)-4H-pyrido[1,2-a]pyrimidin-4-one 2-(4-aminopiperidin-1-yl)-7-(3-fluoro-4-methoxyphenyl)-4H-pyrido[1,2-a]pyrimidin-4-one 2-[(3R)-3-(dimethylamino)pyrrolidin-1-yl]-7-(3-fluoro-4-methoxyphenyl)-4H-pyrido[1,2-a]pyrimidin-4-one 2-[(3S)-3-(dimethylamino)pyrrolidin-1-yl]-7-(3-fluoro-4-methoxyphenyl)-4H-pyrido[1,2-a]pyrimidin-4-one 2-(3-fluoro-4-methoxyphenyl)-7-[(3 aR, 6aS)-5-(2-hydroxyethyl)hexahydropyrrolo[3,4-c]pyrrol-2(1H)-yl]-4H-pyrido[1,2-a]pyrimidin-4-one 2-(3-fluoro-4-methoxyphenyl)-7-[(3aS,6aS)-1-methylhexahydropyrrolo[3,4-b]pyrrol-5(1H)-yl]-4H-pyrido[1,2-a]pyrimidin-4-one 2-(3-fluoro-4-methoxyphenyl)-7-[(3 aR, 6aS)-5-(propan-2-yl)hexahydropyrrolo[3,4-c]pyrrol-2(1H)-yl]-4H-pyrido[1,2-a]pyrimidin-4-one 7-[(3R)-3-(dimethylamino)pyrrolidin-1-yl]-2-(3-fluoro-4-methoxyphenyl)-4H-pyrido[1,2-a]pyrimidin-4-one 7-(3,3-dimethylpiperazin-1-yl)-2-(2-methyl-1,3-benzothiazol-6-yl)-4H-pyrido[1,2-a]pyrimidin-4-one 7-[(8aR)-hexahydropyrrolo[1,2-a]pyrazin-2(1H)-yl]-2-(2-methyl-1,3-benzothiazol-6-yl)-4H-pyrido[1,2-a]pyrimidin-4-one 7-[4-(dimethylamino)piperidin-1-yl]-2-(2-methyl-1,3-benzothiazol-6-yl)-4H-pyrido[1,2-a]pyrimidin-4-one 2-(2-methyl-1,3-benzothiazol-6-yl)-7-(piperidin-4-yloxy)-4H-pyrido[1,2-a]pyrimidin-4-one 2-(8-chloro-2-methylimidazo[1,2-a]pyridin-6-yl)-7-(piperazin-1-yl)-4H-pyrido[1,2-a]pyrimidin-4-one 2-(8-chloro-2-methylimidazo[1,2-a]pyridin-6-yl)-7-[(3R,5S)-3,5-dimethylpiperazin-1-yl]-4H-pyrido[1,2-a]pyrimidin-4-one 2-(8-chloro-2-methylimidazo[1,2-a]pyridin-6-yl)-7-(4-methyl-1,4-diazepan-1-yl)-4H-pyrido[1,2-a]pyrimidin-4-one 2-(8-chloro-2-methylimidazo[1,2-a]pyridin-6-yl)-7-[(3R)-3-methylpiperazin-1-yl]-4H-pyrido[1,2-a]pyrimidin-4-one 2-(8-chloro-2-methylimidazo[1,2-a]pyridin-6-yl)-7-[(3S)-3-methylpiperazin-1-yl]-4H-pyrido[1,2-a]pyrimidin-4-one 2-(8-chloro-2-methylimidazo[1,2-a]pyridin-6-yl)-7-[(8aR)-hexahydropyrrolo[1,2-a]pyrazin-2(1H)-yl]-4H-pyrido[1,2-a]pyrimidin-4-one 2-(8-chloro-2-methylimidazo[1,2-a]pyridin-6-yl)-7-[(8aS)-hexahydropyrrolo[1,2-a]pyrazin-2(1H)-yl]-4H-pyrido[1,2-a]pyrimidin-4-one 7-(3-fluoro-4-methoxyphenyl)-2-(1,2,3,6-tetrahydropyridin-4-yl)-4H-pyrido[1,2-a]pyrimidin-4-one 7-[(3S)-3,4-dimethylpiperazin-1-yl]-2-(8-fluoro-2-methylimidazo[1,2-a]pyridin-6-yl)-4H-pyrido[1,2-a]pyrimidin-4-one 7-[(3R)-3,4-dimethylpiperazin-1-yl]-2-(8-fluoro-2-methylimidazo[1,2-a]pyridin-6-yl)-4H-pyrido[1,2-a]pyrimidin-4-one 7-[4-(dimethylamino)piperidin-1-yl]-2-(8-fluoro-2-methylimidazo[1,2-a]pyridin-6-yl)-4H-pyrido[1,2-a]pyrimidin-4-one 2-[4-(dimethylamino)piperidin-1-yl]-7-(3-fluoro-4-methoxyphenyl)-4H-pyrido[1,2-a]pyrimidin-4-one 2-(4-fluoro-2-methyl-1,3-benzoxazol-6-yl)-7-(1,2,3,6-tetrahydropyridin-4-yl)-4H-pyrido[1,2-a]pyrimidin-4-one 2-(4-fluoro-2-methyl-1,3-benzoxazol-6-yl)-7-(1-methyl-1,2,3,6-tetrahydropyridin-4-yl)-4H-pyrido[1,2-a]pyrimidin-4-one 2-(3-fluoro-4-methoxyphenyl)-7-[(4aR,7aR)-octahydro-6H-pyrrolo[3,4-b]pyridin-6-yl]-4H-pyrido[1,2-a]pyrimidin-4-one 2-(2-methyl-1,3-benzoxazol-6-yl)-7-(1,2,3,6-tetrahydropyridin-4-yl)-4H-pyrido[1,2-a]pyrimidin-4-one 2-(2-methyl-1,3-benzoxazol-6-yl)-7-(1-methyl-1,2,3,6-tetrahydropyridin-4-yl)-4H-pyrido[1,2-a]pyrimidin-4-one 7-(1-ethyl-1,2,3,6-tetrahydropyridin-4-yl)-2-(2-methyl-1,3-benzoxazol-6-yl)-4H-pyrido[1,2-a]pyrimidin-4-one 2-(4-fluoro-2-methyl-1,3-benzoxazol-6-yl)-7-(piperazin-1-yl)-4H-pyrido[1,2-a]pyrimidin-4-one 2-(4-fluoro-2-methyl-1,3-benzoxazol-6-yl)-7-[(3S)-3-methylpiperazin-1-yl]-4H-pyrido[1,2-a]pyrimidin-4-one 7-[(3S)-3,4-dimethylpiperazin-1-yl]-2-(4-fluoro-2-methyl-1,3-benzoxazol-6-yl)-4H-pyrido[1,2-a]pyrimidin-4-one 2-(4-fluoro-2-methyl-1,3-benzoxazol-6-yl)-7-(4-methylpiperazin-1-yl)-4H-pyrido[1,2-a]pyrimidin-4-one 7-(4-ethylpiperazin-1-yl)-2-(4-fluoro-2-methyl-1,3-benzoxazol-6-yl)-4H-pyrido[1,2-a]pyrimidin-4-one 2-(4-fluoro-2-methyl-1,3-benzoxazol-6-yl)-7-(4-propylpiperazin-1-yl)-4H-pyrido[1,2-a]pyrimidin-4-one 7-[(3aR,6aS)-5-ethylhexahydropyrrolo[3,4-c]pyrrol-2(1H)-yl]-2-(3-fluoro-4-methoxyphenyl)-4H-pyrido[1,2-a]pyrimidin-4-one 2-(3-fluoro-4-methoxyphenyl)-9-methyl-7-(1,2,3,6-tetrahydropyridin-4-yl)-4H-pyrido[1,2-a]pyrimidin-4-one 2-(3-fluoro-4-methoxyphenyl)-7-[(4aR,7aR)-1-methyloctahydro-6H-pyrrolo[3,4-b]pyridin-6-yl]-4H-pyrido[1,2-a]pyrimidin-4-one 2-(3,4-dimethoxyphenyl)-9-methyl-7-[(3R)-3-methylpiperazin-1-yl]-4H-pyrido[1,2-a]pyrimidin-4-one 2-(3-fluoro-4-methoxyphenyl)-9-methyl-7-(1-methyl-1,2,3,6-tetrahydropyridin-4-yl)-4H-pyrido[1,2-a]pyrimidin-4-one 7-(3-fluoro-4-methoxyphenyl)-2-(piperidin-4-yl)-4H-pyrido[1,2-a]pyrimidin-4-one 7-(3-fluoro-4-methoxyphenyl)-2-(1-methylpiperidin-4-yl)-4H-pyrido[1,2-a]pyrimidin-4-one 7-(1-ethyl-1,2,3,6-tetrahydropyridin-4-yl)-2-(4-fluoro-2-methyl-1,3-benzoxazol-6-yl)-4H-pyrido[1,2-a]pyrimidin-4-one 2-(4-fluoro-2-methyl-1,3-benzoxazol-6-yl)-7-(1-propyl-1,2,3,6-tetrahydropyridin-4-yl)-4H-pyrido[1,2-a]pyrimidin-4-one 2-(3,4-dimethoxyphenyl)-7-[(1R,5S)-8-methyl-8-azabicyclo[3.2.1]oct-3-yl]-4H-pyrido[1,2-a]pyrimidin-4-one 2-(3,4-dimethoxyphenyl)-7-[(2R)-2-methylpiperazin-1-yl]-4H-pyrido[1,2-a]pyrimidin-4-one 2-(2-methyl-1,3-benzoxazol-6-yl)-7-[(3S)-3-methylpiperazin-1-yl]-4H-quinolizin-4-one 2-(2-methyl-1,3-benzoxazol-6-yl)-7-(4-methylpiperazin-1-yl)-4H-quinolizin-4-one 7-[(3S)-4-ethyl-3-methylpiperazin-1-yl]-2-(2-methyl-1,3-benzoxazol-6-yl)-4H-quinolizin-4-one 7-[(3S)-3,4-dimethylpiperazin-1-yl]-2-(2-methyl-1,3-benzoxazol-6-yl)-4H-quinolizin-4-one 7-(4-aminopiperidin-1-yl)-2-(2-methyl-1,3-benzoxazol-6-yl)-4H-quinolizin-4-one 2-(3-fluoro-4-methoxyphenyl)-9-methyl-7-[(3S)-3-methylpiperazin-1-yl]-4H-pyrido[1,2-a]pyrimidin-4-one 7-[4-(dimethylamino)piperidin-1-yl]-2-(3-fluoro-4-methoxyphenyl)-9-methyl-4H-pyrido[1,2-a]pyrimidin-4-one 2-(3-fluoro-4-methoxyphenyl)-9-methyl-7-(1-methylpiperidin-4-yl)-4H-pyrido[1,2-a]pyrimidin-4-one 7-[4-(cyclopropylamino)piperidin-1-yl]-2-(3,4-dimethoxyphenyl)-9-methyl-4H-pyrido[1,2-a]pyrimidin-4-one 2-(8-chloro-2-methylimidazo[1,2-a]pyridin-6-yl)-7-[(3S)-3,4-dimethylpiperazin-1-yl]-4H-pyrido[1,2-a]pyrimidin-4-one 2-(3,4-dimethoxyphenyl)-7-[(3R,5S)-3,5-dimethylpiperazin-1-yl]-9-methyl-4H-pyrido[1,2-a]pyrimidin-4-one 2-(3,4-dimethoxyphenyl)-7-[(3R)-3,4-dimethylpiperazin-1-yl]-9-methyl-4H-pyrido[1,2-a]pyrimidin-4-one 2-(4,6-dimethylpyrazolo[1,5-a]pyrazin-2-yl)-7-(4-methyl-1,4-diazepan-1-yl)-4H-pyrido[1,2-a]pyrimidin-4-one 2-(4,6-dimethylpyrazolo[1,5-a]pyrazin-2-yl)-7-[(3R)-3-methylpiperazin-1-yl]-4H-pyrido[1,2-a]pyrimidin-4-one 2-(4,6-dimethylpyrazolo[1,5-a]pyrazin-2-yl)-7-[(8aS)-hexahydropyrrolo[1,2-a]pyrazin-2(1H)-yl]-4H-pyrido[1,2-a]pyrimidin-4-one 2-(4,6-dimethylpyrazolo[1,5-a]pyrazin-2-yl)-7-[(8aR)-hexahydropyrrolo[1,2-a]pyrazin-2(1H)-yl]-4H-pyrido[1,2-a]pyrimidin-4-one 2-(4,6-dimethylpyrazolo[1,5-a]pyrazin-2-yl)-7-(4-ethylpiperazin-1-yl)-4H-pyrido[1,2-a]pyrimidin-4-one 7-[4-(dimethylamino)piperidin-1-yl]-2-(4,6-dimethylpyrazolo[1,5-a]pyrazin-2-yl)-4H-pyrido[1,2-a]pyrimidin-4-one 7-(3,3-dimethylpiperazin-1-yl)-2-(4,6-dimethylpyrazolo[1,5-a]pyrazin-2-yl)-4H-pyrido[1,2-a]pyrimidin-4-one 7-(4-cyclopropylpiperazin-1-yl)-2-(4,6-dimethylpyrazolo[1,5-a]pyrazin-2-yl)-4H-pyrido[1,2-a]pyrimidin-4-one 2-(4,6-dimethylpyrazolo[1,5-a]pyrazin-2-yl)-7-(1,2,3,6-tetrahydropyridin-4-yl)-4H-pyrido[1,2-a]pyrimidin-4-one 2-(4,6-dimethylpyrazolo[1,5-a]pyrazin-2-yl)-7-[(3R)-4-ethyl-3-methylpiperazin-1-yl]-4H-pyrido[1,2-a]pyrimidin-4-one 2-(3,4-dimethoxyphenyl)-9-methyl-7-(4-methylpiperazin-1-yl)-4H-pyrido[1,2-a]pyrimidin-4-one 2-(3,4-dimethoxyphenyl)-7-[4-(dimethylamino)piperidin-1-yl]-9-ethyl-4H-pyrido[1,2-a]pyrimidin-4-one 2-(3,4-dimethoxyphenyl)-7-[1-(2-hydroxyethyl)-1,2,3,6-tetrahydropyridin-4-yl]-9-methyl-4H-pyrido[1,2-a]pyrimidin-4-one 7-[4-(dimethylamino)piperidin-1-yl]-2-(2-methyl-1,3-benzothiazol-5-yl)-4H-pyrido[1,2-a]pyrimidin-4-one 7-(4-aminopiperidin-1-yl)-2-(2-methyl-1,3-benzothiazol-5-yl)-4H-pyrido[1,2-a]pyrimidin-4-one 7-[(3 aR,6aS)-hexahydropyrrolo[3,4-c]pyrrol-2(1H)-yl]-2-(2-methyl-1,3-benzothiazol-5-yl)-4H-pyrido[1,2-a]pyrimidin-4-one 2-(4,6-dimethylpyrazolo[1,5-a]pyrazin-2-yl)-7-(1-methyl-1,2,3,6-tetrahydropyridin-4-yl)-4H-pyrido[1,2-a]pyrimidin-4-one 2-(4,6-dimethylpyrazolo[1,5-a]pyrazin-2-yl)-7-(1-ethyl-1,2,3,6-tetrahydropyridin-4-yl)-4H-pyrido[1,2-a]pyrimidin-4-one 2-(4,6-dimethylpyrazolo[1,5-a]pyrazin-2-yl)-7-(1-propyl-1,2,3,6-tetrahydropyridin-4-yl)-4H-pyrido[1,2-a]pyrimidin-4-one 2-(3,4-dimethoxyphenyl)-7-(1,2,3,6-tetrahydropyridin-4-yl)-4H-pyrimido[1,2-a]pyrimidin-4-one 7-(1-cyclopropyl-1,2,3,6-tetrahydropyridin-4-yl)-2-(4,6-dimethylpyrazolo[1,5-a]pyrazin-2-yl)-4H-pyrido[1,2-a]pyrimidin-4-one 2-(4,6-dimethylpyrazolo[1,5-a]pyrazin-2-yl)-7-[1-(propan-2-yl)-1,2,3,6-tetrahydropyridin-4-yl]-4H-pyrido[1,2-a]pyrimidin-4-one 7-(1-cyclobutyl-1,2,3,6-tetrahydropyridin-4-yl)-2-(4,6-dimethylpyrazolo[1,5-a]pyrazin-2-yl)-4H-pyrido[1,2-a]pyrimidin-4-one 2-(4,6-dimethylpyrazolo[1,5-a]pyrazin-2-yl)-7-[1-(oxetan-3-yl)-1,2,3,6-tetrahydropyridin-4-yl]-4H-pyrido[1,2-a]pyrimidin-4-one 2-(3,4-dimethoxyphenyl)-9-methyl-7-[4-(methylamino)piperidin-1-yl]-4H-pyrido[1,2-a]pyrimidin-4-one 2-(3,4-dimethoxyphenyl)-7-[4-(ethylamino)piperidin-1-yl]-9-methyl-4H-pyrido[1,2-a]pyrimidin-4-one 2-(3,4-dimethoxyphenyl)-8-methyl-7-(piperazin-1-yl)-4H-pyrido[1,2-a]pyrimidin-4-one 2-(3,4-dimethoxyphenyl)-7-[4-(propan-2-ylamino)piperidin-1-yl]-4H-pyrido[1,2-a]pyrimidin-4-one 7-(1-cyclobutyl-1,2,3,6-tetrahydropyridin-4-yl)-2-(3,4-dimethoxyphenyl)-4H-pyrido[1,2-a]pyrimidin-4-one 2-(3,4-dimethoxyphenyl)-7-[1-(propan-2-yl)-1,2,3,6-tetrahydropyridin-4-yl]-4H-pyrido[1,2-a]pyrimidin-4-one 2-(3,4-dimethoxyphenyl)-7-[1-(oxetan-3-yl)-1,2,3,6-tetrahydropyridin-4-yl]-4H-pyrido[1,2-a]pyrimidin-4-one 2-(3,4-dimethoxyphenyl)-7-(1-propyl-1,2,3,6-tetrahydropyridin-4-yl)-4H-pyrido[1,2-a]pyrimidin-4-one 2-(3,4-dimethoxyphenyl)-7-[4-(methylamino)cyclohex-1-en-1-yl]-4H-pyrido[1,2-a]pyrimidin-4-one 2-(3,4-dimethoxyphenyl)-7-[4-(dimethylamino)cyclohex-1-en-1-yl]-4H-pyrido[1,2-a]pyrimidin-4-one 2-(3,4-dimethoxyphenyl)-7-{4-[ethyl(methyl)amino]cyclohex-1-en-1-yl}-4H-pyrido[1,2-a]pyrimidin-4-one 2-(3,4-dimethoxyphenyl)-7-{4-[methyl(propyl)amino]cyclohex-1-en-1-yl}-4H-pyrido[1,2-a]pyrimidin-4-one 2-(3,4-dimethoxyphenyl)-7-(1-ethyl-1,2,3,6-tetrahydropyridin-4-yl)-4H-pyrido[1,2-a]pyrimidin-4-one 7-(3,4-dimethoxyphenyl)-2-(1,2,3,6-tetrahydropyridin-4-yl)-4H-pyrido[1,2-a]pyrimidin-4-one 7-(8-fluoro-2-methylimidazo[1,2-a]pyridin-6-yl)-2-(1,2,3,6-tetrahydropyridin-4-yl)-4H-pyrido[1,2-a]pyrimidin-4-one 2-(8-fluoro-2-methylimidazo[1,2-a]pyridin-6-yl)-7-[4-(propan-2-yl)piperazin-1-yl]-4H-pyrido[1,2-a]pyrimidin-4-one 2-(8-chloro-2-methylimidazo[1,2-a]pyridin-6-yl)-7-[4-(propan-2-yl)piperazin-1-yl]-4H-pyrido[1,2-a]pyrimidin-4-one 7-(2-methylimidazo[1,2-a]pyridin-6-yl)-2-(1,2,3,6-tetrahydropyridin-4-yl)-4H-pyrido[1,2-a]pyrimidin-4-one 7-(2-methylimidazo[1,2-a]pyridin-6-yl)-2-(1-methyl-1,2,3,6-tetrahydropyridin-4-yl)-4H-pyrido[1,2-a]pyrimidin-4-one 7-(3,4-dimethoxyphenyl)-2-(1-methyl-1,2,3,6-tetrahydropyridin-4-yl)-4H-pyrido[1,2-a]pyrimidin-4-one 2-(3,4-dimethoxyphenyl)-9-methyl-7-(1-propyl-1,2,3,6-tetrahydropyridin-4-yl)-4H-pyrido[1,2-a]pyrimidin-4-one 7-(1-cyclobutyl-1,2,3,6-tetrahydropyridin-4-yl)-2-(3,4-dimethoxyphenyl)-9-methyl-4H-pyrido[1,2-a]pyrimidin-4-one 2-(2-methyl-1,3-benzothiazol-6-yl)-7-(piperidin-4-yl)-4H-pyrimido[1,2-b]pyridazin-4-one 7-(4-aminopiperidin-1-yl)-2-(2-methyl-1,3-benzothiazol-6-yl)-4H-pyrido[1,2-a]pyrimidin-4-one 7-(3-aminopyrrolidin-1-yl)-2-(2-methyl-1,3-benzothiazol-6-yl)-4H-pyrido[1,2-a]pyrimidin-4-one 7-[(3R)-3-(dimethylamino)pyrrolidin-1-yl]-2-(2-methyl-1,3-benzothiazol-6-yl)-4H-pyrido[1,2-a]pyrimidin-4-one 2-(2-methyl-1,3-benzothiazol-6-yl)-7-(1,2,3,6-tetrahydropyridin-4-yl)-4H-pyrido[1,2-a]pyrimidin-4-one 2-(8-fluoro-2-methylimidazo[1,2-a]pyridin-6-yl)-7-[4-(2-methoxyethyl)piperazin-1-yl]-4H-pyrido[1,2-a]pyrimidin-4-one 2-(3,4-dimethoxyphenyl)-9-methyl-7-[1-(oxetan-3-yl)-1,2,3,6-tetrahydropyridin-4-yl]-4H-pyrido[1,2-a]pyrimidin-4-one 2-(3,4-dimethoxyphenyl)-9-methyl-7-[1-(propan-2-yl)-1,2,3,6-tetrahydropyridin-4-yl]-4H-pyrido[1,2-a]pyrimidin-4-one 2-(3,4-dimethoxyphenyl)-7-(1-ethyl-1,2,3,6-tetrahydropyridin-4-yl)-9-methyl-4H-pyrido[1,2-a]pyrimidin-4-one 2-(3,4-dimethoxyphenyl)-8-methyl-7-(1,2,3,6-tetrahydropyridin-4-yl)-4H-pyrido[1,2-a]pyrimidin-4-one 7-(1-cyclopropyl-1,2,3,6-tetrahydropyridin-4-yl)-2-(3,4-dimethoxyphenyl)-9-methyl-4H-pyrido[1,2-a]pyrimidin-4-one 2-(3,4-dimethoxyphenyl)-8-methyl-7-(1-methyl-1,2,3,6-tetrahydropyridin-4-yl)-4H-pyrido[1,2-a]pyrimidin-4-one 2-(2-methyl-1,3-benzothiazol-6-yl)-7-(1-methyl-1,2,3,6-tetrahydropyridin-4-yl)-4H-pyrido[1,2-a]pyrimidin-4-one 7-[1-(2-hydroxyethyl)-1,2,3,6-tetrahydropyridin-4-yl]-2-(2-methyl-1,3-benzothiazol-6-yl)-4H-pyrido[1,2-a]pyrimidin-4-one 2-(2-methyl-1,3-benzothiazol-6-yl)-7-[1-(propan-2-yl)-1,2,3,6-tetrahydropyridin-4-yl]-4H-pyrido[1,2-a]pyrimidin-4-one 7-(1-cyclopropyl-1,2,3,6-tetrahydropyridin-4-yl)-2-(2-methyl-1,3-benzothiazol-6-yl)-4H-pyrido[1,2-a]pyrimidin-4-one 7-(1-ethyl-1,2,3,6-tetrahydropyridin-4-yl)-2-(2-methyl-1,3-benzothiazol-6-yl)-4H-pyrido[1,2-a]pyrimidin-4-one 7-[(3R)-3,4-dimethylpiperazin-1-yl]-2-(4,6-dimethylpyrazolo[1,5-a]pyrazin-2-yl)-4H-pyrido[1,2-a]pyrimidin-4-one 2-(3,4-dimethoxyphenyl)-7-(1,2,3,6-tetrahydropyridin-4-yl)-4H-pyrimido[1,2-b]pyridazin-4-one 7-[(1 S,4S)-2,5-diazabicyclo[2.2.1]hept-2-yl]-2-(4,6-dimethylpyrazolo[1,5-a]pyrazin-2-yl)-4H-pyrido[1,2-a]pyrimidin-4-one 2-(4,6-dimethylpyrazolo[1,5-a]pyrazin-2-yl)-7-[(1 S,4S)-5-methyl-2,5-diazabicyclo[2.2.1]hept-2-yl]-4H-pyrido[1,2-a]pyrimidin-4-one 2-(4,6-dimethylpyrazolo[1,5-a]pyrazin-2-yl)-7-[(1 S,4S)-5-ethyl-2,5-diazabicyclo[2.2.1]hept-2-yl]-4H-pyrido[1,2-a]pyrimidin-4-one 2-(3,4-dimethoxyphenyl)-7-(1,2,3,6-tetrahydropyridin-4-yl)-4H-pyrazino[1,2-a]pyrimidin-4-one 2-(3-fluoro-4-methoxyphenyl)-7-(piperidin-4-yl)-4H-pyrido[1,2-a]pyrimidin-4-one 2-(3,4-dimethoxyphenyl)-7-(1-ethylpiperidin-4-yl)-4H-pyrido[1,2-a]pyrimidin-4-one 2-(3,4-dimethoxyphenyl)-7-[cis-4-(methylamino)cyclohexyl]-4H-pyrido[1,2-a]pyrimidin-4-one 2-(3,4-dimethoxyphenyl)-7-(piperidin-3-yl)-4H-pyrido[1,2-a]pyrimidin-4-one 2-(3,4-dimethoxyphenyl)-9-methyl-7-[4-(propylamino)piperidin-1-yl]-4H-pyrido[12-a]pyrimidin-4-one 2-(3,4-dimethoxyphenyl)-9-ethyl-7-(1,2,3,6-tetrahydropyridin-4-yl)-4H-pyrido[1,2-a]pyrimidin-4-one 7-(2-methylimidazo[1,2-a]pyridin-6-yl)-2-(piperidin-4-yl)-4H-pyrido[1,2-a]pyrimidin-4-one 7-(8-fluoro-2-methylimidazo[1,2-a]pyridin-6-yl)-2-(piperidin-4-yl)-4H-pyrido[1,2-a]pyrimidin-4-one 7-(8-fluoro-2-methylimidazo[1,2-a]pyridin-6-yl)-2-(1-methyl-1,2,3,6-tetrahydropyridin-4-yl)-4H-pyrido[1,2-a]pyrimidin-4-one 7-(4-cyclopropylpiperazin-1-yl)-2-(8-fluoro-2-methylimidazo[1,2-a]pyridin-6-yl)-4H-pyrido[1,2-a]pyrimidin-4-one 2-(1,3-dimethylpyrrolo[1,2-a]pyrazin-7-yl)-7-(1,2,3,6-tetrahydropyridin-4-yl)-4H-pyrazino[1,2-a]pyrimidin-4-one 2-(3,4-dimethoxyphenyl)-7-[(8aR)-hexahydropyrrolo[1,2-a]pyrazin-2(1H)-yl]-9-methyl-4H-pyrido[1,2-a]pyrimidin-4-one 2-(3,4-dimethoxyphenyl)-9-ethyl-7-(1-methyl-1,2,3,6-tetrahydropyridin-4-yl)-4H-pyrido[1,2-a]pyrimidin-4-one 2-(3,4-dimethoxyphenyl)-9-methyl-7-[4-(propan-2-ylamino)piperidin-1-yl]-4H-pyrido[12-a]pyrimidin-4-one 2-(3,4-dimethoxyphenyl)-7-[(8aS)-hexahydropyrrolxo[1,2-a]pyrazin-2(1H)-yl]-9-methyl-4H-pyrido[1,2-a]pyrimidin-4-one 2-(3,4-dimethoxyphenyl)-9-ethyl-7-(1-ethyl-1,2,3,6-tetrahydropyridin-4-yl)-4H-pyrido[1,2-a]pyrimidin-4-one 2-(3,4-dimethoxyphenyl)-9-methyl-7-[4-(morpholin-4-yl)piperidin-1-yl]-4H-pyrido[1,2-a]pyrimidin-4-one 2-(6-methylpyrazolo[1,5-a]pyrazin-2-yl)-7-(piperazin-1-yl)-4H-pyrido[1,2-a]pyrimidin-4-one 2-(2-methyl-1,3-benzoxazol-6-yl)-7-(1,2,3,6-tetrahydropyridin-4-yl)-4H-pyrazino[1,2-a]pyrimidin-4-one hydrochloride (1:1)

2-(2-methyl-1,3-benzoxazol-6-yl)-7-(1-methyl-1,2,3,6-tetrahydropyridin-4-yl)-4H-pyrazino[1,2-a]pyrimidin-4-one 7-(1-ethyl-1,2,3,6-tetrahydropyridin-4-yl)-2-(2-methyl-1,3-benzoxazol-6-yl)-4H-pyrazino[1,2-a]pyrimidin-4-one 2-(2-methyl-1,3-benzothiazol-6-yl)-7-(piperidin-4-yl)-4H-pyrido[1,2-a]pyrimidin-4-one 2-(4,6-dimethylpyrazolo[1,5-a]pyrazin-2-yl)-7-[4-(pyrrolidin-1-yl)piperidin-1-yl]-4H-pyrido[1,2-a]pyrimidin-4-one 7-(1,4'-bipiperidin-1'-yl)-2-(4,6-dimethylpyrazolo[1,5-a]pyrazin-2-yl)-4H-pyrido[1,2-a]pyrimidin-4-one 2-(4,6-dimethylpyrazolo[1,5-a]pyrazin-2-yl)-7-[4-(4-methylpiperazin-1-yl)piperidin-1-yl]-4H-pyrido[1,2-a]pyrimidin-4-one 2-(4,6-dimethylpyrazolo[1,5-a]pyrazin-2-yl)-7-[4-(morpholin-4-yl)piperidin-1-yl]-4H-pyrido[1,2-a]pyrimidin-4-one 2-(2-methylimidazo[1,2-a]pyridin-6-yl)-7-(1,2,3,6-tetrahydropyridin-4-yl)-4H-pyrido[1,2-a]pyrimidin-4-one 2-(2-methylimidazo[1,2-a]pyridin-6-yl)-7-(1-methyl-1,2,3,6-tetrahydropyridin-4-yl)-4H-pyrido[1,2-a]pyrimidin-4-one 7-(1-ethyl-1,2,3,6-tetrahydropyridin-4-yl)-2-(2-methylimidazo[1,2-a]pyridin-6-yl)-4H-pyrido[1,2-a]pyrimidin-4-one 7-[4-(dimethylamino)piperidin-1-yl]-2-(2-methylimidazo[1,2-a]pyridin-6-yl)-4H-pyrido[1,2-a]pyrimidin-4-one 2-(3,4-dimethoxyphenyl)-7-{4-[(2-hydroxyethyl)amino]piperidin-1-yl)}-9-methyl-4H-pyrido[1,2-a]pyrimidin-4-one 2-(3,4-dimethoxyphenyl)-9-ethyl-7-(1-methylpiperidin-4-yl)-4H-pyrido[1,2-a]pyrimidin-4-one 7-[4-(diethylamino)piperidin-1-yl]-2-(3,4-dimethoxyphenyl)-9-methyl-4H-pyrido[1,2-a]pyrimidin-4-one 2-(3,4-dimethoxyphenyl)-9-ethyl-7-(1-ethylpiperidin-4-yl)-4H-pyrido[1,2-a]pyrimidin-4-one 2-(2-methylimidazo[1,2-a]pyridin-6-yl)-7-[4-(pyrrolidin-1-yl)piperidin-1-yl]-4H-pyrido[12-a]pyrimidin-4-one 2-(2-methylimidazo[1,2-a]pyridin-6-yl)-7-(piperidin-4-yl)-4H-pyrido[1,2-a]pyrimidin-4-one 2-(2-methyl-1,3-benzothiazol-6-yl)-7-(1-methylpiperidin-4-yl)-4H-pyrido[1,2-a]pyrimidin-4-one 7-(4-methylpiperazin-1-yl)-2-(6-methylpyrazolo[1,5-a]pyrazin-2-yl)-4H-pyrido[1,2-a]pyrimidin-4-one 7-[(3S)-3-methylpiperazin-1-yl]-2-(6-methylpyrazolo[1,5-a]pyrazin-2-yl)-4H-pyrido[1,2-a]pyrimidin-4-one 7-[(3R,5S)-3,5-dimethylpiperazin-1-yl]-2-(6-methylpyrazolo[1,5-a]pyrazin-2-yl)-4H-pyrido[1,2-a]pyrimidin-4-one 2-(1-methyl-1H-indazol-5-yl)-7-(1,2,3,6-tetrahydropyridin-4-yl)-4H-pyrido[1,2-a]pyrimidin-4-one 2-[6-(dimethylamino)pyridin-3-yl]-7-(1,2,3,6-tetrahydropyridin-4-yl)-4H-pyrido[1,2-a]pyrimidin-4-one 7-[4-(diethylamino)piperidin-1-yl]-2-(2-methylimidazo[1,2-a]pyridin-6-yl)-4H-pyrido[1,2-a]pyrimidin-4-one 2-(3,4-dimethoxyphenyl)-7-{4-[(2-hydroxyethyl)(methyl)amino]piperidin-1-yl)}-9-methyl-4H-pyrido[1,2-a]pyrimidin-4-one 2-(3,4-dimethoxyphenyl)-9-ethyl-7-[(3R)-3-methylpiperazin-1-yl]-4H-pyrido[1,2-a]pyrimidin-4-one 2-(2-methylimidazo[1,2-a]pyridin-6-yl)-7-(1-methylpiperidin-4-yl)-4H-pyrido[1,2-a]pyrimidin-4-one 2-(1-methyl-1H-indazol-5-yl)-7-(1-methyl-1,2,3,6-tetrahydropyridin-4-yl)-4H-pyrido[1,2-a]pyrimidin-4-one 2-[6-(dimethylamino)pyridin-3-yl]-7-(1-methyl-1,2,3,6-tetrahydropyridin-4-yl)-4H-pyrido[1,2-a]pyrimidin-4-one 7-[4-(diethylamino)piperidin-1-yl]-2-(4,6-dimethylpyrazolo[1,5-a]pyrazin-2-yl)-4H-pyrido[1,2-a]pyrimidin-4-one 2-(4,6-dimethylpyrazolo[1,5-a]pyrazin-2-yl)-7-(piperidin-4-yl)-4H-pyrido[1,2-a]pyrimidin-4-one 2-(4,6-dimethylpyrazolo[1,5-a]pyrazin-2-yl)-7-(1-methylpiperidin-4-yl)-4H-pyrido[1,2-a]pyrimidin-4-one 2-(4,6-dimethylpyrazolo[1,5-a]pyrazin-2-yl)-7-(1-ethylpiperidin-4-yl)-4H-pyrido[1,2-a]pyrimidin-4-one 2-(3,4-dimethoxyphenyl)-9-ethyl-7-[(8aR)-hexahydropyrrolo[1,2-a]pyrazin-2(1H)-yl]-4H-pyrido[1,2-a]pyrimidin-4-one 2-(3,4-dimethoxyphenyl)-7-{4-[(2-methoxyethyl)amino]piperidin-1-yl}-9-methyl-4H-pyrido[1,2-a]pyrimidin-4-one 2-(4,6-dimethylpyrazolo[1,5-a]pyrazin-2-yl)-9-methyl-7-(4-methylpiperazin-1-yl)-4H-pyrido[1,2-a]pyrimidin-4-one 2-(4,6-dimethylpyrazolo[1,5-a]pyrazin-2-yl)-7-[(8aR)-hexahydropyrrolo[1,2-a]pyrazin-2(1H)-yl]-9-methyl-4H-pyrido[1,2-a]pyrimidin-4-one 7-[4-(dimethylamino)piperidin-1-yl]-2-(4,6-dimethylpyrazolo[1,5-a]pyrazin-2-yl)-9-methyl-4H-pyrido[1,2-a]pyrimidin-4-one 7-(2-methylimidazo[1,2-a]pyridin-6-yl)-2-(1-methylpiperidin-4-yl)-4H-pyrido[1,2-a]pyrimidin-4-one 7-(2-methylimidazo[1,2-a]pyridin-6-yl)-2-[1-(propan-2-yl)piperidin-4-yl]-4H-pyrido[1,2-a]pyrimidin-4-one 7-(8-fluoro-2-methylimidazo[1,2-a]pyridin-6-yl)-2-(1-methylpiperidin-4-yl)-4H-pyrido[1,2-a]pyrimidin-4-one 7-(1-ethyl-1,2,3,6-tetrahydropyridin-4-yl)-2-(1-methyl-1H-indazol-5-yl)-4H-pyrido[1,2-a]pyrimidin-4-one 2-(1-methyl-1H-indazol-5-yl)-7-(1-propyl-1,2,3,6-tetrahydropyridin-4-yl)-4H-pyrido[1,2-a]pyrimidin-4-one 2-[6-(dimethylamino)pyridin-3-yl]-7-(piperidin-4-yl)-4H-pyrido[1,2-a]pyrimidin-4-one 7-(4-ethylpiperazin-1-yl)-2-(6-methylpyrazolo[1,5-a]pyrazin-2-yl)-4H-pyrido[1,2-a]pyrimidin-4-one 7-[(8aR)-hexahydropyrrolo[1,2-a]pyrazin-2(1H)-yl]-2-(6-methylpyrazolo[1,5-a]pyrazin-2-yl)-4H-pyrido[1,2-a]pyrimidin-4-one 7-[4-(dimethylamino)piperidin-1-yl]-2-(6-methylpyrazolo[1,5-a]pyrazin-2-yl)-4H-pyrido[1,2-a]pyrimidin-4-one 7-[4-(2-hydroxyethyl)piperazin-1-yl]-2-(6-methylpyrazolo[1,5-a]pyrazin-2-yl)-4H-pyrido[1,2-a]pyrimidin-4-one 2-(2-methylimidazo[1,2-a]pyridin-6-yl)-7-(1-propylpiperidin-4-yl)-4H-pyrido[1,2-a]pyrimidin-4-one 7-[1-(2-hydroxyethyl)-1,2,3,6-tetrahydropyridin-4-yl]-2-(1-methyl-1H-indazol-5-yl)-4H-pyrido[1,2-a]pyrimidin-4-one 7-[(3R)-3-methylpiperazin-1-yl]-2-(6-methylpyrazolo[1,5-a]pyrazin-2-yl)-4H-pyrido[1,2-a]pyrimidin-4-one 2-(6-methylpyrazolo[1,5-a]pyrazin-2-yl)-7-(1,2,3,6-tetrahydropyridin-4-yl)-4H-pyrido[1,2-a]pyrimidin-4-one 2-(2-methyl-2H-indazol-5-yl)-7-(1,2,3,6-tetrahydropyridin-4-yl)-4H-pyrido[1,2-a]pyrimidin-4-one 2-(1-methyl-1H-indazol-5-yl)-7-(1-methylpiperidin-4-yl)-4H-pyrido[1,2-a]pyrimidin-4-one 2-(2-methyl-2H-indazol-5-yl)-7-(1-methyl-1,2,3,6-tetrahydropyridin-4-yl)-4H-pyrido[1,2-a]pyrimidin-4-one 7-(1-ethyl-1,2,3,6-tetrahydropyridin-4-yl)-2-(2-methyl-2H-indazol-5-yl)-4H-pyrido[1,2-a]pyrimidin-4-one 7-(1-ethylpiperidin-4-yl)-2-(2-methylimidazo[1,2-a]pyridin-6-yl)-4H-pyrido[1,2-a]pyrimidin-4-one 2-(1,3-dimethylpyrrolo[1,2-a]pyrazin-7-yl)-7-[1-(propan-2-yl)-1,2,3,6-tetrahydropyridin-4-yl]-4H-pyrazino[1,2-a]pyrimidin-4-one 2-(4,6-dimethylpyrazolo[1,5-a]pyrazin-2-yl)-9-methyl-7-(1,2,3,6-tetrahydropyridin-4-yl)-4H-pyrido[1,2-a]pyrimidin-4-one 2-(4,6-dimethylpyrazolo[1,5-a]pyrazin-2-yl)-9-methyl-7-(1-methyl-1,2,3,6-tetrahydropyridin-4-yl)-4H-pyrido[1,2-a]pyrimidin-4-one 2-(4,6-dimethylpyrazolo[1,5-a]pyrazin-2-yl)-7-(1-ethyl-1,2,3,6-tetrahydropyridin-4-yl)-9-methyl-4H-pyrido[1,2-a]pyrimidin-4-one 7-(1-cyclopropyl-1,2,3,6-tetrahydropyridin-4-yl)-2-(4,6-dimethylpyrazolo[1,5-a]pyrazin-2-yl)-9-methyl-4H-pyrido[1,2-a]pyrimidin-4-one 2-(6-methylpyrazolo[1,5-a]pyrazin-2-yl)-7-(1-methyl-1,2,3,6-tetrahydropyridin-4-yl)-4H-pyrido[1,2-a]pyrimidin-4-one 7-(1-ethyl-1,2,3,6-tetrahydropyridin-4-yl)-2-(6-methylpyrazolo[1,5-a]pyrazin-2-yl)-4H-pyrido[1,2-a]pyrimidin-4-one 2-(5,7-dimethylfuro[2,3-c]pyridin-2-yl)-7-(piperazin-1-yl)-4H-pyrido[1,2-a]pyrimidin-4-one 2-(5,7-dimethylfuro[2,3-c]pyridin-2-yl)-7-(4-methylpiperazin-1-yl)-4H-pyrido[1,2-a]pyrimidin-4-one 2-(5,7-dimethylfuro[2,3-c]pyridin-2-yl)-7-[(3S)-3-methylpiperazin-1-yl]-4H-pyrido[1,2-a]pyrimidin-4-one 2-(1-methyl-1H-indazol-5-yl)-7-(4-methylpiperazin-1-yl)-4H-pyrido[1,2-a]pyrimidin-4-one 2-(1-methyl-1H-indazol-5-yl)-7-(piperazin-1-yl)-4H-pyrido[1,2-a]pyrimidin-4-one 7-[4-(dimethylamino)piperidin-1-yl]-2-(1-methyl-1H-indazol-5-yl)-4H-pyrido[1,2-a]pyrimidin-4-one 7-(4-methyl-1,4-diazepan-1-yl)-2-(1-methyl-1H-indazol-5-yl)-4H-pyrido[1,2-a]pyrimidin-4-one 7-(1-ethyl-1,2,3,6-tetrahydropyridin-4-yl)-2-(2-methyl-1,3-benzoxazol-6-yl)-4H-pyrimido[1,2-b]pyridazin-4-one 2-(8-chloro-2-methylimidazo[1,2-a]pyridin-6-yl)-7-(4-ethylpiperazin-1-yl)-4H-pyrido[1,2-a]pyrimidin-4-one 2-(8-chloro-2-methylimidazo[1,2-a]pyridin-6-yl)-7-[(3R)-4-ethyl-3-methylpiperazin-1-yl]-4H-pyrido[1,2-a]pyrimidin-4-one 2-(8-chloro-2-methylimidazo[1,2-a]pyridin-6-yl)-7-[(3S)-4-ethyl-3-methylpiperazin-1-yl]-4H-pyrido[1,2-a]pyrimidin-4-one 2-(8-chloro-2-methylimidazo[1,2-a]pyridin-6-yl)-7-[(3R)-3-methyl-4-(propan-2-yl)piperazin-1-yl]-4H-pyrido[1,2-a]pyrimidin-4-one 2-(8-chloro-2-methylimidazo[1,2-a]pyridin-6-yl)-7-[(3S)-3-methyl-4-(propan-2-yl)piperazin-1-yl]-4H-pyrido[1,2-a]pyrimidin-4-one 2-(2-methyl-1,3-benzoxazol-6-yl)-7-(piperidin-4-yl)-4H-pyrimido[1,2-b]pyridazin-4-one 2-(2-methyl-1,3-benzoxazol-6-yl)-7-(1-methylpiperidin-4-yl)-4H-pyrimido[1,2-b]pyridazin-4-one 7-(1-ethylpiperidin-4-yl)-2-(2-methyl-1,3-benzoxazol-6-yl)-4H-pyrimido[1,2-b]pyridazin-4-one 2-(4,6-dimethylpyrazolo[1,5-a]pyrazin-2-yl)-7-(piperidin-4-yl)-4H-pyrazino[1,2-a]pyrimidin-4-one 2-(4,6-dimethylpyrazolo[1,5-a]pyrazin-2-yl)-7-(1-methylpiperidin-4-yl)-4H-pyrazino[1,2-a]pyrimidin-4-one 2-(4,6-dimethylpyrazolo[1,5-a]pyrazin-2-yl)-7-(1-ethylpiperidin-4-yl)-4H-pyrazino[1,2-a]pyrimidin-4-one 2-(1-methyl-1H-indazol-5-yl)-7-(1,2,3,6-tetrahydropyridin-4-yl)-4H-pyrazino[1,2-a]pyrimidin-4-one 2-(1-methyl-1H-indazol-5-yl)-7-(1-methyl-1,2,3,6-tetrahydropyridin-4-yl)-4H-pyrazino[1,2-a]pyrimidin-4-one 7-(1-ethyl-1,2,3,6-tetrahydropyridin-4-yl)-2-(1-methyl-1H-indazol-5-yl)-4H-pyrazino[1,2-a]pyrimidin-4-one 2-(4,6-dimethylpyrazolo[1,5-a]pyrazin-2-yl)-7-(4-ethylpiperazin-1-yl)-9-methyl-4H-pyrido[1,2-a]pyrimidin-4-one 2-(4,6-dimethylpyrazolo[1,5-a]pyrazin-2-yl)-9-methyl-7-[(3R)-3-methylpiperazin-1-yl]-4H-pyrido[1,2-a]pyrimidin-4-one 7-[(3R)-3,4-dimethylpiperazin-1-yl]-2-(4,6-dimethylpyrazolo[1,5-a]pyrazin-2-yl)-9-methyl-4H-pyrido[1,2-a]pyrimidin-4-one 2-(4,6-dimethylpyrazolo[1,5-a]pyrazin-2-yl)-7-[(3R)-4-ethyl-3-methylpiperazin-1-yl]-9-methyl-4H-pyrido[1,2-a]pyrimidin-4-one 2-(4,6-dimethylpyrazolo[1,5-a]pyrazin-2-yl)-7-(piperidin-4-yl)-4H-pyrimido[1,2-b]pyridazin-4-one 2-(4,6-dimethylpyrazolo[1,5-a]pyrazin-2-yl)-7-(1-methylpiperidin-4-yl)-4H-pyrimido[1,2-b]pyridazin-4-one 2-(4,6-dimethylpyrazolo[1,5-a]pyrazin-2-yl)-7-(1-ethylpiperidin-4-yl)-4H-pyrimido[1,2-b]pyridazin-4-one 2-(4,6-dimethylpyrazolo[1,5-a]pyrazin-2-yl)-7-(octahydro-5H-pyrrolo[3,2-c]pyridin-5-yl)-4H-pyrido[1,2-a]pyrimidin-4-one 2-(8-chloro-2-methylimidazo[1,2-a]pyridin-6-yl)-7-(piperidin-4-yl)-4H-pyrido[1,2-a]pyrimidin-4-one 2-(8-chloro-2-methylimidazo[1,2-a]pyridin-6-yl)-7-(1-methylpiperidin-4-yl)-4H-pyrido[1,2-a]pyrimidin-4-one 2-(8-chloro-2-methylimidazo[1,2-a]pyridin-6-yl)-7-(1-ethylpiperidin-4-yl)-4H-pyrido[1,2-a]pyrimidin-4-one 2-(8-chloro-2-methylimidazo[1,2-a]pyridin-6-yl)-7-[1-(propan-2-yl)piperidin-4-yl]-4H-pyrido[1,2-a]pyrimidin-4-one 2-(4,6-dimethylpyrazolo[1,5-a]pyrazin-2-yl)-9-methyl-7-(4-methyl-1,4-diazepan-1-yl)-4H-pyrido[1,2-a]pyrimidin-4-one 2-(2-methyl-2H-indazol-5-yl)-7-(piperidin-4-yl)-4H-pyrimido[1,2-b]pyridazin-4-one 2-(2-methyl-2H-indazol-5-yl)-7-(1-methylpiperidin-4-yl)-4H-pyrimido[1,2-b]pyridazin-4-one 7-(1-ethylpiperidin-4-yl)-2-(2-methyl-2H-indazol-5-yl)-4H-pyrimido[1,2-b]pyridazin-4-one 2-(8-chloro-2-methylimidazo[1,2-a]pyridin-6-yl)-7-(1-methylpiperidin-4-yl)-4H-pyrimido[1,2-b]pyridazin-4-one 2-(8-chloro-2-methylimidazo[1,2-a]pyridin-6-yl)-7-(1-ethylpiperidin-4-yl)-4H-pyrimido[1,2-b]pyridazin-4-one 2-(8-chloro-2-methylimidazo[1,2-a]pyridin-6-yl)-7-[1-(2-hydroxyethyl)piperidin-4-yl]-4H-pyrimido[1,2-b]pyridazin-4-one 2-(5,7-dimethylfuro[2,3-c]pyridin-2-yl)-7-[(3R,5S)-3,5-dimethylpiperazin-1-yl]-4H-pyrido[1,2-a]pyrimidin-4-one 7-[4-(dimethylamino)piperidin-1-yl]-2-(5,7-dimethylfuro[2,3-c]pyridin-2-yl)-4H-pyrido[1,2-a]pyrimidin-4-one 2-(5,7-dimethylfuro[2,3-c]pyridin-2-yl)-7-[4-(2-hydroxyethyl)piperazin-1-yl]-4H-pyrido[1,2-a]pyrimidin-4-one 2-(4,6-dimethylpyrazolo[1,5-a]pyrazin-2-yl)-7-[1-(2-hydroxyethyl)piperidin-4-yl]-4H-pyrido[1,2-a]pyrimidin-4-one 2-(4,6-dimethylpyrazolo[1,5-a]pyrazin-2-yl)-7-[4-(2-hydroxyethyl)piperazin-1-yl]-4H-pyrido[1,2-a]pyrimidin-4-one 2-(4,6-dimethylpyrazolo[1,5-a]pyrazin-2-yl)-7-[(3R)-4-(2-hydroxyethyl)-3-methylpiperazin-1-yl]-4H-pyrido[1,2-a]pyrimidin-4-one 2-(8-chloro-2-methylimidazo[1,2-a]pyridin-6-yl)-7-[(3S)-4-(2-methoxyethyl)-3-methylpiperazin-1-yl]-4H-pyrido[1,2-a]pyrimidin-4-one 2-(8-chloro-2-methylimidazo[1,2-a]pyridin-6-yl)-7-{(3S)-4-[2-(2-hydroxyethoxy)ethyl]-3-methylpiperazin-1-yl}-4H-pyrido[1,2-a]pyrimidin-4-one 2-(8-chloro-2-methylimidazo[1,2-a]pyridin-6-yl)-7-[(3S)-4-cyclopropyl-3-methylpiperazin-1-yl]-4H-pyrido[1,2-a]pyrimidin-4-one 2-(8-chloro-2-methylimidazo[1,2-a]pyridin-6-yl)-7-[(3S)-4-cyclobutyl-3-methylpiperazin-1-yl]-4H-pyrido[1,2-a]pyrimidin-4-one 2-(8-chloro-2-methylimidazo[1,2-a]pyridin-6-yl)-7-[(3S)-4-(2-hydroxyethyl)-3-methylpiperazin-1-yl]-4H-pyrido[1,2-a]pyrimidin-4-one 2-(8-fluoro-2-methylimidazo[1,2-a]pyridin-6-yl)-7-[(3S)-4-(2-methoxyethyl)-3-methylpiperazin-1-yl]-4H-pyrido[1,2-a]pyrimidin-4-one 2-(8-fluoro-2-methylimidazo[1,2-a]pyridin-6-yl)-7-[(3S)-4-(2-hydroxyethyl)-3-methylpiperazin-1-yl]-4H-pyrido[1,2-a]pyrimidin-4-one 2-(8-fluoro-2-methylimidazo[1,2-a]pyridin-6-yl)-7-{(3S)-4-[2-(2-hydroxyethoxy)ethyl]-3-methylpiperazin-1-yl}-4H-pyrido[1,2-a]pyrimidin-4-one 2-(8-fluoro-2-methylimidazo[1,2-a]pyridin-6-yl)-7-[(3S)-3-methyl-4-(propan-2-yl)piperazin-1-yl]-4H-pyrido[1,2-a]pyrimidin-4-one 7-[(3S)-4-cyclopropyl-3-methylpiperazin-1-yl]-2-(8-fluoro-2-methylimidazo[1,2-a]pyridin-6-yl)-4H-pyrido[1,2-a]pyrimidin-4-one 7-[(3S)-4-cyclobutyl-3-methylpiperazin-1-yl]-2-(8-fluoro-2-methylimidazo[1,2-a]pyridin-6-yl)-4H-pyrido[1,2-a]pyrimidin-4-one 7-(3,3-dimethylpiperazin-1-yl)-2-(4,6-dimethylpyrazolo[1,5-a]pyrazin-2-yl)-9-methyl-4H-pyrido[1,2-a]pyrimidin-4-one 2-(1-methyl-1H-indazol-5-yl)-7-[(3R)-3-methylpiperazin-1-yl]-4H-pyrido[1,2-a]pyrimidin-4-one 2-(4-ethyl-6-methylpyrazolo[1,5-a]pyrazin-2-yl)-7-(piperazin-1-yl)-4H-pyrido[1,2-a]pyrimidin-4-one 2-(4-ethyl-6-methylpyrazolo[1,5-a]pyrazin-2-yl)-7-(4-methylpiperazin-1-yl)-4H-pyrido[1,2-a]pyrimidin-4-one 2-(4-ethyl-6-methylpyrazolo[1,5-a]pyrazin-2-yl)-7-(4-ethylpiperazin-1-yl)-4H-pyrido[1,2-a]pyrimidin-4-one 2-(4-ethyl-6-methylpyrazolo[1,5-a]pyrazin-2-yl)-7-[4-(2-hydroxyethyl)piperazin-1-yl]-4H-pyrido[1,2-a]pyrimidin-4-one 7-[4-(dimethylamino)piperidin-1-yl]-2-(4-ethyl-6-methylpyrazolo[1,5-a]pyrazin-2-yl)-4H-pyrido[1,2-a]pyrimidin-4-one 7-[4-(diethylamino)piperidin-1-yl]-2-(4-ethyl-6-methylpyrazolo[1,5-a]pyrazin-2-yl)-4H-pyrido[1,2-a]pyrimidin-4-one 7-[(3R,5S)-3,5-dimethylpiperazin-1-yl]-2-(l-methyl-1H-indazol-5-yl)-4H-pyrido[1,2-a]pyrimidin-4-one 2-(1-methyl-1H-indazol-5-yl)-7-[(3S)-3-methylpiperazin-1-yl]-4H-pyrido[1,2-a]pyrimidin-4-one 2-(2-methylimidazo[1,2-a]pyridin-6-yl)-7-[1-(propan-2-yl)piperidin-4-yl]-4H-pyrido[1,2-a]pyrimidin-4-one 2-(2-methylimidazo[1,2-a]pyridin-7-yl)-7-(piperazin-1-yl)-4H-pyrido[1,2-a]pyrimidin-4-one 2-(2-methylimidazo[1,2-a]pyridin-7-yl)-7-(piperidin-4-yl)-4H-pyrido[1,2-a]pyrimidin-4-one 2-(2-methylimidazo[1,2-a]pyridin-7-yl)-7-(4-methylpiperazin-1-yl)-4H-pyrido[1,2-a]pyrimidin-4-one 7-(4-ethylpiperazin-1-yl)-2-(2-methylimidazo[1,2-a]pyridin-7-yl)-4H-pyrido[1,2-a]pyrimidin-4-one 2-(2-methylimidazo[1,2-a]pyridin-7-yl)-7-(1-methylpiperidin-4-yl)-4H-pyrido[1,2-a]pyrimidin-4-one 7-(1-ethylpiperidin-4-yl)-2-(2-methylimidazo[1,2-a]pyridin-7-yl)-4H-pyrido[1,2-a]pyrimidin-4-one 2-(4,6-dimethylpyrazolo[1,5-a]pyrazin-2-yl)-9-methyl-7-[(3S)-3-methylpiperazin-1-yl]-4H-pyrido[1,2-a]pyrimidin-4-one 7-[(3R,5S)-3,5-dimethylpiperazin-1-yl]-2-(4,6-dimethylpyrazolo[1,5-a]pyrazin-2-yl)-9-methyl-4H-pyrido[1,2-a]pyrimidin-4-one 7-[(3S)-3,4-dimethylpiperazin-1-yl]-2-(4,6-dimethylpyrazolo[1,5-a]pyrazin-2-yl)-9-methyl-4H-pyrido[1,2-a]pyrimidin-4-one 2-(4,6-dimethylpyrazolo[1,5-a]pyrazin-2-yl)-9-methyl-7-[(3R,5S)-3,4,5-trimethylpiperazin-1-yl]-4H-pyrido[1,2-a]pyrimidin-4-one 2-(2-methylimidazo[1,2-a]pyridin-6-yl)-7-[1-(propan-2-yl)-1,2,3,6-tetrahydropyridin-4-yl]-4H-pyrido[1,2-a]pyrimidin-4-one 2-(2-methyl-2H-indazol-5-yl)-7-(piperidin-4-yl)-4H-pyrazino[1,2-a]pyrimidin-4-one 2-(2-methyl-2H-indazol-5-yl)-7-(1-methylpiperidin-4-yl)-4H-pyrazino[1,2-a]pyrimidin-4-one 7-(1-ethylpiperidin-4-yl)-2-(2-methyl-2H-indazol-5-yl)-4H-pyrazino[1,2-a]pyrimidin-4-one 7-[1-(2-hydroxyethyl)piperidin-4-yl]-2-(2-methyl-2H-indazol-5-yl)-4H-pyrazino[1,2-a]pyrimidin-4-one 7-{4-[(dimethylamino)methyl]piperidin-1-yl}-2-(4,6-dimethylpyrazolo[1,5-a]pyrazin-2-yl)-4H-pyrido[1,2-a]pyrimidin-4-one 2-(4,6-dimethylpyrazolo[1,5-a]pyrazin-2-yl)-7-[4-(pyrrolidin-1-ylmethyl)piperidin-1-yl]-4H-pyrido[1,2-a]pyrimidin-4-one 2-(4,6-dimethylpyrazolo[1,5-a]pyrazin-2-yl)-7-[4-(piperidin-1-ylmethyl)piperidin-1-yl]-4H-pyrido[1,2-a]pyrimidin-4-one 2-(3,4-dimethoxyphenyl)-7-{4-[(dimethylamino)methyl]piperidin-1-yl}-4H-pyrido[1,2-a]pyrimidin-4-one 2-(3,4-dimethoxyphenyl)-7-[4-(pyrrolidin-1-ylmethyl)piperidin-1-yl]-4H-pyrido[1,2-a]pyrimidin-4-one 2-(3,4-dimethoxyphenyl)-7-[4-(piperidin-1-ylmethyl)piperidin-1-yl]-4H-pyrido[1,2-a]pyrimidin-4-one 7-[1-(2-hydroxyethyl)piperidin-4-yl]-2-(2-methylimidazo[1,2-a]pyridin-6-yl)-4H-pyrido[1,2-a]pyrimidin-4-one 7-[1-(2-hydroxyethyl)-1,2,3,6-tetrahydropyridin-4-yl]-2-(2-methylimidazo[1,2-a]pyridin-6-yl)-4H-pyrido[1,2-a]pyrimidin-4-one 2-(2-methyl-2H-indazol-5-yl)-7-(1-methylpiperidin-4-yl)-4H-pyrido[1,2-a]pyrimidin-4-one 2-(2-methylimidazo[1,2-a]pyridin-6-yl)-7-(1-methylpiperidin-4-yl)-4H-pyrazino[1,2-a]pyrimidin-4-one 7-(1-ethylpiperidin-4-yl)-2-(2-methylimidazo[1,2-a]pyridin-6-yl)-4H-pyrazino[1,2-a]pyrimidin-4-one 7-[1-(2-hydroxyethyl)piperidin-4-yl]-2-(2-methylimidazo[1,2-a]pyridin-6-yl)-4H-pyrazino[1,2-a]pyrimidin-4-one 2-(4,6-dimethylpyrazolo[1,5-a]pyrazin-2-yl)-7-{4-[(2-hydroxyethyl)(methyl)amino]piperidin-1-yl}-9-methyl-4H-pyrido[1,2-a]pyrimidin-4-one 2-(4,6-dimethylpyrazolo[1,5-a]pyrazin-2-yl)-9-methyl-7-[4-(propylamino)piperidin-1-yl]-4H-pyrido[1,2-a]pyrimidin-4-one 7-(4-amino-4-methylpiperidin-1-yl)-2-(4,6-dimethylpyrazolo[1,5-a]pyrazin-2-yl)-4H-pyrido[1,2-a]pyrimidin-4-one 2-(2-methylimidazo[1,2-a]pyridin-6-yl)-7-(piperidin-4-yl)-4H-pyrazino[1,2-a]pyrimidin-4-one 2-(2-methyl-2H-indazol-5-yl)-7-(piperazin-1-yl)-4H-pyrazino[1,2-a]pyrimidin-4-one 2-(8-chloro-2-methylimidazo[1,2-a]pyridin-6-yl)-7-(piperidin-4-yl)-4H-pyrazino[1,2-a]pyrimidin-4-one 2-(2,8-dimethylimidazo[1,2-a]pyridin-6-yl)-7-(piperidin-4-yl)-4H-pyrazino[1,2-a]pyrimidin-4-one 2-(2-methyl-2H-indazol-5-yl)-7-(4-methylpiperazin-1-yl)-4H-pyrazino[1,2-a]pyrimidin-4-one 7-(4-ethylpiperazin-1-yl)-2-(2-methyl-2H-indazol-5-yl)-4H-pyrazino[1,2-a]pyrimidin-4-one 7-[4-(2-hydroxyethyl)piperazin-1-yl]-2-(2-methyl-2H-indazol-5-yl)-4H-pyrazino[1,2-a]pyrimidin-4-one 2-(2,8-dimethylimidazo[1,2-a]pyridin-6-yl)-7-(1-methylpiperidin-4-yl)-4H-pyrazino[1,2-a]pyrimidin-4-one 2-(2,8-dimethylimidazo[1,2-a]pyridin-6-yl)-7-(1-ethylpiperidin-4-yl)-4H-pyrazino[1,2-a]pyrimidin-4-one 2-(2,8-dimethylimidazo[1,2-a]pyridin-6-yl)-7-[1-(2-hydroxyethyl)piperidin-4-yl]-4H-pyrazino[1,2-a]pyrimidin-4-one 2-(8-chloro-2-methylimidazo[1,2-a]pyridin-6-yl)-7-[1-(propan-2-yl)piperidin-4-yl]-4H-pyrazino[1,2-a]pyrimidin-4-one 2-(4,6-dimethylpyrazolo[1,5-a]pyrazin-2-yl)-7-[4-(ethylamino)piperidin-1-yl]-9-methyl-4H-pyrido[1,2-a]pyrimidin-4-one 7-{4-[bis(2-hydroxyethyl)amino]piperidin-1-yl}-2-(4,6-dimethylpyrazolo[1,5-a]pyrazin-2-yl)-9-methyl-4H-pyrido[1,2-a]pyrimidin-4-one 7-[1-(2-hydroxyethyl)piperidin-4-yl]-2-(2-methyl-1,3-benzoxazol-6-yl)-4H-pyrimido[1,2-b]pyridazin-4-one 2-(8-chloro-2-methylimidazo[1,2-a]pyridin-6-yl)-7-[1-(2-hydroxyethyl)piperidin-4-yl]-4H-pyrazino[1,2-a]pyrimidin-4-one 2-(4,6-dimethylpyrazolo[1,5-a]pyrazin-2-yl)-7-[1-(oxetan-3-yl)piperidin-4-yl]-4H-pyrido[1,2-a]pyrimidin-4-one 2-(5,7-dimethylfuro[2,3-c]pyridin-2-yl)-7-(4-ethylpiperazin-1-yl)-4H-pyrido[1,2-a]pyrimidin-4-one 2-(4,6-dimethylpyrazolo[1,5-a]pyrazin-2-yl)-7-(1-methyloctahydro-5H-pyrrolo[3,2-c]pyridin-5-yl)-4H-pyrido[1,2-a]pyrimidin-4-one 2-(1-methyl-1H-indazol-5-yl)-7-(piperidin-4-yl)-4H-pyrido[1,2-a]pyrimidin-4-one 7-(1-ethylpiperidin-4-yl)-2-(1-methyl-1H-indazol-5-yl)-4H-pyrido[1,2-a]pyrimidin-4-one 7-[1-(2-hydroxyethyl)piperidin-4-yl]-2-(1-methyl-1H-indazol-5-yl)-4H-pyrido[1,2-a]pyrimidin-4-one 2-(2-methyl-2H-indazol-5-yl)-7-(piperidin-4-yl)-4H-pyrido[1,2-a]pyrimidin-4-one 2-(2,8-dimethylimidazo[1,2-a]pyridin-6-yl)-7-(piperidin-4-yl)-4H-pyrido[1,2-a]pyrimidin-4-one 2-(2-methyl-2H-indazol-5-yl)-7-[1-(propan-2-yl)piperidin-4-yl]-4H-pyrido[1,2-a]pyrimidin-4-one 2-(4,6-dimethylpyrazolo[1,5-a]pyrazin-2-yl)-7-{4-[(2-hydroxyethyl)amino]piperidin-1-yl}-9-methyl-4H-pyrido[1,2-a]pyrimidin-4-one 2-(4,6-dimethylpyrazolo[1,5-a]pyrazin-2-yl)-9-methyl-7-[4-(methylamino)piperidin-1-yl]-4H-pyrido[1,2-a]pyrimidin-4-one 2-(4,6-dimethylpyrazolo[1,5-a]pyrazin-2-yl)-9-methyl-7-[4-(propan-2-ylamino)piperidin-1-yl]-4H-pyrido[1,2-a]pyrimidin-4-one 7-(1-ethylpiperidin-4-yl)-2-(2-methyl-2H-indazol-5-yl)-4H-pyrido[1,2-a]pyrimidin-4-one 7-[1-(2-hydroxyethyl)piperidin-4-yl]-2-(2-methyl-2H-indazol-5-yl)-4H-pyrido[1,2-a]pyrimidin-4-one 2-(2,8-dimethylimidazo[1,2-a]pyridin-6-yl)-7-(1-methylpiperidin-4-yl)-4H-pyrido[1,2-a]pyrimidin-4-one 2-(2,8-dimethylimidazo[1,2-a]pyridin-6-yl)-7-(1-ethylpiperidin-4-yl)-4H-pyrido[1,2-a]pyrimidin-4-one 2-(2,8-dimethylimidazo[1,2-a]pyridin-6-yl)-7-[1-(propan-2-yl)piperidin-4-yl]-4H-pyrido[1,2-a]pyrimidin-4-one 2-(2,8-dimethylimidazo[1,2-a]pyridin-6-yl)-7-[1-(2-hydroxyethyl)piperidin-4-yl]-4H-pyrido[1,2-a]pyrimidin-4-one 2-(4-ethyl-6-methylpyrazolo[1,5-a]pyrazin-2-yl)-7-(4-propylpiperazin-1-yl)-4H-pyrido[1,2-a]pyrimidin-4-one 2-(4-ethyl-6-methylpyrazolo[1,5-a]pyrazin-2-yl)-7-[4-(propan-2-yl)piperazin-1-yl]-4H-pyrido[1,2-a]pyrimidin-4-one 7-(4-cyclopropylpiperazin-1-yl)-2-(4-ethyl-6-methylpyrazolo[1,5-a]pyrazin-2-yl)-4H-pyrido[1,2-a]pyrimidin-4-one 7-(4-cyclobutylpiperazin-1-yl)-2-(4-ethyl-6-methylpyrazolo[1,5-a]pyrazin-2-yl)-4H-pyrido[1,2-a]pyrimidin-4-one 2-(4-ethyl-6-methylpyrazolo[1,5-a]pyrazin-2-yl)-7-[4-(oxetan-3-yl)piperazin-1-yl]-4H-pyrido[1,2-a]pyrimidin-4-one 2-(4,6-dimethylpyrazolo[1,5-a]pyrazin-2-yl)-7-(1-ethyloctahydro-5H-pyrrolo[3,2-c]pyridin-5-yl)-4H-pyrido[1,2-a]pyrimidin-4-one 2-(4,6-dimethylpyrazolo[1,5-a]pyrazin-2-yl)-7-[1-(2-hydroxyethyl)octahydro-5H-pyrrolo[3,2-c]pyridin-5-yl]-4H-pyrido[1,2-a]pyrimidin-4-one 2-(4-methoxy-6-methylpyrazolo[1,5-a]pyrazin-2-yl)-7-(4-methylpiperazin-1-yl)-4H-pyrido[1,2-a]pyrimidin-4-one 2-(4-hydroxy-6-methylpyrazolo[1,5-a]pyrazin-2-yl)-7-(4-methylpiperazin-1-yl)-4H-pyrido[1,2-a]pyrimidin-4-one 2-(2-methylimidazo[1,2-a]pyridin-6-yl)-7-[1-(propan-2-yl)piperidin-4-yl]-4H-pyrazino[1,2-a]pyrimidin-4-one 7-(1-cyclobutylpiperidin-4-yl)-2-(2-methylimidazo[1,2-a]pyridin-6-yl)-4H-pyrazino[1,2-a]pyrimidin-4-one 7-[(3R)-3,4-dimethylpiperazin-1-yl]-2-(4-ethyl-6-methylpyrazolo[1,5-a]pyrazin-2-yl)-4H-pyrido[1,2-a]pyrimidin-4-one 7-[(3R)-4-ethyl-3-methylpiperazin-1-yl]-2-(4-ethyl-6-methylpyrazolo[1,5-a]pyrazin-2-yl)-4H-pyrido[1,2-a]pyrimidin-4-one 2-(4-ethyl-6-methylpyrazolo[1,5-a]pyrazin-2-yl)-7-[(3R)-3-methyl-4-propylpiperazin-1-yl]-4H-pyrido[1,2-a]pyrimidin-4-one 2-(4-ethyl-6-methylpyrazolo[1,5-a]pyrazin-2-yl)-7-[(3R)-4-(2-hydroxyethyl)-3-methylpiperazin-1-yl]-4H-pyrido[1,2-a]pyrimidin-4-one 7-[(3R,5S)-3,5-dimethylpiperazin-1-yl]-2-(4-ethyl-6-methylpyrazolo[1,5-a]pyrazin-2-yl)-4H-pyrido[1,2-a]pyrimidin-4-one 2-(4-ethyl-6-methylpyrazolo[1,5-a]pyrazin-2-yl)-7-[4-(pyrrolidin-1-yl)piperidin-1-yl]-4H-pyrido[1,2-a]pyrimidin-4-one 2-(4-ethyl-6-methylpyrazolo[1,5-a]pyrazin-2-yl)-7-[(3S)-3-methylpiperazin-1-yl]-4H-pyrido[1,2-a]pyrimidin-4-one 2-(4-ethyl-6-methylpyrazolo[1,5-a]pyrazin-2-yl)-7-(4-methyl-1,4-diazepan-1-yl)-4H-pyrido[12-a]pyrimidin-4-one 2-(8-ethyl-2-methylimidazo[1,2-a]pyridin-6-yl)-7-(piperazin-1-yl)-4H-pyrido[1,2-a]pyrimidin-4-one 2-(8-ethyl-2-methylimidazo[1,2-a]pyridin-6-yl)-7-[(3R)-3-methylpiperazin-1-yl]-4H-pyrido[1,2-a]pyrimidin-4-one 2-(8-ethyl-2-methylimidazo[1,2-a]pyridin-6-yl)-7-[(3S)-3-methylpiperazin-1-yl]-4H-pyrido[1,2-a]pyrimidin-4-one 2-(4,6-dimethylpyrazolo[1,5-a]pyrazin-2-yl)-7-[1-(propan-2-yl)piperidin-4-yl]-4H-pyrido[1,2-a]pyrimidin-4-one 7-(1-cyclopropylpiperidin-4-yl)-2-(4,6-dimethylpyrazolo[1,5-a]pyrazin-2-yl)-4H-pyrido[1,2-a]pyrimidin-4-one 7-(1-cyclobutylpiperidin-4-yl)-2-(4,6-dimethylpyrazolo[1,5-a]pyrazin-2-yl)-4H-pyrido[1,2-a]pyrimidin-4-one 2-(4-ethyl-6-methylpyrazolo[1,5-a]pyrazin-2-yl)-7-[(3R)-3-methyl-4-(propan-2-yl)piperazin-1-yl]-4H-pyrido[1,2-a]pyrimidin-4-one 7-[(3R)-4-cyclopropyl-3-methylpiperazin-1-yl]-2-(4-ethyl-6-methylpyrazolo[1,5-a]pyrazin-2-yl)-4H-pyrido[1,2-a]pyrimidin-4-one 7-[(3R)-4-cyclobutyl-3-methylpiperazin-1-yl]-2-(4-ethyl-6-methylpyrazolo[1,5-a]pyrazin-2-yl)-4H-pyrido[1,2-a]pyrimidin-4-one 2-(4-ethyl-6-methylpyrazolo[1,5-a]pyrazin-2-yl)-7-[(3R)-3-methyl-4-(oxetan-3-yl)piperazin-1-yl]-4H-pyrido[1,2-a]pyrimidin-4-one 2-(8-ethyl-2-methylimidazo[1,2-a]pyridin-6-yl)-7-[4-(2-hydroxyethyl)piperazin-1-yl]-4H-pyrido[1,2-a]pyrimidin-4-one 7-(4-cyclobutylpiperazin-1-yl)-2-(8-ethyl-2-methylimidazo[1,2-a]pyridin-6-yl)-4H-pyrido[1,2-a]pyrimidin-4-one 2-(8-ethyl-2-methylimidazo[1,2-a]pyridin-6-yl)-7-[(3R)-4-(2-hydroxyethyl)-3-methylpiperazin-1-yl]-4H-pyrido[1,2-a]pyrimidin-4-one 7-[(3R)-4-cyclobutyl-3-methylpiperazin-1-yl]-2-(8-ethyl-2-methylimidazo[1,2-a]pyridin-6-yl)-4H-pyrido[1,2-a]pyrimidin-4-one 2-(8-ethyl-2-methylimidazo[1,2-a]pyridin-6-yl)-7-[(3S)-4-(2-hydroxyethyl)-3-methylpiperazin-1-yl]-4H-pyrido[1,2-a]pyrimidin-4-one 7-[(3S)-4-cyclobutyl-3-methylpiperazin-1-yl]-2-(8-ethyl-2-methylimidazo[1,2-a]pyridin-6-yl)-4H-pyrido[1,2-a]pyrimidin-4-one 2-(4-ethyl-6-methylpyrazolo[1,5-a]pyrazin-2-yl)-7-(piperidin-4-yl)-4H-pyrazino[1,2-a]pyrimidin-4-one 2-(4-ethyl-6-methylpyrazolo[1,5-a]pyrazin-2-yl)-7-(1-methylpiperidin-4-yl)-4H-pyrazino[1,2-a]pyrimidin-4-one 2-(4-ethyl-6-methylpyrazolo[1,5-a]pyrazin-2-yl)-7-(1-ethylpiperidin-4-yl)-4H-pyrazino[1,2-a]pyrimidin-4-one 2-(4-ethyl-6-methylpyrazolo[1,5-a]pyrazin-2-yl)-7-(piperidin-4-yl)-4H-pyrido[1,2-a]pyrimidin-4-one 2-(4-ethyl-6-methylpyrazolo[1,5-a]pyrazin-2-yl)-7-(1-methylpiperidin-4-yl)-4H-pyrido[1,2-a]pyrimidin-4-one 2-(4-ethyl-6-methylpyrazolo[1,5-a]pyrazin-2-yl)-7-(1-ethylpiperidin-4-yl)-4H-pyrido[1,2-a]pyrimidin-4-one 2-(4-ethyl-6-methylpyrazolo[1,5-a]pyrazin-2-yl)-7-[1-(2-hydroxyethyl)piperidin-4-yl]-4H-pyrido[1,2-a]pyrimidin-4-one 2-(4-ethyl-6-methylpyrazolo[1,5-a]pyrazin-2-yl)-7-(1-propylpiperidin-4-yl)-4H-pyrido[1,2-a]pyrimidin-4-one 2-(4-ethyl-6-methylpyrazolo[1,5-a]pyrazin-2-yl)-7-[(3R)-3-methylpiperazin-1-yl]-4H-pyrido[1,2-a]pyrimidin-4-one 2-(4,6-dimethylpyrazolo[1,5-a]pyrazin-2-yl)-7-[1-(2-fluoroethyl)piperidin-4-yl]-4H-pyrido[1,2-a]pyrimidin-4-one 2-(4,6-dimethylpyrazolo[1,5-a]pyrazin-2-yl)-7-[1-(3-fluoropropyl)piperidin-4-yl]-4H-pyrido[1,2-a]pyrimidin-4-one 2-(4-ethyl-6-methylpyrazolo[1,5-a]pyrazin-2-yl)-7-[4-(2-fluoroethyl)piperazin-1-yl]-4H-pyrido[1,2-a]pyrimidin-4-one 2-(4-ethyl-6-methylpyrazolo[1,5-a]pyrazin-2-yl)-7-[4-(3-fluoropropyl)piperazin-1-yl]-4H-pyrido[1,2-a]pyrimidin-4-one 2-(4-ethyl-6-methylpyrazolo[1,5-a]pyrazin-2-yl)-7-[(3R)-4-(2-fluoroethyl)-3-methylpiperazin-1-yl]-4H-pyrido[1,2-a]pyrimidin-4-one 2-(4-ethyl-6-methylpyrazolo[1,5-a]pyrazin-2-yl)-7-[(3R)-4-(3-fluoropropyl)-3-methylpiperazin-1-yl]-4H-pyrido[1,2-a]pyrimidin-4-one 2-(4-ethyl-6-methylpyrazolo[1,5-a]pyrazin-2-yl)-7-[1-(2-fluoroethyl)piperidin-4-yl]-4H-pyrido[1,2-a]pyrimidin-4-one 2-(4-ethyl-6-methylpyrazolo[1,5-a]pyrazin-2-yl)-7-[1-(3-fluoropropyl)piperidin-4-yl]-4H-pyrido[1,2-a]pyrimidin-4-one 2-(4,6-dimethylpyrazolo[1,5-a]pyrazin-2-yl)-7-{(3R)-4-[2-(2-hydroxyethoxy)ethyl]-3-methylpiperazin-1-yl}-9-methyl-4H-pyrido[1,2-a]pyrimidin-4-one 2-(4,6-dimethylpyrazolo[1,5-a]pyrazin-2-yl)-9-methyl-7-(piperidin-4-yl)-4H-pyrido[1,2-a]pyrimidin-4-one 2-(4,6-dimethylpyrazolo[1,5-a]pyrazin-2-yl)-9-methyl-7-(1-methylpiperidin-4-yl)-4H-pyrido[1,2-a]pyrimidin-4-one 2-(4,6-dimethylpyrazolo[1,5-a]pyrazin-2-yl)-7-[(3R)-4-(2-hydroxyethyl)-3-methylpiperazin-1-yl]-9-methyl-4H-pyrido[1,2-a]pyrimidin-4-one 2-[8-(hydroxymethyl)-2-methylimidazo[1,2-a]pyridin-6-yl]-7-(piperazin-1-yl)-4H-pyrido[1,2-a]pyrimidin-4-one 7-[(3R,5S)-3,5-dimethylpiperazin-1-yl]-2-(8-ethyl-2-methylimidazo[1,2-a]pyridin-6-yl)-4H-pyrido[1,2-a]pyrimidin-4-one 2-(8-ethyl-2-methylimidazo[1,2-a]pyridin-6-yl)-7-(4-methyl-1,4-diazepan-1-yl)-4H-pyrido[1,2-a]pyrimidin-4-one 2-[8-(hydroxymethyl)-2-methylimidazo[1,2-a]pyridin-6-yl]-7-(4-methylpiperazin-1-yl)-4H-pyrido[1,2-a]pyrimidin-4-one 7-(4-ethylpiperazin-1-yl)-2-[8-(hydroxymethyl)-2-methylimidazo[1,2-a]pyridin-6-yl]-4H-pyrido[1,2-a]pyrimidin-4-one 2-(4-ethyl-6-methylpyrazolo[1,5-a]pyrazin-2-yl)-7-[1-(propan-2-yl)piperidin-4-yl]-4H-pyrido[1,2-a]pyrimidin-4-one 7-(1-cyclopropylpiperidin-4-yl)-2-(4-ethyl-6-methypyrazolo[1,5-a]pyrazin-2-yl)-4H-pyrido[1,2-a]pyrimidin-4-one 7-(1-cyclobutylpiperidin-4-yl)-2-(4-ethyl-6-methylpyrazolo[1,5-a]pyrazin-2-yl)-4H-pyrido[1,2-a]pyrimidin-4-one 2-(4-ethyl-6-methylpyrazolo[1,5-a]pyrazin-2-yl)-7-[1-(oxetan-3-yl)piperidin-4-yl]-4H-pyrido[1,2-a]pyrimidin-4-one 2-(4-cyclopropyl-6-methylpyrazolo[1,5-a]pyrazin-2-yl)-7-(piperazin-1-yl)-4H-pyrido[1,2-a]pyrimidin-4-one 2-(4-cyclopropyl-6-methylpyrazolo[1,5-a]pyrazin-2-yl)-7-(4-methylpiperazin-1-yl)-4H-pyrido[1,2-a]pyrimidin-4-one 2-(4-cyclopropyl-6-methylpyrazolo[1,5-a]pyrazin-2-yl)-7-(4-ethylpiperazin-1-yl)-4H-pyrido[1,2-a]pyrimidin-4-one 2-(4-cyclopropyl-6-methylpyrazolo[1,5-a]pyrazin-2-yl)-7-[4-(2-hydroxyethyl)piperazin-1-yl]-4H-pyrido[1,2-a]pyrimidin-4-one 2-(4,6-dimethylpyrazolo[1,5-a]pyrazin-2-yl)-7-(1-propylpiperidin-4-yl)-4H-pyrido[1,2-a]pyrimidin-4-one 2-[4-(dimethylamino)-6-methylpyrazolo[1,5-a]pyrazin-2-yl]-7-(piperazin-1-yl)-4H-pyrido[1,2-a]pyrimidin-4-one 2-(2-methyl-1H-benzimidazol-6-yl)-7-(4-methylpiperazin-1-yl)-4H-pyrido[1,2-a]pyrimidin-4-one 7-(4-ethylpiperazin-1-yl)-2-(2-methyl-1H-benzimidazol-6-yl)-4H-pyrido[1,2-a]pyrimidin-4-one 2-(2,8-dimethylimidazo[1,2-a]pyridin-6-yl)-7-(piperidin-4-yl)-4H-pyrimido[1,2-b]pyridazin-4-one 2-(2-methylimidazo[1,2-a]pyridin-6-yl)-7-(piperidin-4-yl)-4H-pyrimido[1,2-b]pyridazin-4-one 7-[1-(2,2-dimethyl-1,3-dioxan-5-yl)piperidin-4-yl]-2-(4-ethyl-6-methylpyrazolo[1,5-a]pyrazin-2-yl)-4H-pyrido[1,2-a]pyrimidin-4-one 7-[1-(1,3-dihydroxypropan-2-yl)piperidin-4-yl]-2-(4-ethyl-6-methylpyrazolo[1,5-a]pyrazin-2-yl)-4H-pyrido[1,2-a]pyrimidin-4-one 7-[(3R,5S)-3,5-dimethylpiperazin-1-yl]-2-(1,3-dimethylpyrrolo[1,2-a]pyrazin-7-yl)-4H-pyrido[1,2-a]pyrimidin-4-one 2-(8-ethyl-2-methylimidazo[1,2-a]pyridin-6-yl)-7-(piperidin-4-yl)-4H-pyrido[1,2-a]pyrimidin-4-one 2-(8-ethyl-2-methylimidazo[1,2-a]pyridin-6-yl)-7-(1-methylpiperidin-4-yl)-4H-pyrido[1,2-a]pyrimidin-4-one 2-(8-ethyl-2-methylimidazo[1,2-a]pyridin-6-yl)-7-(1-ethylpiperidin-4-yl)-4H-pyrido[1,2-a]pyrimidin-4-one 2-(8-ethyl-2-methylimidazo[1,2-a]pyridin-6-yl)-7-[1-(2-hydroxyethyl)piperidin-4-yl]-4H-pyrido[1,2-a]pyrimidin-4-one 7-[(3R)-3,4-dimethylpiperazin-1-yl]-2-(8-ethyl-2-methylimidazo[1,2-a]pyridin-6-yl)-4H-pyrido[1,2-a]pyrimidin-4-one 2-(8-ethyl-2-methylimidazo[1,2-a]pyridin-6-yl)-7-[(3R)-4-ethyl-3-methylpiperazin-1-yl]-4H-pyrido[1,2-a]pyrimidin-4-one 2-(4,6-dimethylpyrazolo[1,5-a]pyrazin-2-yl)-7-(1-ethylpiperidin-4-yl)-9-methyl-4H-pyrido[1,2-a]pyrimidin-4-one 2-(4,6-dimethylpyrazolo[1,5-a]pyrazin-2-yl)-7-[1-(2-hydroxyethyl)piperidin-4-yl]-9-methyl-4H-pyrido[1,2-a]pyrimidin-4-one 7-(1-cyclobutylpiperidin-4-yl)-2-(4,6-dimethylpyrazzolo[1,5-a]pyrazin-2-yl)-9-methyl-4H-pyrido[1,2-a]pyrimidin-4-one 9-methyl-2-(2-methyl-2H-indazol-5-yl)-7-(1-methylpiperidin-4-yl)-4H-pyrido[1,2-a]pyrimidin-4-one 7-[4-(dimethylamino)-4-methylpiperidin-1-yl]-2-(4,6-dimethylpyrazolo[1,5-a]pyrazin-2-yl)-4H-pyrido[1,2-a]pyrimidin-4-one 2-(4,6-dimethylpyrazolo[1,5-a]pyrazin-2-yl)-7-[4-(ethylamino)-4-methylpiperidin-1-yl]-4H-pyrido[1,2-a]pyrimidin-4-one 2-(4,6-dimethylpyrazolo[1,5-a]pyrazin-2-yl)-7-[4-methyl-4-(propylamino)piperidin-1-yl]-4H-pyrido[1,2-a]pyrimidin-4-one 2-(4,6-dimethylpyrazolo[1,5-a]pyrazin-2-yl)-7-{4-[(2-hydroxyethyl)amino]-4-methylpiperidin-1-yl}-4H-pyrido[1,2-a]pyrimidin-4-one 7-(1-cyclobutylpiperidin-4-yl)-9-methyl-2-(2-methyl-2H-indazol-5-yl)-4H-pyrido[1,2-a]pyrimidin-4-one 7-[1-(2-hydroxyethyl)piperidin-4-yl]-9-methyl-2-(2-methyl-2H-indazol-5-yl)-4H-pyrido[1,2-a]pyrimidin-4-one 2-(4,6-dimethylpyrazolo[1,5-a]pyrazin-2-yl)-9-methyl-7-(1-propylpiperidin-4-yl)-4H-pyrido[1,2-a]pyrimidin-4-one 2-(1,3-dimethylpyrrolo[1,2-a]pyrazin-7-yl)-7-[(3R)-3-methylpiperazin-1-yl]-4H-pyrido[1,2-a]pyrimidin-4-one 2-(8-cyclopropyl-2-methylimidazo[1,2-a]pyridin-6-yl)-7-(piperazin-1-yl)-4H-pyrido[1,2-a]pyrimidin-4-one 2-(8-cyclopropyl-2-methylimidazo[1,2-a]pyridin-6-yl)-7-[(3R)-3-methylpiperazin-1-yl]-4H-pyrido[1,2-a]pyrimidin-4-one 2-(8-cyclopropyl-2-methylimidazo[1,2-a]pyridin-6-yl)-7-[(3S)-3-methylpiperazin-1-yl]-4H-pyrido[1,2-a]pyrimidin-4-one 2-(8-cyclopropyl-2-methylimidazo[1,2-a]pyridin-6-yl)-7-[(3R,5S)-3,5-dimethylpiperazin-1-yl]-4H-pyrido[1,2-a]pyrimidin-4-one 7-(1-cyclopropylpiperidin-4-yl)-9-methyl-2-(2-methyl-2H-indazol-5-yl)-4H-pyrido[1,2-a]pyrimidin-4-one 7-(1-ethylpiperidin-4-yl)-9-methyl-2-(2-methyl-2H-indazol-5-yl)-4H-pyrido[1,2-a]pyrimidin-4-one 2-(4,6-dimethylpyrazolo[1,5-a]pyrazin-2-yl)-9-methyl-7-(piperazin-1-yl)-4H-pyrido[1,2-a]pyrimidin-4-one 9-methyl-2-(2-methyl-2H-indazol-5-yl)-7-(piperidin-4-yl)-4H-pyrido[1,2-a]pyrimidin-4-one 2-(4,6-dimethylpyrazolo[1,5-a]pyrazin-2-yl)-7-[(1-methylpiperidin-4-yl)oxy]-4H-pyrido[1,2-a]pyrimidin-4-one 2-(6-methyl-4-propylpyrazolo[1,5-a]pyrazin-2-yl)-7-(piperazin-1-yl)-4H-pyrido[1,2-a]pyrimidin-4-one 7-(4-methylpiperazin-1-yl)-2-(6-methyl-4-propylpyrazolo[1,5-a]pyrazin-2-yl)-4H-pyrido[1,2-a]pyrimidin-4-one 7-(4-ethylpiperazin-1-yl)-2-(6-methyl-4-propylpyrazolo[1,5-a]pyrazin-2-yl)-4H-pyrido[1,2-a]pyrimidin-4-one 7-[4-(2-hydroxyethyl)piperazin-1-yl]-2-(6-methyl-4-propylpyrazolo[1,5-a]pyrazin-2-yl)-4H-pyrido[1,2-a]pyrimidin-4-one 7-[(3R)-3-methylpiperazin-1-yl]-2-(6-methyl-4-propylpyrazolo[1,5-a]pyrazin-2-yl)-4H-pyrido[1,2-a]pyrimidin-4-one 7-[(3S)-3-methylpiperazin-1-yl]-2-(6-methyl-4-propylpyrazolo[1,5-a]pyrazin-2-yl)-4H-pyrido[1,2-a]pyrimidin-4-one 7-[(3R,5S)-3,5-dimethylpiperazin-1-yl]-2-(6-methyl-4-propylpyrazolo[1,5-a]pyrazin-2-yl)-4H-pyrido[1,2-a]pyrimidin-4-one 2-(1,3-dimethylpyrrolo[1,2-a]pyrazin-7-yl)-7-[(3R)-3-methyl-4-(propan-2-yl)piperazin-1-yl]-4H-pyrido[1,2-a]pyrimidin-4-one 7-(4-amino-4-methylpiperidin-1-yl)-2-(1,3-dimethylpyrrolo[1,2-a]pyrazin-7-yl)-4H-pyrido[1,2-a]pyrimidin-4-one 2-(4,6-dimethylpyrazolo[1,5-a]pyrazin-2-yl)-7-[(3S)-3-ethylpiperazin-1-yl]-9-methyl-4H-pyrido[1,2-a]pyrimidin-4-one 2-[2-methyl-8-(trifluoromethyl)imidazo[1,2-a]pyridin-6-yl]-7-(piperazin-1-yl)-4H-pyrido[1,2-a]pyrimidin-4-one 7-[(3R)-3-methylpiperazin-1-yl]-2-[2-methyl-8-(trifluoromethyl)imidazo[1,2-a]pyridin-6-yl]-4H-pyrido[1,2-a]pyrimidin-4-one 7-[(3S)-3-methylpiperazin-1-yl]-2-[2-methyl-8-(trifluoromethyl)imidazo[1,2-a]pyridin-6-yl]-4H-pyrido[1,2-a]pyrimidin-4-one 7-[(3R,5S)-3,5-dimethylpiperazin-1-yl]-2-[2-methyl-8-(trifluoromethyl)imidazo[1,2-a]pyridin-6-yl]-4H-pyrido[1,2-a]pyrimidin-4-one 7-(4-amino-4-methylpiperidin-1-yl)-2-(4-ethyl-6-methylpyrazolo[1,5-a]pyrazin-2-yl)-4H-pyrido[1,2-a]pyrimidin-4-one 2-(2,7-dimethyl-2H-indazol-5-yl)-7-(piperazin-1-yl)-4H-pyrido[1,2-a]pyrimidin-4-one 2-(2,7-dimethyl-2H-indazol-5-yl)-7-(piperidin-4-yl)-4H-pyrido[1,2-a]pyrimidin-4-one 7-(3-aminoprop-1-yn-1-yl)-2-(4,6-dimethylpyrazolo[1,5-a]pyrazin-2-yl)-4H-pyrido[1,2-a]pyrimidin-4-one 2-(2,7-dimethyl-2H-indazol-5-yl)-7-[(3R)-3-methylpiperazin-1-yl]-4H-pyrido[1,2-a]pyrimidin-4-one 7-(3-aminopropyl)-2-(4,6-dimethylpyrazolo[1,5-a]pyrazin-2-yl)-4H-pyrido[1,2-a]pyrimidin-4-one 2-(1,3-dimethylpyrrolo[1,2-a]pyrazin-7-yl)-7-(1,2,3,6-tetrahydropyridin-4-yl)-4H-pyrido[1,2-a]pyrimidin-4-one 2-(4,6-dimethylpyrazolo[1,5-a]pyrazin-2-yl)-7-(2,2,6,6-tetramethyl-1,2,3,6-tetrahydropyridin-4-yl)-4H-pyrido[1,2-a]pyrimidin-4-one 2-(4-ethyl-6-methylpyrazolo[1,5-a]pyrazin-2-yl)-7-(2,2,6,6-tetramethyl-1,2,3,6-tetrahydropyridin-4-yl)-4H-pyrido[1,2-a]pyrimidin-4-one 2-(4,6-dimethylpyrazolo[1,5-a]pyrazin-2-yl)-7-[(3aR,6aS)-hexahydropyrrrol[3,4-c]pyrrol-2(1H)-yl]-4H-pyrido[1,2-a]pyrimidin-4-one 2-(4-ethyl-6-methylpyrazolo[1,5-a]pyrazin-2-yl)-7-[(3aR,6aS)-hexahydropyrrolo[3,4-c]pyrrol-2(1H)-yl]-4H-pyrido[1,2-a]pyrimidin-4-one 7-[(3R,5S)-3,5-dimethylpiperazin-1-yl]-2-(1-ethyl-3-methylpyrrolo[1,2-a]pyrazin-7-yl)-4H-pyrido[1,2-a]pyrimidin-4-one 7-(1,4-diazepan-1-yl)-2-(1-ethyl-3-methylpyrrolo[1,2-a]pyrazin-7-yl)-4H-pyrido[1,2-a]pyrimidin-4-one 2-(2,7-dimethyl-2H-indazol-5-yl)-7-[(3S)-3-methylpiperazin-1-yl]-4H-pyrido[1,2-a]pyrimidin-4-one 2-(2,7-dimethyl-2H-indazol-5-yl)-7-[(3S)-3,4-dimethylpiperazin-1-yl]-4H-pyrido[1,2-a]pyrimidin-4-one 2-(2,7-dimethyl-2H-indazol-5-yl)-7-(1-methylpiperidin-4-yl)-4H-pyrido[1,2-a]pyrimidin-4-one 2-(2,7-dimethyl-2H-indazol-5-yl)-7-(1-ethylpiperidin-4-yl)-4H-pyrido[1,2-a]pyrimidin-4-one 9-methyl-2-(2-methyl-2H-indazol-5-yl)-7-(piperazin-1-yl)-4H-pyrido[1,2-a]pyrimidin-4-one 9-methyl-2-(2-methyl-2H-indazol-5-yl)-7-[(3R)-3-methylpiperazin-1-yl]-4H-pyrido[1,2-a]pyrimidin-4-one 9-methyl-2-(2-methyl-2H-indazol-5-yl)-7-[(3S)-3-methylpiperazin-1-yl]-4H-pyrido[1,2-a]pyrimidin-4-one 7-[3-(dimethylamino)azetidin-1-yl]-2-(4,6-dimethylpyrazolo[1,5-a]pyrazin-2-yl)-4H-pyrido[1,2-a]pyrimidin-4-one 7-[3-(diethylamino)azetidin-1-yl]-2-(4,6-dimethylpyrazolo[1,5-a]pyrazin-2-yl)-4H-pyrido[1,2-a]pyrimidin-4-one 2-(4,6-dimethylpyrazolo[1,5-a]pyrazin-2-yl)-7-[3-(pyrrolidin-1-yl)azetidin-1-yl]-4H-pyrido[1,2-a]pyrimidin-4-one 7-(1,4-diazepan-1-yl)-2-(4-ethyl-6-methylpyrazolo[1,5-a]pyrazin-2-yl)-4H-pyrido[1,2-a]pyrimidin-4-one 7-[(3 aR,6aS)-hexahydropyrrolo[3,4-c]pyrrol-2(1H)-yl]-2-(6-methyl-4-propylpyrazolo[1,5-a]pyrazin-2-yl)-4H-pyrido[1,2-a]pyrimidin-4-one 2-(6-methyl-4-propylpyrazolo[1,5-a]pyrazin-2-yl)-7-(1,2,3,6-tetrahydropyridin-4-yl)-4H-pyrido[1,2-a]pyrimidin-4-one 2-(4-ethyl-6-methylpyrazolo[1,5-a]pyrazin-2-yl)-7-(1,2,3,6-tetrahydropyridin-4-yl)-4H-pyrido[1,2-a]pyrimidin-4-one 7-[(3S)-3-(aminomethyl)pyrrolidin-1-yl]-2-(4,6-dimethylpyrazolo[1,5-a]pyrazin-2-yl)-4H-pyrido[1,2-a]pyrimidin-4-one 2-(4,6-dimethylpyrazolo[1,5-a]pyrazin-2-yl)-7-[3-(piperidin-1-yl)azetidin-1-yl]-4H-pyrido[1,2-a]pyrimidin-4-one 2-(6-methyl-4-propylpyrazolo[1,5-a]pyrazin-2-yl)-7-(piperidin-4-yl)-4H-pyrido[1,2-a]pyrimidin-4-one 7-(2,7-diazaspiro[4.4]non-2-yl)-2-(4,6-dimethylpyrazolo[1,5-a]pyrazin-2-yl)-4H-pyrido[1,2-a]pyrimidin-4-one 2-(2,7-dimethyl-2H-indazol-5-yl)-7-(4-methylpiperazin-1-yl)-4H-pyrido[1,2-a]pyrimidin-4-one 7-[3-(dimethylamino)propyl]-2-(4,6-dimethylpyrazolo[1,5-a]pyrazin-2-yl)-4H-pyrido[1,2-a]pyrimidin-4-one 7-{(3S)-3-[(dimethylamino)methyl]pyrrolidin-1-yl}-2-(4,6-dimethylpyrazolo[1,5-a]pyrazin-2-yl)-4H-pyrido[1,2-a]pyrimidin-4-one 2-(4-ethyl-6-methylpyrazolo[1,5-a]pyrazin-2-yl)-9-methyl-7-(piperidin-4-yl)-4H-pyrido[1,2-a]pyrimidin-4-one 9-methyl-2-(1-methyl-1H-indazol-5-yl)-7-(piperidin-4-yl)-4H-pyrido[1,2-a]pyrimidin-4-one 2-(4-ethyl-6-methylpyrazolo[1,5-a]pyrazin-2-yl)-9-methyl-7-(1,2,3,6-tetrahydropyridin-4-yl)-4H-pyrido[1,2-a]pyrimidin-4-one 2-(4-ethyl-6-methylpyrazolo[1,5-a]pyrazin-2-yl)-9-methyl-7-(1-methylpiperidin-4-yl)-4H-pyrido[1,2-a]pyrimidin-4-one 2-(1,7-dimethyl-1H-indazol-5-yl)-7-(piperidin-4-yl)-4H-pyrido[1,2-a]pyrimidin-4-one 2-(1,7-dimethyl-1H-indazol-5-yl)-7-(piperazin-1-yl)-4H-pyrido[1,2-a]pyrimidin-4-one 2-(1,7-dimethyl-1H-indazol-5-yl)-7-[(3S)-3-methylpiperazin-1-yl]-4H-pyrido[1,2-a]pyrimidin-4-one 7-{(3S)-3-[(diethylamino)methyl]pyrrolidin-1-yl}-2-(4,6-dimethylpyrazolo[1,5-a]pyrazin-2-yl)-4H-pyrido[1,2-a]pyrimidin-4-one 2-(4,6-dimethylpyrazolo[1,5-a]pyrazin-2-yl)-7-{(3S)-3-[(ethylamino)methyl]pyrrolidin-1-yl})-4H-pyrido[1,2-a]pyrimidin-4-one 7-{3-[(dimethylamino)methyl]azetidin-1-yl}-2-(4,6-dimethylpyrazolo[1,5-a]pyrazin-2-yl)-4H-pyrido[1,2-a]pyrimidin-4-one 7-{3-[(diethylamino)methyl]azetidin-1-yl}-2-(4,6-dimethylpyrazolo[1,5-a]pyrazin-2-yl)-4H-pyrido[1,2-a]pyrimidin-4-one 2-(1-ethyl-3-methylpyrrolo[1,2-a]pyrazin-7-yl)-7-[(8aS)-hexahydropyrrolo[1,2-a]pyrazin-2(1H)-yl]-4H-pyrido[1,2-a]pyrimidin-4-one 2-(4-ethyl-6-methylpyrazolo[1,5-a]pyrazin-2-yl)-9-methyl-7-[(3R)-3-methylpiperazin-1-yl]-4H-pyrido[1,2-a]pyrimidin-4-one 9-methyl-2-(1-methyl-1H-indazol-5-yl)-7-(1-methylpiperidin-4-yl)-4H-pyrido[1,2-a]pyrimidin-4-one 7-[(3R)-3,4-dimethylpiperazin-1-yl]-2-(4-ethyl-6-methylpyrazolo[1,5-a]pyrazin-2-yl)-9-methyl-4H-pyrido[1,2-a]pyrimidin-4-one 7-(1-ethylpiperidin-4-yl)-9-methyl-2-(1-methyl-1H-indazol-5-yl)-4H-pyrido[1,2-a]pyrimidin-4-one 2-(4-ethyl-6-methylpyrazolo[1,5-a]pyrazin-2-yl)-9-methyl-7-[(3S)-3-methylpiperazin-1-yl]-4H-pyrido[1,2-a]pyrimidin-4-one 7-[1-(2-hydroxyethyl)piperidin-4-yl]-9-methyl-2-(1-methyl-1H-indazol-5-yl)-4H-pyrido[1,2-a]pyrimidin-4-one 7-[(3S)-3,4-dimethylpiperazin-1-yl]-2-(4-ethyl-6-methylpyrazolo[1,5-a]pyrazin-2-yl)-9-methyl-4H-pyrido[1,2-a]pyrimidin-4-one 2-(4-ethyl-6-methylpyrazolo[1,5-a]pyrazin-2-yl)-7-(1-ethylpiperidin-4-yl)-9-methyl-4H-pyrido[1,2-a]pyrimidin-4-one 9-methyl-2-(2-methyl-2H-indazol-5-yl)-7-(1,2,3,6-tetrahydropyridin-4-yl)-4H-pyrazino[1,2-a]pyrimidin-4-one 7-(1-cyclobutylpiperidin-4-yl)-2-(4-ethyl-6-methylpyrazolo[1,5-a]pyrazin-2-yl)-9-methyl-4H-pyrido[1,2-a]pyrimidin-4-one 2-(4-ethyl-6-methylpyrazolo[1,5-a]pyrazin-2-yl)-7-[1-(2-hydroxyethyl)piperidin-4-yl]-9-methyl-4H-pyrido[1,2-a]pyrimidin-4-one 2-(8-ethyl-2-methylimidazo[1,2-a]pyridin-6-yl)-7-[(8aR)-hexahydropyrrolo[1,2-a]pyrazin-2(1H)-yl]-4H-pyrido[1,2-a]pyrimidin-4-one 2-(8-ethyl-2-methylimidazo[1,2-a]pyridin-6-yl)-7-[(8aS)-hexahydropyrrolo[1,2-a]pyrazin-2(1H)-yl]-4H-pyrido[1,2-a]pyrimidin-4-one 9-methyl-2-(2-methyl-2H-indazol-5-yl)-7-(piperidin-4-yl)-4H-pyrazino[1,2-a]pyrimidin-4-one 7-[(3R)-3-(aminomethyl)pyrrolidin-1-yl]-2-(4,6-dimethylpyrazolo[1,5-a]pyrazin-2-yl)-4H-pyrido[1,2-a]pyrimidin-4-one 2-(4,6-dimethylpyrazolo[1,5-a]pyrazin-2-yl)-7-[(2S,6S)-2,6-dimethyl-1,2,3,6-tetrahydropyridin-4-yl]-4H-pyrido[1,2-a]pyrimidin-4-one 7-{(3R)-3-[(dimethylamino)methyl]pyrrolidin-1-yl}-2-(4,6-dimethylpyrazolo[1,5-a]pyrazin-2-yl)-4H-pyrido[1,2-a]pyrimidin-4-one 7-[(2S,6S)-2,6-dimethylpiperidin-4-yl]-2-(4,6-dimethylpyrazolo[1,5-a]pyrazin-2-yl)-4H-pyrido[1,2-a]pyrimidin-4-one 2-(8-fluoro-2-methylimidazo[1,2-a]pyridin-6-yl)-7-[4-(2-hydroxyethyl)piperazin-1-yl]-4H-pyrido[1,2-a]pyrimidin-4-one 2-(imidazo[1,2-a]pyridin-6-yl)-7-(4-methylpiperazin-1-yl)-4H-pyrido[1,2-a]pyrimidin-4-one 2-(4-fluoro-2-methyl-1,3-benzoxazol-6-yl)-7-[(8aS)-hexahydropyrrrolo[1,2-a]pyrazin-2(1H)-yl]-4H-pyrido[1,2-a]pyrimidin-4-one 7-(2,7-diazaspiro[3.5]non-7-yl)-2-(4,6-dimethylpyrazolo[1,5-a]pyrazin-2-yl)-4H-pyrido[1,2-a]pyrimidin-4-one 7-(4-methylpiperazin-1-yl)-2-(2-methyl[1,2,4]triazolo[1,5-a]pyridin-6-yl)-4H-pyrido[1,2-a]pyrimidin-4-one 7-(4-methylpiperazin-1-yl)-2-[2-methyl-8-(trifluoromethyl)imidazo[1,2-a]pyridin-6-yl]-4H-pyrido[1,2-a]pyrimidin-4-one 2-methyl-6-[7-(4-methylpiperazin-1-yl)-4-oxo-4H-pyrido[1,2-a]pyrimidin-2-yl]imidazo[1,2-a]pyridine-8-carbonitrile 2-(2,8-dimethylimidazo[1,2-a]pyridin-6-yl)-7-(4-methylpiperazin-1-yl)-4H-pyrido[1,2-a]pyrimidin-4-one 7-(4,7-diazaspiro[2.5]oct-7-yl)-2-(2,8-dimethylimidazo[1,2-a]pyridin-6-yl)-4H-pyrido[1,2-a]pyrimidin-4-one 2-(8-fluoro-2-methylimidazo[1,2-a]pyridin-6-yl)-7-(1-methylpiperidin-4-yl)-4H-pyrido[1,2-a]pyrimidin-4-one 2-(8-fluoro-2-methylimidazo[1,2-a]pyridin-6-yl)-7-(4-hydroxypiperidin-4-yl)-4H-pyrido[1,2-a]pyrimidin-4-one 2-(4-ethyl-6-methylpyrazolo[1,5-a]pyrazin-2-yl)-7-[(8aS)-hexahydropyrrolo[1,2-a]pyrazin-2(1H)-yl]-4H-pyrido[1,2-a]pyrimidin-4-one 2-(4-ethyl-6-methylpyrazolo[1,5-a]pyrazin-2-yl)-7-[(8aR)-hexahydropyrrolo[1,2-a]pyrazin-2(1H)-yl]-4H-pyrido[1,2-a]pyrimidin-4-one 7-[(3R)-3-(dimethylamino)pyrrolidin-1-yl]-2-(4-ethyl-6-methylpyrazolo[1,5-a]pyrazin-2-yl)-4H-pyrido[1,2-a]pyrimidin-4-one 7-[(3S)-3-(dimethylamino)pyrrolidin-1-yl]-2-(4-ethyl-6-methylpyrazolo[1,5-a]pyrazin-2-yl)-4H-pyrido[1,2-a]pyrimidin-4-one 2-(8-fluoro-2-methylimidazo[1,2-a]pyridin-6-yl)-7-[(8aS)-8a-methylhexahydropyrrolo[1,2-a]pyrazin-2(1H)-yl]-4H-pyrido[1,2-a]pyrimidin-4-one 2-(4-ethyl-6-methylpyrazolo[1,5-a]pyrazin-2-yl)-7-(4-ethylpiperazin-1-yl)-9-methyl-4H-pyrido[1,2-a]pyrimidin-4-one 2-(4-ethyl-6-methylpyrazolo[1,5-a]pyrazin-2-yl)-7-[(8aS)-hexahydropyrrolo[1,2-a]pyrazin-2(1H)-yl]-9-methyl-4H-pyrido[1,2-a]pyrimidin-4-one 2-(2,8-dimethylimidazo[1,2-a]pyridin-6-yl)-7-(4-ethylpiperazin-1-yl)-4H-pyrido[1,2-a]pyrimidin-4-one 2-(2,8-dimethylimidazo[1,2-a]pyridin-6-yl)-7-[(8aS)-hexahydropyrrolo[1,2-a]pyrazin-2(1H)-yl]-4H-pyrido[1,2-a]pyrimidin-4-one 2-(2,8-dimethylimidazo[1,2-a]pyridin-6-yl)-7-(8a-methylhexahydropyrrolo[1,2-a]pyrazin-2(1H)-yl)-4H-pyrido[1,2-a]pyrimidin-4-one 7-[(3R)-3-(dimethylamino)pyrrolidin-1-yl]-2-(4-ethyl-6-methylpyrazolo[1,5-a]pyrazin-2-yl)-9-methyl-4H-pyrido[1,2-a]pyrimidin-4-one 2-(4-ethyl-6-methylpyrazolo[1,5-a]pyrazin-2-yl)-7-{[2-(morpholin-4-yl)ethyl]amino}-4H-pyrido[1,2-a]pyrimidin-4-one 7-{[2-(dimethylamino)ethyl]amino}-2-(4-ethyl-6-methylpyrazolo[1,5-a]pyrazin-2-yl)-4H-pyrido[1,2-a]pyrimidin-4-one 7-{[2-(dimethylamino)ethyl](methyl)amino}-2-(4-ethyl-6-methylpyrazolo[1,5-a]pyrazin-2-yl)-4H-pyrido[1,2-a]pyrimidin-4-one 2-(4-ethyl-6-methylpyrazolo[1,5-a]pyrazin-2-yl)-7-{methyl[2-(methylamino)ethyl]amino}-4H-pyrido[1,2-a]pyrimidin-4-one 7-[(3R)-3-(dimethylamino)pyrrolidin-1-yl]-2-(2,8-dimethylimidazo[1,2-a]pyridin-6-yl)-4H-pyrido[1,2-a]pyrimidin-4-one 7-[(3S)-3-(dimethylamino)pyrrolidin-1-yl]-2-(2,8-dimethylimidazo[1,2-a]pyridin-6-yl)-4H-pyrido[1,2-a]pyrimidin-4-one 7-[2-(dimethylamino)ethoxy]-2-(4-ethyl-6-methylpyrazolo[1,5-a]pyrazin-2-yl)-9-methyl-4H-pyrido[1,2-a]pyrimidin-4-one 7-[2-(dimethylamino)ethoxy]-2-(4-ethyl-6-methylpyrazolo[1,5-a]pyrazin-2-yl)-4H-pyrido[1,2-a]pyrimidin-4-one 2-(4-ethyl-6-methylpyrazolo[1,5-a]pyrazin-2-yl)-7-(piperidin-4-ylmethoxy)-4H-pyrido[1,2-a]pyrimidin-4-one 2-(4-ethyl-6-methylpyrazolo[1,5-a]pyrazin-2-yl)-7-[2-(piperidin-1-yl)ethoxy]-4H-pyrido[1,2-a]pyrimidin-4-one 2-(4-ethyl-6-methylpyrazolo[1,5-a]pyrazin-2-yl)-7-[3-(morpholin-4-yl)propoxy]-4H-pyrido[1,2-a]pyrimidin-4-one 7-[3-(dimethylamino)propoxy]-2-(4-ethyl-6-methylpyrazolo[1,5-a]pyrazin-2-yl)-4H-pyrido[1,2-a]pyrimidin-4-one, or 2-(4,6-dimethylpyrazolo[1,5-a]pyrazin-2-yl)-7-[(3 aR,6aS)-5-methylhexahydropyrrolo[3,4-c]pyrrol-2(1H)-yl]-4H-pyrido[1,2-a]pyrimidin-4-one or a salt, isotopologue, stereoisomer, racemate, enantiomer, diastereomer or tautomer thereof.

In another embodiment, the compound of Formula (I) used in a method disclosed herein is a compound selected from the group consisting of:

2-(3,5-difluoro-4-hydroxyphenyl)-7-(piperazin-1-yl)-4H-pyrido[1,2-a]pyrimidin-4-one hydrochloride 7-[4-(dimethylamino)piperidin-1-yl]-2-(3-fluoro-4-methoxyphenyl)-4H-quinolizin-4-one acetate 2-(2-methyl-1,3-benzothiazol-6-yl)-7-(piperidin-4-yl)-4H-pyrimido[1,2-b]pyridazin-4-one trifluoroacetate (1:1), or 2-(1,3-dimethylpyrrolo[1,2-a]pyrazin-7-yl)-7-(1,2,3,6-tetrahydropyridin-4-yl)-4H-pyrazino[1,2-a]pyrimidin-4-one hydrochloride (1:2)

or a free base, isotopologue, stereoisomer, racemate, enantiomer, diastereomer or tautomer thereof.

Compounds of Formula (I) can be prepared using reagents and methods known in the art, including the methods provided in International Application No. PCT/US2013/025292, filed on Feb. 8, 2013, and published as International Publication No. WO 2013/119916 on Aug. 15, 2013, the entire contents which are incorporated herein by reference (see in particular, General Synthetic Methods, Schemes A-J, at paragraphs [001126] to [001159]; and Specific Synthetic Examples, at paragraphs [001160] to [001573] and Table 1).

Terminology

The chemical terms used above and throughout the description herein, unless specifically defined otherwise, shall be understood by one of ordinary skill in the art to have the following indicated meanings.

As used herein, the term "$C_{1-8}$alkyl" generally refers to saturated hydrocarbon radicals having from one to eight carbon atoms in a straight or branched chain configuration, including, but not limited to, methyl, ethyl, n-propyl (also referred to as propyl or propanyl), isopropyl, n-butyl (also referred to as butyl or butanyl), isobutyl, sec-butyl, tert-butyl, n-pentyl (also referred to as pentyl or pentanyl), n-hexyl (also referred to as hexyl or hexanyl), n-heptyl (also referred to as heptyl or heptanyl), n-octyl and the like. In some embodiments, $C_{1-8}$alkyl includes, but is not limited to, $C_{1-6}$alkyl, $C_{1-4}$alkyl and the like. A $C_{1-8}$alkyl radical is optionally substituted with substituent species as described herein where allowed by available valences.

As used herein, the term "$C_{2-8}$alkenyl" generally refers to partially unsaturated hydrocarbon radicals having from two to eight carbon atoms in a straight or branched chain configuration and one or more carbon-carbon double bonds therein, including, but not limited to, ethenyl (also referred to as vinyl), allyl, propenyl and the like. In some embodiments, $C_{2-8}$alkenyl includes, but is not limited to, $C_{2-6}$alkenyl, $C_{2-4}$alkenyl and the like. A $C_{2-8}$alkenyl radical is optionally substituted with substituent species as described herein where allowed by available valences.

As used herein, the term "$C_{2-8}$alkynyl" generally refers to partially unsaturated hydrocarbon radicals having from two to eight carbon atoms in a straight or branched chain configuration and one or more carbon-carbon triple bonds therein, including, but not limited to, ethynyl, propynyl, butynyl and the like. In some embodiments, $C_{2-8}$alkynyl includes, but is not limited to, $C_{2-6}$alkynyl, $C_{2-4}$alkynyl and the like. A $C_{2-8}$alkynyl radical is optionally substituted with substituent species as described herein where allowed by available valences.

As used herein, the term "$C_{1-8}$alkoxy" generally refers to saturated hydrocarbon radicals having from one to eight carbon atoms in a straight or branched chain configuration of the formula: —O—$C_{1-8}$alkyl, including, but not limited to, methoxy, ethoxy, n-propoxy, isopropoxy, n-butoxy, isobutoxy, sec-butoxy, tert-butoxy, n-pentoxy, n-hexoxy and the like. In some embodiments, $C_{1-8}$alkoxy includes, but is not limited to, $C_{1-6}$alkoxy, $C_{1-4}$alkoxy and the like. A $C_{1-8}$alkoxy radical is optionally substituted with substituent species as described herein where allowed by available valences.

As used herein, the term "$C_{3-14}$cycloalkyl" generally refers to a saturated or partially unsaturated monocyclic, bicyclic or polycyclic hydrocarbon radical, including, but not limited to, cyclopropyl, cyclobutyl, cyclopentyl, cyclohexyl, cyclohexenyl, cycloheptyl, cyclooctyl, 1H-indanyl, indenyl, tetrahydro-naphthalenyl and the like. In some embodiments, $C_{3-14}$cycloalkyl includes, but is not limited to, $C_{3-8}$cycloalkyl, $C_{5-8}$cycloalkyl, $C_{3-10}$cycloalkyl and the like. A $C_{3-14}$cycloalkyl radical is optionally substituted with substituent species as described herein where allowed by available valences.

As used herein, the term "aryl" generally refers to a monocyclic, bicyclic or polycyclic aromatic carbon atom ring structure radical, including, but not limited to, phenyl, naphthyl, anthracenyl, fluorenyl, azulenyl, phenanthrenyl and the like. An aryl radical is optionally substituted with substituent species as described herein where allowed by available valences.

As used herein, the term "heteroaryl" generally refers to a monocyclic, bicyclic or polycyclic aromatic carbon atom ring structure radical in which one or more carbon atom ring members have been replaced, where allowed by structural stability, with one or more heteroatoms, such as an O, S or N atom, including, but not limited to, furanyl (also referred to as furyl), thienyl (also referred to as thiophenyl), pyrrolyl, 2H-pyrrolyl, 3H-pyrrolyl, pyrazolyl, 1H-pyrazolyl, imidazolyl, 1H-imidazolyl, isoxazolyl, isothiazolyl, oxazolyl, 1,3-thiazolyl, triazolyl (such as 1H-1,2,3-triazolyl and the like), oxadiazolyl (such as 1,2,4-oxadiazolyl, 1,3,4-oxadiazolyl and the like), thiadiazolyl, tetrazolyl (such as 1H-tetrazolyl, 2H-tetrazolyl and the like), pyridinyl (also referred to as pyridyl), pyrimidinyl, pyrazinyl, pyridazinyl, triazinyl, indolyl, 1H-indolyl, indazolyl, 1H-indazolyl, 2H-indazolyl, indolizinyl, isoindolyl, benzofuranyl, benzothienyl (also referred to as benzothiophenyl), benzoimidazolyl, 1H-benzoimidazolyl, 1,3-benzothiazolyl, 1,3-benzoxazolyl (also referred to as 1,3-benzooxazolyl), purinyl, 9H-purinyl, quinolinyl, isoquinolinyl, quinazolinyl, quinoxalinyl, 1,3-diazinyl, 1,2-diazinyl, 1,2-diazolyl, 1,4-diazanaphthalenyl, acridinyl, furo[3,2-b]pyridinyl, furo[3,2-c]pyridinyl, furo[2,3-c]pyridinyl, 6H-thieno[2,3-b]pyrrolyl, thieno[3,2-c]pyridinyl, thieno[2,3-d]pyrimidinyl, 1H-pyrrolo[2,3-b]pyridinyl, 1H-pyrrolo[2,3-c]pyridinyl, 1H-pyrrolo[3,2-b]pyridinyl, pyrrolo[1,2-a]pyrazinyl, pyrrolo[1,2-b]pyridazinyl, pyrazolo[1,5-a]pyridinyl, pyrazolo[1,5-a]pyrazinyl, imidazo[1,2-a]pyridinyl, 3H-imidazo[4,5-b]pyridinyl, imidazo[1,2-a]pyrimidinyl, imidazo[1,2-c]pyrimidinyl, imidazo[1,2-b]pyridazinyl, imidazo[1,2-a]pyrazinyl, imidazo[2,1-b][1,3]thiazolyl, imidazo[2,1-b][1,3, 4]thiadiazolyl, [1,2,4]triazolo[1,5-a]pyridinyl, [1,2,4]triazolo[4,3-a]pyridinyl and the like. A heteroaryl radical is optionally substituted on a carbon or nitrogen atom ring member with substituent species as described herein where allowed by available valences.

As used herein, the term "heterocyclyl" generally refers to a saturated or partially unsaturated monocyclic, bicyclic or polycyclic carbon atom ring structure radical in which one or more carbon atom ring members have been replaced, where allowed by structural stability, with a heteroatom, such as an O, S or N atom, including, but not limited to, oxiranyl, oxetanyl, azetidinyl, tetrahydrofuranyl, pyrrolinyl, pyrrolidinyl, pyrazolinyl, pyrazolidinyl, imidazolinyl, imidazolidinyl, isoxazolinyl, isoxazolidinyl, isothiazolinyl, isothiazolidinyl, oxazolinyl, oxazolidinyl, thiazolinyl, thiazolidinyl, triazolinyl, triazolidinyl, oxadiazolinyl, oxadiazolidinyl, thiadiazolinyl, thiadiazolidinyl, tetrazolinyl, tetrazolidinyl, pyranyl, dihydro-2H-pyranyl, thiopyranyl, 1,3-dioxanyl, 1,2,5,6-tetrahydropyridinyl, 1,2,3,6-tetrahydropyridinyl, piperidinyl, piperazinyl, morpholinyl, thiomorpholinyl, 1,4-diazepanyl, 1,3-benzodioxolyl (also referred to as benzo[d][1,3]dioxolyl), 1,4-benzodioxanyl, 2,3-dihydro-1,4-benzodioxinyl (also referred to as 2,3-dihydrobenzo[b][1,4]dioxinyl), hexahydropyrrolo[3,4-b]pyrrol-(1H)-yl, (3aS,6aS)-hexahydropyrrolo[3,4-b]pyrrol-(1H)-yl, (3aR,6aR)-hexahydropyrrolo[3,4-b]pyrrol-(1H)-yl, hexahydropyrrolo[3,4-b]pyrrol-(2H)-yl, (3 aS,6aS)-hexahydropyrrolo[3,4-b]pyrrol-(2H)-yl, (3aR,6aR)-hexahydropyrrolo[3,4-b]pyrrol-(2H)-yl, hexahydropyrrolo[3,4-c]pyrrol-(1H)-yl, (3 aR,6aS)-hexahydropyrrolo[3,4-c]pyrrol-(1H)-yl, (3aR,6aR)-hexahydropyrrolo[3,4-c]pyrrol-(1H)-yl, octahydro-5H-pyrrolo[3,2-c]pyridinyl, octahydro-6H-pyrrolo[3,4-b]pyridinyl, (4aR,7aR)-octahydro-6H-pyrrolo[3,4-b]pyridinyl, (4aS,7aS)-octahydro-6H-pyrrolo[3,4-b]pyridinyl, hexahydropyrrolo[1,2-a]pyrazin-(1H)-yl, (7R,8aS)-hexahydropyrrolo[1,2-a]pyrazin-(1H)-yl, (8aS)-hexahydropyrrolo[1,2-a]pyrazin-(1H)-yl, (8aR)-hexahydropyrrolo[1,2-a]pyrazin-(1H)-yl, (8aS)-octahydropyrrolo[1,2-a]pyrazin-(1H)-yl, (8aR)-octahydropyrrolo[1,2-a]pyrazin-(1H)-yl, hexahydropyrrolo[1,2-a]pyrazin-(2H)-one, octahydro-2H-pyrido[1,2-a]pyrazinyl, 3-azabicyclo[3.1.0]hexyl, (1R,5S)-3-azabicyclo[3.1.0]hexyl, 8-azabicyclo[3.2.1]octyl, (1R,5S)-8-azabicyclo[3.2.1]octyl, 8-azabicyclo[3.2.1]oct-2-enyl, (1R,5S)-8-azabicyclo[3.2.1]oct-2-enyl, 9-azabicyclo[3.3.1]nonyl, (1R,5S)-9-azabicyclo[3.3.1]nonyl, 2,5-diazabicyclo[2.2.1]heptyl, (1S,4S)-2,5-diazabicyclo[2.2.1]heptyl, 2,5-diazabicyclo[2.2.2]octyl, 3,8-diazabicyclo[3.2.1]octyl, (1R,5S)-3,8-diazabicyclo[3.2.1]octyl, 1,4-diazabicyclo[3.2.2]nonyl, azaspiro[3.3]heptyl, 2,6-diazaspiro[3.3]heptyl, 2,7-diazaspiro[3.5]nonyl, 5,8-diazaspiro[3.5]nonyl, 2,7-diazaspiro[4.4]nonyl, 6,9-diazaspiro[4.5]decyl and the like. A heterocyclyl radical is optionally substituted on a carbon or nitrogen atom ring member with substituent species as described herein where allowed by available valences.

As used herein, the term "$C_{1-8}$alkoxy-$C_{1-8}$alkyl" refers to a radical of the formula: —$C_{1-8}$alkyl-O—$C_{1-8}$alkyl.

As used herein, the term "$C_{1-8}$alkoxy-$C_{1-8}$alkyl-amino" refers to a radical of the formula: —NH—$C_{1-8}$alkyl-O—$C_{1-8}$ alkyl.

As used herein, the term "($C_{1-8}$alkoxy-$C_{1-8}$alkyl)$_2$-amino" refers to a radical of the formula: —N($C_{1-8}$alkyl-O—$C_{1-8}$alkyl)$_2$.

As used herein, the term "$C_{1-8}$alkoxy-$C_{1-8}$alkyl-amino-$C_{1-8}$alkoxy" refers to a radical of the formula: —O—$C_{1-8}$alkyl-NH—$C_{1-8}$alkyl-O—$C_{1-8}$alkyl.

As used herein, the term "($C_{1-8}$alkoxy-$C_{1-8}$alkyl)$_2$-amino-$C_{1-8}$alkoxy" refers to a radical of the formula: —O—$C_{1-8}$alkyl-N($C_{1-8}$alkyl-O—$C_{1-8}$alkyl)$_2$.

As used herein, the term "($C_{1-8}$alkoxy-$C_{1-8}$alkyl)($C_{1-8}$alkyl)amino-$C_{1-8}$alkoxy" refers to a radical of the formula: —O—$C_{1-8}$alkyl-N($C_{1-8}$alkyl)($C_{1-8}$alkyl-O—$C_{1-8}$alkyl).

As used herein, the term "$C_{1-8}$alkoxy-$C_{1-8}$alkyl-amino-$C_{1-8}$alkyl" refers to a radical of the formula: —$C_{1-8}$alkyl-NH—$C_{1-8}$alkyl-O—$C_{1-8}$alkyl.

As used herein, the term "($C_{1-8}$alkoxy-$C_{1-8}$alkyl)$_2$-amino-$C_{1-8}$alkyl" refers to a radical of the formula: —$C_{1-8}$alkyl-N($C_{1-8}$alkyl-O—$C_{1-8}$alkyl)$_2$.

As used herein, the term "($C_{1-8}$alkoxy-$C_{1-8}$alkyl)($C_{1-8}$alkyl)amino-$C_{1-8}$alkyl" refers to a radical of the formula: —$C_{1-8}$alkyl-N($C_{1-8}$alkyl)($C_{1-8}$alkyl-O—$C_{1-8}$alkyl).

As used herein, the term "$C_{1-8}$alkoxy-carbonyl" refers to a radical of the formula: —C(O)—O—$C_{1-8}$alkyl.

As used herein, the term "$C_{1-8}$alkoxy-carbonyl-$C_{2-8}$alkenyl" refers to a radical of the formula: —$C_{2-8}$alkenyl-C(O)—O—$C_{1-8}$alkyl.

As used herein, the term "$C_{1-8}$alkoxy-carbonyl-amino" refers to a radical of the formula: —NH—C(O)—O—$C_{1-8}$alkyl.

As used herein, the term "$C_{1-8}$alkyl-amino" refers to a radical of the formula: —NH—$C_{1-8}$alkyl.

As used herein, the term "($C_{1-8}$alkyl)$_2$-amino" refers to a radical of the formula: —N($C_{1-8}$alkyl)$_2$.

As used herein, the term "$C_{1-8}$alkyl-amino-$C_{2-8}$alkenyl" refers to a radical of the formula: —$C_{2-8}$alkenyl-NH—$C_{1-8}$alkyl.

As used herein, the term "($C_{1-8}$alkyl)$_2$-amino-$C_{2-8}$alkenyl" refers to a radical of the formula: —$C_{2-8}$alkenyl-N($C_{1-8}$alkyl)$_2$.

As used herein, the term "$C_{1-8}$alkyl-amino-$C_{1-8}$alkoxy" refers to a radical of the formula: —O—$C_{1-8}$alkyl-NH—$C_{1-8}$ alkyl.

As used herein, the term "($C_{1-8}$alkyl)$_2$-amino-$C_{1-8}$alkoxy" refers to a radical of the formula: —O—$C_{1-8}$alkyl-N($C_{1-8}$alkyl)$_2$.

As used herein, the term "$C_{1-8}$alkyl-amino-$C_{1-8}$alkyl" refers to a radical of the formula: —$C_{1-8}$alkyl-NH—$C_{1-8}$ alkyl.

As used herein, the term "($C_{1-8}$alkyl)$_2$-amino-$C_{1-8}$alkyl" refers to a radical of the formula: —$C_{1-8}$alkyl-N($C_{1-8}$alkyl)$_2$.

As used herein, the term "$C_{1-8}$alkyl-amino-$C_{1-8}$alkyl-amino" refers to a radical of the formula: —NH—$C_{1-8}$alkyl-NH—$C_{1-8}$alkyl.

As used herein, the term "($C_{1-8}$alkyl)$_2$-amino-$C_{1-8}$alkyl-amino" refers to a radical of the formula: —NH—$C_{1-8}$alkyl-N($C_{1-8}$alkyl)$_2$.

As used herein, the term "($C_{1-8}$alkyl-amino-$C_{1-8}$alkyl)$_2$-amino" refers to a radical of the formula: —N($C_{1-8}$alkyl-NH—$C_{1-8}$alkyl)$_2$.

As used herein, the term "[($C_{1-8}$alkyl)$_2$-amino-$C_{1-8}$alkyl]$_2$-amino" refers to a radical of the formula: —N[$C_{1-8}$alkyl-N($C_{1-8}$alkyl)$_2$]$_2$.

As used herein, the term "($C_{1-8}$alkyl-amino-$C_{1-8}$alkyl)($C_{1-8}$alkyl)amino" refers to a radical of the formula: —N($C_{1-8}$ alkyl)($C_{1-8}$alkyl-NH—$C_{1-8}$alkyl).

As used herein, the term "[($C_{1-8}$alkyl)$_2$-amino-$C_{1-8}$alkyl]($C_{1-8}$alkyl)amino" refers to a radical of the formula: —N($C_{1-8}$ alkyl)[$C_{1-8}$alkyl-N($C_{1-8}$alkyl)$_2$].

As used herein, the term "$C_{1-8}$alkyl-amino-$C_{2-8}$alkynyl" refers to a radical of the formula: —$C_{2-8}$alkynyl-NH—$C_{1-8}$ alkyl.

As used herein, the term "($C_{1-8}$alkyl)$_2$-amino-$C_{2-8}$alkynyl" refers to a radical of the formula: —$C_{2-8}$alkynyl-N($C_{1-8}$alkyl)$_2$.

As used herein, the term "$C_{1-8}$alkyl-carbonyl" refers to a radical of the formula: —C(O)—$C_{1-8}$alkyl.

As used herein, the term "$C_{1-8}$alkyl-carbonyl-amino" refers to a radical of the formula: —NH—C(O)—$C_{1-8}$alkyl.

As used herein, the term "$C_{1-8}$alkyl-thio" refers to a radical of the formula: —S—$C_{1-8}$alkyl.

As used herein, the term "amino-$C_{2-8}$alkenyl" refers to a radical of the formula: —$C_{2-8}$alkenyl-NH$_2$.

As used herein, the term "amino-$C_{1-8}$alkoxy" refers to a radical of the formula: —O—$C_{1-8}$alkyl-NH$_2$.

As used herein, the term "amino-$C_{1-8}$alkyl" refers to a radical of the formula: —$C_{1-8}$alkyl-NH$_2$.

As used herein, the term "amino-$C_{1-8}$alkyl-amino" refers to a radical of the formula: —NH—$C_{1-8}$alkyl-NH$_2$.

As used herein, the term "(amino-$C_{1-8}$alkyl)$_2$-amino" refers to a radical of the formula: —N($C_{1-8}$alkyl-NH$_2$)$_2$.

As used herein, the term "(amino-$C_{1-8}$alkyl)($C_{1-8}$alkyl)amino" refers to a radical of the formula: —N($C_{1-8}$alkyl)($C_{1-8}$alkyl-NH$_2$).

As used herein, the term "amino-$C_{2-8}$alkynyl" refers to a radical of the formula: —$C_{2-8}$alkynyl-NH$_2$.

As used herein, the term "aryl-$C_{1-8}$alkoxy-carbonyl" refers to a radical of the formula: —C(O)—O—$C_{1-8}$alkyl-aryl.

As used herein, the term "aryl-$C_{1-8}$alkyl" refers to a radical of the formula: —$C_{1-8}$alkyl-aryl.

As used herein, the term "aryl-$C_{1-8}$alkyl-amino" refers to a radical of the formula: —NH—$C_{1-8}$alkyl-aryl.

As used herein, the term "(aryl-$C_{1-8}$alkyl)$_2$-amino" refers to a radical of the formula: —N($C_{1-8}$alkyl-aryl)$_2$.

As used herein, the term "(aryl-$C_{1-8}$alkyl)($C_{1-8}$alkyl)amino" refers to a radical of the formula: —N($C_{1-8}$alkyl)($C_{1-8}$alkyl-aryl).

As used herein, the term "aryl-$C_{1-8}$alkyl-amino-$C_{1-8}$alkyl" refers to a radical of the formula: —$C_{1-8}$alkyl-NH—$C_{1-8}$alkyl-aryl.

As used herein, the term "(aryl-$C_{1-8}$alkyl)$_2$-amino-$C_{1-8}$alkyl" refers to a radical of the formula: —$C_{1-8}$alkyl-N($C_{1-8}$alkyl-aryl)$_2$.

As used herein, the term "(aryl-$C_{1-8}$alkyl)($C_{1-8}$alkyl)amino-$C_{1-8}$alkyl" refers to a radical of the formula: —$C_{1-8}$alkyl-N($C_{1-8}$alkyl)($C_{1-8}$alkyl-aryl).

As used herein, the term "aryl-amino" refers to a radical of the formula: —NH-aryl.

As used herein, the term "aryl-amino-carbonyl" refers to a radical of the formula: —C(O)—NH-aryl.

As used herein, the term "aryl-sulfonyloxy-$C_{1-8}$alkyl" refers to a radical of the formula: —$C_{1-8}$alkyl-O—SO$_2$-aryl.

As used herein, the term "benzoxy-carbonyl" refers to a radical of the formula: —C(O)O—CH$_2$-phenyl.

As used herein, the term "$C_{3-14}$cycloalkyl-$C_{1-8}$alkyl" refers to a radical of the formula: —$C_{1-8}$alkyl-$C_{3-14}$cycloalkyl.

As used herein, the term "$C_{3-14}$cycloalkyl-amino" refers to a radical of the formula: —NH—$C_{3-14}$cycloalkyl.

As used herein, the term "$C_{3-14}$cycloalkyl-oxy" refers to a radical of the formula: —O—$C_{3-14}$cycloalkyl.

As used herein, the term "halo" or "halogen" generally refers to a halogen atom radical, including fluoro, chloro, bromo and iodo.

As used herein, the term "halo-$C_{1-8}$alkoxy" refers to a radical of the formula: —O—$C_{1-8}$alkyl-halo, wherein $C_{1-8}$alkyl is partially or completely substituted with one or more halogen atoms where allowed by available valences.

As used herein, the term "halo-$C_{1-8}$alkyl" refers to a radical of the formula: —$C_{1-8}$alkyl-halo, wherein $C_{1-8}$alkyl is partially or completely substituted with one or more halogen atoms where allowed by available valences.

As used herein, the term "halo-$C_{1-8}$alkyl-amino" refers to a radical of the formula: —NH—$C_{1-8}$alkyl-halo.

As used herein, the term "(halo-$C_{1-8}$alkyl)($C_{1-8}$alkyl)amino" refers to a radical of the formula: —N($C_{1-8}$alkyl)($C_{1-8}$alkyl-halo).

As used herein, the term "(halo-$C_{1-8}$alkyl)$_2$-amino" refers to a radical of the formula: —N($C_{1-8}$alkyl-halo)$_2$.

As used herein, the term "heteroaryl-$C_{1-8}$alkoxy" refers to a radical of the formula: —O—$C_{1-8}$alkyl-heteroaryl.

As used herein, the term "heteroaryl-$C_{1-8}$alkyl" refers to a radical of the formula: —$C_{1-8}$alkyl-heteroaryl.

As used herein, the term "heteroaryl-$C_{1-8}$alkyl-amino" refers to a radical of the formula: —NH—$C_{1-8}$alkyl-heteroaryl.

As used herein, the term "(heteroaryl-$C_{1-8}$alkyl)$_2$-amino" refers to a radical of the formula: —N($C_{1-8}$alkyl-heteroaryl)$_2$.

As used herein, the term "(heteroaryl-$C_{1-8}$alkyl)($C_{1-8}$alkyl)amino" refers to a radical of the formula: —N($C_{1-8}$alkyl)($C_{1-8}$alkyl-heteroaryl).

As used herein, the term "heteroaryl-$C_{1-8}$alkyl-amino-$C_{1-8}$alkyl" refers to a radical of the formula: —$C_{1-8}$alkyl-NH—$C_{1-8}$alkyl-heteroaryl.

As used herein, the term "(heteroaryl-$C_{1-8}$alkyl)$_2$-amino-$C_{1-8}$alkyl" refers to a radical of the formula: —$C_{1-8}$alkyl-N($C_{1-8}$alkyl-heteroaryl)$_2$.

As used herein, the term "(heteroaryl-$C_{1-8}$alkyl)($C_{1-8}$alkyl)amino-$C_{1-8}$alkyl" refers to a radical of the formula: —$C_{1-8}$alkyl-N($C_{1-8}$alkyl)($C_{1-8}$alkyl-heteroaryl).

As used herein, the term "heteroaryl-amino" refers to a radical of the formula: —NH-heteroaryl.

As used herein, the term "heterocyclyl-$C_{1-8}$alkoxy" refers to a radical of the formula: —O—$C_{1-8}$alkyl-heterocyclyl.

As used herein, the term "heterocyclyl-$C_{1-8}$alkyl" refers to a radical of the formula: —$C_{1-8}$alkyl-heterocyclyl.

As used herein, the term "heterocyclyl-$C_{1-8}$alkyl-amino" refers to a radical of the formula: —NH—$C_{1-8}$alkyl-heterocyclyl.

As used herein, the term "(heterocyclyl-$C_{1-8}$alkyl)$_2$-amino" refers to a radical of the formula: —N($C_{1-8}$alkyl-heterocyclyl)$_2$.

As used herein, the term "(heterocyclyl-$C_{1-8}$alkyl)($C_{1-8}$alkyl)amino" refers to a radical of the formula: —N($C_{1-8}$alkyl)($C_{1-8}$alkyl-heterocyclyl).

As used herein, the term "heterocyclyl-$C_{1-8}$alkyl-amino-$C_{1-8}$alkyl" refers to a radical of the formula: —$C_{1-8}$alkyl-NH—$C_{1-8}$alkyl-heterocyclyl.

As used herein, the term "(heterocyclyl-$C_{1-8}$alkyl)$_2$-amino-$C_{1-8}$alkyl" refers to a radical of the formula: —$C_{1-8}$alkyl-N($C_{1-8}$alkyl-heterocyclyl)$_2$.

As used herein, the term "(heterocyclyl-$C_{1-8}$alkyl)($C_{1-8}$alkyl)amino-$C_{1-8}$alkyl" refers to a radical of the formula: —$C_{1-8}$alkyl-N($C_{1-8}$alkyl)($C_{1-8}$alkyl-heterocyclyl).

As used herein, the term "heterocyclyl-amino" refers to a radical of the formula: —NH-heterocyclyl.

As used herein, the term "(heterocyclyl)($C_{1-8}$alkyl)amino" refers to a radical of the formula: —N($C_{1-8}$alkyl)(heterocyclyl).

As used herein, the term "heterocyclyl-amino-$C_{1-8}$alkyl" refers to a radical of the formula: —$C_{1-8}$alkyl-NH-heterocyclyl.

As used herein, the term "heterocyclyl-carbonyl" refers to a radical of the formula: —C(O)-heterocyclyl.

As used herein, the term "heterocyclyl-carbonyl-oxy" refers to a radical of the formula: —O—C(O)-heterocyclyl.

As used herein, the term "heterocyclyl-oxy" refers to a radical of the formula: —O-heterocyclyl.

As used herein, the term "hydroxy" refers to a radical of the formula: —OH.

As used herein, the term "hydroxy-$C_{1-8}$alkoxy-$C_{1-8}$alkyl" refers to a radical of the formula: —$C_{1-8}$alkyl-O—$C_{1-8}$alkyl-OH.

As used herein, the term "hydroxy-$C_{1-8}$alkyl" refers to a radical of the formula: —$C_{1-8}$alkyl-OH, wherein $C_{1-8}$alkyl is partially or completely substituted with one or more hydroxy radicals where allowed by available valences.

As used herein, the term "hydroxy-$C_{1-8}$alkyl-amino" refers to a radical of the formula: —NH—$C_{1-8}$alkyl-OH.

As used herein, the term "(hydroxy-$C_{1-8}$alkyl)$_2$-amino" refers to a radical of the formula: —N($C_{1-8}$alkyl-OH)$_2$.

As used herein, the term "(hydroxy-$C_{1-8}$alkyl)($C_{1-8}$alkyl)amino" refers to a radical of the formula: —N($C_{1-8}$alkyl)($C_{1-8}$alkyl-OH).

As used herein, the term "hydroxy-$C_{1-8}$alkyl-amino-$C_{1-8}$alkyl" refers to a radical of the formula: —$C_{1-8}$alkyl-NH—$C_{1-8}$alkyl-OH.

As used herein, the term "(hydroxy-$C_{1-8}$alkyl)$_2$-amino-$C_{1-8}$alkyl" refers to a radical of the formula: —$C_{1-8}$alkyl-N($C_{1-8}$alkyl-OH)$_2$.

As used herein, the term "(hydroxy-$C_{1-8}$alkyl)($C_{1-8}$alkyl)amino-$C_{1-8}$alkyl" refers to a radical of the formula: —$C_{1-8}$alkyl-N($C_{1-8}$alkyl)($C_{1-8}$alkyl-OH).

As used herein, the term "hydroxy-$C_{1-8}$alkyl-amino-$C_{1-8}$alkoxy" refers to a radical of the formula: —O—$C_{1-8}$alkyl-NH—$C_{1-8}$alkyl-OH.

As used herein, the term "(hydroxy-$C_{1-8}$alkyl)$_2$-amino-$C_{1-8}$alkoxy" refers to a radical of the formula: —O—$C_{1-8}$alkyl-N($C_{1-8}$alkyl-OH)$_2$.

As used herein, the term "(hydroxy-$C_{1-8}$alkyl)($C_{1-8}$alkyl)amino-$C_{1-8}$alkoxy" refers to a radical of the formula: —O—$C_{1-8}$alkyl-N($C_{1-8}$alkyl)($C_{1-8}$alkyl-OH).

As used herein, the term "hydroxy-$C_{1-8}$alkyl-amino-$C_{1-8}$alkyl-amino" refers to a radical of the formula: —NH—$C_{1-8}$alkyl-NH—$C_{1-8}$alkyl-OH.

As used herein, the term "(hydroxy-$C_{1-8}$alkyl-amino-$C_{1-8}$alkyl)$_2$-amino" refers to a radical of the formula: —N($C_{1-8}$alkyl-NH—$C_{1-8}$alkyl-OH)$_2$.

As used herein, the term "(hydroxy-$C_{1-8}$alkyl-amino-$C_{1-8}$alkyl)$_2$-amino-$C_{1-8}$alkyl-amino" refers to a radical of the formula: —NH—$C_{1-8}$alkyl-N($C_{1-8}$alkyl-OH)$_2$.

As used herein, the term "(hydroxy-$C_{1-8}$alkyl-amino-$C_{1-8}$alkyl)($C_{1-8}$alkyl)amino" refers to a radical of the formula: —N($C_{1-8}$alkyl)($C_{1-8}$alkyl-NH—$C_{1-8}$alkyl-OH).

As used herein, the term "[(hydroxy-$C_{1-8}$alkyl)$_2$-amino-$C_{1-8}$alkyl]($C_{1-8}$alkyl)amino" refers to a radical of the formula: —N($C_{1-8}$alkyl)[$C_{1-8}$alkyl-N($C_{1-8}$alkyl-OH)$_2$].

As used herein, the term "(hydroxy-$C_{1-8}$alkyl)($C_{1-8}$alkyl)amino-$C_{1-8}$alkyl-amino" refers to a radical of the formula: —NH—$C_{1-8}$alkyl-N($C_{1-8}$alkyl, $C_{1-8}$alkyl-OH).

As used herein, the term "[(hydroxy-$C_{1-8}$alkyl)($C_{1-8}$alkyl)amino-$C_{1-8}$alkyl]($C_{1-8}$alkyl)amino" refers to a radical of the formula: —N($C_{1-8}$alkyl)[$C_{1-8}$alkyl-N($C_{1-8}$alkyl)($C_{1-8}$alkyl-OH)].

As used herein, the term "substituent" means positional variables on the atoms of a core molecule that are attached at a designated atom position, replacing one or more hydrogen atoms on the designated atom, provided that the atom of attachment does not exceed the available valence or shared valences, such that the substitution results in a stable compound. Accordingly, combinations of substituents and/or variables are permissible only if such combinations result in stable compounds. It should also be noted that any carbon as well as heteroatom with a valence level that appears to be unsatisfied as described or shown herein is assumed to have a sufficient number of hydrogen atom(s) to satisfy the valences described or shown.

For the purposes of this description, where one or more substituent variables for a compound of Formula (I) encompass functionalities incorporated into a compound of Formula (I), each functionality appearing at any location within the disclosed compound may be independently selected, and as appropriate, independently and/or optionally substituted.

As used herein, the terms "independently selected," or "each selected" refer to functional variables in a substituent list that may be attached more than once on the structure of a core molecule, where the pattern of substitution at each occurrence is independent of the pattern at any other occurrence. Further, the use of a generic substituent on a core structure for a compound provided herein is understood to include the replacement of the generic substituent with specie substituents that are included within the particular genus, e.g., aryl may be independently replaced with phenyl or naphthalenyl (also referred to as naphthyl) and the like, such that the resulting compound is intended to be included within the scope of the compounds described herein.

As used herein, the term "each instance of" when used in a phrase such as " . . . aryl, aryl-$C_{1-8}$alkyl, heterocyclyl and heterocyclyl-$C_{1-8}$alkyl, wherein each instance of aryl and heterocyclyl is optionally substituted with one or two substituents . . . " is intended to include optional, independent substitution on each of the aryl and heterocyclyl rings and on the aryl and heterocyclyl portions of aryl-$C_{1-8}$alkyl and heterocyclyl-$C_{1-8}$alkyl.

As used herein, the term "optionally substituted" means that the specified substituent variables, groups, radicals or moieties represent the scope of the genus and may be independently chosen as needed to replace one or more hydrogen atoms on the designated atom of attachment of a core molecule.

As used herein, the terms "stable compound" or "stable structure" mean a compound that is sufficiently robust to be isolated to a useful degree of purity from a reaction mixture and formulations thereof into an efficacious therapeutic agent.

Compound names provided herein were obtained using ACD Labs Index Name software provided by ACD Labs and/or ChemDraw Ultra software provided by CambridgeSoft®. When the compound name disclosed herein conflicts with the structure depicted, the structure shown will supercede the use of the name to define the compound intended. Nomenclature for substituent radicals defined herein may differ slightly from the chemical name from which they are derived; one skilled in the art will recognize that the definition of the substituent radical is intended to include the radical as found in the chemical name.

As used herein the term "aberrant" refers to a deviation from the norm of, e.g., the average healthy subject or a cell(s) or tissue sample from a healthy subject. The term "aberrant expression," as used herein, refers to abnormal expression (up-regulated or down-regulated resulting in an excessive or deficient amount thereof) of a gene product (e.g., RNA transcript or protein) by a cell, tissue sample, or subject relative to a corresponding normal, healthy cell, tissue sample or subject. In a specific embodiment, the "aberrant expression" refers to an altered level of a gene product (e.g., RNA transcript or protein) in a cell, tissue sample, or subject relative to a corresponding normal, healthy cell, tissue sample or subject. The term "aberrant amount" as used herein refers to an altered level of a gene product (e.g., RNA, protein, polypeptide, or peptide) in a cell, tissue sample, or subject relative to a corresponding normal, healthy cell, tissue sample or subject. In specific embodiments, the amount of a gene product (e.g., RNA, protein, polypeptide, or peptide) in a cell, tissue sample, or subject relative to a corresponding cell or tissue sample from a healthy subject or a healthy subject, is considered aberrant if it is 1, 1.5, 2, 2.5, 3, 3.5, 4, 4.5, 5, 5.5, 6-fold or more above or below the amount of the gene product in the corresponding cell or tissue sample from a healthy subject or healthy subject.

As used herein, the term "substantial change" in the context of the amount of one or more RNA transcripts (e.g., rRNA, tRNA, miRNA, siRNA, lncRNA, pre-mRNA or mRNA transcripts), an alternative splice variant thereof or an isoform thereof, or one or more proteins thereof, each expressed as the product of one or more of genes, means that the amount of such products changes by a statistically significant amount such as, in a nonlimiting example, a p value less than a value selected from 0.1, 0.01, 0.001, or 0.0001.

As used herein, the terms "subject" and "patient" are used interchangeably to refer to an animal or any living organism having sensation and the power of voluntary movement, and which requires for its existence oxygen and organic food. Non-limiting examples include members of the human, equine, porcine, bovine, rattus, murine, canine and feline species. In some embodiments, the subject is a mammal or a warm-blooded vertebrate animal. In certain embodiments, the subject is a non-human animal. In specific embodiments, the subject is a human.

Compound Forms

As used herein, the terms "a compound of Formula (Ia)," "a compound of Formula (Ia1)," "a compound of Formula (Ia2)," "a compound of Formula (Ia3)," "a compound of Formula (Ia4)," "a compound of Formula (II)," "a compound of Formula (IIa)," "a compound of Formula (IIa1)," "a compound of Formula (IIa2)," "a compound of Formula (IIa3)," "a compound of Formula (IIa4)," "a compound of Formula (III)," "a compound of Formula (IIIa)," "a compound of Formula (IIIa1)," "a compound of Formula (IIIa2)," "a compound of Formula (IIIa3)," "a compound of Formula (IIIa4)," "a compound of Formula (IV)," "a compound of Formula (IVa)," "a compound of Formula (IVa1)," "a compound of Formula (IVa2)," "a compound of Formula (V)," "a compound of Formula (Va)," "a compound of Formula (Va1)," "a compound of Formula (Va2)," "a compound of Formula (VI)," "a compound of Formula (VIa)," "a compound of Formula (VIa1)," "a compound of Formula (VIa2)," "a compound of Formula (VIa3)," "a compound of Formula (VIa4)," "a compound of Formula (VII)," "a compound of Formula (VIIa)," "a compound of Formula (VIIa1)," "a compound of Formula (VIIa2)," "a compound of Formula (VIII)," "a compound of Formula (VIIIa)," "a compound of Formula (VIIIa1)," "a compound of Formula (VIIIa2)," "a compound of Formula (IX)," "a compound of Formula (IXa)," "a compound of Formula (IXa1)," "a compound of Formula (IXa2)," "a compound of Formula (IXa3)," "a compound of Formula (IXa4)," "a compound of Formula (X)," "a compound of Formula (Xa)," "a compound of Formula (Xa1)," "a compound of Formula (Xa2)," "a compound of Formula (XI)," "a compound of Formula (XIa)," "a compound of Formula (XIa1)," "a compound of Formula (XIa2)," "a compound of Formula (XII)," "a compound of Formula (XIIa)," "a compound of Formula (XIIa1)," "a compound of Formula (XIIa2)," "a compound of Formula (XIIa3)," "a compound of Formula (XIIa4)," "a compound of Formula (XIII)," "a compound of Formula (XIIIa)," "a compound of Formula (XIIIa1)," "a compound of Formula (XIIIa2)," "a compound of Formula (XIV)," "a compound of Formula (XIVa)," "a compound of Formula (XIVa1)," and "a compound of Formula (XIVa2)," each refer to subgenera of the compound of Formula (I) or a form thereof.

Rather than repeat embodiments for the various subgenera of the compound of Formula (I), in certain embodiments, the term "a compound of Formula (I) or a form thereof" is used to inclusively to refer to a compound of Formula (Ia) or a form thereof, a compound of Formula (Ia1) or a form thereof, a compound of Formula (Ia2) or a form thereof, a compound of Formula (Ia3) or a form thereof, a compound of Formula (Ia4) or a form thereof, a compound of Formula (II) or a form thereof, a compound of Formula (IIa) or a form thereof, a compound of Formula (IIa1) or a form thereof, a compound of Formula (IIa2) or a form thereof, a compound of Formula (IIa3) or a form thereof, a compound of Formula (IIa4) or a form thereof, a compound of Formula (III) or a form thereof, a compound of Formula (IIIa) or a form thereof, a compound of Formula (IIIa1) or a form thereof, a compound of Formula (IIIa2) or a form thereof, a compound of Formula (IIIa3) or a form thereof, a compound of Formula (IIIa4) or a form thereof, a compound of Formula (IV) or a form thereof, a compound of Formula (IVa) or a form thereof, a compound of Formula (IVa1) or a form thereof, a compound of Formula (IVa2) or a form thereof, a compound of Formula (V) or a form thereof, a compound of Formula (Va) or a form thereof, a compound of Formula (Va1) or a form thereof, a compound of Formula (Va2) or a form thereof, a compound of Formula (VI) or a form thereof, a compound of Formula (VIa) or a form thereof, a compound of Formula (VIa1) or a form thereof, a compound of Formula (VIa2) or a form thereof, a compound of Formula (VIa3) or a form thereof, a compound of Formula (VIa4) or a form thereof, a compound of Formula (VII) or a form thereof, a compound of Formula (VIIa) or a form thereof, a compound of Formula (VIIa1) or a form thereof, a compound of Formula (VIIa2) or a form thereof, a compound of Formula (VIII) or a form thereof, a compound of Formula (VIIIa) or a form thereof, a compound of Formula (VIIIa1) or a form thereof, a compound of Formula (VIIIa2) or a form thereof, a compound of Formula (IX) or a form thereof, a compound of Formula (IXa) or a form thereof, a compound of Formula (IXa1) or a form thereof, a compound of Formula (IXa2) or a form thereof, a compound of Formula (IXa3) or a form thereof, a compound of Formula (IXa4) or a form thereof, a compound of Formula (X) or a form thereof, a compound of Formula (Xa) or a form thereof, a compound of Formula (Xa1) or a form thereof, a compound of Formula (Xa2) or a form thereof, a compound of Formula (XI) or a form thereof, a compound of Formula (XIa) or a form thereof, a compound of Formula (XIa1) or a form thereof, a compound of Formula (XIa2) or a form thereof, a compound of Formula (XII) or a form thereof, a compound of Formula (XIIa) or a form thereof, a compound of Formula (XIIa1) or a form thereof, a compound of Formula (XIIa2) or a form thereof, a compound of Formula (XIIa3) or a form thereof, a compound of Formula (XIIa4) or a form thereof, a compound of Formula (XIII) or a form thereof, a compound of Formula (XIIIa) or a form thereof, a compound of Formula (XIIIa1) or a form thereof, a compound of Formula (XIIIa2) or a form thereof, a compound of Formula (XIV) or a form thereof, a compound of Formula (XIVa) or a form thereof, a compound of Formula (XIVa1) or a form thereof or a compound of Formula (XIVa2) or a form thereof, either separately or together.

Thus, embodiments and references to "a compound of Formula (I)" are intended to be inclusive of compounds of Formula (Ia), Formula (Ia1), Formula (Ia2), Formula (Ia3), Formula (Ia4), Formula (II), Formula (IIa), Formula (IIa1), Formula (IIa2), Formula (IIa3), Formula (IIa4), Formula (III), Formula (IIIa), Formula (IIIa1), Formula (IIIa2), Formula (IIIa3), Formula (IIIa4), Formula (IV), Formula (IVa), Formula (IVa1), Formula (IVa2), Formula (V), Formula (Va), Formula (Va1), Formula (Va2), Formula (VI), Formula (VIa), Formula (VIa1), Formula (VIa2), Formula (VIa3), Formula (VIa4), Formula (VII), Formula (VIIa), Formula (VIIa1), Formula (VIIa2), Formula (VIII), Formula (VIIIa), Formula (VIIIa1), Formula (VIIIa2), Formula (IX), Formula (IXa), Formula (IXa1), Formula (IXa2), Formula (IXa3), Formula (IXa4), Formula (X), Formula (Xa), Formula (Xa1), Formula (Xa2), Formula (XI), Formula (XIa), Formula (XIa1), Formula (XIa2), Formula (XII), Formula (XIIa), Formula (XIIa1), Formula (XIIa2), Formula (XIIa3), Formula (XIIa4), Formula (XIII), Formula (XIIIa), Formula (XIIIa1), Formula (XIIIa2), Formula (XIV), Formula (XIVa), Formula (XIVa1) and Formula (XIVa2).

As used herein, the term "form" means a compound of Formula (I) selected from a free acid, free base, salt, isotopologue, stereoisomer, racemate, enantiomer, diastereomer, or tautomer thereof.

In certain embodiments described herein, the form of the compound of Formula (I) is a selected from a salt, isotopologue, stereoisomer, racemate, enantiomer, diastereomer or tautomer thereof.

In certain embodiments described herein, the form of the compound of Formula (I) is a selected from a free acid, isotopologue, stereoisomer, racemate, enantiomer, diastereomer or tautomer thereof.

In certain embodiments described herein, the form of the compound of Formula (I) is a selected from a free base, isotopologue, stereoisomer, racemate, enantiomer, diastereomer or tautomer thereof.

In certain embodiments described herein, the form of the compound of Formula (I) is a free acid, free base or salt thereof.

In certain embodiments described herein, the form of the compound of Formula (I) is an isotopologue thereof.

In certain embodiments described herein, the form of the compound of Formula (I) is a stereoisomer, racemate, enantiomer or diastereomer thereof.

In certain embodiments described herein, the form of the compound of Formula (I) is a tautomer thereof.

In certain embodiments described herein, the form of the compound of Formula (I) is a pharmaceutically acceptable form.

In certain embodiments described herein, the compound of Formula (I) or a form thereof is isolated for use.

As used herein, the term "isolated" means the physical state of a compound of Formula (I) or a form thereof after being isolated and/or purified from a synthetic process (e.g., from a reaction mixture) or natural source or combination thereof according to an isolation or purification process or processes described herein or which are well known to the skilled artisan (e.g., chromatography, recrystallization and the like) in sufficient purity to be characterizable by standard analytical techniques described herein or well known to the skilled artisan.

As used herein, the term "protected" means that a functional group on a compound of Formula (I) is in a form modified to preclude undesired side reactions at the protected site when the compound is subjected to a reaction. Suitable protecting groups will be recognized by those with ordinary skill in the art as well as by reference to standard textbooks such as, for example, T. W. Greene et al, Protective Groups in Organic Synthesis (1991), Wiley, New York.

Prodrugs of a compound of Formula (I) or a form thereof are also contemplated herein.

As used herein, the term "prodrug" means that a functional group on a compound of Formula (I) is in a form (e.g., acting as an active or inactive drug precursor) that is transformed in vivo to yield an active or more active compound of Formula (I) or a form thereof. The transformation may occur by various mechanisms (e.g., by metabolic and/or non-metabolic chemical processes), such as, for example, by hydrolysis and/or metabolism in blood, liver and/or other organs and tissues. A discussion of the use of prodrugs is provided by V. J. Stella, et. al., "Biotechnology: Pharmaceutical Aspects, Prodrugs: Challenges and Rewards," American Association of Pharmaceutical Scientists and Springer Press, 2007.

In one example, when a compound of Formula (I) or a form thereof contains a carboxylic acid functional group, a prodrug can comprise an ester formed by the replacement of the hydrogen atom of the acid group with a functional group such as alkyl and the like. In another example, when a compound of Formula (I) or a form thereof contains an alcohol functional group, a prodrug can be formed by the replacement of the hydrogen atom of the alcohol group with a functional group such as alkyl or substituted carbonyl and the like. In another example, when a compound of Formula (I) or a form thereof contains an amine functional group, a prodrug can be formed by the replacement of one or more amine hydrogen atoms with a functional group such as alkyl or substituted carbonyl. In another example, when a compound of Formula (I) or a form thereof contains a hydrogen substituent, a prodrug can be formed by the replacement of one or more hydrogen atoms with an alkyl substituent.

Pharmaceutically acceptable prodrugs of compounds of Formula (I) or a form thereof include those compounds substituted with one or more of the following groups: carboxylic acid esters, sulfonate esters, amino acid esters phosphonate esters, mono-, di- or triphosphate esters or alkyl substituents where appropriate. As described herein, it is understood by a person of ordinary skill in the art that one or more of such substituents may be used to provide a compound of Formula (I) or a form thereof for use as a prodrug.

The compounds of Formula (I) can form salts which are intended to be included within the scope of this description. Reference to a compound of Formula (I) herein is understood to include reference to salts thereof, unless otherwise indicated. The term "salt(s)", as employed herein, denotes acidic salts formed with inorganic and/or organic acids, as well as basic salts formed with inorganic and/or organic bases. In addition, when a compound of Formula (I) contains both a basic moiety, such as, but not limited to a pyridine or imidazole, and an acidic moiety, such as, but not limited to a carboxylic acid, zwitterions ("inner salts") may be formed and are included within the term "salt(s)" as used herein.

The term "pharmaceutically acceptable salt(s)", as used herein, means those salts of compounds described herein that are safe and effective (i.e., non-toxic, physiologically acceptable) for use in mammals and that possess biological activity, although other salts are also useful. Salts of the compounds of Formula (I) may be formed, for example, by reacting a compound of Formula (I) with an amount of acid or base, such as an equivalent or stoichiometric amount, in a medium such as one in which the salt precipitates or in an aqueous medium followed by lyophilization.

Pharmaceutically acceptable salts include one or more salts of acidic or basic groups present in compounds described herein. Embodiments of acid addition salts include, and are not limited to, acetate, acid phosphate, ascorbate, benzoate, benzenesulfonate, bisulfate, bitartrate, borate, butyrate, chloride, citrate, camphorate, camphorsulfonate, ethanesulfonate, formate, fumarate, gentisinate, gluconate, glucaronate, glutamate, hydrobromide, hydrochloride, dihydrochloride, hydroiodide, isonicotinate, lactate, maleate, methanesulfonate, naphthalenesulfonate, nitrate, oxalate, pamoate, pantothenate, phosphate, propionate, saccharate, salicylate, succinate, sulfate, tartrate, thiocyanate, toluenesulfonate (also known as tosylate), trifluoroacetate salts and the like. One or more embodiments of acid addition salts include a chloride, hydrochloride, dihydrochloride, trihydrochloride, hydrobromide, acetate, diacetate or trifluoroacetate salt. More particular embodiments include a chloride, hydrochloride, dihydrochloride, hydrobromide or trifluoroacetate salt.

Additionally, acids which are generally considered suitable for the formation of pharmaceutically useful salts from basic pharmaceutical compounds are discussed, for example, by P. Stahl et al, Camille G. (eds.) Handbook of Pharmaceutical Salts. Properties, Selection and Use. (2002) Zurich: Wiley-VCH; S. Berge et al, Journal of Pharmaceutical Sciences (1977) 66(1) 1-19; P. Gould, International J. of Pharmaceutics (1986) 33, 201-217; Anderson et al, The Practice of Medicinal Chemistry (1996), Academic Press, New York; and in The Orange Book (see, website for Food & Drug Administration, Washington, D.C.). These disclosures are incorporated herein by reference thereto.

Suitable basic salts include, but are not limited to, aluminum, ammonium, calcium, lithium, magnesium, potassium, sodium, zinc, and diethanolamine salts. Certain compounds described herein can also form pharmaceutically acceptable salts with organic bases (for example, organic amines) such as, but not limited to, dicyclohexylamines, tert-butyl amines and the like, and with various amino acids such as, but not limited to, arginine, lysine and the like. Basic nitrogen-containing groups may be quarternized with agents such as lower alkyl halides (e.g., methyl, ethyl, and butyl chlorides, bromides and iodides), dialkyl sulfates (e.g., dimethyl, diethyl, and dibutyl sulfates), long chain halides (e.g., decyl, lauryl, and stearyl chlorides, bromides and iodides), aralkyl halides (e.g., benzyl and phenethyl bromides), and others.

All such acid salts and base salts are intended to be pharmaceutically acceptable salts within the scope of the description herein and all such acid and base salts are considered equivalent to the free forms of the corresponding compounds for the purposes described herein.

Compounds of Formula I and forms thereof may further exist in a tautomeric form. All such tautomeric forms are contemplated herein as part of the present description.

The compounds of Formula (I) may contain asymmetric or chiral centers, and, therefore, may exist in different stereoisomeric forms. The present description is intended to include all stereoisomeric forms of the compounds of Formula (I) as well as mixtures thereof, including racemic mixtures.

The compounds of Formula (I) described herein may include one or more chiral centers, and as such may exist as racemic mixtures (R/S) or as substantially pure enantiomers and diastereomers. The compounds may also exist as substantially pure (R) or (S) enantiomers (when one chiral center is present). In one embodiment, the compounds of Formula (I) described herein are (S) isomers and may exist as enantiomerically pure compositions substantially comprising only the (S) isomer. In another embodiment, the compounds of Formula (I) described herein are (R) isomers and may exist as enantiomerically pure compositions substantially comprising only the (R) isomer. As one of skill in the art will recognize, when more than one chiral center is present, the compounds of Formula (I) described herein may also include portions described as an (R,R), (R,S), (S,R) or (S,S) isomer, as defined by IUPAC Nomenclature Recommendations.

As used herein, the term "substantially pure" refers to compounds consisting substantially of a single isomer in an amount greater than or equal to 90%, in an amount greater than or equal to 92%, in an amount greater than or equal to 95%, in an amount greater than or equal to 98%, in an amount greater than or equal to 99%, or in an amount equal to 100% of the single isomer.

In one aspect, a compound of Formula (I) is a substantially pure (S) enantiomer present in an amount greater than or equal to 90%, in an amount greater than or equal to 92%, in an amount greater than or equal to 95%, in an amount greater than or equal to 98%, in an amount greater than or equal to 99%, or in an amount equal to 100%.

In one aspect, a compound of Formula (I) is a substantially pure (R) enantiomer present in an amount greater than or equal to 90%, in an amount greater than or equal to 92%, in an amount greater than or equal to 95%, in an amount greater than or equal to 98%, in an amount greater than or equal to 99%, or in an amount equal to 100%.

As used herein, a "racemate" is any mixture of isometric forms that are not "enantiomerically pure", including mixtures such as, without limitation, in a ratio of about 50/50, about 60/40, about 70/30, about 80/20, about 85/15 or about 90/10.

In addition, the present description embraces all geometric and positional isomers. For example, if a compound of Formula (I) incorporates a double bond or a fused ring, both the cis- and trans-forms, as well as mixtures, are embraced within the scope of the description herein.

Diastereomeric mixtures can be separated into their individual diastereomers on the basis of their physical chemical differences by methods well known to those skilled in the art, such as, for example, by chromatography and/or fractional crystallization. Enantiomers can be separated by use of chiral HPLC column or other chromatographic methods known to those skilled in the art.

Enantiomers can also be separated by converting the enantiomeric mixture into a diastereomeric mixture by reaction with an appropriate optically active compound (e.g., chiral auxiliary such as a chiral alcohol or Mosher's acid chloride), separating the diastereomers and converting (e.g., hydrolyzing) the individual diastereomers to the corresponding pure enantiomers. Also, some of the compounds of Formula (I) may be atropisomers (e.g., substituted biaryls) and are considered part of this description.

All stereoisomer forms (for example, geometric isomers, optical isomers, positional isomers and the like) of the present compounds (including salts, solvates, esters and prodrugs and transformed prodrugs thereof) which may exist due to asymmetric carbons on various substituents, including enantiomeric forms (which may exist even in the absence of asymmetric carbons), rotameric forms, atropisomers, diastereomeric forms and regioisomeric forms are contemplated within the scope of the description herein. For example, if a compound of Formula (I) incorporates a double bond or a fused ring, both the cis- and trans-forms, as well as mixtures thereof, are embraced within the scope of the description herein. Also, for example, all keto-enol and imine-enamine tautomeric forms of the compounds are included in the description herein. Individual stereoisomers of the compounds of Formula (I) described herein may, for example, be substantially free of other isomers, or may be present in a racemic mixture, as described supra.

The use of the terms "salt," "prodrug" and "transformed prodrug" are intended to equally apply to the salts, prodrugs and transformed prodrugs of all contemplated isotopologues, stereoisomers, racemates or tautomers of the instant compounds.

The term "isotopologue" refers to isotopically-enriched compounds which are identical to those recited herein, but for the fact that one or more atoms are replaced by an atom having an atomic mass or mass number different from the atomic mass or mass number usually found in nature. Examples of isotopes that can be incorporated into compounds described herein include isotopes of hydrogen, carbon, nitrogen, oxygen, phosphorus, fluorine and chlorine, such as $H^2$, $H^3$, $C^{13}$, $C^{14}$, $N^{15}$, $O^{18}$, $O^{17}$, $P^{31}$, $P^{32}$, $S^{35}$, $F^{18}$, $Cl^{35}$ and $Cl^{36}$, respectively, each of which is also within the scope of this description.

Certain isotopically-enriched compounds described herein (e.g., those labeled with $H^3$ and $C^{14}$) are useful in compound and/or substrate tissue distribution assays. Tritiated (i.e., $H^3$) and carbon-14 (i.e., $C^{14}$) isotopes are particularly preferred for their ease of preparation and detectability. Further, substitution with heavier isotopes such as deuterium (i.e., "deuterium enriched") may afford certain therapeutic advantages resulting from greater metabolic stability (e.g., increased in vivo half-life or reduced dosage requirements) and hence may be preferred in some circumstances. Isotopically-enriched compounds of Formula (I) can generally be prepared using procedures known to persons of ordinary skill in the art by substituting an appropriate isotopically-enriched reagent for a non-isotopically-enriched reagent.

When the compounds are enriched with deuterium, the deuterium-to-hydrogen ratio on the deuterated atoms of the molecule substantially exceeds the naturally occurring deuterium-to-hydrogen ratio.

An embodiment described herein may include an isotopologue form of the compound of Formula (I), wherein the isotopologue is substituted on one or more atom members of the compound of Formula (I) with one or more deuterium atoms in place of one or more hydrogen atoms.

An embodiment described herein may include a compound of Formula (I) and forms thereof, wherein a carbon atom may have from 1 to 3 hydrogen atoms optionally replaced with deuterium.

One or more compounds described herein may exist in unsolvated as well as solvated forms with pharmaceutically acceptable solvents such as water, ethanol, and the like, and the description herein is intended to embrace both solvated and unsolvated forms.

As used herein, the term "solvate" means a physical association of a compound described herein with one or more solvent molecules. This physical association involves varying degrees of ionic and covalent bonding, including hydrogen bonding. In certain instances the solvate will be capable of isolation, for example when one or more solvent molecules are incorporated in the crystal lattice of the crystalline solid. As used herein, "solvate" encompasses both solution-phase and isolatable solvates. Non-limiting examples of suitable solvates include ethanolates, methanolates, and the like.

One or more compounds described herein may optionally be converted to a solvate. Preparation of solvates is generally known. A typical, non-limiting process involves dissolving a compound in a desired amount of the desired solvent (organic or water or mixtures thereof) at a higher than ambient temperature, and cooling the solution at a rate sufficient to form crystals which are then isolated by standard methods. Analytical techniques such as, for example infrared spectroscopy, show the presence of the solvent (or water) in the crystals as a solvate (or hydrate).

As used herein, the term "hydrate" means a solvate wherein the solvent molecule is water.

Polymorphic crystalline and amorphous forms of the compounds of Formula (I), and of the salts, solvates, esters and prodrugs of the compounds of Formula (I), are further intended to be included in the scope of the compounds described herein.

Methods for Determining which Compounds of Formula (I) Modulate the Expression of Certain Genes Provided herein are methods for determining whether a compound of Formula (I) or a form thereof modulates the amount of one, two, three or more RNA transcripts (e.g., pre-mRNA or mRNA transcripts or isoforms thereof) of one, two, three or more genes. In certain embodiments, the gene is not the SMN2 gene. In certain embodiments, provided herein are methods for determining whether a compound of Formula (I) or a form thereof modulates the amount of one, two, three or more RNA transcripts (e.g., pre-mRNA or mRNA transcripts or isoforms thereof) of one, two, three or more of the genes in, by way of nonlimiting example, Tables 1-4, 6 and 8-11, infra. In other embodiments, provided herein are methods for determining whether a compound of Formula (I) or a form thereof modulates the amount of one, two, three or more RNA transcripts (e.g., pre-mRNA or mRNA transcripts or isoforms thereof) of one, two, three or more of the genes in, by way of nonlimiting example, Tables 1-4, 6 and 8-11, infra.

In one embodiment, provided herein is a method for determining whether a compound of Formula (I) or a form thereof modulates the amount of an RNA transcript, comprising: (a) contacting a cell(s) with a compound of Formula (I) or a form thereof, and (b) determining the amount of the RNA transcript produced by the cell(s), wherein an alteration in the amount of the RNA transcript in the presence of the compound relative to the amount of the RNA transcript in the absence of the compound or the presence of a negative control (e.g., a vehicle control such as PBS or DMSO) indicates that the compound of Formula (I) or a form thereof modulates the amount of the RNA transcript. In another embodiment, provided herein is a method for determining whether a compound of Formula (I) or a form thereof modulates the amount of an RNA transcript (e.g., an mRNA transcript), comprising: (a) contacting a first cell(s) with a compound of Formula (I) or a form thereof, (b) contacting a second cell(s) with a negative control (e.g., a vehicle control, such as PBS or DMSO); and (c) determining the amount of the RNA transcript produced by the first cell(s) and the second cell(s); and (d) comparing the amount of the RNA transcript produced by the first cell(s) to the amount of the RNA transcript expressed by the second cell(s), wherein an alteration in the amount of the RNA transcript produced by the first cell(s) relative to the amount of the RNA transcript produced by the second cell(s) indicates that the compound of Formula (I) or a form thereof modulates the amount of the RNA transcript. In certain embodiments, the contacting of the cell(s) with the compound occurs in cell culture. In other embodiments, the contacting of the cell(s) with the compound occurs in a subject, such as a non-human animal subject. In specific embodiments, the RNA transcript is an RNA transcript encoded by a gene in Tables 1-4, 6 and 8-11, infra. In certain embodiments, the amount of 1, 2, 3, 4, 5, 6, 7, 8, 9, 10, 15, 20, 25, 30, 35, 40, 45, 50, 55, 60, 65, 70 or more RNA transcripts encoded by 1, 2, 3, 4, 5, 6, 7, 8, 9, 10, 15, 20, 25, 30, 35, 40, 45, 50, 55, 60, 65, 70 or more of the genes listed in Tables 1-4, 6 and 8-11, infra, is measured. In some embodiments, the amount of 1, 2, 3 or more splice variants of an RNA transcript encoded by a gene in Tables 1-4, 6 and 8-11, infra, is measured. In other embodiments, the amount of 1, 2, 3 or more splice variants of RNA transcripts encoded by 1, 2, 3, 4 or more genes in Tables 1-4, 6 and 8-11, infra, is measured. In certain embodiments, the amount of the RNA transcript(s) or splice variant(s) encoded by the SMN2 gene are not measured.

In another embodiment, provided herein is a method for determining whether a compound of Formula (I) or a form thereof modulates the splicing of an RNA transcript (e.g., an mRNA transcript), comprising: (a) culturing a cell(s) in the presence of a compound of Formula (I) or a form thereof; and (b) determining the amount of the two or more RNA transcript splice variants produced by the cell(s), wherein an alteration in the amount of the two or more RNA transcript in the presence of the compound relative to the amount of the two or more RNA transcript splice variants in the absence of the compound or the presence of a negative control (e.g., a vehicle control such as PBS or DMSO) indicates that the compound of Formula (I) or a form thereof modulates the splicing of the RNA transcript.

In another embodiment, provided herein is a method for determining whether a compound of Formula (I) or a form thereof modulates the splicing of an RNA transcript (e.g., an mRNA transcript), comprising: (a) culturing a cell(s) in the presence of a compound of Formula (I) or a form thereof; (b) isolating two or more RNA transcript splice variants from the cell(s) after a certain period of time; and (c) determining the amount of the two or more RNA transcript splice variants produced by the cell(s), wherein an alteration in the amount of the two or more RNA transcript in the presence of the compound relative to the amount of the two or more RNA transcript splice variants in the absence of the compound or the presence of a negative control (e.g., a vehicle control such as PBS or DMSO) indicates that the compound of Formula (I) or a form thereof modulates the splicing of the RNA transcript. In another embodiment, provided herein is a method for determining whether a compound of Formula (I) or a form thereof modulates the splicing of an RNA transcript (e.g., an mRNA transcript), comprising (a) culturing a first cell(s) in the presence of a compound of Formula (I) or a form thereof; (b) culturing a second cell(s) in the presence of a negative control (e.g., a vehicle control, such as PBS or DMSO); (c) isolating two or more RNA transcript splice variants produced by the first cell(s) and isolating two or more RNA transcript splice variants produced by the second cell(s); (d) determining the amount of the two or more RNA transcript splice variants produced by the first cell(s) and the second cell(s); and (e) comparing the amount of the two or more RNA transcript splice variants produced by the first cell(s) to the amount of the two or more RNA transcript splice variants produced by the second cell(s), wherein an alteration in the amount of the two or more RNA transcript splice variants produced by the first cell(s) relative to the amount of the two or more RNA transcript splice variants produced by the second cell(s) indicates that the compound of Formula (I) or a form thereof modulates the splicing of the RNA transcript. In specific embodiments, the RNA transcript is an RNA transcript encoded by a gene in Tables 1-4, 6 and 8-11, infra. In certain embodiments, the splicing of 1, 2, 3, 4, 5, 6, 7, 8, 9, 10, 15, 20, 25, 30, 35, 40, 45, 50, 55, 60, 65, 70 or more RNA transcripts encoded by 1, 2, 3, 4, 5, 6, 7, 8, 9, 10, 15, 20, 25, 30, 35, 40, 45, 50, 55, 60, 65, 70 or more of the genes listed in Tables 1-4, 6 and 8-11, infra, is measured. In certain embodiments, the amount of the RNA transcript(s) or splice variant(s) encoded by the SMN2 gene are not measured.

In another embodiment, provided herein is a method for determining whether a compound of Formula (I) or a form thereof modulates the amount of an RNA transcript (e.g., an mRNA transcript), comprising: (a) contacting a cell-free system with a compound of Formula (I) or a form thereof, and (b) determining the amount of the RNA transcript produced by the cell-free system, wherein an alteration in the amount of the RNA transcript in the presence of the compound relative to the amount of the RNA transcript in the absence of the compound or the presence of a negative control (e.g., a vehicle control such as PBS or DMSO) indicates that the compound of Formula (I) or a form thereof modulates the amount of the RNA transcript. In another embodiment, provided herein is a method for determining whether a compound of Formula (I) or a form thereof modulates the amount of an RNA transcript (e.g., an mRNA transcript), comprising: (a) contacting a first cell-free system with a compound of Formula (I) or a form thereof, (b) contacting a second cell-free system with a negative control (e.g., a vehicle control, such as PBS or DMSO); and (c) determining the amount of the RNA transcript produced by the first cell-free system and the second cell-free system; and (d) comparing the amount of the RNA transcript produced by the first cell-free system to the amount of the RNA transcript expressed by the second cell-free system, wherein an alteration in the amount of the RNA transcript produced by the first cell-free system relative to the amount of the RNA transcript produced by the second cell-free system indicates that the compound of Formula (I) or a form thereof modulates the amount of the RNA transcript. In certain embodiments, the cell-free system comprises purely synthetic RNA, synthetic or recombinant (purified) enzymes, and protein factors. In other embodiments, the cell-free system comprises RNA transcribed from a synthetic DNA template, synthetic or recombinant (purified) enzymes, and protein factors. In other embodiments, the cell-free system comprises purely synthetic RNA and nuclear extract. In other embodiments, the cell-free system comprises RNA transcribed from a synthetic DNA template and nuclear extract. In other embodiments, the cell-free system comprises purely synthetic RNA and whole cell extract. In other embodiments, the cell-free system comprises RNA transcribed from a synthetic DNA template and whole cell extract. In certain embodiments, the cell-free system additionally comprises regulatory RNAs (e.g., microRNAs). In specific embodiments, the RNA transcript is an RNA transcript encoded by a gene in Tables 1-4, 6 and 8-11, infra. In certain embodiments, the amount of 1, 2, 3, 4, 5, 6, 7, 8, 9, 10, 15, 20, 25, 30, 35, 40, 45, 50, 55, 60, 65, 70 or more RNA transcripts encoded by 1, 2, 3, 4, 5, 6, 7, 8, 9, 10, 15, 20, 25, 30, 35, 40, 45, 50, 55, 60, 65, 70 or more of the genes listed in Tables 1-4, 6 and 8-11, infra, is measured. In some embodiments, the amount of 1, 2, 3 or more splice variants of an RNA transcript encoded by a gene in Tables 1-4, 6 and 8-11, infra, is measured. In other embodiments, the amount of 1, 2, 3 or more splice variants of RNA transcripts encoded by 1, 2, 3, 4 or more genes in Tables 1-4, 6 and 8-11, infra, is measured. In certain embodiments, the amount of the RNA transcript(s) or splice variant(s) encoded by the SMN2 gene are not measured.

In another embodiment, provided herein is a method for determining whether a compound of Formula (I) or a form thereof modulates the splicing of an RNA transcript (e.g., an mRNA transcript), comprising: (a) contacting a cell-free system with a compound of Formula (I) or a form thereof; and (b) determining the amount of two or more RNA transcript splice variants produced by the cell-free system, wherein an alteration in the amount of the two or more RNA transcript splice variants in the presence of the compound relative to the amount of the two or more RNA transcript splice variants in the absence of the compound or the presence of a negative control (e.g., a vehicle control such as PBS or DMSO) indicates that the compound of Formula (I) or a form thereof modulates the splicing of the RNA transcript. In another embodiment, provided herein is a method for determining whether a compound of Formula (I) or a form thereof modulates the splicing of an RNA transcript (e.g., an mRNA transcript), comprising: (a) contacting a first cell-free system with a compound of Formula (I) or a form thereof; (b) contacting a second cell-free system with a negative control (e.g., a vehicle control, such as PBS or DMSO); and (c) determining the amount of two or more RNA transcript splice variants produced by the first cell-free system and the second cell-free system; and (d) comparing the amount of the two or more RNA transcript splice variants produced by the first cell-free system to the amount of the RNA transcript expressed by the second cell-free system, wherein an alteration in the amount of the two or more RNA transcript splice variants produced by the first cell-free system relative to the amount of the two or more RNA transcript splice variants produced by the second cell-free system indicates that the compound of Formula (I) or a form thereof modulates the splicing of the RNA transcript. In certain embodiments, the cell-free system comprises purely synthetic RNA, synthetic or recombinant (purified) enzymes, and protein factors. In other embodiments, the cell-free system comprises RNA transcribed from a synthetic DNA template, synthetic or recombinant (purified) enzymes, and protein factors. In other embodiments, the cell-free system comprises purely synthetic RNA and nuclear extract. In other embodiments, the cell-free system comprises RNA transcribed from a synthetic DNA template and nuclear extract. In other embodiments, the cell-free system comprises purely synthetic RNA and whole cell extract. In other embodiments, the cell-free system comprises RNA transcribed from a synthetic DNA template and whole cell extract. In certain embodiments, the cell-free system additionally comprises regulatory RNAs (e.g., microRNAs). In specific embodiments, the RNA transcript is an RNA transcript encoded by a gene Tables 1-4, 6 and 8-11, infra. In certain embodiments, the amount of 1, 2, 3, 4, 5, 6, 7, 8, 9, 10, 15, 20, 25, 30, 35, 40, 45, 50, 55, 60, 65, 70 or more RNA transcripts encoded by 1, 2, 3, 4, 5, 6, 7, 8, 9, 10, 15, 20, 25, 30, 35, 40, 45, 50, 55, 60, 65, 70 or more of the genes listed in Tables 1-4, 6 and 8-11, infra, is measured. In certain embodiments, the amount of the RNA transcript(s) or splice variant(s) encoded by the SMN2 gene are not measured.

In another embodiment, provided herein is a method for determining whether a compound of Formula (I) or a form thereof modulates the amount of an RNA transcript (e.g., an mRNA transcript), comprising: (a) culturing a cell(s) in the presence of a compound of Formula (I) or a form thereof; (b) isolating the RNA transcript from the cell(s) after a certain period of time; and (c) determining the amount of the RNA transcript produced by the cell(s), wherein an alteration in the amount of the RNA transcript in the presence of the compound relative to the amount of the RNA transcript in the absence of the compound or the presence of a negative control (e.g., a vehicle control such as PBS or DMSO) indicates that the compound of Formula (I) or a form thereof modulates the amount of the RNA transcript. In another embodiment, provided herein is a method for determining whether a compound of Formula (I) or a form thereof modulates the amount of an RNA transcript (e.g., an mRNA transcript), comprising (a) culturing a first cell(s) in the presence of a compound of Formula (I) or a form thereof, (b) culturing a second cell(s) in the presence of a negative control (e.g., a vehicle control, such as PBS or DMSO); (c) isolating the RNA transcript produced by the first cell(s) and isolating the RNA transcript produced by the second cell(s); (d) determining the amount of the RNA transcript produced by the first cell(s) and the second cell(s); and (e) comparing the amount of the RNA transcript produced by the first cell(s) to the amount of the RNA transcript produced by the second cell(s), wherein an alteration in the amount of the RNA transcript produced by the first cell(s) relative to the amount of the RNA transcript produced by the second cell(s) indicates that the compound of Formula (I) or a form thereof modulates the amount of the RNA transcript. In specific embodiments, the RNA transcript is an RNA transcript encoded by a gene in Tables 1-4, 6 and 8-11, infra. In certain embodiments, the amount of 1, 2, 3, 4, 5, 6, 7, 8, 9, 10, 15, 20, 25, 30, 35, 40, 45, 50, 55, 60, 65, 70 or more RNA transcripts encoded by 1, 2, 3, 4, 5, 6, 7, 8, 9, 10, 15, 20, 25, 30, 35, 40, 45, 50, 55, 60, 65, 70 or more of the genes listed in Tables 1-4, 6 and 8-11, infra, is measured. In some embodiments, the amount of 1, 2, 3 or more splice variants of an RNA transcript encoded by a gene in Tables 1-4, 6 and 8-11, infra, is measured. In other embodiments, the amount of 1, 2, 3 or more splice variants of RNA transcripts encoded by 1, 2, 3, 4 or more genes in Tables 1-4, 6 and 8-11, infra, is measured. In certain embodiments, the amount of the RNA transcript(s) or splice variant(s) encoded by the SMN2 gene are not measured.

In certain embodiments, the method for determining whether a compound of Formula (I) or a form thereof modulates the amount of an RNA transcript (e.g., an mRNA transcript) is described in Example 1, infra.

In certain embodiments, the cell(s) contacted or cultured with a compound of Formula (I) or a form thereof is a primary cell(s) from a subject. In some embodiments, the cell(s) contacted or cultured with a compound of Formula (I) or a form thereof is a primary cell(s) from a subject with a disease. In specific embodiments, the cell(s) contacted or cultured with a compound of Formula (I) or a form thereof is a primary cell(s) from a subject with a disease associated with an aberrant amount of an RNA transcript(s) for a particular gene(s), e.g., a gene in Tables 1-4, 6 and 8-11, infra. In some specific embodiments, the cell(s) contacted or cultured with a compound of Formula (I) or a form thereof is a primary cell(s) from a subject with a disease associated with an aberrant amount of an isoform(s) of a particular gene(s), e.g., a gene in Tables 1-4, 6 and 8-11, infra. In some embodiments, the cell(s) contacted or cultured with a compound of Formula (I) or a form thereof is a fibroblast (e.g., GM03813 or PNN 1-46 fibroblasts), an immune cell (e.g., a T cell, B cell, natural killer cell, macrophage), or a muscle cell. In certain embodiments, the cell(s) contacted or cultured with a compound of Formula (I) or a form thereof is a cancer cell.

In certain embodiments, the cell(s) contacted or cultured with a compound of Formula (I) or a form thereof is from a cell line. In some embodiments, the cell(s) contacted or cultured with a compound of Formula (I) or a form thereof is a cell line derived from a subject with a disease. In certain embodiments, the cell(s) contacted or cultured with a compound of Formula (I) or a form thereof is from a cell line known to have aberrant RNA transcript levels for a particular gene(s), e.g., a gene in Tables 1-4, 6 and 8-11, infra. In specific embodiments, the cell(s) contacted or cultured with a compound of Formula (I) or a form thereof is from a cell line derived from a subject with a disease known to have aberrant RNA transcript levels for a particular gene(s), e.g., a gene in Tables 1-4, 6 and 8-11, infra. In certain embodiments, the cell(s) contacted or cultured with a compound of Formula (I) or a form thereof is a cancer cell line. In some specific embodiments, the cell(s) contacted or cultured with the compound of Formula (I) or a form thereof is from a cell line derived from a subject with a disease known to have an aberrant amount of an RNA isoform(s) and/or protein isoform(s) of a particular gene(s), e.g., a gene in Tables 1-4, 6 and 8-11, infra. Non-limiting examples of cell lines include 293, 3T3, 4T1, 721, 9L, A2780, A172, A20, A253, A431, A-549, ALC, B16, B35, BCP-1, BEAS-2B, bEnd.3, BHK, BR 293, BT20, BT483, BxPC3, C2C12, C3H-10T1/2, C6/36, C6, Cal-27, CHO, COR-L23, COS, COV-434, CML Ti, CMT, CRL7030, CT26, D17, DH82, DU145, DuCaP, EL4, EM2, EM3, EMT6, FM3, H1299, H69, HB54, HB55, HCA2, HEK-293, HeLa, Hepa1c1c7, HL-60, HMEC, Hs578T, HsS78Bst, HT-29, HTB2, HUVEC, Jurkat, J558L, JY, K562, Ku812, KCL22, KG1, KYO1, LNCap, Ma-Mel, MC-38, MCF-7, MCF-10A, MDA-MB-231, MDA-MB-468, MDA-MB-435, MDCK, MG63, MOR/0.2R, MONO-MAC6, MRC5, MTD-1A, NCI-H69, NIH-3T3, NALM-1, NSO, NW-145, OPCN, OPCT, PNT-1A, PNT-2, Raji, RBL, RenCa, RIN-5F, RMA, Saos-2, Sf21, Sf9, SiHa, SKBR3, SKOV-3, T2, T-47D, T84, THP1, U373, U87, U937, VCaP, Vero, VERY, W138, WM39, WT-49, X63, YAC-1, or YAR cells. In one embodiment, the cells are from a patient.

In another embodiment, provided herein is a method for determining whether a compound of Formula (I) or a form thereof modulates the amount of an RNA transcript (e.g., an mRNA transcript), comprising: (a) contacting a tissue sample with a compound of Formula (I) or a form thereof; and (b) determining the amount of the RNA transcript produced by the tissue sample, wherein an alteration in the amount of the RNA transcript in the presence of the compound relative to the amount of the RNA transcript in the absence of the compound or the presence of a negative control (e.g., a vehicle control such as PBS or DMSO) indicates that the compound of Formula (I) or a form thereof modulates the amount of the RNA transcript. In another embodiment, provided herein is a method for determining whether a compound of Formula (I) or a form thereof modulates the amount of an RNA transcript (e.g., an mRNA transcript), comprising: (a) contacting a first tissue sample with a compound of Formula (I) or a form thereof, (b) contacting a second tissue sample with a negative control (e.g., a vehicle control, such as PBS or DMSO); and (c) determining the amount of the RNA transcript produced by the first tissue sample and the second tissue sample; and (d) comparing the amount of the RNA transcript produced by the first tissue sample to the amount of the RNA transcript produced by the second tissue sample, wherein an alteration in the amount of the RNA transcript produced by the first tissue sample relative to the amount of the RNA transcript produced by the second tissue sample indicates that the compound of Formula (I) or a form thereof modulates the amount of the RNA transcript. Any tissue sample containing cells may be used in the accordance with these methods. In certain embodiments, the tissue sample is a blood sample, a skin sample, a muscle sample, or a tumor sample. Techniques known to one skilled in the art may be used to obtain a tissue sample from a subject. In specific embodiments, the RNA transcript is an RNA transcript encoded by a gene in Tables 1-4, 6 and 8-11, infra. In certain embodiments, the amount of 1, 2, 3, 4, 5, 6, 7, 8, 9, 10, 15, 20, 25, 30, 35, 40, 45, 50, 55, 60, 65, 70 or more RNA transcripts encoded by 1, 2, 3, 4, 5, 6, 7, 8, 9, 10, 15, 20, 25, 30, 35, 40, 45, 50, 55, 60, 65, 70 or more of the genes listed in Tables 1-4, 6 and 8-11, infra, is measured. In some embodiments, the amount of 1, 2, 3 or more splice variants of an RNA transcript encoded by a gene in Tables 1-4, 6 and 8-11, infra, is measured. In other embodiments, the amount of 1, 2, 3 or more splice variants of RNA transcripts encoded by 1, 2, 3, 4 or more genes in Tables 1-4, 6 and 8-11, infra, is measured. In certain embodiments, the amount of the RNA transcript(s) or splice variant(s) encoded by the SMN2 gene are not measured.

In some embodiments, a dose-response assay is performed. In one embodiment, the dose response assay comprises: (a) contacting a cell(s) with a concentration of a compound of Formula (I) or a form thereof; (b) determining the amount of the RNA transcript produced by the cell(s), wherein an alteration in the amount of the RNA transcript in the presence of the compound relative to the amount of the RNA transcript in the absence of the compound or the presence of a negative control (e.g., a vehicle control such as PBS or DMSO) indicates that the compound of Formula (I) or a form thereof modulates the amount of the RNA transcript; (c) repeating steps (a) and (b), wherein the only experimental variable changed is the concentration of the compound or a form thereof; and (d) comparing the amount of the RNA transcript produced at the different concentrations of the compound or a form thereof. In another embodiment, the dose response assay comprises: (a) culturing a cell(s) in the presence of a compound of Formula (I) or a form thereof, (b) isolating the RNA transcript from the cell(s) after a certain period of time; (c) determining the amount of the RNA transcript produced by the cell(s), wherein an alteration in the amount of the RNA transcript in the presence of the compound relative to the amount of the RNA transcript in the absence of the compound or the presence of a negative control (e.g., a vehicle control such as PBS or DMSO) indicates that the compound of Formula (I) or a form thereof modulates the amount of the RNA transcript; (d) repeating steps (a), (b), and (c), wherein the only experimental variable changed is the concentration of the compound or a form thereof; and (e) comparing the amount of the RNA transcript produced at the different concentrations of the compound or a form thereof. In another embodiments, the dose-response assay comprises: (a) contacting each well of a microtiter plate containing cells with a different concentration of a compound of Formula (I) or a form thereof; (b) determining the amount of an RNA transcript produced by cells in each well; and (c) assessing the change of the amount of the RNA transcript at the different concentrations of the compound or form thereof.

In one embodiment, the dose response assay comprises: (a) contacting a cell(s) with a concentration of a compound of Formula (I) or a form thereof, wherein the cells are within the wells of a tissue culture container (e.g., a 96-well plate) at about the same density within each well, and wherein the cells are contacted with different concentrations of compound in different wells; (b) isolating the RNA from said cells in each well; (c) determining the amount of the RNA transcript produced by the cell(s) in each well; and (d) assessing change in the amount of the RNA transcript in the presence of one or more concentrations of compound relative to the amount of the RNA transcript in the presence of a different concentration of the compound or the absence of the compound or the presence of a negative control (e.g., a vehicle control such as PBS or DMSO).

In certain embodiments, the contacting of the cell(s) with the compound occurs in cell culture. In other embodiments, the contacting of the cell(s) with the compound occurs in a subject, such as a non-human animal subject. In specific embodiments, the RNA transcript is an RNA transcript encoded by a gene in Tables 1-4, 6 and 8-11, infra. In certain embodiments, the amount of 1, 2, 3, 4, 5, 6, 7, 8, 9, 10, 15, 20, 25, 30, 35, 40, 45, 50, 55, 60, 65, 70 or more RNA transcripts encoded by 1, 2, 3, 4, 5, 6, 7, 8, 9, 10, 15, 20, 25, 30, 35, 40, 45, 50, 55, 60, 65, 70 or more of the genes listed in Tables 1-4, 6 and 8-11, infra, is measured. In some embodiments, the amount of 1, 2, 3 or more splice variants of an RNA transcript encoded by a gene in Tables 1-4, 6 and 8-11, infra, is measured. In other embodiments, the amount of 1, 2, 3 or more splice variants of RNA transcripts encoded by 1, 2, 3, 4 or more genes in Tables 1-4, 6 and 8-11, infra, is measured. In certain embodiments, the amount of the RNA transcript(s) or splice variant(s) encoded by the SMN2 gene are not measured.

In certain embodiments, a dose-response assay is performed as described in Example 2, infra.

In certain embodiments described herein, the cell(s) is contacted or cultured with a compound of Formula (I) or a form thereof, or a tissue sample is contacted with a compound of Formula (I) or a form thereof, or a negative control for a period of 15 minutes, 30 minutes, 45 minutes, 1 hour, 2 hours, 3 hours, 4 hours, 5 hours, 6 hours, 8 hours, 12 hours, 18 hours, 24 hours, 48 hours, 72 hours or more. In other embodiments described herein, the cell(s) is contacted or cultured with a compound of Formula (I) or a form thereof, or a tissue sample is contacted with a compound of Formula (I) or a form thereof, or a negative control for a period of 15 minutes to 1 hour, 1 to 2 hours, 2 to 4 hours, 6 to 12 hours, 12 to 18 hours, 12 to 24 hours, 28 to 24 hours, 24 to 48 hours, 48 to 72 hours.

In certain embodiments described herein, the cell(s) is contacted or cultured with certain concentration of a compound of Formula (I) or a form thereof, or a tissue sample is contacted with a certain concentration of a compound of Formula (I) or a form thereof, wherein the certain concentration is 0.01 µM, 0.05 µM, 1 µM, 2 µM, 5 µM, 10 µM, 15 µM, 20 µM, 25 µM, 50 µM, 75 µM, 100 µM, or 150 µM. In other embodiments described herein, the cell(s) is contacted or cultured with certain concentration of a compound of Formula (I) or a form thereof, or a tissue sample is contacted with a certain concentration of a compound of Formula (I) or a form thereof, wherein the certain concentration is 175 µM, 200 µM, 250 µM, 275 µM, 300 µM, 350 µM, 400 µM, 450 µM, 500 µM, 550 µM 600 µM, 650 µM, 700 µM, 750 µM, 800 µM, 850 µM, 900 µM, 950 µM or 1 mM. In some embodiments described herein, the cell(s) is contacted or cultured with certain concentration of a compound of Formula (I) or a form thereof, or a tissue sample is contacted with a certain concentration of a compound of Formula (I) or a form thereof, wherein the certain concentration is 5 nM, 10 nM, 20 nM, 30 nM, 40 nM, 50 nM, 60 nM, 70 nM, 80 nM, 90 nM, 100 nM, 150 nM, 200 nM, 250 nM, 300 nM, 350 nM, 400 nM, 450 nM, 500 nM, 550 nM, 600 nM, 650 nM, 700 nM, 750 nM, 800 nM, 850 nM, 900 nM, or 950 nM. In certain embodiments described herein, the cell(s) is contacted or cultured with certain concentration of a compound of Formula (I) or a form thereof, or a tissue sample is contacted with a certain concentration of a compound of Formula (I) or a form thereof, wherein the certain concentration is between 0.01 µM to 0.1 µM, 0.1 µM to 1 µM, 1 µM to 50 µM, 50 µM to 100 µM, 100 µM to 500 µM, 500 µM to 1 nM, 1 nM to 10 nM, 10 nM to 50 nM, 50 nM to 100 nM, 100 nM to 500 nM, 500 nM to 1000 nM.

In another embodiment, provided herein is a method for determining whether a compound of Formula (I) or a form thereof modulates the amount of an RNA transcript (e.g., an mRNA transcript), comprising: (a) administering a compound of Formula (I) or a form thereof to a subject (in certain embodiments, a non-human animal); and (b) determining the amount of the RNA transcript in a sample obtained from the subject, wherein an alteration in the amount of the RNA transcript measured in the sample from the subject administered the compound or form thereof relative to the amount of the RNA transcript in a sample from the subject prior to administration of the compound or form thereof or a sample from a different subject from the same species not administered the compound or form thereof indicates that the compound of Formula (I) or a form thereof modulates the amount of the RNA transcript. In another embodiment, provided herein is a method for determining whether a compound of Formula (I) or a form thereof modulates the amount of an RNA transcript (e.g., an mRNA transcript), comprising: (a) administering a compound of Formula (I) or a form thereof to a first subject (in certain embodiments, a non-human animal); (b) administering a negative control (e.g., a pharmaceutical carrier) to a second subject (in certain embodiments, a non-human animal) of the same species as the first subject; and (c) determining the amount of the RNA transcript in a first tissue sample from the first subject and the amount of the RNA transcript in the second tissue sample from the second subject; and (d) comparing the amount of the RNA transcript in the first tissue sample to the amount of the RNA transcript in the second tissue sample, wherein an alteration in the amount of the RNA transcript in the first tissue sample relative to the amount of the RNA transcript in the second tissue sample indicates that the compound of Formula (I) or a form thereof modulates the amount of the RNA transcript. In certain embodiments, a compound of Formula (I) or form thereof is administered to a subject at a dose of about 0.001 mg/kg/day to about 500 mg/kg/day. In some embodiments, a single dose of a compound of Formula (I) or a form thereof is administered to a subject in accordance with the methods described herein. In other embodiments, 2, 3, 4, 5 or more doses of a compound of Formula (I) is administered to a subject in accordance with the methods described herein. In specific embodiments, the RNA transcript is an RNA transcript encoded by a gene in Tables 1-4, 6 and 8-11, infra. In certain embodiments, the amount of 1, 2, 3, 4, 5, 6, 7, 8, 9, 10, 15, 20, 25, 30, 35, 40, 45, 50, 55, 60, 65, 70 or more RNA transcripts encoded by 1, 2, 3, 4, 5, 6, 7, 8, 9, 10, 15, 20, 25, 30, 35, 40, 45, 50, 55, 60, 65, 70 or more of the genes listed in Tables 1-4, 6 and 8-11, infra, is measured. In some embodiments, the amount of 1, 2, 3 or more splice variants of an RNA transcript encoded by a gene in Tables 1-4, 6 and 8-11, infra, is measured. In other embodiments, the amount of 1, 2, 3 or more splice variants of RNA transcripts encoded by 1, 2, 3, 4 or more genes in Tables 1-4, 6 and 8-11, infra, is measured. In certain embodiments, the amount of the RNA transcript(s) or splice variant(s) encoded by the SMN2 gene are not measured. In specific embodiments, the compound of Formula (I) or a form thereof is administered in a subject in a pharmaceutically acceptable carrier, excipient or diluent.

In another embodiment, provided herein is a method for determining whether a compound of Formula (I) or a form thereof modulates the splicing of an RNA transcript (e.g., an mRNA transcript), comprising: (a) administering a compound of Formula (I) or a form thereof to a subject (in certain embodiments, a non-human animal); and (b) determining the amount of two or more RNA transcript splice variants in a sample obtained from the subject, wherein an alteration in the amount of the two or more RNA transcript splice variants measured in the sample from the subject administered the compound or form thereof relative to the amount of the two or more RNA transcript splice variants in a sample from the subject prior to administration of the compound or form thereof or a sample from a different subject from the same species not administered the compound or form thereof indicates that the compound of Formula (I) or a form thereof modulates the splicing of the RNA transcript. In another embodiment, provided herein is a method for determining whether a compound of Formula (I) or a form thereof modulates the splicing of an RNA transcript (e.g., an mRNA transcript), comprising: (a) administering a compound of Formula (I) or a form thereof to a first subject (in certain embodiments, a non-human animal); (b) administering a negative control (e.g., a pharmaceutical carrier) to a second subject (in certain embodiments, a non-human animal) of the same species as the first subject; and (c) determining the amount of two or more RNA transcript splice variants in a first tissue sample from the first subject and the amount of two or more RNA transcript splice variants in the second tissue sample from the second subject; and (d) comparing the amount of the two or more RNA transcript splice variants in the first tissue sample to the amount of the two or more RNA transcript splice variants in the second tissue sample, wherein an alteration in the amount of the two or more RNA transcript splice variants in the first tissue sample relative to the amount of the two or more RNA transcript splice variants in the second tissue sample indicates that the compound of Formula (I) or a form thereof modulates the splicing of the RNA transcript. In certain embodiments, a compound of Formula (I) or form thereof is administered to a subject at a dose of about 0.001 mg/kg/day to about 500 mg/kg/day. In some embodiments, a single dose of a compound of Formula (I) or a form thereof is administered to a subject in accordance with the methods described herein. In other embodiments, 2, 3, 4, 5 or more doses of a compound of Formula (I) is administered to a subject in accordance with the methods described herein. In specific embodiments, the RNA transcript is an RNA transcript encoded by a gene in Tables 1-4, 6 and 8-11, infra. In certain embodiments, the amount of 1, 2, 3, 4, 5, 6, 7, 8, 9, 10, 15, 20, 25, 30, 35, 40, 45, 50, 55, 60, 65, 70 or more RNA transcripts encoded by 1, 2, 3, 4, 5, 6, 7, 8, 9, 10, 15, 20, 25, 30, 35, 40, 45, 50, 55, 60, 65, 70 or more of the genes listed in Tables 1-4, 6 and 8-11, infra, is measured. In certain embodiments, the amount of the RNA transcript(s) or splice variant(s) encoded by the SMN2 gene are not measured. In specific embodiments, the compound of Formula (I) or a form thereof is administered in a subject in a pharmaceutically acceptable carrier, excipient or diluent.

In some embodiments, the compound of Formula (I) or a form thereof that is contacted or cultured with a cell(s) or a tissue sample, or administered to a subject is a compound of Formula (II), Formula (III), Formula (IV), Formula (V), Formula (VI), Formula (VII), Formula (VIII), Formula (IX), Formula (X), Formula (XI), Formula (XII), Formula (XIII), or Formula (XIV). In some embodiments, the compound of Formula (I) or a form thereof that is contacted or cultured with a cell(s) or a tissue sample, or administered to a subject is a compound described herein.

Techniques known to one skilled in the art may be used to determine the amount of an RNA transcript(s). In some embodiments, the amount of one, two, three or more RNA transcripts is measured using deep sequencing, such as ILLUMINA® RNASeq, ILLUMINA® next generation sequencing (NGS), ION TORRENT™ RNA next generation sequencing, 454™ pyrosequencing, or Sequencing by Oligo Ligation Detection (SOLID™). In other embodiments, the amount of multiple RNA transcripts is measured using an exon array, such as the GENECHIP® human exon array. In certain embodiments, the amount of one, two, three or more RNA transcripts is determined by RT-PCR. In other embodiments, the amount of one, two, three or more RNA transcripts is measured by RT-qPCR. Techniques for conducting these assays are known to one skilled in the art.

In some embodiments, a statistical analysis or other analysis is performed on data from the assay utilized to measure an RNA transcript. In certain embodiments, a student t-test statistical analysis is performed on data from the assay utilized to measure an RNA transcript to determined those RNA transcripts that have an alternation in amount in the presence of the compound relative to the amount in the absence of the compound or presence of a negative control. In specific embodiments, the student t-test value of those RNA transcripts with the alternation is 10%, 5%, 4%, 3%, 2%, 1%, 0.5% or 0.1%. In some specific embodiments, p value of those RNA transcripts with the alternation is 10%, 5%, 4%, 3%, 2%, 1%, 0.5% or 0.1%. In certain specific embodiments, the student t-test and p values of those RNA transcripts with the alteration are 10%, 5%, 4%, 3%, 2%, 1%, 0.5% or 0.1% and 10%, 5%, 4%, 3%, 2%, 1%, 0.5% or 0.1%, respectively.

In certain embodiments, a further analysis is performed to determine how the compound of Formula (I) or a form thereof is changing the amount of an RNA transcript(s). In specific embodiments, a further analysis is performed to determine if an alternation in the amount of an RNA transcript(s) in the presence of a compound of Formula (I) or a form thereof relative the amount of the RNA transcript(s) in the absence of the compound or a form thereof, or the presence of a negative control is due to changes in transcription, splicing, and/or stability of the RNA transcript(s). Techniques known to one skilled in the art may be used to determine whether a compound of Formula (I) or a form thereof changes, e.g., the transcription, splicing and/or stability of an RNA transcript(s).

In certain embodiments, the stability of one or more RNA transcripts is determined by serial analysis of gene expression (SAGE), differential display analysis (DD), RNA arbitrarily primer (RAP)-PCR, restriction endonuclease-lytic analysis of differentially expressed sequences (READS), amplified restriction fragment-length polymorphism (ALFP), total gene expression analysis (TOGA), RT-PCR, RT-qPCR, high-density cDNA filter hybridization analysis (HDFCA), suppression subtractive hybridization (SSH), differential screening (DS), cDNA arrays, oligonucleotide chips, or tissue microarrays. In other embodiments, the stability of one or more RNA transcripts is determined by Northern blots, RNase protection, or slot blots.

In some embodiments, the transcription in a cell(s) or tissue sample is inhibited before (e.g., 5 minutes, 10 minutes, 30 minutes, 1 hour, 2 hours, 4 hours, 6 hours, 8 hours, 12 hours, 18 hours, 24 hours, 36 hours, 48 hours, or 72 hours before) or after (e.g., 5 minutes, 10 minutes, 30 minutes, 1 hour, 2 hours, 4 hours, 6 hours, 8 hours, 12 hours, 18 hours, 24 hours, 36 hours, 48 hours, or 72 hours after) the cell or the tissue sample is contacted or cultured with an inhibitor of transcription, such as α-amanitin, DRB, flavopiridol, triptolide, or actinomycin-D. In other embodiments, the transcription in a cell(s) or tissue sample is inhibited with an inhibitor of transcription, such as α-amanitin, DRB, flavopiridol, triptolide, or actinomycin-D, while the cell(s) or tissue sample is contacted or cultured with a compound of Formula (I) or a form thereof.

In certain embodiments, the level of transcription of one or more RNA transcripts is determined by nuclear run-on assay or an in vitro transcription initiation and elongation assay. In some embodiments, the detection of transcription is based on measuring radioactivity or fluorescence. In some embodiments, a PCR-based amplification step is used.

In certain embodiments, the amount of alternatively spliced forms of the RNA transcripts of a particular gene, e.g., a gene in Tables 1-4, 6 and 8-11, infra, are measured to see if there is an alteration in the amount of one, two or more alternatively spliced forms of the RNA transcripts of the gene. In some embodiments, the amount of an isoform(s) encoded by a particular gene, e.g., a gene in Tables 1-4, 6 and 8-11, infra, are measured to see if there is an alteration in the amount of the isoform(s). In certain embodiments, the levels of spliced forms of RNA are quantified by RT-PCR, RT-qPCR, or northern blotting. In other embodiments, sequence-specific techniques may be used to detect the levels of an individual spliceoform. In certain embodiments, splicing is measured in vitro using nuclear extracts. In some embodiments, detection is based on measuring radioactivity or fluorescence. Techniques known to one skilled in the art may be used to measure alterations in the amount of alternatively spliced forms of an RNA transcript of a gene and alterations in the amount of an isoform encoded by a gene.

Pharmaceutical Compositions and Modes of Administration

When administered to a patient, a compound of Formula (I) or a form thereof is preferably administered as a component of a composition that optionally comprises a pharmaceutically acceptable carrier, excipient or diluent. The composition can be administered orally, or by any other convenient route, for example, by infusion or bolus injection, by absorption through epithelial or mucocutaneous linings (e.g., oral mucosa, rectal, and intestinal mucosa) and may be administered together with another biologically active agent. Administration can be systemic or local. Various delivery systems are known, e.g., encapsulation in liposomes, microparticles, microcapsules, capsules, and can be used to administer the compound.

Methods of administration include, but are not limited to, parenteral, intradermal, intramuscular, intraperitoneal, intravenous, subcutaneous, intranasal, epidural, oral, sublingual, intranasal, intraocular, intratumoral, intracerebral, intravaginal, transdermal, ocularly, rectally, by inhalation, or topically, particularly to the ears, nose, eyes, or skin. The mode of administration is left to the discretion of the practitioner. In most instances, administration will result in the release of a compound into the bloodstream, tissue or cell(s). In a specific embodiment, a compound is administered orally.

The amount of a compound of Formula (I) or a form thereof that will be effective in the treatment of a disease resulting from an aberrant amount of mRNA transcripts depends, e.g., on the route of administration, the disease being treated, the general health of the subject, ethnicity, age, weight, and gender of the subject, diet, time, and the severity of disease progress, and should be decided according to the judgment of the practitioner and each patient's or subject's circumstances.

In specific embodiments, an "effective amount" in the context of the administration of a compound of Formula (I) or a form thereof, or composition or medicament thereof refers to an amount of a compound of Formula (I) or a form thereof to a patient which has a therapeutic effect and/or beneficial effect. In certain specific embodiments, an "effective amount" in the context of the administration of a compound of Formula (I) or a form thereof, or composition or medicament thereof to a patient results in one, two or more of the following effects: (i) reduces or ameliorates the severity of a disease; (ii) delays onset of a disease; (iii) inhibits the progression of a disease; (iv) reduces hospitalization of a subject; (v) reduces hospitalization length for a subject; (vi) increases the survival of a subject; (vii) improves the quality of life of a subject; (viii) reduces the number of symptoms associated with a disease; (ix) reduces or ameliorates the severity of a symptom(s) associated with a disease; (x) reduces the duration of a symptom associated with a disease associated; (xi) prevents the recurrence of a symptom associated with a disease; (xii) inhibits the development or onset of a symptom of a disease; and/or (xiii) inhibits of the progression of a symptom associated with a disease. In certain embodiments, an effective amount of a compound of Formula (I) or a form thereof is an amount effective to restore the amount of a RNA transcript of a gene (e.g., a gene in Tables 1-4, 6 and 8-11, infra) to the amount of the RNA transcript detectable in healthy patients or cells from healthy patients. In other embodiments, an effective amount of a compound of Formula (I) or a form thereof is an amount effective to restore the amount an RNA isoform and/or protein isoform of gene (e.g., a gene in Tables 1-4, 6 and 8-11, infra) to the amount of the RNA isoform and/or protein isoform detectable in healthy patients or cells from healthy patients.

In certain embodiments, an effective amount of a compound of Formula (I) or a form thereof is an amount effective to decrease the aberrant amount of an RNA transcript of a gene (e.g., a gene in Tables 1-4, 6 and 8-11, infra) which associated with a disease. In certain embodiments, an effective amount of a compound of Formula (I) or a form thereof is an amount effective to decrease the amount of the aberrant expression of an isoform of a gene (e.g., a gene in Tables 1-4, 6 and 8-11, infra). In some embodiments, an effective amount of a compound of Formula (I) or a form thereof is an amount effective to result in a substantial change in the amount of an RNA transcript (e.g., mRNA transcript), alternative splice variant or isoform.

In certain embodiments, an effective amount of a compound of Formula (I) or a form thereof is an amount effective to increase or decrease the amount of an RNA transcript (e.g., an mRNA transcript) of gene (e.g., a gene in Tables 1-4, 6 and 8-11, infra) which is beneficial for the prevention and/or treatment of a disease. In certain embodiments, an effective amount of a compound of Formula (I) or a form thereof is an amount effective to increase or decrease the amount of an alternative splice variant of an RNA transcript of gene (e.g., a gene in Tables 1-4, 6 and 8-11, infra) which is beneficial for the prevention and/or treatment of a disease. In certain embodiments, an effective amount of a compound of Formula (I) or a form thereof is an amount effective to increase or decrease the amount of an isoform of gene (e.g., a gene in Tables 1-4, 6 and 8-11, infra) which is beneficial for the prevention and/or treatment of a disease. Non-limiting examples of effective amounts of a compound of Formula (I) or a form thereof are described herein.

For example, the effective amount may be the amount required to prevent and/or treat a disease associated with the aberrant amount of an mRNA transcript of gene (e.g., a gene in Tables 1-4, 6 and 8-11, infra) in a human subject.

In general, the effective amount will be in a range of from about 0.001 mg/kg/day to about 500 mg/kg/day for a patient having a weight in a range of between about 1 kg to about 200 kg. The typical adult subject is expected to have a median weight in a range of between about 70 and about 100 kg.

Within the scope of the present description, the "effective amount" of a compound of Formula (I) or a form thereof for use in the manufacture of a medicament, the preparation of a pharmaceutical kit or in a method for preventing and/or treating a disease in a human subject in need thereof, is intended to include an amount in a range of from about 0.001 mg to about 35,000 mg.

The compositions described herein are formulated for administration to the subject via any drug delivery route known in the art. Non-limiting examples include oral, ocular, rectal, buccal, topical, nasal, ophthalmic, subcutaneous, intramuscular, intraveneous (bolus and infusion), intracerebral, transdermal, and pulmonary routes of administration.

Embodiments described herein include the use of a compound of Formula (I) or a form thereof in a pharmaceutical composition. In a specific embodiment, described herein is the use of a compound of Formula (I) or a form thereof in a pharmaceutical composition for preventing and/or treating a disease in a human subject in need thereof comprising administering an effective amount of a compound of Formula (I) or a form thereof in admixture with a pharmaceutically acceptable carrier, excipient or diluent. In a specific embodiment, the human subject is a patient with a disease associated with the aberrant amount of an mRNA transcript(s).

A compound of Formula (I) or a form thereof may optionally be in the form of a composition comprising the compound or a form thereof and an optional carrier, excipient or diluent. Other embodiments provided herein include pharmaceutical compositions comprising an effective amount of a compound of Formula (I) or a form thereof and a pharmaceutically acceptable carrier, excipient, or diluent. In a specific embodiment, the pharmaceutical compositions are suitable for veterinary and/or human administration. The pharmaceutical compositions provided herein can be in any form that allows for the composition to be administered to a subject.

In a specific embodiment and in this context, the term "pharmaceutically acceptable carrier, excipient or diluent" means a carrier, excipient or diluent approved by a regulatory agency of the Federal or a state government or listed in the U.S. Pharmacopeia or other generally recognized pharmacopeia for use in animals, and more particularly in humans. The term "carrier" refers to a diluent, adjuvant (e.g., Freund's adjuvant (complete and incomplete)), excipient, or vehicle with which a therapeutic agent is administered. Such pharmaceutical carriers can be sterile liquids, such as water and oils, including those of petroleum, animal, vegetable or synthetic origin, such as peanut oil, soybean oil, mineral oil, sesame oil and the like. Water is a specific carrier for intravenously administered pharmaceutical compositions. Saline solutions and aqueous dextrose and glycerol solutions can also be employed as liquid carriers, particularly for injectable solutions.

Typical compositions and dosage forms comprise one or more excipients. Suitable excipients are well-known to those skilled in the art of pharmacy, and non limiting examples of suitable excipients include starch, glucose, lactose, sucrose, gelatin, malt, rice, flour, chalk, silica gel, sodium stearate, glycerol monostearate, talc, sodium chloride, dried skim milk, glycerol, propylene, glycol, water, ethanol and the like. Whether a particular excipient is suitable for incorporation into a pharmaceutical composition or dosage form depends on a variety of factors well known in the art including, but not limited to, the way in which the dosage form will be administered to a patient and the specific active ingredients in the dosage form. Further provided herein are anhydrous pharmaceutical compositions and dosage forms comprising one or more compounds of Formula (I) or a form thereof as described herein. The compositions and single unit dosage forms can take the form of solutions or syrups (optionally with a flavoring agent), suspensions (optionally with a flavoring agent), emulsions, tablets (e.g., chewable tablets), pills, capsules, granules, powder (optionally for reconstitution), taste-masked or sustained-release formulations and the like.

Pharmaceutical compositions provided herein that are suitable for oral administration can be presented as discrete dosage forms, such as, but are not limited to, tablets, caplets, capsules, granules, powder, and liquids. Such dosage forms contain predetermined amounts of active ingredients, and may be prepared by methods of pharmacy well known to those skilled in the art.

Examples of excipients that can be used in oral dosage forms provided herein include, but are not limited to, binders, fillers, disintegrants, and lubricants.

Methods of Modulating the Amount of RNA Transcripts Encoded by Certain Genes

In one aspect, provided herein is a method for modulating the amount of one or more RNA transcripts (e.g., pre-mRNA or mRNA transcripts or isoforms thereof) of one or more genes, comprising contacting a compound of Formula (I) or a form thereof with a cell(s). In some embodiments, the RNA transcript(s) is not encoded by the SMN2 gene. In one embodiment, provided herein is a method for modulating the amount of one, two or more RNA transcripts (e.g., pre-mRNA or mRNA transcripts or isoforms thereof) of one, two or more genes in Tables 1-4, 6 and 8-11, infra, comprising contacting a compound of Formula (I) or a form thereof with a cell(s). In another embodiment, provided herein is a method for modulating the amount of one, two or more alternatively spliced variants of a gene in Tables 1-4, 6 and 8-11, infra, comprising contacting a compound of Formula (I) or a form thereof with a cell(s). In certain embodiments, the cell(s) is contacted with a compound of Formula (I) or a form thereof in cell culture. In other embodiments, the cell(s) is contacted with a compound of Formula (I) or a form thereof in a subject, such as a non-human animal or a human.

In another aspect, provided herein is a method for modulating the amount of one or more RNA isoforms encoded by one or more genes, comprising contacting a compound of Formula (I) or a form thereof with a cell(s). In some embodiments, the RNA isoform(s) is not encoded by the SMN2 gene. In one embodiment, provided herein is a method for modulating the amount of one or more RNA isoforms of one or more genes in Tables 1-4, 6 and 8-11, infra, comprising contacting a compound of Formula (I) or a form thereof with a cell(s). In certain embodiments, the cell(s) is contacted with a compound of Formula (I) or a form thereof in cell culture. In other embodiments, the cell(s) is contacted with a compound of Formula (I) or a form thereof in a subject, such as a non-human animal or a human.

In another aspect, provided herein is a method for modulating the amount of one or more protein isoforms encoded by one or more genes, comprising contacting a compound of Formula (I) or a form thereof with a cell(s). In some embodiments, the protein isoform(s) is not encoded by the SMN2 gene. In one embodiment, provided herein is a method for modulating the amount of one or more protein isoforms of one or more genes in Tables 1-4, 6 and 8-11, infra, comprising contacting a compound of Formula (I) or a form thereof with a cell(s). In certain embodiments, the cell(s) is contacted with a compound of Formula (I) or a form thereof in cell culture. In other embodiments, the cell(s) is contacted with a compound of Formula (I) or a form thereof in a subject, such as a non-human animal or a human.

In another aspect, provided herein is a method for modulating the amount of one or more RNA transcripts (e.g., pre-mRNA or mRNA transcripts or isoforms thereof) of one or more genes, comprising culturing a cell(s) in the presence of a compound of Formula (I) or a form thereof. In some embodiments, the RNA transcript(s) is not encoded by the SMN2 gene. In one embodiment, provided herein is a methods for modulating the amount of one, two or more RNA transcripts (e.g., pre-mRNA or mRNA transcripts or isoforms thereof) of one, two or more genes in Tables 1-4, 6 and 8-11, infra, comprising culturing a cell(s) in the presence of a compound of Formula (I) or a form thereof. In another embodiment, provided herein is a method for modulating the amount of one, two or more alternatively spliced variants of a gene in Tables 1-4, 6 and 8-11, infra, comprising culturing a cell(s) in the presence of a compound of Formula (I) or a form thereof.

In another aspect, provided herein is a method for modulating the amount of one or more RNA isoforms encoded by one or more genes, comprising culturing a cell(s) in the presence of a compound of Formula (I) or a form thereof. In some embodiments, the RNA isoform(s) is not encoded by the SMN2 gene. In one embodiment, provided herein is a methods for modulating the amount of one or more RNA isoforms of one or more genes in Tables 1-4, 6 and 8-11, infra, comprising culturing a cell(s) in the presence of a compound of Formula (I) or a form thereof. In certain embodiments, the cell(s) is contacted with a compound of Formula (I) or a form thereof in cell culture. In other embodiments, the cell(s) is contacted with a compound of Formula (I) or a form thereof in a subject, such as a non-human animal or a human.

In another aspect, provided herein is a method for modulating the splicing of one or more RNA transcripts encoded by one or more genes, comprising culturing a cell(s) in the presence of a compound of Formula (I) or a form thereof. In some embodiments, the RNA transcript(s) is not encoded by the SMN2 gene. In one embodiment, provided herein is a method for modulating the amount of one or more RNA transcript splice variants of one or more genes in Tables 1-4, 6 and 8-11, infra, comprising culturing a cell(s) in the presence of a compound of Formula (I) or a form thereof. In certain embodiments, the compound upregulates one, two, or more splice variants encoded by the genes identified in Table 6 as upregulated. In certain embodiments, the compound down-regulates one, two, or more of splice variants encoded by the genes identified in Table 6 as down-regulated. In specific embodiments, the compound upregulates one or more splice variants encoded by a gene in Tables 1-4, 6 and 8-11 and down-regulates a corresponding alternative splice variant(s). In certain embodiments, the cell(s) is contacted with a compound of Formula (I) or a form thereof in cell culture. In other embodiments, the cell(s) is contacted with a compound of Formula (I) or a form thereof in a subject, such as a non-human animal or a human.

In another aspect, provided herein is a method for modulating the amount of one or more protein isoforms encoded by one or more genes, comprising culturing a cell(s) in the presence of a compound of Formula (I) or a form thereof. In some embodiments, the protein isoform(s) is not encoded by the SMN2 gene. In one embodiment, provided herein is a methods for modulating the amount of one or more protein isoforms of one or more genes in Tables 1-4, 6 and 8-11, infra, comprising culturing a cell(s) in the presence of a compound of Formula (I) or a form thereof. In certain embodiments, the cell(s) is contacted with a compound of Formula (I) or a form thereof in cell culture. In other embodiments, the cell(s) is contacted with a compound of Formula (I) or a form thereof in a subject, such as a non-human animal or a human.

In certain embodiments, the cell(s) contacted or cultured with a compound of Formula (I) or a form thereof is primary cell(s) or cell(s) from a cell line. In some embodiments, the cell(s) contacted or cultured with a compound of Formula (I) or a form thereof is a fibroblast(s), an immune cell(s), or a muscle cell(s). In certain embodiments, the cell(s) contacted or cultured with a compound of Formula (I) or a form thereof is associated with aberrant expression of a gene, e.g., a gene in Tables 1-4, 6 and 8-11. In some embodiments, the cell(s) contacted or cultured with a compound of Formula (I) or a form thereof is a cancer cell. Non-limiting examples of cell lines include 293, 3T3, 4T1, 721, 9L, A2780, A172, A20, A253, A431, A-549, ALC, B16, B35, BCP-1, BEAS-2B, bEnd.3, BHK, BR 293, BT20, BT483, BxPC3, C2C12, C3H-10T1/2, C6/36, C6, Cal-27, CHO, COR-L23, COS, COV-434, CML T1, CMT, CRL7030, CT26, D17, DH82, DU145, DuCaP, EL4, EM2, EM3, EMT6, FM3, H1299, H69, HB54, HB55, HCA2, HEK-293, HeLa, Hepa1c1c7, HL-60, HMEC, Hs578T, HsS78Bst, HT-29, HTB2, HUVEC, Jurkat, J558L, JY, K562, Ku812, KCL22, KG1, KYO1, LNCap, Ma-Mel, MC-38, MCF-7, MCF-10A, MDA-MB-231, MDA-MB-468, MDA-MB-435, MDCK, MG63, MOR/0.2R, MONO-MAC6, MRC5, MTD-1A, NCI-H69, NIH-3T3, NALM-1, NSO, NW-145, OPCN, OPCT, PNT-1A, PNT-2, Raji, RBL, RenCa, RIN-5F, RMA, Saos-2, Sf21, Sf9, SiHa, SKBR3, SKOV-3, T2, T-47D, T84, THP1, U373, U87, U937, VCaP, Vero, VERY, W138, WM39, WT-49, X63, YAC-1, or YAR cells. In one embodiment, the cells are from a patient.

In certain embodiments described herein, the cell(s) is contacted or cultured with a compound of Formula (I) or a form thereof with a compound of Formula (I) or a form thereof for a period of 15 minutes, 30 minutes, 45 minutes, 1 hour, 2 hours, 3 hours, 4 hours, 5 hours, 6 hours, 8 hours, 12 hours, 18 hours, 24 hours, 48 hours, 72 hours or more. In other embodiments described herein, the cell(s) is contacted or cultured with a compound of Formula (I) or a form thereof with a compound of Formula (I) or a form thereof for a period of 15 minutes to 1 hour, 1 to 2 hours, 2 to 4 hours, 6 to 12 hours, 12 to 18 hours, 12 to 24 hours, 28 to 24 hours, 24 to 48 hours, 48 to 72 hours.

In certain embodiments described herein, the cell(s) is contacted or cultured with certain concentration of a compound of Formula (I) or a form thereof, wherein the certain concentration is 0.01 µM, 0.05 µM, 1 µM, 2 µM, 5 µM, 10 µM, 15 µM, 20 µM, 25 µM, 50 µM, 75 µM, 100 µM, or 150 µM. In other embodiments described herein, the cell(s) is contacted or cultured with certain concentration of a compound of Formula (I) or a form thereof, wherein the certain concentration is 175 µM, 200 µM, 250 µM, 275 µM, 300 µM, 350 µM, 400 µM, 450 µM, 500 µM, 550 µM 600 µM, 650 µM, 700 µM, 750 µM, 800 µM, 850 µM, 900 µM, 950 µM or 1 mM. In some embodiments described herein, the cell(s) is contacted or cultured with certain concentration of a compound of Formula (I) or a form thereof, wherein the certain concentration is 5 nM, 10 nM, 20 nM, 30 nM, 40 nM, 50 nM, 60 nM, 70 nM, 80 nM, 90 nM, 100 nM, 150 nM, 200 nM, 250 nM, 300 nM, 350 nM, 400 nM, 450 nM, 500 nM, 550 nM, 600 nM, 650 nM, 700 nM, 750 nM, 800 nM, 850 nM, 900 nM, or 950 nM. In certain embodiments described herein, the cell(s) is contacted or cultured with certain concentration of a compound of Formula (I) or a form thereof, wherein the certain concentration is between 0.01 µM to 0.1 µM, 0.1 µM to 1 µM, 1 µM to 50 µM, 50 µM to 100 µM, 100 µM to 500 µM, 500 nM to 1 nM, 1 nM to 10 nM, 10 nM to 50 nM, 50 nM to 100 nM, 100 nM to 500 nM, 500 nM to 1000 nM. In certain embodiments described herein, the cell(s) is contacted or cultured with certain concentration of a compound of Formula (I) or a form thereof that results in a substantial change in the amount of an RNA transcript (e.g., an mRNA transcript), an alternatively spliced variant, or an isoform of a gene in Tables 1-4, 6 and 8-11, infra.

In another aspect, provided herein is a method for modulating the amount of one or more RNA transcripts (e.g., pre-mRNA or mRNA transcripts or isoforms thereof) of one or more genes, comprising administering to a subject (e.g., a non-human animal or a human) a compound of Formula (I) or a form thereof, or a pharmaceutical composition comprising a compound of Formula (I) or a form thereof and a pharmaceutically acceptable carrier, excipient, or diluent. In some embodiments, the RNA transcript(s) is not encoded by the SMN2 gene. In one embodiment, provided herein is a methods for modulating the amount of one, two or more RNA transcripts (e.g., pre-mRNA or mRNA transcripts or isoforms thereof) of one, two or more genes in Tables 1-4, 6 and 8-11, infra, comprising administering to a subject (e.g., a non-human animal or a human) an effective amount compound of Formula (I) or a form thereof, or a pharmaceutical composition comprising an effective amount of a compound of Formula (I) or a form thereof and a pharmaceutically acceptable carrier, excipient, or diluent. In another embodiment, provided herein is a method for modulating the amount of one, two or more alternatively spliced variants of a gene in Tables 1-4, 6 and 8-11, infra, comprising administering to a subject (e.g., a non-human animal or a human) an effective amount compound of Formula (I) or a form thereof, or a pharmaceutical composition comprising an effective amount of a compound of Formula (I) or a form thereof and a pharmaceutically acceptable carrier, excipient, or diluent.

In another aspect, provided herein is a method for modulating the amount of one or more RNA isoforms encoded by one or more genes, comprising administering to a subject (e.g., a non-human animal or a human) a compound of Formula (I) or a form thereof, or a pharmaceutical composition comprising a compound of Formula (I) or a form thereof and a pharmaceutically acceptable carrier, excipient, or diluent. In some embodiments, the RNA isoform(s) is not encoded by the SMN2 gene. In one embodiment, provided herein is a methods for modulating the amount of one, two or more RNA isoforms of one, two or more genes in Tables 1-4, 6 and 8-11, infra, comprising administering to a subject (e.g., a non-human animal or a human) an effective amount compound of Formula (I) or a form thereof, or a pharmaceutical composition comprising an effective amount of a compound of Formula (I) or a form thereof and a pharmaceutically acceptable carrier, excipient, or diluent.

In another aspect, provided herein is a method for modulating the splicing of one or more RNA transcripts encoded by one or more genes, comprising administering to a subject (e.g., a non-human animal or a human) a compound of Formula (I) or a form thereof, or a pharmaceutical composition comprising a compound of Formula (I) or a form thereof and a pharmaceutically acceptable carrier, excipient, or diluent. In some embodiments, the RNA transcript(s) is not encoded by the SMN2 gene. In one embodiment, provided herein is a method for modulating the splicing of one, two or more RNA transcripts of one, two or more genes in Tables 1-4, 6 and 8-11, infra, comprising administering to a subject (e.g., a non-human animal or a human) an effective amount compound of Formula (I) or a form thereof, or a pharmaceutical composition comprising an effective amount of a compound of Formula (I) or a form thereof and a pharmaceutically acceptable carrier, excipient, or diluent. In certain embodiments, the compound upregulates one, two, or more splice variants encoded by the genes identified in Table 6 as upregulated. In certain embodiments, the compound down-regulates one, two, or more of splice variants encoded by the genes identified in Table 6 as down-regulated. In specific embodiments, the compound upregulates one or more splice variants encoded by a gene(s) in Tables 1-4, 6 and 8-11 and down-regulates a corresponding alternative splice variant(s).

In another aspect, provided herein is a method for modulating the amount of one or more protein isoforms encoded by one or more genes, comprising administering to a subject (e.g., a non-human animal or a human) a compound of Formula (I) or a form thereof, or a pharmaceutical composition comprising a compound of Formula (I) or a form thereof and a pharmaceutically acceptable carrier, excipient, or diluent. In some embodiments, the protein isoform(s) is not encoded by the SMN2 gene. In one embodiment, provided herein is a methods for modulating the amount of one, two or more protein isoforms of one, two or more genes in Tables 1-4, 6 and 8-11, infra, comprising administering to a subject (e.g., a non-human animal or a human) an effective amount compound of Formula (I) or a form thereof, or a pharmaceutical composition comprising an effective amount of a compound of Formula (I) or a form thereof and a pharmaceutically acceptable carrier, excipient, or diluent.

In certain embodiments, a compound of Formula (I) or a form thereof contacted or cultured with a cell(s), or administered to a subject is a compound of Formula (II), Formula (III), Formula (IV), Formula (V), Formula (VI), Formula (VII), Formula (VIII), Formula (IX), Formula (X), Formula (XI), Formula (XII), Formula (XIII), or Formula (XIV). In some embodiments, a compound of Formula (I) or a form thereof contacted or cultured with a cell(s), or administered to a subject is a compound described herein.

In certain embodiments, a compound of Formula (I) or a form thereof modulates the transcription of one, two, three or more genes in Tables 1-4, 6 and 8-11, infra. In some embodiments, a compound of Formula (I) or a form thereof modulates the stability of an RNA transcript (e.g., mRNA transcript) of one, two, three or more genes in Tables 1-4, 6 and 8-11, infra. In certain embodiments, a compound of Formula (I) or a form thereof modulates the splicing of an RNA transcript of one, two, three or more genes in Tables 1-4, 6 and 8-11, infra. In certain embodiments, a compound of Formula (I) or a form thereof modulates the transport of an RNA transcript of one, two, three or more genes in Tables 1-4, 6 and 8-11, infra. In certain embodiments, a compound of Formula (I) or a form thereof modulates the sequestration of an RNA transcript of one, two, three or more genes in Tables 1-4, 6 and 8-11, infra. In certain embodiments, a compound of Formula (I) or a form thereof modulates the decay of an RNA transcript of one, two, three or more genes in Tables 1-4, 6 and 8-11, infra. In certain embodiments, a compound of Formula (I) or a form thereof modulates the translation of an RNA transcript of one, two, three or more genes in Tables 1-4, 6 and 8-11, infra.

In certain embodiments, a compound of Formula (I) or a form thereof may perturb the transcription process for a particular gene or multiple genes in Tables 1-4, 6 and 8-11, infra. In certain embodiments, a compound of Formula (I) or a form thereof may perturb the activity of a particular transcription factor that regulates transcription of a gene or multiple genes in Tables 1-4, 6 and 8-11, infra. In other embodiments, a compound of Formula (I) or a form thereof may perturb a component of the pre-mRNA splicing process. In other embodiments, a compound of Formula (I) or a form thereof may perturb interaction(s) between RNA transcript(s) of a gene(s) in Tables 1-4, 6 and 8-11, infra, and a protein(s) that stabilizes the transcript(s). In certain embodiments, a compound of Formula (I) or a form thereof may perturb a protein(s) that stabilizes an mRNA transcript(s) of a gene in Tables 1-4, 6 and 8-11, infra.

Based on the data shown in Table 8, Table 1 shows 263 genes that, in the presence of Compound 774 (3 µM), demonstrate an effect on isoform fold increase having a statistically significant adjusted p value of at least 0.01.

TABLE 1

ABCA1, ABCC1, ABL2, ACACA, ACAT2, AFF2, AHRR, AK021888, AK310472, AKAP1, ANK2, ANKHD1-EIF4EBP3, AP2B1, APAF1, APLP2, ARID1A, ARMCX3, ASAP1, ASPH, ATAD2B, ATF7IP, ATG9A, AXIN1, BACE1, BIN1, BNC1, BRPF1, BZW1, C11orf30, C11orf73, C17orf76-AS1, C4orf27, C6orf48, CAB39, CAMKK1, CCDC88A, CCDC92, CDC25B, CDC42BPA, CDCA7, CDH11, CDH13, CEP68, CFLAR, COPS7B, CREB5, CUL2, CUL4A, CUX1, CYP51A1, DCUN1D4, DDR1, DDX39B, DDX42, DENND1A, DENND5A, DGKA, DHCR24, DHCR7, DIAPH1, DIAPH3, DNM2, DOCK1, EFCAB14, EIF2B3, EPN1, EPT1, ERC1, ETV5, FADS1, FADS2, FAF1, FAM198B, FAM219B, FBXO10, FBXO9, FDFT1, FDPS, FER, FEZ1, FHOD3, FLII, FLNB, FNBP1, FOS, FOSB, FOXM1, FYN, GABPB1, GALC, GAS7, GGCT, GJC1, GPSM2, GRK6, HAS2, HAT1, HLTF, HMGA1, HMGB1, HMGCR, HMGCS1, HMOX1, HP1BP3, HSD17B12, HTT, IDI1, INHBA, INSIG1, KANSL3, KIAA1199, KIAA1524, KIAA1715, KIF3A, KLF6, KRT19, KRT34, KRTAP2-3, LAMA2, LARP7, LDLR, LEMD3, LMAN2L, LRCH4, LRP8, LSS, MAGED4, MAGED4B, MAN1A2, MEDAG, MEF2D, MEMO1, MFGE8, MICAL2, MMAB, MMS19, MMS22L, MSL3, MSMO1, MTAP, MTERFD1, MVD, MVK, NASP, NAV2, NEURL1B, NFE2L1, NID1, NPEPPS, NREP, NRG1, NSUN4, NT5C2, NUP153, P4HA1, PABPC1, PAPD4, PCBP2, PCM1, PCSK9, PDXDC1, PEPD, PHF19, PHF8, PHTF2, PIK3C2B, PITPNB, PLEC, PMS1, POU2F1, PPHLN1, PRKDC, PRSS23, PSMC1, PTPN14, PUF60, PVR, RAB23, RAD23B, RAP1A, RASSF8, RBM10, RCC1, RFWD2, RNFT1, RWDD4, SAMD9L, SART3, SCAF4, SCD, SEC22A, SEC61A1, SERPINE2, SF1, SLC25A17, SLC7A6, SLC7A8, SMN2, SMYD3, SMYD5, SNAP23, SNHG16, SQLE, SQRDL, SQSTM1, SRCAP, SREBF1, STARD4, STAT1, STAU1, STEAP2, STRN3, SYNE1, TACC1, TAF2, TANC2, TARBP1, TBC1D15, TEP1, TFCP2, TGFBRAP1, THADA, TIMP2, TLK1, TMEM154, TNS3, TOMM5, TRAF3, TRAK1, TRAPPC12, TRIM2, TRIM26, TRIM65, TSPAN2, U2SURP, UBAP2L, UBE2V1, UCHL5, UHRF1BP1L, VANGL1, VARS2, VPS13A, VPS29, VWA8, WSB1, XIAP, XRN2, YPEL5, ZAK, ZC3H18, ZFAND5, ZMIZ1, ZMYM2, ZNF219, ZNF227, ZNF24, ZNF37A, ZNF37BP, ZNF395, ZNF652, ZNF674, ZNF74 and ZNF778

Based on the data shown in Table 9, Table 2 shows 234 genes that, in the presence of Compound 774 (0.3 µM), demonstrate an effect on isoform fold increase having a statistically significant adjusted p value of at least 0.01.

TABLE 2

ABCC1, ACADVL, ADAM15, AGPAT3, AHRR, AJUBA, AKAP1, AKAP9, ALCAM, ALDH4A1, ANKFY1, AP2B1, APLP2, APP, ARID1A, ARID2, ASPH, ATMIN, BASP1, BC033281, BCAR3, C11orf73, C17orf76-AS1, C5orf24, C6orf48, CAB39, CASP8AP2, CAV1, CCAR1, CCT6A, CD276, CD46, CDC25B, CDK16, CEP68, CHD8, CLIC1, COL12A1, CPEB2, CREB5, CRLS1, CRTAP, CTNND1, CUX1, CYBRD1, DACT1, DCAF10, DCAF11, DDHD2, DDX39B, DIAPH3, DKK3, DLC1, DSTN, EBF1, EGR1, EIF4G1, EIF4G3, ENG, ERC1, ETV5, FAM198B, FAM219A, FAM3C, FEZ1, FGD5-AS1, FLII, FN1, FNBP1, FOS, FOSB, FOXK1, FOXM1, FYN, GABPB1, GALC, GALNT1, GBA2, GGCT, GHDC, GMIP, GNA13, GNAS, GNL3L, GOLGA2, GORASP1, GREM1, GSE1, HAUS6, HDAC7, HEG1, HLA-A, HLA-E, HMGA1, HP1BP3, IL6ST, ITGAV, KIAA1549, KIF14, KLC1, KLF6, KLHL7, KRT18, LAMA2, LAMB1, LARP7, LATS2, LGALS8, LIMS1, LINC00341, LONP1, LOX, MDM2, MEPCE, MINPP1, MLLT4, MPPE1, MRPL3, MSH2, MSH6, MSL3, MTMR9, MTRR, MUM1, MYADM, MYLK, NADK, NAV2, NCSTN, NFE2L1, NID1, NIPA1, NPEPPS, NRD1, NUDT4, NUSAP1, P4HB, PABPC1, PAK4, PAPD4, PCNXL2, PDE4A, PDXDC1, PHRF1, PHTF2, PI4K2A, PIK3C2B, PLAU, PLEKHB2, PLSCR3, PLXNB2, POSTN, POU2F1, PPARA, PPP1R12A, PRKACB, PSMD6, PTPN14, PUS7, QKI, RAB34, RAD1, RAD23B, RASSF8, RBCK1,

TABLE 2-continued

RBFOX2, RFTN1, RNF19A, RNF38, RPS6KC1, RWDD4, SEC14L1, SEC24B, SERPINE2, SF1, SLC39A3, SLC41A1, SLC4A4, SLC7A6, SMARCA4, SMN2, SNHG16, SNX14, SON, SPRED2, STAU1, STEAP2, STRIP1, STRN3, TBL2, TGFBI, TGFBR1, THAP4, TLE3, TMEM47, TNKS1BP1, TOMM40, TOPORS, TRAK1, TRAPPC12, TRIB1, TRIM2, TRIM23, TRIM65, TRMT1L, TRPS1, TXNL1, TXNRD1, U2SURP, UBE2G2, UBE2V1, UHMK1, USP7, VP529, VWA8, WDR19, WDR37, WIPF1, YPEL5, YTHDF3, Z24749, ZBTB10, ZBTB7A, ZFAND5, ZMIZ1, ZNF12, ZNF148, ZNF335, ZNF395, ZNF583, ZNF621, ZNF655, ZNF74 and ZNF780A Based on the data shown in Table 10, Table 3 shows 384 genes that, in the presence of Compound 808 (3 µM), demonstrate an effect on isoform fold increase having a statistically significant adjusted p value of at least 0.01.

TABLE 3

ABCB7, ABHD10, ABLIM3, ACACA, ADAM12, ADAM17, ADAM33, AGK, AGPS, AHCYL2, AHDC1, AHRR, AK021888, AK310472, AKAP1, AKAP9, AKNA, AMPD2, ANKRD17, ANKS6, ANP32A, ANXA11, ANXA6, APLP2, APP, APPL2, APTX, ARHGAP22, ARMCX3, ASAP1, ASNS, ASPH, ATG9A, ATP2C1, AURKA, AXIN1, B4GALT2, BACE1, BASP1, BEND6, BICD1, BIN1, BRD2, BRPF1, BTBD10, C11orf30, C11orf73, C17orf76-AS1, C4orf27, C6orf48, CAB39, CAPNS1, CASC3, CCDC77, CCDC88A, CD46, CDC40, CDC42BPA, CDCA7, CDH13, CDK11B, CEP68, CIZ1, CLK4, CNOT1, COG1, COL12A1, COL1A1, COL6A1, COPS7B, CSDE1, CSNK1A1, CUX1, CYB5B, CYBRD1, DAB2, DARS, DCBLD2, DCUN1D4, DDAH2, DDR1, DDX39B, DDX42, DENND1A, DENND1B, DENND5A, DGKA, DHFR, DHX9, DIAPH1, DIAPH3, DIS3L, DNM2, DOCK1, DPP8, DSEL, EEA1, EFCAB14, EIF2B3, EIF4G1, EIF4G3, ELF2, ENG, ENPP2, EPN1, EXTL2, EYA3, FAF1, FAM198B, FAM3C, FBXO10, FBXO18, FBXO31, FBXO9, FER, FEZ1, FHOD3, FLII, FN1, FNBP1, FOCAD, FOSL1, FOXM1, GABPB1, GALC, GALNT1, GCFC2, GGCT, GIGYF2, GMIP, GNAS, GNL3L, GOLGB1, GPR89A, GPSM2, GREM1, GRK6, GTF2H2B, HAT1, HAUS3, HEG1, HLA-A, HLTF, HP1BP3, HRH1, HSD17B12, HSD17B4, HTT, IARS, IDH1, IGF2BP2, ITM2C, KCNK2, KIAA1033, KIAA1143, KIAA1522, KIAA1524, KIAA1715, KIF3A, KLHL7, LAMA2, LARP4, LARP7, LATS2, LIMS1, LINC00341, LINC00657, LMAN2L, LMO7, LRCH4, LRIG1, LRRC8A, LTBR, LUC7L2, LZTS2, MADD, MAGED4B, MAN1A2, MAP4K4, MED1, MEDAG, MEF2D, MEIS2, MEMO1, MICAL2, MKLN1, MLLT4, MMS19, MPZL1, MSANTD3, MSC, MSL3, MTAP, MTERFD1, MTHFD1L, MYADM, MYLK, MYO9B, MYOF, NASP, NAV2, NCOA3, NCOA4, NELFA, NEO1, NEURL1B, NF2, NID2, NOL10, NPEPPS, NRG1, NSUN4, NT5C2, NT5E, NTNG1, NUP153, NUP35, NUP50, NUSAP1, ODF2, OS9, OSBPL6, P4HA1, P4HB, PABPC1, PAPD4, PARN, PARP4, PCBP2, PCBP4, PCDHGB3, PCGF3, PCM1, PCMTD2, PDE7A, PDXDC1, PEPD, PFKP, PHF19, PHRF1, PHTF2, PIEZO1, PIGU, PITPNA, PITPNB, PITPNM1, PLAU, PLSCR3, PLXNC1, PMS1, POU2F1, PPAPDC1A, PPHLN1, PPIP5K1, PPP1R12A, PRKDC, PRMT1, PRSS23, PSMA4, PTK2B, PUF60, PVR, RAB23, RAB2B, RAD1, RAD23B, RAP1A, RAP1GDS1, RARG, RASSF8, RBCK1, RCC1, RFWD2, RGS3, RNF14, RNFT1, RPL10, RRBP1, RWDD4, SAR1A, SCAF4, SCAF8, SCLT1, SCO1, SDCBP, SEC22A, 9-Sep, SF1, SGOL2, SLC25A17, SLC4A4, SLC7A6, SMARCC2, SMC4, SMC6, SMCHD1, SMN2, SMPD4, SMYD3, SNAP23, SNHG16, SOCS2, SOS2, SPATA20, SPATS2, SPG20, SQRDL, SREBF1, SREK1, SRSF3, STAT1, STAU1, STEAP2, STRN3, STX16, SUPT20H, SYNE1, SYNE2, SYT15, SYTL2, TAF2, TARBP1, TARS, TBL2, TCF7L2, TENC1, TENM2, TEP1, TET3, TGFBR1, THADA, THRB, TJP2, TLE3, TMEM47, TMEM63A, TNFAIP3, TNIP1, TNPO3, TNS1, TNS3, TOE1, TOMM5, TP53INP1, TRAF3, TRAPPC12, TRIM2, TRIM23, TRIM65, TSC2, TSPAN2, TUBB2C, TXNRD1, UBAP2L, UBE2V1, UCHL5, USP19, VANGL1, VIPAS39, VPS29, VPS51, VWA8, WDR48, WNT5B, WSB1, WWTR1, XRN2, YAP1, YES1, YPEL5, YTHDF3, Z24749, ZBTB24, ZC3H14, ZFAND1, ZFAND5, ZHX3, ZMIZ1, ZMYM2, ZNF219, ZNF268, ZNF395, ZNF827 and ZNF91

Based on the data shown in Table 11, Table 4 shows 219 genes that, in the presence of Compound 808 (0.3 µM), demonstrate an effect on isoform fold increase having a statistically significant adjusted p value of at least 0.01.

TABLE 4

ACACA, ACADVL, AFF2, AHCYL2, AHRR, AKAP1, ALDH4A1, ANKRD17, AP2B1, APLP2, ASL, ASPH, ATG9A, ATMIN, ATXN3, BAG2, BASP1, BRPF1, BSCL2, C11orf30, C11orf73, C17orf76-AS1, C6orf48, C9orf69, CAB39, CALU, CDC25B, CDC42BPA, CDKAL1, CLIC1, COL12A1, COL1A1, COL6A1, CSNK1A1, CTDSP2, CUL2, CUL4A, DAXX, DCAF10, DDAH1, DDR1, DDX39B, DENND1A, DGCR2, DKFZp434M1735, DKK3, DNM2, DST, EEF1A1, EFCAB14, EHMT2, EIF4G1, EIF4G2, EIF4G3, ENSA, EXO1, FAM111A, FAM198B, FAM65A, FBXO34, FEZ1, FGD5-AS1, FGFRL1, FLII, FN1, FOXK1, FOXM1, FUS, GALC, GALNT1, GAS7, GCFC2, GGCT, GJC1, GNA13, GNL3L, GOLGA4, GPR1, GREM1, HEG1, HLA-A, HLA-E, HLTF, TABLE 4-continued HNRNPR, HNRNPUL1, IQCE, ITGB5, ITSN1, KIAA1033, KIF2A, KIF3A, KLC2, LATS2,
LIMS1, LINC00341, LINC00657, LONP1, LOX, LUC7L2, MBD1, MBOAT7, MEF2D,
MEIS2, MICAL2, MKL1, MKNK2, MLST8, MPPE1, MSL3, MSRB3, MTRR, MYADM,
MYLK, MYO1D, NAA35, NAV1, NAV2, NCOA1, NFX1, NKX3-1, NOMO3, NRG1,
NUDT4, NUPL1, NUSAP1, OSMR, P4HA1, P4HB, PAPD4, PARD3, PARN, PARP14,
PARVB, PCBP2, PCBP4, PCGF3, PDLIM7, PDXDC1, PEX5, PFKP, PHRF1, PI4K2A,
POLE3, POLR3D, POSTN, PPARA, PPP6R1, PPP6R2, PRNP, PXN, RAB34, RAD23B,
RALB, RAP1A, RASSF8, RBCK1, RBFOX2, RGS10, RIF1, RNF14, RNF19A, SAMD9,
SCAF4, SDCBP, SERPINE2, SF1, SH3RF1, SKIL, SLC25A17, SLC4A4, SMG1, SMN2,
SNHG16, SREBF1, STAT3, STC2, STEAP2, STRN3, SYNE1, SYNE2, TACC1, TARS,
TGFBI, TMEM47, TNC, TNFRSF12A, TNS1, TRAF3, TRIM28, TSC2, TSHZ1, TTC7A,
TUBB2C, TUBB3, TXNL1, TXNRD1, UBE2G2, UBE2V1, UBQLN4, UNC5B, USP19,
VARS2, VCL, VPS29, WDR37, WIPF1, WWTR1, ZC3H12C, ZCCHC11, ZEB1, ZEB2,
ZFAND1, ZFAND5, ZMIZ1, ZNF28, ZNF281, ZNF655, ZNF764 and ZNF839

Methods of Preventing and/or Treating Diseases

In one aspect, presented herein are methods for preventing and/or treating a disease by modulating the amount of one or more RNA transcripts of one or more genes (e.g., a gene(s) in Tables 1-4, 6 and 8-11, supra), comprising administering to a patient in need thereof a compound of Formula (I) or a form thereof. In some embodiments, the RNA transcript(s) is not encoded by the SMN2 gene. In one embodiment, provided herein is a method for preventing and/or treating a disease by modulating the amount of one or more RNA transcripts of a gene(s) in Tables 1-4, 6 and 8-11, supra, comprising administering to a patient in need thereof an effective amount of a compound of Formula (I) or a form thereof, or a pharmaceutical composition comprising an effective amount of a compound of Formula (I) or a form thereof and a pharmaceutically acceptable carrier, excipient or diluent.

In another aspect, presented herein are methods for preventing and/or treating a disease in which there is aberrant expression of an RNA transcript (e.g., an mRNA transcript) of a gene(s) (e.g., a gene in Tables 1-4, 6 and 8-11, supra), comprising administering to a patient in need thereof a compound of Formula (I) or a form thereof. In some embodiments, the RNA transcript(s) is not encoded by the SMN2 gene. In one embodiment, presented herein is a method for preventing and/or treating a disease in which there is aberrant expression of an RNA transcript (e.g., an mRNA transcript) of a gene(s) (e.g., a gene in Tables 1-4, 6 and 8-11, supra), comprising administering to a patient in need thereof an effective amount of a compound of Formula (I) or a form thereof.

In another aspect, presented herein are methods for preventing and/or treating a disease which is associated with aberrant amount of an RNA transcript (e.g., an mRNA transcript) of a gene(s) (e.g., a gene in Tables 1-4, 6 and 8-11, supra), comprising administering to a patient in need thereof a compound of Formula (I) or a form thereof. In some embodiments, the RNA transcript(s) is not encoded by the SMN2 gene. In one embodiment, presented herein is a method for preventing and/or treating a disease which is associated with an aberrant amount of an RNA transcript (e.g., an mRNA transcript) of a gene(s) (e.g., a gene in Tables 1-4, 6 and 8-11, supra), comprising administering to a patient in need thereof an effective amount of a compound of Formula (I) or a form thereof.

In another aspect, presented herein are methods for preventing and/or treating a disease which is associated with a change in the amount of an RNA transcript (e.g., an mRNA transcript) of a gene(s) (e.g., a gene in Tables 1-4, 6 and 8-11, supra) is beneficial to the prevention and/or treatment of the disease, comprising administering to a patient in need thereof a compound of Formula (I) or a form thereof. In some embodiments, the RNA transcript(s) is not encoded by the SMN2 gene. In one embodiment, provided herein is a method for preventing and/or treating a disease which is associated with an increase in the amount of an RNA transcript (e.g., an mRNA transcript) of a gene(s) in Tables 1-4, 6 and 8-11, supra, is beneficial to the prevention and/or treatment of the disease, comprising administering to a patient in need thereof an effective amount of a compound of Formula (I) or a form thereof, or a pharmaceutical composition comprising an effective amount of a compound of Formula (I) or a form thereof and a pharmaceutically acceptable carrier, excipient or diluent. In another embodiment, provided herein is a method for preventing and/or treating a disease in which an decrease in the amount of an RNA transcript (e.g., an mRNA transcript) of a gene(s) in Tables 1-4, 6 and 8-11, supra, is beneficial to the prevention and/or treatment of the disease, comprising administering to a patient in need thereof an effective amount of a compound of Formula (I) or a form thereof, or a pharmaceutical composition comprising an effective amount of a compound of Formula (I) or a form thereof and a pharmaceutically acceptable carrier, excipient or diluent.

In another aspect, presented herein are methods for preventing and/or treating a disease in which a change in the amount of a splice variant of an RNA transcript (e.g., an mRNA transcript) of a gene(s) (e.g., a gene in Tables 1-4, 6 and 8-11, supra) is beneficial to the prevention and/or treatment of the disease, comprising administering to a patient in need thereof a compound of Formula (I) or a form thereof. In some embodiments, the splice variant(s) is not encoded by the SMN2 gene. In one embodiment, provided herein is a method for preventing and/or treating a disease in which an increase in the amount of a splice variant of an RNA transcript (e.g., an mRNA transcript) of a gene(s) in Tables 1-4, 6 and 8-11, supra, is beneficial to the prevention and/or treatment of the disease, comprising administering to a patient in need thereof an effective amount of a compound of Formula (I) or a form thereof, or a pharmaceutical composition comprising an effective amount of a compound of Formula (I) or a form thereof and a pharmaceutically acceptable carrier, excipient or diluent. In another embodiment, provided herein is a method for preventing and/or treating a disease in which an decrease in the amount of a splice variant of an RNA transcript (e.g., an mRNA transcript) of a gene(s) in Tables 1-4, 6 and 8-11, supra, is beneficial to the prevention and/or treatment of the disease, comprising administering to a patient in need thereof an effective amount of a compound of Formula (I) or a form thereof, or a pharmaceutical composition comprising an effective amount of a compound of Formula (I) or a form thereof and a pharmaceutically acceptable carrier, excipient or diluent.

In another aspect, presented herein are methods for preventing and/or treating a disease in which a change in the amount of an alternative splice variant of an RNA transcript (e.g., an mRNA transcript) of a gene(s) (e.g., a gene in Tables 1-4, 6 and 8-11, supra) is beneficial to the prevention and/or treatment of the disease, comprising administering to a patient in need thereof a compound of Formula (I) or a form thereof. In some embodiments, the splice variant(s) is not encoded by the SMN2 gene. In one embodiment, provided herein is a method for preventing and/or treating a disease in which an increase in the amount of an alternative splice variant of an RNA transcript (e.g., an mRNA transcript) of a gene(s) in Tables 1-4, 6 and 8-11, supra, is beneficial to the prevention and/or treatment of the disease, comprising administering to a patient in need thereof an effective amount of a compound of Formula (I) or a form thereof, or a pharmaceutical composition comprising an effective amount of a compound of Formula (I) or a form thereof and a pharmaceutically acceptable carrier, excipient or diluent. In another embodiment, provided herein is a method for preventing and/or treating a disease in which an decrease in the amount of an alternative splice variant of an RNA transcript (e.g., an mRNA transcript) of a gene(s) in Tables 1-4, 6 and 8-11, supra, is beneficial to the prevention and/or treatment of the disease, comprising administering to a patient in need thereof an effective amount of a compound of Formula (I) or a form thereof, or a pharmaceutical composition comprising an effective amount of a compound of Formula (I) or a form thereof and a pharmaceutically acceptable carrier, excipient or diluent.

In another aspect, presented herein are methods for preventing and/or treating a disease in which a change in the level of expression of one, two, three or more RNA isoforms of a gene(s) (e.g., a gene in Tables 1-4, 6 and 8-11, supra), is beneficial to the prevention and/or treatment of the disease, comprising administering to a patient in need thereof a compound of Formula (I) or a form thereof. In some embodiments, the RNA isoform(s) is not encoded by the SMN2 gene. In one embodiment, provided herein is a method for preventing and/or treating a disease in which an increase in the level of expression of one, two, three or more RNA isoforms of a gene(s) in Tables 1-4, 6 and 8-11, supra, is beneficial to the prevention and/or treatment of the disease, comprising administering to a patient in need thereof an effective amount of a compound of Formula (I) or a form thereof, or a pharmaceutical composition comprising an effective amount of a compound of Formula (I) or a form thereof and a pharmaceutically acceptable carrier, excipient or diluent. In another embodiment, provided herein is a method for preventing and/or treating a disease in which an decrease in the level of expression of one, two, three or more RNA isoforms of a gene(s) in Tables 1-4, 6 and 8-11, supra, is beneficial to the prevention and/or treatment of the disease, comprising administering to a patient in need thereof an effective amount of a compound of Formula (I) or a form thereof, or a pharmaceutical composition comprising an effective amount of a compound of Formula (I) or a form thereof and a pharmaceutically acceptable carrier, excipient or diluent.

In another aspect, presented herein are methods for preventing and/or treating a disease in which a change in the level of expression of one, two, three or more protein isoforms of a gene(s) (e.g., a gene in Tables 1-4, 6 and 8-11, supra), is beneficial to the prevention and/or treatment of the disease, comprising administering to a patient in need thereof a compound of Formula (I) or a form thereof. In some embodiments, the protein isoform(s) is not encoded by the SMN2 gene. In one embodiment, provided herein is a method for preventing and/or treating a disease in which an increase in the level of expression of one, two, three or more protein isoforms of a gene(s) in Tables 1-4, 6 and 8-11, supra, is beneficial to the prevention and/or treatment of the disease, comprising administering to a patient in need thereof an effective amount of a compound of Formula (I) or a form thereof, or a pharmaceutical composition comprising an effective amount of a compound of Formula (I) or a form thereof and a pharmaceutically acceptable carrier, excipient or diluent. In another embodiment, provided herein is a method for preventing and/or treating a disease in which an decrease in the level of expression of one, two, three or more protein isoforms of a gene(s) in Tables 1-4, 6 and 8-11, supra, is beneficial to the prevention and/or treatment of the disease, comprising administering to a patient in need thereof an effective amount of a compound of Formula (I) or a form thereof, or a pharmaceutical composition comprising an effective amount of a compound of Formula (I) or a form thereof and a pharmaceutically acceptable carrier, excipient or diluent.

In some embodiments, the compound of Formula (I) or a form thereof that is administered to a subject is a compound of Formula (II), Formula (III), Formula (IV), Formula (V), Formula (VI), Formula (VII), Formula (VIII), Formula (IX), Formula (X), Formula (XI), Formula (XII), Formula (XIII), or Formula (XIV). In some embodiments, the compound of Formula (I) or a form thereof that is administered to a subject is a compound described herein.

In certain embodiments, a compound of Formula (I) or a form thereof modulates the transcription of one, two, three or more genes in Tables 1-4, 6 and 8-11, infra. In some embodiments, a compound of Formula (I) or a form thereof modulates the stability of an RNA transcript (e.g., mRNA transcript) of one, two, three or more genes in Tables 1-4, 6 and 8-11, infra. In certain embodiments, a compound of Formula (I) or a form thereof modulates the splicing of an RNA transcript of one, two, three or more genes in Tables 1-4, 6 and 8-11, infra.

In a specific embodiment, the methods for preventing a disease described herein prevent the onset or development of one or symptoms of the disease. In another embodiment, the methods for preventing a disease described herein prevent the recurrence of the disease or delays the recurrence of the disease. In another embodiment, the methods for treating a disease described herein has one, two or more of the effects: (i) reduce or ameliorates the severity of the disease; (ii) inhibit the progression of the disease; (iii) reduce hospitalization of a subject; (iv) reduce hospitalization length for a subject; (v) increase the survival of a subject; (vi) improve the quality of life of a subject; (vii) reduce the number of symptoms associated with the disease; (viii) reduce or ameliorates the severity of a symptom(s) associated with the disease; (ix) reduce the duration of a symptom(s) associated with the disease; (x) prevent the recurrence of a symptom associated with the disease; (xi) inhibit the development or onset of a symptom of the disease; and/or (xii) inhibit of the progression of a symptom associated with the disease.

In certain embodiments, the disease or disorder prevented and/or treated in accordance with a method described herein is a disease or disorder associated with a gene listed in Tables 1-4, 6 and 8-11. In specific embodiments, the disease or disorder prevented and/or treated in accordance with a method described herein is leukemia, acute myeloid leukemia, colon cancer, gastric cancer, macular degeneration, acute monocytic leukemia, breast cancer, combined methylmalonic aciduria and homocystinuria, cblC type, hepatocellular carcinoma, cone-rod dystrophy, alveolar soft part sarcoma, myeloma, skin melanoma, prostatitis, pancreatitis, pancreatic cancer, retinitis, adenocarcinoma, adenoiditis, adenoid cystic carcinoma, cataract, retinal degeneration, gastrointestinal stromal tumor, Wegener's granulomatosis, sarcoma, myopathy, prostate adenocarcinoma, Alzheimer's disease, hyperprolinemia, acne, tuberculosis, succinic semialdehyde dehydrogenase deficiency, esophagitis, mental retardation, esophageal adenocarcinoma, glycine encephalopathy, Crohn's disease, spina *bifida*, tuberculosis, autosomal recessive disease, schizophrenia, neural tube defects, lung cancer, myelodysplastic syndromes, amyotropic lateral sclerosis, neuronitis, germ cell tumors, Parkinson's disease, talipes equinovarus, dystrophinopathies, Hodgkin's lymphoma, ovarian cancer, non-Hodgkin's lymphoma, multiple myeloma, chronic myeloid leukemia, ischemia, acute lymphoblastic leukemia, renal cell carcinoma, transitional cell carcinoma, colorectal cancer, chronic lymphocytic leukemia, anaplastic large cell lymphoma, kidney cancer, cerebritis, bladder related disorders, breast cancer, cervical cancer, cleft lip, cleft palate, cervicitis, spasticity, lipoma, scleroderma, Gitelman syndrome, poliomyelitis, paralysis, Aagenaes syndrome, or oculomotor nerve paralysis. In specific embodiments, the disease or disorder prevented and/or treated in accordance with a method described herein is basal cell carcinoma, goblet cell metaplasia, or a malignant glioma. In other specific embodiments, the disease or disorder prevented and/or treated in accordance with a method described herein is a cancer of the liver, breast, lung, prostate, cervix, uterus, colon, pancreas, kidney, stomach, bladder, ovary, or brain.

In certain embodiments, the disease prevented and/or treated in accordance with a method described herein is cancer amenable to treatment by upregulation or downregulation of a gene or isoform thereof as described herein. In specific embodiments, cancers that can be prevented and/or treated in accordance with a method described herein include, but are not limited to, cancer of the head, neck, eye, mouth, throat, esophagus, esophagus, chest, bone, lung, kidney, colon, rectum or other gastrointestinal tract organs, stomach, spleen, skeletal muscle, subcutaneous tissue, prostate, breast, ovaries, testicles or other reproductive organs, skin, thyroid, blood, lymph nodes, kidney, liver, pancreas, and brain or central nervous system.

Specific examples of cancers that can be prevented and/or treated in accordance with the methods provided herein include, but are not limited to, the following: renal cancer, kidney cancer, glioblastoma multiforme, metastatic breast cancer; breast carcinoma; breast sarcoma; neurofibroma; neurofibromatosis; pediatric tumors; neuroblastoma; malignant melanoma; carcinomas of the epidermis; leukemias such as but not limited to, acute leukemia, acute lymphocytic leukemia, acute myelocytic leukemias such as myeloblastic, promyelocytic, myelomonocytic, monocytic, erythroleukemia leukemias and myclodysplastic syndrome, chronic leukemias such as but not limited to, chronic myclocytic (granulocytic) leukemia, chronic lymphocytic leukemia, hairy cell leukemia; polycythemia vera; lymphomas such as but not limited to Hodgkin's disease, non-Hodgkin's disease; multiple myelomas such as but not limited to smoldering multiple myeloma, nonsecretory myeloma, osteosclerotic myeloma, plasma cell leukemia, solitary plasmacytoma and extramedullary plasmacytoma; Waldenstrom's macroglobulinemia; monoclonal gammopathy of undetermined significance; benign monoclonal gammopathy; heavy chain disease; bone cancer and connective tissue sarcomas such as but not limited to bone sarcoma, myeloma bone disease, multiple myeloma, cholesteatoma-induced bone osteosarcoma, Paget's disease of bone, osteosarcoma, chondrosarcoma, Ewing's sarcoma, malignant giant cell tumor, fibrosarcoma of bone, chordoma, periosteal sarcoma, soft-tissue sarcomas, angiosarcoma (hemangiosarcoma), fibrosarcoma, Kaposi's sarcoma, leiomyosarcoma, liposarcoma, lymphangiosarcoma, neurilemmoma, rhabdomyosarcoma, and synovial sarcoma; brain tumors such as but not limited to, glioma, astrocytoma, brain stem glioma, ependymoma, oligodendroglioma, nonglial tumor, acoustic neurinoma, craniopharyngioma, medulloblastoma, meningioma, pineocytoma, pineoblastoma, and primary brain lymphoma; breast cancer including but not limited to adenocarcinoma, lobular (small cell) carcinoma, intraductal carcinoma, medullary breast cancer, mucinous breast cancer, tubular breast cancer, papillary breast cancer, Paget's disease (including juvenile Paget's disease) and inflammatory breast cancer; adrenal cancer such as but not limited to pheochromocytom and adrenocortical carcinoma; thyroid cancer such as but not limited to papillary or follicular thyroid cancer, medullary thyroid cancer and anaplastic thyroid cancer; pancreatic cancer such as but not limited to, insulinoma, gastrinoma, glucagonoma, vipoma, somatostatin-secreting tumor, and carcinoid or islet cell tumor; pituitary cancers such as but limited to Cushing's disease, prolactin-secreting tumor, acromegaly, and diabetes insipius; eye cancers such as but not limited to ocular melanoma such as iris melanoma, choroidal melanoma, and cilliary body melanoma, and retinoblastoma; vaginal cancers such as squamous cell carcinoma, adenocarcinoma, and melanoma; vulvar cancer such as squamous cell carcinoma, melanoma, adenocarcinoma, basal cell carcinoma, sarcoma, and Paget's disease; cervical cancers such as but not limited to, squamous cell carcinoma, and adenocarcinoma; uterine cancers such as but not limited to endometrial carcinoma and uterine sarcoma; ovarian cancers such as but not limited to, ovarian epithelial carcinoma, borderline tumor, germ cell tumor, and stromal tumor; cervical carcinoma; esophageal cancers such as but not limited to, squamous cancer, adenocarcinoma, adenoid cyctic carcinoma, mucoepidermoid carcinoma, adenosquamous carcinoma, sarcoma, melanoma, plasmacytoma, verrucous carcinoma, and oat cell (small cell) carcinoma; stomach cancers such as but not limited to, adenocarcinoma, fungating (polypoid), ulcerating, superficial spreading, diffusely spreading, malignant lymphoma, liposarcoma, fibrosarcoma, and carcinosarcoma; colon cancers; KRAS-mutated colorectal cancer; colon carcinoma; rectal cancers; liver cancers such as but not limited to hepatocellular carcinoma and hepatoblastoma, gallbladder cancers such as adenocarcinoma; cholangiocarcinomas such as but not limited to pappillary, nodular, and diffuse; lung cancers such as KRAS-mutated non-small cell lung cancer, non-small cell lung cancer, squamous cell carcinoma (epidermoid carcinoma), adenocarcinoma, large-cell carcinoma and small-cell lung cancer; lung carcinoma; testicular cancers such as but not limited to germinal tumor, seminoma, anaplastic, classic (typical), spermatocytic, nonseminoma, embryonal carcinoma, teratoma carcinoma, choriocarcinoma (yolk-sac tumor), prostate cancers such as but not limited to, androgen-independent prostate cancer, androgen-dependent prostate cancer, adenocarcinoma, leiomyosarcoma, and rhabdomyosarcoma; penal cancers; oral cancers such as but not limited to squamous cell carcinoma; basal cancers; salivary gland cancers such as but not limited to adenocarcinoma, mucoepidermoid carcinoma, and adenoid-cystic carcinoma; pharynx cancers such as but not limited to squamous cell cancer, and verrucous; skin cancers such as but not limited to, basal cell carcinoma, squamous cell carcinoma and melanoma, superficial spreading melanoma, nodular melanoma, lentigo malignant melanoma, acral lentiginous melanoma; kidney cancers such as but not limited to renal cell cancer, adenocarcinoma, hypernephroma, fibrosarcoma, transitional cell cancer (renal pelvis and/or uterer); renal carcinoma; Wilms' tumor; bladder cancers such as but not limited to transitional cell carcinoma, squamous cell cancer, adenocarcinoma, carcinosarcoma. In addition, cancers include myxosarcoma, osteogenic sarcoma, endotheliosarcoma, lymphangioendotheliosarcoma, mesotheliorna, synovioma, hemangioblastoma, epithelial carcinoma, cystadenocarcinoma, bronchogenic carcinoma, sweat gland carcinoma, sebaceous gland carcinoma, papillary carcinoma and papillary adenocarcinomas.

In certain embodiments cancers that can be prevented and/or treated in accordance with the methods provided herein include, the following: pediatric solid tumor, Ewing's sarcoma, Wilms tumor, neuroblastoma, neurofibroma, carcinoma of the epidermis, malignant melanoma, cervical carcinoma, colon carcinoma, lung carcinoma, renal carcinoma, breast carcinoma, breast sarcoma, metastatic breast cancer, HIV-related Kaposi's sarcoma, prostate cancer, androgen-independent prostate cancer, androgen-dependent prostate cancer, neurofibromatosis, lung cancer, non-small cell lung cancer, KRAS-mutated non-small cell lung cancer, malignant melanoma, melanoma, colon cancer, KRAS-mutated colorectal cancer, glioblastoma multiforme, renal cancer, kidney cancer, bladder cancer, ovarian cancer, hepatocellular carcinoma, thyroid carcinoma, rhabdomyosarcoma, acute myeloid leukemia, and multiple myeloma.

In certain embodiments, cancers and conditions associated therewith that are prevented and/or treated in accordance with the methods provided herein are breast carcinomas, lung carcinomas, gastric carcinomas, esophageal carcinomas, colorectal carcinomas, liver carcinomas, ovarian carcinomas, thecomas, arrhenoblastomas, cervical carcinomas, endometrial carcinoma, endometrial hyperplasia, endometriosis, fibrosarcomas, choriocarcinoma, head and neck cancer, nasopharyngeal carcinoma, laryngeal carcinomas, hepatoblastoma, Kaposi's sarcoma, melanoma, skin carcinomas, hemangioma, cavernous hemangioma, hemangioblastoma, pancreas carcinomas, retinoblastoma, astrocytoma, glioblastoma, Schwannoma, oligodendroglioma, medulloblastoma, neuroblastomas, rhabdomyosarcoma, osteogenic sarcoma, leiomyosarcomas, urinary tract carcinomas, thyroid carcinomas, Wilm's tumor, renal cell carcinoma, prostate carcinoma, abnormal vascular proliferation associated with phakomatoses, edema (such as that associated with brain tumors), or Meigs' syndrome. In specific embodiment, the cancer an astrocytoma, an oligodendroglioma, a mixture of oligodendroglioma and an astrocytoma elements, an ependymoma, a meningioma, a pituitary adenoma, a primitive neuroectodermal tumor, a medullblastoma, a primary central nervous system (CNS) lymphoma, or a CNS germ cell tumor. In specific embodiments, the cancer treated in accordance with the methods provided herein is an acoustic neuroma, an anaplastic astrocytoma, a glioblastoma multiforme, or a meningioma. In other specific embodiments, the cancer treated in accordance with the methods provided herein is a brain stem glioma, a craniopharyngioma, an ependymoma, a juvenile pilocytic astrocytoma, a medulloblastoma, an optic nerve glioma, primitive neuroectodermal tumor, or a rhabdoid tumor.

Specific examples of conditions that can be prevented and/or treated in accordance with the methods described herein include cystic fibrosis, muscular dystrophy, polycystic autosomal-dominant kidney disease, cancer-induced cachexia, benign prostatic hyperplasia, rheumatoid arthritis, psoriasis, atherosclerosis, obesity, retinopathies (including diabetic retinopathy and retinopathy of prematurity), retrolental fibroplasia, neovascular glaucoma, age-related macular degeneration, exudative macular degeneration, thyroid hyperplasias (including Grave's disease), corneal and other tissue transplantation, epidemic keratoconjunctivitis, Vitamin A deficiency, contact lens overwear, atopic keratitis, superior limbic keratitis, and pterygium keratitis sicca, viral infections, inflammation associated with viral infections, chronic inflammation, lung inflammation, nephrotic syndrome, preeclampsia, ascites, pericardial effusion (such as that associated with pericarditis), pleural effusion, Sjogren's syndrome, acne rosacea, phylectenulosis, syphilis, lipid degeneration, chemical burns, bacterial ulcers, fungal ulcers, Herpes simplex infection, Herpes zoster infections, protozoan infections, Mooren's ulcer, Terrien's marginal degeneration, marginal keratolysis, systemic lupus, polyarteritis, trauma, Wegener's sarcoidosis, Paget's disease, scleritis, Stevens-Johnson's disease, pemphigoid, radial keratotomy, Eales' disease, Behcet's disease, sickle cell anemia, pseudoxanthoma elasticum, Stargardt's disease, pars planitis, chronic retinal detachment, vein occlusion, artery occlusion, carotid obstructive disease, chronic uveitis/vitritis, ocular histoplasmosis, Mycobacteria infections, Lyme's disease, Best's disease, myopia, optic pits, hyperviscosity syndromes, toxoplasmosis, sarcoidosis, trauma, post-laser complications, diseases associated with rubeosis (neovascularization of the iris and of the angle), and diseases caused by the abnormal proliferation of fibrovascular or fibrous tissue, including all forms of prolific vitreoretinopathy. Certain examples of non-neoplastic conditions that can be prevented and/or treated in accordance with the methods described herein include viral infections, including but not limited to, those associated with viruses belonging to Flaviviridae, flavivirus, pestivirus, hepacivirus, West Nile virus, hepatitis C virus (HCV) or human papilloma virus (HPV).

Kits

In one aspect, provided herein are pharmaceutical or assay kits comprising a compound of Formula (I) or a form thereof, in one or more containers, and instructions for use. In one embodiment, a pharmaceutical or assay kit comprises, in a container, a compound of Formula (I) or a form thereof, or a composition thereof provided herein, a vehicle control or composition of a vehicle control in another container, and instructions for use. In certain embodiments, the compound or the compound and vehicle, in separate containers, are accompanied by a reagent or reagents necessary for carrying out an assay(s) described herein. In a specific embodiment, the pharmaceutical or assay kit comprises, in a container, a compound of Formula (I) or a form thereof, and further comprises, in one or more containers, components for isolating RNA. In another specific embodiment, the pharmaceutical or assay kit comprises, in a container, a compound of Formula (I) or a form thereof, and further comprises, in one or more containers, components for conducting RT-PCR or RT-qPCR. In further embodiments, the compound, in one or more containers, is accompanied by an apparatus or apparati necessary for administering the compound or composition thereof to a subject. In certain embodiments, the compound is chosen from Formulas (II) through (XIV) or forms thereof. In yet other embodiments, the compound is any compound disclosed herein.

EXAMPLES

To describe in more detail and assist in understanding the present description, the following non-limiting biological examples are offered to more fully illustrate the scope of the description and are not to be construed as specifically limiting the scope thereof. Such variations of the present description that may be now known or later developed, which would be within the purview of one skilled in the art to ascertain, are considered to fall within the scope of the present description and as hereinafter claimed. These examples illustrate the testing of certain compounds described herein in vitro and/or in vivo and demonstrate the usefulness of the compounds for treating a disease associated with the aberrant amount of RNA transcripts.

Example 1

Described below is a method of contacting cells with a compound described herein and determining changes in RNA transcript levels of said cells compared to cells that have not been contacted with the compound.

Cells from a cell line of interest are cultured in conditions sufficient to yield the number of cells capable of generating enough RNA for subsequent sequencing steps. Cells from the tested cell line are contacted with a compound described herein.

To culture said cells, they are seeded, at appropriate concentrations in a volume of media in a cell culture container and incubated for 4, 5, 6, 7, 8, 9, 10, or more hours. A concentrated solution of compound in a vehicle (e.g., DMSO) is then added in sufficient volume to result in the intended final concentration of the compound, for example 100 nM, 500 nM, 1 µM, 5 µM, 10 µM, 15 µM, 20 µM, or more. The cells may also be treated with vehicle alone, as a control. A number of replicates of each concentration or control may be made (e.g., 2 replicates). The cells are then incubated at a constant temperature appropriate for cell culture of the particular cell line (e.g., 37° C.) for 6, 12, 18, 24, 48, or more hours. After incubation, the growth medium is removed and the cells are washed with the appropriate buffer (e.g., PBS). Cells are then removed from adherence to the cell culture container by treatment with a solution containing trypsin, and the trypsin subsequently quenched with the appropriate volume of buffer (e.g., DMEM-FBS). The cells are then pelleted with gentle centrifugation (e.g., ≤90×g centrifugal force) and resuspended in a buffer to lyse the cells for extraction of RNA. The cell lysates may then be frozen (e.g., at −80° C.) or, alternately, may immediately be used in a procedure to purify the RNA (e.g. by use of the RNEASY PLUS® minikit). The RNA from cell lysates is eluted in the appropriate volume of buffer (e.g., RNEASE-FREE $H_2O$®). The resulting purified RNA may then be sequenced (e.g., using RNASeq) or analyzed using a human exon array (e.g., by GENECHIP® human exon array) to determine changes in the RNA levels in those cells treated with compound compared to those cells treated only with DMSO. The purified RNA may also be quantified by other methods known in the art.

Using the RNA data obtained from sequencing, exon array, or other methods, a statistical analysis can reveal changes in the RNA levels of compound-treated compared with control. For example, t-test p-values may be calculated for the data obtained through sequencing and exon array methods in order to compare compound-treated cells to those treated with the DMSO control. RNA sequences whose levels have been determined to have significantly changed may then be mapped onto known genes, using an appropriate database. Analysis of the sequencing and exon array data may then also yield predictions about the cause of the aberrant amount of an RNA transcript in the cells (e.g., perturbation of RNA splicing, RNA transcription, or RNA stability). These predictions may be further confirmed by methods known in the art. For example, RT-PCR and RT-qPCR may be used to confirm the change in amount of RNA transcripts for one or more particular transcripts of interest.

Example 2 mRNA RT-qPCR Splicing Assay in Cultured Cells

Described below is a method of contacting cells with varying concentrations of a compound described herein and determining changes in RNA transcript levels of said cells that occur with changes of concentration.

Cells are plated at a certain density in an appropriate medium in 96-well flat-bottom plates. The plate is immediately swirled to ensure even distribution of the cells to ensure the formation of an even monolayer of cells and incubated for 6-24 hrs at 37° C. Cells are then treated with serially diluted test compound (e.g., 3.16-fold dilution factor, 0.5% final concentration of DMSO), in duplicate, for desired time under appropriate conditions (e.g., 37° C., 5% $CO_2$, 100% relative humidity). After supernatant removal, cells are lysed (e.g., in Cells-To-Ct lysis buffer, Life Technologies). The levels of RNA of interest, and a reference RNA (e.g., GAPDH mRNA) are quantified (e.g., by using Taqman-based RT-qPCR) by assays designed to detect each mRNA of interest specifically. The forward and reverse primers are used at the appropriate concentration (e.g., 0.1-1 µM), as well as the probe (e.g., 0.1 to 0.3 µM). GAPDH primers are typically at 0.1 µM and the probe at 0.075 µM. RT-qPCR is carried out using an appropriate protocol. One example of such a protocol is the following temperatures for indicated time: Step 1: 48° C. (15 min); Step 2: 95° C. (10 min); Step 3: 95° C. (15 sec); Step 4: 60° C. (1 min); then, repeat Steps 3 and 4 for a total of 40 cycles. Fluorescence is recorded in each cycle at the end of the Step 4 incubation. Each PCR contains one or more primer(s) and probe(s) for the RNA of interest and reference RNA (multiplex design), allowing simultaneous measurement of the levels of two transcripts. The Ct values for each mRNA are converted to mRNA abundance using actual PCR efficiencies, and may be calculated essentially as described in Liu and Saint (Anal Biochem 302:52). RNA of interest abundance is first normalized to the reference RNA to account for well-to-well variability. The reference RNA-normalized abundances of RNA of interest in compound-treated wells are then normalized to a control (e.g., a DMSO control) and plotted as fold change relative to control (e.g., DMSO).

Example 3

Alterations in Splicing of RNA Transcripts

This example demonstrates that a compound within Formula (I) modulates the splicing of RNA transcripts encoded by certain genes.

Materials and Methods

RT-qPCR Analysis of SMN2 Full Length (FL) and Δ7 mRNAs in Cultured Cells.

GM03813 (Coriell Institute) and PNN 1-46 fibroblasts (Columbia University) derived from SMA Type I patients were plated at 5,000 cells/well in 200 µL Dulbecco's modified Eagle's medium (DMEM) with GlutaMAX and 10% fetal bovine serum (FBS) (Life Technologies, Inc.) in 96-well plates, and incubated for 6 hours in a cell culture incubator (37° C., 5% CO$_2$, 100% relative humidity). Cells were then treated with Compound 702 at different concentrations (0.5% DMSO) in duplicate for 24 hours. After supernatant removal, cells were lysed in Cells-To-Ct lysis buffer (Life Technologies, Inc.) according to the manufacturer's recommendations. The mRNA levels of SMN2 FL, SMN2 Δ7 and GAPDH were quantified using Taqman-based RT-qPCR and SMN2-specific primers and probes in Table 5 (purchased from Life Technologies, Inc.). The SMN forward and reverse primers were each used at a final concentration of 0.4 µM. The SMN probe was used at a final concentration of 0.15 µM. GAPDH primers were used at final concentrations of 0.1 µM and the probe at 0.075 µM. RT-qPCR was carried out at the following temperatures for indicated times: Step 1: 48° C. (15 min); Step 2: 95° C. (10 min); Step 3: 95° C. (15 sec); Step 4: 60° C. (1 min); Steps 3 and 4 were repeated for 40 cycles. The Ct values for each mRNA were converted to mRNA abundance using actual PCR efficiencies. SMN2 FL and Δ7 mRNAs were normalized to GAPDH and DMSO controls and plotted as fold change over DMSO.

and bridge-amplified to create single sequence clusters using the TruSeq Rapid PE Cluster Kit—HS (Illumina Inc., San Diego, Calif.). Amplified clusters in the flow cell were then sequenced with 50-bp paired-end reads using the TruSeq Rapid SBS Kit—HS (Illumina Inc., San Diego, Calif.) in rapid run mode. Real time image analysis and base calling were performed on the the HiSeq 2500 instrument using the HiSeq Sequencing Control Software (HCS). CASAVA software version 1.8 was used for de-multiplexing and production of FASTQ sequence files.

RNA Sequencing and Data Analysis.

In order to estimate gene expression levels, paired-end RNAseq reads were subsequently mapped to RefSeq human transcripts (release 60) and the human genome (hg19) by using the short read aligner Bowtie2 (Langmead et al., 2012. Nature methods 9:357). The number of mapped reads for all transcript variants of a gene (counts) were combined into a single value and normalized denoted as rpkms (number of mapped reads per kilobase transcript per million sequenced reads, (Mortazavi et al., 2008. Nature methods 5:621)). The splice-site analysis was performed by mapping the paired-end RNASeq reads to RefSeq human transcripts using the

TABLE 5

| Primer/Probe | Sequence | Exon/Exon junction | SEQ ID NO. |
|---|---|---|---|
| SMN FL Forward Primer B | GCTCACATTCCTTAAATTAAGGAGAAA | Exon 7-exon 8 | 4 |
| SMNΔ7 Forward Primer B | TGGCTATCATACTGGCTATTATATGGAA | Exon 6-exon 8 | 5 |
| SMN Reverse Primer B | TCCAGATCTGTCTGATCGTTTCTT | Exon 8 | 6 |
| SMN Forward Probe B | 6FAM-CTGGCATAGAGCAGCACTAAATGACACCAC-TAMRA | Exon 8 | 7 |
| hGAPDH Forward Probe | VIC-CGCCTGGTCACCAGGGCTGCT-TAMRA | Exon 3 | 1 |
| hGAPDH Forward Primer | CAACGGATTTGGTCGTATTGG | Exon 2-exon 3 | 2 |
| hGAPDH Reverse Primer | TGATGGCAACAATATCCACTTTACC | Exon 3 | 3 |

RNA Sequencing Data Generation.

PNN 1-46 cells derived from a Type I SMA patient were treated with Compound 702 at 500 nM for 24 hours. RNA was purified with the RNeasy Mini Kit (Qiagen) for mRNA sequencing on HiSeq 2500 (Illumina Inc., San Diego, Calif.). The quality of the total RNA was assessed using UV spectrophotometry and agarose gel electrophoresis. Template DNA molecules suitable for cluster generation were prepared from 1 ug of total RNA samples using the TruSeq RNA Sample Preparation Kit v2 (Illumina Inc., San Diego, Calif.) according to the manufacturer's instructions. The size distribution of the libraries was estimated by electrophoresis on Agilent High Sensitivity Bioanalyzer microfluidic chips. The minimum and average sizes of the amplified libraries were determined to be >200 nucleotides and 300-340 nucleotides, respectively. Libraries were quantified using the KAPA Library Quantification Kit (KK4824, Kapa Biosystems, Boston, Mass.). The libraries were pooled at equimolar concentrations and diluted prior to loading onto the flow cell of the HiSeq 2500 (Illumina Inc., San Diego, Calif.) for both clustering and sequencing. The libraries were extended alignment software GSNAP with default parameters and the option 'sam-multiple-primaries' in order to account for reads that were mapped multiple times to different splice variants. The number of reads spanning splice-sites was determined by applying the samtools mpileup software with default parameters for each transcript. Reads having an alignment start or end exactly on the splice-site were excluded from the analysis (Wu et al., 2005, Bioinformatics 21:1859; Wu et al., 2010, Bioinformatics 26:873; Li et al., 2009, Bioinformatics 25:2078).

Results

Figure 2A:
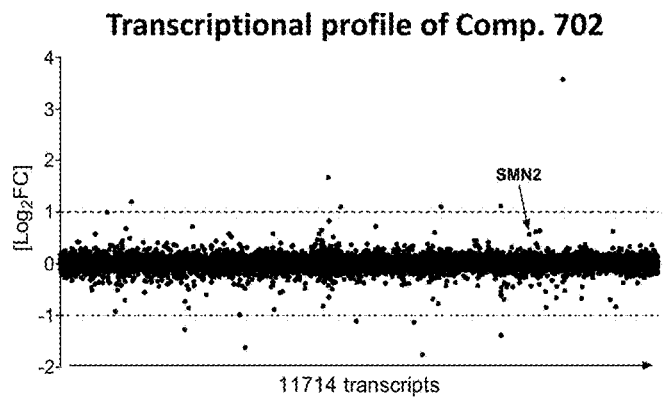
FIG. 2A. Difference in total transcript abundance between samples treated with Compound 702 (500 nM) or DMSO control at the gene level for 11,714 human genes with an rpkm (reads per kilobase per million)>1 in at least one of the conditions studied. Change in abundance of mRNA is shown as log 2 fold change ($Log_2FC$) values (0 represents no change, +1 represents doubling, −1 represents reduction by 50%). SMN2 is highlighted by the arrow, showing no change in total mRNA abundance.
Figure 2B:
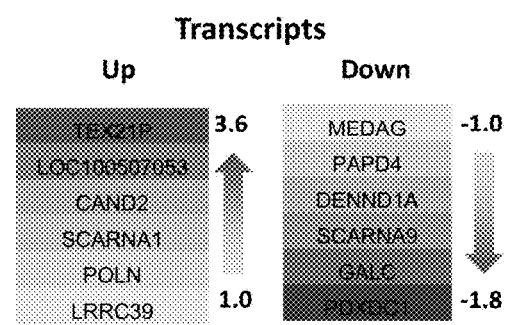
FIG. 2B. Using a threshold of $|Log_2FC| \geqslant 1$, six genes were found to be up- or downregulated, respectively.
Figure 2C:
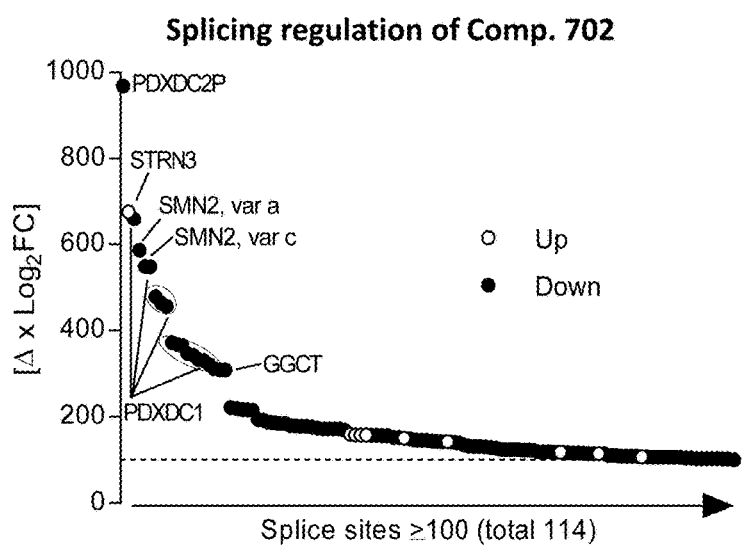
FIG. 2C. Differential effects of treatment on individual splice junctions in human transcripts. For each splice junction, spanning reads were counted in both treated and control conditions. Splice junctions are characterized either by absolute difference in counts ($\Delta$) or by relative changes ($Log_2$ FC). The product $p = \Delta \times Log_2$ FC was used to distinguish splice junctions (upregulated, white; downregulated; black). Certain splice junctions (114 splice junctions out of about 300,000 splice junctions analyzed in total) with p>100 are shown in Table 6 (including a complete list of genes). Additionally, 20 splice junctions had p>300, belonging to the following genes: SMN2, PDXDC1, STRN3, and pseudogene PDXDC2P. Note: two SMN2 transcript variants NM_022875 (SMN2 $\Delta$exon7 mRNA, alternatively referred to as "var a") and NM_022877 (SMN $\Delta$exon5, $\Delta$exon7 mRNA, alternatively referred to as "var c") share the target splice junction 5' of intron 7. For STRN3, a switch between variants NM_014574 and NM_001083893 is observed. 15 splice junctions belong to PDXDC1, with all splice junctions similarly affected. PDXDC2P is a pseudogene, probably identified due to the strong similarity between the PDXDC1 and PDXDC2P transcripts around that junction (not resolved by the mapping algorithm).
Figure 3:
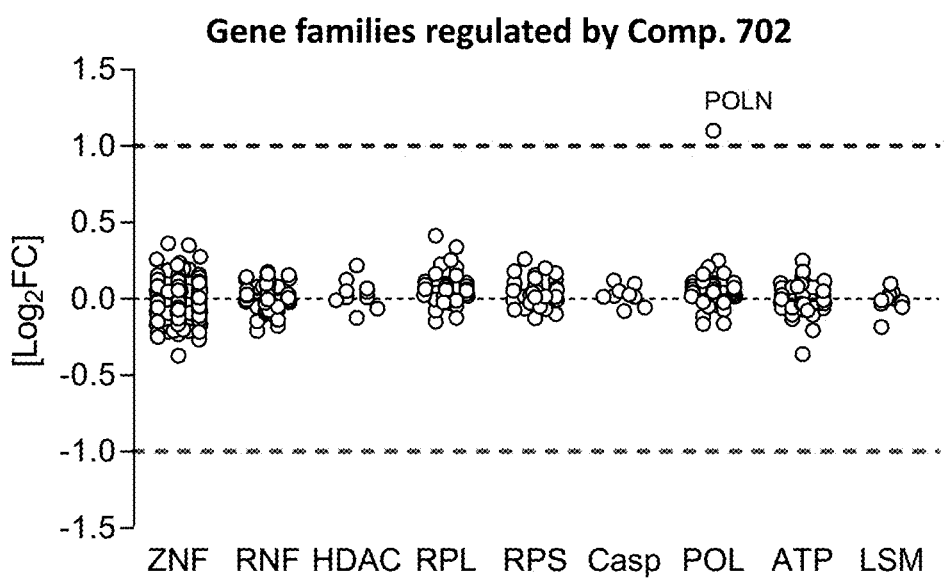
FIG. 3. Difference in total transcript expression between Compound 702 (500 nM) treatment and DMSO controls at the gene level (presented in FIG. 2A). The effect on certain gene families is shown as Log$_2$FC between DMSO control and Compound 702 treatment including (from left to right): zinc finger proteins (ZNF), ring finger proteins (RNF), histone deacetylases (HDAC), ribosomal proteins from large subunit (RPL), ribosomal proteins from small subunit (RPS), caspases (Casp), DNA and RNA polymerases (POL), ATPases (ATP), and LSM proteins involved in the splicing machinery. Only POLN (DNA polymerase nu) is changed with a Log$_2$FC>1 in this collection.

SMA Type I fibroblast cells (PNN 1-46) were treated either with DMSO or Compound 702 (500 nM) for 24 hours to allow complete splicing alteration of all SMN2 transcripts (see FIG. 1). RNA sequencing results of both samples were mapped to the human RefSeq transcript collection (release 60) to quantify transcript abundance, and counts were transformed to reads per kilobase transcript per million reads sequenced (rpkm). For an overall comparison, reads for all transcript variants of a gene were combined into a single value. By defining an rpkm of 1 as threshold for significant expression of a gene, 11,714 human genes were identified that were expressed in at least one of the experimental conditions (FIG. 2A). Genes either up- or downregulated to a factor >2 (log 2>1 or <−1; FIG. 2B) are shown in Table 6. No deregulation in gene families involved in DNA or RNA metabolism or cell survival was detected (FIG. 3).

A separate analysis of annotated splice junctions within the transcripts may be performed to identify splicing events potentially affected by a compound described herein. As shown in Table 6, splice junctions of 16 genes and two pseudogenes (*) are affected, either upregulated (up spl j gene) or down-regulated (down spl j gene), by treatment with a compound described herein without any changes in overall mRNA abundance.

TABLE 6

| down spl j gene | up spl j gene |
|---|---|
| PDXDC2P* | STRN3 |
| PDXDC1 | APLP2 |
| GGCT | TEX21P* |
| SMN2 | RCC1 |
| PAPD4 | FOXM1 |
| C11orf73 | VPS29 |
| DIAPH3 | |
| DENND5A | |
| HLTF | |
| PPHLN1 | |
| GALC | |
| PITPNB | |

Example 4

Following the methods described above in Example 1, PNN 1-46 SMA type I patient-derived fibroblasts were treated with 300 nM or 3 μM Compounds 774 and 808 in 0.5% DMSO.

700,000 cells were seeded in 10 mL of medium (DMEM plus 10% FBS) in a T-75 flask. Cells were allowed to attach for at least 4 hrs, after which 50 μL of a 200× compound solution (100% DMSO) was added to each well, and the plate was incubated at 37° C. for 24 hrs.

At the end of the incubation period, the supernatant was removed and the cells where washed with PBS. TrypLE (Invitrogen) express solution was added (e.g. 1.5 mL per one T75 flask). The flasks were incubated for 3 to 5 min at 37° C. The trypsin was then quenched, e.g., by adding 10 mL DMEM-FBS.

Next, the cells were pelleted using gentle centrifugation without exceeding 90×g centrifugal force. The supernatant was removed and the cell pellet was re-suspended in 600 μL RLT buffer (the RLT buffer was supplemented with beta-mercaptoethanol according to the RNeasy protocol manual) by pipetting up and down until the pellet was completely dissolved The cell lysates were either frozen at −80° C. or RNA purification using the RNeasy plus mini kit was started immediately. RNA was eluted in 50 μL RNease-free $H_2O$, giving a yield of 15 μg of total cellular RNA per 700,000 fibroblasts Purified total cellular RNA was prepared for HiSeq RNA sequencing (ILLUMINA™) using TRUSEQ™ sample preparation kit, or an equivalent procedure, per manufacturer's protocol.

Between 35 and 40 million paired-end reads were obtained. Raw data were mapped to UCSC reference genome (August-September 2011 version) using "TopHat" and "Cufflinks" software packages (Trapnell, et al., (2010) Nat. Biotechnol. 28(5):511-515; Trapnell, et al., (2012) Nat. Protocols 7(3):562-578).

Data for RNA abundance modulation (shown in Table 8, column heading legend in Table 7) demonstrate that Compound 774 (3 μM) modulates RNA abundance, having an effect on isoform fold increase at a statistically significant adjusted p value of at least 0.01, expressed as reads per million bases (RPM) in the filtered perfect match format (FPM). For analysis of RNA isoform abundance, iFPM (isoform filtered perfect match) numbers were generated for each annotated RNA.

Data for RNA abundance modulation (shown in Table 9, column heading legend in Table 7) demonstrate that Compound 774 (0.3 μM) modulates RNA abundance, having an effect on isoform fold increase at a statistically significant adjusted p value of at least 0.01, expressed as reads per million bases (RPM) in the filtered perfect match format (FPM). For analysis of RNA isoform abundance, iFPM (isoform filtered perfect match) numbers were generated for each annotated RNA.

Data for RNA abundance modulation (shown in Table 10, column heading legend in Table 7) demonstrate that Compound 808 (3 μM) modulates RNA abundance, having an effect on isoform fold increase at a statistically significant adjusted p value of at least 0.01, expressed as reads per million bases (RPM) in the filtered perfect match format (FPM). For analysis of RNA isoform abundance, iFPM (isoform filtered perfect match) numbers were generated for each annotated RNA.

Data for RNA abundance modulation (shown in Table 11, column heading legend in Table 7) demonstrate that Compound 808 (0.3 μM) modulates RNA abundance, having an effect on isoform fold increase at a statistically significant adjusted p value of at least 0.01, expressed as reads per million bases (RPM) in the filtered perfect match format (FPM). For analysis of RNA isoform abundance, iFPM (isoform filtered perfect match) numbers were generated for each annotated RNA.

TABLE 7

| Column Heading | Explanation |
|---|---|
| Trx_ID | RNA accession number in GenBank |
| GeneType | Type of gene: protein coding or pseudogene; miscRNA: long noncoding RNA and other miscellaneous RNA |
| description | Name of protein encoded by the RNA |
| aveDMSO | mean RNA counts from three separate cell culture samples treated with DMSO vehicle |
| ave Cpd | mean RNA counts from three separate cell culture samples treated with a test Compound |
| padj (q val, FDR) | q value. The Benjamini and Hochberg adjusted p values OR p value adjusted for multiple comparisons OR false discovery rate |

TABLE 7-continued

| Column Heading | Explanation |
|---|---|
| ttest (p val) | simple Student's t test comparing two groups - treated and control |
| FC(x + 1) | Fold change (counts in DMSO/counts in DMSO), modified as x + 1 to avoid dividing by 0 for entries with 0 counts |
| L₂FC(x + 1) | log2 of data in column FC(x + 1) |
| ampFC(x + 1) | amplitude of fold change, wherein if FC < 1 (i.e., counts in Compound treated sample are lower than that in DMSO), 1/FC is used, ensuring all folds are >1 |
| abs(Cpd-DMSO) | absolute arithmetic difference between DMSO and test Compound |
| L₂abs(Cpd-DMSO) | log2 of data in column abs(Cpd-DMSO) |

TABLE 8

RNA Abundance Modulation

| Gene | Trx_ID | ave DMSO | ave Cpd | padj (q val, FDR) | ttest (p val) | FC (x + 1) | L₂FC (x + 1) | amp FC (x + 1) | abs (Cpd-DMSO) | L₂abs (Cpd-DMSO) |
|---|---|---|---|---|---|---|---|---|---|---|
| ABCA1 | BC034824 | 1 | 0 | 0.2452 | 1.0000 | 0.4966 | −1.010 | 2.01 | 1 | 0.02 |
| ABCA1 | NM_005502 | 622 | 140 | 0.0000 | 0.0000 | 0.2265 | −2.143 | 4.42 | 482 | 8.91 |
| ABCC1 | AB209120 | 101 | 0 | 0.0000 | 0.0000 | 0.0098 | −6.668 | 101.69 | 101 | 6.65 |
| ABCC1 | AK311015 | 5 | 7 | 0.8917 | 1.0000 | 1.1745 | 0.232 | 1.17 | 1 | 0.18 |
| ABCC1 | HQ917064 | 7 | 5 | 0.7400 | 1.0000 | 0.7568 | −0.402 | 1.32 | 2 | 0.90 |
| ABCC1 | HQ917065 | 0 | 0 | 9999 | 9999 | 1.0000 | 0.000 | 1.00 | 0 | 0 |
| ABCC1 | HQ917066 | 1 | 1 | 1.0000 | 1.0000 | 0.9793 | −0.030 | 1.02 | 0 | −4.77 |
| ABCC1 | HQ917067 | 13 | 9 | 0.6494 | 1.0000 | 0.6890 | −0.537 | 1.45 | 4 | 2.15 |
| ABCC1 | NM_004996 | 3220 | 2460 | 0.0081 | 0.1909 | 0.7639 | −0.388 | 1.31 | 760 | 9.57 |
| ABL2 | AK225255 | 10 | 15 | 0.7270 | 1.0000 | 1.3999 | 0.485 | 1.40 | 5 | 2.20 |
| ABL2 | AK309549 | 0 | 0 | 9999 | 9999 | 1.0000 | 0.000 | 1.00 | 0 | 0 |
| ABL2 | NM_001136000 | 78 | 0 | 0.0000 | 0.0000 | 0.0126 | −6.308 | 79.22 | 78 | 6.29 |
| ABL2 | NM_001136001 | 13 | 18 | 0.7289 | 1.0000 | 1.3492 | 0.432 | 1.35 | 5 | 2.33 |
| ABL2 | NM_001168236 | 0 | 12 | 0.0077 | 0.1836 | 13.4034 | 3.745 | 13.40 | 12 | 3.63 |
| ABL2 | NM_001168237 | 2 | 0 | 0.0807 | 0.3033 | −1.721 | 3.30 | 2 | 1.20 |
| ABL2 | NM_001168238 | 0 | 0 | 9999 | 9999 | 1.0000 | 0.000 | 1.00 | 0 | 0 |
| ABL2 | NM_001168239 | 1429 | 1773 | 0.0512 | 0.5451 | 1.2408 | 0.311 | 1.24 | 344 | 8.43 |
| ABL2 | NM_005158 | 1432 | 1498 | 0.6152 | 1.0000 | 1.0464 | 0.065 | 1.05 | 66 | 6.05 |
| ABL2 | NM_007314 | 44 | 92 | 0.0659 | 0.6122 | 2.0636 | 1.045 | 2.06 | 48 | 5.58 |
| ACACA | AB209325 | 52 | 1 | 0.0000 | 0.0010 | 0.0374 | −4.741 | 26.73 | 51 | 5.67 |
| ACACA | AJ564444 | 1 | 1 | 1.0000 | 1.0000 | 0.9988 | −0.002 | 1.00 | 0 | −8.79 |
| ACACA | AK295586 | 54 | 66 | 0.8216 | 1.0000 | 1.2145 | 0.280 | 1.21 | 12 | 3.56 |
| ACACA | AK295735 | 12 | 24 | 0.4266 | 1.0000 | 1.9627 | 0.973 | 1.96 | 12 | 3.64 |
| ACACA | AK308905 | 18 | 25 | 0.6619 | 1.0000 | 1.3739 | 0.458 | 1.37 | 7 | 2.84 |
| ACACA | AK309084 | 13 | 11 | 0.9283 | 1.0000 | 0.8309 | −0.267 | 1.20 | 2 | 1.23 |
| ACACA | AY315622 | 2 | 1 | 0.5425 | 1.0000 | 0.5812 | −0.783 | 1.72 | 1 | 0.25 |
| ACACA | NM_198834 | 1048 | 1206 | 0.2081 | 1.0000 | 1.1508 | 0.203 | 1.15 | 158 | 7.31 |
| ACACA | NM_198836 | 1736 | 1864 | 0.5683 | 1.0000 | 1.0736 | 0.103 | 1.07 | 128 | 7.00 |
| ACACA | NM_198839 | 17 | 14 | 0.7482 | 1.0000 | 0.8234 | −0.280 | 1.21 | 3 | 1.71 |
| ACAT2 | AK055001 | 3 | 11 | 0.3209 | 1.0000 | 2.7403 | 1.454 | 2.74 | 7 | 2.89 |
| ACAT2 | AK294273 | 26 | 62 | 0.1141 | 0.7674 | 2.3168 | 1.212 | 2.32 | 36 | 5.16 |
| ACAT2 | NM_005891 | 1256 | 3214 | 0.0000 | 0.0000 | 2.5583 | 1.355 | 2.56 | 1959 | 10.94 |
| AFF2 | NM_001169122 | 24 | 47 | 0.3213 | 1.0000 | 1.9057 | 0.930 | 1.91 | 23 | 4.52 |
| AFF2 | NM_001169123 | 53 | 41 | 0.7016 | 1.0000 | 0.7828 | −0.353 | 1.28 | 12 | 3.54 |
| AFF2 | NM_001169124 | 68 | 0 | 0.0000 | 0.0000 | 0.0145 | −6.104 | 68.80 | 68 | 6.08 |
| AFF2 | NM_001169125 | 66 | 108 | 0.1689 | 0.9319 | 1.6105 | 0.687 | 1.61 | 41 | 5.36 |
| AFF2 | NM_001170628 | 0 | 0 | 9999 | 9999 | 1.0000 | 0.000 | 1.00 | 0 | 0 |
| AFF2 | NM_002025 | 0 | 0 | 9999 | 9999 | 1.0000 | 0.000 | 1.00 | 0 | 0 |
| AFF2 | X95463 | 0 | 6 | 0.0393 | 0.4829 | 7.3731 | 2.882 | 7.37 | 6 | 2.67 |
| AHRR | AK090508 | 160 | 127 | 0.4487 | 1.0000 | 0.7940 | −0.333 | 1.26 | 33 | 5.05 |
| AHRR | AK127977 | 5 | 4 | 0.8407 | 1.0000 | 0.7910 | −0.338 | 1.26 | 1 | 0.41 |
| AHRR | AK314472 | 111 | 0 | 0.0000 | 0.0000 | 0.0090 | −6.803 | 111.68 | 111 | 6.79 |
| AHRR | BC035358 | 0 | 0 | 9999 | 9999 | 1.0000 | 0.000 | 1.00 | 0 | 0 |
| AHRR | BC121048 | 109 | 18 | 0.0001 | 0.0081 | 0.1747 | −2.517 | 5.72 | 91 | 6.51 |
| AHRR | NM_001242412 | 714 | 775 | 0.4809 | 1.0000 | 1.0853 | 0.118 | 1.09 | 61 | 5.93 |
| AHRR | NM_020731 | 0 | 0 | 9999 | 9999 | 1.0000 | 0.000 | 1.00 | 0 | 0 |
| AK021888 | AK021888 | 312 | 104 | 0.0001 | 0.0058 | 0.3353 | −1.577 | 2.98 | 208 | 7.70 |
| AK310472 | AK310472 | 171 | 37 | 0.0001 | 0.0088 | 0.2209 | −2.178 | 4.53 | 134 | 7.07 |
| AKAP1 | AK292416 | 190 | 0 | 0.0000 | 0.0000 | 0.0052 | −7.581 | 191.46 | 190 | 7.57 |
| AKAP1 | NM_001242902 | 46 | 102 | 0.0685 | 0.6197 | 2.2096 | 1.144 | 2.21 | 56 | 5.82 |
| AKAP1 | NM_001242903 | 4 | 4 | 1.0000 | 1.0000 | 1.1235 | 0.168 | 1.12 | 1 | −0.76 |
| AKAP1 | NM_003488 | 370 | 595 | 0.0031 | 0.0999 | 1.6084 | 0.686 | 1.61 | 226 | 7.82 |
| AKAP1 | U34074 | 4 | 2 | 0.6229 | 1.0000 | 0.5914 | −0.758 | 1.69 | 2 | 1.06 |
| ANK2 | AK294720 | 57 | 102 | 0.2588 | 1.0000 | 1.7586 | 0.814 | 1.76 | 44 | 5.47 |
| ANK2 | AK299767 | 2 | 26 | 0.0059 | 0.1536 | 10.5786 | 3.403 | 10.58 | 24 | 4.60 |
| ANK2 | AK299815 | 176 | 205 | 0.5501 | 1.0000 | 1.1643 | 0.219 | 1.16 | 29 | 4.86 |
| ANK2 | BC125236 | 9 | 56 | 0.0067 | 0.1672 | 5.5640 | 2.476 | 5.56 | 46 | 5.54 |

TABLE 8-continued

RNA Abundance Modulation

| Gene | Trx_ID | ave DMSO | ave Cpd | padj (q val, FDR) | ttest (p val) | FC (x + 1) | L$_2$FC (x + 1) | amp FC (x + 1) | abs (Cpd-DMSO) | L$_2$abs (Cpd-DMSO) |
|---|---|---|---|---|---|---|---|---|---|---|
| ANK2 | BX538132 | 397 | 315 | 0.2835 | 1.0000 | 0.7944 | −0.332 | 1.26 | 82 | 6.35 |
| ANK2 | NM_001127493 | 73 | 0 | 0.0000 | 0.0000 | 0.0135 | −6.209 | 73.99 | 73 | 6.19 |
| ANK2 | NM_001148 | 26 | 0 | 0.0001 | 0.0084 | 0.0372 | −4.750 | 26.91 | 26 | 4.70 |
| ANK2 | NM_020977 | 98 | 108 | 0.7305 | 1.0000 | 1.0984 | 0.135 | 1.10 | 10 | 3.28 |
| ANKHD1-EIF4EBP3 | AK125734 | 153 | 137 | 0.6253 | 1.0000 | 0.8948 | −0.160 | 1.12 | 16 | 4.02 |
| ANKHD1-EIF4EBP3 | BC144623 | 0 | 85 | 0.0000 | 0.0000 | 85.5307 | 6.418 | 85.53 | 85 | 6.40 |
| ANKHD1-EIF4EBP3 | NM_020690 | 691 | 323 | 0.0001 | 0.0051 | 0.4688 | −1.093 | 2.13 | 368 | 8.52 |
| AP2B1 | AK292531 | 1978 | 1282 | 0.0001 | 0.0064 | 0.6484 | −0.625 | 1.54 | 696 | 9.44 |
| AP2B1 | AK301522 | 112 | 77 | 0.2954 | 1.0000 | 0.6880 | −0.540 | 1.45 | 35 | 5.14 |
| AP2B1 | AY341427 | 18 | 11 | 0.6209 | 1.0000 | 0.6347 | −0.656 | 1.58 | 7 | 2.80 |
| AP2B1 | CR749392 | 1146 | 642 | 0.0000 | 0.0018 | 0.5601 | −0.836 | 1.79 | 505 | 8.98 |
| AP2B1 | NM_001030006 | 358 | 1422 | 0.0000 | 0.0000 | 3.9681 | 1.988 | 3.97 | 1064 | 10.06 |
| AP2B1 | NM_001282 | 5514 | 4616 | 0.0468 | 0.5229 | 0.8371 | −0.257 | 1.19 | 899 | 9.81 |
| APAF1 | AJ243107 | 7 | 29 | 0.1033 | 0.7252 | 3.5830 | 1.841 | 3.58 | 21 | 4.42 |
| APAF1 | NM_001160 | 14 | 0 | 0.0019 | 0.0703 | 0.0646 | −3.951 | 15.47 | 14 | 3.85 |
| APAF1 | NM_013229 | 58 | 0 | 0.0000 | 0.0000 | 0.0170 | −5.879 | 58.84 | 58 | 5.85 |
| APAF1 | NM_181861 | 1103 | 1219 | 0.3374 | 1.0000 | 1.1051 | 0.144 | 1.11 | 116 | 6.86 |
| APAF1 | NM_181868 | 230 | 197 | 0.4607 | 1.0000 | 0.8569 | −0.223 | 1.17 | 33 | 5.04 |
| APLP2 | AK308932 | 12 | 7 | 0.4934 | 1.0000 | 0.5986 | −0.740 | 1.67 | 5 | 2.34 |
| APLP2 | L23114 | 4629 | 4770 | 0.8779 | 1.0000 | 1.0305 | 0.043 | 1.03 | 141 | 7.14 |
| APLP2 | NM_001142276 | 4338 | 13521 | 0.0000 | 0.0000 | 3.1161 | 1.640 | 3.12 | 9183 | 13.16 |
| APLP2 | NM_001142277 | 16000 | 8335 | 0.0000 | 0.0000 | 0.5210 | −0.941 | 1.92 | 7665 | 12.90 |
| APLP2 | NM_001142278 | 2 | 3 | 0.8768 | 1.0000 | 1.3381 | 0.420 | 1.34 | 1 | 0.11 |
| APLP2 | NM_001243299 | 79 | 0 | 0.0000 | 0.0000 | 0.0125 | −6.319 | 79.83 | 79 | 6.30 |
| APLP2 | NR_024515 | 186 | 152 | 0.5032 | 1.0000 | 0.8177 | −0.290 | 1.22 | 34 | 5.09 |
| APLP2 | NR_024516 | 0 | 11 | 0.0118 | 0.2422 | 11.9580 | 3.580 | 11.96 | 11 | 3.45 |
| ARID1A | AB001895 | 869 | 801 | 0.5855 | 1.0000 | 0.9218 | −0.118 | 1.08 | 68 | 6.09 |
| ARID1A | AB384378 | 0 | 5 | 0.0541 | 0.5655 | 5.8952 | 2.560 | 5.90 | 5 | 2.29 |
| ARID1A | AK027655 | 326 | 280 | 0.4621 | 1.0000 | 0.8581 | −0.221 | 1.17 | 46 | 5.54 |
| ARID1A | AK223275 | 875 | 831 | 0.8209 | 1.0000 | 0.9499 | −0.074 | 1.05 | 44 | 5.46 |
| ARID1A | AK308363 | 0 | 61 | 0.0000 | 0.0000 | 62.0846 | 5.956 | 62.08 | 61 | 5.93 |
| ARID1A | NM_006015 | 96 | 408 | 0.0000 | 0.0000 | 4.2142 | 2.075 | 4.21 | 312 | 8.29 |
| ARID1A | NM_139135 | 551 | 160 | 0.0000 | 0.0000 | 0.2915 | −1.778 | 3.43 | 391 | 8.61 |
| ARMCX3 | CCDS14489 | 268 | 119 | 0.0035 | 0.1085 | 0.4470 | −1.162 | 2.24 | 149 | 7.22 |
| ARMCX3 | NM_016607 | 479 | 123 | 0.0000 | 0.0000 | 0.2587 | −1.950 | 3.86 | 356 | 8.47 |
| ARMCX3 | NM_177947 | 1421 | 652 | 0.0000 | 0.0000 | 0.4589 | −1.124 | 2.18 | 770 | 9.59 |
| ARMCX3 | NM_177948 | 56 | 40 | 0.4578 | 1.0000 | 0.7140 | −0.486 | 1.40 | 16 | 4.03 |
| ASAP1 | AB033075 | 751 | 676 | 0.4207 | 1.0000 | 0.9001 | −0.152 | 1.11 | 75 | 6.23 |
| ASAP1 | NM_001247996 | 742 | 271 | 0.0000 | 0.0000 | 0.3660 | −1.450 | 2.73 | 471 | 8.88 |
| ASAP1 | NM_018482 | 2807 | 1237 | 0.0000 | 0.0000 | 0.4409 | −1.182 | 2.27 | 1570 | 10.62 |
| ASPH | FJ461473 | 2581 | 2620 | 0.8664 | 1.0000 | 1.0149 | 0.021 | 1.01 | 39 | 5.27 |
| ASPH | NM_001164750 | 1943 | 3545 | 0.0000 | 0.0000 | 1.8244 | 0.867 | 1.82 | 1602 | 10.65 |
| ASPH | NM_001164751 | 926 | 1291 | 0.0132 | 0.2589 | 1.3932 | 0.478 | 1.39 | 365 | 8.51 |
| ASPH | NM_001164752 | 717 | 550 | 0.1573 | 0.9046 | 0.7680 | −0.381 | 1.30 | 166 | 7.38 |
| ASPH | NM_001164753 | 0 | 44 | 0.0000 | 0.0003 | 44.7153 | 5.483 | 44.72 | 44 | 5.45 |
| ASPH | NM_001164754 | 169 | 543 | 0.0000 | 0.0000 | 3.2067 | 1.681 | 3.21 | 374 | 8.55 |
| ASPH | NM_001164755 | 5200 | 4960 | 0.6006 | 1.0000 | 0.9539 | −0.068 | 1.05 | 240 | 7.91 |
| ASPH | NM_001164756 | 18 | 20 | 0.9297 | 1.0000 | 1.0830 | 0.115 | 1.08 | 2 | 0.67 |
| ASPH | NM_004318 | 12376 | 11193 | 0.3255 | 1.0000 | 0.9044 | −0.145 | 1.11 | 1183 | 10.21 |
| ASPH | NM_032466 | 0 | 2035 | 0.0000 | 0.0000 | 2036.0635 | 10.992 | 2036.06 | 2035 | 10.99 |
| ASPH | NM_032467 | 12 | 5 | 0.3559 | 1.0000 | 0.4407 | −1.182 | 2.27 | 7 | 2.90 |
| ATAD2B | AK125718 | 9 | 8 | 0.9078 | 1.0000 | 0.8915 | −0.166 | 1.12 | 1 | 0.07 |
| ATAD2B | BC037408 | 3 | 3 | 0.9379 | 1.0000 | 1.0220 | 0.031 | 1.02 | 0 | −3.57 |
| ATAD2B | BC171846 | 9 | 27 | 0.1360 | 0.8448 | 2.7339 | 1.451 | 2.73 | 18 | 4.14 |
| ATAD2B | NM_001242338 | 85 | 0 | 0.0000 | 0.0000 | 0.0117 | −6.418 | 85.53 | 85 | 6.40 |
| ATAD2B | NM_017552 | 87 | 210 | 0.0102 | 0.2222 | 2.3930 | 1.259 | 2.39 | 123 | 6.94 |
| ATF7IP | AK025060 | 21 | 2 | 0.0290 | 0.4130 | 0.1489 | −2.748 | 6.72 | 19 | 4.23 |
| ATF7IP | AK299320 | 16 | 17 | 0.6841 | 1.0000 | 1.0947 | 0.131 | 1.09 | 2 | 0.66 |
| ATF7IP | AK304184 | 3 | 0 | 0.0717 | 0.6296 | 0.2717 | −1.880 | 3.68 | 3 | 1.42 |
| ATF7IP | AY337596 | 10 | 10 | 0.9750 | 1.0000 | 1.0408 | 0.058 | 1.04 | 0 | −1.15 |
| ATF7IP | BC053625 | 358 | 132 | 0.0001 | 0.0053 | 0.3715 | −1.428 | 2.69 | 225 | 7.82 |
| ATF7IP | BC063855 | 42 | 32 | 0.6432 | 1.0000 | 0.7639 | −0.389 | 1.31 | 10 | 3.33 |
| ATF7IP | BX648096 | 84 | 34 | 0.0613 | 0.5948 | 0.4129 | −1.276 | 2.42 | 50 | 5.64 |
| ATF7IP | NM_018179 | 967 | 997 | 0.8186 | 1.0000 | 1.0307 | 0.044 | 1.03 | 30 | 4.90 |
| ATG9A | BC065534 | 8 | 29 | 0.0892 | 0.6888 | 3.2895 | 1.718 | 3.29 | 21 | 4.37 |
| ATG9A | NM_001077198 | 2319 | 2577 | 0.2984 | 1.0000 | 1.1115 | 0.152 | 1.11 | 259 | 8.01 |
| ATG9A | NM_024085 | 692 | 300 | 0.0000 | 0.0003 | 0.4340 | −1.204 | 2.30 | 392 | 8.62 |
| AXIN1 | NM_003502 | 109 | 329 | 0.0000 | 0.0023 | 3.0076 | 1.589 | 3.01 | 220 | 7.78 |
| AXIN1 | NM_181050 | 586 | 413 | 0.0465 | 0.5213 | 0.7051 | −0.504 | 1.42 | 173 | 7.44 |
| BACE1 | AF527782 | 3 | 3 | 0.9381 | 1.0000 | 0.9598 | −0.059 | 1.04 | 0 | −2.68 |
| BACE1 | NM_001207048 | 2406 | 2519 | 0.7420 | 1.0000 | 1.0469 | 0.066 | 1.05 | 113 | 6.82 |

TABLE 8-continued

RNA Abundance Modulation

| Gene | Trx_ID | ave DMSO | ave Cpd | padj (q val, FDR) | ttest (p val) | FC (x + 1) | L₂FC (x + 1) | amp FC (x + 1) | abs (Cpd-DMSO) | L₂abs (Cpd-DMSO) |
|---|---|---|---|---|---|---|---|---|---|---|
| BACE1 | NM_001207049 | 408 | 34 | 0.0000 | 0.0000 | 0.0861 | −3.537 | 11.61 | 374 | 8.55 |
| BACE1 | NM_012104 | 5807 | 5079 | 0.1540 | 0.8944 | 0.8748 | −0.193 | 1.14 | 727 | 9.51 |
| BACE1 | NM_138971 | 68 | 74 | 0.8031 | 1.0000 | 1.0965 | 0.133 | 1.10 | 7 | 2.72 |
| BACE1 | NM_138972 | 355 | 679 | 0.0001 | 0.0051 | 1.9128 | 0.936 | 1.91 | 325 | 8.34 |
| BACE1 | NM_138973 | 0 | 16 | 0.0024 | 0.0816 | 16.8375 | 4.074 | 16.84 | 16 | 3.99 |
| BIN1 | AF068916 | 0 | 7 | 0.0402 | 0.4904 | 7.9266 | 2.987 | 7.93 | 7 | 2.79 |
| BIN1 | AK301153 | 33 | 50 | 0.5451 | 1.0000 | 1.4727 | 0.558 | 1.47 | 16 | 4.03 |
| BIN1 | NM_004305 | 16 | 0 | 0.0014 | 0.0550 | 0.0573 | −4.125 | 17.45 | 16 | 4.04 |
| BIN1 | NM_139343 | 0 | 0 | 9999 | 9999 | 1.0000 | 0.000 | 1.00 | 0 | 0 |
| BIN1 | NM_139346 | 0 | 3 | 0.0939 | 0.6918 | 4.1675 | 2.059 | 4.17 | 3 | 1.66 |
| BIN1 | NM_139347 | 0 | 0 | 9999 | 9999 | 1.0000 | 0.000 | 1.00 | 0 | 0 |
| BIN1 | NM_139348 | 379 | 381 | 1.0000 | 1.0000 | 1.0052 | 0.007 | 1.01 | 2 | 0.97 |
| BIN1 | NM_139349 | 3 | 3 | 0.9383 | 1.0000 | 0.9409 | −0.088 | 1.06 | 0 | −2.14 |
| BIN1 | NM_139350 | 193 | 227 | 0.5325 | 1.0000 | 1.1723 | 0.229 | 1.17 | 33 | 5.07 |
| BIN1 | NM_139351 | 63 | 0 | 0.0000 | 0.0000 | 0.0156 | −5.998 | 63.93 | 63 | 5.98 |
| BNC1 | AK302992 | 596 | 166 | 0.0000 | 0.0000 | 0.2803 | −1.835 | 3.57 | 429 | 8.75 |
| BNC1 | NM_001717 | 1017 | 1275 | 0.1119 | 0.7573 | 1.2530 | 0.325 | 1.25 | 258 | 8.01 |
| BRPF1 | AK293865 | 109 | 125 | 0.6106 | 1.0000 | 1.1456 | 0.196 | 1.15 | 16 | 4.00 |
| BRPF1 | AL713696 | 340 | 359 | 0.7817 | 1.0000 | 1.0544 | 0.076 | 1.05 | 19 | 4.21 |
| BRPF1 | NM_001003694 | 225 | 270 | 0.4422 | 1.0000 | 1.2008 | 0.264 | 1.20 | 45 | 5.50 |
| BRPF1 | NM_004634 | 85 | 0 | 0.0000 | 0.0000 | 0.0155 | −6.013 | 64.58 | 84 | 6.40 |
| BZW1 | NM_001207067 | 5467 | 5923 | 0.3982 | 1.0000 | 1.0836 | 0.116 | 1.08 | 457 | 8.84 |
| BZW1 | NM_001207068 | 250 | 50 | 0.0000 | 0.0006 | 0.2022 | −2.306 | 4.94 | 200 | 7.65 |
| BZW1 | NM_001207069 | 7454 | 8279 | 0.2361 | 1.0000 | 1.1107 | 0.151 | 1.11 | 825 | 9.69 |
| BZW1 | Z70221 | 25 | 35 | 0.6128 | 1.0000 | 1.4085 | 0.494 | 1.41 | 11 | 3.40 |
| C11orf30 | AK125114 | 53 | 7 | 0.0022 | 0.0792 | 0.1406 | −2.830 | 7.11 | 46 | 5.53 |
| C11orf30 | AK126030 | 42 | 25 | 0.4064 | 1.0000 | 0.6024 | −0.731 | 1.66 | 17 | 4.09 |
| C11orf30 | AK304043 | 19 | 26 | 0.7290 | 1.0000 | 1.3600 | 0.444 | 1.36 | 7 | 2.84 |
| C11orf30 | AK304043 | 63 | 33 | 0.2209 | 1.0000 | 0.5342 | −0.904 | 1.87 | 30 | 4.89 |
| C11orf30 | AK309621 | 2 | 3 | 0.8648 | 1.0000 | 1.2758 | 0.351 | 1.28 | 1 | −0.23 |
| C11orf30 | AY070433 | 2 | 0 | 0.0895 | 0.6888 | 0.3431 | −1.543 | 2.91 | 2 | 0.94 |
| C11orf30 | BC021688 | 0 | 0 | 1.0000 | 1.0000 | 0.9792 | −0.030 | 1.02 | 0 | −5.19 |
| C11orf30 | BC033404 | 7 | 16 | 0.3551 | 1.0000 | 2.1951 | 1.134 | 2.20 | 9 | 3.24 |
| C11orf30 | BC117265 | 257 | 144 | 0.0238 | 0.3686 | 0.5627 | −0.830 | 1.78 | 113 | 6.82 |
| C11orf30 | BC143370 | 0 | 10 | 0.0121 | 0.2461 | 11.3672 | 3.507 | 11.37 | 10 | 3.37 |
| C11orf30 | BC143374 | 61 | 28 | 0.1335 | 0.8340 | 0.4731 | −1.080 | 2.11 | 33 | 5.04 |
| C11orf30 | BC143376 | 76 | 3 | 0.0000 | 0.0006 | 0.0507 | −4.302 | 19.72 | 73 | 6.20 |
| C11orf30 | NM_020193 | 115 | 78 | 0.4065 | 1.0000 | 0.6851 | −0.546 | 1.46 | 36 | 5.19 |
| C11orf73 | NM_016401 | 691 | 168 | 0.0000 | 0.0000 | 0.2447 | −2.031 | 4.09 | 523 | 9.03 |
| C11orf73 | NR_024596 | 10 | 7 | 0.7161 | 1.0000 | 0.7379 | −0.438 | 1.36 | 3 | 1.50 |
| C11orf73 | NR_024598 | 24 | 5 | 0.0651 | 0.6088 | 0.2312 | −2.113 | 4.32 | 19 | 4.25 |
| C17orf76-AS1 | HQ447236 | 16 | 16 | 0.9805 | 1.0000 | 0.9529 | −0.070 | 1.05 | 1 | −0.29 |
| C17orf76-AS1 | NR_027158 | 557 | 558 | 0.9432 | 1.0000 | 1.0022 | 0.003 | 1.00 | 1 | 0.32 |
| C17orf76-AS1 | NR_027163 | 1763 | 1607 | 0.4055 | 1.0000 | 0.9118 | −0.133 | 1.10 | 156 | 7.28 |
| C17orf76-AS1 | NR_027164 | 244 | 67 | 0.0000 | 0.0010 | 0.2754 | −1.861 | 3.63 | 178 | 7.47 |
| C17orf76-AS1 | NR_027165 | 20 | 28 | 0.6749 | 1.0000 | 1.3636 | 0.447 | 1.36 | 8 | 2.93 |
| C17orf76-AS1 | NR_027166 | 5481 | 5706 | 0.6940 | 1.0000 | 1.0411 | 0.058 | 1.04 | 225 | 7.82 |
| C17orf76-AS1 | NR_027167 | 55 | 120 | 0.0543 | 0.5677 | 2.1413 | 1.098 | 2.14 | 64 | 6.01 |
| C17orf76-AS1 | NR_027168 | 572 | 757 | 0.0517 | 0.5472 | 1.3226 | 0.403 | 1.32 | 185 | 7.53 |
| C17orf76-AS1 | NR_027169 | 258 | 219 | 0.4936 | 1.0000 | 0.8502 | −0.234 | 1.18 | 39 | 5.28 |
| C17orf76-AS1 | NR_027170 | 95 | 83 | 0.7304 | 1.0000 | 0.8674 | −0.205 | 1.15 | 13 | 3.68 |
| C17orf76-AS1 | NR_027172 | 1 | 6 | 0.2126 | 1.0000 | 4.0770 | 2.027 | 4.08 | 5 | 2.32 |
| C17orf76-AS1 | NR_027173 | 0 | 2 | 0.1447 | 0.8705 | 2.7277 | 1.448 | 2.73 | 2 | 0.79 |
| C17orf76-AS1 | NR_027174 | 11 | 6 | 0.5143 | 1.0000 | 0.5643 | −0.825 | 1.77 | 5 | 2.44 |
| C17orf76-AS1 | NR_027176 | 0 | 0 | 9999 | 9999 | 1.0000 | 0.000 | 1.00 | 0 | 0 |
| C17orf76-AS1 | NR_027177 | 0 | 3 | 0.1149 | 0.7677 | 3.9377 | 1.977 | 3.94 | 3 | 1.55 |
| C17orf76-AS1 | NR_027178 | 4 | 0 | 0.0511 | 0.5451 | 0.2071 | −2.272 | 4.83 | 4 | 1.94 |
| C17orf76-AS1 | NR_027179 | 49 | 45 | 0.8156 | 1.0000 | 0.9101 | −0.136 | 1.10 | 5 | 2.18 |
| C17orf76-AS1 | NR_027667 | 314 | 264 | 0.4689 | 1.0000 | 0.8411 | −0.250 | 1.19 | 50 | 5.65 |
| C17orf76-AS1 | NR_045022 | 38 | 38 | 0.9885 | 1.0000 | 1.0196 | 0.028 | 1.02 | 1 | −0.41 |
| C17orf76-AS1 | NR_045023 | 3 | 3 | 0.8133 | 1.0000 | 0.7935 | −0.334 | 1.26 | 1 | −0.11 |
| C17orf76-AS1 | NR_045025 | 0 | 0 | 9999 | 9999 | 1.0000 | 0.000 | 1.00 | 0 | 0 |
| C17orf76-AS1 | NR_045026 | 76 | 80 | 0.8622 | 1.0000 | 1.0594 | 0.083 | 1.06 | 5 | 2.18 |
| C17orf76-AS1 | NR_045028 | 32 | 27 | 0.7806 | 1.0000 | 0.8686 | −0.203 | 1.15 | 4 | 2.10 |
| C17orf76-AS1 | NR_045029 | 366 | 403 | 0.6034 | 1.0000 | 1.0994 | 0.137 | 1.10 | 37 | 5.19 |
| C4orf27 | NM_017867 | 637 | 110 | 0.0000 | 0.0000 | 0.1735 | −2.527 | 5.76 | 527 | 9.04 |
| C6orf48 | AJ249732 | 1 | 1 | 0.8418 | 1.0000 | 0.8098 | −0.304 | 1.23 | 0 | −1.43 |
| C6orf48 | AJ249732 | 3 | 1 | 0.3873 | 1.0000 | 0.4171 | −1.262 | 2.40 | 3 | 1.38 |
| C6orf48 | NM_001040437 | 193 | 492 | 0.0000 | 0.0007 | 2.5344 | 1.342 | 2.53 | 298 | 8.22 |
| C6orf48 | NM_001040437 | 581 | 286 | 0.0003 | 0.0169 | 0.4933 | −1.020 | 2.03 | 295 | 8.20 |
| C6orf48 | NM_001040438 | 287 | 763 | 0.0000 | 0.0000 | 2.6510 | 1.407 | 2.65 | 476 | 8.89 |
| C6orf48 | NM_001040438 | 1041 | 478 | 0.0000 | 0.0002 | 0.4594 | −1.122 | 2.18 | 563 | 9.14 |
| C6orf48 | NM_001040438 | 238 | 238 | 0.7372 | 1.0000 | 1.0010 | 0.002 | 1.00 | 0 | −2.00 |
| CAB39 | AF134480 | 553 | 535 | 0.8273 | 1.0000 | 0.9663 | −0.049 | 1.03 | 19 | 4.22 |

TABLE 8-continued

RNA Abundance Modulation

| Gene | Trx_ID | ave DMSO | ave Cpd | padj (q val, FDR) | ttest (p val) | FC (x + 1) | L$_2$FC (x + 1) | amp FC (x + 1) | abs (Cpd-DMSO) | L$_2$abs (Cpd-DMSO) |
|---|---|---|---|---|---|---|---|---|---|---|
| CAB39 | NM_001130849 | 63 | 68 | 0.8894 | 1.0000 | 1.0788 | 0.109 | 1.08 | 5 | 2.34 |
| CAB39 | NM_001130850 | 486 | 223 | 0.0001 | 0.0055 | 0.4593 | −1.123 | 2.18 | 263 | 8.04 |
| CAB39 | NM_016289 | 1421 | 1428 | 0.8678 | 1.0000 | 1.0047 | 0.007 | 1.00 | 7 | 2.75 |
| CAMKK1 | NM_032294 | 533 | 641 | 0.2523 | 1.0000 | 1.2034 | 0.267 | 1.20 | 109 | 6.76 |
| CAMKK1 | NM_172206 | 96 | 0 | 0.0000 | 0.0000 | 0.0103 | −6.599 | 96.91 | 96 | 6.58 |
| CAMKK1 | NM_172207 | 8 | 9 | 0.9422 | 1.0000 | 1.1248 | 0.170 | 1.12 | 1 | 0.16 |
| CCDC88A | AK001254 | 6 | 2 | 0.4199 | 1.0000 | 0.4711 | −1.086 | 2.12 | 4 | 1.84 |
| CCDC88A | AK024717 | 203 | 160 | 0.4276 | 1.0000 | 0.7920 | −0.336 | 1.26 | 42 | 5.41 |
| CCDC88A | AK124603 | 3 | 0 | 0.0717 | 0.6296 | 0.2717 | −1.880 | 3.68 | 3 | 1.42 |
| CCDC88A | AK124761 | 11 | 31 | 0.2059 | 1.0000 | 2.6955 | 1.431 | 2.70 | 20 | 4.34 |
| CCDC88A | BC032683 | 217 | 160 | 0.2957 | 1.0000 | 0.7382 | −0.438 | 1.35 | 57 | 5.84 |
| CCDC88A | BC142700 | 0 | 1 | 0.6865 | 1.0000 | 1.5561 | 0.638 | 1.56 | 1 | −0.38 |
| CCDC88A | BX537985 | 73 | 100 | 0.4570 | 1.0000 | 1.3577 | 0.441 | 1.36 | 27 | 4.73 |
| CCDC88A | BX538154 | 0 | 0 | 9999 | 9999 | 1.0000 | 0.000 | 1.00 | 0 | 0 |
| CCDC88A | NM_001135597 | 810 | 1152 | 0.0136 | 0.2629 | 1.4213 | 0.507 | 1.42 | 342 | 8.42 |
| CCDC88A | NM_001254943 | 271 | 203 | 0.3021 | 1.0000 | 0.7487 | −0.418 | 1.34 | 68 | 6.10 |
| CCDC88A | NM_018084 | 801 | 358 | 0.0000 | 0.0003 | 0.4479 | −1.159 | 2.23 | 443 | 8.79 |
| CCDC92 | AK125866 | 33 | 24 | 0.6485 | 1.0000 | 0.7510 | −0.413 | 1.33 | 8 | 3.07 |
| CCDC92 | AK222661 | 142 | 17 | 0.0000 | 0.0008 | 0.1236 | −3.017 | 8.09 | 125 | 6.97 |
| CCDC92 | NM_025140 | 1590 | 1227 | 0.0336 | 0.4478 | 0.7717 | −0.374 | 1.30 | 363 | 8.50 |
| CDC25B | AK295573 | 3 | 11 | 0.2342 | 1.0000 | 3.1867 | 1.672 | 3.19 | 8 | 3.07 |
| CDC25B | AK299028 | 26 | 0 | 0.0001 | 0.0074 | 0.0375 | −4.739 | 26.70 | 26 | 4.68 |
| CDC25B | AK299192 | 0 | 0 | 9999 | 9999 | 1.0000 | 0.000 | 1.00 | 0 | 0 |
| CDC25B | BX640836 | 57 | 31 | 0.1672 | 0.9262 | 0.5435 | −0.880 | 1.84 | 27 | 4.73 |
| CDC25B | BX647988 | 267 | 0 | 0.0000 | 0.0000 | 0.0037 | −8.068 | 268.31 | 267 | 8.06 |
| CDC25B | FR695900 | 4314 | 3562 | 0.0398 | 0.4878 | 0.8258 | −0.276 | 1.21 | 751 | 9.55 |
| CDC25B | FR695901 | 582 | 528 | 0.5656 | 1.0000 | 0.9077 | −0.140 | 1.10 | 54 | 5.75 |
| CDC25B | NM_004358 | 151 | 104 | 0.2794 | 1.0000 | 0.6931 | −0.529 | 1.44 | 47 | 5.54 |
| CDC25B | NM_021872 | 91 | 24 | 0.0090 | 0.2051 | 0.2665 | −1.908 | 3.75 | 67 | 6.08 |
| CDC25B | NM_021873 | 1150 | 1045 | 0.5281 | 1.0000 | 0.9090 | −0.138 | 1.10 | 105 | 6.71 |
| CDC42BPA | AB007920 | 3 | 10 | 0.2444 | 1.0000 | 2.7359 | 1.452 | 2.74 | 7 | 2.82 |
| CDC42BPA | AB384799 | 70 | 0 | 0.0000 | 0.0000 | 0.0141 | −6.147 | 70.85 | 70 | 6.13 |
| CDC42BPA | AK027000 | 2 | 9 | 0.2299 | 1.0000 | 3.5125 | 1.813 | 3.51 | 7 | 2.86 |
| CDC42BPA | AK098391 | 95 | 89 | 0.8091 | 1.0000 | 0.9323 | −0.101 | 1.07 | 7 | 2.71 |
| CDC42BPA | BC136333 | 0 | 34 | 0.0000 | 0.0025 | 35.2726 | 5.140 | 35.27 | 34 | 5.10 |
| CDC42BPA | CR933723 | 96 | 112 | 0.6628 | 1.0000 | 1.1598 | 0.214 | 1.16 | 16 | 3.96 |
| CDC42BPA | NM_003607 | 3693 | 3088 | 0.0653 | 0.6104 | 0.8364 | −0.258 | 1.20 | 604 | 9.24 |
| CDC42BPA | NM_014826 | 488 | 637 | 0.0969 | 0.7018 | 1.3035 | 0.382 | 1.30 | 148 | 7.21 |
| CDCA7 | AK297097 | 0 | 0 | 9999 | 9999 | 1.0000 | 0.000 | 1.00 | 0 | 0 |
| CDCA7 | AK300949 | 0 | 0 | 9999 | 9999 | 1.0000 | 0.000 | 1.00 | 0 | 0 |
| CDCA7 | NM_031942 | 52 | 12 | 0.0234 | 0.3648 | 0.2433 | −2.039 | 4.11 | 40 | 5.32 |
| CDCA7 | NM_145810 | 321 | 76 | 0.0000 | 0.0001 | 0.2405 | −2.056 | 4.16 | 244 | 7.93 |
| CDH11 | AK294872 | 2 | 1 | 1.0000 | 1.0000 | 0.9523 | −0.070 | 1.05 | 0 | −3.03 |
| CDH11 | AK297377 | 396 | 140 | 0.0000 | 0.0009 | 0.3539 | −1.499 | 2.83 | 257 | 8.00 |
| CDH11 | AK308000 | 0 | 0 | 9999 | 9999 | 1.0000 | 0.000 | 1.00 | 0 | 0 |
| CDH11 | E07383 | 189 | 291 | 0.0905 | 0.6901 | 1.5387 | 0.622 | 1.54 | 102 | 6.67 |
| CDH11 | NM_001797 | 10285 | 9384 | 0.3004 | 1.0000 | 0.9124 | −0.132 | 1.10 | 901 | 9.82 |
| CDH13 | NM_001220488 | 34 | 0 | 0.0000 | 0.0017 | 0.0289 | −5.110 | 34.55 | 34 | 5.07 |
| CDH13 | NM_001220490 | 0 | 0 | 9999 | 9999 | 1.0000 | 0.000 | 1.00 | 0 | 0 |
| CDH13 | NM_001220491 | 36 | 45 | 0.7073 | 1.0000 | 1.2543 | 0.327 | 1.25 | 9 | 3.22 |
| CDH13 | NM_001220492 | 1 | 3 | 0.7641 | 1.0000 | 1.6054 | 0.683 | 1.61 | 1 | 0.45 |
| CDH13 | NM_001257 | 2497 | 1105 | 0.0000 | 0.0000 | 0.4429 | −1.175 | 2.26 | 1391 | 10.44 |
| CEP68 | AK299373 | 241 | 316 | 0.2113 | 1.0000 | 1.3114 | 0.391 | 1.31 | 75 | 6.24 |
| CEP68 | AK301173 | 102 | 77 | 0.4710 | 1.0000 | 0.7546 | −0.406 | 1.33 | 25 | 4.66 |
| CEP68 | AK304110 | 49 | 64 | 0.5189 | 1.0000 | 1.2951 | 0.373 | 1.30 | 15 | 3.89 |
| CEP68 | BC004873 | 0 | 6 | 0.0516 | 0.5467 | 6.5489 | 2.711 | 6.55 | 6 | 2.47 |
| CEP68 | BC030534 | 3 | 5 | 0.7593 | 1.0000 | 1.4652 | 0.551 | 1.47 | 2 | 0.90 |
| CEP68 | NM_015147 | 161 | 0 | 0.0000 | 0.0000 | 0.0062 | −7.344 | 162.44 | 161 | 7.33 |
| CFLAR | AB209600 | 133 | 160 | 0.5498 | 1.0000 | 1.2036 | 0.267 | 1.20 | 27 | 4.77 |
| CFLAR | AF009617 | 8 | 0 | 0.0123 | 0.2481 | 0.1135 | −3.139 | 8.81 | 8 | 2.97 |
| CFLAR | AF009619 | 3 | 0 | 0.0509 | 0.5451 | 0.2408 | −2.054 | 4.15 | 3 | 1.66 |
| CFLAR | AF015451 | 58 | 6 | 0.0011 | 0.0476 | 0.1236 | −3.017 | 8.09 | 51 | 5.68 |
| CFLAR | AF015452 | 84 | 49 | 0.2706 | 1.0000 | 0.5869 | −0.769 | 1.70 | 35 | 5.14 |
| CFLAR | AF041462 | 0 | 0 | 9999 | 9999 | 1.0000 | 0.000 | 1.00 | 0 | 0 |
| CFLAR | AK308767 | 112 | 93 | 0.6485 | 1.0000 | 0.8369 | −0.257 | 1.19 | 18 | 4.20 |
| CFLAR | NM_001127183 | 111 | 3 | 0.0000 | 0.0000 | 0.0371 | −4.752 | 26.94 | 108 | 6.76 |
| CFLAR | NM_001127184 | 265 | 253 | 0.8206 | 1.0000 | 0.9541 | −0.068 | 1.05 | 12 | 3.61 |
| CFLAR | NM_001202515 | 86 | 17 | 0.0025 | 0.0845 | 0.2117 | −2.240 | 4.72 | 69 | 6.11 |
| CFLAR | NM_001202516 | 0 | 6 | 0.0379 | 0.4705 | 7.0471 | 2.817 | 7.05 | 6 | 2.60 |
| CFLAR | NM_001202517 | 121 | 90 | 0.4915 | 1.0000 | 0.7470 | −0.421 | 1.34 | 31 | 4.95 |
| CFLAR | NM_001202518 | 20 | 0 | 0.0008 | 0.0353 | 0.0478 | −4.386 | 20.91 | 20 | 4.32 |
| CFLAR | NM_001202519 | 12 | 97 | 0.0002 | 0.0139 | 7.3344 | 2.875 | 7.33 | 84 | 6.40 |
| CFLAR | NM_003879 | 268 | 498 | 0.0011 | 0.0471 | 1.8545 | 0.891 | 1.85 | 230 | 7.84 |
| CFLAR | U97075 | 14 | 26 | 0.5054 | 1.0000 | 1.7859 | 0.837 | 1.79 | 12 | 3.57 |

TABLE 8-continued

RNA Abundance Modulation

| Gene | Trx_ID | ave DMSO | ave Cpd | padj (q val, FDR) | ttest (p val) | FC (x + 1) | L$_2$FC (x + 1) | amp FC (x + 1) | abs (Cpd-DMSO) | L$_2$abs (Cpd-DMSO) |
|---|---|---|---|---|---|---|---|---|---|---|
| COPS7B | AK024273 | 50 | 13 | 0.0320 | 0.4351 | 0.2696 | −1.891 | 3.71 | 37 | 5.21 |
| COPS7B | AK124133 | 2 | 10 | 0.2001 | 1.0000 | 3.5774 | 1.839 | 3.58 | 8 | 2.99 |
| COPS7B | AK126326 | 13 | 81 | 0.0015 | 0.0580 | 5.9514 | 2.573 | 5.95 | 68 | 6.09 |
| COPS7B | AK307486 | 16 | 4 | 0.1722 | 0.9431 | 0.3050 | −1.713 | 3.28 | 12 | 3.58 |
| COPS7B | BC091493 | 3 | 0 | 0.0558 | 0.5724 | 0.2624 | −1.930 | 3.81 | 3 | 1.49 |
| COPS7B | NM_022730 | 656 | 326 | 0.0001 | 0.0066 | 0.4979 | −1.006 | 2.01 | 330 | 8.37 |
| CREB5 | AK298121 | 0 | 1 | 0.6669 | 1.0000 | 1.6528 | 0.725 | 1.65 | 1 | −0.62 |
| CREB5 | NM_001011666 | 159 | 204 | 0.3386 | 1.0000 | 1.2830 | 0.359 | 1.28 | 45 | 5.50 |
| CREB5 | NM_004904 | 51 | 0 | 0.0000 | 0.0000 | 0.0193 | −5.693 | 51.75 | 51 | 5.67 |
| CREB5 | NM_182899 | 28 | 33 | 0.6907 | 1.0000 | 1.1584 | 0.212 | 1.16 | 5 | 2.20 |
| CUL2 | AK294080 | 533 | 596 | 0.5647 | 1.0000 | 1.1180 | 0.161 | 1.12 | 63 | 5.98 |
| CUL2 | NM_001198777 | 1522 | 1760 | 0.2051 | 1.0000 | 1.1565 | 0.210 | 1.16 | 238 | 7.90 |
| CUL2 | NM_003591 | 83 | 0 | 0.0000 | 0.0000 | 0.0119 | −6.392 | 83.99 | 83 | 6.37 |
| CUL4A | AK296700 | 471 | 387 | 0.3081 | 1.0000 | 0.8208 | −0.285 | 1.22 | 85 | 6.40 |
| CUL4A | AL833355 | 214 | 188 | 0.4789 | 1.0000 | 0.8801 | −0.184 | 1.14 | 26 | 4.69 |
| CUL4A | NM_001008895 | 3631 | 3033 | 0.0757 | 0.6446 | 0.8353 | −0.260 | 1.20 | 598 | 9.22 |
| CUL4A | NM_003589 | 139 | 496 | 0.0000 | 0.0000 | 3.5598 | 1.832 | 3.56 | 357 | 8.48 |
| CUX1 | NM_001202543 | 753 | 240 | 0.0000 | 0.0000 | 0.3203 | −1.642 | 3.12 | 512 | 9.00 |
| CUX1 | NM_001202544 | 11 | 0 | 0.0051 | 0.1388 | 0.0831 | −3.589 | 12.04 | 11 | 3.46 |
| CUX1 | NM_001202545 | 8 | 0 | 0.0137 | 0.2647 | 0.1116 | −3.163 | 8.96 | 8 | 2.99 |
| CUX1 | NM_001202546 | 10 | 6 | 0.5656 | 1.0000 | 0.6435 | −0.636 | 1.55 | 4 | 1.93 |
| CUX1 | NM_001913 | 1271 | 1125 | 0.3804 | 1.0000 | 0.8856 | −0.175 | 1.13 | 146 | 7.18 |
| CUX1 | NM_181500 | 266 | 275 | 0.9632 | 1.0000 | 1.0338 | 0.048 | 1.03 | 9 | 3.17 |
| CUX1 | NM_181552 | 330 | 821 | 0.0000 | 0.0000 | 2.4791 | 1.310 | 2.48 | 490 | 8.94 |
| CYP51A1 | AK091323 | 0 | 0 | 9999 | 9999 | 1.0000 | 0.000 | 1.00 | 0 | 0 |
| CYP51A1 | NM_000786 | 1642 | 3492 | 0.0000 | 0.0000 | 2.1261 | 1.088 | 2.13 | 1850 | 10.85 |
| CYP51A1 | NM_001146152 | 380 | 957 | 0.0000 | 0.0000 | 2.5134 | 1.330 | 2.51 | 577 | 9.17 |
| DCUN1D4 | AK124346 | 0 | 8 | 0.0247 | 0.3768 | 9.1602 | 3.195 | 9.16 | 8 | 3.03 |
| DCUN1D4 | AK294894 | 159 | 21 | 0.0000 | 0.0005 | 0.1395 | −2.842 | 7.17 | 137 | 7.10 |
| DCUN1D4 | AK294896 | 4 | 0 | 0.0342 | 0.4489 | 0.1861 | −2.426 | 5.37 | 4 | 2.13 |
| DCUN1D4 | BC041702 | 22 | 24 | 0.9677 | 1.0000 | 1.1000 | 0.137 | 1.10 | 2 | 1.18 |
| DCUN1D4 | NM_001040402 | 844 | 396 | 0.0000 | 0.0008 | 0.4702 | −1.089 | 2.13 | 448 | 8.81 |
| DCUN1D4 | NM_015115 | 431 | 322 | 0.1344 | 0.8378 | 0.7476 | −0.420 | 1.34 | 109 | 6.77 |
| DDR1 | AK130776 | 0 | 0 | 9999 | 9999 | 1.0000 | 0.000 | 1.00 | 0 | 0 |
| DDR1 | AK291621 | 54 | 0 | 0.0000 | 0.0000 | 0.0181 | −5.791 | 55.35 | 54 | 5.76 |
| DDR1 | AK291621 | 4 | 0 | 0.0417 | 0.4942 | 0.2097 | −2.254 | 4.77 | 4 | 1.91 |
| DDR1 | AK295643 | 1 | 1 | 1.0000 | 1.0000 | 1.0173 | 0.025 | 1.02 | 0 | −5.15 |
| DDR1 | AK295643 | 0 | 0 | 9999 | 9999 | 1.0000 | 0.000 | 1.00 | 0 | 0 |
| DDR1 | BC070070 | 116 | 210 | 0.0318 | 0.4342 | 1.8048 | 0.852 | 1.80 | 94 | 6.55 |
| DDR1 | EU826614 | 0 | 3 | 0.1154 | 0.7701 | 4.0512 | 2.018 | 4.05 | 3 | 1.61 |
| DDR1 | EU826614 | 5 | 4 | 0.8777 | 1.0000 | 0.8323 | −0.265 | 1.20 | 1 | 0.02 |
| DDR1 | EU826614 | 1 | 1 | 1.0000 | 1.0000 | 1.1430 | 0.193 | 1.14 | 0 | −2.10 |
| DDR1 | L20817 | 187 | 47 | 0.0001 | 0.0050 | 0.2565 | −1.963 | 3.90 | 140 | 7.13 |
| DDR1 | L57508 | 23 | 14 | 0.6759 | 1.0000 | 0.6350 | −0.655 | 1.57 | 9 | 3.13 |
| DDR1 | NM_001202521 | 0 | 8 | 0.0300 | 0.4196 | 9.0203 | 3.173 | 9.02 | 8 | 3.00 |
| DDR1 | NM_001202522 | 0 | 0 | 9999 | 9999 | 1.0000 | 0.000 | 1.00 | 0 | 0 |
| DDR1 | NM_001202523 | 7 | 1 | 0.1396 | 0.8558 | 0.1998 | −2.324 | 5.01 | 7 | 2.73 |
| DDR1 | NM_001202523 | 0 | 1 | 0.4902 | 1.0000 | 1.9792 | 0.985 | 1.98 | 1 | −0.03 |
| DDR1 | NM_013993 | 289 | 294 | 0.8938 | 1.0000 | 1.0171 | 0.024 | 1.02 | 5 | 2.31 |
| DDR1 | NM_013994 | 57 | 48 | 0.7719 | 1.0000 | 0.8557 | −0.225 | 1.17 | 8 | 3.06 |
| DDR1 | Z29093 | 3 | 0 | 0.0616 | 0.5948 | 0.2839 | −1.817 | 3.52 | 3 | 1.33 |
| DDR1 | Z29093 | 15 | 9 | 0.4914 | 1.0000 | 0.6682 | −0.582 | 1.50 | 5 | 2.38 |
| DDX39B | AB209217 | 175 | 192 | 0.7525 | 1.0000 | 1.0937 | 0.129 | 1.09 | 17 | 4.05 |
| DDX39B | AB209217 | 188 | 238 | 0.4627 | 1.0000 | 1.2672 | 0.342 | 1.27 | 50 | 5.66 |
| DDX39B | AB209217 | 68 | 65 | 0.8721 | 1.0000 | 0.9596 | −0.060 | 1.04 | 3 | 1.47 |
| DDX39B | AK127767 | 3 | 0 | 0.0643 | 0.6048 | 0.2461 | −2.022 | 4.06 | 3 | 1.61 |
| DDX39B | AK127767 | 144 | 151 | 0.8372 | 1.0000 | 1.0511 | 0.072 | 1.05 | 7 | 2.89 |
| DDX39B | AK127767 | 134 | 90 | 0.2415 | 1.0000 | 0.6727 | −0.572 | 1.49 | 44 | 5.46 |
| DDX39B | AK127767 | 26 | 29 | 0.8870 | 1.0000 | 1.0921 | 0.127 | 1.09 | 2 | 1.32 |
| DDX39B | AK294939 | 13 | 0 | 0.0038 | 0.1140 | 0.0735 | −3.766 | 13.60 | 13 | 3.66 |
| DDX39B | AK295634 | 18 | 18 | 0.9287 | 1.0000 | 0.9687 | −0.046 | 1.03 | 1 | −0.73 |
| DDX39B | AK316469 | 6 | 0 | 0.0211 | 0.3412 | 0.1436 | −2.800 | 6.96 | 6 | 2.58 |
| DDX39B | AK316469 | 7 | 9 | 1.0000 | 1.0000 | 1.2255 | 0.293 | 1.23 | 2 | 0.90 |
| DDX39B | AK316469 | 0 | 0 | 9999 | 9999 | 1.0000 | 0.000 | 1.00 | 0 | 0 |
| DDX39B | NM_004640 | 1902 | 1723 | 0.3332 | 1.0000 | 0.9058 | −0.143 | 1.10 | 179 | 7.49 |
| DDX39B | NM_080598 | 172 | 1 | 0.0000 | 0.0000 | 0.0091 | −6.780 | 109.86 | 172 | 7.42 |
| DDX39B | NM_080598 | 207 | 460 | 0.0003 | 0.0180 | 2.2194 | 1.150 | 2.22 | 253 | 7.98 |
| DDX39B | NM_080598 | 424 | 204 | 0.0023 | 0.0806 | 0.4824 | −1.052 | 2.07 | 220 | 7.78 |
| DDX39B | NM_080598 | 569 | 580 | 0.8552 | 1.0000 | 1.0198 | 0.028 | 1.02 | 11 | 3.50 |
| DDX39B | NM_080598 | 6 | 1 | 0.2809 | 1.0000 | 0.3132 | −1.675 | 3.19 | 5 | 2.24 |
| DDX39B | NR_037852 | 24 | 37 | 0.4811 | 1.0000 | 1.4856 | 0.571 | 1.49 | 12 | 3.62 |
| DDX39B | NR_037852 | 0 | 0 | 9999 | 9999 | 1.0000 | 0.000 | 1.00 | 0 | 0 |
| DDX39B | NR_037852 | 0 | 0 | 9999 | 9999 | 1.0000 | 0.000 | 1.00 | 0 | 0 |
| DDX39B | NR_037853 | 899 | 833 | 0.5285 | 1.0000 | 0.9261 | −0.111 | 1.08 | 67 | 6.06 |

TABLE 8-continued

RNA Abundance Modulation

| Gene | Trx_ID | ave DMSO | ave Cpd | padj (q val, FDR) | ttest (p val) | FC (x + 1) | L$_2$FC (x + 1) | amp FC (x + 1) | abs (Cpd-DMSO) | L$_2$abs (Cpd-DMSO) |
|---|---|---|---|---|---|---|---|---|---|---|
| DDX42 | AK095772 | 48 | 8 | 0.0119 | 0.2432 | 0.1860 | −2.427 | 5.38 | 40 | 5.31 |
| DDX42 | AK122737 | 46 | 30 | 0.4627 | 1.0000 | 0.6680 | −0.582 | 1.50 | 16 | 3.96 |
| DDX42 | AK126480 | 13 | 41 | 0.1066 | 0.7355 | 3.0015 | 1.586 | 3.00 | 28 | 4.82 |
| DDX42 | CU677324 | 105 | 39 | 0.0338 | 0.4489 | 0.3749 | −1.416 | 2.67 | 66 | 6.05 |
| DDX42 | NM_007372 | 639 | 257 | 0.0000 | 0.0002 | 0.4025 | −1.313 | 2.48 | 382 | 8.58 |
| DDX42 | NM_203499 | 2908 | 1212 | 0.0000 | 0.0000 | 0.4169 | −1.262 | 2.40 | 1696 | 10.73 |
| DENND1A | AB046828 | 12 | 0 | 0.0048 | 0.1344 | 0.0777 | −3.686 | 12.87 | 12 | 3.57 |
| DENND1A | AK295710 | 0 | 5 | 0.0618 | 0.5956 | 6.1620 | 2.623 | 6.16 | 5 | 2.37 |
| DENND1A | AK299867 | 8 | 2 | 0.2853 | 1.0000 | 0.3586 | −1.480 | 2.79 | 6 | 2.51 |
| DENND1A | BC009616 | 0 | 0 | 1.0000 | 1.0000 | 1.2880 | 0.365 | 1.29 | 0 | −1.80 |
| DENND1A | BC028061 | 4 | 1 | 0.2647 | 1.0000 | 0.3340 | −1.582 | 2.99 | 3 | 1.79 |
| DENND1A | BC113037 | 0 | 5 | 0.0576 | 0.5792 | 6.0302 | 2.592 | 6.03 | 5 | 2.33 |
| DENND1A | NM_020946 | 356 | 43 | 0.0000 | 0.0000 | 0.1237 | −3.015 | 8.09 | 312 | 8.29 |
| DENND1A | NM_024820 | 187 | 20 | 0.0000 | 0.0000 | 0.1094 | −3.193 | 9.14 | 168 | 7.39 |
| DENND5A | AK125444 | 14 | 5 | 0.3482 | 1.0000 | 0.3973 | −1.332 | 2.52 | 9 | 3.13 |
| DENND5A | AK294016 | 3 | 0 | 0.0643 | 0.6048 | 0.2461 | −2.022 | 4.06 | 3 | 1.61 |
| DENND5A | NM_001243254 | 308 | 0 | 0.0000 | 0.0032 | 8.271 | −8.271 | 309.00 | 308 | 8.27 |
| DENND5A | NM_015213 | 5004 | 828 | 0.0000 | 0.0000 | 0.1656 | −2.594 | 6.04 | 4176 | 12.03 |
| DGKA | AF064770 | 28 | 9 | 0.1919 | 1.0000 | 0.3646 | −1.456 | 2.74 | 18 | 4.19 |
| DGKA | AF064771 | 0 | 7 | 0.0300 | 0.4196 | 8.3133 | 3.055 | 8.31 | 7 | 2.87 |
| DGKA | AK122973 | 12 | 7 | 0.5923 | 1.0000 | 0.6505 | −0.620 | 1.54 | 5 | 2.18 |
| DGKA | AK307685 | 0 | 0 | 9999 | 9999 | 1.0000 | 0.000 | 1.00 | 0 | 0 |
| DGKA | AK309939 | 12 | 22 | 0.4679 | 1.0000 | 1.7735 | 0.827 | 1.77 | 10 | 3.30 |
| DGKA | AK310600 | 4 | 3 | 0.7944 | 1.0000 | 0.7260 | −0.462 | 1.38 | 1 | 0.56 |
| DGKA | AY930112 | 6 | 0 | 0.0261 | 0.3873 | 0.1403 | −2.833 | 7.13 | 6 | 2.61 |
| DGKA | NM_001345 | 39 | 42 | 0.9888 | 1.0000 | 1.0642 | 0.090 | 1.06 | 3 | 1.37 |
| DGKA | NM_201444 | 86 | 51 | 0.1960 | 1.0000 | 0.5939 | −0.752 | 1.68 | 36 | 5.15 |
| DGKA | NM_201445 | 69 | 38 | 0.2138 | 1.0000 | 0.5590 | −0.839 | 1.79 | 31 | 4.95 |
| DGKA | NM_201554 | 655 | 272 | 0.0000 | 0.0005 | 0.4169 | −1.262 | 2.40 | 383 | 8.58 |
| DHCR24 | AK298414 | 97 | 213 | 0.0115 | 0.2379 | 2.1791 | 1.124 | 2.18 | 116 | 6.86 |
| DHCR24 | AK304302 | 47 | 207 | 0.0001 | 0.0044 | 4.3574 | 2.123 | 4.36 | 160 | 7.32 |
| DHCR24 | AK316419 | 0 | 0 | 9999 | 9999 | 1.0000 | 0.000 | 1.00 | 0 | 0 |
| DHCR24 | NM_014762 | 6490 | 15827 | 0.0000 | 0.0000 | 2.4386 | 1.286 | 2.44 | 9338 | 13.19 |
| DHCR7 | NM_001163817 | 26 | 70 | 0.0895 | 0.6888 | 2.6305 | 1.395 | 2.63 | 44 | 5.45 |
| DHCR7 | NM_001360 | 996 | 2736 | 0.0000 | 0.0000 | 2.7456 | 1.457 | 2.75 | 1740 | 10.76 |
| DIAPH1 | AF051782 | 2 | 0 | 0.0669 | 0.6122 | 0.3138 | −1.672 | 3.19 | 2 | 1.13 |
| DIAPH1 | BC143414 | 16 | 9 | 0.3963 | 1.0000 | 0.5847 | −0.774 | 1.71 | 7 | 2.84 |
| DIAPH1 | NM_001079812 | 253 | 0 | 0.0000 | 0.0000 | 0.0039 | −7.988 | 253.81 | 253 | 7.98 |
| DIAPH1 | NM_005219 | 5870 | 5528 | 0.5185 | 1.0000 | 0.9417 | −0.087 | 1.06 | 342 | 8.42 |
| DIAPH3 | BC041395 | 0 | 1 | 0.2667 | 1.0000 | 2.1518 | 1.106 | 2.15 | 1 | 0.20 |
| DIAPH3 | NM_001042517 | 2472 | 253 | 0.0000 | 0.0000 | 0.1027 | −3.284 | 9.74 | 2219 | 11.12 |
| DIAPH3 | NM_001258366 | 761 | 47 | 0.0000 | 0.0000 | 0.0624 | −4.003 | 16.04 | 715 | 9.48 |
| DIAPH3 | NM_001258367 | 55 | 0 | 0.0000 | 0.0000 | 0.0177 | −5.820 | 56.48 | 55 | 5.79 |
| DIAPH3 | NM_001258368 | 41 | 5 | 0.0098 | 0.2158 | 0.1470 | −2.766 | 6.80 | 36 | 5.16 |
| DIAPH3 | NM_001258369 | 562 | 23 | 0.0000 | 0.0000 | 0.0425 | −4.558 | 23.56 | 539 | 9.08 |
| DIAPH3 | NM_001258370 | 12 | 0 | 0.0036 | 0.1112 | 0.0743 | −3.751 | 13.46 | 12 | 3.64 |
| DIAPH3 | NM_030932 | 2 | 14 | 0.1048 | 0.7268 | 5.1176 | 2.355 | 5.12 | 12 | 3.56 |
| DNM2 | AB209213 | 9 | 7 | 0.8198 | 1.0000 | 0.8281 | −0.272 | 1.21 | 2 | 0.78 |
| DNM2 | AK097967 | 163 | 152 | 0.8159 | 1.0000 | 0.9331 | −0.100 | 1.07 | 11 | 3.45 |
| DNM2 | AK097989 | 17 | 27 | 0.5531 | 1.0000 | 1.5801 | 0.660 | 1.58 | 10 | 3.35 |
| DNM2 | AK127033 | 4 | 1 | 0.3544 | 1.0000 | 0.3705 | −1.432 | 2.70 | 3 | 1.66 |
| DNM2 | AK295929 | 0 | 0 | 9999 | 9999 | 1.0000 | 0.000 | 1.00 | 0 | 0 |
| DNM2 | NM_001005360 | 147 | 10 | 0.0000 | 0.0000 | 0.0710 | −3.816 | 14.09 | 137 | 7.10 |
| DNM2 | NM_001005361 | 48 | 149 | 0.0021 | 0.0744 | 3.0750 | 1.621 | 3.08 | 101 | 6.66 |
| DNM2 | NM_001005362 | 418 | 583 | 0.0477 | 0.5297 | 1.3952 | 0.481 | 1.40 | 166 | 7.37 |
| DNM2 | NM_001190716 | 737 | 680 | 0.5726 | 1.0000 | 0.9231 | −0.116 | 1.08 | 57 | 5.83 |
| DNM2 | NM_004945 | 2104 | 2103 | 0.9717 | 1.0000 | 0.9996 | −0.001 | 1.00 | 1 | −0.41 |
| DOCK1 | BC084559 | 5 | 3 | 0.6074 | 1.0000 | 0.6099 | −0.713 | 1.64 | 2 | 1.19 |
| DOCK1 | BC144632 | 621 | 310 | 0.0001 | 0.0087 | 0.4991 | −1.002 | 2.00 | 312 | 8.28 |
| DOCK1 | BX648342 | 9 | 4 | 0.4552 | 1.0000 | 0.5256 | −0.928 | 1.90 | 5 | 2.18 |
| DOCK1 | NM_001380 | 2889 | 1243 | 0.0000 | 0.0000 | 0.4307 | −1.215 | 2.32 | 1645 | 10.68 |
| EFCAB14 | AK295722 | 142 | 458 | 0.0000 | 0.0000 | 3.2080 | 1.682 | 3.21 | 316 | 8.30 |
| EFCAB14 | AK296777 | 265 | 309 | 0.4761 | 1.0000 | 1.1660 | 0.222 | 1.17 | 44 | 5.47 |
| EFCAB14 | NM_014774 | 2212 | 1988 | 0.3138 | 1.0000 | 0.8990 | −0.154 | 1.11 | 223 | 7.80 |
| EIF2B3 | NM_001166588 | 416 | 96 | 0.0000 | 0.0000 | 0.2327 | −2.103 | 4.30 | 320 | 8.32 |
| EIF2B3 | NM_001261418 | 10 | 3 | 0.2556 | 1.0000 | 0.3463 | −1.530 | 2.89 | 7 | 2.89 |
| EIF2B3 | NM_020365 | 586 | 178 | 0.0000 | 0.0000 | 0.3056 | −1.710 | 3.27 | 408 | 8.67 |
| EPN1 | AK314690 | 1042 | 1324 | 0.0557 | 0.5724 | 1.2710 | 0.346 | 1.27 | 283 | 8.14 |
| EPN1 | NM_001130071 | 41 | 214 | 0.0000 | 0.0003 | 5.1536 | 2.366 | 5.15 | 173 | 7.44 |
| EPN1 | NM_001130072 | 2039 | 2064 | 0.9713 | 1.0000 | 1.0122 | 0.018 | 1.01 | 25 | 4.64 |
| EPN1 | NM_013333 | 288 | 54 | 0.0000 | 0.0000 | 0.1894 | −2.401 | 5.28 | 235 | 7.87 |
| EPT1 | BC021229 | 98 | 0 | 0.0000 | 0.0000 | 0.0101 | −6.633 | 99.27 | 98 | 6.62 |
| EPT1 | NM_033505 | 1560 | 2252 | 0.0009 | 0.0401 | 1.4435 | 0.530 | 1.44 | 692 | 9.44 |
| ERC1 | AK294351 | 22 | 10 | 0.3879 | 1.0000 | 0.4804 | −1.058 | 2.08 | 12 | 3.55 |

TABLE 8-continued

| | | | | RNA Abundance Modulation | | | | | |
|---|---|---|---|---|---|---|---|---|---|
| Gene | Trx_ID | ave DMSO | ave Cpd | padj (q val, FDR) | ttest (p val) | FC (x + 1) | L$_2$FC (x + 1) | amp FC (x + 1) | abs (Cpd-DMSO) | L$_2$abs (Cpd-DMSO) |
| ERC1 | AK309992 | 14 | 15 | 0.9185 | 1.0000 | 1.0820 | 0.114 | 1.08 | 1 | 0.28 |
| ERC1 | BC144287 | 67 | 43 | 0.3093 | 1.0000 | 0.6490 | −0.624 | 1.54 | 24 | 4.57 |
| ERC1 | NM_178039 | 665 | 234 | 0.0000 | 0.0000 | 0.3523 | −1.505 | 2.84 | 431 | 8.75 |
| ERC1 | NM_178040 | 2274 | 1482 | 0.0002 | 0.0136 | 0.6517 | −0.618 | 1.53 | 792 | 9.63 |
| ERC1 | NR_027946 | 0 | 2 | 0.1220 | 0.7938 | 3.3036 | 1.724 | 3.30 | 2 | 1.20 |
| ERC1 | NR_027948 | 335 | 233 | 0.1357 | 0.8437 | 0.6959 | −0.523 | 1.44 | 102 | 6.68 |
| ETV5 | AK301878 | 551 | 155 | 0.0000 | 0.0000 | 0.2828 | −1.822 | 3.54 | 396 | 8.63 |
| ETV5 | NM_004454 | 2169 | 2695 | 0.0271 | 0.3963 | 1.2426 | 0.313 | 1.24 | 526 | 9.04 |
| FADS1 | AK096275 | 759 | 1607 | 0.0000 | 0.0000 | 2.1148 | 1.081 | 2.11 | 848 | 9.73 |
| FADS1 | AK298871 | 9 | 9 | 0.9443 | 1.0000 | 0.9406 | −0.088 | 1.06 | 1 | −0.70 |
| FADS1 | NM_013402 | 1235 | 2559 | 0.0000 | 0.0000 | 2.0709 | 1.050 | 2.07 | 1324 | 10.37 |
| FADS2 | AK074991 | 423 | 736 | 0.0006 | 0.0300 | 1.7381 | 0.798 | 1.74 | 313 | 8.29 |
| FADS2 | AK299762 | 37 | 102 | 0.0281 | 0.4040 | 2.6983 | 1.432 | 2.70 | 65 | 6.02 |
| FADS2 | BC009011 | 75 | 248 | 0.0001 | 0.0051 | 3.2816 | 1.714 | 3.28 | 173 | 7.43 |
| FADS2 | NM_004265 | 1405 | 5002 | 0.0000 | 0.0000 | 3.5570 | 1.831 | 3.56 | 3596 | 11.81 |
| FAF1 | AF094700 | 41 | 26 | 0.4325 | 1.0000 | 0.6361 | −0.653 | 1.57 | 15 | 3.94 |
| FAF1 | AK293659 | 12 | 9 | 0.7526 | 1.0000 | 0.7848 | −0.350 | 1.27 | 3 | 1.43 |
| FAF1 | NM_007051 | 1719 | 439 | 0.0000 | 0.0000 | 0.2556 | −1.968 | 3.91 | 1281 | 10.32 |
| FAM198B | AK172805 | 1 | 1 | 0.8462 | 1.0000 | 0.8219 | −0.283 | 1.22 | 0 | −1.48 |
| FAM198B | NM_001031700 | 0 | 4 | 0.0941 | 0.6918 | 4.5905 | 2.199 | 4.59 | 4 | 1.84 |
| FAM198B | NM_001128424 | 79 | 0 | 0.0000 | 0.0000 | 0.0125 | −6.324 | 80.12 | 79 | 6.31 |
| FAM198B | NM016613 | 326 | 240 | 0.2163 | 1.0000 | 0.7385 | −0.437 | 1.35 | 85 | 6.42 |
| FAM219B | BC006348 | 114 | 305 | 0.0002 | 0.0100 | 2.6547 | 1.409 | 2.65 | 191 | 7.57 |
| FAM219B | BC064575 | 67 | 28 | 0.1351 | 0.8409 | 0.4302 | −1.217 | 2.32 | 39 | 5.27 |
| FAM219B | NM_020447 | 550 | 475 | 0.3615 | 1.0000 | 0.8639 | −0.211 | 1.16 | 75 | 6.23 |
| FBXO10 | BC125124 | 0 | 15 | 0.0041 | 0.1209 | 15.6883 | 3.972 | 15.69 | 15 | 3.88 |
| FBXO10 | BC125125 | 51 | 309 | 0.0000 | 0.0000 | 5.9612 | 2.576 | 5.96 | 258 | 8.01 |
| FBXO10 | NM_012166 | 267 | 272 | 0.8333 | 1.0000 | 1.0172 | 0.025 | 1.02 | 5 | 2.21 |
| FBXO9 | NM_012347 | 21 | 11 | 0.3784 | 1.0000 | 0.5321 | −0.910 | 1.88 | 10 | 3.35 |
| FBXO9 | NM_033480 | 1073 | 527 | 0.0000 | 0.0003 | 0.4922 | −1.023 | 2.03 | 545 | 9.09 |
| FBXO9 | NM_033481 | 35 | 6 | 0.0354 | 0.4574 | 0.2022 | −2.306 | 4.94 | 28 | 4.83 |
| FDFT1 | AK057726 | 6 | 9 | 0.8128 | 1.0000 | 1.3413 | 0.424 | 1.34 | 2 | 1.32 |
| FDFT1 | AK296043 | 0 | 20 | 0.0010 | 0.0425 | 21.2109 | 4.407 | 21.21 | 20 | 4.34 |
| FDFT1 | AK297868 | 105 | 181 | 0.0991 | 0.7120 | 1.7107 | 0.775 | 1.71 | 76 | 6.24 |
| FDFT1 | AK300059 | 2 | 0 | 0.0804 | 0.6550 | 0.3881 | −1.365 | 2.58 | 2 | 0.66 |
| FDFT1 | AK300245 | 6 | 24 | 0.1186 | 0.7825 | 3.8106 | 1.930 | 3.81 | 19 | 4.22 |
| FDFT1 | AK301617 | 0 | 6 | 0.1437 | 0.8698 | 5.4553 | 2.448 | 5.46 | 6 | 2.55 |
| FDFT1 | AK311246 | 367 | 805 | 0.0000 | 0.0002 | 2.1901 | 1.131 | 2.19 | 438 | 8.78 |
| FDFT1 | AK315993 | 26 | 31 | 0.8907 | 1.0000 | 1.1754 | 0.233 | 1.18 | 5 | 2.24 |
| FDFT1 | AK316033 | 45 | 75 | 0.2860 | 1.0000 | 1.6594 | 0.731 | 1.66 | 30 | 4.91 |
| FDFT1 | AK316351 | 74 | 80 | 0.8634 | 1.0000 | 1.0871 | 0.121 | 1.09 | 7 | 2.70 |
| FDFT1 | AK316531 | 5 | 12 | 0.4463 | 1.0000 | 2.2247 | 1.154 | 2.22 | 7 | 2.81 |
| FDFT1 | NM_004462 | 2086 | 5917 | 0.0000 | 0.0000 | 2.8352 | 1.503 | 2.84 | 3831 | 11.90 |
| FDPS | NM_001135821 | 373 | 601 | 0.0060 | 0.1557 | 1.6073 | 0.685 | 1.61 | 227 | 7.83 |
| FDPS | NM_001135822 | 1144 | 2398 | 0.0000 | 0.0000 | 2.0949 | 1.067 | 2.09 | 1254 | 10.29 |
| FDPS | NM_001242824 | 1204 | 2103 | 0.0000 | 0.0001 | 1.7469 | 0.805 | 1.75 | 900 | 9.81 |
| FDPS | NM_001242825 | 27 | 59 | 0.1957 | 1.0000 | 2.1126 | 1.079 | 2.11 | 32 | 4.98 |
| FDPS | NM_002004 | 41 | 107 | 0.0314 | 0.4301 | 2.5881 | 1.372 | 2.59 | 66 | 6.05 |
| FER | AK293376 | 10 | 2 | 0.1926 | 1.0000 | 0.2860 | −1.806 | 3.50 | 8 | 2.99 |
| FER | AK296874 | 0 | 2 | 0.1673 | 0.9262 | 2.6320 | 1.396 | 2.63 | 2 | 0.71 |
| FER | AK299855 | 93 | 8 | 0.0000 | 0.0015 | 0.0926 | −3.433 | 10.80 | 85 | 6.41 |
| FER | BC058030 | 3 | 2 | 0.7980 | 1.0000 | 0.7130 | −0.488 | 1.40 | 1 | 0.21 |
| FER | NM_005246 | 341 | 109 | 0.0000 | 0.0018 | 0.3210 | −1.639 | 3.12 | 232 | 7.86 |
| FEZ1 | AK296554 | 0 | 3 | 0.0941 | 0.6918 | 4.2444 | 2.086 | 4.24 | 3 | 1.70 |
| FEZ1 | CCDS44758 | 5 | 7 | 0.8229 | 1.0000 | 1.3473 | 0.430 | 1.35 | 2 | 0.99 |
| FEZ1 | NM_005103 | 267 | 447 | 0.0102 | 0.2222 | 1.6738 | 0.743 | 1.67 | 180 | 7.49 |
| FEZ1 | NM_022549 | 71 | 1 | 0.0000 | 0.0001 | 0.0317 | −4.980 | 31.56 | 69 | 6.11 |
| FHOD3 | AB051482 | 280 | 98 | 0.0003 | 0.0165 | 0.3516 | −1.508 | 2.84 | 182 | 7.51 |
| FHOD3 | AB084087 | 101 | 0 | 0.0000 | 0.0000 | 0.0098 | −6.674 | 102.10 | 101 | 6.66 |
| FHOD3 | AK128053 | 15 | 13 | 0.8731 | 1.0000 | 0.8974 | −0.156 | 1.11 | 2 | 0.72 |
| FHOD3 | AK308859 | 19 | 6 | 0.2234 | 1.0000 | 0.3689 | −1.439 | 2.71 | 13 | 3.68 |
| FHOD3 | BC058897 | 65 | 28 | 0.1097 | 0.7500 | 0.4349 | −1.201 | 2.30 | 37 | 5.22 |
| FHOD3 | HM191478 | 14 | 4 | 0.1952 | 1.0000 | 0.3167 | −1.659 | 3.16 | 10 | 3.38 |
| FHOD3 | NM_025135 | 453 | 250 | 0.0041 | 0.1209 | 0.5522 | −0.857 | 1.81 | 203 | 7.67 |
| FLII | AK295814 | 5 | 13 | 0.3710 | 1.0000 | 2.3273 | 1.219 | 2.33 | 8 | 2.99 |
| FLII | BC021885 | 3458 | 3822 | 0.2913 | 1.0000 | 1.1053 | 0.144 | 1.11 | 364 | 8.51 |
| FLII | NM_001256264 | 156 | 0 | 0.0000 | 0.0000 | 0.0064 | −7.291 | 156.56 | 156 | 7.28 |
| FLII | NM_001256265 | 14 | 0 | 0.0021 | 0.0749 | 0.0658 | −3.925 | 15.19 | 14 | 3.83 |
| FLII | NM_002018 | 3744 | 3619 | 0.7879 | 1.0000 | 0.9666 | −0.049 | 1.03 | 125 | 6.97 |
| FLNB | AF353666 | 1 | 1 | 0.7310 | 1.0000 | 0.7328 | −0.448 | 1.36 | 1 | −0.73 |
| FLNB | NM_001164317 | 681 | 433 | 0.0049 | 0.1359 | 0.6357 | −0.654 | 1.57 | 248 | 7.96 |
| FLNB | NM_001164318 | 1197 | 429 | 0.0000 | 0.0000 | 0.3591 | −1.478 | 2.78 | 768 | 9.58 |
| FLNB | NM_001164319 | 3504 | 3149 | 0.2242 | 1.0000 | 0.8989 | −0.154 | 1.11 | 354 | 8.47 |
| FLNB | NM_001457 | 11022 | 7590 | 0.0000 | 0.0013 | 0.6887 | −0.538 | 1.45 | 3431 | 11.74 |

TABLE 8-continued

RNA Abundance Modulation

| Gene | Trx_ID | ave DMSO | ave Cpd | padj (q val, FDR) | ttest (p val) | FC (x + 1) | L₂FC (x + 1) | amp FC (x + 1) | abs (Cpd-DMSO) | L₂abs (Cpd-DMSO) |
|---|---|---|---|---|---|---|---|---|---|---|
| FNBP1 | AK000975 | 276 | 107 | 0.0008 | 0.0368 | 0.3901 | −1.358 | 2.56 | 169 | 7.40 |
| FNBP1 | AK001616 | 158 | 256 | 0.0671 | 0.6122 | 1.6171 | 0.693 | 1.62 | 98 | 6.61 |
| FNBP1 | AK023681 | 4 | 13 | 0.3625 | 1.0000 | 2.6266 | 1.393 | 2.63 | 9 | 3.14 |
| FNBP1 | BC143513 | 1226 | 825 | 0.0024 | 0.0823 | 0.6734 | −0.571 | 1.49 | 401 | 8.65 |
| FNBP1 | BC143514 | 108 | 0 | 0.0000 | 0.0000 | 0.0091 | −6.774 | 109.46 | 108 | 6.76 |
| FNBP1 | BC143515 | 158 | 16 | 0.0000 | 0.0002 | 0.1056 | −3.243 | 9.47 | 143 | 7.16 |
| FNBP1 | NM_015033 | 263 | 366 | 0.0838 | 0.6689 | 1.3897 | 0.475 | 1.39 | 103 | 6.68 |
| FOS | AK290907 | 239 | 51 | 0.0000 | 0.0003 | 0.2145 | −2.221 | 4.66 | 189 | 7.56 |
| FOS | AK298659 | 39 | 10 | 0.0687 | 0.6206 | 0.2853 | −1.809 | 3.51 | 29 | 4.84 |
| FOS | NM_005252 | 2826 | 344 | 0.0000 | 0.0000 | 0.1221 | −3.034 | 8.19 | 2482 | 11.28 |
| FOSB | AK225070 | 76 | 6 | 0.0000 | 0.0038 | 0.0858 | −3.543 | 11.66 | 70 | 6.13 |
| FOSB | EU178110 | 0 | 6 | 0.0345 | 0.4512 | 7.4119 | 2.890 | 7.41 | 6 | 2.68 |
| FOSB | EU178111 | 40 | 12 | 0.0569 | 0.5766 | 0.3242 | −1.625 | 3.08 | 28 | 4.81 |
| FOSB | EU178112 | 28 | 0 | 0.0001 | 0.0041 | 0.0339 | −4.881 | 29.48 | 28 | 4.83 |
| FOSB | EU178113 | 0 | 0 | 9999 | 9999 | 1.0000 | 0.000 | 1.00 | 0 | 0 |
| FOSB | EU178114 | 7 | 3 | 0.5247 | 1.0000 | 0.4759 | −1.071 | 2.10 | 4 | 2.12 |
| FOSB | EU178115 | 119 | 13 | 0.0000 | 0.0009 | 0.1144 | −3.128 | 8.74 | 106 | 6.73 |
| FOSB | EU178116 | 16 | 1 | 0.0231 | 0.3616 | 0.1191 | −3.070 | 8.40 | 15 | 3.87 |
| FOSB | NM_001114171 | 13 | 5 | 0.2890 | 1.0000 | 0.4559 | −1.133 | 2.19 | 8 | 2.95 |
| FOSB | NM_006732 | 31 | 3 | 0.0113 | 0.2348 | 0.1243 | −3.008 | 8.04 | 28 | 4.80 |
| FOXM1 | NM_001243088 | 1088 | 867 | 0.0714 | 0.6296 | 0.7976 | −0.326 | 1.25 | 220 | 7.78 |
| FOXM1 | NM_001243089 | 497 | 735 | 0.0073 | 0.1773 | 1.4771 | 0.563 | 1.48 | 238 | 7.89 |
| FOXM1 | NM_021953 | 5048 | 1244 | 0.0000 | 0.0000 | 0.2466 | −2.020 | 4.05 | 3804 | 11.89 |
| FOXM1 | NM_202002 | 574 | 4527 | 0.0000 | 0.0000 | 7.8710 | 2.977 | 7.87 | 3953 | 11.95 |
| FYN | AY429536 | 0 | 0 | 0.4919 | 1.0000 | 0.7603 | −0.395 | 1.32 | 0 | −1.67 |
| FYN | BC015055 | 563 | 239 | 0.0000 | 0.0011 | 0.4261 | −1.231 | 2.35 | 324 | 8.34 |
| FYN | NM_002037 | 1377 | 1320 | 0.7880 | 1.0000 | 0.9584 | −0.061 | 1.04 | 57 | 5.84 |
| FYN | NM_153047 | 582 | 521 | 0.5318 | 1.0000 | 0.8952 | −0.160 | 1.12 | 61 | 5.93 |
| FYN | NM_153048 | 0 | 0 | 9999 | 9999 | 1.0000 | 0.000 | 1.00 | 0 | 0 |
| GABPB1 | AK303901 | 15 | 10 | 0.8024 | 1.0000 | 0.6876 | −0.540 | 1.45 | 5 | 2.33 |
| GABPB1 | D13316 | 79 | 48 | 0.3022 | 1.0000 | 0.6120 | −0.708 | 1.63 | 31 | 4.96 |
| GABPB1 | NM_002041 | 38 | 78 | 0.1649 | 0.9215 | 2.0203 | 1.015 | 2.02 | 40 | 5.32 |
| GABPB1 | NM_005254 | 441 | 375 | 0.4349 | 1.0000 | 0.8504 | −0.234 | 1.18 | 66 | 6.05 |
| GABPB1 | NM_016654 | 68 | 263 | 0.0000 | 0.0012 | 3.8139 | 1.931 | 3.81 | 195 | 7.61 |
| GABPB1 | NM_016655 | 90 | 19 | 0.0034 | 0.1051 | 0.2239 | −2.159 | 4.47 | 71 | 6.15 |
| GABPB1 | NM_181427 | 49 | 89 | 0.1884 | 0.9897 | 1.7862 | 0.837 | 1.79 | 40 | 5.30 |
| GALC | AK302683 | 2 | 2 | 0.7036 | 1.0000 | 0.7522 | −0.411 | 1.33 | 1 | −0.21 |
| GALC | D25284 | 2 | 0 | 0.3276 | 1.0000 | 0.4748 | −1.075 | 2.11 | 2 | 0.59 |
| GALC | NM_000153 | 470 | 75 | 0.0000 | 0.0000 | 0.1615 | −2.631 | 6.19 | 395 | 8.63 |
| GALC | NM_001201401 | 0 | 0 | 9999 | 9999 | 1.0000 | 0.000 | 1.00 | 0 | 0 |
| GALC | NM_001201402 | 0 | 31 | 0.0001 | 0.0053 | 31.6822 | 4.986 | 31.68 | 31 | 4.94 |
| GAS7 | AK293755 | 0 | 0 | 9999 | 9999 | 1.0000 | 0.000 | 1.00 | 0 | 0 |
| GAS7 | AK294829 | 155 | 235 | 0.1371 | 0.8483 | 1.5112 | 0.596 | 1.51 | 80 | 6.32 |
| GAS7 | NM_003644 | 62 | 0 | 0.0000 | 0.0000 | 0.0159 | −5.978 | 63.03 | 62 | 5.95 |
| GAS7 | NM_201433 | 889 | 774 | 0.3880 | 1.0000 | 0.8704 | −0.200 | 1.15 | 115 | 6.85 |
| GGCT | AK021779 | 3 | 4 | 0.8939 | 1.0000 | 1.1596 | 0.214 | 1.16 | 1 | −0.63 |
| GGCT | NM_001199815 | 3 | 5 | 0.7440 | 1.0000 | 1.6353 | 0.710 | 1.64 | 2 | 1.16 |
| GGCT | NM_001199816 | 14 | 60 | 0.0223 | 0.3550 | 4.0099 | 2.004 | 4.01 | 46 | 5.51 |
| GGCT | NM_001199817 | 3 | 0 | 0.0643 | 0.6048 | 0.2461 | −2.022 | 4.06 | 3 | 1.61 |
| GGCT | NM_024051 | 542 | 944 | 0.0002 | 0.0121 | 1.7413 | 0.800 | 1.74 | 402 | 8.65 |
| GGCT | NR_037669 | 233 | 9 | 0.0000 | 0.0000 | 0.0433 | −4.528 | 23.07 | 224 | 7.81 |
| GJC1 | AK124339 | 35 | 22 | 0.4901 | 1.0000 | 0.6383 | −0.648 | 1.57 | 13 | 3.69 |
| GJC1 | CCDS11487 | 372 | 342 | 0.6949 | 1.0000 | 0.9189 | −0.122 | 1.09 | 30 | 4.92 |
| GJC1 | NM_001080383 | 76 | 358 | 0.0000 | 0.0000 | 4.6793 | 2.226 | 4.68 | 282 | 8.14 |
| GJC1 | NM_005497 | 1664 | 1804 | 0.4493 | 1.0000 | 1.0836 | 0.116 | 1.08 | 139 | 7.12 |
| GPSM2 | AB445462 | 489 | 353 | 0.0850 | 0.6722 | 0.7229 | −0.468 | 1.38 | 136 | 7.09 |
| GPSM2 | AK295563 | 627 | 213 | 0.0000 | 0.0000 | 0.3409 | −1.552 | 2.93 | 414 | 8.69 |
| GPSM2 | NM_013296 | 929 | 726 | 0.0609 | 0.5948 | 0.7819 | −0.355 | 1.28 | 203 | 7.66 |
| GRK6 | AK056697 | 152 | 9 | 0.0000 | 0.0000 | 0.0663 | −3.915 | 15.09 | 142 | 7.15 |
| GRK6 | NM_001004105 | 318 | 409 | 0.1623 | 0.9132 | 1.2832 | 0.360 | 1.28 | 90 | 6.50 |
| GRK6 | NM_001004106 | 726 | 504 | 0.0179 | 0.3100 | 0.6950 | −0.525 | 1.44 | 222 | 7.79 |
| GRK6 | NM_002082 | 207 | 286 | 0.1606 | 0.9103 | 1.3813 | 0.466 | 1.38 | 79 | 6.31 |
| HAS2 | NM_005328 | 577 | 1329 | 0.0000 | 0.0000 | 2.2996 | 1.201 | 2.30 | 752 | 9.55 |
| HAT1 | AK309001 | 3 | 10 | 0.3073 | 1.0000 | 2.7002 | 1.433 | 2.70 | 7 | 2.78 |
| HAT1 | NM_003642 | 2430 | 3005 | 0.0322 | 0.4366 | 1.2362 | 0.306 | 1.24 | 574 | 9.17 |
| HAT1 | NR_027862 | 70 | 0 | 0.0000 | 0.0000 | 0.0141 | −6.153 | 71.14 | 70 | 6.13 |
| HLTF | BC044659 | 408 | 98 | 0.0000 | 0.0000 | 0.2429 | −2.041 | 4.12 | 310 | 8.27 |
| HLTF | EU446704 | 109 | 0 | 0.0000 | 0.0000 | 0.0091 | −6.783 | 110.14 | 109 | 6.77 |
| HLTF | NM_003071 | 1233 | 178 | 0.0000 | 0.0000 | 0.1448 | −2.787 | 6.90 | 1055 | 10.04 |
| HLTF | NM_139048 | 249 | 33 | 0.0000 | 0.0000 | 0.1355 | −2.883 | 7.38 | 216 | 7.75 |
| HMGA1 | AK301434 | 0 | 5 | 0.0569 | 0.5766 | 6.2225 | 2.637 | 6.22 | 5 | 2.38 |
| HMGA1 | BC008963 | 1258 | 1282 | 0.9493 | 1.0000 | 1.0191 | 0.027 | 1.02 | 24 | 4.59 |
| HMGA1 | BC063434 | 1134 | 1532 | 0.0118 | 0.2427 | 1.3507 | 0.434 | 1.35 | 398 | 8.64 |
| HMGA1 | M23616 | 1601 | 2117 | 0.0072 | 0.1757 | 1.3227 | 0.403 | 1.32 | 517 | 9.01 |

TABLE 8-continued

RNA Abundance Modulation

| Gene | Trx_ID | ave DMSO | ave Cpd | padj (q val, FDR) | ttest (p val) | FC (x + 1) | L$_2$FC (x + 1) | amp FC (x + 1) | abs (Cpd-DMSO) | L$_2$abs (Cpd-DMSO) |
|---|---|---|---|---|---|---|---|---|---|---|
| HMGA1 | M23618 | 623 | 194 | 0.0000 | 0.0000 | 0.3132 | −1.675 | 3.19 | 429 | 8.74 |
| HMGA1 | M23619 | 3944 | 4589 | 0.1000 | 0.7167 | 1.1635 | 0.218 | 1.16 | 645 | 9.33 |
| HMGA1 | NM_002131 | 0 | 11 | 0.0101 | 0.2214 | 11.6543 | 3.543 | 11.65 | 11 | 3.41 |
| HMGA1 | NM_145899 | 2598 | 3278 | 0.0148 | 0.2768 | 1.2617 | 0.335 | 1.26 | 680 | 9.41 |
| HMGA1 | NM_145901 | 187 | 235 | 0.4294 | 1.0000 | 1.2521 | 0.324 | 1.25 | 47 | 5.57 |
| HMGA1 | NM_145903 | 122 | 233 | 0.0248 | 0.3769 | 1.9030 | 0.928 | 1.90 | 111 | 6.80 |
| HMGA1 | NM_145905 | 95 | 60 | 0.3744 | 1.0000 | 0.6341 | −0.657 | 1.58 | 35 | 5.13 |
| HMGB1 | AK304506 | 2725 | 1086 | 0.0000 | 0.0000 | 0.3987 | −1.327 | 2.51 | 1639 | 10.68 |
| HMGB1 | BX647267 | 211 | 157 | 0.2721 | 1.0000 | 0.7428 | −0.429 | 1.35 | 55 | 5.77 |
| HMGB1 | CR749614 | 163 | 116 | 0.3013 | 1.0000 | 0.7119 | −0.490 | 1.40 | 47 | 5.57 |
| HMGB1 | NM_002128 | 15411 | 16310 | 0.5139 | 1.0000 | 1.0583 | 0.082 | 1.06 | 899 | 9.81 |
| HMGCR | AK296499 | 33 | 34 | 1.0000 | 1.0000 | 1.0215 | 0.031 | 1.02 | 1 | −0.44 |
| HMGCR | AY429542 | 0 | 0 | 9999 | 9999 | 1.0000 | 0.000 | 1.00 | 0 | 0 |
| HMGCR | NM_000859 | 1840 | 4261 | 0.0000 | 0.0000 | 2.3153 | 1.211 | 2.32 | 2421 | 11.24 |
| HMGCR | NM_001130996 | 64 | 71 | 0.8869 | 1.0000 | 1.1071 | 0.147 | 1.11 | 7 | 2.80 |
| HMGCS1 | AK025736 | 7 | 21 | 0.2617 | 1.0000 | 2.6409 | 1.401 | 2.64 | 13 | 3.75 |
| HMGCS1 | NM_001098272 | 456 | 1491 | 0.0000 | 0.0000 | 3.2671 | 1.708 | 3.27 | 1035 | 10.02 |
| HMGCS1 | NM_002130 | 390 | 1247 | 0.0000 | 0.0000 | 3.1962 | 1.676 | 3.20 | 858 | 9.74 |
| HMOX1 | NM_002133 | 6214 | 12843 | 0.0000 | 0.0000 | 2.0665 | 1.047 | 2.07 | 6629 | 12.69 |
| HP1BP3 | AF113534 | 956 | 563 | 0.0006 | 0.0284 | 0.5896 | −0.762 | 1.70 | 393 | 8.62 |
| HP1BP3 | AK303456 | 149 | 111 | 0.3462 | 1.0000 | 0.7476 | −0.420 | 1.34 | 38 | 5.24 |
| HP1BP3 | AK304065 | 1904 | 1114 | 0.0000 | 0.0014 | 0.5853 | −0.773 | 1.71 | 790 | 9.63 |
| HP1BP3 | BC032139 | 56 | 46 | 0.6993 | 1.0000 | 0.8160 | −0.293 | 1.23 | 11 | 3.40 |
| HP1BP3 | BC046170 | 219 | 79 | 0.0016 | 0.0608 | 0.3620 | −1.466 | 2.76 | 140 | 7.13 |
| HP1BP3 | BC053327 | 390 | 165 | 0.0002 | 0.0138 | 0.4242 | −1.237 | 2.36 | 225 | 7.81 |
| HP1BP3 | CR749652 | 315 | 503 | 0.0142 | 0.2699 | 1.5954 | 0.674 | 1.60 | 188 | 7.56 |
| HP1BP3 | NM_016287 | 1673 | 362 | 0.0000 | 0.0000 | 0.2167 | −2.206 | 4.61 | 1311 | 10.36 |
| HSD17B12 | BC012536 | 6 | 8 | 0.7735 | 1.0000 | 1.4215 | 0.507 | 1.42 | 3 | 1.46 |
| HSD17B12 | NM_016142 | 1517 | 161 | 0.0000 | 0.0000 | 0.1065 | −3.231 | 9.39 | 1356 | 10.41 |
| HTT | NM_002111 | 3672 | 957 | 0.0000 | 0.0000 | 0.2607 | −1.940 | 3.84 | 2716 | 11.41 |
| IDI1 | AK311110 | 258 | 392 | 0.0450 | 0.5174 | 1.5178 | 0.602 | 1.52 | 134 | 7.07 |
| IDI1 | BC057827 | 41 | 50 | 0.7689 | 1.0000 | 1.2164 | 0.283 | 1.22 | 9 | 3.17 |
| IDI1 | BX648472 | 12 | 26 | 0.3080 | 1.0000 | 2.0519 | 1.037 | 2.05 | 14 | 3.79 |
| IDI1 | NM_004508 | 921 | 2665 | 0.0000 | 0.0000 | 2.8917 | 1.532 | 2.89 | 1744 | 10.77 |
| INHBA | M13436 | 247 | 341 | 0.1280 | 0.8144 | 1.3807 | 0.465 | 1.38 | 94 | 6.56 |
| INHBA | NM_002192 | 291 | 671 | 0.0000 | 0.0002 | 2.2977 | 1.200 | 2.30 | 379 | 8.57 |
| INSIG1 | NM_005542 | 1356 | 6302 | 0.0000 | 0.0000 | 4.6437 | 2.215 | 4.64 | 4946 | 12.27 |
| INSIG1 | NM_198336 | 113 | 496 | 0.0000 | 0.0000 | 4.3684 | 2.127 | 4.37 | 383 | 8.58 |
| INSIG1 | NM_198337 | 16 | 26 | 0.5230 | 1.0000 | 1.6069 | 0.684 | 1.61 | 10 | 3.37 |
| KANSL3 | AF311326 | 10 | 17 | 0.5621 | 1.0000 | 1.7194 | 0.782 | 1.72 | 8 | 2.94 |
| KANSL3 | AK000943 | 2 | 0 | 0.0669 | 0.6122 | 0.3138 | −1.672 | 3.19 | 2 | 1.13 |
| KANSL3 | AL136849 | 9 | 11 | 0.8697 | 1.0000 | 1.1376 | 0.186 | 1.14 | 1 | 0.52 |
| KANSL3 | BC032746 | 19 | 21 | 1.0000 | 1.0000 | 1.0627 | 0.088 | 1.06 | 1 | 0.36 |
| KANSL3 | BC051763 | 20 | 53 | 0.1566 | 0.9030 | 2.5510 | 1.351 | 2.55 | 33 | 5.03 |
| KANSL3 | NM_001115016 | 930 | 463 | 0.0000 | 0.0009 | 0.4978 | −1.006 | 2.01 | 468 | 8.87 |
| KANSL3 | NR_047653 | 296 | 668 | 0.0000 | 0.0003 | 2.2496 | 1.170 | 2.25 | 372 | 8.54 |
| KANSL3 | NR_047654 | 214 | 68 | 0.0008 | 0.0383 | 0.3211 | −1.639 | 3.11 | 146 | 7.19 |
| KANSL3 | NR_047656 | 0 | 192 | 0.0000 | 0.0000 | 193.2775 | 7.595 | 193.28 | 192 | 7.59 |
| KANSL3 | NR_047657 | 30 | 0 | 0.0001 | 0.0046 | 0.0326 | −4.940 | 30.70 | 30 | 4.89 |
| KANSL3 | NR_047658 | 54 | 45 | 0.8451 | 1.0000 | 0.8338 | −0.262 | 1.20 | 9 | 3.20 |
| KIAA1199 | AY581149 | 583 | 167 | 0.0000 | 0.0000 | 0.2869 | −1.801 | 3.49 | 417 | 8.70 |
| KIAA1199 | NM_018689 | 8350 | 4221 | 0.0000 | 0.0000 | 0.5056 | −0.984 | 1.98 | 4129 | 12.01 |
| KIAA1524 | AB040957 | 116 | 25 | 0.0018 | 0.0670 | 0.2206 | −2.181 | 4.53 | 91 | 6.51 |
| KIAA1524 | AK308315 | 15 | 13 | 0.7463 | 1.0000 | 0.9218 | −0.117 | 1.08 | 1 | 0.30 |
| KIAA1524 | AK310446 | 8 | 3 | 0.3898 | 1.0000 | 0.4389 | −1.188 | 2.28 | 5 | 2.32 |
| KIAA1524 | NM_020890 | 1676 | 515 | 0.0000 | 0.0000 | 0.3080 | −1.699 | 3.25 | 1160 | 10.18 |
| KIAA1715 | AK056532 | 165 | 51 | 0.0023 | 0.0796 | 0.3117 | −1.682 | 3.21 | 114 | 6.84 |
| KIAA1715 | AK301947 | 47 | 32 | 0.4379 | 1.0000 | 0.6720 | −0.573 | 1.49 | 16 | 3.99 |
| KIAA1715 | BC110329 | 36 | 1 | 0.0011 | 0.0456 | 0.0660 | −3.922 | 15.16 | 35 | 5.11 |
| KIAA1715 | BC143681 | 25 | 15 | 0.4691 | 1.0000 | 0.6351 | −0.655 | 1.57 | 9 | 3.23 |
| KIAA1715 | BC143683 | 8 | 0 | 0.0122 | 0.2475 | 0.1126 | −3.151 | 8.88 | 8 | 2.98 |
| KIAA1715 | NM_030650 | 2540 | 547 | 0.0000 | 0.0000 | 0.2156 | −2.214 | 4.64 | 1993 | 10.96 |
| KIF3A | AF041853 | 6 | 5 | 0.7645 | 1.0000 | 0.8343 | −0.261 | 1.20 | 1 | 0.15 |
| KIF3A | AK295089 | 6 | 0 | 0.0261 | 0.3873 | 0.1403 | −2.833 | 7.13 | 6 | 2.61 |
| KIF3A | AK313359 | 197 | 516 | 0.0000 | 0.0004 | 2.6091 | 1.384 | 2.61 | 319 | 8.32 |
| KIF3A | AM177178 | 0 | 14 | 0.0058 | 0.1506 | 15.2177 | 3.928 | 15.22 | 14 | 3.83 |
| KIF3A | NM_007054 | 352 | 57 | 0.0000 | 0.0000 | 0.1658 | −2.592 | 6.03 | 294 | 8.20 |
| KLF6 | AK293259 | 290 | 263 | 0.5647 | 1.0000 | 0.9057 | −0.143 | 1.10 | 27 | 4.78 |
| KLF6 | NM_001160124 | 36 | 9 | 0.0387 | 0.4779 | 0.2653 | −1.914 | 3.77 | 27 | 4.76 |
| KLF6 | NM_001160125 | 500 | 199 | 0.0000 | 0.0003 | 0.3991 | −1.325 | 2.51 | 301 | 8.23 |
| KLF6 | NM_001300 | 7240 | 9190 | 0.0033 | 0.1050 | 1.2692 | 0.344 | 1.27 | 1949 | 10.93 |
| KLF6 | NR_027653 | 0 | 34 | 0.0000 | 0.0023 | 34.6933 | 5.117 | 34.69 | 34 | 5.07 |
| KRT19 | NM_002276 | 875 | 2075 | 0.0000 | 0.0000 | 2.3694 | 1.245 | 2.37 | 1200 | 10.23 |
| KRT34 | NM_021013 | 2071 | 4690 | 0.0000 | 0.0000 | 2.2645 | 1.179 | 2.26 | 2619 | 11.36 |

TABLE 8-continued

RNA Abundance Modulation

| Gene | Trx_ID | ave DMSO | ave Cpd | padj (q val, FDR) | ttest (p val) | FC (x + 1) | L₂FC (x + 1) | amp FC (x + 1) | abs (Cpd-DMSO) | L₂abs (Cpd-DMSO) |
|---|---|---|---|---|---|---|---|---|---|---|
| KRTAP2-3 | NM_001165252 | 369 | 992 | 0.0000 | 0.0000 | 2.6856 | 1.425 | 2.69 | 623 | 9.28 |
| LAMA2 | CCDS5138 | 2401 | 2025 | 0.1340 | 0.8364 | 0.8433 | −0.246 | 1.19 | 376 | 8.56 |
| LAMA2 | NM_000426 | 51 | 0 | 0.0000 | 0.0000 | 0.0192 | −5.703 | 52.08 | 51 | 5.67 |
| LAMA2 | NM_001079823 | 25 | 81 | 0.0322 | 0.4366 | 3.1134 | 1.638 | 3.11 | 56 | 5.80 |
| LARP7 | NM_001267039 | 18 | 370 | 0.0000 | 0.0000 | 19.2503 | 4.267 | 19.25 | 351 | 8.46 |
| LARP7 | NM_015454 | 373 | 746 | 0.0000 | 0.0021 | 2.0002 | 1.000 | 2.00 | 374 | 8.55 |
| LARP7 | NM_016648 | 499 | 21 | 0.0000 | 0.0438 | 0.0438 | −4.512 | 22.82 | 478 | 8.90 |
| LARP7 | NR_049768 | 27 | 40 | 0.5808 | 1.0000 | 1.4661 | 0.552 | 1.47 | 13 | 3.69 |
| LDLR | AK295612 | 0 | 3 | 0.1436 | 0.8690 | 3.5519 | 1.829 | 3.55 | 3 | 1.35 |
| LDLR | FW340025 | 7 | 12 | 0.6023 | 1.0000 | 1.5410 | 0.624 | 1.54 | 5 | 2.20 |
| LDLR | NM_000527 | 1917 | 7239 | 0.0000 | 0.0000 | 3.7749 | 1.916 | 3.77 | 5322 | 12.38 |
| LDLR | NM_001195798 | 60 | 73 | 0.3725 | 1.0000 | 1.2058 | 0.270 | 1.21 | 13 | 3.66 |
| LDLR | NM_001195799 | 10 | 73 | 0.0011 | 0.0463 | 6.8857 | 2.784 | 6.89 | 63 | 5.99 |
| LDLR | NM_001195800 | 0 | 0 | 9999 | 9999 | 1.0000 | 0.000 | 1.00 | 0 | 0 |
| LDLR | NM_001195802 | 0 | 0 | 0.4919 | 1.0000 | 0.7231 | −0.468 | 1.38 | 0 | −1.39 |
| LDLR | NM_001195803 | 32 | 152 | 0.0001 | 0.0095 | 4.6826 | 2.227 | 4.68 | 121 | 6.91 |
| LDLR | S70123 | 10 | 37 | 0.0673 | 0.6123 | 3.6431 | 1.865 | 3.64 | 28 | 4.80 |
| LEMD3 | NM_001167614 | 61 | 0 | 0.0000 | 0.0000 | 0.0161 | −5.955 | 62.05 | 61 | 5.93 |
| LEMD3 | NM_014319 | 994 | 1162 | 0.2313 | 1.0000 | 1.1682 | 0.224 | 1.17 | 167 | 7.39 |
| LMAN2L | AK316331 | 8 | 4 | 0.6115 | 1.0000 | 0.5650 | −0.824 | 1.77 | 4 | 1.92 |
| LMAN2L | NM_001142292 | 0 | 4 | 0.0835 | 0.6673 | 5.3747 | 2.426 | 5.37 | 4 | 2.13 |
| LMAN2L | NM_030805 | 938 | 254 | 0.0000 | 0.0000 | 0.2711 | −1.883 | 3.69 | 684 | 9.42 |
| LMAN2L | NR_024518 | 0 | 7 | 0.0319 | 0.4342 | 7.6230 | 2.930 | 7.62 | 7 | 2.73 |
| LMAN2L | NR_024520 | 0 | 8 | 0.0295 | 0.4157 | 8.5073 | 3.089 | 8.51 | 8 | 2.91 |
| LMAN2L | NR_024521 | 6 | 0 | 0.0231 | 0.3616 | 0.1498 | −2.739 | 6.68 | 6 | 2.50 |
| LRCH4 | AF459638 | 59 | 0 | 0.0000 | 0.0000 | 0.0165 | −5.917 | 60.43 | 59 | 5.89 |
| LRCH4 | AK302410 | 131 | 157 | 0.5803 | 1.0000 | 1.1926 | 0.254 | 1.19 | 25 | 4.67 |
| LRCH4 | NM_002319 | 562 | 681 | 0.2201 | 1.0000 | 1.2124 | 0.278 | 1.21 | 119 | 6.90 |
| LRP8 | AK096482 | 262 | 334 | 0.2728 | 1.0000 | 1.2759 | 0.351 | 1.28 | 72 | 6.18 |
| LRP8 | AK122887 | 16 | 25 | 0.5644 | 1.0000 | 1.4916 | 0.577 | 1.49 | 9 | 3.10 |
| LRP8 | NM_001018054 | 0 | 73 | 0.0000 | 0.0000 | 74.4738 | 6.219 | 74.47 | 73 | 6.20 |
| LRP8 | NM_004631 | 194 | 271 | 0.2175 | 1.0000 | 1.3905 | 0.476 | 1.39 | 76 | 6.25 |
| LRP8 | NM_017522 | 40 | 151 | 0.0005 | 0.0268 | 3.7487 | 1.906 | 3.75 | 112 | 6.80 |
| LRP8 | NM_033300 | 304 | 695 | 0.0000 | 0.0001 | 2.2821 | 1.190 | 2.28 | 391 | 8.61 |
| LSS | NM_001001438 | 33 | 78 | 0.1011 | 0.7222 | 2.3001 | 1.202 | 2.30 | 45 | 5.49 |
| LSS | NM_001145436 | 168 | 475 | 0.0000 | 0.0001 | 2.8230 | 1.497 | 2.82 | 308 | 8.27 |
| LSS | NM_001145437 | 462 | 708 | 0.0109 | 0.2312 | 1.5320 | 0.615 | 1.53 | 246 | 7.94 |
| LSS | NM_002340 | 2086 | 3599 | 0.0000 | 0.0000 | 1.7246 | 0.786 | 1.72 | 1512 | 10.56 |
| MAGED4 | AK098830 | 89 | 4 | 0.0000 | 0.0001 | 0.0533 | −4.229 | 18.75 | 85 | 6.41 |
| MAGED4 | AK098830 | 84 | 208 | 0.0047 | 0.1311 | 2.4646 | 1.301 | 2.46 | 124 | 6.96 |
| MAGED4 | NM_001098800 | 84 | 5 | 0.0000 | 0.0008 | 0.0679 | −3.881 | 14.73 | 79 | 6.31 |
| MAGED4 | NM_001272061 | 5 | 14 | 0.2637 | 1.0000 | 2.3820 | 1.252 | 2.38 | 9 | 3.14 |
| MAGED4 | NM_001272061 | 0 | 0 | 1.0000 | 1.0000 | 1.2880 | 0.365 | 1.29 | 0 | −1.80 |
| MAGED4 | NM_001272062 | 104 | 8 | 0.0000 | 0.0007 | 0.0863 | −3.534 | 11.59 | 96 | 6.58 |
| MAGED4 | NM_001272063 | 454 | 26 | 0.0000 | 0.0000 | 0.0604 | −4.049 | 16.55 | 428 | 8.74 |
| MAGED4 | NM_177535 | 189 | 380 | 0.0006 | 0.0314 | 2.0010 | 1.001 | 2.00 | 190 | 7.57 |
| MAGED4B | NM_030801 | 571 | 1225 | 0.0000 | 0.0000 | 2.1426 | 1.099 | 2.14 | 654 | 9.35 |
| MAGED4B | NM_177537 | 171 | 269 | 0.0464 | 0.5211 | 1.5649 | 0.646 | 1.56 | 97 | 6.61 |
| MAN1A2 | AK023308 | 37 | 11 | 0.1219 | 0.7938 | 0.3217 | −1.636 | 3.11 | 26 | 4.69 |
| MAN1A2 | NM_006699 | 2000 | 516 | 0.0000 | 0.0000 | 0.2581 | −1.954 | 3.87 | 1485 | 10.54 |
| MEDAG | NM_032849 | 167 | 36 | 0.0001 | 0.0091 | 0.2182 | −2.197 | 4.58 | 131 | 7.03 |
| MEF2D | AK308641 | 341 | 307 | 0.6677 | 1.0000 | 0.9011 | −0.150 | 1.11 | 34 | 5.08 |
| MEF2D | BC032479 | 0 | 0 | 9999 | 9999 | 1.0000 | 0.000 | 1.00 | 0 | 0 |
| MEF2D | BC064988 | 1350 | 1214 | 0.3747 | 1.0000 | 0.8992 | −0.153 | 1.11 | 136 | 7.09 |
| MEF2D | NM_001271629 | 75 | 285 | 0.0000 | 0.0007 | 3.7809 | 1.919 | 3.78 | 210 | 7.72 |
| MEMO1 | AK022169 | 34 | 16 | 0.2695 | 1.0000 | 0.4847 | −1.045 | 2.06 | 18 | 4.16 |
| MEMO1 | AK057760 | 16 | 2 | 0.0639 | 0.6048 | 0.1869 | −2.419 | 5.35 | 14 | 3.79 |
| MEMO1 | AK290753 | 664 | 212 | 0.0000 | 0.0000 | 0.3208 | −1.640 | 3.12 | 451 | 8.82 |
| MEMO1 | AK295755 | 9 | 8 | 0.8859 | 1.0000 | 0.8905 | −0.167 | 1.12 | 1 | 0.17 |
| MEMO1 | NM_001137602 | 21 | 9 | 0.3147 | 1.0000 | 0.4264 | −1.230 | 2.35 | 13 | 3.68 |
| MEMO1 | NM_015955 | 315 | 82 | 0.0000 | 0.0005 | 0.2636 | −1.924 | 3.79 | 233 | 7.86 |
| MFGE8 | AK095908 | 4 | 4 | 0.9572 | 1.0000 | 0.9364 | −0.095 | 1.07 | 0 | −1.55 |
| MFGE8 | AK304627 | 3 | 26 | 0.0354 | 0.4574 | 6.1423 | 2.619 | 6.14 | 23 | 4.52 |
| MFGE8 | AK310357 | 4 | 6 | 0.8783 | 1.0000 | 1.3638 | 0.448 | 1.36 | 2 | 0.91 |
| MFGE8 | BX537974 | 161 | 461 | 0.0000 | 0.0007 | 2.8412 | 1.506 | 2.84 | 299 | 8.22 |
| MFGE8 | NM_001114614 | 571 | 630 | 0.5731 | 1.0000 | 1.1021 | 0.140 | 1.10 | 58 | 5.87 |
| MFGE8 | NM_005928 | 4339 | 3751 | 0.1466 | 0.8778 | 0.8645 | −0.210 | 1.16 | 588 | 9.20 |
| MICAL2 | AB110785 | 3155 | 3200 | 0.8307 | 1.0000 | 1.0143 | 0.020 | 1.01 | 45 | 5.49 |
| MICAL2 | AB110786 | 9518 | 9176 | 0.7069 | 1.0000 | 0.9640 | −0.053 | 1.04 | 342 | 8.42 |
| MICAL2 | AK294845 | 0 | 0 | 9999 | 9999 | 1.0000 | 0.000 | 1.00 | 0 | 0 |
| MICAL2 | AK302580 | 215 | 43 | 0.0000 | 0.0011 | 0.2053 | −2.284 | 4.87 | 172 | 7.42 |
| MICAL2 | AK302893 | 155 | 146 | 0.9294 | 1.0000 | 0.9411 | −0.088 | 1.06 | 9 | 3.20 |
| MICAL2 | BC015755 | 350 | 325 | 0.7456 | 1.0000 | 0.9280 | −0.108 | 1.08 | 25 | 4.66 |
| MICAL2 | BX538021 | 117 | 192 | 0.0970 | 0.7022 | 1.6292 | 0.704 | 1.63 | 74 | 6.22 |

TABLE 8-continued

RNA Abundance Modulation

| Gene | Trx_ID | ave DMSO | ave Cpd | padj (q val, FDR) | ttest (p val) | FC (x + 1) | L$_2$FC (x + 1) | amp FC (x + 1) | abs (Cpd-DMSO) | L$_2$abs (Cpd-DMSO) |
|---|---|---|---|---|---|---|---|---|---|---|
| MICAL2 | NM_014632 | 44 | 53 | 0.7460 | 1.0000 | 1.2079 | 0.273 | 1.21 | 9 | 3.22 |
| MMAB | AK295211 | 6 | 8 | 0.9326 | 1.0000 | 1.2263 | 0.294 | 1.23 | 2 | 0.74 |
| MMAB | NM_052845 | 288 | 583 | 0.0001 | 0.0089 | 2.0172 | 1.012 | 2.02 | 294 | 8.20 |
| MMAB | NR_038118 | 12 | 39 | 0.1174 | 0.7769 | 3.0406 | 1.604 | 3.04 | 27 | 4.73 |
| MMS19 | AF319947 | 1355 | 313 | 0.0000 | 0.0000 | 0.2314 | −2.112 | 4.32 | 1042 | 10.03 |
| MMS19 | AK025496 | 41 | 26 | 0.3736 | 1.0000 | 0.6532 | −0.614 | 1.53 | 15 | 3.87 |
| MMS19 | AK027710 | 39 | 0 | 0.0248 | 0.0005 | 0.0248 | −5.333 | 40.30 | 39 | 5.30 |
| MMS19 | AK056581 | 22 | 14 | 0.4966 | 1.0000 | 0.6229 | −0.683 | 1.61 | 9 | 3.14 |
| MMS19 | BC007298 | 11 | 8 | 0.7146 | 1.0000 | 0.7665 | −0.384 | 1.30 | 3 | 1.44 |
| MMS19 | BC080532 | 118 | 82 | 0.4678 | 1.0000 | 0.7030 | −0.508 | 1.42 | 35 | 5.14 |
| MMS19 | BC143285 | 44 | 3 | 0.0007 | 0.0339 | 0.0868 | −3.527 | 11.53 | 41 | 5.37 |
| MMS19 | NM_022362 | 73 | 15 | 0.0059 | 0.1528 | 0.2117 | −2.240 | 4.72 | 58 | 5.87 |
| MMS22L | AB385246 | 86 | 315 | 0.0000 | 0.0003 | 3.6207 | 1.856 | 3.62 | 229 | 7.84 |
| MMS22L | BC110860 | 9 | 2 | 0.1863 | 0.9839 | 0.2872 | −1.800 | 3.48 | 7 | 2.81 |
| MMS22L | BC142948 | 56 | 61 | 0.9171 | 1.0000 | 1.0748 | 0.104 | 1.07 | 4 | 2.10 |
| MMS22L | NM_198468 | 866 | 990 | 0.2997 | 1.0000 | 1.1427 | 0.192 | 1.14 | 124 | 6.95 |
| MSL3 | AK294255 | 0 | 6 | 0.0379 | 0.4705 | 7.0471 | 2.817 | 7.05 | 6 | 2.60 |
| MSL3 | AK304419 | 5 | 10 | 0.6175 | 1.0000 | 1.6717 | 0.741 | 1.67 | 4 | 2.09 |
| MSL3 | NM_001193270 | 8 | 21 | 0.2797 | 1.0000 | 2.6043 | 1.381 | 2.60 | 14 | 3.77 |
| MSL3 | NM_006800 | 289 | 329 | 0.4692 | 1.0000 | 1.1402 | 0.189 | 1.14 | 41 | 5.34 |
| MSL3 | NM_078628 | 158 | 22 | 0.0000 | 0.0007 | 0.1422 | −2.814 | 7.03 | 136 | 7.09 |
| MSL3 | NM_078629 | 318 | 514 | 0.0143 | 0.2717 | 1.6177 | 0.694 | 1.62 | 197 | 7.62 |
| MSMO1 | AK309206 | 2 | 7 | 0.4429 | 1.0000 | 2.3910 | 1.258 | 2.39 | 4 | 2.15 |
| MSMO1 | NM_001017369 | 73 | 360 | 0.0000 | 0.0000 | 4.8604 | 2.281 | 4.86 | 287 | 8.16 |
| MSMO1 | NM_006745 | 1034 | 4098 | 0.0000 | 0.0000 | 3.9605 | 1.986 | 3.96 | 3064 | 11.58 |
| MTAP | AF109294 | 0 | 0 | 9999 | 9999 | 1.0000 | 0.000 | 1.00 | 0 | 0 |
| MTAP | AK300592 | 113 | 164 | 0.2183 | 1.0000 | 1.4528 | 0.539 | 1.45 | 51 | 5.69 |
| MTAP | AK309365 | 110 | 24 | 0.0032 | 0.1016 | 0.2278 | −2.134 | 4.39 | 86 | 6.42 |
| MTAP | BC012316 | 49 | 136 | 0.0101 | 0.2213 | 2.7160 | 1.441 | 2.72 | 86 | 6.43 |
| MTAP | CU693137 | 68 | 120 | 0.0806 | 0.6550 | 1.7428 | 0.801 | 1.74 | 51 | 5.68 |
| MTAP | HE654774 | 143 | 406 | 0.0000 | 0.0012 | 2.8277 | 1.500 | 2.83 | 263 | 8.04 |
| MTAP | HE654776 | 31 | 25 | 0.8181 | 1.0000 | 0.8099 | −0.304 | 1.23 | 6 | 2.60 |
| MTAP | HE654777 | 11 | 0 | 0.0051 | 0.1388 | 0.0831 | −3.589 | 12.04 | 11 | 3.46 |
| MTAP | NM_002451 | 1009 | 1625 | 0.0001 | 0.0070 | 1.6097 | 0.687 | 1.61 | 616 | 9.27 |
| MTERFD1 | AK001801 | 1 | 1 | 0.7288 | 1.0000 | 0.6969 | −0.521 | 1.43 | 1 | −0.54 |
| MTERFD1 | AK309002 | 2 | 0 | 0.0669 | 0.6122 | 0.3138 | −1.672 | 3.19 | 2 | 1.13 |
| MTERFD1 | NM_015942 | 366 | 118 | 0.0000 | 0.0010 | 0.3241 | −1.625 | 3.09 | 248 | 7.96 |
| MVD | AY203927 | 8 | 12 | 0.7068 | 1.0000 | 1.4248 | 0.511 | 1.42 | 4 | 1.91 |
| MVD | NM_002461 | 498 | 1316 | 0.0000 | 0.0000 | 2.6383 | 1.400 | 2.64 | 818 | 9.68 |
| MVK | AF217536 | 9 | 4 | 0.4445 | 1.0000 | 0.4726 | −1.081 | 2.12 | 5 | 2.37 |
| MVK | AK293130 | 16 | 15 | 0.9055 | 1.0000 | 0.9104 | −0.135 | 1.10 | 2 | 0.64 |
| MVK | AK295338 | 26 | 47 | 0.3050 | 1.0000 | 1.7845 | 0.836 | 1.78 | 21 | 4.40 |
| MVK | CU677575 | 20 | 48 | 0.1934 | 1.0000 | 2.3646 | 1.242 | 2.36 | 29 | 4.84 |
| MVK | NM_000431 | 166 | 462 | 0.0000 | 0.0003 | 2.7729 | 1.471 | 2.77 | 296 | 8.21 |
| MVK | NM_001114185 | 40 | 60 | 0.3651 | 1.0000 | 1.4706 | 0.556 | 1.47 | 19 | 4.28 |
| NASP | AK056161 | 578 | 576 | 0.9796 | 1.0000 | 0.9973 | −0.004 | 1.00 | 2 | 0.67 |
| NASP | AK092829 | 50 | 51 | 1.0000 | 1.0000 | 1.0105 | 0.015 | 1.01 | 1 | −0.89 |
| NASP | AK308001 | 69 | 59 | 0.8458 | 1.0000 | 0.8568 | −0.223 | 1.17 | 10 | 3.32 |
| NASP | AY700118 | 76 | 57 | 0.5624 | 1.0000 | 0.7635 | −0.389 | 1.31 | 18 | 4.18 |
| NASP | NM_001195193 | 0 | 0 | 9999 | 9999 | 1.0000 | 0.000 | 1.00 | 0 | 0 |
| NASP | NM_002482 | 225 | 0 | 0.0000 | 0.0000 | 0.0044 | −7.819 | 225.79 | 225 | 7.81 |
| NASP | NM_152298 | 1141 | 1675 | 0.0008 | 0.0374 | 1.4683 | 0.554 | 1.47 | 535 | 9.06 |
| NAV2 | AK001495 | 18 | 24 | 0.6259 | 1.0000 | 1.2645 | 0.339 | 1.26 | 5 | 2.36 |
| NAV2 | AK096037 | 10 | 3 | 0.2438 | 1.0000 | 0.3376 | −1.566 | 2.96 | 7 | 2.88 |
| NAV2 | AK290458 | 76 | 111 | 0.4041 | 1.0000 | 1.4527 | 0.539 | 1.45 | 35 | 5.12 |
| NAV2 | AK307574 | 35 | 17 | 0.2723 | 1.0000 | 0.5074 | −0.979 | 1.97 | 18 | 4.14 |
| NAV2 | CCDS58126 | 81 | 61 | 0.5379 | 1.0000 | 0.7572 | −0.401 | 1.32 | 20 | 4.32 |
| NAV2 | CCDS7851 | 844 | 884 | 0.6451 | 1.0000 | 1.0473 | 0.067 | 1.05 | 40 | 5.32 |
| NAV2 | NM_001111018 | 609 | 303 | 0.0002 | 0.0137 | 0.4980 | −1.006 | 2.01 | 306 | 8.26 |
| NAV2 | NM_001111019 | 243 | 122 | 0.0132 | 0.2593 | 0.5063 | −0.982 | 1.98 | 120 | 6.91 |
| NAV2 | NM_001244963 | 41 | 0 | 0.0000 | 0.0003 | 0.0236 | −5.404 | 42.33 | 41 | 5.37 |
| NAV2 | NM_182964 | 377 | 0 | 0.0000 | 0.0000 | 0.0026 | −8.564 | 378.49 | 377 | 8.56 |
| NEURL1B | GQ414758 | 61 | 20 | 0.0556 | 0.5724 | 0.3369 | −1.570 | 2.97 | 41 | 5.36 |
| NEURL1B | GQ414759 | 528 | 143 | 0.0000 | 0.0000 | 0.2716 | −1.881 | 3.68 | 385 | 8.59 |
| NEURL1B | NM_001142651 | 102 | 24 | 0.0038 | 0.1160 | 0.2429 | −2.041 | 4.12 | 78 | 6.28 |
| NFE2L1 | AK294553 | 46 | 51 | 0.7900 | 1.0000 | 1.0946 | 0.130 | 1.09 | 4 | 2.16 |
| NFE2L1 | AK302387 | 222 | 0 | 0.0000 | 0.0000 | 0.0045 | −7.802 | 223.21 | 222 | 7.80 |
| NFE2L1 | AL833530 | 676 | 518 | 0.1042 | 0.7252 | 0.7670 | −0.383 | 1.30 | 158 | 7.30 |
| NFE2L1 | BX647976 | 696 | 659 | 0.8007 | 1.0000 | 0.9466 | −0.079 | 1.06 | 37 | 5.22 |
| NFE2L1 | L24123 | 7197 | 8315 | 0.0718 | 0.6302 | 1.1552 | 0.208 | 1.16 | 1117 | 10.13 |
| NFE2L1 | NM_003204 | 4767 | 4366 | 0.3539 | 1.0000 | 0.9158 | −0.127 | 1.09 | 402 | 8.65 |
| NID1 | AB209448 | 125 | 241 | 0.0370 | 0.4682 | 1.9289 | 0.948 | 1.93 | 117 | 6.87 |
| NID1 | BC045606 | 81 | 5 | 0.0000 | 0.0013 | 0.0791 | −3.660 | 12.64 | 75 | 6.24 |
| NID1 | NM_002508 | 9977 | 9268 | 0.4166 | 1.0000 | 0.9289 | −0.106 | 1.08 | 710 | 9.47 |

TABLE 8-continued

RNA Abundance Modulation

| Gene | Trx_ID | ave DMSO | ave Cpd | padj (q val, FDR) | ttest (p val) | FC (x + 1) | L$_2$FC (x + 1) | amp FC (x + 1) | abs (Cpd-DMSO) | L$_2$abs (Cpd-DMSO) |
|---|---|---|---|---|---|---|---|---|---|---|
| NPEPPS | AK096491 | 34 | 18 | 0.3718 | 1.0000 | 0.5505 | −0.861 | 1.82 | 16 | 3.96 |
| NPEPPS | AK293995 | 28 | 17 | 0.4638 | 1.0000 | 0.6152 | −0.701 | 1.63 | 11 | 3.47 |
| NPEPPS | AK296887 | 77 | 48 | 0.2709 | 1.0000 | 0.6281 | −0.671 | 1.59 | 29 | 4.86 |
| NPEPPS | AK303037 | 1299 | 494 | 0.0000 | 0.0000 | 0.3807 | −1.393 | 2.63 | 805 | 9.65 |
| NPEPPS | AK311414 | 0 | 5 | 0.0622 | 0.5984 | 6.0475 | 2.596 | 6.05 | 5 | 2.34 |
| NPEPPS | NM_006310 | 1601 | 974 | 0.0001 | 0.0080 | 0.6085 | −0.717 | 1.64 | 627 | 9.29 |
| NREP | BX649051 | 15 | 8 | 0.5328 | 1.0000 | 0.5719 | −0.806 | 1.75 | 7 | 2.74 |
| NREP | NM_001142474 | 7 | 18 | 0.3725 | 1.0000 | 2.1851 | 1.128 | 2.19 | 10 | 3.33 |
| NREP | NM_001142475 | 281 | 281 | 1.0000 | 1.0000 | 0.9973 | −0.004 | 1.00 | 1 | −0.39 |
| NREP | NM_001142476 | 6 | 9 | 0.7626 | 1.0000 | 1.4038 | 0.489 | 1.40 | 3 | 1.49 |
| NREP | NM_001142477 | 20 | 5 | 0.2239 | 1.0000 | 0.3059 | −1.709 | 3.27 | 15 | 3.88 |
| NREP | NM_001142478 | 867 | 786 | 0.4826 | 1.0000 | 0.9075 | −0.140 | 1.10 | 80 | 6.33 |
| NREP | NM_001142479 | 73 | 84 | 0.8266 | 1.0000 | 1.1430 | 0.193 | 1.14 | 11 | 3.41 |
| NREP | NM_001142480 | 17 | 0 | 0.0013 | 0.0517 | 0.0562 | −4.153 | 17.79 | 17 | 4.07 |
| NREP | NM_001142481 | 130 | 0 | 0.0000 | 0.0077 | 0.0077 | −7.029 | 130.60 | 130 | 7.02 |
| NREP | NM_001142482 | 343 | 376 | 0.6827 | 1.0000 | 1.0958 | 0.132 | 1.10 | 33 | 5.04 |
| NREP | NM_001142483 | 76 | 61 | 0.6328 | 1.0000 | 0.8018 | −0.319 | 1.25 | 15 | 3.93 |
| NREP | NM_004772 | 7521 | 5219 | 0.0001 | 0.0043 | 0.6940 | −0.527 | 1.44 | 2301 | 11.17 |
| NRG1 | AK293270 | 37 | 15 | 0.2473 | 1.0000 | 0.4318 | −1.212 | 2.32 | 22 | 4.43 |
| NRG1 | AY207002 | 0 | 1 | 0.4902 | 1.0000 | 1.9792 | 0.985 | 1.98 | 1 | −0.03 |
| NRG1 | EF372275 | 0 | 15 | 0.0041 | 0.1209 | 15.6883 | 3.972 | 15.69 | 15 | 3.88 |
| NRG1 | EF372277 | 36 | 0 | 0.0000 | 0.0016 | 0.0273 | −5.194 | 36.60 | 36 | 5.15 |
| NRG1 | NM_001159995 | 99 | 32 | 0.0087 | 0.2000 | 0.3333 | −1.585 | 3.00 | 67 | 6.06 |
| NRG1 | NM_001159996 | 178 | 172 | 0.9125 | 1.0000 | 0.9652 | −0.051 | 1.04 | 6 | 2.64 |
| NRG1 | NM_001160001 | 138 | 79 | 0.1862 | 0.9836 | 0.5727 | −0.804 | 1.75 | 59 | 5.89 |
| NRG1 | NM_001160004 | 20 | 27 | 0.6497 | 1.0000 | 1.2948 | 0.373 | 1.29 | 6 | 2.65 |
| NRG1 | NM_001160007 | 1 | 1 | 0.8635 | 1.0000 | 1.3147 | 0.395 | 1.31 | 1 | −0.91 |
| NRG1 | NM_001160008 | 109 | 59 | 0.1737 | 0.9484 | 0.5496 | −0.864 | 1.82 | 49 | 5.63 |
| NRG1 | NM_004495 | 16 | 13 | 0.7926 | 1.0000 | 0.8446 | −0.244 | 1.18 | 3 | 1.39 |
| NRG1 | NM_013956 | 47 | 41 | 0.7328 | 1.0000 | 0.8878 | −0.172 | 1.13 | 5 | 2.41 |
| NRG1 | NM_013957 | 22 | 115 | 0.0003 | 0.0159 | 5.1294 | 2.359 | 5.13 | 94 | 6.55 |
| NRG1 | NM_013958 | 68 | 57 | 0.7281 | 1.0000 | 0.8464 | −0.241 | 1.18 | 11 | 3.41 |
| NRG1 | NM_013959 | 6 | 6 | 0.9285 | 1.0000 | 0.9539 | −0.068 | 1.05 | 0 | −1.64 |
| NRG1 | NM_013960 | 338 | 97 | 0.0000 | 0.0006 | 0.2878 | −1.797 | 3.47 | 242 | 7.92 |
| NRG1 | NM_013964 | 470 | 515 | 0.5217 | 1.0000 | 1.0965 | 0.133 | 1.10 | 45 | 5.51 |
| NRG1 | U02325 | 0 | 29 | 0.0002 | 0.0103 | 29.8000 | 4.897 | 29.80 | 29 | 4.85 |
| NRG1 | U02327 | 25 | 25 | 1.0000 | 1.0000 | 1.0125 | 0.018 | 1.01 | 0 | −1.63 |
| NSUN4 | AK097524 | 8 | 1 | 0.1448 | 0.8711 | 0.2265 | −2.142 | 4.41 | 7 | 2.84 |
| NSUN4 | AK128066 | 14 | 18 | 0.8286 | 1.0000 | 1.2923 | 0.370 | 1.29 | 4 | 2.08 |
| NSUN4 | NM_001256127 | 22 | 9 | 0.2939 | 1.0000 | 0.4373 | −1.193 | 2.29 | 13 | 3.72 |
| NSUN4 | NM_001256128 | 76 | 47 | 0.2673 | 1.0000 | 0.6194 | −0.691 | 1.61 | 29 | 4.88 |
| NSUN4 | NM_199044 | 337 | 100 | 0.0000 | 0.0015 | 0.2989 | −1.742 | 3.35 | 237 | 7.89 |
| NSUN4 | NR_045789 | 56 | 6 | 0.0019 | 0.0685 | 0.1262 | −2.987 | 7.93 | 50 | 5.63 |
| NSUN4 | NR_045790 | 14 | 7 | 0.3902 | 1.0000 | 0.5550 | −0.849 | 1.80 | 7 | 2.72 |
| NSUN4 | NR_045791 | 1 | 1 | 1.0000 | 1.0000 | 1.1858 | 0.246 | 1.19 | 0 | −1.61 |
| NT5C2 | AK127670 | 104 | 70 | 0.3341 | 1.0000 | 0.6788 | −0.559 | 1.47 | 34 | 5.08 |
| NT5C2 | AK295593 | 0 | 0 | 9999 | 9999 | 1.0000 | 0.000 | 1.00 | 0 | 0 |
| NT5C2 | NM_001134373 | 1643 | 757 | 0.0000 | 0.0000 | 0.4612 | −1.116 | 2.17 | 886 | 9.79 |
| NT5C2 | NM_012229 | 1248 | 596 | 0.0000 | 0.0000 | 0.4781 | −1.065 | 2.09 | 652 | 9.35 |
| NUP153 | NM_001278209 | 29 | 35 | 0.6909 | 1.0000 | 1.1974 | 0.260 | 1.20 | 6 | 2.57 |
| NUP153 | NM_001278210 | 66 | 0 | 0.0000 | 0.0000 | 0.0149 | −6.071 | 67.22 | 66 | 6.05 |
| NUP153 | NM_005124 | 2557 | 2772 | 0.4203 | 1.0000 | 1.0840 | 0.116 | 1.08 | 215 | 7.75 |
| P4HA1 | CCDS41537 | 171 | 406 | 0.0001 | 0.0073 | 2.3621 | 1.240 | 2.36 | 235 | 7.87 |
| P4HA1 | CCDS7320 | 810 | 374 | 0.0000 | 0.0002 | 0.4630 | −1.111 | 2.16 | 435 | 8.77 |
| P4HA1 | NM_000917 | 2558 | 2967 | 0.1057 | 0.7310 | 1.1596 | 0.214 | 1.16 | 408 | 8.67 |
| P4HA1 | NM_001017962 | 2498 | 2208 | 0.2301 | 1.0000 | 0.8841 | −0.178 | 1.13 | 290 | 8.18 |
| P4HA1 | NM_001142595 | 48 | 68 | 0.5869 | 1.0000 | 1.4046 | 0.490 | 1.40 | 20 | 4.32 |
| P4HA1 | NM_001142596 | 30 | 20 | 0.5037 | 1.0000 | 0.6845 | −0.547 | 1.46 | 10 | 3.30 |
| PABPC1 | AK298990 | 322 | 736 | 0.0000 | 0.0001 | 2.2862 | 1.193 | 2.29 | 415 | 8.70 |
| PABPC1 | AK303120 | 5917 | 3202 | 0.0000 | 0.0000 | 0.5411 | −0.886 | 1.85 | 2716 | 11.41 |
| PABPC1 | NM_002568 | 21334 | 19898 | 0.3930 | 1.0000 | 0.9327 | −0.101 | 1.07 | 1436 | 10.49 |
| PABPC1 | Y00345 | 612 | 484 | 0.1606 | 0.9103 | 0.7916 | −0.337 | 1.26 | 128 | 7.00 |
| PABPC1 | Z48501 | 3135 | 1799 | 0.0000 | 0.0000 | 0.5740 | −0.801 | 1.74 | 1336 | 10.38 |
| PAPD4 | AL833136 | 19 | 1 | 0.0110 | 0.2318 | 0.1044 | −3.260 | 9.58 | 18 | 4.17 |
| PAPD4 | BC047581 | 197 | 11 | 0.0000 | 0.0000 | 0.0610 | −4.035 | 16.39 | 186 | 7.54 |
| PAPD4 | NM_001114393 | 0 | 0 | 9999 | 9999 | 1.0000 | 0.000 | 1.00 | 0 | 0 |
| PAPD4 | NM_001114394 | 1038 | 201 | 0.0000 | 0.0000 | 0.1941 | −2.365 | 5.15 | 837 | 9.71 |
| PAPD4 | NM_173797 | 49 | 31 | 0.5000 | 1.0000 | 0.6414 | −0.641 | 1.56 | 18 | 4.17 |
| PCBP2 | AK023529 | 16 | 12 | 0.7018 | 1.0000 | 0.7579 | −0.400 | 1.32 | 4 | 2.01 |
| PCBP2 | AK130583 | 220 | 207 | 0.7738 | 1.0000 | 0.9421 | −0.086 | 1.06 | 13 | 3.68 |
| PCBP2 | AK296930 | 2380 | 2093 | 0.2271 | 1.0000 | 0.8796 | −0.185 | 1.14 | 287 | 8.16 |
| PCBP2 | AK299210 | 54 | 54 | 0.9713 | 1.0000 | 1.0035 | 0.005 | 1.00 | 0 | −2.39 |
| PCBP2 | AK302067 | 5 | 5 | 1.0000 | 1.0000 | 0.9645 | −0.052 | 1.04 | 0 | −2.22 |
| PCBP2 | NM_001098620 | 1274 | 1258 | 0.9178 | 1.0000 | 0.9868 | −0.019 | 1.01 | 17 | 4.07 |

TABLE 8-continued

RNA Abundance Modulation

| Gene | Trx_ID | ave DMSO | ave Cpd | padj (q val, FDR) | ttest (p val) | FC (x + 1) | L₂FC (x + 1) | amp FC (x + 1) | abs (Cpd-DMSO) | L₂abs (Cpd-DMSO) |
|---|---|---|---|---|---|---|---|---|---|---|
| PCBP2 | NM_001128911 | 960 | 639 | 0.0069 | 0.1719 | 0.6657 | −0.587 | 1.50 | 321 | 8.33 |
| PCBP2 | NM_001128912 | 782 | 1304 | 0.0005 | 0.0249 | 1.6670 | 0.737 | 1.67 | 522 | 9.03 |
| PCBP2 | NM_001128913 | 1380 | 1735 | 0.0591 | 0.5884 | 1.2569 | 0.330 | 1.26 | 355 | 8.47 |
| PCBP2 | NM_001128914 | 1427 | 1170 | 0.1046 | 0.7260 | 0.8198 | −0.287 | 1.22 | 257 | 8.01 |
| PCBP2 | NM_005016 | 4680 | 4435 | 0.5266 | 1.0000 | 0.9477 | −0.077 | 1.06 | 245 | 7.93 |
| PCBP2 | NM_031989 | 283 | 1 | 0.0000 | 0.0000 | 0.0057 | −7.457 | 175.70 | 282 | 8.14 |
| PCM1 | AB587340 | 921 | 547 | 0.0006 | 0.0299 | 0.5948 | −0.750 | 1.68 | 374 | 8.55 |
| PCM1 | AK302378 | 18 | 9 | 0.4694 | 1.0000 | 0.5259 | −0.927 | 1.90 | 9 | 3.17 |
| PCM1 | AK307583 | 158 | 47 | 0.0018 | 0.0674 | 0.2988 | −1.743 | 3.35 | 112 | 6.81 |
| PCM1 | BC000453 | 35 | 18 | 0.3344 | 1.0000 | 0.5366 | −0.898 | 1.86 | 16 | 4.04 |
| PCM1 | BC027477 | 22 | 21 | 0.8677 | 1.0000 | 0.9270 | −0.109 | 1.08 | 2 | 0.76 |
| PCM1 | BC133052 | 392 | 246 | 0.0340 | 0.4489 | 0.6272 | −0.673 | 1.59 | 147 | 7.20 |
| PCM1 | BC140946 | 990 | 348 | 0.0000 | 0.0000 | 0.3516 | −1.508 | 2.84 | 643 | 9.33 |
| PCM1 | NM_006197 | 634 | 297 | 0.0000 | 0.0024 | 0.4699 | −1.089 | 2.13 | 336 | 8.39 |
| PCSK9 | AK297473 | 3 | 0 | 0.0572 | 0.5766 | 0.2249 | −2.152 | 4.45 | 3 | 1.78 |
| PCSK9 | NM_174936 | 167 | 534 | 0.0000 | 0.0006 | 3.1844 | 1.671 | 3.18 | 367 | 8.52 |
| PDXDC1 | AK295168 | 862 | 12 | 0.0000 | 0.0000 | 0.0146 | −6.099 | 68.53 | 850 | 9.73 |
| PDXDC1 | AK299111 | 37 | 7 | 0.0198 | 0.3297 | 0.2007 | −2.317 | 4.98 | 30 | 4.91 |
| PDXDC1 | AK299799 | 35 | 3 | 0.0068 | 0.1681 | 0.1196 | −3.064 | 8.36 | 31 | 4.97 |
| PDXDC1 | AY203955 | 10 | 0 | 0.0068 | 0.1687 | 0.0882 | −3.503 | 11.34 | 10 | 3.37 |
| PDXDC1 | BC033748 | 24 | 9 | 0.2572 | 1.0000 | 0.4104 | −1.285 | 2.44 | 15 | 3.91 |
| PDXDC1 | BC053946 | 122 | 11 | 0.0000 | 0.0005 | 0.1008 | −3.310 | 9.92 | 111 | 6.79 |
| PDXDC1 | BX648066 | 115 | 0 | 0.0000 | 0.0000 | 0.0086 | −6.863 | 116.39 | 115 | 6.85 |
| PDXDC1 | NM_015027 | 1737 | 99 | 0.0000 | 0.0000 | 0.0576 | −4.119 | 17.37 | 1638 | 10.68 |
| PEPD | AK057538 | 8 | 3 | 0.4679 | 1.0000 | 0.4841 | −1.047 | 2.07 | 5 | 2.23 |
| PEPD | NM_000285 | 2231 | 926 | 0.0000 | 0.0000 | 0.4153 | −1.268 | 2.41 | 1305 | 10.35 |
| PEPD | NM_001166056 | 3 | 3 | 0.8870 | 1.0000 | 0.8648 | −0.210 | 1.16 | 1 | −0.83 |
| PEPD | NM_001166057 | 4 | 0 | 0.0417 | 0.4942 | 0.2106 | −2.247 | 4.75 | 4 | 1.91 |
| PHF19 | AK302996 | 298 | 543 | 0.0020 | 0.0713 | 1.8209 | 0.865 | 1.82 | 245 | 7.94 |
| PHF19 | BC044224 | 192 | 63 | 0.0028 | 0.0931 | 0.3329 | −1.587 | 3.00 | 129 | 7.01 |
| PHF19 | NM_001009936 | 505 | 140 | 0.0000 | 0.0000 | 0.2791 | −1.841 | 3.58 | 365 | 8.51 |
| PHF19 | NM_015651 | 1311 | 1615 | 0.0815 | 0.6592 | 1.2318 | 0.301 | 1.23 | 304 | 8.25 |
| PHF8 | AF091081 | 0 | 1 | 0.2667 | 1.0000 | 2.1518 | 1.106 | 2.15 | 1 | 0.20 |
| PHF8 | BC017720 | 39 | 26 | 0.4291 | 1.0000 | 0.6644 | −0.590 | 1.51 | 14 | 3.76 |
| PHF8 | NM_001184896 | 84 | 0 | 0.0000 | 0.0000 | 0.0118 | −6.403 | 84.62 | 84 | 6.39 |
| PHF8 | NM_001184897 | 132 | 151 | 0.6957 | 1.0000 | 1.1432 | 0.193 | 1.14 | 19 | 4.25 |
| PHF8 | NM_001184898 | 1 | 1 | 1.0000 | 1.0000 | 1.0196 | 0.028 | 1.02 | 0 | −4.50 |
| PHF8 | NM_015107 | 400 | 454 | 0.5221 | 1.0000 | 1.1350 | 0.183 | 1.14 | 54 | 5.76 |
| PHTF2 | AL136883 | 18 | 58 | 0.0241 | 0.3711 | 3.1505 | 1.656 | 3.15 | 40 | 5.32 |
| PHTF2 | AM393200 | 20 | 0 | 0.0006 | 0.0476 | 0.0474 | −4.392 | 21.00 | 20 | 4.32 |
| PHTF2 | AX746556 | 302 | 297 | 0.9443 | 1.0000 | 0.9833 | −0.024 | 1.02 | 5 | 2.34 |
| PHTF2 | BC018098 | 45 | 35 | 0.7391 | 1.0000 | 0.7888 | −0.342 | 1.27 | 10 | 3.27 |
| PHTF2 | BC032334 | 15 | 8 | 0.4846 | 1.0000 | 0.5616 | −0.832 | 1.78 | 7 | 2.83 |
| PHTF2 | NM_001127357 | 0 | 0 | 9999 | 9999 | 1.0000 | 0.000 | 1.00 | 0 | 0 |
| PHTF2 | NM_001127358 | 1975 | 2641 | 0.0053 | 0.1425 | 1.3371 | 0.419 | 1.34 | 666 | 9.38 |
| PHTF2 | NM_001127360 | 60 | 61 | 0.9638 | 1.0000 | 1.0203 | 0.029 | 1.02 | 1 | 0.31 |
| PHTF2 | NM_020432 | 645 | 207 | 0.0000 | 0.0000 | 0.3222 | −1.634 | 3.10 | 438 | 8.77 |
| PIK3C2B | BC094741 | 1 | 3 | 0.7641 | 1.0000 | 1.6006 | 0.679 | 1.60 | 1 | 0.44 |
| PIK3C2B | BC144342 | 54 | 1 | 0.0000 | 0.0004 | 0.0316 | −4.986 | 31.69 | 53 | 5.73 |
| PIK3C2B | NM_002646 | 0 | 40 | 0.0000 | 0.0008 | 40.6951 | 5.347 | 40.70 | 40 | 5.31 |
| PITPNB | AK302367 | 22 | 0 | 0.0003 | 0.0170 | 0.0440 | −4.505 | 22.70 | 22 | 4.44 |
| PITPNB | BC031427 | 18 | 5 | 0.1570 | 0.9043 | 0.3248 | −1.622 | 3.08 | 13 | 3.67 |
| PITPNB | CU689164 | 0 | 0 | 9999 | 9999 | 1.0000 | 0.000 | 1.00 | 0 | 0 |
| PITPNB | NM_012399 | 2924 | 909 | 0.0000 | 0.0000 | 0.3110 | −1.685 | 3.22 | 2015 | 10.98 |
| PLEC | NM_000445 | 5106 | 4213 | 0.0546 | 0.5689 | 0.8253 | −0.277 | 1.21 | 892 | 9.80 |
| PLEC | NM_201378 | 3797 | 2711 | 0.0006 | 0.0302 | 0.7141 | −0.486 | 1.40 | 1086 | 10.08 |
| PLEC | NM_201379 | 994 | 1011 | 0.8699 | 1.0000 | 1.0169 | 0.024 | 1.02 | 17 | 4.07 |
| PLEC | NM_201380 | 8452 | 7841 | 0.4407 | 1.0000 | 0.9277 | −0.108 | 1.08 | 611 | 9.25 |
| PLEC | NM_201381 | 52 | 0 | 0.0000 | 0.0000 | 0.0189 | −5.729 | 53.03 | 52 | 5.70 |
| PLEC | NM_201382 | 5341 | 3999 | 0.0012 | 0.0502 | 0.7488 | −0.417 | 1.34 | 1342 | 10.39 |
| PLEC | NM_201383 | 2100 | 1289 | 0.0000 | 0.0012 | 0.6138 | −0.704 | 1.63 | 811 | 9.66 |
| PLEC | NM_201384 | 12726 | 9573 | 0.0006 | 0.0283 | 0.7522 | −0.411 | 1.33 | 3153 | 11.62 |
| PMS1 | AB102869 | 34 | 13 | 0.2086 | 1.0000 | 0.4048 | −1.305 | 2.47 | 21 | 4.39 |
| PMS1 | AB102872 | 1 | 0 | 0.3227 | 1.0000 | 0.6155 | −0.700 | 1.62 | 1 | −0.68 |
| PMS1 | AB102874 | 0 | 0 | 9999 | 9999 | 1.0000 | 0.000 | 1.00 | 0 | 0 |
| PMS1 | AK295602 | 0 | 0 | 9999 | 9999 | 1.0000 | 0.000 | 1.00 | 0 | 0 |
| PMS1 | AK304634 | 0 | 0 | 9999 | 9999 | 1.0000 | 0.000 | 1.00 | 0 | 0 |
| PMS1 | AK316215 | 0 | 0 | 9999 | 9999 | 1.0000 | 0.000 | 1.00 | 0 | 0 |
| PMS1 | AY540750 | 14 | 1 | 0.0195 | 0.3256 | 0.1022 | −3.291 | 9.79 | 14 | 3.79 |
| PMS1 | AY540751 | 8 | 12 | 0.7845 | 1.0000 | 1.3729 | 0.457 | 1.37 | 3 | 1.77 |
| PMS1 | BC008410 | 4 | 3 | 0.8496 | 1.0000 | 0.7914 | −0.338 | 1.26 | 1 | 0.19 |
| PMS1 | BC036376 | 17 | 1 | 0.0191 | 0.3225 | 0.1177 | −3.087 | 8.49 | 16 | 3.97 |
| PMS1 | NM_000534 | 336 | 40 | 0.0000 | 0.0000 | 0.1201 | −3.058 | 8.33 | 297 | 8.21 |
| PMS1 | NM_001128143 | 0 | 4 | 0.0840 | 0.6697 | 5.2602 | 2.395 | 5.26 | 4 | 2.09 |

TABLE 8-continued

RNA Abundance Modulation

| Gene | Trx_ID | ave DMSO | ave Cpd | padj (q val, FDR) | ttest (p val) | FC (x + 1) | L$_2$FC (x + 1) | amp FC (x + 1) | abs (Cpd-DMSO) | L$_2$abs (Cpd-DMSO) |
|---|---|---|---|---|---|---|---|---|---|---|
| PMS1 | NM_001128144 | 18 | 0 | 0.0009 | 0.0405 | 0.0536 | −4.222 | 18.66 | 18 | 4.14 |
| POU2F1 | AK091438 | 0 | 13 | 0.0070 | 0.1723 | 13.7298 | 3.779 | 13.73 | 13 | 3.67 |
| POU2F1 | AK302525 | 0 | 0 | 9999 | 9999 | 1.0000 | 0.000 | 1.00 | 0 | 0 |
| POU2F1 | BC007388 | 12 | 8 | 0.7166 | 1.0000 | 0.7335 | −0.447 | 1.36 | 3 | 1.78 |
| POU2F1 | NM_001198786 | 52 | 0 | 0.0000 | 0.0000 | 0.0189 | −5.724 | 52.85 | 52 | 5.70 |
| POU2F1 | NM_002697 | 304 | 251 | 0.5165 | 1.0000 | 0.8257 | −0.276 | 1.21 | 53 | 5.73 |
| POU2F1 | NR_037163 | 0 | 40 | 0.0000 | 0.0008 | 40.9380 | 5.355 | 40.94 | 40 | 5.32 |
| POU2F1 | S66902 | 0 | 0 | 0.4919 | 1.0000 | 0.7231 | −0.468 | 1.38 | 0 | −1.39 |
| PPHLN1 | AK000186 | 4 | 0 | 0.0372 | 0.4696 | 0.1846 | −2.437 | 5.42 | 4 | 2.14 |
| PPHLN1 | AK299682 | 1 | 0 | 0.3227 | 1.0000 | 0.6144 | −0.703 | 1.63 | 1 | −0.67 |
| PPHLN1 | AK299951 | 63 | 118 | 0.1337 | 0.8352 | 1.8458 | 0.884 | 1.85 | 54 | 5.77 |
| PPHLN1 | AK303612 | 10 | 14 | 0.7725 | 1.0000 | 1.3474 | 0.430 | 1.35 | 4 | 1.96 |
| PPHLN1 | NM_001143787 | 296 | 194 | 0.0962 | 0.6986 | 0.6559 | −0.608 | 1.52 | 102 | 6.67 |
| PPHLN1 | NM_001143788 | 0 | 13 | 0.0048 | 0.1344 | 14.2459 | 3.832 | 14.25 | 13 | 3.73 |
| PPHLN1 | NM_001143789 | 251 | 46 | 0.0000 | 0.0001 | 0.1871 | −2.418 | 5.35 | 205 | 7.68 |
| PPHLN1 | NM_201438 | 2 | 8 | 0.3215 | 1.0000 | 2.5800 | 1.367 | 2.58 | 5 | 2.38 |
| PPHLN1 | NM_201439 | 313 | 656 | 0.0000 | 0.0023 | 2.0919 | 1.065 | 2.09 | 343 | 8.42 |
| PPHLN1 | NM_201440 | 260 | 32 | 0.0000 | 0.0000 | 0.1274 | −2.973 | 7.85 | 228 | 7.83 |
| PPHLN1 | NM_201515 | 24 | 82 | 0.0216 | 0.3476 | 3.3823 | 1.758 | 3.38 | 59 | 5.88 |
| PRKDC | NM_001081640 | 945 | 0 | 0.0000 | 0.0000 | 0.0011 | −9.886 | 946.46 | 945 | 9.88 |
| PRKDC | NM_006904 | 11464 | 2505 | 0.0000 | 0.0000 | 0.2186 | −2.194 | 4.57 | 8959 | 13.13 |
| PRSS23 | AK304301 | 4627 | 3518 | 0.0039 | 0.1165 | 0.7603 | −0.395 | 1.32 | 1110 | 10.12 |
| PRSS23 | BC063022 | 538 | 231 | 0.0000 | 0.0023 | 0.4307 | −1.215 | 2.32 | 307 | 8.26 |
| PRSS23 | CCDS8278 | 6499 | 4963 | 0.0026 | 0.0882 | 0.7637 | −0.389 | 1.31 | 1536 | 10.58 |
| PRSS23 | NM_007173 | 5004 | 3900 | 0.0076 | 0.1828 | 0.7794 | −0.360 | 1.28 | 1104 | 10.11 |
| PSMC1 | AK299121 | 4 | 22 | 0.0938 | 0.6918 | 4.3112 | 2.108 | 4.31 | 18 | 4.16 |
| PSMC1 | DQ891703 | 51 | 243 | 0.0000 | 0.0001 | 4.7073 | 2.235 | 4.71 | 192 | 7.59 |
| PSMC1 | NM_002802 | 3923 | 3901 | 0.9393 | 1.0000 | 0.9946 | −0.008 | 1.01 | 21 | 4.41 |
| PTPN14 | AK090596 | 45 | 42 | 0.9037 | 1.0000 | 0.9340 | −0.099 | 1.07 | 3 | 1.62 |
| PTPN14 | AK298120 | 20 | 8 | 0.4620 | 1.0000 | 0.4436 | −1.173 | 2.25 | 12 | 3.55 |
| PTPN14 | HQ116786 | 1284 | 551 | 0.0000 | 0.0000 | 0.4293 | −1.220 | 2.33 | 734 | 9.52 |
| PTPN14 | NM_005401 | 6964 | 6184 | 0.1702 | 0.9364 | 0.8880 | −0.171 | 1.13 | 780 | 9.61 |
| PUF60 | AK055941 | 1 | 0 | 0.3332 | 1.0000 | 0.5664 | −0.820 | 1.77 | 1 | −0.39 |
| PUF60 | NM_001136033 | 25 | 4 | 0.0614 | 0.5948 | 0.2067 | −2.275 | 4.84 | 20 | 4.35 |
| PUF60 | NM_001271096 | 89 | 288 | 0.0000 | 0.0007 | 3.2139 | 1.684 | 3.21 | 199 | 7.64 |
| PUF60 | NM_001271097 | 633 | 582 | 0.6301 | 1.0000 | 0.9199 | −0.120 | 1.09 | 51 | 5.67 |
| PUF60 | NM_001271098 | 181 | 84 | 0.0136 | 0.2632 | 0.4688 | −1.093 | 2.13 | 97 | 6.59 |
| PUF60 | NM_001271099 | 406 | 514 | 0.2267 | 1.0000 | 1.2661 | 0.340 | 1.27 | 108 | 6.76 |
| PUF60 | NM_001271100 | 0 | 25 | 0.0016 | 0.0615 | 20.1334 | 4.332 | 20.13 | 25 | 4.65 |
| PUF60 | NM_014281 | 941 | 931 | 0.8745 | 1.0000 | 0.9887 | −0.016 | 1.01 | 11 | 3.41 |
| PUF60 | NM_078480 | 1005 | 1134 | 0.3154 | 1.0000 | 1.1284 | 0.174 | 1.13 | 129 | 7.01 |
| PVR | AK094177 | 51 | 0 | 0.0000 | 0.0000 | 0.0191 | −5.707 | 52.23 | 51 | 5.68 |
| PVR | NM_001135768 | 494 | 425 | 0.4007 | 1.0000 | 0.8593 | −0.219 | 1.16 | 70 | 6.12 |
| PVR | NM_001135769 | 553 | 564 | 0.8852 | 1.0000 | 1.0202 | 0.029 | 1.02 | 11 | 3.48 |
| PVR | NM_001135770 | 310 | 351 | 0.5459 | 1.0000 | 1.1310 | 0.178 | 1.13 | 41 | 5.35 |
| PVR | NM_006505 | 1592 | 1903 | 0.1058 | 0.7312 | 1.1952 | 0.257 | 1.20 | 311 | 8.28 |
| RAB23 | AF161486 | 718 | 445 | 0.0059 | 0.1532 | 0.6204 | −0.689 | 1.61 | 273 | 8.09 |
| RAB23 | AK311123 | 0 | 0 | 9999 | 9999 | 1.0000 | 0.000 | 1.00 | 0 | 0 |
| RAB23 | NM_016277 | 870 | 1130 | 0.0473 | 0.5263 | 1.2988 | 0.377 | 1.30 | 260 | 8.02 |
| RAB23 | NM_183227 | 115 | 438 | 0.0000 | 0.0000 | 3.7764 | 1.917 | 3.78 | 322 | 8.33 |
| RAD23B | AK293532 | 2603 | 2222 | 0.1240 | 0.8032 | 0.8534 | −0.229 | 1.17 | 382 | 8.58 |
| RAD23B | NM_001244713 | 76 | 253 | 0.0000 | 0.0037 | 3.3065 | 1.725 | 3.31 | 177 | 7.47 |
| RAD23B | NM_001244724 | 7118 | 6344 | 0.1631 | 0.9159 | 0.8914 | −0.166 | 1.12 | 773 | 9.59 |
| RAD23B | NM_002874 | 108 | 282 | 0.0008 | 0.0367 | 2.6058 | 1.382 | 2.61 | 174 | 7.45 |
| RAP1A | M22995 | 1261 | 842 | 0.0037 | 0.1124 | 0.6677 | −0.583 | 1.50 | 419 | 8.71 |
| RAP1A | NM_001010935 | 327 | 1222 | 0.0000 | 0.0000 | 3.7296 | 1.899 | 3.73 | 895 | 9.81 |
| RAP1A | NM_002884 | 870 | 463 | 0.0000 | 0.0034 | 0.5331 | −0.907 | 1.88 | 407 | 8.67 |
| RASSF8 | AY665468 | 378 | 1094 | 0.0000 | 0.0000 | 2.8922 | 1.532 | 2.89 | 716 | 9.48 |
| RASSF8 | AY665470 | 8 | 9 | 0.9123 | 1.0000 | 1.1598 | 0.214 | 1.16 | 1 | 0.47 |
| RASSF8 | NM_001164746 | 5 | 0 | 0.0255 | 0.3818 | 0.1585 | −2.658 | 6.31 | 5 | 2.41 |
| RASSF8 | NM_001164747 | 860 | 642 | 0.0394 | 0.4834 | 0.7460 | −0.423 | 1.34 | 219 | 7.77 |
| RASSF8 | NM_001164748 | 1576 | 1186 | 0.0396 | 0.4858 | 0.7529 | −0.409 | 1.33 | 390 | 8.61 |
| RASSF8 | NM_007211 | 74 | 51 | 0.4125 | 1.0000 | 0.6943 | −0.526 | 1.44 | 23 | 4.52 |
| RBM10 | AK000962 | 2 | 9 | 0.1875 | 0.9872 | 3.5509 | 1.828 | 3.55 | 7 | 2.89 |
| RBM10 | NM_001204466 | 86 | 266 | 0.0001 | 0.0091 | 3.0570 | 1.612 | 3.06 | 179 | 7.49 |
| RBM10 | NM_001204467 | 603 | 407 | 0.0296 | 0.4164 | 0.6747 | −0.568 | 1.48 | 197 | 7.62 |
| RBM10 | NM_001204468 | 409 | 290 | 0.0869 | 0.6782 | 0.7099 | −0.494 | 1.41 | 119 | 6.89 |
| RBM10 | NM_005676 | 144 | 344 | 0.0003 | 0.0165 | 2.3838 | 1.253 | 2.38 | 200 | 7.65 |
| RBM10 | NM_152856 | 393 | 305 | 0.2121 | 1.0000 | 0.7778 | −0.363 | 1.29 | 88 | 6.45 |
| RCC1 | NM_001048194 | 19 | 131 | 0.0000 | 0.0031 | 6.5714 | 2.716 | 6.57 | 112 | 6.81 |
| RCC1 | NM_001048195 | 257 | 649 | 0.0000 | 0.0000 | 2.5191 | 1.333 | 2.52 | 392 | 8.62 |
| RCC1 | NM_001048199 | 84 | 355 | 0.0000 | 0.0000 | 4.1906 | 2.067 | 4.19 | 271 | 8.08 |
| RCC1 | NM_001269 | 1352 | 828 | 0.0002 | 0.0108 | 0.6128 | −0.707 | 1.63 | 524 | 9.03 |
| RCC1 | NR_030725 | 763 | 2501 | 0.0000 | 0.0000 | 3.2725 | 1.710 | 3.27 | 1737 | 10.76 |

TABLE 8-continued

RNA Abundance Modulation

| Gene | Trx_ID | ave DMSO | ave Cpd | padj (q val, FDR) | ttest (p val) | FC (x + 1) | L$_2$FC (x + 1) | amp FC (x + 1) | abs (Cpd-DMSO) | L$_2$abs (Cpd-DMSO) |
|---|---|---|---|---|---|---|---|---|---|---|
| RCC1 | NR_030726 | 144 | 315 | 0.0041 | 0.1210 | 2.1794 | 1.124 | 2.18 | 171 | 7.42 |
| RFWD2 | AK001278 | 463 | 59 | 0.0000 | 0.0000 | 0.1297 | −2.947 | 7.71 | 404 | 8.66 |
| RFWD2 | AK025789 | 86 | 6 | 0.0000 | 0.0014 | 0.0769 | −3.701 | 13.01 | 80 | 6.32 |
| RFWD2 | BC039723 | 37 | 10 | 0.0574 | 0.5776 | 0.2781 | −1.846 | 3.60 | 27 | 4.77 |
| RFWD2 | NM_001001740 | 106 | 6 | 0.0000 | 0.0002 | 0.0676 | −3.887 | 14.80 | 99 | 6.63 |
| RFWD2 | NM_022457 | 533 | 73 | 0.0000 | 0.0000 | 0.1395 | −2.841 | 7.17 | 459 | 8.84 |
| RNFT1 | AF100745 | 15 | 17 | 1.0000 | 1.0000 | 1.1003 | 0.138 | 1.10 | 2 | 0.69 |
| RNFT1 | AK294806 | 3 | 7 | 0.5467 | 1.0000 | 2.0416 | 1.030 | 2.04 | 4 | 2.11 |
| RNFT1 | AK296197 | 32 | 0 | 0.0000 | 0.0019 | 0.0303 | −5.046 | 33.03 | 32 | 5.00 |
| RNFT1 | BC006971 | 5 | 12 | 0.3875 | 1.0000 | 2.2964 | 1.199 | 2.30 | 7 | 2.88 |
| RNFT1 | NM_016125 | 179 | 412 | 0.0001 | 0.0074 | 2.2888 | 1.195 | 2.29 | 232 | 7.86 |
| RWDD4 | AK293274 | 22 | 26 | 0.7662 | 1.0000 | 1.1797 | 0.238 | 1.18 | 4 | 2.02 |
| RWDD4 | CCDS34111 | 414 | 656 | 0.0164 | 0.2935 | 1.5827 | 0.662 | 1.58 | 242 | 7.92 |
| RWDD4 | NM_152682 | 765 | 172 | 0.0000 | 0.0000 | 0.2265 | −2.142 | 4.41 | 592 | 9.21 |
| SAMD9L | AF474973 | 43 | 39 | 0.7598 | 1.0000 | 0.9283 | −0.107 | 1.08 | 3 | 1.64 |
| SAMD9L | AY195582 | 14 | 41 | 0.1511 | 0.8929 | 2.6951 | 1.430 | 2.70 | 26 | 4.71 |
| SAMD9L | AY195583 | 8 | 9 | 0.8792 | 1.0000 | 1.0919 | 0.127 | 1.09 | 1 | −0.21 |
| SAMD9L | AY195584 | 82 | 46 | 0.2972 | 1.0000 | 0.5648 | −0.824 | 1.77 | 36 | 5.17 |
| SAMD9L | AY195585 | 62 | 0 | 0.0000 | 0.0000 | 0.0158 | −5.980 | 63.13 | 62 | 5.96 |
| SAMD9L | CCDS34681 | 174 | 161 | 0.7986 | 1.0000 | 0.9229 | −0.116 | 1.08 | 14 | 3.76 |
| SAMD9L | DQ068177 | 19 | 20 | 1.0000 | 1.0000 | 1.0605 | 0.085 | 1.06 | 1 | 0.28 |
| SAMD9L | NM_152703 | 177 | 205 | 0.6758 | 1.0000 | 1.1619 | 0.216 | 1.16 | 29 | 4.85 |
| SART3 | AK299250 | 181 | 212 | 0.5657 | 1.0000 | 1.1683 | 0.224 | 1.17 | 31 | 4.94 |
| SART3 | AK304834 | 7 | 6 | 0.8219 | 1.0000 | 0.9483 | −0.083 | 1.06 | 0 | −1.24 |
| SART3 | BC024279 | 25 | 14 | 0.4020 | 1.0000 | 0.5573 | −0.844 | 1.79 | 12 | 3.53 |
| SART3 | BC041638 | 1 | 2 | 0.7308 | 1.0000 | 1.7297 | 0.791 | 1.73 | 1 | 0.50 |
| SART3 | BC143253 | 92 | 0 | 0.0000 | 0.0000 | 0.0107 | −6.546 | 93.45 | 92 | 6.53 |
| SART3 | CR933631 | 20 | 18 | 0.9473 | 1.0000 | 0.9350 | −0.097 | 1.07 | 1 | 0.42 |
| SART3 | NM_014706 | 1306 | 1453 | 0.4043 | 1.0000 | 1.1123 | 0.154 | 1.11 | 147 | 7.20 |
| SCAF4 | AK057840 | 3 | 4 | 0.9515 | 1.0000 | 1.2191 | 0.286 | 1.22 | 1 | −0.03 |
| SCAF4 | AL117417 | 13 | 15 | 0.9787 | 1.0000 | 1.1076 | 0.147 | 1.11 | 2 | 0.60 |
| SCAF4 | NM_001145444 | 53 | 0 | 0.0000 | 0.0000 | 0.0184 | −5.763 | 54.29 | 53 | 5.74 |
| SCAF4 | NM_001145445 | 508 | 423 | 0.3219 | 1.0000 | 0.8337 | −0.262 | 1.20 | 85 | 6.40 |
| SCAF4 | NM_020706 | 643 | 672 | 0.8229 | 1.0000 | 1.0441 | 0.062 | 1.04 | 28 | 4.83 |
| SCD | NM_005063 | 6549 | 17564 | 0.0000 | 0.0000 | 2.6816 | 1.423 | 2.68 | 11015 | 13.43 |
| SEC22A | AK057587 | 1 | 0 | 0.0917 | 0.6901 | 0.4445 | −1.170 | 2.25 | 1 | 0.32 |
| SEC22A | NM_012430 | 578 | 179 | 0.0000 | 0.0000 | 0.3105 | −1.687 | 3.22 | 399 | 8.64 |
| SEC61A1 | AK074928 | 0 | 0 | 9999 | 9999 | 1.0000 | 0.000 | 1.00 | 0 | 0 |
| SEC61A1 | AL831940 | 21 | 10 | 0.4084 | 1.0000 | 0.5127 | −0.964 | 1.95 | 11 | 3.43 |
| SEC61A1 | BC002951 | 3906 | 1936 | 0.0000 | 0.0000 | 0.4959 | −1.012 | 2.02 | 1969 | 10.94 |
| SEC61A1 | NM_013336 | 25225 | 26100 | 0.6425 | 1.0000 | 1.0346 | 0.049 | 1.03 | 874 | 9.77 |
| SERPINE2 | NM_001136528 | 16396 | 14840 | 0.2228 | 1.0000 | 0.9051 | −0.144 | 1.10 | 1556 | 10.60 |
| SERPINE2 | NM_001136530 | 1127 | 2465 | 0.0000 | 0.0000 | 2.1852 | 1.128 | 2.19 | 1337 | 10.39 |
| SERPINE2 | NM_006216 | 4286 | 3899 | 0.2686 | 1.0000 | 0.9098 | −0.136 | 1.10 | 387 | 8.59 |
| SERPINE2 | NR_073116 | 3 | 3 | 1.0000 | 1.0000 | 1.0844 | 0.117 | 1.08 | 0 | −1.53 |
| SF1 | CU675924 | 95 | 136 | 0.3281 | 1.0000 | 1.4241 | 0.510 | 1.42 | 41 | 5.35 |
| SF1 | D26121 | 9 | 14 | 0.6401 | 1.0000 | 1.4999 | 0.585 | 1.50 | 5 | 2.35 |
| SF1 | NM_001178030 | 288 | 199 | 0.1410 | 0.8604 | 0.6926 | −0.530 | 1.44 | 89 | 6.47 |
| SF1 | NM_001178031 | 1745 | 1056 | 0.0001 | 0.0043 | 0.6050 | −0.725 | 1.65 | 690 | 9.43 |
| SF1 | NM_004630 | 130 | 968 | 0.0000 | 0.0000 | 7.3874 | 2.885 | 7.39 | 838 | 9.71 |
| SF1 | NM_201995 | 268 | 242 | 0.6874 | 1.0000 | 0.9008 | −0.151 | 1.11 | 27 | 4.74 |
| SF1 | NM_201997 | 513 | 614 | 0.2560 | 1.0000 | 1.1958 | 0.258 | 1.20 | 101 | 6.65 |
| SF1 | NM_201998 | 2585 | 2403 | 0.4370 | 1.0000 | 0.9296 | −0.105 | 1.08 | 182 | 7.51 |
| SF1 | NR_033649 | 32 | 37 | 0.8938 | 1.0000 | 1.1544 | 0.207 | 1.15 | 5 | 2.36 |
| SF1 | NR_033650 | 2 | 9 | 0.2561 | 1.0000 | 3.4130 | 1.771 | 3.41 | 7 | 2.79 |
| SLC25A17 | AK298215 | 24 | 8 | 0.1905 | 0.9955 | 0.3758 | −1.412 | 2.66 | 16 | 3.97 |
| SLC25A17 | AK300553 | 3 | 336 | 0.0000 | 0.0000 | 81.8212 | 6.354 | 81.82 | 333 | 8.38 |
| SLC25A17 | BC024741 | 2 | 12 | 0.1272 | 0.8109 | 4.6272 | 2.210 | 4.63 | 10 | 3.39 |
| SLC25A17 | BX647991 | 10 | 8 | 0.7582 | 1.0000 | 0.8528 | −0.230 | 1.17 | 2 | 0.70 |
| SLC25A17 | NM_006358 | 778 | 221 | 0.0000 | 0.0000 | 0.2854 | −1.809 | 3.50 | 557 | 9.12 |
| SLC7A6 | AK310866 | 7 | 17 | 0.3640 | 1.0000 | 2.2254 | 1.154 | 2.23 | 10 | 3.28 |
| SLC7A6 | AK311610 | 0 | 85 | 0.0000 | 0.0000 | 86.4833 | 6.434 | 86.48 | 85 | 6.42 |
| SLC7A6 | CR749475 | 61 | 25 | 0.1200 | 0.7883 | 0.4202 | −1.251 | 2.38 | 36 | 5.18 |
| SLC7A6 | NM_001076785 | 677 | 262 | 0.0000 | 0.0001 | 0.3874 | −1.368 | 2.58 | 415 | 8.70 |
| SLC7A6 | NM_003983 | 940 | 367 | 0.0000 | 0.0000 | 0.3914 | −1.353 | 2.56 | 573 | 9.16 |
| SLC7A8 | AK094550 | 3 | 7 | 0.4365 | 1.0000 | 2.3549 | 1.236 | 2.35 | 5 | 2.25 |
| SLC7A8 | NM_001267036 | 18 | 11 | 0.4905 | 1.0000 | 0.5935 | −0.753 | 1.68 | 8 | 2.98 |
| SLC7A8 | NM_001267037 | 8 | 11 | 0.9173 | 1.0000 | 1.2904 | 0.368 | 1.29 | 3 | 1.46 |
| SLC7A8 | NM_012244 | 166 | 449 | 0.0000 | 0.0005 | 2.6932 | 1.429 | 2.69 | 283 | 8.14 |
| SLC7A8 | NM_182728 | 143 | 182 | 0.3794 | 1.0000 | 1.2731 | 0.348 | 1.27 | 39 | 5.30 |
| SLC7A8 | NR_049767 | 0 | 7 | 0.0375 | 0.4705 | 7.9096 | 2.984 | 7.91 | 7 | 2.79 |
| SMN2 | JQ657801 | 1 | 0 | 0.3227 | 1.0000 | 0.6132 | −0.705 | 1.63 | 1 | −0.67 |
| SMN2 | JQ657801 | 0 | 0 | 9999 | 9999 | 1.0000 | 0.000 | 1.00 | 0 | 0 |
| SMN2 | JQ690861 | 6 | 12 | 0.5189 | 1.0000 | 1.9932 | 0.995 | 1.99 | 7 | 2.72 |

TABLE 8-continued

RNA Abundance Modulation

| Gene | Trx_ID | ave DMSO | ave Cpd | padj (q val, FDR) | ttest (p val) | FC (x + 1) | L$_2$FC (x + 1) | amp FC (x + 1) | abs (Cpd-DMSO) | L$_2$abs (Cpd-DMSO) |
|---|---|---|---|---|---|---|---|---|---|---|
| SMN2 | JQ690864 | 4 | 0 | 0.0342 | 0.4489 | 0.1861 | −2.426 | 5.37 | 4 | 2.13 |
| SMN2 | JQ690866 | 0 | 2 | 0.1319 | 0.8273 | 3.0157 | 1.592 | 3.02 | 2 | 1.01 |
| SMN2 | JQ690867 | 12 | 0 | 0.0043 | 0.1240 | 0.0796 | −3.651 | 12.56 | 12 | 3.53 |
| SMN2 | JQ690868 | 4 | 0 | 0.0511 | 0.5451 | 0.2071 | −2.272 | 4.83 | 4 | 1.94 |
| SMN2 | JQ732167 | 0 | 0 | 9999 | 9999 | 1.0000 | 0.000 | 1.00 | 0 | 0 |
| SMN2 | JQ732167 | 0 | 0 | 9999 | 9999 | 1.0000 | 0.000 | 1.00 | 0 | 0 |
| SMN2 | JQ745297 | 0 | 0 | 9999 | 9999 | 1.0000 | 0.000 | 1.00 | 0 | 0 |
| SMN2 | NM_017411 | 446 | 756 | 0.0012 | 0.0486 | 1.6941 | 0.761 | 1.69 | 310 | 8.28 |
| SMN2 | NM_017411 | 0 | 8 | 0.0300 | 0.4196 | 9.0203 | 3.173 | 9.02 | 8 | 3.00 |
| SMN2 | NM_022875 | 225 | 0 | 0.0000 | 0.0000 | 0.0044 | −7.818 | 225.61 | 225 | 7.81 |
| SMN2 | NM_022875 | 0 | 0 | 9999 | 9999 | 1.0000 | 0.000 | 1.00 | 0 | 0 |
| SMN2 | NM_022876 | 0 | 28 | 0.0001 | 0.0087 | 29.0977 | 4.863 | 29.10 | 28 | 4.81 |
| SMN2 | NM_022876 | 0 | 0 | 9999 | 9999 | 1.0000 | 0.000 | 1.00 | 0 | 0 |
| SMN2 | NM_022877 | 29 | 0 | 0.0001 | 0.0042 | 0.0336 | −4.895 | 29.74 | 29 | 4.85 |
| SMN2 | NM_022877 | 3 | 0 | 0.0508 | 0.5451 | 0.2425 | −2.044 | 4.12 | 3 | 1.64 |
| SMYD3 | AK023594 | 6 | 12 | 0.4851 | 1.0000 | 1.9207 | 0.942 | 1.92 | 6 | 2.66 |
| SMYD3 | NM_001167740 | 221 | 159 | 0.2785 | 1.0000 | 0.7198 | −0.474 | 1.39 | 62 | 5.96 |
| SMYD3 | NM_022743 | 2835 | 1355 | 0.0000 | 0.0000 | 0.4780 | −1.065 | 2.09 | 1480 | 10.53 |
| SMYD5 | AK300779 | 59 | 0 | 0.0000 | 0.0168 | 0.0168 | −5.897 | 59.59 | 59 | 5.87 |
| SMYD5 | NM_006062 | 830 | 815 | 0.9300 | 1.0000 | 0.9811 | −0.028 | 1.02 | 16 | 3.97 |
| SNAP23 | NM_003825 | 1557 | 251 | 0.0000 | 0.0000 | 0.1619 | −2.627 | 6.18 | 1305 | 10.35 |
| SNAP23 | NM_130798 | 6 | 0 | 0.0261 | 0.3873 | 0.1403 | −2.833 | 7.13 | 6 | 2.61 |
| SNHG16 | BC042949 | 5 | 37 | 0.0187 | 0.3184 | 5.8960 | 2.560 | 5.90 | 31 | 4.96 |
| SNHG16 | NR_038108 | 90 | 7 | 0.0001 | 0.0041 | 0.0868 | −3.526 | 11.52 | 83 | 6.38 |
| SNHG16 | NR_038109 | 1353 | 286 | 0.0000 | 0.0000 | 0.2121 | −2.237 | 4.72 | 1067 | 10.06 |
| SNHG16 | NR_038110 | 0 | 9 | 0.0207 | 0.3394 | 9.8130 | 3.295 | 9.81 | 9 | 3.14 |
| SNHG16 | NR_038111 | 413 | 143 | 0.0000 | 0.0010 | 0.3479 | −1.523 | 2.87 | 270 | 8.08 |
| SQLE | NM_003129 | 1495 | 3560 | 0.0000 | 0.0000 | 2.3806 | 1.251 | 2.38 | 2065 | 11.01 |
| SQRDL | NM_001271213 | 117 | 393 | 0.0000 | 0.0001 | 3.3371 | 1.739 | 3.34 | 276 | 8.11 |
| SQRDL | NM_021199 | 149 | 143 | 0.9211 | 1.0000 | 0.9590 | −0.060 | 1.04 | 6 | 2.63 |
| SQSTM1 | AK098077 | 46 | 85 | 0.1949 | 1.0000 | 1.8146 | 0.860 | 1.81 | 39 | 5.27 |
| SQSTM1 | AX747927 | 40 | 29 | 0.5611 | 1.0000 | 0.7372 | −0.440 | 1.36 | 11 | 3.44 |
| SQSTM1 | NM_001142298 | 426 | 527 | 0.2249 | 1.0000 | 1.2358 | 0.305 | 1.24 | 101 | 6.65 |
| SQSTM1 | NM_001142299 | 1107 | 1301 | 0.1916 | 1.0000 | 1.1748 | 0.232 | 1.17 | 194 | 7.60 |
| SQSTM1 | NM_003900 | 5087 | 10467 | 0.0000 | 0.0000 | 2.0575 | 1.041 | 2.06 | 5380 | 12.39 |
| SRCAP | AB621816 | 420 | 274 | 0.0509 | 0.5451 | 0.6522 | −0.617 | 1.53 | 147 | 7.20 |
| SRCAP | AF143946 | 2826 | 2356 | 0.0788 | 0.6550 | 0.8337 | −0.262 | 1.20 | 470 | 8.88 |
| SRCAP | BC159099 | 416 | 398 | 0.8606 | 1.0000 | 0.9556 | −0.066 | 1.05 | 19 | 4.21 |
| SRCAP | NM_006662 | 325 | 695 | 0.0000 | 0.0004 | 2.1358 | 1.095 | 2.14 | 370 | 8.53 |
| SREBF1 | AB209609 | 4 | 0 | 0.0378 | 0.4705 | 0.1976 | −2.339 | 5.06 | 4 | 2.02 |
| SREBF1 | AB373958 | 54 | 27 | 0.2273 | 1.0000 | 0.5137 | −0.961 | 1.95 | 27 | 4.75 |
| SREBF1 | AB373959 | 152 | 156 | 0.9346 | 1.0000 | 1.0238 | 0.034 | 1.02 | 4 | 1.86 |
| SREBF1 | AK091131 | 117 | 433 | 0.0000 | 0.0000 | 3.6626 | 1.873 | 3.66 | 315 | 8.30 |
| SREBF1 | AK095325 | 47 | 19 | 0.1572 | 0.9046 | 0.4174 | −1.260 | 2.40 | 28 | 4.80 |
| SREBF1 | AK128320 | 20 | 22 | 0.9161 | 1.0000 | 1.0829 | 0.115 | 1.08 | 2 | 0.82 |
| SREBF1 | NM_001005291 | 19 | 0 | 0.0006 | 0.0284 | 0.0496 | −4.335 | 20.18 | 19 | 4.26 |
| SREBF1 | NM_004176 | 904 | 731 | 0.1649 | 0.9215 | 0.8089 | −0.306 | 1.24 | 173 | 7.43 |
| STARD4 | AK125317 | 83 | 182 | 0.0180 | 0.3107 | 2.1662 | 1.115 | 2.17 | 99 | 6.62 |
| STARD4 | AK315863 | 28 | 61 | 0.1387 | 0.8525 | 2.1348 | 1.094 | 2.13 | 33 | 5.04 |
| STARD4 | AK315869 | 27 | 123 | 0.0008 | 0.0380 | 4.4316 | 2.148 | 4.43 | 96 | 6.58 |
| STARD4 | BC042956 | 78 | 143 | 0.0913 | 0.6901 | 1.8195 | 0.864 | 1.82 | 65 | 6.02 |
| STARD4 | NM_139164 | 281 | 596 | 0.0000 | 0.0033 | 2.1202 | 1.084 | 2.12 | 316 | 8.30 |
| STAT1 | AK096686 | 207 | 32 | 0.0000 | 0.0001 | 0.1587 | −2.655 | 6.30 | 175 | 7.45 |
| STAT1 | AK225853 | 0 | 0 | 9999 | 9999 | 1.0000 | 0.000 | 1.00 | 0 | 0 |
| STAT1 | AK292604 | 411 | 64 | 0.0000 | 0.0000 | 0.1579 | −2.663 | 6.33 | 347 | 8.44 |
| STAT1 | GU211348 | 0 | 0 | 9999 | 9999 | 1.0000 | 0.000 | 1.00 | 0 | 0 |
| STAT1 | NM_007315 | 7566 | 1129 | 0.0000 | 0.0000 | 0.1493 | −2.744 | 6.70 | 6437 | 12.65 |
| STAT1 | NM_139266 | 788 | 61 | 0.0000 | 0.0000 | 0.0784 | −3.673 | 12.76 | 727 | 9.51 |
| STAU1 | AB209561 | 469 | 161 | 0.0000 | 0.0005 | 0.3441 | −1.539 | 2.91 | 308 | 8.27 |
| STAU1 | AY546099 | 323 | 359 | 0.4622 | 1.0000 | 1.1122 | 0.153 | 1.11 | 36 | 5.18 |
| STAU1 | NM_001037328 | 220 | 80 | 0.0023 | 0.0796 | 0.3687 | −1.439 | 2.71 | 139 | 7.12 |
| STAU1 | NM_004602 | 390 | 447 | 0.4193 | 1.0000 | 1.1442 | 0.194 | 1.14 | 56 | 5.82 |
| STAU1 | NM_017453 | 136 | 215 | 0.1662 | 0.9262 | 1.5761 | 0.656 | 1.58 | 79 | 6.30 |
| STAU1 | NM_017454 | 324 | 364 | 0.6044 | 1.0000 | 1.1233 | 0.168 | 1.12 | 40 | 5.32 |
| STEAP2 | DQ656062 | 0 | 11 | 0.0113 | 0.2349 | 11.9026 | 3.573 | 11.90 | 11 | 3.45 |
| STEAP2 | NM_001040665 | 109 | 22 | 0.0007 | 0.0320 | 0.2084 | −2.263 | 4.80 | 87 | 6.45 |
| STEAP2 | NM_001040666 | 70 | 8 | 0.0011 | 0.0466 | 0.1295 | −2.949 | 7.72 | 61 | 5.94 |
| STEAP2 | NM_001244944 | 83 | 45 | 0.2508 | 1.0000 | 0.5480 | −0.868 | 1.82 | 38 | 5.25 |
| STEAP2 | NM_001244945 | 0 | 0 | 9999 | 9999 | 1.0000 | 0.000 | 1.00 | 0 | 0 |
| STEAP2 | NM_001244946 | 2 | 0 | 0.2650 | 1.0000 | 0.3900 | −1.358 | 2.56 | 2 | 1.09 |
| STEAP2 | NM_152999 | 124 | 10 | 0.0000 | 0.0002 | 0.0861 | −3.537 | 11.61 | 115 | 6.84 |
| STRN3 | BC143933 | 16 | 6 | 0.3989 | 1.0000 | 0.4155 | −1.267 | 2.41 | 10 | 3.31 |
| STRN3 | NM_001083893 | 116 | 1133 | 0.0000 | 0.0000 | 9.7324 | 3.283 | 9.73 | 1018 | 9.99 |
| STRN3 | NM_014574 | 872 | 225 | 0.0000 | 0.0000 | 0.2593 | −1.947 | 3.86 | 647 | 9.34 |

TABLE 8-continued

RNA Abundance Modulation

| Gene | Trx_ID | ave DMSO | ave Cpd | padj (q val, FDR) | ttest (p val) | FC (x + 1) | L₂FC (x + 1) | amp FC (x + 1) | abs (Cpd-DMSO) | L₂abs (Cpd-DMSO) |
|---|---|---|---|---|---|---|---|---|---|---|
| SYNE1 | AB033088 | 37 | 74 | 0.2090 | 1.0000 | 2.0032 | 1.002 | 2.00 | 38 | 5.23 |
| SYNE1 | AB051543 | 190 | 21 | 0.0000 | 0.0000 | 0.1159 | −3.108 | 8.62 | 169 | 7.40 |
| SYNE1 | AK308717 | 35 | 21 | 0.4236 | 1.0000 | 0.6272 | −0.673 | 1.59 | 13 | 3.74 |
| SYNE1 | AK310977 | 17 | 12 | 0.6535 | 1.0000 | 0.6853 | −0.545 | 1.46 | 6 | 2.52 |
| SYNE1 | AL713682 | 4 | 0 | 0.0373 | 0.4702 | 0.1862 | −2.425 | 5.37 | 4 | 2.13 |
| SYNE1 | AY061755 | 406 | 460 | 0.5417 | 1.0000 | 1.1309 | 0.178 | 1.13 | 53 | 5.74 |
| SYNE1 | BC028616 | 26 | 11 | 0.2624 | 1.0000 | 0.4341 | −1.204 | 2.30 | 15 | 3.92 |
| SYNE1 | BC039121 | 51 | 48 | 0.9295 | 1.0000 | 0.9382 | −0.092 | 1.07 | 3 | 1.68 |
| SYNE1 | BX537517 | 23 | 11 | 0.3514 | 1.0000 | 0.4892 | −1.032 | 2.04 | 12 | 3.59 |
| SYNE1 | BX647837 | 345 | 312 | 0.6676 | 1.0000 | 0.9054 | −0.143 | 1.10 | 33 | 5.03 |
| SYNE1 | CR933676 | 5 | 0 | 0.0363 | 0.4638 | 0.1673 | −2.579 | 5.98 | 5 | 2.32 |
| SYNE1 | FM162565 | 14 | 3 | 0.2234 | 1.0000 | 0.3069 | −1.704 | 3.26 | 10 | 3.34 |
| SYNE1 | JQ740784 | 0 | 4 | 0.0941 | 0.6918 | 4.5905 | 2.199 | 4.59 | 4 | 1.84 |
| SYNE1 | JQ740786 | 2 | 0 | 0.0670 | 0.6122 | 0.3132 | −1.675 | 3.19 | 2 | 1.13 |
| SYNE1 | NM_033071 | 53 | 120 | 0.0666 | 0.6122 | 2.2485 | 1.169 | 2.25 | 67 | 6.07 |
| SYNE1 | NM_182961 | 2331 | 1604 | 0.0023 | 0.0805 | 0.6884 | −0.539 | 1.45 | 726 | 9.50 |
| TACC1 | AB029026 | 0 | 64 | 0.0000 | 0.0000 | 64.9586 | 6.021 | 64.96 | 64 | 6.00 |
| TACC1 | AB463317 | 50 | 2 | 0.0001 | 0.0060 | 0.0623 | −4.004 | 16.04 | 48 | 5.58 |
| TACC1 | AK294931 | 1104 | 1048 | 0.5828 | 1.0000 | 0.9489 | −0.076 | 1.05 | 56 | 5.82 |
| TACC1 | AK295841 | 10 | 12 | 0.8299 | 1.0000 | 1.2664 | 0.341 | 1.27 | 3 | 1.49 |
| TACC1 | AK303596 | 0 | 0 | 9999 | 9999 | 1.0000 | 0.000 | 1.00 | 0 | 0 |
| TACC1 | AK304725 | 65 | 79 | 0.5828 | 1.0000 | 1.2191 | 0.286 | 1.22 | 14 | 3.85 |
| TACC1 | AK308849 | 3 | 3 | 0.9383 | 1.0000 | 0.9336 | −0.099 | 1.07 | 0 | −1.98 |
| TACC1 | AY072874 | 1 | 0 | 0.2609 | 1.0000 | 0.4654 | −1.103 | 2.15 | 1 | 0.20 |
| TACC1 | NM_001122824 | 435 | 327 | 0.1916 | 1.0000 | 0.7533 | −0.409 | 1.33 | 107 | 6.75 |
| TACC1 | NM_001146216 | 0 | 7 | 0.0402 | 0.4904 | 7.9266 | 2.987 | 7.93 | 7 | 2.79 |
| TACC1 | NM_006283 | 2152 | 2506 | 0.1333 | 0.8334 | 1.1645 | 0.220 | 1.16 | 354 | 8.47 |
| TAF2 | NM_003184 | 1576 | 714 | 0.0000 | 0.0000 | 0.4533 | −1.141 | 2.21 | 862 | 9.75 |
| TANC2 | AJ278120 | 133 | 136 | 0.9279 | 1.0000 | 1.0181 | 0.026 | 1.02 | 2 | 1.28 |
| TANC2 | AK001077 | 0 | 4 | 0.0942 | 0.6918 | 4.5130 | 2.174 | 4.51 | 4 | 1.81 |
| TANC2 | AK021886 | 8 | 3 | 0.3647 | 1.0000 | 0.4015 | −1.317 | 2.49 | 5 | 2.40 |
| TANC2 | BC144357 | 470 | 158 | 0.0000 | 0.0004 | 0.3363 | −1.572 | 2.97 | 313 | 8.29 |
| TANC2 | NM_025185 | 1790 | 1812 | 0.8496 | 1.0000 | 1.0124 | 0.018 | 1.01 | 22 | 4.47 |
| TARBP1 | NM_005646 | 415 | 49 | 0.0000 | 0.0000 | 0.1192 | −3.068 | 8.39 | 367 | 8.52 |
| TBC1D15 | AK307922 | 257 | 263 | 0.8907 | 1.0000 | 1.0252 | 0.036 | 1.03 | 6 | 2.70 |
| TBC1D15 | NM_001146213 | 654 | 923 | 0.0181 | 0.3119 | 1.4119 | 0.498 | 1.41 | 270 | 8.07 |
| TBC1D15 | NM_001146214 | 41 | 41 | 0.9353 | 1.0000 | 1.0153 | 0.022 | 1.02 | 1 | −0.65 |
| TBC1D15 | NM_022771 | 80 | 96 | 0.5861 | 1.0000 | 1.1954 | 0.257 | 1.20 | 16 | 3.99 |
| TBC1D15 | NR_027449 | 146 | 23 | 0.0000 | 0.0017 | 0.1625 | −2.621 | 6.15 | 123 | 6.94 |
| TEP1 | AB209669 | 0 | 0 | 9999 | 9999 | 1.0000 | 0.000 | 1.00 | 0 | 0 |
| TEP1 | AK303307 | 10 | 14 | 0.8623 | 1.0000 | 1.3304 | 0.412 | 1.33 | 4 | 1.91 |
| TEP1 | BC143812 | 169 | 137 | 0.7119 | 1.0000 | 0.8125 | −0.300 | 1.23 | 32 | 4.99 |
| TEP1 | BC143815 | 72 | 0 | 0.0000 | 0.0000 | 0.0138 | −6.184 | 72.71 | 72 | 6.16 |
| TEP1 | BX640983 | 12 | 13 | 1.0000 | 1.0000 | 1.1188 | 0.162 | 1.12 | 2 | 0.61 |
| TEP1 | NM_007110 | 388 | 397 | 0.9306 | 1.0000 | 1.0236 | 0.034 | 1.02 | 9 | 3.20 |
| TFCP2 | AK308087 | 118 | 98 | 0.6198 | 1.0000 | 0.8370 | −0.257 | 1.19 | 19 | 4.27 |
| TFCP2 | NM_001173452 | 58 | 239 | 0.0000 | 0.0012 | 4.0384 | 2.014 | 4.04 | 180 | 7.49 |
| TFCP2 | NM_001173453 | 18 | 0 | 0.0010 | 0.0439 | 0.0531 | −4.236 | 18.84 | 18 | 4.16 |
| TFCP2 | NM_005653 | 971 | 808 | 0.1876 | 0.9875 | 0.8324 | −0.265 | 1.20 | 163 | 7.35 |
| TGFBRAP1 | AK021697 | 34 | 9 | 0.0838 | 0.6686 | 0.2793 | −1.840 | 3.58 | 25 | 4.66 |
| TGFBRAP1 | NM_001142621 | 275 | 446 | 0.0121 | 0.2459 | 1.6224 | 0.698 | 1.62 | 172 | 7.42 |
| TGFBRAP1 | NM_004257 | 156 | 0 | 0.0000 | 0.0000 | 0.0064 | −7.294 | 156.98 | 156 | 7.29 |
| THADA | AK025445 | 48 | 12 | 0.0334 | 0.4454 | 0.2651 | −1.915 | 3.77 | 36 | 5.17 |
| THADA | AK126824 | 6 | 0 | 0.1024 | 0.7252 | 0.1808 | −2.468 | 5.53 | 6 | 2.55 |
| THADA | AK307915 | 16 | 2 | 0.1105 | 0.7538 | 0.2071 | −2.272 | 4.83 | 13 | 3.71 |
| THADA | AL832141 | 1 | 3 | 0.6309 | 1.0000 | 1.7328 | 0.793 | 1.73 | 2 | 0.72 |
| THADA | AY149632 | 0 | 0 | 9999 | 9999 | 1.0000 | 0.000 | 1.00 | 0 | 0 |
| THADA | BX641038 | 4 | 2 | 0.7810 | 1.0000 | 0.6958 | −0.523 | 1.44 | 2 | 0.60 |
| THADA | NM_001083953 | 73 | 0 | 0.0000 | 0.0000 | 0.0135 | −6.211 | 74.06 | 73 | 6.19 |
| THADA | NM_001271643 | 33 | 38 | 0.8112 | 1.0000 | 1.1557 | 0.209 | 1.16 | 5 | 2.41 |
| THADA | NM_001271644 | 3 | 17 | 0.0966 | 0.7005 | 4.4176 | 2.143 | 4.42 | 14 | 3.80 |
| THADA | NM_022065 | 961 | 304 | 0.0000 | 0.0000 | 0.3170 | −1.658 | 3.15 | 657 | 9.36 |
| THADA | NR_073394 | 2 | 1 | 0.6136 | 1.0000 | 0.6844 | −0.547 | 1.46 | 1 | −0.13 |
| TIMP2 | AK294290 | 91 | 0 | 0.0000 | 0.0000 | 0.0109 | −6.520 | 91.79 | 91 | 6.50 |
| TIMP2 | BC039613 | 32193 | 29887 | 0.3550 | 1.0000 | 0.9284 | −0.107 | 1.08 | 2306 | 11.17 |
| TIMP2 | NM_003255 | 21111 | 20235 | 0.6448 | 1.0000 | 0.9585 | −0.061 | 1.04 | 876 | 9.77 |
| TLK1 | AK091975 | 326 | 232 | 0.1404 | 0.8584 | 0.7110 | −0.492 | 1.41 | 95 | 6.56 |
| TLK1 | BX537631 | 4 | 5 | 0.9084 | 1.0000 | 1.2332 | 0.302 | 1.23 | 1 | 0.14 |
| TLK1 | E09283 | 27 | 30 | 0.8854 | 1.0000 | 1.1041 | 0.143 | 1.10 | 3 | 1.54 |
| TLK1 | NM_001136554 | 697 | 260 | 0.0000 | 0.0000 | 0.3744 | −1.417 | 2.67 | 437 | 8.77 |
| TLK1 | NM_001136555 | 27 | 111 | 0.0010 | 0.0428 | 4.0350 | 2.013 | 4.04 | 84 | 6.40 |
| TLK1 | NM_012290 | 808 | 1174 | 0.0055 | 0.1467 | 1.4535 | 0.540 | 1.45 | 367 | 8.52 |
| TMEM154 | NM_152680 | 242 | 548 | 0.0000 | 0.0016 | 2.2609 | 1.177 | 2.26 | 306 | 8.26 |
| TNS3 | NM_022748 | 1138 | 167 | 0.0000 | 0.0000 | 0.1472 | −2.764 | 6.79 | 971 | 9.92 |

TABLE 8-continued

RNA Abundance Modulation

| Gene | Trx_ID | ave DMSO | ave Cpd | padj (q val, FDR) | ttest (p val) | FC (x + 1) | L₂FC (x + 1) | amp FC (x + 1) | abs (Cpd-DMSO) | L₂abs (Cpd-DMSO) |
|---|---|---|---|---|---|---|---|---|---|---|
| TOMM5 | CCDS47968 | 1 | 1 | 0.8815 | 1.0000 | 0.9090 | −0.138 | 1.10 | 0 | −2.28 |
| TOMM5 | CR627326 | 10 | 4 | 0.3675 | 1.0000 | 0.4244 | −1.236 | 2.36 | 6 | 2.64 |
| TOMM5 | NM_001001790 | 1959 | 774 | 0.0000 | 0.0000 | 0.3953 | −1.339 | 2.53 | 1185 | 10.21 |
| TOMM5 | NM_001134484 | 13 | 3 | 0.1454 | 0.8735 | 0.2630 | −1.927 | 3.80 | 11 | 3.41 |
| TOMM5 | NM_001134485 | 55 | 25 | 0.1931 | 1.0000 | 0.4705 | −1.088 | 2.13 | 29 | 4.88 |
| TRAF3 | NM_001199427 | 17 | 22 | 0.7495 | 1.0000 | 1.2405 | 0.311 | 1.24 | 4 | 2.15 |
| TRAF3 | NM_003300 | 354 | 57 | 0.0000 | 0.0000 | 0.1622 | −2.624 | 6.17 | 298 | 8.22 |
| TRAF3 | NM_145725 | 1028 | 757 | 0.0191 | 0.3225 | 0.7367 | −0.441 | 1.36 | 271 | 8.08 |
| TRAF3 | NM_145726 | 0 | 0 | 9999 | 9999 | 1.0000 | 0.000 | 1.00 | 0 | 0 |
| TRAK1 | AK295848 | 656 | 755 | 0.3245 | 1.0000 | 1.1521 | 0.204 | 1.15 | 100 | 6.64 |
| TRAK1 | NM_001042646 | 445 | 309 | 0.0557 | 0.5724 | 0.6949 | −0.525 | 1.44 | 136 | 7.09 |
| TRAK1 | NM_001265608 | 793 | 705 | 0.4060 | 1.0000 | 0.8894 | −0.169 | 1.12 | 88 | 6.46 |
| TRAK1 | NM_001265610 | 27 | 18 | 0.5623 | 1.0000 | 0.6862 | −0.543 | 1.46 | 9 | 3.13 |
| TRAK1 | NM_014965 | 52 | 0 | 0.0000 | 0.0000 | 0.0190 | −5.718 | 52.63 | 52 | 5.69 |
| TRAPPC12 | AK094181 | 20 | 24 | 0.8098 | 1.0000 | 1.2209 | 0.288 | 1.22 | 5 | 2.20 |
| TRAPPC12 | AK098327 | 151 | 0 | 0.0000 | 0.0000 | 0.0066 | −7.244 | 151.58 | 151 | 7.23 |
| TRAPPC12 | NM_016030 | 621 | 781 | 0.1298 | 0.8205 | 1.2575 | 0.331 | 1.26 | 160 | 7.32 |
| TRIM2 | BC025417 | 5 | 4 | 0.8162 | 1.0000 | 0.7534 | −0.408 | 1.33 | 2 | 0.61 |
| TRIM2 | NM_001130067 | 53 | 0 | 0.0000 | 0.0000 | 0.0184 | −5.763 | 54.29 | 53 | 5.74 |
| TRIM2 | NM_015271 | 1657 | 1858 | 0.2782 | 1.0000 | 1.1211 | 0.165 | 1.12 | 201 | 7.65 |
| TRIM26 | AK314782 | 182 | 30 | 0.0000 | 0.0016 | 0.1688 | −2.567 | 5.92 | 152 | 7.25 |
| TRIM26 | AK314782 | 38 | 46 | 0.7647 | 1.0000 | 1.1992 | 0.262 | 1.20 | 8 | 2.96 |
| TRIM26 | AK314782 | 38 | 46 | 0.7647 | 1.0000 | 1.1992 | 0.262 | 1.20 | 8 | 2.96 |
| TRIM26 | AK314782 | 38 | 46 | 0.7647 | 1.0000 | 1.1992 | 0.262 | 1.20 | 8 | 2.96 |
| TRIM26 | AK314782 | 0 | 0 | 9999 | 9999 | 1.0000 | 0.000 | 1.00 | 0 | 0 |
| TRIM26 | BC021115 | 4 | 0 | 0.0460 | 0.5174 | 0.2172 | −2.203 | 4.60 | 4 | 1.85 |
| TRIM26 | BC021115 | 2 | 2 | 0.9158 | 1.0000 | 0.9127 | −0.132 | 1.10 | 0 | −1.99 |
| TRIM26 | BC021115 | 2 | 2 | 0.9158 | 1.0000 | 0.9127 | −0.132 | 1.10 | 0 | −1.99 |
| TRIM26 | BC021115 | 2 | 2 | 0.9158 | 1.0000 | 0.9127 | −0.132 | 1.10 | 0 | −1.99 |
| TRIM26 | BC021115 | 0 | 0 | 9999 | 9999 | 1.0000 | 0.000 | 1.00 | 0 | 0 |
| TRIM26 | NM_001242783 | 2 | 0 | 0.0614 | 0.5948 | 0.2858 | −1.807 | 3.50 | 2 | 1.32 |
| TRIM26 | NM_001242783 | 569 | 652 | 0.3966 | 1.0000 | 1.1460 | 0.197 | 1.15 | 83 | 6.38 |
| TRIM26 | NM_001242783 | 61 | 82 | 0.4870 | 1.0000 | 1.3366 | 0.419 | 1.34 | 21 | 4.38 |
| TRIM26 | NM_001242783 | 199 | 179 | 0.7674 | 1.0000 | 0.9032 | −0.147 | 1.11 | 19 | 4.27 |
| TRIM26 | NM_003449 | 4 | 0 | 0.0455 | 0.5174 | 0.1919 | −2.382 | 5.21 | 4 | 2.07 |
| TRIM26 | NM_003449 | 49 | 102 | 0.0619 | 0.5966 | 2.0855 | 1.060 | 2.09 | 54 | 5.75 |
| TRIM26 | NM_003449 | 98 | 53 | 0.1094 | 0.7486 | 0.5395 | −0.890 | 1.85 | 46 | 5.51 |
| TRIM26 | NM_003449 | 71 | 101 | 0.4450 | 1.0000 | 1.4263 | 0.512 | 1.43 | 31 | 4.93 |
| TRIM26 | NM_003449 | 0 | 0 | 9999 | 9999 | 1.0000 | 0.000 | 1.00 | 0 | 0 |
| TRIM26 | U09825 | 166 | 98 | 0.0956 | 0.6963 | 0.5930 | −0.754 | 1.69 | 68 | 6.09 |
| TRIM26 | U09825 | 166 | 98 | 0.0956 | 0.6963 | 0.5930 | −0.754 | 1.69 | 68 | 6.09 |
| TRIM26 | U09825 | 0 | 2 | 0.1389 | 0.8525 | 3.2848 | 1.716 | 3.28 | 2 | 1.19 |
| TRIM65 | NM_001256124 | 182 | 0 | 0.0000 | 0.0000 | 0.0055 | −7.514 | 182.75 | 182 | 7.51 |
| TRIM65 | NM_173547 | 270 | 449 | 0.0094 | 0.2105 | 1.6613 | 0.732 | 1.66 | 179 | 7.49 |
| TSPAN2 | GU971730 | 27 | 9 | 0.1801 | 0.9624 | 0.3567 | −1.487 | 2.80 | 18 | 4.19 |
| TSPAN2 | NM_005725 | 424 | 136 | 0.0000 | 0.0005 | 0.3229 | −1.631 | 3.10 | 288 | 8.17 |
| U2SURP | AK057679 | 197 | 223 | 0.6509 | 1.0000 | 1.1346 | 0.182 | 1.13 | 27 | 4.73 |
| U2SURP | AK296440 | 268 | 261 | 0.8746 | 1.0000 | 0.9747 | −0.037 | 1.03 | 7 | 2.77 |
| U2SURP | BC006474 | 1365 | 1249 | 0.3364 | 1.0000 | 0.9155 | −0.127 | 1.09 | 115 | 6.85 |
| U2SURP | BC111692 | 9 | 18 | 0.5601 | 1.0000 | 1.9191 | 0.940 | 1.92 | 9 | 3.18 |
| U2SURP | NM_001080415 | 173 | 395 | 0.0000 | 0.0017 | 2.2780 | 1.188 | 2.28 | 222 | 7.79 |
| UBAP2L | AJ243668 | 153 | 68 | 0.0350 | 0.4554 | 0.4506 | −1.150 | 2.22 | 84 | 6.40 |
| UBAP2L | AJ243669 | 119 | 31 | 0.0034 | 0.1061 | 0.2687 | −1.896 | 3.72 | 88 | 6.45 |
| UBAP2L | AJ243670 | 0 | 2 | 0.1608 | 0.9103 | 3.1873 | 1.672 | 3.19 | 2 | 1.13 |
| UBAP2L | AK124294 | 68 | 31 | 0.1397 | 0.8559 | 0.4670 | −1.099 | 2.14 | 37 | 5.20 |
| UBAP2L | AK302662 | 393 | 110 | 0.0000 | 0.0001 | 0.2827 | −1.822 | 3.54 | 283 | 8.14 |
| UBAP2L | AK302953 | 780 | 399 | 0.0000 | 0.0038 | 0.5118 | −0.966 | 1.95 | 381 | 8.57 |
| UBAP2L | AK303533 | 20 | 0 | 0.0005 | 0.0239 | 0.0476 | −4.392 | 20.99 | 20 | 4.32 |
| UBAP2L | NM_001127320 | 2001 | 972 | 0.0000 | 0.0000 | 0.4857 | −1.042 | 2.06 | 1030 | 10.01 |
| UBAP2L | NM_014847 | 1764 | 544 | 0.0000 | 0.0000 | 0.3090 | −1.695 | 3.24 | 1219 | 10.25 |
| UBE2V1 | NM_001032288 | 4396 | 4751 | 0.4224 | 1.0000 | 1.0807 | 0.112 | 1.08 | 355 | 8.47 |
| UBE2V1 | NM_001257393 | 12 | 0 | 0.0043 | 0.1240 | 0.0796 | −3.651 | 12.56 | 12 | 3.53 |
| UBE2V1 | NM_001257394 | 18 | 2 | 0.0588 | 0.5875 | 0.1697 | −2.559 | 5.89 | 16 | 4.01 |
| UBE2V1 | NM_001257397 | 20 | 11 | 0.4764 | 1.0000 | 0.5713 | −0.808 | 1.75 | 9 | 3.18 |
| UBE2V1 | NM_001257399 | 157 | 182 | 0.5936 | 1.0000 | 1.1595 | 0.214 | 1.16 | 25 | 4.66 |
| UBE2V1 | NM_021988 | 76 | 69 | 0.7985 | 1.0000 | 0.9186 | −0.122 | 1.09 | 6 | 2.64 |
| UBE2V1 | NM_022442 | 2 | 0 | 0.0614 | 0.5948 | 0.2858 | −1.807 | 3.50 | 2 | 1.32 |
| UBE2V1 | NM_199144 | 0 | 8 | 0.0211 | 0.3412 | 9.0627 | 3.180 | 9.06 | 8 | 3.01 |
| UBE2V1 | NR_047554 | 362 | 25 | 0.0000 | 0.0000 | 0.0730 | −3.777 | 13.71 | 337 | 8.39 |
| UBE2V1 | NR_047555 | 5 | 5 | 0.9187 | 1.0000 | 0.9261 | −0.111 | 1.08 | 0 | −1.09 |
| UBE2V1 | NR_047556 | 30 | 15 | 0.3439 | 1.0000 | 0.5268 | −0.925 | 1.90 | 15 | 3.88 |
| UCHL5 | AK225794 | 51 | 37 | 0.5177 | 1.0000 | 0.7328 | −0.448 | 1.36 | 14 | 3.79 |
| UCHL5 | AK316064 | 76 | 106 | 0.4037 | 1.0000 | 1.3941 | 0.479 | 1.39 | 30 | 4.93 |
| UCHL5 | BC015381 | 10 | 13 | 0.8149 | 1.0000 | 1.2220 | 0.289 | 1.22 | 3 | 1.34 |

TABLE 8-continued

RNA Abundance Modulation

| Gene | Trx_ID | ave DMSO | ave Cpd | padj (q val, FDR) | ttest (p val) | FC (x + 1) | $L_2$FC (x + 1) | amp FC (x + 1) | abs (Cpd-DMSO) | $L_2$abs (Cpd-DMSO) |
|---|---|---|---|---|---|---|---|---|---|---|
| UCHL5 | NM_001199261 | 124 | 324 | 0.0000 | 0.0037 | 2.6069 | 1.382 | 2.61 | 200 | 7.64 |
| UCHL5 | NM_001199262 | 118 | 134 | 0.6310 | 1.0000 | 1.1349 | 0.183 | 1.13 | 16 | 4.00 |
| UCHL5 | NM_001199263 | 214 | 182 | 0.5156 | 1.0000 | 0.8534 | −0.229 | 1.17 | 31 | 4.98 |
| UCHL5 | NM_015984 | 509 | 439 | 0.3456 | 1.0000 | 0.8637 | −0.211 | 1.16 | 69 | 6.12 |
| UCHL5 | NR_037607 | 22 | 24 | 0.9061 | 1.0000 | 1.0924 | 0.127 | 1.09 | 2 | 1.06 |
| UHRF1BP1L | BX647380 | 154 | 20 | 0.0000 | 0.0006 | 0.1346 | −2.894 | 7.43 | 134 | 7.07 |
| UHRF1BP1L | NM_001006947 | 42 | 17 | 0.2239 | 1.0000 | 0.4169 | −1.262 | 2.40 | 25 | 4.65 |
| UHRF1BP1L | NM_015054 | 1589 | 1565 | 0.8930 | 1.0000 | 0.9853 | −0.021 | 1.01 | 23 | 4.55 |
| VANGL1 | NM_001172412 | 70 | 0 | 0.0000 | 0.0000 | 0.0142 | −6.143 | 70.66 | 70 | 6.12 |
| VANGL1 | NM_138959 | 2913 | 2279 | 0.0167 | 0.2972 | 0.7825 | −0.354 | 1.28 | 634 | 9.31 |
| VARS2 | AB067472 | 6 | 0 | 0.0270 | 0.3961 | 0.1508 | −2.729 | 6.63 | 6 | 2.49 |
| VARS2 | AK000511 | 24 | 28 | 0.8152 | 1.0000 | 1.1599 | 0.214 | 1.16 | 4 | 2.00 |
| VARS2 | AK000511 | 12 | 9 | 0.6340 | 1.0000 | 0.7407 | −0.433 | 1.35 | 3 | 1.77 |
| VARS2 | AK094483 | 2 | 0 | 0.1044 | 0.7252 | 0.3950 | −1.340 | 2.53 | 2 | 0.61 |
| VARS2 | AK094483 | 1 | 4 | 0.2990 | 1.0000 | 3.1438 | 1.652 | 3.14 | 3 | 1.81 |
| VARS2 | AK125069 | 1 | 0 | 0.2609 | 1.0000 | 0.4654 | −1.103 | 2.15 | 1 | 0.20 |
| VARS2 | AK125069 | 3 | 3 | 0.9489 | 1.0000 | 0.9655 | −0.051 | 1.04 | 0 | −2.71 |
| VARS2 | AK125069 | 5 | 2 | 0.4235 | 1.0000 | 0.5011 | −0.997 | 2.00 | 3 | 1.67 |
| VARS2 | BC063427 | 8 | 9 | 1.0000 | 1.0000 | 1.1095 | 0.150 | 1.11 | 1 | 0.01 |
| VARS2 | BC143535 | 63 | 3 | 0.0000 | 0.0011 | 0.0553 | −4.177 | 18.08 | 61 | 5.92 |
| VARS2 | BC143535 | 10 | 0 | 0.0095 | 0.2113 | 0.0913 | −3.453 | 10.95 | 10 | 3.32 |
| VARS2 | BC143535 | 23 | 45 | 0.2875 | 1.0000 | 1.8990 | 0.925 | 1.90 | 22 | 4.46 |
| VARS2 | BC143535 | 0 | 0 | 9999 | 9999 | 1.0000 | 0.000 | 1.00 | 0 | 0 |
| VARS2 | BC143536 | 15 | 0 | 0.0025 | 0.0861 | 0.0628 | −3.994 | 15.93 | 15 | 3.90 |
| VARS2 | BC143536 | 0 | 0 | 9999 | 9999 | 1.0000 | 0.000 | 1.00 | 0 | 0 |
| VARS2 | NM_001167733 | 15 | 3 | 0.0980 | 0.7080 | 0.2427 | −2.043 | 4.12 | 12 | 3.61 |
| VARS2 | NM_001167733 | 52 | 46 | 0.5952 | 1.0000 | 0.8815 | −0.182 | 1.13 | 6 | 2.65 |
| VARS2 | NM_001167734 | 45 | 0 | 0.0000 | 0.0002 | 0.0219 | −5.516 | 45.77 | 45 | 5.48 |
| VARS2 | NM_001167734 | 51 | 136 | 0.0108 | 0.2293 | 2.6275 | 1.394 | 2.63 | 85 | 6.40 |
| VARS2 | NM_020442 | 22 | 86 | 0.0087 | 0.2000 | 3.8391 | 1.941 | 3.84 | 64 | 6.00 |
| VARS2 | NM_020442 | 131 | 95 | 0.4088 | 1.0000 | 0.7330 | −0.448 | 1.36 | 35 | 5.13 |
| VPS13A | BC020576 | 6 | 7 | 0.9661 | 1.0000 | 1.1859 | 0.246 | 1.19 | 1 | 0.40 |
| VPS13A | NM_001018037 | 247 | 40 | 0.0000 | 0.0000 | 0.1645 | −2.604 | 6.08 | 207 | 7.70 |
| VPS13A | NM_001018038 | 198 | 152 | 0.3553 | 1.0000 | 0.7668 | −0.383 | 1.30 | 46 | 5.54 |
| VPS13A | NM_015186 | 87 | 120 | 0.3647 | 1.0000 | 1.3794 | 0.464 | 1.38 | 33 | 5.06 |
| VPS13A | NM_033305 | 251 | 297 | 0.3830 | 1.0000 | 1.1805 | 0.239 | 1.18 | 46 | 5.51 |
| VPS29 | AF201936 | 20 | 40 | 0.2834 | 1.0000 | 1.9393 | 0.956 | 1.94 | 20 | 4.31 |
| VPS29 | BC015095 | 7 | 0 | 0.0175 | 0.3050 | 0.1318 | −2.923 | 7.59 | 7 | 2.72 |
| VPS29 | BC017964 | 7 | 11 | 0.6863 | 1.0000 | 1.4999 | 0.585 | 1.50 | 4 | 1.94 |
| VPS29 | NM_016226 | 742 | 57 | 0.0000 | 0.0000 | 0.0776 | −3.687 | 12.88 | 686 | 9.42 |
| VPS29 | NM_057180 | 836 | 1522 | 0.0000 | 0.0003 | 1.8200 | 0.864 | 1.82 | 686 | 9.42 |
| VWA8 | NM_001009814 | 71 | 5 | 0.0001 | 0.0046 | 0.0803 | −3.639 | 12.46 | 66 | 6.05 |
| VWA8 | NM_015058 | 758 | 680 | 0.4777 | 1.0000 | 0.8972 | −0.156 | 1.11 | 78 | 6.29 |
| WSB1 | AK294516 | 26 | 0 | 0.0001 | 0.0065 | 0.0366 | −4.771 | 27.30 | 26 | 4.72 |
| WSB1 | AK300262 | 51 | 69 | 0.5501 | 1.0000 | 1.3457 | 0.428 | 1.35 | 18 | 4.16 |
| WSB1 | AK307114 | 0 | 7 | 0.0319 | 0.4342 | 7.6230 | 2.930 | 7.62 | 7 | 2.73 |
| WSB1 | BC048007 | 160 | 437 | 0.0000 | 0.0007 | 2.7242 | 1.446 | 2.72 | 277 | 8.11 |
| WSB1 | NM_015626 | 1068 | 524 | 0.0000 | 0.0003 | 0.4910 | −1.026 | 2.04 | 544 | 9.09 |
| WSB1 | NM_134265 | 7 | 0 | 0.0134 | 0.2605 | 0.1177 | −3.087 | 8.50 | 7 | 2.91 |
| XIAP | NM_001167 | 1277 | 1537 | 0.1602 | 0.9103 | 1.2033 | 0.267 | 1.20 | 260 | 8.02 |
| XIAP | NM_001204401 | 105 | 6 | 0.0000 | 0.0004 | 0.0652 | −3.940 | 15.35 | 99 | 6.62 |
| XIAP | NR_037916 | 541 | 608 | 0.4720 | 1.0000 | 1.1231 | 0.168 | 1.12 | 67 | 6.06 |
| XRN2 | AK172858 | 1 | 2 | 0.9093 | 1.0000 | 1.2403 | 0.311 | 1.24 | 1 | −0.88 |
| XRN2 | AK302846 | 68 | 30 | 0.1696 | 0.9346 | 0.4535 | −1.141 | 2.21 | 37 | 5.23 |
| XRN2 | AK303312 | 81 | 0 | 0.0000 | 0.0000 | 0.0121 | −6.364 | 82.36 | 81 | 6.35 |
| XRN2 | NM_012255 | 2886 | 1373 | 0.0000 | 0.0000 | 0.4761 | −1.071 | 2.10 | 1513 | 10.56 |
| YPEL5 | AK307099 | 13 | 8 | 0.4816 | 1.0000 | 0.6503 | −0.621 | 1.54 | 5 | 2.34 |
| YPEL5 | BC047237 | 0 | 2 | 0.1673 | 0.9262 | 2.6320 | 1.396 | 2.63 | 2 | 0.71 |
| YPEL5 | NM_001127399 | 33 | 154 | 0.0001 | 0.0089 | 4.5696 | 2.192 | 4.57 | 121 | 6.92 |
| YPEL5 | NM_001127400 | 201 | 890 | 0.0000 | 0.0000 | 4.4164 | 2.143 | 4.42 | 689 | 9.43 |
| YPEL5 | NM_001127401 | 67 | 123 | 0.1616 | 0.9120 | 1.8246 | 0.868 | 1.82 | 56 | 5.80 |
| YPEL5 | NM_016061 | 2607 | 1429 | 0.0000 | 0.0000 | 0.5484 | −0.867 | 1.82 | 1178 | 10.20 |
| ZAK | AF465843 | 92 | 100 | 0.8347 | 1.0000 | 1.0946 | 0.130 | 1.09 | 9 | 3.13 |
| ZAK | AK298634 | 83 | 0 | 0.0000 | 0.0000 | 0.0119 | −6.389 | 83.79 | 83 | 6.37 |
| ZAK | NM_016653 | 929 | 1035 | 0.4451 | 1.0000 | 1.1130 | 0.154 | 1.11 | 105 | 6.72 |
| ZAK | NM_133646 | 4289 | 3946 | 0.3587 | 1.0000 | 0.9200 | −0.120 | 1.09 | 343 | 8.42 |
| ZC3H18 | AK056632 | 72 | 130 | 0.1126 | 0.7609 | 1.7868 | 0.837 | 1.79 | 58 | 5.85 |
| ZC3H18 | AK056632 | 16 | 20 | 0.8521 | 1.0000 | 1.2113 | 0.277 | 1.21 | 4 | 1.87 |
| ZC3H18 | AK300254 | 247 | 10 | 0.0000 | 0.0000 | 0.0434 | −4.525 | 23.02 | 238 | 7.89 |
| ZC3H18 | AK302716 | 12 | 8 | 0.6879 | 1.0000 | 0.7016 | −0.511 | 1.43 | 4 | 1.95 |
| ZC3H18 | AX748097 | 7 | 5 | 0.7714 | 1.0000 | 0.7793 | −0.360 | 1.28 | 2 | 0.73 |
| ZC3H18 | CU690696 | 45 | 28 | 0.4117 | 1.0000 | 0.6389 | −0.646 | 1.57 | 16 | 4.04 |
| ZC3H18 | NM_144604 | 1190 | 1486 | 0.0667 | 0.6122 | 1.2489 | 0.321 | 1.25 | 296 | 8.21 |
| ZFAND5 | AK290849 | 1496 | 850 | 0.0000 | 0.0017 | 0.5682 | −0.816 | 1.76 | 647 | 9.34 |

TABLE 8-continued

RNA Abundance Modulation

| Gene | Trx_ID | ave DMSO | ave Cpd | padj (q val, FDR) | ttest (p val) | FC (x + 1) | L₂FC (x + 1) | amp FC (x + 1) | abs (Cpd-DMSO) | L₂abs (Cpd-DMSO) |
|---|---|---|---|---|---|---|---|---|---|---|
| ZFAND5 | AK307376 | 171 | 98 | 0.0925 | 0.6910 | 0.5768 | −0.794 | 1.73 | 73 | 6.18 |
| ZFAND5 | NM_001102420 | 2058 | 1472 | 0.0032 | 0.1029 | 0.7153 | −0.483 | 1.40 | 586 | 9.19 |
| ZFAND5 | NM_001102421 | 1287 | 1117 | 0.2631 | 1.0000 | 0.8686 | −0.203 | 1.15 | 169 | 7.40 |
| ZFAND5 | NM_001278243 | 271 | 631 | 0.0000 | 0.0022 | 2.3290 | 1.220 | 2.33 | 361 | 8.50 |
| ZFAND5 | NM_001278244 | 0 | 76 | 0.0000 | 0.0000 | 77.2799 | 6.272 | 77.28 | 76 | 6.25 |
| ZFAND5 | NM_001278245 | 326 | 227 | 0.1786 | 0.9580 | 0.6970 | −0.521 | 1.43 | 99 | 6.63 |
| ZFAND5 | NM_006007 | 24 | 14 | 0.3505 | 1.0000 | 0.6020 | −0.732 | 1.66 | 10 | 3.33 |
| ZMIZ1 | AB033050 | 226 | 487 | 0.0000 | 0.0032 | 2.1470 | 1.102 | 2.15 | 261 | 8.03 |
| ZMIZ1 | AK024490 | 20 | 32 | 0.4657 | 1.0000 | 1.6291 | 0.704 | 1.63 | 13 | 3.69 |
| ZMIZ1 | AK025812 | 2 | 4 | 0.7537 | 1.0000 | 1.4407 | 0.527 | 1.44 | 1 | 0.48 |
| ZMIZ1 | AK299728 | 796 | 816 | 0.8018 | 1.0000 | 1.0249 | 0.036 | 1.02 | 20 | 4.31 |
| ZMIZ1 | NM_020338 | 4060 | 3877 | 0.6534 | 1.0000 | 0.9549 | −0.067 | 1.05 | 183 | 7.52 |
| ZMYM2 | AF012126 | 8 | 4 | 0.5559 | 1.0000 | 0.5638 | −0.827 | 1.77 | 4 | 2.04 |
| ZMYM2 | AK302917 | 89 | 88 | 0.9635 | 1.0000 | 0.9917 | −0.012 | 1.01 | 1 | −0.43 |
| ZMYM2 | AK310505 | 49 | 41 | 0.7255 | 1.0000 | 0.8265 | −0.275 | 1.21 | 9 | 3.13 |
| ZMYM2 | AL136621 | 51 | 71 | 0.4683 | 1.0000 | 1.3885 | 0.474 | 1.39 | 20 | 4.33 |
| ZMYM2 | BX648905 | 9 | 7 | 0.7506 | 1.0000 | 0.7902 | −0.340 | 1.27 | 2 | 1.02 |
| ZMYM2 | NM_001190964 | 56 | 238 | 0.0000 | 0.0037 | 4.1811 | 2.064 | 4.18 | 182 | 7.51 |
| ZMYM2 | NM_001190965 | 282 | 241 | 0.7802 | 1.0000 | 0.8547 | −0.226 | 1.17 | 41 | 5.36 |
| ZMYM2 | NM_003453 | 212 | 105 | 0.0429 | 0.5034 | 0.4990 | −1.003 | 2.00 | 107 | 6.74 |
| ZMYM2 | NM_197968 | 142 | 76 | 0.0566 | 0.5766 | 0.5380 | −0.894 | 1.86 | 66 | 6.04 |
| ZNF219 | NM_001101672 | 109 | 0 | 0.0000 | 0.0000 | 0.0091 | −6.783 | 110.14 | 109 | 6.77 |
| ZNF219 | NM_001102454 | 29 | 147 | 0.0000 | 0.0148 | 4.9220 | 2.299 | 4.92 | 118 | 6.88 |
| ZNF219 | NM_016423 | 24 | 27 | 0.9439 | 1.0000 | 1.1046 | 0.144 | 1.10 | 3 | 1.41 |
| ZNF227 | AK299266 | 49 | 45 | 0.9486 | 1.0000 | 0.9090 | −0.138 | 1.10 | 5 | 2.19 |
| ZNF227 | AK300576 | 0 | 4 | 0.0768 | 0.6480 | 5.2433 | 2.390 | 5.24 | 4 | 2.09 |
| ZNF227 | AK316048 | 32 | 62 | 0.2557 | 1.0000 | 1.9108 | 0.934 | 1.91 | 30 | 4.91 |
| ZNF227 | AL833012 | 4 | 0 | 0.0417 | 0.4942 | 0.2090 | −2.258 | 4.78 | 4 | 1.92 |
| ZNF227 | AX721152 | 4 | 10 | 0.3373 | 1.0000 | 2.2780 | 1.188 | 2.28 | 6 | 2.63 |
| ZNF227 | AX747434 | 48 | 98 | 0.1116 | 0.7570 | 2.0351 | 1.025 | 2.04 | 50 | 5.66 |
| ZNF227 | NM_182490 | 91 | 10 | 0.0001 | 0.0085 | 0.1158 | −3.110 | 8.64 | 82 | 6.35 |
| ZNF24 | AF542097 | 52 | 49 | 0.9022 | 1.0000 | 0.9518 | −0.071 | 1.05 | 3 | 1.35 |
| ZNF24 | BC016801 | 1217 | 1584 | 0.0245 | 0.3758 | 1.3014 | 0.380 | 1.30 | 367 | 8.52 |
| ZNF24 | NM_006965 | 591 | 228 | 0.0000 | 0.0002 | 0.3867 | −1.371 | 2.59 | 363 | 8.50 |
| ZNF37A | NM_001007094 | 195 | 224 | 0.6042 | 1.0000 | 1.1455 | 0.196 | 1.15 | 29 | 4.83 |
| ZNF37A | NM_001178101 | 411 | 428 | 0.8211 | 1.0000 | 1.0395 | 0.056 | 1.04 | 16 | 4.03 |
| ZNF37A | NM_003421 | 54 | 0 | 0.0000 | 0.0000 | 0.0180 | −5.792 | 55.41 | 54 | 5.77 |
| ZNF37BP | AX721116 | 55 | 0 | 0.0000 | 0.0000 | 0.0179 | −5.802 | 55.78 | 55 | 5.78 |
| ZNF37BP | BC045697 | 15 | 51 | 0.0724 | 0.6341 | 3.1725 | 1.666 | 3.17 | 36 | 5.16 |
| ZNF37BP | NR_026777 | 101 | 108 | 0.8422 | 1.0000 | 1.0706 | 0.098 | 1.07 | 7 | 2.85 |
| ZNF395 | AK002050 | 172 | 24 | 0.0000 | 0.0014 | 0.1452 | −2.784 | 6.89 | 148 | 7.21 |
| ZNF395 | AK098243 | 0 | 10 | 0.0159 | 0.2884 | 10.7886 | 3.431 | 10.79 | 10 | 3.29 |
| ZNF395 | BC001237 | 298 | 364 | 0.5477 | 1.0000 | 1.2179 | 0.284 | 1.22 | 65 | 6.03 |
| ZNF395 | NM_018660 | 151 | 200 | 0.3410 | 1.0000 | 1.3210 | 0.402 | 1.32 | 49 | 5.61 |
| ZNF652 | BC034987 | 36 | 29 | 0.7205 | 1.0000 | 0.8151 | −0.295 | 1.23 | 7 | 2.77 |
| ZNF652 | NM_001145365 | 157 | 25 | 0.0000 | 0.0009 | 0.1651 | −2.599 | 6.06 | 132 | 7.05 |
| ZNF652 | NM_014897 | 121 | 232 | 0.0219 | 0.3505 | 1.9084 | 0.932 | 1.91 | 111 | 6.79 |
| ZNF674 | AK308986 | 6 | 1 | 0.3368 | 1.0000 | 0.3408 | −1.553 | 2.93 | 5 | 2.26 |
| ZNF674 | NM_001039891 | 21 | 76 | 0.0286 | 0.4100 | 3.4118 | 1.771 | 3.41 | 54 | 5.76 |
| ZNF674 | NM_001146291 | 2 | 0 | 0.0744 | 0.6386 | 0.3458 | −1.532 | 2.89 | 2 | 0.92 |
| ZNF674 | NM_001190417 | 54 | 0 | 0.0000 | 0.0001 | 0.0182 | −5.782 | 55.02 | 54 | 5.76 |
| ZNF74 | NM_001256523 | 69 | 72 | 0.8511 | 1.0000 | 1.0471 | 0.066 | 1.05 | 3 | 1.73 |
| ZNF74 | NM_001256524 | 77 | 4 | 0.0000 | 0.0006 | 0.0641 | −3.963 | 15.60 | 73 | 6.19 |
| ZNF74 | NM_001256525 | 7 | 24 | 0.1192 | 0.7848 | 3.2632 | 1.706 | 3.26 | 17 | 4.09 |
| ZNF74 | NM_003426 | 35 | 81 | 0.0793 | 0.6550 | 2.2628 | 1.178 | 2.26 | 46 | 5.51 |
| ZNF74 | NR_046282 | 3 | 4 | 1.0000 | 1.0000 | 1.0693 | 0.097 | 1.07 | 0 | −1.70 |
| ZNF778 | BC125192 | 30 | 54 | 0.2803 | 1.0000 | 1.7929 | 0.842 | 1.79 | 24 | 4.61 |
| ZNF778 | NM_001201407 | 70 | 64 | 0.7246 | 1.0000 | 0.9169 | −0.125 | 1.09 | 6 | 2.57 |
| ZNF778 | NM_182531 | 50 | 0 | 0.0000 | 0.0001 | 0.0195 | −5.681 | 51.29 | 50 | 5.65 |
| ZNF778 | NR_037705 | 70 | 63 | 0.7554 | 1.0000 | 0.9064 | −0.142 | 1.10 | 7 | 2.73 |

TABLE 9

RNA Abundance Modulation

| Gene | Trx_ID | ave DMSO | ave Cpd | padj (q val, FDR) | ttest (p val) | FC (x + 1) | L₂FC (x + 1) | amp FC (x + 1) | abs (Cpd − DMSO) | L₂abs (Cpd − DMSO) |
|---|---|---|---|---|---|---|---|---|---|---|
| ABCA1 | BC034824 | 100 | 0 | 0.0000 | 0.0000 | 0.0099 | −6.656 | 100.82 | 100 | 6.64 |
| ABCA1 | NM_005502 | 5 | 11 | 1.0000 | 0.4880 | 1.8052 | 0.852 | 1.81 | 5 | 2.38 |

TABLE 9-continued

RNA Abundance Modulation

| Gene | Trx_ID | ave DMSO | ave Cpd | padj (q val, FDR) | ttest (p val) | FC (x + 1) | L$_2$FC (x + 1) | amp FC (x + 1) | abs (Cpd − DMSO) | L$_2$abs (Cpd − DMSO) |
|---|---|---|---|---|---|---|---|---|---|---|
| ABCC1 | AB209120 | 7 | 6 | 1.0000 | 0.8906 | 0.8859 | −0.175 | 1.13 | 1 | −0.20 |
| ABCC1 | AK311015 | 0 | 1 | 1.0000 | 0.4588 | 1.8808 | 0.911 | 1.88 | 1 | −0.18 |
| ABCC1 | HQ917064 | 1 | 2 | 1.0000 | 0.6839 | 1.7981 | 0.846 | 1.80 | 1 | 0.49 |
| ABCC1 | HQ917065 | 13 | 0 | 0.1114 | 0.0032 | 0.0706 | −3.824 | 14.17 | 13 | 3.72 |
| ABCC1 | HQ917066 | 3194 | 3037 | 1.0000 | 0.4410 | 0.9506 | −0.073 | 1.05 | 158 | 7.30 |
| ABCC1 | HQ917067 | 170 | 167 | 1.0000 | 0.9480 | 0.9836 | −0.024 | 1.02 | 3 | 1.49 |
| ABCC1 | NM_004996 | 1465 | 2615 | 0.0000 | 0.0000 | 1.7849 | 0.836 | 1.78 | 1151 | 10.17 |
| ABL2 | AK225255 | 157 | 116 | 1.0000 | 0.4100 | 0.7398 | −0.435 | 1.35 | 41 | 5.36 |
| ABL2 | AK309549 | 2415 | 1132 | 0.0000 | 0.0000 | 0.4688 | −1.093 | 2.13 | 1283 | 10.33 |
| ABL2 | NM_001136000 | 295 | 460 | 0.2561 | 0.0115 | 1.5555 | 0.637 | 1.56 | 165 | 7.36 |
| ABL2 | NM_001136001 | 3 | 5 | 1.0000 | 0.6544 | 1.6207 | 0.697 | 1.62 | 2 | 1.17 |
| ABL2 | NM_001168236 | 16 | 8 | 1.0000 | 0.3581 | 0.4981 | −1.006 | 2.01 | 9 | 3.13 |
| ABL2 | NM_001168237 | 26 | 28 | 1.0000 | 0.9270 | 1.0663 | 0.093 | 1.07 | 2 | 0.83 |
| ABL2 | NM_001168238 | 34 | 19 | 1.0000 | 0.3232 | 0.5676 | −0.817 | 1.76 | 15 | 3.93 |
| ABL2 | NM_001168239 | 0 | 0 | 9999 | 9999 | 1.0000 | 0.000 | 1.00 | 0 | 0 |
| ABL2 | NM_005158 | 12 | 16 | 1.0000 | 0.7920 | 1.3493 | 0.432 | 1.35 | 4 | 2.17 |
| ABL2 | NM_007314 | 1985 | 2095 | 1.0000 | 0.4916 | 1.0555 | 0.078 | 1.06 | 110 | 6.78 |
| ACACA | AB209325 | 92 | 13 | 0.0095 | 0.0001 | 0.1478 | −2.759 | 6.77 | 79 | 6.31 |
| ACACA | AJ564444 | 4 | 9 | 1.0000 | 0.4966 | 1.8777 | 0.909 | 1.88 | 4 | 2.15 |
| ACACA | AK295586 | 69 | 40 | 1.0000 | 0.2757 | 0.5852 | −0.773 | 1.71 | 29 | 4.86 |
| ACACA | AK295735 | 8 | 2 | 1.0000 | 0.1903 | 0.2834 | −1.819 | 3.53 | 7 | 2.76 |
| ACACA | AK308905 | 19 | 12 | 1.0000 | 0.6049 | 0.6874 | −0.541 | 1.45 | 6 | 2.62 |
| ACACA | AK309084 | 14 | 4 | 1.0000 | 0.1881 | 0.3193 | −1.647 | 3.13 | 10 | 3.32 |
| ACACA | AY315622 | 0 | 0 | 9999 | 9999 | 1.0000 | 0.000 | 1.00 | 0 | 0 |
| ACACA | NM_198834 | 0 | 5 | 0.6345 | 0.0668 | 6.0516 | 2.597 | 6.05 | 5 | 2.34 |
| ACACA | NM_198836 | 227 | 224 | 1.0000 | 0.9271 | 0.9865 | −0.020 | 1.01 | 3 | 1.63 |
| ACACA | NM_198839 | 9 | 0 | 0.2467 | 0.0108 | 0.1037 | −3.269 | 9.64 | 9 | 3.11 |
| ACAT2 | AK055001 | 506 | 92 | 0.0000 | 0.0000 | 0.1833 | −2.447 | 5.45 | 414 | 8.69 |
| ACAT2 | AK294273 | 2034 | 2442 | 0.3278 | 0.0176 | 1.2004 | 0.264 | 1.20 | 408 | 8.67 |
| ACAT2 | NM_005891 | 159 | 168 | 1.0000 | 0.8826 | 1.0594 | 0.083 | 1.06 | 9 | 3.25 |
| AFF2 | NM_001169122 | 5 | 21 | 0.9595 | 0.1678 | 3.4115 | 1.770 | 3.41 | 15 | 3.93 |
| AFF2 | NM_001169123 | 110 | 0 | 0.0000 | 0.0000 | 0.0090 | −6.792 | 110.81 | 110 | 6.78 |
| AFF2 | NM_001169124 | 0 | 4 | 0.6897 | 0.0842 | 5.0146 | 2.326 | 5.01 | 4 | 2.01 |
| AFF2 | NM_001169125 | 108 | 11 | 0.0003 | 0.0000 | 0.1083 | −3.207 | 9.23 | 97 | 6.61 |
| AFF2 | NM_001170628 | 708 | 906 | 0.3886 | 0.0244 | 1.2787 | 0.355 | 1.28 | 198 | 7.63 |
| AFF2 | NM_002025 | 0 | 2 | 0.2843 | 0.0137 | 11.8248 | 3.564 | 11.82 | 11 | 3.44 |
| AFF2 | X95463 | 1502 | 1775 | 0.5623 | 0.0495 | 1.1815 | 0.241 | 1.18 | 273 | 8.09 |
| AHRR | AK090508 | 194 | 32 | 0.0000 | 0.0000 | 0.1707 | −2.550 | 5.86 | 161 | 7.33 |
| AHRR | AK127977 | 189 | 0 | 0.0000 | 0.0000 | 0.0053 | −7.570 | 189.97 | 189 | 7.56 |
| AHRR | AK314472 | 45 | 30 | 1.0000 | 0.3917 | 0.6613 | −0.597 | 1.51 | 16 | 3.97 |
| AHRR | BC035358 | 4 | 0 | 0.5166 | 0.0422 | 0.2103 | −2.249 | 4.75 | 4 | 1.91 |
| AHRR | BC121048 | 367 | 631 | 0.0081 | 0.0001 | 1.7195 | 0.782 | 1.72 | 265 | 8.05 |
| AHRR | NM_001242412 | 4 | 0 | 0.4926 | 0.0381 | 0.1973 | −2.341 | 5.07 | 4 | 2.02 |
| AHRR | NM_020731 | 11 | 11 | 1.0000 | 1.0000 | 1.0698 | 0.097 | 1.07 | 1 | −0.31 |
| AK021888 | AK021888 | 75 | 1 | 0.0000 | 0.0000 | 0.0220 | −5.506 | 45.43 | 74 | 6.21 |
| AK310472 | AK310472 | 56 | 54 | 1.0000 | 0.9513 | 0.9649 | −0.052 | 1.04 | 2 | 1.01 |
| AKAP1 | AK292416 | 3 | 1 | 1.0000 | 0.5591 | 0.6276 | −0.672 | 1.59 | 1 | 0.50 |
| AKAP1 | NM_001242902 | 9 | 2 | 1.0000 | 0.2814 | 0.3298 | −1.600 | 3.03 | 6 | 2.69 |
| AKAP1 | NM_001242903 | 0 | 0 | 1.0000 | 1.0000 | 1.3608 | 0.444 | 1.36 | 0 | −1.47 |
| AKAP1 | NM_003488 | 626 | 501 | 0.9361 | 0.1601 | 0.8015 | −0.319 | 1.25 | 124 | 6.96 |
| AKAP1 | U34074 | 0 | 155 | 0.0000 | 0.0000 | 155.9151 | 7.285 | 155.92 | 155 | 7.28 |
| ANK2 | AK294720 | 15 | 28 | 1.0000 | 0.4569 | 1.8463 | 0.885 | 1.85 | 13 | 3.72 |
| ANK2 | AK299767 | 826 | 242 | 0.0000 | 0.0000 | 0.2935 | −1.769 | 3.41 | 585 | 9.19 |
| ANK2 | AK299815 | 88 | 111 | 1.0000 | 0.4990 | 1.2597 | 0.333 | 1.26 | 23 | 4.53 |
| ANK2 | BC125236 | 1842 | 1800 | 1.0000 | 0.6619 | 0.9774 | −0.033 | 1.02 | 42 | 5.38 |
| ANK2 | BX538132 | 82 | 86 | 1.0000 | 0.9115 | 1.0435 | 0.061 | 1.04 | 4 | 1.85 |
| ANK2 | NM_001127493 | 83 | 75 | 1.0000 | 0.7817 | 0.9056 | −0.143 | 1.10 | 8 | 2.99 |
| ANK2 | NM_001148 | 17996 | 18144 | 1.0000 | 0.8071 | 1.0082 | 0.012 | 1.01 | 148 | 7.21 |
| ANK2 | NM_020977 | 39 | 24 | 1.0000 | 0.3418 | 0.6094 | −0.715 | 1.64 | 16 | 3.98 |
| ANKHD1-EIF4BP3 | AK125734 | 233 | 22 | 0.0000 | 0.0000 | 0.0994 | −3.330 | 10.06 | 210 | 7.72 |
| ANKHD1-EIF4BP3 | BC144623 | 640 | 878 | 0.2178 | 0.0087 | 1.3724 | 0.457 | 1.37 | 239 | 7.90 |
| ANKHD1-EIF4BP3 | NM_020690 | 4 | 9 | 1.0000 | 0.4746 | 2.0047 | 1.003 | 2.00 | 5 | 2.26 |
| AP2B1 | AK292531 | 875 | 436 | 0.0001 | 0.0000 | 0.4988 | −1.004 | 2.00 | 439 | 8.78 |
| AP2B1 | AK301522 | 243 | 315 | 0.9035 | 0.1479 | 1.2914 | 0.369 | 1.29 | 71 | 6.15 |
| AP2B1 | AY341427 | 1 | 5 | 1.0000 | 0.4236 | 2.4034 | 1.265 | 2.40 | 3 | 1.74 |
| AP2B1 | CR749392 | 6 | 9 | 1.0000 | 0.7900 | 1.3375 | 0.420 | 1.34 | 2 | 1.28 |
| AP2B1 | NM_001030006 | 56 | 67 | 1.0000 | 0.7063 | 1.2072 | 0.272 | 1.21 | 12 | 3.55 |
| AP2B1 | NM_001282 | 1722 | 1959 | 1.0000 | 0.2029 | 1.1376 | 0.186 | 1.14 | 237 | 7.89 |
| APAF1 | AJ243107 | 48 | 57 | 1.0000 | 0.7700 | 1.1762 | 0.234 | 1.18 | 9 | 3.11 |
| APAF1 | NM_001160 | 1962 | 1376 | 0.0058 | 0.0001 | 0.7014 | −0.512 | 1.43 | 586 | 9.20 |
| APAF1 | NM_013229 | 111 | 127 | 1.0000 | 0.7475 | 1.1486 | 0.200 | 1.15 | 17 | 4.05 |

TABLE 9-continued

RNA Abundance Modulation

| Gene | Trx_ID | ave DMSO | ave Cpd | padj (q val, FDR) | ttest (p val) | FC (x + 1) | L$_2$FC (x + 1) | amp FC (x + 1) | abs (Cpd − DMSO) | L$_2$abs (Cpd − DMSO) |
|---|---|---|---|---|---|---|---|---|---|---|
| APAF1 | NM_181861 | 18 | 21 | 1.0000 | 0.7175 | 1.1680 | 0.224 | 1.17 | 3 | 1.67 |
| APAF1 | NM_181868 | 1137 | 757 | 0.0088 | 0.0001 | 0.6657 | −0.587 | 1.50 | 380 | 8.57 |
| APLP2 | AK308932 | 355 | 1020 | 0.0000 | 0.0000 | 2.8690 | 1.521 | 2.87 | 665 | 9.38 |
| APLP2 | L23114 | 5470 | 5094 | 1.0000 | 0.2534 | 0.9313 | −0.103 | 1.07 | 376 | 8.55 |
| APLP2 | NM_001142276 | 12 | 19 | 1.0000 | 0.5291 | 1.6204 | 0.696 | 1.62 | 8 | 2.96 |
| APLP2 | NM_001142277 | 4591 | 3605 | 0.0095 | 0.0001 | 0.7853 | −0.349 | 1.27 | 986 | 9.95 |
| APLP2 | NM_001142278 | 4304 | 8747 | 0.0000 | 0.0000 | 2.0321 | 1.023 | 2.03 | 4443 | 12.12 |
| APLP2 | NM_001243299 | 15873 | 13379 | 0.0751 | 0.0019 | 0.8429 | −0.247 | 1.19 | 2494 | 11.28 |
| APLP2 | NR_024515 | 2 | 0 | 0.6345 | 0.0671 | 0.3158 | −1.663 | 3.17 | 2 | 1.12 |
| APLP2 | NR_024516 | 78 | 15 | 0.0994 | 0.0028 | 0.1979 | −2.337 | 5.05 | 64 | 5.99 |
| ARID1A | AB001895 | 185 | 188 | 1.0000 | 1.0000 | 1.0166 | 0.024 | 1.02 | 3 | 1.62 |
| ARID1A | AB384378 | 0 | 4 | 0.6476 | 0.0705 | 5.1105 | 2.353 | 5.11 | 4 | 2.04 |
| ARID1A | AK027655 | 2 | 0 | 0.6759 | 0.0808 | 0.3048 | −1.714 | 3.28 | 2 | 1.19 |
| ARID1A | AK223275 | 1 | 3 | 1.0000 | 0.5352 | 1.8886 | 0.917 | 1.89 | 2 | 0.78 |
| ARID1A | AK308363 | 14110 | 14271 | 1.0000 | 0.7753 | 1.0114 | 0.016 | 1.01 | 161 | 7.33 |
| ARID1A | NM_006015 | 28 | 1 | 0.0593 | 0.0013 | 0.0691 | −3.855 | 14.47 | 27 | 4.76 |
| ARID1A | NM_139135 | 32 | 50 | 1.0000 | 0.5420 | 1.5328 | 0.616 | 1.53 | 18 | 4.14 |
| ARMCX3 | CCDS14489 | 222 | 0 | 0.0000 | 0.0000 | 0.0045 | −7.799 | 222.65 | 222 | 7.79 |
| ARMCX3 | NM_016607 | 819 | 826 | 1.0000 | 0.9722 | 1.0078 | 0.011 | 1.01 | 6 | 2.68 |
| ARMCX3 | NM_177947 | 350 | 369 | 1.0000 | 0.7606 | 1.0557 | 0.078 | 1.06 | 20 | 4.29 |
| ARMCX3 | NM_177948 | 12 | 21 | 1.0000 | 0.4590 | 1.7075 | 0.772 | 1.71 | 9 | 3.17 |
| ASAP1 | AB033075 | 6707 | 6964 | 1.0000 | 0.4435 | 1.0383 | 0.054 | 1.04 | 257 | 8.01 |
| ASAP1 | NM_001247996 | 334 | 561 | 0.0248 | 0.0004 | 1.6790 | 0.748 | 1.68 | 227 | 7.83 |
| ASAP1 | NM_018482 | 862 | 744 | 1.0000 | 0.2154 | 0.8631 | −0.212 | 1.16 | 118 | 6.89 |
| ASPH | FJ461473 | 0 | 5 | 0.5987 | 0.0583 | 5.6978 | 2.510 | 5.70 | 5 | 2.23 |
| ASPH | NM_001164750 | 324 | 222 | 0.6377 | 0.0682 | 0.6857 | −0.544 | 1.46 | 102 | 6.67 |
| ASPH | NM_001164751 | 868 | 834 | 1.0000 | 0.7244 | 0.9614 | −0.057 | 1.04 | 34 | 5.07 |
| ASPH | NM_001164752 | 0 | 25 | 0.0149 | 0.0002 | 26.3708 | 4.721 | 26.37 | 25 | 4.67 |
| ASPH | NM_001164753 | 95 | 505 | 0.0000 | 0.0000 | 5.2518 | 2.393 | 5.25 | 410 | 8.68 |
| ASPH | NM_001164754 | 546 | 469 | 1.0000 | 0.1922 | 0.8578 | −0.221 | 1.17 | 78 | 6.28 |
| ASPH | NM_001164755 | 0 | 1 | 1.0000 | 0.6668 | 1.6544 | 0.726 | 1.65 | 1 | −0.61 |
| ASPH | NM_001164756 | 24 | 18 | 1.0000 | 0.7240 | 0.7742 | −0.369 | 1.29 | 6 | 2.48 |
| ASPH | NM_004318 | 79 | 5 | 0.0012 | 0.0000 | 0.0750 | −3.737 | 13.33 | 74 | 6.21 |
| ASPH | NM_032466 | 450 | 389 | 1.0000 | 0.3438 | 0.8658 | −0.208 | 1.16 | 60 | 5.92 |
| ASPH | NM_032467 | 419 | 508 | 1.0000 | 0.2231 | 1.2138 | 0.279 | 1.21 | 90 | 6.49 |
| ATAD2B | AK125718 | 2561 | 2758 | 1.0000 | 0.2653 | 1.0768 | 0.107 | 1.08 | 197 | 7.62 |
| ATAD2B | BC037408 | 1926 | 0 | 0.0000 | 0.0000 | 0.0005 | −10.912 | 1926.86 | 1926 | 10.91 |
| ATAD2B | BC171846 | 919 | 919 | 1.0000 | 1.0000 | 1.0005 | 0.001 | 1.00 | 0 | −1.13 |
| ATAD2B | NM_001242338 | 711 | 575 | 0.7979 | 0.1173 | 0.8085 | −0.307 | 1.24 | 136 | 7.09 |
| ATAD2B | NM_017552 | 0 | 23 | 0.0319 | 0.0006 | 23.5867 | 4.560 | 23.59 | 23 | 4.50 |
| ATF7IP | AK025060 | 167 | 242 | 1.0000 | 0.3007 | 1.4437 | 0.530 | 1.44 | 75 | 6.22 |
| ATF7IP | AK299320 | 5159 | 5313 | 1.0000 | 0.5982 | 1.0299 | 0.042 | 1.03 | 154 | 7.27 |
| ATF7IP | AK304184 | 18 | 18 | 1.0000 | 1.0000 | 0.9961 | −0.006 | 1.00 | 0 | −3.77 |
| ATF7IP | AY337596 | 12279 | 13846 | 0.3371 | 0.0185 | 1.1277 | 0.173 | 1.13 | 1568 | 10.61 |
| ATF7IP | BC053625 | 0 | 110 | 0.0000 | 0.0000 | 111.1435 | 6.796 | 111.14 | 110 | 6.78 |
| ATF7IP | BC063855 | 12 | 6 | 1.0000 | 0.4951 | 0.5424 | −0.882 | 1.84 | 6 | 2.60 |
| ATF7IP | BX648096 | 45 | 30 | 1.0000 | 0.5045 | 0.6791 | −0.558 | 1.47 | 15 | 3.89 |
| ATF7IP | NM_018179 | 0 | 13 | 0.1907 | 0.0072 | 13.6359 | 3.769 | 13.64 | 13 | 3.66 |
| ATG9A | BC065534 | 63 | 0 | 0.0000 | 0.0000 | 0.0156 | −6.006 | 64.27 | 63 | 5.98 |
| ATG9A | NM_001077198 | 1937 | 1737 | 0.9851 | 0.1786 | 0.8967 | −0.157 | 1.12 | 200 | 7.65 |
| ATG9A | NM_024085 | 197 | 0 | 0.0000 | 0.0000 | 0.0051 | −7.629 | 197.89 | 197 | 7.62 |
| AXIN1 | NM_003502 | 4681 | 5238 | 0.6512 | 0.0710 | 1.1189 | 0.162 | 1.12 | 557 | 9.12 |
| AXIN1 | NM_181050 | 116 | 2 | 0.0000 | 0.0000 | 0.0262 | −5.255 | 38.19 | 114 | 6.83 |
| BACE1 | AF527782 | 94 | 8 | 0.0005 | 0.0000 | 0.0978 | −3.355 | 10.23 | 86 | 6.42 |
| BACE1 | NM_001207048 | 3 | 8 | 1.0000 | 0.3931 | 2.5984 | 1.378 | 2.60 | 6 | 2.49 |
| BACE1 | NM_001207049 | 61 | 39 | 1.0000 | 0.3783 | 0.6335 | −0.659 | 1.58 | 23 | 4.51 |
| BACE1 | NM_012104 | 16 | 10 | 1.0000 | 0.4832 | 0.6586 | −0.603 | 1.52 | 6 | 2.57 |
| BACE1 | NM_138971 | 87 | 75 | 1.0000 | 0.7283 | 0.8692 | −0.202 | 1.15 | 11 | 3.52 |
| BACE1 | NM_138972 | 2491 | 2841 | 0.6345 | 0.0668 | 1.1406 | 0.190 | 1.14 | 350 | 8.45 |
| BACE1 | NM_138973 | 686 | 334 | 0.0001 | 0.0000 | 0.4886 | −1.033 | 2.05 | 351 | 8.46 |
| BIN1 | AF068916 | 10 | 3 | 1.0000 | 0.3682 | 0.4108 | −1.284 | 2.43 | 6 | 2.66 |
| BIN1 | AK301153 | 24 | 17 | 1.0000 | 0.6196 | 0.7243 | −0.465 | 1.38 | 7 | 2.76 |
| BIN1 | NM_004305 | 16 | 11 | 1.0000 | 0.7000 | 0.7225 | −0.469 | 1.38 | 5 | 2.26 |
| BIN1 | NM_139343 | 552 | 499 | 1.0000 | 0.4985 | 0.9047 | −0.144 | 1.11 | 53 | 5.72 |
| BIN1 | NM_139346 | 1749 | 1567 | 1.0000 | 0.2194 | 0.8960 | −0.158 | 1.12 | 182 | 7.51 |
| BIN1 | NM_139347 | 243 | 1 | 0.0000 | 0.0000 | 0.0069 | −7.189 | 145.91 | 242 | 7.92 |
| BIN1 | NM_139348 | 20 | 33 | 1.0000 | 0.5305 | 1.6230 | 0.699 | 1.62 | 13 | 3.70 |
| BIN1 | NM_139349 | 5437 | 5032 | 1.0000 | 0.2172 | 0.9255 | −0.112 | 1.08 | 405 | 8.66 |
| BIN1 | NM_139350 | 55 | 100 | 0.9399 | 0.1613 | 1.8102 | 0.856 | 1.81 | 45 | 5.50 |
| BIN1 | NM_139351 | 567 | 728 | 0.5768 | 0.0532 | 1.2821 | 0.359 | 1.28 | 160 | 7.33 |
| BNC1 | AK302992 | 256 | 208 | 1.0000 | 0.3572 | 0.8128 | −0.299 | 1.23 | 48 | 5.59 |
| BNC1 | NM_001717 | 95 | 126 | 1.0000 | 0.3077 | 1.3309 | 0.412 | 1.33 | 32 | 4.98 |
| BRPF1 | AK293865 | 1 | 5 | 1.0000 | 0.2699 | 3.6239 | 1.858 | 3.62 | 4 | 2.09 |
| BRPF1 | AL713696 | 0 | 6 | 0.5661 | 0.0504 | 6.6874 | 2.741 | 6.69 | 6 | 2.51 |

TABLE 9-continued

RNA Abundance Modulation

| Gene | Trx_ID | ave DMSO | ave Cpd | padj (q val, FDR) | ttest (p val) | FC (x + 1) | L$_2$FC (x + 1) | amp FC (x + 1) | abs (Cpd − DMSO) | L$_2$abs (Cpd − DMSO) |
|---|---|---|---|---|---|---|---|---|---|---|
| BRPF1 | NM_001003694 | 11 | 0 | 0.1462 | 0.0048 | 0.0811 | −3.624 | 12.33 | 11 | 3.50 |
| BRPF1 | NM_004634 | 0 | 0 | 9999 | 9999 | 1.0000 | 0.000 | 1.00 | 0 | 0 |
| BZW1 | NM_001207067 | 0 | 2 | 0.8943 | 0.1454 | 2.7617 | 1.466 | 2.76 | 2 | 0.82 |
| BZW1 | NM_001207068 | 4 | 3 | 1.0000 | 1.0000 | 0.9090 | −0.138 | 1.10 | 0 | −1.19 |
| BZW1 | NM_001207069 | 49 | 51 | 1.0000 | 0.9586 | 1.0384 | 0.054 | 1.04 | 2 | 0.94 |
| BZW1 | Z70221 | 312 | 334 | 1.0000 | 0.7293 | 1.0691 | 0.096 | 1.07 | 22 | 4.44 |
| C11orf30 | AK125114 | 37 | 30 | 1.0000 | 0.7510 | 0.8158 | −0.294 | 1.23 | 7 | 2.82 |
| C11orf30 | AK126030 | 3 | 1 | 1.0000 | 0.4189 | 0.4681 | −1.095 | 2.14 | 2 | 1.24 |
| C11orf30 | AK304043 | 0 | 1 | 1.0000 | 0.6668 | 1.5872 | 0.667 | 1.59 | 1 | −0.77 |
| C11orf30 | AK304043 | 75 | 73 | 1.0000 | 0.9408 | 0.9803 | −0.029 | 1.02 | 1 | 0.58 |
| C11orf30 | AK309621 | 31 | 50 | 1.0000 | 0.4037 | 1.5667 | 0.648 | 1.57 | 18 | 4.20 |
| C11orf30 | AY070433 | 363 | 375 | 1.0000 | 0.7918 | 1.0328 | 0.047 | 1.03 | 12 | 3.58 |
| C11orf30 | BC021688 | 13 | 30 | 1.0000 | 0.2183 | 2.2812 | 1.190 | 2.28 | 17 | 4.12 |
| C11orf30 | BC033404 | 119 | 141 | 1.0000 | 0.5642 | 1.1787 | 0.237 | 1.18 | 21 | 4.42 |
| C11orf30 | BC117265 | 1859 | 2234 | 0.3816 | 0.0237 | 1.2014 | 0.265 | 1.20 | 375 | 8.55 |
| C11orf30 | BC143370 | 690 | 191 | 0.0000 | 0.0000 | 0.2777 | −1.848 | 3.60 | 499 | 8.96 |
| C11orf30 | BC143374 | 1 | 3 | 1.0000 | 0.4495 | 2.3146 | 1.211 | 2.31 | 3 | 1.35 |
| C11orf30 | BC143376 | 3 | 3 | 1.0000 | 0.8901 | 0.8839 | −0.178 | 1.13 | 1 | −0.96 |
| C11orf30 | NM_020193 | 192 | 457 | 0.0004 | 0.0000 | 2.3728 | 1.247 | 2.37 | 265 | 8.05 |
| C11orf73 | NM_016401 | 576 | 308 | 0.0019 | 0.0000 | 0.5353 | −0.902 | 1.87 | 268 | 8.07 |
| C11orf73 | NR_024596 | 285 | 774 | 0.0000 | 0.0000 | 2.7095 | 1.438 | 2.71 | 489 | 8.93 |
| C11orf73 | NR_024598 | 1033 | 510 | 0.0000 | 0.0000 | 0.4942 | −1.017 | 2.02 | 523 | 9.03 |
| C17orf76-AS1 | HQ447236 | 236 | 243 | 1.0000 | 0.9238 | 1.0314 | 0.045 | 1.03 | 7 | 2.89 |
| C17orf76-AS1 | NR_027158 | 549 | 478 | 1.0000 | 0.3438 | 0.8719 | −0.198 | 1.15 | 70 | 6.14 |
| C17orf76-AS1 | NR_027163 | 63 | 59 | 1.0000 | 0.8300 | 0.9502 | −0.074 | 1.05 | 3 | 1.66 |
| C17orf76-AS1 | NR_027164 | 482 | 190 | 0.0001 | 0.0000 | 0.3947 | −1.341 | 2.53 | 292 | 8.19 |
| C17orf76-AS1 | NR_027165 | 1410 | 1573 | 1.0000 | 0.2024 | 1.1154 | 0.158 | 1.12 | 163 | 7.35 |
| C17orf76-AS1 | NR_027166 | 1 | 1 | 1.0000 | 0.8816 | 0.9304 | −0.104 | 1.07 | 0 | −2.68 |
| C17orf76-AS1 | NR_027167 | 319 | 407 | 0.8337 | 0.1263 | 1.2733 | 0.349 | 1.27 | 88 | 6.45 |
| C17orf76-AS1 | NR_027168 | 268 | 29 | 0.0000 | 0.0000 | 0.1119 | −3.160 | 8.94 | 239 | 7.90 |
| C17orf76-AS1 | NR_027169 | 110 | 185 | 0.6622 | 0.0748 | 1.6787 | 0.747 | 1.68 | 75 | 6.23 |
| C17orf76-AS1 | NR_027170 | 4 | 0 | 0.4926 | 0.0382 | 0.1990 | −2.329 | 5.02 | 4 | 2.01 |
| C17orf76-AS1 | NR_027172 | 706 | 755 | 1.0000 | 0.5835 | 1.0699 | 0.097 | 1.07 | 49 | 5.63 |
| C17orf76-AS1 | NR_027173 | 18334 | 20220 | 0.6251 | 0.0643 | 1.1029 | 0.141 | 1.10 | 1886 | 10.88 |
| C17orf76-AS1 | NR_027174 | 5413 | 2518 | 0.0000 | 0.0000 | 0.4653 | −1.104 | 2.15 | 2895 | 11.50 |
| C17orf76-AS1 | NR_027176 | 12972 | 10999 | 0.1040 | 0.0029 | 0.8479 | −0.238 | 1.18 | 1973 | 10.95 |
| C17orf76-AS1 | NR_027177 | 43 | 56 | 1.0000 | 0.6310 | 1.2984 | 0.377 | 1.30 | 13 | 3.70 |
| C17orf76-AS1 | NR_027178 | 39 | 129 | 0.0628 | 0.0015 | 3.2188 | 1.687 | 3.22 | 90 | 6.49 |
| C17orf76-AS1 | NR_027179 | 445 | 380 | 1.0000 | 0.3473 | 0.8544 | −0.227 | 1.17 | 65 | 6.02 |
| C17orf76-AS1 | NR_027667 | 0 | 4 | 0.6476 | 0.0705 | 5.1105 | 2.353 | 5.11 | 4 | 2.04 |
| C17orf76-AS1 | NR_045022 | 101 | 10 | 0.0008 | 0.0000 | 0.1093 | −3.194 | 9.15 | 90 | 6.50 |
| C17orf76-AS1 | NR_045023 | 0 | 6 | 0.5326 | 0.0442 | 6.5786 | 2.718 | 6.58 | 6 | 2.48 |
| C17orf76-AS1 | NR_045025 | 1846 | 1816 | 1.0000 | 0.8135 | 0.9839 | −0.023 | 1.02 | 30 | 4.90 |
| C17orf76-AS1 | NR_045026 | 438 | 82 | 0.0000 | 0.0000 | 0.1902 | −2.395 | 5.26 | 355 | 8.47 |
| C17orf76-AS1 | NR_045028 | 108 | 128 | 1.0000 | 0.6085 | 1.1884 | 0.249 | 1.19 | 21 | 4.36 |
| C17orf76-AS1 | NR_045029 | 7346 | 7547 | 1.0000 | 0.6520 | 1.0274 | 0.039 | 1.03 | 201 | 7.65 |
| C4orf27 | NM_017867 | 12 | 12 | 1.0000 | 0.9776 | 0.9895 | −0.015 | 1.01 | 0 | −2.84 |
| C6orf48 | AJ249732 | 2 | 6 | 1.0000 | 0.4673 | 2.3151 | 1.211 | 2.32 | 4 | 2.07 |
| C6orf48 | AJ249732 | 139 | 93 | 0.9229 | 0.1551 | 0.6747 | −0.568 | 1.48 | 46 | 5.51 |
| C6orf48 | NM_001040437 | 2946 | 3733 | 0.0362 | 0.0007 | 1.2672 | 0.342 | 1.27 | 787 | 9.62 |
| C6orf48 | NM_001040437 | 367 | 33 | 0.0000 | 0.0000 | 0.0936 | −3.418 | 10.69 | 334 | 8.38 |
| C6orf48 | NM_001040438 | 135 | 93 | 1.0000 | 0.2694 | 0.6916 | −0.532 | 1.45 | 42 | 5.39 |
| C6orf48 | NM_001040438 | 1081 | 1047 | 1.0000 | 0.8073 | 0.9678 | −0.047 | 1.03 | 35 | 5.12 |
| C6orf48 | NM_001040438 | 0 | 0 | 9999 | 9999 | 1.0000 | 0.000 | 1.00 | 0 | 0 |
| CAB39 | AF134480 | 1397 | 1255 | 1.0000 | 0.2948 | 0.8987 | −0.154 | 1.11 | 142 | 7.15 |
| CAB39 | NM_001130849 | 86 | 299 | 0.0007 | 0.0000 | 3.4606 | 1.791 | 3.46 | 213 | 7.74 |
| CAB39 | NM_001130850 | 372 | 305 | 1.0000 | 0.2716 | 0.8195 | −0.287 | 1.22 | 67 | 6.07 |
| CAB39 | NM_016289 | 13 | 116 | 0.0015 | 0.0000 | 8.3836 | 3.068 | 8.38 | 103 | 6.69 |
| CAMKK1 | NM_032294 | 24 | 34 | 1.0000 | 0.5755 | 1.4147 | 0.500 | 1.41 | 10 | 3.37 |
| CAMKK1 | NM_172206 | 3 | 42 | 0.0777 | 0.0020 | 11.3258 | 3.502 | 11.33 | 39 | 5.30 |
| CAMKK1 | NM_172207 | 25 | 0 | 0.0077 | 0.0001 | 0.0378 | −4.727 | 26.48 | 25 | 4.67 |
| CCDC88A | AK001254 | 0 | 13 | 0.1892 | 0.0071 | 13.7130 | 3.777 | 13.71 | 13 | 3.67 |
| CCDC88A | AK024717 | 57 | 46 | 1.0000 | 0.5531 | 0.8145 | −0.296 | 1.23 | 11 | 3.42 |
| CCDC88A | AK124603 | 265 | 448 | 0.0701 | 0.0017 | 1.6864 | 0.754 | 1.69 | 183 | 7.51 |
| CCDC88A | AK124761 | 4279 | 4062 | 1.0000 | 0.4644 | 0.9492 | −0.075 | 1.05 | 217 | 7.76 |
| CCDC88A | BC032683 | 578 | 411 | 0.3124 | 0.0162 | 0.7115 | −0.491 | 1.41 | 167 | 7.38 |
| CCDC88A | BC142700 | 150 | 166 | 1.0000 | 0.6702 | 1.1110 | 0.152 | 1.11 | 17 | 4.06 |
| CCDC88A | BX537985 | 90 | 307 | 0.0003 | 0.0000 | 3.3721 | 1.754 | 3.37 | 216 | 7.76 |
| CCDC88A | BX538154 | 1141 | 1153 | 1.0000 | 0.8716 | 1.0102 | 0.015 | 1.01 | 12 | 3.54 |
| CCDC88A | NM_001135597 | 90 | 98 | 1.0000 | 0.7704 | 1.0857 | 0.119 | 1.09 | 8 | 2.97 |
| CCDC88A | NM_001254943 | 261 | 194 | 1.0000 | 0.2164 | 0.7444 | −0.426 | 1.34 | 67 | 6.06 |
| CCDC88A | NM_018084 | 1842 | 851 | 0.0000 | 0.0000 | 0.4623 | −1.113 | 2.16 | 991 | 9.95 |
| CCDC92 | AK125866 | 1982 | 2775 | 0.0028 | 0.0000 | 1.3997 | 0.485 | 1.40 | 793 | 9.63 |
| CCDC92 | AK222661 | 686 | 794 | 1.0000 | 0.2735 | 1.1573 | 0.211 | 1.16 | 108 | 6.76 |

TABLE 9-continued

RNA Abundance Modulation

| Gene | Trx_ID | ave DMSO | ave Cpd | padj (q val, FDR) | ttest (p val) | FC (x + 1) | $L_2$FC (x + 1) | amp FC (x + 1) | abs (Cpd − DMSO) | $L_2$abs (Cpd − DMSO) |
|---|---|---|---|---|---|---|---|---|---|---|
| CCDC92 | NM_025140 | 239 | 350 | 0.5661 | 0.0509 | 1.4630 | 0.549 | 1.46 | 111 | 6.80 |
| CDC25B | AK295573 | 101 | 86 | 1.0000 | 0.6331 | 0.8557 | −0.225 | 1.17 | 15 | 3.88 |
| CDC25B | AK299028 | 49 | 56 | 1.0000 | 0.6843 | 1.1458 | 0.196 | 1.15 | 7 | 2.87 |
| CDC25B | AK299192 | 0 | 7 | 0.4039 | 0.0262 | 8.3402 | 3.060 | 8.34 | 7 | 2.88 |
| CDC25B | BX640836 | 3 | 5 | 1.0000 | 0.7100 | 1.5141 | 0.598 | 1.51 | 2 | 1.04 |
| CDC25B | BX647988 | 160 | 3 | 0.0000 | 0.0000 | 0.0267 | −5.226 | 37.44 | 157 | 7.29 |
| CDC25B | FR695900 | 21 | 0 | 0.0234 | 0.0004 | 0.0463 | −4.432 | 21.58 | 21 | 4.36 |
| CDC25B | FR695901 | 1601 | 1829 | 0.8501 | 0.1313 | 1.1428 | 0.193 | 1.14 | 229 | 7.84 |
| CDC25B | NM_004358 | 396 | 183 | 0.0064 | 0.0001 | 0.4626 | −1.112 | 2.16 | 213 | 7.74 |
| CDC25B | NM_021872 | 0 | 0 | 9999 | 9999 | 1.0000 | 0.000 | 1.00 | 0 | 0 |
| CDC25B | NM_021873 | 0 | 0 | 9999 | 9999 | 1.0000 | 0.000 | 1.00 | 0 | 0 |
| CDC42BPA | AB007920 | 0 | 0 | 9999 | 9999 | 1.0000 | 0.000 | 1.00 | 0 | 0 |
| CDC42BPA | AB384799 | 0 | 0 | 9999 | 9999 | 1.0000 | 0.000 | 1.00 | 0 | 0 |
| CDC42BPA | AK027000 | 327 | 0 | 0.0000 | 0.0000 | 0.0030 | −8.359 | 328.22 | 327 | 8.35 |
| CDC42BPA | AK098391 | 3354 | 3382 | 1.0000 | 0.9154 | 1.0081 | 0.012 | 1.01 | 27 | 4.76 |
| CDC42BPA | BC136333 | 3354 | 3382 | 1.0000 | 0.9154 | 1.0081 | 0.012 | 1.01 | 27 | 4.76 |
| CDC42BPA | CR933723 | 3354 | 3382 | 1.0000 | 0.9154 | 1.0081 | 0.012 | 1.01 | 27 | 4.76 |
| CDC42BPA | NM_003607 | 3354 | 3382 | 1.0000 | 0.9154 | 1.0081 | 0.012 | 1.01 | 27 | 4.76 |
| CDC42BPA | NM_014826 | 151 | 22 | 0.0011 | 0.0000 | 0.1534 | −2.704 | 6.52 | 129 | 7.01 |
| CDCA7 | AK297097 | 4447 | 3097 | 0.0000 | 0.0000 | 0.6965 | −0.522 | 1.44 | 1350 | 10.40 |
| CDCA7 | AK300949 | 58866 | 56920 | 1.0000 | 0.3816 | 0.9669 | −0.049 | 1.03 | 1946 | 10.93 |
| CDCA7 | NM_031942 | 0 | 64 | 0.0000 | 0.0000 | 64.7208 | 6.016 | 64.72 | 64 | 5.99 |
| CDCA7 | NM_145810 | 1614 | 1506 | 1.0000 | 0.3798 | 0.9333 | −0.100 | 1.07 | 108 | 6.75 |
| CDH11 | AK294872 | 0 | 66 | 0.0000 | 0.0000 | 67.0893 | 6.068 | 67.09 | 66 | 6.05 |
| CDH11 | AK297377 | 74 | 0 | 0.0000 | 0.0000 | 0.0132 | −6.238 | 75.49 | 74 | 6.22 |
| CDH11 | AK308000 | 33 | 16 | 1.0000 | 0.2873 | 0.4794 | −1.061 | 2.09 | 18 | 4.16 |
| CDH11 | E07383 | 96 | 0 | 0.0000 | 0.0000 | 0.0103 | −6.599 | 96.93 | 96 | 6.58 |
| CDH11 | NM_001797 | 87 | 164 | 0.5661 | 0.0506 | 1.8711 | 0.904 | 1.87 | 77 | 6.27 |
| CDH13 | NM_001220488 | 263 | 335 | 1.0000 | 0.2091 | 1.2728 | 0.348 | 1.27 | 72 | 6.17 |
| CDH13 | NM_001220490 | 0 | 0 | 9999 | 9999 | 1.0000 | 0.000 | 1.00 | 0 | 0 |
| CDH13 | NM_001220491 | 157 | 151 | 1.0000 | 0.9625 | 0.9593 | −0.060 | 1.04 | 6 | 2.69 |
| CDH13 | NM_001220492 | 50 | 0 | 0.0000 | 0.0195 | 0.0195 | −5.681 | 51.31 | 50 | 5.65 |
| CDH13 | NM_001257 | 28 | 83 | 0.3010 | 0.0150 | 2.9122 | 1.542 | 2.91 | 55 | 5.78 |
| CEP68 | AK299373 | 0 | 3 | 0.8871 | 0.1424 | 3.5258 | 1.818 | 3.53 | 3 | 1.34 |
| CEP68 | AK301173 | 125 | 0 | 0.0000 | 0.0000 | 0.0079 | −6.976 | 125.93 | 125 | 6.96 |
| CEP68 | AK304110 | 529 | 640 | 1.0000 | 0.1882 | 1.2091 | 0.274 | 1.21 | 111 | 6.79 |
| CEP68 | BC004873 | 2001 | 60 | 0.0000 | 0.0000 | 0.0303 | −5.044 | 32.98 | 1941 | 10.92 |
| CEP68 | BC030534 | 0 | 3 | 0.7895 | 0.1154 | 4.2474 | 2.087 | 4.25 | 3 | 1.70 |
| CEP68 | NM_015147 | 4916 | 6774 | 0.0000 | 0.0000 | 1.3779 | 0.463 | 1.38 | 1858 | 10.86 |
| CFLAR | AB209600 | 0 | 0 | 9999 | 9999 | 1.0000 | 0.000 | 1.00 | 0 | 0 |
| CFLAR | AF009617 | 36 | 8 | 0.4221 | 0.0283 | 0.2410 | −2.053 | 4.15 | 28 | 4.82 |
| CFLAR | AF009619 | 0 | 0 | 9999 | 9999 | 1.0000 | 0.000 | 1.00 | 0 | 0 |
| CFLAR | AF015451 | 1 | 0 | 1.0000 | 0.2352 | 0.5158 | −0.955 | 1.94 | 1 | −0.09 |
| CFLAR | AF015452 | 0 | 1 | 1.0000 | 0.6668 | 1.6691 | 0.739 | 1.67 | 1 | −0.58 |
| CFLAR | AF041462 | 2262 | 2216 | 1.0000 | 0.7573 | 0.9800 | −0.029 | 1.02 | 45 | 5.50 |
| CFLAR | AK308767 | 179 | 130 | 0.9595 | 0.1685 | 0.7247 | −0.465 | 1.38 | 50 | 5.63 |
| CFLAR | NM_001127183 | 391 | 388 | 1.0000 | 0.9305 | 0.9915 | −0.012 | 1.01 | 3 | 1.73 |
| CFLAR | NM_001127184 | 0 | 5 | 0.5895 | 0.0557 | 6.3529 | 2.667 | 6.35 | 5 | 2.42 |
| CFLAR | NM_001202515 | 37 | 27 | 1.0000 | 0.6510 | 0.7337 | −0.447 | 1.36 | 10 | 3.33 |
| CFLAR | NM_001202516 | 413 | 341 | 1.0000 | 0.2464 | 0.8261 | −0.276 | 1.21 | 72 | 6.17 |
| CFLAR | NM_001202517 | 1369 | 1299 | 1.0000 | 0.6165 | 0.9494 | −0.075 | 1.05 | 69 | 6.11 |
| CFLAR | NM_001202518 | 658 | 559 | 1.0000 | 0.2530 | 0.8507 | −0.233 | 1.18 | 98 | 6.62 |
| CFLAR | NM_001202519 | 0 | 0 | 9999 | 9999 | 1.0000 | 0.000 | 1.00 | 0 | 0 |
| CFLAR | NM_003879 | 0 | 0 | 9999 | 9999 | 1.0000 | 0.000 | 1.00 | 0 | 0 |
| CFLAR | U97075 | 1 | 116 | 0.0000 | 0.0000 | 72.1281 | 6.172 | 72.13 | 115 | 6.85 |
| COPS7B | AK024273 | 136 | 89 | 0.8630 | 0.1351 | 0.6576 | −0.605 | 1.52 | 47 | 5.55 |
| COPS7B | AK124133 | 55 | 0 | 0.0000 | 0.0000 | 0.0180 | −5.797 | 55.61 | 55 | 5.77 |
| COPS7B | AK126326 | 5 | 3 | 1.0000 | 0.6307 | 0.6371 | −0.650 | 1.57 | 2 | 1.12 |
| COPS7B | AK307486 | 746 | 414 | 0.0010 | 0.0000 | 0.5548 | −0.850 | 1.80 | 333 | 8.38 |
| COPS7B | BC091493 | 11 | 8 | 1.0000 | 0.7982 | 0.7471 | −0.421 | 1.34 | 3 | 1.60 |
| COPS7B | NM_022730 | 8 | 0 | 0.2870 | 0.0139 | 0.1124 | −3.153 | 8.90 | 8 | 2.98 |
| CREB5 | AK298121 | 10 | 0 | 0.1947 | 0.0074 | 0.0944 | −3.406 | 10.60 | 10 | 3.26 |
| CREB5 | NM_001011666 | 1261 | 1241 | 1.0000 | 0.8873 | 0.9842 | −0.023 | 1.02 | 20 | 4.32 |
| CREB5 | NM_004904 | 264 | 392 | 0.5143 | 0.0406 | 1.4833 | 0.569 | 1.48 | 128 | 7.00 |
| CREB5 | NM_182899 | 328 | 737 | 0.0000 | 0.0000 | 2.2448 | 1.167 | 2.24 | 409 | 8.68 |
| CUL2 | AK294080 | 368 | 391 | 1.0000 | 0.7023 | 1.0605 | 0.085 | 1.06 | 22 | 4.48 |
| CUL2 | NM_001198777 | 191 | 29 | 0.0001 | 0.0000 | 0.1548 | −2.691 | 6.46 | 163 | 7.34 |
| CUL2 | NM_003591 | 8157 | 8383 | 1.0000 | 0.6271 | 1.0278 | 0.040 | 1.03 | 227 | 7.82 |
| CUL4A | AK296700 | 190 | 505 | 0.0000 | 0.0000 | 2.6526 | 1.407 | 2.65 | 315 | 8.30 |
| CUL4A | AL833355 | 950 | 914 | 1.0000 | 0.7068 | 0.9621 | −0.056 | 1.04 | 36 | 5.17 |
| CUL4A | NM_001008895 | 1557 | 1222 | 0.2282 | 0.0094 | 0.7850 | −0.349 | 1.27 | 335 | 8.39 |
| CUL4A | NM_003589 | 67 | 56 | 1.0000 | 0.6620 | 0.8400 | −0.252 | 1.19 | 11 | 3.45 |
| CUX1 | NM_001202543 | 59 | 0 | 0.0000 | 0.0000 | 0.0168 | −5.896 | 59.54 | 59 | 5.87 |
| CUX1 | NM_001202544 | 150 | 145 | 1.0000 | 0.8720 | 0.9667 | −0.049 | 1.03 | 5 | 2.32 |

TABLE 9-continued

RNA Abundance Modulation

| Gene | Trx_ID | ave DMSO | ave Cpd | padj (q val, FDR) | ttest (p val) | FC (x + 1) | $L_2FC$ (x + 1) | amp FC (x + 1) | abs (Cpd − DMSO) | $L_2$abs (Cpd − DMSO) |
|---|---|---|---|---|---|---|---|---|---|---|
| CUX1 | NM_001202545 | 1193 | 1255 | 1.0000 | 0.6177 | 1.0517 | 0.073 | 1.05 | 62 | 5.95 |
| CUX1 | NM_001202546 | 74 | 0 | 0.0000 | 0.0000 | 0.0133 | −6.229 | 74.99 | 74 | 6.21 |
| CUX1 | NM_001913 | 25 | 79 | 0.4904 | 0.0373 | 3.1152 | 1.639 | 3.12 | 54 | 5.77 |
| CUX1 | NM_181500 | 283 | 176 | 0.4684 | 0.0345 | 0.6226 | −0.684 | 1.61 | 107 | 6.74 |
| CUX1 | NM_181552 | 308 | 399 | 0.8771 | 0.1385 | 1.2928 | 0.370 | 1.29 | 90 | 6.50 |
| CYP51A1 | AK091323 | 875 | 890 | 1.0000 | 0.8093 | 1.0169 | 0.024 | 1.02 | 15 | 3.89 |
| CYP51A1 | NM_000786 | 55 | 41 | 1.0000 | 0.5226 | 0.7561 | −0.403 | 1.32 | 14 | 3.77 |
| CYP51A1 | NM_001146152 | 114 | 24 | 0.0327 | 0.0006 | 0.2213 | −2.176 | 4.52 | 90 | 6.49 |
| DCUN1D4 | AK124346 | 19 | 19 | 1.0000 | 0.9478 | 0.9922 | −0.011 | 1.01 | 0 | −2.67 |
| DCUN1D4 | AK294894 | 45 | 48 | 1.0000 | 0.8608 | 1.0610 | 0.085 | 1.06 | 3 | 1.49 |
| DCUN1D4 | AK294896 | 173 | 0 | 0.0000 | 0.0000 | 0.0057 | −7.445 | 174.19 | 173 | 7.44 |
| DCUN1D4 | BC041702 | 7 | 5 | 1.0000 | 0.7317 | 0.7165 | −0.481 | 1.40 | 2 | 1.16 |
| DCUN1D4 | NM_001040402 | 531 | 650 | 0.8667 | 0.1360 | 1.2237 | 0.291 | 1.22 | 119 | 6.90 |
| DCUN1D4 | NM_015115 | 174 | 158 | 1.0000 | 0.6834 | 0.9060 | −0.142 | 1.10 | 16 | 4.04 |
| DDR1 | AK130776 | 186 | 189 | 1.0000 | 0.9715 | 1.0124 | 0.018 | 1.01 | 2 | 1.22 |
| DDR1 | AK291621 | 67 | 78 | 1.0000 | 0.7037 | 1.1616 | 0.216 | 1.16 | 11 | 3.46 |
| DDR1 | AK291621 | 3 | 0 | 0.6251 | 0.0647 | 0.2475 | −2.015 | 4.04 | 3 | 1.60 |
| DDR1 | AK295643 | 133 | 83 | 0.8537 | 0.1329 | 0.6301 | −0.666 | 1.59 | 49 | 5.63 |
| DDR1 | AK295643 | 143 | 165 | 1.0000 | 0.6376 | 1.1575 | 0.211 | 1.16 | 23 | 4.50 |
| DDR1 | BC070070 | 26 | 46 | 1.0000 | 0.3021 | 1.7611 | 0.816 | 1.76 | 20 | 4.35 |
| DDR1 | EU826614 | 13 | 2 | 0.7955 | 0.1167 | 0.2344 | −2.093 | 4.27 | 10 | 3.37 |
| DDR1 | EU826614 | 18 | 6 | 1.0000 | 0.2512 | 0.3675 | −1.444 | 2.72 | 12 | 3.59 |
| DDR1 | EU826614 | 6 | 0 | 0.3637 | 0.1446 | 0.1447 | −2.790 | 6.91 | 6 | 2.56 |
| DDR1 | L20817 | 7 | 11 | 1.0000 | 0.7034 | 1.5099 | 0.594 | 1.51 | 4 | 2.06 |
| DDR1 | L57508 | 0 | 0 | 9999 | 9999 | 1.0000 | 0.000 | 1.00 | 0 | 0 |
| DDR1 | NM_001202521 | 1887 | 1785 | 1.0000 | 0.5323 | 0.9462 | −0.080 | 1.06 | 102 | 6.67 |
| DDR1 | NM_001202522 | 171 | 11 | 0.0000 | 0.0000 | 0.0727 | −3.781 | 13.75 | 159 | 7.31 |
| DDR1 | NM_001202523 | 205 | 22 | 0.0000 | 0.0000 | 0.1093 | −3.193 | 9.15 | 183 | 7.52 |
| DDR1 | NM_001202523 | 421 | 659 | 0.0327 | 0.0006 | 1.5639 | 0.645 | 1.56 | 238 | 7.89 |
| DDR1 | NM_013993 | 564 | 699 | 0.6900 | 0.0845 | 1.2387 | 0.309 | 1.24 | 135 | 7.08 |
| DDR1 | NM_013994 | 6 | 11 | 1.0000 | 0.5480 | 1.8290 | 0.871 | 1.83 | 6 | 2.50 |
| DDR1 | Z29093 | 24 | 28 | 1.0000 | 0.7081 | 1.1625 | 0.217 | 1.16 | 4 | 2.03 |
| DDR1 | Z29093 | 0 | 0 | 9999 | 9999 | 1.0000 | 0.000 | 1.00 | 0 | 0 |
| DDX39B | AB209217 | 0 | 0 | 9999 | 9999 | 1.0000 | 0.000 | 1.00 | 0 | 0 |
| DDX39B | AB209217 | 892 | 822 | 1.0000 | 0.4119 | 0.9213 | −0.118 | 1.09 | 70 | 6.13 |
| DDX39B | AB209217 | 0 | 0 | 9999 | 9999 | 1.0000 | 0.000 | 1.00 | 0 | 0 |
| DDX39B | AK127767 | 2453 | 1938 | 0.0880 | 0.0023 | 0.7903 | −0.339 | 1.27 | 514 | 9.01 |
| DDX39B | AK127767 | 755 | 296 | 0.0000 | 0.0000 | 0.3924 | −1.350 | 2.55 | 460 | 8.84 |
| DDX39B | AK127767 | 55 | 11 | 0.3570 | 0.0206 | 0.2169 | −2.205 | 4.61 | 44 | 5.46 |
| DDX39B | AK127767 | 41 | 33 | 1.0000 | 0.7135 | 0.8267 | −0.275 | 1.21 | 7 | 2.85 |
| DDX39B | AK294939 | 558 | 363 | 0.1277 | 0.0040 | 0.6519 | −0.617 | 1.53 | 195 | 7.60 |
| DDX39B | AK295634 | 12 | 11 | 1.0000 | 0.8555 | 0.9019 | −0.149 | 1.11 | 1 | 0.39 |
| DDX39B | AK316469 | 2 | 22 | 0.3181 | 0.0168 | 8.1592 | 3.028 | 8.16 | 20 | 4.35 |
| DDX39B | AK316469 | 15 | 36 | 1.0000 | 0.2503 | 2.2974 | 1.200 | 2.30 | 21 | 4.37 |
| DDX39B | AK316469 | 272 | 364 | 0.7564 | 0.1065 | 1.3336 | 0.415 | 1.33 | 91 | 6.51 |
| DDX39B | NM_004640 | 20592 | 20075 | 1.0000 | 0.6731 | 0.9749 | −0.037 | 1.03 | 517 | 9.01 |
| DDX39B | NM_080598 | 773 | 1572 | 0.0000 | 0.0000 | 2.0323 | 1.023 | 2.03 | 799 | 9.64 |
| DDX39B | NM_080598 | 286 | 384 | 0.7356 | 0.0993 | 1.3410 | 0.423 | 1.34 | 98 | 6.61 |
| DDX39B | NM_080598 | 1039 | 1313 | 0.3785 | 0.0230 | 1.2639 | 0.338 | 1.26 | 274 | 8.10 |
| DDX39B | NM_080598 | 3 | 4 | 1.0000 | 0.8934 | 1.3142 | 0.394 | 1.31 | 1 | 0.26 |
| DDX39B | NM_080598 | 791 | 0 | 0.0000 | 0.0000 | 0.0013 | −9.630 | 792.28 | 791 | 9.63 |
| DDX39B | NR_037852 | 4529 | 5500 | 0.0853 | 0.0022 | 1.2143 | 0.280 | 1.21 | 971 | 9.92 |
| DDX39B | NR_037852 | 0 | 0 | 9999 | 9999 | 1.0000 | 0.000 | 1.00 | 0 | 0 |
| DDX39B | NR_037852 | 191 | 137 | 1.0000 | 0.2091 | 0.7189 | −0.476 | 1.39 | 54 | 5.75 |
| DDX39B | NR_037853 | 1012 | 372 | 0.0000 | 0.0000 | 0.3686 | −1.440 | 2.71 | 640 | 9.32 |
| DDX42 | AK095772 | 380 | 311 | 1.0000 | 0.2835 | 0.8178 | −0.290 | 1.22 | 69 | 6.12 |
| DDX42 | AK122737 | 8974 | 9035 | 1.0000 | 0.9473 | 1.0068 | 0.010 | 1.01 | 61 | 5.92 |
| DDX42 | AK126480 | 134 | 22 | 0.0035 | 0.0000 | 0.1710 | −2.548 | 5.85 | 112 | 6.81 |
| DDX42 | CU677324 | 89 | 183 | 0.4670 | 0.0338 | 2.0421 | 1.030 | 2.04 | 94 | 6.55 |
| DDX42 | NM_007372 | 38 | 56 | 1.0000 | 0.4331 | 1.4390 | 0.525 | 1.44 | 17 | 4.11 |
| DDX42 | NM_203499 | 359 | 295 | 1.0000 | 0.2843 | 0.8216 | −0.284 | 1.22 | 64 | 6.01 |
| DENND1A | AB046828 | 4618 | 2067 | 0.0000 | 0.0000 | 0.4477 | −1.159 | 2.23 | 2551 | 11.32 |
| DENND1A | AK295710 | 85 | 32 | 0.5752 | 0.0529 | 0.3891 | −1.362 | 2.57 | 52 | 5.71 |
| DENND1A | AK299867 | 10 | 9 | 1.0000 | 0.9439 | 0.9462 | −0.080 | 1.06 | 1 | −0.78 |
| DENND1A | BC009616 | 37 | 23 | 1.0000 | 0.5075 | 0.6403 | −0.643 | 1.56 | 14 | 3.76 |
| DENND1A | BC028061 | 72 | 96 | 1.0000 | 0.5336 | 1.3323 | 0.414 | 1.33 | 24 | 4.60 |
| DENND1A | BC113037 | 1128 | 1509 | 0.1163 | 0.0034 | 1.3382 | 0.420 | 1.34 | 382 | 8.58 |
| DENND1A | NM_020946 | 337 | 347 | 1.0000 | 0.8293 | 1.0308 | 0.044 | 1.03 | 10 | 3.38 |
| DENND1A | NM_024820 | 0 | 0 | 9999 | 9999 | 1.0000 | 0.000 | 1.00 | 0 | 0 |
| DENND5A | AK125444 | 26 | 0 | 0.0068 | 0.0001 | 0.0370 | −4.755 | 27.00 | 26 | 4.70 |
| DENND5A | AK294016 | 87 | 60 | 1.0000 | 0.3283 | 0.6937 | −0.528 | 1.44 | 27 | 4.75 |
| DENND5A | NM_001243254 | 3711 | 4387 | 0.2077 | 0.0082 | 1.1821 | 0.241 | 1.18 | 676 | 9.40 |
| DENND5A | NM_015213 | 8112 | 9030 | 0.6733 | 0.0797 | 1.1130 | 0.154 | 1.11 | 917 | 9.84 |
| DGKA | AF064770 | 3428 | 1507 | 0.0000 | 0.0000 | 0.4399 | −1.185 | 2.27 | 1921 | 10.91 |

TABLE 9-continued

RNA Abundance Modulation

| Gene | Trx_ID | ave DMSO | ave Cpd | padj (q val, FDR) | ttest (p val) | FC (x + 1) | L$_2$FC (x + 1) | amp FC (x + 1) | abs (Cpd − DMSO) | L$_2$abs (Cpd − DMSO) |
|---|---|---|---|---|---|---|---|---|---|---|
| DGKA | AF064771 | 2932 | 3457 | 0.3360 | 0.0184 | 1.1792 | 0.238 | 1.18 | 526 | 9.04 |
| DGKA | AK122973 | 334 | 50 | 0.0000 | 0.0000 | 0.1517 | −2.721 | 6.59 | 284 | 8.15 |
| DGKA | AK307685 | 138 | 126 | 1.0000 | 0.8819 | 0.9168 | −0.125 | 1.09 | 12 | 3.53 |
| DGKA | AK309939 | 0 | 5 | 0.6377 | 0.0683 | 5.6838 | 2.507 | 5.68 | 5 | 2.23 |
| DGKA | AK310600 | 1387 | 1404 | 1.0000 | 0.8959 | 1.0123 | 0.018 | 1.01 | 17 | 4.10 |
| DGKA | AY930112 | 887 | 1129 | 0.3603 | 0.0209 | 1.2723 | 0.347 | 1.27 | 242 | 7.92 |
| DGKA | NM_001345 | 122 | 148 | 1.0000 | 0.5593 | 1.2077 | 0.272 | 1.21 | 26 | 4.68 |
| DGKA | NM_201444 | 37 | 37 | 1.0000 | 0.9497 | 0.9850 | −0.022 | 1.02 | 1 | −0.80 |
| DGKA | NM_201445 | 860 | 748 | 1.0000 | 0.2241 | 0.8698 | −0.201 | 1.15 | 112 | 6.81 |
| DGKA | NM_201554 | 12 | 16 | 1.0000 | 0.7878 | 1.3288 | 0.410 | 1.33 | 4 | 2.09 |
| DHCR24 | AK298414 | 487 | 436 | 1.0000 | 0.4710 | 0.8948 | −0.160 | 1.12 | 51 | 5.68 |
| DHCR24 | AK304302 | 7559 | 8824 | 0.1672 | 0.0058 | 1.1673 | 0.223 | 1.17 | 1265 | 10.30 |
| DHCR24 | AK316419 | 557 | 0 | 0.0000 | 0.0000 | 0.0018 | −9.123 | 557.61 | 557 | 9.12 |
| DHCR24 | NM_014762 | 21 | 20 | 1.0000 | 0.8930 | 0.9253 | −0.112 | 1.08 | 2 | 0.74 |
| DHCR7 | NM_001163817 | 14 | 14 | 1.0000 | 1.0000 | 1.0299 | 0.042 | 1.03 | 0 | −1.19 |
| DHCR7 | NM_001360 | 66 | 108 | 0.9512 | 0.1646 | 1.6194 | 0.695 | 1.62 | 42 | 5.38 |
| DIAPH1 | AF051782 | 659 | 290 | 0.0000 | 0.0000 | 0.4408 | −1.182 | 2.27 | 369 | 8.53 |
| DIAPH1 | BC143414 | 2256 | 2191 | 1.0000 | 0.6748 | 0.9709 | −0.043 | 1.03 | 66 | 6.04 |
| DIAPH1 | NM_001079812 | 0 | 38 | 0.0008 | 0.0000 | 38.5820 | 5.270 | 38.58 | 38 | 5.23 |
| DIAPH1 | NM_005219 | 333 | 248 | 0.8384 | 0.1284 | 0.7458 | −0.423 | 1.34 | 85 | 6.41 |
| DIAPH3 | BC041395 | 547 | 267 | 0.0014 | 0.0000 | 0.4900 | −1.029 | 2.04 | 279 | 8.13 |
| DIAPH3 | NM_001042517 | 2152 | 2586 | 0.2943 | 0.0144 | 1.2019 | 0.265 | 1.20 | 435 | 8.76 |
| DIAPH3 | NM_001258366 | 1 | 2 | 1.0000 | 0.8049 | 1.4798 | 0.565 | 1.48 | 1 | −0.06 |
| DIAPH3 | NM_001258367 | 0 | 0 | 9999 | 9999 | 1.0000 | 0.000 | 1.00 | 0 | 0 |
| DIAPH3 | NM_001258368 | 78 | 0 | 0.0000 | 0.0000 | 0.0126 | −6.312 | 79.43 | 78 | 6.29 |
| DIAPH3 | NM_001258369 | 323 | 350 | 1.0000 | 0.6206 | 1.0824 | 0.114 | 1.08 | 27 | 4.74 |
| DIAPH3 | NM_001258370 | 10 | 96 | 0.0020 | 0.0000 | 8.6476 | 3.112 | 8.65 | 86 | 6.43 |
| DIAPH3 | NM_030932 | 395 | 152 | 0.0007 | 0.0000 | 0.3858 | −1.374 | 2.59 | 243 | 7.93 |
| DNM2 | AB209213 | 32 | 163 | 0.0070 | 0.0001 | 4.9794 | 2.316 | 4.98 | 131 | 7.03 |
| DNM2 | AK097967 | 0 | 0 | 9999 | 9999 | 1.0000 | 0.000 | 1.00 | 0 | 0 |
| DNM2 | AK097989 | 66 | 27 | 0.8456 | 0.1304 | 0.4160 | −1.265 | 2.40 | 39 | 5.30 |
| DNM2 | AK127033 | 17 | 8 | 1.0000 | 0.5518 | 0.4871 | −1.038 | 2.05 | 9 | 3.18 |
| DNM2 | AK295929 | 123 | 254 | 0.1981 | 0.0075 | 2.0613 | 1.044 | 2.06 | 131 | 7.04 |
| DNM2 | NM_001005360 | 578 | 112 | 0.0000 | 0.0000 | 0.1946 | −2.361 | 5.14 | 466 | 8.87 |
| DNM2 | NM_001005361 | 1647 | 2006 | 0.3782 | 0.0229 | 1.2179 | 0.284 | 1.22 | 359 | 8.49 |
| DNM2 | NM_001005362 | 0 | 5 | 0.5661 | 0.0516 | 6.3977 | 2.678 | 6.40 | 5 | 2.43 |
| DNM2 | NM_001190716 | 5 | 6 | 1.0000 | 0.9227 | 1.1683 | 0.224 | 1.17 | 1 | −0.07 |
| DNM2 | NM_004945 | 265 | 416 | 0.2858 | 0.0138 | 1.5718 | 0.652 | 1.57 | 152 | 7.25 |
| DOCK1 | BC084559 | 70 | 3 | 0.0007 | 0.0000 | 0.0567 | −4.141 | 17.64 | 67 | 6.07 |
| DOCK1 | BC144632 | 2 | 1 | 1.0000 | 0.8195 | 0.8104 | −0.303 | 1.23 | 1 | −0.88 |
| DOCK1 | BX648342 | 414 | 420 | 1.0000 | 0.9061 | 1.0158 | 0.023 | 1.02 | 7 | 2.71 |
| DOCK1 | NM_001380 | 2996 | 3051 | 1.0000 | 0.7659 | 1.0185 | 0.027 | 1.02 | 56 | 5.80 |
| EFCAB14 | AK295722 | 130 | 58 | 0.3257 | 0.0174 | 0.4535 | −1.141 | 2.21 | 71 | 6.16 |
| EFCAB14 | AK296777 | 576 | 534 | 1.0000 | 0.4590 | 0.9260 | −0.111 | 1.08 | 43 | 5.42 |
| EFCAB14 | NM_014774 | 409 | 126 | 0.0000 | 0.0000 | 0.3093 | −1.693 | 3.23 | 283 | 8.14 |
| EIF2B3 | NM_001166588 | 5 | 33 | 0.4099 | 0.0269 | 5.7736 | 2.529 | 5.77 | 28 | 4.83 |
| EIF2B3 | NM_001261418 | 3430 | 3581 | 1.0000 | 0.4979 | 1.0439 | 0.062 | 1.04 | 151 | 7.24 |
| EIF2B3 | NM_020365 | 154 | 0 | 0.0000 | 0.0000 | 0.0064 | −7.278 | 155.17 | 154 | 7.27 |
| EPN1 | AK314690 | 14 | 27 | 1.0000 | 0.5124 | 1.8610 | 0.896 | 1.86 | 13 | 3.70 |
| EPN1 | NM_001130071 | 3715 | 4234 | 0.5421 | 0.0454 | 1.1396 | 0.189 | 1.14 | 519 | 9.02 |
| EPN1 | NM_001130072 | 219939 | 208128 | 1.0000 | 0.2764 | 0.9463 | −0.080 | 1.06 | 11811 | 13.53 |
| EPN1 | NM_013333 | 156 | 62 | 0.1892 | 0.0071 | 0.4017 | −1.316 | 2.49 | 94 | 6.55 |
| EPT1 | BC021229 | 35 | 51 | 1.0000 | 0.5188 | 1.4258 | 0.512 | 1.43 | 15 | 3.95 |
| EPT1 | NM_033505 | 5985 | 4046 | 0.0000 | 0.0000 | 0.6762 | −0.565 | 1.48 | 1939 | 10.92 |
| ERC1 | AK294351 | 9434 | 0 | 0.0000 | 0.0000 | 0.0001 | −13.204 | 9434.90 | 9434 | 13.20 |
| ERC1 | AK309992 | 53333 | 50063 | 1.0000 | 0.2063 | 0.9387 | −0.091 | 1.07 | 3270 | 11.67 |
| ERC1 | BC144287 | 92613 | 93194 | 1.0000 | 0.9879 | 1.0063 | 0.009 | 1.01 | 581 | 9.18 |
| ERC1 | NM_178039 | 15026 | 14267 | 1.0000 | 0.2485 | 0.9495 | −0.075 | 1.05 | 759 | 9.57 |
| ERC1 | NM_178040 | 2691 | 2425 | 0.7974 | 0.1171 | 0.9013 | −0.150 | 1.11 | 266 | 8.05 |
| ERC1 | NR_027946 | 37608 | 35995 | 1.0000 | 0.3111 | 0.9571 | −0.063 | 1.04 | 1614 | 10.66 |
| ERC1 | NR_027948 | 127 | 121 | 1.0000 | 0.8224 | 0.9493 | −0.075 | 1.05 | 6 | 2.70 |
| ETV5 | AK301878 | 570449 | 536948 | 1.0000 | 0.2860 | 0.9413 | −0.087 | 1.06 | 33501 | 15.03 |
| ETV5 | NM_004454 | 6104 | 6474 | 1.0000 | 0.3279 | 1.0607 | 0.085 | 1.06 | 370 | 8.53 |
| FADS1 | AK096275 | 17639 | 14912 | 0.0204 | 0.0003 | 0.8454 | −0.242 | 1.18 | 2728 | 11.41 |
| FADS1 | AK298871 | 331169 | 321899 | 1.0000 | 0.5394 | 0.9720 | −0.041 | 1.03 | 9269 | 13.18 |
| FADS1 | NM_013402 | 147578 | 142887 | 1.0000 | 0.4080 | 0.9682 | −0.047 | 1.03 | 4691 | 12.20 |
| FADS2 | AK074991 | 136635 | 140576 | 1.0000 | 0.7080 | 1.0288 | 0.041 | 1.03 | 3941 | 11.94 |
| FADS2 | AK299762 | 274 | 189 | 0.7088 | 0.0934 | 0.6918 | −0.532 | 1.45 | 85 | 6.40 |
| FADS2 | BC009011 | 156 | 234 | 0.7780 | 0.1109 | 1.4948 | 0.580 | 1.49 | 78 | 6.28 |
| FADS2 | NM_004265 | 4 | 13 | 1.0000 | 0.2938 | 2.6315 | 1.396 | 2.63 | 9 | 3.13 |
| FAF1 | AF094700 | 1217 | 1005 | 0.6177 | 0.0626 | 0.8266 | −0.275 | 1.21 | 211 | 7.72 |
| FAF1 | AK293659 | 108 | 3 | 0.0000 | 0.0000 | 0.0389 | −4.682 | 25.67 | 104 | 6.71 |
| FAF1 | NM_007051 | 157 | 37 | 0.0043 | 0.0000 | 0.2413 | −2.051 | 4.14 | 120 | 6.91 |
| FAM198B | AK172805 | 261 | 552 | 0.0005 | 0.0000 | 2.1113 | 1.078 | 2.11 | 291 | 8.18 |

TABLE 9-continued

RNA Abundance Modulation

| Gene | Trx_ID | ave DMSO | ave Cpd | padj (q val, FDR) | ttest (p val) | FC (x + 1) | L$_2$FC (x + 1) | amp FC (x + 1) | abs (Cpd − DMSO) | L$_2$abs (Cpd − DMSO) |
|---|---|---|---|---|---|---|---|---|---|---|
| FAM198B | NM_001031700 | 237 | 66 | 0.0007 | 0.0000 | 0.2820 | −1.826 | 3.55 | 171 | 7.42 |
| FAM198B | NM_001128424 | 39 | 0 | 0.0004 | 0.0000 | 0.0251 | −5.316 | 39.84 | 39 | 5.28 |
| FAM198B | NM_016613 | 2802 | 267 | 0.0000 | 0.0000 | 0.0957 | −3.386 | 10.45 | 2535 | 11.31 |
| FAM219B | BC006348 | 75 | 7 | 0.0068 | 0.0001 | 0.1106 | −3.176 | 9.04 | 68 | 6.08 |
| FAM219B | BC064575 | 0 | 0 | 9999 | 9999 | 1.0000 | 0.000 | 1.00 | 0 | 0 |
| FAM219B | NM_020447 | 40 | 9 | 0.3436 | 0.0193 | 0.2354 | −2.087 | 4.25 | 31 | 4.97 |
| FBXO10 | BC125124 | 28 | 0 | 0.0042 | 0.0342 | 0.0342 | −4.869 | 29.23 | 28 | 4.82 |
| FBXO10 | BC125125 | 0 | 0 | 9999 | 9999 | 1.0000 | 0.000 | 1.00 | 0 | 0 |
| FBXO10 | NM_012166 | 7 | 4 | 1.0000 | 0.6209 | 0.6044 | −0.726 | 1.65 | 3 | 1.70 |
| FBXO9 | NM_012347 | 118 | 0 | 0.0000 | 0.0000 | 0.0084 | −6.895 | 119.01 | 118 | 6.88 |
| FBXO9 | NM_033480 | 15 | 0 | 0.0600 | 0.0014 | 0.0607 | −4.043 | 16.48 | 15 | 3.95 |
| FBXO9 | NM_033481 | 13 | 0 | 0.0982 | 0.0027 | 0.0710 | −3.815 | 14.08 | 13 | 3.71 |
| FDFT1 | AK057726 | 31 | 25 | 1.0000 | 0.7581 | 0.8381 | −0.255 | 1.19 | 5 | 2.35 |
| FDFT1 | AK296043 | 8 | 10 | 1.0000 | 0.8069 | 1.2673 | 0.342 | 1.27 | 2 | 1.27 |
| FDFT1 | AK297868 | 784 | 265 | 0.0000 | 0.0000 | 0.3391 | −1.560 | 2.95 | 519 | 9.02 |
| FDFT1 | AK300059 | 805 | 1425 | 0.0000 | 0.0000 | 1.7689 | 0.823 | 1.77 | 620 | 9.28 |
| FDFT1 | AK300245 | 1079 | 1116 | 1.0000 | 0.9577 | 1.0340 | 0.048 | 1.03 | 37 | 5.20 |
| FDFT1 | AK301617 | 494 | 399 | 1.0000 | 0.3692 | 0.8097 | −0.305 | 1.24 | 94 | 6.56 |
| FDFT1 | AK311246 | 5008 | 3441 | 0.0000 | 0.0000 | 0.6871 | −0.541 | 1.46 | 1567 | 10.61 |
| FDFT1 | AK315993 | 570 | 2054 | 0.0000 | 0.0000 | 3.6012 | 1.848 | 3.60 | 1485 | 10.54 |
| FDFT1 | AK316033 | 0 | 0 | 1.0000 | 0.4970 | 0.7617 | −0.393 | 1.31 | 0 | −1.68 |
| FDFT1 | AK316351 | 559 | 244 | 0.0000 | 0.0000 | 0.4384 | −1.190 | 2.28 | 314 | 8.30 |
| FDFT1 | AK316531 | 1366 | 1593 | 0.6212 | 0.0632 | 1.1658 | 0.221 | 1.17 | 227 | 7.83 |
| FDFT1 | NM_004462 | 577 | 534 | 1.0000 | 0.6042 | 0.9256 | −0.112 | 1.08 | 43 | 5.43 |
| FDPS | NM_001135821 | 0 | 11 | 0.2639 | 0.0120 | 11.5899 | 3.535 | 11.59 | 11 | 3.40 |
| FDPS | NM_001135822 | 15 | 13 | 1.0000 | 0.8640 | 0.8969 | −0.157 | 1.11 | 2 | 0.72 |
| FDPS | NM_001242824 | 79 | 36 | 0.6857 | 0.0827 | 0.4611 | −1.117 | 2.17 | 43 | 5.43 |
| FDPS | NM_001242825 | 38 | 105 | 0.2960 | 0.0145 | 2.7469 | 1.458 | 2.75 | 68 | 6.08 |
| FDPS | NM_002004 | 437 | 352 | 0.9595 | 0.1682 | 0.8059 | −0.311 | 1.24 | 85 | 6.41 |
| FER | AK293376 | 68 | 168 | 0.1617 | 0.0056 | 2.4584 | 1.298 | 2.46 | 100 | 6.65 |
| FER | AK296874 | 90 | 7 | 0.0009 | 0.0000 | 0.0930 | −3.426 | 10.75 | 82 | 6.36 |
| FER | AK299855 | 49 | 131 | 0.2888 | 0.0140 | 2.6516 | 1.407 | 2.65 | 82 | 6.36 |
| FER | BC058030 | 2 | 2 | 1.0000 | 0.8591 | 0.7944 | −0.332 | 1.26 | 1 | −0.48 |
| FER | NM_005246 | 2 | 1 | 1.0000 | 0.4808 | 0.5841 | −0.776 | 1.71 | 1 | 0.25 |
| FEZ1 | AK296554 | 466 | 112 | 0.0000 | 0.0000 | 0.2412 | −2.052 | 4.15 | 355 | 8.47 |
| FEZ1 | CCDS44758 | 0 | 0 | 9999 | 9999 | 1.0000 | 0.000 | 1.00 | 0 | 0 |
| FEZ1 | NM_005103 | 0 | 0 | 9999 | 9999 | 1.0000 | 0.000 | 1.00 | 0 | 0 |
| FEZ1 | NM_022549 | 53 | 0 | 0.0000 | 0.0000 | 0.0185 | −5.760 | 54.19 | 53 | 5.73 |
| FHOD3 | AB051482 | 15 | 10 | 1.0000 | 0.5153 | 0.6748 | −0.567 | 1.48 | 5 | 2.37 |
| FHOD3 | AB084087 | 4 | 5 | 1.0000 | 0.9538 | 1.0955 | 0.132 | 1.10 | 0 | −1.02 |
| FHOD3 | AK128053 | 2737 | 2810 | 1.0000 | 0.7190 | 1.0269 | 0.038 | 1.03 | 74 | 6.20 |
| FHOD3 | AK308859 | 98 | 2 | 0.0000 | 0.0000 | 0.0303 | −5.042 | 32.95 | 96 | 6.59 |
| FHOD3 | BC058897 | 12 | 13 | 1.0000 | 0.8294 | 1.1145 | 0.156 | 1.11 | 1 | 0.52 |
| FHOD3 | HM191478 | 155 | 170 | 1.0000 | 0.7311 | 1.0972 | 0.134 | 1.10 | 15 | 3.92 |
| FHOD3 | NM_025135 | 21 | 17 | 1.0000 | 0.7955 | 0.8471 | −0.239 | 1.18 | 3 | 1.72 |
| FLII | AK295814 | 399 | 450 | 1.0000 | 0.4392 | 1.1280 | 0.174 | 1.13 | 51 | 5.68 |
| FLII | BC021885 | 3 | 2 | 1.0000 | 0.7301 | 0.7878 | −0.344 | 1.27 | 1 | −0.23 |
| FLII | NM_001256264 | 3 | 4 | 1.0000 | 0.8357 | 1.3614 | 0.445 | 1.36 | 1 | 0.34 |
| FLII | NM_001256265 | 14 | 24 | 1.0000 | 0.4653 | 1.6812 | 0.750 | 1.68 | 10 | 3.36 |
| FLII | NM_002018 | 3 | 0 | 0.6251 | 0.0647 | 0.2475 | −2.015 | 4.04 | 3 | 1.60 |
| FLNB | AF353666 | 538 | 840 | 0.0299 | 0.0005 | 1.5620 | 0.643 | 1.56 | 303 | 8.24 |
| FLNB | NM_001164317 | 231 | 10 | 0.0000 | 0.0000 | 0.0469 | −4.416 | 21.34 | 221 | 7.79 |
| FLNB | NM_001164318 | 10 | 9 | 1.0000 | 0.9472 | 0.9253 | −0.112 | 1.08 | 1 | −0.27 |
| FLNB | NM_001164319 | 157 | 23 | 0.0002 | 0.0000 | 0.1550 | −2.690 | 6.45 | 133 | 7.06 |
| FLNB | NM_001457 | 0 | 7 | 0.4826 | 0.0361 | 8.2165 | 3.039 | 8.22 | 7 | 2.85 |
| FNBP1 | AK000975 | 25 | 50 | 1.0000 | 0.2677 | 1.9550 | 0.967 | 1.96 | 25 | 4.64 |
| FNBP1 | AK001616 | 121 | 283 | 0.0385 | 0.0008 | 2.3297 | 1.220 | 2.33 | 162 | 7.34 |
| FNBP1 | AK023681 | 10 | 8 | 1.0000 | 0.8904 | 0.8249 | −0.278 | 1.21 | 2 | 0.92 |
| FNBP1 | BC143513 | 53 | 0 | 0.0000 | 0.0000 | 0.0187 | −5.742 | 53.53 | 53 | 5.72 |
| FNBP1 | BC143514 | 34 | 43 | 1.0000 | 0.6685 | 1.2647 | 0.339 | 1.26 | 9 | 3.22 |
| FNBP1 | BC143515 | 60 | 138 | 0.3124 | 0.0162 | 2.2677 | 1.181 | 2.27 | 78 | 6.28 |
| FNBP1 | NM_015033 | 69 | 0 | 0.0000 | 0.0000 | 0.0143 | −6.130 | 70.03 | 69 | 6.11 |
| FOS | AK290907 | 2608 | 2653 | 1.0000 | 0.8122 | 1.0171 | 0.024 | 1.02 | 45 | 5.48 |
| FOS | AK298659 | 1 | 2 | 1.0000 | 1.0000 | 1.1224 | 0.167 | 1.12 | 0 | −1.82 |
| FOS | NM_005252 | 53 | 58 | 1.0000 | 0.9214 | 1.0812 | 0.113 | 1.08 | 4 | 2.14 |
| FOSB | AK225070 | 139 | 181 | 1.0000 | 0.3366 | 1.2976 | 0.376 | 1.30 | 42 | 5.38 |
| FOSB | EU178110 | 74 | 0 | 0.0000 | 0.0000 | 0.0134 | −6.226 | 74.83 | 74 | 6.21 |
| FOSB | EU178111 | 3 | 0 | 0.6144 | 0.0620 | 0.2855 | −1.809 | 3.50 | 3 | 1.32 |
| FOSB | EU178112 | 0 | 0 | 1.0000 | 1.0000 | 1.3346 | 0.416 | 1.33 | 0 | −1.58 |
| FOSB | EU178113 | 6762 | 7564 | 0.6144 | 0.0609 | 1.1185 | 0.162 | 1.12 | 801 | 9.65 |
| FOSB | EU178114 | 2496 | 2728 | 1.0000 | 0.2298 | 1.0927 | 0.128 | 1.09 | 232 | 7.86 |
| FOSB | EU178115 | 4712 | 4668 | 1.0000 | 0.8864 | 0.9906 | −0.014 | 1.01 | 44 | 5.47 |
| FOSB | EU178116 | 7 | 10 | 1.0000 | 0.6469 | 1.4433 | 0.529 | 1.44 | 3 | 1.76 |
| FOSB | NM_001114171 | 1 | 0 | 1.0000 | 0.3294 | 0.6151 | −0.701 | 1.63 | 1 | −0.68 |

TABLE 9-continued

RNA Abundance Modulation

| Gene | Trx_ID | ave DMSO | ave Cpd | padj (q val, FDR) | ttest (p val) | FC (x + 1) | L$_2$FC (x + 1) | amp FC (x + 1) | abs (Cpd − DMSO) | L$_2$abs (Cpd − DMSO) |
|---|---|---|---|---|---|---|---|---|---|---|
| FOSB | NM_006732 | 10065 | 9993 | 1.0000 | 0.9874 | 0.9928 | −0.010 | 1.01 | 72 | 6.17 |
| FOXM1 | NM_001243088 | 11239 | 11007 | 1.0000 | 0.7306 | 0.9794 | −0.030 | 1.02 | 231 | 7.85 |
| FOXM1 | NM_001243089 | 276 | 289 | 1.0000 | 0.8118 | 1.0479 | 0.067 | 1.05 | 13 | 3.73 |
| FOXM1 | NM_021953 | 101 | 0 | 0.0000 | 0.0000 | 0.0098 | −6.669 | 101.73 | 101 | 6.65 |
| FOXM1 | NM_202002 | 629 | 769 | 0.9210 | 0.1531 | 1.2218 | 0.289 | 1.22 | 140 | 7.13 |
| FYN | AY429536 | 250 | 235 | 1.0000 | 0.8134 | 0.9388 | −0.091 | 1.07 | 15 | 3.94 |
| FYN | BC015055 | 166 | 154 | 1.0000 | 0.7965 | 0.9287 | −0.107 | 1.08 | 12 | 3.58 |
| FYN | NM_002037 | 8 | 14 | 1.0000 | 0.5181 | 1.6868 | 0.754 | 1.69 | 6 | 2.56 |
| FYN | NM_153047 | 95 | 0 | 0.0000 | 0.0000 | 0.0104 | −6.590 | 96.37 | 95 | 6.58 |
| FYN | NM_153048 | 2193 | 2495 | 0.7212 | 0.0962 | 1.1377 | 0.186 | 1.14 | 302 | 8.24 |
| GABPB1 | AK303901 | 3 | 22 | 0.5166 | 0.0413 | 5.2041 | 2.380 | 5.20 | 19 | 4.22 |
| GABPB1 | D13316 | 158 | 33 | 0.0029 | 0.0000 | 0.2169 | −2.205 | 4.61 | 124 | 6.96 |
| GABPB1 | NM_002041 | 14 | 14 | 1.0000 | 1.0000 | 0.9995 | −0.001 | 1.00 | 0 | −7.17 |
| GABPB1 | NM_005254 | 17 | 19 | 1.0000 | 0.9443 | 1.0975 | 0.134 | 1.10 | 2 | 0.84 |
| GABPB1 | NM_016654 | 124 | 154 | 1.0000 | 0.5614 | 1.2392 | 0.309 | 1.24 | 30 | 4.90 |
| GABPB1 | NM_016655 | 665 | 752 | 1.0000 | 0.2663 | 1.1313 | 0.178 | 1.13 | 87 | 6.45 |
| GABPB1 | NM_181427 | 640 | 1219 | 0.0000 | 0.0000 | 1.9042 | 0.929 | 1.90 | 579 | 9.18 |
| GALC | AK302683 | 13515 | 1562 | 0.0000 | 0.0000 | 0.1157 | −3.112 | 8.65 | 11953 | 13.55 |
| GALC | D25284 | 2846 | 2578 | 1.0000 | 0.1842 | 0.9057 | −0.143 | 1.10 | 268 | 8.07 |
| GALC | NM_000153 | 154914 | 159320 | 1.0000 | 0.5883 | 1.0284 | 0.040 | 1.03 | 4406 | 12.11 |
| GALC | NM_001201401 | 49 | 40 | 1.0000 | 0.6646 | 0.8159 | −0.294 | 1.23 | 9 | 3.20 |
| GALC | NM_001201402 | 91 | 8 | 0.0014 | 0.0000 | 0.1025 | −3.286 | 9.75 | 83 | 6.37 |
| GAS7 | AK293755 | 1171 | 1049 | 1.0000 | 0.2754 | 0.8964 | −0.158 | 1.12 | 121 | 6.92 |
| GAS7 | AK294829 | 120 | 74 | 1.0000 | 0.1870 | 0.6206 | −0.688 | 1.61 | 46 | 5.53 |
| GAS7 | NM_003644 | 447 | 736 | 0.0212 | 0.0003 | 1.6464 | 0.719 | 1.65 | 289 | 8.18 |
| GAS7 | NM_201433 | 439 | 468 | 1.0000 | 0.6647 | 1.0670 | 0.094 | 1.07 | 29 | 4.88 |
| GGCT | AK021779 | 14 | 14 | 1.0000 | 0.9328 | 0.9919 | −0.012 | 1.01 | 0 | −3.08 |
| GGCT | NM_001199815 | 4 | 3 | 1.0000 | 1.0000 | 0.9208 | −0.119 | 1.09 | 0 | −1.39 |
| GGCT | NM_001199816 | 51 | 0 | 0.0000 | 0.0000 | 0.0192 | −5.706 | 52.20 | 51 | 5.68 |
| GGCT | NM_001199817 | 1457 | 1474 | 1.0000 | 0.9049 | 1.0117 | 0.017 | 1.01 | 17 | 4.09 |
| GGCT | NM_024051 | 8 | 1 | 0.9640 | 0.1702 | 0.2535 | −1.980 | 3.95 | 7 | 2.78 |
| GGCT | NR_037669 | 392 | 83 | 0.0000 | 0.0000 | 0.2135 | −2.227 | 4.68 | 309 | 8.27 |
| GJC1 | AK124339 | 976 | 1255 | 0.2912 | 0.0142 | 1.2856 | 0.362 | 1.29 | 279 | 8.12 |
| GJC1 | CCDS11487 | 1663 | 1945 | 0.5912 | 0.0567 | 1.1694 | 0.226 | 1.17 | 282 | 8.14 |
| GJC1 | NM_001080383 | 15334 | 15260 | 1.0000 | 0.9064 | 0.9951 | −0.007 | 1.00 | 75 | 6.22 |
| GJC1 | NM_005497 | 421 | 149 | 0.0000 | 0.0000 | 0.3554 | −1.492 | 2.81 | 272 | 8.09 |
| GPSM2 | AB445462 | 827 | 552 | 0.0455 | 0.0009 | 0.6671 | −0.584 | 1.50 | 276 | 8.11 |
| GPSM2 | AK295563 | 14 | 19 | 1.0000 | 0.5375 | 1.3655 | 0.449 | 1.37 | 5 | 2.42 |
| GPSM2 | NM_013296 | 21 | 43 | 1.0000 | 0.2208 | 1.9837 | 0.988 | 1.98 | 22 | 4.43 |
| GRK6 | AK056697 | 3 | 4 | 1.0000 | 0.9443 | 1.1956 | 0.258 | 1.20 | 1 | −0.33 |
| GRK6 | NM_001004105 | 6 | 3 | 1.0000 | 0.5064 | 0.5460 | −0.873 | 1.83 | 3 | 1.67 |
| GRK6 | NM_001004106 | 1 | 1 | 1.0000 | 0.7315 | 0.7413 | −0.432 | 1.35 | 1 | −0.78 |
| GRK6 | NM_002082 | 1 | 0 | 1.0000 | 0.3294 | 0.6151 | −0.701 | 1.63 | 1 | −0.68 |
| HAS2 | NM_005328 | 67 | 63 | 1.0000 | 0.9187 | 0.9529 | −0.070 | 1.05 | 3 | 1.67 |
| HAT1 | AK309001 | 0 | 1 | 1.0000 | 0.6668 | 1.5872 | 0.667 | 1.59 | 1 | −0.77 |
| HAT1 | NM_003642 | 1 | 0 | 1.0000 | 0.3294 | 0.6176 | −0.695 | 1.62 | 1 | −0.69 |
| HAT1 | NR_027862 | 121 | 123 | 1.0000 | 0.9336 | 1.0209 | 0.030 | 1.02 | 3 | 1.35 |
| HLTF | BC044659 | 0 | 0 | 9999 | 9999 | 1.0000 | 0.000 | 1.00 | 0 | 0 |
| HLTF | EU446704 | 79 | 0 | 0.0000 | 0.0000 | 0.0125 | −6.319 | 79.87 | 79 | 6.30 |
| HLTF | NM_003071 | 2 | 4 | 1.0000 | 0.7543 | 1.5328 | 0.616 | 1.53 | 2 | 0.65 |
| HLTF | NM_139048 | 1 | 0 | 1.0000 | 0.2592 | 0.4672 | −1.098 | 2.14 | 1 | 0.19 |
| HMGA1 | AK301434 | 1 | 9 | 0.8851 | 0.1412 | 4.5132 | 2.174 | 4.51 | 8 | 2.98 |
| HMGA1 | BC008963 | 0 | 0 | 1.0000 | 0.4970 | 0.7617 | −0.393 | 1.31 | 0 | −1.68 |
| HMGA1 | BC063434 | 0 | 0 | 1.0000 | 0.4970 | 0.7617 | −0.393 | 1.31 | 0 | −1.68 |
| HMGA1 | M23616 | 3 | 0 | 0.6144 | 0.0620 | 0.2855 | −1.809 | 3.50 | 3 | 1.32 |
| HMGA1 | M23618 | 18 | 16 | 1.0000 | 0.8986 | 0.9027 | −0.148 | 1.11 | 2 | 0.90 |
| HMGA1 | M23619 | 0 | 1 | 1.0000 | 1.0000 | 1.2433 | 0.314 | 1.24 | 0 | −1.65 |
| HMGA1 | NM_002131 | 73 | 93 | 1.0000 | 0.5384 | 1.2736 | 0.349 | 1.27 | 20 | 4.33 |
| HMGA1 | NM_145899 | 0 | 0 | 9999 | 9999 | 1.0000 | 0.000 | 1.00 | 0 | 0 |
| HMGA1 | NM_145901 | 15 | 16 | 1.0000 | 0.8855 | 1.0904 | 0.125 | 1.09 | 1 | 0.50 |
| HMGA1 | NM_145903 | 3264 | 3635 | 0.7497 | 0.1052 | 1.1138 | 0.155 | 1.11 | 371 | 8.54 |
| HMGA1 | NM_145905 | 8017 | 8282 | 1.0000 | 0.5443 | 1.0331 | 0.047 | 1.03 | 266 | 8.05 |
| HMGB1 | AK304506 | 1 | 0 | 1.0000 | 0.2352 | 0.5158 | −0.955 | 1.94 | 1 | −0.09 |
| HMGB1 | BX647267 | 0 | 1 | 1.0000 | 0.6668 | 1.5872 | 0.667 | 1.59 | 1 | −0.77 |
| HMGB1 | CR749614 | 1 | 3 | 1.0000 | 0.3560 | 2.7135 | 1.440 | 2.71 | 3 | 1.47 |
| HMGB1 | NM_002128 | 3 | 4 | 1.0000 | 0.8552 | 1.3271 | 0.408 | 1.33 | 1 | 0.43 |
| HMGCR | AK296499 | 2 | 1 | 1.0000 | 0.7386 | 0.6831 | −0.550 | 1.46 | 1 | −0.32 |
| HMGCR | AY429542 | 8 | 7 | 1.0000 | 0.8499 | 0.8849 | −0.176 | 1.13 | 1 | 0.12 |
| HMGCR | NM_000859 | 244 | 12 | 0.0000 | 0.0000 | 0.0526 | −4.249 | 19.02 | 232 | 7.86 |
| HMGCR | NM_001130996 | 29 | 154 | 0.0068 | 0.0001 | 5.0981 | 2.350 | 5.10 | 124 | 6.96 |
| HMGCS1 | AK025736 | 29 | 154 | 0.0068 | 0.0001 | 5.0981 | 2.350 | 5.10 | 124 | 6.96 |
| HMGCS1 | NM_001098272 | 31 | 114 | 0.1526 | 0.0051 | 3.5692 | 1.836 | 3.57 | 83 | 6.37 |
| HMGCS1 | NM_002130 | 16 | 40 | 0.8915 | 0.1435 | 2.4361 | 1.285 | 2.44 | 24 | 4.58 |
| HMOX1 | NM_002133 | 16 | 40 | 0.8915 | 0.1435 | 2.4361 | 1.285 | 2.44 | 24 | 4.58 |

TABLE 9-continued

RNA Abundance Modulation

| Gene | Trx_ID | ave DMSO | ave Cpd | padj (q val, FDR) | ttest (p val) | FC (x + 1) | L$_2$FC (x + 1) | amp FC (x + 1) | abs (Cpd − DMSO) | L$_2$abs (Cpd − DMSO) |
|---|---|---|---|---|---|---|---|---|---|---|
| HP1BP3 | AF113534 | 18 | 19 | 1.0000 | 1.0000 | 1.0031 | 0.005 | 1.00 | 0 | −4.03 |
| HP1BP3 | AK303456 | 18 | 19 | 1.0000 | 1.0000 | 1.0031 | 0.005 | 1.00 | 0 | −4.03 |
| HP1BP3 | AK304065 | 1166 | 925 | 0.4316 | 0.0297 | 0.7934 | −0.334 | 1.26 | 241 | 7.91 |
| HP1BP3 | BC032139 | 1166 | 925 | 0.4316 | 0.0297 | 0.7934 | −0.334 | 1.26 | 241 | 7.91 |
| HP1BP3 | BC046170 | 1005 | 1186 | 0.9952 | 0.1815 | 1.1797 | 0.238 | 1.18 | 181 | 7.50 |
| HP1BP3 | BC053327 | 701 | 730 | 1.0000 | 0.4812 | 1.0415 | 0.059 | 1.04 | 29 | 4.87 |
| HP1BP3 | CR749652 | 0 | 4 | 0.6718 | 0.0775 | 4.8169 | 2.268 | 4.82 | 4 | 1.93 |
| HP1BP3 | NM_016287 | 1248 | 972 | 0.2136 | 0.0085 | 0.7789 | −0.361 | 1.28 | 276 | 8.11 |
| HSD17B12 | BC012536 | 1125 | 1434 | 0.2938 | 0.0144 | 1.2749 | 0.350 | 1.27 | 310 | 8.27 |
| HSD17B12 | NM_016142 | 1588 | 2319 | 0.0004 | 0.0000 | 1.4603 | 0.546 | 1.46 | 731 | 9.51 |
| HTT | NM_002111 | 618 | 258 | 0.0000 | 0.0000 | 0.4189 | −1.255 | 2.39 | 360 | 8.49 |
| IDI1 | AK311110 | 3913 | 3944 | 1.0000 | 0.8713 | 1.0080 | 0.011 | 1.01 | 31 | 4.97 |
| IDI1 | BC057827 | 0 | 0 | 9999 | 9999 | 1.0000 | 0.000 | 1.00 | 0 | 0 |
| IDI1 | BX648472 | 2577 | 3575 | 0.0005 | 0.0000 | 1.3872 | 0.472 | 1.39 | 998 | 9.96 |
| IDI1 | NM_004508 | 186 | 261 | 1.0000 | 0.1840 | 1.4038 | 0.489 | 1.40 | 75 | 6.24 |
| INHBA | M13436 | 121 | 154 | 1.0000 | 0.4473 | 1.2717 | 0.347 | 1.27 | 33 | 5.05 |
| INHBA | NM_002192 | 94 | 62 | 1.0000 | 0.3549 | 0.6641 | −0.590 | 1.51 | 32 | 5.00 |
| INSIG1 | NM_005542 | 948 | 783 | 0.7587 | 0.1071 | 0.8260 | −0.276 | 1.21 | 165 | 7.37 |
| INSIG1 | NM_198336 | 148 | 131 | 1.0000 | 0.7198 | 0.8886 | −0.170 | 1.13 | 17 | 4.05 |
| INSIG1 | NM_198337 | 1889 | 1559 | 0.4926 | 0.0380 | 0.8256 | −0.277 | 1.21 | 330 | 8.36 |
| KANSL3 | AF311326 | 56 | 66 | 1.0000 | 0.7059 | 1.1789 | 0.237 | 1.18 | 10 | 3.35 |
| KANSL3 | AK000943 | 217 | 148 | 0.8471 | 0.1308 | 0.6837 | −0.548 | 1.46 | 69 | 6.11 |
| KANSL3 | AL136849 | 386 | 290 | 0.6714 | 0.0772 | 0.7506 | −0.414 | 1.33 | 97 | 6.59 |
| KANSL3 | BC032746 | 313 | 463 | 0.3755 | 0.0227 | 1.4799 | 0.565 | 1.48 | 150 | 7.23 |
| KANSL3 | BC051763 | 1659 | 571 | 0.0000 | 0.0000 | 0.3446 | −1.537 | 2.90 | 1088 | 10.09 |
| KANSL3 | NM_001115016 | 2 | 1 | 1.0000 | 0.6148 | 0.6402 | −0.643 | 1.56 | 1 | 0.11 |
| KANSL3 | NR_047653 | 241 | 69 | 0.0008 | 0.0000 | 0.2892 | −1.790 | 3.46 | 172 | 7.42 |
| KANSL3 | NR_047654 | 240 | 370 | 0.2991 | 0.0149 | 1.5417 | 0.625 | 1.54 | 130 | 7.03 |
| KANSL3 | NR_047656 | 10986 | 10523 | 1.0000 | 0.4284 | 0.9578 | −0.062 | 1.04 | 464 | 8.86 |
| KANSL3 | NR_047657 | 47 | 26 | 1.0000 | 0.2610 | 0.5623 | −0.831 | 1.78 | 21 | 4.39 |
| KANSL3 | NR_047658 | 0 | 0 | 1.0000 | 1.0000 | 1.3608 | 0.444 | 1.36 | 0 | −1.47 |
| KIAA1199 | AY581149 | 2766 | 331 | 0.0000 | 0.0000 | 0.1199 | −3.060 | 8.34 | 2435 | 11.25 |
| KIAA1199 | NM_018689 | 346 | 265 | 0.7330 | 0.0988 | 0.7655 | −0.386 | 1.31 | 81 | 6.35 |
| KIAA1524 | AB040957 | 9847 | 11874 | 0.0345 | 0.0007 | 1.2059 | 0.270 | 1.21 | 2028 | 10.99 |
| KIAA1524 | AK308315 | 0 | 2 | 0.9675 | 0.1718 | 2.7253 | 1.446 | 2.73 | 2 | 0.79 |
| KIAA1524 | AK310446 | 0 | 0 | 1.0000 | 1.0000 | 1.3608 | 0.444 | 1.36 | 0 | −1.47 |
| KIAA1524 | NM_020890 | 273 | 75 | 0.0002 | 0.0000 | 0.2786 | −1.844 | 3.59 | 198 | 7.63 |
| KIAA1715 | AK056532 | 46 | 232 | 0.0002 | 0.0000 | 4.9887 | 2.319 | 4.99 | 186 | 7.54 |
| KIAA1715 | AK301947 | 349 | 82 | 0.0000 | 0.0000 | 0.2367 | −2.079 | 4.22 | 267 | 8.06 |
| KIAA1715 | BC110329 | 2021 | 2067 | 1.0000 | 0.7694 | 1.0225 | 0.032 | 1.02 | 46 | 5.51 |
| KIAA1715 | BC143681 | 376 | 362 | 1.0000 | 0.7827 | 0.9620 | −0.056 | 1.04 | 14 | 3.84 |
| KIAA1715 | BC143683 | 329 | 84 | 0.0000 | 0.0000 | 0.2578 | −1.956 | 3.88 | 245 | 7.94 |
| KIAA1715 | NM_030650 | 81 | 117 | 1.0000 | 0.3044 | 1.4358 | 0.522 | 1.44 | 36 | 5.16 |
| KIF3A | AF041853 | 6 | 7 | 1.0000 | 0.9289 | 1.1723 | 0.229 | 1.17 | 1 | 0.29 |
| KIF3A | AK295089 | 65 | 76 | 1.0000 | 0.7199 | 1.1647 | 0.220 | 1.16 | 11 | 3.45 |
| KIF3A | AK313359 | 2 | 5 | 1.0000 | 0.5603 | 1.7592 | 0.815 | 1.76 | 3 | 1.36 |
| KIF3A | AM177178 | 128 | 137 | 1.0000 | 0.8058 | 1.0744 | 0.103 | 1.07 | 10 | 3.26 |
| KIF3A | NM_007054 | 30 | 38 | 1.0000 | 0.6486 | 1.2487 | 0.320 | 1.25 | 8 | 2.96 |
| KLF6 | AK293259 | 962 | 900 | 1.0000 | 0.6216 | 0.9352 | −0.097 | 1.07 | 62 | 5.96 |
| KLF6 | NM_001160124 | 1294 | 1510 | 0.6932 | 0.0856 | 1.1663 | 0.222 | 1.17 | 215 | 7.75 |
| KLF6 | NM_001160125 | 1805 | 2011 | 1.0000 | 0.1924 | 1.1142 | 0.156 | 1.11 | 206 | 7.69 |
| KLF6 | NM_001300 | 288 | 253 | 1.0000 | 0.4397 | 0.8809 | −0.183 | 1.14 | 34 | 5.10 |
| KLF6 | NR_027653 | 35 | 6 | 0.3419 | 0.0190 | 0.1927 | −2.376 | 5.19 | 29 | 4.88 |
| KRT19 | NM_002276 | 496 | 93 | 0.0000 | 0.0000 | 0.1883 | −2.409 | 5.31 | 403 | 8.66 |
| KRT34 | NM_021013 | 7183 | 7861 | 0.7917 | 0.1159 | 1.0945 | 0.130 | 1.09 | 679 | 9.41 |
| KRTAP2-3 | NM_001165252 | 0 | 11 | 0.2306 | 0.0096 | 11.8635 | 3.568 | 11.86 | 11 | 3.44 |
| LAMA2 | CCDS5138 | 3 | 0 | 0.5661 | 0.0513 | 0.2442 | −2.034 | 4.10 | 3 | 1.63 |
| LAMA2 | NM_000426 | 0 | 5 | 0.5555 | 0.0484 | 6.2850 | 2.652 | 6.28 | 5 | 2.40 |
| LAMA2 | NM_001079823 | 1 | 1 | 1.0000 | 0.8636 | 1.4441 | 0.530 | 1.44 | 1 | −0.48 |
| LARP7 | NM_001267039 | 815 | 874 | 1.0000 | 0.5415 | 1.0718 | 0.100 | 1.07 | 59 | 5.87 |
| LARP7 | NM_015454 | 93 | 47 | 0.8114 | 0.1203 | 0.5112 | −0.968 | 1.96 | 46 | 5.52 |
| LARP7 | NM_016648 | 56 | 57 | 1.0000 | 0.9704 | 1.0099 | 0.014 | 1.01 | 1 | −0.82 |
| LARP7 | NR_049768 | 133 | 3 | 0.0000 | 0.0000 | 0.0294 | −5.090 | 34.05 | 130 | 7.02 |
| LDLR | AK295612 | 0 | 38 | 0.0012 | 0.0000 | 38.6836 | 5.274 | 38.68 | 38 | 5.24 |
| LDLR | FW340025 | 55 | 73 | 1.0000 | 0.5254 | 1.3109 | 0.391 | 1.31 | 17 | 4.13 |
| LDLR | NM_000527 | 2111 | 2445 | 0.6127 | 0.0604 | 1.1579 | 0.212 | 1.16 | 334 | 8.38 |
| LDLR | NM_001195798 | 104 | 9 | 0.0007 | 0.0000 | 0.0910 | −3.458 | 10.99 | 95 | 6.57 |
| LDLR | NM_001195799 | 2382 | 2331 | 1.0000 | 0.7594 | 0.9786 | −0.031 | 1.02 | 51 | 5.67 |
| LDLR | NM_001195800 | 51 | 0 | 0.0000 | 0.0000 | 0.0193 | −5.692 | 51.68 | 51 | 5.66 |
| LDLR | NM_001195802 | 25 | 48 | 1.0000 | 0.3802 | 1.8626 | 0.897 | 1.86 | 22 | 4.49 |
| LDLR | NM_001195803 | 3 | 3 | 1.0000 | 0.8702 | 0.8798 | −0.185 | 1.14 | 0 | −1.05 |
| LDLR | S70123 | 17 | 21 | 1.0000 | 0.8930 | 1.1856 | 0.246 | 1.19 | 3 | 1.76 |
| LEMD3 | NM_001167614 | 1146 | 237 | 0.0000 | 0.0000 | 0.2076 | −2.268 | 4.82 | 909 | 9.83 |
| LEMD3 | NM_014319 | 9677 | 10408 | 1.0000 | 0.2146 | 1.0755 | 0.105 | 1.08 | 730 | 9.51 |

TABLE 9-continued

RNA Abundance Modulation

| Gene | Trx_ID | ave DMSO | ave Cpd | padj (q val, FDR) | ttest (p val) | FC (x + 1) | L₂FC (x + 1) | amp FC (x + 1) | abs (Cpd − DMSO) | L₂abs (Cpd − DMSO) |
|---|---|---|---|---|---|---|---|---|---|---|
| LMAN2L | AK316331 | 18 | 198 | 0.0000 | 0.0000 | 10.4071 | 3.379 | 10.41 | 180 | 7.49 |
| LMAN2L | NM_001142292 | 370 | 458 | 0.9660 | 0.1711 | 1.2389 | 0.309 | 1.24 | 89 | 6.47 |
| LMAN2L | NM_030805 | 495 | 225 | 0.0007 | 0.0000 | 0.4550 | −1.136 | 2.20 | 270 | 8.08 |
| LMAN2L | NR_024518 | 26 | 25 | 1.0000 | 0.8701 | 0.9465 | −0.079 | 1.06 | 1 | 0.55 |
| LMAN2L | NR_024520 | 128 | 0 | 0.0000 | 0.0000 | 0.0077 | −7.017 | 129.47 | 128 | 7.01 |
| LMAN2L | NR_024521 | 2171 | 2386 | 1.0000 | 0.2076 | 1.0991 | 0.136 | 1.10 | 215 | 7.75 |
| LRCH4 | AF459638 | 126 | 125 | 1.0000 | 1.0000 | 0.9926 | −0.011 | 1.01 | 1 | −0.10 |
| LRCH4 | AK302410 | 0 | 3 | 0.7780 | 0.1117 | 3.6425 | 1.865 | 3.64 | 3 | 1.40 |
| LRCH4 | NM_002319 | 354 | 346 | 1.0000 | 0.8688 | 0.9788 | −0.031 | 1.02 | 8 | 2.91 |
| LRP8 | AK096482 | 243 | 518 | 0.0003 | 0.0000 | 2.1257 | 1.088 | 2.13 | 275 | 8.10 |
| LRP8 | AK122887 | 338 | 69 | 0.0000 | 0.0000 | 0.2076 | −2.268 | 4.82 | 269 | 8.07 |
| LRP8 | NM_001018054 | 323 | 0 | 0.0000 | 0.0000 | 0.0031 | −8.339 | 323.88 | 323 | 8.33 |
| LRP8 | NM_004631 | 2674 | 2935 | 0.9614 | 0.1695 | 1.0976 | 0.134 | 1.10 | 261 | 8.03 |
| LRP8 | NM_017522 | 0 | 0 | 9999 | 9999 | 1.0000 | 0.000 | 1.00 | 0 | 0 |
| LRP8 | NM_033300 | 508 | 681 | 0.4926 | 0.0379 | 1.3391 | 0.421 | 1.34 | 173 | 7.43 |
| LSS | NM_001001438 | 43 | 0 | 0.0001 | 0.0000 | 0.0227 | −5.460 | 44.03 | 43 | 5.43 |
| LSS | NM_001145436 | 59 | 2 | 0.0011 | 0.0000 | 0.0489 | −4.353 | 20.43 | 57 | 5.83 |
| LSS | NM_001145437 | 56 | 86 | 1.0000 | 0.3045 | 1.5334 | 0.617 | 1.53 | 30 | 4.93 |
| LSS | NM_002340 | 590 | 233 | 0.0000 | 0.0000 | 0.3966 | −1.334 | 2.52 | 357 | 8.48 |
| MAGED4 | AK098830 | 0 | 5 | 0.6377 | 0.0683 | 5.6838 | 2.507 | 5.68 | 5 | 2.23 |
| MAGED4 | AK098830 | 0 | 0 | 9999 | 9999 | 1.0000 | 0.000 | 1.00 | 0 | 0 |
| MAGED4 | NM_001098800 | 1003 | 1293 | 0.2858 | 0.0138 | 1.2893 | 0.367 | 1.29 | 290 | 8.18 |
| MAGED4 | NM_001272061 | 1981 | 2383 | 0.3858 | 0.0241 | 1.2027 | 0.266 | 1.20 | 402 | 8.65 |
| MAGED4 | NM_001272061 | 1878 | 1283 | 0.0006 | 0.0000 | 0.6833 | −0.549 | 1.46 | 595 | 9.22 |
| MAGED4 | NM_001272062 | 25 | 23 | 1.0000 | 0.9673 | 0.9031 | −0.147 | 1.11 | 3 | 1.36 |
| MAGED4 | NM_001272063 | 4670 | 1833 | 0.0000 | 0.0000 | 0.3927 | −1.349 | 2.55 | 2837 | 11.47 |
| MAGED4 | NM_177535 | 133832 | 137141 | 1.0000 | 0.6390 | 1.0247 | 0.035 | 1.02 | 3309 | 11.69 |
| MAGED4B | NM_030801 | 27 | 33 | 1.0000 | 0.7678 | 1.2137 | 0.279 | 1.21 | 6 | 2.58 |
| MAGED4B | NM_177537 | 214 | 236 | 1.0000 | 0.6930 | 1.1031 | 0.142 | 1.10 | 22 | 4.47 |
| MAN1A2 | AK023308 | 0 | 0 | 9999 | 9999 | 1.0000 | 0.000 | 1.00 | 0 | 0 |
| MAN1A2 | NM_006699 | 0 | 0 | 9999 | 9999 | 1.0000 | 0.000 | 1.00 | 0 | 0 |
| MEDAG | NM_032849 | 24 | 16 | 1.0000 | 0.6408 | 0.6835 | −0.549 | 1.46 | 8 | 2.99 |
| MEF2D | AK308641 | 1 | 1 | 1.0000 | 1.0000 | 1.0309 | 0.044 | 1.03 | 0 | −4.32 |
| MEF2D | BC032479 | 3 | 10 | 1.0000 | 0.3738 | 2.5718 | 1.363 | 2.57 | 7 | 2.79 |
| MEF2D | BC064988 | 8 | 0 | 0.2412 | 0.0105 | 0.1069 | −3.226 | 9.36 | 8 | 3.06 |
| MEF2D | NM_001271629 | 106 | 94 | 1.0000 | 0.7415 | 0.8882 | −0.171 | 1.13 | 12 | 3.58 |
| MEMO1 | AK022169 | 368 | 17 | 0.0000 | 0.0000 | 0.0497 | −4.330 | 20.12 | 350 | 8.45 |
| MEMO1 | AK057760 | 33 | 0 | 0.0017 | 0.0000 | 0.0290 | −5.106 | 34.44 | 33 | 5.06 |
| MEMO1 | AK290753 | 0 | 39 | 0.0011 | 0.0000 | 40.0270 | 5.323 | 40.03 | 39 | 5.29 |
| MEMO1 | AK295755 | 0 | 16 | 0.0872 | 0.0023 | 17.4776 | 4.127 | 17.48 | 16 | 4.04 |
| MEMO1 | NM_001137602 | 1574 | 1913 | 0.3720 | 0.0223 | 1.2151 | 0.281 | 1.22 | 339 | 8.40 |
| MEMO1 | NM_015955 | 0 | 14 | 0.1480 | 0.0049 | 15.0513 | 3.912 | 15.05 | 14 | 3.81 |
| MFGE8 | AK095908 | 438 | 524 | 1.0000 | 0.1949 | 1.1959 | 0.258 | 1.20 | 86 | 6.43 |
| MFGE8 | AK304627 | 22 | 75 | 0.4434 | 0.0310 | 3.2818 | 1.714 | 3.28 | 53 | 5.72 |
| MFGE8 | AK310357 | 261 | 91 | 0.0068 | 0.0001 | 0.3502 | −1.514 | 2.86 | 170 | 7.41 |
| MFGE8 | BX537974 | 1000 | 1244 | 0.4543 | 0.0323 | 1.2444 | 0.315 | 1.24 | 245 | 7.93 |
| MFGE8 | NM_001114614 | 0 | 6 | 0.4670 | 0.0339 | 7.4594 | 2.899 | 7.46 | 6 | 2.69 |
| MFGE8 | NM_005928 | 1 | 0 | 1.0000 | 0.3294 | 0.6176 | −0.695 | 1.62 | 1 | −0.69 |
| MICAL2 | AB110785 | 124 | 3 | 0.0000 | 0.0000 | 0.0292 | −5.098 | 34.25 | 121 | 6.92 |
| MICAL2 | AB110786 | 1027 | 1102 | 1.0000 | 0.4915 | 1.0739 | 0.103 | 1.07 | 76 | 6.25 |
| MICAL2 | AK294845 | 451 | 530 | 1.0000 | 0.2545 | 1.1755 | 0.233 | 1.18 | 79 | 6.31 |
| MICAL2 | AK302580 | 95 | 0 | 0.0000 | 0.0000 | 0.0104 | −6.581 | 95.74 | 95 | 6.57 |
| MICAL2 | AK302893 | 17 | 18 | 1.0000 | 0.8888 | 1.0810 | 0.112 | 1.08 | 1 | 0.52 |
| MICAL2 | BC015755 | 13 | 24 | 1.0000 | 0.4940 | 1.7466 | 0.805 | 1.75 | 11 | 3.40 |
| MICAL2 | BX538021 | 34 | 29 | 1.0000 | 0.7591 | 0.8674 | −0.205 | 1.15 | 5 | 2.21 |
| MICAL2 | NM_014632 | 531 | 513 | 1.0000 | 0.7553 | 0.9671 | −0.048 | 1.03 | 18 | 4.13 |
| MMAB | AK295211 | 172 | 111 | 0.9288 | 0.1570 | 0.6472 | −0.628 | 1.55 | 61 | 5.93 |
| MMAB | NM_052845 | 32 | 23 | 1.0000 | 0.5279 | 0.7162 | −0.482 | 1.40 | 9 | 3.22 |
| MMAB | NR_038118 | 0 | 15 | 0.1354 | 0.0043 | 15.6485 | 3.968 | 15.65 | 15 | 3.87 |
| MMS19 | AF319947 | 27 | 21 | 1.0000 | 0.6883 | 0.7824 | −0.354 | 1.28 | 6 | 2.59 |
| MMS19 | AK025496 | 307 | 284 | 1.0000 | 0.7562 | 0.9248 | −0.113 | 1.08 | 23 | 4.54 |
| MMS19 | AK027710 | 76 | 4 | 0.0017 | 0.0000 | 0.0666 | −3.909 | 15.02 | 72 | 6.16 |
| MMS19 | AK056581 | 4 | 4 | 1.0000 | 1.0000 | 1.0697 | 0.097 | 1.07 | 0 | −1.59 |
| MMS19 | BC007298 | 43 | 116 | 0.3683 | 0.0218 | 2.6408 | 1.401 | 2.64 | 73 | 6.18 |
| MMS19 | BC080532 | 8 | 13 | 1.0000 | 0.6679 | 1.4862 | 0.572 | 1.49 | 5 | 2.20 |
| MMS19 | BC143285 | 237 | 78 | 0.0062 | 0.0001 | 0.3302 | −1.599 | 3.03 | 160 | 7.32 |
| MMS19 | NM_022362 | 2394 | 2459 | 1.0000 | 0.7286 | 1.0270 | 0.038 | 1.03 | 65 | 6.01 |
| MMS22L | AB385246 | 0 | 3 | 0.8871 | 0.1424 | 3.5258 | 1.818 | 3.53 | 3 | 1.34 |
| MMS22L | BC110860 | 0 | 16 | 0.0959 | 0.0026 | 17.3931 | 4.120 | 17.39 | 16 | 4.04 |
| MMS22L | BC142948 | 0 | 0 | 1.0000 | 0.4970 | 0.7246 | −0.465 | 1.38 | 0 | −1.40 |
| MMS22L | NM_198468 | 0 | 0 | 9999 | 9999 | 1.0000 | 0.000 | 1.00 | 0 | 0 |
| MSL3 | AK294255 | 0 | 3 | 0.8347 | 0.1273 | 3.7027 | 1.889 | 3.70 | 3 | 1.43 |
| MSL3 | AK304419 | 842 | 1076 | 0.4015 | 0.0257 | 1.2769 | 0.353 | 1.28 | 234 | 7.87 |
| MSL3 | NM_001193270 | 243 | 18 | 0.0000 | 0.0000 | 0.0786 | −3.670 | 12.73 | 225 | 7.82 |

TABLE 9-continued

| | | | | RNA Abundance Modulation | | | | | |
|---|---|---|---|---|---|---|---|---|---|
| Gene | Trx_ID | ave DMSO | ave Cpd | padj (q val, FDR) | ttest (p val) | FC (x + 1) | L$_2$FC (x + 1) | amp FC (x + 1) | abs (Cpd − DMSO) | L$_2$abs (Cpd − DMSO) |
| MSL3 | NM_006800 | 458 | 147 | 0.0000 | 0.0000 | 0.3223 | −1.633 | 3.10 | 311 | 8.28 |
| MSL3 | NM_078628 | 0 | 11 | 0.2058 | 0.0081 | 12.4508 | 3.638 | 12.45 | 11 | 3.52 |
| MSL3 | NM_078629 | 40 | 23 | 1.0000 | 0.3786 | 0.5966 | −0.745 | 1.68 | 16 | 4.04 |
| MSMO1 | AK309206 | 1923 | 1991 | 1.0000 | 0.6875 | 1.0351 | 0.050 | 1.04 | 68 | 6.08 |
| MSMO1 | NM_001017369 | 0 | 0 | 9999 | 9999 | 1.0000 | 0.000 | 1.00 | 0 | 0 |
| MSMO1 | NM_006745 | 5 | 6 | 1.0000 | 1.0000 | 1.0525 | 0.074 | 1.05 | 0 | −1.60 |
| MTAP | AF109294 | 7 | 18 | 1.0000 | 0.3464 | 2.2808 | 1.190 | 2.28 | 11 | 3.44 |
| MTAP | AK300592 | 286 | 279 | 1.0000 | 0.9654 | 0.9748 | −0.037 | 1.03 | 7 | 2.85 |
| MTAP | AK309365 | 157 | 18 | 0.0000 | 0.0000 | 0.1186 | −3.076 | 8.43 | 139 | 7.12 |
| MTAP | BC012316 | 315 | 507 | 0.1631 | 0.0056 | 1.6063 | 0.684 | 1.61 | 192 | 7.58 |
| MTAP | CU693137 | 171 | 42 | 0.0062 | 0.0001 | 0.2485 | −2.009 | 4.02 | 129 | 7.02 |
| MTAP | HE654774 | 45 | 69 | 1.0000 | 0.4363 | 1.5288 | 0.612 | 1.53 | 24 | 4.60 |
| MTAP | HE654776 | 1285 | 1377 | 1.0000 | 0.4514 | 1.0718 | 0.100 | 1.07 | 92 | 6.53 |
| MTAP | HE654777 | 20 | 28 | 1.0000 | 0.5668 | 1.4190 | 0.505 | 1.42 | 9 | 3.11 |
| MTAP | NM_002451 | 26 | 7 | 0.9568 | 0.1663 | 0.2971 | −1.751 | 3.37 | 19 | 4.25 |
| MTERFD1 | AK001801 | 210 | 178 | 1.0000 | 0.5690 | 0.8480 | −0.238 | 1.18 | 32 | 5.00 |
| MTERFD1 | AK309002 | 31 | 0 | 0.0020 | 0.0000 | 0.0310 | −5.012 | 32.27 | 31 | 4.97 |
| MTERFD1 | NM_015942 | 738 | 646 | 1.0000 | 0.2320 | 0.8763 | −0.191 | 1.14 | 91 | 6.51 |
| MVD | AY203927 | 57 | 208 | 0.0045 | 0.0000 | 3.5960 | 1.846 | 3.60 | 151 | 7.24 |
| MVD | NM_002461 | 43 | 54 | 1.0000 | 0.6407 | 1.2424 | 0.313 | 1.24 | 11 | 3.43 |
| MVK | AF217536 | 5 | 0 | 0.4640 | 0.0334 | 0.1671 | −2.581 | 5.99 | 5 | 2.32 |
| MVK | AK293130 | 576 | 703 | 0.8438 | 0.1300 | 1.2188 | 0.286 | 1.22 | 126 | 6.98 |
| MVK | AK295338 | 168 | 42 | 0.0058 | 0.0001 | 0.2521 | −1.988 | 3.97 | 127 | 6.98 |
| MVK | CU677575 | 39 | 40 | 1.0000 | 0.9883 | 1.0215 | 0.031 | 1.02 | 1 | −0.23 |
| MVK | NM_000431 | 134 | 388 | 0.0002 | 0.0000 | 2.8801 | 1.526 | 2.88 | 254 | 7.99 |
| MVK | NM_001114185 | 195 | 206 | 1.0000 | 0.8306 | 1.0540 | 0.076 | 1.05 | 11 | 3.41 |
| NASP | AK056161 | 1039 | 1308 | 0.3436 | 0.0193 | 1.2583 | 0.332 | 1.26 | 269 | 8.07 |
| NASP | AK092829 | 121 | 132 | 1.0000 | 0.5440 | 1.0957 | 0.132 | 1.10 | 12 | 3.54 |
| NASP | AK308001 | 22 | 40 | 1.0000 | 0.3121 | 1.8026 | 0.850 | 1.80 | 18 | 4.17 |
| NASP | AY700118 | 6530 | 7073 | 0.9770 | 0.1761 | 1.0831 | 0.115 | 1.08 | 543 | 9.08 |
| NASP | NM_001195193 | 2570 | 2681 | 1.0000 | 0.7216 | 1.0434 | 0.061 | 1.04 | 111 | 6.80 |
| NASP | NM_002482 | 34 | 39 | 1.0000 | 0.8763 | 1.1306 | 0.177 | 1.13 | 5 | 2.20 |
| NASP | NM_152298 | 184 | 33 | 0.0001 | 0.0000 | 0.1839 | −2.443 | 5.44 | 151 | 7.24 |
| NAV2 | AK001495 | 8 | 6 | 1.0000 | 0.8693 | 0.7902 | −0.340 | 1.27 | 2 | 0.99 |
| NAV2 | AK096037 | 5 | 5 | 1.0000 | 1.0000 | 0.8956 | −0.159 | 1.12 | 1 | −0.58 |
| NAV2 | AK290458 | 399 | 579 | 0.1714 | 0.0061 | 1.4498 | 0.536 | 1.45 | 180 | 7.49 |
| NAV2 | AK307574 | 21 | 14 | 1.0000 | 0.6321 | 0.6842 | −0.547 | 1.46 | 7 | 2.78 |
| NAV2 | CCDS58126 | 1039 | 854 | 0.8825 | 0.1405 | 0.8224 | −0.282 | 1.22 | 185 | 7.53 |
| NAV2 | CCDS7851 | 3699 | 3764 | 1.0000 | 0.7877 | 1.0176 | 0.025 | 1.02 | 65 | 6.02 |
| NAV2 | NM_001111018 | 0 | 3 | 0.8337 | 0.1270 | 3.6764 | 1.878 | 3.68 | 3 | 1.42 |
| NAV2 | NM_001111019 | 0 | 15 | 0.1159 | 0.0034 | 16.3895 | 4.035 | 16.39 | 15 | 3.94 |
| NAV2 | NM_001244963 | 0 | 3 | 0.7894 | 0.1146 | 4.0110 | 2.004 | 4.01 | 3 | 1.59 |
| NAV2 | NM_182964 | 59 | 38 | 1.0000 | 0.3379 | 0.6450 | −0.633 | 1.55 | 21 | 4.41 |
| NEURL1B | GQ414758 | 28 | 38 | 1.0000 | 0.6201 | 1.3544 | 0.438 | 1.35 | 10 | 3.35 |
| NEURL1B | GQ414759 | 78 | 0 | 0.0000 | 0.0000 | 0.0127 | −6.296 | 78.57 | 78 | 6.28 |
| NEURL1B | NM_001142651 | 22 | 15 | 1.0000 | 0.6758 | 0.6916 | −0.532 | 1.45 | 7 | 2.84 |
| NFE2L1 | AK294553 | 0 | 0 | 9999 | 9999 | 1.0000 | 0.000 | 1.00 | 0 | 0 |
| NFE2L1 | AK302387 | 1686 | 1831 | 1.0000 | 0.3008 | 1.0858 | 0.119 | 1.09 | 145 | 7.18 |
| NFE2L1 | AL833530 | 18 | 17 | 1.0000 | 0.8838 | 0.9528 | −0.070 | 1.05 | 1 | −0.14 |
| NFE2L1 | BX647976 | 10 | 1 | 0.7888 | 0.1139 | 0.1965 | −2.347 | 5.09 | 9 | 3.15 |
| NFE2L1 | L24123 | 75 | 88 | 1.0000 | 0.8426 | 1.1651 | 0.221 | 1.17 | 13 | 3.65 |
| NFE2L1 | NM_003204 | 34 | 33 | 1.0000 | 0.9866 | 0.9582 | −0.062 | 1.04 | 1 | 0.57 |
| NID1 | AB209448 | 81 | 31 | 0.5083 | 0.0399 | 0.3902 | −1.358 | 2.56 | 50 | 5.64 |
| NID1 | BC045606 | 838 | 1130 | 0.1772 | 0.0064 | 1.3488 | 0.432 | 1.35 | 293 | 8.19 |
| NID1 | NM_002508 | 605 | 344 | 0.0312 | 0.0006 | 0.5703 | −0.810 | 1.75 | 260 | 8.02 |
| NPEPPS | AK096491 | 241 | 149 | 0.5166 | 0.0414 | 0.6197 | −0.690 | 1.61 | 92 | 6.52 |
| NPEPPS | AK293995 | 41 | 1 | 0.0098 | 0.0001 | 0.0582 | −4.102 | 17.18 | 40 | 5.30 |
| NPEPPS | AK296887 | 374 | 44 | 0.0000 | 0.0000 | 0.1186 | −3.076 | 8.43 | 331 | 8.37 |
| NPEPPS | AK303037 | 364 | 114 | 0.0000 | 0.0000 | 0.3149 | −1.667 | 3.18 | 250 | 7.96 |
| NPEPPS | AK311414 | 28 | 21 | 1.0000 | 0.7240 | 0.7548 | −0.406 | 1.32 | 7 | 2.81 |
| NPEPPS | NM_006310 | 5 | 3 | 1.0000 | 0.6061 | 0.6441 | −0.635 | 1.55 | 2 | 1.05 |
| NREP | BX649051 | 0 | 3 | 0.7088 | 0.0935 | 4.2297 | 2.081 | 4.23 | 3 | 1.69 |
| NREP | NM_001142474 | 4497 | 4577 | 1.0000 | 0.7708 | 1.0179 | 0.026 | 1.02 | 80 | 6.33 |
| NREP | NM_001142475 | 46 | 49 | 1.0000 | 0.8604 | 1.0638 | 0.089 | 1.06 | 3 | 1.58 |
| NREP | NM_001142476 | 220 | 492 | 0.0065 | 0.0001 | 2.2280 | 1.156 | 2.23 | 272 | 8.09 |
| NREP | NM_001142477 | 671 | 619 | 1.0000 | 0.6710 | 0.9237 | −0.114 | 1.08 | 51 | 5.68 |
| NREP | NM_001142478 | 690 | 638 | 1.0000 | 0.5895 | 0.9242 | −0.114 | 1.08 | 52 | 5.71 |
| NREP | NM_001142479 | 7140 | 7207 | 1.0000 | 0.8182 | 1.0093 | 0.013 | 1.01 | 67 | 6.06 |
| NREP | NM_001142480 | 4729 | 4910 | 1.0000 | 0.5292 | 1.0383 | 0.054 | 1.04 | 181 | 7.50 |
| NREP | NM_001142481 | 124 | 0 | 0.0000 | 0.0000 | 0.0080 | −6.960 | 124.52 | 124 | 6.95 |
| NREP | NM_001142482 | 80 | 46 | 1.0000 | 0.1932 | 0.5784 | −0.790 | 1.73 | 34 | 5.10 |
| NREP | NM_001142483 | 9898 | 10241 | 1.0000 | 0.5557 | 1.0347 | 0.049 | 1.03 | 343 | 8.42 |
| NREP | NM_004772 | 0 | 6 | 0.4883 | 0.0370 | 7.1658 | 2.841 | 7.17 | 6 | 2.62 |
| NRG1 | AK293270 | 192 | 41 | 0.0003 | 0.0000 | 0.2161 | −2.210 | 4.63 | 152 | 7.24 |

TABLE 9-continued

RNA Abundance Modulation

| Gene | Trx_ID | ave DMSO | ave Cpd | padj (q val, FDR) | ttest (p val) | FC (x + 1) | $L_2$FC (x + 1) | amp FC (x + 1) | abs (Cpd − DMSO) | $L_2$abs (Cpd − DMSO) |
|---|---|---|---|---|---|---|---|---|---|---|
| NRG1 | AY207002 | 526 | 554 | 1.0000 | 0.7370 | 1.0536 | 0.075 | 1.05 | 28 | 4.82 |
| NRG1 | EF372275 | 33 | 24 | 1.0000 | 0.5972 | 0.7163 | −0.481 | 1.40 | 10 | 3.29 |
| NRG1 | EF372277 | 28 | 25 | 1.0000 | 0.9105 | 0.9198 | −0.121 | 1.09 | 2 | 1.20 |
| NRG1 | NM_001159995 | 76 | 0 | 0.0000 | 0.0000 | 0.0129 | −6.272 | 77.29 | 76 | 6.25 |
| NRG1 | NM_001159996 | 1288 | 851 | 0.0072 | 0.0001 | 0.6612 | −0.597 | 1.51 | 437 | 8.77 |
| NRG1 | NM_001160001 | 0 | 4 | 0.7088 | 0.0935 | 4.6098 | 2.205 | 4.61 | 4 | 1.85 |
| NRG1 | NM_001160004 | 1588 | 1721 | 1.0000 | 0.4119 | 1.0837 | 0.116 | 1.08 | 133 | 7.05 |
| NRG1 | NM_001160007 | 174 | 14 | 0.0000 | 0.0000 | 0.0829 | −3.593 | 12.07 | 161 | 7.33 |
| NRG1 | NM_001160008 | 22 | 5 | 0.7985 | 0.1175 | 0.2474 | −2.015 | 4.04 | 18 | 4.14 |
| NRG1 | NM_004495 | 97 | 108 | 1.0000 | 0.7656 | 1.1146 | 0.157 | 1.11 | 11 | 3.49 |
| NRG1 | NM_013956 | 41 | 75 | 1.0000 | 0.2062 | 1.8024 | 0.850 | 1.80 | 34 | 5.09 |
| NRG1 | NM_013957 | 5214 | 5346 | 1.0000 | 0.7143 | 1.0253 | 0.036 | 1.03 | 132 | 7.04 |
| NRG1 | NM_013958 | 382 | 356 | 1.0000 | 0.7471 | 0.9322 | −0.101 | 1.07 | 26 | 4.70 |
| NRG1 | NM_013959 | 24 | 0 | 0.0112 | 0.0002 | 0.0405 | −4.626 | 24.69 | 24 | 4.57 |
| NRG1 | NM_013960 | 16 | 0 | 0.0560 | 0.0013 | 0.0574 | −4.123 | 17.42 | 16 | 4.04 |
| NRG1 | NM_013964 | 252 | 196 | 1.0000 | 0.1902 | 0.7784 | −0.361 | 1.28 | 56 | 5.81 |
| NRG1 | U02325 | 422 | 98 | 0.0000 | 0.0000 | 0.2343 | −2.094 | 4.27 | 324 | 8.34 |
| NRG1 | U02327 | 1782 | 1742 | 1.0000 | 0.7564 | 0.9776 | −0.033 | 1.02 | 40 | 5.32 |
| NSUN4 | AK097524 | 1155 | 1328 | 0.8932 | 0.1440 | 1.1496 | 0.201 | 1.15 | 173 | 7.43 |
| NSUN4 | AK128066 | 961 | 820 | 1.0000 | 0.2539 | 0.8540 | −0.228 | 1.17 | 140 | 7.13 |
| NSUN4 | NM_001256127 | 288 | 78 | 0.0002 | 0.0000 | 0.2726 | −1.875 | 3.67 | 210 | 7.71 |
| NSUN4 | NM_001256128 | 77 | 174 | 0.1933 | 0.0073 | 2.2401 | 1.164 | 2.24 | 97 | 6.60 |
| NSUN4 | NM_199044 | 533 | 756 | 0.4163 | 0.0275 | 1.4189 | 0.505 | 1.42 | 224 | 7.80 |
| NSUN4 | NR_045789 | 1974 | 2007 | 1.0000 | 0.6966 | 1.0164 | 0.023 | 1.02 | 32 | 5.01 |
| NSUN4 | NR_045790 | 1003 | 784 | 0.3124 | 0.0162 | 0.7820 | −0.355 | 1.28 | 219 | 7.77 |
| NSUN4 | NR_045791 | 9129 | 10464 | 0.2639 | 0.0120 | 1.1463 | 0.197 | 1.15 | 1335 | 10.38 |
| NT5C2 | AK127670 | 882 | 297 | 0.0000 | 0.0000 | 0.3373 | −1.568 | 2.96 | 585 | 9.19 |
| NT5C2 | AK295593 | 47349 | 50140 | 1.0000 | 0.2403 | 1.0590 | 0.083 | 1.06 | 2791 | 11.45 |
| NT5C2 | NM_001134373 | 319 | 326 | 1.0000 | 0.7319 | 1.0210 | 0.030 | 1.02 | 7 | 2.75 |
| NT5C2 | NM_012229 | 5869 | 1679 | 0.0000 | 0.0000 | 0.2861 | −1.805 | 3.49 | 4190 | 12.03 |
| NUP153 | NM_001278209 | 21164 | 23443 | 0.6144 | 0.0619 | 1.1077 | 0.148 | 1.11 | 2279 | 11.15 |
| NUP153 | NM_001278210 | 607 | 488 | 0.9476 | 0.1635 | 0.8034 | −0.316 | 1.24 | 120 | 6.90 |
| NUP153 | NM_005124 | 3110 | 2684 | 0.5895 | 0.0550 | 0.8630 | −0.212 | 1.16 | 426 | 8.74 |
| P4HA1 | CCDS41537 | 289 | 298 | 1.0000 | 0.8624 | 1.0304 | 0.043 | 1.03 | 9 | 3.14 |
| P4HA1 | CCDS7320 | 2 | 5 | 1.0000 | 0.5957 | 1.7968 | 0.845 | 1.80 | 3 | 1.35 |
| P4HA1 | NM_000917 | 183 | 295 | 0.5845 | 0.0544 | 1.6068 | 0.684 | 1.61 | 112 | 6.81 |
| P4HA1 | NM_001017962 | 65 | 50 | 1.0000 | 0.6448 | 0.7680 | −0.381 | 1.30 | 15 | 3.93 |
| P4HA1 | NM_001142595 | 97 | 13 | 0.0050 | 0.0001 | 0.1432 | −2.804 | 6.98 | 84 | 6.39 |
| P4HA1 | NM_001142596 | 1007 | 1004 | 1.0000 | 1.0000 | 0.9974 | −0.004 | 1.00 | 3 | 1.41 |
| PABPC1 | AK298990 | 19 | 0 | 0.0299 | 0.0005 | 0.0503 | −4.314 | 19.88 | 19 | 4.24 |
| PABPC1 | AK303120 | 195 | 79 | 0.1200 | 0.0036 | 0.4100 | −1.286 | 2.44 | 116 | 6.85 |
| PABPC1 | NM_002568 | 0 | 0 | 9999 | 9999 | 1.0000 | 0.000 | 1.00 | 0 | 0 |
| PABPC1 | Y00345 | 1029 | 406 | 0.0000 | 0.0000 | 0.3945 | −1.342 | 2.53 | 624 | 9.29 |
| PABPC1 | Z48501 | 49 | 23 | 1.0000 | 0.2239 | 0.4839 | −1.047 | 2.07 | 26 | 4.69 |
| PAPD4 | AL833136 | 18 | 20 | 1.0000 | 0.8931 | 1.1270 | 0.172 | 1.13 | 2 | 1.24 |
| PAPD4 | BC047581 | 2 | 0 | 0.6733 | 0.0800 | 0.3900 | −1.359 | 2.56 | 2 | 0.65 |
| PAPD4 | NM_001114393 | 80 | 0 | 0.0000 | 0.0000 | 0.0123 | −6.344 | 81.26 | 80 | 6.33 |
| PAPD4 | NM_001114394 | 3 | 0 | 0.5945 | 0.0576 | 0.2299 | −2.121 | 4.35 | 3 | 1.74 |
| PAPD4 | NM_173797 | 20 | 20 | 1.0000 | 1.0000 | 1.0039 | 0.006 | 1.00 | 0 | −3.66 |
| PCBP2 | AK023529 | 61 | 125 | 0.5421 | 0.0458 | 2.0291 | 1.021 | 2.03 | 64 | 5.99 |
| PCBP2 | AK130583 | 270 | 254 | 1.0000 | 0.7693 | 0.9419 | −0.086 | 1.06 | 16 | 3.98 |
| PCBP2 | AK296930 | 47 | 45 | 1.0000 | 0.7984 | 0.9524 | −0.070 | 1.05 | 2 | 1.19 |
| PCBP2 | AK299210 | 404 | 655 | 0.0352 | 0.0007 | 1.6195 | 0.696 | 1.62 | 251 | 7.97 |
| PCBP2 | AK302067 | 285 | 102 | 0.0036 | 0.0000 | 0.3583 | −1.481 | 2.79 | 184 | 7.52 |
| PCBP2 | NM_001098620 | 0 | 7 | 0.4826 | 0.0361 | 8.2165 | 3.039 | 8.22 | 7 | 2.85 |
| PCBP2 | NM_001128911 | 25 | 30 | 1.0000 | 0.8292 | 1.1790 | 0.238 | 1.18 | 5 | 2.22 |
| PCBP2 | NM_001128912 | 855 | 206 | 0.0000 | 0.0000 | 0.2414 | −2.051 | 4.14 | 649 | 9.34 |
| PCBP2 | NM_001128913 | 36 | 8 | 0.4105 | 0.0269 | 0.2295 | −2.124 | 4.36 | 29 | 4.85 |
| PCBP2 | NM_001128914 | 34 | 6 | 0.4717 | 0.0350 | 0.1943 | −2.364 | 5.15 | 28 | 4.83 |
| PCBP2 | NM_005016 | 10 | 2 | 0.9760 | 0.1746 | 0.2633 | −1.925 | 3.80 | 8 | 3.05 |
| PCBP2 | NM_031989 | 24 | 15 | 1.0000 | 0.5189 | 0.6419 | −0.640 | 1.56 | 9 | 3.18 |
| PCM1 | AB587340 | 121 | 55 | 0.5017 | 0.0392 | 0.4574 | −1.128 | 2.19 | 66 | 6.05 |
| PCM1 | AK302378 | 114 | 59 | 0.6108 | 0.0600 | 0.5235 | −0.934 | 1.91 | 55 | 5.78 |
| PCM1 | AK307583 | 1723 | 442 | 0.0000 | 0.0000 | 0.2570 | −1.960 | 3.89 | 1281 | 10.32 |
| PCM1 | BC000453 | 17 | 9 | 1.0000 | 0.5446 | 0.5542 | −0.852 | 1.80 | 8 | 3.00 |
| PCM1 | BC027477 | 0 | 5 | 0.5675 | 0.0519 | 6.3189 | 2.660 | 6.32 | 5 | 2.41 |
| PCM1 | BC133052 | 1061 | 1130 | 1.0000 | 0.4994 | 1.0656 | 0.092 | 1.07 | 70 | 6.12 |
| PCM1 | BC140946 | 58 | 109 | 0.8735 | 0.1376 | 1.8808 | 0.911 | 1.88 | 52 | 5.69 |
| PCM1 | NM_006197 | 215 | 366 | 0.2045 | 0.0079 | 1.6952 | 0.761 | 1.70 | 150 | 7.23 |
| PCSK9 | AK297473 | 65 | 0 | 0.0000 | 0.0000 | 0.0201 | −5.636 | 49.75 | 65 | 6.02 |
| PCSK9 | NM_174936 | 17 | 27 | 1.0000 | 0.4504 | 1.5329 | 0.616 | 1.53 | 10 | 3.30 |
| PDXDC1 | AK295168 | 20 | 20 | 1.0000 | 0.9297 | 0.9858 | −0.021 | 1.01 | 0 | −1.76 |
| PDXDC1 | AK299111 | 300 | 265 | 1.0000 | 0.5797 | 0.8851 | −0.176 | 1.13 | 35 | 5.11 |
| PDXDC1 | AK299799 | 44 | 46 | 1.0000 | 0.9214 | 1.0294 | 0.042 | 1.03 | 1 | 0.42 |

TABLE 9-continued

RNA Abundance Modulation

| Gene | Trx_ID | ave DMSO | ave Cpd | padj (q val, FDR) | ttest (p val) | FC (x + 1) | L₂FC (x + 1) | amp FC (x + 1) | abs (Cpd − DMSO) | L₂abs (Cpd − DMSO) |
|---|---|---|---|---|---|---|---|---|---|---|
| PDXDC1 | AY203955 | 15 | 9 | 1.0000 | 0.5241 | 0.6038 | −0.728 | 1.66 | 6 | 2.67 |
| PDXDC1 | BC033748 | 0 | 0 | 9999 | 9999 | 1.0000 | 0.000 | 1.00 | 0 | 0 |
| PDXDC1 | BC053946 | 1959 | 2562 | 0.0479 | 0.0010 | 1.3072 | 0.386 | 1.31 | 602 | 9.23 |
| PDXDC1 | BX648066 | 60 | 58 | 1.0000 | 0.9614 | 0.9672 | −0.048 | 1.03 | 2 | 1.00 |
| PDXDC1 | NM_015027 | 640 | 157 | 0.0000 | 0.0000 | 0.2468 | −2.019 | 4.05 | 483 | 8.92 |
| PEPD | AK057538 | 23 | 26 | 1.0000 | 0.8792 | 1.1475 | 0.198 | 1.15 | 4 | 1.81 |
| PEPD | NM_000285 | 198 | 13 | 0.0000 | 0.0000 | 0.0687 | −3.865 | 14.57 | 185 | 7.53 |
| PEPD | NM_001166056 | 1695 | 1900 | 0.9699 | 0.1727 | 1.1206 | 0.164 | 1.12 | 205 | 7.68 |
| PEPD | NM_001166057 | 1 | 4 | 1.0000 | 0.5339 | 2.1667 | 1.116 | 2.17 | 3 | 1.39 |
| PHF19 | AK302996 | 53 | 1 | 0.0014 | 0.0000 | 0.0430 | −4.539 | 23.26 | 52 | 5.70 |
| PHF19 | BC044224 | 0 | 56 | 0.0000 | 0.0000 | 57.3708 | 5.842 | 57.37 | 56 | 5.82 |
| PHF19 | NM_001009936 | 8 | 0 | 0.2412 | 0.0104 | 0.1059 | −3.240 | 9.45 | 8 | 3.08 |
| PHF19 | NM_015651 | 8 | 18 | 1.0000 | 0.3655 | 2.1300 | 1.091 | 2.13 | 10 | 3.37 |
| PHF8 | AF091081 | 121 | 2 | 0.0000 | 0.0000 | 0.0246 | −5.344 | 40.63 | 119 | 6.90 |
| PHF8 | BC017720 | 8 | 4 | 1.0000 | 0.5313 | 0.5121 | −0.965 | 1.95 | 5 | 2.18 |
| PHF8 | NM_001184896 | 242 | 381 | 0.3720 | 0.0222 | 1.5718 | 0.652 | 1.57 | 139 | 7.12 |
| PHF8 | NM_001184897 | 26 | 24 | 1.0000 | 0.9709 | 0.9200 | −0.120 | 1.09 | 2 | 1.10 |
| PHF8 | NM_001184898 | 0 | 1 | 1.0000 | 0.6668 | 1.7217 | 0.784 | 1.72 | 1 | −0.47 |
| PHF8 | NM_015107 | 3261 | 3148 | 1.0000 | 0.5317 | 0.9653 | −0.051 | 1.04 | 113 | 6.82 |
| PHTF2 | AL136883 | 226 | 288 | 1.0000 | 0.2003 | 1.2723 | 0.347 | 1.27 | 62 | 5.95 |
| PHTF2 | AM393200 | 75 | 0 | 0.0000 | 0.0000 | 0.0179 | −5.801 | 55.74 | 74 | 6.22 |
| PHTF2 | AX746556 | 390 | 380 | 1.0000 | 0.8962 | 0.9754 | −0.036 | 1.03 | 10 | 3.27 |
| PHTF2 | BC018098 | 1109 | 882 | 0.5448 | 0.0470 | 0.7957 | −0.330 | 1.26 | 227 | 7.82 |
| PHTF2 | BC032334 | 0 | 0 | 9999 | 9999 | 1.0000 | 0.000 | 1.00 | 0 | 0 |
| PHTF2 | NM_001127357 | 17 | 29 | 1.0000 | 0.4583 | 1.7021 | 0.767 | 1.70 | 12 | 3.63 |
| PHTF2 | NM_001127358 | 0 | 0 | 9999 | 9999 | 1.0000 | 0.000 | 1.00 | 0 | 0 |
| PHTF2 | NM_001127360 | 378 | 420 | 1.0000 | 0.6080 | 1.1116 | 0.153 | 1.11 | 42 | 5.40 |
| PHTF2 | NM_020432 | 50 | 55 | 1.0000 | 0.8852 | 1.0974 | 0.134 | 1.10 | 5 | 2.32 |
| PIK3C2B | BC094741 | 25 | 0 | 0.0097 | 0.0001 | 0.0386 | −4.696 | 25.93 | 25 | 4.64 |
| PIK3C2B | BC144342 | 8 | 8 | 1.0000 | 0.9697 | 0.9908 | −0.013 | 1.01 | 0 | −3.58 |
| PIK3C2B | NM_002646 | 4 | 5 | 1.0000 | 0.9551 | 1.0669 | 0.093 | 1.07 | 0 | −1.49 |
| PITPNB | AK302367 | 295 | 541 | 0.0169 | 0.0003 | 1.8305 | 0.872 | 1.83 | 246 | 7.94 |
| PITPNB | BC031427 | 311 | 284 | 1.0000 | 0.6456 | 0.9143 | −0.129 | 1.09 | 27 | 4.74 |
| PITPNB | CU689164 | 57 | 74 | 1.0000 | 0.5319 | 1.2897 | 0.367 | 1.29 | 17 | 4.07 |
| PITPNB | NM_012399 | 52 | 0 | 0.0000 | 0.0000 | 0.0188 | −5.737 | 53.32 | 52 | 5.71 |
| PLEC | NM_000445 | 1082 | 1051 | 1.0000 | 0.8297 | 0.9715 | −0.042 | 1.03 | 31 | 4.95 |
| PLEC | NM_201378 | 57 | 0 | 0.0000 | 0.0000 | 0.0173 | −5.856 | 57.93 | 57 | 5.83 |
| PLEC | NM_201379 | 837 | 698 | 0.9225 | 0.1550 | 0.8335 | −0.263 | 1.20 | 140 | 7.13 |
| PLEC | NM_201380 | 6254 | 7294 | 0.2350 | 0.0099 | 1.1662 | 0.222 | 1.17 | 1040 | 10.02 |
| PLEC | NM_201381 | 20 | 17 | 1.0000 | 0.8387 | 0.8542 | −0.227 | 1.17 | 3 | 1.61 |
| PLEC | NM_201382 | 298 | 0 | 0.0000 | 0.0000 | 0.0033 | −8.226 | 299.43 | 298 | 8.22 |
| PLEC | NM_201383 | 157 | 59 | 0.1796 | 0.0065 | 0.3791 | −1.399 | 2.64 | 98 | 6.61 |
| PLEC | NM_201384 | 2031 | 2357 | 0.4676 | 0.0339 | 1.1605 | 0.215 | 1.16 | 326 | 8.35 |
| PMS1 | AB102869 | 5250 | 5390 | 1.0000 | 0.5084 | 1.0268 | 0.038 | 1.03 | 141 | 7.14 |
| PMS1 | AB102872 | 4871 | 5251 | 1.0000 | 0.2168 | 1.0780 | 0.108 | 1.08 | 380 | 8.57 |
| PMS1 | AB102874 | 33563 | 34265 | 1.0000 | 0.6816 | 1.0209 | 0.030 | 1.02 | 702 | 9.46 |
| PMS1 | AK295602 | 18046 | 16942 | 1.0000 | 0.2629 | 0.9388 | −0.091 | 1.07 | 1104 | 10.11 |
| PMS1 | AK304634 | 996 | 980 | 1.0000 | 0.8094 | 0.9832 | −0.024 | 1.02 | 17 | 4.06 |
| PMS1 | AK316215 | 0 | 0 | 9999 | 9999 | 1.0000 | 0.000 | 1.00 | 0 | 0 |
| PMS1 | AY540750 | 0 | 1 | 1.0000 | 0.4588 | 1.8808 | 0.911 | 1.88 | 1 | −0.18 |
| PMS1 | AY540751 | 12 | 10 | 1.0000 | 0.8731 | 0.8902 | −0.168 | 1.12 | 1 | 0.49 |
| PMS1 | BC008410 | 51 | 0 | 0.0000 | 0.0000 | 0.0191 | −5.711 | 52.39 | 51 | 5.68 |
| PMS1 | BC036376 | 302 | 328 | 1.0000 | 0.5964 | 1.0848 | 0.117 | 1.08 | 26 | 4.68 |
| PMS1 | NM_000534 | 0 | 0 | 9999 | 9999 | 1.0000 | 0.000 | 1.00 | 0 | 0 |
| PMS1 | NM_001128143 | 0 | 0 | 1.0000 | 1.0000 | 0.9670 | −0.048 | 1.03 | 0 | −4.46 |
| PMS1 | NM_001128144 | 8 | 31 | 0.7917 | 0.1159 | 3.5036 | 1.809 | 3.50 | 23 | 4.52 |
| POU2F1 | AK091438 | 0 | 0 | 9999 | 9999 | 1.0000 | 0.000 | 1.00 | 0 | 0 |
| POU2F1 | AK302525 | 4 | 3 | 1.0000 | 0.8409 | 0.8056 | −0.312 | 1.24 | 1 | −0.10 |
| POU2F1 | BC007388 | 42 | 40 | 1.0000 | 0.9306 | 0.9680 | −0.047 | 1.03 | 1 | 0.44 |
| POU2F1 | NM_001198786 | 222 | 270 | 1.0000 | 0.3696 | 1.2189 | 0.286 | 1.22 | 49 | 5.61 |
| POU2F1 | NM_002697 | 311 | 282 | 1.0000 | 0.6423 | 0.9064 | −0.142 | 1.10 | 29 | 4.87 |
| POU2F1 | NR_037163 | 192 | 320 | 0.3378 | 0.0186 | 1.6604 | 0.732 | 1.66 | 128 | 7.00 |
| POU2F1 | S66902 | 223 | 48 | 0.0001 | 0.0000 | 0.2180 | −2.198 | 4.59 | 175 | 7.45 |
| PPHLN1 | AK000186 | 26 | 29 | 1.0000 | 0.8992 | 1.0880 | 0.122 | 1.09 | 2 | 1.26 |
| PPHLN1 | AK299682 | 14 | 80 | 0.0793 | 0.0020 | 5.3446 | 2.418 | 5.34 | 66 | 6.03 |
| PPHLN1 | AK299951 | 59 | 0 | 0.0000 | 0.0000 | 0.0166 | −5.912 | 60.22 | 59 | 5.89 |
| PPHLN1 | AK303612 | 18 | 13 | 1.0000 | 0.5401 | 0.7262 | −0.462 | 1.38 | 5 | 2.40 |
| PPHLN1 | NM_001143787 | 2118 | 2093 | 1.0000 | 0.9838 | 0.9884 | −0.017 | 1.01 | 25 | 4.62 |
| PPHLN1 | NM_001143788 | 3140 | 3340 | 1.0000 | 0.4063 | 1.0637 | 0.089 | 1.06 | 200 | 7.64 |
| PPHLN1 | NM_001143789 | 3 | 5 | 1.0000 | 0.7730 | 1.4951 | 0.580 | 1.50 | 2 | 1.03 |
| PPHLN1 | NM_201438 | 40 | 0 | 0.0003 | 0.0000 | 0.0242 | −5.370 | 41.36 | 40 | 5.33 |
| PPHLN1 | NM_201439 | 484 | 192 | 0.0001 | 0.0000 | 0.3978 | −1.330 | 2.51 | 292 | 8.19 |
| PPHLN1 | NM_201440 | 0 | 0 | 9999 | 9999 | 1.0000 | 0.000 | 1.00 | 0 | 0 |
| PPHLN1 | NM_201515 | 0 | 0 | 9999 | 9999 | 1.0000 | 0.000 | 1.00 | 0 | 0 |

TABLE 9-continued

RNA Abundance Modulation

| Gene | Trx_ID | ave DMSO | ave Cpd | padj (q val, FDR) | ttest (p val) | FC (x + 1) | L₂FC (x + 1) | amp FC (x + 1) | abs (Cpd − DMSO) | L₂abs (Cpd − DMSO) |
|---|---|---|---|---|---|---|---|---|---|---|
| PRKDC | NM_001081640 | 1090 | 1385 | 0.2686 | 0.0124 | 1.2703 | 0.345 | 1.27 | 295 | 8.20 |
| PRKDC | NM_006904 | 11 | 23 | 1.0000 | 0.4041 | 1.9679 | 0.977 | 1.97 | 12 | 3.56 |
| PRSS23 | AK304301 | 6 | 5 | 1.0000 | 0.8393 | 0.7595 | −0.397 | 1.32 | 2 | 0.82 |
| PRSS23 | BC063022 | 46 | 40 | 1.0000 | 0.8232 | 0.8897 | −0.169 | 1.12 | 5 | 2.36 |
| PRSS23 | CCDS8278 | 101 | 124 | 1.0000 | 0.5442 | 1.2287 | 0.297 | 1.23 | 23 | 4.54 |
| PRSS23 | NM_007173 | 395 | 167 | 0.0023 | 0.0000 | 0.4240 | −1.238 | 2.36 | 228 | 7.83 |
| PSMC1 | AK299121 | 1570 | 1675 | 1.0000 | 0.4636 | 1.0672 | 0.094 | 1.07 | 106 | 6.72 |
| PSMC1 | DQ891703 | 45 | 43 | 1.0000 | 0.9101 | 0.9555 | −0.066 | 1.05 | 2 | 1.04 |
| PSMC1 | NM_002802 | 20 | 30 | 1.0000 | 0.4784 | 1.4777 | 0.563 | 1.48 | 10 | 3.32 |
| PTPN14 | AK090596 | 1274 | 209 | 0.0000 | 0.0000 | 0.1651 | −2.599 | 6.06 | 1064 | 10.06 |
| PTPN14 | AK298120 | 6908 | 7352 | 1.0000 | 0.3466 | 1.0642 | 0.090 | 1.06 | 443 | 8.79 |
| PTPN14 | HQ116786 | 245 | 58 | 0.0004 | 0.0000 | 0.2389 | −2.065 | 4.19 | 187 | 7.55 |
| PTPN14 | NM_005401 | 30 | 71 | 0.6800 | 0.0815 | 2.3112 | 1.209 | 2.31 | 41 | 5.35 |
| PUF60 | AK055941 | 291 | 366 | 1.0000 | 0.2168 | 1.2556 | 0.328 | 1.26 | 75 | 6.22 |
| PUF60 | NM_001136033 | 2 | 271 | 0.0000 | 0.0000 | 95.3473 | 6.575 | 95.35 | 270 | 8.07 |
| PUF60 | NM_001271096 | 352 | 134 | 0.0004 | 0.0000 | 0.3841 | −1.380 | 2.60 | 217 | 7.76 |
| PUF60 | NM_001271097 | 2362 | 2395 | 1.0000 | 0.8192 | 1.0140 | 0.020 | 1.01 | 33 | 5.05 |
| PUF60 | NM_001271098 | 1555 | 1556 | 1.0000 | 0.9858 | 1.0001 | 0.000 | 1.00 | 0 | −2.19 |
| PUF60 | NM_001271099 | 336 | 143 | 0.0014 | 0.0000 | 0.4264 | −1.230 | 2.35 | 193 | 7.59 |
| PUF60 | NM_001271100 | 166 | 168 | 1.0000 | 0.9826 | 1.0120 | 0.017 | 1.01 | 2 | 0.99 |
| PUF60 | NM_014281 | 225 | 74 | 0.0099 | 0.0001 | 0.3300 | −1.600 | 3.03 | 152 | 7.24 |
| PUF60 | NM_078480 | 59 | 41 | 1.0000 | 0.4924 | 0.7064 | −0.501 | 1.42 | 18 | 4.13 |
| PVR | AK094177 | 348 | 615 | 0.0088 | 0.0001 | 1.7655 | 0.820 | 1.77 | 267 | 8.06 |
| PVR | NM_001135768 | 679 | 812 | 0.7913 | 0.1158 | 1.1952 | 0.257 | 1.20 | 133 | 7.05 |
| PVR | NM_001135769 | 169 | 128 | 1.0000 | 0.3296 | 0.7623 | −0.392 | 1.31 | 40 | 5.33 |
| PVR | NM_001135770 | 795 | 938 | 0.9728 | 0.1738 | 1.1787 | 0.237 | 1.18 | 142 | 7.15 |
| PVR | NM_006505 | 255 | 189 | 0.9435 | 0.1623 | 0.7410 | −0.433 | 1.35 | 66 | 6.05 |
| RAB23 | AF161486 | 717 | 623 | 1.0000 | 0.2880 | 0.8696 | −0.202 | 1.15 | 94 | 6.55 |
| RAB23 | AK311123 | 206 | 50 | 0.0007 | 0.0000 | 0.2471 | −2.017 | 4.05 | 156 | 7.29 |
| RAB23 | NM_016277 | 592 | 705 | 1.0000 | 0.1849 | 1.1893 | 0.250 | 1.19 | 112 | 6.81 |
| RAB23 | NM_183227 | 341 | 333 | 1.0000 | 0.9558 | 0.9769 | −0.034 | 1.02 | 8 | 2.98 |
| RAD23B | AK293532 | 2583 | 2653 | 1.0000 | 0.6965 | 1.0272 | 0.039 | 1.03 | 70 | 6.14 |
| RAD23B | NM_001244713 | 75 | 0 | 0.0000 | 0.0000 | 0.0131 | −6.250 | 76.09 | 75 | 6.23 |
| RAD23B | NM_001244724 | 7060 | 5751 | 0.0293 | 0.0005 | 0.8146 | −0.296 | 1.23 | 1309 | 10.35 |
| RAD23B | NM_002874 | 107 | 906 | 0.0000 | 0.0000 | 8.4226 | 3.074 | 8.42 | 799 | 9.64 |
| RAP1A | M22995 | 375 | 1020 | 0.0000 | 0.0000 | 2.7193 | 1.443 | 2.72 | 646 | 9.33 |
| RAP1A | NM_001010935 | 8 | 6 | 1.0000 | 0.9015 | 0.8630 | −0.212 | 1.16 | 1 | 0.23 |
| RAP1A | NM_002884 | 5 | 0 | 0.4015 | 0.0259 | 0.1597 | −2.647 | 6.26 | 5 | 2.40 |
| RASSF8 | AY665468 | 853 | 764 | 1.0000 | 0.1912 | 0.8949 | −0.160 | 1.12 | 90 | 6.49 |
| RASSF8 | AY665470 | 1564 | 912 | 0.0000 | 0.0000 | 0.5839 | −0.776 | 1.71 | 651 | 9.35 |
| RASSF8 | NM_001164746 | 74 | 57 | 1.0000 | 0.5275 | 0.7712 | −0.375 | 1.30 | 17 | 4.09 |
| RASSF8 | NM_001164747 | 11 | 8 | 1.0000 | 0.7359 | 0.7803 | −0.358 | 1.28 | 3 | 1.38 |
| RASSF8 | NM_001164748 | 569 | 517 | 1.0000 | 0.4950 | 0.9083 | −0.139 | 1.10 | 52 | 5.71 |
| RASSF8 | NM_007211 | 50 | 49 | 1.0000 | 0.8554 | 0.9797 | −0.030 | 1.02 | 1 | 0.05 |
| RBM10 | AK000962 | 62 | 0 | 0.0000 | 0.0000 | 0.0158 | −5.985 | 63.33 | 62 | 5.96 |
| RBM10 | NM_001204466 | 1 | 16 | 0.4695 | 0.0347 | 7.8851 | 2.979 | 7.89 | 15 | 3.88 |
| RBM10 | NM_001204467 | 1725 | 1835 | 1.0000 | 0.5122 | 1.0639 | 0.089 | 1.06 | 110 | 6.79 |
| RBM10 | NM_001204468 | 286 | 198 | 0.8622 | 0.1348 | 0.6937 | −0.528 | 1.44 | 88 | 6.46 |
| RBM10 | NM_005676 | 0 | 0 | 9999 | 9999 | 1.0000 | 0.000 | 1.00 | 0 | 0 |
| RBM10 | NM_152856 | 555 | 260 | 0.0001 | 0.0000 | 0.4696 | −1.090 | 2.13 | 295 | 8.20 |
| RCC1 | NM_001048194 | 2116 | 2431 | 0.6207 | 0.0631 | 1.1488 | 0.200 | 1.15 | 315 | 8.30 |
| RCC1 | NM_001048195 | 808 | 820 | 1.0000 | 0.8188 | 1.0149 | 0.021 | 1.01 | 12 | 3.59 |
| RCC1 | NM_001048199 | 1888 | 2090 | 1.0000 | 0.1884 | 1.1071 | 0.147 | 1.11 | 202 | 7.66 |
| RCC1 | NM_001269 | 474 | 422 | 1.0000 | 0.3963 | 0.8906 | −0.167 | 1.12 | 52 | 5.70 |
| RCC1 | NR_030725 | 312 | 70 | 0.0000 | 0.0000 | 0.2251 | −2.152 | 4.44 | 243 | 7.92 |
| RCC1 | NR_030726 | 1574 | 1687 | 1.0000 | 0.4220 | 1.0718 | 0.100 | 1.07 | 113 | 6.82 |
| RFWD2 | AK001278 | 0 | 0 | 9999 | 9999 | 1.0000 | 0.000 | 1.00 | 0 | 0 |
| RFWD2 | AK025789 | 99 | 0 | 0.0000 | 0.0000 | 0.0100 | −6.647 | 100.21 | 99 | 6.63 |
| RFWD2 | BC039723 | 1502 | 1586 | 1.0000 | 0.6004 | 1.0563 | 0.079 | 1.06 | 85 | 6.40 |
| RFWD2 | NM_001001740 | 6 | 0 | 0.3813 | 0.0236 | 0.1340 | −2.899 | 7.46 | 6 | 2.69 |
| RFWD2 | NM_022457 | 15 | 10 | 1.0000 | 0.7096 | 0.7110 | −0.492 | 1.41 | 5 | 2.20 |
| RNFT1 | AF100745 | 40 | 64 | 1.0000 | 0.2421 | 1.6063 | 0.684 | 1.61 | 25 | 4.62 |
| RNFT1 | AK294806 | 288 | 97 | 0.0071 | 0.0001 | 0.3381 | −1.565 | 2.96 | 191 | 7.58 |
| RNFT1 | AK296197 | 232 | 261 | 1.0000 | 0.8643 | 1.1233 | 0.168 | 1.12 | 29 | 4.84 |
| RNFT1 | BC006971 | 358 | 490 | 0.5615 | 0.0494 | 1.3674 | 0.451 | 1.37 | 132 | 7.04 |
| RNFT1 | NM_016125 | 95 | 98 | 1.0000 | 0.9408 | 1.0367 | 0.052 | 1.04 | 4 | 1.82 |
| RWDD4 | AK293274 | 28 | 20 | 1.0000 | 0.7449 | 0.7389 | −0.436 | 1.35 | 8 | 2.92 |
| RWDD4 | CCDS34111 | 85 | 64 | 1.0000 | 0.4621 | 0.7579 | −0.400 | 1.32 | 21 | 4.38 |
| RWDD4 | NM_152682 | 60 | 59 | 1.0000 | 0.9716 | 0.9952 | −0.007 | 1.00 | 0 | −1.77 |
| SAMD9L | AF474973 | 87 | 1 | 0.0000 | 0.0000 | 0.0278 | −5.169 | 35.97 | 85 | 6.42 |
| SAMD9L | AY195582 | 0 | 0 | 1.0000 | 1.0000 | 1.3608 | 0.444 | 1.36 | 0 | −1.47 |
| SAMD9L | AY195583 | 0 | 0 | 9999 | 9999 | 1.0000 | 0.000 | 1.00 | 0 | 0 |
| SAMD9L | AY195584 | 0 | 48 | 0.0001 | 0.0000 | 49.1441 | 5.619 | 49.14 | 48 | 5.59 |
| SAMD9L | AY195585 | 678 | 721 | 1.0000 | 0.6506 | 1.0630 | 0.088 | 1.06 | 43 | 5.42 |

TABLE 9-continued

RNA Abundance Modulation

| Gene | Trx_ID | ave DMSO | ave Cpd | padj (q val, FDR) | ttest (p val) | FC (x + 1) | $L_2FC$ (x + 1) | amp FC (x + 1) | abs (Cpd − DMSO) | $L_2$abs (Cpd − DMSO) |
|---|---|---|---|---|---|---|---|---|---|---|
| SAMD9L | CCDS34681 | 21 | 31 | 1.0000 | 0.5046 | 1.4540 | 0.540 | 1.45 | 10 | 3.34 |
| SAMD9L | DQ068177 | 410 | 808 | 0.0004 | 0.0000 | 1.9676 | 0.976 | 1.97 | 398 | 8.64 |
| SAMD9L | NM_152703 | 759 | 158 | 0.0000 | 0.0000 | 0.2094 | −2.256 | 4.78 | 601 | 9.23 |
| SART3 | AK299250 | 23 | 31 | 1.0000 | 0.6605 | 1.3178 | 0.398 | 1.32 | 8 | 2.94 |
| SART3 | AK304834 | 12 | 9 | 1.0000 | 0.8236 | 0.7885 | −0.343 | 1.27 | 3 | 1.49 |
| SART3 | BC024279 | 7 | 17 | 1.0000 | 0.3614 | 2.3605 | 1.239 | 2.36 | 11 | 3.41 |
| SART3 | BC041638 | 387 | 347 | 1.0000 | 0.5400 | 0.8991 | −0.153 | 1.11 | 39 | 5.29 |
| SART3 | BC143253 | 2516 | 2782 | 0.9925 | 0.1808 | 1.1059 | 0.145 | 1.11 | 266 | 8.06 |
| SART3 | CR933631 | 59 | 46 | 1.0000 | 0.8704 | 0.7799 | −0.359 | 1.28 | 13 | 3.72 |
| SART3 | NM_014706 | 2 | 0 | 0.6144 | 0.0618 | 0.2876 | −1.798 | 3.48 | 2 | 1.31 |
| SCAF4 | AK057840 | 0 | 0 | 9999 | 9999 | 1.0000 | 0.000 | 1.00 | 0 | 0 |
| SCAF4 | AL117417 | 182 | 40 | 0.0047 | 0.0001 | 0.2256 | −2.148 | 4.43 | 141 | 7.14 |
| SCAF4 | NM_001145444 | 349 | 115 | 0.0015 | 0.0000 | 0.3321 | −1.590 | 3.01 | 234 | 7.87 |
| SCAF4 | NM_001145445 | 162 | 208 | 1.0000 | 0.5662 | 1.2804 | 0.357 | 1.28 | 46 | 5.52 |
| SCAF4 | NM_020706 | 40 | 44 | 1.0000 | 0.7530 | 1.0917 | 0.127 | 1.09 | 4 | 1.91 |
| SCD | NM_005063 | 1059 | 1228 | 1.0000 | 0.2139 | 1.1591 | 0.213 | 1.16 | 169 | 7.40 |
| SEC22A | AK057587 | 127 | 96 | 1.0000 | 0.6314 | 0.7596 | −0.397 | 1.32 | 31 | 4.94 |
| SEC22A | NM_012430 | 16265 | 16003 | 1.0000 | 0.7923 | 0.9839 | −0.023 | 1.02 | 262 | 8.04 |
| SEC61A1 | AK074928 | 1117 | 244 | 0.0000 | 0.0000 | 0.2194 | −2.188 | 4.56 | 873 | 9.77 |
| SEC61A1 | AL831940 | 4251 | 3829 | 0.8648 | 0.1355 | 0.9006 | −0.151 | 1.11 | 423 | 8.72 |
| SEC61A1 | BC002951 | 3 | 2 | 1.0000 | 0.6477 | 0.6865 | −0.543 | 1.46 | 1 | 0.36 |
| SEC61A1 | NM_013336 | 95 | 167 | 0.6144 | 0.0607 | 1.7575 | 0.814 | 1.76 | 72 | 6.18 |
| SERPINE2 | NM_001136528 | 9 | 17 | 1.0000 | 0.4950 | 1.7841 | 0.835 | 1.78 | 8 | 2.99 |
| SERPINE2 | NM_001136530 | 285 | 304 | 1.0000 | 0.6831 | 1.0643 | 0.090 | 1.06 | 18 | 4.20 |
| SERPINE2 | NM_006216 | 1731 | 1232 | 0.0226 | 0.0004 | 0.7117 | −0.491 | 1.41 | 499 | 8.96 |
| SERPINE2 | NR_073116 | 129 | 906 | 0.0000 | 0.0000 | 6.9672 | 2.801 | 6.97 | 777 | 9.60 |
| SF1 | CU675924 | 266 | 299 | 1.0000 | 0.5318 | 1.1234 | 0.168 | 1.12 | 33 | 5.04 |
| SF1 | D26121 | 509 | 596 | 1.0000 | 0.2608 | 1.1696 | 0.226 | 1.17 | 87 | 6.43 |
| SF1 | NM_001178030 | 2565 | 2427 | 1.0000 | 0.4360 | 0.9465 | −0.079 | 1.06 | 137 | 7.10 |
| SF1 | NM_001178031 | 32 | 34 | 1.0000 | 0.9875 | 1.0738 | 0.103 | 1.07 | 2 | 1.28 |
| SF1 | NM_004630 | 2 | 7 | 1.0000 | 0.3445 | 2.8663 | 1.519 | 2.87 | 5 | 2.41 |
| SF1 | NM_201995 | 109 | 11 | 0.0008 | 0.0000 | 0.1121 | −3.157 | 8.92 | 98 | 6.62 |
| SF1 | NM_201997 | 3 | 4 | 1.0000 | 0.6718 | 1.3873 | 0.472 | 1.39 | 1 | 0.48 |
| SF1 | NM_201998 | 495 | 631 | 0.7040 | 0.0877 | 1.2736 | 0.349 | 1.27 | 136 | 7.09 |
| SF1 | NR_033649 | 228 | 203 | 1.0000 | 0.5766 | 0.8930 | −0.163 | 1.12 | 24 | 4.61 |
| SF1 | NR_033650 | 67 | 5 | 0.0042 | 0.0000 | 0.0888 | −3.494 | 11.26 | 62 | 5.96 |
| SLC25A17 | AK298215 | 2680 | 2749 | 1.0000 | 0.6848 | 1.0255 | 0.036 | 1.03 | 68 | 6.10 |
| SLC25A17 | AK300553 | 60 | 48 | 1.0000 | 0.6331 | 0.8055 | −0.312 | 1.24 | 12 | 3.57 |
| SLC25A17 | BC024741 | 532 | 89 | 0.0000 | 0.0000 | 0.1689 | −2.566 | 5.92 | 443 | 8.79 |
| SLC25A17 | BX647991 | 15 | 25 | 1.0000 | 0.5471 | 1.5866 | 0.666 | 1.59 | 10 | 3.25 |
| SLC25A17 | NM_006358 | 5 | 13 | 1.0000 | 0.3012 | 2.4115 | 1.270 | 2.41 | 8 | 3.07 |
| SLC7A6 | AK310866 | 0 | 0 | 9999 | 9999 | 1.0000 | 0.000 | 1.00 | 0 | 0 |
| SLC7A6 | AK311610 | 1028 | 1684 | 0.0001 | 0.0000 | 1.6371 | 0.711 | 1.64 | 656 | 9.36 |
| SLC7A6 | CR749475 | 1 | 13 | 0.1892 | 0.0071 | 13.7130 | 3.777 | 13.71 | 13 | 3.67 |
| SLC7A6 | NM_001076785 | 23 | 0 | 0.0144 | 0.0002 | 0.0424 | −4.560 | 23.59 | 23 | 4.50 |
| SLC7A6 | NM_003983 | 7 | 13 | 1.0000 | 0.5558 | 1.7891 | 0.839 | 1.79 | 6 | 2.64 |
| SLC7A8 | AK094550 | 0 | 23 | 0.0206 | 0.0003 | 24.1704 | 4.595 | 24.17 | 23 | 4.53 |
| SLC7A8 | NM_001267036 | 61 | 37 | 1.0000 | 0.4030 | 0.6156 | −0.700 | 1.62 | 24 | 4.57 |
| SLC7A8 | NM_001267037 | 671 | 600 | 1.0000 | 0.3846 | 0.8945 | −0.161 | 1.12 | 71 | 6.15 |
| SLC7A8 | NM_012244 | 932 | 441 | 0.0000 | 0.0000 | 0.4741 | −1.077 | 2.11 | 491 | 8.94 |
| SLC7A8 | NM_182728 | 19 | 9 | 1.0000 | 0.3743 | 0.4887 | −1.033 | 2.05 | 10 | 3.34 |
| SLC7A8 | NR_049767 | 36 | 31 | 1.0000 | 0.8706 | 0.8687 | −0.203 | 1.15 | 5 | 2.29 |
| SMN2 | JQ657801 | 3 | 3 | 1.0000 | 0.9319 | 0.9364 | −0.095 | 1.07 | 0 | −2.06 |
| SMN2 | JQ657801 | 24 | 32 | 1.0000 | 0.7250 | 1.2992 | 0.378 | 1.30 | 8 | 2.92 |
| SMN2 | JQ690861 | 17 | 24 | 1.0000 | 0.5611 | 1.4170 | 0.503 | 1.42 | 7 | 2.90 |
| SMN2 | JQ690864 | 29 | 36 | 1.0000 | 0.7692 | 1.2324 | 0.301 | 1.23 | 7 | 2.80 |
| SMN2 | JQ690866 | 790 | 448 | 0.0056 | 0.0001 | 0.5677 | −0.817 | 1.76 | 342 | 8.42 |
| SMN2 | JQ690867 | 341 | 707 | 0.0003 | 0.0000 | 2.0704 | 1.050 | 2.07 | 366 | 8.52 |
| SMN2 | JQ690868 | 1173 | 1441 | 0.5141 | 0.0406 | 1.2282 | 0.297 | 1.23 | 268 | 8.07 |
| SMN2 | JQ732167 | 683 | 560 | 0.9816 | 0.1775 | 0.8213 | −0.284 | 1.22 | 122 | 6.93 |
| SMN2 | JQ732167 | 136 | 145 | 1.0000 | 0.7895 | 1.0628 | 0.088 | 1.06 | 9 | 3.11 |
| SMN2 | JQ745297 | 273 | 262 | 1.0000 | 0.7360 | 0.9591 | −0.060 | 1.04 | 11 | 3.48 |
| SMN2 | NM_017411 | 1 | 0 | 1.0000 | 0.3294 | 0.6151 | −0.701 | 1.63 | 1 | −0.68 |
| SMN2 | NM_017411 | 0 | 0 | 9999 | 9999 | 1.0000 | 0.000 | 1.00 | 0 | 0 |
| SMN2 | NM_022875 | 6 | 4 | 1.0000 | 0.8006 | 0.7311 | −0.452 | 1.37 | 2 | 0.83 |
| SMN2 | NM_022875 | 4 | 0 | 0.4684 | 0.0346 | 0.1875 | −2.415 | 5.33 | 4 | 2.12 |
| SMN2 | NM_022876 | 0 | 0 | 9999 | 9999 | 1.0000 | 0.000 | 1.00 | 0 | 0 |
| SMN2 | NM_022876 | 11 | 0 | 0.1350 | 0.0043 | 0.0803 | −3.639 | 12.45 | 11 | 3.52 |
| SMN2 | NM_022877 | 4 | 0 | 0.5661 | 0.0515 | 0.2083 | −2.263 | 4.80 | 4 | 1.93 |
| SMN2 | NM_022877 | 0 | 1 | 1.0000 | 0.5116 | 2.0825 | 1.058 | 2.08 | 1 | 0.11 |
| SMYD3 | AK023594 | 0 | 0 | 9999 | 9999 | 1.0000 | 0.000 | 1.00 | 0 | 0 |
| SMYD3 | NM_001167740 | 0 | 1 | 1.0000 | 0.6668 | 1.6691 | 0.739 | 1.67 | 1 | −0.58 |
| SMYD3 | NM_022743 | 442 | 662 | 0.1428 | 0.0047 | 1.4956 | 0.581 | 1.50 | 220 | 7.78 |
| SMYD5 | AK300779 | 0 | 0 | 9999 | 9999 | 1.0000 | 0.000 | 1.00 | 0 | 0 |

TABLE 9-continued

RNA Abundance Modulation

| Gene | Trx_ID | ave DMSO | ave Cpd | padj (q val, FDR) | ttest (p val) | FC (x + 1) | L$_2$FC (x + 1) | amp FC (x + 1) | abs (Cpd − DMSO) | L$_2$abs (Cpd − DMSO) |
|---|---|---|---|---|---|---|---|---|---|---|
| SMYD5 | NM_006062 | 223 | 14 | 0.0000 | 0.0000 | 0.0672 | −3.895 | 14.87 | 209 | 7.71 |
| SNAP23 | NM_003825 | 0 | 0 | 9999 | 9999 | 1.0000 | 0.000 | 1.00 | 0 | 0 |
| SNAP23 | NM_130798 | 0 | 16 | 0.1107 | 0.0032 | 16.9149 | 4.080 | 16.91 | 16 | 3.99 |
| SNHG16 | BC042949 | 0 | 1 | 1.0000 | 0.5116 | 2.0825 | 1.058 | 2.08 | 1 | 0.11 |
| SNHG16 | NR_038108 | 29 | 0 | 0.0042 | 0.0000 | 0.0339 | −4.883 | 29.52 | 29 | 4.83 |
| SNHG16 | NR_038109 | 3 | 0 | 0.5661 | 0.0513 | 0.2442 | −2.034 | 4.10 | 3 | 1.63 |
| SNHG16 | NR_038110 | 5 | 26 | 0.6589 | 0.0727 | 4.1981 | 2.070 | 4.20 | 20 | 4.34 |
| SNHG16 | NR_038111 | 89 | 7 | 0.0008 | 0.0000 | 0.0908 | −3.461 | 11.01 | 82 | 6.36 |
| SQLE | NM_003129 | 1342 | 914 | 0.0084 | 0.0001 | 0.6811 | −0.554 | 1.47 | 428 | 8.74 |
| SQRDL | NM_001271213 | 0 | 30 | 0.0058 | 0.0001 | 31.2059 | 4.964 | 31.21 | 30 | 4.92 |
| SQRDL | NM_021199 | 410 | 322 | 1.0000 | 0.1907 | 0.7857 | −0.348 | 1.27 | 88 | 6.46 |
| SQSTM1 | AK098077 | 9 | 9 | 1.0000 | 0.9146 | 1.0937 | 0.129 | 1.09 | 1 | −0.16 |
| SQSTM1 | AX747927 | 1 | 4 | 1.0000 | 0.4973 | 2.1410 | 1.098 | 2.14 | 3 | 1.35 |
| SQSTM1 | NM_001142298 | 390 | 157 | 0.0020 | 0.0000 | 0.4041 | −1.307 | 2.47 | 233 | 7.86 |
| SQSTM1 | NM_001142299 | 150 | 106 | 1.0000 | 0.4288 | 0.7120 | −0.490 | 1.40 | 43 | 5.44 |
| SQSTM1 | NM_003900 | 204 | 205 | 1.0000 | 0.9048 | 1.0018 | 0.003 | 1.00 | 0 | −1.47 |
| SRCAP | AB621816 | 943 | 1092 | 1.0000 | 0.2087 | 1.1568 | 0.210 | 1.16 | 148 | 7.21 |
| SRCAP | AF143946 | 77 | 0 | 0.0000 | 0.0000 | 0.0128 | −6.285 | 77.99 | 77 | 6.27 |
| SRCAP | BC159099 | 390 | 498 | 0.8984 | 0.1463 | 1.2762 | 0.352 | 1.28 | 108 | 6.76 |
| SRCAP | NM_006662 | 146 | 107 | 1.0000 | 0.2969 | 0.7328 | −0.449 | 1.36 | 39 | 5.30 |
| SREBF1 | AB209609 | 1082 | 1366 | 0.4042 | 0.0263 | 1.2626 | 0.336 | 1.26 | 284 | 8.15 |
| SREBF1 | AB373958 | 17 | 23 | 1.0000 | 0.6446 | 1.3145 | 0.395 | 1.31 | 6 | 2.54 |
| SREBF1 | AB373959 | 850 | 771 | 1.0000 | 0.3933 | 0.9066 | −0.142 | 1.10 | 80 | 6.31 |
| SREBF1 | AK091131 | 6892 | 6111 | 0.4704 | 0.0348 | 0.8866 | −0.174 | 1.13 | 782 | 9.61 |
| SREBF1 | AK095325 | 5 | 2 | 1.0000 | 0.5159 | 0.5315 | −0.912 | 1.88 | 3 | 1.49 |
| SREBF1 | AK128320 | 287 | 60 | 0.0000 | 0.0000 | 0.2104 | −2.249 | 4.75 | 228 | 7.83 |
| SREBF1 | NM_001005291 | 1156 | 1443 | 0.3720 | 0.0223 | 1.2477 | 0.319 | 1.25 | 287 | 8.16 |
| SREBF1 | NM_004176 | 465 | 206 | 0.0025 | 0.0000 | 0.4438 | −1.172 | 2.25 | 259 | 8.02 |
| STARD4 | AK125317 | 321 | 470 | 0.2412 | 0.0103 | 1.4647 | 0.551 | 1.46 | 149 | 7.22 |
| STARD4 | AK315863 | 218 | 90 | 0.0802 | 0.0021 | 0.4164 | −1.264 | 2.40 | 128 | 7.00 |
| STARD4 | AK315869 | 387 | 435 | 1.0000 | 0.5083 | 1.1221 | 0.166 | 1.12 | 47 | 5.57 |
| STARD4 | BC042956 | 135 | 237 | 0.6021 | 0.0589 | 1.7548 | 0.811 | 1.75 | 102 | 6.68 |
| STARD4 | NM_139164 | 321 | 289 | 1.0000 | 0.6342 | 0.9004 | −0.151 | 1.11 | 32 | 5.00 |
| STAT1 | AK096686 | 0 | 7 | 0.4864 | 0.0366 | 8.0558 | 3.010 | 8.06 | 7 | 2.82 |
| STAT1 | AK225853 | 108 | 12 | 0.0004 | 0.0000 | 0.1147 | −3.125 | 8.72 | 97 | 6.60 |
| STAT1 | AK292604 | 69 | 30 | 0.7895 | 0.1154 | 0.4360 | −1.198 | 2.29 | 40 | 5.30 |
| STAT1 | GU211348 | 82 | 98 | 1.0000 | 0.6258 | 1.1857 | 0.246 | 1.19 | 15 | 3.95 |
| STAT1 | NM_007315 | 0 | 3 | 0.7425 | 0.1038 | 4.3455 | 2.120 | 4.35 | 3 | 1.74 |
| STAT1 | NM_139266 | 2 | 0 | 0.6144 | 0.0618 | 0.2876 | −1.798 | 3.48 | 2 | 1.31 |
| STAU1 | AB209561 | 123 | 46 | 0.3118 | 0.0160 | 0.3763 | −1.410 | 2.66 | 78 | 6.28 |
| STAU1 | AY546099 | 470 | 197 | 0.0004 | 0.0000 | 0.4195 | −1.253 | 2.38 | 273 | 8.10 |
| STAU1 | NM_001037328 | 812 | 1128 | 0.0920 | 0.0025 | 1.3888 | 0.474 | 1.39 | 316 | 8.30 |
| STAU1 | NM_004602 | 0 | 0 | 9999 | 9999 | 1.0000 | 0.000 | 1.00 | 0 | 0 |
| STAU1 | NM_017453 | 16 | 8 | 1.0000 | 0.4053 | 0.5095 | −0.973 | 1.96 | 8 | 3.05 |
| STAU1 | NM_017454 | 115 | 624 | 0.0000 | 0.0000 | 5.4076 | 2.435 | 5.41 | 510 | 8.99 |
| STEAP2 | DQ656062 | 865 | 528 | 0.0053 | 0.0001 | 0.6113 | −0.710 | 1.64 | 337 | 8.40 |
| STEAP2 | NM_001040665 | 49 | 12 | 0.5421 | 0.0461 | 0.2641 | −1.921 | 3.79 | 37 | 5.21 |
| STEAP2 | NM_001040666 | 7 | 14 | 1.0000 | 0.5831 | 1.8050 | 0.852 | 1.81 | 7 | 2.76 |
| STEAP2 | NM_001244944 | 237 | 90 | 0.0095 | 0.0001 | 0.3815 | −1.390 | 2.62 | 147 | 7.20 |
| STEAP2 | NM_001244945 | 1558 | 1783 | 0.7753 | 0.1103 | 1.1442 | 0.194 | 1.14 | 225 | 7.81 |
| STEAP2 | NM_001244946 | 7418 | 6882 | 1.0000 | 0.1988 | 0.9277 | −0.108 | 1.08 | 536 | 9.07 |
| STEAP2 | NM_152999 | 7661 | 6550 | 0.1635 | 0.0057 | 0.8550 | −0.226 | 1.17 | 1111 | 10.12 |
| STRN3 | BC143933 | 6625 | 2763 | 0.0000 | 0.0000 | 0.4171 | −1.261 | 2.40 | 3862 | 11.92 |
| STRN3 | NM_001083893 | 957 | 1194 | 0.4394 | 0.0306 | 1.2480 | 0.320 | 1.25 | 238 | 7.89 |
| STRN3 | NM_014574 | 477802 | 485681 | 1.0000 | 0.7895 | 1.0165 | 0.024 | 1.02 | 7879 | 12.94 |
| SYNE1 | AB033088 | 510 | 463 | 1.0000 | 0.5829 | 0.9093 | −0.137 | 1.10 | 46 | 5.53 |
| SYNE1 | AB051543 | 1389 | 364 | 0.0000 | 0.0000 | 0.2627 | −1.929 | 3.81 | 1025 | 10.00 |
| SYNE1 | AK308717 | 163 | 39 | 0.0118 | 0.0002 | 0.2413 | −2.051 | 4.14 | 125 | 6.96 |
| SYNE1 | AK310977 | 1523 | 2486 | 0.0000 | 0.0000 | 1.6321 | 0.707 | 1.63 | 963 | 9.91 |
| SYNE1 | AL713682 | 59 | 3 | 0.0058 | 0.0001 | 0.0656 | −3.931 | 15.25 | 56 | 5.81 |
| SYNE1 | AY061755 | 1240 | 1294 | 1.0000 | 0.6514 | 1.0434 | 0.061 | 1.04 | 54 | 5.75 |
| SYNE1 | BC028616 | 84 | 72 | 1.0000 | 0.6914 | 0.8570 | −0.223 | 1.17 | 12 | 3.60 |
| SYNE1 | BC039121 | 303 | 204 | 0.5976 | 0.0580 | 0.6733 | −0.571 | 1.49 | 99 | 6.64 |
| SYNE1 | BX537517 | 0 | 1 | 1.0000 | 0.6668 | 1.6282 | 0.703 | 1.63 | 1 | −0.67 |
| SYNE1 | BX647837 | 231 | 261 | 1.0000 | 0.5742 | 1.1285 | 0.174 | 1.13 | 30 | 4.90 |
| SYNE1 | CR933676 | 59 | 24 | 0.7666 | 0.1087 | 0.4218 | −1.245 | 2.37 | 35 | 5.12 |
| SYNE1 | FM162565 | 34 | 41 | 1.0000 | 0.7287 | 1.2135 | 0.279 | 1.21 | 7 | 2.90 |
| SYNE1 | JQ740784 | 25 | 193 | 0.0000 | 0.0000 | 7.5349 | 2.914 | 7.53 | 168 | 7.39 |
| SYNE1 | JQ740786 | 73 | 7 | 0.0090 | 0.0001 | 0.1064 | −3.232 | 9.40 | 66 | 6.04 |
| SYNE1 | NM_033071 | 1 | 1 | 1.0000 | 1.0000 | 1.0962 | 0.133 | 1.10 | 0 | −2.21 |
| SYNE1 | NM_182961 | 569 | 66 | 0.0000 | 0.0000 | 0.1170 | −3.095 | 8.54 | 503 | 8.97 |
| TACC1 | AB029026 | 7585 | 8216 | 0.8932 | 0.1440 | 1.0832 | 0.115 | 1.08 | 631 | 9.30 |
| TACC1 | AB463317 | 73 | 109 | 1.0000 | 0.2149 | 1.4897 | 0.575 | 1.49 | 36 | 5.17 |
| TACC1 | AK294931 | 401 | 120 | 0.0000 | 0.0000 | 0.3022 | −1.726 | 3.31 | 281 | 8.13 |

TABLE 9-continued

RNA Abundance Modulation

| Gene | Trx_ID | ave DMSO | ave Cpd | padj (q val, FDR) | ttest (p val) | FC (x + 1) | L$_2$FC (x + 1) | amp FC (x + 1) | abs (Cpd − DMSO) | L$_2$abs (Cpd − DMSO) |
|---|---|---|---|---|---|---|---|---|---|---|
| TACC1 | AK295841 | 70 | 91 | 1.0000 | 0.5134 | 1.3050 | 0.384 | 1.30 | 22 | 4.43 |
| TACC1 | AK303596 | 4709 | 5237 | 0.7076 | 0.0905 | 1.1121 | 0.153 | 1.11 | 528 | 9.04 |
| TACC1 | AK304725 | 11 | 15 | 1.0000 | 0.7150 | 1.3062 | 0.385 | 1.31 | 4 | 1.88 |
| TACC1 | AK308849 | 678 | 1199 | 0.0001 | 0.0000 | 1.7670 | 0.821 | 1.77 | 521 | 9.02 |
| TACC1 | AY072874 | 205 | 276 | 1.0000 | 0.1957 | 1.3434 | 0.426 | 1.34 | 71 | 6.15 |
| TACC1 | NM_001122824 | 677 | 93 | 0.0000 | 0.0000 | 0.1388 | −2.849 | 7.20 | 584 | 9.19 |
| TACC1 | NM_001146216 | 273 | 39 | 0.0000 | 0.0000 | 0.1450 | −2.786 | 6.90 | 234 | 7.87 |
| TACC1 | NM_006283 | 813 | 950 | 0.9055 | 0.1485 | 1.1674 | 0.223 | 1.17 | 136 | 7.09 |
| TAF2 | NM_003184 | 650 | 768 | 1.0000 | 0.1950 | 1.1802 | 0.239 | 1.18 | 117 | 6.87 |
| TANC2 | AJ278120 | 441 | 293 | 0.3490 | 0.0199 | 0.6651 | −0.588 | 1.50 | 148 | 7.21 |
| TANC2 | AK001077 | 787 | 761 | 1.0000 | 0.7397 | 0.9673 | −0.048 | 1.03 | 26 | 4.69 |
| TANC2 | AK021886 | 27 | 21 | 1.0000 | 0.6461 | 0.7792 | −0.360 | 1.28 | 6 | 2.61 |
| TANC2 | BC144357 | 51 | 0 | 0.0000 | 0.0000 | 0.0191 | −5.707 | 52.22 | 51 | 5.68 |
| TANC2 | NM_025185 | 20 | 20 | 1.0000 | 0.9828 | 1.0054 | 0.008 | 1.01 | 0 | −3.17 |
| TARBP1 | NM_005646 | 149 | 0 | 0.0000 | 0.0000 | 0.0066 | −7.233 | 150.39 | 149 | 7.22 |
| TBC1D15 | AK307922 | 616 | 787 | 0.5421 | 0.0457 | 1.2775 | 0.353 | 1.28 | 171 | 7.42 |
| TBC1D15 | NM_001146213 | 67 | 119 | 0.8682 | 0.1363 | 1.7610 | 0.816 | 1.76 | 52 | 5.69 |
| TBC1D15 | NM_001146214 | 79 | 7 | 0.0063 | 0.0001 | 0.0967 | −3.370 | 10.34 | 72 | 6.18 |
| TBC1D15 | NM_022771 | 81 | 111 | 1.0000 | 0.3975 | 1.3716 | 0.456 | 1.37 | 30 | 4.92 |
| TBC1D15 | NR_027449 | 5 | 5 | 1.0000 | 1.0000 | 0.9533 | −0.069 | 1.05 | 0 | −1.80 |
| TEP1 | AB209669 | 53 | 371 | 0.0000 | 0.0000 | 6.8994 | 2.786 | 6.90 | 318 | 8.31 |
| TEP1 | AK303307 | 1644 | 1381 | 0.5895 | 0.0551 | 0.8404 | −0.251 | 1.19 | 262 | 8.04 |
| TEP1 | BC143812 | 697 | 691 | 1.0000 | 0.9217 | 0.9914 | −0.012 | 1.01 | 6 | 2.59 |
| TEP1 | BC143815 | 20 | 122 | 0.0116 | 0.0002 | 5.8028 | 2.537 | 5.80 | 101 | 6.66 |
| TEP1 | BX640983 | 57 | 1 | 0.0008 | 0.0000 | 0.0372 | −4.749 | 26.88 | 56 | 5.81 |
| TEP1 | NM_007110 | 180 | 17 | 0.0000 | 0.0000 | 0.0975 | −3.358 | 10.25 | 164 | 7.35 |
| TFCP2 | AK308087 | 268 | 454 | 0.0919 | 0.0025 | 1.6931 | 0.760 | 1.69 | 186 | 7.54 |
| TFCP2 | NM_001173452 | 68 | 0 | 0.0000 | 0.0000 | 0.0145 | −6.103 | 68.74 | 68 | 6.08 |
| TFCP2 | NM_001173453 | 610 | 692 | 1.0000 | 0.3207 | 1.1340 | 0.181 | 1.13 | 82 | 6.36 |
| TFCP2 | NM_005653 | 236 | 324 | 0.9548 | 0.1658 | 1.3718 | 0.456 | 1.37 | 88 | 6.46 |
| TGFBRAP1 | AK021697 | 228 | 43 | 0.0001 | 0.0000 | 0.1936 | −2.369 | 5.17 | 185 | 7.53 |
| TGFBRAP1 | NM_001142621 | 117 | 34 | 0.0844 | 0.0022 | 0.2934 | −1.769 | 3.41 | 83 | 6.38 |
| TGFBRAP1 | NM_004257 | 197 | 344 | 0.1474 | 0.0049 | 1.7435 | 0.802 | 1.74 | 147 | 7.20 |
| THADA | AK025445 | 32 | 23 | 1.0000 | 0.6102 | 0.7216 | −0.471 | 1.39 | 9 | 3.22 |
| THADA | AK126824 | 0 | 1 | 1.0000 | 0.4588 | 1.8808 | 0.911 | 1.88 | 1 | −0.18 |
| THADA | AK307915 | 338 | 107 | 0.0002 | 0.0000 | 0.3196 | −1.646 | 3.13 | 231 | 7.85 |
| THADA | AL832141 | 1535 | 1636 | 1.0000 | 0.4836 | 1.0656 | 0.092 | 1.07 | 101 | 6.66 |
| THADA | AY149632 | 7 | 3 | 1.0000 | 0.5276 | 0.5781 | −0.791 | 1.73 | 3 | 1.67 |
| THADA | BX641038 | 2381 | 2200 | 1.0000 | 0.2621 | 0.9237 | −0.115 | 1.08 | 182 | 7.51 |
| THADA | NM_001083953 | 2709 | 1353 | 0.0000 | 0.0000 | 0.4999 | −1.000 | 2.00 | 1355 | 10.40 |
| THADA | NM_001271643 | 4 | 5 | 1.0000 | 0.8686 | 1.2492 | 0.321 | 1.25 | 1 | 0.34 |
| THADA | NM_001271644 | 97 | 53 | 0.6251 | 0.0647 | 0.5540 | −0.852 | 1.81 | 44 | 5.45 |
| THADA | NM_022065 | 369 | 485 | 0.7425 | 0.1022 | 1.3126 | 0.392 | 1.31 | 116 | 6.86 |
| THADA | NR_073394 | 88 | 150 | 0.7325 | 0.0987 | 1.6964 | 0.762 | 1.70 | 62 | 5.96 |
| TIMP2 | AK294290 | 8394 | 9342 | 0.6251 | 0.0643 | 1.1129 | 0.154 | 1.11 | 948 | 9.89 |
| TIMP2 | BC039613 | 13044 | 11478 | 0.3735 | 0.0225 | 0.8800 | −0.184 | 1.14 | 1566 | 10.61 |
| TIMP2 | NM_003255 | 1813 | 1969 | 1.0000 | 0.2219 | 1.0859 | 0.119 | 1.09 | 156 | 7.28 |
| TLK1 | AK091975 | 2403 | 2538 | 1.0000 | 0.4878 | 1.0561 | 0.079 | 1.06 | 135 | 7.07 |
| TLK1 | BX537631 | 195 | 234 | 1.0000 | 0.4463 | 1.2015 | 0.265 | 1.20 | 39 | 5.30 |
| TLK1 | E09283 | 266 | 257 | 1.0000 | 0.8575 | 0.9671 | −0.048 | 1.03 | 9 | 3.14 |
| TLK1 | NM_001136554 | 1354 | 971 | 0.0353 | 0.0007 | 0.7176 | −0.479 | 1.39 | 383 | 8.58 |
| TLK1 | NM_001136555 | 9 | 39 | 0.5627 | 0.0496 | 4.0581 | 2.021 | 4.06 | 30 | 4.90 |
| TLK1 | NM_012290 | 171 | 393 | 0.0018 | 0.0000 | 2.2865 | 1.193 | 2.29 | 222 | 7.79 |
| TMEM154 | NM_152680 | 60 | 0 | 0.0000 | 0.0000 | 0.0164 | −5.934 | 61.12 | 60 | 5.91 |
| TNS3 | NM_022748 | 2025 | 2216 | 1.0000 | 0.2765 | 1.0947 | 0.130 | 1.09 | 192 | 7.58 |
| TOMM5 | CCDS47968 | 55 | 39 | 1.0000 | 0.4596 | 0.7088 | −0.497 | 1.41 | 16 | 4.02 |
| TOMM5 | CR627326 | 4361 | 4985 | 0.4900 | 0.0372 | 1.1429 | 0.193 | 1.14 | 624 | 9.28 |
| TOMM5 | NM_001001790 | 11 | 3 | 1.0000 | 0.2059 | 0.3221 | −1.635 | 3.11 | 8 | 3.08 |
| TOMM5 | NM_001134484 | 18 | 3 | 0.6994 | 0.0869 | 0.1896 | −2.399 | 5.27 | 16 | 3.96 |
| TOMM5 | NM_001134485 | 20 | 29 | 1.0000 | 0.6056 | 1.4359 | 0.522 | 1.44 | 9 | 3.19 |
| TRAF3 | NM_001199427 | 156 | 169 | 1.0000 | 0.7567 | 1.0842 | 0.117 | 1.08 | 13 | 3.72 |
| TRAF3 | NM_003300 | 75 | 84 | 1.0000 | 0.7839 | 1.1213 | 0.165 | 1.12 | 9 | 3.20 |
| TRAF3 | NM_145725 | 2 | 2 | 1.0000 | 0.7032 | 0.8066 | −0.310 | 1.24 | 1 | −0.57 |
| TRAF3 | NM_145726 | 0 | 0 | 9999 | 9999 | 1.0000 | 0.000 | 1.00 | 0 | 0 |
| TRAK1 | AK295848 | 359 | 75 | 0.0000 | 0.0000 | 0.2097 | −2.254 | 4.77 | 285 | 8.15 |
| TRAK1 | NM_001042646 | 5 | 3 | 1.0000 | 0.6828 | 0.6550 | −0.611 | 1.53 | 2 | 1.13 |
| TRAK1 | NM_001265608 | 30 | 29 | 1.0000 | 0.9727 | 0.9899 | −0.015 | 1.01 | 0 | −1.68 |
| TRAK1 | NM_001265610 | 1082 | 75 | 0.0000 | 0.0000 | 0.0700 | −3.836 | 14.28 | 1007 | 9.98 |
| TRAK1 | NM_014965 | 17 | 1 | 0.0466 | 0.0010 | 0.0564 | −4.147 | 17.72 | 17 | 4.06 |
| TRAPPC12 | AK094181 | 4679 | 5581 | 0.1502 | 0.0050 | 1.1927 | 0.254 | 1.19 | 902 | 9.82 |
| TRAPPC12 | AK098327 | 965 | 910 | 1.0000 | 0.5763 | 0.9438 | −0.083 | 1.06 | 54 | 5.76 |
| TRAPPC12 | NM_016030 | 131 | 162 | 1.0000 | 0.4393 | 1.2325 | 0.302 | 1.23 | 31 | 4.94 |
| TRIM2 | BC025417 | 0 | 5 | 0.5895 | 0.0557 | 6.3529 | 2.667 | 6.35 | 5 | 2.42 |
| TRIM2 | NM_001130067 | 479 | 54 | 0.0000 | 0.0000 | 0.1135 | −3.139 | 8.81 | 426 | 8.73 |

TABLE 9-continued

RNA Abundance Modulation

| Gene | Trx_ID | ave DMSO | ave Cpd | padj (q val, FDR) | ttest (p val) | FC (x + 1) | L$_2$FC (x + 1) | amp FC (x + 1) | abs (Cpd − DMSO) | L$_2$abs (Cpd − DMSO) |
|---|---|---|---|---|---|---|---|---|---|---|
| TRIM2 | NM_015271 | 2424 | 2671 | 1.0000 | 0.1838 | 1.1018 | 0.140 | 1.10 | 247 | 7.95 |
| TRIM26 | AK314782 | 20 | 28 | 1.0000 | 0.6163 | 1.4031 | 0.489 | 1.40 | 8 | 3.08 |
| TRIM26 | AK314782 | 7 | 0 | 0.3283 | 0.0177 | 0.1328 | −2.913 | 7.53 | 7 | 2.71 |
| TRIM26 | AK314782 | 7 | 11 | 1.0000 | 0.6341 | 1.5492 | 0.632 | 1.55 | 4 | 2.07 |
| TRIM26 | AK314782 | 736 | 324 | 0.0000 | 0.0000 | 0.4412 | −1.181 | 2.27 | 412 | 8.69 |
| TRIM26 | AK314782 | 829 | 1137 | 0.1289 | 0.0040 | 1.3709 | 0.455 | 1.37 | 308 | 8.27 |
| TRIM26 | BC021115 | 71 | 3 | 0.0013 | 0.0000 | 0.0590 | −4.082 | 16.94 | 67 | 6.08 |
| TRIM26 | BC021115 | 752 | 746 | 1.0000 | 0.9030 | 0.9914 | −0.012 | 1.01 | 6 | 2.70 |
| TRIM26 | BC021115 | 5 | 14 | 1.0000 | 0.3372 | 2.6034 | 1.380 | 2.60 | 9 | 3.19 |
| TRIM26 | BC021115 | 11 | 0 | 0.1781 | 0.0064 | 0.0854 | −3.549 | 11.71 | 11 | 3.42 |
| TRIM26 | BC021115 | 57 | 0 | 0.0000 | 0.0000 | 0.0173 | −5.857 | 57.95 | 57 | 5.83 |
| TRIM26 | NM_001242783 | 0 | 2 | 0.8778 | 0.1389 | 3.3241 | 1.733 | 3.32 | 2 | 1.22 |
| TRIM26 | NM_001242783 | 399 | 437 | 1.0000 | 0.5548 | 1.0950 | 0.131 | 1.10 | 38 | 5.25 |
| TRIM26 | NM_001242783 | 143 | 36 | 0.0078 | 0.0001 | 0.2594 | −1.946 | 3.85 | 107 | 6.74 |
| TRIM26 | NM_001242783 | 18 | 14 | 1.0000 | 0.7273 | 0.7812 | −0.356 | 1.28 | 4 | 2.06 |
| TRIM26 | NM_003449 | 491 | 418 | 1.0000 | 0.2291 | 0.8517 | −0.232 | 1.17 | 73 | 6.19 |
| TRIM26 | NM_003449 | 96 | 120 | 1.0000 | 0.4687 | 1.2497 | 0.322 | 1.25 | 24 | 4.60 |
| TRIM26 | NM_003449 | 28 | 34 | 1.0000 | 0.7745 | 1.2088 | 0.274 | 1.21 | 6 | 2.59 |
| TRIM26 | NM_003449 | 0 | 129 | 0.0000 | 0.0000 | 130.1883 | 7.024 | 130.19 | 129 | 7.01 |
| TRIM26 | NM_003449 | 2 | 0 | 0.6618 | 0.0746 | 0.3480 | −1.523 | 2.87 | 2 | 0.91 |
| TRIM26 | U09825 | 67 | 72 | 1.0000 | 0.8681 | 1.0718 | 0.100 | 1.07 | 5 | 2.29 |
| TRIM26 | U09825 | 296 | 405 | 0.6172 | 0.0625 | 1.3644 | 0.448 | 1.36 | 108 | 6.76 |
| TRIM26 | U09825 | 1682 | 1922 | 0.7723 | 0.1097 | 1.1425 | 0.192 | 1.14 | 240 | 7.91 |
| TRIM65 | NM_001256124 | 379 | 100 | 0.0000 | 0.0000 | 0.2648 | −1.917 | 3.78 | 279 | 8.13 |
| TRIM65 | NM_173547 | 12 | 12 | 1.0000 | 0.9534 | 0.9724 | −0.040 | 1.03 | 0 | −1.43 |
| TSPAN2 | GU971730 | 13 | 6 | 1.0000 | 0.3482 | 0.4673 | −1.098 | 2.14 | 8 | 2.93 |
| TSPAN2 | NM_005725 | 0 | 0 | 9999 | 9999 | 1.0000 | 0.000 | 1.00 | 0 | 0 |
| U2SURP | AK057679 | 33 | 55 | 1.0000 | 0.3131 | 1.6641 | 0.735 | 1.66 | 22 | 4.48 |
| U2SURP | AK296440 | 199 | 441 | 0.0041 | 0.0000 | 2.2099 | 1.144 | 2.21 | 242 | 7.92 |
| U2SURP | BC006474 | 66 | 108 | 1.0000 | 0.2405 | 1.6221 | 0.698 | 1.62 | 42 | 5.39 |
| U2SURP | BC111692 | 2586 | 2241 | 0.6345 | 0.0660 | 0.8668 | −0.206 | 1.15 | 345 | 8.43 |
| U2SURP | NM_001080415 | 143 | 116 | 1.0000 | 0.4124 | 0.8116 | −0.301 | 1.23 | 27 | 4.76 |
| UBAP2L | AJ243668 | 33 | 11 | 0.8943 | 0.1453 | 0.3477 | −1.524 | 2.88 | 22 | 4.48 |
| UBAP2L | AJ243669 | 599 | 703 | 1.0000 | 0.2382 | 1.1732 | 0.230 | 1.17 | 104 | 6.70 |
| UBAP2L | AJ243670 | 179 | 169 | 1.0000 | 0.7220 | 0.9437 | −0.084 | 1.06 | 10 | 3.34 |
| UBAP2L | AK124294 | 1041 | 805 | 0.3152 | 0.0164 | 0.7735 | −0.371 | 1.29 | 236 | 7.88 |
| UBAP2L | AK302662 | 68 | 0 | 0.0000 | 0.0000 | 0.0145 | −6.107 | 68.92 | 68 | 6.09 |
| UBAP2L | AK302953 | 1547 | 1608 | 1.0000 | 0.6412 | 1.0391 | 0.055 | 1.04 | 61 | 5.92 |
| UBAP2L | AK303533 | 3 | 0 | 0.5661 | 0.0517 | 0.2248 | −2.153 | 4.45 | 3 | 1.79 |
| UBAP2L | NM_001127320 | 404 | 0 | 0.0000 | 0.0000 | 0.0025 | −8.663 | 405.30 | 404 | 8.66 |
| UBAP2L | NM_014847 | 1 | 1 | 1.0000 | 1.0000 | 1.0590 | 0.083 | 1.06 | 0 | −3.38 |
| UBE2V1 | NM_001032288 | 401 | 421 | 1.0000 | 0.7636 | 1.0512 | 0.072 | 1.05 | 21 | 4.36 |
| UBE2V1 | NM_001257393 | 66 | 4 | 0.0039 | 0.0000 | 0.0675 | −3.889 | 14.82 | 63 | 5.97 |
| UBE2V1 | NM_001257394 | 0 | 14 | 0.1390 | 0.0045 | 15.3858 | 3.944 | 15.39 | 14 | 3.85 |
| UBE2V1 | NM_001257397 | 1214 | 1190 | 1.0000 | 0.8291 | 0.9796 | −0.030 | 1.02 | 25 | 4.63 |
| UBE2V1 | NM_001257399 | 116 | 370 | 0.0001 | 0.0000 | 3.1666 | 1.663 | 3.17 | 254 | 7.99 |
| UBE2V1 | NM_021988 | 1484 | 555 | 0.0000 | 0.0000 | 0.3741 | −1.418 | 2.67 | 930 | 9.86 |
| UBE2V1 | NM_022442 | 169 | 74 | 0.2306 | 0.0096 | 0.4385 | −1.190 | 2.28 | 96 | 6.58 |
| UBE2V1 | NM_199144 | 2041 | 2338 | 0.6345 | 0.0660 | 1.1454 | 0.196 | 1.15 | 297 | 8.21 |
| UBE2V1 | NR_047554 | 1276 | 1621 | 0.2538 | 0.0113 | 1.2702 | 0.345 | 1.27 | 345 | 8.43 |
| UBE2V1 | NR_047555 | 268 | 320 | 1.0000 | 0.7850 | 1.1925 | 0.254 | 1.19 | 52 | 5.69 |
| UBE2V1 | NR_047556 | 0 | 27 | 0.0100 | 0.0001 | 28.2228 | 4.819 | 28.22 | 27 | 4.77 |
| UCHL5 | AK225794 | 323 | 137 | 0.0221 | 0.0004 | 0.4262 | −1.230 | 2.35 | 186 | 7.54 |
| UCHL5 | AK316064 | 24 | 39 | 1.0000 | 0.4709 | 1.5961 | 0.675 | 1.60 | 15 | 3.90 |
| UCHL5 | BC015381 | 225 | 499 | 0.0003 | 0.0000 | 2.2185 | 1.150 | 2.22 | 275 | 8.10 |
| UCHL5 | NM_001199261 | 19 | 30 | 1.0000 | 0.5180 | 1.5420 | 0.625 | 1.54 | 11 | 3.47 |
| UCHL5 | NM_001199262 | 2 | 4 | 1.0000 | 0.6052 | 1.6239 | 0.699 | 1.62 | 2 | 0.97 |
| UCHL5 | NM_001199263 | 789 | 651 | 0.7506 | 0.1053 | 0.8246 | −0.278 | 1.21 | 139 | 7.12 |
| UCHL5 | NM_015984 | 4028 | 4407 | 1.0000 | 0.1900 | 1.0942 | 0.130 | 1.09 | 379 | 8.57 |
| UCHL5 | NR_037607 | 211 | 48 | 0.0007 | 0.0000 | 0.2318 | −2.109 | 4.31 | 163 | 7.35 |
| UHRF1BP1L | BX647380 | 40 | 31 | 1.0000 | 0.9749 | 0.7950 | −0.331 | 1.26 | 8 | 3.06 |
| UHRF1BP1L | NM_001006947 | 457 | 590 | 0.7648 | 0.1083 | 1.2893 | 0.367 | 1.29 | 132 | 7.05 |
| UHRF1BP1L | NM_015054 | 126 | 25 | 0.0076 | 0.0001 | 0.2071 | −2.271 | 4.83 | 101 | 6.65 |
| VANGL1 | NM_001172412 | 49 | 89 | 0.8820 | 0.1402 | 1.8011 | 0.849 | 1.80 | 40 | 5.32 |
| VANGL1 | NM_138959 | 243 | 354 | 0.5229 | 0.0429 | 1.4537 | 0.540 | 1.45 | 111 | 6.79 |
| VARS2 | AB067472 | 1568 | 1485 | 0.4899 | 0.4899 | 0.9476 | −0.078 | 1.06 | 82 | 6.36 |
| VARS2 | AK000511 | 1 | 3 | 1.0000 | 0.4888 | 2.0809 | 1.057 | 2.08 | 2 | 1.11 |
| VARS2 | AK000511 | 6 | 3 | 1.0000 | 0.5793 | 0.5967 | −0.745 | 1.68 | 3 | 1.59 |
| VARS2 | AK094483 | 112 | 13 | 0.0009 | 0.0000 | 0.1214 | −3.042 | 8.23 | 99 | 6.63 |
| VARS2 | AK094483 | 0 | 1 | 1.0000 | 0.6668 | 1.7217 | 0.784 | 1.72 | 1 | −0.47 |
| VARS2 | AK125069 | 261 | 381 | 0.5073 | 0.0397 | 1.4594 | 0.545 | 1.46 | 120 | 6.91 |
| VARS2 | AK125069 | 171 | 39 | 0.0046 | 0.0000 | 0.2302 | −2.119 | 4.34 | 132 | 7.05 |
| VARS2 | AK125069 | 0 | 7 | 0.4221 | 0.0285 | 8.0466 | 3.008 | 8.05 | 7 | 2.82 |
| VARS2 | BC063427 | 296 | 368 | 1.0000 | 0.2477 | 1.2419 | 0.312 | 1.24 | 72 | 6.17 |

TABLE 9-continued

RNA Abundance Modulation

| Gene | Trx_ID | ave DMSO | ave Cpd | padj (q val, FDR) | ttest (p val) | FC (x + 1) | L$_2$FC (x + 1) | amp FC (x + 1) | abs (Cpd − DMSO) | L$_2$abs (Cpd − DMSO) |
|---|---|---|---|---|---|---|---|---|---|---|
| VARS2 | BC143535 | 150 | 233 | 0.9034 | 0.1479 | 1.5539 | 0.636 | 1.55 | 84 | 6.39 |
| VARS2 | BC143535 | 0 | 19 | 0.0615 | 0.0014 | 20.4846 | 4.356 | 20.48 | 19 | 4.28 |
| VARS2 | BC143535 | 55 | 0 | 0.0000 | 0.0000 | 0.0178 | −5.812 | 56.20 | 55 | 5.79 |
| VARS2 | BC143535 | 63 | 87 | 1.0000 | 0.4324 | 1.3771 | 0.462 | 1.38 | 24 | 4.59 |
| VARS2 | BC143536 | 51 | 0 | 0.0000 | 0.0000 | 0.0192 | −5.704 | 52.14 | 51 | 5.68 |
| VARS2 | BC143536 | 141 | 239 | 0.5579 | 0.0489 | 1.6877 | 0.755 | 1.69 | 98 | 6.61 |
| VARS2 | NM_001167733 | 160 | 124 | 1.0000 | 0.4073 | 0.7792 | −0.360 | 1.28 | 36 | 5.15 |
| VARS2 | NM_001167733 | 640 | 585 | 1.0000 | 0.5143 | 0.9138 | −0.130 | 1.09 | 55 | 5.79 |
| VARS2 | NM_001167734 | 63 | 69 | 1.0000 | 0.8839 | 1.0870 | 0.120 | 1.09 | 6 | 2.48 |
| VARS2 | NM_001167734 | 24 | 11 | 1.0000 | 0.3062 | 0.4731 | −1.080 | 2.11 | 13 | 3.73 |
| VARS2 | NM_020442 | 334 | 229 | 0.6523 | 0.0712 | 0.6872 | −0.541 | 1.46 | 105 | 6.71 |
| VARS2 | NM_020442 | 23 | 0 | 0.0138 | 0.0002 | 0.0414 | −4.595 | 24.16 | 23 | 4.53 |
| VPS13A | BC020576 | 47 | 122 | 0.3603 | 0.0209 | 2.5809 | 1.368 | 2.58 | 75 | 6.24 |
| VPS13A | NM_001018037 | 165 | 256 | 0.5661 | 0.0501 | 1.5525 | 0.635 | 1.55 | 91 | 6.51 |
| VPS13A | NM_001018038 | 18 | 53 | 0.7023 | 0.0874 | 2.8067 | 1.489 | 2.81 | 34 | 5.11 |
| VPS13A | NM_015186 | 56 | 87 | 1.0000 | 0.2864 | 1.5529 | 0.635 | 1.55 | 31 | 4.97 |
| VPS13A | NM_033305 | 31 | 0 | 0.0023 | 0.0000 | 0.0313 | −4.999 | 31.97 | 31 | 4.95 |
| VPS29 | AF201936 | 131 | 117 | 1.0000 | 0.7310 | 0.8888 | −0.170 | 1.13 | 15 | 3.88 |
| VPS29 | BC015095 | 216 | 64 | 0.0018 | 0.0000 | 0.3012 | −1.731 | 3.32 | 151 | 7.24 |
| VPS29 | BC017964 | 69 | 106 | 1.0000 | 0.2413 | 1.5358 | 0.619 | 1.54 | 37 | 5.22 |
| VPS29 | NM_016226 | 76 | 1 | 0.0000 | 0.0000 | 0.0259 | −5.273 | 38.67 | 75 | 6.24 |
| VPS29 | NM_057180 | 6 | 26 | 0.6654 | 0.0759 | 3.5882 | 1.843 | 3.59 | 19 | 4.27 |
| VWA8 | NM_001009814 | 35 | 51 | 1.0000 | 0.4194 | 1.4556 | 0.542 | 1.46 | 16 | 4.03 |
| VWA8 | NM_015058 | 3 | 8 | 1.0000 | 0.5496 | 2.0393 | 1.028 | 2.04 | 5 | 2.19 |
| WSB1 | AK294516 | 11 | 38 | 0.5826 | 0.0540 | 3.1112 | 1.637 | 3.11 | 26 | 4.71 |
| WSB1 | AK300262 | 117 | 0 | 0.0000 | 0.0000 | 0.0085 | −6.877 | 117.58 | 117 | 6.87 |
| WSB1 | AK307114 | 75 | 166 | 0.3050 | 0.0153 | 2.2074 | 1.142 | 2.21 | 92 | 6.52 |
| WSB1 | BC048007 | 116 | 134 | 1.0000 | 0.6432 | 1.1503 | 0.202 | 1.15 | 18 | 4.14 |
| WSB1 | NM_015626 | 100 | 0 | 0.0000 | 0.0000 | 0.0099 | −6.656 | 100.82 | 100 | 6.64 |
| WSB1 | NM_134265 | 5 | 11 | 1.0000 | 0.4880 | 1.8052 | 0.852 | 1.81 | 5 | 2.38 |
| XIAP | NM_001167 | 7 | 6 | 1.0000 | 0.8906 | 0.8859 | −0.175 | 1.13 | 1 | −0.20 |
| XIAP | NM_001204401 | 0 | 1 | 1.0000 | 0.4588 | 1.8808 | 0.911 | 1.88 | 1 | −0.18 |
| XIAP | NR_037916 | 1 | 2 | 1.0000 | 0.6839 | 1.7981 | 0.846 | 1.80 | 1 | 0.49 |
| XRN2 | AK172858 | 13 | 0 | 0.1114 | 0.0032 | 0.0706 | −3.824 | 14.17 | 13 | 3.72 |
| XRN2 | AK302846 | 3194 | 3037 | 1.0000 | 0.4410 | 0.9506 | −0.073 | 1.05 | 158 | 7.30 |
| XRN2 | AK303312 | 170 | 167 | 1.0000 | 0.9480 | 0.9836 | −0.024 | 1.02 | 3 | 1.49 |
| XRN2 | NM_012255 | 1465 | 2615 | 0.0000 | 0.0000 | 1.7849 | 0.836 | 1.78 | 1151 | 10.17 |
| YPEL5 | AK307099 | 157 | 116 | 1.0000 | 0.4100 | 0.7398 | −0.435 | 1.35 | 41 | 5.36 |
| YPEL5 | BC047237 | 2415 | 1132 | 0.0000 | 0.0000 | 0.4688 | −1.093 | 2.13 | 1283 | 10.33 |
| YPEL5 | NM_001127399 | 295 | 460 | 0.2561 | 0.0115 | 1.5555 | 0.637 | 1.56 | 165 | 7.36 |
| YPEL5 | NM_001127400 | 3 | 5 | 1.0000 | 0.6544 | 1.6207 | 0.697 | 1.62 | 2 | 1.17 |
| YPEL5 | NM_001127401 | 16 | 8 | 1.0000 | 0.3581 | 0.4981 | −1.006 | 2.01 | 9 | 3.13 |
| YPEL5 | NM_016061 | 26 | 28 | 1.0000 | 0.9270 | 1.0663 | 0.093 | 1.07 | 2 | 0.83 |
| ZAK | AF465843 | 34 | 19 | 1.0000 | 0.3232 | 0.5676 | −0.817 | 1.76 | 15 | 3.93 |
| ZAK | AK298634 | 0 | 0 | 9999 | 9999 | 1.0000 | 0.000 | 1.00 | 0 | 0 |
| ZAK | NM_016653 | 12 | 16 | 1.0000 | 0.7920 | 1.3493 | 0.432 | 1.35 | 4 | 2.17 |
| ZAK | NM_133646 | 1985 | 2095 | 1.0000 | 0.4916 | 1.0555 | 0.078 | 1.06 | 110 | 6.78 |
| ZC3H18 | AK056632 | 92 | 13 | 0.0095 | 0.0001 | 0.1478 | −2.759 | 6.77 | 79 | 6.31 |
| ZC3H18 | AK056632 | 4 | 9 | 1.0000 | 0.4966 | 1.8777 | 0.909 | 1.88 | 4 | 2.15 |
| ZC3H18 | AK300254 | 69 | 40 | 1.0000 | 0.2757 | 0.5852 | −0.773 | 1.71 | 29 | 4.86 |
| ZC3H18 | AK302716 | 8 | 2 | 1.0000 | 0.1903 | 0.2834 | −1.819 | 3.53 | 7 | 2.76 |
| ZC3H18 | AX748097 | 19 | 12 | 1.0000 | 0.6049 | 0.6874 | −0.541 | 1.45 | 6 | 2.62 |
| ZC3H18 | CU690696 | 14 | 4 | 1.0000 | 0.1881 | 0.3193 | −1.647 | 3.13 | 10 | 3.32 |
| ZC3H18 | NM_144604 | 0 | 0 | 9999 | 9999 | 1.0000 | 0.000 | 1.00 | 0 | 0 |
| ZFAND5 | AK290849 | 0 | 5 | 0.6345 | 0.0668 | 6.0516 | 2.597 | 6.05 | 5 | 2.34 |
| ZFAND5 | AK307376 | 227 | 224 | 1.0000 | 0.9271 | 0.9865 | −0.020 | 1.01 | 3 | 1.63 |
| ZFAND5 | NM_001102420 | 9 | 0 | 0.2467 | 0.0108 | 0.1037 | −3.269 | 9.64 | 9 | 3.11 |
| ZFAND5 | NM_001102421 | 506 | 92 | 0.0000 | 0.0000 | 0.1833 | −2.447 | 5.45 | 414 | 8.69 |
| ZFAND5 | NM_001278243 | 2034 | 2442 | 0.3278 | 0.0176 | 1.2004 | 0.264 | 1.20 | 408 | 8.67 |
| ZFAND5 | NM_001278244 | 159 | 168 | 1.0000 | 0.8826 | 1.0594 | 0.083 | 1.06 | 9 | 3.25 |
| ZFAND5 | NM_001278245 | 5 | 21 | 0.9595 | 0.1678 | 3.4115 | 1.770 | 3.41 | 15 | 3.93 |
| ZFAND5 | NM_006007 | 110 | 0 | 0.0000 | 0.0000 | 0.0090 | −6.792 | 110.81 | 110 | 6.78 |
| ZMIZ1 | AB033050 | 0 | 4 | 0.6897 | 0.0842 | 5.0146 | 2.326 | 5.01 | 4 | 2.01 |
| ZMIZ1 | AK024490 | 108 | 11 | 0.0003 | 0.0000 | 0.1083 | −3.207 | 9.23 | 97 | 6.61 |
| ZMIZ1 | AK025812 | 708 | 906 | 0.3886 | 0.0244 | 1.2787 | 0.355 | 1.28 | 198 | 7.63 |
| ZMIZ1 | AK299728 | 0 | 11 | 0.2843 | 0.0137 | 11.8248 | 3.564 | 11.82 | 11 | 3.44 |
| ZMIZ1 | NM_020338 | 1502 | 1775 | 0.5623 | 0.0495 | 1.1815 | 0.241 | 1.18 | 273 | 8.09 |
| ZMYM2 | AF012126 | 194 | 32 | 0.0000 | 0.0000 | 0.1707 | −2.550 | 5.86 | 161 | 7.33 |
| ZMYM2 | AK302917 | 189 | 0 | 0.0000 | 0.0000 | 0.0053 | −7.570 | 189.97 | 189 | 7.56 |
| ZMYM2 | AK310505 | 45 | 30 | 1.0000 | 0.3917 | 0.6613 | −0.597 | 1.51 | 16 | 3.97 |
| ZMYM2 | AL136621 | 4 | 0 | 0.5166 | 0.0422 | 0.2103 | −2.249 | 4.75 | 4 | 1.91 |
| ZMYM2 | BX648905 | 367 | 631 | 0.0081 | 0.0001 | 1.7195 | 0.782 | 1.72 | 265 | 8.05 |
| ZMYM2 | NM_001190964 | 4 | 0 | 0.4926 | 0.0381 | 0.1973 | −2.341 | 5.07 | 4 | 2.02 |
| ZMYM2 | NM_001190965 | 11 | 11 | 1.0000 | 1.0000 | 1.0698 | 0.097 | 1.07 | 1 | −0.31 |

TABLE 9-continued

RNA Abundance Modulation

| Gene | Trx_ID | ave DMSO | ave Cpd | padj (q val, FDR) | ttest (p val) | FC (x + 1) | $L_2$FC (x + 1) | amp FC (x + 1) | abs (Cpd − DMSO) | $L_2$abs (Cpd − DMSO) |
|---|---|---|---|---|---|---|---|---|---|---|
| ZMYM2 | NM_003453 | 75 | 1 | 0.0000 | 0.0000 | 0.0220 | −5.506 | 45.43 | 74 | 6.21 |
| ZMYM2 | NM_197968 | 56 | 54 | 1.0000 | 0.9513 | 0.9649 | −0.052 | 1.04 | 2 | 1.01 |
| ZNF219 | NM_001101672 | 3 | 1 | 1.0000 | 0.5591 | 0.6276 | −0.672 | 1.59 | 1 | 0.50 |
| ZNF219 | NM_001102454 | 9 | 2 | 1.0000 | 0.2814 | 0.3298 | −1.600 | 3.03 | 6 | 2.69 |
| ZNF219 | NM_016423 | 0 | 0 | 1.0000 | 1.0000 | 1.3608 | 0.444 | 1.36 | 0 | −1.47 |
| ZNF227 | AK299266 | 626 | 501 | 0.9361 | 0.1601 | 0.8015 | −0.319 | 1.25 | 124 | 6.96 |
| ZNF227 | AK300576 | 0 | 155 | 0.0000 | 0.0000 | 155.9151 | 7.285 | 155.92 | 155 | 7.28 |
| ZNF227 | AK316048 | 15 | 28 | 1.0000 | 0.4569 | 1.8463 | 0.885 | 1.85 | 13 | 3.72 |
| ZNF227 | AL833012 | 826 | 242 | 0.0000 | 0.0000 | 0.2935 | −1.769 | 3.41 | 585 | 9.19 |
| ZNF227 | AX721152 | 88 | 111 | 1.0000 | 0.4990 | 1.2597 | 0.333 | 1.26 | 23 | 4.53 |
| ZNF227 | AX747434 | 1842 | 1800 | 1.0000 | 0.6619 | 0.9774 | −0.033 | 1.02 | 42 | 5.38 |
| ZNF227 | NM_182490 | 82 | 86 | 1.0000 | 0.9115 | 1.0435 | 0.061 | 1.04 | 4 | 1.85 |
| ZNF24 | AF542097 | 83 | 75 | 1.0000 | 0.7817 | 0.9056 | −0.143 | 1.10 | 8 | 2.99 |
| ZNF24 | BC016801 | 17996 | 18144 | 1.0000 | 0.8071 | 1.0082 | 0.012 | 1.01 | 148 | 7.21 |
| ZNF24 | NM_006965 | 39 | 24 | 1.0000 | 0.3418 | 0.6094 | −0.715 | 1.64 | 16 | 3.98 |
| ZNF37A | NM_001007094 | 233 | 22 | 0.0000 | 0.0000 | 0.0994 | −3.330 | 10.06 | 210 | 7.72 |
| ZNF37A | NM_001178101 | 640 | 878 | 0.2178 | 0.0087 | 1.3724 | 0.457 | 1.37 | 239 | 7.90 |
| ZNF37A | NM_003421 | 4 | 9 | 1.0000 | 0.4746 | 2.0047 | 1.003 | 2.00 | 5 | 2.26 |
| ZNF37BP | AX721116 | 875 | 436 | 0.0001 | 0.0000 | 0.4988 | −1.004 | 2.00 | 439 | 8.78 |
| ZNF37BP | BC045697 | 243 | 315 | 0.9035 | 0.1479 | 1.2914 | 0.369 | 1.29 | 71 | 6.15 |
| ZNF37BP | NR_026777 | 1 | 5 | 1.0000 | 0.4236 | 2.4034 | 1.265 | 2.40 | 3 | 1.74 |
| ZNF395 | AK002050 | 6 | 9 | 1.0000 | 0.7900 | 1.3375 | 0.420 | 1.34 | 2 | 1.28 |
| ZNF395 | AK098243 | 56 | 67 | 1.0000 | 0.7063 | 1.2072 | 0.272 | 1.21 | 12 | 3.55 |
| ZNF395 | BC001237 | 1722 | 1959 | 1.0000 | 0.2029 | 1.1376 | 0.186 | 1.14 | 237 | 7.89 |
| ZNF395 | NM_018660 | 48 | 57 | 1.0000 | 0.7700 | 1.1762 | 0.234 | 1.18 | 9 | 3.11 |
| ZNF652 | BC034987 | 1962 | 1376 | 0.0058 | 0.0001 | 0.7014 | −0.512 | 1.43 | 586 | 9.20 |
| ZNF652 | NM_001145365 | 111 | 127 | 1.0000 | 0.7475 | 1.1486 | 0.200 | 1.15 | 17 | 4.05 |
| ZNF652 | NM_014897 | 18 | 21 | 1.0000 | 0.7175 | 1.1680 | 0.224 | 1.17 | 3 | 1.67 |
| ZNF674 | AK308986 | 1137 | 757 | 0.0088 | 0.0001 | 0.6657 | −0.587 | 1.50 | 380 | 8.57 |
| ZNF674 | NM_001039891 | 355 | 1020 | 0.0000 | 0.0000 | 2.8690 | 1.521 | 2.87 | 665 | 9.38 |
| ZNF674 | NM_001146291 | 5470 | 5094 | 1.0000 | 0.2534 | 0.9313 | −0.103 | 1.07 | 376 | 8.55 |
| ZNF674 | NM_001190417 | 12 | 19 | 1.0000 | 0.5291 | 1.6204 | 0.696 | 1.62 | 8 | 2.96 |
| ZNF74 | NM_001256523 | 4591 | 3605 | 0.0095 | 0.0001 | 0.7853 | −0.349 | 1.27 | 986 | 9.95 |
| ZNF74 | NM_001256524 | 4304 | 8747 | 0.0000 | 0.0000 | 2.0321 | 1.023 | 2.03 | 4443 | 12.12 |
| ZNF74 | NM_001256525 | 15873 | 13379 | 0.0751 | 0.0019 | 0.8429 | −0.247 | 1.19 | 2494 | 11.28 |
| ZNF74 | NM_003426 | 2 | 0 | 0.6345 | 0.0671 | 0.3158 | −1.663 | 3.17 | 2 | 1.12 |
| ZNF74 | NR_046282 | 78 | 15 | 0.0994 | 0.0028 | 0.1979 | −2.337 | 5.05 | 64 | 5.99 |
| ZNF778 | BC125192 | 185 | 188 | 1.0000 | 1.0000 | 1.0166 | 0.024 | 1.02 | 3 | 1.62 |
| ZNF778 | NM_001201407 | 0 | 4 | 0.6476 | 0.0705 | 5.1105 | 2.353 | 5.11 | 4 | 2.04 |
| ZNF778 | NM_182531 | 2 | 0 | 0.6759 | 0.0808 | 0.3048 | −1.714 | 3.28 | 2 | 1.19 |
| ZNF778 | NR_037705 | 1 | 3 | 1.0000 | 0.5352 | 1.8886 | 0.917 | 1.89 | 2 | 0.78 |

TABLE 10

RNA Abundance Modulation

| Gene | Trx_ID | ave DMSO | ave Cpd | padj (q val, FDR) | ttest (p val) | FC (x + 1) | $L_2$FC (x + 1) | amp FC (x + 1) | abs (Cpd− DMSO) | $L_2$abs (Cpd− DMSO) |
|---|---|---|---|---|---|---|---|---|---|---|
| ABCB7 | NM_001271696 | 266 | 109 | 0.0303 | 0.0010 | 0.4098 | −1.287 | 2.44 | 158 | 7.30 |
| ABCB7 | NM_001271697 | 0 | 0 | 9999 | 9999 | 1.0000 | 0.000 | 1.00 | 0 | 0 |
| ABCB7 | NM_001271698 | 6 | 0 | 0.2687 | 0.0210 | 0.1434 | −2.802 | 6.97 | 6 | 2.58 |
| ABCB7 | NM_001271699 | 0 | 1 | 1.0000 | 0.6737 | 1.7648 | 0.820 | 1.76 | 1 | −0.39 |
| ABCB7 | NM_004299 | 94 | 276 | 0.0051 | 0.0001 | 2.9285 | 1.550 | 2.93 | 183 | 7.51 |
| ABHD10 | NM_001272069 | 26 | 725 | 0.0000 | 0.0000 | 26.6095 | 4.734 | 26.61 | 698 | 9.45 |
| ABHD10 | NM_018394 | 765 | 277 | 0.0000 | 0.0000 | 0.3630 | −1.462 | 2.75 | 488 | 8.93 |
| ABHD10 | NR_073570 | 19 | 30 | 1.0000 | 0.4844 | 1.6028 | 0.681 | 1.60 | 12 | 3.56 |
| ABHD10 | NR_073571 | 18 | 20 | 1.0000 | 0.9287 | 1.1414 | 0.191 | 1.14 | 3 | 1.40 |
| ABLIM3 | AM393559 | 99 | 349 | 0.0001 | 0.0000 | 3.4996 | 1.807 | 3.50 | 250 | 7.96 |
| ABLIM3 | AM393658 | 671 | 436 | 0.0712 | 0.0030 | 0.6499 | −0.622 | 1.54 | 235 | 7.88 |
| ABLIM3 | BC001665 | 170 | 124 | 1.0000 | 0.2938 | 0.7310 | −0.452 | 1.37 | 46 | 5.53 |
| ABLIM3 | BC014463 | 54 | 22 | 0.6887 | 0.1302 | 0.4282 | −1.224 | 2.34 | 31 | 4.97 |
| ABLIM3 | NM_014945 | 238 | 129 | 0.2471 | 0.0183 | 0.5432 | −0.881 | 1.84 | 109 | 6.77 |
| ACACA | AB209325 | 52 | 0 | 0.0000 | 0.0000 | 0.0189 | −5.722 | 52.79 | 52 | 5.69 |
| ACACA | AJ564444 | 1 | 0 | 0.9218 | 0.2323 | 0.5154 | −0.956 | 1.94 | 1 | −0.09 |
| ACACA | AK295586 | 54 | 24 | 0.7838 | 0.1698 | 0.4599 | −1.121 | 2.17 | 30 | 4.88 |
| ACACA | AK295735 | 12 | 37 | 0.6325 | 0.1103 | 2.9346 | 1.553 | 2.93 | 25 | 4.65 |
| ACACA | AK308905 | 18 | 15 | 1.0000 | 0.8727 | 0.8593 | −0.219 | 1.16 | 3 | 1.42 |
| ACACA | AK309084 | 13 | 9 | 1.0000 | 0.7999 | 0.7092 | −0.496 | 1.41 | 4 | 2.01 |
| ACACA | AY315622 | 2 | 4 | 1.0000 | 0.6118 | 1.8355 | 0.876 | 1.84 | 2 | 1.24 |

TABLE 10-continued

RNA Abundance Modulation

| Gene | Trx_ID | ave DMSO | ave Cpd | padj (q val, FDR) | ttest (p val) | FC (x + 1) | L₂FC (x + 1) | amp FC (x + 1) | abs (Cpd-DMSO) | L₂abs (Cpd-DMSO) |
|---|---|---|---|---|---|---|---|---|---|---|
| ACACA | NM_198834 | 1045 | 1089 | 1.0000 | 0.7296 | 1.0426 | 0.060 | 1.04 | 45 | 5.48 |
| ACACA | NM_198836 | 1730 | 1900 | 1.0000 | 0.3605 | 1.0981 | 0.135 | 1.10 | 170 | 7.41 |
| ACACA | NM_198839 | 17 | 22 | 1.0000 | 0.7498 | 1.2712 | 0.346 | 1.27 | 5 | 2.32 |
| ADAM12 | AB384856 | 2673 | 1864 | 0.0016 | 0.0000 | 0.6973 | -0.520 | 1.43 | 810 | 9.66 |
| ADAM12 | AK127856 | 270 | 77 | 0.0011 | 0.0000 | 0.2877 | -1.798 | 3.48 | 193 | 7.59 |
| ADAM12 | AK291629 | 518 | 379 | 0.3935 | 0.0396 | 0.7315 | -0.451 | 1.37 | 139 | 7.12 |
| ADAM12 | NM_003474 | 12100 | 8011 | 0.0000 | 0.0000 | 0.6621 | -0.595 | 1.51 | 4088 | 12.00 |
| ADAM17 | AK289829 | 7 | 6 | 1.0000 | 0.9330 | 0.9677 | -0.047 | 1.03 | 0 | -2.03 |
| ADAM17 | AY422721 | 0 | 0 | 9999 | 9999 | 1.0000 | 0.000 | 1.00 | 0 | 0 |
| ADAM17 | BC062687 | 0 | 1 | 1.0000 | 0.6668 | 1.6070 | 0.684 | 1.61 | 1 | -0.72 |
| ADAM17 | BC146658 | 0 | 0 | 1.0000 | 0.4930 | 0.7623 | -0.391 | 1.31 | 0 | -1.68 |
| ADAM17 | NM_003183 | 1431 | 699 | 0.0000 | 0.0000 | 0.4885 | -1.033 | 2.05 | 732 | 9.52 |
| ADAM17 | U69612 | 0 | 0 | 9999 | 9999 | 1.0000 | 0.000 | 1.00 | 0 | 0 |
| ADAM33 | AF466287 | 95 | 14 | 0.0090 | 0.0002 | 0.1526 | -2.712 | 6.55 | 82 | 6.35 |
| ADAM33 | AK095953 | 34 | 48 | 1.0000 | 0.5346 | 1.4226 | 0.509 | 1.42 | 15 | 3.88 |
| ADAM33 | AK095953 | 4 | 1 | 1.0000 | 0.3517 | 0.3655 | -1.452 | 2.74 | 3 | 1.73 |
| ADAM33 | AK123015 | 32 | 28 | 1.0000 | 0.8278 | 0.8864 | -0.174 | 1.13 | 4 | 1.92 |
| ADAM33 | AK300429 | 5 | 3 | 1.0000 | 0.9025 | 0.7979 | -0.326 | 1.25 | 1 | 0.18 |
| ADAM33 | AK304037 | 15 | 8 | 1.0000 | 0.4570 | 0.5356 | -0.901 | 1.87 | 8 | 2.92 |
| ADAM33 | AL117415 | 0 | 0 | 9999 | 9999 | 1.0000 | 0.000 | 1.00 | 0 | 0 |
| ADAM33 | AY223854 | 1 | 1 | 1.0000 | 1.0000 | 1.0836 | 0.116 | 1.08 | 0 | -2.88 |
| ADAM33 | BC062663 | 0 | 1 | 1.0000 | 1.0000 | 1.1550 | 0.208 | 1.15 | 0 | -2.22 |
| ADAM33 | NM_025220 | 177 | 181 | 1.0000 | 0.8192 | 1.0231 | 0.033 | 1.02 | 4 | 2.04 |
| ADAM33 | NM_153202 | 5 | 1 | 0.8789 | 0.2068 | 0.2792 | -1.841 | 3.58 | 4 | 2.04 |
| AGK | AK299131 | 0 | 2 | 0.7358 | 0.1484 | 2.8211 | 1.496 | 2.82 | 2 | 0.86 |
| AGK | BC009775 | 2 | 1 | 1.0000 | 0.5362 | 0.6582 | -0.603 | 1.52 | 1 | -0.19 |
| AGK | NM_018238 | 685 | 273 | 0.0000 | 0.0000 | 0.3992 | -1.325 | 2.50 | 412 | 8.69 |
| AGPS | AK296239 | 354 | 246 | 0.6092 | 0.1037 | 0.6959 | -0.523 | 1.44 | 108 | 6.75 |
| AGPS | NM_003659 | 1958 | 653 | 0.0000 | 0.0000 | 0.3339 | -1.583 | 3.00 | 1305 | 10.35 |
| AHCYL2 | NM_001130720 | 250 | 383 | 0.3500 | 0.0321 | 1.5343 | 0.618 | 1.53 | 134 | 7.06 |
| AHCYL2 | NM_001130722 | 37 | 75 | 0.7337 | 0.1461 | 1.9703 | 0.978 | 1.97 | 37 | 5.22 |
| AHCYL2 | NM_015328 | 116 | 0 | 0.0000 | 0.0000 | 0.0086 | -6.866 | 116.64 | 116 | 6.85 |
| AHDC1 | BC042058 | 115 | 151 | 1.0000 | 0.4117 | 1.3083 | 0.388 | 1.31 | 36 | 5.17 |
| AHDC1 | BC064935 | 10 | 19 | 1.0000 | 0.4349 | 1.8866 | 0.916 | 1.89 | 9 | 3.25 |
| AHDC1 | CCDS30652 | 126 | 18 | 0.0012 | 0.0000 | 0.1457 | -2.779 | 6.86 | 108 | 6.76 |
| AHDC1 | NM_001029882 | 504 | 562 | 1.0000 | 0.4430 | 1.1147 | 0.157 | 1.11 | 58 | 5.86 |
| AHRR | AK090508 | 160 | 137 | 1.0000 | 0.6402 | 0.8588 | -0.220 | 1.16 | 23 | 4.50 |
| AHRR | AK127977 | 5 | 10 | 1.0000 | 0.5961 | 1.6592 | 0.730 | 1.66 | 4 | 2.06 |
| AHRR | AK314472 | 110 | 0 | 0.0000 | 0.0000 | 0.0090 | -6.799 | 111.33 | 110 | 6.79 |
| AHRR | BC035358 | 0 | 0 | 9999 | 9999 | 1.0000 | 0.000 | 1.00 | 0 | 0 |
| AHRR | BC121048 | 109 | 44 | 0.2687 | 0.0211 | 0.4132 | -1.275 | 2.42 | 64 | 6.01 |
| AHRR | NM_001242412 | 712 | 662 | 1.0000 | 0.6696 | 0.9304 | -0.104 | 1.07 | 50 | 5.63 |
| AHRR | NM_020731 | 0 | 8 | 0.2643 | 0.0204 | 9.3343 | 3.223 | 9.33 | 8 | 3.06 |
| AK021888 | AK021888 | 311 | 68 | 0.0000 | 0.0000 | 0.2211 | -2.177 | 4.52 | 243 | 7.92 |
| AK310472 | AK310472 | 171 | 17 | 0.0000 | 0.0000 | 0.1056 | -3.244 | 9.47 | 154 | 7.26 |
| AKAP1 | AK292416 | 190 | 0 | 0.0000 | 0.0000 | 0.0052 | -7.576 | 190.85 | 190 | 7.57 |
| AKAP1 | NM_001242902 | 46 | 40 | 1.0000 | 0.7878 | 0.8852 | -0.176 | 1.13 | 5 | 2.42 |
| AKAP1 | NM_001242903 | 4 | 0 | 0.3999 | 0.0415 | 0.2096 | -2.255 | 4.77 | 4 | 1.92 |
| AKAP1 | NM_003488 | 369 | 643 | 0.0068 | 0.0002 | 1.7420 | 0.801 | 1.74 | 274 | 8.10 |
| AKAP1 | U34074 | 4 | 2 | 1.0000 | 0.6854 | 0.6740 | -0.569 | 1.48 | 2 | 0.73 |
| AKAP9 | AF026245 | 11 | 1 | 0.6131 | 0.1049 | 0.1910 | -2.389 | 5.24 | 9 | 3.23 |
| AKAP9 | AF083037 | 75 | 20 | 0.1025 | 0.0049 | 0.2740 | -1.868 | 3.65 | 55 | 5.79 |
| AKAP9 | AF091711 | 57 | 55 | 1.0000 | 0.9027 | 0.9643 | -0.052 | 1.04 | 2 | 1.04 |
| AKAP9 | AK000270 | 3 | 2 | 1.0000 | 0.9384 | 0.8935 | -0.163 | 1.12 | 0 | -1.30 |
| AKAP9 | AK026444 | 9 | 6 | 1.0000 | 0.8162 | 0.7558 | -0.404 | 1.32 | 2 | 1.24 |
| AKAP9 | BC015533 | 0 | 0 | 9999 | 9999 | 1.0000 | 0.000 | 1.00 | 0 | 0 |
| AKAP9 | NM_005751 | 629 | 295 | 0.0007 | 0.0000 | 0.4705 | -1.088 | 2.13 | 333 | 8.38 |
| AKAP9 | NM_147185 | 0 | 296 | 0.0000 | 0.0000 | 296.9704 | 8.214 | 296.97 | 296 | 8.21 |
| AKNA | AB075848 | 41 | 48 | 1.0000 | 0.7799 | 1.1697 | 0.226 | 1.17 | 7 | 2.83 |
| AKNA | AK126136 | 4 | 0 | 0.4212 | 0.0452 | 0.1926 | -2.377 | 5.19 | 4 | 2.07 |
| AKNA | AK160382 | 128 | 110 | 1.0000 | 0.5874 | 0.8642 | -0.211 | 1.16 | 17 | 4.13 |
| AKNA | AY703040 | 76 | 21 | 0.2237 | 0.0156 | 0.2853 | -1.809 | 3.50 | 55 | 5.78 |
| AKNA | AY703043 | 119 | 0 | 0.0000 | 0.0000 | 0.0083 | -6.908 | 120.09 | 119 | 6.90 |
| AKNA | AY703044 | 16 | 0 | 0.0460 | 0.0017 | 0.0575 | -4.120 | 17.39 | 16 | 4.03 |
| AKNA | AY703045 | 0 | 3 | 0.6461 | 0.1156 | 4.4417 | 2.151 | 4.44 | 3 | 1.78 |
| AKNA | NM_030767 | 108 | 192 | 0.4053 | 0.0424 | 1.7717 | 0.825 | 1.77 | 84 | 6.40 |
| AMPD2 | AK302939 | 77 | 77 | 1.0000 | 0.9592 | 1.0019 | 0.003 | 1.00 | 0 | -2.75 |
| AMPD2 | AK308907 | 26 | 21 | 1.0000 | 0.8920 | 0.8294 | -0.270 | 1.21 | 5 | 2.19 |
| AMPD2 | BC030217 | 68 | 50 | 1.0000 | 0.5539 | 0.7350 | -0.444 | 1.36 | 18 | 4.19 |
| AMPD2 | NM_001257360 | 43 | 5 | 0.0437 | 0.0016 | 0.1263 | -2.985 | 7.92 | 39 | 5.27 |
| AMPD2 | NM_001257361 | 448 | 223 | 0.0059 | 0.0001 | 0.4985 | -1.004 | 2.01 | 225 | 7.81 |
| AMPD2 | NM_004037 | 205 | 253 | 1.0000 | 0.3083 | 1.2326 | 0.302 | 1.23 | 48 | 5.58 |
| AMPD2 | NM_139156 | 899 | 893 | 1.0000 | 0.9861 | 0.9936 | -0.009 | 1.01 | 6 | 2.52 |
| AMPD2 | NM_203404 | 49 | 30 | 1.0000 | 0.4703 | 0.6312 | -0.664 | 1.58 | 18 | 4.20 |

TABLE 10-continued

RNA Abundance Modulation

| Gene | Trx_ID | ave DMSO | ave Cpd | padj (q val, FDR) | ttest (p val) | FC (x + 1) | L₂FC (x + 1) | amp FC (x + 1) | abs (Cpd-DMSO) | L₂abs (Cpd-DMSO) |
|---|---|---|---|---|---|---|---|---|---|---|
| ANKRD17 | AK299046 | 77 | 100 | 1.0000 | 0.5556 | 1.2923 | 0.370 | 1.29 | 23 | 4.51 |
| ANKRD17 | BX648035 | 1821 | 2040 | 0.8998 | 0.2161 | 1.1203 | 0.164 | 1.12 | 219 | 7.78 |
| ANKRD17 | NM_032217 | 251 | 0 | 0.0000 | 0.0000 | 0.0040 | −7.978 | 252.15 | 251 | 7.97 |
| ANKRD17 | NM_198889 | 1279 | 1675 | 0.1820 | 0.0113 | 1.3095 | 0.389 | 1.31 | 396 | 8.63 |
| ANKS6 | AK094247 | 9 | 23 | 0.9405 | 0.2433 | 2.4875 | 1.315 | 2.49 | 14 | 3.86 |
| ANKS6 | AK126614 | 5 | 6 | 1.0000 | 0.8477 | 1.1456 | 0.196 | 1.15 | 1 | −0.18 |
| ANKS6 | AK127702 | 44 | 23 | 1.0000 | 0.3284 | 0.5422 | −0.883 | 1.84 | 21 | 4.37 |
| ANKS6 | CR749472 | 119 | 11 | 0.0002 | 0.0000 | 0.1022 | −3.291 | 9.79 | 108 | 6.76 |
| ANKS6 | NM_173551 | 498 | 616 | 0.6959 | 0.1322 | 1.2369 | 0.307 | 1.24 | 118 | 6.89 |
| ANP32A | NM_006305 | 2377 | 731 | 0.0000 | 0.0000 | 0.3077 | −1.700 | 3.25 | 1647 | 10.69 |
| ANXA11 | AK056107 | 2196 | 1059 | 0.0000 | 0.0000 | 0.4826 | −1.051 | 2.07 | 1137 | 10.15 |
| ANXA11 | AK126287 | 235 | 242 | 1.0000 | 0.9377 | 1.0292 | 0.042 | 1.03 | 7 | 2.78 |
| ANXA11 | AK300509 | 14 | 4 | 0.9736 | 0.2649 | 0.3559 | −1.490 | 2.81 | 9 | 3.24 |
| ANXA11 | AK301047 | 4 | 2 | 1.0000 | 0.5890 | 0.6949 | −0.525 | 1.44 | 1 | 0.53 |
| ANXA11 | NM_001157 | 1495 | 712 | 0.0000 | 0.0000 | 0.4765 | −1.070 | 2.10 | 783 | 9.61 |
| ANXA11 | NM_145868 | 2036 | 1269 | 0.0000 | 0.0000 | 0.6235 | −0.682 | 1.60 | 767 | 9.58 |
| ANXA11 | NM_145869 | 48 | 33 | 1.0000 | 0.3792 | 0.6900 | −0.535 | 1.45 | 15 | 3.93 |
| ANXA6 | NM_001155 | 11010 | 4287 | 0.0000 | 0.0000 | 0.3894 | −1.361 | 2.57 | 6723 | 12.71 |
| ANXA6 | NM_001193544 | 16 | 0 | 0.0357 | 0.0012 | 0.0587 | −4.090 | 17.03 | 16 | 4.00 |
| APLP2 | AK308932 | 12 | 14 | 1.0000 | 0.8409 | 1.2300 | 0.299 | 1.23 | 3 | 1.53 |
| APLP2 | L23114 | 4615 | 5066 | 0.8055 | 0.1775 | 1.0978 | 0.135 | 1.10 | 452 | 8.82 |
| APLP2 | NM_001142276 | 4325 | 13306 | 0.0000 | 0.0000 | 3.0763 | 1.621 | 3.08 | 8981 | 13.13 |
| APLP2 | NM_001142277 | 15948 | 6741 | 0.0000 | 0.0000 | 0.4227 | −1.242 | 2.37 | 9207 | 13.17 |
| APLP2 | NM_001142278 | 2 | 2 | 1.0000 | 1.0000 | 1.0662 | 0.093 | 1.07 | 0 | −2.25 |
| APLP2 | NM_001243299 | 79 | 59 | 1.0000 | 0.3777 | 0.7602 | −0.396 | 1.32 | 19 | 4.25 |
| APLP2 | NR_024515 | 185 | 142 | 1.0000 | 0.3786 | 0.7690 | −0.379 | 1.30 | 43 | 5.43 |
| APLP2 | NR_024516 | 0 | 3 | 0.5802 | 0.0937 | 4.3387 | 2.117 | 4.34 | 3 | 1.74 |
| APP | AK295373 | 2 | 0 | 0.5415 | 0.0800 | 0.3042 | −1.717 | 3.29 | 2 | 1.19 |
| APP | BC004369 | 1 | 1 | 1.0000 | 1.0000 | 1.1441 | 0.194 | 1.14 | 0 | −1.84 |
| APP | NM_000484 | 14177 | 14292 | 1.0000 | 0.8669 | 1.0081 | 0.012 | 1.01 | 114 | 6.84 |
| APP | NM_001136129 | 28 | 1 | 0.0388 | 0.0014 | 0.0704 | −3.828 | 14.20 | 27 | 4.77 |
| APP | NM_001136130 | 32 | 89 | 0.4924 | 0.0627 | 2.6929 | 1.429 | 2.69 | 57 | 5.82 |
| APP | NM_001136131 | 223 | 1 | 0.0000 | 0.0000 | 0.0098 | −6.670 | 101.80 | 222 | 7.79 |
| APP | NM_001204301 | 823 | 975 | 0.7943 | 0.1737 | 1.1849 | 0.245 | 1.18 | 152 | 7.25 |
| APP | NM_001204302 | 351 | 401 | 1.0000 | 0.4677 | 1.1423 | 0.192 | 1.14 | 50 | 5.65 |
| APP | NM_001204303 | 12 | 25 | 1.0000 | 0.3269 | 2.0267 | 1.019 | 2.03 | 13 | 3.71 |
| APP | NM_201413 | 6738 | 6518 | 1.0000 | 0.6727 | 0.9673 | −0.048 | 1.03 | 220 | 7.78 |
| APP | NM_201414 | 335 | 564 | 0.0249 | 0.0008 | 1.6794 | 0.748 | 1.68 | 228 | 7.84 |
| APPL2 | AK310377 | 13 | 2 | 0.7687 | 0.1640 | 0.2494 | −2.004 | 4.01 | 10 | 3.37 |
| APPL2 | BC028008 | 0 | 10 | 0.1926 | 0.0123 | 11.1202 | 3.475 | 11.12 | 10 | 3.34 |
| APPL2 | NM_001251904 | 182 | 44 | 0.0016 | 0.0000 | 0.2466 | −2.020 | 4.06 | 138 | 7.11 |
| APPL2 | NM_001251905 | 63 | 247 | 0.0002 | 0.0000 | 3.9000 | 1.963 | 3.90 | 184 | 7.53 |
| APPL2 | NM_018171 | 4100 | 981 | 0.0000 | 0.0000 | 0.2396 | −2.061 | 4.17 | 3118 | 11.61 |
| APTX | AJ565850 | 54 | 59 | 1.0000 | 0.8438 | 1.0933 | 0.129 | 1.09 | 5 | 2.35 |
| APTX | AJ565855 | 0 | 0 | 9999 | 9999 | 1.0000 | 0.000 | 1.00 | 0 | 0 |
| APTX | AY302067 | 0 | 2 | 0.7347 | 0.1468 | 2.7859 | 1.478 | 2.79 | 2 | 0.84 |
| APTX | AY302068 | 3 | 0 | 0.4643 | 0.0555 | 0.2628 | −1.928 | 3.81 | 3 | 1.49 |
| APTX | AY302069 | 0 | 1 | 0.9827 | 0.2720 | 2.1906 | 1.131 | 2.19 | 1 | 0.25 |
| APTX | AY302070 | 0 | 0 | 9999 | 9999 | 1.0000 | 0.000 | 1.00 | 0 | 0 |
| APTX | BC032650 | 105 | 16 | 0.0080 | 0.0002 | 0.1583 | −2.659 | 6.32 | 89 | 6.48 |
| APTX | CCDS47956 | 39 | 27 | 1.0000 | 0.5057 | 0.6956 | −0.524 | 1.44 | 12 | 3.61 |
| APTX | NM_001195248 | 256 | 298 | 1.0000 | 0.4279 | 1.1623 | 0.217 | 1.16 | 42 | 5.38 |
| APTX | NM_001195249 | 11 | 4 | 1.0000 | 0.3918 | 0.4406 | −1.182 | 2.27 | 7 | 2.74 |
| APTX | NM_001195250 | 22 | 14 | 1.0000 | 0.4543 | 0.6496 | −0.622 | 1.54 | 8 | 3.04 |
| APTX | NM_001195251 | 15 | 7 | 1.0000 | 0.4081 | 0.5220 | −0.938 | 1.92 | 8 | 2.93 |
| APTX | NM_001195252 | 3 | 13 | 0.9819 | 0.2694 | 3.2105 | 1.683 | 3.21 | 9 | 3.22 |
| APTX | NM_001195254 | 0 | 31 | 0.0026 | 0.0000 | 31.6596 | 4.985 | 31.66 | 31 | 4.94 |
| APTX | NM_175069 | 39 | 29 | 1.0000 | 0.5603 | 0.7553 | −0.405 | 1.32 | 10 | 3.29 |
| APTX | NM_175073 | 87 | 102 | 1.0000 | 0.7157 | 1.1663 | 0.222 | 1.17 | 15 | 3.88 |
| APTX | NR_036576 | 9 | 21 | 1.0000 | 0.3468 | 2.1234 | 1.086 | 2.12 | 12 | 3.54 |
| APTX | NR_036577 | 53 | 22 | 0.7298 | 0.1447 | 0.4178 | −1.259 | 2.39 | 31 | 4.97 |
| APTX | NR_036578 | 30 | 68 | 0.7140 | 0.1391 | 2.2640 | 1.179 | 2.26 | 39 | 5.28 |
| APTX | NR_036579 | 0 | 18 | 0.0418 | 0.0015 | 19.1114 | 4.256 | 19.11 | 18 | 4.18 |
| ARHGAP22 | AB385228 | 71 | 227 | 0.0033 | 0.0001 | 3.1888 | 1.673 | 3.19 | 157 | 7.29 |
| ARHGAP22 | NM_001256024 | 118 | 164 | 1.0000 | 0.3091 | 1.3875 | 0.472 | 1.39 | 46 | 5.52 |
| ARHGAP22 | NM_001256025 | 2 | 5 | 1.0000 | 0.4112 | 2.2968 | 1.200 | 2.30 | 3 | 1.77 |
| ARHGAP22 | NM_021226 | 226 | 223 | 1.0000 | 1.0000 | 0.9860 | −0.020 | 1.01 | 3 | 1.67 |
| ARHGAP22 | NR_045675 | 13 | 18 | 1.0000 | 0.7715 | 1.3339 | 0.416 | 1.33 | 5 | 2.21 |
| ARHGAP22 | U90908 | 32 | 34 | 1.0000 | 0.9473 | 1.0655 | 0.092 | 1.07 | 2 | 1.09 |
| ARMCX3 | CCDS14489 | 267 | 64 | 0.0001 | 0.0000 | 0.2431 | −2.040 | 4.11 | 203 | 7.67 |
| ARMCX3 | NM_016607 | 477 | 88 | 0.0000 | 0.0000 | 0.1856 | −2.430 | 5.39 | 390 | 8.61 |
| ARMCX3 | NM_177947 | 1417 | 296 | 0.0000 | 0.0000 | 0.2093 | −2.257 | 4.78 | 1121 | 10.13 |
| ARMCX3 | NM_177948 | 56 | 0 | 0.0000 | 0.0000 | 0.0175 | −5.833 | 57.01 | 56 | 5.81 |
| ASAP1 | AB033075 | 749 | 389 | 0.0005 | 0.0000 | 0.5196 | −0.944 | 1.92 | 360 | 8.49 |

TABLE 10-continued

RNA Abundance Modulation

| Gene | Trx_ID | ave DMSO | ave Cpd | padj (q val, FDR) | ttest (p val) | FC (x + 1) | L₂FC (x + 1) | amp FC (x + 1) | abs (Cpd-DMSO) | L₂abs (Cpd-DMSO) |
|---|---|---|---|---|---|---|---|---|---|---|
| ASAP1 | NM_001247996 | 740 | 244 | 0.0000 | 0.0000 | 0.3309 | −1.596 | 3.02 | 496 | 8.95 |
| ASAP1 | NM_018482 | 2798 | 508 | 0.0000 | 0.0000 | 0.1819 | −2.459 | 5.50 | 2290 | 11.16 |
| ASNS | NM_001178075 | 86 | 33 | 0.4677 | 0.0563 | 0.3965 | −1.335 | 2.52 | 52 | 5.71 |
| ASNS | NM_001178076 | 75 | 5 | 0.0018 | 0.0000 | 0.0792 | −3.658 | 12.62 | 70 | 6.12 |
| ASNS | NM_001673 | 7904 | 1510 | 0.0000 | 0.0000 | 0.1912 | −2.387 | 5.23 | 6393 | 12.64 |
| ASNS | NM_133436 | 61 | 39 | 1.0000 | 0.3619 | 0.6552 | −0.610 | 1.53 | 21 | 4.41 |
| ASNS | NM_183356 | 334 | 133 | 0.0024 | 0.0000 | 0.3996 | −1.323 | 2.50 | 201 | 7.65 |
| ASPH | FJ461473 | 2573 | 2897 | 0.6693 | 0.1234 | 1.1262 | 0.171 | 1.13 | 325 | 8.34 |
| ASPH | NM_001164750 | 1938 | 4496 | 0.0000 | 0.0000 | 2.3189 | 1.213 | 2.32 | 2558 | 11.32 |
| ASPH | NM_001164751 | 923 | 1247 | 0.1450 | 0.0081 | 1.3501 | 0.433 | 1.35 | 324 | 8.34 |
| ASPH | NM_001164752 | 714 | 563 | 0.6231 | 0.1075 | 0.7881 | −0.344 | 1.27 | 152 | 7.24 |
| ASPH | NM_001164753 | 0 | 42 | 0.0003 | 0.0000 | 42.9159 | 5.423 | 42.92 | 42 | 5.39 |
| ASPH | NM_001164754 | 168 | 328 | 0.0648 | 0.0026 | 1.9416 | 0.957 | 1.94 | 159 | 7.32 |
| ASPH | NM_001164755 | 5184 | 4772 | 0.9174 | 0.2244 | 0.9207 | −0.119 | 1.09 | 411 | 8.68 |
| ASPH | NM_001164756 | 18 | 22 | 1.0000 | 0.8115 | 1.2248 | 0.293 | 1.22 | 4 | 2.10 |
| ASPH | NM_004318 | 12335 | 9732 | 0.0026 | 0.0000 | 0.7890 | −0.342 | 1.27 | 2603 | 11.35 |
| ASPH | NM_032466 | 0 | 1822 | 0.0000 | 0.0000 | 1823.2737 | 10.832 | 1823.27 | 1822 | 10.83 |
| ASPH | NM_032467 | 12 | 12 | 1.0000 | 0.9533 | 0.9551 | −0.066 | 1.05 | 1 | −0.74 |
| ATG9A | BC065534 | 8 | 7 | 1.0000 | 0.8908 | 0.8754 | −0.192 | 1.14 | 1 | 0.17 |
| ATG9A | NM_001077198 | 2311 | 2454 | 1.0000 | 0.4863 | 1.0616 | 0.086 | 1.06 | 142 | 7.15 |
| ATG9A | NM_024085 | 690 | 328 | 0.0002 | 0.0000 | 0.4754 | −1.073 | 2.10 | 363 | 8.50 |
| ATP2C1 | AB209265 | 45 | 59 | 1.0000 | 0.5643 | 1.3035 | 0.382 | 1.30 | 14 | 3.81 |
| ATP2C1 | NM_001001485 | 185 | 207 | 1.0000 | 0.6888 | 1.1200 | 0.163 | 1.12 | 22 | 4.48 |
| ATP2C1 | NM_001001486 | 2390 | 2288 | 1.0000 | 0.6008 | 0.9574 | −0.063 | 1.04 | 102 | 6.67 |
| ATP2C1 | NM_001001487 | 1171 | 928 | 0.4216 | 0.0458 | 0.7929 | −0.335 | 1.26 | 243 | 7.92 |
| ATP2C1 | NM_001199179 | 382 | 414 | 1.0000 | 0.8570 | 1.0841 | 0.116 | 1.08 | 32 | 5.01 |
| ATP2C1 | NM_001199181 | 0 | 0 | 9999 | 9999 | 1.0000 | 0.000 | 1.00 | 0 | 0 |
| ATP2C1 | NM_001199184 | 1180 | 1132 | 1.0000 | 0.8895 | 0.9597 | −0.059 | 1.04 | 48 | 5.57 |
| ATP2C1 | NM_014382 | 429 | 180 | 0.0004 | 0.0000 | 0.4211 | −1.248 | 2.37 | 249 | 7.96 |
| AURKA | AK301769 | 0 | 4 | 0.5170 | 0.0705 | 5.1671 | 2.369 | 5.17 | 4 | 2.06 |
| AURKA | BC001280 | 288 | 577 | 0.0031 | 0.0001 | 1.9992 | 0.999 | 2.00 | 289 | 8.17 |
| AURKA | NM_003600 | 364 | 410 | 1.0000 | 0.5769 | 1.1253 | 0.170 | 1.13 | 46 | 5.52 |
| AURKA | NM_198433 | 970 | 993 | 1.0000 | 0.9300 | 1.0231 | 0.033 | 1.02 | 22 | 4.49 |
| AURKA | NM_198434 | 553 | 456 | 0.9218 | 0.2279 | 0.8240 | −0.279 | 1.21 | 98 | 6.61 |
| AURKA | NM_198435 | 1058 | 1307 | 0.4530 | 0.0526 | 1.2345 | 0.304 | 1.23 | 248 | 7.96 |
| AURKA | NM_198436 | 523 | 590 | 1.0000 | 0.3915 | 1.1270 | 0.173 | 1.13 | 67 | 6.06 |
| AURKA | NM_198437 | 858 | 1322 | 0.0053 | 0.0001 | 1.5404 | 0.623 | 1.54 | 464 | 8.86 |
| AXIN1 | NM_003502 | 108 | 488 | 0.0000 | 0.0000 | 4.4740 | 2.162 | 4.47 | 379 | 8.57 |
| AXIN1 | NM_181050 | 584 | 174 | 0.0000 | 0.0000 | 0.2982 | −1.745 | 3.35 | 411 | 8.68 |
| B4GALT2 | BC002431 | 0 | 0 | 9999 | 9999 | 1.0000 | 0.000 | 1.00 | 0 | 0 |
| B4GALT2 | NM_001005417 | 1356 | 657 | 0.0000 | 0.0000 | 0.4849 | −1.044 | 2.06 | 699 | 9.45 |
| B4GALT2 | NM_003780 | 579 | 475 | 0.8274 | 0.1861 | 0.8207 | −0.285 | 1.22 | 104 | 6.70 |
| B4GALT2 | NM_030587 | 1222 | 1704 | 0.0064 | 0.0001 | 1.3938 | 0.479 | 1.39 | 482 | 8.91 |
| BACE1 | AF527782 | 3 | 2 | 1.0000 | 0.9383 | 0.9020 | −0.149 | 1.11 | 0 | −1.40 |
| BACE1 | NM_001207048 | 2399 | 3513 | 0.0002 | 0.0000 | 1.4641 | 0.550 | 1.46 | 1114 | 10.12 |
| BACE1 | NM_001207049 | 407 | 11 | 0.0000 | 0.0000 | 0.0297 | −5.073 | 33.67 | 396 | 8.63 |
| BACE1 | NM_012104 | 5788 | 4616 | 0.0216 | 0.0006 | 0.7975 | −0.326 | 1.25 | 1172 | 10.19 |
| BACE1 | NM_138971 | 67 | 33 | 0.7961 | 0.1743 | 0.4972 | −1.008 | 2.01 | 34 | 5.10 |
| BACE1 | NM_138972 | 353 | 994 | 0.0000 | 0.0000 | 2.8104 | 1.491 | 2.81 | 641 | 9.32 |
| BACE1 | NM_138973 | 0 | 9 | 0.2486 | 0.0185 | 9.8020 | 3.293 | 9.80 | 9 | 3.14 |
| BASP1 | NM_001271606 | 198 | 2 | 0.0000 | 0.0000 | 0.0170 | −5.881 | 58.93 | 196 | 7.61 |
| BASP1 | NM_006317 | 4703 | 5010 | 1.0000 | 0.3579 | 1.0653 | 0.091 | 1.07 | 307 | 8.26 |
| BEND6 | BC022988 | 6 | 30 | 0.4300 | 0.0471 | 4.1405 | 2.050 | 4.14 | 23 | 4.55 |
| BEND6 | BC036119 | 299 | 241 | 0.9827 | 0.2716 | 0.8064 | −0.310 | 1.24 | 58 | 5.86 |
| BEND6 | NM_152731 | 388 | 100 | 0.0000 | 0.0000 | 0.2598 | −1.944 | 3.85 | 288 | 8.17 |
| BICD1 | BC136372 | 32 | 20 | 1.0000 | 0.5146 | 0.6295 | −0.668 | 1.59 | 12 | 3.62 |
| BICD1 | NM_001003398 | 506 | 186 | 0.0000 | 0.0000 | 0.3679 | −1.443 | 2.72 | 321 | 8.33 |
| BICD1 | NM_001714 | 100 | 86 | 1.0000 | 0.8463 | 0.8587 | −0.220 | 1.16 | 14 | 3.83 |
| BICD1 | U90030 | 64 | 20 | 0.3740 | 0.0361 | 0.3215 | −1.637 | 3.11 | 44 | 5.47 |
| BIN1 | AF068916 | 0 | 6 | 0.3963 | 0.0400 | 7.0703 | 2.822 | 7.07 | 6 | 2.60 |
| BIN1 | AK301153 | 33 | 46 | 1.0000 | 0.6047 | 1.3545 | 0.438 | 1.35 | 12 | 3.61 |
| BIN1 | NM_004305 | 16 | 7 | 1.0000 | 0.4038 | 0.4510 | −1.149 | 2.22 | 10 | 3.26 |
| BIN1 | NM_139343 | 0 | 0 | 9999 | 9999 | 1.0000 | 0.000 | 1.00 | 0 | 0 |
| BIN1 | NM_139346 | 0 | 5 | 0.5506 | 0.0822 | 5.5890 | 2.483 | 5.59 | 5 | 2.20 |
| BIN1 | NM_139347 | 0 | 0 | 9999 | 9999 | 1.0000 | 0.000 | 1.00 | 0 | 0 |
| BIN1 | NM_139348 | 377 | 340 | 1.0000 | 0.5608 | 0.9020 | −0.149 | 1.11 | 37 | 5.21 |
| BIN1 | NM_139349 | 3 | 3 | 1.0000 | 1.0000 | 1.0386 | 0.055 | 1.04 | 0 | −2.76 |
| BIN1 | NM_139350 | 193 | 204 | 1.0000 | 0.8229 | 1.0600 | 0.084 | 1.06 | 12 | 3.54 |
| BIN1 | NM_139351 | 63 | 1 | 0.0000 | 0.0000 | 0.0277 | −5.174 | 36.10 | 62 | 5.95 |
| BRD2 | AK056504 | 1155 | 1054 | 1.0000 | 0.4133 | 0.9123 | −0.132 | 1.10 | 101 | 6.66 |
| BRD2 | AK309797 | 230 | 238 | 1.0000 | 0.8771 | 1.0336 | 0.048 | 1.03 | 8 | 2.96 |
| BRD2 | NM_001199455 | 280 | 254 | 1.0000 | 0.5948 | 0.9061 | −0.142 | 1.10 | 26 | 4.72 |
| BRD2 | NM_001199455 | 0 | 0 | 9999 | 9999 | 1.0000 | 0.000 | 1.00 | 0 | 0 |
| BRD2 | NM_001199456 | 4152 | 4247 | 1.0000 | 0.7603 | 1.0228 | 0.033 | 1.02 | 95 | 6.56 |

TABLE 10-continued

RNA Abundance Modulation

| Gene | Trx_ID | ave DMSO | ave Cpd | padj (q val, FDR) | ttest (p val) | FC (x + 1) | L₂FC (x + 1) | amp FC (x + 1) | abs (Cpd-DMSO) | L₂abs (Cpd-DMSO) |
|---|---|---|---|---|---|---|---|---|---|---|
| BRD2 | NM_005104 | 49 | 0 | 0.0000 | 0.0000 | 0.0198 | −5.656 | 50.43 | 49 | 5.63 |
| BRD2 | NM_005104 | 0 | 30 | 0.0042 | 0.0001 | 31.0960 | 4.959 | 31.10 | 30 | 4.91 |
| BRD2 | NM_005104 | 75 | 70 | 1.0000 | 0.9316 | 0.9417 | −0.087 | 1.06 | 4 | 2.14 |
| BRD2 | NM_005104 | 0 | 0 | 9999 | 9999 | 1.0000 | 0.000 | 1.00 | 0 | 0 |
| BRD2 | NR_037625 | 451 | 219 | 0.0069 | 0.0002 | 0.4866 | −1.039 | 2.05 | 232 | 7.86 |
| BRD2 | NR_037625 | 54 | 195 | 0.0083 | 0.0002 | 3.5383 | 1.823 | 3.54 | 140 | 7.13 |
| BRD2 | NR_037625 | 157 | 200 | 1.0000 | 0.3183 | 1.2720 | 0.347 | 1.27 | 43 | 5.42 |
| BRD2 | NR_037625 | 23 | 14 | 1.0000 | 0.5038 | 0.6344 | −0.656 | 1.58 | 9 | 3.11 |
| BRD2 | NR_037625 | 0 | 0 | 9999 | 9999 | 1.0000 | 0.000 | 1.00 | 0 | 0 |
| BRPF1 | AK293865 | 108 | 172 | 0.6254 | 0.1082 | 1.5841 | 0.664 | 1.58 | 64 | 6.00 |
| BRPF1 | AL713696 | 339 | 306 | 1.0000 | 0.5643 | 0.9028 | −0.148 | 1.11 | 33 | 5.05 |
| BRPF1 | NM_001003694 | 224 | 288 | 0.8432 | 0.1924 | 1.2851 | 0.362 | 1.29 | 64 | 6.01 |
| BRPF1 | NM_004634 | 84 | 0 | 0.0000 | 0.0000 | 0.0117 | −6.418 | 85.48 | 84 | 6.40 |
| BTBD10 | AK294768 | 1 | 0 | 0.9601 | 0.2573 | 0.4665 | −1.100 | 2.14 | 1 | 0.19 |
| BTBD10 | AK298226 | 700 | 429 | 0.0256 | 0.0008 | 0.6134 | −0.705 | 1.63 | 271 | 8.08 |
| BTBD10 | AK310935 | 9 | 1 | 0.8120 | 0.1805 | 0.2548 | −1.972 | 3.92 | 7 | 2.86 |
| BTBD10 | AK316163 | 2 | 0 | 0.5018 | 0.0664 | 0.3142 | −1.670 | 3.18 | 2 | 1.13 |
| BTBD10 | NM_032320 | 696 | 341 | 0.0003 | 0.0000 | 0.4906 | −1.027 | 2.04 | 355 | 8.47 |
| C11orf30 | AK125114 | 53 | 6 | 0.0726 | 0.0031 | 0.1375 | −2.862 | 7.27 | 46 | 5.53 |
| C11orf30 | AK126030 | 42 | 17 | 0.8756 | 0.2054 | 0.4243 | −1.237 | 2.36 | 25 | 4.62 |
| C11orf30 | AK304043 | 19 | 4 | 0.6232 | 0.1076 | 0.2456 | −2.025 | 4.07 | 15 | 3.90 |
| C11orf30 | AK304043 | 63 | 40 | 1.0000 | 0.3574 | 0.6384 | −0.648 | 1.57 | 23 | 4.52 |
| C11orf30 | AK309621 | 2 | 0 | 0.5390 | 0.0772 | 0.3248 | −1.622 | 3.08 | 2 | 1.06 |
| C11orf30 | AY070433 | 2 | 2 | 1.0000 | 0.9026 | 0.8705 | −0.200 | 1.15 | 0 | −1.41 |
| C11orf30 | BC021688 | 0 | 0 | 1.0000 | 0.4930 | 0.7608 | −0.394 | 1.31 | 0 | −1.67 |
| C11orf30 | BC033404 | 7 | 11 | 1.0000 | 0.6288 | 1.5469 | 0.629 | 1.55 | 4 | 2.11 |
| C11orf30 | BC117265 | 256 | 101 | 0.0250 | 0.0008 | 0.3970 | −1.333 | 2.52 | 155 | 7.28 |
| C11orf30 | BC143370 | 0 | 0 | 9999 | 9999 | 1.0000 | 0.000 | 1.00 | 0 | 0 |
| C11orf30 | BC143374 | 61 | 31 | 0.7717 | 0.1648 | 0.5194 | −0.945 | 1.93 | 30 | 4.90 |
| C11orf30 | BC143376 | 76 | 0 | 0.0000 | 0.0000 | 0.0130 | −6.266 | 76.96 | 76 | 6.25 |
| C11orf30 | NM_020193 | 114 | 152 | 1.0000 | 0.4054 | 1.3215 | 0.402 | 1.32 | 37 | 5.21 |
| C11orf73 | NM_016401 | 689 | 129 | 0.0000 | 0.0000 | 0.1879 | −2.412 | 5.32 | 560 | 9.13 |
| C11orf73 | NR_024596 | 10 | 4 | 1.0000 | 0.4020 | 0.4661 | −1.101 | 2.15 | 6 | 2.52 |
| C11orf73 | NR_024598 | 24 | 4 | 0.4216 | 0.0456 | 0.2162 | −2.210 | 4.63 | 19 | 4.27 |
| C17orf76-AS1 | HQ447236 | 16 | 13 | 1.0000 | 0.8780 | 0.8303 | −0.268 | 1.20 | 3 | 1.56 |
| C17orf76-AS1 | NR_027158 | 555 | 581 | 1.0000 | 0.7204 | 1.0476 | 0.067 | 1.05 | 26 | 4.72 |
| C17orf76-AS1 | NR_027163 | 1757 | 1513 | 0.6163 | 0.1057 | 0.8609 | −0.216 | 1.16 | 245 | 7.93 |
| C17orf76-AS1 | NR_027164 | 244 | 40 | 0.0000 | 0.0000 | 0.1695 | −2.561 | 5.90 | 203 | 7.67 |
| C17orf76-AS1 | NR_027165 | 20 | 13 | 1.0000 | 0.3969 | 0.6497 | −0.622 | 1.54 | 7 | 2.88 |
| C17orf76-AS1 | NR_027166 | 5464 | 5709 | 1.0000 | 0.5515 | 1.0450 | 0.063 | 1.04 | 246 | 7.94 |
| C17orf76-AS1 | NR_027167 | 55 | 69 | 1.0000 | 0.6611 | 1.2455 | 0.317 | 1.25 | 14 | 3.79 |
| C17orf76-AS1 | NR_027168 | 570 | 825 | 0.1142 | 0.0058 | 1.4465 | 0.533 | 1.45 | 255 | 7.99 |
| C17orf76-AS1 | NR_027169 | 257 | 213 | 1.0000 | 0.4300 | 0.8313 | −0.267 | 1.20 | 44 | 5.44 |
| C17orf76-AS1 | NR_027170 | 95 | 206 | 0.1280 | 0.0068 | 2.1575 | 1.109 | 2.16 | 111 | 6.80 |
| C17orf76-AS1 | NR_027172 | 1 | 8 | 0.6364 | 0.1112 | 5.4442 | 2.445 | 5.44 | 7 | 2.85 |
| C17orf76-AS1 | NR_027173 | 0 | 0 | 9999 | 9999 | 1.0000 | 0.000 | 1.00 | 0 | 0 |
| C17orf76-AS1 | NR_027174 | 11 | 5 | 1.0000 | 0.4183 | 0.5152 | −0.957 | 1.94 | 6 | 2.59 |
| C17orf76-AS1 | NR_027176 | 0 | 1 | 0.7536 | 0.1556 | 2.4883 | 1.315 | 2.49 | 1 | 0.57 |
| C17orf76-AS1 | NR_027177 | 0 | 1 | 0.9827 | 0.2760 | 2.2141 | 1.147 | 2.21 | 1 | 0.28 |
| C17orf76-AS1 | NR_027178 | 4 | 1 | 1.0000 | 0.4167 | 0.3934 | −1.346 | 2.54 | 3 | 1.55 |
| C17orf76-AS1 | NR_027179 | 49 | 28 | 1.0000 | 0.3134 | 0.5714 | −0.807 | 1.75 | 22 | 4.43 |
| C17orf76-AS1 | NR_027667 | 313 | 184 | 0.2168 | 0.0149 | 0.5889 | −0.764 | 1.70 | 129 | 7.01 |
| C17orf76-AS1 | NR_045022 | 37 | 22 | 1.0000 | 0.3950 | 0.5994 | −0.738 | 1.67 | 15 | 3.95 |
| C17orf76-AS1 | NR_045023 | 3 | 0 | 0.4439 | 0.0509 | 0.2240 | −2.159 | 4.46 | 3 | 1.79 |
| C17orf76-AS1 | NR_045025 | 0 | 3 | 0.7290 | 0.1445 | 3.6769 | 1.878 | 3.68 | 3 | 1.42 |
| C17orf76-AS1 | NR_045026 | 75 | 37 | 0.6987 | 0.1338 | 0.4927 | −1.021 | 2.03 | 39 | 5.27 |
| C17orf76-AS1 | NR_045028 | 32 | 27 | 1.0000 | 0.8641 | 0.8583 | −0.220 | 1.17 | 5 | 2.21 |
| C17orf76-AS1 | NR_045029 | 365 | 286 | 0.8314 | 0.1876 | 0.7848 | −0.350 | 1.27 | 79 | 6.30 |
| C4orf27 | NM_017867 | 635 | 51 | 0.0000 | 0.0000 | 0.0823 | −3.604 | 12.16 | 583 | 9.19 |
| C6orf48 | AJ249732 | 3 | 0 | 0.8554 | 0.1974 | 0.2911 | −1.780 | 3.44 | 3 | 1.66 |
| C6orf48 | AJ249732 | 1 | 1 | 1.0000 | 1.0000 | 1.1275 | 0.173 | 1.13 | 0 | −2.01 |
| C6orf48 | NM_001040437 | 193 | 322 | 0.1700 | 0.0101 | 1.6677 | 0.738 | 1.67 | 129 | 7.02 |
| C6orf48 | NM_001040437 | 579 | 503 | 0.8432 | 0.1924 | 0.8692 | −0.202 | 1.15 | 76 | 6.25 |
| C6orf48 | NM_001040438 | 237 | 498 | 0.0014 | 0.0000 | 2.0967 | 1.068 | 2.10 | 261 | 8.03 |
| C6orf48 | NM_001040438 | 286 | 155 | 0.1421 | 0.0078 | 0.5437 | −0.879 | 1.84 | 131 | 7.03 |
| C6orf48 | NM_001040438 | 1038 | 922 | 0.8557 | 0.1975 | 0.8882 | −0.171 | 1.13 | 116 | 6.86 |
| CAB39 | AF134480 | 552 | 525 | 1.0000 | 0.7322 | 0.9509 | −0.073 | 1.05 | 27 | 4.76 |
| CAB39 | NM_001130849 | 63 | 119 | 0.6089 | 0.1034 | 1.8875 | 0.916 | 1.89 | 57 | 5.82 |
| CAB39 | NM_001130850 | 485 | 29 | 0.0000 | 0.0000 | 0.0611 | −4.032 | 16.36 | 456 | 8.83 |
| CAB39 | NM_016289 | 1417 | 1314 | 1.0000 | 0.5408 | 0.9279 | −0.108 | 1.08 | 102 | 6.67 |
| CAPNS1 | BC011903 | 248 | 295 | 1.0000 | 0.4143 | 1.1884 | 0.249 | 1.19 | 47 | 5.55 |
| CAPNS1 | BC064998 | 5720 | 8456 | 0.0000 | 0.0000 | 1.4783 | 0.564 | 1.48 | 2736 | 11.42 |
| CAPNS1 | NM_001003962 | 3366 | 486 | 0.0000 | 0.0000 | 0.1445 | −2.790 | 6.92 | 2880 | 11.49 |
| CAPNS1 | NM_001749 | 1777 | 1927 | 1.0000 | 0.7816 | 1.0844 | 0.117 | 1.08 | 150 | 7.23 |

TABLE 10-continued

RNA Abundance Modulation

| Gene | Trx_ID | ave DMSO | ave Cpd | padj (q val, FDR) | ttest (p val) | FC (x + 1) | $L_2$FC (x + 1) | amp FC (x + 1) | abs (Cpd-DMSO) | $L_2$abs (Cpd-DMSO) |
|---|---|---|---|---|---|---|---|---|---|---|
| CASC3 | AK292425 | 94 | 30 | 0.1929 | 0.0124 | 0.3209 | −1.640 | 3.12 | 65 | 6.02 |
| CASC3 | AK310635 | 14 | 4 | 0.9105 | 0.2210 | 0.3076 | −1.701 | 3.25 | 10 | 3.37 |
| CASC3 | NM_007359 | 2776 | 1302 | 0.0000 | 0.0000 | 0.4691 | −1.092 | 2.13 | 1474 | 10.53 |
| CCDC77 | NM_001130146 | 192 | 425 | 0.0042 | 0.0001 | 2.2059 | 1.141 | 2.21 | 233 | 7.86 |
| CCDC77 | NM_001130147 | 24 | 49 | 1.0000 | 0.2891 | 1.9620 | 0.972 | 1.96 | 24 | 4.61 |
| CCDC77 | NM_001130148 | 103 | 35 | 0.1259 | 0.0066 | 0.3511 | −1.510 | 2.85 | 67 | 6.07 |
| CCDC77 | NM_032358 | 345 | 387 | 1.0000 | 0.4426 | 1.1217 | 0.166 | 1.12 | 42 | 5.39 |
| CCDC88A | AK001254 | 6 | 13 | 1.0000 | 0.3778 | 2.1126 | 1.079 | 2.11 | 8 | 2.91 |
| CCDC88A | AK024717 | 202 | 224 | 1.0000 | 0.6788 | 1.1089 | 0.149 | 1.11 | 22 | 4.47 |
| CCDC88A | AK124603 | 3 | 0 | 0.5184 | 0.0711 | 0.2726 | −1.875 | 3.67 | 3 | 1.42 |
| CCDC88A | AK124761 | 11 | 30 | 0.9508 | 0.2498 | 2.5696 | 1.362 | 2.57 | 19 | 4.23 |
| CCDC88A | BC032683 | 217 | 180 | 1.0000 | 0.4922 | 0.8319 | −0.265 | 1.20 | 37 | 5.19 |
| CCDC88A | BC142700 | 0 | 3 | 1.0000 | 0.3451 | 2.7104 | 1.439 | 2.71 | 2 | 1.24 |
| CCDC88A | BX537985 | 73 | 98 | 1.0000 | 0.4777 | 1.3416 | 0.424 | 1.34 | 25 | 4.66 |
| CCDC88A | BX538154 | 0 | 0 | 9999 | 9999 | 1.0000 | 0.000 | 1.00 | 0 | 0 |
| CCDC88A | NM_001135597 | 808 | 1387 | 0.0004 | 0.0000 | 1.7161 | 0.779 | 1.72 | 579 | 9.18 |
| CCDC88A | NM_001254943 | 270 | 334 | 0.9662 | 0.2605 | 1.2340 | 0.303 | 1.23 | 63 | 5.99 |
| CCDC88A | NM_018084 | 799 | 307 | 0.0000 | 0.0000 | 0.3851 | −1.377 | 2.60 | 492 | 8.94 |
| CD46 | NM_002389 | 135 | 132 | 1.0000 | 0.8407 | 0.9749 | −0.037 | 1.03 | 3 | 1.78 |
| CD46 | NM_153826 | 1087 | 1466 | 0.1462 | 0.0082 | 1.3486 | 0.431 | 1.35 | 379 | 8.57 |
| CD46 | NM_172350 | 0 | 0 | 9999 | 9999 | 1.0000 | 0.000 | 1.00 | 0 | 0 |
| CD46 | NM_172351 | 1404 | 1134 | 0.6226 | 0.1074 | 0.8078 | −0.308 | 1.24 | 270 | 8.08 |
| CD46 | NM_172352 | 86 | 351 | 0.0000 | 0.0000 | 4.0433 | 2.016 | 4.04 | 265 | 8.05 |
| CD46 | NM_172353 | 374 | 293 | 0.9698 | 0.2622 | 0.7842 | −0.351 | 1.28 | 81 | 6.34 |
| CD46 | NM_172359 | 13 | 61 | 0.2102 | 0.0141 | 4.4073 | 2.140 | 4.41 | 48 | 5.58 |
| CD46 | NM_172361 | 24 | 13 | 1.0000 | 0.3658 | 0.5388 | −0.892 | 1.86 | 12 | 3.53 |
| CDC40 | NM_015891 | 916 | 277 | 0.0000 | 0.0000 | 0.3027 | −1.724 | 3.30 | 639 | 9.32 |
| CDC42BPA | AB007920 | 3 | 7 | 1.0000 | 0.4433 | 1.8842 | 0.914 | 1.88 | 4 | 1.84 |
| CDC42BPA | AB384799 | 70 | 213 | 0.0090 | 0.0002 | 3.0344 | 1.601 | 3.03 | 144 | 7.17 |
| CDC42BPA | AK027000 | 2 | 6 | 1.0000 | 0.4681 | 2.2863 | 1.193 | 2.29 | 4 | 1.89 |
| CDC42BPA | AK098391 | 95 | 146 | 0.9332 | 0.2376 | 1.5323 | 0.616 | 1.53 | 51 | 5.68 |
| CDC42BPA | BC136333 | 0 | 87 | 0.0000 | 0.0000 | 87.5738 | 6.452 | 87.57 | 87 | 6.44 |
| CDC42BPA | CR933723 | 96 | 82 | 1.0000 | 0.7933 | 0.8586 | −0.220 | 1.16 | 14 | 3.78 |
| CDC42BPA | NM_003607 | 3681 | 2992 | 0.1032 | 0.0050 | 0.8130 | −0.299 | 1.23 | 689 | 9.43 |
| CDC42BPA | NM_014826 | 487 | 800 | 0.0196 | 0.0006 | 1.6420 | 0.715 | 1.64 | 313 | 8.29 |
| CDCA7 | AK297097 | 0 | 2 | 0.6693 | 0.1228 | 3.3812 | 1.758 | 3.38 | 2 | 1.25 |
| CDCA7 | AK300949 | 0 | 0 | 9999 | 9999 | 1.0000 | 0.000 | 1.00 | 0 | 0 |
| CDCA7 | NM_031942 | 51 | 11 | 0.1650 | 0.0097 | 0.2305 | −2.117 | 4.34 | 40 | 5.34 |
| CDCA7 | NM_145810 | 320 | 23 | 0.0000 | 0.0000 | 0.0755 | −3.727 | 13.24 | 297 | 8.21 |
| CDH13 | NM_001220488 | 33 | 13 | 0.8785 | 0.2066 | 0.3967 | −1.334 | 2.52 | 21 | 4.38 |
| CDH13 | NM_001220490 | 0 | 8 | 0.3124 | 0.0266 | 8.9156 | 3.156 | 8.92 | 8 | 2.98 |
| CDH13 | NM_001220491 | 35 | 40 | 1.0000 | 0.8478 | 1.1376 | 0.186 | 1.14 | 5 | 2.33 |
| CDH13 | NM_001220492 | 1 | 0 | 0.5736 | 0.0906 | 0.4450 | −1.168 | 2.25 | 1 | 0.32 |
| CDH13 | NM_001257 | 2489 | 880 | 0.0000 | 0.0000 | 0.3538 | −1.499 | 2.83 | 1609 | 10.65 |
| CDK11B | AF067515 | 323 | 392 | 1.0000 | 0.3054 | 1.2138 | 0.280 | 1.21 | 69 | 6.11 |
| CDK11B | AF067517 | 40 | 19 | 0.9467 | 0.2467 | 0.4931 | −1.020 | 2.03 | 21 | 4.39 |
| CDK11B | AF067526 | 4 | 12 | 1.0000 | 0.3625 | 2.6704 | 1.417 | 2.67 | 8 | 3.08 |
| CDK11B | AF067528 | 19 | 31 | 1.0000 | 0.4731 | 1.5507 | 0.633 | 1.55 | 11 | 3.49 |
| CDK11B | BC009375 | 6 | 4 | 1.0000 | 0.8339 | 0.8261 | −0.276 | 1.21 | 1 | 0.18 |
| CDK11B | NM_033486 | 213 | 28 | 0.0000 | 0.0000 | 0.1347 | −2.893 | 7.43 | 185 | 7.53 |
| CDK11B | NM_033487 | 48 | 61 | 1.0000 | 0.7423 | 1.2616 | 0.335 | 1.26 | 13 | 3.67 |
| CDK11B | NM_033488 | 113 | 11 | 0.0002 | 0.0000 | 0.1010 | −3.308 | 9.90 | 102 | 6.68 |
| CDK11B | NM_033489 | 124 | 213 | 0.3882 | 0.0387 | 1.7068 | 0.771 | 1.71 | 89 | 6.47 |
| CDK11B | NM_033492 | 19 | 48 | 0.7586 | 0.1592 | 2.3902 | 1.257 | 2.39 | 28 | 4.82 |
| CDK11B | NM_033493 | 473 | 485 | 1.0000 | 0.8226 | 1.0257 | 0.037 | 1.03 | 12 | 3.61 |
| CDK11B | U04819 | 51 | 86 | 0.8169 | 0.1821 | 1.6680 | 0.738 | 1.67 | 35 | 5.12 |
| CEP68 | AK299373 | 240 | 273 | 1.0000 | 0.5077 | 1.1375 | 0.186 | 1.14 | 33 | 5.05 |
| CEP68 | AK301173 | 101 | 82 | 1.0000 | 0.5298 | 0.8082 | −0.307 | 1.24 | 20 | 4.30 |
| CEP68 | AK304110 | 49 | 35 | 1.0000 | 0.5489 | 0.7136 | −0.487 | 1.40 | 14 | 3.85 |
| CEP68 | BC004873 | 0 | 14 | 0.1222 | 0.0063 | 15.1493 | 3.921 | 15.15 | 14 | 3.82 |
| CEP68 | BC030534 | 3 | 3 | 1.0000 | 0.9379 | 0.9130 | −0.131 | 1.10 | 0 | −1.52 |
| CEP68 | NM_015147 | 161 | 7 | 0.0000 | 0.0000 | 0.0485 | −4.367 | 20.64 | 154 | 7.27 |
| CIZ1 | AF234161 | 271 | 138 | 0.2311 | 0.0165 | 0.5105 | −0.970 | 1.96 | 133 | 7.06 |
| CIZ1 | BC004119 | 787 | 790 | 1.0000 | 0.9377 | 1.0042 | 0.006 | 1.00 | 3 | 1.72 |
| CIZ1 | NM_001131015 | 56 | 22 | 0.4894 | 0.0620 | 0.3986 | −1.327 | 2.51 | 34 | 5.10 |
| CIZ1 | NM_001131016 | 1776 | 1770 | 1.0000 | 0.9270 | 0.9971 | −0.004 | 1.00 | 5 | 2.39 |
| CIZ1 | NM_001131017 | 90 | 264 | 0.0083 | 0.0002 | 2.9182 | 1.545 | 2.92 | 174 | 7.44 |
| CIZ1 | NM_001131018 | 166 | 50 | 0.0544 | 0.0021 | 0.3082 | −1.698 | 3.24 | 115 | 6.85 |
| CIZ1 | NM_001257975 | 27 | 13 | 1.0000 | 0.3532 | 0.4947 | −1.015 | 2.02 | 14 | 3.80 |
| CIZ1 | NM_001257976 | 46 | 116 | 0.3523 | 0.0325 | 2.5242 | 1.336 | 2.52 | 71 | 6.15 |
| CLK4 | AK294921 | 7 | 12 | 1.0000 | 0.5875 | 1.5630 | 0.644 | 1.56 | 5 | 2.19 |
| CLK4 | AK304614 | 4 | 24 | 0.5508 | 0.0822 | 4.6400 | 2.214 | 4.64 | 20 | 4.29 |
| CLK4 | AK310427 | 0 | 1 | 1.0000 | 0.6938 | 1.7957 | 0.845 | 1.80 | 1 | 0.06 |
| CLK4 | AK311485 | 5 | 6 | 1.0000 | 0.9268 | 1.2333 | 0.302 | 1.23 | 1 | 0.49 |

TABLE 10-continued

RNA Abundance Modulation

| Gene | Trx_ID | ave DMSO | ave Cpd | padj (q val, FDR) | ttest (p val) | FC (x + 1) | L$_2$FC (x + 1) | amp FC (x + 1) | abs (Cpd-DMSO) | L$_2$abs (Cpd-DMSO) |
|---|---|---|---|---|---|---|---|---|---|---|
| CLK4 | BC063116 | 15 | 16 | 1.0000 | 0.9797 | 1.0308 | 0.044 | 1.03 | 1 | −0.99 |
| CLK4 | BC143538 | 32 | 31 | 1.0000 | 0.9349 | 0.9632 | −0.054 | 1.04 | 1 | 0.28 |
| CLK4 | BC143547 | 3 | 0 | 0.4853 | 0.0612 | 0.2845 | −1.813 | 3.51 | 3 | 1.33 |
| CLK4 | BC151233 | 0 | 3 | 0.6450 | 0.1149 | 4.0472 | 2.017 | 4.05 | 3 | 1.61 |
| CLK4 | CR749504 | 7 | 13 | 1.0000 | 0.5589 | 1.7869 | 0.837 | 1.79 | 6 | 2.63 |
| CLK4 | NM_020666 | 86 | 259 | 0.0050 | 0.0001 | 2.9956 | 1.583 | 3.00 | 173 | 7.44 |
| CNOT1 | AK056927 | 0 | 2 | 0.6970 | 0.1332 | 3.0836 | 1.625 | 3.08 | 2 | 1.06 |
| CNOT1 | AK092885 | 11 | 14 | 1.0000 | 0.8164 | 1.2706 | 0.345 | 1.27 | 3 | 1.64 |
| CNOT1 | AK302495 | 55 | 15 | 0.3797 | 0.0373 | 0.2962 | −1.755 | 3.38 | 39 | 5.29 |
| CNOT1 | NM_001265612 | 1453 | 2948 | 0.0000 | 0.0000 | 2.0281 | 1.020 | 2.03 | 1495 | 10.55 |
| CNOT1 | NM_016284 | 5036 | 3835 | 0.0040 | 0.0001 | 0.7616 | −0.393 | 1.31 | 1201 | 10.23 |
| CNOT1 | NM_206999 | 285 | 294 | 1.0000 | 0.8584 | 1.0312 | 0.044 | 1.03 | 9 | 3.16 |
| CNOT1 | NR_049763 | 22 | 7 | 0.8508 | 0.1954 | 0.3333 | −1.585 | 3.00 | 15 | 3.94 |
| COG1 | AB037802 | 65 | 22 | 0.3966 | 0.0401 | 0.3468 | −1.528 | 2.88 | 43 | 5.44 |
| COG1 | BC047465 | 11 | 10 | 1.0000 | 0.9451 | 0.8699 | −0.201 | 1.15 | 2 | 0.69 |
| COG1 | NM_018714 | 951 | 452 | 0.0000 | 0.0000 | 0.4759 | −1.071 | 2.10 | 499 | 8.96 |
| COL12A1 | CCDS43481 | 152 | 32 | 0.0079 | 0.0002 | 0.2189 | −2.192 | 4.57 | 119 | 6.90 |
| COL12A1 | CCDS43482 | 4466 | 3132 | 0.0011 | 0.0000 | 0.7014 | −0.512 | 1.43 | 1334 | 10.38 |
| COL12A1 | NM_004370 | 59155 | 56036 | 0.8481 | 0.1944 | 0.9473 | −0.078 | 1.06 | 3119 | 11.61 |
| COL12A1 | NM_080645 | 0 | 32 | 0.0022 | 0.0000 | 33.4940 | 5.066 | 33.49 | 32 | 5.02 |
| COL12A1 | U68139 | 1622 | 1519 | 1.0000 | 0.4516 | 0.9365 | −0.095 | 1.07 | 103 | 6.69 |
| COL1A1 | JQ236861 | 293 | 84 | 0.0001 | 0.0000 | 0.2877 | −1.797 | 3.48 | 210 | 7.71 |
| COL1A1 | NM_000088 | 1247334 | 850699 | 0.0000 | 0.0000 | 0.6820 | −0.552 | 1.47 | 396635 | 18.60 |
| COL6A1 | BC022236 | 783 | 2147 | 0.0000 | 0.0000 | 2.7404 | 1.454 | 2.74 | 1364 | 10.41 |
| COL6A1 | NM_001848 | 72992 | 59182 | 0.0042 | 0.0001 | 0.8108 | −0.303 | 1.23 | 13810 | 13.75 |
| COPS7B | AK024273 | 49 | 37 | 1.0000 | 0.5675 | 0.7572 | −0.401 | 1.32 | 12 | 3.61 |
| COPS7B | AK124133 | 2 | 12 | 0.7358 | 0.1478 | 4.0852 | 2.030 | 4.09 | 9 | 3.25 |
| COPS7B | AK126326 | 13 | 98 | 0.0051 | 0.0001 | 7.2463 | 2.857 | 7.25 | 85 | 6.42 |
| COPS7B | AK307486 | 16 | 9 | 1.0000 | 0.4037 | 0.5936 | −0.752 | 1.68 | 7 | 2.80 |
| COPS7B | BC091493 | 3 | 2 | 1.0000 | 0.9384 | 0.9008 | −0.151 | 1.11 | 0 | −1.41 |
| COPS7B | NM_022730 | 654 | 259 | 0.0000 | 0.0000 | 0.3961 | −1.336 | 2.52 | 396 | 8.63 |
| CSDE1 | AY049788 | 1397 | 1600 | 0.9129 | 0.2222 | 1.1459 | 0.196 | 1.15 | 204 | 7.67 |
| CSDE1 | NM_001007553 | 2904 | 1980 | 0.0002 | 0.0000 | 0.6817 | −0.553 | 1.47 | 925 | 9.85 |
| CSDE1 | NM_001130523 | 55 | 40 | 1.0000 | 0.6318 | 0.7325 | −0.449 | 1.37 | 15 | 3.89 |
| CSDE1 | NM_001242891 | 109 | 60 | 0.5711 | 0.0880 | 0.5586 | −0.840 | 1.79 | 49 | 5.60 |
| CSDE1 | NM_001242892 | 10 | 681 | 0.0000 | 0.0000 | 59.6504 | 5.898 | 59.65 | 670 | 9.39 |
| CSDE1 | NM_001242893 | 893 | 123 | 0.0000 | 0.0000 | 0.1382 | −2.855 | 7.24 | 770 | 9.59 |
| CSDE1 | NM_007158 | 14613 | 16000 | 0.6970 | 0.1329 | 1.0949 | 0.131 | 1.09 | 1387 | 10.44 |
| CSNK1A1 | AK294099 | 84 | 284 | 0.0007 | 0.0000 | 3.3457 | 1.742 | 3.35 | 200 | 7.64 |
| CSNK1A1 | NM_001025105 | 267 | 162 | 0.3696 | 0.0355 | 0.6102 | −0.713 | 1.64 | 104 | 6.70 |
| CSNK1A1 | NM_001271741 | 1563 | 1042 | 0.0044 | 0.0001 | 0.6672 | −0.584 | 1.50 | 520 | 9.02 |
| CSNK1A1 | NM_001271742 | 546 | 505 | 1.0000 | 0.6241 | 0.9262 | −0.111 | 1.08 | 40 | 5.34 |
| CSNK1A1 | NM_001892 | 4939 | 5068 | 1.0000 | 0.6896 | 1.0261 | 0.037 | 1.03 | 129 | 7.01 |
| CSNK1A1 | X80693 | 164 | 189 | 1.0000 | 0.6032 | 1.1530 | 0.205 | 1.15 | 25 | 4.66 |
| CUX1 | NM_001202543 | 750 | 119 | 0.0000 | 0.0000 | 0.1596 | −2.647 | 6.26 | 631 | 9.30 |
| CUX1 | NM_001202544 | 11 | 0 | 0.1038 | 0.0050 | 0.0833 | −3.585 | 12.00 | 11 | 3.46 |
| CUX1 | NM_001202545 | 8 | 11 | 1.0000 | 0.8020 | 1.3756 | 0.460 | 1.38 | 3 | 1.75 |
| CUX1 | NM_001202546 | 10 | 18 | 1.0000 | 0.4873 | 1.7532 | 0.810 | 1.75 | 8 | 3.01 |
| CUX1 | NM_001913 | 1267 | 947 | 0.1499 | 0.0085 | 0.7475 | −0.420 | 1.34 | 320 | 8.32 |
| CUX1 | NM_181500 | 265 | 192 | 0.6874 | 0.1296 | 0.7250 | −0.464 | 1.38 | 73 | 6.19 |
| CUX1 | NM_181552 | 329 | 1017 | 0.0000 | 0.0000 | 3.0815 | 1.624 | 3.08 | 687 | 9.43 |
| CYB5B | BX647922 | 22 | 72 | 0.3248 | 0.0283 | 3.1660 | 1.663 | 3.17 | 50 | 5.65 |
| CYB5B | NM_030579 | 2915 | 1359 | 0.0000 | 0.0000 | 0.4665 | −1.100 | 2.14 | 1555 | 10.60 |
| CYBRD1 | NM_001127383 | 370 | 451 | 0.8386 | 0.1904 | 1.2177 | 0.284 | 1.22 | 81 | 6.34 |
| CYBRD1 | NM_001256909 | 193 | 840 | 0.0000 | 0.0000 | 4.3429 | 2.119 | 4.34 | 647 | 9.34 |
| CYBRD1 | NM_024843 | 8196 | 7343 | 0.5514 | 0.0825 | 0.8960 | −0.158 | 1.12 | 853 | 9.74 |
| DAB2 | NM_001244871 | 881 | 423 | 0.0000 | 0.0000 | 0.4808 | −1.056 | 2.08 | 458 | 8.84 |
| DAB2 | NM_001343 | 14708 | 12518 | 0.1032 | 0.0050 | 0.8511 | −0.233 | 1.17 | 2190 | 11.10 |
| DARS | CR749809 | 0 | 16 | 0.0799 | 0.0035 | 17.4438 | 4.125 | 17.44 | 16 | 4.04 |
| DARS | NM_001349 | 2087 | 420 | 0.0000 | 0.0000 | 0.2017 | −2.309 | 4.96 | 1666 | 10.70 |
| DCBLD2 | BC007117 | 7 | 3 | 1.0000 | 0.4532 | 0.4758 | −1.072 | 2.10 | 4 | 2.01 |
| DCBLD2 | DQ894997 | 169 | 392 | 0.0069 | 0.0002 | 2.3080 | 1.207 | 2.31 | 222 | 7.80 |
| DCBLD2 | NM_080927 | 6950 | 9171 | 0.0008 | 0.0000 | 1.3196 | 0.400 | 1.32 | 2221 | 11.12 |
| DCUN1D4 | AK124346 | 0 | 0 | 9999 | 9999 | 1.0000 | 0.000 | 1.00 | 0 | 0 |
| DCUN1D4 | AK294894 | 158 | 48 | 0.0196 | 0.0006 | 0.3048 | −1.714 | 3.28 | 111 | 6.79 |
| DCUN1D4 | AK294896 | 4 | 0 | 0.3594 | 0.0340 | 0.1864 | −2.423 | 5.36 | 4 | 2.13 |
| DCUN1D4 | BC041702 | 22 | 34 | 1.0000 | 0.4737 | 1.5710 | 0.652 | 1.57 | 13 | 3.69 |
| DCUN1D4 | NM_001040402 | 841 | 311 | 0.0000 | 0.0000 | 0.3705 | −1.432 | 2.70 | 530 | 9.05 |
| DCUN1D4 | NM_015115 | 429 | 231 | 0.0417 | 0.0015 | 0.5382 | −0.894 | 1.86 | 199 | 7.63 |
| DDAH2 | AK026191 | 4 | 0 | 0.3797 | 0.0375 | 0.1966 | −2.347 | 5.09 | 4 | 2.03 |
| DDAH2 | AK026191 | 30 | 24 | 1.0000 | 0.7583 | 0.8155 | −0.294 | 1.23 | 6 | 2.50 |
| DDAH2 | AK026191 | 30 | 24 | 1.0000 | 0.7583 | 0.8155 | −0.294 | 1.23 | 6 | 2.50 |
| DDAH2 | AK026191 | 30 | 24 | 1.0000 | 0.7583 | 0.8155 | −0.294 | 1.23 | 6 | 2.50 |
| DDAH2 | NM_013974 | 286 | 112 | 0.0079 | 0.0002 | 0.3926 | −1.349 | 2.55 | 174 | 7.45 |

TABLE 10-continued

RNA Abundance Modulation

| Gene | Trx_ID | ave DMSO | ave Cpd | padj (q val, FDR) | ttest (p val) | FC (x + 1) | L₂FC (x + 1) | amp FC (x + 1) | abs (Cpd-DMSO) | L₂abs (Cpd-DMSO) |
|---|---|---|---|---|---|---|---|---|---|---|
| DDAH2 | NM_013974 | 286 | 112 | 0.0079 | 0.0002 | 0.3926 | −1.349 | 2.55 | 174 | 7.45 |
| DDAH2 | NM_013974 | 286 | 112 | 0.0079 | 0.0002 | 0.3926 | −1.349 | 2.55 | 174 | 7.45 |
| DDAH2 | NM_013974 | 3 | 7 | 1.0000 | 0.4895 | 2.1707 | 1.118 | 2.17 | 4 | 2.16 |
| DDR1 | AK130776 | 0 | 2 | 0.6970 | 0.1332 | 3.0836 | 1.625 | 3.08 | 2 | 1.06 |
| DDR1 | AK291621 | 4 | 0 | 0.3999 | 0.0415 | 0.2101 | −2.251 | 4.76 | 4 | 1.91 |
| DDR1 | AK291621 | 54 | 47 | 1.0000 | 0.5678 | 0.8706 | −0.200 | 1.15 | 7 | 2.84 |
| DDR1 | AK295643 | 1 | 0 | 1.0000 | 0.3241 | 0.6160 | −0.699 | 1.62 | 1 | −0.68 |
| DDR1 | AK295643 | 0 | 0 | 9999 | 9999 | 1.0000 | 0.000 | 1.00 | 0 | 0 |
| DDR1 | BC070070 | 115 | 183 | 0.5018 | 0.0665 | 1.5823 | 0.662 | 1.58 | 68 | 6.08 |
| DDR1 | EU826614 | 5 | 0 | 0.3223 | 0.0279 | 0.1659 | −2.592 | 6.03 | 5 | 2.33 |
| DDR1 | EU826614 | 1 | 0 | 1.0000 | 0.3241 | 0.6140 | −0.704 | 1.63 | 1 | −0.67 |
| DDR1 | EU826614 | 0 | 0 | 9999 | 9999 | 1.0000 | 0.000 | 1.00 | 0 | 0 |
| DDR1 | L20817 | 187 | 41 | 0.0008 | 0.0000 | 0.2215 | −2.174 | 4.51 | 146 | 7.19 |
| DDR1 | L57508 | 23 | 0 | 0.0118 | 0.0003 | 0.0419 | −4.578 | 23.89 | 23 | 4.52 |
| DDR1 | NM_001202521 | 0 | 0 | 9999 | 9999 | 1.0000 | 0.000 | 1.00 | 0 | 0 |
| DDR1 | NM_001202522 | 0 | 0 | 9999 | 9999 | 1.0000 | 0.000 | 1.00 | 0 | 0 |
| DDR1 | NM_001202523 | 7 | 0 | 0.2531 | 0.0190 | 0.1213 | −3.043 | 8.24 | 7 | 2.86 |
| DDR1 | NM_001202523 | 0 | 0 | 9999 | 9999 | 1.0000 | 0.000 | 1.00 | 0 | 0 |
| DDR1 | NM_013993 | 288 | 235 | 1.0000 | 0.3201 | 0.8163 | −0.293 | 1.23 | 53 | 5.73 |
| DDR1 | NM_013994 | 57 | 69 | 1.0000 | 0.6875 | 1.2201 | 0.287 | 1.22 | 13 | 3.67 |
| DDR1 | Z29093 | 3 | 0 | 0.4853 | 0.0612 | 0.2845 | −1.813 | 3.51 | 3 | 1.33 |
| DDR1 | Z29093 | 15 | 20 | 1.0000 | 0.7682 | 1.3546 | 0.438 | 1.35 | 6 | 2.47 |
| DDX39B | AB209217 | 187 | 296 | 0.3999 | 0.0415 | 1.5790 | 0.659 | 1.58 | 109 | 6.77 |
| DDX39B | AB209217 | 175 | 220 | 1.0000 | 0.3120 | 1.2574 | 0.330 | 1.26 | 45 | 5.50 |
| DDX39B | AB209217 | 68 | 69 | 1.0000 | 0.9569 | 1.0278 | 0.040 | 1.03 | 2 | 0.93 |
| DDX39B | AK127767 | 3 | 0 | 0.4939 | 0.0639 | 0.2469 | −2.018 | 4.05 | 3 | 1.61 |
| DDX39B | AK127767 | 133 | 93 | 0.9964 | 0.2840 | 0.6984 | −0.518 | 1.43 | 41 | 5.34 |
| DDX39B | AK127767 | 143 | 107 | 1.0000 | 0.4311 | 0.7502 | −0.415 | 1.33 | 36 | 5.17 |
| DDX39B | AK127767 | 26 | 47 | 1.0000 | 0.3021 | 1.7755 | 0.828 | 1.78 | 21 | 4.39 |
| DDX39B | AK294939 | 13 | 0 | 0.0830 | 0.0037 | 0.0738 | −3.761 | 13.56 | 13 | 3.65 |
| DDX39B | AK295634 | 18 | 33 | 1.0000 | 0.3296 | 1.7596 | 0.815 | 1.76 | 15 | 3.87 |
| DDX39B | AK316469 | 0 | 4 | 0.6088 | 0.1033 | 4.8241 | 2.270 | 4.82 | 4 | 1.94 |
| DDX39B | AK316469 | 6 | 9 | 1.0000 | 0.7310 | 1.4471 | 0.533 | 1.45 | 3 | 1.64 |
| DDX39B | AK316469 | 7 | 9 | 1.0000 | 0.8595 | 1.2280 | 0.296 | 1.23 | 2 | 0.91 |
| DDX39B | NM_004640 | 1896 | 2199 | 0.6693 | 0.1234 | 1.1597 | 0.214 | 1.16 | 303 | 8.24 |
| DDX39B | NM_080598 | 172 | 0 | 0.0000 | 0.0000 | 0.0058 | −7.433 | 172.77 | 172 | 7.42 |
| DDX39B | NM_080598 | 206 | 412 | 0.0231 | 0.0007 | 1.9931 | 0.995 | 1.99 | 206 | 7.69 |
| DDX39B | NM_080598 | 6 | 0 | 0.2832 | 0.0227 | 0.1460 | −2.776 | 6.85 | 6 | 2.55 |
| DDX39B | NM_080598 | 567 | 778 | 0.3127 | 0.0266 | 1.3717 | 0.456 | 1.37 | 211 | 7.72 |
| DDX39B | NM_080598 | 423 | 447 | 1.0000 | 0.5375 | 1.0572 | 0.080 | 1.06 | 24 | 4.60 |
| DDX39B | NR_037852 | 0 | 7 | 0.3236 | 0.0282 | 8.2844 | 3.050 | 8.28 | 7 | 2.86 |
| DDX39B | NR_037852 | 24 | 21 | 1.0000 | 0.8839 | 0.8797 | −0.185 | 1.14 | 3 | 1.61 |
| DDX39B | NR_037852 | 0 | 0 | 9999 | 9999 | 1.0000 | 0.000 | 1.00 | 0 | 0 |
| DDX39B | NR_037853 | 897 | 1017 | 1.0000 | 0.3027 | 1.1342 | 0.182 | 1.13 | 120 | 6.91 |
| DDX42 | AK095772 | 47 | 7 | 0.1462 | 0.0082 | 0.1630 | −2.617 | 6.13 | 41 | 5.34 |
| DDX42 | AK122737 | 46 | 20 | 0.8481 | 0.1944 | 0.4466 | −1.163 | 2.24 | 26 | 4.70 |
| DDX42 | AK126480 | 13 | 80 | 0.0463 | 0.0017 | 5.7184 | 2.516 | 5.72 | 66 | 6.05 |
| DDX42 | CU677324 | 105 | 22 | 0.0357 | 0.0012 | 0.2178 | −2.199 | 4.59 | 83 | 6.37 |
| DDX42 | NM_007372 | 637 | 93 | 0.0000 | 0.0000 | 0.1480 | −2.756 | 6.76 | 544 | 9.09 |
| DDX42 | NM_203499 | 2898 | 761 | 0.0000 | 0.0000 | 0.2628 | −1.928 | 3.80 | 2137 | 11.06 |
| DENND1A | AB046828 | 12 | 2 | 0.7189 | 0.1407 | 0.2323 | −2.106 | 4.31 | 10 | 3.30 |
| DENND1A | AK295710 | 0 | 0 | 9999 | 9999 | 1.0000 | 0.000 | 1.00 | 0 | 0 |
| DENND1A | AK299867 | 8 | 0 | 0.2071 | 0.0138 | 0.1128 | −3.148 | 8.86 | 8 | 2.98 |
| DENND1A | BC009616 | 0 | 0 | 9999 | 9999 | 1.0000 | 0.000 | 1.00 | 0 | 0 |
| DENND1A | BC028061 | 4 | 0 | 0.3999 | 0.0410 | 0.1937 | −2.368 | 5.16 | 4 | 2.06 |
| DENND1A | BC113037 | 0 | 0 | 9999 | 9999 | 1.0000 | 0.000 | 1.00 | 0 | 0 |
| DENND1A | NM_020946 | 354 | 49 | 0.0000 | 0.0000 | 0.1412 | −2.824 | 7.08 | 305 | 8.25 |
| DENND1A | NM_024820 | 187 | 27 | 0.0000 | 0.0000 | 0.1481 | −2.756 | 6.75 | 160 | 7.32 |
| DENND1B | AL831839 | 2 | 0 | 1.0000 | 0.3757 | 0.4810 | −1.056 | 2.08 | 1 | 0.49 |
| DENND1B | AX746849 | 97 | 65 | 0.9566 | 0.2529 | 0.6707 | −0.576 | 1.49 | 32 | 5.02 |
| DENND1B | BC022561 | 8 | 3 | 1.0000 | 0.4975 | 0.4987 | −1.004 | 2.01 | 4 | 2.12 |
| DENND1B | NM_001195215 | 352 | 134 | 0.0014 | 0.0000 | 0.3816 | −1.390 | 2.62 | 218 | 7.77 |
| DENND1B | NM_001195216 | 25 | 19 | 1.0000 | 0.6982 | 0.7764 | −0.365 | 1.29 | 6 | 2.51 |
| DENND5A | AK125444 | 13 | 14 | 1.0000 | 0.8899 | 1.0116 | 0.017 | 1.01 | 0 | −2.57 |
| DENND5A | AK294016 | 3 | 8 | 1.0000 | 0.4512 | 2.2299 | 1.157 | 2.23 | 5 | 2.32 |
| DENND5A | NM_001243254 | 307 | 28 | 0.0000 | 0.0000 | 0.0946 | −3.401 | 10.57 | 279 | 8.12 |
| DENND5A | NM_015213 | 4989 | 608 | 0.0000 | 0.0000 | 0.1220 | −3.036 | 8.20 | 4381 | 12.10 |
| DGKA | AF064770 | 28 | 8 | 0.7154 | 0.1396 | 0.3184 | −1.651 | 3.14 | 20 | 4.29 |
| DGKA | AF064771 | 0 | 1 | 0.9827 | 0.2720 | 2.1906 | 1.131 | 2.19 | 1 | 0.25 |
| DGKA | AK122973 | 12 | 10 | 1.0000 | 0.8817 | 0.8766 | −0.190 | 1.14 | 2 | 0.67 |
| DGKA | AK307685 | 0 | 0 | 9999 | 9999 | 1.0000 | 0.000 | 1.00 | 0 | 0 |
| DGKA | AK309939 | 12 | 27 | 0.9625 | 0.2584 | 2.2069 | 1.142 | 2.21 | 15 | 3.94 |
| DGKA | AK310600 | 4 | 3 | 1.0000 | 0.7951 | 0.6872 | −0.541 | 1.46 | 2 | 0.74 |
| DGKA | AY930112 | 6 | 7 | 1.0000 | 0.8573 | 1.0632 | 0.088 | 1.06 | 0 | −1.16 |

TABLE 10-continued

RNA Abundance Modulation

| Gene | Trx_ID | ave DMSO | ave Cpd | padj (q val, FDR) | ttest (p val) | FC (x + 1) | L$_2$FC (x + 1) | amp FC (x + 1) | abs (Cpd-DMSO) | L$_2$abs (Cpd-DMSO) |
|---|---|---|---|---|---|---|---|---|---|---|
| DGKA | NM_001345 | 39 | 19 | 0.7631 | 0.1611 | 0.4990 | −1.003 | 2.00 | 20 | 4.33 |
| DGKA | NM_201444 | 86 | 38 | 0.5720 | 0.0885 | 0.4516 | −1.147 | 2.21 | 48 | 5.58 |
| DGKA | NM_201445 | 69 | 29 | 0.5736 | 0.0896 | 0.4329 | −1.208 | 2.31 | 40 | 5.31 |
| DGKA | NM_201554 | 653 | 205 | 0.0000 | 0.0000 | 0.3153 | −1.665 | 3.17 | 448 | 8.81 |
| DHFR | AK293146 | 20 | 0 | 0.0181 | 0.0005 | 0.0478 | −4.386 | 20.90 | 20 | 4.31 |
| DHFR | AK297302 | 7 | 0 | 0.2391 | 0.0174 | 0.1316 | −2.926 | 7.60 | 7 | 2.72 |
| DHFR | AK308492 | 0 | 8 | 0.2938 | 0.0241 | 8.7390 | 3.127 | 8.74 | 8 | 2.95 |
| DHFR | NM_000791 | 3624 | 1520 | 0.0000 | 0.0000 | 0.4197 | −1.253 | 2.38 | 2104 | 11.04 |
| DHX9 | AK096582 | 7 | 8 | 1.0000 | 1.0000 | 1.0051 | 0.007 | 1.01 | 0 | −4.54 |
| DHX9 | NM_001357 | 7449 | 6751 | 0.6208 | 0.1069 | 0.9063 | −0.142 | 1.10 | 698 | 9.45 |
| DHX9 | NR_033302 | 166 | 367 | 0.0094 | 0.0002 | 2.2016 | 1.139 | 2.20 | 201 | 7.65 |
| DHX9 | U03643 | 4 | 0 | 0.3797 | 0.0375 | 0.1973 | −2.341 | 5.07 | 4 | 2.02 |
| DIAPH1 | AF051782 | 2 | 3 | 1.0000 | 0.9359 | 1.1561 | 0.209 | 1.16 | 0 | −1.01 |
| DIAPH1 | BC143414 | 16 | 30 | 1.0000 | 0.4591 | 1.8220 | 0.866 | 1.82 | 14 | 3.83 |
| DIAPH1 | NM_001079812 | 252 | 0 | 0.0000 | 0.0000 | 0.0040 | −7.983 | 253.08 | 252 | 7.98 |
| DIAPH1 | NM_005219 | 5852 | 5621 | 1.0000 | 0.5328 | 0.9607 | −0.058 | 1.04 | 230 | 7.85 |
| DIAPH3 | BC041395 | 0 | 5 | 0.5253 | 0.0734 | 5.9714 | 2.578 | 5.97 | 5 | 2.31 |
| DIAPH3 | NM_001042517 | 2464 | 107 | 0.0000 | 0.0000 | 0.0437 | −4.517 | 22.90 | 2358 | 11.20 |
| DIAPH3 | NM_001258366 | 759 | 21 | 0.0000 | 0.0000 | 0.0290 | −5.108 | 34.50 | 738 | 9.53 |
| DIAPH3 | NM_001258367 | 55 | 0 | 0.0000 | 0.0000 | 0.0178 | −5.815 | 56.30 | 55 | 5.79 |
| DIAPH3 | NM_001258368 | 41 | 12 | 0.5030 | 0.0668 | 0.2988 | −1.743 | 3.35 | 29 | 4.88 |
| DIAPH3 | NM_001258369 | 561 | 25 | 0.0000 | 0.0000 | 0.0472 | −4.406 | 21.20 | 535 | 9.06 |
| DIAPH3 | NM_001258370 | 12 | 0 | 0.0810 | 0.0036 | 0.0745 | −3.747 | 13.43 | 12 | 3.64 |
| DIAPH3 | NM_030932 | 2 | 6 | 1.0000 | 0.4633 | 2.4951 | 1.319 | 2.50 | 4 | 2.10 |
| DIS3L | AB075835 | 133 | 19 | 0.0023 | 0.0000 | 0.1526 | −2.712 | 6.55 | 113 | 6.82 |
| DIS3L | AK095407 | 35 | 8 | 0.3603 | 0.0342 | 0.2507 | −1.996 | 3.99 | 27 | 4.75 |
| DIS3L | AK295392 | 13 | 2 | 0.5142 | 0.0693 | 0.1740 | −2.523 | 5.75 | 12 | 3.58 |
| DIS3L | NM_001143688 | 421 | 262 | 0.1005 | 0.0048 | 0.6217 | −0.686 | 1.61 | 160 | 7.32 |
| DIS3L | NM_133375 | 195 | 149 | 1.0000 | 0.4160 | 0.7664 | −0.384 | 1.30 | 46 | 5.52 |
| DNM2 | AB209213 | 9 | 12 | 1.0000 | 0.7319 | 1.3171 | 0.397 | 1.32 | 3 | 1.66 |
| DNM2 | AK097967 | 162 | 147 | 1.0000 | 0.7751 | 0.9074 | −0.140 | 1.10 | 15 | 3.92 |
| DNM2 | AK097989 | 17 | 24 | 1.0000 | 0.6293 | 1.4063 | 0.492 | 1.41 | 7 | 2.84 |
| DNM2 | AK127033 | 4 | 1 | 0.9752 | 0.2661 | 0.3202 | −1.643 | 3.12 | 3 | 1.77 |
| DNM2 | AK295929 | 0 | 26 | 0.0069 | 0.0002 | 27.3766 | 4.775 | 27.38 | 26 | 4.72 |
| DNM2 | NM_001005360 | 147 | 6 | 0.0000 | 0.0000 | 0.0464 | −4.430 | 21.55 | 141 | 7.14 |
| DNM2 | NM_001005361 | 48 | 120 | 0.2232 | 0.0155 | 2.4893 | 1.316 | 2.49 | 72 | 6.18 |
| DNM2 | NM_001005362 | 416 | 513 | 0.7358 | 0.1482 | 1.2303 | 0.299 | 1.23 | 96 | 6.59 |
| DNM2 | NM_001190716 | 734 | 727 | 1.0000 | 0.9716 | 0.9898 | −0.015 | 1.01 | 7 | 2.90 |
| DNM2 | NM_004945 | 2097 | 2205 | 1.0000 | 0.6075 | 1.0515 | 0.072 | 1.05 | 108 | 6.75 |
| DOCK1 | BC084559 | 5 | 3 | 1.0000 | 0.7204 | 0.7149 | −0.484 | 1.40 | 2 | 0.74 |
| DOCK1 | BC144632 | 619 | 175 | 0.0000 | 0.0000 | 0.2839 | −1.817 | 3.52 | 444 | 8.80 |
| DOCK1 | BX648342 | 9 | 1 | 0.6677 | 0.1216 | 0.1983 | −2.334 | 5.04 | 8 | 2.94 |
| DOCK1 | NM_001380 | 2879 | 1057 | 0.0000 | 0.0000 | 0.3671 | −1.446 | 2.72 | 1823 | 10.83 |
| DPP8 | AF221635 | 3 | 0 | 0.4939 | 0.0639 | 0.2469 | −2.018 | 4.05 | 3 | 1.61 |
| DPP8 | AF221637 | 0 | 1 | 0.7536 | 0.1556 | 2.4883 | 1.315 | 2.49 | 1 | 0.57 |
| DPP8 | AK291057 | 0 | 0 | 9999 | 9999 | 1.0000 | 0.000 | 1.00 | 0 | 0 |
| DPP8 | AK296915 | 52 | 15 | 0.4870 | 0.0615 | 0.2987 | −1.743 | 3.35 | 37 | 5.22 |
| DPP8 | AK302638 | 31 | 56 | 1.0000 | 0.3050 | 1.7418 | 0.801 | 1.74 | 24 | 4.59 |
| DPP8 | BC040203 | 15 | 20 | 1.0000 | 0.7285 | 1.3128 | 0.393 | 1.31 | 5 | 2.29 |
| DPP8 | NM_017743 | 83 | 50 | 0.9406 | 0.2435 | 0.6102 | −0.713 | 1.64 | 33 | 5.03 |
| DPP8 | NM_130434 | 919 | 1097 | 0.6479 | 0.1161 | 1.1942 | 0.256 | 1.19 | 179 | 7.48 |
| DPP8 | NM_197960 | 50 | 0 | 0.0000 | 0.0000 | 0.0196 | −5.673 | 51.03 | 50 | 5.64 |
| DPP8 | NM_197961 | 148 | 181 | 1.0000 | 0.5905 | 1.2269 | 0.295 | 1.23 | 34 | 5.08 |
| DSEL | CCDS11995 | 613 | 333 | 0.0044 | 0.0001 | 0.5446 | −0.877 | 1.84 | 280 | 8.13 |
| DSEL | NM_032160 | 3514 | 1726 | 0.0000 | 0.0000 | 0.4915 | −1.025 | 2.03 | 1787 | 10.80 |
| EEA1 | NM_003566 | 1886 | 638 | 0.0000 | 0.0000 | 0.3386 | −1.562 | 2.95 | 1248 | 10.29 |
| EFCAB14 | AK295722 | 142 | 442 | 0.0000 | 0.0000 | 3.1079 | 1.636 | 3.11 | 301 | 8.23 |
| EFCAB14 | AK296777 | 264 | 366 | 0.5749 | 0.0914 | 1.3839 | 0.469 | 1.38 | 102 | 6.67 |
| EFCAB14 | NM_014774 | 2205 | 2166 | 1.0000 | 0.8137 | 0.9825 | −0.026 | 1.02 | 39 | 5.27 |
| EIF2B3 | NM_001166588 | 415 | 71 | 0.0000 | 0.0000 | 0.1736 | −2.526 | 5.76 | 344 | 8.43 |
| EIF2B3 | NM_001261418 | 10 | 0 | 0.1188 | 0.0061 | 0.0882 | −3.504 | 11.34 | 10 | 3.37 |
| EIF2B3 | NM_020365 | 585 | 119 | 0.0000 | 0.0000 | 0.2051 | −2.285 | 4.87 | 465 | 8.86 |
| EIF4G1 | AB210013 | 85 | 32 | 0.3996 | 0.0409 | 0.3868 | −1.370 | 2.59 | 53 | 5.72 |
| EIF4G1 | AF002815 | 10 | 13 | 1.0000 | 0.7826 | 1.3193 | 0.400 | 1.32 | 3 | 1.80 |
| EIF4G1 | AK096719 | 37 | 0 | 0.0005 | 0.0000 | 0.0265 | −5.239 | 37.76 | 37 | 5.20 |
| EIF4G1 | AK128378 | 72 | 508 | 0.0000 | 0.0000 | 6.9237 | 2.792 | 6.92 | 435 | 8.77 |
| EIF4G1 | AK226160 | 1133 | 1225 | 1.0000 | 0.4230 | 1.0814 | 0.113 | 1.08 | 92 | 6.53 |
| EIF4G1 | BC065256 | 339 | 215 | 0.3318 | 0.0294 | 0.6366 | −0.652 | 1.57 | 123 | 6.95 |
| EIF4G1 | NM_001194946 | 0 | 0 | 9999 | 9999 | 1.0000 | 0.000 | 1.00 | 0 | 0 |
| EIF4G1 | NM_001194947 | 26 | 15 | 1.0000 | 0.4213 | 0.5727 | −0.804 | 1.75 | 12 | 3.54 |
| EIF4G1 | NM_004953 | 87 | 135 | 1.0000 | 0.3950 | 1.5432 | 0.626 | 1.54 | 48 | 5.58 |
| EIF4G1 | NM_182917 | 3728 | 3653 | 1.0000 | 0.8630 | 0.9798 | −0.029 | 1.02 | 75 | 6.24 |
| EIF4G1 | NM_198241 | 8151 | 6747 | 0.0567 | 0.0022 | 0.8278 | −0.273 | 1.21 | 1404 | 10.46 |
| EIF4G1 | NM_198242 | 3446 | 2843 | 0.1410 | 0.0077 | 0.8249 | −0.278 | 1.21 | 603 | 9.24 |

TABLE 10-continued

RNA Abundance Modulation

| Gene | Trx_ID | ave DMSO | ave Cpd | padj (q val, FDR) | ttest (p val) | FC (x + 1) | L$_2$FC (x + 1) | amp FC (x + 1) | abs (Cpd-DMSO) | L$_2$abs (Cpd-DMSO) |
|---|---|---|---|---|---|---|---|---|---|---|
| EIF4G1 | NM_198244 | 2947 | 4416 | 0.0000 | 0.0000 | 1.4982 | 0.583 | 1.50 | 1469 | 10.52 |
| EIF4G3 | AK294883 | 336 | 117 | 0.0008 | 0.0000 | 0.3507 | −1.512 | 2.85 | 219 | 7.77 |
| EIF4G3 | AK302087 | 139 | 124 | 1.0000 | 0.7603 | 0.8922 | −0.165 | 1.12 | 15 | 3.91 |
| EIF4G3 | BC094683 | 0 | 0 | 9999 | 9999 | 1.0000 | 0.000 | 1.00 | 0 | 0 |
| EIF4G3 | BC144335 | 1393 | 1789 | 0.1462 | 0.0082 | 1.2841 | 0.361 | 1.28 | 396 | 8.63 |
| EIF4G3 | NM_001198801 | 891 | 970 | 1.0000 | 0.4450 | 1.0875 | 0.121 | 1.09 | 78 | 6.29 |
| EIF4G3 | NM_001198802 | 123 | 262 | 0.1063 | 0.0052 | 2.1198 | 1.084 | 2.12 | 139 | 7.12 |
| EIF4G3 | NM_001198803 | 37 | 43 | 1.0000 | 0.7222 | 1.1602 | 0.214 | 1.16 | 6 | 2.62 |
| EIF4G3 | NM_003760 | 864 | 719 | 0.6708 | 0.1241 | 0.8323 | −0.265 | 1.20 | 145 | 7.18 |
| ELF2 | AK303782 | 30 | 30 | 1.0000 | 0.9736 | 0.9981 | −0.003 | 1.00 | 0 | −4.08 |
| ELF2 | DQ359746 | 5 | 5 | 1.0000 | 1.0000 | 1.0612 | 0.086 | 1.06 | 0 | −1.52 |
| ELF2 | NM_001276457 | 35 | 25 | 1.0000 | 0.8733 | 0.7383 | −0.438 | 1.35 | 9 | 3.22 |
| ELF2 | NM_001276458 | 189 | 33 | 0.0000 | 0.0000 | 0.1768 | −2.500 | 5.66 | 156 | 7.29 |
| ELF2 | NM_001276459 | 53 | 78 | 1.0000 | 0.4779 | 1.4662 | 0.552 | 1.47 | 25 | 4.64 |
| ELF2 | NM_006874 | 237 | 335 | 0.5557 | 0.0835 | 1.4087 | 0.494 | 1.41 | 97 | 6.61 |
| ELF2 | NM_201999 | 460 | 426 | 1.0000 | 0.6418 | 0.9267 | −0.110 | 1.08 | 34 | 5.08 |
| ENG | BC031967 | 12 | 14 | 1.0000 | 0.8712 | 1.1637 | 0.219 | 1.16 | 2 | 1.09 |
| ENG | NM_000118 | 489 | 322 | 0.2259 | 0.0159 | 0.6583 | −0.603 | 1.52 | 168 | 7.39 |
| ENG | NM_001114753 | 7595 | 7226 | 1.0000 | 0.4532 | 0.9515 | −0.072 | 1.05 | 369 | 8.53 |
| ENG | NM_001278138 | 561 | 5 | 0.0000 | 0.0000 | 0.0113 | −6.465 | 88.32 | 555 | 9.12 |
| ENPP2 | AK296027 | 48 | 39 | 1.0000 | 0.6544 | 0.8110 | −0.302 | 1.23 | 9 | 3.22 |
| ENPP2 | NM_001040092 | 3415 | 3117 | 0.8634 | 0.2005 | 0.9129 | −0.131 | 1.10 | 297 | 8.22 |
| ENPP2 | NM_001130863 | 95 | 3 | 0.0000 | 0.0000 | 0.0382 | −4.709 | 26.15 | 92 | 6.53 |
| ENPP2 | NM_006209 | 2380 | 2186 | 1.0000 | 0.3420 | 0.9187 | −0.122 | 1.09 | 194 | 7.60 |
| ENPP2 | NR_045555 | 409 | 310 | 0.7290 | 0.1441 | 0.7592 | −0.397 | 1.32 | 99 | 6.63 |
| EPN1 | AK314690 | 1038 | 1237 | 0.5128 | 0.0689 | 1.1913 | 0.253 | 1.19 | 199 | 7.64 |
| EPN1 | NM_001130071 | 41 | 288 | 0.0000 | 0.0000 | 6.9465 | 2.796 | 6.95 | 247 | 7.95 |
| EPN1 | NM_001130072 | 2032 | 1844 | 0.8726 | 0.2041 | 0.9076 | −0.140 | 1.10 | 188 | 7.55 |
| EPN1 | NM_013333 | 287 | 52 | 0.0000 | 0.0000 | 0.1827 | −2.452 | 5.47 | 236 | 7.88 |
| EXTL2 | NM_001033025 | 757 | 259 | 0.0000 | 0.0000 | 0.3428 | −1.545 | 2.92 | 498 | 8.96 |
| EXTL2 | NM_001261440 | 74 | 30 | 0.6227 | 0.1074 | 0.4153 | −1.268 | 2.41 | 44 | 5.46 |
| EXTL2 | NM_001261441 | 20 | 99 | 0.0332 | 0.0011 | 4.6888 | 2.229 | 4.69 | 78 | 6.29 |
| EXTL2 | NM_001261442 | 0 | 9 | 0.2243 | 0.0157 | 10.3680 | 3.374 | 10.37 | 9 | 3.23 |
| EXTL2 | NM_001439 | 151 | 13 | 0.0000 | 0.0000 | 0.0922 | −3.438 | 10.84 | 138 | 7.11 |
| EYA3 | AK295745 | 524 | 716 | 0.2302 | 0.0164 | 1.3652 | 0.449 | 1.37 | 192 | 7.58 |
| EYA3 | AK298129 | 67 | 0 | 0.0000 | 0.0000 | 0.0148 | −6.079 | 67.62 | 67 | 6.06 |
| EYA3 | AK303664 | 0 | 0 | 9999 | 9999 | 1.0000 | 0.000 | 1.00 | 0 | 0 |
| EYA3 | BC029500 | 20 | 29 | 1.0000 | 0.4970 | 1.4823 | 0.568 | 1.48 | 10 | 3.31 |
| EYA3 | BC041667 | 19 | 10 | 1.0000 | 0.4409 | 0.5374 | −0.896 | 1.86 | 9 | 3.20 |
| EYA3 | NM_001990 | 256 | 250 | 1.0000 | 0.6909 | 0.9778 | −0.032 | 1.02 | 6 | 2.51 |
| FAF1 | AF094700 | 41 | 20 | 0.9827 | 0.2735 | 0.4927 | −1.021 | 2.03 | 21 | 4.42 |
| FAF1 | AK293659 | 12 | 7 | 1.0000 | 0.6425 | 0.6599 | −0.600 | 1.52 | 4 | 2.09 |
| FAF1 | NM_007051 | 1714 | 374 | 0.0000 | 0.0000 | 0.2186 | −2.193 | 4.57 | 1340 | 10.39 |
| FAM198B | AK172805 | 1 | 1 | 1.0000 | 0.8442 | 0.7977 | −0.326 | 1.25 | 0 | −1.30 |
| FAM198B | NM_001031700 | 0 | 9 | 0.2691 | 0.0211 | 10.0951 | 3.336 | 10.10 | 9 | 3.19 |
| FAM198B | NM_001128424 | 79 | 11 | 0.0079 | 0.0002 | 0.1560 | −2.680 | 6.41 | 67 | 6.08 |
| FAM198B | NM_016613 | 325 | 205 | 0.3999 | 0.0412 | 0.6342 | −0.657 | 1.58 | 119 | 6.90 |
| FAM3C | NM_001040020 | 581 | 278 | 0.0030 | 0.0001 | 0.4791 | −1.062 | 2.09 | 303 | 8.24 |
| FAM3C | NM_014888 | 1655 | 2132 | 0.1336 | 0.0072 | 1.2882 | 0.365 | 1.29 | 477 | 8.90 |
| FBXO10 | BC125124 | 0 | 11 | 0.1698 | 0.0101 | 11.9266 | 3.576 | 11.93 | 11 | 3.45 |
| FBXO10 | BC125125 | 51 | 289 | 0.0000 | 0.0000 | 5.5859 | 2.482 | 5.59 | 238 | 7.90 |
| FBXO10 | NM_012166 | 266 | 427 | 0.1916 | 0.0123 | 1.6033 | 0.681 | 1.60 | 161 | 7.33 |
| FBXO18 | NM_001258452 | 36 | 33 | 1.0000 | 0.8620 | 0.9167 | −0.125 | 1.09 | 3 | 1.62 |
| FBXO18 | NM_001258453 | 9 | 15 | 1.0000 | 0.5412 | 1.6800 | 0.748 | 1.68 | 7 | 2.73 |
| FBXO18 | NM_032807 | 78 | 20 | 0.1027 | 0.0049 | 0.2659 | −1.911 | 3.76 | 58 | 5.85 |
| FBXO18 | NM_178150 | 1840 | 644 | 0.0000 | 0.0000 | 0.3501 | −1.514 | 2.86 | 1197 | 10.22 |
| FBXO31 | AF318348 | 8 | 134 | 0.0000 | 0.0000 | 15.8665 | 3.988 | 15.87 | 126 | 6.98 |
| FBXO31 | NM_024735 | 566 | 136 | 0.0000 | 0.0000 | 0.2416 | −2.049 | 4.14 | 430 | 8.75 |
| FBXO31 | NR_024568 | 264 | 66 | 0.0002 | 0.0000 | 0.2551 | −1.971 | 3.92 | 197 | 7.62 |
| FBXO9 | NM_012347 | 21 | 7 | 0.7719 | 0.1650 | 0.3811 | −1.392 | 2.62 | 13 | 3.75 |
| FBXO9 | NM_033480 | 1069 | 399 | 0.0000 | 0.0000 | 0.3739 | −1.419 | 2.67 | 670 | 9.39 |
| FBXO9 | NM_033481 | 35 | 4 | 0.2034 | 0.0134 | 0.1451 | −2.785 | 6.89 | 30 | 4.93 |
| FER | AK293376 | 10 | 4 | 1.0000 | 0.4556 | 0.4452 | −1.167 | 2.25 | 6 | 2.62 |
| FER | AK296874 | 0 | 0 | 9999 | 9999 | 1.0000 | 0.000 | 1.00 | 0 | 0 |
| FER | AK299855 | 92 | 8 | 0.0015 | 0.0000 | 0.0978 | −3.354 | 10.23 | 84 | 6.39 |
| FER | BC058030 | 3 | 1 | 1.0000 | 0.3526 | 0.3959 | −1.337 | 2.53 | 2 | 1.28 |
| FER | NM_005246 | 340 | 67 | 0.0000 | 0.0000 | 0.1992 | −2.328 | 5.02 | 273 | 8.09 |
| FEZ1 | AK296554 | 0 | 3 | 0.6797 | 0.1270 | 3.6648 | 1.874 | 3.66 | 3 | 1.41 |
| FEZ1 | CCDS44758 | 5 | 7 | 1.0000 | 0.8228 | 1.3371 | 0.419 | 1.34 | 2 | 0.94 |
| FEZ1 | NM_005103 | 266 | 466 | 0.0569 | 0.0022 | 1.7509 | 0.808 | 1.75 | 200 | 7.65 |
| FEZ1 | NM_022549 | 70 | 0 | 0.0000 | 0.0000 | 0.0194 | −5.689 | 51.59 | 70 | 6.13 |
| FHOD3 | AB051482 | 279 | 72 | 0.0001 | 0.0000 | 0.2600 | −1.943 | 3.85 | 207 | 7.70 |
| FHOD3 | AB084087 | 101 | 0 | 0.0000 | 0.0000 | 0.0098 | −6.669 | 101.76 | 101 | 6.65 |
| FHOD3 | AK128053 | 15 | 15 | 1.0000 | 0.9584 | 0.9777 | −0.032 | 1.02 | 0 | −1.49 |

TABLE 10-continued

RNA Abundance Modulation

| Gene | Trx_ID | ave DMSO | ave Cpd | padj (q val, FDR) | ttest (p val) | FC (x + 1) | $L_2$FC (x + 1) | amp FC (x + 1) | abs (Cpd-DMSO) | $L_2$abs (Cpd-DMSO) |
|---|---|---|---|---|---|---|---|---|---|---|
| FHOD3 | AK308859 | 19 | 0 | 0.0216 | 0.0006 | 0.0496 | −4.335 | 20.18 | 19 | 4.26 |
| FHOD3 | BC058897 | 65 | 8 | 0.0204 | 0.0006 | 0.1396 | −2.841 | 7.17 | 56 | 5.82 |
| FHOD3 | HM191478 | 14 | 2 | 0.5465 | 0.0809 | 0.1852 | −2.433 | 5.40 | 12 | 3.63 |
| FHOD3 | NM_025135 | 452 | 123 | 0.0000 | 0.0000 | 0.2740 | −1.868 | 3.65 | 329 | 8.36 |
| FLII | AK295814 | 5 | 15 | 1.0000 | 0.3214 | 2.6518 | 1.407 | 2.65 | 10 | 3.31 |
| FLII | BC021885 | 3447 | 3763 | 0.9644 | 0.2594 | 1.0918 | 0.127 | 1.09 | 317 | 8.31 |
| FLII | NM_001256264 | 155 | 0 | 0.0000 | 0.0000 | 0.0083 | −6.912 | 120.41 | 155 | 7.28 |
| FLII | NM_001256265 | 14 | 0 | 0.0533 | 0.0020 | 0.0660 | −3.921 | 15.14 | 14 | 3.82 |
| FLII | NM_002018 | 3732 | 3091 | 0.2184 | 0.0150 | 0.8283 | −0.272 | 1.21 | 641 | 9.32 |
| FN1 | AB385106 | 220995 | 182630 | 0.0167 | 0.0005 | 0.8264 | −0.275 | 1.21 | 38365 | 15.23 |
| FN1 | AJ320525 | 157 | 61 | 0.1521 | 0.0087 | 0.3908 | −1.355 | 2.56 | 96 | 6.59 |
| FN1 | AJ320526 | 35 | 18 | 1.0000 | 0.3824 | 0.5268 | −0.925 | 1.90 | 17 | 4.11 |
| FN1 | AJ320527 | 6017 | 2876 | 0.0000 | 0.0000 | 0.4780 | −1.065 | 2.09 | 3142 | 11.62 |
| FN1 | AK300246 | 9500 | 0 | 0.0000 | 0.0000 | 0.0001 | −13.214 | 9501.09 | 9500 | 13.21 |
| FN1 | BC143754 | 53588 | 45132 | 0.0269 | 0.0009 | 0.8422 | −0.248 | 1.19 | 8457 | 13.05 |
| FN1 | BX537590 | 93054 | 84328 | 0.4776 | 0.0588 | 0.9062 | −0.142 | 1.10 | 8726 | 13.09 |
| FN1 | BX641150 | 15100 | 13018 | 0.1342 | 0.0072 | 0.8621 | −0.214 | 1.16 | 2082 | 11.02 |
| FN1 | CR749316 | 2703 | 1933 | 0.0017 | 0.0000 | 0.7153 | −0.483 | 1.40 | 770 | 9.59 |
| FN1 | EF550133 | 37795 | 33001 | 0.1287 | 0.0068 | 0.8732 | −0.196 | 1.15 | 4794 | 12.23 |
| FN1 | EF550135 | 128 | 110 | 1.0000 | 0.6686 | 0.8605 | −0.217 | 1.16 | 18 | 4.17 |
| FN1 | NM_002026 | 573237 | 476364 | 0.0584 | 0.0023 | 0.8310 | −0.267 | 1.20 | 96874 | 16.56 |
| FN1 | NM_054034 | 6130 | 4137 | 0.0000 | 0.0000 | 0.6749 | −0.567 | 1.48 | 1993 | 10.96 |
| FN1 | NM_212474 | 17723 | 11620 | 0.0000 | 0.0000 | 0.6557 | −0.609 | 1.53 | 6103 | 12.58 |
| FN1 | NM_212476 | 332753 | 273686 | 0.0207 | 0.0006 | 0.8225 | −0.282 | 1.22 | 59068 | 15.85 |
| FN1 | NM_212478 | 148299 | 127827 | 0.1013 | 0.0049 | 0.8620 | −0.214 | 1.16 | 20472 | 14.32 |
| FN1 | NM_212482 | 137283 | 123048 | 0.3966 | 0.0401 | 0.8963 | −0.158 | 1.12 | 14235 | 13.80 |
| FNBP1 | AK000975 | 275 | 256 | 1.0000 | 0.8255 | 0.9310 | −0.103 | 1.07 | 19 | 4.25 |
| FNBP1 | AK001616 | 157 | 161 | 1.0000 | 0.9748 | 1.0235 | 0.034 | 1.02 | 4 | 1.89 |
| FNBP1 | AK023681 | 4 | 8 | 1.0000 | 0.7719 | 1.6722 | 0.742 | 1.67 | 4 | 1.86 |
| FNBP1 | BC143513 | 1223 | 965 | 0.4217 | 0.0458 | 0.7896 | −0.341 | 1.27 | 257 | 8.01 |
| FNBP1 | BC143514 | 108 | 145 | 1.0000 | 0.3025 | 1.3375 | 0.419 | 1.34 | 37 | 5.20 |
| FNBP1 | BC143515 | 158 | 39 | 0.0096 | 0.0002 | 0.2547 | −1.973 | 3.93 | 118 | 6.89 |
| FNBP1 | NM_015033 | 262 | 252 | 1.0000 | 0.4206 | 0.9609 | −0.057 | 1.04 | 10 | 3.36 |
| FOCAD | AB058700 | 300 | 118 | 0.0062 | 0.0001 | 0.3941 | −1.343 | 2.54 | 183 | 7.51 |
| FOCAD | NM_017794 | 1268 | 775 | 0.0009 | 0.0000 | 0.6116 | −0.709 | 1.64 | 493 | 8.95 |
| FOSL1 | AK299050 | 476 | 1156 | 0.0000 | 0.0000 | 2.4253 | 1.278 | 2.43 | 680 | 9.41 |
| FOSL1 | NM_005438 | 4404 | 5566 | 0.0256 | 0.0008 | 1.2638 | 0.338 | 1.26 | 1162 | 10.18 |
| FOXM1 | NM_001243088 | 1084 | 1360 | 0.3799 | 0.0376 | 1.2539 | 0.326 | 1.25 | 276 | 8.11 |
| FOXM1 | NM_001243089 | 496 | 438 | 1.0000 | 0.4323 | 0.8836 | −0.178 | 1.13 | 58 | 5.85 |
| FOXM1 | NM_021953 | 5033 | 1391 | 0.0000 | 0.0000 | 0.2765 | −1.855 | 3.62 | 3642 | 11.83 |
| FOXM1 | NM_202002 | 573 | 5340 | 0.0000 | 0.0000 | 9.3116 | 3.219 | 9.31 | 4767 | 12.22 |
| GABPB1 | AK303901 | 15 | 29 | 1.0000 | 0.4389 | 1.8458 | 0.884 | 1.85 | 14 | 3.76 |
| GABPB1 | D13316 | 79 | 48 | 0.8864 | 0.2102 | 0.6131 | −0.706 | 1.63 | 31 | 4.96 |
| GABPB1 | NM_002041 | 38 | 152 | 0.0147 | 0.0004 | 3.9294 | 1.974 | 3.93 | 114 | 6.83 |
| GABPB1 | NM_005254 | 440 | 274 | 0.2168 | 0.0148 | 0.6249 | −0.678 | 1.60 | 165 | 7.37 |
| GABPB1 | NM_016654 | 68 | 290 | 0.0000 | 0.0000 | 4.2214 | 2.078 | 4.22 | 222 | 7.80 |
| GABPB1 | NM_016655 | 90 | 15 | 0.0184 | 0.0005 | 0.1780 | −2.490 | 5.62 | 75 | 6.23 |
| GABPB1 | NM_181427 | 49 | 65 | 1.0000 | 0.4851 | 1.3070 | 0.386 | 1.31 | 15 | 3.94 |
| GALC | AK302683 | 2 | 0 | 0.4853 | 0.0610 | 0.2862 | −1.805 | 3.49 | 2 | 1.32 |
| GALC | D25284 | 2 | 0 | 0.5253 | 0.0735 | 0.3484 | −1.521 | 2.87 | 2 | 0.90 |
| GALC | NM_000153 | 469 | 95 | 0.0000 | 0.0000 | 0.2045 | −2.289 | 4.89 | 374 | 8.55 |
| GALC | NM_001201401 | 0 | 0 | 9999 | 9999 | 1.0000 | 0.000 | 1.00 | 0 | 0 |
| GALC | NM_001201402 | 0 | 0 | 9999 | 9999 | 1.0000 | 0.000 | 1.00 | 0 | 0 |
| GALNT1 | AK293062 | 53 | 0 | 0.0000 | 0.0000 | 0.0184 | −5.766 | 54.43 | 53 | 5.74 |
| GALNT1 | BC038440 | 15 | 14 | 1.0000 | 0.7915 | 0.9199 | −0.120 | 1.09 | 1 | 0.36 |
| GALNT1 | BC047746 | 4 | 3 | 1.0000 | 0.8962 | 0.8411 | −0.250 | 1.19 | 1 | −0.29 |
| GALNT1 | NM_020474 | 2750 | 2824 | 1.0000 | 0.7666 | 1.0267 | 0.038 | 1.03 | 74 | 6.20 |
| GCFC2 | EF158468 | 0 | 15 | 0.0810 | 0.0036 | 15.5688 | 3.961 | 15.57 | 15 | 3.86 |
| GCFC2 | EF158469 | 0 | 40 | 0.0005 | 0.0000 | 40.5213 | 5.341 | 40.52 | 40 | 5.30 |
| GCFC2 | NM_001201334 | 119 | 65 | 0.7058 | 0.1364 | 0.5494 | −0.864 | 1.82 | 54 | 5.75 |
| GCFC2 | NM_001201335 | 43 | 22 | 0.9601 | 0.2566 | 0.5138 | −0.961 | 1.95 | 21 | 4.42 |
| GCFC2 | NM_003203 | 106 | 0 | 0.0000 | 0.0094 | 0.0094 | −6.739 | 106.82 | 106 | 6.73 |
| GGCT | AK021779 | 3 | 3 | 1.0000 | 1.0000 | 0.9804 | −0.029 | 1.02 | 0 | −3.66 |
| GGCT | NM_001199815 | 3 | 15 | 0.6970 | 0.1326 | 4.4152 | 2.142 | 4.42 | 12 | 3.59 |
| GGCT | NM_001199816 | 14 | 48 | 0.5149 | 0.0695 | 3.2301 | 1.692 | 3.23 | 34 | 5.07 |
| GGCT | NM_001199817 | 3 | 0 | 0.9777 | 0.2675 | 0.3219 | −1.635 | 3.11 | 3 | 1.46 |
| GGCT | NM_024051 | 540 | 915 | 0.0037 | 0.0001 | 1.6920 | 0.759 | 1.69 | 375 | 8.55 |
| GGCT | NR_037669 | 232 | 0 | 0.0000 | 0.0000 | 0.0043 | −7.865 | 233.21 | 232 | 7.86 |
| GIGYF2 | AK299418 | 78 | 47 | 0.8891 | 0.2112 | 0.6148 | −0.702 | 1.63 | 30 | 4.92 |
| GIGYF2 | AK302998 | 343 | 352 | 1.0000 | 0.8814 | 1.0257 | 0.037 | 1.03 | 9 | 3.14 |
| GIGYF2 | BC043402 | 183 | 172 | 1.0000 | 0.8675 | 0.9390 | −0.091 | 1.06 | 11 | 3.49 |
| GIGYF2 | BX647172 | 4 | 7 | 1.0000 | 0.7814 | 1.5076 | 0.592 | 1.51 | 3 | 1.45 |
| GIGYF2 | NM_001103146 | 1241 | 881 | 0.0420 | 0.0015 | 0.7100 | −0.494 | 1.41 | 360 | 8.49 |
| GIGYF2 | NM_001103147 | 45 | 47 | 1.0000 | 0.8566 | 1.0454 | 0.064 | 1.05 | 2 | 1.05 |

TABLE 10-continued

RNA Abundance Modulation

| Gene | Trx_ID | ave DMSO | ave Cpd | padj (q val, FDR) | ttest (p val) | FC (x + 1) | L₂FC (x + 1) | amp FC (x + 1) | abs (Cpd-DMSO) | L₂abs (Cpd-DMSO) |
|---|---|---|---|---|---|---|---|---|---|---|
| GIGYF2 | NM_001103148 | 101 | 108 | 1.0000 | 0.7882 | 1.0657 | 0.092 | 1.07 | 7 | 2.75 |
| GIGYF2 | NM_015575 | 209 | 556 | 0.0000 | 0.0000 | 2.6539 | 1.408 | 2.65 | 347 | 8.44 |
| GIGYF2 | NR_103492 | 3 | 0 | 0.5184 | 0.0711 | 0.2726 | −1.875 | 3.67 | 3 | 1.42 |
| GIGYF2 | NR_103493 | 16 | 20 | 1.0000 | 0.8220 | 1.2237 | 0.291 | 1.22 | 4 | 1.96 |
| GIGYF2 | NR_103494 | 9 | 2 | 0.7754 | 0.1662 | 0.2660 | −1.911 | 3.76 | 7 | 2.80 |
| GIGYF2 | NR_103495 | 0 | 2 | 0.7358 | 0.1484 | 2.8211 | 1.496 | 2.82 | 2 | 0.86 |
| GMIP | AK297220 | 53 | 0 | 0.0000 | 0.0000 | 0.0186 | −5.751 | 53.85 | 53 | 5.72 |
| GMIP | BC144142 | 34 | 67 | 0.7054 | 0.1362 | 1.9199 | 0.941 | 1.92 | 32 | 5.02 |
| GMIP | NM_016573 | 61 | 107 | 0.7634 | 0.1612 | 1.7519 | 0.809 | 1.75 | 46 | 5.53 |
| GNAS | AJ224867 | 1 | 2 | 1.0000 | 0.9094 | 1.2716 | 0.347 | 1.27 | 1 | −0.66 |
| GNAS | AK054862 | 54 | 63 | 1.0000 | 0.7344 | 1.1709 | 0.228 | 1.17 | 9 | 3.22 |
| GNAS | AK122771 | 140 | 130 | 1.0000 | 0.8583 | 0.9268 | −0.110 | 1.08 | 10 | 3.37 |
| GNAS | AK315874 | 74 | 0 | 0.0000 | 0.0000 | 0.0133 | −6.233 | 75.24 | 74 | 6.21 |
| GNAS | BC036081 | 3 | 0 | 0.4853 | 0.0612 | 0.2845 | −1.813 | 3.51 | 3 | 1.33 |
| GNAS | CCDS13471 | 0 | 0 | 9999 | 9999 | 1.0000 | 0.000 | 1.00 | 0 | 0 |
| GNAS | NM_000516 | 6795 | 6567 | 1.0000 | 0.5789 | 0.9664 | −0.049 | 1.03 | 228 | 7.83 |
| GNAS | NM_001077488 | 2509 | 2733 | 1.0000 | 0.2932 | 1.0895 | 0.124 | 1.09 | 225 | 7.81 |
| GNAS | NM_001077489 | 4736 | 4158 | 0.4409 | 0.0493 | 0.8780 | −0.188 | 1.14 | 578 | 9.17 |
| GNAS | NM_016592 | 7 | 6 | 1.0000 | 1.0000 | 0.9649 | −0.051 | 1.04 | 0 | −1.89 |
| GNAS | NM_080425 | 1 | 1 | 1.0000 | 1.0000 | 0.9867 | −0.019 | 1.01 | 0 | −5.53 |
| GNAS | NM_080426 | 10113 | 8794 | 0.2687 | 0.0209 | 0.8696 | −0.202 | 1.15 | 1319 | 10.36 |
| GNAS | NR_003259 | 11294 | 13286 | 0.1275 | 0.0067 | 1.1764 | 0.234 | 1.18 | 1992 | 10.96 |
| GNL3L | BC011720 | 277 | 279 | 1.0000 | 1.0000 | 1.0060 | 0.009 | 1.01 | 2 | 0.75 |
| GNL3L | NM_001184819 | 101 | 12 | 0.0021 | 0.0000 | 0.1297 | −2.946 | 7.71 | 89 | 6.47 |
| GNL3L | NM_019067 | 632 | 856 | 0.3100 | 0.0263 | 1.3536 | 0.437 | 1.35 | 224 | 7.81 |
| GOLGB1 | AK296903 | 111 | 48 | 0.4850 | 0.0602 | 0.4382 | −1.190 | 2.28 | 63 | 5.97 |
| GOLGB1 | BC065301 | 2 | 25 | 0.2173 | 0.0149 | 10.0548 | 3.330 | 10.05 | 23 | 4.54 |
| GOLGB1 | NM_001256486 | 648 | 240 | 0.0000 | 0.0000 | 0.3718 | −1.427 | 2.69 | 408 | 8.67 |
| GOLGB1 | NM_001256487 | 6 | 0 | 0.2535 | 0.0192 | 0.1382 | −2.855 | 7.23 | 6 | 2.64 |
| GOLGB1 | NM_001256488 | 673 | 352 | 0.0018 | 0.0000 | 0.5243 | −0.932 | 1.91 | 320 | 8.32 |
| GOLGB1 | NM_004487 | 446 | 288 | 0.1005 | 0.0048 | 0.6462 | −0.630 | 1.55 | 158 | 7.30 |
| GPR89A | AK001354 | 2 | 5 | 1.0000 | 0.5657 | 1.8754 | 0.907 | 1.88 | 3 | 1.40 |
| GPR89A | AK094228 | 1 | 3 | 1.0000 | 0.7635 | 1.4980 | 0.583 | 1.50 | 1 | 0.25 |
| GPR89A | AK299995 | 0 | 0 | 9999 | 9999 | 1.0000 | 0.000 | 1.00 | 0 | 0 |
| GPR89A | AK301939 | 44 | 32 | 1.0000 | 0.6967 | 0.7276 | −0.459 | 1.37 | 12 | 3.61 |
| GPR89A | AK302266 | 13 | 32 | 0.9827 | 0.2715 | 2.2851 | 1.192 | 2.29 | 19 | 4.21 |
| GPR89A | NM_001097612 | 602 | 667 | 1.0000 | 0.4175 | 1.1091 | 0.149 | 1.11 | 66 | 6.04 |
| GPR89A | NM_001097613 | 7 | 0 | 0.2259 | 0.0160 | 0.1273 | −2.974 | 7.86 | 7 | 2.78 |
| GPR89A | NR_036541 | 54 | 0 | 0.0000 | 0.0000 | 0.0182 | −5.783 | 55.08 | 54 | 5.76 |
| GPSM2 | AB445462 | 488 | 361 | 0.5390 | 0.0771 | 0.7410 | −0.432 | 1.35 | 127 | 6.98 |
| GPSM2 | AK295563 | 625 | 277 | 0.0000 | 0.0000 | 0.4438 | −1.172 | 2.25 | 348 | 8.44 |
| GPSM2 | NM_013296 | 926 | 687 | 0.2280 | 0.0162 | 0.7418 | −0.431 | 1.35 | 239 | 7.90 |
| GREM1 | CCDS10029 | 642 | 119 | 0.0000 | 0.0000 | 0.1867 | −2.422 | 5.36 | 523 | 9.03 |
| GREM1 | NM_001191322 | 13598 | 16405 | 0.0852 | 0.0038 | 1.2064 | 0.271 | 1.21 | 2807 | 11.45 |
| GREM1 | NM_001191323 | 2860 | 2090 | 0.0079 | 0.0002 | 0.7308 | −0.452 | 1.37 | 770 | 9.59 |
| GREM1 | NM_013372 | 155658 | 116514 | 0.0000 | 0.0000 | 0.7485 | −0.418 | 1.34 | 39143 | 15.26 |
| GRK6 | AK056697 | 151 | 0 | 0.0000 | 0.0000 | 0.0066 | −7.249 | 152.12 | 151 | 7.24 |
| GRK6 | NM_001004105 | 317 | 407 | 0.6693 | 0.1234 | 1.2813 | 0.358 | 1.28 | 90 | 6.48 |
| GRK6 | NM_001004106 | 723 | 538 | 0.2769 | 0.0220 | 0.7446 | −0.425 | 1.34 | 185 | 7.53 |
| GRK6 | NM_002082 | 206 | 204 | 1.0000 | 0.9291 | 0.9887 | −0.016 | 1.01 | 2 | 1.23 |
| GTF2H2B | BC141603 | 119 | 279 | 0.0216 | 0.0006 | 2.3278 | 1.219 | 2.33 | 159 | 7.32 |
| GTF2H2B | BT006773 | 10 | 9 | 1.0000 | 0.9212 | 0.9285 | −0.107 | 1.08 | 1 | −0.34 |
| GTF2H2B | BX537982 | 1 | 0 | 1.0000 | 0.7343 | 0.8029 | −0.317 | 1.25 | 0 | −1.64 |
| GTF2H2B | NR_033417 | 84 | 0 | 0.0000 | 0.0000 | 0.0118 | −6.411 | 85.11 | 84 | 6.39 |
| HAT1 | AK309001 | 3 | 9 | 1.0000 | 0.3739 | 2.4649 | 1.302 | 2.46 | 6 | 2.56 |
| HAT1 | NM_003642 | 2423 | 3039 | 0.0974 | 0.0046 | 1.2542 | 0.327 | 1.25 | 616 | 9.27 |
| HAT1 | NR_027862 | 70 | 6 | 0.0074 | 0.0002 | 0.0997 | −3.326 | 10.03 | 64 | 6.00 |
| HAUS3 | AK293948 | 283 | 202 | 0.6916 | 0.1311 | 0.7153 | −0.483 | 1.40 | 81 | 6.34 |
| HAUS3 | BC003648 | 55 | 90 | 0.8135 | 0.1810 | 1.6260 | 0.701 | 1.63 | 35 | 5.14 |
| HAUS3 | NM_024511 | 290 | 112 | 0.0041 | 0.0001 | 0.3879 | −1.366 | 2.58 | 178 | 7.48 |
| HEG1 | AB384586 | 15408 | 15673 | 1.0000 | 0.8960 | 1.0172 | 0.025 | 1.02 | 265 | 8.05 |
| HEG1 | AK074987 | 424 | 183 | 0.0005 | 0.0000 | 0.4337 | −1.205 | 2.31 | 241 | 7.91 |
| HEG1 | NM_020733 | 832 | 1390 | 0.0006 | 0.0000 | 1.6707 | 0.740 | 1.67 | 558 | 9.13 |
| HLA-A | AF287958 | 1 | 0 | 0.5736 | 0.0911 | 0.4430 | −1.175 | 2.26 | 1 | 0.33 |
| HLA-A | AF287958 | 14 | 5 | 1.0000 | 0.3829 | 0.3771 | −1.407 | 2.65 | 9 | 3.20 |
| HLA-A | AF287958 | 21 | 21 | 1.0000 | 0.9162 | 1.0130 | 0.019 | 1.01 | 0 | −1.80 |
| HLA-A | AF287958 | 3 | 1 | 1.0000 | 0.4593 | 0.4872 | −1.037 | 2.05 | 2 | 1.07 |
| HLA-A | AF287958 | 6 | 2 | 1.0000 | 0.3380 | 0.3572 | −1.485 | 2.80 | 5 | 2.18 |
| HLA-A | AF287958 | 1 | 0 | 1.0000 | 0.3241 | 0.6140 | −0.704 | 1.63 | 1 | −0.67 |
| HLA-A | AK125608 | 67 | 56 | 1.0000 | 0.7026 | 0.8379 | −0.255 | 1.19 | 11 | 3.46 |
| HLA-A | AK125608 | 1 | 1 | 1.0000 | 1.0000 | 1.3226 | 0.403 | 1.32 | 1 | −0.93 |
| HLA-A | AK125608 | 121 | 124 | 1.0000 | 0.9737 | 1.0198 | 0.028 | 1.02 | 2 | 1.28 |
| HLA-A | AK125608 | 0 | 0 | 9999 | 9999 | 1.0000 | 0.000 | 1.00 | 0 | 0 |
| HLA-A | AK125608 | 0 | 0 | 9999 | 9999 | 1.0000 | 0.000 | 1.00 | 0 | 0 |

TABLE 10-continued

RNA Abundance Modulation

| Gene | Trx_ID | ave DMSO | ave Cpd | padj (q val, FDR) | ttest (p val) | FC (x + 1) | L₂FC (x + 1) | amp FC (x + 1) | abs (Cpd-DMSO) | L₂abs (Cpd-DMSO) |
|---|---|---|---|---|---|---|---|---|---|---|
| HLA-A | AK296091 | 79 | 492 | 0.0000 | 0.0000 | 6.1389 | 2.618 | 6.14 | 413 | 8.69 |
| HLA-A | AK296091 | 2 | 2 | 1.0000 | 1.0000 | 0.9474 | −0.078 | 1.06 | 0 | −2.69 |
| HLA-A | AK301014 | 1 | 0 | 0.9601 | 0.2573 | 0.4665 | −1.100 | 2.14 | 1 | 0.19 |
| HLA-A | AK301019 | 1 | 29 | 0.0772 | 0.0033 | 13.1853 | 3.721 | 13.19 | 27 | 4.78 |
| HLA-A | AK301019 | 0 | 0 | 1.0000 | 0.4930 | 0.7608 | −0.394 | 1.31 | 0 | −1.67 |
| HLA-A | AK301019 | 0 | 0 | 1.0000 | 0.4930 | 0.7608 | −0.394 | 1.31 | 0 | −1.67 |
| HLA-A | AY786588 | 3 | 0 | 0.4853 | 0.0612 | 0.2845 | −1.813 | 3.51 | 3 | 1.33 |
| HLA-A | AY786588 | 18 | 4 | 0.7803 | 0.1682 | 0.2686 | −1.897 | 3.72 | 14 | 3.81 |
| HLA-A | AY787587 | 0 | 0 | 1.0000 | 0.4930 | 0.7623 | −0.391 | 1.31 | 0 | −1.68 |
| HLA-A | DQ580344 | 73 | 60 | 1.0000 | 0.6646 | 0.8297 | −0.269 | 1.21 | 13 | 3.66 |
| HLA-A | JQ313909 | 0 | 0 | 1.0000 | 1.0000 | 1.2977 | 0.376 | 1.30 | 0 | −1.75 |
| HLA-A | M27539 | 15 | 65 | 0.2124 | 0.0143 | 4.1853 | 2.065 | 4.19 | 50 | 5.65 |
| HLA-A | NM_002116 | 8055 | 6479 | 0.0225 | 0.0007 | 0.8043 | −0.314 | 1.24 | 1576 | 10.62 |
| HLA-A | NM_002116 | 1 | 0 | 0.9218 | 0.2327 | 0.5147 | −0.958 | 1.94 | 1 | −0.08 |
| HLA-A | NM_002116 | 1 | 5 | 0.9471 | 0.2469 | 3.8882 | 1.959 | 3.89 | 5 | 2.23 |
| HLA-A | NM_002116 | 0 | 1 | 1.0000 | 0.6737 | 1.7648 | 0.820 | 1.76 | 1 | −0.39 |
| HLA-A | NM_002116 | 3280 | 3023 | 1.0000 | 0.3117 | 0.9219 | −0.117 | 1.08 | 256 | 8.00 |
| HLA-A | NM_002116 | 3 | 4 | 1.0000 | 0.9483 | 1.2467 | 0.318 | 1.25 | 1 | 0.03 |
| HLA-A | NM_002116 | 2 | 2 | 1.0000 | 0.8317 | 1.2375 | 0.307 | 1.24 | 1 | −0.74 |
| HLA-A | Y17224 | 8 | 20 | 1.0000 | 0.4044 | 2.2106 | 1.144 | 2.21 | 11 | 3.52 |
| HLTF | BC044659 | 407 | 31 | 0.0000 | 0.0000 | 0.0780 | −3.680 | 12.82 | 376 | 8.55 |
| HLTF | EU446704 | 109 | 5 | 0.0000 | 0.0000 | 0.0534 | −4.228 | 18.74 | 104 | 6.70 |
| HLTF | NM_003071 | 1229 | 194 | 0.0000 | 0.0000 | 0.1584 | −2.659 | 6.31 | 1035 | 10.02 |
| HLTF | NM_139048 | 248 | 31 | 0.0000 | 0.0000 | 0.1274 | −2.973 | 7.85 | 217 | 7.76 |
| HP1BP3 | AF113534 | 953 | 625 | 0.0252 | 0.0008 | 0.6568 | −0.607 | 1.52 | 327 | 8.35 |
| HP1BP3 | AK303456 | 148 | 145 | 1.0000 | 0.9702 | 0.9746 | −0.037 | 1.03 | 4 | 1.92 |
| HP1BP3 | AK304065 | 1898 | 1064 | 0.0000 | 0.0000 | 0.5611 | −0.834 | 1.78 | 833 | 9.70 |
| HP1BP3 | BC032139 | 56 | 63 | 1.0000 | 0.7451 | 1.1263 | 0.172 | 1.13 | 7 | 2.85 |
| HP1BP3 | BC046170 | 218 | 81 | 0.0225 | 0.0007 | 0.3728 | −1.424 | 2.68 | 137 | 7.10 |
| HP1BP3 | BC053327 | 388 | 159 | 0.0012 | 0.0000 | 0.4114 | −1.282 | 2.43 | 229 | 7.84 |
| HP1BP3 | CR749652 | 314 | 512 | 0.0606 | 0.0024 | 1.6270 | 0.702 | 1.63 | 198 | 7.63 |
| HP1BP3 | NM_016287 | 1668 | 340 | 0.0000 | 0.0000 | 0.2045 | −2.290 | 4.89 | 1328 | 10.37 |
| HRH1 | CCDS2604 | 146 | 142 | 1.0000 | 0.8986 | 0.9727 | −0.040 | 1.03 | 4 | 2.01 |
| HRH1 | NM_000861 | 9 | 17 | 1.0000 | 0.5529 | 1.8091 | 0.855 | 1.81 | 8 | 3.03 |
| HRH1 | NM_001098211 | 56 | 0 | 0.0000 | 0.0000 | 0.0175 | −5.836 | 57.13 | 56 | 5.81 |
| HRH1 | NM_001098212 | 683 | 642 | 1.0000 | 0.7237 | 0.9396 | −0.090 | 1.06 | 41 | 5.37 |
| HRH1 | NM_001098213 | 87 | 38 | 0.4440 | 0.0510 | 0.4398 | −1.185 | 2.27 | 50 | 5.63 |
| HSD17B12 | BC012536 | 6 | 12 | 1.0000 | 0.5068 | 1.9298 | 0.948 | 1.93 | 6 | 2.60 |
| HSD17B12 | NM016142 | 1512 | 125 | 0.0000 | 0.0000 | 0.0831 | −3.590 | 12.04 | 1388 | 10.44 |
| HSD17B4 | AK094049 | 48 | 15 | 0.4086 | 0.0429 | 0.3314 | −1.593 | 3.02 | 33 | 5.03 |
| HSD17B4 | AK295440 | 0 | 2 | 0.6970 | 0.1332 | 3.0836 | 1.625 | 3.08 | 2 | 1.06 |
| HSD17B4 | AK299685 | 4 | 33 | 0.2679 | 0.0208 | 6.3549 | 2.668 | 6.35 | 29 | 4.84 |
| HSD17B4 | AK308968 | 0 | 0 | 9999 | 9999 | 1.0000 | 0.000 | 1.00 | 0 | 0 |
| HSD17B4 | NM_000414 | 2136 | 913 | 0.0000 | 0.0000 | 0.4279 | −1.225 | 2.34 | 1222 | 10.26 |
| HSD17B4 | NM_001199291 | 4 | 31 | 0.2482 | 0.0184 | 6.3887 | 2.676 | 6.39 | 27 | 4.78 |
| HTT | NM_002111 | 3661 | 827 | 0.0000 | 0.0000 | 0.2261 | −2.145 | 4.42 | 2834 | 11.47 |
| IARS | AK057920 | 17 | 19 | 1.0000 | 1.0000 | 1.0635 | 0.089 | 1.06 | 1 | 0.23 |
| IARS | AK308202 | 17 | 16 | 1.0000 | 0.9064 | 0.9688 | −0.046 | 1.03 | 1 | −0.87 |
| IARS | BC065552 | 0 | 13 | 0.1105 | 0.0055 | 14.0512 | 3.813 | 14.05 | 13 | 3.71 |
| IARS | NM_002161 | 10457 | 10305 | 1.0000 | 0.8057 | 0.9855 | −0.021 | 1.01 | 152 | 7.25 |
| IARS | NM_013417 | 4618 | 4842 | 1.0000 | 0.5764 | 1.0486 | 0.069 | 1.05 | 225 | 7.81 |
| IARS | NR_073446 | 58 | 0 | 0.0000 | 0.0000 | 0.0168 | −5.892 | 59.38 | 58 | 5.87 |
| IDH1 | BC012846 | 13 | 5 | 0.9649 | 0.2599 | 0.4121 | −1.279 | 2.43 | 9 | 3.09 |
| IDH1 | BX537411 | 37 | 22 | 1.0000 | 0.3155 | 0.6018 | −0.733 | 1.66 | 15 | 3.91 |
| IDH1 | NM_005896 | 2400 | 962 | 0.0000 | 0.0000 | 0.4013 | −1.317 | 2.49 | 1438 | 10.49 |
| IGF2BP2 | BC012322 | 181 | 23 | 0.0000 | 0.0000 | 0.1339 | −2.901 | 7.47 | 158 | 7.30 |
| IGF2BP2 | EU408701 | 1 | 61 | 0.0001 | 0.0000 | 38.1049 | 5.252 | 38.10 | 60 | 5.91 |
| IGF2BP2 | EU408702 | 277 | 210 | 1.0000 | 0.3042 | 0.7588 | −0.398 | 1.32 | 67 | 6.07 |
| IGF2BP2 | EU408703 | 109 | 141 | 1.0000 | 0.3315 | 1.2924 | 0.370 | 1.29 | 32 | 5.00 |
| IGF2BP2 | EU408704 | 0 | 12 | 0.1725 | 0.0104 | 13.2372 | 3.727 | 13.24 | 12 | 3.61 |
| IGF2BP2 | NM_001007225 | 717 | 966 | 0.2048 | 0.0135 | 1.3468 | 0.429 | 1.35 | 249 | 7.96 |
| IGF2BP2 | NM_006548 | 1521 | 1305 | 0.6025 | 0.0995 | 0.8580 | −0.221 | 1.17 | 216 | 7.76 |
| ITM2C | AB003629 | 457 | 221 | 0.0039 | 0.0001 | 0.4852 | −1.043 | 2.06 | 236 | 7.88 |
| ITM2C | EU832488 | 0 | 0 | 9999 | 9999 | 1.0000 | 0.000 | 1.00 | 0 | 0 |
| ITM2C | NM_001012514 | 95 | 124 | 1.0000 | 0.3486 | 1.2980 | 0.376 | 1.30 | 29 | 4.84 |
| ITM2C | NM_001012516 | 6 | 0 | 0.2862 | 0.0230 | 0.1502 | −2.735 | 6.66 | 6 | 2.50 |
| ITM2C | NM_030926 | 2210 | 2148 | 1.0000 | 0.7943 | 0.9719 | −0.041 | 1.03 | 62 | 5.96 |
| KCNK2 | AK294780 | 134 | 115 | 1.0000 | 0.7016 | 0.8623 | −0.214 | 1.16 | 19 | 4.22 |
| KCNK2 | AY552981 | 242 | 244 | 1.0000 | 0.8474 | 1.0050 | 0.007 | 1.01 | 1 | 0.30 |
| KCNK2 | NM_001017424 | 896 | 362 | 0.0000 | 0.0000 | 0.4043 | −1.306 | 2.47 | 534 | 9.06 |
| KCNK2 | NM_001017425 | 483 | 602 | 0.7536 | 0.1548 | 1.2469 | 0.318 | 1.25 | 119 | 6.90 |
| KCNK2 | NM_014217 | 1957 | 2382 | 0.2770 | 0.0220 | 1.2170 | 0.283 | 1.22 | 425 | 8.73 |
| KIAA1033 | AL137753 | 145 | 296 | 0.1015 | 0.0049 | 2.0388 | 1.028 | 2.04 | 151 | 7.24 |
| KIAA1033 | BC143373 | 344 | 167 | 0.0081 | 0.0002 | 0.4872 | −1.037 | 2.05 | 177 | 7.47 |

TABLE 10-continued

RNA Abundance Modulation

| Gene | Trx_ID | ave DMSO | ave Cpd | padj (q val, FDR) | ttest (p val) | FC (x + 1) | $L_2$FC (x + 1) | amp FC (x + 1) | abs (Cpd-DMSO) | $L_2$abs (Cpd-DMSO) |
|---|---|---|---|---|---|---|---|---|---|---|
| KIAA1033 | NM_015275 | 2872 | 2225 | 0.0684 | 0.0028 | 0.7750 | −0.368 | 1.29 | 646 | 9.34 |
| KIAA1143 | NM_020696 | 1206 | 504 | 0.0000 | 0.0000 | 0.4180 | −1.258 | 2.39 | 703 | 9.46 |
| KIAA1522 | AB384615 | 306 | 90 | 0.0002 | 0.0000 | 0.2959 | −1.757 | 3.38 | 216 | 7.76 |
| KIAA1522 | NM_001198973 | 63 | 64 | 1.0000 | 0.9732 | 1.0083 | 0.012 | 1.01 | 1 | −0.90 |
| KIAA1522 | NM_020888 | 316 | 450 | 0.3886 | 0.0389 | 1.4233 | 0.509 | 1.42 | 134 | 7.07 |
| KIAA1524 | AB040957 | 115 | 20 | 0.0077 | 0.0002 | 0.1836 | −2.445 | 5.45 | 95 | 6.57 |
| KIAA1524 | AK308315 | 15 | 10 | 1.0000 | 0.5634 | 0.6854 | −0.545 | 1.46 | 5 | 2.30 |
| KIAA1524 | AK310446 | 8 | 0 | 0.1914 | 0.0122 | 0.1129 | −3.147 | 8.86 | 8 | 2.97 |
| KIAA1524 | NM_020890 | 1671 | 249 | 0.0000 | 0.0000 | 0.1497 | −2.740 | 6.68 | 1421 | 10.47 |
| KIAA1715 | AK056532 | 165 | 16 | 0.0000 | 0.0000 | 0.1022 | −3.291 | 9.79 | 149 | 7.22 |
| KIAA1715 | AK301947 | 47 | 16 | 0.5105 | 0.0684 | 0.3583 | −1.481 | 2.79 | 31 | 4.95 |
| KIAA1715 | BC110329 | 36 | 1 | 0.0283 | 0.0009 | 0.0675 | −3.889 | 14.82 | 34 | 5.10 |
| KIAA1715 | BC143681 | 25 | 7 | 0.8234 | 0.1848 | 0.3182 | −1.652 | 3.14 | 17 | 4.12 |
| KIAA1715 | BC143683 | 8 | 0 | 0.1914 | 0.0122 | 0.1129 | −3.147 | 8.86 | 8 | 2.97 |
| KIAA1715 | NM_030650 | 2532 | 246 | 0.0000 | 0.0000 | 0.0974 | −3.361 | 10.27 | 2287 | 11.16 |
| KIF3A | AF041853 | 6 | 0 | 0.2862 | 0.0230 | 0.1502 | −2.735 | 6.66 | 6 | 2.50 |
| KIF3A | AK295089 | 6 | 67 | 0.0054 | 0.0001 | 9.5596 | 3.257 | 9.56 | 61 | 5.93 |
| KIF3A | AK313359 | 197 | 529 | 0.0000 | 0.0000 | 2.6832 | 1.424 | 2.68 | 333 | 8.38 |
| KIF3A | AM177178 | 0 | 0 | 9999 | 9999 | 1.0000 | 0.000 | 1.00 | 0 | 0 |
| KIF3A | NM_007054 | 350 | 15 | 0.0000 | 0.0000 | 0.0443 | −4.496 | 22.57 | 336 | 8.39 |
| KLHL7 | AK296219 | 3 | 3 | 1.0000 | 0.8811 | 0.9284 | −0.107 | 1.08 | 0 | −1.76 |
| KLHL7 | AK297595 | 0 | 0 | 9999 | 9999 | 1.0000 | 0.000 | 1.00 | 0 | 0 |
| KLHL7 | AK302995 | 1 | 2 | 1.0000 | 0.4698 | 2.1044 | 1.073 | 2.10 | 2 | 0.84 |
| KLHL7 | NM_001031710 | 820 | 1021 | 0.5253 | 0.0734 | 1.2458 | 0.317 | 1.25 | 202 | 7.66 |
| KLHL7 | NM_001172428 | 93 | 35 | 0.3736 | 0.0360 | 0.3771 | −1.407 | 2.65 | 59 | 5.87 |
| KLHL7 | NM_018846 | 57 | 96 | 0.8641 | 0.2008 | 1.6840 | 0.752 | 1.68 | 39 | 5.30 |
| KLHL7 | NR_033328 | 134 | 1 | 0.0000 | 0.0000 | 0.0159 | −5.970 | 62.70 | 132 | 7.05 |
| KLHL7 | NR_033329 | 0 | 39 | 0.0006 | 0.0000 | 39.9041 | 5.318 | 39.90 | 39 | 5.28 |
| LAMA2 | CCDS5138 | 2394 | 2320 | 1.0000 | 0.7308 | 0.9693 | −0.045 | 1.03 | 74 | 6.20 |
| LAMA2 | NM_000426 | 51 | 0 | 0.0000 | 0.0000 | 0.0193 | −5.698 | 51.92 | 51 | 5.67 |
| LAMA2 | NM_001079823 | 25 | 132 | 0.0162 | 0.0005 | 5.0788 | 2.344 | 5.08 | 107 | 6.74 |
| LARP4 | AK055521 | 19 | 49 | 0.8505 | 0.1952 | 2.4884 | 1.315 | 2.49 | 30 | 4.90 |
| LARP4 | AK125113 | 141 | 363 | 0.0031 | 0.0001 | 2.5699 | 1.362 | 2.57 | 222 | 7.80 |
| LARP4 | NM_001170803 | 0 | 47 | 0.0002 | 0.0000 | 47.6545 | 5.575 | 47.65 | 47 | 5.54 |
| LARP4 | NM_001170804 | 18 | 6 | 0.8295 | 0.1869 | 0.3728 | −1.424 | 2.68 | 12 | 3.58 |
| LARP4 | NM_001170808 | 68 | 59 | 1.0000 | 0.9030 | 0.8734 | −0.195 | 1.14 | 9 | 3.12 |
| LARP4 | NM_052879 | 1382 | 1231 | 0.9243 | 0.2339 | 0.8910 | −0.166 | 1.12 | 151 | 7.24 |
| LARP4 | NM_199188 | 158 | 250 | 0.5538 | 0.0830 | 1.5740 | 0.654 | 1.57 | 91 | 6.51 |
| LARP4 | NM_199190 | 228 | 201 | 1.0000 | 0.6806 | 0.8826 | −0.180 | 1.13 | 27 | 4.75 |
| LARP4 | NR_033200 | 110 | 166 | 0.7823 | 0.1692 | 1.5009 | 0.586 | 1.50 | 56 | 5.80 |
| LARP7 | NM_001267039 | 18 | 441 | 0.0000 | 0.0000 | 23.0098 | 4.524 | 23.01 | 423 | 8.72 |
| LARP7 | NM_015454 | 371 | 822 | 0.0000 | 0.0000 | 2.2110 | 1.145 | 2.21 | 451 | 8.82 |
| LARP7 | NM_016648 | 498 | 8 | 0.0000 | 0.0000 | 0.0183 | −5.775 | 54.77 | 490 | 8.94 |
| LARP7 | NR_049768 | 27 | 41 | 1.0000 | 0.5777 | 1.5065 | 0.591 | 1.51 | 14 | 3.80 |
| LATS2 | AK314235 | 129 | 729 | 0.0000 | 0.0000 | 5.6012 | 2.486 | 5.60 | 600 | 9.23 |
| LATS2 | NM_014572 | 2181 | 1723 | 0.0908 | 0.0042 | 0.7901 | −0.340 | 1.27 | 458 | 8.84 |
| LIMS1 | NM_001193482 | 325 | 0 | 0.0000 | 0.0000 | 0.0031 | −8.349 | 326.15 | 325 | 8.34 |
| LIMS1 | NM_001193483 | 2686 | 2812 | 1.0000 | 0.5117 | 1.0466 | 0.066 | 1.05 | 125 | 6.97 |
| LIMS1 | NM_001193484 | 0 | 0 | 9999 | 9999 | 1.0000 | 0.000 | 1.00 | 0 | 0 |
| LIMS1 | NM_001193485 | 511 | 446 | 1.0000 | 0.3999 | 0.8725 | −0.197 | 1.15 | 65 | 6.03 |
| LIMS1 | NM_004987 | 43 | 0 | 0.0001 | 0.0000 | 0.0226 | −5.470 | 44.33 | 43 | 5.44 |
| LINC00341 | NR_026779 | 59 | 1 | 0.0001 | 0.0000 | 0.0328 | −4.929 | 30.46 | 58 | 5.87 |
| LINC00657 | NR_027451 | 1615 | 4003 | 0.0000 | 0.0000 | 2.4772 | 1.309 | 2.48 | 2388 | 11.22 |
| LMAN2L | AK316331 | 8 | 2 | 1.0000 | 0.3173 | 0.3799 | −1.396 | 2.63 | 5 | 2.43 |
| LMAN2L | NM_001142292 | 0 | 0 | 9999 | 9999 | 1.0000 | 0.000 | 1.00 | 0 | 0 |
| LMAN2L | NM_030805 | 935 | 138 | 0.0000 | 0.0000 | 0.1483 | −2.754 | 6.74 | 797 | 9.64 |
| LMAN2L | NR_024518 | 0 | 0 | 9999 | 9999 | 1.0000 | 0.000 | 1.00 | 0 | 0 |
| LMAN2L | NR_024520 | 0 | 0 | 1.0000 | 1.0000 | 1.3035 | 0.382 | 1.30 | 0 | −1.72 |
| LMAN2L | NR_024521 | 6 | 13 | 1.0000 | 0.4058 | 2.1561 | 1.108 | 2.16 | 8 | 2.94 |
| LMO7 | AK055465 | 0 | 0 | 9999 | 9999 | 1.0000 | 0.000 | 1.00 | 0 | 0 |
| LMO7 | AK304051 | 6881 | 3304 | 0.0000 | 0.0000 | 0.4802 | −1.058 | 2.08 | 3577 | 11.80 |
| LMO7 | AX747335 | 5387 | 2770 | 0.0000 | 0.0000 | 0.5143 | −0.959 | 1.94 | 2617 | 11.35 |
| LMO7 | BC036428 | 0 | 1 | 1.0000 | 0.4688 | 1.9106 | 0.934 | 1.91 | 1 | −0.14 |
| LMO7 | FJ711162 | 0 | 0 | 9999 | 9999 | 1.0000 | 0.000 | 1.00 | 0 | 0 |
| LMO7 | NM_005358 | 26 | 10 | 0.9601 | 0.2558 | 0.4133 | −1.275 | 2.42 | 16 | 4.00 |
| LMO7 | NM_015842 | 110 | 84 | 1.0000 | 0.3991 | 0.7633 | −0.390 | 1.31 | 26 | 4.72 |
| LRCH4 | AF459638 | 59 | 0 | 0.0000 | 0.0000 | 0.0166 | −5.914 | 60.29 | 59 | 5.89 |
| LRCH4 | AK302410 | 131 | 120 | 1.0000 | 0.7506 | 0.9183 | −0.123 | 1.09 | 11 | 3.43 |
| LRCH4 | NM_002319 | 560 | 671 | 0.7804 | 0.1683 | 1.1991 | 0.262 | 1.20 | 112 | 6.80 |
| LRIG1 | AK294984 | 4 | 19 | 0.6051 | 0.1003 | 4.3037 | 2.106 | 4.30 | 15 | 3.92 |
| LRIG1 | AY730707 | 142 | 33 | 0.0070 | 0.0002 | 0.2359 | −2.084 | 4.24 | 109 | 6.77 |
| LRIG1 | BC071561 | 0 | 0 | 9999 | 9999 | 1.0000 | 0.000 | 1.00 | 0 | 0 |
| LRIG1 | NM_015541 | 328 | 387 | 1.0000 | 0.3573 | 1.1809 | 0.240 | 1.18 | 59 | 5.89 |
| LRRC8A | NM_001127244 | 24 | 47 | 1.0000 | 0.2882 | 1.9223 | 0.943 | 1.92 | 23 | 4.52 |

TABLE 10-continued

RNA Abundance Modulation

| Gene | Trx_ID | ave DMSO | ave Cpd | padj (q val, FDR) | ttest (p val) | FC (x + 1) | L$_2$FC (x + 1) | amp FC (x + 1) | abs (Cpd-DMSO) | L$_2$abs (Cpd-DMSO) |
|---|---|---|---|---|---|---|---|---|---|---|
| LRRC8A | NM_001127245 | 232 | 0 | 0.0000 | 0.0000 | 0.0043 | −7.863 | 232.77 | 232 | 7.86 |
| LRRC8A | NM_019594 | 2314 | 2457 | 1.0000 | 0.4605 | 1.0620 | 0.087 | 1.06 | 143 | 7.16 |
| LTBR | AK095418 | 122 | 167 | 1.0000 | 0.3119 | 1.3670 | 0.451 | 1.37 | 45 | 5.50 |
| LTBR | NM_001270987 | 644 | 239 | 0.0000 | 0.0000 | 0.3725 | −1.425 | 2.68 | 405 | 8.66 |
| LTBR | NM_002342 | 2419 | 2748 | 0.7556 | 0.1568 | 1.1361 | 0.184 | 1.14 | 329 | 8.36 |
| LUC7L2 | AK092044 | 28 | 13 | 0.9004 | 0.2166 | 0.4782 | −1.064 | 2.09 | 15 | 3.93 |
| LUC7L2 | AK095839 | 46 | 52 | 1.0000 | 0.7205 | 1.1283 | 0.174 | 1.13 | 6 | 2.60 |
| LUC7L2 | NM_001244585 | 59 | 210 | 0.0044 | 0.0001 | 3.4963 | 1.806 | 3.50 | 151 | 7.24 |
| LUC7L2 | NM_001270643 | 25 | 26 | 1.0000 | 0.9691 | 1.0526 | 0.074 | 1.05 | 1 | 0.43 |
| LUC7L2 | NM_016019 | 2003 | 2270 | 0.7146 | 0.1393 | 1.1336 | 0.181 | 1.13 | 268 | 8.06 |
| LZTS2 | AB058716 | 63 | 45 | 1.0000 | 0.4917 | 0.7101 | −0.494 | 1.41 | 19 | 4.22 |
| LZTS2 | AK097997 | 65 | 57 | 1.0000 | 0.7627 | 0.8722 | −0.197 | 1.15 | 8 | 3.08 |
| LZTS2 | AK298208 | 418 | 35 | 0.0000 | 0.0000 | 0.0870 | −3.524 | 11.50 | 383 | 8.58 |
| LZTS2 | BC058938 | 726 | 892 | 0.5253 | 0.0735 | 1.2289 | 0.297 | 1.23 | 166 | 7.38 |
| LZTS2 | NM_032429 | 205 | 182 | 1.0000 | 0.5331 | 0.8871 | −0.173 | 1.13 | 23 | 4.54 |
| MADD | AK308780 | 4 | 5 | 1.0000 | 0.9216 | 1.1894 | 0.250 | 1.19 | 1 | 0.03 |
| MADD | NM_001135943 | 141 | 76 | 0.4375 | 0.0487 | 0.5436 | −0.879 | 1.84 | 65 | 6.02 |
| MADD | NM_001135944 | 93 | 135 | 1.0000 | 0.3915 | 1.4500 | 0.536 | 1.45 | 42 | 5.40 |
| MADD | NM_003682 | 6 | 144 | 0.0000 | 0.0000 | 19.3635 | 4.275 | 19.36 | 137 | 7.10 |
| MADD | NM_130470 | 26 | 18 | 1.0000 | 0.6185 | 0.7037 | −0.507 | 1.42 | 8 | 3.02 |
| MADD | NM_130471 | 163 | 61 | 0.0489 | 0.0018 | 0.3745 | −1.417 | 2.67 | 103 | 6.68 |
| MADD | NM_130472 | 5 | 257 | 0.0000 | 0.0000 | 43.1299 | 5.431 | 43.13 | 252 | 7.98 |
| MADD | NM_130473 | 275 | 96 | 0.0011 | 0.0000 | 0.3537 | −1.499 | 2.83 | 178 | 7.48 |
| MADD | NM_130474 | 118 | 0 | 0.0000 | 0.0000 | 0.0084 | −6.901 | 119.48 | 118 | 6.89 |
| MADD | NM_130475 | 0 | 150 | 0.0000 | 0.0000 | 151.0139 | 7.239 | 151.01 | 150 | 7.23 |
| MADD | NM_130476 | 342 | 254 | 0.6907 | 0.1308 | 0.7435 | −0.428 | 1.34 | 88 | 6.46 |
| MAGED4B | NM_030801 | 569 | 337 | 0.0051 | 0.0001 | 0.5929 | −0.754 | 1.69 | 232 | 7.86 |
| MAGED4B | NM_177537 | 171 | 38 | 0.0017 | 0.0000 | 0.2287 | −2.128 | 4.37 | 132 | 7.05 |
| MAN1A2 | AK023308 | 37 | 16 | 0.9601 | 0.2553 | 0.4525 | −1.144 | 2.21 | 21 | 4.37 |
| MAN1A2 | NM_006699 | 1994 | 377 | 0.0000 | 0.0000 | 0.1897 | −2.398 | 5.27 | 1617 | 10.66 |
| MAP4K4 | AK025610 | 391 | 51 | 0.0000 | 0.0000 | 0.1330 | −2.910 | 7.52 | 340 | 8.41 |
| MAP4K4 | AK074900 | 3 | 2 | 1.0000 | 0.7982 | 0.7786 | −0.361 | 1.28 | 1 | −0.25 |
| MAP4K4 | AK295610 | 1136 | 1243 | 1.0000 | 0.4984 | 1.0941 | 0.130 | 1.09 | 107 | 6.74 |
| MAP4K4 | AK307879 | 102 | 125 | 1.0000 | 0.6537 | 1.2210 | 0.288 | 1.22 | 23 | 4.51 |
| MAP4K4 | AY834276 | 1318 | 1581 | 0.5650 | 0.0866 | 1.1991 | 0.262 | 1.20 | 263 | 8.04 |
| MAP4K4 | BC156887 | 100 | 55 | 0.6138 | 0.1051 | 0.5597 | −0.837 | 1.79 | 44 | 5.47 |
| MAP4K4 | NM_001242559 | 1528 | 1874 | 0.3397 | 0.0304 | 1.2261 | 0.294 | 1.23 | 346 | 8.43 |
| MAP4K4 | NM_004834 | 2799 | 3427 | 0.1875 | 0.0118 | 1.2243 | 0.292 | 1.22 | 628 | 9.29 |
| MAP4K4 | NM_145686 | 5570 | 5893 | 1.0000 | 0.4519 | 1.0580 | 0.081 | 1.06 | 323 | 8.34 |
| MAP4K4 | NM_145687 | 0 | 5 | 0.5018 | 0.0658 | 6.3538 | 2.668 | 6.35 | 5 | 2.42 |
| MED1 | AK299789 | 153 | 388 | 0.0003 | 0.0000 | 2.5317 | 1.340 | 2.53 | 235 | 7.88 |
| MED1 | JF432429 | 41 | 41 | 1.0000 | 0.9659 | 1.0143 | 0.021 | 1.01 | 1 | −0.74 |
| MED1 | NM_004774 | 2847 | 3107 | 1.0000 | 0.3284 | 1.0915 | 0.126 | 1.09 | 261 | 8.03 |
| MEDAG | NM_032849 | 166 | 27 | 0.0003 | 0.0000 | 0.1664 | −2.587 | 6.01 | 139 | 7.12 |
| MEF2D | AK308641 | 340 | 217 | 0.3291 | 0.0290 | 0.6378 | −0.649 | 1.57 | 124 | 6.95 |
| MEF2D | BC032479 | 0 | 4 | 0.5592 | 0.0853 | 4.5718 | 2.193 | 4.57 | 4 | 1.84 |
| MEF2D | BC064988 | 1345 | 1108 | 0.4814 | 0.0596 | 0.8239 | −0.279 | 1.21 | 237 | 7.89 |
| MEF2D | NM_001271629 | 74 | 233 | 0.0085 | 0.0002 | 3.1031 | 1.634 | 3.10 | 159 | 7.31 |
| MEIS2 | AK055936 | 124 | 202 | 0.6137 | 0.1051 | 1.6314 | 0.706 | 1.63 | 79 | 6.30 |
| MEIS2 | AY349358 | 2 | 0 | 0.5415 | 0.0800 | 0.3042 | −1.717 | 3.29 | 2 | 1.19 |
| MEIS2 | NM_001220482 | 79 | 53 | 1.0000 | 0.5288 | 0.6821 | −0.552 | 1.47 | 25 | 4.66 |
| MEIS2 | NM_002399 | 52 | 130 | 0.3469 | 0.0316 | 2.4509 | 1.293 | 2.45 | 77 | 6.27 |
| MEIS2 | NM_170674 | 232 | 167 | 0.8972 | 0.2149 | 0.7216 | −0.471 | 1.39 | 65 | 6.02 |
| MEIS2 | NM_170675 | 104 | 69 | 0.9726 | 0.2642 | 0.6661 | −0.586 | 1.50 | 35 | 5.13 |
| MEIS2 | NM_170676 | 0 | 23 | 0.0135 | 0.0004 | 24.2588 | 4.600 | 24.26 | 23 | 4.54 |
| MEIS2 | NM_170677 | 0 | 0 | 9999 | 9999 | 1.0000 | 0.000 | 1.00 | 0 | 0 |
| MEIS2 | NM_172315 | 132 | 7 | 0.0000 | 0.0000 | 0.0566 | −4.143 | 17.67 | 125 | 6.97 |
| MEIS2 | NM_172316 | 41 | 34 | 1.0000 | 0.7793 | 0.8357 | −0.259 | 1.20 | 7 | 2.78 |
| MEMO1 | AK022169 | 34 | 2 | 0.0899 | 0.0041 | 0.0990 | −3.337 | 10.10 | 31 | 4.96 |
| MEMO1 | AK057760 | 16 | 7 | 1.0000 | 0.3896 | 0.4890 | −1.032 | 2.05 | 9 | 3.12 |
| MEMO1 | AK290753 | 662 | 152 | 0.0000 | 0.0000 | 0.2309 | −2.114 | 4.33 | 510 | 8.99 |
| MEMO1 | AK295755 | 9 | 16 | 1.0000 | 0.5618 | 1.7009 | 0.766 | 1.70 | 7 | 2.85 |
| MEMO1 | NM_001137602 | 21 | 8 | 0.8179 | 0.1825 | 0.3879 | −1.366 | 2.58 | 14 | 3.77 |
| MEMO1 | NM_015955 | 314 | 89 | 0.0002 | 0.0000 | 0.2856 | −1.808 | 3.50 | 225 | 7.81 |
| MICAL2 | AB110785 | 3145 | 2729 | 0.4922 | 0.0626 | 0.8677 | −0.205 | 1.15 | 416 | 8.70 |
| MICAL2 | AB110786 | 9488 | 9071 | 1.0000 | 0.5318 | 0.9560 | −0.065 | 1.05 | 417 | 8.70 |
| MICAL2 | AK294845 | 0 | 0 | 9999 | 9999 | 1.0000 | 0.000 | 1.00 | 0 | 0 |
| MICAL2 | AK302580 | 214 | 0 | 0.0000 | 0.0000 | 0.0046 | −7.750 | 215.28 | 214 | 7.74 |
| MICAL2 | AK302893 | 155 | 171 | 1.0000 | 0.7732 | 1.1046 | 0.143 | 1.10 | 16 | 4.03 |
| MICAL2 | BC015755 | 349 | 348 | 1.0000 | 0.9807 | 0.9962 | −0.006 | 1.00 | 1 | 0.42 |
| MICAL2 | BX538021 | 117 | 111 | 1.0000 | 0.8173 | 0.9470 | −0.079 | 1.06 | 6 | 2.64 |
| MICAL2 | NM_014632 | 44 | 57 | 1.0000 | 0.5929 | 1.3056 | 0.385 | 1.31 | 14 | 3.77 |
| MKLN1 | AK310452 | 423 | 435 | 1.0000 | 0.9154 | 1.0296 | 0.042 | 1.03 | 13 | 3.65 |
| MKLN1 | BX537433 | 0 | 4 | 0.5170 | 0.0705 | 5.1671 | 2.369 | 5.17 | 4 | 2.06 |

TABLE 10-continued

RNA Abundance Modulation

| Gene | Trx_ID | ave DMSO | ave Cpd | padj (q val, FDR) | ttest (p val) | FC (x + 1) | L$_2$FC (x + 1) | amp FC (x + 1) | abs (Cpd-DMSO) | L$_2$abs (Cpd-DMSO) |
|---|---|---|---|---|---|---|---|---|---|---|
| MKLN1 | NM_001145354 | 72 | 0 | 0.0000 | 0.0000 | 0.0137 | −6.186 | 72.82 | 72 | 6.17 |
| MKLN1 | NM_013255 | 1139 | 1110 | 1.0000 | 0.7485 | 0.9752 | −0.036 | 1.03 | 28 | 4.82 |
| MLLT4 | AB621809 | 453 | 541 | 0.9601 | 0.2548 | 1.1944 | 0.256 | 1.19 | 88 | 6.46 |
| MLLT4 | AL161973 | 95 | 7 | 0.0003 | 0.0000 | 0.0791 | −3.661 | 12.65 | 89 | 6.47 |
| MLLT4 | BC014505 | 17 | 18 | 1.0000 | 0.9080 | 1.0975 | 0.134 | 1.10 | 2 | 0.79 |
| MLLT4 | BX649158 | 13 | 29 | 1.0000 | 0.3571 | 2.0872 | 1.062 | 2.09 | 15 | 3.95 |
| MLLT4 | NM_001040000 | 34 | 22 | 1.0000 | 0.5091 | 0.6439 | −0.635 | 1.55 | 13 | 3.65 |
| MLLT4 | NM_001207008 | 534 | 586 | 1.0000 | 0.5433 | 1.0986 | 0.136 | 1.10 | 53 | 5.72 |
| MLLT4 | U02478 | 173 | 200 | 1.0000 | 0.6053 | 1.1564 | 0.210 | 1.16 | 27 | 4.76 |
| MMS19 | AF319947 | 1351 | 113 | 0.0000 | 0.0000 | 0.0841 | −3.571 | 11.89 | 1238 | 10.27 |
| MMS19 | AK025496 | 41 | 6 | 0.1353 | 0.0073 | 0.1726 | −2.534 | 5.79 | 35 | 5.12 |
| MMS19 | AK027710 | 39 | 14 | 0.6924 | 0.1313 | 0.3805 | −1.394 | 2.63 | 25 | 4.64 |
| MMS19 | AK056581 | 22 | 20 | 1.0000 | 0.9183 | 0.8855 | −0.175 | 1.13 | 3 | 1.42 |
| MMS19 | BC007298 | 11 | 9 | 1.0000 | 0.7944 | 0.8321 | −0.265 | 1.20 | 2 | 0.96 |
| MMS19 | BC080532 | 117 | 43 | 0.2531 | 0.0191 | 0.3718 | −1.427 | 2.69 | 74 | 6.21 |
| MMS19 | BC143285 | 44 | 19 | 0.7320 | 0.1454 | 0.4394 | −1.186 | 2.28 | 25 | 4.66 |
| MMS19 | NM_022362 | 73 | 5 | 0.0024 | 0.0000 | 0.0782 | −3.676 | 12.78 | 68 | 6.09 |
| MPZL1 | AF181660 | 25 | 20 | 1.0000 | 0.8412 | 0.8355 | −0.259 | 1.20 | 4 | 2.07 |
| MPZL1 | AK307250 | 7 | 22 | 0.8374 | 0.1896 | 2.9169 | 1.544 | 2.92 | 15 | 3.91 |
| MPZL1 | AL035308 | 29 | 33 | 1.0000 | 0.9588 | 1.1509 | 0.203 | 1.15 | 4 | 2.17 |
| MPZL1 | NM_001146191 | 53 | 55 | 1.0000 | 0.9319 | 1.0498 | 0.070 | 1.05 | 3 | 1.42 |
| MPZL1 | NM_003953 | 4959 | 4839 | 1.0000 | 0.7342 | 0.9759 | −0.035 | 1.02 | 119 | 6.90 |
| MPZL1 | NM_024569 | 183 | 431 | 0.0029 | 0.0001 | 2.3457 | 1.230 | 2.35 | 248 | 7.95 |
| MSANTD3 | AK092292 | 54 | 54 | 1.0000 | 0.9805 | 0.9957 | −0.006 | 1.00 | 0 | −2.09 |
| MSANTD3 | NM_001198805 | 398 | 664 | 0.0196 | 0.0006 | 1.6666 | 0.737 | 1.67 | 266 | 8.05 |
| MSANTD3 | NM_001198806 | 378 | 162 | 0.0009 | 0.0000 | 0.4299 | −1.218 | 2.33 | 216 | 7.75 |
| MSANTD3 | NM_001198807 | 8 | 18 | 1.0000 | 0.3513 | 2.1414 | 1.099 | 2.14 | 10 | 3.36 |
| MSANTD3 | NM_080655 | 665 | 712 | 1.0000 | 0.5579 | 1.0693 | 0.097 | 1.07 | 46 | 5.53 |
| MSC | NM_005098 | 451 | 225 | 0.0089 | 0.0002 | 0.5007 | −0.998 | 2.00 | 225 | 7.82 |
| MSL3 | AK294255 | 0 | 7 | 0.3427 | 0.0310 | 7.8460 | 2.972 | 7.85 | 7 | 2.78 |
| MSL3 | AK304419 | 5 | 7 | 1.0000 | 0.9638 | 1.2274 | 0.296 | 1.23 | 1 | 0.52 |
| MSL3 | NM_001193270 | 8 | 15 | 1.0000 | 0.4653 | 1.8828 | 0.913 | 1.88 | 8 | 2.91 |
| MSL3 | NM_006800 | 288 | 345 | 1.0000 | 0.3271 | 1.1994 | 0.262 | 1.20 | 58 | 5.85 |
| MSL3 | NM_078628 | 158 | 20 | 0.0001 | 0.0000 | 0.1300 | −2.943 | 7.69 | 138 | 7.11 |
| MSL3 | NM_078629 | 317 | 515 | 0.1292 | 0.0068 | 1.6240 | 0.700 | 1.62 | 198 | 7.63 |
| MTAP | AF109294 | 0 | 1 | 1.0000 | 0.5246 | 2.1472 | 1.102 | 2.15 | 1 | 0.20 |
| MTAP | AK300592 | 112 | 197 | 0.4845 | 0.0601 | 1.7445 | 0.803 | 1.74 | 84 | 6.40 |
| MTAP | AK309365 | 109 | 36 | 0.1918 | 0.0123 | 0.3308 | −1.596 | 3.02 | 74 | 6.21 |
| MTAP | BC012316 | 49 | 94 | 0.6472 | 0.1160 | 1.8826 | 0.913 | 1.88 | 44 | 5.47 |
| MTAP | CU693137 | 68 | 131 | 0.2544 | 0.0193 | 1.9154 | 0.938 | 1.92 | 63 | 5.98 |
| MTAP | HE654774 | 142 | 464 | 0.0000 | 0.0000 | 3.2437 | 1.698 | 3.24 | 322 | 8.33 |
| MTAP | HE654776 | 31 | 15 | 1.0000 | 0.4021 | 0.5192 | −0.946 | 1.93 | 15 | 3.93 |
| MTAP | HE654777 | 11 | 0 | 0.1038 | 0.0050 | 0.0833 | −3.585 | 12.00 | 11 | 3.46 |
| MTAP | NM_002451 | 1006 | 1354 | 0.1247 | 0.0065 | 1.3458 | 0.429 | 1.35 | 348 | 8.44 |
| MTERFD1 | AK001801 | 1 | 4 | 1.0000 | 0.4985 | 2.0462 | 1.033 | 2.05 | 2 | 1.24 |
| MTERFD1 | AK309002 | 2 | 0 | 0.5018 | 0.0664 | 0.3142 | −1.670 | 3.18 | 2 | 1.13 |
| MTERFD1 | NM_015942 | 365 | 75 | 0.0000 | 0.0000 | 0.2066 | −2.275 | 4.84 | 290 | 8.18 |
| MTHFD1L | AK127089 | 9 | 5 | 1.0000 | 0.5058 | 0.5317 | −0.911 | 1.88 | 5 | 2.28 |
| MTHFD1L | AK310342 | 33 | 22 | 1.0000 | 0.5608 | 0.6901 | −0.535 | 1.45 | 10 | 3.38 |
| MTHFD1L | BC144369 | 5 | 0 | 0.3038 | 0.0254 | 0.1587 | −2.655 | 6.30 | 5 | 2.41 |
| MTHFD1L | NM_001242768 | 2475 | 1302 | 0.0000 | 0.0000 | 0.5263 | −0.926 | 1.90 | 1173 | 10.20 |
| MTHFD1L | NM_001242769 | 199 | 173 | 1.0000 | 0.5348 | 0.8683 | −0.204 | 1.15 | 26 | 4.72 |
| MTHFD1L | NM_015440 | 404 | 156 | 0.0002 | 0.0000 | 0.3879 | −1.366 | 2.58 | 248 | 7.95 |
| MYADM | CCDS12866 | 135 | 0 | 0.0000 | 0.0000 | 0.0074 | −7.083 | 135.58 | 135 | 7.07 |
| MYADM | NM_001020818 | 196 | 261 | 1.0000 | 0.3295 | 1.3260 | 0.407 | 1.33 | 64 | 6.01 |
| MYADM | NM_001020819 | 1044 | 1075 | 1.0000 | 0.7752 | 1.0289 | 0.041 | 1.03 | 30 | 4.92 |
| MYADM | NM_001020820 | 121 | 185 | 0.6287 | 0.1091 | 1.5253 | 0.609 | 1.53 | 64 | 6.00 |
| MYADM | NM_001020821 | 22 | 32 | 1.0000 | 0.5184 | 1.4509 | 0.537 | 1.45 | 10 | 3.35 |
| MYADM | NM_138373 | 6562 | 5963 | 0.7652 | 0.1623 | 0.9089 | −0.138 | 1.10 | 598 | 9.22 |
| MYLK | AB384705 | 2583 | 2276 | 0.6158 | 0.1056 | 0.8813 | −0.182 | 1.13 | 307 | 8.26 |
| MYLK | AF069604 | 34 | 116 | 0.1160 | 0.0059 | 3.3100 | 1.727 | 3.31 | 82 | 6.35 |
| MYLK | AK300610 | 186 | 269 | 0.8731 | 0.2044 | 1.4470 | 0.533 | 1.45 | 83 | 6.38 |
| MYLK | AK311053 | 8 | 7 | 1.0000 | 0.9375 | 0.8866 | −0.174 | 1.13 | 1 | 0.10 |
| MYLK | BC040115 | 5 | 3 | 1.0000 | 0.6019 | 0.5772 | −0.793 | 1.73 | 3 | 1.45 |
| MYLK | BC064695 | 401 | 410 | 1.0000 | 0.6223 | 1.0225 | 0.032 | 1.02 | 9 | 3.17 |
| MYLK | DQ642691 | 21 | 10 | 1.0000 | 0.3671 | 0.4861 | −1.041 | 2.06 | 11 | 3.49 |
| MYLK | NM_053025 | 1043 | 331 | 0.0000 | 0.0000 | 0.3183 | −1.651 | 3.14 | 712 | 9.48 |
| MYLK | NM_053026 | 3717 | 2884 | 0.0310 | 0.0010 | 0.7761 | −0.366 | 1.29 | 832 | 9.70 |
| MYLK | NM_053027 | 0 | 0 | 9999 | 9999 | 1.0000 | 0.000 | 1.00 | 0 | 0 |
| MYLK | NM_053028 | 0 | 0 | 9999 | 9999 | 1.0000 | 0.000 | 1.00 | 0 | 0 |
| MYLK | NM_053031 | 0 | 6 | 0.3966 | 0.0404 | 6.9530 | 2.798 | 6.95 | 6 | 2.57 |
| MYLK | NM_053032 | 59 | 42 | 1.0000 | 0.4724 | 0.7069 | −0.500 | 1.41 | 18 | 4.14 |
| MYO9B | AK002201 | 398 | 420 | 1.0000 | 0.8200 | 1.0546 | 0.077 | 1.05 | 22 | 4.44 |
| MYO9B | AY927576 | 89 | 66 | 1.0000 | 0.4725 | 0.7454 | −0.424 | 1.34 | 23 | 4.52 |

TABLE 10-continued

RNA Abundance Modulation

| Gene | Trx_ID | ave DMSO | ave Cpd | padj (q val, FDR) | ttest (p val) | FC (x + 1) | $L_2$FC (x + 1) | amp FC (x + 1) | abs (Cpd-DMSO) | $L_2$abs (Cpd-DMSO) |
|---|---|---|---|---|---|---|---|---|---|---|
| MYO9B | NM_001130065 | 899 | 280 | 0.0000 | 0.0000 | 0.3117 | −1.682 | 3.21 | 619 | 9.27 |
| MYO9B | NM_004145 | 1079 | 1759 | 0.0000 | 0.0000 | 1.6287 | 0.704 | 1.63 | 679 | 9.41 |
| MYO9B | U42391 | 1976 | 1900 | 1.0000 | 0.5793 | 0.9615 | −0.057 | 1.04 | 76 | 6.25 |
| MYOF | AL096713 | 1552 | 766 | 0.0000 | 0.0000 | 0.4936 | −1.019 | 2.03 | 786 | 9.62 |
| MYOF | BC033616 | 117 | 120 | 1.0000 | 0.9334 | 1.0294 | 0.042 | 1.03 | 3 | 1.79 |
| MYOF | BC040110 | 21 | 24 | 1.0000 | 0.8859 | 1.1491 | 0.201 | 1.15 | 3 | 1.68 |
| MYOF | NM_013451 | 25516 | 15755 | 0.0000 | 0.0000 | 0.6175 | −0.696 | 1.62 | 9761 | 13.25 |
| MYOF | NM_133337 | 449 | 261 | 0.0345 | 0.0012 | 0.5808 | −0.784 | 1.72 | 189 | 7.56 |
| NASP | AK056161 | 576 | 562 | 1.0000 | 0.9346 | 0.9763 | −0.035 | 1.02 | 14 | 3.77 |
| NASP | AK092829 | 50 | 58 | 1.0000 | 0.7310 | 1.1638 | 0.219 | 1.16 | 8 | 3.06 |
| NASP | AK308001 | 69 | 17 | 0.2240 | 0.0156 | 0.2581 | −1.954 | 3.88 | 52 | 5.69 |
| NASP | AY700118 | 75 | 59 | 1.0000 | 0.6126 | 0.7874 | −0.345 | 1.27 | 16 | 4.02 |
| NASP | NM_001195193 | 0 | 0 | 9999 | 9999 | 1.0000 | 0.000 | 1.00 | 0 | 0 |
| NASP | NM_002482 | 224 | 0 | 0.0000 | 0.0000 | 0.0044 | −7.815 | 225.24 | 224 | 7.81 |
| NASP | NM_152298 | 1137 | 1528 | 0.0686 | 0.0029 | 1.3435 | 0.426 | 1.34 | 391 | 8.61 |
| NAV2 | AK001495 | 18 | 23 | 1.0000 | 0.5717 | 1.2471 | 0.319 | 1.25 | 5 | 2.25 |
| NAV2 | AK096037 | 10 | 1 | 0.5528 | 0.0827 | 0.1931 | −2.372 | 5.18 | 9 | 3.17 |
| NAV2 | AK290458 | 76 | 142 | 0.6144 | 0.1053 | 1.8622 | 0.897 | 1.86 | 66 | 6.05 |
| NAV2 | AK307574 | 35 | 8 | 0.5566 | 0.0841 | 0.2582 | −1.954 | 3.87 | 26 | 4.72 |
| NAV2 | CCDS58126 | 81 | 97 | 1.0000 | 0.6546 | 1.1898 | 0.251 | 1.19 | 16 | 3.96 |
| NAV2 | CCDS7851 | 842 | 807 | 1.0000 | 0.6939 | 0.9587 | −0.061 | 1.04 | 35 | 5.12 |
| NAV2 | NM_001111018 | 607 | 345 | 0.0132 | 0.0003 | 0.5693 | −0.813 | 1.76 | 262 | 8.03 |
| NAV2 | NM_001111019 | 242 | 137 | 0.2983 | 0.0246 | 0.5687 | −0.814 | 1.76 | 105 | 6.71 |
| NAV2 | NM_001244963 | 41 | 0 | 0.0001 | 0.0000 | 0.0237 | −5.400 | 42.23 | 41 | 5.37 |
| NAV2 | NM_182964 | 376 | 0 | 0.0000 | 0.0000 | 0.0026 | −8.560 | 377.48 | 376 | 8.56 |
| NCOA3 | AK302595 | 250 | 268 | 1.0000 | 0.7892 | 1.0731 | 0.102 | 1.07 | 18 | 4.20 |
| NCOA3 | BC122547 | 528 | 241 | 0.0001 | 0.0000 | 0.4586 | −1.125 | 2.18 | 286 | 8.16 |
| NCOA3 | NM_001174087 | 931 | 1204 | 0.1820 | 0.0112 | 1.2929 | 0.371 | 1.29 | 273 | 8.09 |
| NCOA3 | NM_001174088 | 112 | 110 | 1.0000 | 0.9122 | 0.9816 | −0.027 | 1.02 | 2 | 1.06 |
| NCOA3 | NM_006534 | 567 | 547 | 1.0000 | 0.7097 | 0.9643 | −0.052 | 1.04 | 20 | 4.34 |
| NCOA4 | AK293978 | 8 | 20 | 1.0000 | 0.3022 | 2.3459 | 1.230 | 2.35 | 12 | 3.57 |
| NCOA4 | AK302794 | 2 | 3 | 1.0000 | 0.9356 | 1.1122 | 0.153 | 1.11 | 0 | −1.42 |
| NCOA4 | NM_001145260 | 0 | 11 | 0.1916 | 0.0122 | 11.5683 | 3.532 | 11.57 | 11 | 3.40 |
| NCOA4 | NM_001145261 | 66 | 2 | 0.0003 | 0.0000 | 0.0466 | −4.425 | 21.48 | 64 | 6.00 |
| NCOA4 | NM_001145262 | 33 | 6 | 0.3505 | 0.0322 | 0.1937 | −2.368 | 5.16 | 28 | 4.79 |
| NCOA4 | NM_001145263 | 6548 | 6756 | 1.0000 | 0.7404 | 1.0318 | 0.045 | 1.03 | 208 | 7.70 |
| NCOA4 | NM_005437 | 550 | 548 | 1.0000 | 0.9780 | 0.9960 | −0.006 | 1.00 | 2 | 1.13 |
| NELFA | AF131751 | 16 | 15 | 1.0000 | 0.8428 | 0.9191 | −0.122 | 1.09 | 1 | 0.45 |
| NELFA | AK094040 | 0 | 0 | 9999 | 9999 | 1.0000 | 0.000 | 1.00 | 0 | 0 |
| NELFA | AK095737 | 7 | 47 | 0.1881 | 0.0119 | 5.6769 | 2.505 | 5.68 | 40 | 5.31 |
| NELFA | NM_005663 | 445 | 215 | 0.0063 | 0.0001 | 0.4850 | −1.044 | 2.06 | 230 | 7.84 |
| NEO1 | AB528479 | 1149 | 559 | 0.0000 | 0.0000 | 0.4871 | −1.038 | 2.05 | 590 | 9.20 |
| NEO1 | NM_001172623 | 23 | 27 | 1.0000 | 0.7835 | 1.1364 | 0.184 | 1.14 | 3 | 1.72 |
| NEO1 | NM_001172624 | 86 | 40 | 0.4939 | 0.0641 | 0.4754 | −1.073 | 2.10 | 46 | 5.51 |
| NEO1 | NM_002499 | 72 | 11 | 0.0359 | 0.0012 | 0.1715 | −2.543 | 5.83 | 60 | 5.91 |
| NEURL1B | GQ414758 | 61 | 65 | 1.0000 | 0.9167 | 1.0672 | 0.094 | 1.07 | 4 | 2.05 |
| NEURL1B | GQ414759 | 526 | 56 | 0.0000 | 0.0000 | 0.1072 | −3.222 | 9.33 | 471 | 8.88 |
| NEURL1B | NM_001142651 | 101 | 48 | 0.5695 | 0.0877 | 0.4810 | −1.056 | 2.08 | 53 | 5.73 |
| NF2 | AF122828 | 7 | 4 | 1.0000 | 0.5643 | 0.5394 | −0.891 | 1.85 | 4 | 1.97 |
| NF2 | AF369666 | 31 | 27 | 1.0000 | 0.7916 | 0.8752 | −0.192 | 1.14 | 4 | 2.02 |
| NF2 | AF369667 | 154 | 35 | 0.0087 | 0.0002 | 0.2346 | −2.092 | 4.26 | 119 | 6.89 |
| NF2 | AF369700 | 28 | 5 | 0.3762 | 0.0364 | 0.1913 | −2.386 | 5.23 | 23 | 4.55 |
| NF2 | AK297116 | 2 | 2 | 1.0000 | 1.0000 | 0.9764 | −0.035 | 1.02 | 0 | −3.73 |
| NF2 | NM_000268 | 1107 | 1307 | 0.5679 | 0.0873 | 1.1808 | 0.240 | 1.18 | 200 | 7.65 |
| NF2 | NM_016418 | 1137 | 962 | 0.6693 | 0.1226 | 0.8463 | −0.241 | 1.18 | 175 | 7.45 |
| NF2 | NM_181825 | 13 | 39 | 0.6450 | 0.1149 | 2.8205 | 1.496 | 2.82 | 26 | 4.71 |
| NF2 | NM_181828 | 6 | 21 | 0.8319 | 0.1877 | 2.9929 | 1.582 | 2.99 | 15 | 3.86 |
| NF2 | NM_181829 | 24 | 54 | 0.6693 | 0.1236 | 2.1724 | 1.119 | 2.17 | 30 | 4.90 |
| NF2 | NM_181831 | 373 | 381 | 1.0000 | 0.8661 | 1.0193 | 0.028 | 1.02 | 7 | 2.85 |
| NF2 | NM_181832 | 128 | 170 | 0.9601 | 0.2555 | 1.3259 | 0.407 | 1.33 | 42 | 5.39 |
| NID2 | AB385187 | 313 | 112 | 0.0019 | 0.0000 | 0.3589 | −1.478 | 2.79 | 201 | 7.65 |
| NID2 | AK300462 | 659 | 744 | 1.0000 | 0.3276 | 1.1295 | 0.176 | 1.13 | 85 | 6.42 |
| NID2 | BX648241 | 8 | 12 | 1.0000 | 0.7265 | 1.4074 | 0.493 | 1.41 | 4 | 1.93 |
| NID2 | NM_007361 | 1396 | 1041 | 0.1102 | 0.0055 | 0.7458 | −0.423 | 1.34 | 355 | 8.47 |
| NOL10 | AK024000 | 7 | 6 | 1.0000 | 0.8351 | 0.8284 | −0.272 | 1.21 | 1 | 0.53 |
| NOL10 | NM_001261392 | 0 | 0 | 9999 | 9999 | 1.0000 | 0.000 | 1.00 | 0 | 0 |
| NOL10 | NM_001261394 | 36 | 9 | 0.5404 | 0.0793 | 0.2823 | −1.825 | 3.54 | 26 | 4.73 |
| NOL10 | NM_024894 | 1247 | 434 | 0.0000 | 0.0000 | 0.3485 | −1.521 | 2.87 | 813 | 9.67 |
| NOL10 | NR_048552 | 47 | 12 | 0.3914 | 0.0393 | 0.2675 | −1.902 | 3.74 | 35 | 5.14 |
| NPEPPS | AK096491 | 34 | 18 | 1.0000 | 0.3638 | 0.5517 | −0.858 | 1.81 | 16 | 3.96 |
| NPEPPS | AK293995 | 28 | 22 | 1.0000 | 0.6941 | 0.7929 | −0.335 | 1.26 | 6 | 2.58 |
| NPEPPS | AK296887 | 77 | 50 | 1.0000 | 0.3414 | 0.6597 | −0.600 | 1.52 | 26 | 4.72 |
| NPEPPS | AK303037 | 1295 | 365 | 0.0000 | 0.0000 | 0.2822 | −1.825 | 3.54 | 930 | 9.86 |
| NPEPPS | AK311414 | 0 | 14 | 0.1023 | 0.0049 | 14.8487 | 3.892 | 14.85 | 14 | 3.79 |

TABLE 10-continued

RNA Abundance Modulation

| Gene | Trx_ID | ave DMSO | ave Cpd | padj (q val, FDR) | ttest (p val) | FC (x + 1) | $L_2$FC (x + 1) | amp FC (x + 1) | abs (Cpd-DMSO) | $L_2$abs (Cpd-DMSO) |
|---|---|---|---|---|---|---|---|---|---|---|
| NPEPPS | NM_006310 | 1595 | 411 | 0.0000 | 0.0000 | 0.2580 | −1.954 | 3.88 | 1185 | 10.21 |
| NRG1 | AK293270 | 37 | 29 | 1.0000 | 0.8115 | 0.8046 | −0.314 | 1.24 | 7 | 2.88 |
| NRG1 | AY207002 | 0 | 1 | 1.0000 | 0.6737 | 1.7648 | 0.820 | 1.76 | 1 | −0.39 |
| NRG1 | EF372275 | 0 | 8 | 0.3076 | 0.0258 | 8.5879 | 3.102 | 8.59 | 8 | 2.92 |
| NRG1 | EF372277 | 35 | 35 | 1.0000 | 0.7611 | 0.9746 | −0.037 | 1.03 | 1 | −0.11 |
| NRG1 | NM_001159995 | 99 | 109 | 1.0000 | 1.0000 | 1.1092 | 0.149 | 1.11 | 11 | 3.44 |
| NRG1 | NM_001159996 | 178 | 131 | 0.9383 | 0.2404 | 0.7369 | −0.440 | 1.36 | 47 | 5.56 |
| NRG1 | NM_001160001 | 138 | 34 | 0.0374 | 0.0013 | 0.2501 | −1.999 | 4.00 | 104 | 6.70 |
| NRG1 | NM_001160004 | 20 | 27 | 1.0000 | 0.5943 | 1.3418 | 0.424 | 1.34 | 7 | 2.86 |
| NRG1 | NM_001160007 | 1 | 0 | 1.0000 | 0.3241 | 0.5907 | −0.760 | 1.69 | 1 | −0.53 |
| NRG1 | NM_001160008 | 108 | 40 | 0.2416 | 0.0177 | 0.3735 | −1.421 | 2.68 | 68 | 6.10 |
| NRG1 | NM_004495 | 16 | 15 | 1.0000 | 0.9399 | 0.9618 | −0.056 | 1.04 | 1 | −0.64 |
| NRG1 | NM_013956 | 46 | 9 | 0.2266 | 0.0161 | 0.2033 | −2.298 | 4.92 | 38 | 5.24 |
| NRG1 | NM_013957 | 22 | 59 | 0.5253 | 0.0727 | 2.6630 | 1.413 | 2.66 | 38 | 5.23 |
| NRG1 | NM_013958 | 68 | 42 | 1.0000 | 0.3312 | 0.6235 | −0.682 | 1.60 | 26 | 4.69 |
| NRG1 | NM_013959 | 6 | 9 | 1.0000 | 0.7300 | 1.4799 | 0.566 | 1.48 | 3 | 1.74 |
| NRG1 | NM_013960 | 337 | 119 | 0.0015 | 0.0000 | 0.3561 | −1.490 | 2.81 | 218 | 7.77 |
| NRG1 | NM_013964 | 468 | 312 | 0.2769 | 0.0220 | 0.6659 | −0.587 | 1.50 | 157 | 7.29 |
| NRG1 | U02325 | 0 | 7 | 0.3588 | 0.0335 | 7.6774 | 2.941 | 7.68 | 7 | 2.74 |
| NRG1 | U02327 | 25 | 24 | 1.0000 | 0.9696 | 0.9550 | −0.066 | 1.05 | 1 | 0.22 |
| NSUN4 | AK097524 | 8 | 5 | 1.0000 | 0.7640 | 0.6933 | −0.528 | 1.44 | 3 | 1.50 |
| NSUN4 | AK128066 | 13 | 23 | 1.0000 | 0.6243 | 1.6272 | 0.702 | 1.63 | 9 | 3.18 |
| NSUN4 | NM_001256127 | 22 | 14 | 1.0000 | 0.4754 | 0.6254 | −0.677 | 1.60 | 9 | 3.13 |
| NSUN4 | NM_001256128 | 76 | 9 | 0.0180 | 0.0005 | 0.1264 | −2.984 | 7.91 | 67 | 6.07 |
| NSUN4 | NM_199044 | 336 | 43 | 0.0000 | 0.0000 | 0.1297 | −2.947 | 7.71 | 293 | 8.19 |
| NSUN4 | NR_045789 | 56 | 9 | 0.0755 | 0.0032 | 0.1732 | −2.530 | 5.77 | 47 | 5.55 |
| NSUN4 | NR_045790 | 14 | 21 | 1.0000 | 0.6784 | 1.4599 | 0.546 | 1.46 | 7 | 2.76 |
| NSUN4 | NR_045791 | 1 | 3 | 1.0000 | 0.5221 | 2.0863 | 1.061 | 2.09 | 2 | 0.94 |
| NT5C2 | AK127670 | 104 | 59 | 0.8309 | 0.1874 | 0.5749 | −0.799 | 1.74 | 45 | 5.48 |
| NT5C2 | AK295593 | 0 | 0 | 9999 | 9999 | 1.0000 | 0.000 | 1.00 | 0 | 0 |
| NT5C2 | NM_001134373 | 1638 | 390 | 0.0000 | 0.0000 | 0.2388 | −2.066 | 4.19 | 1248 | 10.29 |
| NT5C2 | NM_012229 | 1244 | 276 | 0.0000 | 0.0000 | 0.2221 | −2.170 | 4.50 | 969 | 9.92 |
| NT5E | BC015940 | 125 | 145 | 1.0000 | 0.6168 | 1.1622 | 0.217 | 1.16 | 20 | 4.35 |
| NT5E | NM_001204813 | 447 | 904 | 0.0000 | 0.0000 | 2.0193 | 1.014 | 2.02 | 457 | 8.84 |
| NT5E | NM_002526 | 11095 | 12429 | 0.4920 | 0.0626 | 1.1202 | 0.164 | 1.12 | 1334 | 10.38 |
| NTNG1 | AB023193 | 514 | 242 | 0.0013 | 0.0000 | 0.4717 | −1.084 | 2.12 | 272 | 8.09 |
| NTNG1 | AK296533 | 14 | 4 | 0.7798 | 0.1680 | 0.3394 | −1.559 | 2.95 | 10 | 3.34 |
| NTNG1 | AY764263 | 5 | 0 | 0.3344 | 0.0297 | 0.1583 | −2.659 | 6.32 | 5 | 2.41 |
| NTNG1 | AY764264 | 14 | 0 | 0.0635 | 0.0026 | 0.0675 | −3.890 | 14.82 | 14 | 3.79 |
| NTNG1 | AY781194 | 21 | 1 | 0.1387 | 0.0076 | 0.0842 | −3.569 | 11.87 | 21 | 4.36 |
| NTNG1 | NM_001113226 | 17 | 2 | 0.5620 | 0.0861 | 0.1864 | −2.424 | 5.37 | 15 | 3.88 |
| NTNG1 | NM_001113228 | 0 | 0 | 9999 | 9999 | 1.0000 | 0.000 | 1.00 | 0 | 0 |
| NTNG1 | NM_014917 | 1186 | 483 | 0.0000 | 0.0000 | 0.4080 | −1.293 | 2.45 | 702 | 9.46 |
| NUP153 | NM_001278209 | 29 | 20 | 1.0000 | 0.6748 | 0.6928 | −0.529 | 1.44 | 9 | 3.21 |
| NUP153 | NM_001278210 | 66 | 0 | 0.0000 | 0.0000 | 0.0149 | −6.068 | 67.09 | 66 | 6.05 |
| NUP153 | NM_005124 | 2549 | 3284 | 0.0492 | 0.0018 | 1.2884 | 0.366 | 1.29 | 735 | 9.52 |
| NUP35 | AK289601 | 13 | 6 | 1.0000 | 0.4529 | 0.5254 | −0.928 | 1.90 | 7 | 2.72 |
| NUP35 | AK298199 | 2 | 2 | 1.0000 | 1.0000 | 0.9839 | −0.023 | 1.02 | 0 | −4.60 |
| NUP35 | NM_138285 | 505 | 100 | 0.0000 | 0.0000 | 0.1995 | −2.325 | 5.01 | 405 | 8.66 |
| NUP50 | AK304223 | 7 | 18 | 1.0000 | 0.4803 | 2.2591 | 1.176 | 2.26 | 10 | 3.37 |
| NUP50 | BC016055 | 33 | 54 | 1.0000 | 0.3634 | 1.5993 | 0.677 | 1.60 | 20 | 4.35 |
| NUP50 | NM_007172 | 2806 | 3088 | 0.8287 | 0.1865 | 1.1003 | 0.138 | 1.10 | 281 | 8.14 |
| NUP50 | NM_153645 | 260 | 799 | 0.0000 | 0.0000 | 3.0664 | 1.617 | 3.07 | 539 | 9.07 |
| NUSAP1 | BC010838 | 965 | 1099 | 0.9875 | 0.2785 | 1.1382 | 0.187 | 1.14 | 134 | 7.06 |
| NUSAP1 | BC012887 | 289 | 249 | 1.0000 | 0.5572 | 0.8608 | −0.216 | 1.16 | 40 | 5.34 |
| NUSAP1 | NM_001243142 | 78 | 71 | 1.0000 | 0.9159 | 0.9114 | −0.134 | 1.10 | 7 | 2.80 |
| NUSAP1 | NM_001243143 | 535 | 1260 | 0.0000 | 0.0000 | 2.3508 | 1.233 | 2.35 | 725 | 9.50 |
| NUSAP1 | NM_016359 | 1984 | 1840 | 1.0000 | 0.3557 | 0.9272 | −0.109 | 1.08 | 144 | 7.17 |
| NUSAP1 | NM_018454 | 1008 | 862 | 0.8192 | 0.1830 | 0.8549 | −0.226 | 1.17 | 146 | 7.19 |
| ODF2 | AK126816 | 17 | 34 | 1.0000 | 0.3097 | 1.9044 | 0.929 | 1.90 | 16 | 4.04 |
| ODF2 | AK295662 | 0 | 0 | 1.0000 | 1.0000 | 1.2977 | 0.376 | 1.30 | 0 | −1.75 |
| ODF2 | AK308278 | 47 | 52 | 1.0000 | 0.8356 | 1.1138 | 0.155 | 1.11 | 5 | 2.45 |
| ODF2 | AK309917 | 51 | 60 | 1.0000 | 0.7427 | 1.1809 | 0.240 | 1.18 | 9 | 3.23 |
| ODF2 | NM_001242352 | 1718 | 1600 | 1.0000 | 0.4571 | 0.9311 | −0.103 | 1.07 | 118 | 6.89 |
| ODF2 | NM_001242353 | 93 | 1 | 0.0000 | 0.0000 | 0.0200 | −5.641 | 49.91 | 93 | 6.53 |
| ODF2 | NM_001242354 | 178 | 171 | 1.0000 | 0.8548 | 0.9576 | −0.063 | 1.04 | 8 | 2.93 |
| ODF2 | NM_002540 | 12 | 95 | 0.0070 | 0.0002 | 7.4973 | 2.906 | 7.50 | 83 | 6.38 |
| ODF2 | NM_153432 | 0 | 0 | 9999 | 9999 | 1.0000 | 0.000 | 1.00 | 0 | 0 |
| ODF2 | NM_153435 | 229 | 161 | 0.6874 | 0.1296 | 0.7064 | −0.501 | 1.42 | 67 | 6.08 |
| ODF2 | NM_153436 | 38 | 104 | 0.3046 | 0.0255 | 2.6962 | 1.431 | 2.70 | 66 | 6.04 |
| ODF2 | NM_153437 | 10 | 0 | 0.1421 | 0.0078 | 0.0910 | −3.457 | 10.98 | 10 | 3.32 |
| ODF2 | NM_153439 | 15 | 9 | 1.0000 | 0.5401 | 0.6556 | −0.609 | 1.53 | 5 | 2.44 |
| OS9 | AK304533 | 0 | 0 | 9999 | 9999 | 1.0000 | 0.000 | 1.00 | 0 | 0 |
| OS9 | NM_001017956 | 654 | 1337 | 0.0000 | 0.0000 | 2.0418 | 1.030 | 2.04 | 683 | 9.41 |

TABLE 10-continued

RNA Abundance Modulation

| Gene | Trx_ID | ave DMSO | ave Cpd | padj (q val, FDR) | ttest (p val) | FC (x + 1) | $L_2$FC (x + 1) | amp FC (x + 1) | abs (Cpd-DMSO) | $L_2$abs (Cpd-DMSO) |
|---|---|---|---|---|---|---|---|---|---|---|
| OS9 | NM_001017957 | 590 | 643 | 1.0000 | 0.5306 | 1.0897 | 0.124 | 1.09 | 53 | 5.73 |
| OS9 | NM_001017958 | 443 | 365 | 1.0000 | 0.3646 | 0.8252 | −0.277 | 1.21 | 78 | 6.28 |
| OS9 | NM_001261420 | 3367 | 2722 | 0.1785 | 0.0109 | 0.8085 | −0.307 | 1.24 | 645 | 9.33 |
| OS9 | NM_001261423 | 22 | 11 | 1.0000 | 0.3722 | 0.5389 | −0.892 | 1.86 | 11 | 3.41 |
| OS9 | NM_006812 | 4099 | 3302 | 0.0587 | 0.0023 | 0.8056 | −0.312 | 1.24 | 797 | 9.64 |
| OSBPL6 | BC052259 | 247 | 242 | 1.0000 | 0.9709 | 0.9790 | −0.031 | 1.02 | 5 | 2.38 |
| OSBPL6 | NM_001201480 | 73 | 9 | 0.0073 | 0.0002 | 0.1327 | −2.913 | 7.53 | 64 | 6.00 |
| OSBPL6 | NM_001201481 | 789 | 585 | 0.3558 | 0.0330 | 0.7425 | −0.430 | 1.35 | 203 | 7.67 |
| OSBPL6 | NM_001201482 | 117 | 27 | 0.0370 | 0.0013 | 0.2397 | −2.061 | 4.17 | 90 | 6.49 |
| OSBPL6 | NM_032523 | 118 | 225 | 0.2422 | 0.0178 | 1.9099 | 0.934 | 1.91 | 108 | 6.75 |
| OSBPL6 | NM_145739 | 0 | 6 | 0.3770 | 0.0366 | 7.3739 | 2.882 | 7.37 | 6 | 2.67 |
| P4HA1 | CCDS41537 | 171 | 425 | 0.0020 | 0.0000 | 2.4832 | 1.312 | 2.48 | 255 | 7.99 |
| P4HA1 | CCDS7320 | 807 | 569 | 0.1820 | 0.0112 | 0.7057 | −0.503 | 1.42 | 238 | 7.89 |
| P4HA1 | NM_000917 | 2550 | 2824 | 0.9034 | 0.2180 | 1.1074 | 0.147 | 1.11 | 274 | 8.10 |
| P4HA1 | NM_001017962 | 2490 | 1974 | 0.1502 | 0.0085 | 0.7930 | −0.335 | 1.26 | 516 | 9.01 |
| P4HA1 | NM_001142595 | 48 | 68 | 1.0000 | 0.5517 | 1.4011 | 0.487 | 1.40 | 20 | 4.30 |
| P4HA1 | NM_001142596 | 30 | 32 | 1.0000 | 0.9719 | 1.0506 | 0.071 | 1.05 | 2 | 0.65 |
| P4HB | AK095938 | 9175 | 11668 | 0.0066 | 0.0001 | 1.2717 | 0.347 | 1.27 | 2493 | 11.28 |
| P4HB | BC014504 | 886 | 2736 | 0.0000 | 0.0000 | 3.0848 | 1.625 | 3.08 | 1850 | 10.85 |
| P4HB | NM_000918 | 47574 | 38200 | 0.0024 | 0.0000 | 0.8030 | −0.317 | 1.25 | 9373 | 13.19 |
| PABPC1 | AK298990 | 320 | 777 | 0.0000 | 0.0000 | 2.4200 | 1.275 | 2.42 | 457 | 8.83 |
| PABPC1 | AK303120 | 5900 | 7354 | 0.0559 | 0.0022 | 1.2463 | 0.318 | 1.25 | 1453 | 10.51 |
| PABPC1 | NM_002568 | 21266 | 17608 | 0.0208 | 0.0006 | 0.8280 | −0.272 | 1.21 | 3658 | 11.84 |
| PABPC1 | Y00345 | 610 | 490 | 0.6898 | 0.1305 | 0.8039 | −0.315 | 1.24 | 120 | 6.91 |
| PABPC1 | Z48501 | 3126 | 2134 | 0.0001 | 0.0000 | 0.6827 | −0.551 | 1.46 | 992 | 9.95 |
| PAPD4 | AL833136 | 19 | 0 | 0.0187 | 0.0005 | 0.0500 | −4.323 | 20.02 | 19 | 4.25 |
| PAPD4 | BC047581 | 196 | 0 | 0.0000 | 0.0000 | 0.0051 | −7.622 | 196.96 | 196 | 7.61 |
| PAPD4 | NM_001114393 | 0 | 26 | 0.0091 | 0.0002 | 27.1201 | 4.761 | 27.12 | 26 | 4.71 |
| PAPD4 | NM_001114394 | 1034 | 222 | 0.0000 | 0.0000 | 0.2158 | −2.213 | 4.63 | 812 | 9.67 |
| PAPD4 | NM_173797 | 49 | 1 | 0.0020 | 0.0000 | 0.0437 | −4.515 | 22.86 | 48 | 5.58 |
| PARN | AK299653 | 0 | 18 | 0.0474 | 0.0017 | 19.0990 | 4.255 | 19.10 | 18 | 4.18 |
| PARN | AK303348 | 0 | 0 | 9999 | 9999 | 1.0000 | 0.000 | 1.00 | 0 | 0 |
| PARN | NM_001134477 | 197 | 412 | 0.0029 | 0.0001 | 2.0841 | 1.059 | 2.08 | 215 | 7.75 |
| PARN | NM_001242992 | 19 | 0 | 0.0217 | 0.0007 | 0.0505 | −4.308 | 19.81 | 19 | 4.23 |
| PARN | NM_002582 | 1113 | 955 | 0.7600 | 0.1597 | 0.8581 | −0.221 | 1.17 | 158 | 7.30 |
| PARP4 | AK304399 | 13 | 16 | 1.0000 | 0.8777 | 1.2421 | 0.313 | 1.24 | 3 | 1.74 |
| PARP4 | NM_006437 | 2380 | 873 | 0.0000 | 0.0000 | 0.3670 | −1.446 | 2.72 | 1507 | 10.56 |
| PCBP2 | AK023529 | 16 | 16 | 1.0000 | 0.9805 | 1.0035 | 0.005 | 1.00 | 0 | −4.11 |
| PCBP2 | AK130583 | 219 | 184 | 1.0000 | 0.3967 | 0.8382 | −0.255 | 1.19 | 36 | 5.16 |
| PCBP2 | AK296930 | 2373 | 2055 | 0.5544 | 0.0831 | 0.8662 | −0.207 | 1.15 | 318 | 8.31 |
| PCBP2 | AK299210 | 54 | 60 | 1.0000 | 0.8087 | 1.1105 | 0.151 | 1.11 | 6 | 2.60 |
| PCBP2 | AK302067 | 5 | 2 | 1.0000 | 0.4154 | 0.4171 | −1.262 | 2.40 | 4 | 1.82 |
| PCBP2 | NM_001098620 | 1270 | 1278 | 1.0000 | 0.7989 | 1.0061 | 0.009 | 1.01 | 8 | 2.95 |
| PCBP2 | NM_001128911 | 957 | 799 | 0.3514 | 0.0324 | 0.8352 | −0.260 | 1.20 | 158 | 7.30 |
| PCBP2 | NM_001128912 | 780 | 1211 | 0.0039 | 0.0001 | 1.5514 | 0.634 | 1.55 | 431 | 8.75 |
| PCBP2 | NM_001128913 | 1376 | 1921 | 0.0298 | 0.0010 | 1.3961 | 0.481 | 1.40 | 545 | 9.09 |
| PCBP2 | NM_001128914 | 1423 | 1074 | 0.1598 | 0.0092 | 0.7553 | −0.405 | 1.32 | 348 | 8.44 |
| PCBP2 | NM_005016 | 4665 | 4296 | 1.0000 | 0.3076 | 0.9208 | −0.119 | 1.09 | 370 | 8.53 |
| PCBP2 | NM_031989 | 282 | 643 | 0.0001 | 0.0000 | 2.2781 | 1.188 | 2.28 | 361 | 8.50 |
| PCBP4 | AF092441 | 17 | 14 | 1.0000 | 0.8162 | 0.8389 | −0.253 | 1.19 | 3 | 1.55 |
| PCBP4 | AF257770 | 8 | 21 | 1.0000 | 0.3218 | 2.3108 | 1.208 | 2.31 | 12 | 3.63 |
| PCBP4 | AF257771 | 10 | 0 | 0.3594 | 0.0338 | 0.1206 | −3.052 | 8.29 | 10 | 3.33 |
| PCBP4 | AK001244 | 15 | 18 | 1.0000 | 0.9227 | 1.1506 | 0.202 | 1.15 | 2 | 1.29 |
| PCBP4 | BX647811 | 19 | 14 | 1.0000 | 0.6940 | 0.7462 | −0.422 | 1.34 | 5 | 2.37 |
| PCBP4 | NM_001174100 | 80 | 88 | 1.0000 | 0.7572 | 1.0999 | 0.137 | 1.10 | 8 | 3.01 |
| PCBP4 | NM_020418 | 34 | 25 | 1.0000 | 0.6176 | 0.7344 | −0.445 | 1.36 | 9 | 3.21 |
| PCBP4 | NM_033008 | 674 | 443 | 0.1311 | 0.0070 | 0.6582 | −0.603 | 1.52 | 231 | 7.85 |
| PCBP4 | NM_033010 | 130 | 331 | 0.0088 | 0.0002 | 2.5372 | 1.343 | 2.54 | 201 | 7.65 |
| PCDHGB3 | NM_018924 | 79 | 10 | 0.0079 | 0.0002 | 0.1408 | −2.828 | 7.10 | 69 | 6.11 |
| PCDHGB3 | NM_032097 | 20 | 51 | 0.6946 | 0.1319 | 2.4620 | 1.300 | 2.46 | 31 | 4.96 |
| PCGF3 | AK057124 | 2 | 10 | 0.9511 | 0.2504 | 3.3211 | 1.732 | 3.32 | 7 | 2.89 |
| PCGF3 | AK125801 | 86 | 91 | 1.0000 | 0.8642 | 1.0568 | 0.080 | 1.06 | 5 | 2.30 |
| PCGF3 | AK225892 | 199 | 131 | 0.8763 | 0.2057 | 0.6613 | −0.597 | 1.51 | 68 | 6.08 |
| PCGF3 | AK300290 | 182 | 155 | 1.0000 | 0.5251 | 0.8511 | −0.233 | 1.17 | 27 | 4.77 |
| PCGF3 | BX648409 | 68 | 2 | 0.0003 | 0.0000 | 0.0488 | −4.357 | 20.49 | 66 | 6.04 |
| PCGF3 | NM_006315 | 974 | 1164 | 0.7386 | 0.1494 | 1.1950 | 0.257 | 1.20 | 190 | 7.57 |
| PCM1 | AB587340 | 918 | 137 | 0.0000 | 0.0000 | 0.1506 | −2.731 | 6.64 | 780 | 9.61 |
| PCM1 | AK302378 | 18 | 2 | 0.5184 | 0.0708 | 0.1795 | −2.478 | 5.57 | 16 | 3.96 |
| PCM1 | AK307583 | 158 | 44 | 0.0263 | 0.0008 | 0.2821 | −1.825 | 3.54 | 114 | 6.83 |
| PCM1 | BC000453 | 34 | 11 | 0.5353 | 0.0760 | 0.3299 | −1.600 | 3.03 | 24 | 4.57 |
| PCM1 | BC027477 | 22 | 2 | 0.3566 | 0.0331 | 0.1481 | −2.755 | 6.75 | 20 | 4.30 |
| PCM1 | BC133052 | 391 | 106 | 0.0000 | 0.0000 | 0.2733 | −1.871 | 3.66 | 285 | 8.15 |
| PCM1 | BC140946 | 987 | 218 | 0.0000 | 0.0000 | 0.2218 | −2.173 | 4.51 | 769 | 9.59 |
| PCM1 | NM_006197 | 632 | 197 | 0.0000 | 0.0000 | 0.3121 | −1.680 | 3.20 | 435 | 8.77 |

TABLE 10-continued

RNA Abundance Modulation

| Gene | Trx_ID | ave DMSO | ave Cpd | padj (q val, FDR) | ttest (p val) | FC (x + 1) | L₂FC (x + 1) | amp FC (x + 1) | abs (Cpd-DMSO) | L₂abs (Cpd-DMSO) |
|---|---|---|---|---|---|---|---|---|---|---|
| PCMTD2 | NM_001104925 | 58 | 0 | 0.0000 | 0.0000 | 0.0170 | −5.879 | 58.85 | 58 | 5.85 |
| PCMTD2 | NM_018257 | 583 | 598 | 1.0000 | 0.8553 | 1.0266 | 0.038 | 1.03 | 16 | 3.95 |
| PDE7A | AF332652 | 24 | 35 | 1.0000 | 0.5837 | 1.4117 | 0.497 | 1.41 | 10 | 3.38 |
| PDE7A | NM_001242318 | 316 | 106 | 0.0004 | 0.0000 | 0.3380 | −1.565 | 2.96 | 210 | 7.71 |
| PDE7A | NM_002603 | 22 | 240 | 0.0000 | 0.0000 | 10.5931 | 3.405 | 10.59 | 218 | 7.77 |
| PDXDC1 | AK295168 | 859 | 33 | 0.0000 | 0.0000 | 0.0400 | −4.645 | 25.02 | 826 | 9.69 |
| PDXDC1 | AK299111 | 37 | 0 | 0.0004 | 0.0000 | 0.0266 | −5.232 | 37.58 | 37 | 5.19 |
| PDXDC1 | AK299799 | 35 | 0 | 0.0007 | 0.0000 | 0.0281 | −5.152 | 35.55 | 35 | 5.11 |
| PDXDC1 | AY203955 | 10 | 3 | 0.9827 | 0.2755 | 0.3628 | −1.463 | 2.76 | 7 | 2.85 |
| PDXDC1 | BC033748 | 24 | 10 | 0.9936 | 0.2820 | 0.4361 | −1.197 | 2.29 | 14 | 3.84 |
| PDXDC1 | BC053946 | 122 | 14 | 0.0003 | 0.0000 | 0.1183 | −3.079 | 8.45 | 108 | 6.76 |
| PDXDC1 | BX648066 | 115 | 18 | 0.0044 | 0.0001 | 0.1630 | −2.617 | 6.14 | 97 | 6.60 |
| PDXDC1 | NM_015027 | 1731 | 67 | 0.0000 | 0.0000 | 0.0393 | −4.670 | 25.45 | 1664 | 10.70 |
| PEPD | AK057538 | 8 | 2 | 0.9316 | 0.2368 | 0.3017 | −1.729 | 3.31 | 6 | 2.67 |
| PEPD | NM_000285 | 2224 | 572 | 0.0000 | 0.0000 | 0.2577 | −1.956 | 3.88 | 1652 | 10.69 |
| PEPD | NM_001166056 | 3 | 2 | 1.0000 | 0.8160 | 0.7442 | −0.426 | 1.34 | 1 | 0.08 |
| PEPD | NM_001166057 | 4 | 3 | 1.0000 | 0.8418 | 0.7760 | −0.366 | 1.29 | 1 | 0.09 |
| PFKP | AK128373 | 48 | 43 | 1.0000 | 0.8264 | 0.8948 | −0.160 | 1.12 | 5 | 2.36 |
| PFKP | AK308003 | 50 | 68 | 1.0000 | 0.3181 | 1.3483 | 0.431 | 1.35 | 18 | 4.16 |
| PFKP | AK308226 | 278 | 16 | 0.0000 | 0.0000 | 0.0611 | −4.033 | 16.37 | 262 | 8.04 |
| PFKP | NM_002627 | 6314 | 5353 | 0.2160 | 0.0148 | 0.8479 | −0.238 | 1.18 | 960 | 9.91 |
| PHF19 | AK302996 | 297 | 545 | 0.0158 | 0.0004 | 1.8325 | 0.874 | 1.83 | 248 | 7.95 |
| PHF19 | BC044224 | 191 | 147 | 1.0000 | 0.3370 | 0.7690 | −0.379 | 1.30 | 44 | 5.47 |
| PHF19 | NM_001009936 | 504 | 116 | 0.0000 | 0.0000 | 0.2326 | −2.104 | 4.30 | 387 | 8.60 |
| PHF19 | NM_015651 | 1307 | 1801 | 0.0339 | 0.0011 | 1.3775 | 0.462 | 1.38 | 494 | 8.95 |
| PHRF1 | BC041631 | 17 | 10 | 1.0000 | 0.6421 | 0.6214 | −0.686 | 1.61 | 7 | 2.77 |
| PHRF1 | BC112931 | 0 | 2 | 0.7358 | 0.1484 | 2.8211 | 1.496 | 2.82 | 2 | 0.86 |
| PHRF1 | BC136615 | 1066 | 1067 | 1.0000 | 0.9871 | 1.0017 | 0.002 | 1.00 | 2 | 0.85 |
| PHRF1 | BC144294 | 58 | 34 | 1.0000 | 0.3262 | 0.5934 | −0.753 | 1.69 | 24 | 4.58 |
| PHRF1 | BC144295 | 216 | 376 | 0.1259 | 0.0066 | 1.7316 | 0.792 | 1.73 | 159 | 7.31 |
| PHRF1 | NM_020901 | 66 | 0 | 0.0000 | 0.0000 | 0.0150 | −6.059 | 66.69 | 66 | 6.04 |
| PHTF2 | AL136883 | 18 | 14 | 1.0000 | 0.9585 | 0.7908 | −0.339 | 1.26 | 4 | 1.96 |
| PHTF2 | AM393200 | 20 | 17 | 1.0000 | 0.9279 | 0.8456 | −0.242 | 1.18 | 3 | 1.69 |
| PHTF2 | AX746556 | 301 | 301 | 1.0000 | 1.0000 | 0.9997 | 0.000 | 1.00 | 0 | −3.54 |
| PHTF2 | BC018098 | 45 | 37 | 1.0000 | 0.8037 | 0.8296 | −0.270 | 1.21 | 8 | 2.96 |
| PHTF2 | BC032334 | 15 | 9 | 1.0000 | 0.5780 | 0.6501 | −0.621 | 1.54 | 6 | 2.50 |
| PHTF2 | NM_001127357 | 0 | 0 | 9999 | 9999 | 1.0000 | 0.000 | 1.00 | 0 | 0 |
| PHTF2 | NM_001127358 | 1969 | 2708 | 0.0063 | 0.0001 | 1.3749 | 0.459 | 1.37 | 739 | 9.53 |
| PHTF2 | NM_001127360 | 60 | 73 | 1.0000 | 0.6468 | 1.2109 | 0.276 | 1.21 | 13 | 3.68 |
| PHTF2 | NM_020432 | 643 | 0 | 0.0000 | 0.0000 | 0.0016 | −9.331 | 643.84 | 643 | 9.33 |
| PIEZO1 | AX747306 | 36 | 13 | 0.7518 | 0.1539 | 0.3830 | −1.385 | 2.61 | 23 | 4.49 |
| PIEZO1 | BC008073 | 53 | 58 | 1.0000 | 0.8453 | 1.0952 | 0.131 | 1.10 | 5 | 2.36 |
| PIEZO1 | BC016983 | 206 | 230 | 1.0000 | 0.5962 | 1.1133 | 0.155 | 1.11 | 23 | 4.55 |
| PIEZO1 | BC141877 | 1229 | 532 | 0.0000 | 0.0000 | 0.4331 | −1.207 | 2.31 | 697 | 9.45 |
| PIEZO1 | NM_001142864 | 14246 | 6714 | 0.0000 | 0.0000 | 0.4713 | −1.085 | 2.12 | 7532 | 12.88 |
| PIGU | AK301900 | 2 | 0 | 0.5404 | 0.0787 | 0.3908 | −1.355 | 2.56 | 2 | 0.64 |
| PIGU | AK308627 | 1 | 2 | 1.0000 | 0.6809 | 1.8219 | 0.865 | 1.82 | 1 | 0.42 |
| PIGU | AY339061 | 0 | 0 | 9999 | 9999 | 1.0000 | 0.000 | 1.00 | 0 | 0 |
| PIGU | NM_080476 | 638 | 290 | 0.0001 | 0.0000 | 0.4556 | −1.134 | 2.20 | 348 | 8.44 |
| PITPNA | BC027177 | 96 | 265 | 0.0028 | 0.0001 | 2.7335 | 1.451 | 2.73 | 169 | 7.40 |
| PITPNA | CCDS45563 | 300 | 305 | 1.0000 | 0.9879 | 1.0173 | 0.025 | 1.02 | 5 | 2.38 |
| PITPNA | NM_006224 | 2284 | 2324 | 1.0000 | 0.9848 | 1.0177 | 0.025 | 1.02 | 40 | 5.34 |
| PITPNB | AK302367 | 22 | 5 | 0.5018 | 0.0665 | 0.2637 | −1.923 | 3.79 | 17 | 4.06 |
| PITPNB | BC031427 | 18 | 0 | 0.0277 | 0.0009 | 0.0534 | −4.227 | 18.73 | 18 | 4.15 |
| PITPNB | CU689164 | 0 | 0 | 9999 | 9999 | 1.0000 | 0.000 | 1.00 | 0 | 0 |
| PITPNB | NM_012399 | 2915 | 352 | 0.0000 | 0.0000 | 0.1211 | −3.045 | 8.26 | 2563 | 11.32 |
| PITPNM1 | AK126944 | 8 | 9 | 1.0000 | 0.8905 | 1.1202 | 0.164 | 1.12 | 1 | 0.17 |
| PITPNM1 | NM_001130848 | 203 | 222 | 1.0000 | 0.6465 | 1.0932 | 0.129 | 1.09 | 19 | 4.25 |
| PITPNM1 | NM_004910 | 577 | 287 | 0.0059 | 0.0001 | 0.4988 | −1.004 | 2.00 | 289 | 8.18 |
| PITPNM1 | X98654 | 143 | 457 | 0.0000 | 0.0000 | 3.1893 | 1.673 | 3.19 | 314 | 8.30 |
| PLAU | AK297940 | 8 | 15 | 1.0000 | 0.5040 | 1.7370 | 0.797 | 1.74 | 7 | 2.81 |
| PLAU | E06063 | 8 | 13 | 1.0000 | 0.6488 | 1.4999 | 0.585 | 1.50 | 5 | 2.20 |
| PLAU | M15476 | 122 | 99 | 1.0000 | 0.3510 | 0.8131 | −0.298 | 1.23 | 23 | 4.52 |
| PLAU | NM_001145031 | 8 | 19 | 1.0000 | 0.3052 | 2.1857 | 1.128 | 2.19 | 11 | 3.47 |
| PLAU | NM_002658 | 243 | 592 | 0.0000 | 0.0000 | 2.4286 | 1.280 | 2.43 | 349 | 8.45 |
| PLSCR3 | AK314643 | 296 | 418 | 0.4108 | 0.0433 | 1.4076 | 0.493 | 1.41 | 121 | 6.92 |
| PLSCR3 | BC014989 | 312 | 329 | 1.0000 | 0.7541 | 1.0538 | 0.076 | 1.05 | 17 | 4.08 |
| PLSCR3 | BC028080 | 57 | 95 | 0.9546 | 0.2521 | 1.6491 | 0.722 | 1.65 | 38 | 5.24 |
| PLSCR3 | NM_001201576 | 53 | 0 | 0.0000 | 0.0000 | 0.0187 | −5.745 | 53.62 | 53 | 5.72 |
| PLSCR3 | NM_020360 | 1087 | 816 | 0.1616 | 0.0094 | 0.7511 | −0.413 | 1.33 | 271 | 8.08 |
| PLXNC1 | AK295226 | 14 | 5 | 0.8893 | 0.2113 | 0.3876 | −1.367 | 2.58 | 9 | 3.24 |
| PLXNC1 | NM_005761 | 283 | 50 | 0.0000 | 0.0000 | 0.1794 | −2.479 | 5.57 | 233 | 7.87 |
| PLXNC1 | NR_037687 | 35 | 18 | 1.0000 | 0.3288 | 0.5404 | −0.888 | 1.85 | 17 | 4.05 |
| PMS1 | AB102869 | 34 | 3 | 0.1472 | 0.0083 | 0.1233 | −3.019 | 8.11 | 31 | 4.95 |

TABLE 10-continued

RNA Abundance Modulation

| Gene | Trx_ID | ave DMSO | ave Cpd | padj (q val, FDR) | ttest (p val) | FC (x + 1) | L$_2$FC (x + 1) | amp FC (x + 1) | abs (Cpd-DMSO) | L$_2$abs (Cpd-DMSO) |
|---|---|---|---|---|---|---|---|---|---|---|
| PMS1 | AB102872 | 1 | 1 | 1.0000 | 1.0000 | 1.1660 | 0.222 | 1.17 | 0 | −1.89 |
| PMS1 | AB102874 | 0 | 0 | 9999 | 9999 | 1.0000 | 0.000 | 1.00 | 0 | 0 |
| PMS1 | AK295602 | 0 | 0 | 9999 | 9999 | 1.0000 | 0.000 | 1.00 | 0 | 0 |
| PMS1 | AK304634 | 0 | 0 | 1.0000 | 1.0000 | 1.2977 | 0.376 | 1.30 | 0 | −1.75 |
| PMS1 | AK316215 | 0 | 0 | 9999 | 9999 | 1.0000 | 0.000 | 1.00 | 0 | 0 |
| PMS1 | AY540750 | 14 | 6 | 1.0000 | 0.3678 | 0.4594 | −1.122 | 2.18 | 8 | 3.06 |
| PMS1 | AY540751 | 8 | 0 | 0.1967 | 0.0127 | 0.1097 | −3.189 | 9.12 | 8 | 3.02 |
| PMS1 | BC008410 | 4 | 13 | 1.0000 | 0.2944 | 2.6080 | 1.383 | 2.61 | 9 | 3.14 |
| PMS1 | BC036376 | 17 | 7 | 1.0000 | 0.3082 | 0.4567 | −1.131 | 2.19 | 10 | 3.27 |
| PMS1 | NM_000534 | 335 | 31 | 0.0000 | 0.0000 | 0.0942 | −3.408 | 10.61 | 305 | 8.25 |
| PMS1 | NM_001128143 | 0 | 0 | 9999 | 9999 | 1.0000 | 0.000 | 1.00 | 0 | 0 |
| PMS1 | NM_001128144 | 18 | 2 | 0.4162 | 0.0443 | 0.1498 | −2.739 | 6.68 | 16 | 3.98 |
| POU2F1 | AK091438 | 0 | 10 | 0.1897 | 0.0120 | 11.3196 | 3.501 | 11.32 | 10 | 3.37 |
| POU2F1 | AK302525 | 0 | 0 | 9999 | 9999 | 1.0000 | 0.000 | 1.00 | 0 | 0 |
| POU2F1 | BC007388 | 12 | 7 | 1.0000 | 0.6607 | 0.6362 | −0.652 | 1.57 | 5 | 2.22 |
| POU2F1 | NM_001198786 | 52 | 0 | 0.0000 | 0.0000 | 0.0190 | −5.721 | 52.75 | 52 | 5.69 |
| POU2F1 | NM_002697 | 303 | 327 | 1.0000 | 0.6858 | 1.0771 | 0.107 | 1.08 | 23 | 4.55 |
| POU2F1 | NR_037163 | 0 | 10 | 0.2012 | 0.0131 | 11.0161 | 3.462 | 11.02 | 10 | 3.32 |
| POU2F1 | S66902 | 0 | 2 | 1.0000 | 0.7030 | 1.8315 | 0.873 | 1.83 | 1 | 0.20 |
| PPAPDC1A | AK098668 | 341 | 168 | 0.0378 | 0.0013 | 0.4932 | −1.020 | 2.03 | 173 | 7.44 |
| PPAPDC1A | AK310178 | 87 | 35 | 0.4425 | 0.0495 | 0.4072 | −1.296 | 2.46 | 52 | 5.70 |
| PPAPDC1A | BC101268 | 45 | 44 | 1.0000 | 0.9563 | 0.9653 | −0.051 | 1.04 | 2 | 0.68 |
| PPAPDC1A | BC101269 | 118 | 104 | 1.0000 | 0.7218 | 0.8787 | −0.187 | 1.14 | 14 | 3.85 |
| PPAPDC1A | BC122535 | 7 | 9 | 1.0000 | 0.8180 | 1.2675 | 0.342 | 1.27 | 2 | 1.05 |
| PPAPDC1A | NM_001030059 | 593 | 223 | 0.0000 | 0.0000 | 0.3767 | −1.409 | 2.65 | 370 | 8.53 |
| PPHLN1 | AK000186 | 4 | 5 | 1.0000 | 1.0000 | 1.0300 | 0.043 | 1.03 | 0 | −2.62 |
| PPHLN1 | AK299682 | 1 | 1 | 1.0000 | 1.0000 | 1.1677 | 0.224 | 1.17 | 0 | −1.87 |
| PPHLN1 | AK299951 | 63 | 132 | 0.3349 | 0.0298 | 2.0777 | 1.055 | 2.08 | 69 | 6.11 |
| PPHLN1 | AK303612 | 10 | 14 | 1.0000 | 0.6924 | 1.3715 | 0.456 | 1.37 | 4 | 2.05 |
| PPHLN1 | NM_001143787 | 295 | 231 | 0.8665 | 0.2019 | 0.7859 | −0.348 | 1.27 | 63 | 5.98 |
| PPHLN1 | NM_001143788 | 0 | 14 | 0.1308 | 0.0070 | 14.7669 | 3.884 | 14.77 | 14 | 3.78 |
| PPHLN1 | NM_001143789 | 251 | 10 | 0.0000 | 0.0000 | 0.0450 | −4.475 | 22.24 | 240 | 7.91 |
| PPHLN1 | NM_201438 | 2 | 8 | 0.9418 | 0.2441 | 2.8395 | 1.506 | 2.84 | 6 | 2.60 |
| PPHLN1 | NM_201439 | 312 | 710 | 0.0000 | 0.0000 | 2.2687 | 1.182 | 2.27 | 397 | 8.63 |
| PPHLN1 | NM_201440 | 260 | 22 | 0.0000 | 0.0000 | 0.0899 | −3.476 | 11.13 | 237 | 7.89 |
| PPHLN1 | NM_201515 | 24 | 147 | 0.0016 | 0.0000 | 6.0199 | 2.590 | 6.02 | 123 | 6.95 |
| PPIP5K1 | AF502586 | 7 | 29 | 0.5720 | 0.0885 | 3.6751 | 1.878 | 3.68 | 22 | 4.45 |
| PPIP5K1 | AF502589 | 30 | 53 | 0.9532 | 0.2516 | 1.7375 | 0.797 | 1.74 | 23 | 4.52 |
| PPIP5K1 | AF502589 | 0 | 0 | 9999 | 9999 | 1.0000 | 0.000 | 1.00 | 0 | 0 |
| PPIP5K1 | AK307438 | 57 | 0 | 0.0000 | 0.0000 | 0.0173 | −5.850 | 57.67 | 57 | 5.82 |
| PPIP5K1 | AK307438 | 16 | 8 | 1.0000 | 0.4394 | 0.5171 | −0.951 | 1.93 | 8 | 3.03 |
| PPIP5K1 | BC050263 | 0 | 0 | 9999 | 9999 | 1.0000 | 0.000 | 1.00 | 0 | 0 |
| PPIP5K1 | NM_001130858 | 68 | 148 | 0.3772 | 0.0366 | 2.1726 | 1.119 | 2.17 | 81 | 6.33 |
| PPIP5K1 | NM_001130859 | 260 | 154 | 0.3325 | 0.0295 | 0.5927 | −0.755 | 1.69 | 106 | 6.73 |
| PPIP5K1 | NM_001190214 | 42 | 36 | 1.0000 | 0.8260 | 0.8512 | −0.232 | 1.17 | 6 | 2.69 |
| PPIP5K1 | NM_014659 | 104 | 127 | 1.0000 | 0.5154 | 1.2218 | 0.289 | 1.22 | 23 | 4.54 |
| PPP1R12A | AK057712 | 26 | 27 | 1.0000 | 0.9567 | 1.0170 | 0.024 | 1.02 | 0 | −1.10 |
| PPP1R12A | BC047898 | 14 | 73 | 0.0772 | 0.0034 | 4.9192 | 2.298 | 4.92 | 59 | 5.89 |
| PPP1R12A | NM_001143885 | 59 | 0 | 0.0165 | 0.0000 | 0.0165 | −5.917 | 60.43 | 59 | 5.89 |
| PPP1R12A | NM_001244990 | 18 | 13 | 1.0000 | 0.6738 | 0.7269 | −0.460 | 1.38 | 5 | 2.40 |
| PPP1R12A | NM_001244992 | 2128 | 1872 | 0.7259 | 0.1429 | 0.8797 | −0.185 | 1.14 | 256 | 8.00 |
| PPP1R12A | NM_002480 | 3155 | 2995 | 1.0000 | 0.4802 | 0.9494 | −0.075 | 1.05 | 160 | 7.32 |
| PRKDC | NM_001081640 | 943 | 0 | 0.0000 | 0.0000 | 0.0011 | −9.882 | 943.63 | 943 | 9.88 |
| PRKDC | NM_006904 | 11429 | 920 | 0.0000 | 0.0000 | 0.0806 | −3.633 | 12.41 | 10508 | 13.36 |
| PRMT1 | AK295973 | 26 | 90 | 0.1497 | 0.0085 | 3.4342 | 1.780 | 3.43 | 65 | 6.01 |
| PRMT1 | NM_001207042 | 6 | 4 | 1.0000 | 0.7111 | 0.6972 | −0.520 | 1.43 | 2 | 1.09 |
| PRMT1 | NM_001536 | 245 | 107 | 0.0754 | 0.0032 | 0.4403 | −1.183 | 2.27 | 137 | 7.10 |
| PRMT1 | NM_198318 | 2555 | 862 | 0.0000 | 0.0000 | 0.3378 | −1.566 | 2.96 | 1692 | 10.72 |
| PRMT1 | NR_033397 | 23 | 13 | 1.0000 | 0.5401 | 0.5987 | −0.740 | 1.67 | 10 | 3.27 |
| PRSS23 | AK304301 | 4613 | 3696 | 0.0370 | 0.0013 | 0.8013 | −0.320 | 1.25 | 917 | 9.84 |
| PRSS23 | BC063022 | 536 | 265 | 0.0017 | 0.0000 | 0.4946 | −1.016 | 2.02 | 271 | 8.08 |
| PRSS23 | CCDS8278 | 6478 | 5453 | 0.1178 | 0.0060 | 0.8418 | −0.248 | 1.19 | 1025 | 10.00 |
| PRSS23 | NM_007173 | 4988 | 4184 | 0.1526 | 0.0088 | 0.8389 | −0.253 | 1.19 | 804 | 9.65 |
| PSMA4 | AK055714 | 24 | 25 | 1.0000 | 0.9401 | 1.0450 | 0.063 | 1.04 | 1 | 0.17 |
| PSMA4 | BC030529 | 7 | 0 | 0.2217 | 0.0153 | 0.1188 | −3.073 | 8.41 | 7 | 2.89 |
| PSMA4 | NM_001102667 | 41 | 53 | 1.0000 | 0.7567 | 1.2864 | 0.363 | 1.29 | 12 | 3.58 |
| PSMA4 | NM_001102668 | 69 | 0 | 0.0000 | 0.0000 | 0.0144 | −6.122 | 69.66 | 69 | 6.10 |
| PSMA4 | NM_002789 | 3108 | 3624 | 0.4406 | 0.0492 | 1.1657 | 0.221 | 1.17 | 515 | 9.01 |
| PTK2B | AK128371 | 0 | 0 | 1.0000 | 1.0000 | 1.0539 | 0.076 | 1.05 | 0 | −3.82 |
| PTK2B | AK128371 | 0 | 0 | 9999 | 9999 | 1.0000 | 0.000 | 1.00 | 0 | 0 |
| PTK2B | AY429564 | 1 | 2 | 1.0000 | 0.6804 | 1.5874 | 0.667 | 1.59 | 1 | 0.05 |
| PTK2B | NM_004103 | 65 | 0 | 0.0000 | 0.0000 | 0.0152 | −6.037 | 65.65 | 65 | 6.01 |
| PTK2B | NM_173174 | 63 | 66 | 1.0000 | 1.0000 | 1.0530 | 0.074 | 1.05 | 3 | 1.76 |
| PTK2B | NM_173175 | 14 | 0 | 0.0726 | 0.0031 | 0.0686 | −3.866 | 14.58 | 14 | 3.76 |

TABLE 10-continued

RNA Abundance Modulation

| Gene | Trx_ID | ave DMSO | ave Cpd | padj (q val, FDR) | ttest (p val) | FC (x + 1) | L₂FC (x + 1) | amp FC (x + 1) | abs (Cpd-DMSO) | L₂abs (Cpd-DMSO) |
|---|---|---|---|---|---|---|---|---|---|---|
| PTK2B | NM_173176 | 36 | 82 | 0.5319 | 0.0752 | 2.2575 | 1.175 | 2.26 | 46 | 5.52 |
| PUF60 | AK055941 | 1 | 0 | 1.0000 | 0.3296 | 0.5674 | -0.818 | 1.76 | 1 | -0.39 |
| PUF60 | NM_001136033 | 25 | 10 | 0.9714 | 0.2634 | 0.4228 | -1.242 | 2.37 | 15 | 3.89 |
| PUF60 | NM_001271096 | 88 | 190 | 0.1389 | 0.0076 | 2.1303 | 1.091 | 2.13 | 101 | 6.66 |
| PUF60 | NM_001271097 | 631 | 919 | 0.0737 | 0.0031 | 1.4547 | 0.541 | 1.45 | 287 | 8.17 |
| PUF60 | NM_001271098 | 180 | 39 | 0.0013 | 0.0000 | 0.2182 | -2.196 | 4.58 | 142 | 7.15 |
| PUF60 | NM_001271099 | 404 | 367 | 1.0000 | 0.4654 | 0.9079 | -0.139 | 1.10 | 37 | 5.22 |
| PUF60 | NM_001271100 | 0 | 38 | 0.0042 | 0.0001 | 29.7092 | 4.893 | 29.71 | 38 | 5.24 |
| PUF60 | NM_014281 | 938 | 510 | 0.0002 | 0.0000 | 0.5439 | -0.879 | 1.84 | 428 | 8.74 |
| PUF60 | NM_078480 | 1002 | 1253 | 0.3025 | 0.0250 | 1.2507 | 0.323 | 1.25 | 251 | 7.97 |
| PVR | AK094177 | 51 | 0 | 0.0000 | 0.0000 | 0.0192 | -5.704 | 52.13 | 51 | 5.68 |
| PVR | NM_001135768 | 493 | 465 | 1.0000 | 0.6674 | 0.9438 | -0.083 | 1.06 | 28 | 4.79 |
| PVR | NM_001135769 | 551 | 562 | 1.0000 | 0.8399 | 1.0192 | 0.027 | 1.02 | 11 | 3.41 |
| PVR | NM_001135770 | 309 | 263 | 1.0000 | 0.5222 | 0.8522 | -0.231 | 1.17 | 46 | 5.52 |
| PVR | NM_006505 | 1587 | 1814 | 0.7428 | 0.1507 | 1.1427 | 0.192 | 1.14 | 227 | 7.82 |
| RAB23 | AF161486 | 716 | 324 | 0.0000 | 0.0000 | 0.4529 | -1.143 | 2.21 | 392 | 8.62 |
| RAB23 | AK311123 | 0 | 1 | 1.0000 | 0.4633 | 1.8930 | 0.921 | 1.89 | 1 | -0.16 |
| RAB23 | NM_016277 | 867 | 893 | 1.0000 | 0.7026 | 1.0294 | 0.042 | 1.03 | 26 | 4.67 |
| RAB23 | NM_183227 | 115 | 636 | 0.0000 | 0.0000 | 5.4994 | 2.459 | 5.50 | 521 | 9.03 |
| RAB2B | AK307349 | 0 | 1 | 0.9827 | 0.2720 | 2.1906 | 1.131 | 2.19 | 1 | 0.25 |
| RAB2B | NM_001163380 | 141 | 63 | 0.2810 | 0.0225 | 0.4493 | -1.154 | 2.23 | 78 | 6.29 |
| RAB2B | NM_032846 | 228 | 38 | 0.0000 | 0.0000 | 0.1687 | -2.567 | 5.93 | 191 | 7.57 |
| RAB2B | NR_028074 | 16 | 0 | 0.0428 | 0.0015 | 0.0601 | -4.057 | 16.64 | 16 | 3.97 |
| RAD1 | AF030933 | 207 | 53 | 0.0014 | 0.0000 | 0.2570 | -1.960 | 3.89 | 155 | 7.27 |
| RAD1 | NM_002853 | 595 | 872 | 0.0908 | 0.0042 | 1.4645 | 0.550 | 1.46 | 277 | 8.11 |
| RAD1 | NR_026591 | 343 | 394 | 1.0000 | 0.4089 | 1.1476 | 0.199 | 1.15 | 51 | 5.67 |
| RAD23B | AK293532 | 2595 | 2634 | 1.0000 | 0.8868 | 1.0151 | 0.022 | 1.02 | 39 | 5.29 |
| RAD23B | NM_001244713 | 75 | 0 | 0.0000 | 0.0000 | 0.0131 | -6.256 | 76.44 | 75 | 6.24 |
| RAD23B | NM_001244724 | 7096 | 7447 | 1.0000 | 0.5183 | 1.0494 | 0.070 | 1.05 | 351 | 8.45 |
| RAD23B | NM_002874 | 107 | 0 | 0.0000 | 0.0000 | 0.0092 | -6.757 | 108.18 | 107 | 6.74 |
| RAP1A | M22995 | 1257 | 459 | 0.0000 | 0.0000 | 0.3657 | -1.451 | 2.73 | 798 | 9.64 |
| RAP1A | NM_001010935 | 326 | 1739 | 0.0000 | 0.0000 | 5.3227 | 2.412 | 5.32 | 1413 | 10.46 |
| RAP1A | NM_002884 | 867 | 284 | 0.0000 | 0.0000 | 0.3277 | -1.609 | 3.05 | 584 | 9.19 |
| RAP1GDS1 | NM_001100426 | 427 | 509 | 0.7358 | 0.1480 | 1.1925 | 0.254 | 1.19 | 82 | 6.36 |
| RAP1GDS1 | NM_001100427 | 1299 | 1499 | 0.7652 | 0.1619 | 1.1532 | 0.206 | 1.15 | 199 | 7.64 |
| RAP1GDS1 | NM_001100428 | 273 | 75 | 0.0002 | 0.0000 | 0.2759 | -1.858 | 3.62 | 198 | 7.63 |
| RAP1GDS1 | NM_001100429 | 309 | 247 | 0.9827 | 0.2713 | 0.8000 | -0.322 | 1.25 | 62 | 5.95 |
| RAP1GDS1 | NM_001100430 | 0 | 0 | 9999 | 9999 | 1.0000 | 0.000 | 1.00 | 0 | 0 |
| RAP1GDS1 | NM_021159 | 233 | 262 | 1.0000 | 0.7948 | 1.1216 | 0.166 | 1.12 | 28 | 4.83 |
| RARG | AK301057 | 9 | 15 | 1.0000 | 0.5816 | 1.5731 | 0.654 | 1.57 | 6 | 2.58 |
| RARG | M24857 | 223 | 44 | 0.0000 | 0.0000 | 0.1987 | -2.331 | 5.03 | 180 | 7.49 |
| RARG | NM_000966 | 360 | 475 | 0.5555 | 0.0835 | 1.3191 | 0.400 | 1.32 | 115 | 6.85 |
| RARG | NM_001042728 | 600 | 466 | 0.5404 | 0.0793 | 0.7770 | -0.364 | 1.29 | 134 | 7.07 |
| RARG | NM_001243730 | 186 | 94 | 0.3108 | 0.0264 | 0.5056 | -0.984 | 1.98 | 93 | 6.53 |
| RARG | NM_001243732 | 25 | 35 | 1.0000 | 0.6069 | 1.3829 | 0.468 | 1.38 | 10 | 3.30 |
| RASSF8 | AY665468 | 376 | 1559 | 0.0000 | 0.0000 | 4.1347 | 2.048 | 4.13 | 1183 | 10.21 |
| RASSF8 | AY665470 | 8 | 11 | 1.0000 | 0.7796 | 1.3994 | 0.485 | 1.40 | 3 | 1.78 |
| RASSF8 | NM_001164746 | 5 | 5 | 1.0000 | 0.9623 | 0.9778 | -0.032 | 1.02 | 0 | -2.84 |
| RASSF8 | NM_001164747 | 858 | 495 | 0.0009 | 0.0000 | 0.5776 | -0.792 | 1.73 | 363 | 8.50 |
| RASSF8 | NM_001164748 | 1571 | 913 | 0.0000 | 0.0000 | 0.5812 | -0.783 | 1.72 | 658 | 9.36 |
| RASSF8 | NM_007211 | 74 | 48 | 1.0000 | 0.3766 | 0.6496 | -0.622 | 1.54 | 26 | 4.71 |
| RBCK1 | AK303357 | 11 | 14 | 1.0000 | 0.7655 | 1.2879 | 0.365 | 1.29 | 3 | 1.78 |
| RBCK1 | AK309414 | 572 | 447 | 0.5836 | 0.0948 | 0.7818 | -0.355 | 1.28 | 125 | 6.97 |
| RBCK1 | BC000983 | 50 | 6 | 0.1105 | 0.0055 | 0.1414 | -2.822 | 7.07 | 44 | 5.46 |
| RBCK1 | BC014116 | 63 | 0 | 0.0000 | 0.0000 | 0.0157 | -5.991 | 63.59 | 63 | 5.97 |
| RBCK1 | NM_006462 | 1 | 70 | 0.0000 | 0.0000 | 33.3081 | 5.058 | 33.31 | 69 | 6.11 |
| RBCK1 | NM_031229 | 1734 | 1512 | 0.7172 | 0.1402 | 0.8722 | -0.197 | 1.15 | 222 | 7.79 |
| RCC1 | NM_001048194 | 19 | 190 | 0.0000 | 0.0000 | 9.5321 | 3.253 | 9.53 | 171 | 7.42 |
| RCC1 | NM_001048195 | 256 | 829 | 0.0000 | 0.0000 | 3.2240 | 1.689 | 3.22 | 572 | 9.16 |
| RCC1 | NM_001048199 | 84 | 836 | 0.0000 | 0.0000 | 9.8794 | 3.304 | 9.88 | 753 | 9.56 |
| RCC1 | NM_001269 | 1347 | 434 | 0.0000 | 0.0000 | 0.3223 | -1.633 | 3.10 | 914 | 9.84 |
| RCC1 | NR_030725 | 761 | 4646 | 0.0000 | 0.0000 | 6.0970 | 2.608 | 6.10 | 3885 | 11.92 |
| RCC1 | NR_030726 | 144 | 608 | 0.0000 | 0.0000 | 4.2112 | 2.074 | 4.21 | 464 | 8.86 |
| RFWD2 | AK001278 | 462 | 20 | 0.0000 | 0.0000 | 0.0461 | -4.439 | 21.69 | 441 | 8.79 |
| RFWD2 | AK025789 | 85 | 5 | 0.0006 | 0.0000 | 0.0748 | -3.740 | 13.37 | 80 | 6.32 |
| RFWD2 | BC039723 | 37 | 12 | 0.6051 | 0.1003 | 0.3534 | -1.501 | 2.83 | 24 | 4.61 |
| RFWD2 | NM_001001740 | 105 | 16 | 0.0047 | 0.0001 | 0.1558 | -2.683 | 6.42 | 90 | 6.49 |
| RFWD2 | NM_022457 | 531 | 23 | 0.0000 | 0.0000 | 0.0447 | -4.484 | 22.37 | 508 | 8.99 |
| RGS3 | AK125094 | 3 | 1 | 1.0000 | 0.3195 | 0.4001 | -1.322 | 2.50 | 3 | 1.40 |
| RGS3 | AK222888 | 0 | 0 | 1.0000 | 1.0000 | 1.3824 | 0.467 | 1.38 | 0 | -1.39 |
| RGS3 | AK226153 | 1 | 2 | 1.0000 | 1.0000 | 1.3020 | 0.381 | 1.30 | 1 | -0.77 |
| RGS3 | AK289666 | 312 | 112 | 0.0024 | 0.0000 | 0.3628 | -1.463 | 2.76 | 199 | 7.64 |
| RGS3 | AK310705 | 132 | 388 | 0.0001 | 0.0000 | 2.9126 | 1.542 | 2.91 | 255 | 8.00 |
| RGS3 | NM_001276261 | 0 | 3 | 0.6088 | 0.1029 | 3.9882 | 1.996 | 3.99 | 3 | 1.58 |

TABLE 10-continued

RNA Abundance Modulation

| Gene | Trx_ID | ave DMSO | ave Cpd | padj (q val, FDR) | ttest (p val) | FC (x + 1) | L₂FC (x + 1) | amp FC (x + 1) | abs (Cpd-DMSO) | L₂abs (Cpd-DMSO) |
|---|---|---|---|---|---|---|---|---|---|---|
| RGS3 | NM_001276262 | 48 | 26 | 1.0000 | 0.3348 | 0.5666 | −0.820 | 1.76 | 21 | 4.39 |
| RGS3 | NM_017790 | 1 | 0 | 0.5736 | 0.0911 | 0.4430 | −1.175 | 2.26 | 1 | 0.33 |
| RGS3 | NM_130795 | 2 | 0 | 0.4853 | 0.0610 | 0.2862 | −1.805 | 3.49 | 2 | 1.32 |
| RGS3 | NM_134427 | 0 | 0 | 9999 | 9999 | 1.0000 | 0.000 | 1.00 | 0 | 0 |
| RGS3 | NM_144489 | 230 | 303 | 0.9218 | 0.2277 | 1.3168 | 0.397 | 1.32 | 73 | 6.19 |
| RGS3 | NR_074077 | 0 | 0 | 9999 | 9999 | 1.0000 | 0.000 | 1.00 | 0 | 0 |
| RGS3 | NR_074078 | 21 | 5 | 0.6088 | 0.1029 | 0.2718 | −1.879 | 3.68 | 16 | 4.02 |
| RNF14 | AK294262 | 6 | 21 | 0.9176 | 0.2246 | 2.9667 | 1.569 | 2.97 | 14 | 3.84 |
| RNF14 | AK295965 | 6 | 10 | 1.0000 | 0.6800 | 1.4762 | 0.562 | 1.48 | 3 | 1.78 |
| RNF14 | NM_001201365 | 644 | 267 | 0.0000 | 0.0000 | 0.4161 | −1.265 | 2.40 | 376 | 8.56 |
| RNF14 | NM_004290 | 433 | 417 | 1.0000 | 1.0000 | 0.9632 | −0.054 | 1.04 | 16 | 4.00 |
| RNF14 | NM_183398 | 344 | 316 | 1.0000 | 0.5550 | 0.9184 | −0.123 | 1.09 | 28 | 4.81 |
| RNF14 | NM_183400 | 238 | 180 | 0.9658 | 0.2603 | 0.7577 | −0.400 | 1.32 | 58 | 5.86 |
| RNF14 | NM_183401 | 816 | 1122 | 0.0564 | 0.0022 | 1.3753 | 0.460 | 1.38 | 307 | 8.26 |
| RNFT1 | AF100745 | 15 | 14 | 1.0000 | 0.8362 | 0.9168 | −0.125 | 1.09 | 1 | 0.42 |
| RNFT1 | AK294806 | 3 | 4 | 1.0000 | 0.9487 | 1.1529 | 0.205 | 1.15 | 1 | −0.66 |
| RNFT1 | AK296197 | 32 | 0 | 0.0011 | 0.0000 | 0.0304 | −5.042 | 32.95 | 32 | 5.00 |
| RNFT1 | BC006971 | 5 | 16 | 0.9383 | 0.2420 | 3.0731 | 1.620 | 3.07 | 12 | 3.56 |
| RNFT1 | NM_016125 | 179 | 409 | 0.0020 | 0.0000 | 2.2804 | 1.189 | 2.28 | 230 | 7.85 |
| RPL10 | AK026568 | 23382 | 23998 | 1.0000 | 0.6965 | 1.0263 | 0.038 | 1.03 | 616 | 9.27 |
| RPL10 | AY927536 | 67 | 0 | 0.0000 | 0.0000 | 0.0148 | −6.079 | 67.61 | 67 | 6.06 |
| RPL10 | AY927570 | 52 | 47 | 1.0000 | 0.8970 | 0.9041 | −0.145 | 1.11 | 5 | 2.33 |
| RPL10 | NM_001256577 | 48 | 39 | 1.0000 | 0.6320 | 0.7999 | −0.322 | 1.25 | 10 | 3.31 |
| RPL10 | NM_001256580 | 2 | 4 | 1.0000 | 0.7520 | 1.5885 | 0.668 | 1.59 | 2 | 0.86 |
| RPL10 | NM_006013 | 2409 | 2272 | 1.0000 | 0.5693 | 0.9432 | −0.084 | 1.06 | 137 | 7.10 |
| RRBP1 | AB037819 | 468 | 557 | 0.9827 | 0.2749 | 1.1904 | 0.251 | 1.19 | 89 | 6.48 |
| RRBP1 | AB384598 | 7097 | 5787 | 0.0397 | 0.0014 | 0.8154 | −0.294 | 1.23 | 1310 | 10.36 |
| RRBP1 | AB384598 | 4007 | 3245 | 0.0922 | 0.0043 | 0.8098 | −0.304 | 1.23 | 762 | 9.57 |
| RRBP1 | AK093465 | 15 | 13 | 1.0000 | 0.9565 | 0.8992 | −0.153 | 1.11 | 2 | 0.66 |
| RRBP1 | AK098319 | 42 | 50 | 1.0000 | 0.7553 | 1.1631 | 0.218 | 1.16 | 7 | 2.82 |
| RRBP1 | AK309197 | 25 | 21 | 1.0000 | 0.8148 | 0.8406 | −0.251 | 1.19 | 4 | 2.07 |
| RRBP1 | BC128577 | 824 | 757 | 1.0000 | 0.4973 | 0.9190 | −0.122 | 1.09 | 67 | 6.06 |
| RRBP1 | BC128578 | 0 | 10 | 0.2527 | 0.0190 | 10.5623 | 3.401 | 10.56 | 10 | 3.26 |
| RRBP1 | NM_001042576 | 153 | 156 | 1.0000 | 0.9942 | 1.0230 | 0.033 | 1.02 | 4 | 1.82 |
| RRBP1 | NM_004587 | 234 | 59 | 0.0005 | 0.0000 | 0.2530 | −1.983 | 3.95 | 176 | 7.46 |
| RWDD4 | AK293274 | 21 | 33 | 1.0000 | 0.4656 | 1.5308 | 0.614 | 1.53 | 12 | 3.57 |
| RWDD4 | CCDS34111 | 413 | 196 | 0.0097 | 0.0002 | 0.4750 | −1.074 | 2.11 | 217 | 7.76 |
| RWDD4 | NM_152682 | 762 | 585 | 0.4649 | 0.0557 | 0.7673 | −0.382 | 1.30 | 178 | 7.47 |
| SAR1A | AK298591 | 18 | 19 | 1.0000 | 0.9334 | 1.0581 | 0.081 | 1.06 | 1 | 0.16 |
| SAR1A | NM_001142648 | 127 | 344 | 0.0017 | 0.0000 | 2.6918 | 1.429 | 2.69 | 217 | 7.76 |
| SAR1A | NM_020150 | 5062 | 5168 | 1.0000 | 0.7749 | 1.0208 | 0.030 | 1.02 | 105 | 6.72 |
| SCAF4 | AK057840 | 3 | 9 | 1.0000 | 0.4099 | 2.3523 | 1.234 | 2.35 | 6 | 2.59 |
| SCAF4 | AL117417 | 13 | 23 | 1.0000 | 0.4918 | 1.7073 | 0.772 | 1.71 | 10 | 3.31 |
| SCAF4 | NM_001145444 | 53 | 0 | 0.0000 | 0.0000 | 0.0185 | −5.758 | 54.12 | 53 | 5.73 |
| SCAF4 | NM_001145445 | 506 | 496 | 1.0000 | 0.9876 | 0.9797 | −0.030 | 1.02 | 10 | 3.36 |
| SCAF4 | NM_020706 | 641 | 838 | 0.4728 | 0.0577 | 1.3060 | 0.385 | 1.31 | 197 | 7.62 |
| SCAF8 | AK302969 | 1257 | 1441 | 1.0000 | 0.3230 | 1.1459 | 0.196 | 1.15 | 184 | 7.52 |
| SCAF8 | AK303001 | 141 | 3 | 0.0000 | 0.0000 | 0.0305 | −5.037 | 32.83 | 138 | 7.11 |
| SCAF8 | AK307815 | 9 | 45 | 0.2810 | 0.0225 | 4.4149 | 2.142 | 4.41 | 36 | 5.15 |
| SCAF8 | BC070071 | 314 | 226 | 0.8724 | 0.2040 | 0.7205 | −0.473 | 1.39 | 88 | 6.46 |
| SCAF8 | NM_014892 | 319 | 327 | 1.0000 | 0.8203 | 1.0253 | 0.036 | 1.03 | 8 | 3.02 |
| SCLT1 | AK122852 | 2 | 6 | 1.0000 | 0.3905 | 2.2753 | 1.186 | 2.28 | 4 | 2.01 |
| SCLT1 | AX748077 | 2 | 3 | 1.0000 | 0.6298 | 1.4779 | 0.564 | 1.48 | 1 | 0.27 |
| SCLT1 | BC040258 | 20 | 15 | 1.0000 | 0.7442 | 0.7846 | −0.350 | 1.27 | 4 | 2.16 |
| SCLT1 | BC064428 | 70 | 45 | 1.0000 | 0.3388 | 0.6586 | −0.603 | 1.52 | 24 | 4.59 |
| SCLT1 | BC121058 | 0 | 0 | 9999 | 9999 | 1.0000 | 0.000 | 1.00 | 0 | 0 |
| SCLT1 | BC128051 | 1 | 0 | 0.5736 | 0.0911 | 0.4430 | −1.175 | 2.26 | 1 | 0.33 |
| SCLT1 | NM_144643 | 459 | 105 | 0.0000 | 0.0000 | 0.2309 | −2.115 | 4.33 | 354 | 8.47 |
| SCO1 | NM_004589 | 940 | 249 | 0.0000 | 0.0000 | 0.2659 | −1.911 | 3.76 | 691 | 9.43 |
| SDCBP | AK128645 | 103 | 94 | 1.0000 | 0.7636 | 0.9182 | −0.123 | 1.09 | 8 | 3.09 |
| SDCBP | NM_001007067 | 207 | 303 | 0.4681 | 0.0568 | 1.4591 | 0.545 | 1.46 | 96 | 6.58 |
| SDCBP | NM_001007068 | 0 | 7 | 0.3427 | 0.0310 | 7.8460 | 2.972 | 7.85 | 7 | 2.78 |
| SDCBP | NM_001007069 | 825 | 989 | 0.8402 | 0.1911 | 1.1987 | 0.261 | 1.20 | 164 | 7.36 |
| SDCBP | NM_001007070 | 138 | 24 | 0.0021 | 0.0000 | 0.1779 | −2.491 | 5.62 | 114 | 6.83 |
| SDCBP | NM_005625 | 2945 | 3026 | 1.0000 | 0.7783 | 1.0275 | 0.039 | 1.03 | 81 | 6.34 |
| SEC22A | AK057587 | 1 | 0 | 0.5736 | 0.0906 | 0.4450 | −1.168 | 2.25 | 1 | 0.32 |
| SEC22A | NM_012430 | 576 | 127 | 0.0000 | 0.0000 | 0.2226 | −2.168 | 4.49 | 448 | 8.81 |
| 41891 | AK299828 | 19 | 0 | 0.0211 | 0.0006 | 0.0490 | −4.351 | 20.40 | 19 | 4.28 |
| 41891 | AK300270 | 0 | 198 | 0.0000 | 0.0000 | 199.2127 | 7.638 | 199.21 | 198 | 7.63 |
| 41891 | AK303449 | 2522 | 1910 | 0.0385 | 0.0013 | 0.7572 | −0.401 | 1.32 | 613 | 9.26 |
| 41891 | AK316473 | 0 | 3 | 0.6088 | 0.1031 | 4.0352 | 2.013 | 4.04 | 3 | 1.60 |
| 41891 | BC114550 | 15 | 12 | 1.0000 | 0.8459 | 0.8164 | −0.293 | 1.22 | 3 | 1.52 |
| 41891 | NM_001113491 | 179 | 292 | 0.3804 | 0.0377 | 1.6308 | 0.706 | 1.63 | 113 | 6.83 |
| 41891 | NM_001113492 | 153 | 22 | 0.0002 | 0.0000 | 0.1503 | −2.734 | 6.65 | 131 | 7.03 |

TABLE 10-continued

RNA Abundance Modulation

| Gene | Trx_ID | ave DMSO | ave Cpd | padj (q val, FDR) | ttest (p val) | FC (x + 1) | $L_2$FC (x + 1) | amp FC (x + 1) | abs (Cpd-DMSO) | $L_2$abs (Cpd-DMSO) |
|---|---|---|---|---|---|---|---|---|---|---|
| 41891 | NM_001113493 | 516 | 407 | 0.6734 | 0.1249 | 0.7890 | −0.342 | 1.27 | 109 | 6.77 |
| 41891 | NM_001113494 | 106 | 79 | 1.0000 | 0.3807 | 0.7481 | −0.419 | 1.34 | 27 | 4.75 |
| 41891 | NM_001113495 | 2 | 2 | 1.0000 | 1.0000 | 0.8475 | −0.239 | 1.18 | 1 | −1.00 |
| 41891 | NM_001113496 | 16 | 5 | 0.9411 | 0.2438 | 0.3367 | −1.571 | 2.97 | 11 | 3.51 |
| 41891 | NM_006640 | 5227 | 4821 | 0.9827 | 0.2720 | 0.9223 | −0.117 | 1.08 | 406 | 8.67 |
| SF1 | CU675924 | 95 | 102 | 1.0000 | 0.8538 | 1.0693 | 0.097 | 1.07 | 7 | 2.73 |
| SF1 | D26121 | 9 | 16 | 1.0000 | 0.5371 | 1.6358 | 0.710 | 1.64 | 6 | 2.69 |
| SF1 | NM_001178030 | 287 | 198 | 0.5998 | 0.0989 | 0.6914 | −0.533 | 1.45 | 89 | 6.47 |
| SF1 | NM_001178031 | 1740 | 1625 | 1.0000 | 0.4551 | 0.9343 | −0.098 | 1.07 | 114 | 6.84 |
| SF1 | NM_004630 | 130 | 3 | 0.0000 | 0.0000 | 0.0311 | −5.008 | 32.19 | 127 | 6.98 |
| SF1 | NM_201995 | 268 | 293 | 1.0000 | 0.5626 | 1.0955 | 0.132 | 1.10 | 26 | 4.68 |
| SF1 | NM_201997 | 511 | 777 | 0.0390 | 0.0014 | 1.5193 | 0.603 | 1.52 | 266 | 8.05 |
| SF1 | NM_201998 | 2577 | 2806 | 1.0000 | 0.3592 | 1.0886 | 0.123 | 1.09 | 229 | 7.84 |
| SF1 | NR_033649 | 32 | 53 | 1.0000 | 0.4850 | 1.6331 | 0.708 | 1.63 | 21 | 4.39 |
| SF1 | NR_033650 | 2 | 13 | 0.6660 | 0.1211 | 4.9210 | 2.299 | 4.92 | 11 | 3.49 |
| SGOL2 | BC048349 | 4 | 4 | 1.0000 | 0.9530 | 0.9718 | −0.041 | 1.03 | 0 | −2.81 |
| SGOL2 | NM_001160033 | 76 | 0 | 0.0000 | 0.0000 | 0.0129 | −6.275 | 77.42 | 76 | 6.26 |
| SGOL2 | NM_001160046 | 1018 | 1265 | 0.4439 | 0.0508 | 1.2430 | 0.314 | 1.24 | 247 | 7.95 |
| SGOL2 | NM_152524 | 1071 | 1419 | 0.1465 | 0.0082 | 1.3252 | 0.406 | 1.33 | 349 | 8.45 |
| SLC25A17 | AK298215 | 24 | 4 | 0.4398 | 0.0491 | 0.2086 | −2.261 | 4.79 | 20 | 4.30 |
| SLC25A17 | AK300553 | 3 | 421 | 0.0000 | 0.0000 | 102.5693 | 6.680 | 102.57 | 418 | 8.71 |
| SLC25A17 | BC024741 | 2 | 20 | 0.3483 | 0.0319 | 7.2446 | 2.857 | 7.24 | 18 | 4.17 |
| SLC25A17 | BX647991 | 10 | 7 | 1.0000 | 0.6719 | 0.6845 | −0.547 | 1.46 | 3 | 1.80 |
| SLC25A17 | NM_006358 | 775 | 82 | 0.0000 | 0.0000 | 0.1065 | −3.231 | 9.39 | 694 | 9.44 |
| SLC4A4 | AF004813 | 60 | 84 | 1.0000 | 0.4580 | 1.3892 | 0.474 | 1.39 | 24 | 4.58 |
| SLC4A4 | AF069510 | 534 | 210 | 0.0000 | 0.0000 | 0.3937 | −1.345 | 2.54 | 325 | 8.34 |
| SLC4A4 | AF157492 | 15 | 58 | 0.4518 | 0.0523 | 3.6294 | 1.860 | 3.63 | 43 | 5.42 |
| SLC4A4 | BC030977 | 5 | 0 | 0.3736 | 0.0361 | 0.1679 | −2.574 | 5.96 | 5 | 2.31 |
| SLC4A4 | CR749482 | 0 | 0 | 9999 | 9999 | 1.0000 | 0.000 | 1.00 | 0 | 0 |
| SLC4A4 | NM_001098484 | 1033 | 1561 | 0.0038 | 0.0001 | 1.5101 | 0.595 | 1.51 | 528 | 9.04 |
| SLC4A4 | NM_001134742 | 0 | 0 | 9999 | 9999 | 1.0000 | 0.000 | 1.00 | 0 | 0 |
| SLC4A4 | NM_003759 | 23 | 7 | 0.8336 | 0.1884 | 0.3496 | −1.516 | 2.86 | 15 | 3.95 |
| SLC7A6 | AK310866 | 7 | 20 | 0.9432 | 0.2450 | 2.6153 | 1.387 | 2.62 | 13 | 3.68 |
| SLC7A6 | AK311610 | 0 | 88 | 0.0000 | 0.0000 | 88.9898 | 6.476 | 88.99 | 88 | 6.46 |
| SLC7A6 | CR749475 | 61 | 39 | 1.0000 | 0.5013 | 0.6392 | −0.646 | 1.56 | 22 | 4.49 |
| SLC7A6 | NM_001076785 | 674 | 310 | 0.0001 | 0.0000 | 0.4612 | −1.117 | 2.17 | 364 | 8.51 |
| SLC7A6 | NM_003983 | 937 | 308 | 0.0000 | 0.0000 | 0.3298 | −1.601 | 3.03 | 629 | 9.30 |
| SMARCC2 | AB384911 | 80 | 116 | 1.0000 | 0.2922 | 1.4399 | 0.526 | 1.44 | 36 | 5.16 |
| SMARCC2 | AK293896 | 0 | 12 | 0.1725 | 0.0104 | 13.2372 | 3.727 | 13.24 | 12 | 3.61 |
| SMARCC2 | NM_001130420 | 60 | 1 | 0.0002 | 0.0000 | 0.0365 | −4.775 | 27.37 | 58 | 5.87 |
| SMARCC2 | NM_003075 | 1343 | 1394 | 1.0000 | 0.7856 | 1.0374 | 0.053 | 1.04 | 50 | 5.65 |
| SMARCC2 | NM_139067 | 808 | 683 | 0.9218 | 0.2281 | 0.8461 | −0.241 | 1.18 | 125 | 6.96 |
| SMC4 | AK002200 | 25 | 29 | 1.0000 | 0.7754 | 1.1646 | 0.220 | 1.16 | 4 | 2.07 |
| SMC4 | AK122939 | 213 | 183 | 1.0000 | 0.5272 | 0.8574 | −0.222 | 1.17 | 31 | 4.93 |
| SMC4 | AK128143 | 998 | 1267 | 0.1897 | 0.0120 | 1.2699 | 0.345 | 1.27 | 269 | 8.07 |
| SMC4 | AK307508 | 529 | 699 | 0.3904 | 0.0391 | 1.3211 | 0.402 | 1.32 | 170 | 7.41 |
| SMC4 | AL833949 | 0 | 0 | 9999 | 9999 | 1.0000 | 0.000 | 1.00 | 0 | 0 |
| SMC4 | BC065259 | 48 | 38 | 1.0000 | 0.6682 | 0.7987 | −0.324 | 1.25 | 10 | 3.30 |
| SMC4 | NM_001002800 | 5978 | 6659 | 0.6987 | 0.1338 | 1.1139 | 0.156 | 1.11 | 681 | 9.41 |
| SMC4 | NM_005496 | 350 | 795 | 0.0000 | 0.0000 | 2.2678 | 1.181 | 2.27 | 445 | 8.80 |
| SMC6 | AK098325 | 255 | 329 | 0.8524 | 0.1962 | 1.2900 | 0.367 | 1.29 | 74 | 6.21 |
| SMC6 | AX747768 | 8 | 20 | 0.9956 | 0.2836 | 2.4100 | 1.269 | 2.41 | 12 | 3.63 |
| SMC6 | NM_001142286 | 245 | 601 | 0.0001 | 0.0000 | 2.4497 | 1.293 | 2.45 | 356 | 8.48 |
| SMC6 | NM_024624 | 962 | 852 | 1.0000 | 0.3947 | 0.8861 | −0.174 | 1.13 | 110 | 6.78 |
| SMCHD1 | AK126324 | 87 | 0 | 0.0000 | 0.0000 | 0.0114 | −6.457 | 87.85 | 87 | 6.44 |
| SMCHD1 | NM_015295 | 2390 | 2839 | 0.3788 | 0.0370 | 1.1879 | 0.248 | 1.19 | 449 | 8.81 |
| SMN2 | JQ657801 | 0 | 1 | 0.9827 | 0.2760 | 2.2141 | 1.147 | 2.21 | 1 | 0.28 |
| SMN2 | JQ657801 | 1 | 0 | 1.0000 | 0.3241 | 0.6140 | −0.704 | 1.63 | 1 | −0.67 |
| SMN2 | JQ690861 | 6 | 5 | 1.0000 | 0.8395 | 0.9592 | −0.060 | 1.04 | 0 | −1.89 |
| SMN2 | JQ690864 | 4 | 0 | 0.3594 | 0.0340 | 0.1864 | −2.423 | 5.36 | 4 | 2.13 |
| SMN2 | JQ690866 | 0 | 0 | 9999 | 9999 | 1.0000 | 0.000 | 1.00 | 0 | 0 |
| SMN2 | JQ690867 | 12 | 0 | 0.0918 | 0.0042 | 0.0798 | −3.648 | 12.53 | 12 | 3.53 |
| SMN2 | JQ690868 | 4 | 0 | 0.4439 | 0.0508 | 0.2078 | −2.267 | 4.81 | 4 | 1.93 |
| SMN2 | JQ732167 | 0 | 7 | 0.3415 | 0.0307 | 7.9809 | 2.997 | 7.98 | 7 | 2.80 |
| SMN2 | JQ732167 | 0 | 3 | 0.7247 | 0.1425 | 3.5191 | 1.815 | 3.52 | 3 | 1.33 |
| SMN2 | JQ745297 | 0 | 0 | 1.0000 | 1.0000 | 1.2977 | 0.376 | 1.30 | 0 | −1.75 |
| SMN2 | NM_017411 | 444 | 858 | 0.0003 | 0.0000 | 1.9286 | 0.948 | 1.93 | 414 | 8.69 |
| SMN2 | NM_017411 | 0 | 0 | 9999 | 9999 | 1.0000 | 0.000 | 1.00 | 0 | 0 |
| SMN2 | NM_022875 | 224 | 0 | 0.0000 | 0.0000 | 0.0044 | −7.813 | 224.87 | 224 | 7.81 |
| SMN2 | NM_022875 | 0 | 0 | 9999 | 9999 | 1.0000 | 0.000 | 1.00 | 0 | 0 |
| SMN2 | NM_022876 | 0 | 5 | 0.4533 | 0.0527 | 6.1598 | 2.623 | 6.16 | 5 | 2.37 |
| SMN2 | NM_022876 | 0 | 0 | 9999 | 9999 | 1.0000 | 0.000 | 1.00 | 0 | 0 |
| SMN2 | NM_022877 | 29 | 0 | 0.0024 | 0.0000 | 0.0337 | −4.890 | 29.66 | 29 | 4.84 |
| SMN2 | NM_022877 | 3 | 0 | 0.4439 | 0.0505 | 0.2429 | −2.042 | 4.12 | 3 | 1.64 |

TABLE 10-continued

RNA Abundance Modulation

| Gene | Trx_ID | ave DMSO | ave Cpd | padj (q val, FDR) | ttest (p val) | FC (x + 1) | $L_2$FC (x + 1) | amp FC (x + 1) | abs (Cpd-DMSO) | $L_2$abs (Cpd-DMSO) |
|---|---|---|---|---|---|---|---|---|---|---|
| SMPD4 | AK000763 | 1149 | 1139 | 1.0000 | 0.9032 | 0.9908 | −0.013 | 1.01 | 11 | 3.40 |
| SMPD4 | AK056501 | 32 | 0 | 0.0017 | 0.0000 | 0.0299 | −5.062 | 33.40 | 32 | 5.02 |
| SMPD4 | AK126920 | 42 | 48 | 1.0000 | 0.8192 | 1.1402 | 0.189 | 1.14 | 6 | 2.58 |
| SMPD4 | AK297257 | 0 | 0 | 9999 | 9999 | 1.0000 | 0.000 | 1.00 | 0 | 0 |
| SMPD4 | AK298609 | 4 | 0 | 0.3797 | 0.0375 | 0.1975 | −2.340 | 5.06 | 4 | 2.02 |
| SMPD4 | AK301576 | 0 | 2 | 0.6693 | 0.1236 | 3.4281 | 1.777 | 3.43 | 2 | 1.28 |
| SMPD4 | AK303427 | 1 | 4 | 1.0000 | 0.4961 | 2.1756 | 1.121 | 2.18 | 3 | 1.41 |
| SMPD4 | NM_001171083 | 3 | 4 | 1.0000 | 0.8029 | 1.3793 | 0.464 | 1.38 | 1 | 0.53 |
| SMPD4 | NM_017751 | 872 | 1771 | 0.0000 | 0.0000 | 2.0289 | 1.021 | 2.03 | 899 | 9.81 |
| SMPD4 | NR_033230 | 1198 | 731 | 0.0011 | 0.0000 | 0.6106 | −0.712 | 1.64 | 467 | 8.87 |
| SMPD4 | NR_033231 | 0 | 0 | 9999 | 9999 | 1.0000 | 0.000 | 1.00 | 0 | 0 |
| SMPD4 | NR_033232 | 24 | 28 | 1.0000 | 0.8972 | 1.1525 | 0.205 | 1.15 | 4 | 1.95 |
| SMYD3 | AK023594 | 6 | 15 | 1.0000 | 0.3199 | 2.3399 | 1.226 | 2.34 | 9 | 3.20 |
| SMYD3 | NM_001167740 | 220 | 123 | 0.3696 | 0.0355 | 0.5607 | −0.835 | 1.78 | 97 | 6.60 |
| SMYD3 | NM_022743 | 2826 | 711 | 0.0000 | 0.0000 | 0.2518 | −1.990 | 3.97 | 2115 | 11.05 |
| SNAP23 | NM_003825 | 1552 | 233 | 0.0000 | 0.0000 | 0.1506 | −2.731 | 6.64 | 1319 | 10.37 |
| SNAP23 | NM_130798 | 6 | 2 | 1.0000 | 0.3773 | 0.4102 | −1.286 | 2.44 | 4 | 2.07 |
| SNHG16 | BC042949 | 5 | 27 | 0.4939 | 0.0637 | 4.3573 | 2.123 | 4.36 | 21 | 4.41 |
| SNHG16 | NR_038108 | 90 | 18 | 0.0695 | 0.0029 | 0.2105 | −2.248 | 4.75 | 72 | 6.16 |
| SNHG16 | NR_038109 | 1349 | 184 | 0.0000 | 0.0000 | 0.1372 | −2.865 | 7.29 | 1165 | 10.19 |
| SNHG16 | NR_038110 | 0 | 4 | 0.5592 | 0.0853 | 4.6422 | 2.215 | 4.64 | 4 | 1.86 |
| SNHG16 | NR_038111 | 411 | 37 | 0.0000 | 0.0000 | 0.0929 | −3.428 | 10.76 | 374 | 8.55 |
| SOCS2 | BC070039 | 5 | 11 | 1.0000 | 0.5130 | 1.9971 | 0.998 | 2.00 | 6 | 2.61 |
| SOCS2 | NM_001270467 | 8 | 4 | 1.0000 | 0.5007 | 0.5415 | −0.885 | 1.85 | 4 | 2.07 |
| SOCS2 | NM_001270468 | 85 | 132 | 0.9454 | 0.2461 | 1.5562 | 0.638 | 1.56 | 48 | 5.58 |
| SOCS2 | NM_001270469 | 15 | 22 | 1.0000 | 0.6209 | 1.4390 | 0.525 | 1.44 | 7 | 2.78 |
| SOCS2 | NM_001270470 | 10 | 4 | 1.0000 | 0.4736 | 0.5009 | −0.998 | 2.00 | 5 | 2.42 |
| SOCS2 | NM_001270471 | 77 | 0 | 0.0000 | 0.0000 | 0.0128 | −6.288 | 78.15 | 77 | 6.27 |
| SOCS2 | NM_003877 | 15 | 12 | 1.0000 | 0.7310 | 0.7760 | −0.366 | 1.29 | 4 | 1.85 |
| SOS2 | AK302825 | 60 | 14 | 0.2045 | 0.0135 | 0.2398 | −2.060 | 4.17 | 46 | 5.53 |
| SOS2 | AK308978 | 51 | 33 | 1.0000 | 0.4584 | 0.6609 | −0.598 | 1.51 | 17 | 4.13 |
| SOS2 | BC143367 | 0 | 14 | 0.1222 | 0.0063 | 15.1493 | 3.921 | 15.15 | 14 | 3.82 |
| SOS2 | NM_006939 | 894 | 327 | 0.0000 | 0.0000 | 0.3671 | −1.446 | 2.72 | 566 | 9.15 |
| SPATA20 | AK302850 | 25 | 27 | 1.0000 | 0.9259 | 1.0833 | 0.115 | 1.08 | 2 | 1.11 |
| SPATA20 | DQ238597 | 64 | 69 | 1.0000 | 0.8953 | 1.0779 | 0.108 | 1.08 | 5 | 2.34 |
| SPATA20 | NM_001258372 | 93 | 163 | 0.5942 | 0.0974 | 1.7353 | 0.795 | 1.74 | 69 | 6.12 |
| SPATA20 | NM_001258373 | 542 | 466 | 1.0000 | 0.3134 | 0.8599 | −0.218 | 1.16 | 76 | 6.25 |
| SPATA20 | NM_022827 | 316 | 117 | 0.0060 | 0.0001 | 0.3720 | −1.427 | 2.69 | 199 | 7.64 |
| SPATS2 | AK095582 | 18 | 53 | 0.5820 | 0.0945 | 2.7512 | 1.460 | 2.75 | 34 | 5.09 |
| SPATS2 | AL833614 | 10 | 14 | 1.0000 | 0.6598 | 1.4506 | 0.537 | 1.45 | 5 | 2.26 |
| SPATS2 | BX648916 | 441 | 340 | 0.7105 | 0.1380 | 0.7701 | −0.377 | 1.30 | 102 | 6.67 |
| SPATS2 | NM_023071 | 358 | 141 | 0.0022 | 0.0000 | 0.3948 | −1.341 | 2.53 | 217 | 7.76 |
| SPG20 | AK001949 | 147 | 168 | 1.0000 | 0.6690 | 1.1407 | 0.190 | 1.14 | 21 | 4.38 |
| SPG20 | AK302119 | 24 | 0 | 0.0063 | 0.0001 | 0.0400 | −4.644 | 25.00 | 24 | 4.59 |
| SPG20 | NM_001142294 | 89 | 421 | 0.0000 | 0.0000 | 4.7166 | 2.238 | 4.72 | 333 | 8.38 |
| SPG20 | NM_001142295 | 338 | 278 | 1.0000 | 0.4123 | 0.8226 | −0.282 | 1.22 | 60 | 5.91 |
| SPG20 | NM_001142296 | 151 | 240 | 0.6088 | 0.1029 | 1.5861 | 0.666 | 1.59 | 89 | 6.48 |
| SPG20 | NM_015087 | 824 | 758 | 1.0000 | 0.4028 | 0.9203 | −0.120 | 1.09 | 66 | 6.04 |
| SQRDL | NM_001271213 | 117 | 434 | 0.0000 | 0.0000 | 3.7013 | 1.888 | 3.70 | 318 | 8.31 |
| SQRDL | NM_021199 | 149 | 89 | 0.7168 | 0.1399 | 0.6019 | −0.732 | 1.66 | 60 | 5.90 |
| SREBF1 | AB209609 | 4 | 0 | 0.3797 | 0.0375 | 0.1979 | −2.337 | 5.05 | 4 | 2.02 |
| SREBF1 | AB373958 | 54 | 62 | 1.0000 | 0.5698 | 1.1448 | 0.195 | 1.14 | 8 | 3.00 |
| SREBF1 | AB373959 | 152 | 105 | 0.8374 | 0.1897 | 0.6962 | −0.522 | 1.44 | 46 | 5.53 |
| SREBF1 | AK091131 | 117 | 367 | 0.0002 | 0.0000 | 3.1134 | 1.638 | 3.11 | 250 | 7.96 |
| SREBF1 | AK095325 | 47 | 33 | 1.0000 | 0.5968 | 0.7218 | −0.470 | 1.39 | 13 | 3.73 |
| SREBF1 | AK128320 | 20 | 15 | 1.0000 | 0.8007 | 0.7532 | −0.409 | 1.33 | 5 | 2.39 |
| SREBF1 | NM_001005291 | 19 | 26 | 1.0000 | 0.8523 | 1.3570 | 0.440 | 1.36 | 7 | 2.84 |
| SREBF1 | NM_004176 | 901 | 583 | 0.0167 | 0.0005 | 0.6471 | −0.628 | 1.55 | 318 | 8.31 |
| SREK1 | NM_001077199 | 1553 | 496 | 0.0000 | 0.0000 | 0.3197 | −1.645 | 3.13 | 1057 | 10.05 |
| SREK1 | NM_001270492 | 139 | 63 | 0.4340 | 0.0479 | 0.4596 | −1.122 | 2.18 | 76 | 6.24 |
| SREK1 | NM_001270493 | 31 | 18 | 1.0000 | 0.4271 | 0.5919 | −0.757 | 1.69 | 13 | 3.70 |
| SREK1 | NM_139168 | 0 | 0 | 9999 | 9999 | 1.0000 | 0.000 | 1.00 | 0 | 0 |
| SRSF3 | AK304097 | 629 | 401 | 0.0915 | 0.0042 | 0.6380 | −0.648 | 1.57 | 228 | 7.83 |
| SRSF3 | NM_003017 | 8115 | 9085 | 0.4929 | 0.0629 | 1.1195 | 0.163 | 1.12 | 970 | 9.92 |
| SRSF3 | NR_036610 | 567 | 274 | 0.0008 | 0.0000 | 0.4832 | −1.049 | 2.07 | 294 | 8.20 |
| STAT1 | AK096686 | 207 | 20 | 0.0000 | 0.0000 | 0.0999 | −3.324 | 10.01 | 187 | 7.55 |
| STAT1 | AK225853 | 0 | 14 | 0.1081 | 0.0053 | 14.9432 | 3.901 | 14.94 | 14 | 3.80 |
| STAT1 | AK292604 | 410 | 45 | 0.0000 | 0.0000 | 0.1125 | −3.152 | 8.89 | 365 | 8.51 |
| STAT1 | GU211348 | 0 | 17 | 0.0670 | 0.0028 | 17.8715 | 4.160 | 17.87 | 17 | 4.08 |
| STAT1 | NM_007315 | 7542 | 467 | 0.0000 | 0.0000 | 0.0621 | −4.009 | 16.10 | 7075 | 12.79 |
| STAT1 | NM_139266 | 786 | 31 | 0.0000 | 0.0000 | 0.0403 | −4.632 | 24.80 | 755 | 9.56 |
| STAU1 | AB209561 | 467 | 111 | 0.0000 | 0.0000 | 0.2401 | −2.058 | 4.16 | 356 | 8.47 |
| STAU1 | AY546099 | 322 | 353 | 1.0000 | 0.4446 | 1.0954 | 0.131 | 1.10 | 31 | 4.95 |
| STAU1 | NM_001037328 | 219 | 128 | 0.3271 | 0.0286 | 0.5881 | −0.766 | 1.70 | 91 | 6.50 |

TABLE 10-continued

RNA Abundance Modulation

| Gene | Trx_ID | ave DMSO | ave Cpd | padj (q val, FDR) | ttest (p val) | FC (x + 1) | L$_2$FC (x + 1) | amp FC (x + 1) | abs (Cpd-DMSO) | L$_2$abs (Cpd-DMSO) |
|---|---|---|---|---|---|---|---|---|---|---|
| STAU1 | NM_004602 | 389 | 384 | 1.0000 | 0.8794 | 0.9876 | −0.018 | 1.01 | 5 | 2.27 |
| STAU1 | NM_017453 | 135 | 273 | 0.1530 | 0.0088 | 2.0070 | 1.005 | 2.01 | 137 | 7.10 |
| STAU1 | NM_017454 | 322 | 370 | 1.0000 | 0.4665 | 1.1479 | 0.199 | 1.15 | 48 | 5.58 |
| STEAP2 | DQ656062 | 0 | 5 | 0.4489 | 0.0518 | 6.3991 | 2.678 | 6.40 | 5 | 2.43 |
| STEAP2 | NM_001040665 | 109 | 13 | 0.0018 | 0.0000 | 0.1313 | −2.929 | 7.62 | 96 | 6.58 |
| STEAP2 | NM_001040666 | 69 | 6 | 0.0071 | 0.0002 | 0.0955 | −3.388 | 10.47 | 64 | 5.99 |
| STEAP2 | NM_001244944 | 83 | 36 | 0.5736 | 0.0905 | 0.4397 | −1.185 | 2.27 | 47 | 5.55 |
| STEAP2 | NM_001244945 | 0 | 1 | 1.0000 | 0.6737 | 1.7648 | 0.820 | 1.76 | 1 | −0.39 |
| STEAP2 | NM_001244946 | 2 | 0 | 0.4853 | 0.0610 | 0.2862 | −1.805 | 3.49 | 2 | 1.32 |
| STEAP2 | NM_152999 | 124 | 12 | 0.0001 | 0.0000 | 0.1049 | −3.254 | 9.54 | 112 | 6.80 |
| STRN3 | BC143933 | 16 | 2 | 0.6206 | 0.1068 | 0.2028 | −2.302 | 4.93 | 13 | 3.75 |
| STRN3 | NM_001083893 | 115 | 1330 | 0.0000 | 0.0000 | 11.4539 | 3.518 | 11.45 | 1215 | 10.25 |
| STRN3 | NM_014574 | 869 | 90 | 0.0000 | 0.0000 | 0.1042 | −3.262 | 9.59 | 780 | 9.61 |
| STX16 | NM_001001433 | 291 | 411 | 0.4985 | 0.0650 | 1.4118 | 0.497 | 1.41 | 120 | 6.91 |
| STX16 | NM_001134772 | 132 | 258 | 0.1725 | 0.0104 | 1.9459 | 0.960 | 1.95 | 126 | 6.97 |
| STX16 | NM_001134773 | 247 | 80 | 0.0024 | 0.0000 | 0.3248 | −1.622 | 3.08 | 168 | 7.39 |
| STX16 | NM_001204868 | 48 | 72 | 1.0000 | 0.3845 | 1.4876 | 0.573 | 1.49 | 24 | 4.57 |
| STX16 | NM_003763 | 1013 | 884 | 1.0000 | 0.3024 | 0.8724 | −0.197 | 1.15 | 129 | 7.02 |
| STX16 | NR_037941 | 349 | 417 | 1.0000 | 0.3109 | 1.1945 | 0.256 | 1.19 | 68 | 6.09 |
| STX16 | NR_037942 | 10 | 47 | 0.3567 | 0.0331 | 4.3442 | 2.119 | 4.34 | 37 | 5.20 |
| STX16 | NR_037943 | 62 | 84 | 1.0000 | 0.5587 | 1.3519 | 0.435 | 1.35 | 22 | 4.47 |
| SUPT20H | AF093250 | 156 | 130 | 1.0000 | 0.4963 | 0.8362 | −0.258 | 1.20 | 26 | 4.68 |
| SUPT20H | AF370384 | 14 | 10 | 1.0000 | 0.7986 | 0.7518 | −0.412 | 1.33 | 4 | 1.89 |
| SUPT20H | AK026091 | 74 | 58 | 1.0000 | 0.5805 | 0.7875 | −0.345 | 1.27 | 16 | 4.00 |
| SUPT20H | AK027554 | 108 | 208 | 0.2683 | 0.0208 | 1.9244 | 0.944 | 1.92 | 100 | 6.65 |
| SUPT20H | AK056121 | 37 | 71 | 0.7950 | 0.1739 | 1.8976 | 0.924 | 1.90 | 34 | 5.10 |
| SUPT20H | AK225376 | 336 | 120 | 0.0005 | 0.0000 | 0.3584 | −1.480 | 2.79 | 216 | 7.76 |
| SUPT20H | AK292376 | 22 | 19 | 1.0000 | 0.6728 | 0.8411 | −0.250 | 1.19 | 4 | 1.90 |
| SUPT20H | AK304227 | 84 | 78 | 1.0000 | 0.8643 | 0.9294 | −0.106 | 1.08 | 6 | 2.58 |
| SUPT20H | BC001145 | 121 | 59 | 0.5113 | 0.0685 | 0.4931 | −1.020 | 2.03 | 62 | 5.95 |
| SUPT20H | NM_001014286 | 129 | 143 | 1.0000 | 0.6982 | 1.1037 | 0.142 | 1.10 | 14 | 3.76 |
| SUPT20H | NM_017569 | 46 | 30 | 1.0000 | 0.4469 | 0.6630 | −0.593 | 1.51 | 16 | 4.00 |
| SYNE1 | AB033088 | 36 | 51 | 1.0000 | 0.6914 | 1.3827 | 0.467 | 1.38 | 14 | 3.84 |
| SYNE1 | AB051543 | 189 | 17 | 0.0000 | 0.0000 | 0.0928 | −3.429 | 10.77 | 173 | 7.43 |
| SYNE1 | AK308717 | 35 | 10 | 0.6687 | 0.1219 | 0.3214 | −1.637 | 3.11 | 24 | 4.60 |
| SYNE1 | AK310977 | 17 | 12 | 1.0000 | 0.6478 | 0.7289 | −0.456 | 1.37 | 5 | 2.30 |
| SYNE1 | AL713682 | 4 | 3 | 1.0000 | 0.8509 | 0.7428 | −0.429 | 1.35 | 1 | 0.46 |
| SYNE1 | AY061755 | 405 | 320 | 0.9318 | 0.2369 | 0.7917 | −0.337 | 1.26 | 85 | 6.40 |
| SYNE1 | BC028616 | 26 | 12 | 1.0000 | 0.3528 | 0.4871 | −1.038 | 2.05 | 14 | 3.77 |
| SYNE1 | BC039121 | 51 | 33 | 1.0000 | 0.4241 | 0.6497 | −0.622 | 1.54 | 18 | 4.18 |
| SYNE1 | BX537517 | 22 | 16 | 1.0000 | 0.6366 | 0.7276 | −0.459 | 1.37 | 6 | 2.68 |
| SYNE1 | BX647837 | 344 | 290 | 1.0000 | 0.3837 | 0.8425 | −0.247 | 1.19 | 54 | 5.76 |
| SYNE1 | CR933676 | 5 | 3 | 1.0000 | 0.6771 | 0.6683 | −0.581 | 1.50 | 2 | 0.98 |
| SYNE1 | FM162565 | 14 | 8 | 1.0000 | 0.5276 | 0.6117 | −0.709 | 1.63 | 6 | 2.50 |
| SYNE1 | JQ740784 | 0 | 9 | 0.2492 | 0.0185 | 9.7668 | 3.288 | 9.77 | 9 | 3.13 |
| SYNE1 | JQ740786 | 2 | 0 | 0.5018 | 0.0665 | 0.3137 | −1.672 | 3.19 | 2 | 1.13 |
| SYNE1 | NM_033071 | 53 | 40 | 1.0000 | 0.4535 | 0.7582 | −0.399 | 1.32 | 13 | 3.70 |
| SYNE1 | NM_182961 | 2323 | 1738 | 0.0233 | 0.0007 | 0.7483 | −0.418 | 1.34 | 585 | 9.19 |
| SYNE2 | AF357236 | 0 | 0 | 9999 | 9999 | 1.0000 | 0.000 | 1.00 | 0 | 0 |
| SYNE2 | AK074055 | 0 | 0 | 9999 | 9999 | 1.0000 | 0.000 | 1.00 | 0 | 0 |
| SYNE2 | AK127612 | 9 | 2 | 0.9782 | 0.2677 | 0.3125 | −1.678 | 3.20 | 7 | 2.76 |
| SYNE2 | AK128631 | 1 | 0 | 1.0000 | 0.3241 | 0.6160 | −0.699 | 1.62 | 1 | −0.68 |
| SYNE2 | AK297874 | 4 | 0 | 0.3999 | 0.0415 | 0.2109 | −2.245 | 4.74 | 4 | 1.90 |
| SYNE2 | AY061759 | 2 | 33 | 0.0590 | 0.0023 | 11.7249 | 3.551 | 11.72 | 31 | 4.95 |
| SYNE2 | AY184205 | 0 | 1 | 0.7536 | 0.1556 | 2.4883 | 1.315 | 2.49 | 1 | 0.57 |
| SYNE2 | BC036941 | 6 | 0 | 0.2833 | 0.0227 | 0.1461 | −2.775 | 6.85 | 6 | 2.55 |
| SYNE2 | BX537642 | 54 | 18 | 0.4673 | 0.0562 | 0.3528 | −1.503 | 2.83 | 36 | 5.16 |
| SYNE2 | BX538095 | 13 | 0 | 0.0791 | 0.0035 | 0.0692 | −3.853 | 14.45 | 13 | 3.75 |
| SYNE2 | CR749324 | 0 | 2 | 0.6693 | 0.1228 | 3.3812 | 1.758 | 3.38 | 2 | 1.25 |
| SYNE2 | NM_015180 | 253 | 10 | 0.0000 | 0.0000 | 0.0427 | −4.551 | 23.44 | 243 | 7.92 |
| SYNE2 | NM_182910 | 2 | 0 | 0.6088 | 0.1029 | 0.3961 | −1.336 | 2.52 | 2 | 0.61 |
| SYNE2 | NM_182913 | 0 | 7 | 0.3969 | 0.0405 | 7.7573 | 2.956 | 7.76 | 7 | 2.76 |
| SYNE2 | NM_182914 | 142 | 233 | 0.4084 | 0.0428 | 1.6359 | 0.710 | 1.64 | 91 | 6.51 |
| SYT15 | AK127436 | 357 | 254 | 0.5786 | 0.0923 | 0.7121 | −0.490 | 1.40 | 103 | 6.69 |
| SYT15 | AK293632 | 51 | 0 | 0.0000 | 0.0000 | 0.0192 | −5.704 | 52.13 | 51 | 5.68 |
| SYT15 | NM_031912 | 1143 | 709 | 0.0045 | 0.0001 | 0.6204 | −0.689 | 1.61 | 434 | 8.76 |
| SYT15 | NM_181519 | 618 | 477 | 0.5404 | 0.0784 | 0.7726 | −0.372 | 1.29 | 141 | 7.14 |
| SYTL2 | AK127504 | 0 | 7 | 0.3785 | 0.0370 | 8.0171 | 3.003 | 8.02 | 7 | 2.81 |
| SYTL2 | AK131365 | 4 | 6 | 1.0000 | 0.8377 | 1.2269 | 0.295 | 1.23 | 1 | 0.31 |
| SYTL2 | AK296224 | 8 | 0 | 0.2375 | 0.0172 | 0.1159 | −3.108 | 8.62 | 8 | 2.93 |
| SYTL2 | AK296740 | 23 | 6 | 0.7823 | 0.1693 | 0.2897 | −1.788 | 3.45 | 17 | 4.11 |
| SYTL2 | AK298604 | 19 | 31 | 1.0000 | 0.5135 | 1.5498 | 0.632 | 1.55 | 11 | 3.49 |
| SYTL2 | BC068495 | 0 | 0 | 9999 | 9999 | 1.0000 | 0.000 | 1.00 | 0 | 0 |
| SYTL2 | NM_001162952 | 29 | 20 | 1.0000 | 0.5323 | 0.7089 | −0.496 | 1.41 | 9 | 3.13 |

TABLE 10-continued

RNA Abundance Modulation

| Gene | Trx_ID | ave DMSO | ave Cpd | padj (q val, FDR) | ttest (p val) | FC (x + 1) | L$_2$FC (x + 1) | amp FC (x + 1) | abs (Cpd-DMSO) | L$_2$abs (Cpd-DMSO) |
|---|---|---|---|---|---|---|---|---|---|---|
| SYTL2 | NM_001162953 | 21 | 76 | 0.2433 | 0.0179 | 3.5124 | 1.812 | 3.51 | 55 | 5.79 |
| SYTL2 | NM_032379 | 0 | 3 | 0.6461 | 0.1156 | 4.4417 | 2.151 | 4.44 | 3 | 1.78 |
| SYTL2 | NM_032943 | 71 | 263 | 0.0004 | 0.0000 | 3.6876 | 1.883 | 3.69 | 193 | 7.59 |
| SYTL2 | NM_206927 | 0 | 0 | 1.0000 | 0.4930 | 0.7608 | −0.394 | 1.31 | 0 | −1.67 |
| SYTL2 | NM_206929 | 20 | 8 | 0.9218 | 0.2296 | 0.4206 | −1.249 | 2.38 | 12 | 3.64 |
| SYTL2 | NM_206930 | 8 | 3 | 1.0000 | 0.3918 | 0.4168 | −1.263 | 2.40 | 5 | 2.36 |
| TAF2 | NM_003184 | 1571 | 285 | 0.0000 | 0.0000 | 0.1821 | −2.457 | 5.49 | 1286 | 10.33 |
| TARBP1 | NM_005646 | 414 | 40 | 0.0000 | 0.0000 | 0.0983 | −3.347 | 10.18 | 374 | 8.55 |
| TARS | NM_001258437 | 747 | 2392 | 0.0000 | 0.0000 | 3.1988 | 1.678 | 3.20 | 1645 | 10.68 |
| TARS | NM_001258438 | 0 | 3 | 0.6088 | 0.1028 | 3.9765 | 1.992 | 3.98 | 3 | 1.57 |
| TARS | NM_152295 | 6669 | 5602 | 0.1253 | 0.0065 | 0.8400 | −0.252 | 1.19 | 1067 | 10.06 |
| TARS | NR_047676 | 35 | 30 | 1.0000 | 0.7335 | 0.8618 | −0.215 | 1.16 | 5 | 2.33 |
| TARS | NR_047677 | 18 | 6 | 0.9601 | 0.2546 | 0.3753 | −1.414 | 2.66 | 12 | 3.53 |
| TARS | NR_047678 | 94 | 70 | 1.0000 | 0.3728 | 0.7462 | −0.422 | 1.34 | 24 | 4.59 |
| TBL2 | AK000536 | 50 | 36 | 1.0000 | 0.6129 | 0.7240 | −0.466 | 1.38 | 14 | 3.81 |
| TBL2 | AK130791 | 7 | 23 | 0.9649 | 0.2599 | 2.7838 | 1.477 | 2.78 | 15 | 3.92 |
| TBL2 | AK302265 | 239 | 73 | 0.0031 | 0.0001 | 0.3075 | −1.701 | 3.25 | 166 | 7.37 |
| TBL2 | NM_012453 | 1565 | 1775 | 0.7928 | 0.1729 | 1.1338 | 0.181 | 1.13 | 210 | 7.71 |
| TCF7L2 | AK296305 | 11 | 12 | 1.0000 | 0.9059 | 1.0781 | 0.108 | 1.08 | 1 | −0.05 |
| TCF7L2 | AK301483 | 114 | 62 | 0.7631 | 0.1610 | 0.5437 | −0.879 | 1.84 | 52 | 5.71 |
| TCF7L2 | AK303684 | 8 | 0 | 0.2375 | 0.0172 | 0.1159 | −3.108 | 8.62 | 8 | 2.93 |
| TCF7L2 | AK316111 | 18 | 4 | 0.6987 | 0.1343 | 0.2446 | −2.032 | 4.09 | 14 | 3.84 |
| TCF7L2 | FJ010164 | 2 | 0 | 0.5404 | 0.0787 | 0.3908 | −1.355 | 2.56 | 2 | 0.64 |
| TCF7L2 | FJ010165 | 29 | 24 | 1.0000 | 0.8767 | 0.8515 | −0.232 | 1.17 | 4 | 2.13 |
| TCF7L2 | FJ010173 | 165 | 164 | 1.0000 | 0.8603 | 0.9925 | −0.011 | 1.01 | 1 | 0.31 |
| TCF7L2 | HM352838 | 42 | 63 | 1.0000 | 0.5054 | 1.4989 | 0.584 | 1.50 | 21 | 4.41 |
| TCF7L2 | HM352839 | 4 | 8 | 1.0000 | 0.5037 | 1.9039 | 0.929 | 1.90 | 4 | 2.06 |
| TCF7L2 | HM352840 | 23 | 114 | 0.0174 | 0.0005 | 4.7734 | 2.255 | 4.77 | 91 | 6.51 |
| TCF7L2 | HM352841 | 48 | 35 | 1.0000 | 0.5395 | 0.7332 | −0.448 | 1.36 | 13 | 3.71 |
| TCF7L2 | HM352843 | 60 | 4 | 0.0041 | 0.0001 | 0.0853 | −3.552 | 11.73 | 56 | 5.80 |
| TCF7L2 | HM352844 | 41 | 41 | 1.0000 | 0.9881 | 1.0224 | 0.032 | 1.02 | 1 | −0.11 |
| TCF7L2 | HM352845 | 5 | 0 | 0.3415 | 0.0308 | 0.1750 | −2.515 | 5.71 | 5 | 2.24 |
| TCF7L2 | HM352849 | 36 | 65 | 0.9355 | 0.2386 | 1.7805 | 0.832 | 1.78 | 29 | 4.85 |
| TCF7L2 | HM352851 | 5 | 4 | 1.0000 | 0.9076 | 0.8590 | −0.219 | 1.16 | 1 | −0.27 |
| TCF7L2 | NM_001146274 | 14 | 7 | 1.0000 | 0.4419 | 0.5165 | −0.953 | 1.94 | 7 | 2.88 |
| TCF7L2 | NM_001146283 | 5 | 10 | 1.0000 | 0.6000 | 1.8721 | 0.905 | 1.87 | 5 | 2.38 |
| TCF7L2 | NM_001146284 | 21 | 5 | 0.6345 | 0.1108 | 0.2930 | −1.771 | 3.41 | 15 | 3.94 |
| TCF7L2 | NM_001146285 | 111 | 84 | 1.0000 | 0.5590 | 0.7570 | −0.402 | 1.32 | 27 | 4.77 |
| TCF7L2 | NM_001146286 | 119 | 65 | 0.5390 | 0.0772 | 0.5470 | −0.870 | 1.83 | 54 | 5.77 |
| TCF7L2 | NM_001198525 | 48 | 33 | 1.0000 | 0.4136 | 0.6871 | −0.541 | 1.46 | 15 | 3.94 |
| TCF7L2 | NM_001198526 | 13 | 13 | 1.0000 | 1.0000 | 0.9885 | −0.017 | 1.01 | 0 | −2.61 |
| TCF7L2 | NM_001198529 | 38 | 78 | 0.7290 | 0.1445 | 2.0412 | 1.029 | 2.04 | 40 | 5.33 |
| TCF7L2 | NM_001198530 | 0 | 9 | 0.2510 | 0.0188 | 9.6319 | 3.268 | 9.63 | 9 | 3.11 |
| TCF7L2 | NM_001198531 | 127 | 33 | 0.0244 | 0.0008 | 0.2654 | −1.914 | 3.77 | 94 | 6.56 |
| TENC1 | AK172747 | 2 | 4 | 1.0000 | 0.6049 | 1.6993 | 0.765 | 1.70 | 2 | 1.11 |
| TENC1 | AL137564 | 8 | 0 | 0.1720 | 0.0103 | 0.1062 | −3.235 | 9.42 | 8 | 3.07 |
| TENC1 | BC054099 | 60 | 15 | 0.2972 | 0.0244 | 0.2718 | −1.879 | 3.68 | 44 | 5.46 |
| TENC1 | CR936725 | 8 | 22 | 0.9668 | 0.2608 | 2.5056 | 1.325 | 2.51 | 14 | 3.81 |
| TENC1 | CR936725 | 22 | 34 | 1.0000 | 0.4720 | 1.5302 | 0.614 | 1.53 | 12 | 3.61 |
| TENC1 | NM_015319 | 22 | 18 | 1.0000 | 0.8200 | 0.8269 | −0.274 | 1.21 | 4 | 1.98 |
| TENC1 | NM_170754 | 424 | 200 | 0.0033 | 0.0001 | 0.4721 | −1.083 | 2.12 | 225 | 7.81 |
| TENC1 | NM_198316 | 582 | 576 | 1.0000 | 1.0000 | 0.9913 | −0.013 | 1.01 | 5 | 2.35 |
| TENM2 | AB032953 | 2485 | 1493 | 0.0000 | 0.0000 | 0.6009 | −0.735 | 1.66 | 992 | 9.95 |
| TENM2 | AK056053 | 1477 | 1123 | 0.1394 | 0.0076 | 0.7601 | −0.396 | 1.32 | 355 | 8.47 |
| TENM2 | BC172353 | 1987 | 1611 | 0.2740 | 0.0217 | 0.8111 | −0.302 | 1.23 | 376 | 8.55 |
| TENM2 | BX648178 | 5263 | 4479 | 0.2416 | 0.0177 | 0.8511 | −0.233 | 1.17 | 784 | 9.61 |
| TENM2 | NM_001122679 | 76 | 0 | 0.0000 | 0.0000 | 0.0130 | −6.264 | 76.82 | 76 | 6.25 |
| TEP1 | AB209669 | 0 | 6 | 0.3966 | 0.0404 | 6.9530 | 2.798 | 6.95 | 6 | 2.57 |
| TEP1 | AK303307 | 10 | 15 | 1.0000 | 0.7608 | 1.3892 | 0.474 | 1.39 | 4 | 2.14 |
| TEP1 | BC143812 | 168 | 174 | 1.0000 | 0.7994 | 1.0344 | 0.049 | 1.03 | 6 | 2.54 |
| TEP1 | BC143815 | 72 | 0 | 0.0000 | 0.0000 | 0.0138 | −6.181 | 72.54 | 72 | 6.16 |
| TEP1 | BX640983 | 12 | 9 | 1.0000 | 0.8116 | 0.8094 | −0.305 | 1.24 | 2 | 1.29 |
| TEP1 | NM_007110 | 387 | 337 | 1.0000 | 0.4400 | 0.8729 | −0.196 | 1.15 | 49 | 5.62 |
| TET3 | HQ220209 | 137 | 33 | 0.0093 | 0.0002 | 0.2453 | −2.027 | 4.08 | 104 | 6.71 |
| TET3 | NM_144993 | 211 | 245 | 1.0000 | 0.5051 | 1.1606 | 0.215 | 1.16 | 34 | 5.09 |
| TGFBR1 | AJ619019 | 512 | 655 | 0.6187 | 0.1063 | 1.2781 | 0.354 | 1.28 | 143 | 7.16 |
| TGFBR1 | AK302234 | 1396 | 1330 | 1.0000 | 0.7800 | 0.9524 | −0.070 | 1.05 | 66 | 6.06 |
| TGFBR1 | NM_001130916 | 164 | 21 | 0.0000 | 0.0000 | 0.1327 | −2.913 | 7.53 | 143 | 7.16 |
| TGFBR1 | NM_004612 | 1530 | 2061 | 0.0581 | 0.0023 | 1.3475 | 0.430 | 1.35 | 532 | 9.05 |
| THADA | AK025445 | 48 | 15 | 0.6092 | 0.1038 | 0.3284 | −1.606 | 3.04 | 33 | 5.04 |
| THADA | AK126824 | 6 | 4 | 1.0000 | 0.6607 | 0.6850 | −0.546 | 1.46 | 2 | 1.16 |
| THADA | AK307915 | 15 | 5 | 0.9827 | 0.2738 | 0.3541 | −1.498 | 2.82 | 11 | 3.41 |
| THADA | AL832141 | 1 | 0 | 0.5736 | 0.0906 | 0.4450 | −1.168 | 2.25 | 1 | 0.32 |
| THADA | AY149632 | 0 | 5 | 0.4533 | 0.0527 | 6.1598 | 2.623 | 6.16 | 5 | 2.37 |

TABLE 10-continued

RNA Abundance Modulation

| Gene | Trx_ID | ave DMSO | ave Cpd | padj (q val, FDR) | ttest (p val) | FC (x + 1) | L$_2$FC (x + 1) | amp FC (x + 1) | abs (Cpd-DMSO) | L$_2$abs (Cpd-DMSO) |
|---|---|---|---|---|---|---|---|---|---|---|
| THADA | BX641038 | 4 | 1 | 1.0000 | 0.4372 | 0.4466 | -1.163 | 2.24 | 3 | 1.46 |
| THADA | NM_001083953 | 73 | 0 | 0.0000 | 0.0000 | 0.0135 | -6.207 | 73.85 | 73 | 6.19 |
| THADA | NM_001271643 | 33 | 49 | 1.0000 | 0.5217 | 1.4608 | 0.547 | 1.46 | 16 | 3.97 |
| THADA | NM_001271644 | 3 | 14 | 0.6381 | 0.1120 | 3.7958 | 1.924 | 3.80 | 11 | 3.50 |
| THADA | NM_022065 | 958 | 171 | 0.0000 | 0.0000 | 0.1789 | -2.483 | 5.59 | 788 | 9.62 |
| THADA | NR_073394 | 2 | 0 | 0.5253 | 0.0738 | 0.3465 | -1.529 | 2.89 | 2 | 0.92 |
| THRB | AY286466 | 4 | 0 | 0.7634 | 0.1612 | 0.2366 | -2.080 | 4.23 | 4 | 2.07 |
| THRB | AY286470 | 0 | 0 | 9999 | 9999 | 1.0000 | 0.000 | 1.00 | 0 | 0 |
| THRB | GQ456949 | 0 | 0 | 9999 | 9999 | 1.0000 | 0.000 | 1.00 | 0 | 0 |
| THRB | NM_000461 | 14 | 77 | 0.0783 | 0.0034 | 5.2932 | 2.404 | 5.29 | 63 | 5.98 |
| THRB | NM_001128176 | 88 | 11 | 0.0077 | 0.0002 | 0.1343 | -2.897 | 7.45 | 77 | 6.27 |
| THRB | NM_001128177 | 20 | 23 | 1.0000 | 0.7873 | 1.1544 | 0.207 | 1.15 | 3 | 1.71 |
| THRB | NM_001252634 | 15 | 15 | 1.0000 | 0.8162 | 0.9958 | -0.006 | 1.00 | 0 | -3.87 |
| TJP2 | AF083893 | 3 | 0 | 0.4920 | 0.0625 | 0.2695 | -1.891 | 3.71 | 3 | 1.44 |
| TJP2 | AK304447 | 0 | 0 | 9999 | 9999 | 1.0000 | 0.000 | 1.00 | 0 | 0 |
| TJP2 | AK308564 | 10 | 16 | 1.0000 | 0.5964 | 1.5795 | 0.659 | 1.58 | 6 | 2.63 |
| TJP2 | NM_001170414 | 26 | 13 | 1.0000 | 0.5195 | 0.5294 | -0.918 | 1.89 | 12 | 3.64 |
| TJP2 | NM_001170415 | 6 | 40 | 0.2597 | 0.0199 | 5.6895 | 2.508 | 5.69 | 34 | 5.09 |
| TJP2 | NM_001170416 | 341 | 825 | 0.0000 | 0.0000 | 2.4180 | 1.274 | 2.42 | 485 | 8.92 |
| TJP2 | NM_001170630 | 6 | 9 | 1.0000 | 0.6874 | 1.5241 | 0.608 | 1.52 | 3 | 1.77 |
| TJP2 | NM_004817 | 984 | 780 | 0.4533 | 0.0528 | 0.7930 | -0.335 | 1.26 | 204 | 7.67 |
| TJP2 | NM_201629 | 20 | 26 | 1.0000 | 0.7707 | 1.3146 | 0.395 | 1.31 | 7 | 2.70 |
| TLE3 | AK096779 | 84 | 92 | 1.0000 | 0.8689 | 1.0917 | 0.127 | 1.09 | 8 | 2.97 |
| TLE3 | AK298482 | 305 | 202 | 0.5168 | 0.0701 | 0.6646 | -0.589 | 1.50 | 103 | 6.68 |
| TLE3 | AY566265 | 0 | 0 | 9999 | 9999 | 1.0000 | 0.000 | 1.00 | 0 | 0 |
| TLE3 | AY583459 | 232 | 158 | 0.6044 | 0.1001 | 0.6824 | -0.551 | 1.47 | 74 | 6.21 |
| TLE3 | AY583460 | 59 | 94 | 0.8904 | 0.2120 | 1.5688 | 0.650 | 1.57 | 34 | 5.10 |
| TLE3 | BC041831 | 34 | 45 | 1.0000 | 0.7278 | 1.2993 | 0.378 | 1.30 | 11 | 3.39 |
| TLE3 | NM_001105192 | 25 | 128 | 0.0045 | 0.0001 | 4.9848 | 2.318 | 4.98 | 103 | 6.68 |
| TLE3 | NM_005078 | 73 | 0 | 0.0000 | 0.0000 | 0.0135 | -6.207 | 73.87 | 73 | 6.19 |
| TLE3 | NM_020908 | 1 | 0 | 0.5736 | 0.0911 | 0.4430 | -1.175 | 2.26 | 1 | 0.33 |
| TMEM47 | AK311054 | 572 | 1151 | 0.0000 | 0.0000 | 2.0109 | 1.008 | 2.01 | 579 | 9.18 |
| TMEM47 | NM_031442 | 7621 | 6021 | 0.0102 | 0.0003 | 0.7902 | -0.340 | 1.27 | 1599 | 10.64 |
| TMEM63A | CU688864 | 24 | 17 | 1.0000 | 0.6332 | 0.7200 | -0.474 | 1.39 | 7 | 2.79 |
| TMEM63A | NM_014698 | 557 | 274 | 0.0019 | 0.0000 | 0.4926 | -1.022 | 2.03 | 283 | 8.14 |
| TNFAIP3 | BC041790 | 74 | 0 | 0.0000 | 0.0000 | 0.0133 | -6.237 | 75.44 | 74 | 6.22 |
| TNFAIP3 | FJ434418 | 2 | 0 | 0.5720 | 0.0887 | 0.3441 | -1.539 | 2.91 | 2 | 0.93 |
| TNFAIP3 | NM_001270507 | 18 | 0 | 0.0339 | 0.0011 | 0.0529 | -4.242 | 18.92 | 18 | 4.16 |
| TNFAIP3 | NM_001270508 | 41 | 141 | 0.0785 | 0.0034 | 3.3351 | 1.738 | 3.34 | 99 | 6.63 |
| TNFAIP3 | NM_006290 | 50 | 138 | 0.1377 | 0.0075 | 2.7130 | 1.440 | 2.71 | 88 | 6.46 |
| TNIP1 | AB252978 | 8 | 0 | 0.2237 | 0.0156 | 0.1110 | -3.171 | 9.01 | 8 | 3.00 |
| TNIP1 | AB252979 | 24 | 39 | 1.0000 | 0.3526 | 1.5938 | 0.672 | 1.59 | 15 | 3.89 |
| TNIP1 | AB252981 | 1 | 3 | 1.0000 | 0.4496 | 2.2962 | 1.199 | 2.30 | 3 | 1.33 |
| TNIP1 | CU680235 | 6 | 2 | 1.0000 | 0.5134 | 0.5163 | -0.954 | 1.94 | 3 | 1.68 |
| TNIP1 | NM_001252385 | 81 | 145 | 0.5316 | 0.0752 | 1.7799 | 0.832 | 1.78 | 64 | 6.00 |
| TNIP1 | NM_001252386 | 174 | 74 | 0.1898 | 0.0120 | 0.4303 | -1.217 | 2.32 | 100 | 6.64 |
| TNIP1 | NM_001252390 | 348 | 287 | 0.7504 | 0.1531 | 0.8231 | -0.281 | 1.21 | 62 | 5.95 |
| TNIP1 | NM_001252391 | 0 | 0 | 9999 | 9999 | 1.0000 | 0.000 | 1.00 | 0 | 0 |
| TNIP1 | NM_001252392 | 0 | 0 | 9999 | 9999 | 1.0000 | 0.000 | 1.00 | 0 | 0 |
| TNIP1 | NM_001252393 | 111 | 41 | 0.2329 | 0.0167 | 0.3727 | -1.424 | 2.68 | 71 | 6.14 |
| TNIP1 | NM_001258454 | 15 | 0 | 0.0468 | 0.0017 | 0.0634 | -3.979 | 15.77 | 15 | 3.88 |
| TNIP1 | NM_001258455 | 116 | 15 | 0.0018 | 0.0000 | 0.1355 | -2.883 | 7.38 | 101 | 6.66 |
| TNIP1 | NM_001258456 | 10 | 0 | 0.1616 | 0.0094 | 0.0916 | -3.448 | 10.91 | 10 | 3.31 |
| TNIP1 | NM_006058 | 931 | 407 | 0.0000 | 0.0000 | 0.4373 | -1.193 | 2.29 | 524 | 9.03 |
| TNPO3 | AF145029 | 142 | 83 | 0.6677 | 0.1216 | 0.5870 | -0.769 | 1.70 | 59 | 5.89 |
| TNPO3 | BC009221 | 14 | 8 | 1.0000 | 0.6953 | 0.6087 | -0.716 | 1.64 | 6 | 2.56 |
| TNPO3 | NM_001191028 | 0 | 23 | 0.0170 | 0.0005 | 23.7438 | 4.569 | 23.74 | 23 | 4.51 |
| TNPO3 | NM_012470 | 3208 | 2533 | 0.0611 | 0.0024 | 0.7899 | -0.340 | 1.27 | 674 | 9.40 |
| TNPO3 | NR_034053 | 178 | 398 | 0.0079 | 0.0002 | 2.2300 | 1.157 | 2.23 | 220 | 7.78 |
| TNS1 | AK001785 | 2 | 0 | 1.0000 | 0.3247 | 0.4521 | -1.145 | 2.21 | 2 | 0.65 |
| TNS1 | AK024948 | 1219 | 1343 | 1.0000 | 0.4318 | 1.1015 | 0.140 | 1.10 | 124 | 6.95 |
| TNS1 | AK300345 | 518 | 390 | 0.4858 | 0.0613 | 0.7535 | -0.408 | 1.33 | 128 | 7.00 |
| TNS1 | AK309785 | 382 | 399 | 1.0000 | 0.8717 | 1.0452 | 0.064 | 1.05 | 17 | 4.11 |
| TNS1 | BC071905 | 5 | 5 | 1.0000 | 1.0000 | 1.0519 | 0.073 | 1.05 | 0 | -1.73 |
| TNS1 | BC116187 | 164 | 313 | 0.0580 | 0.0023 | 1.9057 | 0.930 | 1.91 | 149 | 7.22 |
| TNS1 | BC126910 | 4988 | 3825 | 0.0057 | 0.0001 | 0.7669 | -0.383 | 1.30 | 1163 | 10.18 |
| TNS1 | BC141869 | 9 | 8 | 1.0000 | 0.8595 | 0.8764 | -0.190 | 1.14 | 1 | 0.35 |
| TNS1 | NM_022648 | 1143 | 462 | 0.0000 | 0.0000 | 0.4044 | -1.306 | 2.47 | 681 | 9.41 |
| TNS3 | NM_022748 | 1134 | 98 | 0.0000 | 0.0000 | 0.0873 | -3.518 | 11.45 | 1036 | 10.02 |
| TOE1 | AK093320 | 85 | 79 | 1.0000 | 0.9609 | 0.9317 | -0.102 | 1.07 | 6 | 2.56 |
| TOE1 | AK293704 | 2 | 2 | 1.0000 | 0.9254 | 0.8865 | -0.174 | 1.13 | 0 | -1.47 |
| TOE1 | AK298162 | 23 | 5 | 0.5018 | 0.0661 | 0.2534 | -1.980 | 3.95 | 18 | 4.19 |
| TOE1 | NM_025077 | 373 | 90 | 0.0000 | 0.0000 | 0.2427 | -2.043 | 4.12 | 283 | 8.15 |
| TOMM5 | CCDS47968 | 1 | 0 | 1.0000 | 0.4255 | 0.6124 | -0.707 | 1.63 | 1 | -0.19 |

TABLE 10-continued

RNA Abundance Modulation

| Gene | Trx_ID | ave DMSO | ave Cpd | padj (q val, FDR) | ttest (p val) | FC (x + 1) | L₂FC (x + 1) | amp FC (x + 1) | abs (Cpd-DMSO) | L₂abs (Cpd-DMSO) |
|---|---|---|---|---|---|---|---|---|---|---|
| TOMM5 | CR627326 | 10 | 5 | 1.0000 | 0.4810 | 0.5481 | −0.868 | 1.82 | 5 | 2.29 |
| TOMM5 | NM_001001790 | 1953 | 369 | 0.0000 | 0.0000 | 0.1896 | −2.399 | 5.27 | 1584 | 10.63 |
| TOMM5 | NM_001134484 | 13 | 3 | 0.7849 | 0.1702 | 0.2741 | −1.867 | 3.65 | 10 | 3.39 |
| TOMM5 | NM_001134485 | 54 | 10 | 0.1333 | 0.0071 | 0.1938 | −2.367 | 5.16 | 45 | 5.48 |
| TP53INP1 | NM_001135733 | 284 | 525 | 0.0154 | 0.0004 | 1.8440 | 0.883 | 1.84 | 241 | 7.91 |
| TP53INP1 | NM_033285 | 300 | 102 | 0.0019 | 0.0000 | 0.3426 | −1.545 | 2.92 | 198 | 7.63 |
| TRAF3 | NM_001199427 | 17 | 0 | 0.0269 | 0.0009 | 0.0543 | −4.204 | 18.42 | 17 | 4.12 |
| TRAF3 | NM_003300 | 353 | 25 | 0.0000 | 0.0000 | 0.0721 | −3.794 | 13.87 | 328 | 8.36 |
| TRAF3 | NM_145725 | 1025 | 584 | 0.0003 | 0.0000 | 0.5700 | −0.811 | 1.75 | 441 | 8.79 |
| TRAF3 | NM_145726 | 0 | 0 | 9999 | 9999 | 1.0000 | 0.000 | 1.00 | 0 | 0 |
| TRAPPC12 | AK094181 | 20 | 18 | 1.0000 | 0.9124 | 0.9211 | −0.119 | 1.09 | 2 | 0.71 |
| TRAPPC12 | AK098327 | 150 | 0 | 0.0000 | 0.0000 | 0.0066 | −7.239 | 151.10 | 150 | 7.23 |
| TRAPPC12 | NM_016030 | 619 | 640 | 1.0000 | 0.8006 | 1.0335 | 0.048 | 1.03 | 21 | 4.38 |
| TRIM2 | BC025417 | 5 | 6 | 1.0000 | 1.0000 | 1.0870 | 0.120 | 1.09 | 1 | −0.90 |
| TRIM2 | NM_001130067 | 53 | 194 | 0.0053 | 0.0001 | 3.6097 | 1.852 | 3.61 | 141 | 7.14 |
| TRIM2 | NM_015271 | 1652 | 1637 | 1.0000 | 0.8241 | 0.9909 | −0.013 | 1.01 | 15 | 3.92 |
| TRIM23 | NM_001656 | 700 | 861 | 0.6224 | 0.1073 | 1.2290 | 0.297 | 1.23 | 161 | 7.33 |
| TRIM23 | NM_033227 | 20 | 79 | 0.2237 | 0.0155 | 3.7709 | 1.915 | 3.77 | 59 | 5.88 |
| TRIM23 | NM_033228 | 58 | 1 | 0.0001 | 0.0000 | 0.0274 | −5.190 | 36.50 | 57 | 5.83 |
| TRIM65 | NM_001256124 | 181 | 0 | 0.0000 | 0.0000 | 0.0055 | −7.509 | 182.20 | 181 | 7.50 |
| TRIM65 | NM_173547 | 269 | 378 | 0.4922 | 0.0626 | 1.4015 | 0.487 | 1.40 | 108 | 6.76 |
| TSC2 | AK094152 | 12 | 11 | 1.0000 | 0.9077 | 0.9242 | −0.114 | 1.08 | 1 | −0.01 |
| TSC2 | AK294548 | 2 | 1 | 1.0000 | 0.8194 | 0.7842 | −0.351 | 1.28 | 1 | −0.62 |
| TSC2 | AK295672 | 363 | 321 | 1.0000 | 0.5371 | 0.8849 | −0.176 | 1.13 | 42 | 5.39 |
| TSC2 | AK299343 | 397 | 373 | 1.0000 | 0.7414 | 0.9402 | −0.089 | 1.06 | 24 | 4.57 |
| TSC2 | BX647816 | 0 | 0 | 9999 | 9999 | 1.0000 | 0.000 | 1.00 | 0 | 0 |
| TSC2 | NM_000548 | 96 | 10 | 0.0007 | 0.0000 | 0.1123 | −3.154 | 8.90 | 86 | 6.43 |
| TSC2 | NM_001077183 | 1284 | 1266 | 1.0000 | 0.9219 | 0.9860 | −0.020 | 1.01 | 18 | 4.17 |
| TSC2 | NM_001114382 | 124 | 115 | 1.0000 | 0.7284 | 0.9280 | −0.108 | 1.08 | 9 | 3.17 |
| TSPAN2 | GU971730 | 27 | 8 | 0.7513 | 0.1536 | 0.3238 | −1.627 | 3.09 | 19 | 4.26 |
| TSPAN2 | NM_005725 | 422 | 50 | 0.0000 | 0.0000 | 0.1193 | −3.068 | 8.38 | 373 | 8.54 |
| TUBB2C | CU691671 | 188 | 0 | 0.0000 | 0.0000 | 0.0053 | −7.562 | 188.98 | 188 | 7.55 |
| TXNRD1 | AK128515 | 2394 | 2200 | 0.8584 | 0.1984 | 0.9192 | −0.122 | 1.09 | 194 | 7.60 |
| TXNRD1 | AK308881 | 2723 | 1982 | 0.0082 | 0.0002 | 0.7279 | −0.458 | 1.37 | 741 | 9.53 |
| TXNRD1 | AY344069 | 4 | 7 | 1.0000 | 0.6512 | 1.5941 | 0.673 | 1.59 | 3 | 1.60 |
| TXNRD1 | NM_001093771 | 98 | 0 | 0.0000 | 0.0000 | 0.0101 | −6.628 | 98.89 | 98 | 6.61 |
| TXNRD1 | NM_001261445 | 371 | 307 | 0.9885 | 0.2789 | 0.8274 | −0.273 | 1.21 | 64 | 6.01 |
| TXNRD1 | NM_001261446 | 89 | 181 | 0.3678 | 0.0352 | 2.0255 | 1.018 | 2.03 | 92 | 6.52 |
| TXNRD1 | NM_003330 | 8434 | 8482 | 1.0000 | 0.8749 | 1.0057 | 0.008 | 1.01 | 48 | 5.58 |
| TXNRD1 | NM_182729 | 13106 | 12023 | 0.6842 | 0.1282 | 0.9173 | −0.124 | 1.09 | 1084 | 10.08 |
| TXNRD1 | NM_182742 | 1822 | 1688 | 1.0000 | 0.3704 | 0.9269 | −0.110 | 1.08 | 133 | 7.06 |
| TXNRD1 | NM_182743 | 2414 | 2420 | 1.0000 | 0.9384 | 1.0024 | 0.003 | 1.00 | 6 | 2.51 |
| UBAP2L | AJ243668 | 152 | 41 | 0.0239 | 0.0007 | 0.2748 | −1.864 | 3.64 | 111 | 6.79 |
| UBAP2L | AJ243669 | 118 | 28 | 0.0385 | 0.0014 | 0.2405 | −2.056 | 4.16 | 91 | 6.50 |
| UBAP2L | AJ243670 | 0 | 0 | 9999 | 9999 | 1.0000 | 0.000 | 1.00 | 0 | 0 |
| UBAP2L | AK124294 | 68 | 16 | 0.1619 | 0.0095 | 0.2411 | −2.052 | 4.15 | 52 | 5.70 |
| UBAP2L | AK302662 | 392 | 85 | 0.0000 | 0.0000 | 0.2191 | −2.190 | 4.56 | 307 | 8.26 |
| UBAP2L | AK302953 | 777 | 317 | 0.0000 | 0.0000 | 0.4088 | −1.291 | 2.45 | 460 | 8.85 |
| UBAP2L | AK303533 | 20 | 31 | 1.0000 | 0.5216 | 1.5186 | 0.603 | 1.52 | 11 | 3.44 |
| UBAP2L | NM_001127320 | 1995 | 452 | 0.0000 | 0.0000 | 0.2270 | −2.139 | 4.41 | 1543 | 10.59 |
| UBAP2L | NM_014847 | 1758 | 358 | 0.0000 | 0.0000 | 0.2043 | −2.291 | 4.90 | 1400 | 10.45 |
| UBE2V1 | NM_001032288 | 4383 | 5291 | 0.1446 | 0.0081 | 1.2072 | 0.272 | 1.21 | 908 | 9.83 |
| UBE2V1 | NM_001257393 | 12 | 0 | 0.0918 | 0.0042 | 0.0798 | −3.648 | 12.53 | 12 | 3.53 |
| UBE2V1 | NM_001257394 | 18 | 0 | 0.0270 | 0.0009 | 0.0518 | −4.270 | 19.29 | 18 | 4.19 |
| UBE2V1 | NM_001257397 | 20 | 32 | 1.0000 | 0.5282 | 1.5474 | 0.630 | 1.55 | 12 | 3.53 |
| UBE2V1 | NM_001257399 | 156 | 157 | 1.0000 | 0.9823 | 1.0066 | 0.009 | 1.01 | 1 | 0.05 |
| UBE2V1 | NM_021988 | 75 | 63 | 1.0000 | 0.6655 | 0.8353 | −0.260 | 1.20 | 13 | 3.65 |
| UBE2V1 | NM_022442 | 2 | 0 | 0.4853 | 0.0610 | 0.2862 | −1.805 | 3.49 | 2 | 1.32 |
| UBE2V1 | NM_199144 | 0 | 9 | 0.2687 | 0.0209 | 9.6358 | 3.268 | 9.64 | 9 | 3.11 |
| UBE2V1 | NR_047554 | 361 | 35 | 0.0000 | 0.0000 | 0.1003 | −3.318 | 9.97 | 326 | 8.35 |
| UBE2V1 | NR_047555 | 5 | 6 | 1.0000 | 1.0000 | 1.1214 | 0.165 | 1.12 | 1 | −0.38 |
| UBE2V1 | NR_047556 | 30 | 36 | 1.0000 | 0.7111 | 1.1947 | 0.257 | 1.19 | 6 | 2.59 |
| UCHL5 | AK225794 | 50 | 45 | 1.0000 | 0.7871 | 0.9013 | −0.150 | 1.11 | 5 | 2.34 |
| UCHL5 | AK316064 | 76 | 129 | 0.7547 | 0.1561 | 1.6957 | 0.762 | 1.70 | 53 | 5.74 |
| UCHL5 | BC015381 | 10 | 16 | 1.0000 | 0.6184 | 1.4726 | 0.558 | 1.47 | 5 | 2.43 |
| UCHL5 | NM_001199261 | 123 | 330 | 0.0009 | 0.0000 | 2.6635 | 1.413 | 2.66 | 206 | 7.69 |
| UCHL5 | NM_001199262 | 117 | 160 | 1.0000 | 0.2952 | 1.3576 | 0.441 | 1.36 | 42 | 5.40 |
| UCHL5 | NM_001199263 | 213 | 156 | 0.9637 | 0.2589 | 0.7357 | −0.443 | 1.36 | 57 | 5.82 |
| UCHL5 | NM_015984 | 507 | 451 | 1.0000 | 0.4070 | 0.8889 | −0.170 | 1.13 | 56 | 5.82 |
| UCHL5 | NR_037607 | 22 | 17 | 1.0000 | 0.6837 | 0.8001 | −0.322 | 1.25 | 5 | 2.17 |
| USP19 | AK296447 | 76 | 82 | 1.0000 | 0.9425 | 1.0851 | 0.118 | 1.09 | 7 | 2.70 |
| USP19 | BC082241 | 258 | 332 | 0.9255 | 0.2345 | 1.2841 | 0.361 | 1.28 | 74 | 6.20 |
| USP19 | BC128088 | 154 | 110 | 1.0000 | 0.2991 | 0.7136 | −0.487 | 1.40 | 44 | 5.47 |
| USP19 | NM_001199160 | 0 | 107 | 0.0000 | 0.0000 | 107.9183 | 6.754 | 107.92 | 107 | 6.74 |

TABLE 10-continued

RNA Abundance Modulation

| Gene | Trx_ID | ave DMSO | ave Cpd | padj (q val, FDR) | ttest (p val) | FC (x + 1) | L$_2$FC (x + 1) | amp FC (x + 1) | abs (Cpd-DMSO) | L$_2$abs (Cpd-DMSO) |
|---|---|---|---|---|---|---|---|---|---|---|
| USP19 | NM_001199161 | 792 | 653 | 0.7944 | 0.1738 | 0.8247 | −0.278 | 1.21 | 139 | 7.12 |
| USP19 | NM_001199162 | 89 | 32 | 0.2360 | 0.0170 | 0.3645 | −1.456 | 2.74 | 57 | 5.84 |
| USP19 | NM_006677 | 98 | 0 | 0.0000 | 0.0000 | 0.0140 | −6.163 | 71.65 | 98 | 6.61 |
| VANGL1 | NM_001172412 | 70 | 0 | 0.0000 | 0.0000 | 0.0142 | −6.140 | 70.52 | 70 | 6.12 |
| VANGL1 | NM_138959 | 2904 | 2545 | 0.5732 | 0.0889 | 0.8765 | −0.190 | 1.14 | 359 | 8.49 |
| VIPAS39 | NM_001193314 | 37 | 30 | 1.0000 | 0.7423 | 0.8265 | −0.275 | 1.21 | 7 | 2.71 |
| VIPAS39 | NM_001193315 | 772 | 358 | 0.0000 | 0.0000 | 0.4642 | −1.107 | 2.15 | 414 | 8.69 |
| VIPAS39 | NM_001193316 | 4 | 8 | 1.0000 | 0.6094 | 1.6933 | 0.760 | 1.69 | 4 | 1.89 |
| VIPAS39 | NM_001193317 | 9 | 6 | 1.0000 | 0.7524 | 0.7223 | −0.469 | 1.38 | 3 | 1.43 |
| VIPAS39 | NM_022067 | 44 | 30 | 1.0000 | 0.4680 | 0.6932 | −0.529 | 1.44 | 14 | 3.79 |
| VPS29 | AF201936 | 20 | 43 | 0.8670 | 0.2020 | 2.0984 | 1.069 | 2.10 | 23 | 4.53 |
| VPS29 | BC015095 | 7 | 0 | 0.2391 | 0.0175 | 0.1321 | −2.920 | 7.57 | 7 | 2.72 |
| VPS29 | BC017964 | 7 | 8 | 1.0000 | 0.8462 | 1.2348 | 0.304 | 1.23 | 2 | 0.85 |
| VPS29 | NM_016226 | 740 | 17 | 0.0000 | 0.0000 | 0.0246 | −5.347 | 40.71 | 723 | 9.50 |
| VPS29 | NM_057180 | 833 | 1554 | 0.0000 | 0.0000 | 1.8631 | 0.898 | 1.86 | 720 | 9.49 |
| VPS51 | AF289557 | 24 | 28 | 1.0000 | 0.8244 | 1.1883 | 0.249 | 1.19 | 5 | 2.21 |
| VPS51 | NM_013265 | 1259 | 1305 | 1.0000 | 0.7344 | 1.0367 | 0.052 | 1.04 | 46 | 5.53 |
| VPS51 | NR_073519 | 114 | 12 | 0.0006 | 0.0000 | 0.1095 | −3.191 | 9.13 | 103 | 6.68 |
| VWA8 | NM_001009814 | 71 | 0 | 0.0000 | 0.0000 | 0.0139 | −6.170 | 71.99 | 71 | 6.15 |
| VWA8 | NM_015058 | 756 | 737 | 1.0000 | 0.8217 | 0.9748 | −0.037 | 1.03 | 19 | 4.25 |
| WDR48 | AK297349 | 71 | 116 | 0.7479 | 0.1524 | 1.6147 | 0.691 | 1.61 | 44 | 5.47 |
| WDR48 | AK298810 | 0 | 0 | 9999 | 9999 | 1.0000 | 0.000 | 1.00 | 0 | 0 |
| WDR48 | AK302307 | 52 | 0 | 0.0000 | 0.0000 | 0.0189 | −5.723 | 52.80 | 52 | 5.69 |
| WDR48 | BC037168 | 339 | 426 | 0.9260 | 0.2346 | 1.2556 | 0.328 | 1.26 | 87 | 6.44 |
| WDR48 | NM_020839 | 768 | 762 | 1.0000 | 0.9199 | 0.9919 | −0.012 | 1.01 | 6 | 2.64 |
| WNT5B | AB209228 | 92 | 70 | 1.0000 | 0.5664 | 0.7677 | −0.381 | 1.30 | 22 | 4.43 |
| WNT5B | NM_030775 | 5796 | 5090 | 0.4783 | 0.0590 | 0.8782 | −0.187 | 1.14 | 706 | 9.46 |
| WNT5B | NM_032642 | 81 | 0 | 0.0000 | 0.0000 | 0.0122 | −6.358 | 82.04 | 81 | 6.34 |
| WSB1 | AK294516 | 26 | 6 | 0.5802 | 0.0934 | 0.2707 | −1.885 | 3.69 | 20 | 4.31 |
| WSB1 | AK300262 | 51 | 74 | 1.0000 | 0.3839 | 1.4571 | 0.543 | 1.46 | 24 | 4.56 |
| WSB1 | AK307114 | 0 | 2 | 0.7652 | 0.1625 | 3.2945 | 1.720 | 3.29 | 2 | 1.20 |
| WSB1 | BC048007 | 159 | 460 | 0.0000 | 0.0000 | 2.8794 | 1.526 | 2.88 | 301 | 8.23 |
| WSB1 | NM_015626 | 1065 | 382 | 0.0000 | 0.0000 | 0.3589 | −1.478 | 2.79 | 683 | 9.42 |
| WSB1 | NM_134265 | 7 | 3 | 1.0000 | 0.4132 | 0.4337 | −1.205 | 2.31 | 5 | 2.26 |
| WWTR1 | AJ299431 | 645 | 899 | 0.2486 | 0.0184 | 1.3939 | 0.479 | 1.39 | 254 | 7.99 |
| WWTR1 | NM_001168278 | 0 | 5 | 0.4533 | 0.0531 | 6.0601 | 2.599 | 6.06 | 5 | 2.34 |
| WWTR1 | NM_001168280 | 419 | 0 | 0.0000 | 0.0000 | 0.0024 | −8.714 | 419.80 | 419 | 8.71 |
| WWTR1 | NM_015472 | 1122 | 1068 | 1.0000 | 0.6290 | 0.9516 | −0.072 | 1.05 | 54 | 5.76 |
| XRN2 | AK172858 | 1 | 1 | 1.0000 | 0.7292 | 0.7119 | −0.490 | 1.40 | 1 | −0.62 |
| XRN2 | AK302846 | 67 | 4 | 0.0026 | 0.0000 | 0.0670 | −3.900 | 14.93 | 64 | 5.99 |
| XRN2 | AK303312 | 81 | 2 | 0.0000 | 0.0000 | 0.0355 | −4.818 | 28.20 | 79 | 6.31 |
| XRN2 | NM_012255 | 2877 | 506 | 0.0000 | 0.0000 | 0.1763 | −2.504 | 5.67 | 2371 | 11.21 |
| YAP1 | AB567720 | 94 | 61 | 1.0000 | 0.3062 | 0.6520 | −0.617 | 1.53 | 33 | 5.04 |
| YAP1 | AK304485 | 565 | 585 | 1.0000 | 0.8945 | 1.0360 | 0.051 | 1.04 | 20 | 4.35 |
| YAP1 | AL832620 | 2741 | 2997 | 0.9534 | 0.2516 | 1.0935 | 0.129 | 1.09 | 256 | 8.00 |
| YAP1 | HE864159 | 25 | 7 | 0.8225 | 0.1844 | 0.3204 | −1.642 | 3.12 | 18 | 4.16 |
| YAP1 | HE864161 | 0 | 9 | 0.2366 | 0.0171 | 10.0586 | 3.330 | 10.06 | 9 | 3.18 |
| YAP1 | HE864162 | 97 | 125 | 1.0000 | 0.5205 | 1.2893 | 0.367 | 1.29 | 28 | 4.82 |
| YAP1 | HE864163 | 54 | 27 | 0.9949 | 0.2828 | 0.5058 | −0.983 | 1.98 | 27 | 4.77 |
| YAP1 | NM_001130145 | 358 | 97 | 0.0000 | 0.0000 | 0.2742 | −1.866 | 3.65 | 260 | 8.02 |
| YAP1 | NM_001195044 | 2287 | 1851 | 0.2750 | 0.0218 | 0.8096 | −0.305 | 1.24 | 436 | 8.77 |
| YAP1 | NM_001195045 | 52 | 44 | 1.0000 | 0.7493 | 0.8451 | −0.243 | 1.18 | 8 | 3.03 |
| YAP1 | NM_006106 | 1115 | 1040 | 1.0000 | 0.4283 | 0.9332 | −0.100 | 1.07 | 75 | 6.22 |
| YES1 | M15990 | 404 | 167 | 0.0039 | 0.0001 | 0.4162 | −1.265 | 2.40 | 236 | 7.88 |
| YES1 | NM_005433 | 1372 | 1773 | 0.1846 | 0.0115 | 1.2919 | 0.369 | 1.29 | 401 | 8.65 |
| YPEL5 | AK307099 | 13 | 0 | 0.0617 | 0.0025 | 0.0694 | −3.848 | 14.41 | 13 | 3.74 |
| YPEL5 | BC047237 | 0 | 2 | 0.7557 | 0.1579 | 2.5176 | 1.332 | 2.52 | 2 | 0.60 |
| YPEL5 | NM_001127399 | 33 | 170 | 0.0010 | 0.0000 | 5.0391 | 2.333 | 5.04 | 137 | 7.09 |
| YPEL5 | NM_001127400 | 200 | 1094 | 0.0000 | 0.0000 | 5.4458 | 2.445 | 5.45 | 894 | 9.80 |
| YPEL5 | NM_001127401 | 67 | 160 | 0.2273 | 0.0161 | 2.3777 | 1.250 | 2.38 | 93 | 6.54 |
| YPEL5 | NM_016061 | 2598 | 1003 | 0.0000 | 0.0000 | 0.3864 | −1.372 | 2.59 | 1595 | 10.64 |
| YTHDF3 | NM_001277813 | 144 | 111 | 1.0000 | 0.3994 | 0.7762 | −0.366 | 1.29 | 32 | 5.02 |
| YTHDF3 | NM_001277814 | 33 | 7 | 0.4676 | 0.0563 | 0.2464 | −2.021 | 4.06 | 26 | 4.69 |
| YTHDF3 | NM_001277815 | 602 | 520 | 1.0000 | 0.2888 | 0.8644 | −0.210 | 1.16 | 82 | 6.35 |
| YTHDF3 | NM_001277816 | 180 | 270 | 0.7557 | 0.1573 | 1.4961 | 0.581 | 1.50 | 90 | 6.49 |
| YTHDF3 | NM_001277817 | 1047 | 1043 | 1.0000 | 0.8720 | 0.9970 | −0.004 | 1.00 | 3 | 1.67 |
| YTHDF3 | NM_001277818 | 68 | 0 | 0.0000 | 0.0000 | 0.0188 | −5.732 | 53.15 | 68 | 6.09 |
| YTHDF3 | NM_152758 | 1555 | 1819 | 0.5467 | 0.0810 | 1.1699 | 0.226 | 1.17 | 264 | 8.05 |
| YTHDF3 | NR_102434 | 3 | 7 | 1.0000 | 0.5391 | 1.7024 | 0.768 | 1.70 | 3 | 1.65 |
| Z24749 | Z24749 | 407 | 0 | 0.0000 | 0.0000 | 0.0025 | −8.673 | 408.14 | 407 | 8.67 |
| ZBTB24 | AK309697 | 27 | 20 | 1.0000 | 0.7020 | 0.7544 | −0.407 | 1.33 | 7 | 2.77 |
| ZBTB24 | BC143843 | 77 | 0 | 0.0000 | 0.0000 | 0.0128 | −6.287 | 78.06 | 77 | 6.27 |
| ZBTB24 | BX648883 | 50 | 52 | 1.0000 | 0.8050 | 1.0514 | 0.072 | 1.05 | 3 | 1.38 |
| ZBTB24 | NM_001164313 | 50 | 44 | 1.0000 | 0.8236 | 0.8882 | −0.171 | 1.13 | 6 | 2.51 |

TABLE 10-continued

RNA Abundance Modulation

| Gene | Trx_ID | ave DMSO | ave Cpd | padj (q val, FDR) | ttest (p val) | FC (x + 1) | $L_2$FC (x + 1) | amp FC (x + 1) | abs (Cpd-DMSO) | $L_2$abs (Cpd-DMSO) |
|---|---|---|---|---|---|---|---|---|---|---|
| ZBTB24 | NM_014797 | 231 | 278 | 1.0000 | 0.5475 | 1.2023 | 0.266 | 1.20 | 47 | 5.55 |
| ZC3H14 | AF474376 | 0 | 0 | 9999 | 9999 | 1.0000 | 0.000 | 1.00 | 0 | 0 |
| ZC3H14 | AK302136 | 12 | 18 | 1.0000 | 0.4932 | 1.5151 | 0.599 | 1.52 | 7 | 2.70 |
| ZC3H14 | AK303123 | 3 | 5 | 1.0000 | 0.7986 | 1.6695 | 0.739 | 1.67 | 3 | 1.35 |
| ZC3H14 | BX248281 | 14 | 22 | 1.0000 | 0.6289 | 1.4923 | 0.578 | 1.49 | 8 | 2.93 |
| ZC3H14 | NM_001160103 | 554 | 620 | 1.0000 | 0.3884 | 1.1196 | 0.163 | 1.12 | 66 | 6.05 |
| ZC3H14 | NM_001160104 | 157 | 32 | 0.0042 | 0.0001 | 0.2103 | −2.250 | 4.76 | 125 | 6.97 |
| ZC3H14 | NM_024824 | 899 | 905 | 1.0000 | 0.8554 | 1.0057 | 0.008 | 1.01 | 5 | 2.37 |
| ZC3H14 | NM_207660 | 233 | 213 | 1.0000 | 0.7525 | 0.9169 | −0.125 | 1.09 | 19 | 4.28 |
| ZC3H14 | NM_207661 | 305 | 323 | 1.0000 | 0.7382 | 1.0579 | 0.081 | 1.06 | 18 | 4.15 |
| ZC3H14 | NM_207662 | 2 | 1 | 1.0000 | 0.6657 | 0.7454 | −0.424 | 1.34 | 1 | −0.30 |
| ZFAND1 | NM_001170796 | 6 | 15 | 1.0000 | 0.5067 | 2.2366 | 1.161 | 2.24 | 9 | 3.17 |
| ZFAND1 | NM_001170797 | 70 | 24 | 0.4615 | 0.0543 | 0.3499 | −1.515 | 2.86 | 46 | 5.53 |
| ZFAND1 | NM_024699 | 180 | 304 | 0.2985 | 0.0246 | 1.6866 | 0.754 | 1.69 | 124 | 6.96 |
| ZFAND1 | NR_033193 | 14 | 37 | 0.8192 | 0.1830 | 2.5026 | 1.323 | 2.50 | 23 | 4.52 |
| ZFAND1 | NR_033194 | 140 | 28 | 0.0081 | 0.0002 | 0.2039 | −2.294 | 4.90 | 112 | 6.81 |
| ZFAND1 | NR_033195 | 74 | 44 | 1.0000 | 0.3158 | 0.5988 | −0.740 | 1.67 | 30 | 4.91 |
| ZFAND1 | NR_033196 | 43 | 86 | 0.8209 | 0.1838 | 1.9615 | 0.972 | 1.96 | 42 | 5.41 |
| ZFAND5 | AK290849 | 1492 | 1208 | 0.6427 | 0.1141 | 0.8096 | −0.305 | 1.24 | 284 | 8.15 |
| ZFAND5 | AK307376 | 170 | 75 | 0.1749 | 0.0106 | 0.4468 | −1.162 | 2.24 | 95 | 6.56 |
| ZFAND5 | NM_001102420 | 2051 | 1427 | 0.0031 | 0.0001 | 0.6960 | −0.523 | 1.44 | 624 | 9.28 |
| ZFAND5 | NM_001102421 | 1282 | 1215 | 1.0000 | 0.5211 | 0.9474 | −0.078 | 1.06 | 68 | 6.08 |
| ZFAND5 | NM_001278243 | 270 | 632 | 0.0025 | 0.0000 | 2.3378 | 1.225 | 2.34 | 363 | 8.50 |
| ZFAND5 | NM_001278244 | 0 | 29 | 0.0040 | 0.0001 | 29.5746 | 4.886 | 29.57 | 29 | 4.84 |
| ZFAND5 | NM_001278245 | 324 | 123 | 0.0058 | 0.0001 | 0.3802 | −1.395 | 2.63 | 202 | 7.66 |
| ZFAND5 | NM_006007 | 24 | 57 | 0.7344 | 0.1462 | 2.3067 | 1.206 | 2.31 | 33 | 5.04 |
| ZHX3 | AB007855 | 529 | 869 | 0.0143 | 0.0004 | 1.6397 | 0.713 | 1.64 | 339 | 8.41 |
| ZHX3 | AK097523 | 0 | 0 | 9999 | 9999 | 1.0000 | 0.000 | 1.00 | 0 | 0 |
| ZHX3 | AK122905 | 734 | 702 | 1.0000 | 0.7309 | 0.9566 | −0.064 | 1.05 | 32 | 5.00 |
| ZHX3 | BC020258 | 523 | 236 | 0.0006 | 0.0000 | 0.4516 | −1.147 | 2.21 | 288 | 8.17 |
| ZHX3 | BC047070 | 134 | 127 | 1.0000 | 0.6761 | 0.9527 | −0.070 | 1.05 | 6 | 2.67 |
| ZHX3 | BC068569 | 92 | 102 | 1.0000 | 0.7284 | 1.1114 | 0.152 | 1.11 | 9 | 3.37 |
| ZHX3 | NM_015035 | 1022 | 1134 | 0.9974 | 0.2845 | 1.1089 | 0.149 | 1.11 | 111 | 6.80 |
| ZMIZ1 | AB033050 | 226 | 466 | 0.0010 | 0.0000 | 2.0636 | 1.045 | 2.06 | 241 | 7.91 |
| ZMIZ1 | AK024490 | 19 | 28 | 1.0000 | 0.5842 | 1.4091 | 0.495 | 1.41 | 8 | 3.07 |
| ZMIZ1 | AK025812 | 2 | 5 | 1.0000 | 0.5654 | 1.7586 | 0.814 | 1.76 | 2 | 1.26 |
| ZMIZ1 | AK299728 | 793 | 746 | 1.0000 | 0.6980 | 0.9403 | −0.089 | 1.06 | 47 | 5.57 |
| ZMIZ1 | NM_020338 | 4047 | 3543 | 0.4388 | 0.0489 | 0.8753 | −0.192 | 1.14 | 505 | 8.98 |
| ZMYM2 | AF012126 | 8 | 0 | 0.1720 | 0.0103 | 0.1062 | −3.235 | 9.42 | 8 | 3.07 |
| ZMYM2 | AK302917 | 88 | 119 | 1.0000 | 0.4337 | 1.3395 | 0.422 | 1.34 | 30 | 4.92 |
| ZMYM2 | AK310505 | 49 | 38 | 1.0000 | 0.6309 | 0.7866 | −0.346 | 1.27 | 11 | 3.42 |
| ZMYM2 | AL136621 | 51 | 76 | 1.0000 | 0.3758 | 1.4965 | 0.582 | 1.50 | 26 | 4.68 |
| ZMYM2 | BX648905 | 9 | 14 | 1.0000 | 0.6067 | 1.5384 | 0.621 | 1.54 | 5 | 2.38 |
| ZMYM2 | NM_001190964 | 56 | 219 | 0.0042 | 0.0001 | 3.8547 | 1.947 | 3.85 | 163 | 7.35 |
| ZMYM2 | NM_001190965 | 281 | 243 | 1.0000 | 0.5316 | 0.8654 | −0.208 | 1.16 | 38 | 5.25 |
| ZMYM2 | NM_003453 | 211 | 138 | 0.8835 | 0.2091 | 0.6554 | −0.609 | 1.53 | 73 | 6.19 |
| ZMYM2 | NM_197968 | 142 | 56 | 0.1765 | 0.0108 | 0.3968 | −1.334 | 2.52 | 86 | 6.43 |
| ZNF219 | NM_001101672 | 109 | 0 | 0.0000 | 0.0000 | 0.0091 | −6.778 | 109.73 | 109 | 6.76 |
| ZNF219 | NM_001102454 | 29 | 133 | 0.0229 | 0.0007 | 4.4608 | 2.157 | 4.46 | 104 | 6.70 |
| ZNF219 | NM_016423 | 24 | 38 | 1.0000 | 0.5729 | 1.5214 | 0.605 | 1.52 | 13 | 3.73 |
| ZNF268 | AK027712 | 174 | 136 | 1.0000 | 0.3118 | 0.7832 | −0.353 | 1.28 | 38 | 5.25 |
| ZNF268 | AK302159 | 0 | 14 | 0.1013 | 0.0049 | 14.6346 | 3.871 | 14.63 | 14 | 3.77 |
| ZNF268 | AY583691 | 77 | 45 | 1.0000 | 0.3126 | 0.5961 | −0.746 | 1.68 | 31 | 4.97 |
| ZNF268 | DQ057359 | 0 | 4 | 0.5390 | 0.0775 | 4.8695 | 2.284 | 4.87 | 4 | 1.95 |
| ZNF268 | NM_001165881 | 72 | 214 | 0.0109 | 0.0003 | 2.9348 | 1.553 | 2.93 | 142 | 7.15 |
| ZNF268 | NM_001165882 | 12 | 0 | 0.0849 | 0.0038 | 0.0773 | −3.694 | 12.94 | 12 | 3.58 |
| ZNF268 | NM_001165883 | 13 | 12 | 1.0000 | 0.8633 | 0.9449 | −0.082 | 1.06 | 1 | −0.43 |
| ZNF268 | NM_001165884 | 0 | 0 | 9999 | 9999 | 1.0000 | 0.000 | 1.00 | 0 | 0 |
| ZNF268 | NM_001165885 | 0 | 0 | 9999 | 9999 | 1.0000 | 0.000 | 1.00 | 0 | 0 |
| ZNF268 | NM_001165886 | 0 | 0 | 9999 | 9999 | 1.0000 | 0.000 | 1.00 | 0 | 0 |
| ZNF268 | NM_001165887 | 7 | 34 | 0.4577 | 0.0537 | 4.0815 | 2.029 | 4.08 | 26 | 4.71 |
| ZNF268 | NM_003415 | 88 | 0 | 0.0000 | 0.0000 | 0.0113 | −6.473 | 88.83 | 88 | 6.46 |
| ZNF268 | NM_152943 | 158 | 56 | 0.0388 | 0.0014 | 0.3562 | −1.489 | 2.81 | 102 | 6.68 |
| ZNF395 | AK002050 | 172 | 0 | 0.0000 | 0.0000 | 0.0058 | −7.431 | 172.55 | 172 | 7.42 |
| ZNF395 | AK098243 | 0 | 5 | 0.4533 | 0.0530 | 6.0953 | 2.608 | 6.10 | 5 | 2.35 |
| ZNF395 | BC001237 | 297 | 462 | 0.3243 | 0.0282 | 1.5496 | 0.632 | 1.55 | 164 | 7.36 |
| ZNF395 | NM_018660 | 151 | 46 | 0.0103 | 0.0003 | 0.3066 | −1.705 | 3.26 | 105 | 6.72 |
| ZNF827 | AB074279 | 8 | 5 | 1.0000 | 0.6662 | 0.6816 | −0.553 | 1.47 | 3 | 1.44 |
| ZNF827 | AF450485 | 78 | 39 | 0.8626 | 0.2000 | 0.5127 | −0.964 | 1.95 | 38 | 5.26 |
| ZNF827 | BC143577 | 128 | 290 | 0.0475 | 0.0018 | 2.2591 | 1.176 | 2.26 | 162 | 7.34 |
| ZNF827 | NM_178835 | 232 | 63 | 0.0017 | 0.0000 | 0.2757 | −1.859 | 3.63 | 169 | 7.40 |
| ZNF91 | AK300294 | 77 | 8 | 0.0066 | 0.0002 | 0.1134 | −3.140 | 8.82 | 70 | 6.12 |
| ZNF91 | NM_003430 | 85 | 187 | 0.1733 | 0.0105 | 2.1762 | 1.122 | 2.18 | 101 | 6.66 |

TABLE 11

RNA Abundance Modulation

| Gene | Trx_ID | ave DMSO | ave Cpd | padj (q val, FDR) | ttest (p val) | FC (x + 1) | $L_2$FC (x + 1) | amp FC (x + 1) | abs (Cpd − DMSO) | $L_2$abs (Cpd − DMSO) |
|---|---|---|---|---|---|---|---|---|---|---|
| ACACA | AB209325 | 51 | 0 | 0.0001 | 0.0000 | 0.0194 | −5.690 | 51.64 | 51 | 5.66 |
| ACACA | AJ564444 | 1 | 0 | 1.0000 | 0.7967 | 0.6854 | −0.545 | 1.46 | 1 | −0.73 |
| ACACA | AK295586 | 52 | 15 | 0.5023 | 0.0418 | 0.3039 | −1.718 | 3.29 | 37 | 5.22 |
| ACACA | AK295735 | 12 | 53 | 0.3866 | 0.0250 | 4.2336 | 2.082 | 4.23 | 41 | 5.36 |
| ACACA | AK308905 | 18 | 18 | 1.0000 | 0.9645 | 1.0414 | 0.059 | 1.04 | 1 | −0.37 |
| ACACA | AK309084 | 13 | 21 | 1.0000 | 0.4674 | 1.5959 | 0.674 | 1.60 | 8 | 3.01 |
| ACACA | AY315622 | 2 | 5 | 1.0000 | 0.3872 | 2.3117 | 1.209 | 2.31 | 4 | 1.88 |
| ACACA | NM_198834 | 1022 | 1135 | 1.0000 | 0.3057 | 1.1102 | 0.151 | 1.11 | 113 | 6.82 |
| ACACA | NM_198836 | 1693 | 1801 | 1.0000 | 0.5837 | 1.0638 | 0.089 | 1.06 | 108 | 6.76 |
| ACACA | NM_198839 | 17 | 8 | 1.0000 | 0.3905 | 0.4907 | −1.027 | 2.04 | 9 | 3.20 |
| ACADVL | AK302653 | 167 | 154 | 1.0000 | 0.7764 | 0.9238 | −0.114 | 1.08 | 13 | 3.68 |
| ACADVL | NM_000018 | 1440 | 589 | 0.0000 | 0.0000 | 0.4096 | −1.288 | 2.44 | 851 | 9.73 |
| ACADVL | NM_001033859 | 154 | 104 | 1.0000 | 0.2680 | 0.6791 | −0.558 | 1.47 | 50 | 5.64 |
| ACADVL | NM_001270447 | 2374 | 3411 | 0.0023 | 0.0000 | 1.4368 | 0.523 | 1.44 | 1037 | 10.02 |
| ACADVL | NM_001270448 | 290 | 264 | 1.0000 | 0.6593 | 0.9086 | −0.138 | 1.10 | 27 | 4.73 |
| AFF2 | NM_001169122 | 24 | 35 | 1.0000 | 0.5806 | 1.4462 | 0.532 | 1.45 | 11 | 3.47 |
| AFF2 | NM_001169123 | 51 | 37 | 1.0000 | 0.5836 | 0.7206 | −0.473 | 1.39 | 15 | 3.87 |
| AFF2 | NM_001169124 | 66 | 0 | 0.0000 | 0.0000 | 0.0149 | −6.069 | 67.13 | 66 | 6.05 |
| AFF2 | NM_001169125 | 65 | 103 | 0.9839 | 0.1962 | 1.5737 | 0.654 | 1.57 | 38 | 5.24 |
| AFF2 | NM_001170628 | 0 | 0 | 9999 | 9999 | 1.0000 | 0.000 | 1.00 | 0 | 0 |
| AFF2 | NM_002025 | 0 | 17 | 0.0497 | 0.0011 | 18.0825 | 4.177 | 18.08 | 17 | 4.09 |
| AFF2 | X95463 | 0 | 6 | 0.3811 | 0.0242 | 6.6631 | 2.736 | 6.66 | 6 | 2.50 |
| AHCYL2 | NM_001130720 | 244 | 48 | 0.0001 | 0.0000 | 0.1999 | −2.322 | 5.00 | 196 | 7.62 |
| AHCYL2 | NM_001130722 | 37 | 245 | 0.0000 | 0.0000 | 6.5390 | 2.709 | 6.54 | 208 | 7.70 |
| AHCYL2 | NM_015328 | 113 | 144 | 1.0000 | 0.4391 | 1.2738 | 0.349 | 1.27 | 31 | 4.97 |
| AHRR | AK090508 | 156 | 152 | 1.0000 | 0.9198 | 0.9765 | −0.034 | 1.02 | 4 | 1.88 |
| AHRR | AK127977 | 5 | 17 | 1.0000 | 0.2266 | 2.9457 | 1.559 | 2.95 | 12 | 3.60 |
| AHRR | AK314472 | 108 | 56 | 0.7347 | 0.1041 | 0.5196 | −0.944 | 1.92 | 52 | 5.71 |
| AHRR | BC035358 | 0 | 0 | 9999 | 9999 | 1.0000 | 0.000 | 1.00 | 0 | 0 |
| AHRR | BC121048 | 106 | 12 | 0.0023 | 0.0000 | 0.1182 | −3.081 | 8.46 | 95 | 6.57 |
| AHRR | NM_001242412 | 696 | 694 | 1.0000 | 0.9316 | 0.9969 | −0.005 | 1.00 | 2 | 1.13 |
| AHRR | NM_020731 | 0 | 11 | 0.1568 | 0.0057 | 11.9737 | 3.582 | 11.97 | 11 | 3.46 |
| AKAP1 | AK292416 | 186 | 0 | 0.0000 | 0.0000 | 0.0054 | −7.545 | 186.77 | 186 | 7.54 |
| AKAP1 | NM_001242902 | 45 | 11 | 0.5008 | 0.0415 | 0.2704 | −1.887 | 3.70 | 33 | 5.05 |
| AKAP1 | NM_001242903 | 4 | 0 | 0.6786 | 0.0865 | 0.2132 | −2.230 | 4.69 | 4 | 1.88 |
| AKAP1 | NM_003488 | 361 | 591 | 0.0539 | 0.0012 | 1.6374 | 0.711 | 1.64 | 230 | 7.85 |
| AKAP1 | U34074 | 4 | 0 | 0.6590 | 0.0785 | 0.2001 | −2.321 | 5.00 | 4 | 2.00 |
| ALDH4A1 | FJ462711 | 39 | 41 | 1.0000 | 0.9555 | 1.0562 | 0.079 | 1.06 | 2 | 1.16 |
| ALDH4A1 | NM_001161504 | 229 | 341 | 0.5649 | 0.0527 | 1.4877 | 0.573 | 1.49 | 112 | 6.81 |
| ALDH4A1 | NM_003748 | 629 | 299 | 0.0011 | 0.0000 | 0.4758 | −1.072 | 2.10 | 330 | 8.37 |
| ALDH4A1 | NM_170726 | 4 | 3 | 1.0000 | 1.0000 | 0.9103 | −0.136 | 1.10 | 0 | −1.24 |
| ANKRD17 | AK299046 | 75 | 82 | 1.0000 | 0.8641 | 1.0853 | 0.118 | 1.09 | 7 | 2.70 |
| ANKRD17 | BX648035 | 1781 | 2089 | 0.7037 | 0.0970 | 1.1729 | 0.230 | 1.17 | 308 | 8.27 |
| ANKRD17 | NM_032217 | 246 | 39 | 0.0000 | 0.0000 | 0.1615 | −2.631 | 6.19 | 207 | 7.69 |
| ANKRD17 | NM_198889 | 1251 | 1355 | 1.0000 | 0.4984 | 1.0836 | 0.116 | 1.08 | 105 | 6.71 |
| AP2B1 | AK292531 | 1929 | 1748 | 1.0000 | 0.2548 | 0.9058 | −0.143 | 1.10 | 182 | 7.51 |
| AP2B1 | AK301522 | 109 | 126 | 1.0000 | 0.7475 | 1.1543 | 0.207 | 1.15 | 17 | 4.08 |
| AP2B1 | AY341427 | 18 | 12 | 1.0000 | 0.7018 | 0.6988 | −0.517 | 1.43 | 6 | 2.49 |
| AP2B1 | CR749392 | 1118 | 1153 | 1.0000 | 0.8206 | 1.0309 | 0.044 | 1.03 | 35 | 5.11 |
| AP2B1 | NM_001030006 | 349 | 843 | 0.0000 | 0.0000 | 2.4125 | 1.271 | 2.41 | 494 | 8.95 |
| AP2B1 | NM_001282 | 5378 | 5349 | 1.0000 | 0.9183 | 0.9947 | −0.008 | 1.01 | 28 | 4.83 |
| APLP2 | AK308932 | 11 | 5 | 1.0000 | 0.4590 | 0.4217 | −1.123 | 2.18 | 7 | 2.74 |
| APLP2 | L23114 | 4514 | 5905 | 0.0270 | 0.0005 | 1.3080 | 0.387 | 1.31 | 1391 | 10.44 |
| APLP2 | NM_001142276 | 4231 | 8573 | 0.0000 | 0.0000 | 2.0260 | 1.019 | 2.03 | 4342 | 12.08 |
| APLP2 | NM_001142277 | 15603 | 10914 | 0.0000 | 0.0000 | 0.6995 | −0.516 | 1.43 | 4689 | 12.19 |
| APLP2 | NM_001142278 | 2 | 11 | 0.9571 | 0.1864 | 3.8954 | 1.962 | 3.90 | 9 | 3.18 |
| APLP2 | NM_001243299 | 77 | 144 | 0.8014 | 0.1220 | 1.8607 | 0.896 | 1.86 | 67 | 6.07 |
| APLP2 | NR_024515 | 181 | 142 | 1.0000 | 0.3947 | 0.7821 | −0.355 | 1.28 | 40 | 5.31 |
| APLP2 | NR_024516 | 0 | 0 | 9999 | 9999 | 1.0000 | 0.000 | 1.00 | 0 | 0 |
| ASL | AK300519 | 2 | 0 | 0.8529 | 0.1419 | 0.2935 | −1.768 | 3.41 | 2 | 1.27 |
| ASL | AK310912 | 18 | 11 | 1.0000 | 0.5797 | 0.6400 | −0.644 | 1.56 | 7 | 2.75 |
| ASL | AK316334 | 0 | 3 | 0.9220 | 0.1724 | 3.0080 | 1.589 | 3.01 | 3 | 1.39 |
| ASL | NM_000048 | 704 | 702 | 1.0000 | 0.9801 | 0.9969 | −0.004 | 1.00 | 2 | 1.11 |
| ASL | NM_001024943 | 242 | 62 | 0.0014 | 0.0000 | 0.2572 | −1.959 | 3.89 | 181 | 7.50 |
| ASL | NM_001024944 | 44 | 24 | 1.0000 | 0.3041 | 0.5497 | −0.863 | 1.82 | 20 | 4.34 |
| ASL | NM_001024946 | 129 | 181 | 1.0000 | 0.2492 | 1.4024 | 0.488 | 1.40 | 52 | 5.71 |
| ASPH | FJ461473 | 2517 | 2684 | 1.0000 | 0.4411 | 1.0664 | 0.093 | 1.07 | 167 | 7.39 |
| ASPH | NM_001164750 | 1895 | 6887 | 0.0000 | 0.0000 | 3.6325 | 1.861 | 3.63 | 4992 | 12.29 |
| ASPH | NM_001164751 | 903 | 1193 | 0.3749 | 0.0233 | 1.3205 | 0.401 | 1.32 | 290 | 8.18 |
| ASPH | NM_001164752 | 699 | 582 | 1.0000 | 0.2587 | 0.8332 | −0.263 | 1.20 | 117 | 6.87 |
| ASPH | NM_001164753 | 0 | 38 | 0.0007 | 0.0000 | 38.6537 | 5.273 | 38.65 | 38 | 5.23 |
| ASPH | NM_001164754 | 165 | 33 | 0.0031 | 0.0000 | 0.2026 | −2.303 | 4.94 | 132 | 7.04 |
| ASPH | NM_001164755 | 5071 | 4917 | 1.0000 | 0.7425 | 0.9697 | −0.044 | 1.03 | 154 | 7.27 |
| ASPH | NM_001164756 | 18 | 19 | 1.0000 | 0.8926 | 1.0939 | 0.130 | 1.09 | 2 | 0.81 |

TABLE 11-continued

RNA Abundance Modulation

| Gene | Trx_ID | ave DMSO | ave Cpd | padj (q val, FDR) | ttest (p val) | FC (x + 1) | L$_2$FC (x + 1) | amp FC (x + 1) | abs (Cpd − DMSO) | L$_2$abs (Cpd − DMSO) |
|---|---|---|---|---|---|---|---|---|---|---|
| ASPH | NM_004318 | 12069 | 8083 | 0.0000 | 0.0000 | 0.6698 | −0.578 | 1.49 | 3985 | 11.96 |
| ASPH | NM_032466 | 0 | 2380 | 0.0000 | 0.0000 | ####### | 11.218 | 2381.38 | 2380 | 11.22 |
| ASPH | NM_032467 | 12 | 7 | 1.0000 | 0.6348 | 0.6347 | −0.656 | 1.58 | 5 | 2.25 |
| ATG9A | BC065534 | 8 | 13 | 1.0000 | 0.4903 | 1.5603 | 0.642 | 1.56 | 5 | 2.31 |
| ATG9A | NM_001077198 | 2261 | 2224 | 1.0000 | 0.8935 | 0.9835 | −0.024 | 1.02 | 37 | 5.22 |
| ATG9A | NM_024085 | 675 | 325 | 0.0009 | 0.0000 | 0.4817 | −1.054 | 2.08 | 351 | 8.45 |
| ATMIN | AB007891 | 45 | 25 | 1.0000 | 0.3360 | 0.5769 | −0.794 | 1.73 | 19 | 4.27 |
| ATMIN | AK301781 | 0 | 36 | 0.0008 | 0.0000 | 37.0250 | 5.210 | 37.03 | 36 | 5.17 |
| ATMIN | CR749457 | 62 | 0 | 0.0000 | 0.0000 | 0.0158 | −5.981 | 63.18 | 62 | 5.96 |
| ATMIN | NM_015251 | 1905 | 1969 | 1.0000 | 0.7814 | 1.0338 | 0.048 | 1.03 | 64 | 6.01 |
| ATXN3 | GQ176512 | 35 | 2 | 0.1223 | 0.0040 | 0.0901 | −3.473 | 11.10 | 32 | 5.02 |
| ATXN3 | GQ176529 | 3 | 0 | 0.8600 | 0.1452 | 0.2769 | −1.853 | 3.61 | 3 | 1.38 |
| ATXN3 | GQ176602 | 5 | 6 | 1.0000 | 0.8158 | 1.3379 | 0.420 | 1.34 | 2 | 0.91 |
| ATXN3 | GQ176613 | 6 | 0 | 0.5441 | 0.0491 | 0.1362 | −2.876 | 7.34 | 6 | 2.67 |
| ATXN3 | GQ176624 | 47 | 25 | 1.0000 | 0.2860 | 0.5379 | −0.894 | 1.86 | 22 | 4.47 |
| ATXN3 | GQ176650 | 0 | 2 | 0.6432 | 0.0750 | 3.0499 | 1.609 | 3.05 | 2 | 1.04 |
| ATXN3 | GQ176668 | 0 | 0 | 9999 | 9999 | 1.0000 | 0.000 | 1.00 | 0 | 0 |
| ATXN3 | GQ176673 | 26 | 83 | 0.3423 | 0.0200 | 3.1289 | 1.646 | 3.13 | 57 | 5.84 |
| ATXN3 | GQ176681 | 5 | 5 | 1.0000 | 0.9572 | 1.0126 | 0.018 | 1.01 | 0 | −3.74 |
| ATXN3 | GQ176694 | 0 | 0 | 1.0000 | 0.4944 | 1.3160 | 0.396 | 1.32 | 0 | −1.66 |
| ATXN3 | GQ176708 | 0 | 2 | 0.6432 | 0.0750 | 3.0499 | 1.609 | 3.05 | 2 | 1.04 |
| ATXN3 | GQ176709 | 0 | 0 | 9999 | 9999 | 1.0000 | 0.000 | 1.00 | 0 | 0 |
| ATXN3 | GQ176739 | 2 | 0 | 1.0000 | 0.4288 | 0.4720 | −1.083 | 2.12 | 2 | 0.59 |
| ATXN3 | GQ176768 | 1 | 0 | 1.0000 | 0.3131 | 0.4012 | −1.318 | 2.49 | 1 | 0.58 |
| ATXN3 | GQ176769 | 0 | 2 | 0.6432 | 0.0752 | 3.0576 | 1.612 | 3.06 | 2 | 1.04 |
| ATXN3 | GQ176792 | 0 | 0 | 9999 | 9999 | 1.0000 | 0.000 | 1.00 | 0 | 0 |
| ATXN3 | GQ176799 | 6 | 3 | 1.0000 | 0.6458 | 0.6293 | −0.668 | 1.59 | 3 | 1.40 |
| ATXN3 | GQ176811 | 2 | 0 | 0.8367 | 0.1356 | 0.3191 | −1.648 | 3.13 | 2 | 1.09 |
| ATXN3 | GQ176814 | 0 | 3 | 0.5441 | 0.0499 | 4.1601 | 2.057 | 4.16 | 3 | 1.66 |
| ATXN3 | GQ176822 | 0 | 0 | 1.0000 | 1.0000 | 0.7648 | −0.387 | 1.31 | 0 | −1.70 |
| ATXN3 | GQ176826 | 66 | 69 | 1.0000 | 0.9659 | 1.0487 | 0.069 | 1.05 | 3 | 1.71 |
| ATXN3 | GQ176833 | 0 | 0 | 9999 | 9999 | 1.0000 | 0.000 | 1.00 | 0 | 0 |
| ATXN3 | GQ176839 | 1 | 0 | 1.0000 | 0.4730 | 0.5201 | −0.943 | 1.92 | 1 | −0.12 |
| ATXN3 | GQ176844 | 10 | 22 | 1.0000 | 0.3515 | 2.0305 | 1.022 | 2.03 | 12 | 3.54 |
| ATXN3 | GQ176847 | 0 | 0 | 9999 | 9999 | 1.0000 | 0.000 | 1.00 | 0 | 0 |
| ATXN3 | NM_001127696 | 34 | 40 | 1.0000 | 0.8929 | 1.1763 | 0.234 | 1.18 | 6 | 2.62 |
| ATXN3 | NM_001127697 | 0 | 0 | 9999 | 9999 | 1.0000 | 0.000 | 1.00 | 0 | 0 |
| ATXN3 | NM_001164779 | 0 | 0 | 9999 | 9999 | 1.0000 | 0.000 | 1.00 | 0 | 0 |
| ATXN3 | NM_001164781 | 0 | 0 | 9999 | 9999 | 1.0000 | 0.000 | 1.00 | 0 | 0 |
| ATXN3 | NM_004993 | 270 | 324 | 1.0000 | 0.3138 | 1.1964 | 0.259 | 1.20 | 53 | 5.74 |
| ATXN3 | NM_030660 | 80 | 0 | 0.0000 | 0.0000 | 0.0123 | −6.341 | 81.05 | 80 | 6.32 |
| ATXN3 | NR_028453 | 0 | 21 | 0.0220 | 0.0004 | 21.5406 | 4.429 | 21.54 | 21 | 4.36 |
| ATXN3 | NR_028454 | 0 | 0 | 9999 | 9999 | 1.0000 | 0.000 | 1.00 | 0 | 0 |
| ATXN3 | NR_028458 | 0 | 0 | 9999 | 9999 | 1.0000 | 0.000 | 1.00 | 0 | 0 |
| ATXN3 | NR_028468 | 0 | 0 | 9999 | 9999 | 1.0000 | 0.000 | 1.00 | 0 | 0 |
| ATXN3 | NR_028469 | 0 | 0 | 9999 | 9999 | 1.0000 | 0.000 | 1.00 | 0 | 0 |
| ATXN3 | U64821 | 16 | 29 | 1.0000 | 0.4026 | 1.7678 | 0.822 | 1.77 | 13 | 3.68 |
| BAG2 | AK301934 | 76 | 317 | 0.0001 | 0.0000 | 4.1158 | 2.041 | 4.12 | 241 | 7.91 |
| BAG2 | NM_004282 | 1118 | 913 | 0.7057 | 0.0975 | 0.8172 | −0.291 | 1.22 | 205 | 7.68 |
| BASP1 | NM_001271606 | 194 | 519 | 0.0002 | 0.0000 | 2.6666 | 1.415 | 2.67 | 325 | 8.34 |
| BASP1 | NM_006317 | 4601 | 4316 | 1.0000 | 0.4072 | 0.9379 | −0.092 | 1.07 | 286 | 8.16 |
| BRPF1 | AK293865 | 106 | 151 | 1.0000 | 0.2383 | 1.4223 | 0.508 | 1.42 | 45 | 5.50 |
| BRPF1 | AL713696 | 332 | 317 | 1.0000 | 0.8505 | 0.9554 | −0.066 | 1.05 | 15 | 3.89 |
| BRPF1 | NM_001003694 | 219 | 269 | 1.0000 | 0.3401 | 1.2232 | 0.291 | 1.22 | 49 | 5.62 |
| BRPF1 | NM_004634 | 83 | 0 | 0.0000 | 0.0000 | 0.0120 | −6.385 | 83.60 | 83 | 6.37 |
| BSCL2 | NM_001122955 | 3 | 3 | 1.0000 | 1.0000 | 0.9733 | −0.039 | 1.03 | 0 | −3.12 |
| BSCL2 | NM_001130702 | 52 | 0 | 0.0001 | 0.0000 | 0.0187 | −5.738 | 53.58 | 52 | 5.71 |
| BSCL2 | NM_032667 | 25 | 67 | 0.6613 | 0.0790 | 2.6105 | 1.384 | 2.61 | 42 | 5.39 |
| BSCL2 | NR_037948 | 0 | 22 | 0.0153 | 0.0002 | 23.4539 | 4.552 | 23.45 | 22 | 4.49 |
| BSCL2 | NR_037949 | 81 | 62 | 1.0000 | 0.5360 | 0.7782 | −0.362 | 1.28 | 18 | 4.18 |
| C11orf30 | AK125114 | 51 | 0 | 0.0001 | 0.0000 | 0.0191 | −5.714 | 52.48 | 51 | 5.69 |
| C11orf30 | AK126030 | 41 | 20 | 1.0000 | 0.2614 | 0.4907 | −1.027 | 2.04 | 21 | 4.41 |
| C11orf30 | AK304043 | 18 | 12 | 1.0000 | 0.5269 | 0.6498 | −0.622 | 1.54 | 7 | 2.77 |
| C11orf30 | AK304043 | 61 | 55 | 1.0000 | 0.8578 | 0.9076 | −0.140 | 1.10 | 6 | 2.52 |
| C11orf30 | AK309621 | 2 | 2 | 1.0000 | 1.0000 | 0.9800 | −0.029 | 1.02 | 0 | −4.04 |
| C11orf30 | AY070433 | 2 | 7 | 1.0000 | 0.2958 | 2.6709 | 1.417 | 2.67 | 5 | 2.26 |
| C11orf30 | BC021688 | 0 | 1 | 1.0000 | 0.7372 | 1.2481 | 0.320 | 1.25 | 0 | −1.62 |
| C11orf30 | BC033404 | 7 | 10 | 1.0000 | 0.6824 | 1.4248 | 0.511 | 1.42 | 3 | 1.72 |
| C11orf30 | BC117265 | 250 | 171 | 0.6696 | 0.0819 | 0.6830 | −0.550 | 1.46 | 80 | 6.32 |
| C11orf30 | BC143370 | 0 | 0 | 9999 | 9999 | 1.0000 | 0.000 | 1.00 | 0 | 0 |
| C11orf30 | BC143374 | 60 | 41 | 1.0000 | 0.4193 | 0.6902 | −0.535 | 1.45 | 19 | 4.23 |
| C11orf30 | BC143376 | 74 | 138 | 0.5201 | 0.0439 | 1.8486 | 0.886 | 1.85 | 64 | 6.00 |
| C11orf30 | NM_020193 | 112 | 154 | 1.0000 | 0.2623 | 1.3708 | 0.455 | 1.37 | 42 | 5.39 |
| C11orf73 | NM_016401 | 674 | 313 | 0.0005 | 0.0000 | 0.4656 | −1.103 | 2.15 | 361 | 8.49 |

TABLE 11-continued

RNA Abundance Modulation

| Gene | Trx_ID | ave DMSO | ave Cpd | padj (q val, FDR) | ttest (p val) | FC (x + 1) | $L_2$FC (x + 1) | amp FC (x + 1) | abs (Cpd − DMSO) | $L_2$abs (Cpd − DMSO) |
|---|---|---|---|---|---|---|---|---|---|---|
| C11orf73 | NR_024596 | 10 | 13 | 1.0000 | 0.7621 | 1.3220 | 0.403 | 1.32 | 3 | 1.76 |
| C11orf73 | NR_024598 | 23 | 17 | 1.0000 | 0.6367 | 0.7298 | −0.454 | 1.37 | 7 | 2.71 |
| C17orf76-AS1 | HQ447236 | 16 | 18 | 1.0000 | 0.8484 | 1.1398 | 0.189 | 1.14 | 2 | 1.25 |
| C17orf76-AS1 | NR_027158 | 543 | 646 | 1.0000 | 0.2327 | 1.1904 | 0.251 | 1.19 | 104 | 6.69 |
| C17orf76-AS1 | NR_027163 | 1719 | 1896 | 1.0000 | 0.3185 | 1.1029 | 0.141 | 1.10 | 177 | 7.47 |
| C17orf76-AS1 | NR_027164 | 238 | 13 | 0.0000 | 0.0000 | 0.0570 | −4.134 | 17.56 | 226 | 7.82 |
| C17orf76-AS1 | NR_027165 | 20 | 75 | 0.3368 | 0.0193 | 3.6856 | 1.882 | 3.69 | 55 | 5.78 |
| C17orf76-AS1 | NR_027166 | 5345 | 5519 | 1.0000 | 0.7117 | 1.0325 | 0.046 | 1.03 | 174 | 7.44 |
| C17orf76-AS1 | NR_027167 | 54 | 90 | 1.0000 | 0.2089 | 1.6483 | 0.721 | 1.65 | 36 | 5.16 |
| C17orf76-AS1 | NR_027168 | 558 | 837 | 0.1060 | 0.0032 | 1.4994 | 0.584 | 1.50 | 279 | 8.12 |
| C17orf76-AS1 | NR_027169 | 251 | 177 | 0.8649 | 0.1488 | 0.7059 | −0.503 | 1.42 | 74 | 6.21 |
| C17orf76-AS1 | NR_027170 | 93 | 65 | 1.0000 | 0.4357 | 0.6972 | −0.520 | 1.43 | 28 | 4.83 |
| C17orf76-AS1 | NR_027172 | 1 | 3 | 1.0000 | 0.3256 | 2.6515 | 1.407 | 2.65 | 3 | 1.41 |
| C17orf76-AS1 | NR_027173 | 0 | 0 | 9999 | 9999 | 1.0000 | 0.000 | 1.00 | 0 | 0 |
| C17orf76-AS1 | NR_027174 | 11 | 2 | 0.8875 | 0.1602 | 0.2513 | −1.992 | 3.98 | 9 | 3.18 |
| C17orf76-AS1 | NR_027176 | 0 | 0 | 9999 | 9999 | 1.0000 | 0.000 | 1.00 | 0 | 0 |
| C17orf76-AS1 | NR_027177 | 0 | 2 | 0.6266 | 0.0665 | 3.2121 | 1.683 | 3.21 | 2 | 1.15 |
| C17orf76-AS1 | NR_027178 | 4 | 8 | 1.0000 | 0.4457 | 1.9155 | 0.938 | 1.92 | 4 | 2.11 |
| C17orf76-AS1 | NR_027179 | 48 | 34 | 1.0000 | 0.5413 | 0.7168 | −0.480 | 1.40 | 14 | 3.80 |
| C17orf76-AS1 | NR_027667 | 307 | 197 | 0.5773 | 0.0561 | 0.6449 | −0.633 | 1.55 | 109 | 6.77 |
| C17orf76-AS1 | NR_045022 | 37 | 54 | 1.0000 | 0.4628 | 1.4606 | 0.547 | 1.46 | 17 | 4.12 |
| C17orf76-AS1 | NR_045023 | 3 | 1 | 1.0000 | 0.3923 | 0.3835 | −1.383 | 2.61 | 3 | 1.44 |
| C17orf76-AS1 | NR_045025 | 0 | 0 | 9999 | 9999 | 1.0000 | 0.000 | 1.00 | 0 | 0 |
| C17orf76-AS1 | NR_045026 | 74 | 13 | 0.0887 | 0.0025 | 0.1922 | −2.379 | 5.20 | 60 | 5.91 |
| C17orf76-AS1 | NR_045028 | 31 | 20 | 1.0000 | 0.5406 | 0.6650 | −0.588 | 1.50 | 11 | 3.42 |
| C17orf76-AS1 | NR_045029 | 357 | 265 | 0.8559 | 0.1432 | 0.7438 | −0.427 | 1.34 | 92 | 6.52 |
| C6orf48 | AJ249732 | 1 | 0 | 1.0000 | 0.4730 | 0.5201 | −0.943 | 1.92 | 1 | −0.12 |
| C6orf48 | AJ249732 | 3 | 3 | 1.0000 | 0.9455 | 0.8770 | −0.189 | 1.14 | 1 | −0.89 |
| C6orf48 | NM_001040437 | 189 | 235 | 1.0000 | 0.3828 | 1.2466 | 0.318 | 1.25 | 47 | 5.55 |
| C6orf48 | NM_001040437 | 566 | 493 | 1.0000 | 0.4146 | 0.8708 | −0.200 | 1.15 | 73 | 6.20 |
| C6orf48 | NM_001040438 | 1016 | 524 | 0.0003 | 0.0000 | 0.5166 | −0.953 | 1.94 | 491 | 8.94 |
| C6orf48 | NM_001040438 | 232 | 524 | 0.0031 | 0.0000 | 2.2552 | 1.173 | 2.26 | 292 | 8.19 |
| C6orf48 | NM_001040438 | 280 | 480 | 0.0823 | 0.0022 | 1.7117 | 0.775 | 1.71 | 200 | 7.64 |
| C9orf69 | BC092490 | 11 | 6 | 1.0000 | 0.6093 | 0.6086 | −0.716 | 1.64 | 5 | 2.24 |
| C9orf69 | NM_001256526 | 103 | 359 | 0.0002 | 0.0000 | 3.4559 | 1.789 | 3.46 | 256 | 8.00 |
| C9orf69 | NM_152833 | 1651 | 1067 | 0.0050 | 0.0001 | 0.6466 | −0.629 | 1.55 | 584 | 9.19 |
| CAB39 | AF134480 | 540 | 435 | 0.9466 | 0.1823 | 0.8063 | −0.311 | 1.24 | 105 | 6.71 |
| CAB39 | NM_001130849 | 61 | 58 | 1.0000 | 0.9078 | 0.9431 | −0.085 | 1.06 | 4 | 1.83 |
| CAB39 | NM_001130850 | 474 | 948 | 0.0003 | 0.0000 | 1.9983 | 0.999 | 2.00 | 474 | 8.89 |
| CAB39 | NM_016289 | 1386 | 1111 | 0.6179 | 0.0647 | 0.8015 | −0.319 | 1.25 | 275 | 8.10 |
| CALU | HM002613 | 4 | 10 | 1.0000 | 0.5175 | 1.9945 | 0.996 | 1.99 | 5 | 2.40 |
| CALU | HM002614 | 321 | 347 | 1.0000 | 0.6787 | 1.0812 | 0.113 | 1.08 | 26 | 4.71 |
| CALU | HM002615 | 8 | 20 | 1.0000 | 0.3066 | 2.2625 | 1.178 | 2.26 | 12 | 3.57 |
| CALU | NM_001130674 | 12823 | 15299 | 0.2138 | 0.0092 | 1.1930 | 0.255 | 1.19 | 2475 | 11.27 |
| CALU | NM_001199671 | 881 | 1776 | 0.0000 | 0.0000 | 2.0146 | 1.010 | 2.01 | 895 | 9.81 |
| CALU | NM_001199672 | 338 | 128 | 0.0067 | 0.0001 | 0.3808 | −1.393 | 2.63 | 210 | 7.71 |
| CALU | NM_001199673 | 25 | 50 | 1.0000 | 0.2270 | 2.0034 | 1.002 | 2.00 | 26 | 4.69 |
| CALU | NM_001219 | 55590 | 56963 | 1.0000 | 0.7083 | 1.0247 | 0.035 | 1.02 | 1374 | 10.42 |
| CALU | NR_074086 | 69 | 35 | 0.8749 | 0.1523 | 0.5089 | −0.974 | 1.96 | 35 | 5.11 |
| CDC25B | AK295573 | 3 | 0 | 1.0000 | 0.3149 | 0.3492 | −1.518 | 2.86 | 2 | 1.29 |
| CDC25B | AK299028 | 25 | 23 | 1.0000 | 0.8663 | 0.9261 | −0.111 | 1.08 | 2 | 0.95 |
| CDC25B | AK299192 | 0 | 2 | 0.6428 | 0.0725 | 2.8961 | 1.534 | 2.90 | 2 | 0.92 |
| CDC25B | BX640836 | 56 | 23 | 0.7347 | 0.1034 | 0.4245 | −1.236 | 2.36 | 33 | 5.03 |
| CDC25B | BX647988 | 261 | 676 | 0.0000 | 0.0000 | 2.5895 | 1.373 | 2.59 | 416 | 8.70 |
| CDC25B | FR695900 | 4207 | 3076 | 0.0095 | 0.0001 | 0.7311 | −0.452 | 1.37 | 1132 | 10.14 |
| CDC25B | FR695901 | 568 | 622 | 1.0000 | 0.5674 | 1.0950 | 0.131 | 1.10 | 54 | 5.76 |
| CDC25B | NM_004358 | 147 | 109 | 1.0000 | 0.4261 | 0.7411 | −0.432 | 1.35 | 38 | 5.26 |
| CDC25B | NM_021872 | 89 | 43 | 0.8600 | 0.1458 | 0.4868 | −1.039 | 2.05 | 46 | 5.52 |
| CDC25B | NM_021873 | 1121 | 906 | 0.6837 | 0.0874 | 0.8084 | −0.307 | 1.24 | 215 | 7.75 |
| CDC42BPA | AB007920 | 3 | 5 | 1.0000 | 0.6418 | 1.4535 | 0.540 | 1.45 | 2 | 0.85 |
| CDC42BPA | AB384799 | 68 | 0 | 0.0000 | 0.0000 | 0.0145 | −6.111 | 69.10 | 68 | 6.09 |
| CDC42BPA | AK027000 | 2 | 5 | 1.0000 | 0.4848 | 2.1281 | 1.090 | 2.13 | 3 | 1.68 |
| CDC42BPA | AK098391 | 93 | 178 | 0.5406 | 0.0478 | 1.8967 | 0.924 | 1.90 | 84 | 6.40 |
| CDC42BPA | BC136333 | 0 | 22 | 0.0209 | 0.0004 | 22.5239 | 4.493 | 22.52 | 22 | 4.43 |
| CDC42BPA | CR933723 | 94 | 98 | 1.0000 | 0.9057 | 1.0390 | 0.055 | 1.04 | 4 | 1.89 |
| CDC42BPA | NM_003607 | 3601 | 3896 | 1.0000 | 0.3331 | 1.0818 | 0.113 | 1.08 | 295 | 8.20 |
| CDC42BPA | NM_014826 | 476 | 423 | 1.0000 | 0.4797 | 0.8891 | −0.170 | 1.12 | 53 | 5.73 |
| CDKAL1 | AK000349 | 97 | 8 | 0.0010 | 0.0000 | 0.0906 | −3.465 | 11.04 | 89 | 6.48 |
| CDKAL1 | AK024151 | 0 | 0 | 9999 | 9999 | 1.0000 | 0.000 | 1.00 | 0 | 0 |
| CDKAL1 | AK128546 | 15 | 10 | 1.0000 | 0.6784 | 0.6751 | −0.567 | 1.48 | 5 | 2.35 |
| CDKAL1 | AK310219 | 11 | 9 | 1.0000 | 0.8971 | 0.8664 | −0.207 | 1.15 | 2 | 0.67 |
| CDKAL1 | BC064145 | 14 | 8 | 1.0000 | 0.5534 | 0.5864 | −0.770 | 1.71 | 6 | 2.67 |
| CDKAL1 | NM_017774 | 164 | 259 | 0.6232 | 0.0656 | 1.5754 | 0.656 | 1.58 | 95 | 6.57 |
| CLIC1 | BC064527 | 0 | 0 | 9999 | 9999 | 1.0000 | 0.000 | 1.00 | 0 | 0 |

TABLE 11-continued

RNA Abundance Modulation

| Gene | Trx_ID | ave DMSO | ave Cpd | padj (q val, FDR) | ttest (p val) | FC (x + 1) | L₂FC (x + 1) | amp FC (x + 1) | abs (Cpd − DMSO) | L₂abs (Cpd − DMSO) |
|---|---|---|---|---|---|---|---|---|---|---|
| CLIC1 | BC064527 | 0 | 0 | 9999 | 9999 | 1.0000 | 0.000 | 1.00 | 0 | 0 |
| CLIC1 | BC064527 | 0 | 0 | 9999 | 9999 | 1.0000 | 0.000 | 1.00 | 0 | 0 |
| CLIC1 | BC064527 | 0 | 0 | 9999 | 9999 | 1.0000 | 0.000 | 1.00 | 0 | 0 |
| CLIC1 | NM_001288 | 322 | 0 | 0.0000 | 0.0000 | 0.0042 | −7.912 | 240.78 | 322 | 8.33 |
| CLIC1 | NM_001288 | 3298 | 3771 | 0.7032 | 0.0952 | 1.1435 | 0.193 | 1.14 | 473 | 8.89 |
| CLIC1 | NM_001288 | 3298 | 3771 | 0.7032 | 0.0952 | 1.1435 | 0.193 | 1.14 | 473 | 8.89 |
| CLIC1 | NM_001288 | 3298 | 3013 | 1.0000 | 0.2509 | 0.9137 | −0.130 | 1.09 | 285 | 8.15 |
| CLIC1 | NM_001288 | 3298 | 3013 | 1.0000 | 0.2509 | 0.9137 | −0.130 | 1.09 | 285 | 8.15 |
| COL12A1 | CCDS43481 | 148 | 22 | 0.0019 | 0.0000 | 0.1568 | −2.673 | 6.38 | 126 | 6.98 |
| COL12A1 | CCDS43482 | 4370 | 4998 | 0.4511 | 0.0336 | 1.1437 | 0.194 | 1.14 | 628 | 9.29 |
| COL12A1 | NM_004370 | 57872 | 61957 | 1.0000 | 0.2808 | 1.0706 | 0.098 | 1.07 | 4085 | 12.00 |
| COL12A1 | NM_080645 | 0 | 63 | 0.0000 | 0.0000 | 63.9888 | 6.000 | 63.99 | 63 | 5.98 |
| COL12A1 | U68139 | 1587 | 2235 | 0.0228 | 0.0004 | 1.4087 | 0.494 | 1.41 | 649 | 9.34 |
| COL1A1 | JQ236861 | 287 | 88 | 0.0015 | 0.0000 | 0.3090 | −1.694 | 3.24 | 199 | 7.64 |
| COL1A1 | NM_000088 | 1220314 | 895805 | 0.2868 | 0.0150 | 0.7341 | −0.446 | 1.36 | 324509 | 18.31 |
| COL6A1 | BC022236 | 766 | 1799 | 0.0000 | 0.0000 | 2.3478 | 1.231 | 2.35 | 1034 | 10.01 |
| COL6A1 | NM_001848 | 71411 | 59992 | 0.2247 | 0.0100 | 0.8401 | −0.251 | 1.19 | 11419 | 13.48 |
| CSNK1A1 | AK294099 | 82 | 377 | 0.0000 | 0.0000 | 4.5220 | 2.177 | 4.52 | 294 | 8.20 |
| CSNK1A1 | NM_001025105 | 261 | 88 | 0.0123 | 0.0002 | 0.3408 | −1.553 | 2.93 | 173 | 7.43 |
| CSNK1A1 | NM_001271741 | 1529 | 1186 | 0.2527 | 0.0120 | 0.7761 | −0.366 | 1.29 | 342 | 8.42 |
| CSNK1A1 | NM_001271742 | 534 | 557 | 1.0000 | 0.8636 | 1.0426 | 0.060 | 1.04 | 23 | 4.51 |
| CSNK1A1 | NM_001892 | 4832 | 4849 | 1.0000 | 0.8880 | 1.0036 | 0.005 | 1.00 | 17 | 4.11 |
| CSNK1A1 | X80693 | 160 | 226 | 0.9517 | 0.1843 | 1.4088 | 0.494 | 1.41 | 66 | 6.04 |
| CTDSP2 | AK294930 | 515 | 229 | 0.0013 | 0.0000 | 0.4459 | −1.165 | 2.24 | 286 | 8.16 |
| CTDSP2 | AK310183 | 30 | 63 | 0.9126 | 0.1680 | 2.0620 | 1.044 | 2.06 | 33 | 5.04 |
| CTDSP2 | AK310873 | 4153 | 4415 | 1.0000 | 0.4494 | 1.0630 | 0.088 | 1.06 | 262 | 8.03 |
| CTDSP2 | NM_005730 | 2591 | 2356 | 1.0000 | 0.3296 | 0.9094 | −0.137 | 1.10 | 235 | 7.87 |
| CUL2 | AK294080 | 520 | 650 | 0.8875 | 0.1604 | 1.2495 | 0.321 | 1.25 | 130 | 7.02 |
| CUL2 | NM_001198777 | 1484 | 1598 | 1.0000 | 0.5056 | 1.0769 | 0.107 | 1.08 | 114 | 6.83 |
| CUL2 | NM_003591 | 81 | 0 | 0.0000 | 0.0000 | 0.0122 | −6.356 | 81.89 | 81 | 6.34 |
| CUL4A | AK296700 | 460 | 517 | 1.0000 | 0.4650 | 1.1238 | 0.168 | 1.12 | 57 | 5.83 |
| CUL4A | AL833355 | 209 | 245 | 1.0000 | 0.6594 | 1.1748 | 0.232 | 1.17 | 37 | 5.20 |
| CUL4A | NM_001008895 | 3541 | 2653 | 0.0406 | 0.0008 | 0.7495 | −0.416 | 1.33 | 887 | 9.79 |
| CUL4A | NM_003589 | 135 | 790 | 0.0000 | 0.0000 | 5.8054 | 2.537 | 5.81 | 654 | 9.35 |
| DAXX | AK309612 | 20 | 29 | 1.0000 | 0.5759 | 1.4573 | 0.543 | 1.46 | 10 | 3.25 |
| DAXX | HQ436528 | 0 | 0 | 9999 | 9999 | 1.0000 | 0.000 | 1.00 | 0 | 0 |
| DAXX | HQ436529 | 5 | 4 | 1.0000 | 0.8321 | 0.8275 | −0.273 | 1.21 | 1 | 0.09 |
| DAXX | HQ436529 | 0 | 0 | 9999 | 9999 | 1.0000 | 0.000 | 1.00 | 0 | 0 |
| DAXX | NM_001141969 | 6 | 0 | 0.5441 | 0.0487 | 0.1530 | −2.708 | 6.54 | 6 | 2.47 |
| DAXX | NM_001141969 | 1021 | 1167 | 1.0000 | 0.2559 | 1.1436 | 0.194 | 1.14 | 147 | 7.20 |
| DAXX | NM_001141970 | 55 | 0 | 0.0000 | 0.0000 | 0.0178 | −5.814 | 56.26 | 55 | 5.79 |
| DAXX | NM_001141970 | 0 | 0 | 9999 | 9999 | 1.0000 | 0.000 | 1.00 | 0 | 0 |
| DAXX | NM_001254717 | 58 | 23 | 0.7347 | 0.1039 | 0.4086 | −1.291 | 2.45 | 35 | 5.12 |
| DAXX | NM_001254717 | 0 | 0 | 1.0000 | 1.0000 | 0.7648 | −0.387 | 1.31 | 0 | −1.70 |
| DAXX | NM_001350 | 473 | 321 | 0.4941 | 0.0407 | 0.6794 | −0.558 | 1.47 | 152 | 7.25 |
| DAXX | NM_001350 | 1 | 0 | 1.0000 | 0.2791 | 0.4484 | −1.157 | 2.23 | 1 | 0.30 |
| DCAF10 | AK309712 | 58 | 343 | 0.0000 | 0.0000 | 5.8684 | 2.553 | 5.87 | 285 | 8.16 |
| DCAF10 | CU678477 | 147 | 192 | 1.0000 | 0.3633 | 1.3054 | 0.384 | 1.31 | 45 | 5.50 |
| DCAF10 | NM_024345 | 1173 | 947 | 0.6266 | 0.0665 | 0.8077 | −0.308 | 1.24 | 226 | 7.82 |
| DDAH1 | AK294752 | 2108 | 3681 | 0.0000 | 0.0000 | 1.7464 | 0.804 | 1.75 | 1574 | 10.62 |
| DDAH1 | AK302531 | 687 | 299 | 0.0003 | 0.0000 | 0.4361 | −1.197 | 2.29 | 388 | 8.60 |
| DDAH1 | NM_001134445 | 7992 | 7477 | 1.0000 | 0.3597 | 0.9356 | −0.096 | 1.07 | 515 | 9.01 |
| DDAH1 | NM_012137 | 722 | 799 | 1.0000 | 0.4671 | 1.1059 | 0.145 | 1.11 | 77 | 6.26 |
| DDR1 | AK130776 | 0 | 2 | 0.6696 | 0.0839 | 2.7082 | 1.437 | 2.71 | 2 | 0.77 |
| DDR1 | AK291621 | 53 | 0 | 0.0000 | 0.0000 | 0.0185 | −5.756 | 54.03 | 53 | 5.73 |
| DDR1 | AK291621 | 4 | 0 | 0.6786 | 0.0865 | 0.2138 | −2.226 | 4.68 | 4 | 1.88 |
| DDR1 | AK295643 | 1 | 1 | 1.0000 | 0.7383 | 1.4735 | 0.559 | 1.47 | 1 | −0.39 |
| DDR1 | AK295643 | 0 | 0 | 9999 | 9999 | 1.0000 | 0.000 | 1.00 | 0 | 0 |
| DDR1 | BC070070 | 113 | 221 | 0.2628 | 0.0129 | 1.9533 | 0.966 | 1.95 | 109 | 6.76 |
| DDR1 | EU826614 | 5 | 0 | 0.5948 | 0.0588 | 0.1689 | −2.566 | 5.92 | 5 | 2.30 |
| DDR1 | EU826614 | 1 | 0 | 0.6668 | 0.6668 | 0.6191 | −0.692 | 1.62 | 1 | −0.70 |
| DDR1 | EU826614 | 0 | 0 | 9999 | 9999 | 1.0000 | 0.000 | 1.00 | 0 | 0 |
| DDR1 | L20817 | 183 | 48 | 0.0135 | 0.0002 | 0.2665 | −1.908 | 3.75 | 135 | 7.07 |
| DDR1 | L57508 | 22 | 7 | 1.0000 | 0.2362 | 0.3495 | −1.517 | 2.86 | 15 | 3.93 |
| DDR1 | NM_001202521 | 0 | 14 | 0.0811 | 0.0022 | 14.9044 | 3.898 | 14.90 | 14 | 3.80 |
| DDR1 | NM_001202522 | 0 | 25 | 0.0113 | 0.0002 | 25.6908 | 4.683 | 25.69 | 25 | 4.63 |
| DDR1 | NM_001202523 | 7 | 5 | 1.0000 | 0.9628 | 0.7878 | −0.344 | 1.27 | 2 | 0.78 |
| DDR1 | NM_001202523 | 0 | 0 | 9999 | 9999 | 1.0000 | 0.000 | 1.00 | 0 | 0 |
| DDR1 | NM_013993 | 282 | 290 | 1.0000 | 0.8398 | 1.0270 | 0.038 | 1.03 | 8 | 2.93 |
| DDR1 | NM_013994 | 55 | 0 | 0.0000 | 0.0000 | 0.0177 | −5.818 | 56.42 | 55 | 5.79 |
| DDR1 | Z29093 | 14 | 4 | 1.0000 | 0.2258 | 0.3551 | −1.494 | 2.82 | 10 | 3.31 |
| DDR1 | Z29093 | 2 | 3 | 1.0000 | 1.0000 | 1.0803 | 0.111 | 1.08 | 0 | −1.85 |
| DDX39B | AB209217 | 183 | 130 | 0.9290 | 0.1754 | 0.7096 | −0.495 | 1.41 | 54 | 5.74 |
| DDX39B | AB209217 | 171 | 152 | 1.0000 | 0.6727 | 0.8917 | −0.165 | 1.12 | 19 | 4.22 |

TABLE 11-continued

RNA Abundance Modulation

| Gene | Trx_ID | ave DMSO | ave Cpd | padj (q val, FDR) | ttest (p val) | FC (x + 1) | L₂FC (x + 1) | amp FC (x + 1) | abs (Cpd − DMSO) | L₂abs (Cpd − DMSO) |
|---|---|---|---|---|---|---|---|---|---|---|
| DDX39B | AB209217 | 66 | 45 | 1.0000 | 0.4220 | 0.6906 | −0.534 | 1.45 | 21 | 4.38 |
| DDX39B | AK127767 | 25 | 61 | 0.7495 | 0.1081 | 2.3329 | 1.222 | 2.33 | 35 | 5.14 |
| DDX39B | AK127767 | 3 | 0 | 0.8226 | 0.1302 | 0.2510 | −1.995 | 3.98 | 3 | 1.58 |
| DDX39B | AK127767 | 131 | 77 | 0.8311 | 0.1328 | 0.5939 | −0.752 | 1.68 | 53 | 5.74 |
| DDX39B | AK127767 | 140 | 169 | 1.0000 | 0.4572 | 1.2051 | 0.269 | 1.21 | 29 | 4.85 |
| DDX39B | AK294939 | 12 | 18 | 1.0000 | 0.6212 | 1.4393 | 0.525 | 1.44 | 6 | 2.55 |
| DDX39B | AK295634 | 18 | 16 | 1.0000 | 0.9282 | 0.9282 | −0.107 | 1.08 | 1 | 0.43 |
| DDX39B | AK316469 | 7 | 0 | 0.4336 | 0.0310 | 0.1239 | −3.013 | 8.07 | 7 | 2.82 |
| DDX39B | AK316469 | 0 | 4 | 0.4941 | 0.0403 | 5.0998 | 2.350 | 5.10 | 4 | 2.04 |
| DDX39B | AK316469 | 6 | 0 | 0.5204 | 0.0445 | 0.1467 | −2.770 | 6.82 | 6 | 2.54 |
| DDX39B | NM_004640 | 1855 | 1582 | 0.7433 | 0.1069 | 0.8529 | −0.230 | 1.17 | 273 | 8.09 |
| DDX39B | NM_080598 | 168 | 0 | 0.0000 | 0.0000 | 0.0059 | −7.400 | 168.95 | 168 | 7.39 |
| DDX39B | NM_080598 | 202 | 575 | 0.0000 | 0.0000 | 2.8400 | 1.506 | 2.84 | 373 | 8.54 |
| DDX39B | NM_080598 | 413 | 243 | 0.4470 | 0.0330 | 0.5880 | −0.766 | 1.70 | 171 | 7.42 |
| DDX39B | NM_080598 | 555 | 678 | 0.8600 | 0.1459 | 1.2217 | 0.289 | 1.22 | 123 | 6.94 |
| DDX39B | NM_080598 | 6 | 2 | 1.0000 | 0.4433 | 0.4499 | −1.152 | 2.22 | 4 | 1.89 |
| DDX39B | NR_037852 | 24 | 30 | 1.0000 | 0.6285 | 1.2611 | 0.335 | 1.26 | 6 | 2.69 |
| DDX39B | NR_037852 | 0 | 0 | 9999 | 9999 | 1.0000 | 0.000 | 1.00 | 0 | 0 |
| DDX39B | NR_037852 | 0 | 0 | 9999 | 9999 | 1.0000 | 0.000 | 1.00 | 0 | 0 |
| DDX39B | NR_037853 | 877 | 918 | 1.0000 | 0.7759 | 1.0469 | 0.066 | 1.05 | 41 | 5.36 |
| DENND1A | AB046828 | 12 | 3 | 1.0000 | 0.2249 | 0.2977 | −1.748 | 3.36 | 9 | 3.14 |
| DENND1A | AK295710 | 0 | 0 | 9999 | 9999 | 1.0000 | 0.000 | 1.00 | 0 | 0 |
| DENND1A | AK299867 | 8 | 4 | 1.0000 | 0.5949 | 0.5884 | −0.765 | 1.70 | 4 | 1.84 |
| DENND1A | BC009616 | 0 | 0 | 9999 | 9999 | 1.0000 | 0.000 | 1.00 | 0 | 0 |
| DENND1A | BC028061 | 4 | 3 | 1.0000 | 0.9485 | 0.8620 | −0.214 | 1.16 | 1 | −0.51 |
| DENND1A | BC113037 | 0 | 4 | 0.5204 | 0.0449 | 4.7722 | 2.255 | 4.77 | 4 | 1.92 |
| DENND1A | NM_020946 | 347 | 136 | 0.0074 | 0.0001 | 0.3943 | −1.343 | 2.54 | 211 | 7.72 |
| DENND1A | NM_024820 | 183 | 92 | 0.3987 | 0.0264 | 0.5055 | −0.984 | 1.98 | 91 | 6.51 |
| DGCR2 | CR936871 | 16 | 10 | 1.0000 | 0.5606 | 0.6373 | −0.650 | 1.57 | 6 | 2.59 |
| DGCR2 | NM_001173533 | 0 | 24 | 0.0122 | 0.0002 | 25.3479 | 4.664 | 25.35 | 24 | 4.61 |
| DGCR2 | NM_001173534 | 61 | 0 | 0.0000 | 0.0000 | 0.0160 | −5.963 | 62.38 | 61 | 5.94 |
| DGCR2 | NM_001184781 | 391 | 316 | 1.0000 | 0.2566 | 0.8084 | −0.307 | 1.24 | 75 | 6.23 |
| DGCR2 | NM_005137 | 2056 | 1798 | 0.9208 | 0.1713 | 0.8746 | −0.193 | 1.14 | 258 | 8.01 |
| DGCR2 | NR_033674 | 66 | 87 | 1.0000 | 0.4724 | 1.3101 | 0.390 | 1.31 | 21 | 4.38 |
| DKFZp434M1735 | BC056905 | 93 | 4 | 0.0001 | 0.0000 | 0.0545 | −4.197 | 18.34 | 89 | 6.47 |
| DKK3 | AK295441 | 15 | 27 | 1.0000 | 0.4915 | 1.7622 | 0.817 | 1.76 | 12 | 3.58 |
| DKK3 | AK295539 | 268 | 223 | 1.0000 | 0.4501 | 0.8324 | −0.265 | 1.20 | 45 | 5.49 |
| DKK3 | NM_001018057 | 20244 | 19710 | 1.0000 | 0.7254 | 0.9737 | −0.039 | 1.03 | 533 | 9.06 |
| DKK3 | NM_013253 | 760 | 351 | 0.0002 | 0.0000 | 0.4633 | −1.110 | 2.16 | 408 | 8.67 |
| DKK3 | NM_015881 | 281 | 164 | 0.4402 | 0.0318 | 0.5867 | −0.769 | 1.70 | 116 | 6.86 |
| DNM2 | AB209213 | 9 | 12 | 1.0000 | 0.7218 | 1.3391 | 0.421 | 1.34 | 3 | 1.73 |
| DNM2 | AK097967 | 159 | 134 | 1.0000 | 0.5832 | 0.8462 | −0.241 | 1.18 | 25 | 4.62 |
| DNM2 | AK097989 | 16 | 19 | 1.0000 | 0.8716 | 1.1685 | 0.225 | 1.17 | 3 | 1.54 |
| DNM2 | AK127033 | 4 | 0 | 1.0000 | 0.2373 | 0.2724 | −1.876 | 3.67 | 4 | 1.84 |
| DNM2 | AK295929 | 0 | 71 | 0.0000 | 0.0000 | 72.1743 | 6.173 | 72.17 | 71 | 6.15 |
| DNM2 | NM_001005360 | 143 | 11 | 0.0000 | 0.0000 | 0.0830 | −3.591 | 12.05 | 132 | 7.05 |
| DNM2 | NM_001005361 | 47 | 30 | 1.0000 | 0.5675 | 0.6521 | −0.617 | 1.53 | 17 | 4.05 |
| DNM2 | NM_001005362 | 407 | 455 | 1.0000 | 0.5093 | 1.1161 | 0.158 | 1.12 | 47 | 5.57 |
| DNM2 | NM_001190716 | 718 | 663 | 1.0000 | 0.5596 | 0.9234 | −0.115 | 1.08 | 55 | 5.78 |
| DNM2 | NM_004945 | 2052 | 2022 | 1.0000 | 0.8747 | 0.9856 | −0.021 | 1.01 | 30 | 4.89 |
| DST | AF400227 | 1926 | 2848 | 0.0017 | 0.0000 | 1.4785 | 0.564 | 1.48 | 922 | 9.85 |
| DST | AK023487 | 52 | 85 | 1.0000 | 0.2597 | 1.6338 | 0.708 | 1.63 | 33 | 5.07 |
| DST | AK025142 | 19 | 35 | 1.0000 | 0.3324 | 1.7847 | 0.836 | 1.78 | 16 | 4.00 |
| DST | AK056797 | 26 | 23 | 1.0000 | 0.8483 | 0.8940 | −0.162 | 1.12 | 3 | 1.50 |
| DST | AK294830 | 0 | 3 | 0.5205 | 0.0452 | 4.4761 | 2.162 | 4.48 | 3 | 1.80 |
| DST | AK295864 | 39 | 67 | 1.0000 | 0.3042 | 1.6875 | 0.755 | 1.69 | 28 | 4.79 |
| DST | BC004912 | 54 | 2 | 0.0022 | 0.0000 | 0.0491 | −4.347 | 20.35 | 52 | 5.71 |
| DST | BC016991 | 8 | 67 | 0.0525 | 0.0012 | 7.2807 | 2.864 | 7.28 | 58 | 5.86 |
| DST | BC065536 | 11 | 14 | 1.0000 | 0.7925 | 1.2274 | 0.296 | 1.23 | 3 | 1.45 |
| DST | NM_001144769 | 4370 | 5847 | 0.0076 | 0.0001 | 1.3379 | 0.420 | 1.34 | 1477 | 10.53 |
| DST | NM_001144770 | 796 | 1045 | 0.4336 | 0.0309 | 1.3129 | 0.393 | 1.31 | 249 | 7.96 |
| DST | NM_001723 | 57 | 79 | 1.0000 | 0.4615 | 1.3863 | 0.471 | 1.39 | 22 | 4.48 |
| DST | NM_015548 | 2167 | 2316 | 1.0000 | 0.4647 | 1.0687 | 0.096 | 1.07 | 149 | 7.22 |
| DST | NM_183380 | 944 | 1405 | 0.0304 | 0.0006 | 1.4875 | 0.573 | 1.49 | 461 | 8.85 |
| EEF1A1 | AK058082 | 2 | 0 | 0.8810 | 0.1542 | 0.3296 | −1.601 | 3.03 | 2 | 1.02 |
| EEF1A1 | AY043301 | 1798 | 3795 | 0.0000 | 0.0000 | 2.1101 | 1.077 | 2.11 | 1997 | 10.96 |
| EEF1A1 | BC070131 | 27019 | 28941 | 1.0000 | 0.2864 | 1.0711 | 0.099 | 1.07 | 1922 | 10.91 |
| EEF1A1 | BC070500 | 748 | 810 | 1.0000 | 0.5293 | 1.0818 | 0.113 | 1.08 | 61 | 5.94 |
| EEF1A1 | NM_001402 | 345479 | 339076 | 1.0000 | 0.8374 | 0.9815 | −0.027 | 1.02 | 6403 | 12.64 |
| EFCAB14 | AK295722 | 139 | 352 | 0.0077 | 0.0001 | 2.5310 | 1.340 | 2.53 | 214 | 7.74 |
| EFCAB14 | AK296777 | 259 | 313 | 1.0000 | 0.3570 | 1.2096 | 0.274 | 1.21 | 54 | 5.77 |
| EFCAB14 | NM_014774 | 2157 | 2077 | 1.0000 | 0.6722 | 0.9631 | −0.054 | 1.04 | 80 | 6.32 |
| EHMT2 | AB209433 | 23 | 76 | 0.4019 | 0.0267 | 3.2208 | 1.687 | 3.22 | 53 | 5.74 |
| EHMT2 | AB209433 | 88 | 37 | 0.7140 | 0.0992 | 0.4253 | −1.233 | 2.35 | 51 | 5.67 |

TABLE 11-continued

RNA Abundance Modulation

| Gene | Trx_ID | ave DMSO | ave Cpd | padj (q val, FDR) | ttest (p val) | FC (x + 1) | L₂FC (x + 1) | amp FC (x + 1) | abs (Cpd − DMSO) | L₂abs (Cpd − DMSO) |
|---|---|---|---|---|---|---|---|---|---|---|
| EHMT2 | AK056936 | 2 | 2 | 1.0000 | 0.9164 | 1.1677 | 0.224 | 1.17 | 0 | −1.24 |
| EHMT2 | AK092866 | 2 | 2 | 1.0000 | 1.0000 | 1.0272 | 0.039 | 1.03 | 0 | −3.62 |
| EHMT2 | AK092866 | 2 | 2 | 1.0000 | 1.0000 | 1.0272 | 0.039 | 1.03 | 0 | −3.62 |
| EHMT2 | AK092866 | 2 | 2 | 1.0000 | 1.0000 | 1.0272 | 0.039 | 1.03 | 0 | −3.62 |
| EHMT2 | AK092866 | 2 | 2 | 1.0000 | 1.0000 | 1.0272 | 0.039 | 1.03 | 0 | −3.62 |
| EHMT2 | AK092866 | 2 | 2 | 1.0000 | 1.0000 | 1.0272 | 0.039 | 1.03 | 0 | −3.62 |
| EHMT2 | AK302904 | 37 | 37 | 1.0000 | 0.9631 | 1.0193 | 0.028 | 1.02 | 1 | −0.46 |
| EHMT2 | NM_006709 | 237 | 64 | 0.0048 | 0.0001 | 0.2746 | −1.864 | 3.64 | 173 | 7.43 |
| EHMT2 | NM_006709 | 120 | 110 | 1.0000 | 0.7159 | 0.9201 | −0.120 | 1.09 | 10 | 3.27 |
| EHMT2 | NM_025256 | 647 | 617 | 1.0000 | 0.7521 | 0.9537 | −0.068 | 1.05 | 30 | 4.91 |
| EIF4G1 | AB210013 | 83 | 38 | 0.7363 | 0.1055 | 0.4687 | −1.093 | 2.13 | 45 | 5.48 |
| EIF4G1 | AF002815 | 10 | 11 | 1.0000 | 0.8465 | 1.1644 | 0.220 | 1.16 | 2 | 0.81 |
| EIF4G1 | AK096719 | 36 | 230 | 0.0000 | 0.0000 | 6.2486 | 2.644 | 6.25 | 194 | 7.60 |
| EIF4G1 | AK128378 | 71 | 341 | 0.0000 | 0.0000 | 4.7608 | 2.251 | 4.76 | 271 | 8.08 |
| EIF4G1 | AK226160 | 1108 | 1098 | 1.0000 | 0.9624 | 0.9903 | −0.014 | 1.01 | 11 | 3.42 |
| EIF4G1 | BC065256 | 331 | 332 | 1.0000 | 0.9668 | 1.0035 | 0.005 | 1.00 | 1 | 0.21 |
| EIF4G1 | NM_001194946 | 0 | 5 | 0.3987 | 0.0264 | 6.4664 | 2.693 | 6.47 | 5 | 2.45 |
| EIF4G1 | NM_001194947 | 26 | 14 | 1.0000 | 0.3499 | 0.5532 | −0.854 | 1.81 | 12 | 3.57 |
| EIF4G1 | NM_004953 | 85 | 98 | 1.0000 | 0.7228 | 1.1469 | 0.198 | 1.15 | 13 | 3.66 |
| EIF4G1 | NM_182917 | 3648 | 3672 | 1.0000 | 0.8743 | 1.0066 | 0.010 | 1.01 | 24 | 4.60 |
| EIF4G1 | NM_198241 | 7974 | 5531 | 0.0001 | 0.0000 | 0.6936 | −0.528 | 1.44 | 2443 | 11.25 |
| EIF4G1 | NM_198242 | 3371 | 2219 | 0.0002 | 0.0000 | 0.6584 | −0.603 | 1.52 | 1152 | 10.17 |
| EIF4G1 | NM_198244 | 2883 | 4717 | 0.0000 | 0.0000 | 1.6361 | 0.710 | 1.64 | 1835 | 10.84 |
| EIF4G2 | AK123338 | 16 | 0 | 0.1014 | 0.0030 | 0.0576 | −4.119 | 17.37 | 16 | 4.03 |
| EIF4G2 | AK302886 | 850 | 1979 | 0.0000 | 0.0000 | 2.3272 | 1.219 | 2.33 | 1129 | 10.14 |
| EIF4G2 | NM_001042559 | 5884 | 6640 | 0.7143 | 0.0992 | 1.1284 | 0.174 | 1.13 | 756 | 9.56 |
| EIF4G2 | NM_001172705 | 16 | 62 | 0.4021 | 0.0268 | 3.6845 | 1.881 | 3.68 | 46 | 5.51 |
| EIF4G2 | NM_001418 | 41570 | 41658 | 1.0000 | 0.9921 | 1.0021 | 0.003 | 1.00 | 88 | 6.47 |
| EIF4G3 | AK294883 | 329 | 70 | 0.0000 | 0.0000 | 0.2149 | −2.218 | 4.65 | 259 | 8.02 |
| EIF4G3 | AK302087 | 136 | 85 | 0.9768 | 0.1938 | 0.6264 | −0.675 | 1.60 | 51 | 5.67 |
| EIF4G3 | BC094683 | 0 | 15 | 0.0753 | 0.0019 | 15.7184 | 3.974 | 15.72 | 15 | 3.88 |
| EIF4G3 | BC144335 | 1363 | 1701 | 0.4297 | 0.0304 | 1.2480 | 0.320 | 1.25 | 338 | 8.40 |
| EIF4G3 | NM_001198801 | 872 | 1126 | 0.4206 | 0.0288 | 1.2907 | 0.368 | 1.29 | 254 | 7.99 |
| EIF4G3 | NM_001198802 | 120 | 160 | 1.0000 | 0.4400 | 1.3263 | 0.407 | 1.33 | 40 | 5.31 |
| EIF4G3 | NM_001198803 | 37 | 50 | 1.0000 | 0.4884 | 1.3623 | 0.446 | 1.36 | 14 | 3.77 |
| EIF4G3 | NM_003760 | 845 | 799 | 1.0000 | 0.7207 | 0.9459 | −0.080 | 1.06 | 46 | 5.52 |
| ENSA | CR749580 | 10 | 15 | 1.0000 | 0.6929 | 1.4783 | 0.564 | 1.48 | 5 | 2.41 |
| ENSA | EU832387 | 18 | 15 | 1.0000 | 0.8439 | 0.8371 | −0.256 | 1.19 | 3 | 1.62 |
| ENSA | NM_004436 | 1209 | 1155 | 1.0000 | 0.6697 | 0.9554 | −0.066 | 1.05 | 54 | 5.75 |
| ENSA | NM_207042 | 37 | 35 | 1.0000 | 0.9392 | 0.9438 | −0.083 | 1.06 | 2 | 1.08 |
| ENSA | NM_207043 | 1 | 9 | 0.8875 | 0.1597 | 4.4312 | 2.148 | 4.43 | 8 | 2.94 |
| ENSA | NM_207044 | 1221 | 1443 | 0.7870 | 0.1186 | 1.1810 | 0.240 | 1.18 | 221 | 7.79 |
| ENSA | NM_207045 | 0 | 9 | 0.2262 | 0.0101 | 9.8829 | 3.305 | 9.88 | 9 | 3.15 |
| ENSA | NM_207046 | 39 | 42 | 1.0000 | 0.8146 | 1.0736 | 0.102 | 1.07 | 3 | 1.57 |
| ENSA | NM_207047 | 72 | 0 | 0.0000 | 0.0000 | 0.0137 | −6.192 | 73.10 | 72 | 6.17 |
| ENSA | NM_207168 | 87 | 108 | 1.0000 | 0.5880 | 1.2400 | 0.310 | 1.24 | 21 | 4.40 |
| EXO1 | AK291291 | 392 | 276 | 0.6583 | 0.0779 | 0.7045 | −0.505 | 1.42 | 116 | 6.86 |
| EXO1 | NM_006027 | 62 | 306 | 0.0000 | 0.0000 | 4.8786 | 2.286 | 4.88 | 244 | 7.93 |
| EXO1 | NM_130398 | 388 | 512 | 0.6950 | 0.0895 | 1.3194 | 0.400 | 1.32 | 124 | 6.96 |
| FAM111A | AX747422 | 115 | 137 | 1.0000 | 0.5981 | 1.1895 | 0.250 | 1.19 | 22 | 4.46 |
| FAM111A | NM_001142519 | 232 | 319 | 1.0000 | 0.2190 | 1.3753 | 0.460 | 1.38 | 87 | 6.45 |
| FAM111A | NM_001142520 | 347 | 275 | 1.0000 | 0.3315 | 0.7944 | −0.332 | 1.26 | 71 | 6.16 |
| FAM111A | NM_001142521 | 10 | 15 | 1.0000 | 0.7771 | 1.3743 | 0.459 | 1.37 | 4 | 2.10 |
| FAM111A | NM_022074 | 346 | 702 | 0.0010 | 0.0000 | 2.0271 | 1.019 | 2.03 | 356 | 8.48 |
| FAM111A | NM_198847 | 631 | 720 | 1.0000 | 0.3246 | 1.1402 | 0.189 | 1.14 | 89 | 6.47 |
| FAM198B | AK172805 | 1 | 2 | 1.0000 | 0.7116 | 1.5232 | 0.607 | 1.52 | 1 | 0.05 |
| FAM198B | NM_001031700 | 0 | 0 | 9999 | 9999 | 1.0000 | 0.000 | 1.00 | 0 | 0 |
| FAM198B | NM_001128424 | 77 | 0 | 0.0000 | 0.0000 | 0.0172 | −5.864 | 58.23 | 77 | 6.26 |
| FAM198B | NM_016613 | 318 | 357 | 1.0000 | 0.4894 | 1.1243 | 0.169 | 1.12 | 40 | 5.31 |
| FAM65A | AB067517 | 401 | 159 | 0.0023 | 0.0000 | 0.3973 | −1.332 | 2.52 | 242 | 7.92 |
| FAM65A | AK097087 | 19 | 15 | 1.0000 | 0.8138 | 0.8236 | −0.280 | 1.21 | 3 | 1.79 |
| FAM65A | AK307467 | 197 | 235 | 1.0000 | 0.4946 | 1.1920 | 0.253 | 1.19 | 38 | 5.25 |
| FAM65A | BC021284 | 232 | 280 | 1.0000 | 0.3482 | 1.2068 | 0.271 | 1.21 | 48 | 5.59 |
| FAM65A | NM_001193522 | 165 | 174 | 1.0000 | 0.7169 | 1.0527 | 0.074 | 1.05 | 9 | 3.13 |
| FAM65A | NM_001193523 | 61 | 15 | 0.3742 | 0.0232 | 0.2605 | −1.941 | 3.84 | 46 | 5.52 |
| FAM65A | NM_001193524 | 50 | 55 | 1.0000 | 0.8991 | 1.0991 | 0.136 | 1.10 | 5 | 2.35 |
| FAM65A | NM_024519 | 2071 | 1900 | 1.0000 | 0.3864 | 0.9178 | −0.124 | 1.09 | 170 | 7.41 |
| FBXO34 | BX648092 | 1 | 2 | 1.0000 | 0.7111 | 1.5677 | 0.649 | 1.57 | 1 | 0.12 |
| FBXO34 | CCDS32086 | 98 | 112 | 1.0000 | 0.6310 | 1.1388 | 0.188 | 1.14 | 14 | 3.78 |
| FBXO34 | NM_017943 | 470 | 235 | 0.0190 | 0.0003 | 0.5017 | −0.995 | 1.99 | 235 | 7.87 |
| FBXO34 | NM_152231 | 209 | 517 | 0.0004 | 0.0000 | 2.4630 | 1.300 | 2.46 | 308 | 8.27 |
| FEZ1 | AK296554 | 0 | 3 | 0.5441 | 0.0499 | 4.4254 | 2.146 | 4.43 | 3 | 1.78 |
| FEZ1 | CCDS44758 | 5 | 16 | 1.0000 | 0.2278 | 3.1246 | 1.644 | 3.12 | 12 | 3.57 |
| FEZ1 | NM_005103 | 260 | 427 | 0.2354 | 0.0108 | 1.6381 | 0.712 | 1.64 | 167 | 7.38 |

TABLE 11-continued

RNA Abundance Modulation

| Gene | Trx_ID | ave DMSO | ave Cpd | padj (q val, FDR) | ttest (p val) | FC (x + 1) | L₂FC (x + 1) | amp FC (x + 1) | abs (Cpd − DMSO) | L₂abs (Cpd − DMSO) |
|---|---|---|---|---|---|---|---|---|---|---|
| FEZ1 | NM_022549 | 69 | 2 | 0.0004 | 0.0000 | 0.0430 | −4.539 | 23.25 | 67 | 6.06 |
| FGD5-AS1 | BC033386 | 2 | 2 | 1.0000 | 1.0000 | 0.9370 | −0.094 | 1.07 | 0 | −2.48 |
| FGD5-AS1 | NR_046251 | 407 | 322 | 1.0000 | 0.2333 | 0.7922 | −0.336 | 1.26 | 85 | 6.40 |
| FGD5-AS1 | NR_046252 | 2945 | 2929 | 1.0000 | 0.9341 | 0.9948 | −0.008 | 1.01 | 15 | 3.95 |
| FGD5-AS1 | NR_046253 | 128 | 89 | 1.0000 | 0.3055 | 0.7015 | −0.512 | 1.43 | 38 | 5.26 |
| FGD5-AS1 | NR_046254 | 567 | 315 | 0.0355 | 0.0007 | 0.5559 | −0.847 | 1.80 | 252 | 7.98 |
| FGD5-AS1 | NR_046255 | 402 | 925 | 1.0000 | 0.0000 | 2.2983 | 1.201 | 2.30 | 523 | 9.03 |
| FGFRL1 | AK314365 | 40 | 53 | 1.0000 | 0.7007 | 1.3149 | 0.395 | 1.31 | 13 | 3.69 |
| FGFRL1 | BC036769 | 39 | 16 | 0.9539 | 0.1853 | 0.4271 | −1.227 | 2.34 | 23 | 4.52 |
| FGFRL1 | NM_001004356 | 465 | 158 | 0.0000 | 0.0000 | 0.3420 | −1.548 | 2.92 | 306 | 8.26 |
| FGFRL1 | NM_001004358 | 5550 | 4782 | 0.6226 | 0.0654 | 0.8617 | −0.215 | 1.16 | 767 | 9.58 |
| FLII | AK295814 | 5 | 20 | 0.8411 | 0.1376 | 3.5696 | 1.836 | 3.57 | 15 | 3.92 |
| FLII | BC021885 | 3372 | 3578 | 1.0000 | 0.4660 | 1.0612 | 0.086 | 1.06 | 206 | 7.69 |
| FLII | NM_001256264 | 152 | 0 | 0.0000 | 0.0000 | 0.0065 | −7.255 | 152.79 | 152 | 7.25 |
| FLII | NM_001256265 | 14 | 20 | 1.0000 | 0.7207 | 1.4076 | 0.493 | 1.41 | 6 | 2.60 |
| FLII | NM_002018 | 3651 | 2941 | 0.2640 | 0.0130 | 0.8056 | −0.312 | 1.24 | 710 | 9.47 |
| FN1 | AB385106 | 216204 | 222513 | 1.0000 | 0.6552 | 1.0292 | 0.041 | 1.03 | 6309 | 12.62 |
| FN1 | AJ320525 | 153 | 53 | 0.1483 | 0.0053 | 0.3488 | −1.520 | 2.87 | 101 | 6.65 |
| FN1 | AJ320526 | 35 | 19 | 1.0000 | 0.4239 | 0.5639 | −0.826 | 1.77 | 16 | 3.96 |
| FN1 | AJ320527 | 5886 | 3336 | 0.0000 | 0.0000 | 0.5669 | −0.819 | 1.76 | 2550 | 11.32 |
| FN1 | AK300246 | 9288 | 0 | 0.0000 | 0.0000 | 0.0001 | 13.181 | 9289.22 | 9288 | 13.18 |
| FN1 | BC143754 | 52427 | 56111 | 1.0000 | 0.2405 | 1.0703 | 0.098 | 1.07 | 3685 | 11.85 |
| FN1 | BX537590 | 91038 | 101984 | 0.6664 | 0.0810 | 1.1202 | 0.164 | 1.12 | 10946 | 13.42 |
| FN1 | BX641150 | 14772 | 14944 | 1.0000 | 0.8383 | 1.0117 | 0.017 | 1.01 | 172 | 7.43 |
| FN1 | CR749316 | 2645 | 2365 | 1.0000 | 0.2434 | 0.8941 | −0.162 | 1.12 | 280 | 8.13 |
| FN1 | EF550133 | 36974 | 39644 | 1.0000 | 0.2601 | 1.0722 | 0.101 | 1.07 | 2670 | 11.38 |
| FN1 | EF550135 | 125 | 121 | 1.0000 | 0.9043 | 0.9705 | −0.043 | 1.03 | 4 | 1.90 |
| FN1 | NM_002026 | 560801 | 534565 | 1.0000 | 0.6707 | 0.9532 | −0.069 | 1.05 | 26235 | 14.68 |
| FN1 | NM_054034 | 5998 | 4288 | 0.0021 | 0.0000 | 0.7149 | −0.484 | 1.40 | 1710 | 10.74 |
| FN1 | NM_212474 | 17340 | 13197 | 0.0048 | 0.0001 | 0.7611 | −0.394 | 1.31 | 4142 | 12.02 |
| FN1 | NM_212476 | 325543 | 318200 | 1.0000 | 0.8589 | 0.9774 | −0.033 | 1.02 | 7343 | 12.84 |
| FN1 | NM_212478 | 145082 | 143669 | 1.0000 | 0.9579 | 0.9903 | −0.014 | 1.01 | 1412 | 10.46 |
| FN1 | NM_212482 | 134310 | 142310 | 1.0000 | 0.3769 | 1.0596 | 0.083 | 1.06 | 7999 | 12.97 |
| FOXK1 | AX721089 | 8 | 8 | 1.0000 | 0.9694 | 1.0209 | 0.030 | 1.02 | 0 | −2.43 |
| FOXK1 | BC038434 | 771 | 376 | 0.0005 | 0.0000 | 0.4885 | −1.034 | 2.05 | 395 | 8.62 |
| FOXK1 | NM_001037165 | 791 | 1006 | 0.4941 | 0.0399 | 1.2706 | 0.345 | 1.27 | 214 | 7.74 |
| FOXM1 | NM_001243088 | 1061 | 1053 | 1.0000 | 0.8545 | 0.9927 | −0.011 | 1.01 | 8 | 2.95 |
| FOXM1 | NM_001243089 | 485 | 400 | 1.0000 | 0.4454 | 0.8240 | −0.279 | 1.21 | 86 | 6.42 |
| FOXM1 | NM_021953 | 4923 | 3498 | 0.0015 | 0.0000 | 0.7105 | −0.493 | 1.41 | 1426 | 10.48 |
| FOXM1 | NM_202002 | 560 | 2348 | 0.0000 | 0.0000 | 4.1865 | 2.066 | 4.19 | 1788 | 10.80 |
| FUS | AJ549096 | 1233 | 1078 | 1.0000 | 0.2323 | 0.8743 | −0.194 | 1.14 | 155 | 7.28 |
| FUS | AK301110 | 89 | 64 | 1.0000 | 0.4304 | 0.7236 | −0.467 | 1.38 | 25 | 4.64 |
| FUS | NM_001170634 | 3092 | 3245 | 1.0000 | 0.5819 | 1.0494 | 0.070 | 1.05 | 153 | 7.26 |
| FUS | NM_001170937 | 94 | 0 | 0.0000 | 0.0000 | 0.0105 | −6.577 | 95.45 | 94 | 6.56 |
| FUS | NM_004960 | 6619 | 6638 | 1.0000 | 0.9729 | 1.0029 | 0.004 | 1.00 | 19 | 4.24 |
| FUS | NR_028388 | 60 | 69 | 1.0000 | 0.7801 | 1.1327 | 0.180 | 1.13 | 8 | 3.03 |
| GALC | AK302683 | 2 | 5 | 1.0000 | 0.6455 | 1.6853 | 0.753 | 1.69 | 2 | 1.24 |
| GALC | D25284 | 2 | 3 | 1.0000 | 0.7997 | 1.4405 | 0.527 | 1.44 | 1 | 0.32 |
| GALC | NM_000153 | 459 | 117 | 0.0000 | 0.0000 | 0.2576 | −1.957 | 3.88 | 341 | 8.41 |
| GALC | NM_001201401 | 0 | 1 | 1.0000 | 0.3259 | 1.6859 | 0.753 | 1.69 | 1 | −0.54 |
| GALC | NM_001201402 | 0 | 0 | 9999 | 9999 | 1.0000 | 0.000 | 1.00 | 0 | 0 |
| GALNT1 | AK293062 | 52 | 0 | 0.0000 | 0.0000 | 0.0188 | −5.736 | 53.29 | 52 | 5.71 |
| GALNT1 | BC038440 | 15 | 19 | 1.0000 | 0.7669 | 1.2959 | 0.374 | 1.30 | 5 | 2.21 |
| GALNT1 | BC047746 | 4 | 3 | 1.0000 | 0.8354 | 0.7214 | −0.471 | 1.39 | 1 | 0.50 |
| GALNT1 | NM_020474 | 2690 | 2966 | 1.0000 | 0.2766 | 1.1022 | 0.140 | 1.10 | 275 | 8.10 |
| GAS7 | AK293755 | 0 | 0 | 9999 | 9999 | 1.0000 | 0.000 | 1.00 | 0 | 0 |
| GAS7 | AK294829 | 151 | 313 | 0.1132 | 0.0035 | 2.0577 | 1.041 | 2.06 | 161 | 7.33 |
| GAS7 | NM_003644 | 61 | 0 | 0.0000 | 0.0000 | 0.0163 | −5.943 | 61.50 | 61 | 5.92 |
| GAS7 | NM_201433 | 867 | 729 | 1.0000 | 0.2339 | 0.8411 | −0.250 | 1.19 | 138 | 7.11 |
| GCFC2 | EF158468 | 0 | 18 | 0.0361 | 0.0007 | 19.0638 | 4.253 | 19.06 | 18 | 4.18 |
| GCFC2 | EF158469 | 0 | 28 | 0.0049 | 0.0001 | 29.0498 | 4.860 | 29.05 | 28 | 4.81 |
| GCFC2 | NM_001201334 | 116 | 150 | 1.0000 | 0.3828 | 1.2894 | 0.367 | 1.29 | 34 | 5.08 |
| GCFC2 | NM_001201335 | 42 | 35 | 1.0000 | 0.7675 | 0.8422 | −0.248 | 1.19 | 7 | 2.77 |
| GCFC2 | NM_003203 | 103 | 8 | 0.0004 | 0.0000 | 0.0844 | −3.567 | 11.85 | 96 | 6.58 |
| GGCT | AK021779 | 3 | 4 | 1.0000 | 0.7960 | 1.3088 | 0.388 | 1.31 | 1 | 0.29 |
| GGCT | NM_001199815 | 2 | 3 | 1.0000 | 0.9387 | 1.1553 | 0.208 | 1.16 | 1 | −0.90 |
| GGCT | NM_001199816 | 14 | 27 | 1.0000 | 0.3643 | 1.8841 | 0.914 | 1.88 | 13 | 3.71 |
| GGCT | NM_001199817 | 3 | 2 | 1.0000 | 0.9291 | 0.7673 | −0.382 | 1.30 | 1 | −0.11 |
| GGCT | NM_024051 | 529 | 888 | 0.0165 | 0.0003 | 1.6795 | 0.748 | 1.68 | 360 | 8.49 |
| GGCT | NR_037669 | 227 | 16 | 0.0000 | 0.0000 | 0.0758 | −3.721 | 13.19 | 211 | 7.72 |
| GJC1 | AK124339 | 34 | 90 | 0.4941 | 0.0403 | 2.6117 | 1.385 | 2.61 | 56 | 5.81 |
| GJC1 | CCDS11487 | 363 | 396 | 1.0000 | 0.5939 | 1.0920 | 0.127 | 1.09 | 33 | 5.06 |
| GJC1 | NM_001080383 | 74 | 317 | 0.0001 | 0.0000 | 4.2499 | 2.087 | 4.25 | 244 | 7.93 |
| GJC1 | NM_005497 | 1623 | 1602 | 1.0000 | 0.9637 | 0.9871 | −0.019 | 1.01 | 21 | 4.39 |

TABLE 11-continued

RNA Abundance Modulation

| Gene | Trx_ID | ave DMSO | ave Cpd | padj (q val, FDR) | ttest (p val) | FC (x + 1) | L$_2$FC (x + 1) | amp FC (x + 1) | abs (Cpd − DMSO) | L$_2$abs (Cpd − DMSO) |
|---|---|---|---|---|---|---|---|---|---|---|
| GNA13 | AK302400 | 68 | 252 | 0.0023 | 0.0000 | 3.6738 | 1.877 | 3.67 | 184 | 7.53 |
| GNA13 | NM_006572 | 2564 | 2498 | 1.0000 | 0.7653 | 0.9743 | −0.038 | 1.03 | 66 | 6.04 |
| GNL3L | BC011720 | 271 | 260 | 1.0000 | 0.8707 | 0.9569 | −0.064 | 1.05 | 12 | 3.55 |
| GNL3L | NM_001184819 | 99 | 0 | 0.0000 | 0.0000 | 0.0100 | −6.642 | 99.87 | 99 | 6.63 |
| GNL3L | NM_019067 | 618 | 783 | 0.8115 | 0.1260 | 1.2648 | 0.339 | 1.26 | 164 | 7.36 |
| GOLGA4 | AK307429 | 0 | 0 | 9999 | 9999 | 1.0000 | 0.000 | 1.00 | 0 | 0 |
| GOLGA4 | BC023648 | 31 | 37 | 1.0000 | 0.7453 | 1.1831 | 0.243 | 1.18 | 6 | 2.54 |
| GOLGA4 | NM_001172713 | 291 | 587 | 0.0062 | 0.0001 | 2.0120 | 1.009 | 2.01 | 296 | 8.21 |
| GOLGA4 | NM_002078 | 817 | 880 | 1.0000 | 0.6238 | 1.0767 | 0.107 | 1.08 | 63 | 5.97 |
| GOLGA4 | U31906 | 1073 | 1409 | 0.2187 | 0.0096 | 1.3135 | 0.393 | 1.31 | 337 | 8.39 |
| GPR1 | CCDS2368 | 193 | 192 | 1.0000 | 1.0000 | 0.9940 | −0.009 | 1.01 | 1 | 0.22 |
| GPR1 | NM_001098199 | 4 | 0 | 0.6590 | 0.0785 | 0.2001 | −2.321 | 5.00 | 4 | 2.00 |
| GPR1 | NM_001261454 | 150 | 0 | 0.0000 | 0.0000 | 0.0066 | −7.238 | 150.96 | 150 | 7.23 |
| GPR1 | NM_001261455 | 668 | 856 | 0.5482 | 0.0506 | 1.2815 | 0.358 | 1.28 | 188 | 7.56 |
| GPR1 | NM_005279 | 0 | 0 | 9999 | 9999 | 1.0000 | 0.000 | 1.00 | 0 | 0 |
| GREM1 | CCDS10029 | 629 | 233 | 0.0000 | 0.0000 | 0.3715 | −1.429 | 2.69 | 396 | 8.63 |
| GREM1 | NM_001191322 | 13298 | 38145 | 0.0000 | 0.0000 | 2.8683 | 1.520 | 2.87 | 24846 | 14.60 |
| GREM1 | NM_001191323 | 2798 | 1930 | 0.0039 | 0.0000 | 0.6898 | −0.536 | 1.45 | 868 | 9.76 |
| GREM1 | NM_013372 | 152286 | 138765 | 0.9894 | 0.1984 | 0.9112 | −0.134 | 1.10 | 13521 | 13.72 |
| HEG1 | AB384586 | 15074 | 15725 | 1.0000 | 0.4922 | 1.0431 | 0.061 | 1.04 | 650 | 9.35 |
| HEG1 | AK074987 | 415 | 155 | 0.0006 | 0.0000 | 0.3748 | −1.416 | 2.67 | 260 | 8.02 |
| HEG1 | NM_020733 | 813 | 1213 | 0.0604 | 0.0015 | 1.4906 | 0.576 | 1.49 | 400 | 8.64 |
| HLA-A | AF287958 | 13 | 0 | 0.1861 | 0.0074 | 0.0693 | −3.851 | 14.43 | 13 | 3.75 |
| HLA-A | AF287958 | 21 | 7 | 1.0000 | 0.2443 | 0.3559 | −1.490 | 2.81 | 14 | 3.80 |
| HLA-A | AF287958 | 3 | 5 | 1.0000 | 0.6651 | 1.5000 | 0.585 | 1.50 | 2 | 1.01 |
| HLA-A | AF287958 | 6 | 3 | 1.0000 | 0.6580 | 0.6130 | −0.706 | 1.63 | 3 | 1.42 |
| HLA-A | AF287958 | 1 | 0 | 1.0000 | 0.2791 | 0.4484 | −1.157 | 2.23 | 1 | 0.30 |
| HLA-A | AF287958 | 1 | 0 | 1.0000 | 0.6668 | 0.6191 | −0.692 | 1.62 | 1 | −0.70 |
| HLA-A | AK125608 | 0 | 0 | 1.0000 | 0.4944 | 1.3160 | 0.396 | 1.32 | 0 | −1.66 |
| HLA-A | AK125608 | 65 | 68 | 1.0000 | 0.9127 | 1.0443 | 0.062 | 1.04 | 3 | 1.56 |
| HLA-A | AK125608 | 0 | 0 | 1.0000 | 0.4944 | 1.3160 | 0.396 | 1.32 | 0 | −1.66 |
| HLA-A | AK125608 | 1 | 0 | 1.0000 | 0.6668 | 0.6213 | −0.687 | 1.61 | 1 | −0.71 |
| HLA-A | AK125608 | 119 | 111 | 1.0000 | 0.8413 | 0.9313 | −0.103 | 1.07 | 8 | 3.04 |
| HLA-A | AK296091 | 78 | 626 | 0.0000 | 0.0000 | 7.9804 | 2.996 | 7.98 | 549 | 9.10 |
| HLA-A | AK296091 | 2 | 6 | 1.0000 | 0.4262 | 2.2705 | 1.183 | 2.27 | 4 | 1.89 |
| HLA-A | AK301014 | 1 | 0 | 1.0000 | 0.5202 | 0.4719 | −1.084 | 2.12 | 1 | 0.16 |
| HLA-A | AK301019 | 1 | 33 | 0.0428 | 0.0009 | 15.5320 | 3.957 | 15.53 | 32 | 5.01 |
| HLA-A | AK301019 | 0 | 0 | 1.0000 | 1.0000 | 0.7648 | −0.387 | 1.31 | 0 | −1.70 |
| HLA-A | AK301019 | 0 | 0 | 1.0000 | 1.0000 | 0.7648 | −0.387 | 1.31 | 0 | −1.70 |
| HLA-A | AY786588 | 2 | 0 | 0.8060 | 0.1246 | 0.2890 | −1.791 | 3.46 | 2 | 1.30 |
| HLA-A | AY786588 | 18 | 16 | 1.0000 | 0.9400 | 0.8900 | −0.168 | 1.12 | 2 | 1.05 |
| HLA-A | AY787587 | 0 | 0 | 1.0000 | 1.0000 | 0.7664 | −0.384 | 1.30 | 0 | −1.71 |
| HLA-A | DQ580344 | 71 | 64 | 1.0000 | 0.8009 | 0.8959 | −0.159 | 1.12 | 8 | 2.91 |
| HLA-A | JQ313909 | 0 | 0 | 1.0000 | 0.4944 | 1.3429 | 0.425 | 1.34 | 0 | −1.54 |
| HLA-A | M27539 | 14 | 39 | 0.8875 | 0.1591 | 2.6166 | 1.388 | 2.62 | 25 | 4.64 |
| HLA-A | NM_002116 | 7881 | 6356 | 0.1088 | 0.0033 | 0.8065 | −0.310 | 1.24 | 1525 | 10.57 |
| HLA-A | NM_002116 | 3 | 0 | 0.7347 | 0.1044 | 0.2454 | −2.027 | 4.08 | 3 | 1.62 |
| HLA-A | NM_002116 | 1 | 6 | 1.0000 | 0.2404 | 3.4705 | 1.769 | 3.41 | 5 | 2.21 |
| HLA-A | NM_002116 | 3208 | 3026 | 1.0000 | 0.5299 | 0.9433 | −0.084 | 1.06 | 182 | 7.51 |
| HLA-A | NM_002116 | 1 | 1 | 1.0000 | 1.0000 | 1.0458 | 0.065 | 1.05 | 0 | −3.76 |
| HLA-A | NM_002116 | 1 | 0 | 1.0000 | 0.3131 | 0.4012 | −1.318 | 2.49 | 1 | 0.58 |
| HLA-A | NM_002116 | 0 | 0 | 9999 | 9999 | 1.0000 | 0.000 | 1.00 | 0 | 0 |
| HLA-A | Y17224 | 8 | 2 | 1.0000 | 0.2614 | 0.3278 | −1.609 | 3.05 | 6 | 2.64 |
| HLA-E | AK296822 | 240 | 72 | 0.0042 | 0.0000 | 0.3041 | −1.717 | 3.29 | 168 | 7.39 |
| HLA-E | AK296822 | 29 | 88 | 0.4247 | 0.0296 | 2.9664 | 1.569 | 2.97 | 59 | 5.88 |
| HLA-E | AK296822 | 29 | 88 | 0.4247 | 0.0296 | 2.9664 | 1.569 | 2.97 | 59 | 5.88 |
| HLA-E | AK300906 | 15 | 0 | 0.1255 | 0.0041 | 0.0610 | −4.035 | 16.39 | 15 | 3.94 |
| HLA-E | AK300906 | 15 | 0 | 0.1255 | 0.0041 | 0.0610 | −4.035 | 16.39 | 15 | 3.94 |
| HLA-E | AK300906 | 31 | 6 | 0.5278 | 0.0462 | 0.2109 | −2.245 | 4.74 | 25 | 4.65 |
| HLA-E | AK301125 | 18 | 25 | 1.0000 | 0.6455 | 1.3416 | 0.424 | 1.34 | 7 | 2.71 |
| HLA-E | AK301125 | 18 | 25 | 1.0000 | 0.6455 | 1.3416 | 0.424 | 1.34 | 7 | 2.71 |
| HLA-E | NM_005516 | 1147 | 974 | 0.9231 | 0.1731 | 0.8492 | −0.236 | 1.18 | 173 | 7.43 |
| HLA-E | NM_005516 | 1147 | 974 | 0.9231 | 0.1731 | 0.8492 | −0.236 | 1.18 | 173 | 7.43 |
| HLA-E | NM_005516 | 689 | 627 | 1.0000 | 0.6499 | 0.9105 | −0.135 | 1.10 | 62 | 5.95 |
| HLA-E | NM_005516 | 988 | 1104 | 1.0000 | 0.4072 | 1.1176 | 0.160 | 1.12 | 116 | 6.86 |
| HLTF | BC044659 | 398 | 499 | 0.8875 | 0.1596 | 1.2523 | 0.325 | 1.25 | 101 | 6.65 |
| HLTF | EU446704 | 106 | 5 | 0.0000 | 0.0000 | 0.0604 | −4.050 | 16.56 | 101 | 6.66 |
| HLTF | NM_003071 | 1202 | 876 | 0.1937 | 0.0080 | 0.7290 | −0.456 | 1.37 | 326 | 8.35 |
| HLTF | NM_139048 | 242 | 238 | 1.0000 | 0.9022 | 0.9801 | −0.029 | 1.02 | 5 | 2.27 |
| HNRNPR | AK297382 | 55 | 238 | 0.0011 | 0.0000 | 4.2987 | 2.104 | 4.30 | 183 | 7.52 |
| HNRNPR | AK297405 | 184 | 214 | 1.0000 | 0.5358 | 1.1651 | 0.220 | 1.17 | 30 | 4.93 |
| HNRNPR | AK300029 | 436 | 189 | 0.0035 | 0.0000 | 0.4344 | −1.203 | 2.30 | 247 | 7.95 |
| HNRNPR | BX538163 | 0 | 0 | 9999 | 9999 | 1.0000 | 0.000 | 1.00 | 0 | 0 |
| HNRNPR | NM_001102397 | 3725 | 4318 | 0.6400 | 0.0708 | 1.1593 | 0.213 | 1.16 | 594 | 9.21 |

TABLE 11-continued

RNA Abundance Modulation

| Gene | Trx_ID | ave DMSO | ave Cpd | padj (q val, FDR) | ttest (p val) | FC (x + 1) | $L_2$FC (x + 1) | amp FC (x + 1) | abs (Cpd − DMSO) | $L_2$abs (Cpd − DMSO) |
|---|---|---|---|---|---|---|---|---|---|---|
| HNRNPR | NM_001102398 | 448 | 402 | 1.0000 | 0.4755 | 0.8969 | −0.157 | 1.11 | 46 | 5.53 |
| HNRNPR | NM_001102399 | 1096 | 920 | 0.9226 | 0.1727 | 0.8397 | −0.252 | 1.19 | 176 | 7.46 |
| HNRNPR | NM_005826 | 1687 | 1844 | 1.0000 | 0.3982 | 1.0930 | 0.128 | 1.09 | 157 | 7.29 |
| HNRNPUL1 | AK021455 | 72 | 56 | 1.0000 | 0.5812 | 0.7847 | −0.350 | 1.27 | 16 | 3.97 |
| HNRNPUL1 | AK127057 | 48 | 65 | 1.0000 | 0.5176 | 1.3344 | 0.416 | 1.33 | 17 | 4.05 |
| HNRNPUL1 | AK297127 | 622 | 693 | 1.0000 | 0.4603 | 1.1149 | 0.157 | 1.11 | 72 | 6.16 |
| HNRNPUL1 | AK308078 | 151 | 376 | 0.0036 | 0.0000 | 2.4869 | 1.314 | 2.49 | 225 | 7.82 |
| HNRNPUL1 | AK308156 | 1785 | 2074 | 0.7167 | 0.0997 | 1.1619 | 0.216 | 1.16 | 289 | 8.18 |
| HNRNPUL1 | BC004242 | 0 | 0 | 9999 | 9999 | 1.0000 | 0.000 | 1.00 | 0 | 0 |
| HNRNPUL1 | BC014232 | 2379 | 2248 | 1.0000 | 0.6165 | 0.9450 | −0.082 | 1.06 | 131 | 7.03 |
| HNRNPUL1 | BC027713 | 15 | 53 | 0.5565 | 0.0517 | 3.4445 | 1.784 | 3.44 | 39 | 5.27 |
| HNRNPUL1 | BC129981 | 52 | 89 | 1.0000 | 0.2347 | 1.6895 | 0.757 | 1.69 | 37 | 5.19 |
| HNRNPUL1 | NM_007040 | 2621 | 2123 | 0.4021 | 0.0268 | 0.8101 | −0.304 | 1.23 | 498 | 8.96 |
| HNRNPUL1 | NM_144732 | 1521 | 1227 | 0.3260 | 0.0183 | 0.8068 | −0.310 | 1.24 | 294 | 8.20 |
| IQCE | AK293372 | 1 | 14 | 0.4774 | 0.0377 | 6.9589 | 2.799 | 6.96 | 13 | 3.66 |
| IQCE | AK302053 | 8 | 13 | 1.0000 | 0.4868 | 1.6269 | 0.702 | 1.63 | 6 | 2.47 |
| IQCE | AK309646 | 8 | 0 | 0.4342 | 0.0311 | 0.1145 | −3.126 | 8.73 | 8 | 2.95 |
| IQCE | AX747526 | 79 | 20 | 0.2082 | 0.0089 | 0.2594 | −1.947 | 3.86 | 59 | 5.88 |
| IQCE | BC043150 | 40 | 53 | 1.0000 | 0.5271 | 1.3436 | 0.426 | 1.34 | 14 | 3.80 |
| IQCE | NM_001100390 | 96 | 279 | 0.0040 | 0.0000 | 2.8735 | 1.523 | 2.87 | 182 | 7.51 |
| IQCE | NM_152558 | 517 | 293 | 0.0632 | 0.0015 | 0.5681 | −0.816 | 1.76 | 224 | 7.81 |
| ITGB5 | AK309551 | 985 | 444 | 0.0000 | 0.0000 | 0.4515 | −1.147 | 2.21 | 541 | 9.08 |
| ITGB5 | NM_002213 | 13463 | 12899 | 1.0000 | 0.5237 | 0.9581 | −0.062 | 1.04 | 564 | 9.14 |
| ITSN1 | AY340593 | 0 | 0 | 9999 | 9999 | 1.0000 | 0.000 | 1.00 | 0 | 0 |
| ITSN1 | AY603418 | 0 | 0 | 1.0000 | 1.0000 | 0.7283 | −0.457 | 1.37 | 0 | −1.42 |
| ITSN1 | AY639649 | 1 | 0 | 1.0000 | 0.6668 | 0.6213 | −0.687 | 1.61 | 1 | −0.71 |
| ITSN1 | BC116185 | 1 | 0 | 1.0000 | 0.4730 | 0.5201 | −0.943 | 1.92 | 1 | −0.12 |
| ITSN1 | DQ340865 | 25 | 0 | 0.0143 | 0.0002 | 0.0379 | −4.722 | 26.40 | 25 | 4.67 |
| ITSN1 | DQ386455 | 104 | 104 | 1.0000 | 1.0000 | 1.0006 | 0.001 | 1.00 | 0 | −3.97 |
| ITSN1 | DQ679754 | 327 | 341 | 1.0000 | 0.8793 | 1.0427 | 0.060 | 1.04 | 14 | 3.81 |
| ITSN1 | DQ679755 | 15 | 36 | 0.9741 | 0.1930 | 2.3488 | 1.232 | 2.35 | 21 | 4.41 |
| ITSN1 | DQ679756 | 78 | 0 | 0.0000 | 0.0000 | 0.0126 | −6.308 | 79.21 | 78 | 6.29 |
| ITSN1 | DQ679757 | 1029 | 1229 | 0.8192 | 0.1284 | 1.1944 | 0.256 | 1.19 | 200 | 7.65 |
| ITSN1 | EU117382 | 0 | 0 | 9999 | 9999 | 1.0000 | 0.000 | 1.00 | 0 | 0 |
| ITSN1 | EU120734 | 4 | 4 | 1.0000 | 1.0000 | 1.0801 | 0.111 | 1.08 | 0 | −1.42 |
| ITSN1 | EU120735 | 20 | 0 | 0.0492 | 0.0011 | 0.0468 | −4.418 | 21.37 | 20 | 4.35 |
| ITSN1 | EU140799 | 0 | 19 | 0.0335 | 0.0006 | 20.2040 | 4.337 | 20.20 | 19 | 4.26 |
| ITSN1 | EU140800 | 0 | 53 | 0.0000 | 0.0000 | 54.1511 | 5.759 | 54.15 | 53 | 5.73 |
| ITSN1 | EU152331 | 31 | 0 | 0.0074 | 0.0001 | 0.0313 | −4.999 | 31.97 | 31 | 4.95 |
| ITSN1 | EU191901 | 2 | 9 | 1.0000 | 0.3239 | 2.8558 | 1.514 | 2.86 | 6 | 2.68 |
| ITSN1 | GU939616 | 16 | 6 | 1.0000 | 0.3105 | 0.4299 | −1.218 | 2.33 | 10 | 3.25 |
| KIAA1033 | AL137753 | 141 | 380 | 0.0031 | 0.0000 | 2.6790 | 1.422 | 2.68 | 239 | 7.90 |
| KIAA1033 | BC143373 | 337 | 352 | 1.0000 | 0.9054 | 1.0462 | 0.065 | 1.05 | 16 | 3.96 |
| KIAA1033 | NM_015275 | 2809 | 2801 | 1.0000 | 0.9843 | 0.9969 | −0.005 | 1.00 | 9 | 3.14 |
| KIF2A | AY317140 | 136 | 356 | 0.0050 | 0.0001 | 2.6153 | 1.387 | 2.62 | 221 | 7.79 |
| KIF2A | NM_001098511 | 4 | 0 | 0.6400 | 0.0712 | 0.1885 | −2.408 | 5.31 | 4 | 2.11 |
| KIF2A | NM_001243952 | 3 | 11 | 1.0000 | 0.3339 | 2.6612 | 1.412 | 2.66 | 7 | 2.86 |
| KIF2A | NM_001243953 | 697 | 764 | 1.0000 | 0.4874 | 1.0954 | 0.132 | 1.10 | 67 | 6.06 |
| KIF2A | NM_004520 | 818 | 718 | 1.0000 | 0.3267 | 0.8779 | −0.188 | 1.14 | 100 | 6.64 |
| KIF3A | AF041853 | 6 | 9 | 1.0000 | 0.7144 | 1.4759 | 0.562 | 1.48 | 3 | 1.64 |
| KIF3A | AK295089 | 6 | 6 | 1.0000 | 0.9603 | 0.9799 | −0.029 | 1.02 | 0 | −2.84 |
| KIF3A | AK313359 | 192 | 431 | 0.0095 | 0.0001 | 2.2358 | 1.161 | 2.24 | 239 | 7.90 |
| KIF3A | AM177178 | 0 | 0 | 9999 | 9999 | 1.0000 | 0.000 | 1.00 | 0 | 0 |
| KIF3A | NM_007054 | 343 | 161 | 0.0605 | 0.0015 | 0.4720 | −1.083 | 2.12 | 182 | 7.50 |
| KLC2 | AK094593 | 4 | 0 | 0.6400 | 0.0713 | 0.1899 | −2.397 | 5.27 | 4 | 2.09 |
| KLC2 | AK126489 | 36 | 26 | 1.0000 | 0.6179 | 0.7406 | −0.433 | 1.35 | 10 | 3.27 |
| KLC2 | BC034373 | 612 | 721 | 1.0000 | 0.2883 | 1.1769 | 0.235 | 1.18 | 108 | 6.76 |
| KLC2 | NM_001134775 | 0 | 0 | 9999 | 9999 | 1.0000 | 0.000 | 1.00 | 0 | 0 |
| KLC2 | NM_001134776 | 185 | 25 | 0.0001 | 0.0000 | 0.1394 | −2.843 | 7.18 | 161 | 7.33 |
| KLC2 | NM_022822 | 309 | 264 | 1.0000 | 0.4840 | 0.8529 | −0.230 | 1.17 | 46 | 5.51 |
| LATS2 | AK314235 | 126 | 580 | 0.0000 | 0.0000 | 4.5537 | 2.187 | 4.55 | 453 | 8.82 |
| LATS2 | NM_014572 | 2134 | 1739 | 0.5006 | 0.0415 | 0.8150 | −0.295 | 1.23 | 395 | 8.63 |
| LIMS1 | NM_001193482 | 318 | 35 | 0.0000 | 0.0000 | 0.1141 | −3.131 | 8.76 | 283 | 8.14 |
| LIMS1 | NM_001193483 | 2628 | 3034 | 0.6612 | 0.0790 | 1.1544 | 0.207 | 1.15 | 406 | 8.67 |
| LIMS1 | NM_001193484 | 0 | 11 | 0.1469 | 0.0052 | 12.2744 | 3.618 | 12.27 | 11 | 3.49 |
| LIMS1 | NM_001193485 | 500 | 644 | 0.7347 | 0.1037 | 1.2881 | 0.365 | 1.29 | 144 | 7.17 |
| LIMS1 | NM_004987 | 42 | 0 | 0.0004 | 0.0000 | 0.0231 | −5.438 | 43.37 | 42 | 5.40 |
| LINC00341 | NR_026779 | 58 | 1 | 0.0007 | 0.0000 | 0.0392 | −4.673 | 25.51 | 57 | 5.83 |
| LINC00657 | NR_027451 | 1580 | 75 | 0.0000 | 0.0000 | 0.0478 | −4.387 | 20.92 | 1506 | 10.56 |
| LONP1 | AK309720 | 55 | 84 | 1.0000 | 0.3058 | 1.5202 | 0.604 | 1.52 | 29 | 4.87 |
| LONP1 | BC109218 | 580 | 271 | 0.0046 | 0.0001 | 0.4675 | −1.097 | 2.14 | 309 | 8.27 |
| LONP1 | NM_001276479 | 0 | 0 | 9999 | 9999 | 1.0000 | 0.000 | 1.00 | 0 | 0 |
| LONP1 | NM_001276480 | 0 | 0 | 9999 | 9999 | 1.0000 | 0.000 | 1.00 | 0 | 0 |
| LONP1 | NM_004793 | 986 | 566 | 0.0033 | 0.0000 | 0.5749 | −0.799 | 1.74 | 419 | 8.71 |

TABLE 11-continued

RNA Abundance Modulation

| Gene | Trx_ID | ave DMSO | ave Cpd | padj (q val, FDR) | ttest (p val) | FC (x + 1) | L₂FC (x + 1) | amp FC (x + 1) | abs (Cpd − DMSO) | L₂abs (Cpd − DMSO) |
|---|---|---|---|---|---|---|---|---|---|---|
| LONP1 | NR_076392 | 1948 | 2038 | 1.0000 | 0.6707 | 1.0462 | 0.065 | 1.05 | 90 | 6.49 |
| LOX | AK307559 | 1848 | 2177 | 0.7870 | 0.1186 | 1.1782 | 0.237 | 1.18 | 329 | 8.36 |
| LOX | AK315873 | 25 | 131 | 0.0045 | 0.0000 | 5.0709 | 2.342 | 5.07 | 106 | 6.72 |
| LOX | NM_001178102 | 4593 | 12429 | 0.0000 | 0.0000 | 2.7055 | 1.436 | 2.71 | 7836 | 12.94 |
| LOX | NM_002317 | 131562 | 118708 | 0.8865 | 0.1559 | 0.9023 | −0.148 | 1.11 | 12854 | 13.65 |
| LUC7L2 | AK092044 | 28 | 8 | 0.8902 | 0.1612 | 0.3215 | −1.637 | 3.11 | 19 | 4.28 |
| LUC7L2 | AK095839 | 45 | 49 | 1.0000 | 0.8718 | 1.0780 | 0.108 | 1.08 | 4 | 1.85 |
| LUC7L2 | NM_001244585 | 58 | 233 | 0.0010 | 0.0000 | 3.9496 | 1.982 | 3.95 | 175 | 7.45 |
| LUC7L2 | NM_001270643 | 24 | 31 | 1.0000 | 0.6824 | 1.2814 | 0.358 | 1.28 | 7 | 2.82 |
| LUC7L2 | NM_016019 | 1959 | 1929 | 1.0000 | 0.8774 | 0.9847 | −0.022 | 1.02 | 30 | 4.91 |
| MBD1 | AB209765 | 31 | 12 | 0.9582 | 0.1869 | 0.4153 | −1.268 | 2.41 | 19 | 4.22 |
| MBD1 | AK225948 | 0 | 3 | 0.5735 | 0.0554 | 3.9723 | 1.990 | 3.97 | 3 | 1.57 |
| MBD1 | AK295401 | 91 | 92 | 1.0000 | 1.0000 | 1.0097 | 0.014 | 1.01 | 1 | −0.16 |
| MBD1 | NM_001204136 | 294 | 277 | 1.0000 | 0.6769 | 0.9416 | −0.087 | 1.06 | 17 | 4.11 |
| MBD1 | NM_001204137 | 144 | 60 | 0.3987 | 0.0264 | 0.4197 | −1.253 | 2.38 | 84 | 6.39 |
| MBD1 | NM_001204138 | 0 | 0 | 9999 | 9999 | 1.0000 | 0.000 | 1.00 | 0 | 0 |
| MBD1 | NM_001204139 | 11 | 0 | 0.2277 | 0.0103 | 0.0835 | −3.582 | 11.97 | 11 | 3.46 |
| MBD1 | NM_001204140 | 65 | 138 | 0.6179 | 0.0648 | 2.0978 | 1.069 | 2.10 | 73 | 6.18 |
| MBD1 | NM_001204141 | 38 | 66 | 1.0000 | 0.2197 | 1.7375 | 0.797 | 1.74 | 28 | 4.83 |
| MBD1 | NM_001204142 | 109 | 113 | 1.0000 | 0.9333 | 1.0418 | 0.059 | 1.04 | 5 | 2.20 |
| MBD1 | NM_001204143 | 154 | 159 | 1.0000 | 0.8580 | 1.0341 | 0.048 | 1.03 | 5 | 2.40 |
| MBD1 | NM_001204151 | 11 | 9 | 1.0000 | 1.0000 | 0.8065 | −0.310 | 1.24 | 2 | 1.19 |
| MBD1 | NM_002384 | 9 | 15 | 1.0000 | 0.4799 | 1.6162 | 0.693 | 1.62 | 6 | 2.62 |
| MBD1 | NM_015844 | 246 | 71 | 0.0028 | 0.0000 | 0.2922 | −1.775 | 3.42 | 175 | 7.45 |
| MBD1 | NM_015845 | 10 | 12 | 1.0000 | 0.9511 | 1.1409 | 0.190 | 1.14 | 2 | 0.64 |
| MBD1 | NM_015846 | 95 | 183 | 0.3930 | 0.0255 | 1.9196 | 0.941 | 1.92 | 88 | 6.46 |
| MBOAT7 | AK122789 | 1046 | 895 | 1.0000 | 0.2544 | 0.8560 | −0.224 | 1.17 | 151 | 7.24 |
| MBOAT7 | AK293199 | 885 | 656 | 0.3728 | 0.0231 | 0.7413 | −0.432 | 1.35 | 229 | 7.84 |
| MBOAT7 | AK311493 | 132 | 276 | 0.1363 | 0.0046 | 2.0810 | 1.057 | 2.08 | 144 | 7.17 |
| MBOAT7 | NM_001146056 | 15 | 15 | 1.0000 | 0.9115 | 0.9862 | −0.020 | 1.01 | 0 | −2.18 |
| MBOAT7 | NM_001146082 | 56 | 60 | 1.0000 | 0.8569 | 1.0750 | 0.104 | 1.07 | 4 | 2.09 |
| MBOAT7 | NM_001146083 | 96 | 138 | 1.0000 | 0.2938 | 1.4347 | 0.521 | 1.43 | 42 | 5.40 |
| MBOAT7 | NM_024298 | 337 | 120 | 0.0029 | 0.0000 | 0.3571 | −1.486 | 2.80 | 217 | 7.76 |
| MEF2D | AK308641 | 333 | 252 | 1.0000 | 0.2129 | 0.7579 | −0.400 | 1.32 | 81 | 6.34 |
| MEF2D | BC032479 | 0 | 0 | 9999 | 9999 | 1.0000 | 0.000 | 1.00 | 0 | 0 |
| MEF2D | BC064988 | 1316 | 839 | 0.0143 | 0.0002 | 0.6377 | −0.649 | 1.57 | 477 | 8.90 |
| MEF2D | NM_001271629 | 73 | 412 | 0.0000 | 0.0000 | 5.5960 | 2.484 | 5.60 | 339 | 8.41 |
| MEIS2 | AK055936 | 121 | 162 | 1.0000 | 0.3907 | 1.3341 | 0.416 | 1.33 | 41 | 5.35 |
| MEIS2 | AY349358 | 2 | 4 | 1.0000 | 0.6328 | 1.4735 | 0.559 | 1.47 | 2 | 0.62 |
| MEIS2 | NM_001220482 | 77 | 20 | 0.2936 | 0.0155 | 0.2723 | −1.877 | 3.67 | 57 | 5.83 |
| MEIS2 | NM_002399 | 51 | 92 | 1.0000 | 0.2273 | 1.7906 | 0.840 | 1.79 | 41 | 5.36 |
| MEIS2 | NM_170674 | 227 | 246 | 1.0000 | 0.7419 | 1.0817 | 0.113 | 1.08 | 19 | 4.22 |
| MEIS2 | NM_170675 | 101 | 6 | 0.0001 | 0.0000 | 0.0667 | −3.906 | 14.99 | 96 | 6.58 |
| MEIS2 | NM_170676 | 0 | 34 | 0.0015 | 0.0000 | 34.8566 | 5.123 | 34.86 | 34 | 5.08 |
| MEIS2 | NM_170677 | 0 | 2 | 0.6428 | 0.0725 | 2.8961 | 1.534 | 2.90 | 2 | 0.92 |
| MEIS2 | NM_172315 | 129 | 22 | 0.0093 | 0.0001 | 0.1786 | −2.486 | 5.60 | 107 | 6.74 |
| MEIS2 | NM_172316 | 40 | 46 | 1.0000 | 0.7229 | 1.1590 | 0.213 | 1.16 | 6 | 2.70 |
| MICAL2 | AB110785 | 3077 | 3071 | 1.0000 | 0.9901 | 0.9979 | −0.003 | 1.00 | 7 | 2.72 |
| MICAL2 | AB110786 | 9282 | 9913 | 1.0000 | 0.3296 | 1.0679 | 0.095 | 1.07 | 631 | 9.30 |
| MICAL2 | AK294845 | 0 | 3 | 0.5441 | 0.0499 | 4.1601 | 2.057 | 4.16 | 3 | 1.66 |
| MICAL2 | AK302580 | 210 | 10 | 0.0000 | 0.0000 | 0.0513 | −4.286 | 19.51 | 200 | 7.64 |
| MICAL2 | AK302893 | 151 | 225 | 0.8600 | 0.1449 | 1.4863 | 0.572 | 1.49 | 74 | 6.21 |
| MICAL2 | BC015755 | 342 | 376 | 1.0000 | 0.6129 | 1.0989 | 0.136 | 1.10 | 34 | 5.08 |
| MICAL2 | BX538021 | 114 | 233 | 0.1776 | 0.0069 | 2.0324 | 1.023 | 2.03 | 119 | 6.90 |
| MICAL2 | NM_014632 | 43 | 59 | 1.0000 | 0.5087 | 1.3740 | 0.458 | 1.37 | 16 | 4.03 |
| MKL1 | AF448806 | 28 | 20 | 1.0000 | 0.6475 | 0.7142 | −0.486 | 1.40 | 8 | 3.05 |
| MKL1 | AJ297257 | 10 | 0 | 0.2958 | 0.0157 | 0.0949 | −3.397 | 10.53 | 10 | 3.25 |
| MKL1 | BC064620 | 54 | 1 | 0.0020 | 0.0000 | 0.0433 | −4.528 | 23.08 | 52 | 5.71 |
| MKL1 | BC114364 | 11 | 4 | 1.0000 | 0.3893 | 0.4463 | −1.164 | 2.24 | 7 | 2.76 |
| MKL1 | BC115039 | 39 | 11 | 0.7073 | 0.0979 | 0.3101 | −1.689 | 3.22 | 27 | 4.78 |
| MKL1 | NM_020831 | 1364 | 1312 | 1.0000 | 0.7115 | 0.9618 | −0.056 | 1.04 | 52 | 5.70 |
| MKNK2 | AB209074 | 29 | 22 | 1.0000 | 0.6618 | 0.7504 | −0.414 | 1.33 | 7 | 2.90 |
| MKNK2 | AK001730 | 5 | 4 | 1.0000 | 0.9112 | 0.8442 | −0.244 | 1.18 | 1 | −0.13 |
| MKNK2 | AK293742 | 77 | 23 | 0.2726 | 0.0138 | 0.3008 | −1.733 | 3.32 | 55 | 5.78 |
| MKNK2 | AK303393 | 212 | 11 | 0.0000 | 0.0000 | 0.0552 | −4.180 | 18.13 | 201 | 7.65 |
| MKNK2 | NM_017572 | 1496 | 839 | 0.0001 | 0.0000 | 0.5611 | −0.834 | 1.78 | 657 | 9.36 |
| MKNK2 | NM_199054 | 1539 | 1409 | 1.0000 | 0.4119 | 0.9154 | −0.128 | 1.09 | 130 | 7.03 |
| MLST8 | AK022227 | 44 | 38 | 1.0000 | 0.8403 | 0.8798 | −0.185 | 1.14 | 5 | 2.42 |
| MLST8 | AK302201 | 56 | 73 | 1.0000 | 0.5734 | 1.2872 | 0.364 | 1.29 | 16 | 4.04 |
| MLST8 | AK304390 | 1 | 0 | 1.0000 | 0.6885 | 0.6031 | −0.730 | 1.66 | 1 | −0.18 |
| MLST8 | AY223837 | 39 | 14 | 0.8264 | 0.1314 | 0.3871 | −1.369 | 2.58 | 24 | 4.61 |
| MLST8 | BC020499 | 24 | 24 | 1.0000 | 0.9532 | 1.0203 | 0.029 | 1.02 | 1 | −0.98 |
| MLST8 | BC052292 | 46 | 20 | 0.9583 | 0.1869 | 0.4444 | −1.170 | 2.25 | 26 | 4.70 |
| MLST8 | NM_001199173 | 21 | 11 | 1.0000 | 0.4424 | 0.5700 | −0.811 | 1.75 | 9 | 3.24 |

TABLE 11-continued

RNA Abundance Modulation

| Gene | Trx_ID | ave DMSO | ave Cpd | padj (q val, FDR) | ttest (p val) | FC (x + 1) | L$_2$FC (x + 1) | amp FC (x + 1) | abs (Cpd − DMSO) | L$_2$abs (Cpd − DMSO) |
|---|---|---|---|---|---|---|---|---|---|---|
| MLST8 | NM_001199174 | 537 | 461 | 1.0000 | 0.3505 | 0.8573 | −0.222 | 1.17 | 77 | 6.26 |
| MLST8 | NM_001199175 | 40 | 31 | 1.0000 | 0.7641 | 0.7849 | −0.349 | 1.27 | 9 | 3.13 |
| MLST8 | NM_022372 | 61 | 2 | 0.0017 | 0.0000 | 0.0548 | −4.190 | 18.25 | 59 | 5.87 |
| MPPE1 | AK309948 | 31 | 22 | 1.0000 | 0.5986 | 0.7224 | −0.469 | 1.38 | 9 | 3.16 |
| MPPE1 | AX775855 | 0 | 13 | 0.1134 | 0.0035 | 13.6883 | 3.775 | 13.69 | 13 | 3.67 |
| MPPE1 | NM_001242904 | 26 | 17 | 1.0000 | 0.5735 | 0.6790 | −0.559 | 1.47 | 9 | 3.13 |
| MPPE1 | NM_023075 | 302 | 277 | 1.0000 | 0.6835 | 0.9176 | −0.124 | 1.09 | 25 | 4.64 |
| MPPE1 | NR_040241 | 74 | 0 | 0.0000 | 0.0000 | 0.0133 | −6.238 | 75.47 | 74 | 6.22 |
| MPPE1 | NR_040242 | 4 | 2 | 1.0000 | 0.5786 | 0.5773 | −0.792 | 1.73 | 2 | 0.99 |
| MPPE1 | NR_040243 | 43 | 125 | 0.2180 | 0.0095 | 2.8910 | 1.532 | 2.89 | 82 | 6.36 |
| MSL3 | AK294255 | 0 | 0 | 9999 | 9999 | 1.0000 | 0.000 | 1.00 | 0 | 0 |
| MSL3 | AK304419 | 5 | 10 | 1.0000 | 0.6045 | 1.6953 | 0.762 | 1.70 | 4 | 2.11 |
| MSL3 | NM_001193270 | 7 | 11 | 1.0000 | 0.7047 | 1.4741 | 0.560 | 1.47 | 4 | 1.98 |
| MSL3 | NM_006800 | 281 | 272 | 1.0000 | 0.9516 | 0.9659 | −0.050 | 1.04 | 10 | 3.27 |
| MSL3 | NM_078628 | 154 | 24 | 0.0012 | 0.0000 | 0.1606 | −2.639 | 6.23 | 130 | 7.02 |
| MSL3 | NM_078629 | 310 | 541 | 0.0804 | 0.0021 | 1.7448 | 0.803 | 1.74 | 231 | 7.85 |
| MSRB3 | NM_001031679 | 783 | 623 | 0.7626 | 0.1108 | 0.7959 | −0.329 | 1.26 | 160 | 7.32 |
| MSRB3 | NM_001193460 | 58 | 64 | 1.0000 | 0.9375 | 1.1018 | 0.140 | 1.10 | 6 | 2.60 |
| MSRB3 | NM_001193461 | 151 | 432 | 0.0001 | 0.0000 | 2.8564 | 1.514 | 2.86 | 281 | 8.14 |
| MSRB3 | NM_198080 | 3988 | 4164 | 1.0000 | 0.6382 | 1.0441 | 0.062 | 1.04 | 176 | 7.46 |
| MTRR | AK311663 | 19 | 32 | 1.0000 | 0.4367 | 1.6464 | 0.719 | 1.65 | 13 | 3.71 |
| MTRR | BC035977 | 26 | 60 | 0.7199 | 0.1003 | 2.3071 | 1.206 | 2.31 | 35 | 5.12 |
| MTRR | BC062577 | 206 | 174 | 1.0000 | 0.5339 | 0.8456 | −0.242 | 1.18 | 32 | 5.00 |
| MTRR | BC109217 | 31 | 0 | 0.0046 | 0.0001 | 0.0315 | −4.990 | 31.78 | 31 | 4.94 |
| MTRR | NM_002454 | 725 | 600 | 0.9239 | 0.1736 | 0.8277 | −0.273 | 1.21 | 125 | 6.97 |
| MTRR | NM_024010 | 56 | 256 | 0.0001 | 0.0000 | 4.5038 | 2.171 | 4.50 | 200 | 7.64 |
| MYADM | CCDS12866 | 132 | 0 | 0.0000 | 0.0000 | 0.0075 | −7.052 | 132.67 | 132 | 7.04 |
| MYADM | NM_001020818 | 192 | 192 | 1.0000 | 0.9896 | 0.9992 | −0.001 | 1.00 | 0 | −2.65 |
| MYADM | NM_001020819 | 1022 | 838 | 0.7726 | 0.1144 | 0.8200 | −0.286 | 1.22 | 184 | 7.52 |
| MYADM | NM_001020820 | 119 | 148 | 1.0000 | 0.3777 | 1.2491 | 0.321 | 1.25 | 30 | 4.90 |
| MYADM | NM_001020821 | 21 | 4 | 0.6786 | 0.0859 | 0.2165 | −2.208 | 4.62 | 17 | 4.12 |
| MYADM | NM_138373 | 6419 | 5807 | 0.9722 | 0.1924 | 0.9046 | −0.145 | 1.11 | 613 | 9.26 |
| MYLK | AB384705 | 2526 | 2466 | 1.0000 | 0.7460 | 0.9762 | −0.035 | 1.02 | 60 | 5.91 |
| MYLK | AF069604 | 34 | 89 | 0.4941 | 0.0405 | 2.6005 | 1.379 | 2.60 | 55 | 5.79 |
| MYLK | AK300610 | 181 | 573 | 0.0000 | 0.0000 | 3.1478 | 1.654 | 3.15 | 392 | 8.61 |
| MYLK | AK311053 | 8 | 9 | 1.0000 | 0.8818 | 1.0861 | 0.119 | 1.09 | 1 | −0.32 |
| MYLK | BC040115 | 5 | 4 | 1.0000 | 0.9562 | 0.8436 | −0.245 | 1.19 | 1 | −0.01 |
| MYLK | BC064695 | 392 | 432 | 1.0000 | 0.3915 | 1.1029 | 0.141 | 1.10 | 40 | 5.34 |
| MYLK | DQ642691 | 20 | 13 | 1.0000 | 0.5716 | 0.6394 | −0.645 | 1.56 | 8 | 2.95 |
| MYLK | NM_053025 | 1021 | 1007 | 1.0000 | 1.0000 | 0.9861 | −0.020 | 1.01 | 14 | 3.83 |
| MYLK | NM_053026 | 3636 | 3084 | 0.6030 | 0.0620 | 0.8483 | −0.237 | 1.18 | 552 | 9.11 |
| MYLK | NM_053027 | 0 | 3 | 0.6006 | 0.0615 | 3.7332 | 1.900 | 3.73 | 3 | 1.45 |
| MYLK | NM_053028 | 0 | 36 | 0.0010 | 0.0000 | 37.2148 | 5.218 | 37.21 | 36 | 5.18 |
| MYLK | NM_053031 | 0 | 24 | 0.0129 | 0.0002 | 24.8443 | 4.634 | 24.84 | 24 | 4.58 |
| MYLK | NM_053032 | 58 | 41 | 1.0000 | 0.4682 | 0.7060 | −0.502 | 1.42 | 17 | 4.11 |
| MYO1D | AK127942 | 51 | 369 | 0.0000 | 0.0000 | 7.1787 | 2.844 | 7.18 | 318 | 8.31 |
| MYO1D | BC030602 | 0 | 5 | 0.4446 | 0.0325 | 5.8010 | 2.536 | 5.80 | 5 | 2.26 |
| MYO1D | NM_015194 | 5216 | 4859 | 1.0000 | 0.3968 | 0.9316 | −0.102 | 1.07 | 357 | 8.48 |
| NAA35 | AK056059 | 44 | 45 | 1.0000 | 0.9891 | 1.0181 | 0.026 | 1.02 | 1 | −0.29 |
| NAA35 | BC117429 | 153 | 372 | 0.0039 | 0.0000 | 2.4163 | 1.273 | 2.42 | 219 | 7.77 |
| NAA35 | NM_024635 | 584 | 385 | 0.2146 | 0.0093 | 0.6600 | −0.599 | 1.52 | 199 | 7.64 |
| NAV1 | AB033039 | 10 | 8 | 1.0000 | 0.8872 | 0.8561 | −0.224 | 1.17 | 2 | 0.62 |
| NAV1 | AK056158 | 16 | 19 | 1.0000 | 0.7807 | 1.2097 | 0.275 | 1.21 | 3 | 1.81 |
| NAV1 | BC069250 | 679 | 676 | 1.0000 | 1.0000 | 0.9952 | −0.007 | 1.00 | 3 | 1.70 |
| NAV1 | CCDS1414 | 76 | 265 | 0.0005 | 0.0000 | 3.4512 | 1.787 | 3.45 | 189 | 7.56 |
| NAV1 | NM_001167738 | 1425 | 2029 | 0.0372 | 0.0007 | 1.4237 | 0.510 | 1.42 | 604 | 9.24 |
| NAV1 | NM_020443 | 4072 | 3939 | 1.0000 | 0.7072 | 0.9675 | −0.048 | 1.03 | 132 | 7.05 |
| NAV2 | AK001495 | 18 | 56 | 0.4639 | 0.0352 | 3.0091 | 1.589 | 3.01 | 38 | 5.25 |
| NAV2 | AK096037 | 10 | 4 | 1.0000 | 0.4138 | 0.4613 | −1.116 | 2.17 | 6 | 2.55 |
| NAV2 | AK290458 | 74 | 68 | 1.0000 | 0.7737 | 0.9272 | −0.109 | 1.08 | 5 | 2.45 |
| NAV2 | AK307574 | 34 | 34 | 1.0000 | 0.8954 | 1.0097 | 0.014 | 1.01 | 0 | −1.56 |
| NAV2 | CCDS58126 | 79 | 113 | 1.0000 | 0.3461 | 1.4235 | 0.509 | 1.42 | 34 | 5.09 |
| NAV2 | CCDS7851 | 823 | 925 | 1.0000 | 0.2885 | 1.1232 | 0.168 | 1.12 | 102 | 6.67 |
| NAV2 | NM_001111018 | 594 | 666 | 1.0000 | 0.3822 | 1.1204 | 0.164 | 1.12 | 72 | 6.16 |
| NAV2 | NM_001111019 | 237 | 202 | 1.0000 | 0.5030 | 0.8537 | −0.228 | 1.17 | 35 | 5.12 |
| NAV2 | NM_001244963 | 40 | 16 | 0.8520 | 0.1414 | 0.4226 | −1.243 | 2.37 | 24 | 4.58 |
| NAV2 | NM_182964 | 368 | 81 | 0.0000 | 0.0000 | 0.2219 | −2.172 | 4.51 | 287 | 8.17 |
| NCOA1 | AK226063 | 31 | 64 | 0.8362 | 0.1342 | 2.0092 | 1.007 | 2.01 | 33 | 5.03 |
| NCOA1 | AK290019 | 339 | 396 | 1.0000 | 0.3929 | 1.1694 | 0.226 | 1.17 | 58 | 5.85 |
| NCOA1 | NM_003743 | 92 | 283 | 0.0082 | 0.0001 | 3.0397 | 1.604 | 3.04 | 190 | 7.57 |
| NCOA1 | NM_147223 | 121 | 0 | 0.0000 | 0.0000 | 0.0082 | −6.933 | 122.17 | 121 | 6.92 |
| NCOA1 | NM_147233 | 131 | 28 | 0.0196 | 0.0003 | 0.2206 | −2.180 | 4.53 | 103 | 6.68 |
| NCOA1 | U19177 | 0 | 2 | 0.6432 | 0.0739 | 2.9768 | 1.574 | 2.98 | 2 | 0.98 |
| NFX1 | AB385216 | 72 | 0 | 0.0000 | 0.0000 | 0.0137 | −6.189 | 72.95 | 72 | 6.17 |

TABLE 11-continued

RNA Abundance Modulation

| Gene | Trx_ID | ave DMSO | ave Cpd | padj (q val, FDR) | ttest (p val) | FC (x + 1) | L₂FC (x + 1) | amp FC (x + 1) | abs (Cpd − DMSO) | L₂abs (Cpd − DMSO) |
|---|---|---|---|---|---|---|---|---|---|---|
| NFX1 | AK291643 | 16 | 16 | 1.0000 | 0.9594 | 1.0137 | 0.020 | 1.01 | 0 | −2.13 |
| NFX1 | AL832342 | 259 | 323 | 1.0000 | 0.2796 | 1.2494 | 0.321 | 1.25 | 65 | 6.02 |
| NFX1 | NM_002504 | 294 | 248 | 1.0000 | 0.4463 | 0.8434 | −0.246 | 1.19 | 46 | 5.53 |
| NFX1 | NM_147133 | 15 | 12 | 1.0000 | 0.8672 | 0.8215 | −0.284 | 1.22 | 3 | 1.50 |
| NFX1 | NM_147134 | 523 | 633 | 1.0000 | 0.2050 | 1.2096 | 0.275 | 1.21 | 110 | 6.78 |
| NKX3-1 | NM_001256339 | 177 | 479 | 0.0003 | 0.0000 | 2.6956 | 1.431 | 2.70 | 302 | 8.24 |
| NKX3-1 | NM_006167 | 621 | 413 | 0.2478 | 0.0117 | 0.6656 | −0.587 | 1.50 | 208 | 7.70 |
| NKX3-1 | NR_046072 | 99 | 94 | 1.0000 | 0.8748 | 0.9504 | −0.073 | 1.05 | 5 | 2.31 |
| NOMO3 | AL832855 | 365 | 1076 | 0.0000 | 0.0000 | 2.9444 | 1.558 | 2.94 | 711 | 9.47 |
| NOMO3 | BC028389 | 15 | 0 | 0.1443 | 0.0050 | 0.0628 | −3.993 | 15.92 | 15 | 3.90 |
| NOMO3 | NM_001004067 | 3350 | 2388 | 0.0062 | 0.0001 | 0.7130 | −0.488 | 1.40 | 962 | 9.91 |
| NRG1 | AK293270 | 36 | 0 | 0.0024 | 0.0000 | 0.0271 | −5.206 | 36.91 | 36 | 5.17 |
| NRG1 | AY207002 | 0 | 1 | 1.0000 | 0.3259 | 1.6833 | 0.751 | 1.68 | 1 | −0.55 |
| NRG1 | EF372275 | 0 | 19 | 0.0356 | 0.0007 | 19.8611 | 4.312 | 19.86 | 19 | 4.24 |
| NRG1 | EF372277 | 35 | 0 | 0.0035 | 0.0000 | 0.0280 | −5.158 | 35.70 | 35 | 5.12 |
| NRG1 | NM_001159995 | 96 | 236 | 0.1141 | 0.0036 | 2.4316 | 1.282 | 2.43 | 139 | 7.12 |
| NRG1 | NM_001159996 | 174 | 256 | 0.8060 | 0.1239 | 1.4722 | 0.558 | 1.47 | 83 | 6.37 |
| NRG1 | NM_001160001 | 135 | 14 | 0.0003 | 0.0000 | 0.1106 | −3.177 | 9.04 | 121 | 6.92 |
| NRG1 | NM_001160004 | 20 | 43 | 0.9231 | 0.1732 | 2.1374 | 1.096 | 2.14 | 24 | 4.56 |
| NRG1 | NM_001160007 | 1 | 0 | 1.0000 | 0.6668 | 0.5960 | −0.747 | 1.68 | 1 | −0.56 |
| NRG1 | NM_001160008 | 106 | 84 | 1.0000 | 0.5897 | 0.7968 | −0.328 | 1.25 | 22 | 4.44 |
| NRG1 | NM_004495 | 15 | 15 | 1.0000 | 1.0000 | 0.9934 | −0.010 | 1.01 | 0 | −3.19 |
| NRG1 | NM_013956 | 45 | 50 | 1.0000 | 0.8988 | 1.1032 | 0.142 | 1.10 | 5 | 2.26 |
| NRG1 | NM_013957 | 21 | 92 | 0.0903 | 0.0025 | 4.1855 | 2.065 | 4.19 | 71 | 6.14 |
| NRG1 | NM_013958 | 66 | 58 | 1.0000 | 0.7898 | 0.8795 | −0.185 | 1.14 | 8 | 3.02 |
| NRG1 | NM_013959 | 6 | 7 | 1.0000 | 0.9654 | 1.1164 | 0.159 | 1.12 | 1 | −0.33 |
| NRG1 | NM_013960 | 330 | 142 | 0.0350 | 0.0007 | 0.4322 | −1.210 | 2.31 | 188 | 7.55 |
| NRG1 | NM_013964 | 458 | 460 | 1.0000 | 0.9381 | 1.0045 | 0.006 | 1.00 | 2 | 1.05 |
| NRG1 | U02325 | 0 | 16 | 0.0590 | 0.0014 | 17.1176 | 4.097 | 17.12 | 16 | 4.01 |
| NRG1 | U02327 | 24 | 27 | 1.0000 | 0.8673 | 1.1045 | 0.143 | 1.10 | 3 | 1.40 |
| NUDT4 | AF067803 | 16 | 5 | 1.0000 | 0.2840 | 0.3534 | −1.501 | 2.83 | 11 | 3.47 |
| NUDT4 | AK304296 | 248 | 138 | 0.2907 | 0.0152 | 0.5570 | −0.844 | 1.80 | 110 | 6.78 |
| NUDT4 | CR749445 | 415 | 991 | 0.0000 | 0.0000 | 2.3856 | 1.254 | 2.39 | 576 | 9.17 |
| NUDT4 | NM_019094 | 1752 | 1224 | 0.0333 | 0.0006 | 0.6987 | −0.517 | 1.43 | 528 | 9.04 |
| NUDT4 | NR_002212 | 1136 | 1344 | 0.8245 | 0.1308 | 1.1833 | 0.243 | 1.18 | 208 | 7.70 |
| NUPL1 | AB383875 | 292 | 319 | 1.0000 | 0.6809 | 1.0908 | 0.125 | 1.09 | 27 | 4.73 |
| NUPL1 | NM_001008564 | 177 | 0 | 0.0000 | 0.0000 | 0.0056 | −7.479 | 178.46 | 177 | 7.47 |
| NUPL1 | NM_014089 | 1703 | 2145 | 0.3538 | 0.0211 | 1.2591 | 0.332 | 1.26 | 442 | 8.79 |
| NUSAP1 | BC010838 | 944 | 818 | 1.0000 | 0.2585 | 0.8666 | −0.207 | 1.15 | 126 | 6.98 |
| NUSAP1 | BC012887 | 283 | 83 | 0.0014 | 0.0000 | 0.2965 | −1.754 | 3.37 | 200 | 7.64 |
| NUSAP1 | NM_001243142 | 76 | 178 | 0.2130 | 0.0092 | 2.3185 | 1.213 | 2.32 | 102 | 6.67 |
| NUSAP1 | NM_001243143 | 524 | 1073 | 0.0001 | 0.0000 | 2.0459 | 1.033 | 2.05 | 549 | 9.10 |
| NUSAP1 | NM_016359 | 1941 | 1884 | 1.0000 | 0.8045 | 0.9708 | −0.043 | 1.03 | 57 | 5.82 |
| NUSAP1 | NM_018454 | 986 | 1213 | 0.6400 | 0.0713 | 1.2294 | 0.298 | 1.23 | 226 | 7.82 |
| OSMR | AK304016 | 237 | 49 | 0.0002 | 0.0000 | 0.2103 | −2.250 | 4.76 | 188 | 7.55 |
| OSMR | NM_001168355 | 166 | 177 | 1.0000 | 0.8140 | 1.0651 | 0.091 | 1.07 | 11 | 3.44 |
| OSMR | NM_003999 | 4297 | 4855 | 0.8030 | 0.1224 | 1.1297 | 0.176 | 1.13 | 558 | 9.12 |
| P4HA1 | CCDS41537 | 167 | 452 | 0.0006 | 0.0000 | 2.6951 | 1.430 | 2.70 | 285 | 8.15 |
| P4HA1 | CCDS7320 | 789 | 907 | 1.0000 | 0.2375 | 1.1492 | 0.201 | 1.15 | 118 | 6.88 |
| P4HA1 | NM_000917 | 2495 | 2391 | 1.0000 | 0.6671 | 0.9582 | −0.062 | 1.04 | 104 | 6.70 |
| P4HA1 | NM_001017962 | 2436 | 2626 | 1.0000 | 0.3995 | 1.0781 | 0.109 | 1.08 | 190 | 7.57 |
| P4HA1 | NM_001142595 | 47 | 53 | 1.0000 | 0.8605 | 1.1169 | 0.160 | 1.12 | 6 | 2.49 |
| P4HA1 | NM_001142596 | 29 | 11 | 0.9839 | 0.1962 | 0.3928 | −1.348 | 2.55 | 18 | 4.21 |
| P4HB | AK095938 | 8975 | 14414 | 0.0000 | 0.0000 | 1.6059 | 0.683 | 1.61 | 5439 | 12.41 |
| P4HB | BC014504 | 867 | 2319 | 0.0000 | 0.0000 | 2.6730 | 1.418 | 2.67 | 1452 | 10.50 |
| P4HB | NM_000918 | 46544 | 35567 | 0.0032 | 0.0000 | 0.7642 | −0.388 | 1.31 | 10977 | 13.42 |
| PAPD4 | AL833136 | 19 | 15 | 1.0000 | 0.7662 | 0.8087 | −0.306 | 1.24 | 4 | 1.91 |
| PAPD4 | BC047581 | 192 | 119 | 0.7176 | 0.0999 | 0.6201 | −0.689 | 1.61 | 73 | 6.19 |
| PAPD4 | NM_001114393 | 0 | 0 | 9999 | 9999 | 1.0000 | 0.000 | 1.00 | 0 | 0 |
| PAPD4 | NM_001114394 | 1012 | 432 | 0.0000 | 0.0000 | 0.4270 | −1.228 | 2.34 | 580 | 9.18 |
| PAPD4 | NM_173797 | 48 | 9 | 0.2999 | 0.0160 | 0.1971 | −2.343 | 5.07 | 39 | 5.30 |
| PARD3 | AF177228 | 50 | 92 | 0.8949 | 0.1629 | 1.8404 | 0.880 | 1.84 | 43 | 5.42 |
| PARD3 | AF454057 | 161 | 129 | 1.0000 | 0.4838 | 0.8026 | −0.317 | 1.25 | 32 | 5.00 |
| PARD3 | AF454058 | 5 | 0 | 0.6179 | 0.0647 | 0.1781 | −2.489 | 5.61 | 5 | 2.21 |
| PARD3 | AF454059 | 47 | 83 | 1.0000 | 0.2307 | 1.7521 | 0.809 | 1.75 | 36 | 5.17 |
| PARD3 | NM_001184785 | 0 | 5 | 0.3987 | 0.0264 | 6.4664 | 2.693 | 6.47 | 5 | 2.45 |
| PARD3 | NM_001184786 | 45 | 176 | 0.0194 | 0.0003 | 3.8376 | 1.940 | 3.84 | 131 | 7.03 |
| PARD3 | NM_001184787 | 0 | 0 | 9999 | 9999 | 1.0000 | 0.000 | 1.00 | 0 | 0 |
| PARD3 | NM_001184788 | 0 | 10 | 0.1777 | 0.0069 | 11.2495 | 3.492 | 11.25 | 10 | 3.36 |
| PARD3 | NM_001184789 | 0 | 0 | 9999 | 9999 | 1.0000 | 0.000 | 1.00 | 0 | 0 |
| PARD3 | NM_001184791 | 100 | 120 | 1.0000 | 0.5787 | 1.2039 | 0.268 | 1.20 | 21 | 4.36 |
| PARD3 | NM_001184792 | 297 | 399 | 0.8060 | 0.1245 | 1.3419 | 0.424 | 1.34 | 102 | 6.67 |
| PARD3 | NM_001184794 | 187 | 41 | 0.0025 | 0.0000 | 0.2233 | −2.163 | 4.48 | 146 | 7.19 |
| PARD3 | NM_019619 | 226 | 98 | 0.1255 | 0.0041 | 0.4369 | −1.194 | 2.29 | 128 | 7.00 |

TABLE 11-continued

RNA Abundance Modulation

| Gene | Trx_ID | ave DMSO | ave Cpd | padj (q val, FDR) | ttest (p val) | FC (x + 1) | L$_2$FC (x + 1) | amp FC (x + 1) | abs (Cpd − DMSO) | L$_2$abs (Cpd − DMSO) |
|---|---|---|---|---|---|---|---|---|---|---|
| PARN | AK299653 | 0 | 11 | 0.1469 | 0.0052 | 12.2744 | 3.618 | 12.27 | 11 | 3.49 |
| PARN | AK303348 | 0 | 1 | 1.0000 | 0.2461 | 2.0249 | 1.018 | 2.02 | 1 | 0.04 |
| PARN | NM_001134477 | 193 | 491 | 0.0000 | 0.0000 | 2.5379 | 1.344 | 2.54 | 298 | 8.22 |
| PARN | NM_001242992 | 18 | 11 | 1.0000 | 0.5048 | 0.5975 | −0.743 | 1.67 | 8 | 2.96 |
| PARN | NM_002582 | 1089 | 758 | 0.0796 | 0.0021 | 0.6962 | −0.522 | 1.44 | 331 | 8.37 |
| PARP14 | AB033094 | 3 | 7 | 1.0000 | 0.4576 | 2.1930 | 1.133 | 2.19 | 4 | 2.16 |
| PARP14 | AY134858 | 50 | 0 | 0.0001 | 0.0000 | 0.0195 | −5.682 | 51.35 | 50 | 5.65 |
| PARP14 | DQ063585 | 2 | 10 | 0.9380 | 0.1788 | 3.9533 | 1.983 | 3.95 | 8 | 3.07 |
| PARP14 | FW340085 | 3 | 0 | 0.7032 | 0.0952 | 0.2297 | −2.122 | 4.35 | 3 | 1.75 |
| PARP14 | NM_017554 | 540 | 614 | 1.0000 | 0.3959 | 1.1376 | 0.186 | 1.14 | 74 | 6.22 |
| PARVB | NM_001003828 | 0 | 2 | 0.6428 | 0.0725 | 2.8961 | 1.534 | 2.90 | 2 | 0.92 |
| PARVB | NM_001243385 | 112 | 310 | 0.0088 | 0.0001 | 2.7483 | 1.459 | 2.75 | 198 | 7.63 |
| PARVB | NM_001243386 | 61 | 46 | 1.0000 | 0.5336 | 0.7490 | −0.417 | 1.34 | 16 | 3.96 |
| PARVB | NM_013327 | 1673 | 1357 | 0.5229 | 0.0456 | 0.8113 | −0.302 | 1.23 | 316 | 8.30 |
| PCBP2 | AK023529 | 15 | 15 | 1.0000 | 0.9796 | 0.9717 | −0.041 | 1.03 | 0 | −1.12 |
| PCBP2 | AK130583 | 215 | 218 | 1.0000 | 0.9951 | 1.0151 | 0.022 | 1.02 | 3 | 1.71 |
| PCBP2 | AK296930 | 2321 | 1808 | 0.2067 | 0.0088 | 0.7788 | −0.361 | 1.28 | 514 | 9.00 |
| PCBP2 | AK299210 | 53 | 69 | 1.0000 | 0.5350 | 1.3031 | 0.382 | 1.30 | 16 | 4.02 |
| PCBP2 | AK302067 | 5 | 5 | 1.0000 | 0.9900 | 0.9857 | −0.014 | 1.01 | 0 | −4.08 |
| PCBP2 | NM_001098620 | 1243 | 1032 | 0.8226 | 0.1295 | 0.8306 | −0.268 | 1.20 | 211 | 7.72 |
| PCBP2 | NM_001128911 | 936 | 1399 | 0.0201 | 0.0003 | 1.4947 | 0.580 | 1.49 | 463 | 8.86 |
| PCBP2 | NM_001128912 | 763 | 358 | 0.0002 | 0.0000 | 0.4706 | −1.088 | 2.13 | 404 | 8.66 |
| PCBP2 | NM_001128913 | 1346 | 1597 | 0.8699 | 0.1505 | 1.1863 | 0.247 | 1.19 | 251 | 7.97 |
| PCBP2 | NM_001128914 | 1392 | 1357 | 1.0000 | 0.8432 | 0.9746 | −0.037 | 1.03 | 35 | 5.14 |
| PCBP2 | NM_005016 | 4564 | 3961 | 0.6566 | 0.0775 | 0.8678 | −0.205 | 1.15 | 603 | 9.24 |
| PCBP2 | NM_031989 | 276 | 849 | 0.0000 | 0.0000 | 3.0743 | 1.620 | 3.07 | 574 | 9.16 |
| PCBP4 | AF092441 | 17 | 0 | 0.0901 | 0.0025 | 0.0564 | −4.149 | 17.74 | 17 | 4.07 |
| PCBP4 | AF257770 | 8 | 21 | 1.0000 | 0.3173 | 2.3339 | 1.223 | 2.33 | 12 | 3.63 |
| PCBP4 | AF257771 | 10 | 0 | 0.2813 | 0.0144 | 0.0890 | −3.490 | 11.24 | 10 | 3.36 |
| PCBP4 | AK001244 | 15 | 11 | 1.0000 | 0.7200 | 0.7410 | −0.432 | 1.35 | 4 | 2.04 |
| PCBP4 | BX647811 | 19 | 3 | 0.7032 | 0.0919 | 0.2217 | −2.173 | 4.51 | 16 | 3.96 |
| PCBP4 | NM_001174100 | 78 | 94 | 1.0000 | 0.5962 | 1.2067 | 0.271 | 1.21 | 16 | 4.03 |
| PCBP4 | NM_020418 | 33 | 27 | 1.0000 | 0.7949 | 0.8263 | −0.275 | 1.21 | 6 | 2.56 |
| PCBP4 | NM_033008 | 659 | 362 | 0.0153 | 0.0002 | 0.5502 | −0.862 | 1.82 | 297 | 8.21 |
| PCBP4 | NM_033010 | 127 | 365 | 0.0018 | 0.0000 | 2.8621 | 1.517 | 2.86 | 238 | 7.90 |
| PCGF3 | AK057124 | 2 | 4 | 1.0000 | 0.7658 | 1.4684 | 0.554 | 1.47 | 1 | 0.56 |
| PCGF3 | AK125801 | 84 | 134 | 0.9732 | 0.1927 | 1.5867 | 0.666 | 1.59 | 50 | 5.64 |
| PCGF3 | AK225892 | 195 | 158 | 1.0000 | 0.5325 | 0.8134 | −0.298 | 1.23 | 37 | 5.19 |
| PCGF3 | AK300290 | 178 | 140 | 1.0000 | 0.3790 | 0.7884 | −0.343 | 1.27 | 38 | 5.25 |
| PCGF3 | BX648409 | 67 | 1 | 0.0000 | 0.0000 | 0.0248 | −5.331 | 40.26 | 66 | 6.05 |
| PCGF3 | NM_006315 | 952 | 976 | 1.0000 | 0.9332 | 1.0246 | 0.035 | 1.02 | 23 | 4.55 |
| PDLIM7 | AF345906 | 6 | 32 | 0.5316 | 0.0467 | 4.6716 | 2.224 | 4.67 | 26 | 4.71 |
| PDLIM7 | AK096826 | 173 | 201 | 1.0000 | 0.5444 | 1.1641 | 0.219 | 1.16 | 29 | 4.83 |
| PDLIM7 | BC067806 | 246 | 232 | 1.0000 | 0.8635 | 0.9429 | −0.085 | 1.06 | 14 | 3.82 |
| PDLIM7 | BC084575 | 48 | 57 | 1.0000 | 0.7145 | 1.2020 | 0.265 | 1.20 | 10 | 3.30 |
| PDLIM7 | NM_005451 | 3811 | 3864 | 1.0000 | 0.8329 | 1.0139 | 0.020 | 1.01 | 53 | 5.72 |
| PDLIM7 | NM_203352 | 380 | 122 | 0.0002 | 0.0000 | 0.3224 | −1.633 | 3.10 | 258 | 8.01 |
| PDLIM7 | NM_213636 | 380 | 270 | 0.7032 | 0.0922 | 0.7129 | −0.488 | 1.40 | 109 | 6.77 |
| PDXDC1 | AK295168 | 841 | 193 | 0.0000 | 0.0000 | 0.2305 | −2.117 | 4.34 | 648 | 9.34 |
| PDXDC1 | AK299111 | 36 | 8 | 0.5277 | 0.0462 | 0.2416 | −2.049 | 4.14 | 28 | 4.80 |
| PDXDC1 | AK299799 | 34 | 19 | 1.0000 | 0.3780 | 0.5741 | −0.801 | 1.74 | 15 | 3.89 |
| PDXDC1 | AY203955 | 10 | 4 | 1.0000 | 0.4123 | 0.4515 | −1.147 | 2.21 | 6 | 2.60 |
| PDXDC1 | BC033748 | 24 | 15 | 1.0000 | 0.5359 | 0.6442 | −0.634 | 1.55 | 9 | 3.14 |
| PDXDC1 | BC053946 | 119 | 33 | 0.1138 | 0.0036 | 0.2862 | −1.805 | 3.49 | 86 | 6.42 |
| PDXDC1 | BX648066 | 113 | 21 | 0.0144 | 0.0002 | 0.1900 | −2.396 | 5.26 | 92 | 6.52 |
| PDXDC1 | NM_015027 | 1694 | 326 | 0.0000 | 0.0000 | 0.1932 | −2.372 | 5.18 | 1367 | 10.42 |
| PEX5 | AK303515 | 71 | 0 | 0.0000 | 0.0000 | 0.0140 | −6.161 | 71.53 | 71 | 6.14 |
| PEX5 | NM_000319 | 91 | 72 | 1.0000 | 0.6505 | 0.7951 | −0.331 | 1.26 | 19 | 4.23 |
| PEX5 | NM_001131023 | 211 | 260 | 1.0000 | 0.3472 | 1.2334 | 0.303 | 1.23 | 49 | 5.63 |
| PEX5 | NM_001131024 | 449 | 469 | 1.0000 | 0.8258 | 1.0445 | 0.063 | 1.04 | 20 | 4.32 |
| PEX5 | NM_001131025 | 112 | 100 | 1.0000 | 0.7945 | 0.9001 | −0.152 | 1.11 | 11 | 3.49 |
| PEX5 | NM_001131026 | 2 | 4 | 1.0000 | 0.5198 | 1.9625 | 0.973 | 1.96 | 2 | 1.29 |
| PFKP | AK128373 | 47 | 57 | 1.0000 | 0.7030 | 1.2082 | 0.273 | 1.21 | 10 | 3.31 |
| PFKP | AK308003 | 49 | 45 | 1.0000 | 0.9779 | 0.9227 | −0.116 | 1.08 | 4 | 1.96 |
| PFKP | AK308226 | 272 | 67 | 0.0004 | 0.0000 | 0.2502 | −1.999 | 4.00 | 205 | 7.68 |
| PFKP | NM_002627 | 6177 | 6027 | 1.0000 | 0.7297 | 0.9758 | −0.035 | 1.02 | 149 | 7.22 |
| PHRF1 | BC041631 | 17 | 5 | 1.0000 | 0.2781 | 0.3679 | −1.442 | 2.72 | 11 | 3.48 |
| PHRF1 | BC112931 | 0 | 0 | 9999 | 9999 | 1.0000 | 0.000 | 1.00 | 0 | 0 |
| PHRF1 | BC136615 | 1043 | 1062 | 1.0000 | 0.8084 | 1.0181 | 0.026 | 1.02 | 19 | 4.24 |
| PHRF1 | BC144294 | 57 | 31 | 1.0000 | 0.2040 | 0.5513 | −0.859 | 1.81 | 26 | 4.69 |
| PHRF1 | BC144295 | 212 | 206 | 1.0000 | 0.9389 | 0.9742 | −0.038 | 1.03 | 5 | 2.46 |
| PHRF1 | NM_020901 | 64 | 0 | 0.0000 | 0.0000 | 0.0153 | −6.029 | 65.28 | 64 | 6.01 |
| PI4K2A | AK293733 | 22 | 21 | 1.0000 | 0.9682 | 0.9506 | −0.073 | 1.05 | 1 | 0.21 |
| PI4K2A | AK309343 | 194 | 15 | 0.0000 | 0.0000 | 0.0812 | −3.622 | 12.31 | 179 | 7.49 |

TABLE 11-continued

RNA Abundance Modulation

| Gene | Trx_ID | ave DMSO | ave Cpd | padj (q val, FDR) | ttest (p val) | FC (x + 1) | L₂FC (x + 1) | amp FC (x + 1) | abs (Cpd − DMSO) | L₂abs (Cpd − DMSO) |
|---|---|---|---|---|---|---|---|---|---|---|
| PI4K2A | NM_018425 | 1666 | 1840 | 1.0000 | 0.3428 | 1.1039 | 0.143 | 1.10 | 173 | 7.44 |
| POLE3 | NM_001278255 | 2029 | 2938 | 0.0070 | 0.0001 | 1.4476 | 0.534 | 1.45 | 909 | 9.83 |
| POLE3 | NM_017443 | 923 | 256 | 0.0000 | 0.0000 | 0.2777 | −1.848 | 3.60 | 667 | 9.38 |
| POLE3 | NR_027261 | 92 | 58 | 1.0000 | 0.2398 | 0.6323 | −0.661 | 1.58 | 34 | 5.09 |
| POLR3D | AK295725 | 1 | 2 | 1.0000 | 0.7889 | 1.4180 | 0.504 | 1.42 | 1 | −0.32 |
| POLR3D | BC004484 | 612 | 752 | 0.8543 | 0.1425 | 1.2290 | 0.298 | 1.23 | 140 | 7.13 |
| POLR3D | NM_001722 | 285 | 94 | 0.0043 | 0.0000 | 0.3318 | −1.591 | 3.01 | 191 | 7.58 |
| POSTN | AK300261 | 20 | 17 | 1.0000 | 0.8757 | 0.8620 | −0.214 | 1.16 | 3 | 1.51 |
| POSTN | AK304640 | 294 | 87 | 0.0003 | 0.0000 | 0.2977 | −1.748 | 3.36 | 207 | 7.69 |
| POSTN | EU262884 | 154 | 121 | 1.0000 | 0.4511 | 0.7899 | −0.340 | 1.27 | 33 | 5.03 |
| POSTN | EU262886 | 1996 | 1731 | 1.0000 | 0.2412 | 0.8670 | −0.206 | 1.15 | 266 | 8.05 |
| POSTN | GU354210 | 5160 | 5416 | 1.0000 | 0.4640 | 1.0497 | 0.070 | 1.05 | 256 | 8.00 |
| POSTN | NM_001135934 | 4788 | 5956 | 0.0968 | 0.0028 | 1.2440 | 0.315 | 1.24 | 1168 | 10.19 |
| POSTN | NM_001135935 | 32995 | 36035 | 0.8749 | 0.1523 | 1.0921 | 0.127 | 1.09 | 3040 | 11.57 |
| POSTN | NM_001135936 | 17741 | 16271 | 1.0000 | 0.2086 | 0.9171 | −0.125 | 1.09 | 1470 | 10.52 |
| POSTN | NM_006475 | 980 | 1033 | 1.0000 | 0.7279 | 1.0539 | 0.076 | 1.05 | 53 | 5.72 |
| PPARA | AK289821 | 8 | 37 | 0.5448 | 0.0500 | 4.2131 | 2.075 | 4.21 | 29 | 4.85 |
| PPARA | AY258329 | 0 | 0 | 1.0000 | 0.4944 | 1.3416 | 0.424 | 1.34 | 0 | −1.55 |
| PPARA | AY258331 | 4 | 1 | 1.0000 | 0.3301 | 0.3493 | −1.517 | 2.86 | 3 | 1.63 |
| PPARA | BC000052 | 41 | 34 | 1.0000 | 0.7645 | 0.8460 | −0.241 | 1.18 | 6 | 2.69 |
| PPARA | EU395809 | 218 | 309 | 0.8226 | 0.1296 | 1.4146 | 0.500 | 1.41 | 91 | 6.50 |
| PPARA | NM_001001928 | 306 | 311 | 1.0000 | 0.8791 | 1.0166 | 0.024 | 1.02 | 5 | 2.35 |
| PPARA | NM_005036 | 189 | 269 | 0.8269 | 0.1316 | 1.4227 | 0.509 | 1.42 | 80 | 6.33 |
| PPARA | S74349 | 219 | 44 | 0.0002 | 0.0000 | 0.2031 | −2.300 | 4.92 | 176 | 7.46 |
| PPP6R1 | BC113443 | 186 | 0 | 0.0000 | 0.0000 | 0.0054 | −7.546 | 186.86 | 186 | 7.54 |
| PPP6R1 | NM_014931 | 2807 | 2637 | 1.0000 | 0.4956 | 0.9396 | −0.090 | 1.06 | 170 | 7.41 |
| PPP6R2 | AK022669 | 0 | 0 | 9999 | 9999 | 1.0000 | 0 | 1.00 | 0 | 0 |
| PPP6R2 | BC000976 | 42 | 70 | 1.0000 | 0.2962 | 1.6548 | 0.727 | 1.65 | 28 | 4.82 |
| PPP6R2 | NM_001242898 | 657 | 635 | 1.0000 | 0.8475 | 0.9659 | −0.050 | 1.04 | 22 | 4.49 |
| PPP6R2 | NM_001242899 | 238 | 63 | 0.0015 | 0.0000 | 0.2673 | −1.904 | 3.74 | 175 | 7.45 |
| PPP6R2 | NM_001242900 | 102 | 120 | 1.0000 | 0.6501 | 1.1737 | 0.231 | 1.17 | 18 | 4.17 |
| PPP6R2 | NM_014678 | 96 | 142 | 1.0000 | 0.2594 | 1.4720 | 0.558 | 1.47 | 46 | 5.52 |
| PRNP | AB300826 | 38 | 37 | 1.0000 | 0.9880 | 0.9823 | −0.026 | 1.02 | 1 | −0.53 |
| PRNP | AX746518 | 1544 | 1725 | 1.0000 | 0.2934 | 1.1172 | 0.160 | 1.12 | 181 | 7.50 |
| PRNP | CCDS13080 | 495 | 142 | 0.0000 | 0.0000 | 0.2887 | −1.792 | 3.46 | 353 | 8.46 |
| PRNP | NM_001080121 | 124 | 84 | 1.0000 | 0.2827 | 0.6770 | −0.563 | 1.48 | 40 | 5.33 |
| PRNP | NM_001080122 | 25 | 51 | 1.0000 | 0.2209 | 2.0037 | 1.003 | 2.00 | 26 | 4.70 |
| PRNP | NM_001080123 | 2303 | 3504 | 0.0005 | 0.0000 | 1.5211 | 0.605 | 1.52 | 1201 | 10.23 |
| PRNP | NM_001271561 | 4158 | 3170 | 0.0497 | 0.0011 | 0.7624 | −0.391 | 1.31 | 988 | 9.95 |
| PXN | AB209034 | 35 | 31 | 1.0000 | 0.8058 | 0.8695 | −0.202 | 1.15 | 5 | 2.25 |
| PXN | AK122964 | 1205 | 1609 | 0.1818 | 0.0071 | 1.3351 | 0.417 | 1.34 | 404 | 8.66 |
| PXN | AK128712 | 107 | 75 | 1.0000 | 0.3642 | 0.7071 | −0.500 | 1.41 | 32 | 4.98 |
| PXN | BC052611 | 45 | 30 | 1.0000 | 0.4921 | 0.6770 | −0.563 | 1.48 | 15 | 3.89 |
| PXN | NM_001080855 | 201 | 0 | 0.0000 | 0.0000 | 0.0049 | −7.658 | 202.03 | 201 | 7.65 |
| PXN | NM_001243756 | 1224 | 907 | 0.2526 | 0.0120 | 0.7414 | −0.432 | 1.35 | 317 | 8.31 |
| PXN | NM_002859 | 4244 | 4157 | 1.0000 | 0.7776 | 0.9797 | −0.030 | 1.02 | 86 | 6.43 |
| PXN | NM_025157 | 11 | 18 | 1.0000 | 0.6065 | 1.5410 | 0.624 | 1.54 | 7 | 2.70 |
| RAB34 | NM_001142624 | 221 | 310 | 1.0000 | 0.2105 | 1.3997 | 0.485 | 1.40 | 89 | 6.47 |
| RAB34 | NM_001142625 | 58 | 45 | 1.0000 | 0.6369 | 0.7896 | −0.341 | 1.27 | 12 | 3.63 |
| RAB34 | NM_001144942 | 342 | 311 | 1.0000 | 0.8146 | 0.9095 | −0.137 | 1.10 | 31 | 4.95 |
| RAB34 | NM_001144943 | 667 | 360 | 0.0203 | 0.0003 | 0.5400 | −0.889 | 1.85 | 307 | 8.26 |
| RAB34 | NM_001256276 | 166 | 111 | 0.9898 | 0.1986 | 0.6702 | −0.577 | 1.49 | 55 | 5.78 |
| RAB34 | NM_001256277 | 782 | 941 | 0.9128 | 0.1680 | 1.2030 | 0.267 | 1.20 | 159 | 7.31 |
| RAB34 | NM_001256278 | 251 | 624 | 0.0001 | 0.0000 | 2.4830 | 1.312 | 2.48 | 373 | 8.54 |
| RAB34 | NM_031934 | 705 | 651 | 1.0000 | 0.4942 | 0.9233 | −0.115 | 1.08 | 54 | 5.76 |
| RAD23B | AK293532 | 2539 | 2261 | 1.0000 | 0.2029 | 0.8906 | −0.167 | 1.12 | 278 | 8.12 |
| RAD23B | NM_001244713 | 74 | 177 | 0.3221 | 0.0180 | 2.3750 | 1.248 | 2.37 | 103 | 6.68 |
| RAD23B | NM_001244724 | 6941 | 7235 | 0.5714 | 1.0423 | 0.060 | 1.04 | 293 | 8.20 | |
| RAD23B | NM_002874 | 105 | 0 | 0.0000 | 0.0000 | 0.0094 | −6.726 | 105.88 | 105 | 6.71 |
| RALB | AK127675 | 3 | 3 | 1.0000 | 1.0000 | 1.0176 | 0.025 | 1.02 | 0 | −3.71 |
| RALB | AK303214 | 341 | 868 | 0.0000 | 0.0000 | 2.5380 | 1.344 | 2.54 | 526 | 9.04 |
| RALB | AK304588 | 24 | 22 | 1.0000 | 0.9217 | 0.9422 | −0.086 | 1.06 | 1 | 0.52 |
| RALB | NM_002881 | 2417 | 1862 | 0.1759 | 0.0068 | 0.7704 | −0.376 | 1.30 | 555 | 9.12 |
| RAP1A | M22995 | 1230 | 1097 | 1.0000 | 0.3602 | 0.8917 | −0.165 | 1.12 | 133 | 7.06 |
| RAP1A | NM_001010935 | 319 | 781 | 0.0000 | 0.0000 | 2.4453 | 1.290 | 2.45 | 462 | 8.85 |
| RAP1A | NM_002884 | 848 | 585 | 0.1466 | 0.0051 | 0.6904 | −0.534 | 1.45 | 263 | 8.04 |
| RASSF8 | AY665468 | 368 | 939 | 0.0000 | 0.0000 | 2.5446 | 1.347 | 2.54 | 570 | 9.16 |
| RASSF8 | AY665470 | 7 | 12 | 1.0000 | 0.6101 | 1.5298 | 0.613 | 1.53 | 4 | 2.16 |
| RASSF8 | NM_001164746 | 5 | 6 | 1.0000 | 1.0000 | 1.1014 | 0.139 | 1.10 | 1 | −0.67 |
| RASSF8 | NM_001164747 | 839 | 819 | 1.0000 | 0.8121 | 0.9757 | −0.036 | 1.02 | 20 | 4.35 |
| RASSF8 | NM_001164748 | 1537 | 1316 | 0.9380 | 0.1787 | 0.8566 | −0.223 | 1.17 | 221 | 7.79 |
| RASSF8 | NM_007211 | 72 | 50 | 1.0000 | 0.4225 | 0.6930 | −0.529 | 1.44 | 23 | 4.49 |
| RBCK1 | AK303357 | 11 | 10 | 1.0000 | 0.9495 | 0.9556 | −0.066 | 1.05 | 1 | −0.94 |
| RBCK1 | AK309414 | 559 | 452 | 0.9630 | 0.1884 | 0.8086 | −0.307 | 1.24 | 107 | 6.74 |

TABLE 11-continued

RNA Abundance Modulation

| Gene | Trx_ID | ave DMSO | ave Cpd | padj (q val, FDR) | ttest (p val) | FC (x + 1) | $L_2$FC (x + 1) | amp FC (x + 1) | abs (Cpd − DMSO) | $L_2$abs (Cpd − DMSO) |
|---|---|---|---|---|---|---|---|---|---|---|
| RBCK1 | BC000983 | 49 | 47 | 1.0000 | 0.9575 | 0.9632 | −0.054 | 1.04 | 2 | 0.89 |
| RBCK1 | BC014116 | 61 | 0 | 0.0000 | 0.0000 | 0.0161 | −5.960 | 62.24 | 61 | 5.94 |
| RBCK1 | NM_006462 | 1 | 5 | 1.0000 | 0.3000 | 2.7372 | 1.453 | 2.74 | 4 | 1.88 |
| RBCK1 | NM_031229 | 1696 | 1373 | 0.5175 | 0.0435 | 0.8098 | −0.304 | 1.23 | 323 | 8.33 |
| RBFOX2 | AM419009 | 281 | 657 | 0.0001 | 0.0000 | 2.3351 | 1.223 | 2.34 | 376 | 8.56 |
| RBFOX2 | DQ894898 | 0 | 0 | 9999 | 9999 | 1.0000 | 0.000 | 1.00 | 0 | 0 |
| RBFOX2 | NM_001031695 | 546 | 623 | 1.0000 | 0.5931 | 1.1399 | 0.189 | 1.14 | 77 | 6.26 |
| RBFOX2 | NM_001082576 | 2080 | 2057 | 1.0000 | 0.9838 | 0.9891 | −0.016 | 1.01 | 23 | 4.51 |
| RBFOX2 | NM_001082577 | 794 | 681 | 1.0000 | 0.3228 | 0.8581 | −0.221 | 1.17 | 113 | 6.82 |
| RBFOX2 | NM_001082578 | 1855 | 1840 | 1.0000 | 0.9965 | 0.9917 | −0.012 | 1.01 | 15 | 3.95 |
| RBFOX2 | NM_014309 | 467 | 537 | 1.0000 | 0.4441 | 1.1500 | 0.202 | 1.15 | 70 | 6.13 |
| RGS10 | AF368902 | 87 | 0 | 0.0000 | 0.0000 | 0.0113 | −6.465 | 88.33 | 87 | 6.45 |
| RGS10 | NM_001005339 | 596 | 755 | 0.7482 | 0.1079 | 1.2656 | 0.340 | 1.27 | 159 | 7.31 |
| RGS10 | NM_002925 | 0 | 4 | 0.4480 | 0.0333 | 5.4241 | 2.439 | 5.42 | 4 | 2.15 |
| RIF1 | AK299572 | 3 | 4 | 1.0000 | 0.8421 | 1.3213 | 0.402 | 1.32 | 1 | 0.27 |
| RIF1 | AL080129 | 16 | 46 | 0.8192 | 0.1284 | 2.7042 | 1.435 | 2.70 | 29 | 4.87 |
| RIF1 | CR933663 | 0 | 0 | 9999 | 9999 | 1.0000 | 0.000 | 1.00 | 0 | 0 |
| RIF1 | NM_001177664 | 430 | 1010 | 0.0000 | 0.0000 | 2.3440 | 1.229 | 2.34 | 579 | 9.18 |
| RIF1 | NM_001177665 | 755 | 703 | 1.0000 | 0.5935 | 0.9314 | −0.103 | 1.07 | 52 | 5.70 |
| RIF1 | NM_018151 | 1315 | 1041 | 0.4941 | 0.0407 | 0.7916 | −0.337 | 1.26 | 274 | 8.10 |
| RNF14 | AK294262 | 6 | 11 | 1.0000 | 0.5448 | 1.7498 | 0.807 | 1.75 | 5 | 2.42 |
| RNF14 | AK295965 | 6 | 4 | 1.0000 | 0.6731 | 0.6714 | −0.575 | 1.49 | 2 | 1.22 |
| RNF14 | NM_001201365 | 629 | 298 | 0.0002 | 0.0000 | 0.4741 | −1.077 | 2.11 | 332 | 8.37 |
| RNF14 | NM_004290 | 423 | 334 | 1.0000 | 0.2458 | 0.7888 | −0.342 | 1.27 | 90 | 6.49 |
| RNF14 | NM_183398 | 337 | 324 | 1.0000 | 0.8529 | 0.9633 | −0.054 | 1.04 | 12 | 3.63 |
| RNF14 | NM_183400 | 233 | 263 | 1.0000 | 0.6405 | 1.1259 | 0.171 | 1.13 | 29 | 4.88 |
| RNF14 | NM_183401 | 798 | 1230 | 0.0097 | 0.0001 | 1.5405 | 0.623 | 1.54 | 432 | 8.75 |
| RNF19A | AB271913 | 0 | 7 | 0.3058 | 0.0165 | 7.9182 | 2.985 | 7.92 | 7 | 2.79 |
| RNF19A | NM_015435 | 97 | 0 | 0.0000 | 0.0000 | 0.0102 | −6.620 | 98.38 | 97 | 6.61 |
| RNF19A | NM_183419 | 1476 | 1709 | 0.9359 | 0.1777 | 1.1575 | 0.211 | 1.16 | 233 | 7.86 |
| SAMD9 | CCDS34680 | 87 | 87 | 1.0000 | 0.8229 | 1.0057 | 0.008 | 1.01 | 0 | −1.00 |
| SAMD9 | NM_001193307 | 104 | 0 | 0.0000 | 0.0000 | 0.0095 | −6.715 | 105.03 | 104 | 6.70 |
| SAMD9 | NM_017654 | 1361 | 1566 | 1.0000 | 0.2169 | 1.1506 | 0.202 | 1.15 | 205 | 7.68 |
| SCAF4 | AK057840 | 3 | 2 | 1.0000 | 0.8243 | 0.7587 | −0.398 | 1.32 | 1 | 0.08 |
| SCAF4 | AL117417 | 13 | 14 | 1.0000 | 0.9142 | 1.1151 | 0.157 | 1.12 | 2 | 0.66 |
| SCAF4 | NM_001145444 | 52 | 0 | 0.0000 | 0.0000 | 0.0189 | −5.727 | 52.98 | 52 | 5.70 |
| SCAF4 | NM_001145445 | 495 | 496 | 1.0000 | 0.9666 | 1.0007 | 0.001 | 1.00 | 0 | −1.56 |
| SCAF4 | NM_020706 | 627 | 590 | 1.0000 | 0.6797 | 0.9410 | −0.088 | 1.06 | 37 | 5.21 |
| SDCBP | AK128645 | 101 | 93 | 1.0000 | 0.8359 | 0.9295 | −0.106 | 1.08 | 7 | 2.84 |
| SDCBP | NM_001007067 | 203 | 259 | 1.0000 | 0.2279 | 1.2759 | 0.352 | 1.28 | 56 | 5.81 |
| SDCBP | NM_001007068 | 0 | 9 | 0.2136 | 0.0092 | 10.2591 | 3.359 | 10.26 | 9 | 3.21 |
| SDCBP | NM_001007069 | 807 | 856 | 1.0000 | 0.6344 | 1.0611 | 0.086 | 1.06 | 49 | 5.63 |
| SDCBP | NM_001007070 | 135 | 25 | 0.0064 | 0.0001 | 0.1926 | −2.376 | 5.19 | 110 | 6.78 |
| SDCBP | NM_005625 | 2881 | 2919 | 1.0000 | 0.9255 | 1.0133 | 0.019 | 1.01 | 38 | 5.26 |
| SERPINE2 | NM_001136528 | 15990 | 12207 | 0.0050 | 0.0001 | 0.7634 | −0.389 | 1.31 | 3783 | 11.89 |
| SERPINE2 | NM_001136530 | 1100 | 3121 | 0.0000 | 0.0000 | 2.8358 | 1.504 | 2.84 | 2021 | 10.98 |
| SERPINE2 | NM_006216 | 4180 | 3736 | 0.8752 | 0.1525 | 0.8937 | −0.162 | 1.12 | 444 | 8.80 |
| SERPINE2 | NR_073116 | 3 | 0 | 0.7796 | 0.1163 | 0.2481 | −2.011 | 4.03 | 3 | 1.60 |
| SF1 | CU675924 | 93 | 71 | 1.0000 | 0.5581 | 0.7701 | −0.377 | 1.30 | 22 | 4.43 |
| SF1 | D26121 | 9 | 14 | 1.0000 | 0.6271 | 1.5041 | 0.589 | 1.50 | 5 | 2.33 |
| SF1 | NM_001178030 | 280 | 237 | 1.0000 | 0.4893 | 0.8445 | −0.244 | 1.18 | 44 | 5.45 |
| SF1 | NM_001178031 | 1702 | 1467 | 0.8752 | 0.1525 | 0.8618 | −0.215 | 1.16 | 235 | 7.88 |
| SF1 | NM_004630 | 127 | 14 | 0.0006 | 0.0000 | 0.1178 | −3.086 | 8.49 | 113 | 6.82 |
| SF1 | NM_201995 | 262 | 239 | 1.0000 | 0.7712 | 0.9115 | −0.134 | 1.10 | 23 | 4.54 |
| SF1 | NM_201997 | 500 | 365 | 0.7152 | 0.0994 | 0.7294 | −0.455 | 1.37 | 136 | 7.08 |
| SF1 | NM_201998 | 2521 | 2574 | 1.0000 | 0.8849 | 1.0210 | 0.030 | 1.02 | 53 | 5.72 |
| SF1 | NR_033649 | 31 | 44 | 1.0000 | 0.6270 | 1.3906 | 0.476 | 1.39 | 13 | 3.66 |
| SF1 | NR_033650 | 2 | 6 | 1.0000 | 0.4267 | 2.3455 | 1.230 | 2.35 | 4 | 1.93 |
| SH3RF1 | BC041023 | 132 | 13 | 0.0002 | 0.0000 | 0.1056 | −3.243 | 9.47 | 119 | 6.89 |
| SH3RF1 | NM_020870 | 2418 | 2465 | 1.0000 | 0.8304 | 1.0194 | 0.028 | 1.02 | 47 | 5.55 |
| SKIL | NM_001145097 | 72 | 0 | 0.0000 | 0.0000 | 0.0137 | −6.190 | 72.99 | 72 | 6.17 |
| SKIL | NM_001145098 | 31 | 23 | 1.0000 | 0.6222 | 0.7527 | −0.410 | 1.33 | 8 | 2.97 |
| SKIL | NM_001248008 | 651 | 672 | 1.0000 | 0.9525 | 1.0319 | 0.045 | 1.03 | 21 | 4.38 |
| SKIL | NM_005414 | 1145 | 1266 | 1.0000 | 0.3488 | 1.1056 | 0.145 | 1.11 | 121 | 6.92 |
| SLC25A17 | AK298215 | 23 | 18 | 1.0000 | 0.6477 | 0.7691 | −0.379 | 1.30 | 6 | 2.50 |
| SLC25A17 | AK300553 | 3 | 280 | 0.0000 | 0.0000 | 69.5208 | 6.119 | 69.52 | 277 | 8.12 |
| SLC25A17 | BC024741 | 2 | 4 | 1.0000 | 0.5542 | 1.8867 | 0.916 | 1.89 | 3 | 1.34 |
| SLC25A17 | BX647991 | 10 | 7 | 1.0000 | 0.6883 | 0.7270 | −0.460 | 1.38 | 3 | 1.56 |
| SLC25A17 | NM_006358 | 758 | 351 | 0.0002 | 0.0000 | 0.4631 | −1.111 | 2.16 | 408 | 8.67 |
| SLC4A4 | AF004813 | 59 | 73 | 1.0000 | 0.6485 | 1.2312 | 0.300 | 1.23 | 14 | 3.79 |
| SLC4A4 | AF069510 | 523 | 12 | 0.0000 | 0.0000 | 0.0248 | −5.332 | 40.27 | 511 | 9.00 |
| SLC4A4 | AF157492 | 15 | 43 | 0.7509 | 0.1085 | 2.7644 | 1.467 | 2.76 | 28 | 4.82 |
| SLC4A4 | BC030977 | 5 | 0 | 0.6432 | 0.0752 | 0.1709 | −2.549 | 5.85 | 5 | 2.28 |
| SLC4A4 | CR749482 | 0 | 6 | 0.3799 | 0.0238 | 6.8298 | 2.772 | 6.83 | 6 | 2.54 |

TABLE 11-continued

RNA Abundance Modulation

| Gene | Trx_ID | ave DMSO | ave Cpd | padj (q val, FDR) | ttest (p val) | FC (x + 1) | L$_2$FC (x + 1) | amp FC (x + 1) | abs (Cpd − DMSO) | L$_2$abs (Cpd − DMSO) |
|---|---|---|---|---|---|---|---|---|---|---|
| SLC4A4 | NM_001098484 | 1011 | 2047 | 0.0000 | 0.0000 | 2.0239 | 1.017 | 2.02 | 1036 | 10.02 |
| SLC4A4 | NM_001134742 | 0 | 0 | 9999 | 9999 | 1.0000 | 0.000 | 1.00 | 0 | 0 |
| SLC4A4 | NM_003759 | 22 | 8 | 1.0000 | 0.2051 | 0.3816 | −1.390 | 2.62 | 14 | 3.84 |
| SMG1 | AF186377 | 840 | 615 | 0.4240 | 0.0295 | 0.7320 | −0.450 | 1.37 | 225 | 7.82 |
| SMG1 | AF395444 | 739 | 1812 | 0.0000 | 0.0000 | 2.4482 | 1.292 | 2.45 | 1072 | 10.07 |
| SMG1 | AK074359 | 0 | 0 | 9999 | 9999 | 1.0000 | 0.000 | 1.00 | 0 | 0 |
| SMG1 | NM_015092 | 3095 | 3078 | 1.0000 | 0.9254 | 0.9944 | −0.008 | 1.01 | 17 | 4.13 |
| SMN2 | JQ657801 | 1 | 1 | 1.0000 | 1.0000 | 1.0104 | 0.015 | 1.01 | 0 | −5.89 |
| SMN2 | JQ657801 | 0 | 0 | 9999 | 9999 | 1.0000 | 0.000 | 1.00 | 0 | 0 |
| SMN2 | JQ690861 | 6 | 0 | 0.5441 | 0.0489 | 0.1538 | −2.700 | 6.50 | 6 | 2.46 |
| SMN2 | JQ690864 | 4 | 0 | 0.6400 | 0.0713 | 0.1899 | −2.397 | 5.27 | 4 | 2.09 |
| SMN2 | JQ690866 | 0 | 0 | 9999 | 9999 | 1.0000 | 0.000 | 1.00 | 0 | 0 |
| SMN2 | JQ690867 | 11 | 0 | 0.2168 | 0.0094 | 0.0815 | −3.618 | 12.28 | 11 | 3.50 |
| SMN2 | JQ690868 | 4 | 0 | 0.7347 | 0.1048 | 0.2114 | −2.242 | 4.73 | 4 | 1.90 |
| SMN2 | JQ732167 | 0 | 1 | 1.0000 | 0.2461 | 2.0249 | 1.018 | 2.02 | 1 | 0.04 |
| SMN2 | JQ732167 | 0 | 0 | 9999 | 9999 | 1.0000 | 0.000 | 1.00 | 0 | 0 |
| SMN2 | JQ745297 | 0 | 0 | 9999 | 9999 | 1.0000 | 0.000 | 1.00 | 0 | 0 |
| SMN2 | NM_017411 | 435 | 742 | 0.0255 | 0.0005 | 1.7056 | 0.770 | 1.71 | 307 | 8.26 |
| SMN2 | NM_017411 | 0 | 0 | 9999 | 9999 | 1.0000 | 0.000 | 1.00 | 0 | 0 |
| SMN2 | NM_022875 | 219 | 12 | 0.0000 | 0.0000 | 0.0591 | −4.080 | 16.91 | 207 | 7.69 |
| SMN2 | NM_022875 | 0 | 0 | 9999 | 9999 | 1.0000 | 0.000 | 1.00 | 0 | 0 |
| SMN2 | NM_022876 | 0 | 16 | 0.0579 | 0.0014 | 16.9889 | 4.087 | 16.99 | 16 | 4.00 |
| SMN2 | NM_022876 | 0 | 0 | 9999 | 9999 | 1.0000 | 0.000 | 1.00 | 0 | 0 |
| SMN2 | NM_022877 | 28 | 5 | 0.5697 | 0.0535 | 0.2234 | −2.162 | 4.48 | 23 | 4.50 |
| SMN2 | NM_022877 | 3 | 0 | 0.7347 | 0.1043 | 0.2470 | −2.017 | 4.05 | 3 | 1.61 |
| SNHG16 | BC042949 | 5 | 17 | 1.0000 | 0.2267 | 2.9270 | 1.549 | 2.93 | 12 | 3.59 |
| SNHG16 | NR_038108 | 88 | 40 | 0.7366 | 0.1056 | 0.4658 | −1.102 | 2.15 | 47 | 5.57 |
| SNHG16 | NR_038109 | 1320 | 1062 | 0.5889 | 0.0579 | 0.8050 | −0.313 | 1.24 | 258 | 8.01 |
| SNHG16 | NR_038110 | 0 | 0 | 9999 | 9999 | 1.0000 | 0.000 | 1.00 | 0 | 0 |
| SNHG16 | NR_038111 | 403 | 164 | 0.0031 | 0.0000 | 0.4100 | −1.286 | 2.44 | 238 | 7.90 |
| SREBF1 | AB209609 | 4 | 0 | 0.6590 | 0.0787 | 0.2015 | −2.311 | 4.96 | 4 | 1.99 |
| SREBF1 | AB373958 | 53 | 0 | 0.0001 | 0.0000 | 0.0185 | −5.754 | 53.96 | 53 | 5.73 |
| SREBF1 | AB373959 | 148 | 164 | 0.7631 | 0.1177 | 1.1044 | 0.143 | 1.10 | 16 | 3.96 |
| SREBF1 | AK091131 | 115 | 135 | 1.0000 | 0.7851 | 1.1761 | 0.234 | 1.18 | 20 | 4.35 |
| SREBF1 | AK095325 | 46 | 33 | 1.0000 | 0.5430 | 0.7256 | −0.463 | 1.38 | 13 | 3.68 |
| SREBF1 | AK128320 | 20 | 9 | 1.0000 | 0.3710 | 0.4752 | −1.073 | 2.10 | 11 | 3.45 |
| SREBF1 | NM_001005291 | 19 | 27 | 1.0000 | 0.6387 | 1.4191 | 0.505 | 1.42 | 8 | 3.05 |
| SREBF1 | NM_004176 | 882 | 721 | 0.9174 | 0.1701 | 0.8184 | −0.289 | 1.22 | 160 | 7.32 |
| STAT3 | AK297994 | 6 | 33 | 0.4711 | 0.0365 | 4.7354 | 2.243 | 4.74 | 27 | 4.74 |
| STAT3 | L29277 | 1107 | 542 | 0.0000 | 0.0000 | 0.4897 | −1.030 | 2.04 | 565 | 9.14 |
| STAT3 | NM_003150 | 542 | 583 | 1.0000 | 0.6380 | 1.0747 | 0.104 | 1.07 | 41 | 5.34 |
| STAT3 | NM_139276 | 1497 | 2016 | 0.0928 | 0.0026 | 1.3462 | 0.429 | 1.35 | 519 | 9.02 |
| STAT3 | NM_213662 | 274 | 202 | 1.0000 | 0.2100 | 0.7388 | −0.437 | 1.35 | 72 | 6.17 |
| STC2 | AK095862 | 476 | 1101 | 0.0000 | 0.0000 | 2.3136 | 1.210 | 2.31 | 626 | 9.29 |
| STC2 | NM_003714 | 7245 | 5768 | 0.1106 | 0.0034 | 0.7961 | −0.329 | 1.26 | 1477 | 10.53 |
| STEAP2 | DQ656062 | 0 | 4 | 0.5204 | 0.0449 | 4.7722 | 2.255 | 4.77 | 4 | 1.92 |
| STEAP2 | NM_001040665 | 107 | 2 | 0.0000 | 0.0000 | 0.0284 | −5.138 | 35.22 | 105 | 6.71 |
| STEAP2 | NM_001040666 | 68 | 36 | 1.0000 | 0.2225 | 0.5414 | −0.885 | 1.85 | 32 | 4.98 |
| STEAP2 | NM_001244944 | 81 | 54 | 1.0000 | 0.3873 | 0.6665 | −0.585 | 1.50 | 27 | 4.77 |
| STEAP2 | NM_001244945 | 0 | 0 | 9999 | 9999 | 1.0000 | 0.000 | 1.00 | 0 | 0 |
| STEAP2 | NM_001244946 | 2 | 0 | 0.8060 | 0.1242 | 0.2908 | −1.782 | 3.44 | 2 | 1.29 |
| STEAP2 | NM_152999 | 121 | 150 | 1.0000 | 0.5185 | 1.2360 | 0.306 | 1.24 | 29 | 4.85 |
| STRN3 | BC143933 | 16 | 21 | 1.0000 | 0.6667 | 1.3236 | 0.404 | 1.32 | 5 | 2.42 |
| STRN3 | NM_001083893 | 113 | 750 | 0.0000 | 0.0000 | 6.6038 | 2.723 | 6.60 | 637 | 9.32 |
| STRN3 | NM_014574 | 850 | 477 | 0.0053 | 0.0001 | 0.5610 | −0.834 | 1.78 | 374 | 8.55 |
| SYNE1 | AB033088 | 36 | 52 | 1.0000 | 0.5112 | 1.4565 | 0.542 | 1.46 | 17 | 4.06 |
| SYNE1 | AB051543 | 185 | 98 | 0.4720 | 0.0370 | 0.5297 | −0.917 | 1.89 | 88 | 6.45 |
| SYNE1 | AK308717 | 34 | 8 | 0.6179 | 0.0644 | 0.2635 | −1.924 | 3.80 | 26 | 4.68 |
| SYNE1 | AK310977 | 17 | 13 | 1.0000 | 0.7740 | 0.7755 | −0.367 | 1.29 | 4 | 2.00 |
| SYNE1 | AL713682 | 4 | 4 | 1.0000 | 0.9516 | 0.9072 | −0.141 | 1.10 | 0 | −1.03 |
| SYNE1 | AY061755 | 396 | 426 | 1.0000 | 0.6728 | 1.0755 | 0.105 | 1.08 | 30 | 4.91 |
| SYNE1 | BC028616 | 25 | 17 | 1.0000 | 0.6701 | 0.7104 | −0.493 | 1.41 | 8 | 2.91 |
| SYNE1 | BC039121 | 50 | 53 | 1.0000 | 0.8884 | 1.0588 | 0.082 | 1.06 | 3 | 1.57 |
| SYNE1 | BX537517 | 22 | 20 | 1.0000 | 0.9331 | 0.9278 | −0.108 | 1.08 | 2 | 0.73 |
| SYNE1 | BX647837 | 336 | 359 | 1.0000 | 0.7213 | 1.0670 | 0.094 | 1.07 | 23 | 4.50 |
| SYNE1 | CR933676 | 5 | 8 | 1.0000 | 0.5456 | 1.6041 | 0.682 | 1.60 | 4 | 1.82 |
| SYNE1 | FM162565 | 13 | 5 | 1.0000 | 0.3544 | 0.4197 | −1.252 | 2.38 | 8 | 3.05 |
| SYNE1 | JQ740784 | 0 | 1 | 0.7032 | 0.0967 | 2.3666 | 1.243 | 2.37 | 1 | 0.45 |
| SYNE1 | JQ740786 | 2 | 3 | 1.0000 | 0.8719 | 1.3018 | 0.380 | 1.30 | 1 | −0.08 |
| SYNE1 | NM_033071 | 52 | 286 | 0.0000 | 0.0000 | 5.4600 | 2.449 | 5.46 | 235 | 7.87 |
| SYNE1 | NM_182961 | 2273 | 2826 | 0.2136 | 0.0092 | 1.2432 | 0.314 | 1.24 | 553 | 9.11 |
| SYNE2 | AF357236 | 0 | 3 | 0.6006 | 0.0604 | 3.5281 | 1.819 | 3.53 | 3 | 1.34 |
| SYNE2 | AK074055 | 0 | 4 | 0.5204 | 0.0449 | 4.7581 | 2.250 | 4.76 | 4 | 1.91 |
| SYNE2 | AK127612 | 9 | 10 | 1.0000 | 0.8660 | 1.1535 | 0.206 | 1.15 | 1 | 0.57 |

TABLE 11-continued

RNA Abundance Modulation

| Gene | Trx_ID | ave DMSO | ave Cpd | padj (q val, FDR) | ttest (p val) | FC (x + 1) | L₂FC (x + 1) | amp FC (x + 1) | abs (Cpd − DMSO) | L₂abs (Cpd − DMSO) |
|---|---|---|---|---|---|---|---|---|---|---|
| SYNE2 | AK128631 | 1 | 0 | 1.0000 | 0.6668 | 0.6213 | −0.687 | 1.61 | 1 | −0.71 |
| SYNE2 | AK297874 | 4 | 0 | 0.6786 | 0.0865 | 0.2147 | −2.220 | 4.66 | 4 | 1.87 |
| SYNE2 | AY061759 | 2 | 17 | 0.5715 | 0.0539 | 6.3697 | 2.671 | 6.37 | 15 | 3.93 |
| SYNE2 | AY184205 | 0 | 0 | 9999 | 9999 | 1.0000 | 0.000 | 1.00 | 0 | 0 |
| SYNE2 | BC036941 | 6 | 4 | 1.0000 | 0.7080 | 0.6891 | −0.537 | 1.45 | 2 | 1.06 |
| SYNE2 | BX537642 | 53 | 37 | 1.0000 | 0.4793 | 0.7043 | −0.506 | 1.42 | 16 | 4.00 |
| SYNE2 | BX538095 | 13 | 8 | 1.0000 | 0.6485 | 0.6017 | −0.733 | 1.66 | 6 | 2.50 |
| SYNE2 | CR749324 | 0 | 0 | 9999 | 9999 | 1.0000 | 0.000 | 1.00 | 0 | 0 |
| SYNE2 | NM_015180 | 247 | 99 | 0.0361 | 0.0007 | 0.4018 | −1.315 | 2.49 | 148 | 7.21 |
| SYNE2 | NM_182910 | 1 | 1 | 1.0000 | 1.0000 | 0.9516 | −0.072 | 1.05 | 0 | −3.05 |
| SYNE2 | NM_182913 | 0 | 1 | 1.0000 | 0.3259 | 1.6833 | 0.751 | 1.68 | 1 | −0.55 |
| SYNE2 | NM_182914 | 139 | 474 | 0.0000 | 0.0000 | 3.3883 | 1.761 | 3.39 | 335 | 8.39 |
| TACC1 | AB029026 | 0 | 0 | 9999 | 9999 | 1.0000 | 0.000 | 1.00 | 0 | 0 |
| TACC1 | AB463317 | 49 | 0 | 0.0005 | 0.0000 | 0.0264 | −5.245 | 37.92 | 49 | 5.60 |
| TACC1 | AK294931 | 1077 | 1393 | 0.4170 | 0.0284 | 1.2932 | 0.371 | 1.29 | 316 | 8.30 |
| TACC1 | AK295841 | 9 | 5 | 1.0000 | 0.5266 | 0.5502 | −0.862 | 1.82 | 5 | 2.21 |
| TACC1 | AK303596 | 0 | 0 | 9999 | 9999 | 1.0000 | 0.000 | 1.00 | 0 | 0 |
| TACC1 | AK304725 | 63 | 260 | 0.0004 | 0.0000 | 4.0780 | 2.028 | 4.08 | 197 | 7.62 |
| TACC1 | AK308849 | 3 | 4 | 1.0000 | 0.8907 | 1.2467 | 0.318 | 1.25 | 1 | −0.11 |
| TACC1 | AY072874 | 1 | 0 | 1.0000 | 0.8105 | 0.6337 | −0.658 | 1.58 | 1 | −0.37 |
| TACC1 | NM_001122824 | 424 | 369 | 1.0000 | 0.4640 | 0.8715 | −0.198 | 1.15 | 55 | 5.77 |
| TACC1 | NM_001146216 | 0 | 0 | 9999 | 9999 | 1.0000 | 0.000 | 1.00 | 0 | 0 |
| TACC1 | NM_006283 | 2099 | 2205 | 1.0000 | 0.6051 | 1.0508 | 0.071 | 1.05 | 107 | 6.74 |
| TARS | NM_001258437 | 731 | 1844 | 0.0000 | 0.0000 | 2.5202 | 1.334 | 2.52 | 1113 | 10.12 |
| TARS | NM_001258438 | 0 | 0 | 9999 | 9999 | 1.0000 | 0.000 | 1.00 | 0 | 0 |
| TARS | NM_152295 | 6524 | 5710 | 0.6400 | 0.0711 | 0.8753 | −0.192 | 1.14 | 814 | 9.67 |
| TARS | NR_047676 | 35 | 30 | 1.0000 | 0.8689 | 0.8745 | −0.193 | 1.14 | 4 | 2.16 |
| TARS | NR_047677 | 17 | 12 | 1.0000 | 0.6288 | 0.7331 | −0.448 | 1.36 | 5 | 2.28 |
| TARS | NR_047678 | 92 | 57 | 1.0000 | 0.2300 | 0.6296 | −0.667 | 1.59 | 34 | 5.10 |
| TGFBI | AK094055 | 7294 | 8871 | 0.1961 | 0.0081 | 1.2163 | 0.282 | 1.22 | 1578 | 10.62 |
| TGFBI | AK303643 | 7532 | 8784 | 0.4394 | 0.0317 | 1.1662 | 0.222 | 1.17 | 1252 | 10.29 |
| TGFBI | BC007229 | 6519 | 13175 | 0.0000 | 0.0000 | 2.0209 | 1.015 | 2.02 | 6656 | 12.70 |
| TGFBI | BC026352 | 941 | 538 | 0.0054 | 0.0001 | 0.5728 | −0.804 | 1.75 | 402 | 8.65 |
| TGFBI | NM_000358 | 469691 | 442492 | 1.0000 | 0.5665 | 0.9421 | −0.086 | 1.06 | 27199 | 14.73 |
| TMEM47 | AK311054 | 559 | 2376 | 0.0000 | 0.0000 | 4.2407 | 2.084 | 4.24 | 1816 | 10.83 |
| TMEM47 | NM_031442 | 7456 | 6214 | 0.2627 | 0.0129 | 0.8334 | −0.263 | 1.20 | 1242 | 10.28 |
| TNC | BC151843 | 786 | 352 | 0.0001 | 0.0000 | 0.4490 | −1.155 | 2.23 | 433 | 8.76 |
| TNC | GU473235 | 4687 | 4810 | 1.0000 | 0.6762 | 1.0262 | 0.037 | 1.03 | 123 | 6.94 |
| TNC | NM_002160 | 25928 | 24245 | 1.0000 | 0.3289 | 0.9351 | −0.097 | 1.07 | 1682 | 10.72 |
| TNFRSF12A | AB035481 | 203 | 46 | 0.0020 | 0.0000 | 0.2318 | −2.109 | 4.31 | 156 | 7.29 |
| TNFRSF12A | BC020538 | 151 | 128 | 1.0000 | 0.5854 | 0.8482 | −0.238 | 1.18 | 23 | 4.53 |
| TNFRSF12A | NM_016639 | 6358 | 5835 | 1.0000 | 0.2578 | 0.9177 | −0.124 | 1.09 | 523 | 9.03 |
| TNS1 | AK001785 | 2 | 6 | 1.0000 | 0.3986 | 2.5356 | 1.342 | 2.54 | 4 | 2.12 |
| TNS1 | AK024948 | 1192 | 1186 | 1.0000 | 0.9311 | 0.9947 | −0.008 | 1.01 | 6 | 2.67 |
| TNS1 | AK300345 | 507 | 233 | 0.0031 | 0.0000 | 0.4603 | −1.119 | 2.17 | 274 | 8.10 |
| TNS1 | AK309785 | 374 | 473 | 0.8949 | 0.1628 | 1.2641 | 0.338 | 1.26 | 99 | 6.63 |
| TNS1 | BC071905 | 5 | 13 | 1.0000 | 0.3495 | 2.4257 | 1.278 | 2.43 | 8 | 3.03 |
| TNS1 | BC116187 | 160 | 279 | 0.2534 | 0.0121 | 1.7369 | 0.796 | 1.74 | 119 | 6.89 |
| TNS1 | BC126910 | 4880 | 4409 | 1.0000 | 0.2287 | 0.9035 | −0.146 | 1.11 | 471 | 8.88 |
| TNS1 | BC141869 | 9 | 8 | 1.0000 | 0.8850 | 0.8517 | −0.232 | 1.17 | 2 | 0.59 |
| TNS1 | NM_022648 | 1118 | 1181 | 1.0000 | 0.5380 | 1.0563 | 0.079 | 1.06 | 63 | 5.98 |
| TRAF3 | NM_001199427 | 17 | 11 | 1.0000 | 0.5583 | 0.6438 | −0.635 | 1.55 | 6 | 2.68 |
| TRAF3 | NM_003300 | 345 | 80 | 0.0000 | 0.0000 | 0.2333 | −2.100 | 4.29 | 266 | 8.05 |
| TRAF3 | NM_145725 | 1002 | 1203 | 0.8774 | 0.1531 | 1.1993 | 0.262 | 1.20 | 200 | 7.64 |
| TRAF3 | NM_145726 | 0 | 0 | 9999 | 9999 | 1.0000 | 0.000 | 1.00 | 0 | 0 |
| TRIM28 | AK131063 | 645 | 175 | 0.0000 | 0.0000 | 0.2716 | −1.880 | 3.68 | 471 | 8.88 |
| TRIM28 | BC052986 | 29 | 10 | 0.2153 | 0.3769 | 0.3769 | −1.408 | 2.65 | 19 | 4.21 |
| TRIM28 | NM_005762 | 8430 | 7572 | 0.7817 | 0.1176 | 0.8982 | −0.155 | 1.11 | 858 | 9.75 |
| TSC2 | AK094152 | 12 | 8 | 1.0000 | 0.6446 | 0.6781 | −0.561 | 1.47 | 4 | 2.05 |
| TSC2 | AK294548 | 2 | 2 | 1.0000 | 1.0000 | 1.0129 | 0.019 | 1.01 | 0 | −4.70 |
| TSC2 | AK295672 | 355 | 118 | 0.0005 | 0.0000 | 0.3338 | −1.583 | 3.00 | 237 | 7.89 |
| TSC2 | AK299343 | 388 | 347 | 1.0000 | 0.5415 | 0.8946 | −0.161 | 1.12 | 41 | 5.36 |
| TSC2 | BX647816 | 0 | 0 | 9999 | 9999 | 1.0000 | 0.000 | 1.00 | 0 | 0 |
| TSC2 | NM_000548 | 94 | 35 | 0.5023 | 0.0418 | 0.3798 | −1.397 | 2.63 | 59 | 5.89 |
| TSC2 | NM_001077183 | 1256 | 1258 | 1.0000 | 0.9215 | 1.0016 | 0.002 | 1.00 | 2 | 0.97 |
| TSC2 | NM_001114382 | 122 | 165 | 1.0000 | 0.3649 | 1.3527 | 0.436 | 1.35 | 43 | 5.44 |
| TSHZ1 | CCDS12009 | 145 | 18 | 0.0003 | 0.0000 | 0.1291 | −2.954 | 7.75 | 128 | 6.99 |
| TSHZ1 | NM_005786 | 728 | 802 | 1.0000 | 0.4429 | 1.1022 | 0.140 | 1.10 | 74 | 6.22 |
| TTC7A | AB032966 | 0 | 0 | 9999 | 9999 | 1.0000 | 0.000 | 1.00 | 0 | 0 |
| TTC7A | AK056464 | 96 | 86 | 1.0000 | 0.6962 | 0.8888 | −0.170 | 1.13 | 11 | 3.44 |
| TTC7A | BC035708 | 107 | 16 | 0.0086 | 0.0001 | 0.1593 | −2.650 | 6.28 | 91 | 6.51 |
| TTC7A | BC047709 | 91 | 75 | 1.0000 | 0.6108 | 0.8268 | −0.274 | 1.21 | 16 | 3.99 |
| TTC7A | BC082965 | 12 | 4 | 1.0000 | 0.3988 | 0.4058 | −1.301 | 2.46 | 7 | 2.90 |
| TTC7A | BC111487 | 7 | 0 | 0.4691 | 0.0363 | 0.1182 | −3.081 | 8.46 | 7 | 2.90 |

TABLE 11-continued

RNA Abundance Modulation

| Gene | Trx_ID | ave DMSO | ave Cpd | padj (q val, FDR) | ttest (p val) | FC (x + 1) | L$_2$FC (x + 1) | amp FC (x + 1) | abs (Cpd − DMSO) | L$_2$abs (Cpd − DMSO) |
|---|---|---|---|---|---|---|---|---|---|---|
| TTC7A | BC114365 | 0 | 12 | 0.1206 | 0.0039 | 13.3454 | 3.738 | 13.35 | 12 | 3.63 |
| TTC7A | NM_020458 | 641 | 717 | 1.0000 | 0.3632 | 1.1186 | 0.162 | 1.12 | 76 | 6.25 |
| TUBB2C | CU691671 | 184 | 0 | 0.0000 | 0.0000 | 0.0054 | −7.530 | 184.79 | 184 | 7.52 |
| TUBB3 | AK122757 | 31 | 19 | 1.0000 | 0.4782 | 0.6353 | −0.655 | 1.57 | 12 | 3.54 |
| TUBB3 | AK127418 | 15 | 11 | 1.0000 | 0.7192 | 0.7690 | −0.379 | 1.30 | 4 | 1.87 |
| TUBB3 | AK307201 | 3 | 2 | 1.0000 | 0.9357 | 0.8116 | −0.301 | 1.23 | 1 | −0.38 |
| TUBB3 | BT006971 | 42 | 52 | 1.0000 | 0.6340 | 1.2322 | 0.301 | 1.23 | 10 | 3.33 |
| TUBB3 | CU674385 | 74 | 6 | 0.0054 | 0.0001 | 0.0959 | −3.382 | 10.43 | 68 | 6.08 |
| TUBB3 | NM_001197181 | 52 | 63 | 1.0000 | 0.6932 | 1.2118 | 0.277 | 1.21 | 11 | 3.48 |
| TUBB3 | NM_006086 | 9562 | 8223 | 0.4561 | 0.0343 | 0.8599 | −0.218 | 1.16 | 1340 | 10.39 |
| TXNL1 | AB209263 | 32 | 25 | 1.0000 | 0.7503 | 0.8052 | −0.313 | 1.24 | 6 | 2.68 |
| TXNL1 | AK094926 | 0 | 0 | 9999 | 9999 | 1.0000 | 0.000 | 1.00 | 0 | 0 |
| TXNL1 | BC025017 | 333 | 790 | 0.0000 | 0.0000 | 2.3702 | 1.245 | 2.37 | 457 | 8.84 |
| TXNL1 | NM_004786 | 1509 | 1072 | 0.0807 | 0.0021 | 0.7108 | −0.493 | 1.41 | 437 | 8.77 |
| TXNL1 | NR_024546 | 6 | 14 | 1.0000 | 0.4627 | 1.9923 | 0.994 | 1.99 | 7 | 2.88 |
| TXNRD1 | AK128515 | 2342 | 2598 | 1.0000 | 0.2962 | 1.1094 | 0.150 | 1.11 | 256 | 8.00 |
| TXNRD1 | AK308881 | 2664 | 2692 | 1.0000 | 0.9662 | 1.0106 | 0.015 | 1.01 | 28 | 4.82 |
| TXNRD1 | AY344069 | 4 | 6 | 1.0000 | 0.7126 | 1.3823 | 0.467 | 1.38 | 2 | 0.94 |
| TXNRD1 | NM_001093771 | 96 | 0 | 0.0000 | 0.0000 | 0.0103 | −6.596 | 96.70 | 96 | 6.58 |
| TXNRD1 | NM_001261445 | 363 | 295 | 1.0000 | 0.2865 | 0.8132 | −0.298 | 1.23 | 68 | 6.09 |
| TXNRD1 | NM_001261446 | 87 | 63 | 1.0000 | 0.4120 | 0.7261 | −0.462 | 1.38 | 24 | 4.59 |
| TXNRD1 | NM_003330 | 8252 | 7230 | 0.6078 | 0.0627 | 0.8763 | −0.191 | 1.14 | 1021 | 10.00 |
| TXNRD1 | NM_182729 | 12823 | 14180 | 0.8111 | 0.1260 | 1.1059 | 0.145 | 1.11 | 1357 | 10.41 |
| TXNRD1 | NM_182742 | 1782 | 1637 | 1.0000 | 0.4098 | 0.9186 | −0.122 | 1.09 | 145 | 7.18 |
| TXNRD1 | NM_182743 | 2362 | 2682 | 0.9028 | 0.1654 | 1.1355 | 0.183 | 1.14 | 320 | 8.32 |
| UBE2G2 | NM_001202489 | 59 | 0 | 0.0000 | 0.0000 | 0.0167 | −5.908 | 60.05 | 59 | 5.88 |
| UBE2G2 | NM_003343 | 1990 | 2240 | 1.0000 | 0.2362 | 1.1252 | 0.170 | 1.13 | 249 | 7.96 |
| UBE2G2 | NM_182688 | 54 | 67 | 1.0000 | 0.6718 | 1.2470 | 0.318 | 1.25 | 14 | 3.76 |
| UBE2V1 | NM_001032288 | 4288 | 5135 | 0.3726 | 0.0230 | 1.1977 | 0.260 | 1.20 | 848 | 9.73 |
| UBE2V1 | NM_001257393 | 11 | 11 | 1.0000 | 0.9525 | 1.0013 | 0.002 | 1.00 | 0 | −5.94 |
| UBE2V1 | NM_001257394 | 18 | 1 | 0.2793 | 0.0142 | 0.0892 | −3.487 | 11.21 | 17 | 4.11 |
| UBE2V1 | NM_001257397 | 20 | 25 | 1.0000 | 0.7933 | 1.2418 | 0.312 | 1.24 | 5 | 2.32 |
| UBE2V1 | NM_001257399 | 153 | 214 | 0.9916 | 0.1993 | 1.3974 | 0.483 | 1.40 | 61 | 5.94 |
| UBE2V1 | NM_021988 | 74 | 62 | 1.0000 | 0.6795 | 0.8449 | −0.243 | 1.18 | 12 | 3.54 |
| UBE2V1 | NM_022442 | 2 | 0 | 0.8060 | 0.1242 | 0.2908 | −1.782 | 3.44 | 2 | 1.29 |
| UBE2V1 | NM_199144 | 0 | 12 | 0.1240 | 0.0040 | 12.6923 | 3.666 | 12.69 | 12 | 3.55 |
| UBE2V1 | NR_047554 | 353 | 92 | 0.0000 | 0.0000 | 0.2632 | −1.926 | 3.80 | 261 | 8.03 |
| UBE2V1 | NR_047555 | 5 | 2 | 1.0000 | 0.5004 | 0.4906 | −1.027 | 2.04 | 3 | 1.67 |
| UBE2V1 | NR_047556 | 29 | 10 | 0.9231 | 0.1732 | 0.3704 | −1.433 | 2.70 | 19 | 4.25 |
| UBQLN4 | AK302895 | 59 | 290 | 0.0000 | 0.0000 | 4.8383 | 2.274 | 4.84 | 231 | 7.85 |
| UBQLN4 | NM_020131 | 1732 | 1384 | 0.4249 | 0.0297 | 0.7989 | −0.324 | 1.25 | 349 | 8.45 |
| UNC5B | NM_001244889 | 94 | 328 | 0.0002 | 0.0000 | 3.4699 | 1.795 | 3.47 | 234 | 7.87 |
| UNC5B | NM_170744 | 3374 | 2399 | 0.0122 | 0.0002 | 0.7113 | −0.491 | 1.41 | 974 | 9.93 |
| USP19 | AK296447 | 74 | 57 | 1.0000 | 0.5491 | 0.7767 | −0.365 | 1.29 | 17 | 4.07 |
| USP19 | BC082241 | 252 | 325 | 1.0000 | 0.2703 | 1.2869 | 0.364 | 1.29 | 73 | 6.18 |
| USP19 | BC128088 | 151 | 109 | 1.0000 | 0.3255 | 0.7263 | −0.461 | 1.38 | 42 | 5.38 |
| USP19 | NM_001199160 | 0 | 78 | 0.0000 | 0.0000 | 78.8241 | 6.301 | 78.82 | 78 | 6.28 |
| USP19 | NM_001199161 | 775 | 636 | 0.9964 | 0.2010 | 0.8216 | −0.283 | 1.22 | 138 | 7.11 |
| USP19 | NM_001199162 | 87 | 94 | 1.0000 | 0.9172 | 1.0804 | 0.112 | 1.08 | 7 | 2.83 |
| USP19 | NM_006677 | 96 | 0 | 0.0000 | 0.0000 | 0.0103 | −6.598 | 96.90 | 96 | 6.58 |
| VARS2 | AB067472 | 5 | 2 | 1.0000 | 0.5589 | 0.5225 | −0.937 | 1.91 | 3 | 1.63 |
| VARS2 | AK000511 | 23 | 28 | 1.0000 | 0.8207 | 1.1695 | 0.226 | 1.17 | 4 | 2.05 |
| VARS2 | AK000511 | 12 | 14 | 1.0000 | 0.8440 | 1.1544 | 0.207 | 1.15 | 2 | 0.99 |
| VARS2 | AK094483 | 1 | 2 | 1.0000 | 0.8214 | 1.2031 | 0.267 | 1.20 | 1 | −0.98 |
| VARS2 | AK094483 | 1 | 1 | 1.0000 | 1.0000 | 1.0438 | 0.062 | 1.04 | 0 | −3.82 |
| VARS2 | AK125069 | 1 | 0 | 1.0000 | 0.5202 | 0.4719 | −1.084 | 2.12 | 1 | 0.16 |
| VARS2 | AK125069 | 3 | 2 | 1.0000 | 0.6968 | 0.7007 | −0.513 | 1.43 | 1 | 0.38 |
| VARS2 | AK125069 | 5 | 8 | 1.0000 | 0.7348 | 1.4127 | 0.498 | 1.41 | 3 | 1.36 |
| VARS2 | BC063427 | 8 | 8 | 1.0000 | 1.0000 | 0.9824 | −0.026 | 1.02 | 0 | −2.65 |
| VARS2 | BC143535 | 10 | 0 | 0.3437 | 0.0202 | 0.0935 | −3.420 | 10.70 | 10 | 3.28 |
| VARS2 | BC143535 | 0 | 5 | 0.3987 | 0.0264 | 6.4869 | 2.698 | 6.49 | 5 | 2.46 |
| VARS2 | BC143535 | 62 | 55 | 1.0000 | 0.6744 | 0.8897 | −0.169 | 1.12 | 7 | 2.79 |
| VARS2 | BC143535 | 23 | 34 | 1.0000 | 0.4719 | 1.4590 | 0.545 | 1.46 | 11 | 3.45 |
| VARS2 | BC143536 | 0 | 44 | 0.0002 | 0.0000 | 45.0489 | 5.493 | 45.05 | 44 | 5.46 |
| VARS2 | BC143536 | 15 | 42 | 0.6696 | 0.0840 | 2.7546 | 1.462 | 2.75 | 27 | 4.77 |
| VARS2 | NM_001167733 | 51 | 0 | 0.0001 | 0.0000 | 0.0194 | −5.688 | 51.56 | 51 | 5.66 |
| VARS2 | NM_001167733 | 15 | 0 | 0.1145 | 0.0036 | 0.0634 | −3.979 | 15.76 | 15 | 3.88 |
| VARS2 | NM_001167734 | 50 | 50 | 1.0000 | 0.9258 | 1.0112 | 0.016 | 1.01 | 1 | −0.82 |
| VARS2 | NM_001167734 | 44 | 33 | 1.0000 | 0.6320 | 0.7683 | −0.380 | 1.30 | 10 | 3.37 |
| VARS2 | NM_020442 | 21 | 0 | 0.0348 | 0.0007 | 0.0454 | −4.461 | 22.03 | 21 | 4.39 |
| VARS2 | NM_020442 | 127 | 78 | 1.0000 | 0.2076 | 0.6148 | −0.702 | 1.63 | 49 | 5.63 |
| VCL | AK300280 | 14 | 10 | 1.0000 | 0.7302 | 0.7290 | −0.456 | 1.37 | 4 | 2.04 |
| VCL | AK304823 | 64 | 0 | 0.0000 | 0.0000 | 0.0155 | −6.015 | 64.67 | 64 | 5.99 |
| VCL | BX537994 | 22 | 26 | 1.0000 | 0.8468 | 1.1651 | 0.220 | 1.17 | 4 | 1.91 |

TABLE 11-continued

RNA Abundance Modulation

| Gene | Trx_ID | ave DMSO | ave Cpd | padj (q val, FDR) | ttest (p val) | FC (x + 1) | L₂FC (x + 1) | amp FC (x + 1) | abs (Cpd − DMSO) | L₂abs (Cpd − DMSO) |
|---|---|---|---|---|---|---|---|---|---|---|
| VCL | NM_003373 | 15482 | 15153 | 1.0000 | 0.7513 | 0.9787 | −0.031 | 1.02 | 329 | 8.36 |
| VCL | NM_014000 | 110 | 172 | 0.7032 | 0.0049 | 1.5587 | 0.640 | 1.56 | 62 | 5.96 |
| VPS29 | AF201936 | 20 | 66 | 0.4079 | 0.0275 | 3.2422 | 1.697 | 3.24 | 46 | 5.53 |
| VPS29 | BC015095 | 6 | 0 | 0.4720 | 0.0371 | 0.1347 | −2.893 | 7.43 | 6 | 2.68 |
| VPS29 | BC017964 | 7 | 8 | 1.0000 | 0.8413 | 1.2474 | 0.319 | 1.25 | 2 | 0.89 |
| VPS29 | NM_016226 | 724 | 317 | 0.0001 | 0.0000 | 0.4385 | −1.189 | 2.28 | 407 | 8.67 |
| VPS29 | NM_057180 | 815 | 1321 | 0.0052 | 0.0001 | 1.6193 | 0.695 | 1.62 | 506 | 8.98 |
| WDR37 | AB023199 | 141 | 21 | 0.0009 | 0.0000 | 0.1544 | −2.696 | 6.48 | 120 | 6.91 |
| WDR37 | AK128194 | 18 | 20 | 1.0000 | 0.8935 | 1.1280 | 0.174 | 1.13 | 2 | 1.26 |
| WDR37 | AK292591 | 482 | 462 | 1.0000 | 0.8227 | 0.9582 | −0.062 | 1.04 | 20 | 4.34 |
| WDR37 | AK307259 | 94 | 71 | 1.0000 | 0.5465 | 0.7507 | −0.414 | 1.33 | 24 | 4.57 |
| WDR37 | BC018044 | 27 | 19 | 1.0000 | 0.6213 | 0.7220 | −0.470 | 1.39 | 8 | 2.98 |
| WDR37 | NM_014023 | 0 | 175 | 0.0000 | 0.0000 | 176.3373 | 7.462 | 176.34 | 175 | 7.45 |
| WIPF1 | AK304194 | 2 | 1 | 1.0000 | 0.8059 | 0.7137 | −0.487 | 1.40 | 1 | −0.30 |
| WIPF1 | BC110288 | 66 | 50 | 1.0000 | 0.5729 | 0.7656 | −0.385 | 1.31 | 16 | 3.97 |
| WIPF1 | BX640870 | 291 | 97 | 0.0045 | 0.0000 | 0.3357 | −1.575 | 2.98 | 194 | 7.60 |
| WIPF1 | NM_001077269 | 1653 | 1951 | 0.6674 | 0.0812 | 1.1798 | 0.239 | 1.18 | 297 | 8.22 |
| WIPF1 | NM_003387 | 373 | 366 | 1.0000 | 0.7787 | 0.9814 | −0.027 | 1.02 | 7 | 2.79 |
| WIPF1 | X86019 | 12 | 6 | 1.0000 | 0.5291 | 0.5475 | −0.869 | 1.83 | 6 | 2.58 |
| WWTR1 | AJ299431 | 631 | 1394 | 0.0000 | 0.0000 | 2.2084 | 1.143 | 2.21 | 763 | 9.58 |
| WWTR1 | NM_001168278 | 0 | 0 | 9999 | 9999 | 1.0000 | 0.000 | 1.00 | 0 | 0 |
| WWTR1 | NM_001168280 | 410 | 53 | 0.0000 | 0.0000 | 0.1315 | −2.927 | 7.61 | 357 | 8.48 |
| WWTR1 | NM_015472 | 1098 | 768 | 0.1013 | 0.0030 | 0.6994 | −0.516 | 1.43 | 330 | 8.37 |
| ZC3H12C | AB096241 | 0 | 4 | 0.4941 | 0.0403 | 5.0998 | 2.350 | 5.10 | 4 | 2.04 |
| ZC3H12C | AB384628 | 417 | 583 | 0.4496 | 0.0334 | 1.3962 | 0.481 | 1.40 | 166 | 7.37 |
| ZC3H12C | AK095101 | 7 | 3 | 1.0000 | 0.5942 | 0.5395 | −0.890 | 1.85 | 4 | 1.83 |
| ZC3H12C | NM_033390 | 76 | 0 | 0.0000 | 0.0000 | 0.0130 | −6.260 | 76.66 | 76 | 6.24 |
| ZCCHC11 | AK307579 | 110 | 130 | 1.0000 | 0.6219 | 1.1884 | 0.249 | 1.19 | 21 | 4.38 |
| ZCCHC11 | AK308427 | 15 | 21 | 1.0000 | 0.6799 | 1.3722 | 0.457 | 1.37 | 6 | 2.57 |
| ZCCHC11 | BC048301 | 10 | 8 | 1.0000 | 0.9112 | 0.8078 | −0.308 | 1.24 | 2 | 1.04 |
| ZCCHC11 | BX648783 | 11 | 12 | 1.0000 | 0.9531 | 1.0666 | 0.093 | 1.07 | 1 | −0.33 |
| ZCCHC11 | NM_001009881 | 568 | 387 | 0.4458 | 0.0329 | 0.6817 | −0.553 | 1.47 | 181 | 7.50 |
| ZCCHC11 | NM_015269 | 95 | 311 | 0.0023 | 0.0000 | 3.2556 | 1.703 | 3.26 | 216 | 7.75 |
| ZEB1 | AK294775 | 98 | 88 | 1.0000 | 0.7965 | 0.9007 | −0.151 | 1.11 | 10 | 3.29 |
| ZEB1 | AK299541 | 0 | 28 | 0.0043 | 0.0000 | 29.4408 | 4.880 | 29.44 | 28 | 4.83 |
| ZEB1 | AK307510 | 406 | 430 | 1.0000 | 0.7663 | 1.0586 | 0.082 | 1.06 | 24 | 4.58 |
| ZEB1 | AK308785 | 0 | 0 | 9999 | 9999 | 1.0000 | 0.000 | 1.00 | 0 | 0 |
| ZEB1 | AK308822 | 2 | 0 | 0.8875 | 0.1595 | 0.3962 | −1.336 | 2.52 | 2 | 0.61 |
| ZEB1 | AK309399 | 2 | 2 | 1.0000 | 0.9216 | 0.8610 | −0.216 | 1.16 | 0 | −1.19 |
| ZEB1 | AK310924 | 22 | 28 | 1.0000 | 0.6684 | 1.2326 | 0.302 | 1.23 | 5 | 2.45 |
| ZEB1 | AK311137 | 37 | 29 | 1.0000 | 0.7729 | 0.7833 | −0.352 | 1.28 | 8 | 3.05 |
| ZEB1 | AK311557 | 1 | 1 | 1.0000 | 1.0000 | 0.9573 | −0.063 | 1.04 | 0 | −3.47 |
| ZEB1 | AL831979 | 38 | 52 | 1.0000 | 0.4994 | 1.3634 | 0.447 | 1.36 | 14 | 3.83 |
| ZEB1 | BX647794 | 22 | 37 | 1.0000 | 0.3537 | 1.6718 | 0.741 | 1.67 | 15 | 3.94 |
| ZEB1 | NM_001128128 | 22 | 16 | 1.0000 | 0.6206 | 0.7225 | −0.469 | 1.38 | 6 | 2.68 |
| ZEB1 | NM_001174093 | 81 | 0 | 0.0000 | 0.0000 | 0.0122 | −6.362 | 82.25 | 81 | 6.34 |
| ZEB1 | NM_001174094 | 9 | 0 | 0.3298 | 0.0187 | 0.1016 | −3.299 | 9.84 | 9 | 3.14 |
| ZEB1 | NM_001174095 | 0 | 8 | 0.2835 | 0.0147 | 8.5444 | 3.095 | 8.54 | 8 | 2.92 |
| ZEB1 | NM_001174096 | 1527 | 1923 | 0.3894 | 0.0252 | 1.2588 | 0.332 | 1.26 | 396 | 8.63 |
| ZEB1 | NM_030751 | 625 | 504 | 0.8751 | 0.1524 | 0.8070 | −0.309 | 1.24 | 121 | 6.92 |
| ZEB2 | AK308445 | 741 | 840 | 1.0000 | 0.3452 | 1.1321 | 0.179 | 1.13 | 98 | 6.62 |
| ZEB2 | BC025730 | 52 | 52 | 1.0000 | 0.9899 | 1.0112 | 0.016 | 1.01 | 1 | −0.76 |
| ZEB2 | BC037975 | 0 | 0 | 9999 | 9999 | 1.0000 | 0.000 | 1.00 | 0 | 0 |
| ZEB2 | BC060819 | 2 | 2 | 1.0000 | 1.0000 | 1.0044 | 0.006 | 1.00 | 0 | −6.13 |
| ZEB2 | BC070275 | 1 | 1 | 1.0000 | 1.0000 | 0.8361 | −0.258 | 1.20 | 0 | −1.62 |
| ZEB2 | NM_001171653 | 260 | 540 | 0.0070 | 0.0001 | 2.0741 | 1.053 | 2.07 | 280 | 8.13 |
| ZEB2 | NM_014795 | 1306 | 1163 | 0.3373 | 0.0219 | 0.8910 | −0.167 | 1.12 | 142 | 7.15 |
| ZEB2 | NR_033258 | 0 | 2 | 0.6268 | 0.0683 | 3.3915 | 1.762 | 3.39 | 2 | 1.26 |
| ZFAND1 | NM_001170796 | 6 | 11 | 1.0000 | 0.5647 | 1.7025 | 0.768 | 1.70 | 5 | 2.33 |
| ZFAND1 | NM_001170797 | 69 | 52 | 1.0000 | 0.5509 | 0.7648 | −0.387 | 1.31 | 16 | 4.03 |
| ZFAND1 | NM_024699 | 176 | 291 | 0.4720 | 0.0368 | 1.6512 | 0.724 | 1.65 | 115 | 6.85 |
| ZFAND1 | NR_033193 | 14 | 8 | 1.0000 | 0.6261 | 0.6162 | −0.699 | 1.62 | 6 | 2.52 |
| ZFAND1 | NR_033194 | 137 | 21 | 0.0021 | 0.0000 | 0.1586 | −2.656 | 6.30 | 116 | 6.86 |
| ZFAND1 | NR_033195 | 72 | 84 | 1.0000 | 0.7127 | 1.1562 | 0.209 | 1.16 | 11 | 3.52 |
| ZFAND1 | NR_033196 | 42 | 69 | 1.0000 | 0.3483 | 1.6093 | 0.686 | 1.61 | 26 | 4.72 |
| ZFAND5 | AK290849 | 1459 | 1448 | 1.0000 | 0.8761 | 0.9921 | −0.011 | 1.01 | 11 | 3.52 |
| ZFAND5 | AK307376 | 166 | 73 | 0.3307 | 0.0188 | 0.4450 | −1.168 | 2.25 | 93 | 6.54 |
| ZFAND5 | NM_001102420 | 2007 | 1383 | 0.0158 | 0.0002 | 0.6894 | −0.537 | 1.45 | 624 | 9.28 |
| ZFAND5 | NM_001102421 | 1255 | 1209 | 1.0000 | 0.7216 | 0.9638 | −0.053 | 1.04 | 45 | 5.50 |
| ZFAND5 | NM_001278243 | 264 | 1201 | 0.0000 | 0.0000 | 4.5357 | 2.181 | 4.54 | 937 | 9.87 |
| ZFAND5 | NM_001278244 | 0 | 50 | 0.0001 | 0.0000 | 50.5391 | 5.659 | 50.54 | 50 | 5.63 |
| ZFAND5 | NM_001278245 | 317 | 146 | 0.0650 | 0.0016 | 0.4612 | −1.117 | 2.17 | 172 | 7.42 |
| ZFAND5 | NM_006007 | 24 | 73 | 0.5204 | 0.0448 | 3.0120 | 1.591 | 3.01 | 50 | 5.63 |
| ZMIZ1 | AB033050 | 221 | 497 | 0.0009 | 0.0000 | 2.2461 | 1.167 | 2.25 | 276 | 8.11 |

TABLE 11-continued

RNA Abundance Modulation

| Gene | Trx_ID | ave DMSO | ave Cpd | padj (q val, FDR) | ttest (p val) | FC (x + 1) | L$_2$FC (x + 1) | amp FC (x + 1) | abs (Cpd − DMSO) | L$_2$abs (Cpd − DMSO) |
|---|---|---|---|---|---|---|---|---|---|---|
| ZMIZ1 | AK024490 | 19 | 23 | 1.0000 | 0.7846 | 1.2123 | 0.278 | 1.21 | 4 | 2.09 |
| ZMIZ1 | AK025812 | 2 | 11 | 0.8600 | 0.1456 | 3.9689 | 1.989 | 3.97 | 9 | 3.20 |
| ZMIZ1 | AK299728 | 776 | 793 | 1.0000 | 0.8083 | 1.0218 | 0.031 | 1.02 | 17 | 4.08 |
| ZMIZ1 | NM_020338 | 3960 | 3424 | 0.6696 | 0.0821 | 0.8647 | −0.210 | 1.16 | 536 | 9.07 |
| ZNF28 | NM_006969 | 144 | 23 | 0.0030 | 0.0000 | 0.1640 | −2.609 | 6.10 | 121 | 6.92 |
| ZNF28 | NR_036599 | 314 | 358 | 1.0000 | 0.4743 | 1.1378 | 0.186 | 1.14 | 43 | 5.44 |
| ZNF28 | NR_036600 | 31 | 115 | 0.1403 | 0.0048 | 3.5865 | 1.843 | 3.59 | 84 | 6.39 |
| ZNF281 | AJ132592 | 138 | 12 | 0.0001 | 0.0000 | 0.0958 | −3.383 | 10.44 | 125 | 6.97 |
| ZNF281 | AK094701 | 152 | 281 | 0.2072 | 0.0088 | 1.8502 | 0.888 | 1.85 | 130 | 7.02 |
| ZNF281 | CCDS1402 | 105 | 201 | 0.3799 | 0.0239 | 1.8989 | 0.925 | 1.90 | 96 | 6.58 |
| ZNF281 | NM_012482 | 1475 | 1398 | 1.0000 | 0.5915 | 0.9481 | −0.077 | 1.05 | 77 | 6.26 |
| ZNF655 | AK128057 | 62 | 62 | 1.0000 | 1.0000 | 1.0047 | 0.007 | 1.00 | 0 | −1.74 |
| ZNF655 | AK225976 | 24 | 13 | 1.0000 | 0.4360 | 0.5558 | −0.847 | 1.80 | 11 | 3.46 |
| ZNF655 | CR749270 | 328 | 319 | 1.0000 | 0.8571 | 0.9727 | −0.040 | 1.03 | 9 | 3.17 |
| ZNF655 | NM_001009958 | 23 | 39 | 1.0000 | 0.3865 | 1.6969 | 0.763 | 1.70 | 17 | 4.05 |
| ZNF655 | NM_001009960 | 46 | 0 | 0.0010 | 0.0000 | 0.0286 | −5.128 | 34.96 | 46 | 5.51 |
| ZNF655 | NM_001083956 | 162 | 24 | 0.0006 | 0.0000 | 0.1532 | −2.707 | 6.53 | 138 | 7.11 |
| ZNF655 | NM_001085366 | 18 | 19 | 1.0000 | 1.0000 | 1.0567 | 0.080 | 1.06 | 1 | 0.09 |
| ZNF655 | NM_001085367 | 55 | 81 | 1.0000 | 0.3456 | 1.4750 | 0.561 | 1.48 | 27 | 4.73 |
| ZNF655 | NM_001085368 | 30 | 165 | 0.0030 | 0.0000 | 5.2819 | 2.401 | 5.28 | 135 | 7.07 |
| ZNF655 | NM_024061 | 129 | 122 | 1.0000 | 0.8558 | 0.9443 | −0.083 | 1.06 | 7 | 2.86 |
| ZNF655 | NM_138494 | 212 | 319 | 0.6281 | 0.0685 | 1.5045 | 0.589 | 1.50 | 107 | 6.75 |
| ZNF764 | NM_001172679 | 93 | 134 | 1.0000 | 0.2912 | 1.4297 | 0.516 | 1.43 | 41 | 5.34 |
| ZNF764 | NM_033410 | 58 | 0 | 0.0000 | 0.0000 | 0.0171 | −5.871 | 58.55 | 58 | 5.85 |
| ZNF839 | AF155112 | 44 | 64 | 1.0000 | 0.5121 | 1.4433 | 0.529 | 1.44 | 20 | 4.32 |
| ZNF839 | AK127821 | 4 | 0 | 0.7347 | 0.1048 | 0.2114 | −2.242 | 4.73 | 4 | 1.90 |
| ZNF839 | AL137478 | 42 | 34 | 1.0000 | 0.6516 | 0.8027 | −0.317 | 1.25 | 9 | 3.09 |
| ZNF839 | BC042659 | 0 | 0 | 9999 | 9999 | 1.0000 | 0.000 | 1.00 | 0 | 0 |
| ZNF839 | BC073137 | 21 | 49 | 1.0000 | 0.2144 | 2.2210 | 1.151 | 2.22 | 27 | 4.77 |
| ZNF839 | NM_001267827 | 0 | 19 | 0.0304 | 0.0006 | 19.9605 | 4.319 | 19.96 | 19 | 4.24 |
| ZNF839 | NM_001267828 | 61 | 0 | 0.0000 | 0.0000 | 0.0161 | −5.955 | 62.02 | 61 | 5.93 |
| ZNF839 | NM_018335 | 74 | 60 | 1.0000 | 0.8970 | 0.8164 | −0.293 | 1.22 | 14 | 3.78 |

Data Analysis

Two statistical stringency criteria were used:

q value (The Benjamini and Hochberg adjusted p value, also referred to as the p value adjusted for multiple comparisons or the false discovery rate [FDR]) and p value per Student's t-test were calculated on iFPM data for each annotated isoform.

The level of significance cut off (stringency level) may be set at different levels.

The genes in Table 1, 2, 3 and 4 were obtained from Tables 8, 9, 10 and 11, respectively, via the following stringency cut off criteria: fold change in mRNA abundance >2, Student's t-test p value <0.01, and the false discovery rate (also known as padj) at a q value of p<0.01.

Without regard to whether a document cited herein was specifically and individually indicated as being incorporated by reference, all documents referred to herein are incorporated by reference into the present application for any and all purposes to the same extent as if each individual reference was fully set forth herein.

Although certain embodiments have been described in detail above, those having ordinary skill in the art will clearly understand that many modifications are possible in the embodiments without departing from the teachings thereof. All such modifications are intended to be encompassed within the claims as described herein.

What is claimed is:

1. A method of modulating the amount of one or more RNA transcripts of one or more genes, comprising administering to a subject in need thereof a compound of Formula (IIa1):

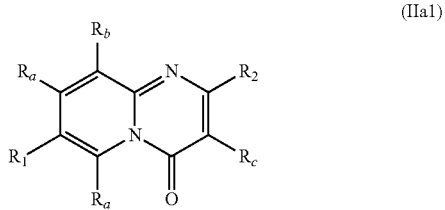

or a free acid, free base, salt, isotopologue, stereoisomer, racemate, enantiomer, diastereomer or tautomer thereof, wherein:

$R_1$ is heterocyclyl;
wherein heterocyclyl is optionally substituted with one, two or three $R_3$ substituents and optionally, with one additional $R_4$ substituent; or,
wherein heterocyclyl is optionally substituted with one, two, three or four $R_3$ substituents;

$R_2$ is phenyl;
wherein phenyl is optionally substituted with one, two or three $R_6$ substituents and optionally, with one additional $R_7$ substituent;

$R_a$ is, in each instance, independently selected from hydrogen, halogen, $C_{1-8}$alkyl or deuterium;

$R_b$ is hydrogen, halogen, $C_{1-8}$alkyl, $C_{1-8}$alkoxy or deuterium;

$R_c$ is hydrogen, halogen, $C_{1-8}$alkyl or deuterium;

$R_3$ is, in each instance, independently selected from cyano, halogen, hydroxy, oxo, $C_{1-8}$alkyl, halo-$C_{1-8}$alkyl, $C_{1-8}$alkyl-carbonyl, $C_{1-8}$alkoxy, halo-$C_{1-8}$alkoxy, $C_{1-8}$alkoxy-$C_{1-8}$alkyl, $C_{1-8}$alkoxy-carbonyl, amino, $C_{1-8}$alkyl-amino, $(C_{1-8}$alkyl$)_2$-amino, amino-$C_{1-8}$alkyl, $C_{1-8}$alkyl-amino-$C_{1-8}$alkyl, $(C_{1-8}$alkyl$)_2$-amino-$C_{1-8}$alkyl, amino-$C_{1-8}$alkyl-amino, $C_{1-8}$alkyl-amino-$C_{1-8}$alkyl-amino, $(C_{1-8}$alkyl-amino-$C_{1-8}$alkyl$)_2$-amino, $(C_{1-8}$ alkyl$)_2$-amino-$C_{1-8}$alkyl-amino, $[(C_{1-8}$alkyl$)_2$-amino-$C_{1-8}$alkyl$]_2$-amino, $(C_{1-8}$alkyl-amino-$C_{1-8}$alkyl)$(C_{1-8}$alkyl)amino, $[(C_{1-8}$alkyl$)_2$-amino-$C_{1-8}$alkyl$](C_{1-8}$ alkyl)amino, $C_{1-8}$alkoxy-$C_{1-8}$alkyl-amino, $(C_{1-8}$ alkoxy-$C_{1-8}$alkyl$)_2$-amino, $(C_{1-8}$alkoxy-$C_{1-8}$alkyl)$(C_{1-8}$alkyl)amino, $C_{1-8}$alkyl-carbonyl-amino, $C_{1-8}$alkoxy-carbonyl-amino, hydroxy-$C_{1-8}$alkyl, hydroxy-$C_{1-8}$alkoxy-$C_{1-8}$alkyl, hydroxy-$C_{1-8}$alkyl-amino, (hydroxy-$C_{1-8}$alkyl$)_2$-amino or (hydroxy-$C_{1-8}$alkyl)$(C_{1-8}$alkyl)amino;

$R_4$ is $C_{3-14}$cycloalkyl, $C_{3-14}$cycloalkyl-$C_{1-8}$alkyl, $C_{3-14}$cycloalkyl-amino, aryl-$C_{1-8}$alkyl, aryl-$C_{1-8}$alkoxy-carbonyl, aryl-sulfonyloxy-$C_{1-8}$alkyl, heterocyclyl or heterocyclyl-$C_{1-8}$alkyl; wherein, each instance of $C_{3-14}$cycloalkyl, aryl and heterocyclyl is optionally substituted with one, two or three $R_5$ substituents;

$R_5$ is, in each instance, independently selected from halogen, hydroxy, cyano, nitro, $C_{1-8}$alkyl, halo-$C_{1-8}$alkyl, $C_{1-8}$alkoxy, halo-$C_{1-8}$alkoxy, amino, $C_{1-8}$alkyl-amino, $(C_{1-8}$alkyl$)_2$-amino or $C_{1-8}$alkyl-thio;

$R_6$ is, in each instance, independently selected from halogen, hydroxy, cyano, nitro, $C_{1-8}$alkyl, $C_{2-8}$alkenyl, halo-$C_{1-8}$alkyl, hydroxy-$C_{1-8}$alkyl, $C_{1-8}$alkoxy, halo-$C_{1-8}$alkoxy, $C_{1-8}$alkoxy-$C_{1-8}$alkyl, amino, $C_{1-8}$alkylamino, $(C_{1-8}$alkyl$)_2$-amino or $C_{1-8}$alkyl-thio; and, $R_7$ is $C_{3-14}$cycloalkyl, $C_{3-14}$cycloalkyl-oxy, aryl, heterocyclyl or heteroaryl, wherein the gene is selected from the group consisting of ABCA1, ABCB7, ABCC1, ABHD10, ABL2, ABLIM3, ACACA, ACADVL, ACAT2, ADAM12, ADAM15, ADAM17, ADAM33, AFF2, AGK, AGPAT3, AGPS, AHCYL2, AHDC1, AHRR, AJUBA, AK021888, AK310472, AKAP1, AKAP9, AKNA, ALCAM, ALDH4A1, AMPD2, ANK2, ANKFY1, ANKHD1-EIF4EBP3, ANKRD17, ANKS6, ANP32A, ANXA11, ANXA6, AP2B1, APAF1, APLP2, APP, APPL2, APTX, ARHGAP22, ARID1A, ARID2, ARMCX3, ASAP1, ASL, ASNS, ASPH, ATAD2B, ATF7IP, ATG9A, ATMIN, ATP2C1, ATXN3, AURKA, AXIN1, B4GALT2, BACE1, BAG2, BASP1, BC033281, BCAR3, BEND6, BICD1, BIN1, BNC1, BRD2, BRPF1, BSCL2, BTBD10, BZW1, C11orf30, C11orf73, C17orf76-AS1, C4orf27, C5orf24, C6orf48, C9orf69, CAB39, CALU, CAMKK1, CAPNS1, CASC3, CASP8AP2, CAV1, CCAR1, CCDC77, CCDC88A, CCDC92, CCT6A, CD276, CD46, CDC25B, CDC40, CDC42BPA, CDCA7, CDH11, CDH13, CDK11B, CDK16, CDKAL1, CEP68, CFLAR, CHD8, CIZ1, CLIC1, CLK4, CNOT1, COG1, COL12A1, COL1A1, COL6A1, COPS7B, CPEB2, CREB5, CRLS1, CRTAP, CSDE1, CSNK1A1, CTDSP2, CTNND1, CUL2, CUL4A, CUX1, CYB5B, CYBRD1, CYP51A1, DAB2, DACT1, DARS, DAXX, DCAF10, DCAF11, DCBLD2, DCUN1D4, DDAH1, DDAH2, DDHD2, DDR1, DDX39B, DDX42, DENND1A, DENND1B, DENND5A, DGCR2, DGKA, DHCR24, DHCR7, DHFR, DHX9, DIAPH1, DIAPH3, DIS3L, DKFZp434M1735, DKK3, DLC1, DNM2, DOCK1, DPP8, DSEL, DST, DSTN, EBF1, EEA1, EEF1A1, EFCAB14, EGR1, EHMT2, EIF2B3, EIF4G1, EIF4G2, EIF4G3, ELF2, ENG, ENPP2, ENSA, EPN1, EPT1, ERC1, ETV5, EXO1, EXTL2, EYA3, FADS1, FADS2, FAF1, FAM111A, FAM198B, FAM219A, FAM219B, FAM3C, FAM65A, FBXO10, FBXO18, FBXO31, FBXO34, FBXO9, FDFT1, FDPS, FER, FEZ1, FGD5-AS1, FGFRL1, FHOD3, FLII, FLNB, FN1, FNBP1, FOCAD, FOS, FOSB, FOSL1, FOXK1, FUS, FYN, GABPB1, GALC, GALNT1, GAS7, GBA2, GCFC2, GGCT, GHDC, GIGYF2, GJC1, GMIP, GNA13, GNAS, GNL3L, GOLGA2, GOLGA4, GOLGB1, GORASP1, GPR1, GPR89A, GPSM2, GREM1, GRK6, GSE1, GTF2H2B, HAS2, HAT1, HAUS3, HAUS6, HDAC7, HEG1, HLA-A, HLA-E, HLTF, HMGA1, HMGB1, HMGCR, HMGCS1, HMOX1, HNRNPR, HNRNPUL1, HP1BP3, HRH1, HSD17B12, HSD17B4, HTT, IARS, IDH1, IDI1, IGF2BP2, IL6ST, INHBA, INSIG1, IQCE, ITGAV, ITGB5, ITM2C, ITSN1, KANSL3, KCNK2, KIAA1033, KIAA1143, KIAA1199, KIAA1522, KIAA1524, KIAA1549, KIAA1715, KIF14, KIF2A, KIF3A, KLC1, KLC2, KLF6, KLHL7, KRT18, KRT19, KRT34, KRTAP2-3, LAMA2, LAMB1, LARP4, LARP7, LATS2, LDLR, LEMD3, LGALS8, LIMS1, LINC00341, LINC00657, LMAN2L, LMO7, LONP1, LOX, LRCH4, LRIG1, LRP8, LRRC8A, LSS, LTBR, LUC7L2, LZTS2, MADD, MAGED4, MAGED4B, MAN1A2, MAP4K4, MBD1, MBOAT7, MDM2, MED1, MEDAG, MEF2D, MEIS2, MEMO1, MEPCE, MFGE8, MICAL2, MINPP1, MKL1, MKLN1, MKNK2, MLLT4, MLST8, MMAB, MMS19, MMS22L, MPPE1, MPZL1, MRPL3, MSANTD3, MSC, MSH2, MSH6, MSL3, MSMO1, MSRB3, MTAP, MTERFD1, MTHFD1L, MTMR9, MTRR, MUM1, MVD, MVK, MYADM, MYLK, MYO1D, MYO9B, MYOF, NAA35, NADK, NASP, NAV1, NAV2, NCOA1, NCOA3, NCOA4, NCSTN, NELFA, NEO1, NEURL1B, NF2, NFE2L1, NFX1, NID1, NID2, NIPA1, NKX3-1, NOL10, NOMO3, NPEPPS, NRD1, NREP, NRG1, NSUN4, NT5C2, NT5E, NTNG1, NUDT4, NUP153, NUP35, NUP50, NUPL1, NUSAP1, ODF2, OS9, OSBPL6, OSMR, P4HA1, P4HB, PABPC1, PAK4, PAPD4, PARD3, PARN, PARP14, PARP4, PARVB, PCBP2, PCBP4, PCDHGB3, PCGF3, PCM1, PCMTD2, PCNXL2, PCSK9, PDE4A, PDE7A, PDLIM7, PDXDC1, PEPD, PEX5, PFKP, PHF19, PHF8, PHRF1, PHTF2, PI4K2A, PIEZO1, PIGU, PIK3C2B, PITPNA, PITPNB, PITPNM1, PLAU, PLEC, PLEKHB2, PLSCR3, PLXNB2, PLXNC1, PMS1, POLE3, POLR3D, POSTN, POU2F1, PPAPDC1A, PPARA, PPHLN1, PPIP5K1, PPP1R12A, PPP6R1, PPP6R2, PRKACB, PRKDC, PRMT1, PRNP, PRSS23, PSMA4, PSMC1, PSMD6, PTK2B, PTPN14, PUF60, PUS7, PVR, PXN, QKI, RAB23, RAB2B, RAB34, RAD1, RAD23B, RALB, RAP1A, RAP1GDS1, RARG, RASSF8, RBCK1, RBFOX2, RBM10, RCC1, RFTN1, RFWD2, RGS10, RGS3, RIF1, RNF14, RNF19A, RNF38, RNFT1, RPL10, RPS6KC1, RRBP1, RWDD4, SAMD9, SAMD9L, SAR1A, SART3, SCAF4, SCAF8, SCD, SCLT1, SCO1, SDCBP, SEC14L1, SEC22A, SEC24B, SEC61A1, SEPT9, SERPINE2, SF1, SGOL2, SH3RF1, SKIL, SLC25A17, SLC39A3, SLC41A1, SLC4A4, SLC7A6, SLC7A8, SMARCA4, SMARCC2, SMC4, SMC6, SMCHD1, SMG1, SMPD4, SMYD3, SMYD5, SNAP23, SNHG16, SNX14, SOCS2, SON, SOS2, SPATA20, SPATS2, SPG20, SPRED2, SQLE, SQRDL, SQSTM1, SRCAP, SREBF1, SREK1, SRSF3, STARD4, STAT1, STAT3, STAU1, STC2, STEAP2, STRIP1, STRN3, STX16, SUPT20H, SYNE1, SYNE2, SYT15, SYTL2, TACC1, TAF2, TANC2, TARBP1, TARS, TBC1D15, TBL2, TCF7L2, TENC1, TENM2, TEP1, TET3, TFCP2, TGFBI, TGFBR1, TGFBRAP1, THADA, THAP4, THRB, TIMP2, TJP2, TLE3, TLK1, TMEM154, TMEM47, TMEM63A, TNC, TNFAIP3, TNFRSF12A, TNIP1, TNKS1BP1, TNPO3, TNS1, TNS3, TOE1, TOMM40, TOMM5, TOPORS, TP53INP1, TRAF3, TRAK1, TRAPPC12, TRIB1, TRIM2, TRIM23, TRIM26, TRIM28, TRIM65, TRMT1L, TRPS1, TSC2, TSHZ1, TSPAN2, TTC7A, TUBB2C, TUBB3, TXNL1, TXNRD1, U2SURP, UBAP2L, UBE2G2, UBE2V1, UBQLN4, UCHL5, UHMK1, UHRF1BPL1L, UNC5B, USP19, USP7, VANGL1, VARS2, VCL, VIPAS39, VPS13A, VPS29, VPS51, VWA8, WDR19, WDR37, WDR48, WIPF1, WNT5B, WSB1, WWTR1, XIAP, XRN2, YAP1, YES1, YPEL5, YTHDF3, Z24749, ZAK, ZBTB10, ZBTB24, ZBTB7A, ZC3H12C, ZC3H14, ZC3H18, ZCCHC11, ZEB1, ZEB2, ZFAND1, ZFAND5, ZHX3, ZMIZ1, ZMYM2, ZNF12, ZNF148, ZNF219, ZNF227, ZNF24, ZNF268, ZNF28, ZNF281, ZNF335, ZNF37A, ZNF37BP, ZNF395, ZNF583, ZNF621, ZNF652, ZNF655, ZNF674, ZNF74, ZNF764, ZNF778, ZNF780A, ZNF827, ZNF839 and ZNF91.

2. The method of claim 1, wherein the salt is a chloride, hydrobromide, hydrochloride, dihydrochloride, acetate or trifluoroacetic acid salt.

3. The method of claim 1, wherein the gene is selected from the group consisting of: ABCA1, ABCC1, ABL2, ACACA, ACAT2, AFF2, AHRR, AK021888, AK310472, AKAP1, ANK2, ANKHD1-EIF4EBP3, AP2B1, APAF1, APLP2, ARID1A, ARMCX3, ASAP1, ASPH, ATAD2B, ATF7IP, ATG9A, AXIN1, BACE1, BIN1, BNC1, BRPF1, BZW1, C11orf30, C11orf73, C17orf76-AS1, C4orf27, C6orf48, CAB39, CAMKK1, CCDC88A, CCDC92, CDC25B, CDC42BPA, CDCA7, CDH11, CDH13, CEP68, CFLAR, COPS7B, CREB5, CUL2, CUL4A, CUX1, CYP51A1, DCUN1D4, DDR1, DDX39B, DDX42, DENND1A, DENND5A, DGKA, DHCR24, DHCR7, DIAPH1, DIAPH3, DNM2, DOCK1, EFCAB14, EIF2B3, EPN1, EPT1, ERC1, ETV5, FADS1, FADS2, FAF1, FAM198B, FAM219B, FBXO10, FBXO9, FDFT1, FDPS, FER, FEZ1, FHOD3, FLII, FLNB, FNBP1, FOS, FOSB, FYN, GABPB1, GALC, GAS7, GGCT, GJC1, GPSM2, GRK6, HAS2, HAT1, HLTF, HMGA1, HMGB1, HMGCR, HMGCS1, HMOX1, HP1BP3, HSD17B12, HTT, IDI1, INHBA, INSIG1, KANSL3, KIAA1199, KIAA1524, KIAA1715, KIF3A, KLF6, KRT19, KRT34, KRTAP2-3, LAMA2, LARP7, LDLR, LEMD3, LMAN2L, LRCH4, LRP8, LSS, MAGED4, MAGED4B, MAN1A2, MEDAG, MEF2D, MEMO1, MFGE8, MICAL2, MMAB, MMS19, MMS22L, MSL3, MSMO1, MTAP, MTERFDI, MVD, MVK, NASP, NAV2, NEURL1B, NFE2L1, NID1, NPEPPS, NREP, NRG1, NSUN4, NT5C2, NUP153, P4HA1, PABPC1, PAPD4, PCBP2, PCM1, PCSK9, PDXDC1, PEPD, PHF19, PHF8, PHTF2, PIK3C2B, PITPNB, PLEC, PMS1, POU2F1, PPHLN1, PRKDC, PRSS23, PSMC1, PTPN14, PUF60, PVR, RAB23, RAD23B, RAP1A, RASSF8, RBM10, RCC1, RFWD2, RNFT1, RWDD4, SAMD9L, SART3, SCAF4, SCD, SEC22A, SEPT9, SEC61A1, SERPINE2, SF1, SLC25A17, SLC7A6, SLC7A8, SMYD3, SMYD5, SNAP23, SNHG16, SQLE, SQRDL, SQSTM1, SRCAP, SREBF1, STARD4, STAT1, STAU1, STEAP2, STRN3, SYNE1, TACC1, TAF2, TANC2, TARBP1, TBC1D15, TEP1, TFCP2, TGFBRAP1, THADA, TIMP2, TLK1, TMEM154, TNS3, TOMM5, TRAF3, TRAK1, TRAPPC12, TRIM2, TRIM26, TRIM65, TSPAN2, U2SURP, UBAP2L, UBE2V1, UCHL5, UHRF1BPL1, VANGL1, VARS2, VPS13A, VPS29, VWA8, WSB1, XIAP, XRN2, YPEL5, ZAK, ZC3H18, ZFAND5, ZMIZ1, ZMYM2, ZNF219, ZNF227, ZNF24, ZNF37A, ZNF37BP, ZNF395, ZNF652, ZNF674, ZNF74 and ZNF778.

4. The method of claim 1, wherein the gene is selected from the group consisting of: ABCC1, ACADVL, ADAM15, AGPAT3, AHRR, AJUBA, AKAP1, AKAP9, ALCAM, ALDH4A1, ANKFY1, AP2B1, APLP2, APP, ARID1A, ARID2, ASPH, ATMIN, BASP1, BC033281, BCAR3, C11orf73, C17orf76-AS1, C5orf24, C6orf48, CAB39, CASP8AP2, CAV1, CCAR1, CCT6A, CD276, CD46, CDC25B, CDK16, CEP68, CHD8, CLIC1, COL12A1, CPEB2, CREB5, CRLS1, CRTAP, CTNND1, CUX1, CYBRD1, DACT1, DCAF10, DCAF11, DDHD2, DDX39B, DIAPH3, DKK3, DLC1, DSTN, EBF1, EGR1, EIF4G1, EIF4G3, ENG, ERC1, ETV5, FAM198B, FAM219A, FAM3C, FEZ1, FGD5-AS1, FLII, FN1, FNBP1, FOS, FOSB, FOXK1, FYN, GABPB1, GALC, GALNT1, GBA2, GGCT, GHDC, GMIP, GNA13, GNAS, GNL3L, GOLGA2, GORASP1, GREM1, GSE1, HAUS6, HDAC7, HEG1, HLA-A, HLA-E, HMGA1, HP1BP3, IL6ST, ITGAV, KIAA1549, KIF14, KLC1, KLF6, KLHL7, KRT18, LAMA2, LAMB1, LARP7, LATS2, LGALS8, LIMS1, LINC00341, LONP1, LOX, MDM2, MEPCE, MINPP1, MLLT4, MPPE1, MRPL3, MSH2, MSH6, MSL3, MTMR9, MTRR, MUM1, MYADM, MYLK, NADK, NAV2, NCSTN, NFE2L1, NID1, NIPA1, NPEPPS, NRD1, NUDT4, NUSAP1, P4HB, PABPC1, PAK4, PAPD4, PCNXL2, PDE4A, PDXDC1, PHRF1, PHTF2, PI4K2A, PIK3C2B, PLAU, PLEKHB2, PLSCR3, PLXNB2, POSTN, POU2F1, PPARA, PPP1R12A, PRKACB, PSMD6, PTPN14, PUS7, QKI, RAB34, RAD1, RAD23B, RASSF8, RBCK1, RBFOX2, RFTN1, RNF19A, RNF38, RPS6KC1, RWDD4, SEC14L1, SEC24B, SERPINE2, SF1, SLC39A3, SLC41A1, SLC4A4, SLC7A6, SMARCA4, SNHG16, SNX14, SON, SPRED2, STAU1, STEAP2, STRIP1, STRN3, TBL2, TGFBI, TGFBR1, THAP4, TLE3, TMEM47, TNKS1BP1, TOMM40, TOPORS, TRAK1, TRAPPC12, TRIB1, TRIM2, TRIM23, TRIM65, TRMT1L, TRPS1, TXNL1, TXNRD1, U2SURP, UBE2G2, UBE2V1, UHMK1, USP7, VPS29, VWA8, WDR19, WDR37, WIPF1, YPEL5, YTHDF3, Z24749, ZBTB10, ZBTB7A, ZFAND5, ZMIZ1, ZNF12, ZNF148, ZNF335, ZNF395, ZNF583, ZNF621, ZNF655, ZNF74 and ZNF780A.

5. The method of claim 1, wherein the gene is selected from the group consisting of: ABCB7, ABHD10, ABLIM3, ACACA, ADAM12, ADAM17, ADAM33, AGK, AGPS, AHCYL2, AHDC1, AHRR, AK021888, AK310472, AKAP1, AKAP9, AKNA, AMPD2, ANKRD17, ANKS6, ANP32A, ANXA11, ANXA6, APLP2, APP, APPL2, APTX, ARHGAP22, ARMCX3, ASAP1, ASNS, ASPH, ATG9A, ATP2C1, AURKA, AXIN1, B4GALT2, BACE1, BASP1, BEND6, BICD1, BIN1, BRD2, BRPF1, BTBD10, C11orf30, C11orf73, C17orf76-AS1, C4orf27, C6orf48, CAB39, CAPNS1, CASC3, CCDC77, CCDC88A, CD46, CDC40, CDC42BPA, CDCA7, CDH13, CDK11B, CEP68, CIZ1, CLK4, CNOT1, COG1, COL12A1, COL1A1, COL6A1, COPS7B, CSDE1, CSNK1A1, CUX1, CYB5B, CYBRD1, DAB2, DARS, DCBLD2, DCUN1D4, DDAH2, DDR1, DDX39B, DDX42, DENND1A, DENND1B, DENND5A, DGKA, DHFR, DHX9, DIAPH1, DIAPH3, DIS3L, DNM2, DOCK1, DPP8, DSEL, EEA1, EFCAB14, EIF2B3, EIF4G1, EIF4G3, ELF2, ENG, ENPP2, EPN1, EXTL2, EYA3, FAFi, FAM198B, FAM3C, FBXO10, FBXO18, FBXO31, FBXO9, FER, FEZ1, FHOD3, FLII, FN1, FNBP1, FOCAD, FOSL1, GABPB1, GALC, GALNT1, GCFC2, GGCT, GIGYF2, GMIP, GNAS, GNL3L, GOLGB1, GPR89A, GPSM2, GREM1, GRK6, GTF2H2B, HAT1, HAUS3, HEG1, HLA-A, HLTF, HP1BP3, HRH1, HSD17B12, HSD17B4, HTT, IARS, IDH1, IGF2BP2, ITM2C, KCNK2, KIAA1033, KIAA1143, KIAA1522, KIAA1524, KIAA1715, KIF3A, KLHL7, LAMA2, LARP4, LARP7, LATS2, LIMS1, LINC00341, LINC00657, LMAN2L, LMO7, LRCH4, LRIG1, LRRC8A, LTBR, LUC7L2, LZTS2, MADD, MAGED4B, MAN1A2, MAP4K4, MED1, MEDAG, MEF2D, MEIS2, MEMO1, MICAL2, MKLN1, MLLT4, MMS19, MPZL1, MSANTD3, MSC, MSL3, MTAP, MTERFD1, MTHFD1L, MYADM, MYLK, MYO9B, MYOF, NASP, NAV2, NCOA3, NCOA4, NELFA, NEO1, NEURL1B, NF2, NID2, NOL10, NPEPPS, NRG1, NSUN4, NT5C2, NT5E, NTNG1, NUP153, NUP35, NUP50, NUSAP1, ODF2, OS9, OSBPL6, P4HA1, P4HB, PABPC1, PAPD4, PARN, PARP4, PCBP2, PCBP4, PCDHGB3, PCGF3, PCM1, PCMTD2, PDE7A, PDXDC1, PEPD, PFKP, PHF19, PHRFi, PHTF2, PIEZO1, PIGU, PITPNA, PITPNB, PITPNM1, PLAU, PLSCR3, PLXNC1, PMS1, POU2F1, PPAPDC1A, PPHLN1, PPIP5K1, PPP1R12A, PRKDC, PRMT1, PRSS23, PSMA4, PTK2B, PUF60, PVR, RAB23, RAB2B, RAD1, RAD23B, RAP1A, RAP1GDS1, RARG, RASSF8, RBCK1, RCC1, RFWD2, RGS3, RNF14, RNFT1, RPL10, RRBP1, RWDD4, SAR1A, SCAF4, SCAF8, SCLT1, SCO1, SDCBP, SEC22A, SEPT9, SF1, SGOL2, SLC25A17, SLC4A4, SLC7A6, SMARCC2, SMC4, SMC6, SMCHD1, SMPD4, SMYD3, SNAP23, SNHG16, SOCS2, SOS2, SPATA20, SPATS2, SPG20, SQRDL, SREBF1, SREK1, SRSF3, STAT1, STAU1, STEAP2, STRN3, STX16, SUPT20H, SYNE1, SYNE2, SYT15, SYTL2, TAF2, TARBP1, TARS, TBL2, TCF7L2, TENC1, TENM2, TEP1, TET3, TGFBR1, THADA, THRB, TJP2, TLE3, TMEM47, TMEM63A, TNFAIP3, TNIP1, TNPO3, TNS1, TNS3, TOE1, TOMM5, TP53INP1, TRAF3, TRAPPC12, TRIM2, TRIM23, TRIM65, TSC2, TSPAN2, TUBB2C, TXNRD1, UBAP2L, UBE2V1, UCHL5, USP19, VANGL1, VIPAS39, VPS29, VPS51, VWA8, WDR48, WNT5B, WSB1, WWTR1, XRN2, YAP1, YES1, YPEL5, YTHDF3, Z24749, ZBTB24, ZC3H14, ZFAND1, ZFAND5, ZHX3, ZMIZ1, ZMYM2, ZNF219, ZNF268, ZNF395, ZNF827 and ZNF91.

6. The method of claim 1, wherein the gene is selected from the group consisting of: ACACA, ACADVL, AFF2, AHCYL2, AHRR, AKAP1, ALDH4A1, ANKRD17, AP2B1, APLP2, ASL, ASPH, ATG9A, ATMIN, ATXN3, BAG2, BASP1, BRPF1, BSCL2, C11orf30, C11orf73, C17orf76-AS1, C6orf48, C9orf69, CAB39, CALU, CDC25B, CDC42BPA, CDKAL1, CLIC1, COL12A1, COL1A1, COL6A1, CSNK1A1, CTDSP2, CUL2, CUL4A, DAXX, DCAF10, DDAH1, DDR1, DDX39B, DENND1A, DGCR2, DKFZp434M1735, DKK3, DNM2, DST, EEF1A1, EFCAB14, EHMT2, EIF4G1, EIF4G2, EIF4G3, ENSA, EXO1, FAM111A, FAM198B, FAM65A, FBXO34, FEZ1, FGD5-AS1, FGFRL1, FLII, FN1, FOXK1, FUS, GALC, GALNT1, GAS7, GCFC2, GGCT, GJC1, GNA13, GNL3L, GOLGA4, GPR1, GREM1, HEG1, HLA-A, HLA-E, HLTF, HNRNPR, HNRNPUL1, IQCE, ITGB5, ITSN1, KIAA1033, KIF2A, KIF3A, KLC2, LATS2, LIMS1, LINC00341, LINC00657, LONP1, LOX, LUC7L2, MBD1, MBOAT7, MEF2D, MEIS2, MICAL2, MKL1, MKNK2, MLST8, MPPE1, MSL3, MSRB3, MTRR, MYADM, MYLK, MYO1D, NAA35, NAV1, NAV2, NCOA1, NFX1, NKX3-1, NOMO3, NRG1, NUDT4, NUPL1, NUSAP1, OSMR, P4HA1, P4HB, PAPD4, PARD3, PARN, PARP14, PARVB, PCBP2, PCBP4, PCGF3, PDLIM7, PDXDC1, PEX5, PFKP, PHRF1, PI4K2A, POLE3, POLR3D, POSTN, PPARA, PPP6R1, PPP6R2, PRNP, PXN, RAB34, RAD23B, RALB, RAP1A, RASSF8, RBCK1, RBFOX2, RGS10, RIF1, RNF14, RNF19A, SAMD9, SCAF4, SDCBP, SERPINE2, SF1, SH3RF1, SKIL, SLC25A17, SLC4A4, SMG1, SNHG16, SREBF1, STAT3, STC2, STEAP2, STRN3, SYNE1, SYNE2, TACC1, TARS, TGFBI, TMEM47, TNC, TNFRSF12A, TNS1, TRAF3, TRIM28, TSC2, TSHZ1, TTC7A, TUBB2C, TUBB3, TXNL1, TXNRD1, UBE2G2, UBE2V1, UBQLN4, UNC5B, USP19, VARS2, VCL, VPS29, WDR37, WIPF1, WWTR1, ZC3H12C, ZCCHC11, ZEB1, ZEB2, ZFAND1, ZFAND5, ZMIZ1, ZNF28, ZNF281, ZNF655, ZNF764 and ZNF839.

7. The method of claim 1, wherein the gene is selected from the group consisting of: PDXDC2P, PDXDC1, GGCT, PAPD4, C11orf73, DIAPH3, DENND5A, HLTF, PPHNL1, GALC, PITPNB, STRN3, APLP2, TEX21P, RCC1, and VPS29.

* * * * *

SEQUENCE LISTING

<160> NUMBER OF SEQ ID NOS: 7

<210> SEQ ID NO 1
<211> LENGTH: 21
<212> TYPE: DNA
<213> ORGANISM: Artificial Sequence
<220> FEATURE:
<223> OTHER INFORMATION: hGAPDH Forward Probe

<400> SEQUENCE: 1
cgcctggtca ccagggctgc t          21

<210> SEQ ID NO 2
<211> LENGTH: 21
<212> TYPE: DNA

```
<213> ORGANISM: Artificial Sequence
<220> FEATURE:
<223> OTHER INFORMATION: hGAPDH Forward Primer

<400> SEQUENCE: 2
caacggattt ggtcgtattg g                                              21

<210> SEQ ID NO 3
<211> LENGTH: 25
<212> TYPE: DNA
<213> ORGANISM: Artificial Sequence
<220> FEATURE:
<223> OTHER INFORMATION: hGAPDH Reverse Primer

<400> SEQUENCE: 3
tgatggcaac aatatccact ttacc                                          25

<210> SEQ ID NO 4
<211> LENGTH: 27
<212> TYPE: DNA
<213> ORGANISM: Artificial Sequence
<220> FEATURE:
<223> OTHER INFORMATION: SMN FL Forward Primer B

<400> SEQUENCE: 4
gctcacattc cttaaattaa ggagaaa                                        27

<210> SEQ ID NO 5
<211> LENGTH: 28
<212> TYPE: DNA
<213> ORGANISM: Artificial Sequence
<220> FEATURE:
<223> OTHER INFORMATION: SMN delta-7 Forward Primer B

<400> SEQUENCE: 5
tggctatcat actggctatt atatggaa                                       28

<210> SEQ ID NO 6
<211> LENGTH: 24
<212> TYPE: DNA
<213> ORGANISM: Artificial Sequence
<220> FEATURE:
<223> OTHER INFORMATION: SMN Reverse Primer B

<400> SEQUENCE: 6
tccagatctg tctgatcgtt tctt                                           24

<210> SEQ ID NO 7
<211> LENGTH: 30
<212> TYPE: DNA
<213> ORGANISM: Artificial Sequence
<220> FEATURE:
<223> OTHER INFORMATION: SMN Forward Probe B

<400> SEQUENCE: 7
ctggcataga gcagcactaa atgacaccac                                     30
```